(12) United States Patent
Schøller et al.

(10) Patent No.: US 10,336,808 B2
(45) Date of Patent: Jul. 2, 2019

(54) MHC PEPTIDE COMPLEXES AND USES THEREOF IN INFECTIOUS DISEASES

(75) Inventors: Jøgen Schøller, Lyngby (DK); Henrik Pedersen, Lynge (DK); Liselotte Brix, Bagsværd (DK)

(73) Assignee: Dako Denmark A/S, Glostrup (DK)

( * ) Notice: Subject to any disclaimer, the term of this patent is extended or adjusted under 35 U.S.C. 154(b) by 0 days.

(21) Appl. No.: 13/482,472

(22) Filed: May 29, 2012

(65) Prior Publication Data

US 2012/0264161 A1  Oct. 18, 2012

Related U.S. Application Data

(63) Continuation of application No. 12/619,039, filed on Nov. 16, 2009, now Pat. No. 8,268,964, which is a continuation of application No. PCT/DK2008/000118, filed on Mar. 26, 2008.

(60) Provisional application No. 60/907,217, filed on Mar. 26, 2007, provisional application No. 60/929,583, filed on Jul. 3, 2007, provisional application No. 60/929,581, filed on Jul. 3, 2007, provisional application No. 60/929,582, filed on Jul. 3, 2007, provisional application No. 60/929,586, filed on Jul. 3, 2007.

(30) Foreign Application Priority Data

| Mar. 26, 2007 | (DK) | ................................. | 2007 00461 |
| Jul. 3, 2007 | (DK) | ................................. | 2007 00972 |
| Jul. 3, 2007 | (DK) | ................................. | 2007 00973 |
| Jul. 3, 2007 | (DK) | ................................. | 2007 00974 |
| Jul. 3, 2007 | (DK) | ................................. | 2007 00975 |

(51) Int. Cl.
| C07K 14/74 | (2006.01) |
| A61K 47/64 | (2017.01) |
| G01N 33/569 | (2006.01) |
| A61K 49/18 | (2006.01) |
| G01N 33/574 | (2006.01) |
| A61K 47/61 | (2017.01) |
| A61K 38/00 | (2006.01) |

(52) U.S. Cl.
CPC ........ *C07K 14/70539* (2013.01); *A61K 47/61* (2017.08); *A61K 47/6425* (2017.08); *A61K 49/1896* (2013.01); *G01N 33/56905* (2013.01); *G01N 33/56911* (2013.01); *G01N 33/56972* (2013.01); *G01N 33/56977* (2013.01); *G01N 33/574* (2013.01); *A61K 38/00* (2013.01); *G01N 2333/70539* (2013.01); *G01N 2800/24* (2013.01)

(58) Field of Classification Search
None
See application file for complete search history.

(56) References Cited

U.S. PATENT DOCUMENTS

| 4,281,061 A | 7/1981 | Zuk et al. |
| 4,336,173 A | 6/1982 | Ugelstad |
| 4,387,164 A | 6/1983 | Hevey et al. |
| 4,459,378 A | 7/1984 | Ugelstad |
| 4,654,267 A | 3/1987 | Ugelstad et al. |
| 4,876,190 A | 10/1989 | Recktenwald |
| 5,039,487 A | 8/1991 | Smith |
| 5,130,297 A | 7/1992 | Sharma et al. |
| 5,194,425 A | 3/1993 | Sharma et al. |
| 5,260,422 A | 11/1993 | Clark et al. |
| 5,284,935 A | 2/1994 | Clark et al. |
| 5,312,744 A | 5/1994 | Shibata |
| 5,468,481 A | 11/1995 | Sharma et al. |
| 5,583,031 A | 12/1996 | Stern |
| 5,627,037 A | 5/1997 | Ward et al. |
| 5,635,363 A | 7/1997 | Altman et al. |
| 5,652,342 A | 7/1997 | Zimmerman et al. |
| 5,807,552 A | 9/1998 | Stanton et al. |
| 5,869,270 A | 2/1999 | Rhode et al. |
| 5,891,741 A | 4/1999 | Siiman et al. |

(Continued)

FOREIGN PATENT DOCUMENTS

| DE | 197 40 735 | 3/1999 |
| DE | 102 47 014 | 4/2004 |

(Continued)

OTHER PUBLICATIONS

Karin et al (J.Exp. Med., 1994, 180: 2227-2237).*

(Continued)

*Primary Examiner* — G. R. Ewoldt
*Assistant Examiner* — Marianne DiBrino
(74) *Attorney, Agent, or Firm* — Arent Fox LLP

(57) ABSTRACT

Novel compounds carrying ligands capable of binding to counter receptors on relevant target cells are disclosed. The compounds possess a number of advantageous features, rendering them very suitable for a wide range of applications, including use as detection systems, detection of relevant target cells as well as a number of other methods. In particular, novel MHC complexes comprising one or more MHC molecules are disclosed. The affinity and specificity of the MHC-peptide complexes are surprisingly high. The possibility of presenting to the target cells a plurality of MHC-peptide complexes makes the MHC complexes according to the present invention an extremely powerful tool e.g. in the field of therapy and diagnosis. The invention generally relates to the field of therapy, including therapeutic methods and therapeutic compositions. Also comprised by the present invention is the sample-mounted use of MHC complexes and MHC multimers.

8 Claims, 76 Drawing Sheets

Specification includes a Sequence Listing.

(56) References Cited

U.S. PATENT DOCUMENTS

| | | | |
|---|---|---|---|
| 5,955,079 A | 9/1999 | Mond et al. | |
| 5,994,089 A | 11/1999 | Siiman et al. | |
| 5,998,204 A | 12/1999 | Tsien et al. | |
| 6,015,884 A | 1/2000 | Schnek et al. | |
| 6,096,315 A | 1/2000 | Zimmerman et al. | |
| 6,074,645 A | 6/2000 | Diamond et al. | |
| 6,090,587 A | 7/2000 | Rhodes et al. | |
| 6,106,840 A | 8/2000 | Clark et al. | |
| 6,129,916 A | 10/2000 | Chang | |
| 6,140,113 A | 10/2000 | Schnek et al. | |
| 6,156,317 A | 12/2000 | Diamond et al. | |
| 6,156,514 A | 12/2000 | Acevedo et al. | |
| 6,197,302 B1 | 3/2001 | Hirsch et al. | |
| 6,197,928 B1 | 3/2001 | Tsien et al. | |
| 6,211,342 B1 | 4/2001 | Hirsch et al. | |
| 6,232,445 B1 | 5/2001 | Rhode et al. | |
| 6,248,564 B1 | 6/2001 | Walter et al. | |
| 6,251,399 B1 | 6/2001 | Diamond et al. | |
| 6,268,411 B1 | 7/2001 | Schneck et al. | |
| 6,306,605 B1 | 10/2001 | Acevedo et al. | |
| 6,309,645 B1 | 10/2001 | Rhode et al. | |
| 6,335,173 B1 | 1/2002 | Kaplan | |
| 6,387,622 B1 | 5/2002 | Siiman et al. | |
| 6,448,071 B1 | 9/2002 | Schneck et al. | |
| 6,451,314 B1 | 9/2002 | Clark et al. | |
| 6,451,769 B1 | 9/2002 | Huebner et al. | |
| 6,458,354 B1 | 10/2002 | Schneck et al. | |
| 6,458,933 B1 | 10/2002 | Hansen | |
| 6,486,130 B1 | 11/2002 | Livey et al. | |
| 6,517,838 B1 | 2/2003 | Hook et al. | |
| 6,534,633 B1 | 3/2003 | Weidanz et al. | |
| 6,548,067 B1 | 4/2003 | Seeman et al. | |
| 6,605,711 B1 | 8/2003 | Valmori et al. | |
| 6,734,013 B2 | 5/2004 | Schneck et al. | |
| 7,041,442 B1 | 5/2006 | Kern et al. | |
| 7,060,869 B2 | 6/2006 | Tsien et al. | |
| 7,064,190 B1 | 6/2006 | Endl et al. | |
| 7,074,904 B2 | 6/2006 | Wong et al. | |
| 7,094,555 B2 | 8/2006 | Kwok et al. | |
| 7,116,407 B2 | 10/2006 | Hansen et al. | |
| 7,141,656 B2 | 11/2006 | Rhode et al. | |
| 7,202,349 B2 | 4/2007 | Davis | |
| 7,364,869 B2 | 4/2008 | Nixon et al. | |
| 7,502,580 B2 | 3/2009 | Hays | |
| 7,519,318 B2 | 4/2009 | Kurogawa et al. | |
| 7,524,503 B2 | 4/2009 | Khanna et al. | |
| 7,706,782 B1 | 4/2010 | Hosmer et al. | |
| 7,902,121 B2 | 3/2011 | Chen et al. | |
| 8,114,669 B2 | 2/2012 | Choo | |
| 8,268,964 B2 * | 9/2012 | Scholler et al. | 530/350 |
| 8,298,782 B2 | 10/2012 | Busch et al. | |
| 2002/0006903 A1 | 1/2002 | Schneck et al. | |
| 2002/0034513 A1 | 3/2002 | Rhode et al. | |
| 2002/0058787 A1 | 5/2002 | Strominger | |
| 2002/0082411 A1 | 6/2002 | Carter et al. | |
| 2002/0091079 A1 | 7/2002 | Rhode et al. | |
| 2002/0119149 A1 | 8/2002 | Jakobsen et al. | |
| 2002/0127231 A1 | 9/2002 | Schneck | |
| 2002/0164340 A1 | 11/2002 | Brumeanu et al. | |
| 2002/0165364 A1 | 11/2002 | Tsien et al. | |
| 2002/0198144 A1 | 12/2002 | Wong et al. | |
| 2003/0017447 A1 | 1/2003 | Barnardo et al. | |
| 2003/0073102 A1 | 4/2003 | Kwok et al. | |
| 2003/0096432 A1 | 5/2003 | Jakobsen et al. | |
| 2003/0104635 A1 | 6/2003 | Jakobsen et al. | |
| 2003/0118594 A1 | 6/2003 | Nag et al. | |
| 2003/0171290 A1 | 9/2003 | Carr et al. | |
| 2003/0199438 A1 | 10/2003 | Shaw et al. | |
| 2003/0228258 A1 | 12/2003 | Scheinberg et al. | |
| 2004/0068100 A1 | 4/2004 | Mach et al. | |
| 2004/0072262 A1 | 4/2004 | Montero-Julian et al. | |
| 2004/0082012 A1 | 4/2004 | Busch et al. | |
| 2004/0086520 A1 | 5/2004 | Diamond | |
| 2004/0137642 A1 | 7/2004 | Erfle et al. | |
| 2004/0141958 A1 | 7/2004 | Steinaa et al. | |
| 2004/0143094 A1 | 7/2004 | Donda et al. | |
| 2004/0204565 A1 | 10/2004 | Schneck et al. | |
| 2004/0209295 A1 | 10/2004 | Schwabe et al. | |
| 2004/0209314 A1 | 10/2004 | Lang et al. | |
| 2004/0223977 A1 | 11/2004 | Diamond | |
| 2004/0253632 A1 | 12/2004 | Rhode et al. | |
| 2005/0003431 A1 | 1/2005 | Wucherpfennig et al. | |
| 2005/0074822 A1 | 4/2005 | Nixon et al. | |
| 2005/0074848 A1 | 4/2005 | Schwabe | |
| 2005/0079152 A1 | 4/2005 | Bot et al. | |
| 2005/0095655 A1 | 5/2005 | Montero-Julian et al. | |
| 2005/0208529 A1 | 9/2005 | Winther et al. | |
| 2005/0214284 A1 | 9/2005 | Price-Schiavi et al. | |
| 2005/0214852 A1 | 9/2005 | Gaynor et al. | |
| 2005/0239160 A1 | 10/2005 | Shaw et al. | |
| 2006/0018878 A1 | 1/2006 | Cooper et al. | |
| 2006/0018929 A1 | 1/2006 | Zaia et al. | |
| 2006/0073159 A1 | 4/2006 | Vonderheide et al. | |
| 2006/0078563 A1 | 4/2006 | Srivastava | |
| 2006/0084116 A1 | 4/2006 | Muchhal et al. | |
| 2006/0112440 A1 | 5/2006 | Tsien et al. | |
| 2006/0141540 A1 | 6/2006 | Miltenyi et al. | |
| 2006/0155115 A1 | 7/2006 | Jakobsen et al. | |
| 2006/0166214 A1 | 7/2006 | Kato et al. | |
| 2006/0166875 A1 | 7/2006 | Jakobsen et al. | |
| 2006/0171954 A1 | 8/2006 | Endl et al. | |
| 2006/0228758 A1 | 10/2006 | Muchhal et al. | |
| 2006/0228759 A1 | 10/2006 | Muchhal et al. | |
| 2006/0234309 A1 | 10/2006 | Shankar et al. | |
| 2006/0234310 A1 | 10/2006 | Cai et al. | |
| 2006/0240482 A1 | 10/2006 | Kwok et al. | |
| 2007/0026503 A1 | 2/2007 | Lacey | |
| 2007/0134814 A1 | 6/2007 | Kajander et al. | |
| 2007/0154953 A1 | 7/2007 | Brunner et al. | |
| 2007/0178532 A1 | 8/2007 | Jacobson et al. | |
| 2007/0184022 A1 | 8/2007 | Wang et al. | |
| 2007/0280957 A1 | 12/2007 | Falk et al. | |
| 2008/0219947 A1 | 9/2008 | Linette et al. | |
| 2009/0004213 A1 | 1/2009 | Singh et al. | |
| 2009/0061478 A1 | 3/2009 | Poulsen et al. | |
| 2009/0232766 A1 | 9/2009 | Wang et al. | |
| 2009/0324630 A1 | 12/2009 | Jensen | |
| 2010/0159594 A1 | 6/2010 | Hansen et al. | |
| 2012/0020998 A1 | 1/2012 | Plumas et al. | |

FOREIGN PATENT DOCUMENTS

| | | |
|---|---|---|
| EP | 0 106 873 | 5/1984 |
| EP | 0 352 761 | 1/1990 |
| EP | 0 516 953 | 12/1992 |
| EP | 0 633 028 | 1/1995 |
| EP | 0 636 696 | 2/1995 |
| EP | 0 420 913 | 11/1995 |
| EP | 0 423 201 | 6/1996 |
| EP | 0 742 014 | 11/1996 |
| EP | 0 949 508 | 10/1999 |
| EP | 0946592 | 10/1999 |
| EP | 1023319 | 8/2000 |
| EP | 0 776 339 | 10/2000 |
| EP | 1 051 619 | 11/2000 |
| EP | 1181313 | 2/2002 |
| EP | 0 981 747 | 7/2002 |
| EP | 1 227 321 | 7/2002 |
| EP | 0 630 255 | 12/2002 |
| EP | 0 812 331 | 5/2004 |
| EP | 0 935 607 | 7/2004 |
| EP | 1 437 366 | 7/2004 |
| EP | 0 877 760 | 9/2004 |
| EP | 1 526 141 | 8/2005 |
| EP | 0 997 477 | 3/2006 |
| EP | 1 017 799 | 3/2006 |
| EP | 1 349 569 | 4/2007 |
| EP | 0 665 289 | 5/2007 |
| EP | 1 012 320 | 10/2007 |
| RU | 2 260 047 | 4/2005 |
| WO | WO 89/12458 | 12/1989 |
| WO | WO 89/12459 | 12/1989 |
| WO | WO 90/04411 | 5/1990 |
| WO | WO 91/09870 | 7/1991 |

(56) References Cited

FOREIGN PATENT DOCUMENTS

| | | |
|---|---|---|
| WO | WO 91/15766 | 10/1991 |
| WO | WO 92/00055 | 1/1992 |
| WO | WO 92/08983 | 5/1992 |
| WO | WO 92/18150 | 10/1992 |
| WO | WO 92/21972 | 12/1992 |
| WO | WO 93/01498 | 1/1993 |
| WO | WO 93/01498 A1 * | 1/1993 |
| WO | WO 93/04175 | 3/1993 |
| WO | WO 93/08306 | 4/1993 |
| WO | WO 93/10220 | 5/1993 |
| WO | WO 94/11078 | 5/1994 |
| WO | WO 94/12196 | 6/1994 |
| WO | WO 95/11998 | 5/1995 |
| WO | WO 95/12676 | 5/1995 |
| WO | WO 95/14781 | 6/1995 |
| WO | WO 96/04314 | 2/1996 |
| WO | WO 96/26962 | 9/1996 |
| WO | WO 97/05239 | 2/1997 |
| WO | WO 97/28191 | 8/1997 |
| WO | WO 97/35991 | 10/1997 |
| WO | WO 97/42221 | 11/1997 |
| WO | WO 97/44667 | 11/1997 |
| WO | WO 98/03552 | 1/1998 |
| WO | WO 98/05965 | 2/1998 |
| WO | WO 98/06749 | 2/1998 |
| WO | WO 98/05684 | 5/1998 |
| WO | WO 1999/002183 | 1/1999 |
| WO | WO 99/11661 | 3/1999 |
| WO | WO 99/11775 | 3/1999 |
| WO | WO 99/14236 | 3/1999 |
| WO | 199924577 A1 | 5/1999 |
| WO | WO 99/21572 | 5/1999 |
| WO | WO 99/13095 | 7/1999 |
| WO | WO 1999/36568 | 7/1999 |
| WO | WO 99/42597 | 8/1999 |
| WO | WO 99/50637 | 10/1999 |
| WO | WO 99/58557 | 11/1999 |
| WO | WO 99/60119 | 11/1999 |
| WO | WO 2000/006745 | 2/2000 |
| WO | WO 00/15665 | 3/2000 |
| WO | 200021989 A1 | 4/2000 |
| WO | WO 00/23053 | 4/2000 |
| WO | WO 2000/075180 | 12/2000 |
| WO | WO 2000/078966 | 12/2000 |
| WO | WO 2003/000720 | 1/2001 |
| WO | WO 2001/63286 | 8/2001 |
| WO | 2001073443 A3 | 10/2001 |
| WO | WO 01/72782 | 10/2001 |
| WO | WO 01/70245 | 11/2001 |
| WO | WO 01/80833 | 11/2001 |
| WO | WO 01/90198 | 11/2001 |
| WO | WO 01/90747 | 11/2001 |
| WO | WO 2002/016422 | 2/2002 |
| WO | WO 02/054065 | 7/2002 |
| WO | WO 02/072631 | 9/2002 |
| WO | WO 02/089837 | 11/2002 |
| WO | WO 03/016905 | 2/2003 |
| WO | WO 02/055992 | 3/2003 |
| WO | WO 03/073097 | 9/2003 |
| WO | WO 02/083906 | 10/2003 |
| WO | WO 03/101473 | 12/2003 |
| WO | WO 2004/000873 | 12/2003 |
| WO | WO 2004/014957 | 2/2004 |
| WO | WO 2004/018520 | 3/2004 |
| WO | WO 2004/033497 | 4/2004 |
| WO | WO 2004/093905 | 11/2004 |
| WO | WO 05/002621 | 1/2005 |
| WO | WO 2005/007689 | 1/2005 |
| WO | WO 2005/035567 | 4/2005 |
| WO | WO 2005/049073 | 6/2005 |
| WO | WO 2005/116051 | 12/2005 |
| WO | WO 2006/009838 | 1/2006 |
| WO | WO 2006/014292 | 2/2006 |
| WO | WO 2006/056027 | 6/2006 |
| WO | WO 2006/071990 | 7/2006 |
| WO | WO 06/082387 | 8/2006 |
| WO | WO 2006/081826 | 8/2006 |
| WO | WO 2006/090283 | 8/2006 |
| WO | WO 2006/113622 | 10/2006 |
| WO | 2007015168 A2 | 2/2007 |
| WO | WO 2007/065098 | 6/2007 |
| WO | WO 2007/085266 | 8/2007 |
| WO | WO 2007/136778 | 11/2007 |
| WO | WO 2008/019366 | 2/2008 |
| WO | WO 2008/031133 | 3/2008 |
| WO | WO 2008/116468 | 10/2008 |
| WO | WO 2009/003492 | 1/2009 |
| WO | WO 2009/003493 | 1/2009 |
| WO | WO 2009/039854 | 4/2009 |
| WO | 2009077173 A2 | 6/2009 |
| WO | WO 2009/106073 | 9/2009 |
| WO | WO 2009/114207 | 9/2009 |
| WO | 2009126828 A2 | 10/2009 |
| WO | WO 2009/125231 | 10/2009 |
| WO | WO 2009/126816 | 10/2009 |
| WO | WO 2009/155535 | 11/2009 |
| WO | WO 2010/009735 | 1/2010 |
| WO | WO 2010/032022 | 3/2010 |
| WO | WO 2010/037395 | 4/2010 |
| WO | WO 2010/037397 | 4/2010 |
| WO | WO 2010/037402 | 4/2010 |
| WO | 2012044999 A2 | 4/2012 |
| WO | 2012094492 A2 | 7/2012 |

OTHER PUBLICATIONS

Celis et al (Mol. Immunol. 1994 31(18): 1423-1430).*
Busch et al (J. Immunol. 1996, 157: 3534-3541).*
Schueler-Furman et al (Protein Science, 2000, 9: 1838-1846).*
Theisen et al (J. Bacter. 1995, 177: 3036-3044).*
DiBrino et al (J. Immunology 151(11) 5930-5935, 1993).*
HLA Nomenclature (world wide web at hla.alles.org/nomenclature/stats.html, 2010).*
HLA Nomenclature 2015.*
DiBrino et al (J. Immunology 151(11) 5390-5935, 1993) (Year: 1993).*
Celis et al (Molecular Immunol. 3: 1423-1430, 1994 (Year: 1994).*
Ochoa-Garay et al (Mol. Immunol., 1997, 34(3): 273-281 )(Year: 1997).*
U.S. Appl. No. 08/374,468, Endl.
Altman, et al., "Formation of functional peptide complexes of class II major histocompatibility complex proteins from subunits produced in *Escherichia coli*," Proc. Natl. Acad. Sci. USA, pp. 10330-10334, Nov. 1993, vol. 90.
Altman, et al., "Phenotypic Analysis of Antigen-Specific T Lymphocytes," Science 274:94-97, 1996.
Andersen, et al., "Spontaneous cytotoxic T-cell responses against survivin MHC class I-restricted T-cell epttopes in situ as well as ex vivo in cancer patients," Cancer Res., vol. 61, pp. 5964-5968, Aug. 15, 2001.
Appel, et al., "Kinetics of T-cell receptor binding by bivalent HLA-DR-peptide complexes that activate antigen-specific human T-cells," J. Biol. Chem., pp. 312-321, Jan. 7, 2000, vol. 275.
Appel, et al., "Anergy induction by dimeric TCR ligands," J. Immunol., pp. 5279-5285, Apr. 15, 2001, vol. 166.
Ausubel, et al., "Characterization of in vivo expanded OspA-specific human T-cell clones," Clinical Immunology, Academic Press, pp. 313-322, Jun. 1, 2005 (Jun. 6, 2005), vol. 115, No. 3, US.
Bakker, et al., "MHC multimer technology: Current status and future prospects," Current Opinion in Immunology, 17:428-433, 2005.
Barany, et al., "Solid-phase peptide synthesis: A silver anniversary report," Int. J. Peptide Protein Res., 30:705-739, 1987.
Batard, et al., "Dextramers: New generation of fluorescent MHC class I/ peptide multimers for visualization of antigen-specific CD8< + > T cells," Journal of Immunological Methods, Elsevier Science Publishers, pp. 136-148, Mar. 20, 2006 (Mar. 20, 2006), vol. 310, No. 1-2, Amsterdam, NL.
Berger, et al., "Circulation and homing of melanoma-reactive T cells to both cutaneous and visceral metastases after vaccinnation with

(56) References Cited

OTHER PUBLICATIONS monocyte-derived dendritic cells," Int. J. Cancer, pp. 229-237, 2004, vol. 111.
Bergmeier, et al., "Innate and adoptive mucosal immunity in protection against HIV infection," Advances in Dental Research 2006, pp. 21-28, 2006, vol. 19, No. 1, XP002562924.
Bill, et al., "Use of soluble MHC class II/peptide multimers to detect antigen-specific T cells in human disease," Arthritis Res., pp. 261-265, Feb. 28, 2002, vol. 4.
Bjorkman, et al., "The foreign antigen binding site and T cell recognition regions of class I histocompatibility antigen," Nature 329:512-518, 1987.
Bogers, "CCR5 targeted SIV vaccination strategy preventing or inhabiting SIV infection," Vaccine, Butterworth Scientific, pp. 2974-2984, Aug. 13, 2004 (Aug. 13, 2004), vol. 22, No. 23-24. Guildford, GB.
Bross, et al., "Approval summary: Gemtuzumab ozogamicin in relapsed acute myeloid leukemia", Clin. Cancer Res., 2001, 7:1490-1496.
Burlingham, et al., "Soluble MHC, Immunoregulation, and tolerance: A progress report," Human Immunol., pp. 1316-1319, Dec. 2000, vol. 61.
Callan, et al., "Direct Visualizing of Antigen.specific CD8+ T Cells during th ePRimary Immune Response to Epstein-Barr Virus in Vivo," J. Exp. Med., May 1998, pp. 1395-1402, vol. 187, No. 9.
Cameron, et al., "Labeling antigen-specific DC4(+) T cells with class II MHC oligomers," J. Immunol. Methods, pp. 51-69, Oct. 1, 2002, vol. 268.
Carena, et al., "Major Histocompatibility Complex Class I Molecules Modulate Activation Threshold and Early Signaling of T-Cell Antigen Receptor-γδ Stimulated by Nonpeptidic Ligands," J. Exp. Med., Nov. 17, 1997, pp. 1769-1774, 186 (10).
Casares, et al., "Antigen-specific downregulation of T cells by doxorubicin delivered through a recombinant MHC II-peptide chimera," Nature Biotech., pp. 142-147, Feb. 2001, vol. 19.
Cochran, et al., "Receptor clustering and transmembrane signaling T cells," TIBS, pp. 304-310, May 2001, vol. 26.
Coles, et al., "Memory CD8 T lymphocytes express inhibitory MHC-specific Ly49 receptors," Eur. J. Immunol. 30:236-244, 2000.
Constantin, et al., "Major histocompatibility complex (MHC) tetramer technologt: An evaluation," Biol. Res. Nursing, pp. 115-127, Oct. 2002, vol. 4.
Dako: "MHC Dextramers" Internet Article Jul. 6, 2006 URL: pri.dako.com/00207_mhcdex_0406.pdf.
Dal Porto et al, "A soluble divalent class I major histocompatibility complex molecule inhibits alloreactive T cells at nanomolar concentrations," Porc. Natl. Acad. Sci. 90.6671-6675, 1993.
Devito-Haynes, et al., "Soluble donor HLA class I and β2-m-free heavy chain in serum of lung transplant recipients: Steady-state levels and increases in patients with recurrent CMV infection, acute rejection episodes, and poor outcome," Human Immunol., pp. 1370-1382, Dec. 2000, vol. 61.
Drouin, et al., "Searching for borrelial T-cell epitopes associated with antibiotic-refractory Lyme arthritis," Molecular Immunology, pp. 2323-2332, Jan. 11, 2008 (Jan. 11, 2008), vol. 45, No. 8, GB.
Ed. Charron, "HLA: Genetic diversity of HLA. Functional and Medical Implication," EDK Press, pages corresponding to Tables 1A and 1B, 1997.
Erout, et al., "Preparation of Conjugates between Oligonucleotide and N-Vinylpyrrolidone/N-Acryoxysuccinimide Coplymers and Applications in Nucleic Acid Assays to Improve Sensitivity," Bioconjugate Chem. 1996, pp. 568-575, vol. 7.
Fields, et al., "Solid phase peptide synthesis utilizing 9-fluorenylmethoxycarbonyl amino acids," Int. J. Peptide Res., 353:161-214, 1990.
Frayser, et al., "Empty and peptide-loaded class II major histocompatibility complex proteins produced by expression in *Escherichia coli* and folding in vitro," Protein Expression and Purification, pp. 105-114, Feb. 1999, vol. 15.

Garboczi, et al., "HlA-A2.peptide complexes: Refolding and crystallization of molecules expressed in *Escherichia coli* and complexed with single antigenic peptides," Proc. Natl. Acad. Sci., 89:3429-3433, 1992.
Gordon, et al., "Applications of Combinatorial Technologies to Drug Discovery. 2. Combinatorial Organic Synthesis, Library Screening Strategies, and Future Directions," Journal of Medicinal Chemistry, 37 (10):1385-1401, 1994.
Hadrup, et al., "Persistence of survivin specific T cells for seven years in a melanoma patient during complete remission," Cancer Biol. Ther., pp. 480-482, May 2006, vol. 5.
Houghten, et al., "Generation and use of synthetic peptide combinatorial libraries for basic research and drug discovery," Nature, 354:84-86, 1991.
Huges, et al., "Generation and use of alternative multimers of peptide/MHC complexes," Journal of Immunological Methods, 268:83-92, 2002.
Haanen, et al., "In situ detection of virus- and tumor-specific T-cell Immunity," Nature Medicine, Sep. 2000, pp. 1056-1060, vol. 6.
International Search report dated May 6, 2007 in International Application No. PCT/DK2007/000045.
Jung, et al., "Multiple Peptide Synthesis Methods and their Applications," Angewandte Chemie, 31 (4):367-486, 1992.
Kalandadze, et al., "Expression of Recombinant HLA-DR2 molecules," J. Biol. Chem., pp. 20156-20162, Aug. 16, 1996, vol. 271.
Knabel, et al., "Reversible MHC multimer staining for functional isolation of T-cell populations and effective adoptive transfer," Nature Medicine, Nature Publishing Group, pp. 631-637, Jun. 1, 2002 (Jun. 1, 2002), vol. 8, No. 6, New York, NY, USA.
Kozono, et al., "Production of soluble MHC class II proteins with covalently bound single peptides," Nature, pp. 151-154, May 12, 1994, vol. 369.
Kuroda, et al., "Analysis of Gag-specific Cytotoxic T Lymphocytes in Simian Immunodeficiency Virus-intected Rhesus Monkeys by Cell Staining with Tetrameric Major Histocompatibility Complex Class I-Peptide Complex," J.Exp. Med., May 4, 1998, 1373-1381, vol. 187, No. 9.
Kuttler, et al., "An Algorithm for the Prediction of Proteasomal Cleavages," J. Miol. Biol., 298:417-429, 2000.
König, "Interactions between MHC molecules and co-receptors of the TCR," Current Opinion in Immunology, pp. 75-83, 2002, vol. 14.
Larsson, "Immunocytochemical detection systems," in Immunocytohemistry: Theory and Practice, pp. 77-145, CRC Press, 1988.
Lee, et al., "Characterizatio of circulating T cells specific for tumor-associateda ntigens in melanoma patients," Nature Medicine, Jun. 1999, pp. 677-685, vol. 5, No. 6.
Lehner, "Allomicrovac: A combined microbicidal-immunising strategy against SIV and HIV infection," Vaccines for Humans, pp. 64-65, Dec. 5, 2008 (Dec. 5, 2008), XP0025629223, URL: biblioteca.porto.ucp.pt/docbweb/MULTIMEDIA/ASSOCIA/PDF/VAC.PDF.
Ljunggren, et al., "Empty MHC class I molecules come out in the cold," Nature 346:476-480, 1990.
Mallone, et al., "MHC class II tetramers and the pursuit of antigen-specific T cells: Define, deviate, delete," Clin. Immunol., pp. 232-242, 2004, vol. 110.
Marchand, et al., "Tumor regression responses in melanoma patients treated with a peptide encoded by gene MAGE-3," Int. J. Cancer, 63:883-885, 1995.
Matsumura, et al., "Emerging Principles for the Recognition of Peptide Antigen by MHC class I Molecules," Science 257:927-934, 1992.
Matsumura, et al., "In vitro peptide binding to soluble empty class I major histocompatibility complex molecules isolated from transfected *Drosophila melanogaster* cells," J. Biol. Chem., pp. 23589-23595, Nov. 25, 1992, vol. 267.
McCluskey, et al., "T-cell activation by purified, soluble, class I MHC molecules: Requirement for polyvalency," J. Immunol. 141(5): 1451-55, 1988.
McHeyzer-Williams, et al., "Tracking antigen-specific helper T cell responses," Current Opinion in Immunology, pp. 278-284, 1996, vol. 8.

(56) References Cited

OTHER PUBLICATIONS

Melenhorst, et al.,"Detection of Low Avidity CD8+ T Cell Populations with Coreceptor-Enhanced Peptide-Major Histompatibility Complex Class I Tetramers," j. Immunol. Methods, 2008, vol. 338, No. 1-2, pp. 31-39.

Merrifield, "Solid Phase Synthesis," Science 232:341-347, 1986.

Merrifield, et al., "Instrument for Automated Synthesis of peptides," Analytical Chemistry, 38 (13):1905-1914, 1966.

Meyer, et al., "Direct enumeration of Borrelia-reactive CD4 T-cell ex vivo by using MHC class II tetramers," Proceedings of the National Academy of Sciences of USA. (PNAS), National Academy of Science, pp. 11433-11438, Oct. 10, 2000 (Oct. 10, 2000), vol. 97, No. 21, Washington D.C., US.

Mutis, et al., "Tetrameric HLA class I-minor histocompatibility antigen peptide complexes demonstrate minor histocompatibility antigen-specific cytoxic T lymphocytes in patients with graft-visus-host disease," Nature Medicine, Jul. 1999, pp. 839-842, vol. 5, No. 7.

Neudorfer, et al., "Reversible HLA multimers (streptamers) for the isolation of human cytotoxic T lymphocytes functionally active against tumor- and virus-derived antigens," Journal of Immunological Methods, 320:119-131, 2007.

O'Herrin, et al., "Analysis of the Expression of Peptide-Major Histocaompatibility Complexes using high affinity Soluble Divalent T-Cell Receptors," The Journal of Biological Chemistry, Oct. 20, 1997, pp. 1333-1345, vol. 186, No. 8.

Reich, et al., "Stability of empty and peptide-loaded class II major histocompatibility complex molecules at neutral and endosomal pH: Comparison to class I proteins," Proc. Natl. Acad. Sci. USA, pp. 2495-2500, Mar. 1997, vol. 94.

Reijonen, et al., "Use of HLA class II tetramers in tracking antigen-specific T cell and mapping T-call epitopes," pp. 282-288, 2003, vol. 29.

Scheffold, et al., "Recent Development in Flow Cytometry," Journal of Clinical Immunology, Aug. 2000, vol. 20, No. 6.

Scheirle, et al., "Peptide binding to soluble HLA-DR4 molecules produced by insect cells," J. Immunol., pp. 1994-1999, Sep. 15, 1992, vol. 149.

Sengupta, et al., "Heat shock protein-mediated cross-presentation of exogenous HIV antigen on HLA class I and class II," Journal of Immunology, American Association of Immunologists, pp. 1987-1993, Aug. 1, 2004 (Aug. 1, 2004), vol. 173, No. 3.

Shambrook, Fritsch and Maniatis, "Molecular Cloning," Cold Spring Harbor Press, 1989, Index and Table of Contents pp. xi to xxxviii and I-1 to I-47.

Shields, et al., "The Effect of Human β2-Microglobulin on Major Histocompatibility Complex I Peptide Loading and the Engineering of a High Affinity Variant," The Journal of Biological Chemistry, Oct. 23, 1998, pp. 28010-28018, vol. 273, No. 43.

Siiman, et al., Bioconjugate Chem. 1999, vol. 10, pp. 1090-1106.

Skinner, et al., "In situ tetramer staining," J. Immunol. Meth., pp. 29-34, 2002, vol. 268.

Stern, et al., "The human class II MHC protein HLA-DR1 assembles as empty alpha beta heterodimers in the absence of antigenic peptide," Cell, pp. 465-477, Feb. 7, 1992, vol. 68.

Stratmann, et al., "Susceptible MHC Alleles, not background genes, select an autoimmune T cell reactivity," The Journal of Clinical Investigation, pp. 902-914, Sep. 2003, vol. 112, No. 6.

Stockel, et al., "Refolding of human class II major histocompatibility complex molecules isolated from *Escherichia coli*", J. Biol. Chem., pp. 29571-29578, Nov. 25, 1994, vol. 269.

Sun, et al., "MHC class I multimers," Arthritis Res., pp. 265-269, Jul. 2001, vol. 3.

Sørensen, et al., "Efficient tumor cell lysis mediated by a bcl-X(L) specific T cell clone isolated from a breast cancer patient," Cancer Immunol., Immunotherapy, Springer, pp. 527-533, Jul. 19, 2006, vol. 56, No. 4, Berlin, DE.

Ugolini, et al., "Regulation of T cell function by NK cell receptors for classical MHC class I molecules," Current Opinion in Immunology 12:295-300, 2000.

Valmori, et al., "Enhanced generation of specific tumor-reactive CTL in vitro by selected Melan-A/MART-1 immunodominant peptide analogues," J. Immunol., pp. 1750-1758, Feb. 15, 1998, vol. 160.

Viola, et al., "T-cell activation and the dynamic world of rafts.," APMIS 107:615-623, 1999.

Vollers, et al.,"Class II Major Histocompatibility Complex Tetramer Staining: Progress, Problems, and Prospects," Immunology, 2008, vol. 123, pp. 305-313.

Vyth-Dreese, et al., "In situ visualization of antigen specific T cells in cryopreserved human tissues," J. Immunol. Meth., pp. 78-85, 2006, vol. 310.

White, et al., "Soluble class I MHC with β2-microglobulin covalently linked peptides: Specific binding to a T cell hybridoma," J. Immunol., pp. 2671-2676, Mar. 1, 1999, vol. 162.

Xu, et al., "MHC/peptide tetramer-based studies of T cell function," J. Immunol Meth., pp. 21-28, 2002, vol. 268.

Zhang, et al., "Essential role of LAT in T cell development," Immunity 10:323-332, 1999.

Bleesing, et al., "Cell Function-Based Flow Cytometry" Seminars in Hematology, Apr. 2001, pp. 169-178, vol. 38, No. 2.

Drouin, et al., "Molecular characterization of the OspA161-175 T cell epitope associated with treatment-resistant Lyme arthritis: differences among the three pathogenic species of *Borrelia burgdorferi* sensu lato", Journal of Autoimmunity, 2004, vol. 23, pp. 281-292.

Fornas, et al., Flow Cytometry Counting of CD34+ cells in whole blood, Nature Medicine, 6 (2000) 7:833-836.

Heijnen, et al., "Enumeration of Antigen-Specific CD8+ T Lymphocytes by Single-Platform, HLA Tetramer-Based Flow Cytometry: A European Multicenter Evaluation", Clinical Cytometry, 2004, pp. 1-13, vol. 62B.

Marsh, et al., "12th International Histocompatibility Workshop Cell Lines Panel: List of Cell Lines", Genetic diversity of HLA Functional and Medical Implication, (Charron ed.), pp. 26-28, 1997.

Wolfl, et al., "Quantitation of MHC Tetramer-Positive Cells From Whole Blood: Evaluation of Single-Platform, Six-parameter Flow Cytometric Method", Cytometry Part A, 2004, pp. 120-130, vol. 57A.

Cecconi, et al., "Use of MHC Class II Tetramers to Investigate CD4 + T Cell Responses: Problems and Solutions," Cytometry, 2008, Part A 73, No. 11, pp. 1010-1018.

Chattopadhyay, et al., "Techniques to improve the direct Ex Vivo detection of low frequency antigen-specific CD8+T cells with peptide-major histocompatibility complex class I tetramers," Cytometry, 2008, Part A, vol. 73, pp. 1001-1009.

Lissina, et al.,"Protein Kinase Inhibitors Substantially Improve the Physical Detection of T-Cells with Peptide-MHC Tetramers," J. Immunol. Methods, 2009, vol. 340, pp. 11-24.

Melenhorst, et al.,"Detection of Low Avidity CD8+ T Cell Populations with Coreceptor-Enhanced Peptide-Major Histocompatibility Complex Class I Tetramers," J. Immunol. Methods, 2008, vol. 338, No. 1-2, pp. 31-39.

Weichsel, et al.,"Profound Inhibition of Antigen-Specific T-Cell Effector Functions by Dasatinib," Clin. Cancer Res.2008, vol. 14, pp. 2484-2491.

Alp, et al., "Fine specificity of cellular immune responses in humans to human cytomegalovirus immediate-early 1 protein", Journal of Virology, vol. 65, No. 9, 1991 pp. 4812-4820.

Ferré, et al., "Purification of correctly oxidized MHC class I heavy-chain molecules under denaturing conditions: A novel strategy exploiting disulfide assisted protein folding", Protein Science, 2003, 12, pp. 551-559.

Dibrino et al., "Endogenous peptides bound to HLA-A3 possess a specific combination of anchor residues that permit identification of potential antigenic peptides", PNAS USA, 1993, vol. 90, pp. 1508-1512.

Parker et al, "Peptide binding to HLA-A2 and HLA-B27 isolated from *Escherichia coli*", JBC, 1992, vol. 267, pp. 5451-5459.

IEBD Analysis Ressource, Jul. 2012, 3 pages, world wide web at tools.immuneepitiope.org/tools/population/tutorial.jsp.

Akiyama et al. "Analysis of HLA-A24-restricted CMVpp65 peptide-specific CTL with HLA-A*2402-CMVpp65 tetramer," Immunology Letters, vol. 95, pp. 199-205, (2004).

(56) References Cited

OTHER PUBLICATIONS

Chen et al. "Modulation of CD1d-restricted NKT cell responses by CD4," Journal of Leukocyte Biology, vol. 82, pp. 1455-1465 (2007).

Denkberg et al. "Recombinant human single-chain MHC-peptide complexes made from E. coli by in vitro refolding: functional single-chain MHC-peptide complexes and tetramers with tumor associated antigens," Eur. J. Immunol., vol. 30, pp. 3522-3532 (2000).

Drake et al. "Cutting Edge: Lipid Raft Integrity Affects the Efficiency of MHC Class I Tetramer Binding and Cell Surface TCR Arrangement on CD8+ T Cells1," The Journal of Immunology, vol. 166, No. 12, pp. 7009-7013 (2001).

He et al. "Procedure for preparing peptide-major histocompatibility complex tetramers for direct quantification of antigen-specific cytotoxic T lymphocytes," World J Gastroenterol, vol. 11, No. 27, pp. 4180-4187 (2005).

Kao et al. "Loss of CD8 and TCR binding to Class I MHC ligands following T cell activation," International Immunology, vol. 17, No. 12, pp. 1607-1617 (2005).

Kronenberg et al. "The unconventional lifestyle of NKT cells," Nature Reviews Immunology vol. 2 No. 8 pp. 557-568 (2002).

Nepom "MHC multimers: expanding the clinical toolkit," Clinical Immunology, vol. 106, pp. 1-4 (2003).

Rognan et al., "Rational design of nonnatural peptides as high-affinity ligands for the HLA-B*2705 human leukocyte antigen", Proc. Natl. Acad. Sci., vol. 92, 1995, pp. 753-757 (1995).

Ruan et al. "Preparation of HLA-A*0201 NLVPMVATV peptide tetramers and application to detect cytomegalovirus specific CTL," Chin J Microbiol Immunol., vol. 26., No. 9, pp. 855-858 (2006)—English Abstract Only.

Ruan et al. "Improved preparation of class I HLA tetramers and their use in detecting CMV-specific CTL," Journal of Immunological Methods, vol. 312, pp. 148-156 (2006).

Weinberg "The Biology of Cancer," Garland Science, pp. 737-747 (2007).

Wulff, "Guide to Flow Cytometry," Dako Educational Guide, www.dako.com, (2006), pp. i to 117.

Andersen et al., "Parallel detection of antigen-specific T-cell responses by combinatorial encoding of MHC multimers," Nat Protoc. vol. 7, No. 5, pp. 891-902 (2012).

Bauer et al., Maximizing Immune Responses: The Effects of Covalent Peptide Linkage to Beta-2-Microglobulin, Oncology Research, vol. 17, pp. 205-216 (2008).

Celis et al., "Induction of anti-tumor cytotoxic T lymphocytes in normal humans using primary cultures and synthetic peptide epitopes," Proc. Natl. Acad. Sci. USA, vol. 91, pp. 2105-2109 (1994).

Cortez-Gonzales et al., Immunogenic HLA-B7-restricted peptides of hTRT. Intl Immunology, vol. 18 No. 12 pp. 1707-1718 (2006).

Desrosiers, "Prospects for an AIDS vaccine," Nature Medicine, vol. 10, No. 3, (2004).

Greten et al., "Peptide-beta-2-microglubulin-MHC fusion molecules bind antigen-specific T cells and can be used for multivalent MHC-Ig complexes," J. Immunological Methods, 27(1-2):125-135 (2002).

Hackett et al., "Frontiers in peptide-MHC class II multimer technology," Nature Immunology, vol. 3, No. 10 (2002).

Karin et al., "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," J. Exp. Med., vol. 180, pp. 2227-2237 (1994).

Larsen, MV, "Prediction of T-cell epitopes for therapeutic and prophylactic vaccines," Ph.D. thesis, Center for Biological Sequence Analysis BioCentrum DTU—Denmark. (2007).

Lauritsen et al., Two distinct pathways exist for down-regulation of the TCR, J, Immunology, 161:260-7 (1998).

Maher, Liposomes and Micelles, Dynamic Chiropractic. www.dynamicchirpractic.com (2016).

Matthews et al., "Prospects for Development of a Vaccine Against HTLV-III-Related Disorders," AIDS Research and Human Retroviruses, vol. 3 Supplement I, (1987).

Nikolich-Zugich et al., "The many important facets of t-cell repertoire diversity, Nature Reviews Immunology," vol. 4, 123-132 (2004).

Ochoa-Garay et al., "The ability of peptides to induce cytotoxic T cells in vitro does not strongly correlate with their affinity for the H-2Ld molecule: Implications for vaccine design and immunotherapy," Molecular Immunology vol. 34, No. 3 273-281, (1997).

Oka et al., "Induction of WT1 (Wilms' tumor gene)-specific cytotoxic T lymphocytes by WT1 peptide vaccine and the resultant cancer regression," PNAS, vol. 101 No. 38, 13885-13890 (2004).

Rammensee et al., "MHC ligands and peptide motifs: first listing. Immunogenetics," 41:178-228 (1995).

Hadrup et al., "Parallel detection of antigen-specific T-cell responses by multidimensional encoding of MHC multimers", Nature Methods (Nature Publishing Group), Basingstoke GB, vol. 6, No. 7, doi:10.1038/NMETH.1345, ISSN 1548-7091, pp. 520-528, (2009).

Schueler-Furman et al., "Structure-based prediction of binding peptides to MHC class I molecules: Application to a broad range of MHC alleles," Protein Science, vol. 9, pp. 1838-1846 (2000).

Schroers et al., "Identification of HLA DR7-restricted epitopes from human telomerase reverse transcriptase recognized by CD4+ T-helper cells," Cancer Research 62, 2600-2605, (2002).

Speiser et al., In Vivo Activation of Melanoma-Specific CD8(+) T Cells by Endogenous Tumor Antigen and Peptide Vaccines. A Comparison to Virus-Specific T Cells, Eur. J. Immunol. 32: 731-741 (2002).

Stoeva et al., "Multiplexed Detection of Protein Cancer Markers with Biobarcoded Nanoparticle Probes", J. American Chemical Society, vol. 128, No. 26, doi:10.1021/JA0613106, ISSN 0002-7863, pp. 8378-8379, (2006).

Sano et al., "Immuno-PCR: Very sensitive antigen detection by means of specific antibody-DNA conjugates," Science American Association for the Advancement of Science, US, vol. 258, No. 5079, 120-122 (1992).

Xu et al., "Preparation and Characterization of HLA-A *0201 Tretamer Loaded with IE-1 316-324 Antigenic Peptide of Human Cytomegalovirus," Cullular & Molecular Immunology, vol. 3, No. 5, pp. 367-371 (2006).

Yang et al. "Immunization with recombinant macaque major histocompatibility complex class I and II and human immunodeficiency virus gp140 inhibits simian-human immunodeficiency virus infection in macaques," Journal of General Virology, vol. 93, pp. 1506-1518 (2012).

* cited by examiner

Fig 1. Schematic representation of MHC multimer

Figure 2: Program for peptide sequence motifs prediction

```
Imports System.IO

Public Class Form1

Dim TRACE_LOG = ""
    Dim CR = "-"
    Dim BACKSLASH = "\"
    Dim COLON = ":"
    Dim SPACE = " "

Private Sub Button_valgmappe_Click(ByVal sender As System.Object, ByVal e As
System.EventArgs) Handles Button_valgmappe.Click
        Dim fdlg As FolderBrowserDialog = New FolderBrowserDialog()

If fdlg.ShowDialog() = Windows.Forms.DialogResult.OK Then
            Txt_mappe.Text = fdlg.SelectedPath
        End If
    End Sub Private Sub Button_gem_Click(ByVal sender As System.Object, ByVal e As
System.EventArgs) Handles Button_gem.Click
        If Txt_sekvens.Text = Nothing Then
            MessageBox.Show("Indtast sekvens")
            Exit Sub
        End If
        If Txt_fil.Text = Nothing Then
            MessageBox.Show("Indtast filnavn")
            Exit Sub
        End If
        If Txt_mappe.Text = Nothing Then
            MessageBox.Show("Vælg mappe")
            Exit Sub
        End If TRACE_LOG = Txt_mappe.Text + "/" + Txt_fil.Text + ".txt"
        If File.Exists(TRACE_LOG) Then
            MessageBox.Show("Filen findes allerede og kan ikke overskrives")
            Exit Sub
        End If
```

Figure 2 cont.

```
    Dim n = Txt_sekvens.Text.Length
    Trace_skriv("Sequence length: " & n)

Trace_skriv("CR")
    Trace_skriv("CR")

Dim min = CInt(Txt_min.Text)
    Dim max = CInt(Txt_max.Text)
    Dim j As Integer
    Dim i As Integer
    Dim tmptxt As String
    Dim peptid As String For j = min To max
       Trace_skriv(j & " mers:")
       Trace_skriv("CR")
       tmptxt = ""
       For i = 0 To n - j
          peptid = Txt_sekvens.Text.Substring(i, j)
          If CheckBox_validering.Checked Then
             If valideret(peptid) Then
                tmptxt = tmptxt + peptid & CR
             End If
          Else
             tmptxt = tmptxt + peptid & CR
          End If
       Next
       Trace_skriv(tmptxt)
       Trace_skriv("CR")
       Trace_skriv("CR")
    Next End Sub Private Function valideret(ByVal peptid As String)
   If CheckBox_validering_stopkodon.Checked Then
      If InStr(peptid, "*") Then
         Return False
      Else
```

Figure 2 cont.

```
            Return True
        End If
    Else
        Return True
    End If
End Function Private Sub Form1_Load(ByVal sender As System.Object, ByVal e As
System.EventArgs) Handles MyBase.Load
    Txt_min.Text = 8

Txt_max.Text = 11
End Sub

Friend Sub Trace_skriv(ByVal texttoadd As String)
    Dim logtext() As String
    Dim fileline() As String
    Dim fs As StreamWriter
    Dim strace As New StackTrace(True)
    Try
        If Not File.Exists(TRACE_LOG) Then
            fs = File.CreateText(TRACE_LOG)
            'fs.Write("Trace Log " & Format(Now) & CR & CR)
            fs.Flush()
            fs.Close()
        End If
        logtext = strace.GetFrame(1).ToString.Split(Space)
        fileline = logtext(6).Split(BACKSLASH)
        Dim i As Integer = fileline.GetUpperBound(0)
        fs = File.AppendText(TRACE_LOG)
        If texttoadd = "CR" Then
            fs.WriteLine()
        Else
            Dim tmp = Split(texttoadd, CR)
            If UBound(tmp) = 0 Then
                fs.Write(tmp(0))
            Else
                For i = LBound(tmp) To UBound(tmp) - 1
                    fs.Write(tmp(i))
```

Figure 2 cont.

```
            If Me.CheckBox_semikolon.Checked Then
               fs.Write("; ")
            End If
            If Me.CheckBox_linie.Checked And i < UBound(tmp) - 1 Then
               fs.WriteLine()
            End If
          Next
        End If
      End If
      fs.Flush()
      fs.Close()
    Catch ex As Exception
      MsgBox(ex.ToString)
    End Try
  End Sub
End Class
```

Figure 3

Full List of HLA Class I alleles assigned as of January 2007 from
http://www.anthonynolan.org.uk/HIG/lists/class1list.html

```
HLA-AHLA-BHLA-CHLA-EHLA-FHLA-G
A*01010101B*070201Cw*010201E*01010101F*01010101G*01010101
A*01010102NB*070202Cw*010202E*01010102F*01010102G*01010102
A*010102B*070203Cw*010203E*01010103F*01010103G*01010103
A*010103B*070204Cw*010204E*01030101F*01010104G*01010104
A*010104B*0703Cw*0103E*01030102F*01010105G*01010105
A*0102B*0704Cw*0104E*010302F*01010106G*01010201
A*0103B*070501Cw*0105E*010303F*01010107G*01010202
A*0104NB*070502Cw*0106E*010304F*01010108G*010103
A*0106B*070503Cw*0107E*0104F*01010201G*010104
A*0107B*0706Cw*0108F*01010202G*010105
A*0108B*0707Cw*0109F*01010203G*010106
A*0109B*0708Cw*0110F*01010204G*010107
A*0110B*0709Cw*0111F*01010205G*010108
A*0111NB*0710Cw*0112F*01010301G*010109
A*0112B*0711Cw*0113F*01010302G*010110
A*0113B*0712Cw*020201F*01010303G*0102
A*0114B*0713Cw*020202F*01010304G*0103
A*0115NB*0714Cw*020203F*0102G*010401
A*0116NB*0715Cw*020205F*01030101G*010402
A*0117B*0716Cw*0203F*01030102G*010403
A*0118NB*0717Cw*0204F*0104G*0105N
A*0119B*0718Cw*0205G*0106
A*0120B*0719Cw*0206G*0107
A*02010101B*0720Cw*0207
A*02010102LB*0721Cw*0208
A*020102B*0722Cw*0209
A*020103B*0723Cw*0210
A*020104B*0724Cw*0211
A*020105B*0725Cw*0212
A*020106B*0726Cw*0213
A*020107B*0727Cw*0214
A*020108B*0728Cw*0215
A*020109B*0729Cw*0216
A*020110B*0730Cw*0217
A*020111B*0731Cw*030201
```

Figure 3 cont.

```
A*020112B*0732Cw*030202
A*0202B*0733Cw*030301
A*020301B*0734Cw*030302
A*020302B*0735Cw*030303
A*0204B*0736Cw*030304
A*0205B*0737Cw*030305
A*020601B*0738Cw*030401
A*020602B*0739Cw*030402
A*020603B*0740Cw*030403
A*0207B*0741Cw*030404
A*0208B*0742Cw*030405
A*0209B*0743Cw*0305
A*0210B*0744Cw*0306
A*0211B*0745Cw*0307
A*0212B*0746Cw*0308
A*0213B*0747Cw*0309
A*0214B*0748Cw*0310
A*0215NB*0749NCw*031101
A*0216B*0750Cw*031102
A*021701B*0751Cw*0312
A*021702B*080101Cw*0313
A*0218B*080102Cw*0314
A*0219B*080103Cw*0315
A*022001B*0802Cw*0316
A*022002B*0803Cw*0317
A*0221B*0804Cw*0318
A*0222B*0805Cw*0319
A*0224B*0806Cw*0320N
A*0225B*0807Cw*0321
A*0226B*0808NCw*0322Q
A*0227B*0809Cw*0323
A*0228B*0810Cw*0324
A*0229B*0811Cw*0325
A*0230B*0812Cw*0326
A*0231B*0813Cw*0327
A*0232NB*0814Cw*0328
A*0233B*0815Cw*0329
A*0234B*0816Cw*0330
A*023501B*0817Cw*0331
```

Figure 3 cont.

```
A*023502B*0818Cw*0332
A*0236B*0819NCw*0333
A*0237B*0820Cw*0334
A*0238B*0821Cw*0335
A*0239B*0822Cw*04010101
A*0240B*0823Cw*04010102
A*0241B*0824Cw*040102
A*0242B*0825Cw*040103
A*0243NB*0826Cw*040104
A*0244B*0827Cw*0403
A*0245B*0828Cw*040401
A*0246B*0829Cw*040402
A*0247B*0830NCw*0405
A*0248B*0831Cw*0406
A*0249B*1301Cw*0407
A*0250B*130201Cw*0408
A*0251B*130202Cw*0409N
A*0252B*130203Cw*0410
A*0253NB*1303Cw*0411
A*0254B*1304Cw*0412
A*0255B*1306Cw*0413
A*0256B*1307NCw*0414
A*0257B*1308Cw*0415
A*0258B*1309Cw*0416
A*0259B*1310Cw*0417
A*0260B*1311Cw*0418
A*0261B*1312Cw*0419
A*0262B*1313Cw*0420
A*0263B*1314Cw*0421
A*0264B*1315Cw*0423
A*0265B*1316Cw*0424
A*0266B*1317Cw*050101
A*0267B*1401Cw*050102
A*0268B*140201Cw*050103
A*0269B*140202Cw*0502
A*0270B*1403Cw*0503
A*0271B*1404Cw*0504
A*0272B*1405Cw*0505
A*0273B*140601Cw*0506
```

Figure 3 cont.

A*027401B*140602Cw*0507N
    A*027402B*1407NCw*0508
    A*0275B*15010101Cw*0509
    A*0276B*15010102NCw*0510
    A*0277B*150102Cw*0511
    A*0278B*150103Cw*0512
    A*0279B*150104Cw*0513
    A*0280B*1502Cw*0514
    A*0281B*1503Cw*0515
    A*0282NB*1504Cw*06020101
    A*0283NB*1505Cw*06020102
    A*0284B*1506Cw*060202
    A*0285B*1507Cw*0603
    A*0286B*1508Cw*0604
    A*0287B*1509Cw*0605
    A*0288NB*1510Cw*0606
    A*0289B*151101Cw*0607
    A*0290B*151102Cw*0608
    A*0291B*151103Cw*0609
    A*0292B*1512Cw*0610
    A*0293B*1513Cw*0611
    A*0294NB*1514Cw*0612
    A*0295B*1515Cw*0613
    A*0296B*1516Cw*0614
    A*0297B*15170101Cw*070101
    A*0299B*15170102Cw*070102
    A*03010101B*151702Cw*070103
    A*03010102NB*1518Cw*070104
    A*03010103B*1519Cw*070105
    A*030102B*1520Cw*070106
    A*030103B*1521Cw*070107
    A*030104B*1523Cw*07020101
    A*030105B*1524Cw*07020102
    A*0302B*1525Cw*07020103
    A*0303NB*1526NCw*0703
    A*0304B*1527Cw*070401
    A*0305B*1528Cw*070402
    A*0306B*1529Cw*0705
    A*0307B*1530Cw*0706

```
A*1115B*1572Cw*080101
A*1116B*1573Cw*080102
A*1117B*1574Cw*0802
A*1118B*1575Cw*0803
A*1119B*1576Cw*0804
A*1120B*1577Cw*0805
A*1121NB*1578Cw*0806
A*1122B*1579NCw*0807
A*1123B*1580Cw*0808
A*1124B*1581Cw*0809
A*1125B*1582Cw*0810
A*1126B*1583Cw*0811
A*1127B*1584Cw*0812
A*1128B*1585Cw*0813
A*1129B*1586Cw*0814
A*2301B*1587Cw*120201
A*2302B*1588Cw*120202
A*2303B*1589Cw*120203
A*2304B*1590Cw*12030101
A*2305B*1591Cw*12030102
A*2306B*1592Cw*120302
A*2307NB*1593Cw*120303
A*2308NB*1594NCw*120304
A*2309B*1595Cw*120401
A*2310B*1596Cw*120402
A*2311NB*1597Cw*1205
A*2312B*1598Cw*1206
A*2313B*1599Cw*1207
A*2314B*9501Cw*1208
A*24020101B*9502Cw*1209
A*24020102LB*9503Cw*1210
A*240202B*9504Cw*1211
A*240203B*9505Cw*1212
A*240204B*9506Cw*1213
A*240205B*9507Cw*1214
A*240206B*9508Cw*1215
A*240207B*9509Cw*1216
A*240208B*9510Cw*1217
A*240209B*9511NCw*1218
```

Figure 3 cont.

A*240210B*9512Cw*1219
A*240211B*9513Cw*140201
A*240212B*9514Cw*140202
A*240213B*9515Cw*140203
A*240301B*9516Cw*140204
A*240302B*9517Cw*1403
A*2404B*9518Cw*1404
A*2405B*9519Cw*1405
A*2406B*9520Cw*1406
A*2407B*9521Cw*1407N
A*2408B*9522Cw*1408
A*2409NB*180101Cw*150201
A*2410B*180102Cw*150202
A*2411NB*180103Cw*150203
A*2413B*1802Cw*1503
A*2414B*1803Cw*1504
A*2415B*1804Cw*150501
A*2417B*1805Cw*150502
A*2418B*1806Cw*150503
A*2419B*1807Cw*150504
A*2420B*1808Cw*1506
A*2421B*1809Cw*1507
A*2422B*1810Cw*1508
A*2423B*1811Cw*1509
A*2424B*1812Cw*1510
A*2425B*1813Cw*1511
A*2426B*1814Cw*1512
A*2427B*1815Cw*1513
A*2428B*1817NCw*1514
A*2429B*1818Cw*1515
A*2430B*1819Cw*1516
A*2431B*1820Cw*1517
A*2432B*1821Cw*160101
A*2433B*1822Cw*160102
A*2434B*1823NCw*1602
A*2435B*1824Cw*160401
A*2436NB*2701Cw*1606
A*2437B*2702Cw*1607
A*2438B*2703Cw*1608

B*5706
B*5707
B*5708
B*5709
B*5710
B*5711
B*5801
B*5802
B*5804
B*5805
B*5806
B*5807
B*5808
B*5809
B*5810N
B*5811
B*5812
B*5813
B*5814
B*5901
B*5902
B*670101
B*670102
B*6702
B*7301
B*7801
B*780201
B*780202
B*7803
B*7804
B*7805
B*8101
B*8102
B*8201
B*8202
B*8301
HLA-HHLA-JHLA-KHLA-LHLA-P
H*01010101J*01010101K*01010101L*01010101P*01010101
H*01010102J*01010102K*01010102L*01010102P*01010102

Figure 4: Top 30 HLA class 1 allele frequency in human ethnic groups

Data from HLA Matchmaker, http://tpis.upmc.edu/tpis/HLAMatchmaker/

| % chance of allele expressed in an individual | | | | | | | |
|---|---|---|---|---|---|---|---|
| Top 30 expressed alleles | | | | | | | |
| Allele | Caucasian | Allele | African-American | Allele | Hispanic | Allele | Oriental |
| A*0201 | 45.6% | C*0401 | 29.0% | A*0201 | 37.1% | A*1101 | 38.4% |
| C*0701 | 27.7% | C*0701 | 25.4% | C*0401 | 25.4% | A*2402 | 33.7% |
| A*0101 | 27.4% | C*0602 | 23.0% | A*2402 | 24.9% | C*0702 | 33.3% |
| A*0301 | 23.8% | A*0201 | 22.3% | C*0702 | 24.2% | C*0102 | 27.7% |
| C*0702 | 21.5% | A*2301 | 20.7% | C*0701 | 20.8% | A*3303 | 23.3% |
| C*0401 | 21.2% | C*0202 | 19.0% | C*0304 | 14.4% | C*0801 | 21.6% |
| B*4402 | 20.2% | A*0301 | 18.7% | A*0301 | 14.3% | C*0304 | 19.9% |
| B*0702 | 18.1% | C*0702 | 18.1% | B*0702 | 13.2% | A*0201 | 18.1% |
| B*0801 | 18.1% | B*5301 | 18.1% | B*3501 | 12.8% | B*4001 | 15.2% |
| C*0501 | 17.2% | B*0702 | 15.8% | C*0602 | 12.3% | C*0401 | 14.0% |
| C*0304 | 16.8% | C*1601 | 15.7% | C*0501 | 11.9% | B*5801 | 13.3% |
| C*0602 | 15.7% | B*1503 | 13.9% | A*0101 | 11.4% | B*4601 | 12.7% |
| A*1101 | 15.3% | B*5801 | 13.5% | A*1101 | 11.0% | B*5101 | 12.4% |
| B*4001 | 13.6% | A*6802 | 12.7% | B*5101 | 10.8% | C*0302 | 12.0% |
| A*2402 | 12.1% | C*1701 | 11.7% | C*1601 | 10.6% | B*3802 | 11.4% |
| B*3501 | 10.7% | B*4501 | 10.8% | B*4403 | 9.9% | A*0207 | 11.0% |
| C*0303 | 10.6% | B*4201 | 10.5% | C*0102 | 9.7% | B*1501 | 9.4% |
| B*5101 | 10.4% | A*3001 | 10.4% | A*2902 | 9.7% | A*0206 | 9.3% |
| C*1203 | 9.9% | B*3501 | 10.1% | C*0802 | 9.3% | C*0303 | 9.2% |
| B*1501 | 9.6% | A*0101 | 10.0% | B*1801 | 9.1% | B*1502 | 9.1% |
| A*2902 | 8.9% | C*0304 | 9.3% | A*3101 | 8.9% | A*0203 | 8.8% |
| A*2601 | 8.2% | A*3002 | 9.2% | B*5201 | 8.6% | B*4403 | 8.6% |
| A*3201 | 8.2% | B*0801 | 8.5% | B*1402 | 8.6% | C*1402 | 8.4% |
| C*0802 | 7.7% | A*3402 | 8.4% | C*0202 | 7.6% | B*3501 | 7.2% |
| A*2501 | 7.5% | A*7401 | 8.4% | C*1203 | 7.6% | C*0602 | 7.0% |
| B*5701 | 7.1% | A*3303 | 8.0% | A*2601 | 7.6% | B*5401 | 6.9% |
| B*1402 | 6.7% | C*1801 | 7.3% | A*6801 | 7.1% | B*1301 | 6.6% |
| C*0202 | 6.6% | A*2902 | 7.2% | B*0801 | 7.0% | B*4002 | 6.3% |
| B*1801 | 6.4% | B*4403 | 6.9% | A*3002 | 6.8% | B*5502 | 6.3% |
| B*4403 | 6.4% | B*4901 | 6.9% | B*4402 | 6.5% | A*2601 | 6.0% |

Figure 5: Reactive groups and the bonds formed upon their reaction.

A

Nucleophilic substitution reaction

Figure 5 cont.

Aromatic nucleophilic substitution

SUBSTITUTED AROMATIC COMPOUNDS

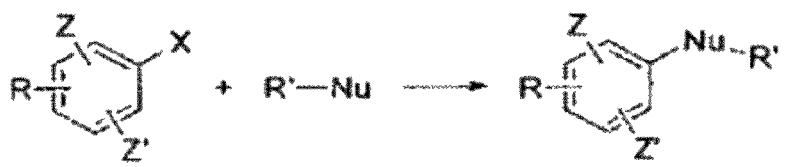

Nu = Oxygen-, Nitrogen-, Sulfur- and Carbon Nucleophiles
X = F, Cl, Br, I, $OSO_2CH_3$, $OSO_2CF_3$, $OSO_2TOL$, . , etc.
Z', Z = COOR, CHO, COR, $CONR"_2$, $COO^-$, CN,
$NO_2$, SOR, $SO_2R$, $SO_2NR"_2$.. ect.

Transition metal catalysed reactions

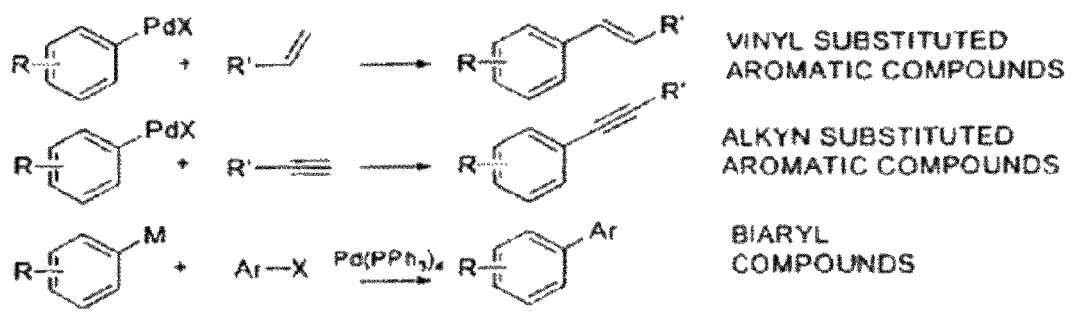

VINYL SUBSTITUTED AROMATIC COMPOUNDS

ALKYN SUBSTITUTED AROMATIC COMPOUNDS

BIARYL COMPOUNDS

Addition to carbon-carbon multiplebonds

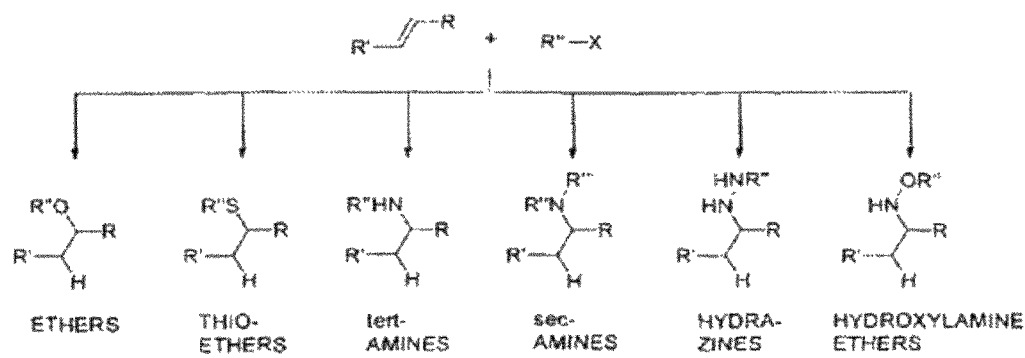

ETHERS  THIO-ETHERS  tert-AMINES  sec-AMINES  HYDRA-ZINES  HYDROXYLAMINE ETHERS

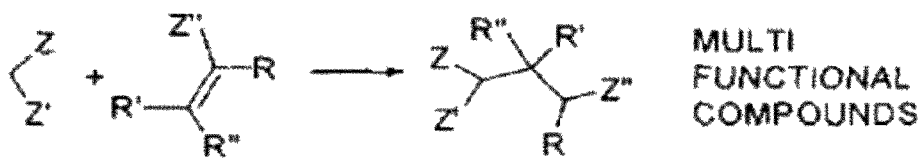

MULTI FUNCTIONAL COMPOUNDS $Z$ = H, Alkyl, $Z'$, Ar $Z''$ = COOR, CHO, COR, CONR''$_2$, CN, NO$_2$, SOR, SO$_2$R, SO$_2$NR''$_2$,. ect.

$Z' = Z''$ $\quad R = R', = R'', = Z$

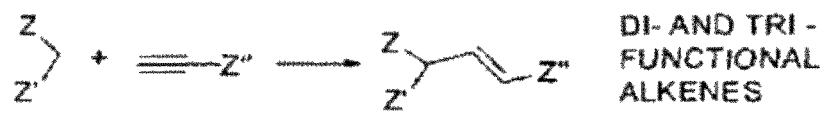

DI- AND TRI- FUNCTIONAL ALKENES $Z$ = H, Alkyl, Ar, $Z'' = Z'$, Alkyl, Ar, $Z'$ = COOR, CHO, COR, CONR''$_2$, CN, NO$_2$, SOR, SO$_2$R, SO$_2$NR''$_2$. ect.

Figure 5 cont.
C
Addition to carbon-hetero multiple bonds
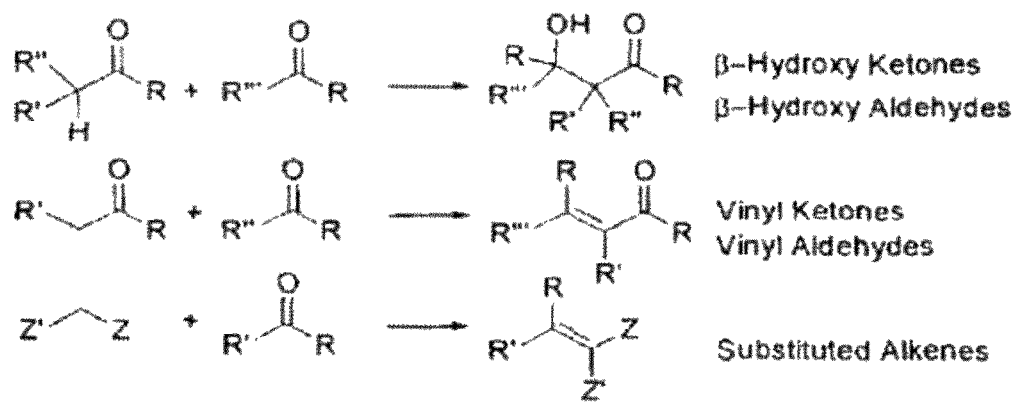
β-Hydroxy Ketones
β-Hydroxy Aldehydes
Vinyl Ketones
Vinyl Aldehydes
Substituted Alkenes
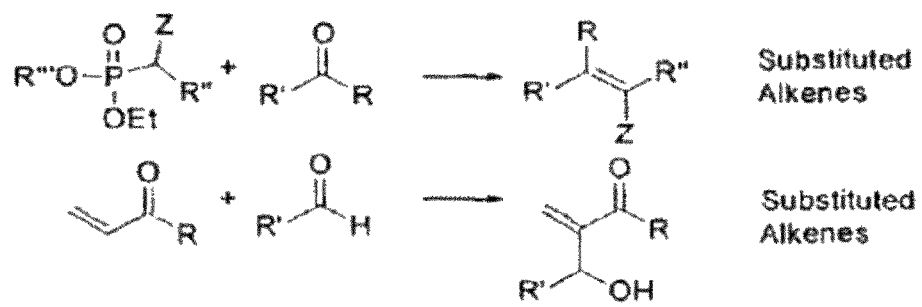
Substituted Alkenes
Substituted Alkenes
Z, Z' = COOR, CHO, COR, CONR''$_2$, CN, NO$_2$, SOR, SO$_2$R, SO$_2$NR''$_2$, ect.    R'' = H, Alkyl, Aryl Z = COOR, CHO, COR, SOR, SO$_2$R, CN, NO$_2$, ect.

R = R', H, Alkyl, Ar,

R" = R'", H, Alkyl, COR,

Figure 6: Cleavable linkers, conditions for cleaving them and the resulting products of the cleavage.
A. Linker for the formation of Ketones, Aldehydes, Amid and Acids
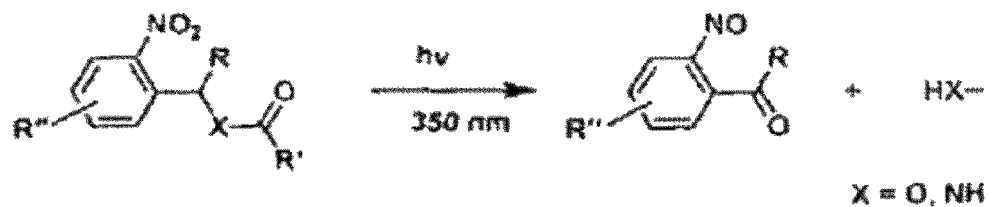
B. Linker for the formation of Ketones, Amides and Acid
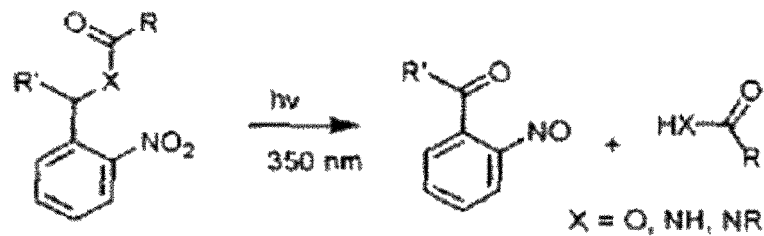
C. Linker for the formation of Aldehydes and Ketones
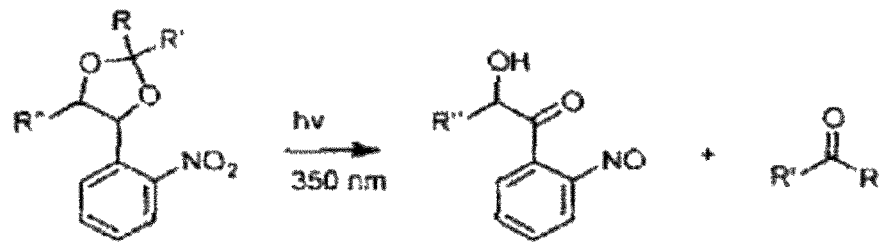

Figure 6 cont.
D. Linker for the formation of Alcohols and Acids
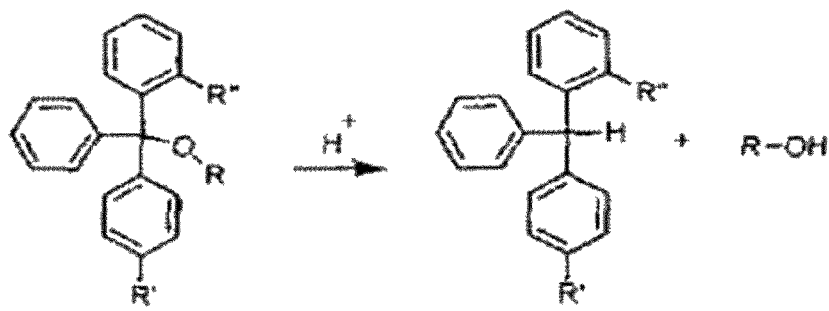
E. Linker for the formation of Amines and Alcohols
F. Linker for the formation of Esters, Thioesters, Amides and Alcohols
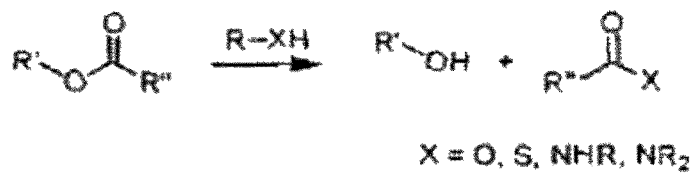
X = O, S, NHR, NR$_2$
G. Linker for the formation of Sulfonamides and Alcohols
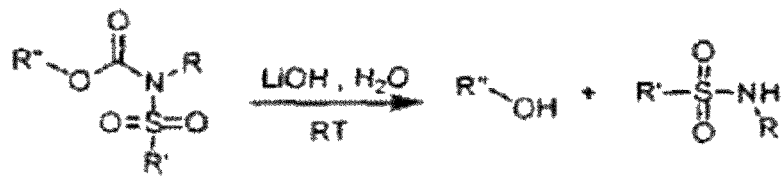

Figure 6 cont.
H. Linker for the formation of Ketones, Amines and Alcohols
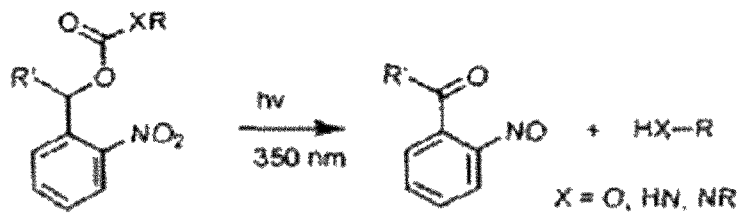
I. Linker for the formation of Ketones, Amines, Alcohols and Mercaptanes
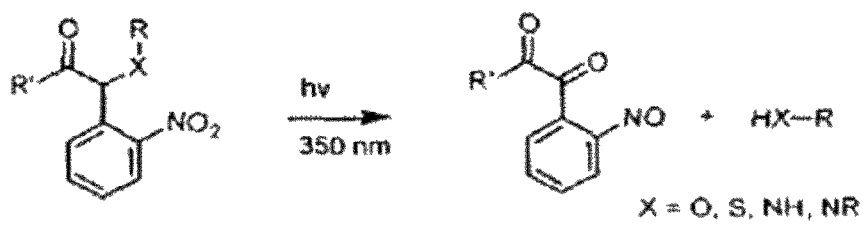
J. Linker for the formation of Biaryl and Bihetaryl
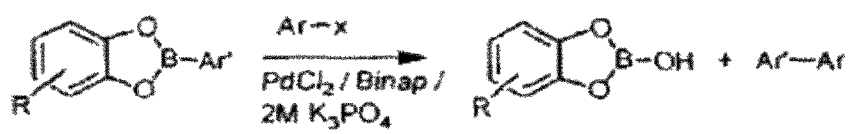
K. Linker for the formation of Benzyles, Amines, Anilins Alcohols and Phenoles
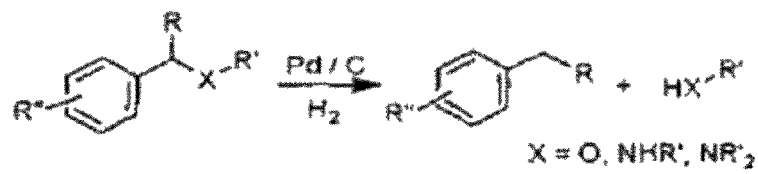

Figure 6 cont.
L. Linker for the formation of Mercaptanes
TCEP = tris(2-carboxyethyl)phosphine
M. Linker for the formation of Glycosides
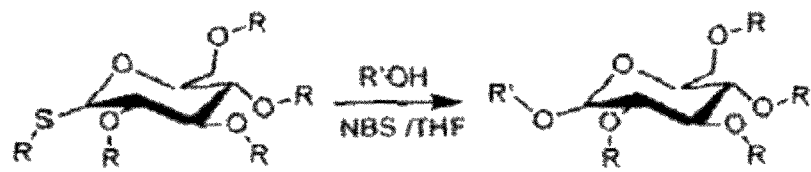
N. Linker for the formation of Aldehydes and Glyoxylamides
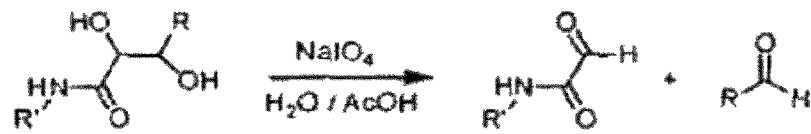
O. Linker for the formation of Aldehydes, Ketones and Aminoalcohols
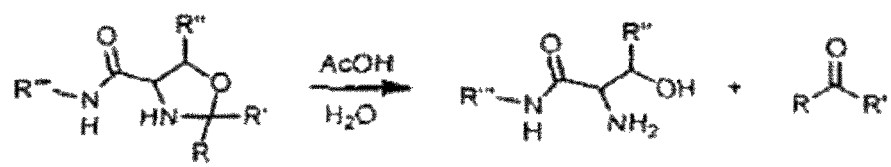

Figure 7: Prediction of MHC class 1 mouse virus LCMV gp 1 protein nonamer peptide binders for H-2Kd using the Syfpeithi database

```
Pos 1 2 3 4 5 6 7 8 9 score
179 S F S D A Q S A L 22
289 G Y C L T K W M I 22
65  M Y G L D G P D I 21
139 T F D H T L M S I 21
30  I V L I I I T S I 20
41  V Y N F A T C G I 20
105 H Y I S M G K S G 19
43  N F A T C G I L A 18
108 S M G K S G L E L 18
143 T L M S I V S S L 18
175 Q Y N L S F S D A 18
226 C S Q T S Y Q Y L 18
13  M F E A L P H I I 17
33  I I I T S I K A V 17
73  I Y K G V Y Q F K 17
84  E F D M S H L N L 17
230 S Y Q Y L I I Q N 17
48  G I L A L V S F L 16
50  L A L V S F L F L 16
75  K G V Y Q F K S V 16
99  S V N N S H H Y I 16
147 I V S S L H L S I 16
208 K Y M R S G W G W 16
227 S Q T S Y Q Y L I 16
9   Q I V T M F E A L 15
25  I N I V I I V L I 15
92  L T M P N A C S V 15
160 N Y K P V S C D F 15
246 T Y A G P F R I S 15
284 V E S P G G Y C L 15
290 Y C L T K W M I L 15
294 K W M I L A A E L 15
54  S F L F L A G K S 14
258 F A Q E K T K F L 14
12  T M F E A L P H I 13
19  H I I D E V I N I 13
```

Figure 8. Size exclusion chromatography of folded HLA-A*0201-β2m-QLFEELQEL-complex.
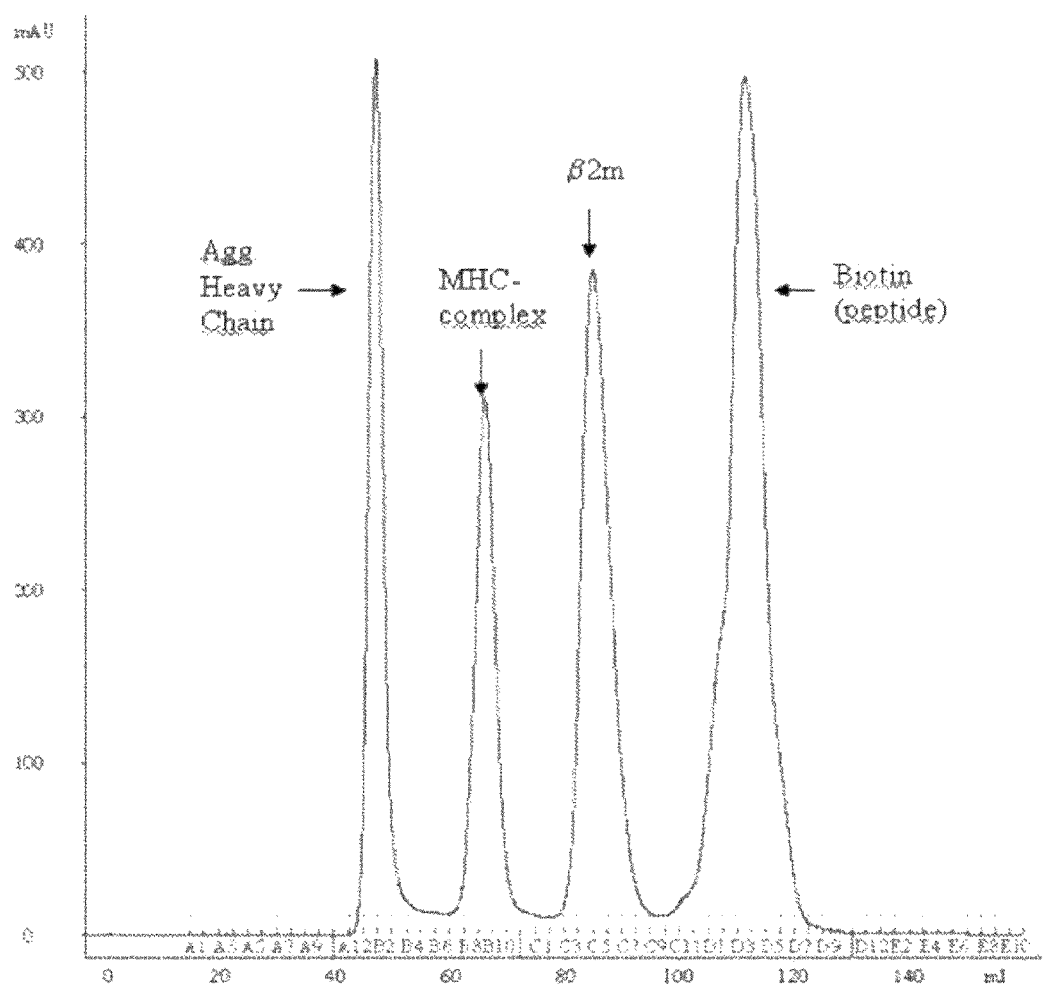

Figure 9: MHC-SHIFT Assay
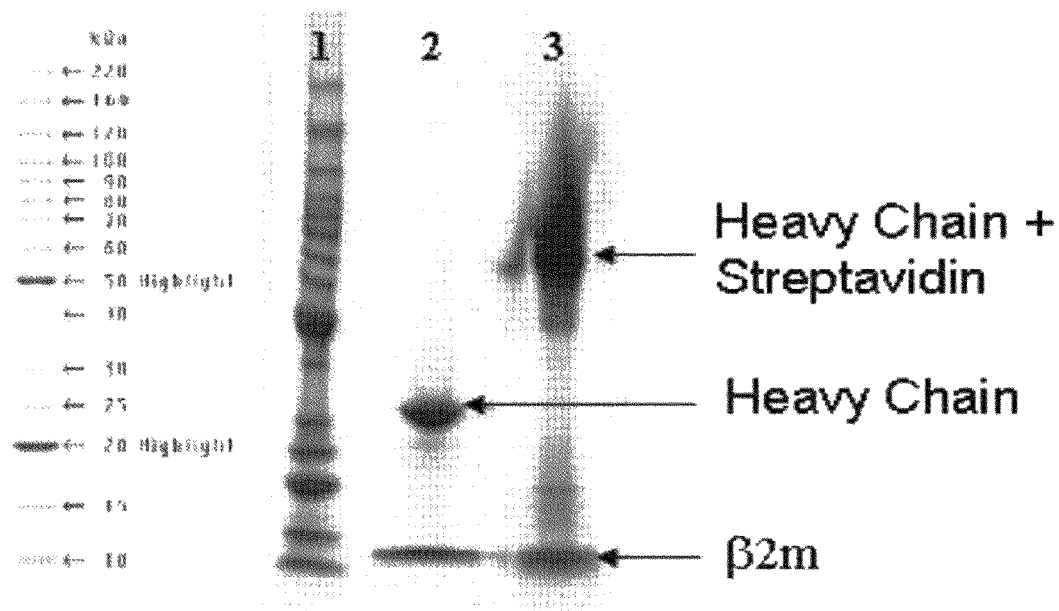

Figure 10: Composition of a Fluorescein-linker molecule
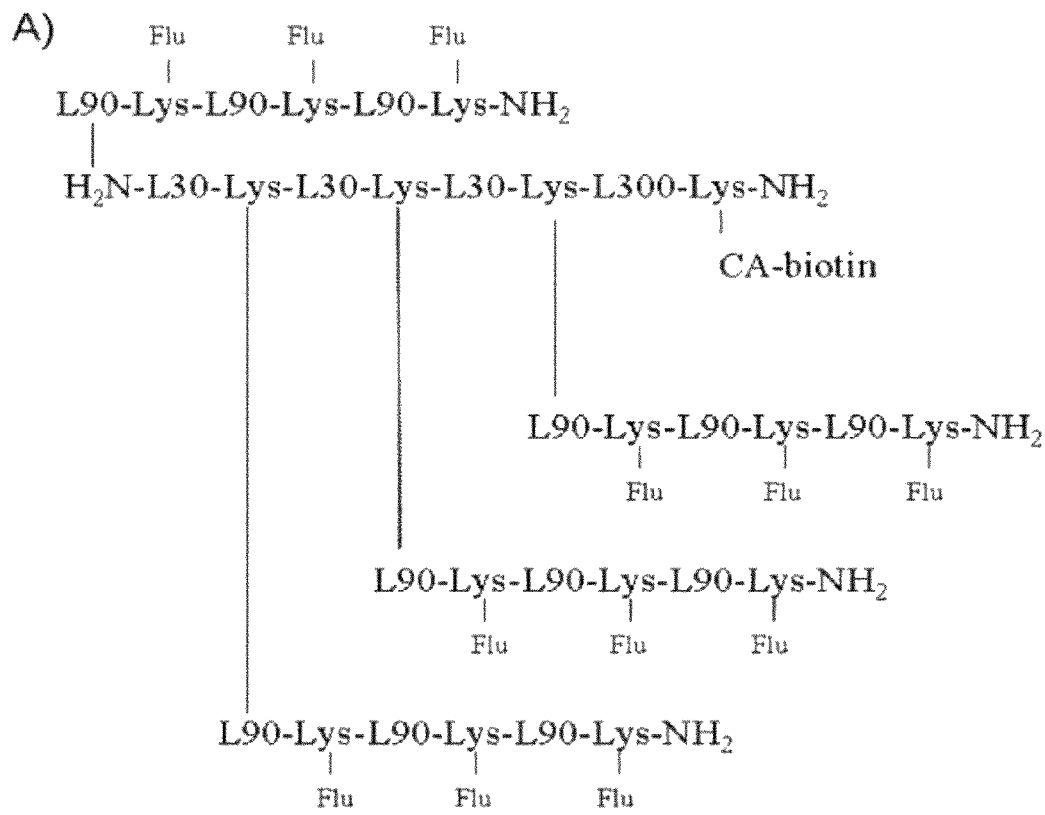
B)   L15 linker composition:
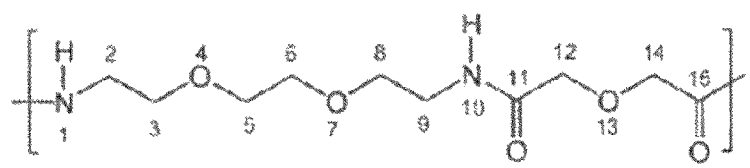

Figure 11: HLA alleles of the NetMHC databases

| Database | Alleles |
|---|---|
| http://www.cbs.dtu.dk/services/NetMHC/ | HLA-A0101, HLA-A0201, HLA-A0202, HLA-A0203, HLA-A0204, HLA-A0206, HLA-A0211, HLA-A0212, HLA-A0216, HLA-A0219, HLA-A0301, HLA-A1101, HLA-A2301, HLA-A2402, HLA-A2403, HLA-A2601, HLA-A2602, HLA-A2902, HLA-A3002, HLA-A3101, HLA-A3301, HLA-A6801, HLA-A6802, HLA-A6901 |
| http://www.cbs.dtu.dk/services/NetMHCII/ | HLA-DRB1*0101, HLA-DRB1*0301, HLA-DRB1*0401, HLA-DRB1*0404, HLA-DRB1*0405, HLA-DRB1*0701, HLA-DRB1*0802, HLA-DRB1*0901, HLA-DRB1*1101, HLA-DRB1*1302, HLA-DRB1*1501, HLA-DRB3*0101, HLA-DRB4*0101, HLA-DRB1*0501 |

Figure 12: Prediction of MHC class 1 mouse virus LCMV gp 1 protein nonamer peptide binders for H-2Kd using the Syfpeithi database

| Pos | 1 | 2 | 3 | 4 | 5 | 6 | 7 | 8 | 9 | score |
|---|---|---|---|---|---|---|---|---|---|---|
| 179 | S | F | S | D | A | Q | S | A | L | 22 |
| 289 | G | Y | C | L | T | K | W | M | I | 22 |
| 65 | M | Y | G | L | D | G | P | D | I | 21 |
| 139 | T | F | D | H | T | L | M | S | I | 21 |
| 30 | I | V | L | I | I | I | T | S | I | 20 |
| 41 | V | Y | N | F | A | T | C | G | I | 20 |
| 105 | H | Y | I | S | M | G | K | S | G | 19 |
| 43 | N | F | A | T | C | G | I | L | A | 18 |
| 108 | S | M | G | K | S | G | L | E | L | 18 |
| 143 | T | L | M | S | I | V | S | S | L | 18 |
| 175 | Q | Y | N | L | S | F | S | D | A | 18 |
| 226 | C | S | Q | T | S | Y | Q | Y | L | 18 |
| 13 | M | F | E | A | L | P | H | I | I | 17 |
| 33 | I | I | I | T | S | I | K | A | V | 17 |
| 73 | I | Y | K | G | V | Y | Q | F | K | 17 |
| 84 | E | F | D | M | S | H | L | N | L | 17 |
| 230 | S | Y | Q | Y | L | I | I | Q | N | 17 |
| 48 | G | I | L | A | L | V | S | F | L | 16 |
| 50 | L | A | L | V | S | F | L | F | L | 16 |
| 75 | K | G | V | Y | Q | F | K | S | V | 16 |
| 99 | S | V | N | N | S | H | H | Y | I | 16 |
| 147 | I | V | S | S | L | H | L | S | I | 16 |
| 208 | K | Y | M | R | S | G | W | G | W | 16 |
| 227 | S | Q | T | S | Y | Q | Y | L | I | 16 |
| 9 | Q | I | V | T | M | F | E | A | L | 15 |
| 25 | I | N | I | V | I | I | V | L | I | 15 |
| 92 | L | T | M | P | N | A | C | S | V | 15 |
| 160 | N | Y | K | P | V | S | C | D | F | 15 |
| 246 | T | Y | A | G | P | F | R | I | S | 15 |
| 284 | V | E | S | P | G | G | Y | C | L | 15 |
| 290 | Y | C | L | T | K | W | M | I | L | 15 |
| 294 | K | W | M | I | L | A | A | E | L | 15 |
| 54 | S | F | L | F | L | A | G | K | S | 14 |
| 258 | F | A | Q | E | K | T | K | F | L | 14 |
| 12 | T | M | F | E | A | L | P | H | I | 13 |

| | | |
|---|---|---|
| 19 | HIIDEVINI | 13 |
| 27 | IVIIVL III | 13 |
| 82 | SVEFDMSHL | 13 |
| 116 | LTFINDSIL | 13 |
| 145 | MSIVSSLHL | 13 |
| 156 | RGNSNYKPV | 13 |
| 170 | NGITIQYNL | 13 |
| 178 | LSFSDAQSA | 13 |
| 240 | TWENHCTYA | 13 |
| 257 | LFAQEK TKF | 13 |
| 262 | KTKFLTRRL | 13 |
| 264 | KFL TRRLAG | 13 |
| 276 | WTLSDSSGV | 13 |
| 20 | II DEVINIV | 12 |
| 21 | I DEVINIVI | 12 |
| 22 | DEVINIVII | 12 |
| 24 | VINIVIIVL | 12 |
| 26 | NIVIIVL II | 12 |
| 37 | SIKAVYNF A | 12 |
| 56 | LFLAGKSCG | 12 |
| 106 | YISMGKSGL | 12 |
| 115 | ELIFINDS I | 12 |
| 126 | HNHCNLTSA | 12 |
| 136 | NKKTFDHTL | 12 |
| 140 | FDHTLMS IV | 12 |
| 166 | CDFNNGITI | 12 |
| 232 | QYLIIQNRT | 12 |

| HLA-A | HLA-B | HLA-C | HLA-E | HLA-F | HLA-G |
|---|---|---|---|---|---|
| A*01010101 | B*070201 | Cw*010201 | E*01010101 | F*01010101 | G*01010101 |
| A*01010102N | B*070202 | Cw*010202 | E*01010102 | F*01010102 | G*01010102 |
| A*010102 | B*070203 | Cw*010203 | E*01010103 | F*01010103 | G*01010103 |
| A*010103 | B*070204 | Cw*010204 | E*01030101 | F*01010104 | G*01010104 |
| A*010104 | B*0703 | Cw*0103 | E*01030102 | F*01010105 | G*01010105 |
| A*0102 | B*0704 | Cw*0104 | E*010302 | F*01010106 | G*01010201 |
| A*0103 | B*070501 | Cw*0105 | E*010303 | F*01010107 | G*01010202 |
| A*0104N | B*070502 | Cw*0106 | E*010304 | F*01010108 | G*010103 |
| A*0106 | B*070503 | Cw*0107 | E*0104 | F*01010201 | G*010104 |
| A*0107 | B*0706 | Cw*0108 | | F*01010202 | G*010105 |
| A*0108 | B*0707 | Cw*0109 | | F*01010203 | G*010106 |
| A*0109 | B*0708 | Cw*0110 | | F*01010204 | G*010107 |
| A*0110 | B*0709 | Cw*0111 | | F*01010205 | G*010108 |
| A*0111N | B*0710 | Cw*0112 | | F*01010301 | G*010109 |
| A*0112 | B*0711 | Cw*0113 | | F*01010302 | G*010110 |
| A*0113 | B*0712 | Cw*020201 | | F*01010303 | G*0102 |
| A*0114 | B*0713 | Cw*020202 | | F*01010304 | G*0103 |
| A*0115N | B*0714 | Cw*020203 | | F*0102 | G*010401 |
| A*0116N | B*0715 | Cw*020205 | | F*01030101 | G*010402 |
| A*0117 | B*0716 | Cw*0203 | | F*01030102 | G*010403 |
| A*0118N | B*0717 | Cw*0204 | | F*0104 | G*0105N |
| A*0119 | B*0718 | Cw*0205 | | | G*0106 |
| A*0120 | B*0719 | Cw*0206 | | | G*0107 |
| A*02010101 | B*0720 | Cw*0207 | | | |
| A*02010102L | B*0721 | Cw*0208 | | | |
| A*020102 | B*0722 | Cw*0209 | | | |
| A*020103 | B*0723 | Cw*0210 | | | |
| A*020104 | B*0724 | Cw*0211 | | | |
| A*020105 | B*0725 | Cw*0212 | | | |
| A*020106 | B*0726 | Cw*0213 | | | |
| A*020107 | B*0727 | Cw*0214 | | | |
| A*020108 | B*0728 | Cw*0215 | | | |
| A*020109 | B*0729 | Cw*0216 | | | |
| A*020110 | B*0730 | Cw*0217 | | | |
| A*020111 | B*0731 | Cw*030201 | | | |
| A*020112 | B*0732 | Cw*030202 | | | |
| A*0202 | B*0733 | Cw*030301 | | | |
| A*020301 | B*0734 | Cw*030302 | | | |
| A*020302 | B*0735 | Cw*030303 | | | |
| A*0204 | B*0736 | Cw*030304 | | | |
| A*0205 | B*0737 | Cw*030305 | | | |
| A*020601 | B*0738 | Cw*030401 | | | |
| A*020602 | B*0739 | Cw*030402 | | | |
| A*020603 | B*0740 | Cw*030403 | | | |
| A*0207 | B*0741 | Cw*030404 | | | |
| A*0208 | B*0742 | Cw*030405 | | | |
| A*0209 | B*0743 | Cw*0305 | | | |
| A*0210 | B*0744 | Cw*0306 | | | |
| A*0211 | B*0745 | Cw*0307 | | | |
| A*0212 | B*0746 | Cw*0308 | | | |
| A*0213 | B*0747 | Cw*0309 | | | |
| A*0214 | B*0748 | Cw*0310 | | | |
| A*0215N | B*0749N | Cw*031101 | | | |
| A*0216 | B*0750 | Cw*031102 | | | |
| A*021701 | B*0751 | Cw*0312 | | | |

Figure 13 cont.

| | | |
|---|---|---|
| A*0217O2 | B*080101 | Cw*0313 |
| A*0218 | B*080102 | Cw*0314 |
| A*0219 | B*080103 | Cw*0315 |
| A*022001 | B*0802 | Cw*0316 |
| A*022002 | B*0803 | Cw*0317 |
| A*0221 | B*0804 | Cw*0318 |
| A*0222 | B*0805 | Cw*0319 |
| A*0224 | B*0806 | Cw*0320N |
| A*0225 | B*0807 | Cw*0321 |
| A*0226 | B*0808N | Cw*0322Q |
| A*0227 | B*0809 | Cw*0323 |
| A*0228 | B*0810 | Cw*0324 |
| A*0229 | B*0811 | Cw*0325 |
| A*0230 | B*0812 | Cw*0326 |
| A*0231 | B*0813 | Cw*0327 |
| A*0232N | B*0814 | Cw*0328 |
| A*0233 | B*0815 | Cw*0329 |
| A*0234 | B*0816 | Cw*0330 |
| A*023501 | B*0817 | Cw*0331 |
| A*023502 | B*0818 | Cw*0332 |
| A*0236 | B*0819N | Cw*0333 |
| A*0237 | B*0820 | Cw*0334 |
| A*0238 | B*0821 | Cw*0335 |
| A*0239 | B*0822 | Cw*04010101 |
| A*0240 | B*0823 | Cw*04010102 |
| A*0241 | B*0824 | Cw*040102 |
| A*0242 | B*0825 | Cw*040103 |
| A*0243N | B*0826 | Cw*040104 |
| A*0244 | B*0827 | Cw*0403 |
| A*0245 | B*0828 | Cw*040401 |
| A*0246 | B*0829 | Cw*040402 |
| A*0247 | B*0830N | Cw*0405 |
| A*0248 | B*0831 | Cw*0406 |
| A*0249 | B*1301 | Cw*0407 |
| A*0250 | B*130201 | Cw*0408 |
| A*0251 | B*130202 | Cw*0409N |
| A*0252 | B*130203 | Cw*0410 |
| A*0253N | B*1303 | Cw*0411 |
| A*0254 | B*1304 | Cw*0412 |
| A*0255 | B*1306 | Cw*0413 |
| A*0256 | B*1307N | Cw*0414 |
| A*0257 | B*1308 | Cw*0415 |
| A*0258 | B*1309 | Cw*0416 |
| A*0259 | B*1310 | Cw*0417 |
| A*0260 | B*1311 | Cw*0418 |
| A*0261 | B*1312 | Cw*0419 |
| A*0262 | B*1313 | Cw*0420 |
| A*0263 | B*1314 | Cw*0421 |
| A*0264 | B*1315 | Cw*0423 |
| A*0265 | B*1316 | Cw*0424 |
| A*0266 | B*1317 | Cw*050101 |
| A*0267 | B*1401 | Cw*050102 |
| A*0268 | B*140201 | Cw*050103 |
| A*0269 | B*140202 | Cw*0502 |
| A*0270 | B*1403 | Cw*0503 |
| A*0271 | B*1404 | Cw*0504 |

Figure 13 cont.

| | | |
|---|---|---|
| A*0272 | B*1405 | Cw*0505 |
| A*0273 | B*140601 | Cw*0506 |
| A*027401 | B*140602 | Cw*0507N |
| A*027402 | B*1407N | Cw*0508 |
| A*0275 | B*15010101 | Cw*0509 |
| A*0276 | B*15010102N | Cw*0510 |
| A*0277 | B*150102 | Cw*0511 |
| A*0278 | B*150103 | Cw*0512 |
| A*0279 | B*150104 | Cw*0513 |
| A*0280 | B*1502 | Cw*0514 |
| A*0281 | B*1503 | Cw*0515 |
| A*0282N | B*1504 | Cw*06020101 |
| A*0283N | B*1505 | Cw*06020102 |
| A*0284 | B*1506 | Cw*060202 |
| A*0285 | B*1507 | Cw*0603 |
| A*0286 | B*1508 | Cw*0604 |
| A*0287 | B*1509 | Cw*0605 |
| A*0288N | B*1510 | Cw*0606 |
| A*0289 | B*151101 | Cw*0607 |
| A*0290 | B*151102 | Cw*0608 |
| A*0291 | B*151103 | Cw*0609 |
| A*0292 | B*1512 | Cw*0610 |
| A*0293 | B*1513 | Cw*0611 |
| A*0294N | B*1514 | Cw*0612 |
| A*0295 | B*1515 | Cw*0613 |
| A*0296 | B*1516 | Cw*0614 |
| A*0297 | B*15170101 | Cw*070101 |
| A*0299 | B*15170102 | Cw*070102 |
| A*03010101 | B*151702 | Cw*070103 |
| A*03010102N | B*1518 | Cw*070104 |
| A*03010103 | B*1519 | Cw*070105 |
| A*030102 | B*1520 | Cw*070106 |
| A*030103 | B*1521 | Cw*070107 |
| A*030104 | B*1523 | Cw*07020101 |
| A*030105 | B*1524 | Cw*07020102 |
| A*0302 | B*1525 | Cw*07020103 |
| A*0303N | B*1526N | Cw*0703 |
| A*0304 | B*1527 | Cw*070401 |
| A*0305 | B*1528 | Cw*070402 |
| A*0306 | B*1529 | Cw*0705 |
| A*0307 | B*1530 | Cw*0706 |
| A*0308 | B*1531 | Cw*0707 |
| A*0309 | B*1532 | Cw*0708 |
| A*0310 | B*1533 | Cw*0709 |
| A*0311N | B*1534 | Cw*0710 |
| A*0312 | B*1535 | Cw*0711 |
| A*0313 | B*1536 | Cw*0712 |
| A*0314 | B*1537 | Cw*0713 |
| A*0315 | B*1538 | Cw*0714 |
| A*0316 | B*1539 | Cw*0715 |
| A*0317 | B*1540 | Cw*0716 |
| A*0318 | B*1542 | Cw*0717 |
| A*0319 | B*1543 | Cw*0718 |
| A*0320 | B*1544 | Cw*0719 |
| A*0321N | B*1545 | Cw*0720 |
| A*0322 | B*1546 | Cw*0721 |

Figure 13 cont.

| | | |
|---|---|---|
| A*0323 | B*1547 | Cw*0722 |
| A*0324 | B*1548 | Cw*0723 |
| A*0325 | B*1549 | Cw*0724 |
| A*0326 | B*1550 | Cw*0725 |
| A*110101 | B*1551 | Cw*0726 |
| A*110102 | B*1552 | Cw*0727 |
| A*110103 | B*1553 | Cw*0728 |
| A*110104 | B*1554 | Cw*0729 |
| A*110105 | B*1555 | Cw*0730 |
| A*110106 | B*1556 | Cw*0731 |
| A*110201 | B*1557 | Cw*0732N |
| A*110202 | B*1558 | Cw*0733N |
| A*1103 | B*1560 | Cw*0734 |
| A*1104 | B*1561 | Cw*0735 |
| A*1105 | B*1562 | Cw*0736 |
| A*1106 | B*1563 | Cw*0737 |
| A*1107 | B*1564 | Cw*0738 |
| A*1108 | B*1565 | Cw*0739 |
| A*1109 | B*1566 | Cw*0740 |
| A*1110 | B*1567 | Cw*0741 |
| A*1111 | B*1568 | Cw*0742 |
| A*1112 | B*1569 | Cw*0743 |
| A*1113 | B*1570 | Cw*0744 |
| A*1114 | B*1571 | Cw*0745 |
| A*1115 | B*1572 | Cw*080101 |
| A*1116 | B*1573 | Cw*080102 |
| A*1117 | B*1574 | Cw*0802 |
| A*1118 | B*1575 | Cw*0803 |
| A*1119 | B*1576 | Cw*0804 |
| A*1120 | B*1577 | Cw*0805 |
| A*1121N | B*1578 | Cw*0806 |
| A*1122 | B*1579N | Cw*0807 |
| A*1123 | B*1580 | Cw*0808 |
| A*1124 | B*1581 | Cw*0809 |
| A*1125 | B*1582 | Cw*0810 |
| A*1126 | B*1583 | Cw*0811 |
| A*1127 | B*1584 | Cw*0812 |
| A*1128 | B*1585 | Cw*0813 |
| A*1129 | B*1586 | Cw*0814 |
| A*2301 | B*1587 | Cw*120201 |
| A*2302 | B*1588 | Cw*120202 |
| A*2303 | B*1589 | Cw*120203 |
| A*2304 | B*1590 | Cw*12030101 |
| A*2305 | B*1591 | Cw*12030102 |
| A*2306 | B*1592 | Cw*120302 |
| A*2307N | B*1593 | Cw*120303 |
| A*2308N | B*1594N | Cw*120304 |
| A*2309 | B*1595 | Cw*120401 |
| A*2310 | B*1596 | Cw*120402 |
| A*2311N | B*1597 | Cw*1205 |
| A*2312 | B*1598 | Cw*1206 |
| A*2313 | B*1599 | Cw*1207 |
| A*2314 | B*9501 | Cw*1208 |
| A*24020101 | B*9502 | Cw*1209 |
| A*24020102L | B*9503 | Cw*1210 |
| A*240202 | B*9504 | Cw*1211 |

Figure 13 cont.

| | | |
|---|---|---|
| A*240203 | B*9505 | Cw*1212 |
| A*240204 | B*9506 | Cw*1213 |
| A*240205 | B*9507 | Cw*1214 |
| A*240206 | B*9508 | Cw*1215 |
| A*240207 | B*9509 | Cw*1216 |
| A*240208 | B*9510 | Cw*1217 |
| A*240209 | B*9511N | Cw*1218 |
| A*240210 | B*9512 | Cw*1219 |
| A*240211 | B*9513 | Cw*140201 |
| A*240212 | B*9514 | Cw*140202 |
| A*240213 | B*9515 | Cw*140203 |
| A*240301 | B*9516 | Cw*140204 |
| A*240302 | B*9517 | Cw*1403 |
| A*2404 | B*9518 | Cw*1404 |
| A*2405 | B*9519 | Cw*1405 |
| A*2406 | B*9520 | Cw*1406 |
| A*2407 | B*9521 | Cw*1407N |
| A*2408 | B*9522 | Cw*1408 |
| A*2409N | B*180101 | Cw*150201 |
| A*2410 | B*180102 | Cw*150202 |
| A*2411N | B*180103 | Cw*150203 |
| A*2413 | B*1802 | Cw*1503 |
| A*2414 | B*1803 | Cw*1504 |
| A*2415 | B*1804 | Cw*150501 |
| A*2417 | B*1805 | Cw*150502 |
| A*2418 | B*1806 | Cw*150503 |
| A*2419 | B*1807 | Cw*150504 |
| A*2420 | B*1808 | Cw*1506 |
| A*2421 | B*1809 | Cw*1507 |
| A*2422 | B*1810 | Cw*1508 |
| A*2423 | B*1811 | Cw*1509 |
| A*2424 | B*1812 | Cw*1510 |
| A*2425 | B*1813 | Cw*1511 |
| A*2426 | B*1814 | Cw*1512 |
| A*2427 | B*1815 | Cw*1513 |
| A*2428 | B*1817N | Cw*1514 |
| A*2429 | B*1818 | Cw*1515 |
| A*2430 | B*1819 | Cw*1516 |
| A*2431 | B*1820 | Cw*1517 |
| A*2432 | B*1821 | Cw*160101 |
| A*2433 | B*1822 | Cw*160102 |
| A*2434 | B*1823N | Cw*1602 |
| A*2435 | B*1824 | Cw*160401 |
| A*2436N | B*2701 | Cw*1606 |
| A*2437 | B*2702 | Cw*1607 |
| A*2438 | B*2703 | Cw*1608 |
| A*2439 | B*270401 | Cw*1609 |
| A*2440N | B*270402 | Cw*1701 |
| A*2441 | B*270502 | Cw*1702 |
| A*2442 | B*270503 | Cw*1703 |
| A*2443 | B*270504 | Cw*1704 |
| A*2444 | B*270505 | Cw*1801 |
| A*2445N | B*270506 | Cw*1802 |
| A*2446 | B*270507 | |
| A*2447 | B*270508 | |
| A*2448N | B*270509 | |

Figure 13 cont.

| | |
|---|---|
| A*2449 | B*2706 |
| A*2450 | B*2707 |
| A*2451 | B*2708 |
| A*2452 | B*2709 |
| A*2453 | B*2710 |
| A*2454 | B*2711 |
| A*2455 | B*2712 |
| A*2456 | B*2713 |
| A*2457 | B*2714 |
| A*2458 | B*2715 |
| A*2459 | B*2716 |
| A*2460N | B*2717 |
| A*2461 | B*2718 |
| A*2462 | B*2719 |
| A*2463 | B*2720 |
| A*2464 | B*2721 |
| A*2465 | B*2723 |
| A*2466 | B*2724 |
| A*2467 | B*2725 |
| A*2468 | B*2726 |
| A*250101 | B*2727 |
| A*250102 | B*2728 |
| A*2502 | B*2729 |
| A*2503 | B*2730 |
| A*2504 | B*2731 |
| A*2505 | B*2732 |
| A*2506 | B*2733 |
| A*260101 | B*2734 |
| A*260102 | B*2735 |
| A*260103 | B*2736 |
| A*260104 | B*350101 |
| A*2602 | B*350102 |
| A*2603 | B*350103 |
| A*2604 | B*350104 |
| A*2605 | B*350105 |
| A*2606 | B*350106 |
| A*260701 | B*350201 |
| A*260702 | B*350202 |
| A*2608 | B*3503 |
| A*2609 | B*350401 |
| A*2610 | B*350402 |
| A*2611N | B*3505 |
| A*2612 | B*3506 |
| A*2613 | B*3507 |
| A*2614 | B*350801 |
| A*2615 | B*350802 |
| A*2616 | B*350901 |
| A*2617 | B*350902 |
| A*2618 | B*3510 |
| A*2619 | B*3511 |
| A*2620 | B*3512 |
| A*2621 | B*3513 |
| A*2622 | B*351401 |
| A*2623 | B*351402 |
| A*2624 | B*3515 |
| A*2625N | B*3516 |

Figure 13 cont.

| | |
|---|---|
| A*2626 | B*3517 |
| A*2627 | B*3518 |
| A*2628 | B*3519 |
| A*2629 | B*3520 |
| A*2630 | B*3521 |
| A*2631 | B*3522 |
| A*2632 | B*3523 |
| A*2633 | B*3524 |
| A*2634 | B*3525 |
| A*29010101 | B*3526 |
| A*29010102N | B*3527 |
| A*290201 | B*3528 |
| A*290202 | B*3529 |
| A*290203 | B*3530 |
| A*2903 | B*3531 |
| A*2904 | B*3532 |
| A*2905 | B*3533 |
| A*2906 | B*3534 |
| A*2907 | B*3535 |
| A*2908N | B*3536 |
| A*2909 | B*3537 |
| A*2910 | B*3538 |
| A*2911 | B*3539 |
| A*2912 | B*3540N |
| A*2913 | B*3541 |
| A*2914 | B*3542 |
| A*2915 | B*3543 |
| A*2916 | B*3544 |
| A*300101 | B*3545 |
| A*300102 | B*3546 |
| A*300201 | B*3547 |
| A*300202 | B*3548 |
| A*300203 | B*3549 |
| A*3003 | B*3550 |
| A*3004 | B*3551 |
| A*3006 | B*3552 |
| A*3007 | B*3553N |
| A*3008 | B*3554 |
| A*3009 | B*3555 |
| A*3010 | B*3556 |
| A*3011 | B*3557 |
| A*3012 | B*3558 |
| A*3013 | B*3559 |
| A*3014L | B*3560 |
| A*3015 | B*3561 |
| A*3016 | B*3562 |
| A*3017 | B*3563 |
| A*3018 | B*3564 |
| A*3019 | B*3565Q |
| A*310102 | B*3566 |
| A*3102 | B*3567 |
| A*3103 | B*3568 |
| A*3104 | B*3569 |
| A*3105 | B*3570 |
| A*3106 | B*3571 |
| A*3107 | B*3572 |

Figure 13 cont.

| | |
|---|---|
| A*3108 | B*370101 |
| A*3109 | B*370102 |
| A*3110 | B*370103 |
| A*3111 | B*370104 |
| A*3112 | B*3702 |
| A*3113 | B*3703N |
| A*3114N | B*3704 |
| A*3115 | B*3705 |
| A*3201 | B*3706 |
| A*3202 | B*3707 |
| A*3203 | B*3708 |
| A*3204 | B*3709 |
| A*3205 | B*3710 |
| A*3206 | B*3711 |
| A*3207 | B*3712 |
| A*3208 | B*380101 |
| A*3209 | B*380102 |
| A*3210 | B*380201 |
| A*3211Q | B*380202 |
| A*3212 | B*3803 |
| A*3213 | B*3804 |
| A*3214 | B*3805 |
| A*3301 | B*3806 |
| A*330301 | B*3807 |
| A*330302 | B*3808 |
| A*3304 | B*3809 |
| A*3305 | B*3810 |
| A*3306 | B*3811 |
| A*3307 | B*3812 |
| A*3308 | B*3813 |
| A*3309 | B*3814 |
| A*3401 | B*3815 |
| A*3402 | B*39010101 |
| A*3403 | B*39010102L |
| A*3404 | B*390103 |
| A*3405 | B*390104 |
| A*3406 | B*390201 |
| A*3407 | B*390202 |
| A*3408 | B*3903 |
| A*3601 | B*3904 |
| A*3602 | B*3905 |
| A*3603 | B*390601 |
| A*3604 | B*390602 |
| A*4301 | B*3907 |
| A*6601 | B*3908 |
| A*6602 | B*3909 |
| A*6603 | B*3910 |
| A*6604 | B*3911 |
| A*6605 | B*3912 |
| A*6606 | B*391301 |
| A*680101 | B*391302 |
| A*680102 | B*3914 |
| A*680103 | B*3915 |
| A*680104 | B*3916 |
| A*680105 | B*3917 |
| A*68020101 | B*3918 |

HLA-H       HLA-J       HLA-K       HLA-L       HLA-P
H*01010101  J*01010101  K*01010101  L*01010101  P*01010101
H*01010102  J*01010102  K*01010102  L*01010102  P*01010102
H*01010103  J*01010103  K*01010103  L*01010103  P*02010101
H*0102      J*01010104  K*01010104  L*010102    P*02010102
H*02010101  J*01010105  K*0102                  L*0102
H*02010102  J*01010106  K*0103
H*0202      J*01010107
H*0203      J*01010108
H*0204      J*0201
H*0205
H*0206
H*0301
```

Figure 14: Top 30 HLA class 1 allele frequency in human ethnic groups

| % chance of allele expressed in an individual | | | | | | | |
|---|---|---|---|---|---|---|---|
| Top 30 expressed alleles | | | | | | | |
| Allele | Caucasian | Allele | African-American | Allele | Hispanic | Allele | Oriental |
| A*0201 | 45.6% | C*0401 | 29.0% | A*0201 | 37.1% | A*1101 | 38.4% |
| C*0701 | 27.7% | C*0701 | 25.4% | C*0401 | 25.4% | A*2402 | 33.7% |
| A*0101 | 27.4% | C*0602 | 23.0% | A*2402 | 24.9% | C*0702 | 33.3% |
| A*0301 | 23.8% | A*0201 | 22.3% | C*0702 | 24.2% | C*0102 | 27.7% |
| C*0702 | 21.5% | A*2301 | 20.7% | C*0701 | 20.8% | A*3303 | 23.3% |
| C*0401 | 21.2% | C*0202 | 19.0% | C*0304 | 14.4% | C*0801 | 21.6% |
| B*4402 | 20.2% | A*0301 | 18.7% | A*0301 | 14.3% | C*0304 | 19.9% |
| B*0702 | 18.1% | C*0702 | 18.1% | B*0702 | 13.2% | A*0201 | 18.1% |
| B*0801 | 18.1% | B*5301 | 18.1% | B*3501 | 12.8% | B*4001 | 15.2% |
| C*0501 | 17.2% | B*0702 | 15.8% | C*0602 | 12.3% | C*0401 | 14.0% |
| C*0304 | 16.8% | C*1601 | 15.7% | C*0501 | 11.9% | B*5801 | 13.3% |
| C*0602 | 15.7% | B*1503 | 13.9% | A*0101 | 11.4% | B*4601 | 12.7% |
| A*1101 | 15.3% | B*5801 | 13.5% | A*1101 | 11.0% | B*5101 | 12.4% |
| B*4001 | 13.6% | A*6802 | 12.7% | B*5101 | 10.8% | C*0302 | 12.0% |
| A*2402 | 12.1% | C*1701 | 11.7% | C*1601 | 10.6% | B*3802 | 11.4% |
| B*3501 | 10.7% | B*4501 | 10.8% | B*4403 | 9.9% | A*0207 | 11.0% |
| C*0303 | 10.6% | B*4201 | 10.5% | C*0102 | 9.7% | B*1501 | 9.4% |
| B*5101 | 10.4% | A*3001 | 10.4% | A*2902 | 9.7% | A*0206 | 9.3% |
| C*1203 | 9.9% | B*3501 | 10.1% | C*0802 | 9.3% | C*0303 | 9.2% |
| B*1501 | 9.6% | A*0101 | 10.0% | B*1801 | 9.1% | B*1502 | 9.1% |
| A*2902 | 8.9% | C*0304 | 9.3% | A*3101 | 8.9% | A*0203 | 8.8% |
| A*2601 | 8.2% | A*3002 | 9.2% | B*5201 | 8.6% | B*4403 | 8.6% |
| A*3201 | 8.2% | B*0801 | 8.5% | B*1402 | 8.6% | C*1402 | 8.4% |
| C*0802 | 7.7% | A*3402 | 8.4% | C*0202 | 7.6% | B*3501 | 7.2% |
| A*2501 | 7.5% | A*7401 | 8.4% | C*1203 | 7.6% | C*0602 | 7.0% |
| B*5701 | 7.1% | A*3303 | 8.0% | A*2601 | 7.6% | B*5401 | 6.9% |
| B*1402 | 6.7% | C*1801 | 7.3% | A*6801 | 7.1% | B*1301 | 6.6% |
| C*0202 | 6.6% | A*2902 | 7.2% | B*0801 | 7.0% | B*4002 | 6.3% |
| B*1801 | 6.4% | B*4403 | 6.9% | A*3002 | 6.8% | B*5502 | 6.3% |
| B*4403 | 6.4% | B*4901 | 6.9% | B*4402 | 6.5% | A*2601 | 6.0% |

Figure 19: Detection of Borrelia specific T cells using MHC dextramers
A)
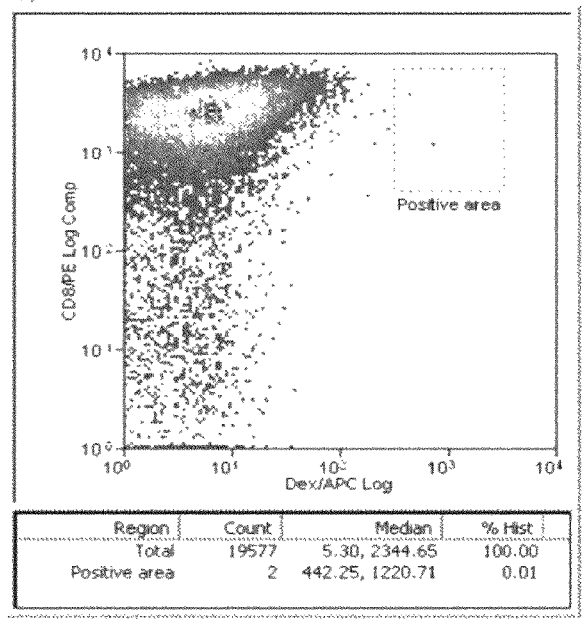
B)
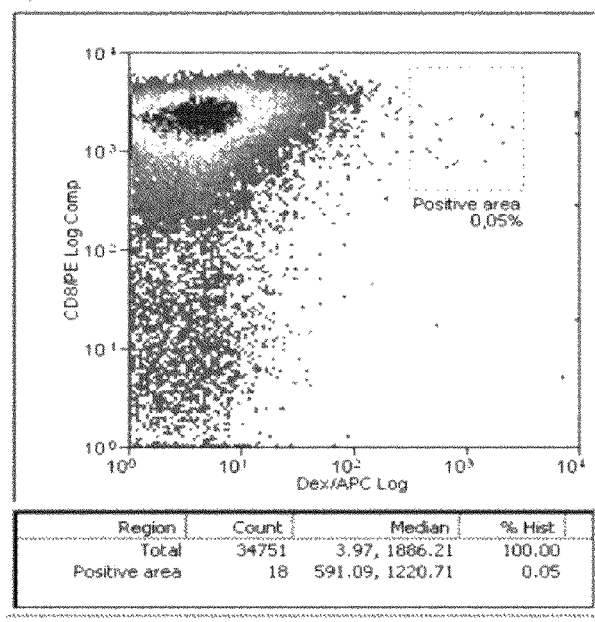

Figure 20: Detection of CMV specific T cells using MHC dextramers
A)
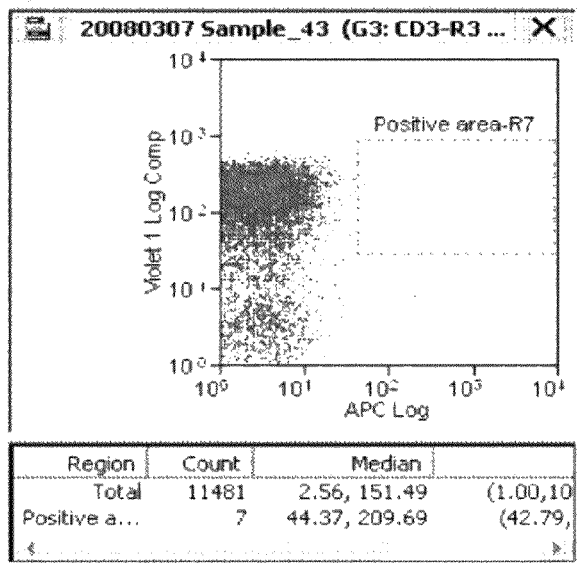
B)
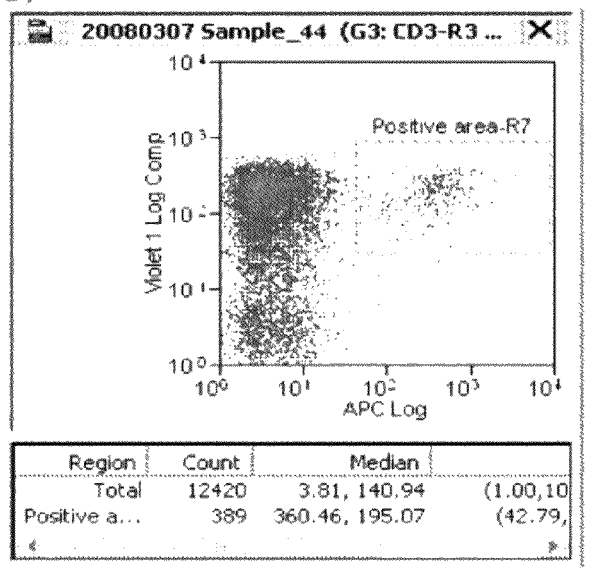

MHC PEPTIDE COMPLEXES AND USES THEREOF IN INFECTIOUS DISEASES

This application claims priority under 35 U.S.C. § 120 as a continuation of U.S. application Ser. No. 12/619,039 filed Nov. 16, 2009, which is a continuation of PCT Application No. PCT/DK2008/000118 filed Mar. 26, 2008, which claims priority to the following Danish Patent applications Nos.—PA 2007 00461, filed Mar. 26, 2007, PA 2007 00973, filed Jul. 3, 2007, PA 2007 00975, filed Jul. 3, 2007, PA 2007 00972, filed Jul. 3, 2007, and PA 2007 00974, filed Jul. 3, 2007 and also claims priority to the following U.S. Provisional Patent Application Nos.—U.S. 60/907,217 filed Mar. 26, 2007, U.S. 60/929,583, filed Jul. 3, 2007, U.S. 60/929,581, filed Jul. 3, 2007, U.S. 60/929,582, filed Jul. 3, 2007, and U.S. 60/929,586, Jul. 3, 2007, the contents of each of which are hereby incorporated by reference.

All patent and non-patent references cited in U.S. 60/907,217 as well as in this application are hereby incorporated by reference in their entirety. U.S. 60/907,217 is hereby also incorporated herein by reference in its entirety.

FIELD OF INVENTION

The present invention relates to MHC-peptide complexes and uses thereof in the treatment of a disease in an individual.

BACKGROUND OF THE INVENTION

Biochemical interactions between peptide epitope specific membrane molecules encoded by the Major Histocompatibility Complex (MHC, in humans HLA) and T-cell receptors (TCR) are required to elicit specific immune responses. This requires activation of T-cells by presentation to the T-cells of peptides against which a T-cell response should be raised. The peptides are presented to the T-cells by the MHC complexes.

The Immune Response

The immune response is divided into two parts termed the innate immune response and the adaptive immune response. Both responses work together to eliminate pathogens (antigens). Innate immunity is present at all times and is the first line of defense against invading pathogens. The immediate response by means of pre-existing elements, i.e. various proteins and phagocytic cells that recognize conserved features on the pathogens, is important in clearing and control of spreading of pathogens. If a pathogen is persistent in the body and thus only partially cleared by the actions of the innate immune system, the adaptive immune system initiate a response against the pathogen. The adaptive immune system is capable of eliciting a response against virtually any type of pathogen and is unlike the innate immune system capable of establishing immunological memory.

The adaptive response is highly specific to the particular pathogen that activated it but it is not so quickly launched as the innate when first encountering a pathogen. However, due to the generation of memory cells, a fast and more efficient response is generated upon repeated exposure to the same pathogen. The adaptive response is carried out by two distinct sets of lymphocytes, the B cells producing antibodies leading to the humoral or antibody mediated immune response, and the T cells leading to the cell mediated immune response.

T cells express a clonotypic T cell receptor (TCR) on the surface. This receptor enable the T cell to recognize peptide antigens bound to major histocompatibility complex (MHC) molecules, called human leukocyte antigens (HLA) in man. Depending on the type of pathogen, being intracellular or extracellular, the antigenic peptides are bound to MHC class I or MHC class II, respectively. The two classes of MHC complexes are recognized by different subsets of T cells; Cytotoxic CD8+ T cells recognizing MHC class I and CD4+ helper cells recognizing MHC class II. In general, TCR recognition of MHC-peptide complexes result in T cell activation, clonal expansion and differentiation of the T cells into effector, memory and regulatory T cells.

B cells express a membrane bound form of immunoglobulin (Ig) called the B cell receptor (BCR). The BCR recognizes an epitope that is part of an intact three dimensional antigenic molecule. Upon BCR recognition of an antigen the BCR:antigen complex is internalized and fragments from the internalized antigen is presented in the context of MHC class II on the surface of the B cell to CD4+ helper T-cells (Th). The specific Th cell will then activate the B cell leading to differentiation into an antibody producing plasma cell.

A very important feature of the adaptive immune system is its ability to distinguish between self and non-self antigens, and preferably respond against non-self. If the immune system fails to discriminate between the two, specific immune responses against self-antigens are generated. These autoimmune reactions can lead to damage of self-tissue.

The adaptive immune response is initiated when antigens are taken up by professional antigen presenting cells such as dendritic cells, Macrophages, Langerhans cells and B-cells. These cells present peptide fragments, resulting from the degradation of proteins, in the context of MHC class II proteins (Major Histocompatibility Complex) to helper T cells. The T helper cells then mediate help to B-cells and antigen specific cytotoxic T cells, both of which have received primary activation signals via their BCR respective TCR. The help from the Th-cell is mediated by means of soluble mediators e.g. cytokines.

In general the interactions between the various cells of the cellular immune response is governed by receptor-ligand interactions directly between the cells and by production of various soluble reporter substances e.g. cytokines by activated cells.

MHC-Peptide Complexes.

MHC complexes function as antigenic peptide receptors, collecting peptides inside the cell and transporting them to the cell surface, where the MHC-peptide complex can be recognized by T-lymphocytes. Two classes of classical MHC complexes exist, MHC class I and II. The most important difference between these two molecules lies in the protein source from which they obtain their associated peptides. MHC class I molecules present peptides derived from endogenous antigens degraded in the cytosol and are thus able to display fragments of viral proteins and unique proteins derived from cancerous cells. Almost all nucleated cells express MHC class I on their surface even though the expression level varies among different cell types. MHC class II molecules bind peptides derived from exogenous antigens. Exogenous proteins enter the cells by endocytosis or phagocytosis, and these proteins are degraded by proteases in acidified intracellular vesicles before presentation by MHC class II molecules. MHC class II molecules are only expressed on professional antigen presenting cells like B cells and macrophages.

The three-dimensional structure of MHC class I and II molecules are very similar but important differences exist. MHC class I molecules consist of two polypeptide chains, a heavy chain, α, spanning the membrane and a light chain, β2-microglobulin (β2m). The heavy chain is encoded in the gene complex termed the major histocompatibility complex (MHC), and its extracellular portion comprises three domains, α1, α2 and α3. The β2m chain is not encoded in the MHC gene and consists of a single domain, which together with the α3 domain of the heavy chain make up a folded structure that closely resembles that of the immunoglobulin. The α1 and α2 domains pair to form the peptide binding cleft, consisting of two segmented α helices lying on a sheet of eight β-strands. In humans as well as in mice three different types of MHC class I molecule exist. HLA-A, B, C are found in humans while MHC class I molecules in mice are designated H-2K, H-2D and H-2L.

The MHC class II molecule is composed of two membrane spanning polypeptide chains, α and β, of similar size (about 30000 Da). Genes located in the major histocompatibility complex encode both chains. Each chain consists of two domains, where α1 and β1 forms a 9-pocket peptide-binding cleft, where pocket 1, 4, 6 and 9 are considered as major peptide binding pockets. The α2 and β2, like the α2 and β2m in the MHC class I molecules, have amino acid sequence and structural similarities to immunoglobulin constant domains. In contrast to MHC class I complexes, where the ends of the antigenic peptide is buried, peptide-ends in MHC class II complexes are not. HLA-DR, DQ and DP are the human class II molecules, H-2A, M and E are those of the mice.

A remarkable feature of MHC genes is their polymorphism accomplished by multiple alleles at each gene. The polygenic and polymorphic nature of MHC genes is reflected in the peptide-binding cleft so that different MHC complexes bind different sets of peptides. The variable amino acids in the peptide binding cleft form pockets where the amino acid side chains of the bound peptide can be buried. This permits a specific variant of MHC to bind some peptides better than others.

MHC Multimers

Due to the short half-life of the peptide-MHC-T cell receptor ternary complex (typically between 10 and 25 seconds) it is difficult to label specific T cells with labelled MHC-peptide complexes, and like-wise, it is difficult to employ such monomers of MHC-peptide for therapeutic and vaccine purposes because of their weak binding. In order to circumvent this problem, MHC multimers have been developed. These are complexes that include multiple copies of MHC-peptide complexes, providing these complexes with an increased affinity and half-life of interaction, compared to that of the monomer MHC-peptide complex. The multiple copies of MHC-peptide complexes are attached, covalently or non-covalently, to a multimerization domain. Known examples of such MHC multimers include the following:

MHC-dimers: Each MHC dimer contains two copies of MHC-peptide. IgG is used as multimerization domain, and one of the domains of the MHC protein is covalently linked to IgG.

MHC-tetramers: Each MHC-tetramer contains four copies of MHC-peptide, each of which is biotinylated. The MHC complexes are held together in a complex by the streptavidin tetramer protein, providing a non-covalent linkage between a streptavidin monomer and the MHC protein. Tetramers are described in U.S. Pat. No. 5,635,363.

MHC pentamers: Five copies of MHC-peptide complexes are multimerised by a self-assembling coiled-coil domain, to form a MHC pentamer. MHC pentamers are described in the US patent 2004209295

MHC dextramers: A large number of MHC-peptide complexes, typically more than ten, are attached to a dextran polymer. MHC-dextramers are described in the patent application WO 02/072631 A2.

MHC streptamers: 8-12 MHC-peptide complexes attached to Streptactin. MHC streptamers are described in Knabel M et al. Reversible MHC multimer staining for functional isolation of T-cell populations and effective adoptive transfer. Nature medicine 6. 631-637 (2002).

Use of MHC Multimers in Flow Cytometry and Related Techniques

The concentration of antigen specific T-cells in samples from e.g. peripheral blood can be very low. Flow cytometry and related methods offer the ability to analyze a large number of cells and simultaneously identify the few of interest. MHC multimers have turned out to be very valuable reagents for detection and characterization of antigen specific T-cells in flow cytometer experiments. The relative amount of antigen specific T cells in a sample can be determined and also the affinity of the binding of MHC multimer to the T-cell receptor can be determined.

The basic function of a flow cytometer is its ability to analyse and identify fluorochrome labelled entities in a liquid sample, by means of its excitation, using a light source such as a laser beam and the light emission from the bound fluorochrome.

MHC multimers is used as detections molecule for identification of antigen specific T-cells in flow cytometry, by labelling the MHC multimer with a specific fluorochrome, which is detectable, by the flow cytometer used.

In order to facilitate the identification of a small amount of cells, the cells can be sub-categorized using antibodies or other fluorochrome labelled detections molecules directed against surface markers other than the TCR on the specific T-cells population. Antibodies or other fluorochrome labelled detections molecules can also be used to identify cells known not to be antigen specific T-cells. Both kinds of detections molecules are in the following referred to as gating reagents. Gating reagents, helps identify the "true" antigen specific T cells bound by MHC multimers by identifying specific subpopulations in a sample, e.g. T cells and by excluding cells that for some reason bind MHC multimers without being antigen specific T-cells. Other cytometry methods, e.g. fluorescence microscopy and IHC can like flow cytometry be employed in identification of antigen specific T cells in a cell sample using MHC multimers.

Application of MHC Multimers in Immune Monitoring, Diagnostics, Prognostics, Therapy and Vaccines T cells are pivotal for mounting an adaptive immune response. It is therefore of importance to be able to measure the number of specific T cells when performing a monitoring of a given immune response, for example in connection with vaccine development, autologous cancer therapy, transplantation, infectious diseases, toxicity studies etc.

Accordingly, the present invention further provides powerful tools in the fields of vaccines, therapy and diagnosis. One objective of the present invention is to provide methods for anti-tumour and anti-virus immunotherapy by generating antigen-specific T-cells capable of inactivating or eliminating undesirable target cells. Another objective is to isolate antigen-specific T-cells and culture these in the presence of co-stimulatory molecules. Ex vivo priming and expansion of T-cell populations allows the T-cells to be used in immunotherapy of various types of cancer and infectious diseases. A third objective of the present invention is to identify and label specific subsets of cells with relevance for the development or treatment of diseases.

SUMMARY OF THE INVENTION

Measurement of antigen specific T cells during an immune response are important parameters in vaccine development, autologous cancer therapy, transplantation, infectious diseases, inflammation, autoimmunity, toxicity studies etc. MHC multimers are crucial reagents in monitoring of antigen specific T cells. The present invention describes novel methods to generate MHC multimers and methods to improve existing and new MHC multimers. The invention also describes improved methods for the use of MHC multimers in analysis of T cells in samples including diagnostic and prognostic methods. Furthermore the use of MHC multimers in therapy are described, e.g. anti-tumour and anti-virus therapy, including isolation of antigen specific T cells capable of inactivation or elimination of undesirable target cells or isolation of specific T cells capable of regulation of other immune cells.

The present invention in one aspect refers to a MHC monomer comprising a-b-P, or a MHC multimer comprising $(a-b-P)_n$, wherein n>1,
wherein a and b together form a functional MHC protein capable of binding the peptide P,
wherein (a-b-P) is the MHC-peptide complex formed when the peptide P binds to the functional MHC protein, and
wherein each MHC peptide complex of a MHC multimer is associated with one or more multimerization domains.

MHC monomers and MHC multimers comprising one or more MHC peptide complexes of class 1 or class 2 MHC are covered by the present invention. Accordingly, the peptide P can have a length of e.g. 8, 9, 10, 11, 12, 13, 14, 15, 16, 16-20, or 20-30 amino acid residues.

Examples of the peptide P is provided herein below. In one embodiment, the peptide P can be selected from the group consisting of sequences disclosed in the electronically enclosed "Sequence Listing" and annotated consecutively (using integers) starting with SEQ ID NO:1 and ending with SEQ ID NO:52252.

In another aspect the present invention is directed to a composition comprising a plurality of MHC monomers and/or MHC multimers according to the present invention, wherein the MHC multimers are identical or different, and a carrier.

In yet another aspect there is provided a kit comprising a MHC monomer or a MHC multimer according to the present invention, or a composition according to the present invention, and at least one additional component, such as a positive control and/or instructions for use.

In a still further aspect there is provided a method for immune monitoring one or more diseases comprising monitoring of antigen specific T cells, said method comprising the steps of
i) providing the MHC monomer or MHC multimer or individual components thereof according to the present invention, or the individual components thereof,
ii) providing a population of antigen specific T cells or individual antigen specific T cells, and
iii) measuring the number, activity or state and/or presence of antigen specific of T cells specific for the peptide P of the said MHC monomer or MHC multimer, thereby immune monitoring said one or more diseases.

In yet another aspect there is provided a method for diagnosing one or more diseases comprising immune monitoring of antigen specific T cells, said method comprising the following steps: of
i) providing the MHC monomer or MHC multimer or individual components thereof according to the present invention, or individual components thereof,
ii) providing a population of antigen specific T cells or individual antigen specific T cells, and
iii) measuring the number, activity or state and/or presence of T cells specific for said MHC monomer or the peptide P of the MHC multimer, thereby diagnosing said one or more diseases.

There is also provided a method for isolation of one or more antigen specific T cells, said method comprising the steps of
i) providing the MHC monomer or MHC multimer or individual components thereof according to the present invention, or individual components thereof, and
ii) providing a population of antigen specific T cells or individual antigen specific T cells, and
iii) thereby isolating said T cells specific for the peptide P of the said MHC monomer or MHC multimer.

The present invention makes it possible to pursue different immune monitoring methods using the MHC monomers and MHC multimers according to the present invention. The immune monitoring methods include e.g. flow cytometry, ELISPOT, LDA, Quantaferon and Quantaferon-like methods. Using the above-cited methods, the MHC monomers and/or the MHC multimers can be provided as a MHC peptide complex, or the peptide and the MHC monomer and/or multimer can be provided separately.

Accordingly, recognition of TCR's can be achieved by direct or indirect detection, e.g. by using one or more of the following methods:

ELISPOT technique using indirect detection, e.g. by adding the antigenic peptide optionally associated with a MHC monomer or MHC multimer, followed by measurement of INF-gamma secretion from a population of cells or from individual cells.

Another technique involves a Quantaferon-like detection assays, e.g. by using indirect detection, e.g. by adding the antigenic peptide optionally associated with a MHC monomer or MHC multimer, followed by measurement of INF-gamma secretion from a population of cells or from individual cells.

Flow cytometry offers another alternative for performing detection assays, e.g. by using direct detection (e.g. of MHC tetramers), e.g. by adding the antigenic peptide optionally associated with a MHC monomer or MHC multimer, followed by detection of a fluorescein label, thereby measuring the number of TCRs on specific T-cells.

Flow cytometry can also be used for indirect detection, e.g. by adding the antigenic peptide optionally associated with a MHC monomer or MHC multimer, followed by addition of a "cell-permeabilizing factor", and subsequent measurement of an intracellular component (e.g. INF-gamma mRNA), from individual cells or populations of cells.

By using the above-mentioned and other techniques, one can diagnose and/or monitor e.g. infectious diseases caused e.g. by mycobacetrium, Gram positive bacteria, Gram negative bacteria, Spirochetes, intracellular bacterium, extracellular bacterium, *Borrelia*, TB, CMV, HPV, Hepatitis, BK, fungal organisms and microorganisms. The diagnosis and/or monitoring of a particular disease can greatly aid in directing an optimal treatment of said disease in an individual. Cancer diagnostic methods and/or cancer monitoring methods also fall within the scope of the present invention.

In still further aspects of the present invention there is provided a method for performing a vaccination of an individual in need thereof, said method comprising the steps of
- providing a MHC monomer or a MHC multimer according to the present invention, or the individual components thereof, and
- administering said MHC monomer or MHC multimer to said individual and obtaining a protective immune response, thereby performing a vaccination of the said individual.

In yet another embodiment there is provided a method for performing therapeutic treatment of an individual comprising the steps of
- Providing the MHC multimer according to the present invention, or individual components thereof, and
- Isolating or obtaining T-cells from a source, such as an individual or an ex-vivo library or cell bank, wherein said isolated or obtained T-cells are specific for said provided MHC multimer,
- Optionally manipulating said T-cells, and
- Introducing said isolated or obtained T-cells into an individual to be subjected to a therapeutic treatment, wherein the individual can be the same individual or a different individual from the source individual.

There is also provided in accordance with the present invention a method for immune monitoring one or more cancer diseases comprising the step of monitoring one or more cancer antigen specific T-cells, said method comprising the steps of
- providing a MHC monomer or MHC multimer, or individual components thereof, as described herein,
- providing a population of cancer antigen specific T cells, or individual cancer antigen specific T cells, and
- measuring the number and/or presence of cancer antigen specific T cells specific for the peptide P of the MHC monomer or MHC multimer, thereby immune monitoring said one or more cancer diseases.

In a still further aspect there is provided a method for diagnosing one or more cancer diseases in an individual, said method comprising the step of performing an immune monitoration of one or more cancer antigen specific T cell(s), said method comprising the further steps of
- providing the MHC multimer or individual components thereof according to the present invention,
- providing a population of cancer antigen specific T cells, or individual cancer antigen specific T cells, and
- measuring the number and/or presence of T cells specific for the peptide P of the MHC monomer or MHC multimer, thereby diagnosing said one or more cancer diseases.

In yet another aspect of the present invention there is provided a method for performing a cancer vaccination of an individual in need thereof, said method comprising the steps of
- providing a MHC monomer or MHC multimer according to any of the present invention, and
- administering said MHC monomer or said MHC multimer to said individual, thereby performing a cancer vaccination of the said individual.

In a still further aspect of the present invention there is provided a method for performing a cancer therapeutic treatment of an individual comprising the steps of
- Providing the MHC multimer according to the present invention, and
- Isolation of T cells specific for said MHC multimer, and
- Optionally manipulation of said T cell and
- Introduction of said T cells into the same or a different individual to obtain a cancer therapeutic treatment.

There is also provided a method comprising one or more steps for minimizing undesired binding of the MHC multimer according to the present invention. This method is disclosed herein below in more detail.

In further aspects the present invention provides:

A method for performing a control experiment comprising the step of counting of particles comprising the MHC multimer according to the present invention.

A method for performing a control experiment comprising the step of sorting of particles comprising the MHC multimer according to the present invention.

A method for performing a control experiment comprising the step of performing flow cytometry analysis of particles comprising the MHC multimer according to the present invention.

A method for performing a control experiment comprising the step of performing a immunohistochemistry analysis comprising the MHC multimer according to the present invention.

A method for performing a control experiment comprising the step of performing a immunocytochemistry analysis comprising the MHC multimer according to the present invention.

A method for performing a control experiment comprising the step of performing an ELISA analysis comprising the MHC multimer according to the present invention.

In a still further aspect of the present invention there is provided a method for generating MHC multimers according to the present invention, said method comprising the steps of
i) providing one or more peptides P; and/or
ii) providing one or more functional MHC proteins,
iii) optionally providing one or more multimerization domains, and
iv) contacting the one or more peptides P and the one or more functional MHC proteins and the one or more multimerization domains simultaneously or sequentially in any order, thereby obtaining MHC multimers according to the present invention.

The method can also be performed by initially providing one or more antigenic peptide(s) P and one or more functional MHC proteins to generate a MHC-peptide complex (a-b-P); subsequently providing one or more multimerisation domain(s); and reacting the one or more MHC-peptide complexes and the one or more multimerization domain(s) to generate a MHC multimer according to the present invention.

Definitions

As used everywhere herein, the term "a", "an" or "the" is meant to be one or more, i.e. at least one.

Adjuvant: adjuvants are drugs that have few or no pharmacological effects by themselves, but can increase the efficacy or potency of other drugs when given at the same time. In another embodiment, an adjuvant is an agent which, while not having any specific antigenic effect in itself, can stimulate the immune system, increasing the response to a vaccine.

Agonist: agonist as used herein is a substance that binds to a specific receptor and triggers a response in the cell. It mimics the action of an endogenous ligand that binds to the same receptor.

Antagonist: antagonist as used herein is a substance that binds to a specific receptor and blocks the response in the cell. It blocks the action of an endogenous ligand that binds to the same receptor.

Antibodies: As used herein, the term "antibody" means an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Antibodies can derive from multiple species. For example, antibodies include rodent (such as mouse and rat), rabbit, sheep, camel, and human antibodies. Antibodies can also include chimeric antibodies, which join variable regions from one species to constant regions from another species. Likewise, antibodies can be humanized, that is constructed by recombinant DNA technology to produce immunoglobulins which have human framework regions from one species combined with complementarity determining regions (CDR's) from a another species' immunoglobulin. The antibody can be monoclonal or polyclonal.

Antibodies can be divided into isotypes (IgA, IgG, IgM, IgD, IgE, IgG1, IgG2, IgG3, IgG4, IgA1, IgA2, IgM1, IgM2)

Antibodies: In another embodiment the term "antibody" refers to an intact antibody, or a fragment of an antibody that competes with the intact antibody for antigen binding. In certain embodiments, antibody fragments are produced by recombinant DNA techniques. In certain embodiments, antibody fragments are produced by enzymatic or chemical cleavage of intact antibodies. Exemplary antibody fragments include, but are not limited to, Fab, Fab', F(ab')2, Fv, and scFv. Exemplary antibody fragments also include, but are not limited to, domain antibodies, nanobodies, minibodies ((scFv-C.sub.H3).sub.2), maxibodies ((scFv-C.sub.H2-C.sub.H3).sub.2), diabodies (noncovalent dimer of scFv).

Antigen presenting cell: An antigen-presenting cell (APC) as used herein is a cell that displays foreign antigen complexed with MHC on its surface.

Antigenic peptide: Any peptide molecule that is bound or able to bind into the binding groove of either MHC class 1 or MHC class 2.

Aptamer: the term aptamer as used herein is defined as oligonucleic acid or peptide molecules that bind a specific target molecule. Aptamers are usually created by selecting them from a large random sequence pool, but natural aptamers also exist. Aptamers can be divided into DNA amtamers, RNA aptamers and peptide aptamers.

Avidin: Avidin as used herein is a glycoprotein found in the egg white and tissues of birds, reptiles and amphibians. It contains four identical subunits having a combined mass of 67,000-68,000 daltons. Each subunit consists of 128 amino acids and binds one molecule of biotin.

Biologically active molecule: A biologically active molecule is a molecule having itself a biological activity/effect or is able to induce a biological activity/effect when administered to a biological system. Biologically active molecules include adjuvants, immune targets (e.g. antigens), enzymes, regulators of receptor activity, receptor ligands, immune potentiators, drugs, toxins, cytotoxic molecules, co-receptors, proteins and peptides in general, sugar moieties, lipid groups, nucleic acids including siRNA, nanoparticles, small molecules.

Bioluminescent: Bioluminescence, as used herein, is the production and emission of light by a living organism as the result of a chemical reaction during which chemical energy is converted to light energy.

Biotin: Biotin, as used herein, is also known as vitamin H or $B_7$. Niotin has the chemical formula $C_{10}H_{16}N_2O_3S$.

Bispecific antibodies: The term bispecific antibodies as used herein is defined as monoclonal, preferably but not limited to human or humanized, antibodies that have binding specificities for at least two different antigens. The antibody can also be trispecific or multispecific.

Carrier: A carrier as used herein can be any type of molecule that is directly or indirectly associated with the MHC peptide complex. In this invention, a carrier will typically refer to a functionalized polymer (e.g. dextran) that is capable of reacting with MHC-peptide complexes, thus covalently attaching the MHC-peptide complex to the carrier, or that is capable of reacting with scaffold molecules (e.g. streptavidin), thus covalently attaching streptavidin to the carrier; the streptavidin then may bind MHC-peptide complexes. Carrier and scaffold are used interchangeably herein where scaffold typically refers to smaller molecules of a multimerization domain and carrier typically refers to larger molecule and/or cell like structures.

Chelating chemical compound: Chelating chemical compound, as used herein, is the process of reversible binding of a ligand to a metal ion, forming a metal complex.

Chemiluminescent: Chemiluminescence, as used herein, is the emission of light (luminescence) without emission of heat as the result of a chemical reaction.

Chromophore: A chromophore, as used herein, is the part of a visibly coloured molecule responsible for light absorption over a range of wavelengths thus giving rise to the colour. By extension the term can be applied to uv or it absorbing parts of molecules.

Coiled-coil polypeptide: the term coiled-coil polypeptide as used herein is a structural motif in proteins, in which 2-7 alpha-helices are coiled together like the strands of a rope Covalent binding: The term covalent binding is used herein to describe a form of chemical bonding that is characterized by the sharing of pairs of electrons between atoms. Attraction-to-repulsion stability that forms between atoms when they share electrons is known as covalent bonding.

Crosslinking is the process of chemically joining two or more molecules by a covalent bond. Crosslinking reagents contain reactive ends to specific functional groups (primary amines, sulfhydryls, etc.) on proteins or other molecules.

Diagnosis: The act or process of identifying or determining the nature and cause of a disease or injury through evaluation Diabodies: The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Dendritic cell: The term dendritic cell as used herein is a type of immune cells. Their main function is to process antigen material and present it on the surface to other cells of the immune system, thus functioning as antigen-presenting cells.

Detection: In this invention detection means any method capable of measuring one molecule bound to another molecule. The molecules are typically proteins but can be any type of molecule Dextran: the term dextran as used herein is a complex, branched polysaccharide made of many glucose molecules joined into chains of varying lengths. The straight chain consists of α1→6 glycosidic linkages between glucose molecules, while branches begin from α1→3 linkages (and in some cases, α1→2 and α1→4 linkages as well).

Direct detection of T cells: Direct detection of T cells is used herein interchangeably with direct detection of TCR and direct detection of T cell receptor. As used herein direct detection of T cells is detection directly of the binding interaction between a specific T cell receptor and a MHC multimer.

DNA: The term DNA (Deoxyribonucleic acid) duplex as used herein is a polymer of simple units called nucleotides, with a backbone made of sugars and phosphate atoms joined by ester bonds. Attached to each sugar is one of four types of molecules called bases.

DNA duplex: In living organisms, DNA does not usually exist as a single molecule, but instead as a tightly-associated pair of molecules. These two long strands entwine like vines, in the shape of a double helix.

Electrophilic: electrophile, as used herein, is a reagent attracted to electrons that participates in a chemical reaction by accepting an electron pair in order to bond to a nucleophile.

Enzyme label: enzyme labelling, as used herein, involves a detection method comprising a reaction catalysed by an enzyme.

Epitope-focused antibody: Antibodies also include epitope-focused antibodies, which have at least one minimal essential binding specificity determinant from a heavy chain or light chain CDR3 from a reference antibody, methods for making such epitope-focused antibodies are described in U.S. patent application Ser. No. 11/040,159, which is incorporated herein by reference in its entirety.

Flow cytometry: The analysis of single cells using a flow cytometer.

Flow cytometer: Instrument that measures cell size, granularity and fluorescence due to bound fluorescent marker molecules as single cells pass in a stream past photodectors. A flow cytometer carry out the measurements and/or sorting of individual cells.

Fluorescent: the term fluorescent as used herein is to have the ability to emit light of a certain wavelength when activated by light of another wavelength.

Fluorochromes: fluorochrome, as used herein, is any fluorescent compound used as a dye to mark e.g. protein with a fluorescent label.

Fluorophore: A fluorophore, as used herein, is a component of a molecule which causes a molecule to be fluorescent.

Folding: In this invention folding means in vitro or in vivo folding of proteins in a tertiary structure.

Fusion antibody: As used herein, the term "fusion antibody" refers to a molecule in which an antibody is fused to a non-antibody polypeptide at the N- or C-terminus of the antibody polypeptide.

Glycosylated: Glycosylation, as used herein, is the process or result of addition of saccharides to proteins and lipids.

Hapten: A residue on a molecule for which there is a specific molecule that can bind, e.g. an antibody.

Heteroconjugate antibodies are composed of two covalently joined antibodies. Such antibodies have, for example, been proposed to target immune system cells to unwanted cells.

IgG: IgG as used herein is a monomeric immunoglobulin, built of two heavy chains and two light chains. Each molecule has two antigen binding sites.

Isolated antibody: The term "isolated" antibody as used herein is an antibody which has been identified and separated and/or recovered from a component of its natural environment.

Immunoconjugates: The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate) Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Immune monitoring: Immune monitoring of the present invention refers to testing of immune status in the diagnosis and therapy of diseases like but not limited to cancer, immunoproliferative and immunodeficiency disorders, autoimmune abnormalities, and infectious disease. It also refers to testing of immune status before, during and after vaccination and transplantation procedures.

Immune monitoring process: a series of one or more immune monitoring analysis

Indirect detection of T cells: Indirect detection of T cells is used interchangeably herein with Indirect detection of TCR and indirect detection of T cell receptor. As used herein indirect detection of T cells is detection of the binding interaction between a specific T cell receptor and a MHC multimer by measurement of the effect of the binding interaction.

Ionophore: ionophore, as used herein, is a lipid-soluble molecule usually synthesized by microorganisms capable of transporting ions.

Label: Label herein is used interchangeable with labeling molecule. Label as described herein is an identifiable substance that is detectable in an assay and that can be attached to a molecule creating a labeled molecule. The behavior of the labeled molecule can then be studied.

Labelling: Labelling herein means attachment of a label to a molecule.

Lanthanide: lanthanide, as used herein, series comprises the 15 elements with atomic numbers 57 through 71, from lanthanum to lutetium.

Linker molecule: Linker molecule and linker is used interchangeable herein. A linker molecule is a molecule that covalently or non-covalently connects two or more molecules, thereby creating a larger complex consisting of all molecules including the linker molecule.

Liposomes: The term liposomes as used herein is defined as a spherical vesicle with a membrane composed of a phospholipid and cholesterol bilayer. Liposomes, usually but not by definition, contain a core of aqueous solution; lipid spheres that contain no aqueous material are called micelles.

Immunoliposomes: The antibodies disclosed herein can also be formulated as immunoliposomes. Liposomes comprising the antibody are prepared by methods known in the art, such as described in Epstein et al., Proc. Natl. Acad. Sci. USA 82: 3688 (1985); Hwang et al., Proc. Natl. Acad. Sci. USA 77: 4030 (1980); and U.S. Pat. Nos. 4,485,045 and 4,544,545. Particularly useful liposomes can be generated by the reverse-phase evaporation method with a lipid composition comprising phosphatidylcholine, cholesterol, and PEG-derivatized phosphatidylethanolamine (PEG-PE).

Marker: Marker is used interchangeably with marker molecule herein. A marker is molecule that specifically associates covalently or non-covalently with a molecule belonging to or associated with an entity.

MHC: Denotes the major histocompatibility complex.

A "MHC Class I molecule" as used everywhere herein is defined as a molecule which comprises 1-3 subunits, including a heavy chain, a heavy chain combined with a light chain (beta$_2$m), a heavy chain combined with a light chain (beta$_2$m) through a flexible linker, a heavy chain combined with a peptide, a heavy chain combined with a peptide through a flexible linker, a heavy chain/beta$_2$m dimer combined with a peptide, and a heavy chain/beta$_2$m dimer with a peptide through a flexible linker to the heavy or light chain. The MHC molecule chain can be changed by substitution of single or by cohorts of native amino acids or by inserts, or deletions to enhance or impair the functions attributed to said molecule. By example, it has been shown that substitution of XX with YY in position nn of human beta$_2$m enhance the biochemical stability of MHC Class I molecule complexes and thus can lead to more efficient antigen presentation of subdominant peptide epitopes.

MHC complex: MHC complex is herein used interchangeably with MHC-peptide complex, unless it is specified that the MHC complex is empty, i.e. is not complexed with peptide.

MHC Class I like molecules (including non-classical MHC Class I molecules) include CD1d, HLA E, HLA G, HLA F, HLA H, MIC A, MIC B, ULBP-1, ULBP-2, and ULBP-3.

A "MHC Class II molecule" as used everywhere herein is defined as a molecule which comprises 2-3 subunits including an alpha-chain and a beta-chain (alpha/beta-dimer), an alpha/beta dimer with a peptide, and an alpha/beta dimer combined with a peptide through a flexible linker to the alpha or beta chain, an alpha/beta dimer combined through an interaction by affinity tags e.g. jun-fos, an alpha/beta dimer combined through an interaction by affinity tags e.g. jun-fos and further combined with a peptide through a flexible linker to the alpha or beta chain. The MHC molecule chains can be changed by substitution of single or by cohorts of native amino acids or by inserts, or deletions to enhance or impair the functions attributed to said molecule. Under circumstances where the alpha-chain and beta-chain have been fused, to form one subunit, the "MHC Class II molecule" can comprise only 1 subunit.

MHC Class II like molecules (including non-classical MHC Class II molecules) include HLA DM, HLA DO, I-A beta2, and I-E beta2.

A "peptide free MHC Class I molecule" as used everywhere herein is meant to be a MHC Class I molecule as defined above with no peptide.

A "peptide free MHC Class II molecule" as used everywhere herein is meant to be a MHC Class II molecule as defined above with no peptide.

Such peptide free MHC Class I and II molecules are also called "empty" MHC Class I and II molecules.

The MHC molecule may suitably be a vertebrate MHC molecule such as a human, a mouse, a rat, a porcine, a bovine or an avian MHC molecule. Such MHC complexes from different species have different names. E.g. in humans, MHC complexes are denoted HLA. The person skilled in the art will readily know the name of the MHC complexes from various species.

In general, the term "MHC molecule" is intended to include alleles. By way of example, in humans e.g. HLA A, HLA B, HLA C, HLA D, HLA E, HLA F, HLA G, HLA H, HLA DR, HLA DQ and HLA DP alleles are of interest, and in the mouse system, H-2 alleles are of interest. Likewise, in the rat system RT1-alleles, in the porcine system SLA-alleles, in the bovine system BoLA, in the avian system e.g. chicken-B alleles, are of interest.

"MHC complexes" and "MHC constructs" are used interchangeably herein.

"MHC protein" and "MHC molecule" are used interchangeably herein. Accordingly, a functional MHC peptide complex comprises a MHC protein or MHC molecule associated with a peptide to be presented for cells or binding partners having an affinity for said peptide.

By the terms "MHC complexes" and "MHC multimers" as used herein are meant such complexes and multimers thereof, which are capable of performing at least one of the functions attributed to said complex or multimer. The terms include both classical and non-classical MHC complexes. The meaning of "classical" and "non-classical" in connection with MHC complexes is well known to the person skilled in the art. Non-classical MHC complexes are subgroups of MHC-like complexes. The term "MHC complex" includes MHC Class I molecules, MHC Class II molecules, as well as MHC-like molecules (both Class I and Class II), including the subgroup non-classical MHC Class I and Class II molecules.

The MHC molecule can suitably be a vertebrate MHC molecule such as a human, a mouse, a rat, a porcine, a bovine or an avian MHC molecule. Such MHC complexes from different species have different names. E.g. in humans, MHC complexes are denoted HLA. The person skilled in the art will readily know the name of the MHC complexes from various species.

MHC multimer: The terms MHC multimer, MHCmer and MHC'mer herein are used interchangeably, to denote a complex comprising more than one MHC-peptide complexes, held together by covalent or non-covalent bonds.

Monoclonal antibodies: Monoclonal antibodies, as used herein, are antibodies that are identical because they were produced by one type of immune cell and are all clones of a single parent cell.

Monovalent antibodies: The antibodies in the present invention can be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

Multimerization domain: A multimerization domain is a molecule, a complex of molecules, or a solid support, to which one or more MHC or MHC-peptide complexes can be attached. A multimerization domain consist of one or more carriers and/or one or more scaffolds and may also contain one or more linkers connecting carrier to scaffold, carrier to carrier, scaffold to scaffold. The multimerization domain may also contain one or more linkers that can be used for attachment of MHC complexes and/or other molecules to the multimerization domain. Multimerization domains thus include IgG, streptavidin, streptactin, micelles, cells, polymers, beads and other types of solid support, and small organic molecules carrying reactive groups or carrying chemical motifs that can bind MHC complexes and other molecules.

Nanobodies: Nanobodies as used herein is a type of antibodies derived from camels, and are much smaller than traditional antibodies.

Neutralizing antibodies: neutralizing antibodies as used herein is an antibody which, on mixture with the homologous infectious agent, reduces the infectious titer.

NMR: NMR (Nuclear magnetic resonance), as used herein, is a physical phenomenon based upon the quantum mechanical magnetic properties of an atom's nucleus. NMR refers to a family of scientific methods that exploit nuclear magnetic resonance to study molecules.

Non-covalent: The term noncovalent bond as used herein is a type of chemical bond, that does not involve the sharing of pairs of electrons, but rather involves more dispersed variations of electromagnetic interactions.

Nucleic acid duplex: A nucleic acid is a complex, high-molecular-weight biochemical macromolecule composed of nucleotide chains that convey genetic information. The most common nucleic acids are deoxyribonucleic acid (DNA) and ribonucleic acid (RNA).

Nucleophilic: a nucleophile, as used herein, is a reagent that forms a chemical bond to its reaction partner (the electrophile) by donating both bonding electrons.

"One or more" as used everywhere herein is intended to include one and a plurality.

A "peptide free MHC Class I molecule" as used everywhere herein is meant to be a MHC Class I molecule as defined above with no peptide.

A "peptide free MHC Class II molecule" as used everywhere herein is meant to be a MHC Class II molecule as defined above with no peptide.

Such peptide free MHC Class I and II molecules are also called "empty" MHC Class I and II molecules.

Pegylated: pegylated, as used herein, is conjugation of Polyethylene glycol (PEG) to proteins.

Peptide or protein: Any molecule composed of at least two amino acids. Peptide normally refers to smaller molecules of up to around 30 amino acids and protein to larger molecules containing more amino acids.

Phosphorylated; phosphorylated, as used herein, is the addition of a phosphate ($PO_4$) group to a protein molecule or a small molecule.

"A plurality" as used everywhere herein should be interpreted as two or more.

PNA: PNA (Peptide nucleic acid) as used herein is a chemical similar to DNA or RNA. PNA is not known to occur naturally in existing life on Earth but is artificially synthesized and used in some biological research and medical treatments. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right.

"A plurality" as used everywhere herein should be interpreted as two or more. This applies i.a. to the MHC peptide complex and the binding entity. When a plurality of MHC peptide complexes is attached to the multimerization domain, such as a scaffold or a carrier molecule, the number of MHC peptide complexes need only be limited by the capacity of the multimerization domain.

Polyclonal antibodies: a polyclonal antibody as used herein is an antibody that is derived from different B-cell lines. They are a mixture of immunoglobulin molecules secreted against a specific antigen, each recognising a different epitope.

Polymer: the term polymer as used herein is defined as a compound composed of repeating structural units, or monomers, connected by covalent chemical bonds.

Polypeptide: Peptides are the family of short molecules formed from the linking, in a defined order, of various α-amino acids. The link between one amino acid residue and the next is an amide bond and is sometimes referred to as a peptide bond. Longer peptides are referred to as proteins or polypeptide.

Polysaccharide: The term polysaccharide as used herein is defined as polymers made up of many monosaccharides joined together by glycosidic linkages.

Radicals: radicals, as used herein, are atomic or molecular species with unpaired electrons on an otherwise open shell configuration. These unpaired electrons are usually highly reactive, so radicals are likely to take part in chemical reactions.

Radioactivity: Radioactive decay is the process in which an unstable atomic nucleus loses energy by emitting radiation in the form of particles or electromagnetic waves.

RNA: RNA (Ribonucleic acid) as used herein is a nucleic acid polymer consisting of nucleotide monomers that plays several important roles in the processes that translate genetic information from deoxyribonucleic acid (DNA) into protein products Scaffold: A scaffold is typically an organic molecule carrying reactive groups, capable of reacting with reactive groups on a MHC-peptide complex. Particularly small organic molecules of cyclic structure (e.g. functionalized cycloalkanes or functionalized aromatic ring structures) are termed scaffolds. Scaffold and carrier are used interchangeably herein where scaffold typically refers to smaller molecules of a multimerization domain and carrier typically refers to larger molecule and/or cell like structures.

Staining: In this invention staining means specific or unspecific labelling of cells by binding labeled molecules to defined proteins or other structures on the surface of cells or inside cells. The cells are either in suspension or part of a tissue. The labeled molecules can be MHC multimers, antibodies or similar molecules capable of binding specific structures on the surface of cells.

Streptavidin: Streptavidin as used herein is a tetrameric protein purified from the bacterium *Streptomyces avidinii*. Streptavidin is widely use in molecular biology through its extraordinarily strong affinity for biotin.

Sugar: Sugars as used herein include monosaccharides, disaccharides, trisaccharides and the oligosaccharides—comprising 1, 2, 3, and 4 or more monosaccharide units respectively.

Therapy: Treatment of illness or disability

Vaccine: A vaccine is an antigenic preparation used to establish immunity to a disease or illness and thereby protects or cure the body from a specific disease or illness. Vaccines are either prophylactic and prevent disease or therapeutic and treat disease. Vaccines may contain more than one type of antigen and is then called a combined vaccine.

Vaccination: The introduction of vaccine into the body of human or animals for the purpose of inducing immunity.

B.L. is an abbreviation for Bind level.

Aff. is an abbreviation for affinity.

BRIEF DESCRIPTION OF THE DRAWINGS

FIG. 2. Program for peptide sequence motifs prediction.

FIG. 3. Full List of HLA Class I alleles assigned as of January 2007 from www.anthonynolan.org.uk/HIG/lists/class1list.html.

FIG. 6. Illustration of selected cleavable linkers.

FIG. 7. Prediction of MHC class 1 mouse virus LCMV gp 1 protein nonamer peptide binders for H-2Kd using the Syfpeithi database. Peptides are ranked according to their binding score. Only peptides with binding scores above the value of 11 are listed. The peptides listed in FIG. 7 correspond to SEQ ID NO:61368 to SEQ ID NO:61663.

FIG. 8. Size exclusion chromatography of folded HLA-A*0201-β2m QLFEELQEL peptide-complex (SEQ ID NO:61664). Purification of HLA-A*0201-β2m QLFEELQEL peptide-complex (SEQ ID NO:61664) by size exclusion chromatography on a HiLoad 16/60 Superdex 75 column. Eluted protein was followed by measurement of the absorbance at 280 nm. The elution profile consisted of 4 peaks, corresponding to aggregated Heavy Chain, correctly folded MHC-complex, β2m and excess biotin and peptide.

FIG. 9. MHC-SHIFT Assay. The SHIFT Assay shows that heavy chain is efficiently biotinylated, since the band corresponding to biotinylated heavy chain (lane 2) is shifted up-wards upon incubation with streptavidin.

Lane 1: Benchmark protein-ladder.

Lane 2: Folded HLA-A*0201-β2m-QLFEELQEL peptide-complex (SEQ ID NO:61664).

Lane 3: Folded HLA-A*0201-β2m-QLFEELQEL peptide-complex (SEQ ID NO:61664) incubated with molar excess Streptavidin.

FIG. 10. Composition of Fluorescein-linker molecule. (A) Schematic representation of an example of a Fluorescein-linker molecule. (B) Composition of a L15 linker.

FIG. 11. List of the 24 MHC class 1 alleles used for peptide prediction by the database www.cbs.dtu.dk/services/NetMHC/ and the 14 MHC class 2 alleles used for peptide prediction by the database www.cbs.dtu.dk/services/NetMHCII/.

FIG. 12. Prediction of MHC class 1 mouse virus LCMV gp 1 protein nonamer peptide binders for H-2Kd using the Syfpeithi database. Peptides are ranked according to their binding score. Only peptides with binding scores above the value of 11 are listed. The peptides listed in FIG. 12 correspond to SEQ ID NO:61665 to SEQ ID NO:61726.

FIG. 13. Full List of HLA Class I alleles assigned as of January 2007 from www.anthonynolan.org.uk/HIG/lists/class1list.html.

FIG. 14. List of top 30 HLA class 1 alleles in different human ethnic groups.

Figure 15:
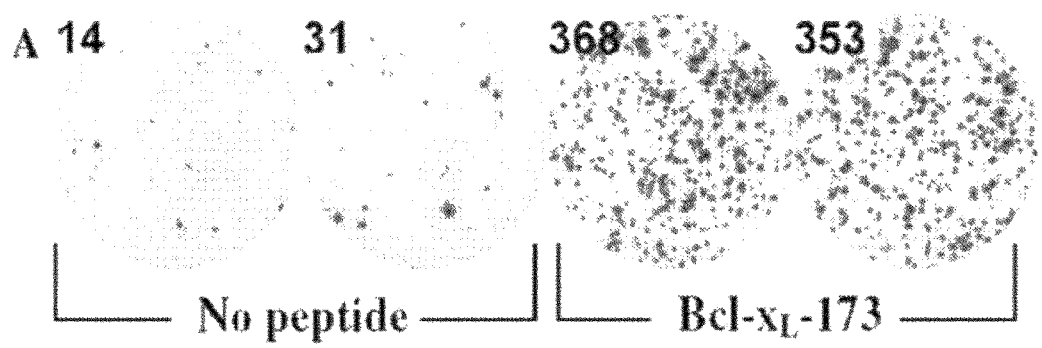

FIG. 15. Ex vivo ELISPOT analysis of BclX(L)-specific, CD8 positive T cells in PBL from a breast cancer patient either with or without the BclX(L) YLNDHLEPWI peptide (SEQ ID NO:61727). Analysis were performed in doublets and number of IFN-gamma producing T-cells are presented. (Reference: Sorensen R B, Hadrup S R, Kollgaard T, Svane I M, Thor Straten P, Andersen M H (2006) Efficient tumor cell lysis mediated by a Bcl-X(L) specific T cell clone isolated from a breast cancer patient. Cancer Immunol Immunother April; 56 (4) 527-33).

Figure 16:
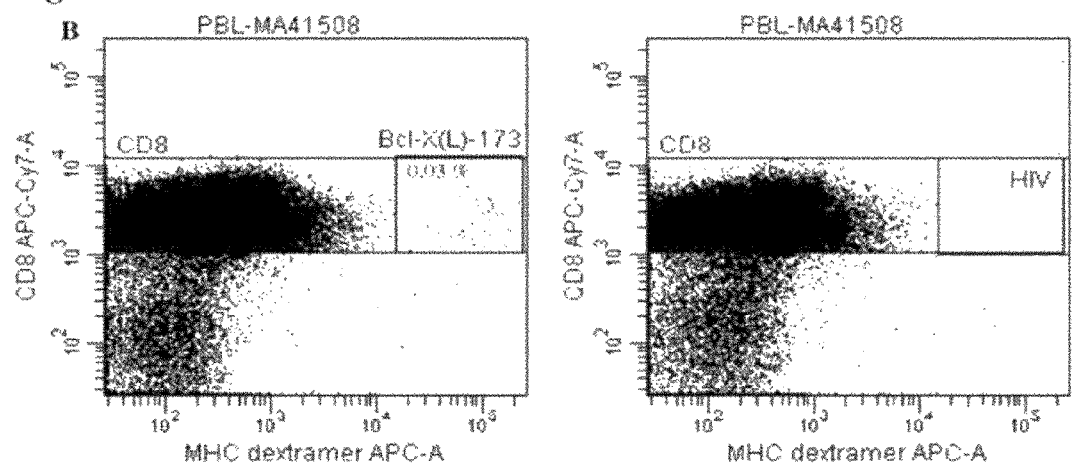

FIG. 16. PBL from a breast cancer patient was analyzed by flow cytometry to identify Bcl-X(L)173-182 (peptide YLNDHLEPWI) (SEQ ID NO:61727) specific CD8 T cells using the dextramer complex HLA-A2/Bcl-X(L)173-182-APC, 7-AAD-PerCP, CD3-FITC, and CD8-APC-Cy7. The dextramer complex HLA-A2/HIV-1 pol476-484-APC was used as negative control. (Reference: Sorensen R B, Hadrup S R, Kollgaard T, Svane I M, Thor Straten P, Andersen M H (2006) Efficient tumor cell lysis mediated by a Bcl-X(L) specific T cell clone isolated from a breast cancer patient. Cancer Immunol Immunother April; 56 (4) 527-33).

Figure 17:
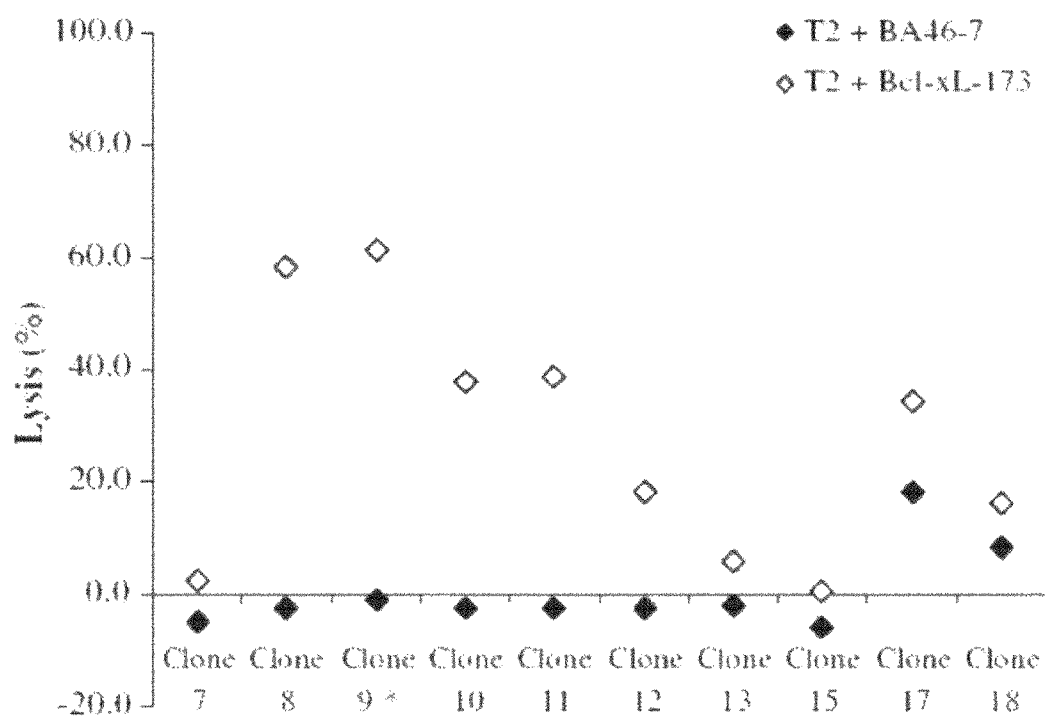

FIG. 17. Ten expanded T cell clones isolated by Flow sorting and then expanded were tested for their specificity by analysis in a standard 51-Cr release assay. For this purpose, T2 cells loaded with either Bcl-X(L)173-182, YLNDHLEPWI peptide (SEQ ID NO:61727) or an irrelevant peptide (BA4697-105, GLQHWVPEL) (SEQ ID NO:61728) were used as target cells. Reference: Sorensen R B, Hadrup S R, Kollgaard T, Svane I M, Thor Straten P, Andersen M H (2006) Efficient tumor cell lysis mediated by a Bcl-X(L) specific T cell clone isolated from a breast cancer patient. Cancer Immunol Immunother April; 56 (4) 527-33).

Figure 18:
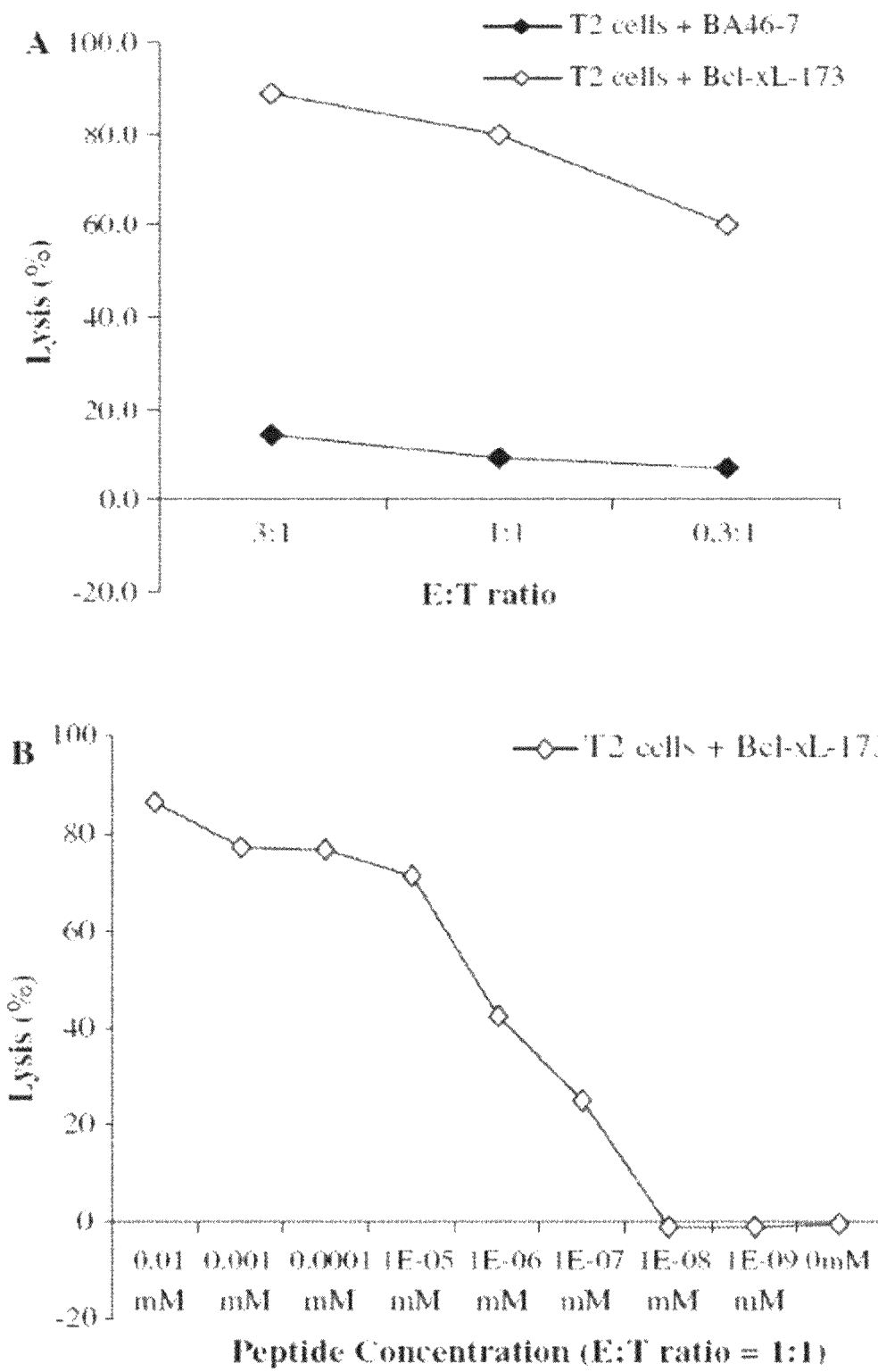

FIG. 18. A Bcl-X(L)173-182 specific clone was tested for its cytotoxic potential in 51Cr-release assays. Two assays were performed a Cell lysis of T2 cells pulsed with Bcl-X(L)173-182 peptide or an irrelevant peptide (BA4697-105, GLQHWVPEL) (SEQ ID NO:61728) in three E:T ratios. b Cell lysis of T2 cells pulsed with different concentrations of Bcl-X(L)173-182 peptide at the E:T ratio 1:1. (Reference: Sorensen R B, Hadrup S R, Kollgaard T, Svane I M, Thor Straten P, Andersen M H (2006) Efficient tumor cell lysis mediated by a Bcl-X(L) specific T cell clone isolated from a breast cancer patient. Cancer Immunol Immunother April; 56 (4) 527-33).

FIG. 19. Detection of *Borrelia* specific T cells using MHC dextramers. Dot plots showing live gated CD3+/CD4− lymphocytes from *Borrelia* patient stained with (A) Negative Control MHC Dextramer (HLA-A*0201(GLAGDVSAV) (SEQ ID NO:61729) or (B) pool of MHC Dextramers containing peptides from *Borrelia* antigen Osp A and Fla B. pool of MHC Dextramers containing peptides from *Borrelia* antigen. 0.05% of the live gated CD3+/CD4− lymphocytes are positive for one or more of the MHC Dextramers in the pool.

FIG. 20. Detection of CMV specific T cells using MHC dextramers Dot plots showing live gated CD3+/CD4− lymphocytes from CMV infected patient stained with (A) Negative Control MHC Dextramers (HLA-A*0201(GLAGDVSAV)) (SEQ ID NO:61729) or (B) MHC Dextramers containing peptides from CMV pp65 antigen (HLA-A*0201 (NLVPMVATV)) (SEQ ID NO:61730).

DETAILED DESCRIPTION OF THE INVENTION

In one aspect, the present invention is directed to novel MHC complexes optionally comprising a multimerization domain preferably comprising a carrier molecule and/or a scaffold.

There is also provided a MHC multimer comprising 2 or more MHC-peptide complexes and a multimerization domain to which the 2 or more MHC-peptide complexes are associated. The MHC multimer can generally be formed by association of the 2 or more MHC-peptide complexes with the multimerization domain to which the 2 or more MHC-peptide complexes are capable of associating.

The multimerization domain can be a scaffold associated with one or more MHC-peptide complexes, or a carrier associated with one or more, preferably more than one, MHC-peptide complex(es), or a carrier associated with a plurality of scaffolds each associated with one or more MHC-peptide complexes, such as 2 MHC-peptide complexes, 3 MHC-peptide complexes, 4 MHC-peptide complexes, 5 MHC-peptide complexes or more than 5 MHC-peptide complexes. Accordingly, multimerization domain collectively refers to each and every of the above. It will be clear from the detailed description of the invention provided herein below when the multimerization domain refers to a scaffold or a carrier or a carrier comprising one or more scaffolds.

Generally, when a multimerization domain comprising a carrier and/or a scaffold is present, the MHC complexes can be associated with this domain either directly or via one or more binding entities. The association can be covalent or non-covalent.

Accordingly, there is provided in one embodiment a MHC complex comprising one or more entities (a-b-P)$_n$, wherein a and b together form a functional MHC protein capable of binding a peptide P, and wherein (a-b-P) is the MHC-peptide complex formed when the peptide P binds to the functional MHC protein, said MHC complex optionally further comprising a multimerization domain comprising a carrier molecule and/or a scaffold. "MHC complex" refers to any MHC complex, including MHC monomers in the form of a single MHC-peptide complex and MHC multimers comprising a multimerization domain to which more than one MHC peptide complex is associated.

When the invention is directed to complexes comprising a MHC multimer, i.e. a plurality of MHC peptide complexes of the general composition (a-b-P)$_n$ associated with a multimerization domain, n is by definition more than 1, i.e. at least 2 or more. Accordingly, the term "MHC multimer" is used herein specifically to indicate that more than one MHC-peptide complex is associated with a multimerization domain, such as a scaffold or carrier or carrier comprising one or more scaffolds. Accordingly, a single MHC-peptide complex can be associated with a scaffold or a carrier or a carrier comprising a scaffold and a MHC-multimer comprising 2 or more MHC-peptide complexes can be formed by association of the individual MHC-peptide complexes with a scaffold or a carrier or a carrier comprising one or more scaffolds each associated with one or more MHC-peptide complexes.

When the MHC complex comprises a multimerization domain to which the n MHC-peptide complexes are associated, the association can be a covalent linkage so that each or at least some of the n MHC-peptide complexes is covalently linked to the multimerization domain, or the association can be a non-covalent association so that each or at least some of the n MHC-peptide complexes are non-covalently associated with the multimerization domain.

The MHC complexes of the invention may be provided in non-soluble or soluble form, depending on the intended application.

Effective methods to produce a variety of MHC complexes comprising highly polymorphic human HLA encoded proteins makes it possible to perform advanced analyses of complex immune responses, which may comprise a variety of peptide epitope specific T-cell clones.

One of the benefits of the MHC complexes of the present invention is that the MHC complexes overcome low intrinsic affinities of monomer ligands and counter receptors. The MHC complexes have a large variety of applications that include targeting of high affinity receptors (e.g. hormone peptide receptors for insulin) on target cells. Taken together poly-ligand binding to target cells has numerous practical, clinical and scientifically uses.

Thus, the present invention provides MHC complexes which present mono-valent or multivalent binding sites for MHC recognising cells, such as MHC complexes optionally comprising a multimerization domain, such as a scaffold or a carrier molecule, which multimerization domain have attached thereto, directly or indirectly via one or more linkers, covalently or non-covalently, one or more MHC peptide complexes. "One or more" as used herein is intended to include one as well as a plurality, such as at least 2. This applies i.a. to the MHC peptide complexes and to the binding entities of the multimerization domain. The scaffold or carrier molecule may thus have attached thereto a MHC peptide complex or a plurality of such MHC peptide complexes, and/or a linker or a plurality of linkers.

Product

Figure 1:
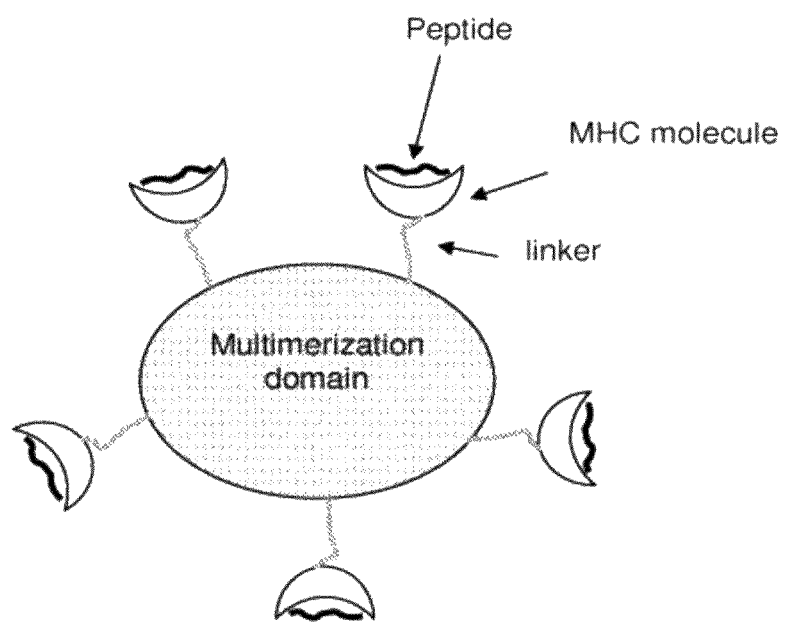
FIG. 1. Schematic representation of MHC multimer. A MHC multimer consist of a multimerization domain whereto one or more MHC-peptide complexes are attached through one or more linkers. The multimerization domain comprise one or more carriers and/or one or more scaffolds. The MHC-peptide complexes comprise a peptide and a MHC molecule.

The product of the present invention is a MHC multimer as described above. As used in the description of this invention, the term "MHC multimers" will be used interchangeably with the terms MHC'mers and MHCmers, and will include any number, (larger than one) of MHC-peptide complexes, held together in a large complex by covalent or non-covalent interactions between a multimerization domain and one or more MHC-peptide complexes, and will also include the monomeric form of the MHC-peptide complex, i.e. a MHC-peptide complex that is not attached to a multimerization domain. The multimerization domain consists of one or more carriers and/or one or more scaffolds while the MHC-peptide complex consists of MHC molecule and antigenic peptide. MHC-peptide complexes may be attached to the multimerization domain through one or more linkers. A schematic representation of a MHC multimer is presented in FIG. 1.

In one preferred embodiment the MHC multimer is between 50,000 Da and 1,000,000 Da, such as from 50,000 Da to 980,000; for example from 50,000 Da to 960,000; such as from 50,000 Da to 940,000; for example from 50,000 Da to 920,000; such as from 50,000 Da to 900,000; for example from 50,000 Da to 880,000; such as from 50,000 Da to 860,000; for example from 50,000 Da to 840,000; such as from 50,000 Da to 820,000; for example from 50,000 Da to 800,000; such as from 50,000 Da to 780,000; for example from 50,000 Da to 760,000; such as from 50,000 Da to 740,000; for example from 50,000 Da to 720,000; such as from 50,000 Da to 700,000; for example from 50,000 Da to 680,000; such as from 50,000 Da to 660,000; for example from 50,000 Da to 640,000; such as from 50,000 Da to 620,000; for example from 50,000 Da to 600,000; such as from 50,000 Da to 580,000; for example from 50,000 Da to 560,000; such as from 50,000 Da to 540,000; for example from 50,000 Da to 520,000; such as from 50,000 Da to 500,000; for example from 50,000 Da to 480,000; such as from 50,000 Da to 460,000; for example from 50,000 Da to 440,000; such as from 50,000 Da to 420,000; for example from 50,000 Da to 400,000; such as from 50,000 Da to 380,000; for example from 50,000 Da to 360,000; such as from 50,000 Da to 340,000; for example from 50,000 Da to 320,000; such as from 50,000 Da to 300,000; for example from 50,000 Da to 280,000; such as from 50,000 Da to 260,000; for example from 50,000 Da to 240,000; such as from 50,000 Da to 220,000; for example from 50,000 Da to 200,000; such as from 50,000 Da to 180,000; for example from 50,000 Da to 160,000; such as from 50,000 Da to 140,000; for example from 50,000 Da to 120,000; such as from 50,000 Da to 100,000; for example from 50,000 Da to 80,000; such as from 50,000 Da to 60,000; such as from 100,000 Da to 980,000; for example from 100,000 Da to 960,000; such as from 100,000 Da to 940,000; for example from 100,000 Da to 920,000; such as from 100,000 Da to 900,000; for example from 100,000 Da to 880,000; such as from 100,000 Da to 860,000; for example from 100,000 Da to 840,000; such as from 100,000 Da to 820,000; for example from 100,000 Da to 800,000; such as from 100,000 Da to 780,000; for example from 100,000 Da to 760,000; such as from 100,000 Da to 740,000; for example from 100,000 Da to 720,000; such as from 100,000 Da to 700,000; for example from 100,000 Da to 680,000; such as from 100,000 Da to 660,000; for example from 100,000 Da to 640,000; such as from 100,000 Da to 620,000; for example from 100,000 Da to 600,000; such as from 100,000 Da to 580,000; for example from 100,000 Da to 560,000; such as from 100,000 Da to 540,000; for example from 100,000 Da to 520,000; such as from 100,000 Da to 500,000; for example from 100,000 Da to 480,000; such as from 100,000 Da to 460,000; for example from 100,000 Da to 440,000; such as from 100,000 Da to 420,000; for example from 100,000 Da to 400,000; such as from 100,000 Da to 380,000; for example from 100,000 Da to 360,000; such as from 100,000 Da to 340,000; for example from 100,000 Da to 320,000; such as from 100,000 Da to 300,000; for example from 100,000 Da to 280,000; such as from 100,000 Da to 260,000; for example from 100,000 Da to 240,000; such as from 100,000 Da to 220,000; for example from 100,000 Da to 200,000; such as from 100,000 Da to 180,000; for example from 100,000 Da to 160,000; such as from 100,000 Da to 140,000; for example from 100,000 Da to 120,000; such as from 150,000 Da to 980,000; for example from 150,000 Da to 960,000; such as from 150,000 Da to 940,000; for example from 150,000 Da to 920,000; such as from 150,000 Da to 900,000; for example from 150,000 Da to 880,000; such as from 150,000 Da to 860,000; for example from 150,000 Da to 840,000; such as from 150,000 Da to 820,000; for example from 150,000 Da to 800,000; such as from 150,000 Da to 780,000; for example from 150,000 Da to 760,000; such as from 150,000 Da to 740,000; for example from 150,000 Da to 720,000; such as from 150,000 Da to 700,000; for example from 150,000 Da to 680,000; such as from 150,000 Da to 660,000; for example from 150,000 Da to 640,000; such as from 150,000 Da to 620,000; for example from 150,000 Da to 600,000; such as from 150,000 Da to 580,000; for example from 150,000 Da to 560,000; such as from 150,000 Da to 540,000; for example from 150,000 Da to 520,000; such as from 150,000 Da to 500,000; for example from 150,000 Da to 480,000; such as from 150,000 Da to 460,000; for example from 150,000 Da to 440,000; such as from 150,000 Da to 420,000; for example from 150,000 Da to 400,000; such as from 150,000 Da to 380,000; for example from 150,000 Da to 360,000; such as from 150,000 Da to 340,000; for example from 150,000 Da to 320,000; such as from 150,000 Da to 300,000; for example from 150,000 Da to 280,000; such as from 150,000 Da to 260,000; for example from 150,000 Da to 240,000; such as from 150,000 Da to 220,000; for example from 150,000 Da to 200,000; such as from 150,000 Da to 180,000; for example from 150,000 Da to 160,000.

In another preferred embodiment the MHC multimer is between 1,000,000 Da and 3,000,000 Da, such as from 1,000,000 Da to 2,800,000; for example from 1,000,000 Da to 2,600,000; such as from 1,000,000 Da to 2,400,000; for example from 1,000,000 Da to 2,200,000; such as from 1,000,000 Da to 2,000,000; for example from 1,000,000 Da to 1,800,000; such as from 1,000,000 Da to 1,600,000; for example from 1,000,000 Da to 1,400,000.

In the following it is described how to generate the product of the present invention.

Number of MHC Complexes pr Multimer

A non-exhaustive list of possible MHC mono- and multimers illustrates the possibilities.

n indicates the number of MHC complexes comprised in the multimer:

a) n=1, Monomers
b) n=2, Dimers, multimerization can be based on IgG scaffold, SA with two MHC's, coiled-coil dimerization e.g. Fos.Jun dimerization
c) n=3, Trimers, multimerization can be based on SA as scaffold with three MHC's, TNFalpha-MHC hybrids, triplex DNA-MHC conjugates or other trimer structures
d) n=4, Tetramers, multimerization can be based on SA with all four binding sites occupied by MHC molecules or on dimeric IgA
e) n=5, Pentamers, multimerization can take place around a pentameric coil-coil structure
f) n=6, Hexamers
g) n=7, Heptamers
h) n=8-12, Octa-dodecamers, multimerization can take place using Streptactin
i) n=10, Decamers, multimerization could take place using IgM
j) 1<n<100, Dextramers, as multimerization domain polymers such as polypeptide, polysaccharides and Dextrans can be used.
k) 1<n<1000, Multimerization make use of DC, APC, micelles, liposomes, beads, surfaces e.g. microtiterplate, tubes, microarray devices, micro-fluidic systems
l) 1<n, n in billions or trillions or higher, multimerization take place on beads, and surfaces e.g. microtiterplate, tubes, microarray devices, micro-fluidic systems MHC Origin Any of the three components of a MHC complex can be of any of the below mentioned origins. The list is non-exhaustive. A complete list would encompass all Chordate species. By origin is meant that the sequence is identical or highly homologous to a naturally occurring sequence of the specific species.

List of Origins:
   Human
   Mouse
   Primate
      Chimpansee
      Gorilla
      Orang Utan Monkey
  Macaques
Porcine (Swine/Pig)
Bovine (Cattle/Antilopes)
Equine (Horse)
Camelides (Camels)
Ruminants (Deears)
Canine (Dog)
Feline (Cat)
Bird
  Chicken
  Turkey
Fish
Reptiles
Amphibians Generation of MHC Multimers Different approaches to the generation of various types of MHC multimers are described in U.S. Pat. No. 5,635,363 (Altmann et al.), patent application WO 02/072631 A2 (Winther et al.), patent application WO 99/42597, US patent 2004209295, U.S. Pat. No. 5,635,363, and is described elsewhere in the present patent application as well. In brief, MHC multimers can be generated by first expressing and purifying the individual protein components of the MHC protein, and then combining the MHC protein components and the peptide, to form the MHC-peptide complex. Then an appropriate number of MHC-peptide complexes are linked together by covalent or non-covalent bonds to a multimerization domain. This can be done by chemical reactions between reactive groups of the multimerization domain (e.g. vinyl sulfone functionalities on a dextran polymer) and reactive groups on the MHC protein (e.g. amino groups on the protein surface), or by non-covalent interaction between a part of the MHC protein (e.g. a biotinylated peptide component) and the multimerization domain (e.g. four binding sites for biotin on the strepavidin tetrameric protein). As an alternative, the MHC multimer can be formed by the non-covalent association of amino acid helices fused to one component of the MHC protein, to form a pentameric MHC multimer, held together by five helices in a coiled-coil structure making up the multimerization domain.

Appropriate chemical reactions for the covalent coupling of MHC and the multimerization domain include nucleophilic substitution by activation of electrophiles (e.g. acylation such as amide formation, pyrazolone formation, isoxazolone formation; alkylation; vinylation; disulfide formation), addition to carbon-hetero multiple bonds (e.g. alkene formation by reaction of phosphonates with aldehydes or ketones; arylation; alkylation of arenes/hetarenes by reaction with alkyl boronates or enolethers), nucleophilic substitution using activation of nucleophiles (e.g. condensations; alkylation of aliphatic halides or tosylates with enolethers or enamines), and cycloadditions.

Appropriate molecules, capable of providing non covalent interactions between the multimerization domain and the MHC-peptide complex, involve the following molecule pairs and molecules: streptavidin/biotin, avidin/biotin, antibody/antigen, DNA/DNA, DNA/PNA, DNA/RNA, PNA/PNA, LNA/DNA, leucine zipper e.g. Fos/Jun, IgG dimeric protein, IgM multivalent protein, acid/base coiled-coil helices, chelate/metal ion-bound chelate, streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-transferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). Combinations of such binding entities are also comprised. In particular, when the MHC complex is tagged, the binding entity can be an "anti-tag". By "anti-tag" is meant an antibody binding to the tag and any other molecule capable of binding to such tag.

Generation of Components of MHC

When employing MHC multimers for diagnostic purposes, it is preferable to use a MHC allele that corresponds to the tissue type of the person or animal to be diagnosed. Once the MHC allele has been chosen, a peptide derived from the antigenic protein may be chosen. The choice will depend on factors such as known or expected binding affinity of the MHC protein and the various possible peptide fragments that may be derived from the full sequence of the antigenic peptide, and will depend on the expected or known binding affinity and specificity of the MHC-peptide complex for the TCR. Preferably, the affinity of the peptide for the MHC molecule, and the affinity and specificity of the MHC-peptide complex for the TCR, should be high.

Similar considerations apply to the choice of MHC allele and peptide for therapeutic and vaccine purposes. In addition, for some of these applications the effect of binding the MHC multimer to the TCR is also important. Thus, in these cases the effect on the T-cell's general state must be considered, e.g. it must be decided whether the desired end result is apoptosis or proliferation of the T-cell.

Likewise, it must be decided whether stability is important. For some applications low stability may be an advantage, e.g. when a short-term effect is desired; in other instances, a long-term effect is desired and MHC multimers of high stability is desired. Stabilities of the MHC protein and of the MHC-peptide complex may be modified as described elsewhere herein.

Finally, modifications to the protein structure may be advantageous for some diagnostics purposes, because of e.g. increased stability, while in for vaccine purposes modifications to the MHC protein structure may induce undesired allergenic responses.

Generation of Protein Chains of MHC

Generation of MHC Class I Heavy Chain and β2-Microglobulin

MHC class I heavy chain (HC) and β2-mircroglobulin (β2m) can be obtained from a variety of sources.

a) Natural sources by means of purification from eukaryotic cells naturally expressing the MHC class 1 or β2m molecules in question.
b) The molecules can be obtained by recombinant means e.g. using.
   a. in vitro translation of mRNA obtained from cells naturally expressing the MHC or β2m molecules in question
   b. by expression and purification of HC and/or β2m gene transfected cells of mammalian, yeast, bacterial or other origin. This last method will normally be the method of choice. The genetic material used for transfection/transformation can be:

i. of natural origin isolated from cells, tissue or organisms
ii. of synthetical origin i.e. synthetic genes identical to the natural DNA sequence or it could be modified to introduce molecular changes or to ease recombinant expression.

The genetic material can encode all or only a fragment of β2m, all or only a fragment of MHC class 1 heavy chain. Of special interest are MHC class 1 heavy chain fragments consisting of, the complete chain minus the intramembrane domain, a chain consisting of only the extracellular α1 and α2 class 1 heavy chain domains, or any of the mentioned β2m and heavy chain fragments containing modified or added designer domain(s) or sequence(s).

Generation of MHC Class 2 α- and β-Chains

MHC class 2 α- and β-chains can be obtained from a variety of sources:

a) Natural sources by means of purification from eukaryotic cells naturally expressing the MHC class 2 molecules in question.
b) By recombinant means e.g. using:
  a. in vitro translation of mRNA obtained from cells naturally expressing the MHC class 2 molecules in question
  b. By purification from MHC class 2 gene transfected cells of mammalian, yeast, bacterial or other origin. This last method will normally be the method of choice. The genetic material used for transfection/transformation can be
    i. of natural origin isolated from cells, tissue or organisms
    ii. of synthetical origin i.e. synthetic genes identical to the natural DNA sequence or it could be modified to introduce molecular changes or to ease recombinant expression.

The genetic material can encode all or only a fragment of MHC class 2 α- and β-chains. Of special interest are MHC class 2 α- and β-chain fragments consisting of, the complete α- and β-chains minus the intramembrane domains of either or both chains; and α- and β-chains consisting of only the extracellular domains of either or both, i.e α1 plus α2 and β1 plus β2 domains, respectively.

The genetic material can be modified to encode the interesting MHC class 2 molecule fragments consisting of domains starting from the amino terminal in consecutive order, MHC class 2 β1 plus MHC class 2 α1 plus MHC class 1 α3 domains or in alternative order, MHC class 2 α1 plus MHC class 2 β1 plus MHC class 1 α3 domains.

Lastly, the genetic material can encode any of the above mentioned MHC class 2 α- and β-chain molecules or fragments containing modified or added designer domain(s) or sequence(s).

c) The MHC material may also be of exclusively synthetic origin manufactured by solid phase protein synthesis. Any of the above mentioned molecules can be made this way.

Modified MHC I or MHC II Complexes

MHC I and MHC II complexes modified in any way as described above, can bind TCR. Modifications include mutations (substitutions, deletions or insertions of natural or non-natural amino acids, or any other organic molecule. The mutations are not limited to those that increase the stability of the MHC complex, and could be introduced anywhere in the MHC complex. One example of special interest is mutations introduced in the α3 subunit of MHC I heavy chain. The α3-subunit interacts with CD8 molecules on the surface of T cells. To minimize binding of MHC multimer to CD8 molecules on the surface of non-specific T cells, amino acids in α3 domain involved in the interaction with CD8 can be mutated. Such a mutation can result in altered or abrogated binding of MHC to CD8 molecules. Another example of special interest is mutations in areas of the β2-domain of MHC II molecules responsible for binding CD4 molecules.

Another embodiment is chemically modified MHC complexes where the chemical modification could be introduced anywhere in the complex, e.g. a MHC complex where the peptide in the peptide-binding cleft has a dinitrophenyl group attached.

Modified MHC complexes could also be MHC I or MHC II fusion proteins where the fusion protein is not necessarily more stable than the native protein. Of special interest is MHC complexes fused with genes encoding an amino acid sequence capable of being biotinylated with a Bir A enzyme (Schatz, P. J., (1993), Biotechnology 11(10):1138-1143). This biotinylation sequence could be fused with the COOH-terminal of β2m or the heavy chain of MHC I molecules or the COOH-terminal of either the α-chain or β-chain of MHC II. Similarly, other sequences capable of being enzymatically or chemically modified, can be fused to the $NH_2$ or COOH-terminal ends of the MHC complex.

Stabilization of Empty MHC Complexes and MHC-Peptide Complexes.

Classical MHC complexes are in nature embedded in the membrane. A preferred embodiment includes multimers comprising a soluble form of MHC II or I where the transmembrane and cytosolic domains of the membrane-anchored MHC complexes are removed. The removal of the membrane-anchoring parts of the molecules can influence the stability of the MHC complexes. The stability of MHC complexes is an important parameter when generating and using MHC multimers.

MHC I complexes consist of a single membrane-anchored heavy chain that contains the complete peptide binding groove and is stable in the soluble form when complexed with β2m. The long-term stability is dependent on the binding of peptide in the peptide-binding groove. Without a peptide in the peptide binding groove the heavy chain and β2m tend to dissociate. Similarly, peptides with high affinity for binding in the peptide-binding groove will typically stabilize the soluble form of the MHC complex while peptides with low affinity for the peptide-binding groove will typically have a smaller stabilizing effect.

In contrast, MHC II complexes consist of two membrane-anchored chains of almost equal size. When not attached to the cell membrane the two chains tend to dissociate and are therefore not stable in the soluble form unless a high affinity peptide is bound in the peptide-binding groove or the two chains are held together in another way.

In nature MHC I molecules consist of a heavy chain combined with β2m, and a peptide of typically 8-11 amino acids. Herein, MHC I molecules also include molecules consisting of a heavy chain and β2m (empty MHC), or a heavy chain combined with a peptide or a truncated heavy chain comprising α1 and α2 subunits combined with a peptide, or a full-length or truncated heavy chain combined with a full-length or truncated β2m chain. These MHC I molecules can be produced in *E. coli* as recombinant proteins, purified and refolded in vitro (Garboczi et al., (1992), Proc. Natl. Acad. Sci. 89, 3429-33). Alternatively, insect cell systems or mammalian cell systems can be used. To produce stable MHC I complexes and thereby generate reliable MHC I multimers several strategies can be followed. Stabilization strategies for MHC I complexes are described in the following.

Stabilization Strategies for MHC I Complexes
  Generation of Covalent Protein-Fusions.
    MHC I molecules can be stabilized by introduction of one or more linkers between the individual components of the MHC I complex. This could be a complex consisting of a heavy chain fused with β2m through a linker and a soluble peptide, a heavy chain fused to β2m through a linker, a heavy chain/β2m dimer covalently linked to a peptide through a linker to either heavy chain or β2m, and where there can or can not be a linker between the heavy chain and β2m, a heavy chain fused to a peptide through a linker, or the α1 and α2 subunits of the heavy chain fused to a peptide through a linker. In all of these example protein-fusions, each of the heavy chain, β2m and the peptide can be truncated.
    The linker could be a flexible linker, e.g. made of glycine and serine and e.g. between 5-20 residues long. The linker could also be rigid with a defined structure, e.g. made of amino acids like glutamate, alanine, lysine, and leucine creating e.g. a more rigid structure.
    In heavy chain-β2m fusion proteins the COOH terminus of β2m can be covalently linked to the NH$_2$ terminus of the heavy chain, or the NH$_2$ terminus of β2m can be linked to the COOH terminus of the heavy chain. The fusion-protein can also comprise a β2m domain, or a truncated β2m domain, inserted into the heavy chain, to form a fusion-protein of the form "heavy chain (first part)-β2m-heavy chain (last part)".
    Likewise, the fusion-protein can comprise a heavy chain domain, or a truncated heavy chain, inserted into the β2m chain, to form a fusion-protein of the form "β2m (first part)-heavy chain-β2m(last part)".
    In peptide-β2m fusion proteins the COOH terminus of the peptide is preferable linked to the NH$_2$ terminus of β2m but the peptide can also be linked to the COOH terminal of β2m via its NH$_2$ terminus. In heavy chain-peptide fusion proteins it is preferred to fuse the NH$_2$ terminus of the heavy chain to the COOH terminus of the peptide, but the fusion can also be between the COOH terminus of the heavy chain and the NH$_2$ terminus of the peptide. In heavy chain-β2m-peptide fusion proteins the NH$_2$ terminus of the heavy chain can be fused to the COOH terminus of β2m and the NH$_2$ terminus of β2m can be fused to the COOH terminus of the peptide.
  Non-Covalent Stabilization by Binding to an Unnatural Component
    Non-covalent binding of unnatural components to the MHC I complexes can lead to increased stability. The unnatural component can bind to both the heavy chain and the β2m, and in this way promote the assemble of the complex, and/or stabilize the formed complex. Alternatively, the unnatural component can bind to either β2m or heavy chain, and in this way stabilize the polypeptide in its correct conformation, and in this way increase the affinity of the heavy chain for β2m and/or peptide, or increase the affinity of β2m for peptide.
    Here, unnatural components mean antibodies, peptides, aptamers or any other molecule with the ability to bind peptides stretches of the MHC complex. Antibody is here to be understood as truncated or full-length antibodies (of isotype IgG, IgM, IgA, IgE), Fab, scFv or bi-Fab fragments or diabodies.
    An example of special interest is an antibody binding the MHC I molecule by interaction with the heavy chain as well as β2m. The antibody can be a bispecific antibody that binds with one arm to the heavy chain and the other arm to the β2m of the MHC complex. Alternatively the antibody can be monospecific, and bind at the interface between heavy chain and β2m.
    Another example of special interest is an antibody binding the heavy chain but only when the heavy chain is correct folded. Correct folded is here a conformation where the MHC complex is able to bind and present peptide in such a way that a restricted T cell can recognize the MHC-peptide complex and be activated. This type of antibody can be an antibody like the one produced by the clone W6/32 (M0736 from Dako, Denmark) that recognizes a conformational epitope on intact human and some monkey MHC complexes containing β2m, heavy chain and peptide.
  Generation of Modified Proteins or Protein Components
    One way to improve stability of a MHC I complex am to increase the affinity of the binding peptide for the MHC complex. This can be done by mutation/substitution of amino acids at relevant positions in the peptide, by chemical modifications of amino acids at relevant positions in the peptide or introduction by synthesis of non-natural amino acids at relevant positions in the peptide. Alternatively, mutations, chemical modifications, insertion of natural or non-natural amino acids or deletions could be introduced in the peptide binding cleft, i.e. in the binding pockets that accommodate peptide side chains responsible for anchoring the peptide to the peptide binding cleft. Moreover, reactive groups can be introduced into the antigenic peptide; before, during or upon binding of the peptide, the reactive groups can react with amino acid residues of the peptide binding cleft, thus covalently linking the peptide to the binding pocket.
    Mutations/substitutions, chemical modifications, insertion of natural or non-natural amino acids or deletions could also be introduced in the heavy chain and/or β2m at positions outside the peptide-binding cleft. By example, it has been shown that substitution of XX with YY in position nn of human β$_2$m enhance the biochemical stability of MHC Class I molecule complexes and thus may lead to more efficient antigen presentation of subdominant peptide epitopes.
    A preferred embodiment is removal of "unwanted cysteine residues" in the heavy chain by mutation, chemical modification, amino acid exchange or deletion. "Unwanted cysteine residues" is here to be understood as cysteines not involved in the correct folding of the final MHC I molecule. The presence of cysteine not directly involved in the formation of correctly folded MHC I molecules can lead to formation of intra molecular disulfide bridges resulting in a non correct folded MHC complex during in vitro refolding.
    Another method for covalent stabilization of MHC I complex am to covalently attach a linker between two of the subunits of the MHC complex. This can be a linker between peptide and heavy chain or between heavy chain and beta2microglobulin.
Stabilization with Soluble Additives.
  The stability of proteins in aqueous solution depends on the composition of the solution. Addition of salts, detergents organic solvent, polymers etc. can influence the stability. Of special interest are additives that increase surface tension of the MHC molecule without binding the molecule. Examples are sucrose, mannose, glycine, betaine, alanine, glutamine, glutamic acid and ammoniumsulfate. Glycerol, mannitol and sorbitol are also included in this group even though they are able to bind polar regions.

Another group of additives of special interest are able to increase surface tension of the MHC molecule and simultaneously interact with charged groups in the protein. Examples are $MgSO_4$, NaCl, polyethylenglycol, 2-methyl-2,4-pentandiol and guanidiniumsulfate.

Correct folding of MHC I complexes is very dependent on binding of peptide in the peptide-binding cleft and the peptide binding stabilises correct conformation. Addition of molar excess of peptide will force the equilibrium against correct folded MHC-peptide complexes. Likewise is excess β2m also expected to drive the folding process in direction of correct folded MHC I complexes. Therefore peptide identical to the peptide bound in the peptide-binding cleft and β2m are included as stabilizing soluble additives.

Other additives of special interest for stabilization of MHC I molecules are BSA, fetal and bovine calf serum or individual protein components in serum with a protein stabilizing effect.

All of the above mentioned soluble additives could be added to any solution containing MHC I molecules in order to increase the stability of the molecule. That could be during the refolding process, to the soluble monomer or to a solutions containing MHC I bound to a carrier.

MHC II molecules as used herein are defined as classical MHC II molecule consisting of a α-chain and a β-chain combined with a peptide. It could also be a molecule only consisting of α-chain and β-chain (α/β dimer or empty MHC II), a truncated α-chain (e.g. α1 domain alone) combined with full-length β-chain either empty or loaded with a peptide, a truncated β-chain (e.g. β1 domain alone) combined with a full-length α-chain either empty or loaded with a peptide or a truncated α-chain combined with a truncated β-chain (e.g. α1 and β1 domain) either empty or loaded with a peptide.

In contrast to MHC I molecules MHC II molecules are not easily refolded in vitro. Only some MHC II alleles may be produced in *E. coli* followed by refolding in vitro.

Therefore preferred expression systems for production of MHC II molecules are eukaryotic systems where refolding after expression of protein is not necessary. Such expression systems could be stable *Drosophila* cell transfectants, baculovirus infected insect cells, CHO cells or other mammalian cell lines suitable for expression of proteins.

Stabilization of soluble MHC II molecules is even more important than for MHC I molecules since both α- and β-chain are participants in formation of the peptide binding groove and tend to dissociate when not embedded in the cell membrane.

Stabilization Strategies for MHC II Complexes
  Generation of Covalent Protein-Fusions.
    MHC II complexes can be stabilized by introduction of one or more linkers between the individual components of the MHC II complex. This can be a α/β dimer with a linker between α-chain and β-chain; a α/β dimer covalently linked to the peptide via a linker to either the α-chain or β-chain; a α/β dimer, covalently linked by a linker between the α-chain and β-chain, and where the dimer is covalently linked to the peptide; a α/β dimer with a linker between α-chain and β-chain, where the dimer is combined with a peptide covalently linked to either α-chain or β-chain.

The linker can be a flexible linker, e.g. made of glycine and serine, and is typically between 5-20 residues long, but can be shorter or longer. The linker can also be more rigid with a more defined structure, e.g. made of amino acids like glutamate, alanine, lysine, and leucine.

The peptides can be linked to the $NH_2$- or COOH-terminus of either α-chain or β-chain. Of special interest are peptides linked to the $NH_2$-terminus of the β-chain via their COOH-terminus, since the linker required is shorter than if the peptide is linked to the COOH-terminus of the β-chain.

Linkage of α-chain to β-chain can be via the COOH-terminus of the β-chain to the $NH_2$-terminus of the α-chain or from the COOH-terminus of the α-chain to the $NH_2$-terminus of the β-chain.

In a three-molecule fusion protein consisting of α-chain, β-chain and peptide a preferred construct is where one linker connect the COOH-terminus of the β-chain with the $NH_2$-terminus of the α-chain and another linker connects the COOH-terminal of the peptide with the $NH_2$-terminal of the β-chain. Alternatively one linker joins the COOH-terminus of the α-chain with the $NH_2$-terminus of the β-chain and the second linker joins the $NH_2$-terminus of the peptide with the COOH-terminus of the β-chain. The three peptides of the MHC complex can further be linked as described above for the three peptides of the MHC complex, including internal fusion points for the proteins.

Non-Covalent Stabilization by Binding Ligand.
Non-covalent binding of ligands to the MHC II complex can promote assembly of α- and β-chain by bridging the two chains, or by binding to either of the α- or β-chains, and in this way stabilize the conformation of α or β, that binds β or α, respectively, and/or that binds the peptide. Ligands here mean antibodies, peptides, aptamers or any other molecules with the ability to bind proteins.

A particular interesting example is an antibody binding the MHC complex distal to the interaction site with TCR, i.e. distal to the peptide-binding cleft. An antibody in this example can be any truncated or full length antibody of any isotype (e.g. IgG, IgM, IgA or IgE), a bi-Fab fragment or a diabody. The antibody could be bispecific with one arm binding to the α-chain and the other arm binding to the β-chain. Alternatively the antibody could be monospecific and directed to a sequence fused to the α-chain as well as to the β-chain.

Another example of interest is an antibody binding more central in the MHC II molecule, but still interacting with both α- and β-chain. Preferable the antibody binds a conformational epitope, thereby forcing the MHC molecule into a correct folded configuration. The antibody can be bispecific binding with one arm to the α-chain and the other arm to the β-chain. Alternatively the antibody is monospecific and binds to a surface of the complex that involves both the α- and β-chain, e.g. both the α2- and β2-domain or both the α1- and β1-domain.

The antibodies described above can be substituted with any other ligand that binds at the α-/β-chain interface, e.g. peptides and aptamers. The ligand can also bind the peptide, although, in this case it is important that the ligand does not interfere with the interaction of the peptide or binding cleft with the TCR.

Non-Covalent Stabilization by Induced Multimerization.

In nature the anchoring of the α- and β-chains in the cell membrane stabilizes the MHC II complexes considerably. As mentioned above, a similar concept for stabilization of the α/β-dimer was employed by attachment of the MHC II chains to the Fc regions of an antibody, leading to a stable α/β-dimer, where α and β are held together by the tight interactions between two Fc domains of an antibody. Other dimerization domains can be used as well.

In one other example of special interest MHC II molecules are incorporated into artificial membrane spheres like liposomes or lipospheres. MHC II molecules can be incorporated as monomers in the membrane or as dimers like the MHC II-antibody constructs describes above. In addition to stabilization of the MHC II complex an increased avidity is obtained. The stabilization of the dimer will in most cases also stabilize the trimeric MHC-peptide complex.

Induced multimerization can also be achieved by biotinylation of α- as well as β-chain and the two chains brought together by binding to streptavidin. Long flexible linkers such as extended glycine-serine tracts can be used to extend both chains, and the chains can be biotinylated at the end of such extended linkers. Then streptavidin can be used as a scaffold to bring the chains together in the presence of the peptide, while the flexible linkers still allow the chains to orientate properly.

Generation of Modified Proteins or Protein Components

Stability of MHC II complexes can be increased by covalent modifications of the protein. One method is to increase the affinity of the peptide for the MHC complex. This can be done by exchange of the natural amino acids with other natural or non-natural amino acids at relevant positions in the peptide or by chemical modifications of amino acids at relevant positions in the peptide. Alternatively, mutations, chemical modifications, insertion of natural or non-natural amino acids or deletions can be introduced in the peptide-binding cleft.

Mutations, chemical modifications, insertion of natural or non-natural amino acids or deletions can alternatively be introduced in α- and/or β-chain at positions outside the peptide-binding cleft.

In this respect a preferred embodiment is to replace the hydrophobic transmembrane regions of α-chain and β-chain by leucine zipper dimerisation domains (e.g. Fos-Jun leucine zipper; acid-base coiled-coil structure) to promote assembly of α-chain and β-chain.

Another preferred embodiment is to introduce one or more cysteine residues by amino acid exchange at the COOH-terminal of both α-chain and β-chain, to create disulfide bridges between the two chains upon assembly of the MHC complex.

Another embodiment is removal of "unwanted cysteine residues" in either of the chains by mutation, chemical modification, amino acid exchange or deletion. "Unwanted cysteine residues" is here to be understood as cysteines not involved in correct folding of the MHC II-peptide complex. The presence of cysteines not directly involved in the formation of correctly folded MHC II complexes can lead to formation of intra molecular disulfide bridges and incorrectly folded MHC complexes.

MHC II complexes can also be stabilized by chemically linking together the subunits and the peptide. That can be a linker between peptide and α-chain, between peptide and β-chain, between α-chain and β-chain, and combination thereof.

Such linkages can be introduced prior to folding by linking two of the complex constituents together, then folding this covalent hetero-dimer in the presence of the third constituent. An advantage of this method is that it only requires complex formation between two, rather than three species.

Another possibility is to allow all three constituents to fold, and then to introduce covalent cross-links on the folded MHC-complex, stabilizing the structure. An advantage of this method is that the two chains and the peptide will be correctly positioned relatively to each other when the cross linkages are introduced.

Stabilization with Soluble Additives.

Salts, detergents, organic solvent, polymers and any other soluble additives can be added to increase the stability of MHC complexes. Of special interest are additives that increase surface tension of the MHC complex. Examples are sucrose, mannose, glycine, betaine, alanine, glutamine, glutamic acid and ammonium sulfate. Glycerol, mannitol and sorbitol are also included in this group even though they are able to bind polar regions.

Another group of additives of special interest increases surface tension of the MHC complex and simultaneously can interact with charged groups in the protein. Examples are $MgSO_4$, NaCl, polyethylenglycol, 2-methyl-2,4-pentanediol and guanidiniumsulphate.

Correct formation of MHC complexes is dependent on binding of peptide in the peptide-binding cleft; the bound peptide appears to stabilize the complex in its correct conformation. Addition of molar excess of peptide will force the equilibrium towards correctly folded MHC-peptide complexes. Likewise, excess β2m is also expected to drive the folding process in direction of correctly folded MHC complexes. Therefore peptide identical to the peptide bound in the peptide-binding cleft and β2m can be included as stabilizing soluble additives.

Other additives of special interest for stabilization of MHC complexes are BSA, fetal and bovine calf serum, and other protein components in serum with a protein stabilizing effect.

All of the above mentioned soluble additives could be added to any solution containing MHC complexes in order to increase the stability of the molecule. This can be during the refolding process, to the formed MHC complex or to a solution of MHC multimers comprising several MHC complexes That could be to the soluble monomer, to a solution containing MHC II bound to a carrier or to solutions used during analysis of MHC II specific T cells with MHC II multimers.

Other additives of special interest for stabilization of MHC II molecules are BSA, fetal and bovine calf serum or individual protein components in serum with a protein stabilizing effect.

All of the above mentioned soluble additives could be added to any solution containing MHC II molecules in order to increase the stability of the molecule. That could be to the soluble monomer, to a solution containing MHC II bound to a carrier or to solutions used during analysis of MHC II specific T cells with MHC II multimers.

Chemically Modified MHC I and II Complexes

There are a number of amino acids that are particularly reactive towards chemical cross linkers. In the following, chemical reactions are described that are particularly preferable for the cross-linking or modification of MHC I or MHC II complexes.

The amino group at the N-terminal of both chains and of the peptide, as well as amino groups of lysine side chains, are nucleophilic and can be used in a number of chemical reactions, including nucleophilic substitution by activation of electrophiles (e.g. acylation such as amide formation, pyrazolone formation, isoxazolone formation; alkylation; vinylation; disulfide formation), addition to carbon-hetero multiple bonds (e.g. alkene formation by reaction of phosphonates with aldehydes or ketones; arylation; alkylation of arenes/hetarenes by reaction with alkyl boronates or enolethers), nucleophilic substitution using activation of nucleophiles (e.g. condensations; alkylation of aliphatic halides or tosylates with enolethers or enamines), and cycloadditions. Example reagents that can be used in a reaction with the amino groups are activated carboxylic acids such as NHS-ester, tetra and pentafluoro phenolic esters, anhydrides, acid chlorides and fluorides, to form stable amide bonds. Likewise, sulphonyl chlorides can react with these amino groups to form stable sulphoneamides. Iso-Cyanates can also react with amino groups to form stable ureas, and isothiocyanates can be used to introduce thio-urea linkages.

Aldehydes, such as formaldehyde and glutardialdehyde will react with amino groups to form shiff's bases, than can be further reduced to secondary amines.

The guanidino group on the side chain of arginine will undergo similar reactions with the same type of reagents.

Another very useful amino acid is cysteine. The thiol on the side chain is readily alkylated by maleimides, vinyl sulphones and halides to form stable thioethers, and reaction with other thiols will give rise to disulphides.

Carboxylic acids at the C-terminal of both chains and peptide, as well as on the side chains of glutamic and aspartic acid, can also be used to introduce cross-links. They will require activation with reagents such as carbodiimides, and can then react with amino groups to give stable amides.

Thus, a large number of chemistries can be employed to form covalent cross-links. The crucial point is that the chemical reagents are bi-functional, being capable of reacting with two amino acid residues.

They can be either homo bi-functional, possessing two identical reactive moieties, such as glutardialdehyde or can be hetero bi-functional with two different reactive moieties, such as GMBS (MaleimidoButyryloxy-Succinimide ester).

Alternatively, two or more reagents can be used; i.e. GMBS can be used to introduce maleimides on the α-chain, and iminothiolane can be used to introduce thiols on the β-chain; the malemide and thiol can then form a thioether link between the two chains. For the present invention some types of cross-links are particularly useful. The folded MHC-complex can be reacted with dextrans possessing a large number (up to many hundreds) of vinyl sulphones. These can react with lysine residues on both the α and β chains as well as with lysine residues on the peptide protruding from the binding site, effectively cross linking the entire MHC-complex. Such cross linking is indeed a favored reaction because as the first lysine residue reacts with the dextran, the MHC-complex becomes anchored to the dextran favoring further reactions between the MHC complex and the dextran multimerization domain. Another great advantage of this dextran chemistry is that it can be combined with fluorochrome labelling; i.e. the dextran is reacted both with one or several MHC-complexes and one or more fluorescent protein such as APC.

Another valuable approach is to combine the molecular biological tools described above with chemical cross linkers. As an example, one or more lysine residues can be inserted into the α-chain, juxtaposed with glutamic acids in the β-chain, where after the introduced amino groups and carboxylic acids are reacted by addition of carbodiimide. Such reactions are usually not very effective in water, unless as in this case, the groups are well positioned towards reaction. This implies that one avoids excessive reactions that could otherwise end up denaturing or changing the conformation of the MHC-complex.

Likewise a dextran multimerization domain can be cross-linked with appropriately modified MHC-complexes; i.e. one or both chains of the MHC complex can be enriched with lysine residues, increasing reactivity towards the vinylsulphone dextran. The lysine's can be inserted at positions opposite the peptide binding cleft, orienting the MHC-complexes favorably for T-cell recognition.

Another valuable chemical tool is to use extended and flexible cross-linkers. An extended linker will allow the two chains to interact with little or no strain resulting from the linker that connects them, while keeping the chains in the vicinity of each other should the complex dissociate. An excess of peptide should further favor reformation of dissociated MHC-complex.

Other TCR Binding Molecules

MHC I and MHC II complexes bind to TCRs. However, other molecules also bind TCR. Some TCR-biding molecules are described in the following. MHC I and MHC II complexes binding to TCRs may be substituted with other molecules capable of binding TCR or molecules that have homology to the classical MHC molecules and therefore potentially could be TCR binding molecules. These other TCR binding or MHC like molecules include:

Non-Classical MHC Complexes and Other MHC-Like Molecules:

Non-classical MHC complexes include protein products of MHC Ib and MHC IIb genes. MHC Ib genes encode β2m-associated cell-surface molecules but show little polymorphism in contrast to classical MHC class I genes. Protein products of MHC class Ib genes include HLA-E, HLA-G, HLA-F, HLA-H, MIC A, MIC B, ULBP-1, ULBP-2, ULBP-3 in humans and H2-M, H2-Q, H2-T and Rae1 in mice.

Non-classical MHC II molecules (protein products of MHC IIb genes) include HLA-DM, HLA-DO in humans and H2-DM and H2-DO in mice that are involved in regulation of peptide loading into MHC II molecules.

Another MHC-like molecule of special interest is the MHC I-like molecule CD1. CD1 is similar to MHC I molecules in its organization of subunits and association with β2m but presents glycolipids and lipids instead of peptides.

Artificial Molecules Capable of Binding Specific TCRs

Of special interest are antibodies that bind TCRs. Antibodies herein include full length antibodies of isotype IgG, IgM, IgE, IgA and truncated versions of these, antibody fragments like Fab fragments and scFv. Antibodies also include antibodies of antibody fragments displayed on various supramolecular structures or solid supports, including filamentous phages, yeast, mammalian cells, fungi, artificial cells or micelles, and beads with various surface chemistries.

Peptide Binding TCR

Another embodiment of special interest is peptides that bind TCRs. Peptides herein include peptides composed of natural, non-natural and/or chemically modified amino acids with a length of 8-20 amino acid. The peptides could also be longer than 20 amino acids or shorter than 8 amino acids. The peptides can or can not have a defined tertiary structure.

Aptamers

Aptamers are another preferred group of TCR ligands. Aptamers are herein understood as natural nucleic acids (e.g. RNA and DNA) or unnatural nucleic acids (e.g. PNA, LNA, morpholinos) capable of binding TCR. The aptamer molecules consist of natural or modified nucleotides in various lengths.

Other TCR-binding molecules can be ankyrin repeat proteins or other repeat proteins, Avimers, or small chemical molecules, as long as they are capable of binding TCR with a dissociation constant smaller than $10^{-3}$ M.

Generation of Antigenic Peptide

Approaches and Methods for the Identification and Design of Appropriate Peptides MHC class 1 molecules normally binds octa-, nona-, deca- or ondecamer (8-, 9-, 10, -11-mer) peptides in their peptide binding groove. The individual MHC class 1 alleles have individual preferences for the peptide length within the given range. MHC class 2 molecules bind peptides most often with a total length of 13-18 amino acids around a 9-mer core motif containing the important amino acid anchor residues. However the total length is not strictly defined as for most MHC class 1 molecules.

For some of the MHC alleles the optimal peptide length is known and also the demands for specific amino acid residues in the so called anchor positions.

To identify binding peptides derived from a specific protein for a given MHC allele it is necessary to systematically work through the amino acid sequence of the protein to identify the putative binding peptides. Although a given peptide is a binder it is not necessarily a functional T-cell epitope. Functionality needs to be confirmed by a functional analysis e.g. ELISPOT, CTL killing assay or flow cytometry assay.

A measure for binding affinity of the peptide to the MHC molecules can for some MHC molecules be found in databases such as www.syfpeithi.de; www-bimas.cit.nih.gov/molbio/hla_bind/; www.cbs.dtu.dk/services/NetMHC/; www.cbs.dtu.dk/services/NetMHCII/.

Design of Binding Peptides a) From Genomic DNA Sequences without Introns

When only the genomic DNA sequences are known and thereby reading frame and direction of transcription of the genes are unknown, the DNA sequence needs to be translated in all three reading frames in both directions leading to a total of six amino acid sequences for a given genome. From these amino acid sequences binding peptides can then be identified.

b) From Genomic DNA Sequences with Introns

In organisms having intron/exon gene structure the present approach will not be able to identify peptide sequence motifs that are derived by combination of amino acid sequences derived partly from two separate introns.

c) From cDNA Sequences cDNA sequences can be translated into the actual amino acid sequences to allow peptide identification.

d) From Known Amino Acid Sequences

In the case of known protein sequences these can directly be applied to software analysis for prediction of peptide epitopes.

Binding peptide sequences can be predicted from any protein sequence by either a total approach generating binding peptide sequences for potentially any MHC allele or by a directed approach using software that specifically can predict the binding peptide sequences for a subset of MHC alleles for which the binding characteristics of the peptide is known.

Design of MHC Class 1 Binding Peptide Sequence a) Total Approach

The MHC class 1 binding peptide prediction is done as follows using the total approach. The actual protein sequence is split up into 8-, 9-, 10-, and 11-mer peptide sequences. This is performed by starting at amino acid position 1 identifying the first 8-mer; then move the start position by one amino acid identifying the second 8-mer; then move the start position by one amino acid, identifying the third 8-mer. This procedure continues by moving start position by one amino acid for each round of peptide identification. Generated peptides will be amino acid position 1-8, 2-9, 3-10 etc. All peptides carrying one or more stop codons are omitted for further consideration. This procedure can be carried out manually or by means of a software program (FIG. 2). This procedure is then repeated in an identical fashion for 9-, 10 and 11-mers, respectively.

b) Directed Approach

Using a directed approach is only possible when working on prediction of peptide sequences binding to MHC class I alleles with known binding preferences. Examples of such programs are www.syfpeithi.de; www.imtech.res.in/raghava/propred1/index.html; www.cbs.dtu.dk/services/NetMHC/. Identified peptides can then be tested for biological relevance in functional assays such as Cytokine release assays, ELISPOT and CTL killing assays.

Prediction of good HLA class 1 peptide binders can be done at the HLA superfamily level even taking the combined action of endocolic and membrane bound protease activities as well as the TAP1 and TAP2 transporter specificities into consideration using the program www.cbs.dtu.dk/services/NetCTL/.

Design of MHC Class 2 Binding Peptide Sequence.

a) Total Approach and b) Directed Approach

The approach to predict putative peptide binders for MHC class 2 is similar as given above for MHC class 1 binding peptide prediction. The only change is the different size of the peptides, which is preferably 13-16 amino acids long for MHC class 2. The putative binding peptide sequences only describe the central part of the peptide including the 9-mer core peptide; in other words, the peptide sequences shown represent the core of the binding peptide with a few important flanking amino acids, which in some cases may be of considerably length generating binding peptides longer than the 13-16 amino acids.

Choice of MHC Allele

Figure 4:
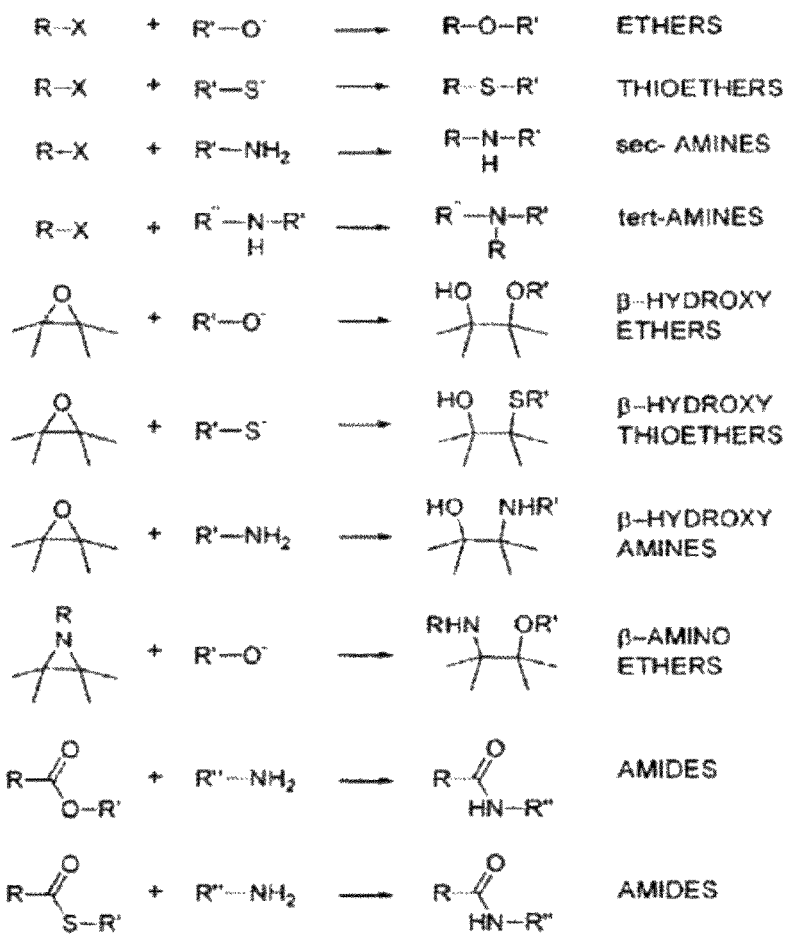
FIG. 4. List of top 30 HLA class 1 alleles in different human ethnic groups.

More than 600 MHC alleles (class 1 and 2) are known in humans; for many of these, the peptide binding characteristics are known. FIG. 3 presents an updated list of the HLA class 1 alleles. The frequency of the different HLA alleles varies considerably, also between different ethnic groups (FIG. 4). Thus it is of outmost importance to carefully select the MHC alleles that corresponds to the human group that one wish to study.

Peptide Modifications
Homologous Peptides

Predictions of the primary amino acid sequence for the binding peptides of MHC class I and class II molecules can be done as described above on the basis of the genetic information. Peptides homologous to the predicted peptide sequences may also be bound if they are sufficiently homologous i.e. are having an amino acid sequence identity greater than e.g. more than 90%, more than 80% or more than 70%. Identity being most important for the anchor residues.

Homologues MHC peptide sequences may arise from the existence of multiple strongly homologous alleles, from small insertions, deletions, inversions or substitutions.

Uncommon Amino Acids

Peptides having un-common amino acids may be bound in the MHC groove as well. Two un-common amino acids found in nature are selenocysteine and pyrrolysine.

Artificial Amino Acids

Artificial amino acids e.g. having the isomeric D-form may also make up isomeric D-peptides that can bind in the binding groove of the MHC molecules.

Chemically Modified Amino Acids

Bound peptides may also contain amino acids that are chemically modified or being linked to reactive groups that can be activated to induce changes in or disrupt the peptide.

Split or Combinatorial Peptide

A MHC binding peptide may also be of split- or combinatorial epitope origin i.e. formed by linkage of peptide fragments derived from two different peptide fragments and/or proteins. Such peptides can be the result of either genetic recombination on the DNA level or due to peptide fragment association during the complex break down of proteins during protein turnover. Possibly it could also be the result of faulty reactions during protein synthesis i.e. caused by some kind of mixed RNA handling. A kind of combinatorial peptide epitope can also be seen if a portion of a longer peptide make a loop out leaving only the terminal part of the peptide bound in the groove.

Position in Peptide of Amino Acid Change

Any of the mentioned changes of the bound peptide amino acid sequence, can be found individually or in combination at any position of the peptide e.g. position 1, 2, 3, 4, 5, 6, etc up to n, n being the final amino acid of the peptide.

TABLE 1

Post translational modification of peptides
Protein primary structure and posttranslational modifications

| | |
|---|---|
| N-terminus | Acetylation, Formylation, Pyroglutamate, Methylation, Glycation, Myristoylation (Gly), carbamylation |
| C-terminus | Amidation, Glycosyl phosphatidylinositol (GPI), O-methylation, Glypiation, Ubiquitmation, Sumoylation. |
| Lysine | Methylation, Acetylation, Acylation, Hydroxylation, Ubiquitination, SUMOylation, Desmosine formation, ADP-ribosylation, Deamination and Oxidation to aldehyde |
| Cysteine | Disulfide bond, Prenylation, Palmitoylation |
| Serine/Threonine | Phosphorylation, Glycosylation |
| Tyrosine | Phosphorylation, Sulfation, Porphyrin ring linkage, Flavin linkage GFP prosthetic group (Thr-Tyr-Gly sequence) formation, Lysine tyrosine quinone (LTQ) formation, Topaquinone (TPQ) formation |
| Asparagine | Deamidation, Glycosylation |
| Aspartate | Succinimide formation |
| Glutamine | Transglutamination |
| Glutamate | Carboxylation, Methylation, Polyglutamylation, Polyglycylation |
| Arginine | Citrullination, Methylation |
| Proline | Hydroxylation |

Post Translationally Modified Peptides

The amino acids of the MHC bound peptides can also be modified in various ways dependent on the amino acid in question or the modification can affect the amino- or carboxy-terminal end of the peptide. See table 1. Such peptide modifications are occurring naturally as the result of post translational processing of the parental protein. A non-exhaustive description of the major post translational modifications is given below, divided into three main types a) Involving Addition Include:
   acylation, the addition of an acetyl group, usually at the N-terminus of the protein
   alkylation, the addition of an alkyl group (e.g. methyl, ethyl). Methylation, the addition of a methyl group, usually at lysine or arginine residues is a type of alkylation. Demethylation involves the removal of a methyl-group.
   amidation at C-terminus
   biotinylation, acylation of conserved lysine residues with a biotin appendage
   formylation
   gamma-carboxylation dependent on Vitamin K
   glutamylation, covalent linkage of glutamic acid residues to tubulin and some other proteins by means of tubulin polyglutamylase
   glycosylation, the addition of a glycosyl group to either asparagine, hydroxylysine, serine, or threonine, resulting in a glycoprotein. Distinct from glycation, which is regarded as a nonenzymatic attachment of sugars.
   glycylation, covalent linkage of one to more than 40 glycine residues to the tubulin C-terminal tail
   heme moiety may be covalently attached
   hydroxylation, is any chemical process that introduces one or more hydroxyl groups (—OH) into a compound (or radical) thereby oxidizing it. The principal residue to be hydroxylated is Proline. The hydroxilation occurs at the $C^\gamma$ atom, forming hydroxyproline (Hyp). In some cases, proline may be hydroxylated instead on its $C^\beta$ atom. Lysine may also be hydroxylated on its $C^\delta$ atom, forming hydroxylysine (Hyl).
   iodination (e.g. of thyroid hormones)
   isoprenylation, the addition of an isoprenoid group (e.g. farnesol and geranylgeraniol)
   lipoylation, attachment of a lipoate functionality, as in prenylation, GPI anchor formation, myristoylation, farnesylation, geranylation
   nucleotides or derivatives thereof may be covalently attached, as in ADP-ribosylation and flavin attachment
   oxidation, lysine can be oxidized to aldehyde
   pegylation, addition of poly-ethylen-glycol groups to a protein. Typical reactive amino acids include lysine, cysteine, histidine, arginine, aspartic acid, glutamic acid, serine, threonine, tyrosine. The N-terminal amino group and the C-terminal carboxylic acid can also be used
   phosphatidylinositol may be covalently attached
   phosphopantetheinylation, the addition of a 4'-phosphopantetheinyl moiety from coenzyme A, as in fatty acid, polyketide, non-ribosomal peptide and leucine biosynthesis phosphorylation, the addition of a phosphate group, usually to serine, tyrosine, threonine or histidine pyroglutamate formation as a result of N-terminal glutamine self-attack, resulting in formation of a cyclic pyroglutamate group.

racemization of proline by prolyl isomerase tRNA-mediated addition of amino acids such as arginylation sulfation, the addition of a sulfate group to a tyrosine.

Selenoylation (co-translational incorporation of selenium in selenoproteins)

b) Involving Addition of Other Proteins or Peptides

ISGylation, the covalent linkage to the ISG15 protein (Interferon-Stimulated Gene 15)

SUMOylation, the covalent linkage to the SUMO protein (Small Ubiquitin-related MOdifier)

ubiquitination, the covalent linkage to the protein ubiquitin.

c) Involving Changing the Chemical Nature of Amino Acids citrullination, or deimination the conversion of arginine to citrulline deamidation, the conversion of glutamine to glutamic acid or asparagine to aspartic acid The peptide modifications can occur as modification of a single amino acid or more than one i.e. in combinations. Modifications can be present on any position within the peptide i.e. on position 1, 2, 3, 4, 5, etc. for the entire length of the peptide.

Sources of Peptides a) From Natural Sources

Peptides can be obtained from natural sources by enzymatic digestion or proteolysis of natural proteins or proteins derived by in vitro translation of mRNA. Peptides may also be eluted from the MHC binding groove.

b) From Recombinant Sources

1) As Monomeric or Multimeric Peptide

Alternatively peptides can be produced recombinantly by transfected cells either as monomeric antigenic peptides or as multimeric (contatemeric) antigenic peptides.

2) As Part of a Bigger Recombinant Protein

Binding peptides may also constitute a part of a bigger recombinant protein e.g. consisting of, 2a) For MHC Class 1 Binding Peptides, Peptide-linker-β2m, β2m being full length or truncated;

Peptide-linker-MHC class 1 heavy chain, the heavy chain being full length or truncated. Most importantly the truncated class I heavy chain will consist of the extracellular part i.e the α1, α2, and a domains. The heavy chain fragment may also only contain the α1 and α2 domains, or α1 domain alone, or any fragment or full length β2m or heavy chain attached to a designer domain(s) or protein fragment(s).

2b) for MHC Class 2 Binding Peptides the Recombinant Construction can Consist of, Peptide-linker-MHC class 2 □-chain, full length or truncated;

Peptide-linker-MHC class 2 □-chain, full length or truncated;

Peptide-linker-MHC class 2 □-chain-linker-MHC class 2 □-chain, both chains can be full length or truncated, truncation may involve, omission of □- and/or □-chain intermembrane domain, or omission of □- and/or □-chain intermembrane plus cytoplasmic domains. MHC class 2 part of the construction may consist of fused domains from NH2-terminal, MHC class 2 □/domain-MHC class 2 □/domain-constant □3 of MHC class 1, or alternatively of fused domains from NH2-terminal, MHC class 2 □1domain-MHC class 2 □1domain-constant □3 of MHC class 1. In both cases □2m will be associated non-covalently in the folded MHC complex. □2m can also be covalently associated in the folded MHC class 2 complex if the following constructs are used from NH2 terminal, MHC class 2 □1domain-MHC class 2 □1domain-constant □3 of MHC class 1-linker-□2m, or alternatively of fused domains from NH2-terminal, MHC class 2 □1domain-MHC class 2 □1domain-constant □3 of MHC class 1-linker-□2m; the construct may also consist of any of the above MHC class 2 constructs with added designer domain(s) or sequence(s).

c) From Chemical Synthesis

MHC binding peptide may also be chemically synthesized by solid phase or fluid phase synthesis.

Loading of the Peptide into the MHCmer

Loading of the peptides into the MHCmer being either MHC class 1 or class 2 can be performed in a number of ways depending on the source of the peptide and the MHC. MHC class 2 molecules can in principle be loaded with peptides in similar ways as MHC class 1. However, due to complex instability the most successful approach have been to make the complexes recombinant in toto in eukaryotic cells from a gene construct encoding the following form □ chain-flexible linker-□ chain-flexible linker-peptide a) During MHC Complex Folding a1) As a Free Peptide MHC class I molecules are most often loaded with peptide during assembly in vitro by the individual components in a folding reaction i.e. consisting of purified recombinant heavy chain □ with the purified recombinant □2 microglobulin and a peptide or a peptide mix.

a2) As Part of a Recombinant Protein Construct

Alternatively the peptide to be folded into the binding groove can be encoded together with e.g. the □ heavy chain or fragment hereof by a gene construct having the structure, heavy chain-flexible linker-peptide. This recombinant molecule is then folded in vitro with □2-microglobulin.

b) By Exchange Reaction b1) In Solution

Loading of desired peptide can also be made by an in vitro exchange reaction where a peptide already in place in the binding groove are being exchanged by another peptide species.

b2) "In Situ"

Peptide exchange reactions can also take place when the parent molecule is attached to other molecules, structures, surfaces, artificial or natural membranes and nano-particles.

b3) By Aided Exchange

This method can be refined by making the parent construct with a peptide containing a meta-stable amino acid analog that is split by either light or chemically induction thereby leaving the parent structure free for access of the desired peptide in the binding groove.

b4) By In Vivo Loading

Loading of MHC class I and II molecules expressed on the cell surface with the desired peptides can be performed by an exchange reaction. Alternatively cells can be transfected by the peptides themselves or by the mother proteins that are then being processed leading to an in vivo analogous situation where the peptides are bound in the groove during the natural cause of MHC expression by the transfected cells. In the case of professional antigen presenting cells e.g. dendritic cells, macrophages, Langerhans cells, the proteins and peptides can be taken up by the cells themselves by phagocytosis and then bound to the MHC complexes the natural way and expressed on the cell surface in the correct MHC context.

Verification of Correctly Folded MHC-Peptide Complexes
Quantitative ELISA and Other Techniques to Quantify Correctly Folded MHC Complexes When producing MHC multimers, it is desirable to determine the degree of correctly folded MHC.

The fraction or amount of functional and/or correctly folded MHC can be tested in a number of different ways, including:

- Measurement of correctly folded MHC in a quantitative ELISA, e.g. where the MHC bind to immobilized molecules recognizing the correctly folded complex.
- Measurement of functional MHC in an assay where the total protein concentration is measured before functional MHC is captured, by binding to e.g. immobilized TCR, and the excess, non-bound protein are measured. If the dissociation constant for the interaction is known, the amount of total and the amount of non-bound protein can be determined. From these numbers, the fraction of functional MHC complex can be determined.
- Measurement of functional MHC complex by a non-denaturing gel-shift assay, where functional MHC complexes bind to TCR (or another molecule that recognize correctly folded MHC complex), and thereby shifts the TCR to another position in the gel.

Multimerization Domain

A number of MHC complexes associate with a multimerization domain to form a MHC multimer. The size of the multimerization domain spans a wide range, from multimerisation domains based on small organic molecule scaffolds to large multimers based on a cellular structure or solid support. The multimerization domain may thus be based on different types of carriers or scaffolds, and likewise, the attachment of MHC complexes to the multimerization domain may involve covalent or non-covalent linkers.

Characteristics of different kinds of multimerization domains are described below.

Molecular Weight of Multimerization Domain.

- In one embodiment the multimerization domain(s) in the present invention is preferably less than 1,000 Da (small molecule scaffold). Examples include short peptides (e.g. comprising 10 amino acids), and various small molecule scaffolds (e.g. aromatic ring structures).
- In another embodiment the multimerization domain(s) is preferably between 1,000 Da and 10,000 Da (small molecule scaffold, small peptides, small polymers). Examples include polycyclic structures of both aliphatic and aromatic compounds, peptides comprising e.g. 10-100 amino acids, and other polymers such as dextran, polyethylenglycol, and polyureas.
- In another embodiment the multimerization domain(s) is between 10,000 Da and 100,000 Da (Small molecule scaffold, polymers e.g. dextran, streptavidin, IgG, pentamer structure). Examples include proteins and large polypeptides, small molecule scaffolds such as steroids, dextran, dimeric streptavidin, and multi-subunit proteins such as used in Pentamers.
- In another embodiment the multimerization domain(s) is preferably between 100,000 Da and 1,000,000 Da (Small molecule scaffold, polymers e.g. dextran, streptavidin, IgG, pentamer structure). Typical examples include larger polymers such as dextran (used in e.g. Dextramers), and streptavidin tetramers.
- In another embodiment the multimerization domain(s) is preferably larger than 1,000,000 Da (Small molecule scaffold, polymers e.g. dextran, streptavidin, IgG, pentamer structure, cells, liposomes, artificial lipid bilayers, polystyrene beads and other beads. Most examples of this size involve cells or cell-based structures such as micelles and liposomes, as well as beads and other solid supports.

As mentioned elsewhere herein multimerisation domains can comprise carrier molecules, scaffolds or combinations of the two.

Type of Multimerization Domain.

In principle any kind of carrier or scaffold can be used as multimerization domain, including any kind of cell, polymer, protein or other molecular structure, or particles and solid supports. Below different types and specific examples of multimerization domains are listed.

- Cell. Cells can be used as carriers. Cells can be either alive and mitotic active, alive and mitotic inactive as a result of irradiation or chemically treatment, or the cells may be dead. The MHC expression may be natural (i.e. not stimulated) or may be induced/stimulated by e.g. Inf-γ. Of special interest are natural antigen presenting cells (APCs) such as dendritic cells, macrophages, Kupfer cells, Langerhans cells, B-cells and any MHC expressing cell either naturally expressing, being transfected or being a hybridoma.
- Cell-like structures. Cell-like carriers include membrane-based structures carrying MHC-peptide complexes in their membranes such as micelles, liposomes, and other structures of membranes, and phages such as filamentous phages.
- Solid support. Solid support includes beads, particulate matters and other surfaces. A preferred embodiment include beads (magnetic or non-magnetic beads) that carry electrophilic groups e.g. divinyl sulfone activated polysaccharide, polystyrene beads that have been functionalized with tosyl-activated esters, magnetic polystyrene beads functionalized with tosyl-activated esters), and where MHC complexes may be covalently immobilized to these by reaction of nucleophiles comprised within the MHC complex with the electrophiles of the beads. Beads may be made of sepharose, sephacryl, polystyrene, agarose, polysaccharide, polycarbamate or any other kind of beads that can be suspended in aqueous buffer.
- Another embodiment includes surfaces, i.e. solid supports and particles carrying immobilized MHC complexes on the surface. Of special interest are wells of a microtiter plate or other plate formats, reagent tubes, glass slides or other supports for use in microarray analysis, tubings or channels of micro fluidic chambers or devices, Biacore chips and beads
- Molecule. Multimerization domains may also be molecules or complexes of molecules held together by non-covalent bonds. The molecules constituting the multimerization domain can be small organic molecules or large polymers, and may be flexible linear molecules or rigid, globular structures such as e.g. proteins. Different kinds of molecules used in multimerization domains are described below.
  - Small organic molecules. Small organic molecules here includes steroids, peptides, linear or cyclic structures, and aromatic or aliphatic structures, and many others. The prototypical small organic scaffold is a functionalized benzene ring, i.e. a benzene ring functionalized with a number of reactive groups such as amines, to which a number of MHC molecules may be covalently linked. However, the types of reactive groups constituting the linker connecting the MHC complex and the multimerization domain, as well as the type of scaffold structure, can be chosen from a long list of chemical structures. A non-comprehensive list of scaffold structures are listed below.

Typical scaffolds include aromatic structures, benzodiazepines, hydantoins, piperazines, indoles, furans, thiazoles, steroids, diketopiperazines, morpholines, tropanes, coumarines, qinolines, pyrroles, oxazoles, amino acid precursors, cyclic or aromatic ring structures, and many others.

Typical carriers include linear and branched polymers such as peptides, polysaccharides, nucleic acids, and many others. Multimerization domains based on small organic or polymer molecules thus include a wealth of different structures, including small compact molecules, linear structures, polymers, polypeptides, polyureas, polycarbamates, cyclic structures, natural compound derivatives, alpha-, beta-, gamma-, and omega-peptides, mono-, di- and tri-substituted peptides, L- and D-form peptides, cyclohexane- and cyclopentane-backbone modified beta-peptides, vinylogous polypeptides, glycopolypeptides, polyamides, vinylogous sulfonamide peptide, Polysulfonamide-conjugated peptide (i.e., having prosthetic groups), Polyesters, Polysaccharides such as dextran and aminodextran, polycarbamates, polycarbonates, polyureas, poly-peptidyl-phosphonates, Azatides, peptoids (oligo N-substituted glycines), Polyethers, ethoxyformacetal oligomers, poly-thioethers, polyethylene, glycols (PEG), polyethylenes, polydisulfides, polyarylene sulfides, Polynucleotides, PNAs, LNAs, Morpholinos, oligo pyrrolinone, polyoximes, Poly-imines, Polyethyleneimine, Polyacetates, Polystyrenes, Polyacetylene, Polyvinyl, Lipids, Phospholipids, Glycolipids, polycycles, (aliphatic), polycycles (aromatic), polyheterocycles, Proteoglycan, Polysi-loxanes, Polyisocyanides, Polyisocyanates, polymethacrylates, Monofunctional, Difunctional, Trifunctional and Oligofunctional open-chain hydrocarbons, Monofunctional, Difunctional, Trifunctional and Oligofunctional Nonaromat Carbocycles, Monocyclic, Bicyclic, Tricyclic and Polycyclic Hydrocarbons, Bridged Polycyclic Hydrocarbones, Monofunctional, Difunctional, Trifunctional and Oligofunctional Nonaromatic, Heterocycles, Monocyclic, Bicyclic, Tricyclic and Polycyclic Heterocycles, bridged Polycyclic Heterocycles, Monofunctional, Difunctional, Trifunctional and Oligofunctional Aromatic Carbocycles, Monocyclic, Bicyclic, Tricyclic and Polycyclic Aromatic Carbocycles, Monofunctional, Difunctional, Trifunctional and Oligofunctional Aromatic Hetero-cycles. Monocyclic, Bicyclic, Tricyclic and Polycyclic Hetero-cycles. Chelates, fullerenes, and any combination of the above and many others.

Biological polymers. Biological molecules here include peptides, proteins (including antibodies, coiled-coil helices, streptavidin and many others), nucleic acids such as DNA and RNA, and polysaccharides such as dextran. The biological polymers may be reacted with MHC complexes (e.g. a number of MHC complexes chemically coupled to e.g. the amino groups of a protein), or may be linked through e.g. DNA duplex formation between a carrier DNA molecule and a number of DNA oligonucleotides each coupled to a MHC complex. Another type of multimerization domain based on a biological polymer is the streptavidin-based tetramer, where a streptavidin binds up to four biotinylated MHC complexes, as described above (see Background of the invention).

Self-assembling multimeric structures. Several examples of commercial MHC multimers exist where the multimer is formed through self-assembling. Thus, the Pentamers are formed through formation of a coiled-coil structure that holds together 5 MHC complexes in an apparently planar structure. In a similar way, the Streptamers are based on the Streptactin protein which oligomerizes to form a MHC multimer comprising several MHC complexes (see Background of the invention).

In the following, alternative ways to make MHC multimers based on a molecule multimerization domain are described. They involve one or more of the abovementioned types of multimerization domains.

MHC dextramers can be made by coupling MHC complexes to dextran via a streptavidin-biotin interaction. In principle, biotin-streptavidin can be replaced by any dimerization domain, where one half of the dimerization domain is coupled to the MHC-peptide complex and the other half is coupled to dextran. For example, an acidic helix (one half of a coiled-coil dimer) is coupled or fused to MHC, and a basic helix (other half of a coiled-coil dimmer) is coupled to dextran. Mixing the two results in MHC binding to dextran by forming the acid/base coiled-coil structure.

Antibodies can be used as scaffolds by using their capacity to bind to a carefully selected antigen found naturally or added as a tag to a part of the MHC molecule not involved in peptide binding. For example, IgG and IgE will be able to bind two MHC molecules, IgM having a pentameric structure will be able to bind 10 MHC molecules. The antibodies can be full-length or truncated; a standard antibody-fragment includes the Fab2 fragment.

Peptides involved in coiled-coil structures can act as scaffold by making stable dimeric, trimeric, tetrameric and pentameric interactions. Examples hereof are the Fos-Jun heterodimeric coiled coil, the *E. coli* homo-trimeric coiled-coil domain Lpp-56, the engineered Trp-zipper protein forming a discrete, stable, α-helical pentamer in water at physiological pH.

Further examples of suitable scaffolds, carriers and linkers are streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase), glutathione, Calmodulin-binding peptide (CBP), Strep-tag, Cellulose Binding Domain, Maltose Binding Protein, S-Peptide Tag, Chitin Binding Tag, Immunoreactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). Combinations of such binding entities are also comprised. Non-limiting examples are streptavidin-biotin and jun-fos. In particular, when the MHC molecule is tagged, the binding entity may be an "anti-tag". By "anti-tag" is meant an antibody binding to the tag, or any other molecule capable of binding to such tag.

MHC complexes can be multimerized by other means than coupling or binding to a multimerization domain. Thus, the multimerization domain may be formed during the multimerization of MHCs. One such method is to extend the bound antigenic peptide with dimerization domains. One end of the antigenic peptide is extended with dimerization domain A (e.g. acidic helix, half of a coiled-coil dimer) and the other end is extended with dimerization domain B (e.g. basic helix, other half of a coiled-coil dimer). When MHC complexes are loaded/mixed with these extended peptides the following multimer structure will be formed: A-MHC-BA-MHC-BA-MHC-B etc. The antigenic peptides in the mixture can either be identical or a mixture of peptides with comparable extended dimerization domains. Alternatively both ends of a peptide are extended with the same dimerization domain A and another peptide (same amino acid sequence or a different amino acid sequence) is extended with dimerization domain B. When MHC and peptides are mixed the following structures are formed: A-MHC-AB-MHC-BA-MHC-AB-MHC-B etc. Multimerization of MHC complexes by extension of peptides are restricted to MHC II molecules since the peptide binding groove of MHC I molecules is typically closed in both ends thereby limiting the size of peptide that can be embedded in the groove, and therefore preventing the peptide from extending out of the groove.

Another multimerization approach applicable to both MHC I and MHC II complexes is based on extension of N- and C-terminal of the MHC complex. For example the N-terminal of the MHC complex is extended with dimerization domain A and the C-terminal is extended with dimerization domain B. When MHC complexes are incubated together they pair with each other and form multimers like: A-MHC-BA-MHC-BA-MHC-BA-MHC-B etc. Alternatively the N-terminal and the C-terminal of a MHC complex are both extended with dimerization domain A and the N-terminal and C-terminal of another preparation of MHC complex (either the same or a different MHC) are extended with dimerization domain B. When these two types of MHC complexes are incubated together multimers will be formed: A-MHC-AB-MHC-BA-MHC-AB-MHC-B etc.

In all the above-described examples the extension can be either chemically coupled to the peptide/MHC complex or introduced as extension by gene fusion.

Dimerization domain AB can be any molecule pair able to bind to each other, such as acid/base coiled-coil helices, antibody-antigen, DNA-DNA, PNA-PNA, DNA-PNA, DNA-RNA, LNA-DNA, leucine zipper e.g. Fos/Jun, streptavidin-biotin and other molecule pairs as described elsewhere herein.

Linker Molecules.

A number of MHC complexes associate with a multimerization domain to form a MHC multimer. The attachment of MHC complexes to the multimerization domain may involve covalent or non-covalent linkers, and may involve small reactive groups as well as large protein-protein interactions.

The coupling of multimerization domains and MHC complexes involve the association of an entity X (attached to or part of the multimerization domain) and an entity Y (attached to or part of the MHC complex). Thus, the linker that connects the multimerization domain and the MHC complex comprises an XY portion.

Figure 5:
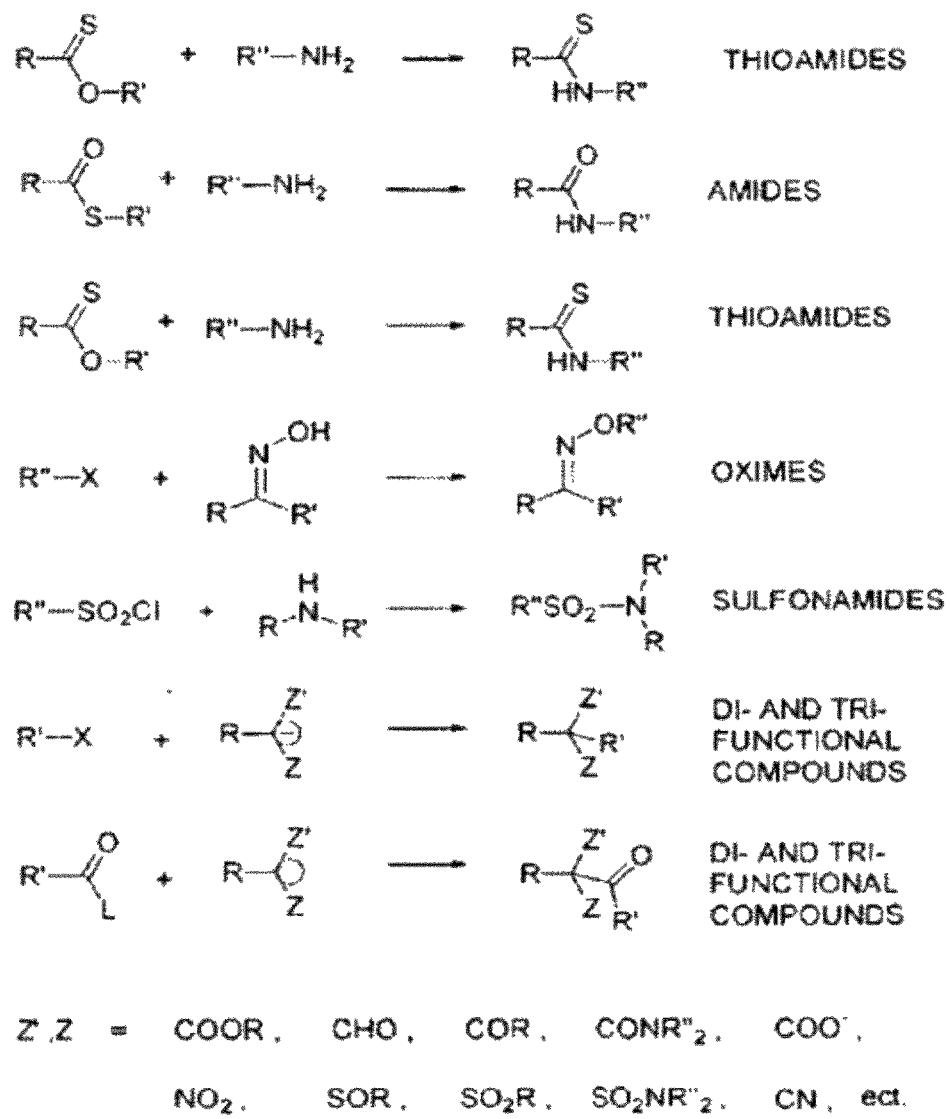
FIG. 5. Illustration of selected reaction groups.
Figure 5:
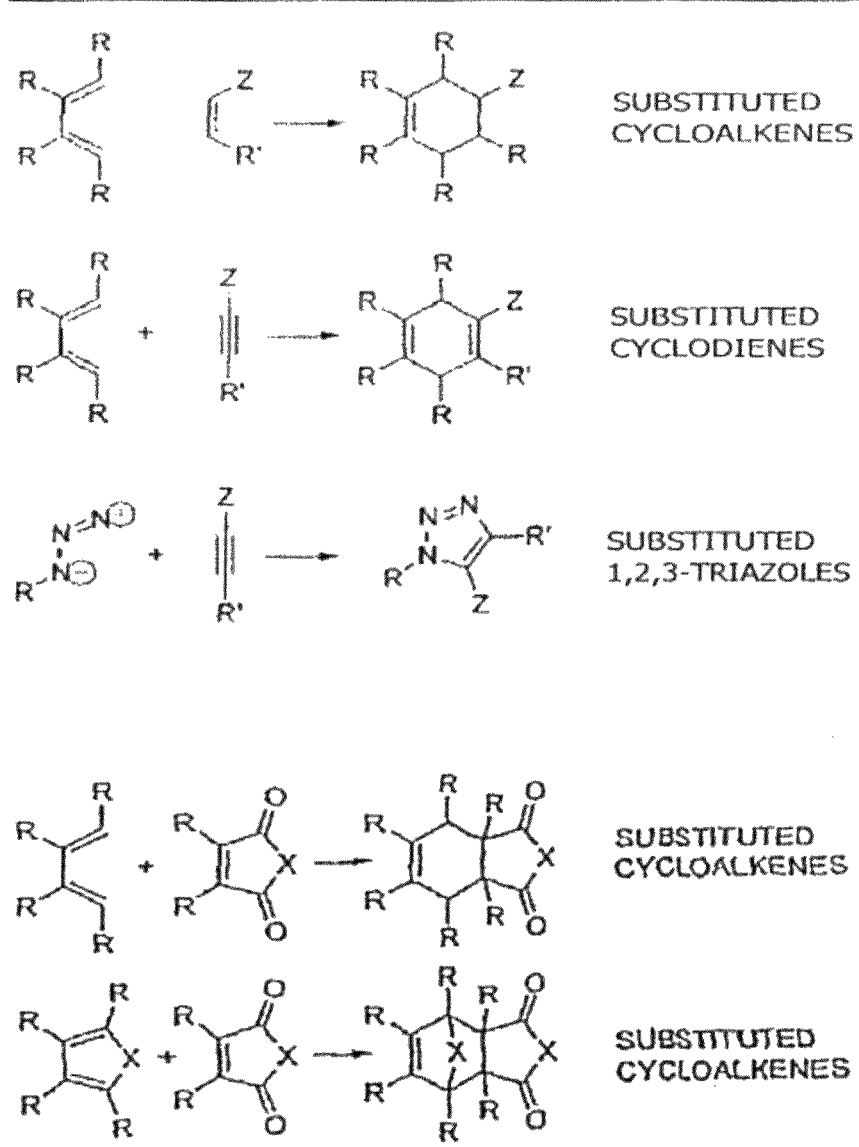
Figure 5:
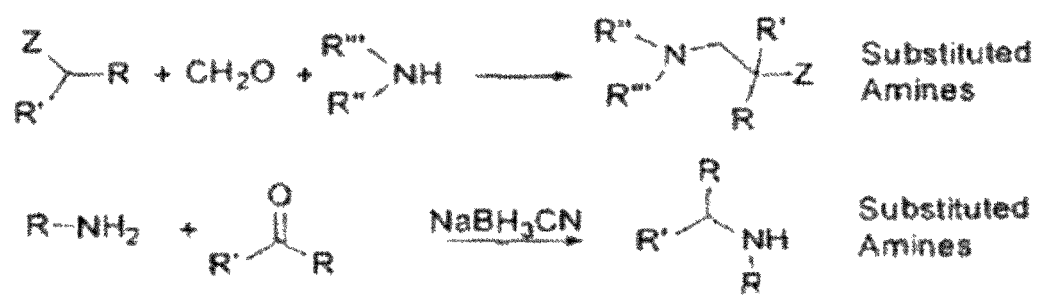

Covalent linker. The XY linkage can be covalent, in which case X and Y are reactive groups. In this case, X can be a nucleophilic group (such as —$NH_2$, —OH, —SH, —NH—$NH_2$), and Y an electrophilic group (such as CHO, COOH, CO) that react to form a covalent bond XY; or Y can be a nucleophilic group and X an electrophilic group that react to form a covalent bond XY. Other possibilities exist, e.g either of the reactive groups can be a radical, capable of reacting with the other reactive group. A number of reactive groups X and Y, and the bonds that are formed upon reaction of X and Y, are shown in FIG. 5.

X and Y can be reactive groups naturally comprised within the multimerization domain and/or the MHC complex, or they can be artificially added reactive groups. Thus, linkers containing reactive groups can be linked to either of the multimerization domain and MHC complex; subsequently the introduced reactive group(s) can be used to covalently link the multimerization domain and MHC complex.

Example natural reactive groups of MHC complexes include amino acid side chains comprising —$NH_2$, —OH, —SH, and —NH—. Example natural reactive groups of multimerization domains include hydroxyls of polysaccharides such as dextrans, but also include amino acid side chains comprising —$NH_2$, —OH, —SH, and —NH— of polypeptides, when the polypeptide is used as a multimerization domain. In some MHC multimers, one of the polypeptides of the MHC complex (i.e. the β2M, heavy chain or the antigenic peptide) is linked by a protein fusion to the multimerization domain. Thus, during the translation of the fusion protein, an acyl group (reactive group X or Y) and an amino group (reactive group Y or X) react to form an amide bond. Example MHC multimers where the bond between the multimerization domain and the MHC complex is covalent and results from reaction between natural reactive groups, include MHC-pentamers (described in US patent 2004209295) and MHC-dimers, where the linkage between multimerization domain and MHC complex is in both cases generated during the translation of the fusion protein.

Example artificial reactive groups include reactive groups that are attached to the multimerization domain or MHC complex, through association of a linker molecule comprising the reactive group. The activation of dextran by reaction of the dextran hydroxyls with divinyl sulfone, introduces a reactive vinyl group that can react with e.g. amines of the MHC complex, to form an amine that now links the multimerization domain (the dextran polymer) and the MHC complex. An alternative activation of the dextran multimerization domain involves a multistep reaction that results in the decoration of the dextran with maleimide groups, as described in the patent Siiman et al. U.S. Pat. No. 6,387,622. In this approach, the amino groups of MHC complexes are converted to —SH groups, capable of reacting with the maleimide groups of the activated dextran. Thus, in the latter example, both the reactive group of the multimerization domain (the maleimide) and the reactive group of the MHC complex (the thiol) are artificially introduced.

Sometimes activating reagents are used in order to make the reactive groups more reactive. For example, acids such as glutamate or aspartate can be converted to activated esters by addition of e.g. carbodiimid and NHS or nitrophenol, or by converting the acid moiety to a tosyl-activated ester. The activated ester reacts efficiently with a nucleophile such as —$NH_2$, —SH, —OH, etc.

For the purpose of this invention, the multimerization domains (including small organic scaffold molecules, proteins, protein complexes, polymers, beads, liposomes, micelles, cells) that form a covalent bond with the MHC complexes can be divided into separate groups, depending on the nature of the reactive group that the multimerization domain contains. One group comprise multimerization domains that carry nucleophilic groups (e.g. —$NH_2$, —OH, —SH, —CN, —NH—$NH_2$), exemplified by polysaccharides, polypeptides containing e.g. lysine, serine, and cysteine; another group of multimerization domains carry electrophilic groups (e.g. —COOH, —CHO, —CO, NHS-ester, tosyl-activated ester, and other activated esters, acid-anhydrides), exemplified by polypeptides containing e.g. glutamate and aspartate, or vinyl sulfone activated dextran; yet another group of multimerization domains carry radicals or conjugated double bonds.

The multimerization domains appropriate for this invention thus include those that contain any of the reactive groups shown in FIG. 5 or that can react with other reactive groups to form the bonds shown in FIG. 5.

Likewise, MHC complexes can be divided into separate groups, depending on the nature of the reactive group comprised within the MHC complex. One group comprise MHCs that carry nucleophilic groups (e.g. —$NH_2$, —OH, —SH, —CN, —NH—$NH_2$), e.g. lysine, serine, and cysteine; another group of MHCs carry electrophilic groups (e.g. —COOH, —CHO, —CO, NHS-ester, tosyl-activated ester, and other activated esters, acid-anhydrides), exemplified by e.g. glutamate and aspartate; yet another group of MHCs carry radicals or conjugated double bonds.

The reactive groups of the MHC complex are either carried by the amino acids of the MHC-peptide complex (and may be comprised by any of the peptides of the MHC-peptide complex, including the antigenic peptide), or alternatively, the reactive group of the MHC complex has been introduced by covalent or non-covalent attachment of a molecule containing the appropriate reactive group.

Preferred reactive groups in this regard include —$CSO_2OH$, phenylchloride, —SH, —SS, aldehydes, hydroxyls, isocyanate, thiols, amines, esters, thioesters, carboxylic acids, triple bonds, double bonds, ethers, acid chlorides, phosphates, imidazoles, halogenated aromatic rings, any precursors thereof, or any protected reactive groups, and many others. Example pairs of reactive groups, and the resulting bonds formed, are shown in FIG. 5.

Reactions that may be employed include acylation (formation of amide, pyrazolone, isoxazolone, pyrimidine, comarine, quinolinon, phthalhydrazide, diketopiperazine, benzodiazepinone, and hydantoin), alkylation, vinylation, disulfide formation, Wittig reaction, Horner-Wittig-Emmans reaction, arylation (formation of biaryl or vinylarene), condensation reactions, cycloadditions ((2+4), (3+2)), addition to carbon-carbon multiplebonds, cycloaddition to multiple bonds, addition to carbon-hetero multiple bonds, nucleophilic aromatic substitution, transition metal catalyzed reactions, and may involve formation of ethers, thioethers, secondary amines, tertiary amines, beta-hydroxy ethers, beta-hydroxy thioethers, beta-hydroxy amines, beta-amino ethers, amides, thioamides, oximes, sulfonamides, di- and tri-functional compounds, substituted aromatic compounds, vinyl substituted aromatic compounds, alkyn substituted aromatic compounds, biaryl compounds, hydrazines, hydroxylamine ethers, substituted cycloalkenes, substituted cyclodienes, substituted 1, 2, 3 triazoles, substituted cycloalkenes, beta-hydroxy ketones, beta-hydroxy aldehydes, vinyl ketones, vinyl aldehydes, substituted alkenes, substituted alkenes, substituted amines, and many others.

MHC dextramers can be made by covalent coupling of MHC complexes to the dextran backbone, e.g. by chemical coupling of MHC complexes to dextran backbones. The MHC complexes can be coupled through either heavy chain or β2-microglobulin if the MHC complexes are MHC I or through α-chain or β-chain if the MHC complexes are MHC II. MHC complexes can be coupled as folded complexes comprising heavy chain/beta2microglobulin or α-chain/β-chain or either combination together with peptide in the peptide-binding cleft. Alternatively either of the protein chains can be coupled to dextran and then folded in vitro together with the other chain of the MHC complex not coupled to dextran and together with peptide. Direct coupling of MHC complexes to dextran multimerization domain can be via an amino group or via a sulphide group. Either group can be a natural component of the MHC complex or attached to the MHC complex chemically. Alternatively, a cysteine may be introduced into the genes of either chain of the MHC complex.

Another way to covalently link MHC complexes to dextran multimerization domains is to use the antigenic peptide as a linker between MHC and dextran. Linker containing antigenic peptide at one end is coupled to dextran. Antigenic peptide here means a peptide able to bind MHC complexes in the peptide-binding cleft. As an example, 10 or more antigenic peptides may be coupled to one dextran molecule. When MHC complexes are added to such peptide-dextran construct the MHC complexes will bind the antigenic peptides and thereby MHC-peptide complexes are displayed around the dextran multimerization domain. The antigenic peptides can be identical or different from each other. Similarly MHC complexes can be either identical or different from each other as long as they are capable of binding one or more of the peptides on the dextran multimerization domain.

Non-covalent linker. The linker that connects the multimerization domain and the MHC complex comprises an XY portion. Above different kinds of covalent linkages XY were described. However, the XY linkage can also be non-covalent.

Non-covalent XY linkages can comprise natural dimerization pairs such as antigen-antibody pairs, DNA-DNA interactions, or can include natural interactions between small molecules and proteins, e.g. between biotin and streptavidin. Artificial XY examples include XY pairs such as $His_6$ tag (X) interacting with Ni-NTA (Y) and PNA-PNA interactions.

Protein-protein interactions. The non-covalent linker may comprise a complex of two or more polypeptides or proteins, held together by non-covalent interactions. Example polypeptides and proteins belonging to this group include Fos/Jun, Acid/Base coiled coil structure, antibody/antigen (where the antigen is a peptide), and many others.

A preferred embodiment involving non-covalent interactions between polypeptides and/or proteins are represented by the Pentamer structure described in US patent 2004209295.

Another preferred embodiment involves the use of antibodies, with affinity for the surface of MHC opposite to the peptide-binding groove. Thus, an anti-MHC antibody, with its two binding site, will bind two MHC complexes and in this way generate a bivalent MHC multimer. In addition, the antibody can stabilize the MHC complex through the binding interactions. This is particularly relevant for MHC class II complexes, as these are less stable than class I MHC complexes.

Polynucleotide-polynucleotide interactions. The non-covalent linker may comprise nucleotides that interact non-covalently. Example interactions include PNA/PNA, DNA/DNA, RNA/RNA, LNA/DNA, and any other nucleic acid duplex structure, and any combination of such natural and unnatural polynucleotides such as DNA/PNA, RNA/DNA, and PNA/LNA.

Protein-small molecule interactions. The non-covalent linker may comprise a macromolecule (e.g. protein, polynucleotide) and a small molecule ligand of the macromolecule. The interaction may be natural (i.e., found in Nature, such as the Streptavidin/biotin interaction) or non-natural (e.g. His-tag peptide/Ni-NTA interaction). Example interactions include Streptavidin/biotin and anti-biotin antibody/biotin.

Combinations—non-covalent linker molecules. Other combinations of proteins, polynucleotides, small organic molecules, and other molecules, may be used to link the MHC to the multimerization domain. These other combinations include protein-DNA interactions (e.g. DNA binding protein such as the gene regulatory protein CRP interacting with its DNA recognition sequence), RNA aptamer-protein interactions (e.g. RNA aptamer specific for growth hormone interacting with growth hormone)

Synthetic molecule-synthetic molecule interaction. The non-covalent linker may comprise a complex of two or more organic molecules, held together by non-covalent interactions. Example interactions are two chelate molecules binding to the same metal ion (e.g. EDTA-$Ni^{++}$-NTA), or a short polyhistidine peptide (e.g. $His_6$) bound to NTA-$Ni^{++}$.

In another preferred embodiment the multimerization domain is a bead. The bead is covalently or non-covalently coated with MHC multimers or single MHC complexes, through non-cleavable or cleavable linkers. As an example, the bead can be coated with streptavidin monomers, which in turn are associated with biotinylated MHC complexes; or the bead can be coated with streptavidin tetramers, each of which are associated with 0, 1, 2, 3, or 4 biotinylated MHC complexes; or the bead can be coated with MHC-dextramers where e.g. the reactive groups of the MHC-dextramer (e.g. the divinyl sulfone-activated dextran backbone) has reacted with nucleophilic groups on the bead, to form a covalent linkage between the dextran of the dextramer and the beads.

In another preferred embodiment, the MHC multimers described above (e.g. where the multimerization domain is a bead) further contains a flexible or rigid, and water soluble, linker that allows for the immobilized MHC complexes to interact efficiently with cells, such as T-cells with affinity for the MHC complexes. In yet another embodiment, the linker is cleavable, allowing for release of the MHC complexes from the bead. If T-cells have been immobilized, by binding to the MHC complexes, the T-cells can very gently be released by cleavage of this cleavable linker Appropriate cleavable linkers are shown in FIG. 6. Most preferably, the linker is cleaved at physiological conditions, allowing for the integrity of the isolated cells.

Further examples of linker molecules that may be employed in the present invention include Calmodulin-binding peptide (CBP), 6×HIS, Protein A, Protein G, biotin, Avidine, Streptavidine, Strep-tag, Cellulose Binding Domain, Maltose Binding Protein, S-Peptide Tag, Chitin Binding Tag, Immuno-reactive Epitopes, Epitope Tags, GST tagged proteins, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope.

The list of dimerization- and multimerization domains, described elsewhere in this document, define alternative non-covalent linkers between the multimerization domain and the MHC complex.

The abovementioned dimerization- and multimerization domains represent specific binding interactions. Another type of non-covalent interactions involves the non-specific adsorption of e.g. proteins onto surfaces. As an example, the non-covalent adsorption of proteins onto glass beads represents this class of XY interactions. Likewise, the interaction of MHC complexes (comprising full-length polypeptide chains, including the transmembrane portion) with the cell membrane of for example dendritic cells is an example of a non-covalent, primarily non-specific XY interaction.

In some of the abovementioned embodiments, several multimerization domains (e.g. streptavidin tetramers bound to biotinylated MHC complexes) are linked to another multimerization domain (e.g. the bead). For the purpose of this invention we shall call both the smaller and the bigger multimerization domain, as well as the combined multimerization domain, for multimerization domain Additional Features of Product Additional components may be coupled to carrier or added as individual components not coupled to carrier Attachment of Biologically Active Molecules to MHC Multimers Engagement of MHC complex to the specific T cell receptor leads to a signaling cascade in the T cell. However, T-cells normally respond to a single signal stimulus by going into apoptosis. T cells needs a second signal in order to become activated and start development into a specific activation state e.g. become an active cytotoxic T cell, helper T cell or regulatory T cell.

It is to be understood that the MHC multimer of the invention may further comprise one or more additional substituents. The definition of the terms "one or more", "a plurality", "a", "an", and "the" also apply here. Such biologically active molecules may be attached to the construct in order to affect the characteristics of the constructs, e.g. with respect to binding properties, effects, MHC molecule specificities, solubility, stability, or detectability. For instance, spacing could be provided between the MHC complexes, one or both chromophores of a Fluorescence Resonance Energy Transfer (FRET) donor/acceptor pair could be inserted, functional groups could be attached, or groups having a biological activity could be attached.

MHC multimers can be covalently or non-covalently associated with various molecules: having adjuvant effects; being immune targets e.g. antigens; having biological activity e.g. enzymes, regulators of receptor activity, receptor ligands, immune potentiators, drugs, toxins, co-receptors, proteins and peptides in general; sugar moieties; lipid groups; nucleic acids including siRNA; nano particles; small molecules. In the following these molecules are collectively called biologically active molecules. Such molecules can be attached to the MHC multimer using the same principles as those described for attachment of MHC complexes to multimerisation domains as described elsewhere herein. In brief, attachment can be done by chemical reactions between reactive groups on the biologically active molecule and reactive groups of the multimerisation domain and/or between reactive groups on the biologically active molecule and reactive groups of the MHC-peptide complex. Alternatively, attachment is done by non-covalent interaction between part of the multimerisation domain and part of the biological active molecule or between part of the MHC-peptide complex and part of the biological active molecule. In both covalent and non-covalent attachment of the biologically molecule to the multimerisation domain a linker molecule can connect the two. The linker molecule can be covalent or non-covalent attached to both molecules. Examples of linker molecules are described elsewhere herein. Some of the MHCmer structures better allows these kind of modifications than others.

Biological active molecules can be attached repetitively aiding to recognition by and stimulation of the innate immune system via Toll or other receptors.

MHC multimers carrying one or more additional groups can be used as therapeutic or vaccine reagents.

In particular, the biologically active molecule may be selected from
proteins such as MHC Class I-like proteins like MIC A, MIC B, CD1d, HLA E, HLA F, HLA G, HLA H, ULBP-1, ULBP-2, and ULBP-3,
co-stimulatory molecules such as CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells,
cell modulating molecules such as CD16, NKp30, NKp44, NKp46, NKp80, 2B4, KIR, LIR, CD94/NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin,
accessory molecules such as LFA-1, CD11a/18, CD54 (ICAM-1), CD106 (VCAM), and CD49a,b,c,d,e,f/CD29 (VLA-4),
adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P,
toxic molecules selected from toxins, enzymes, antibodies, radioisotopes, chemiluminescent substances, bioluminescent substances, polymers, metal particles, and haptens, such as cyclophosphamide, methrotrexate, Azathioprine, mizoribine, 15-deoxyspergualin, neomycin, staurosporine, genestein, herbimycin A, *Pseudomonas* exotoxin A, saporin, Rituxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin,
and combinations of any of the foregoing, as well as antibodies (monoclonal, polyclonal, and recombinant) to the foregoing, where relevant. Antibody derivatives or fragments thereof may also be used.

Design and Generation of Product to be Used for Immune Monitoring, Diagnosis, Therapy or Vaccination The product of the present invention may be used for immune monitoring, diagnosis, therapy and/or vaccination. Generation of a useful product includes the following basic steps:

1. Design of antigenic peptides
2. Choice of MHC allele
3. Generation of product
4. Validation and optimization of product In the following strategies for generation of products are given:

How to Make a MHC Multimer Diagnostic or Immune Monitoring Reagent

1. Identify disease of interest. Most relevant diseases in this regard are infectious-, cancer-, auto immune-, transplantation-, or immuno-suppression-related diseases.
2. Identify relevant protein targets. This may be individual proteins, a group of proteins from a given tissue or all or subgroups of proteins from a complete organism.
3. Identify the protein sequence. Amino acid sequences can be directly found in databases or deduced from gene- or mRNA sequence e.g. using the following link www.ncbi.nlm.nih.gov/Genbank/index.html. If not in databases relevant proteins or genes encoding relevant proteins may be isolated and sequenced. In some cases only DNA sequences will be available without knowing which part of the sequence is protein coding. Then DNA sequence is translated into amino acid sequence in all reading frames.
4. Choose MHC allele. Decide on needed MHC allele population coverage. If a broad coverage of a given population is needed (i.e. when a generally applicable reagent is sought) the most frequently expressed MHC alleles by the population of interest may be chosen e.g. using the database www.allelefrequencies.net/test/default1.asp or epitope.liai.org:8080/tools/population/iedb_input.

In case of personalized medicine the patient is tissue typed (HLA type) and then MHC alleles may be selected according to that.
5. Run the general peptide epitope generator program described elsewhere herein on all selected amino acid sequences from step 3, thereby generating all possible epitopes of defined length (8, 9, 10 and/or 11'mers). This procedure is particularly useful when the amino acid sequence is derived from a DNA sequence not knowing the protein encoding areas.
6. If searching for broadly applicable epitope sequences, a good alternative to step 5 is to run the "intelligent" peptide epitope prediction programs on the selected amino acid sequences of step 3 using the selected MHC alleles from step 4 e.g. using epitope prediction programs like www.syfpeithi.de/, www.cbs.dtu.dk/services/NetMHC/, and www.cbs.dtu.dk/services/NetMHCII/.
7. If searching for broadly applicable epitope sequences, select the best peptide epitopes (the epitopes with highest binding score) for the chosen MHC alleles and run them through the BLAST program (www.ncbi.nlm.nih.gov/blast/Blast.cgi) to validate the uniqueness of the peptides. If the peptide sequences are present in other species, evaluate the potential risk of disease states caused by the non-relevant species in relation to causing false positive results. If considered being a potential problem for evaluating the future analysis outcome, leave out the peptide. In general, favour unique peptide sequences only present in the selected protein.
8. Make selected peptides as described elsewhere herein, and optionally test for binding to the desired MHC alleles by e.g in vitro folding, peptide exchange of already preloaded MHC complexes or another method able to test of peptide binding to MHC I or II molecules.

9. Generate desired MHC multimer as described elsewhere herein and test efficacy in detecting specific T-cells using methods described in the section "Detection".

The MHC multimer reagents may be used in a diagnostic procedure or kit for testing patient and control samples e.g. by flow cytometry, immune histochemistry, Elispot or other methods as described herein.

How to Make a MHC Multimer Therapeutic Reagent

1. As step 1-8 above for diagnostic reagent.
9. Select additional molecules (e.g. biologically active molecules, toxins) to attach to the MHC multimer as described elsewhere herein. The additional molecules can have different functionalities as e.g. adjuvants, specific activators, toxins etc.
10. Test the therapeutic reagent following general guidelines
11. Use for therapy Processes Involving MHC Multimers Thus, the present invention relates to methods for detecting the presence of MHC recognising cells in a sample comprising the steps of
(a) providing a sample suspected of comprising MHC recognising cells,
(b) contacting the sample with a MHC multimer as defined above, and
(c) determining any binding of the MHC multimer, which binding indicates the presence of MHC recognising cells.

Such methods are a powerful tool in diagnosing various diseases. Establishing a diagnosis is important in several ways. A diagnosis gives information about the disease, thus the patient can be offered a suitable treatment regime. Also, establishing a more specific diagnosis may give important information about a subtype of a disease for which a particular treatment will be beneficial (i.e. various subtypes of diseases may involve display of different peptides which are recognised by MHC recognising cells, and thus treatment can be targeted effectively against a particular subtype). In this way, it may also be possible to gain information about aberrant cells, which emerge through the progress of the disease or condition, or to investigate whether and how T-cell specificity is affected. The binding of the MHC multimer makes possible these options, since the binding is indicative for the presence of the MHC recognising cells in the sample, and accordingly the presence of MHC multimeres displaying the peptide.

The present invention also relates to methods for monitoring MHC recognising cells comprising the steps of
(a) providing a sample suspected of comprising MHC recognising cells,
(b) contacting the sample with a MHC complex as defined above, and
(c) determining any binding of the MHC multimer, thereby monitoring MHC recognising cells.

Such methods are a powerful tool in monitoring the progress of a disease, e.g. to closely follow the effect of a treatment. The method can i.a. be used to manage or control the disease in a better way, to ensure the patient receives the optimum treatment regime, to adjust the treatment, to confirm remission or recurrence, and to ensure the patient is not treated with a medicament which does not cure or alleviate the disease. In this way, it may also be possible to monitor aberrant cells, which emerge through the progress of the disease or condition, or to investigate whether and how T-cell specificity is affected during treatment. The binding of the MHC multimer makes possible these options, since the binding is indicative for the presence of the MHC recognising cells in the sample, and accordingly the presence of MHC multimers displaying the peptide.

The present invention also relates to methods for establishing a prognosis of a disease involving MHC recognising cells comprising the steps of
(a) providing a sample suspected of comprising MHC recognising cells,
(b) contacting the sample with a MHC multimer as defined above, and
(c) determining any binding of the MHC multimer, thereby establishing a prognosis of a disease involving MHC recognising cells.

Such methods are a valuable tool in order to manage diseases, i.a. to ensure the patient is not treated without effect, to ensure the disease is treated in the optimum way, and to predict the chances of survival or cure. In this way, it may also be possible to gain information about aberrant cells, which emerge through the progress of the disease or condition, or to investigate whether and how T-cell specificity is affected, thereby being able to establish a prognosis. The binding of the MHC multimer makes possible these options, since the binding is indicative for the presence of the MHC recognising cells in the sample, and accordingly the presence of MHC complexes displaying the peptide.

The present invention also relates to methods for determining the status of a disease involving MHC recognising cells comprising the steps of
(a) providing a sample suspected of comprising MHC recognising cells,
(b) contacting the sample with a MHC complex as defined above, and
(c) determining any binding of the MHC complex, thereby determining the status of a disease involving MHC recognising cells.

Such methods are a valuable tool in managing and controlling various diseases. A disease could, e.g. change from one stage to another, and thus it is important to be able to determine the disease status. In this way, it may also be possible to gain information about aberrant cells which emerge through the progress of the disease or condition, or to investigate whether and how T-cell specificity is affected, thereby determining the status of a disease or condition. The binding of the MHC complex makes possible these options, since the binding is indicative for the presence of the MHC recognising cells in the sample, and accordingly the presence of MHC complexes displaying the peptide.

The present invention also relates to methods for the diagnosis of a disease involving MHC recognising cells comprising the steps of
(a) providing a sample suspected of comprising MHC recognising cells,
(b) contacting the sample with a MHC multimer as defined above, and
(c) determining any binding of the MHC multimer, thereby diagnosing a disease involving MHC recognising cells.

Such diagnostic methods are a powerful tool in the diagnosis of various diseases. Establishing a diagnosis is important in several ways. A diagnosis gives information about the disease, thus the patient can be offered a suitable treatment regime. Also, establishing a more specific diagnosis may give important information about a subtype of a disease for which a particular treatment will be beneficial (i.e. various subtypes of diseases may involve display of different peptides which are recognised by MHC recognising cells, and thus treatment can be targeted effectively against a particular subtype). Valuable information may also be obtained about aberrant cells emerging through the progress of the disease or condition as well as whether and how T-cell specificity is affected. The binding of the MHC multimer makes possible these options, since the binding is indicative for the presence of the MHC recognising cells in the sample, and accordingly the presence of MHC multimers displaying the peptide.

The present invention also relates to methods of correlating cellular morphology with the presence of MHC recognising cells in a sample comprising the steps of
(a) providing a sample suspected of comprising MHC recognising cells,
(b) contacting the sample with a MHC multimer as defined above, and
(c) determining any binding of the MHC multimer, thereby correlating the binding of the MHC multimer with the cellular morphology.

Such methods are especially valuable as applied in the field of histochemical methods, as the binding pattern and distribution of the MHC multimeres can be observed directly. In such methods, the sample is treated so as to preserve the morphology of the individual cells of the sample. The information gained is important i.a. in diagnostic procedures as sites affected can be observed directly.

The present invention also relates to methods for determining the effectiveness of a medicament against a disease involving MHC recognising cells comprising the steps of
(a) providing a sample from a subject receiving treatment with a medicament,
(b) contacting the sample with a as defined herein, and
(c) determining any binding of the MHC multimer, thereby determining the effectiveness of the medicament.

Such methods are a valuable tool in several ways. The methods may be used to determine whether a treatment is effectively combating the disease. The method may also provide information about aberrant cells which emerge through the progress of the disease or condition as well as whether and how T-cell specificity is affected, thereby providing information of the effectiveness of a medicament in question. The binding of the MHC multimer makes possible these options, since the binding is indicative for the presence of the MHC recognising cells in the sample, and accordingly the presence of MHC multimeres displaying the peptide.

The present invention also relates to methods for manipulating MHC recognising cells populations comprising the steps of
(a) providing a sample comprising MHC recognising cells,
(b) contacting the sample with a MHC multimer immobilised onto a solid support as defined above,
(c) isolating the relevant MHC recognising cells, and
(d) expanding such cells to a clinically relevant number, with or without further manipulation.

Such ex vivo methods are a powerful tool to generate antigen-specific, long-lived human effector T-cell populations that, when re-introduced to the subject, enable killing of target cells and has a great potential for use in immunotherapy applications against various types of cancer and infectious diseases.

As used everywhere herein, the term "MHC recognising cells" are intended to mean such which are able to recognise and bind to MHC multimeres. The intended meaning of "MHC multimeres" is given above. Such MHC recognising cells may also be called MHC recognising cell clones, target cells, target MHC recognising cells, target MHC molecule recognising cells, MHC molecule receptors, MHC receptors, MHC peptide specific receptors, or peptide-specific cells. The term "MHC recognising cells" is intended to include all subsets of normal, abnormal and defect cells, which recognise and bind to the MHC molecule. Actually, it is the receptor on the MHC recognising cell that binds to the MHC molecule.

As described above, in diseases and various conditions, peptides are displayed by means of MHC multimeres, which are recognised by the immune system, and cells targeting such MHC multimeres are produced (MHC recognising cells). Thus, the presence of such MHC protein recognising cells is a direct indication of the presence of MHC multimeres displaying the peptides recognised by the MHC protein recognising cells. The peptides displayed are indicative and may involved in various diseases and conditions.

For instance, such MHC recognising cells may be involved in diseases of inflammatory, auto-immune, allergic, viral, cancerous, infectious, allo- or xenogene (graft versus host and host versus graft) origin.

The MHC multimeres of the present invention have numerous uses and are a valuable and powerful tool e.g. in the fields of therapy, diagnosis, prognosis, monitoring, stratification, and determining the status of diseases or conditions. Thus, the MHC multimeres may be applied in the various methods involving the detection of MHC recognising cells.

Furthermore, the present invention relates to compositions comprising the MHC multimeres in a solubilising medium. The present invention also relates to compositions comprising the MHC multimeres immobilised onto a solid or semi-solid support.

The MHC multimers can be used in a number of applications, including analyses such as flow cytometry, immunohistochemistry (IHC), and ELISA-like analyses, and can be used for diagnostic, prognostic or therapeutic purposes including autologous cancer therapy or vaccines such as HIV vaccine or cancer vaccine.

The MHC multimeres are very suitable as detection systems. Thus, the present invention relates to the use of the MHC multimeres as defined herein as detection systems.

In another aspect, the present invention relates to the general use of MHC peptide complexes and multimers of such MHC peptide complexes in various methods. These methods include therapeutic methods, diagnostic methods, prognostic methods, methods for determining the progress and status of a disease or condition, and methods for the stratification of a patient.

The MHC multimeres of the present invention are also of value in testing the expected efficacy of medicaments against or for the treatment of various diseases. Thus, the present invention relates to methods of testing the effect of medicaments or treatments, the methods comprising detecting the binding of the MHC multimeres to MHC recognising cells and establishing the effectiveness of the medicament or the treatment in question based on the specificity of the MHC recognising cells.

As mentioned above, the present invention also relates generally to the field of therapy. Thus, the present invention relates per se to the MHC multimer as defined herein for use as medicaments, and to the MHC multimeres for use in in vivo and ex vivo therapy.

The present invention relates to therapeutic compositions comprising as active ingredients the MHC multimeres as defined herein.

An important aspect of the present invention is therapeutic compositions comprising as active ingredients effective amounts of MHC recognising cells obtained using the MHC multimeres as defined herein to isolate relevant MHC recognising cells, and expanding such cells to a clinically relevant number.

The present invention further relates to methods for treating, preventing or alleviating diseases, methods for inducing anergy of cells, as well as to methods for up-regulating, down-regulating, modulating, stimulating, inhibiting, restoring, enhancing and/or otherwise manipulating immune responses.

The invention also relates to methods for obtaining MHC recognising cells by using the MHC multimeres as described herein.

Also encompassed by the present invention are methods for preparing the therapeutic compositions of the invention.

The present invention is also directed to generating MHC multimeres for detecting and analysing receptors on MHC recognising cells, such as epitope specific T-cell clones or other immune competent effector cells.

It is a further object of the present invention to provide new and powerful strategies for the development of curative vaccines. This in turn will improve the possibilities for directed and efficient immune manipulations against diseases caused by tumour genesis or infection by pathogenic agent like viruses and bacteria. HIV is an important example. The ability to generate and optionally attach recombinant MHC multimeres to multimerization domains, such as scaffolds and/or carrier molecules, will enable the development of a novel analytical and therapeutic tool for monitoring immune responses and contribute to a rational platform for novel therapy and "vaccine" applications.

Therapeutic compositions (e.g. "therapeutical vaccines") that stimulate specific T-cell proliferation by peptide-specific stimulation is indeed a possibility within the present invention. Thus, quantitative analysis and ligand-based detection of specific T-cells that proliferate by the peptide specific stimulation should be performed simultaneously to monitoring the generated response.

For all of those applications, it is important to choose the right MHC allele as well as a peptide that binds well to the MHC protein. It is also important that the chosen MHC allele and peptide forms a MHC-peptide complex that is efficiently and specifically recognized by the TCR. For applications that involve binding as well as activation of cells, further restrictions on the choice of MHC and peptide can apply.

Application of MHC Multimers in Immune Monitoring, Diagnostics, Therapy, Vaccine MHC multimers detect antigen specific T cells of the various T cell subsets. T cells are pivotal for mounting an adaptive immune response. It is therefore of importance to be able to measure the number of specific T cells when performing a monitoring of a given immune response. Typically, the adaptive immune response is monitored by measuring the specific antibody response, which is only one of the effector arms of the immune system. This can lead to miss-interpretation of the actual clinical immune status.

In many cases intruders of the organism can hide away inside the cells, which can not provoke a humoral response. In other cases, e.g. in the case of certain viruses the intruder mutates fast, particularly in the genes encoding the proteins that are targets for the humoral response. Examples include the influenza and HIV viruses. The high rate of mutagenesis renders the humoral response unable to cope with the infection. In these cases the immune system relies on the cellular immune response. When developing vaccines against such targets one needs to provoke the cellular response in order to get an efficient vaccine.

Developing vaccines that should give rise to lifelong protection is another case where the cellular immune system needs to be activated. Commonly, various childhood vaccines are expected to give lifelong protection but will only come to trial many years after the vaccination has been performed and then there is only to hope that it actually have created effective immunity.

Therapeutically cancer vaccines generally rely on cytotoxic effector T cells and have short duration of function. Therefore, continuous monitoring is important.

MHC multimers are therefore very important for immune monitoring of vaccine responses both during vaccine development, as a means to verify the obtained immunity for lifelong vaccines and to follow cancer patients under treatment with therapeutically cancer vaccines.

The number of antigen specific cytotoxic T cells can be used as surrogate markers for the overall wellness of the immune system. The immune system can be compromised severely by natural causes such as HIV infections or big traumas or by immuno suppressive therapy in relation to transplantation. The efficacy of an anti HIV treatment can be evaluated by studying the number of common antigen-specific cytotoxic T cells, specific against for example Cytomegalovirus (CMV) and Epstein-Barr virus. In this case the measured T cells can be conceived as surrogate markers. The treatment can then be corrected accordingly and a prognosis can be made.

A similar situation is found for patients undergoing transplantation as they are severely immune compromised due to pharmaceutical immune suppression to avoid organ rejection. The suppression can lead to outbreak of opportunistic infections caused by reactivation of otherwise dormant viruses residing in the transplanted patients or the grafts. This can be the case for CMV and EBV viruses. Therefore measurement of the number of virus specific T cells can be used to give a prognosis for the outcome of the transplantation and adjustment of the immune suppressive treatment. Similarly, the BK virus has been implied as a causative reagent for kidney rejection. Therefore measurement of BK-virus specific T cells can have prognostic value.

In relation to transplantation, the presence of specific T cells directed against minor histocompatibility antigens (mHAgs) are important as they can cause graft versus host reaction/disease that can develop to a fatal situation for the patient. Again, a well-adjusted immune suppressive treatment is important. A similar reaction denoted graft versus cancer is sometimes employed in the treatment of malignancies of the lymphoid system. It is evident that such treatment is balancing on the edge of a knife and will benefit of specific measurement of relevant effector T cells.

Due to lack of organs, transplantations across greater mismatches are increasingly making harsher immune suppressive treatment more common. This calls for more efficient methods to monitor the immune status of the patient so that corrective measures in the treatment can be applied in due cause.

MHC multimers can be of importance in diagnosis of infections caused by bacteria, virus and parasites that hide away inside cells. Serum titers can be very low and direct measurement of the disease-causing organisms by PCR can be very difficult because the host cells are not identified or are inaccessible. Other clinical symptoms of a chronical infection can be unrecognizable in an otherwise healthy individuals, even though such persons still are disease-carriers and at risk of becoming spontaneously ill if being compromised by other diseases or stress. Likewise, cancers can also be diagnosed early in its development if increased numbers of cancer specific T cells can be measured in circulation, even though the tumor is not yet localized.

Antigen specific tumor infiltrating lymphocytes can be used to identify tumor lesions and metastases as the antigen specific T cells will migrate/home to the tumor site to exert their help or immuno modulatory action (CD4+ T helper cells) or cytotoxic killing of tumor cells expressing the tumor specific/tumor associated peptide MHC multimer (CD8+ T-cells). Likewise identification of sites of infection tumor lesions can be identified as they typically attract antigen specific T-cells.

Localization of tumors and sites of infection can be carried out using antigen specific T-cells labelled with a paramagnetic isotope in conjunction with magnetic resonance imaging (MRI) or electron spin resonance (ESR). In general, any conventional method for diagnostic imaging visualization can be utilized. Usually gamma and positron emitting radioisotopes are used for camera and paramagnetic isotopes for MRI.

For peripheral cancer lesion in skin (e.g. melanoma) fluorescently labeled antigen specific T-cells can be used likewise.

MHC multimers may be used to label the tumor infiltration lymphocytes, e.g. MHC multimers may be labeled with a paramagnetic isotope are injected into the patient, the labeled MHC multimer binds specific T cells and are then internalized thereby introducing the paragmagnetic isotope to the T cell in this way labelling the T cell.

Antigen-specific T helper cells and regulatory T cells have been implicated in the development of autoimmune disorders. In most cases the timing of events leading to autoimmune disease is unknown and the exact role of the immune cells not clear. Use of MHC multimers to study these diseases will lead to greater understanding of the disease-causing scenario and make provisions for development of therapies and vaccines for these diseases.

Therapeutically use of MHC multimers can be possible, either directly or as part of therapeutically vaccines. When performing autologous cancer therapy it is often recognized that the in vitro amplified cancer-specific effector T cells do not home effectively to the correct target sites but ends up in the lungs. If the molecules responsible for interaction with the correct homing receptor can be identified these can be added to the MHC multimer making a dual, triple or multiple molecular structure that are able to aid the antigen-specific T cells home to the correct target, as the MHC multimer will bind to the specific T cell and the additional molecules will mediate binding to the target cells.

In a preferable embodiment, MHC multimers bound to other functional molecules are employed to directly block, regulate or kill these cells.

When it become possible to identify and pinpoint the exact function of regulatory T cells it may be possible to directly block, regulate or kill these cells by means of MHCmers bound other functional molecules. The MHC multimeres specifically recognize the target T cells and direct the action of the other molecules to the target.

Derivatives of MHC multimers can be useful as vaccines, as vaccine components or as engineered intelligent adjuvant. The possibility of combining MHC multimeres that specifically bind certain T cells with molecules that trigger, e.g. the humoral response or the innate immune response, can accelerate vaccine development and improve the efficiency of vaccines.

Diseases

In relation to the use and application of MHCmers in immune monitoring, diagnostics, prognostics, therapy and vaccines in relation to diseases several organisms and human proteins are of relevance, comprising but not limited to the following;

Infectious Diseases a) caused by virus such as,
Adenovirus (subgropus A-F), BK-virus, CMV (Cytomegalo virus, HHV-5), EBV (Epstein Barr Virus, HHV-4), HBV (Hepatitis B Virus), HCV (Hepatitis C virus), HHV-6a and b (Human Herpes Virus-6a and b), HHV-7, HHV-8, HSV-1 (Herpes simplex virus-1, HHV-1), HSV-2 (HHV-2), JC-virus, SV-40 (Simian virus 40), VZV (Varizella-Zoster-Virus, HHV-3), Parvovirus B19, *Haemophilus influenza*, HIV-1 (Human immunodeficiency Virus-1), HTLV-1 (Human T-lymphotrophic virus-1), HPV (Human Papillomavirus giving rise to clinical manifestions such as Hepatitis, AIDS, Measles, Pox, Chicken pox, Rubella, Herpes and others b) caused by bacteria such as,
Gram positive bacteria, gram negative bacteria, intracellular bacterium, extracellular bacterium, *Mycobacterium tuberculosis, Mycobacterium bovis, Mycobacterium avium* subsp. paratuberculosis *Borrelia burgdorferi*, other spirochetes, *Helicobacter pylori, Streptococcus pneumoniae, Listeria monocytogenes, Histoplasma capsulatum, Bartonella henselae, Bartonella quintana* giving rise to clinical manifestations such as Tuberculosis, Pneumonia, Stomach ulcers, Paratuberculosis and others c) caused by fungus such as,
*Aspergillus fumigatus, Candida albicans, Cryptococcus neoformans, Pneumocystis carinii* giving rise to clinical manifestations such as skin-, nail-, and mucosal infections, Meningitis, Sepsis and others Parasitic diseases caused by parasites such as,
*Plasmodium falciparum, Plasmodium vivax, Plasmodium malariae, Schistosoma mansoni, Schistosoma japonicum, Schistosoma haematobium, Trypanosoma cruzi, Trypanosoma rhodesiense, Trypanosoma gambiense, Leishmania donovani, Leishmania tropica* giving rise to clinical manifestations such as Allergic diseases caused by allergens such as,
Birch, Hazel, Elm, Ragweed, Wormwood, Grass, Mould, Dust Mite giving rise to clinical manifestations such as Asthma Transplantation related disease caused by
reactions to minor histocompatibility antigens such as HA-1, HA-8, USP9Y, SMCY, TPR-protein, HB-1Y and other antigens in relation to, Graft-versus-host-related disease, allo- or xenogene reactions i.e. graft-versus-host and host-versus-graft disease.

Cancerous diseases associated with antigens such as
Survivin, Survivin-2B, Livin/ML-IAP, Bcl-2, Mcl-1, Bcl-X (L), Mucin-1, NY-ESO-1, Telomerase, CEA, MART-1, HER-2/neu, bcr-abl, PSA, PSCA, Tyrosinase, p53, hTRT, Leukocyte Proteinase-3, hTRT, gp100, MAGE antigens, GASC, JMJD2C, JARD2 (JMJ), JHDM3a, WT-1, CA 9, Protein kinases, in relation to clinical manifestations such as malignant melanoma, renal carcinoma, breast cancer, lung cancer, cancer of the uterus, cervical cancer, prostatic cancer, pancreatic cancer, brain cancer, head and neck cancer, leukemia, cutaneous lymphoma, hepatic carcinoma, colorectal cancer, bladder cancer Autoimmune and inflammatory diseases, associated with antigens such as GAD64, Collagen, human cartilage glycoprotein 39, □-amyloid, A□42, APP, Presenilin 1, in relation to clinical manifestations such as Diabetes type 1, Rheumatoid arthritis, Alzheimer, chronic inflammatory bowel disease, Crohn's disease, ulcerative colitis uterosa, Multiple Sclerosis, Psoriasis Approaches to the Analysis or Treatment of Diseases.

For each application of a MHC multimer, a number of choices must be made. These include:
- A. Disease (to be e.g. treated, prevented, diagnosed, monitored).
- B. Application (e.g. analyze by flow cytometry, isolate specific cells, induce an immune response)
- C. Label (e.g. should the MHC multimer be labelled with a fluorophore or a chromophore)
- D. Biologically active molecule (e.g. should a biologically active molecule such as an interleukin be added or chemically linked to the complex)
- E. Peptide (e.g. decide on a peptide to be complexed with MHC)
- F. MHC (e.g. use a MHC allele that does not interfere with the patient's immune system in an undesired way).

A number of diseases $A_1$-$A_n$, relevant in connection with MHC multimeres, have been described herein; a number of applications $B_1$-$B_n$, relevant in connection with MHC multimeres, have been described herein; a number of Labels $C_1$-$C_n$, relevant in connection with MHC multimeres, have been described herein; a number of biologically active molecules $D_1$-$D_n$, relevant in connection with MHC multimeres, have been described herein; a number of peptides $E_1$-$E_n$, relevant in connection with MHC multimeres, have been described herein; and a number of MHC molecules $F_1$-$F_n$, relevant in connection with MHC multimeres, have been described herein.

Thus, each approach involves a choice to be made regarding all or some of the parameters A-F. A given application and the choices it involves can thus be described as follows:

$$Ai \times Bi \times Ci \times Di \times Ei \times Fi$$

Where i specifies a number between 1 and n. n is different for different choices A, B, C, D, E, or F. Consequently, the present invention describes a large number of approaches to the diagnosis, monitoring, prognosis, therapeutic or vaccine treatment of diseases. The total number of approaches, as defined by these parameters, are $$n(A) \times n(B) \times n(C) \times n(D) \times n(E) \times n(F),$$

where n(A) describes the number of different diseases A described herein, n(B) describes the number of different applications B described herein, etc.

Detection

Diagnostic procedures, immune monitoring and some therapeutic processes all involve identification and/or enumeration and/or isolation of antigen specific T cells. Identification and enumeration of antigen specific T cells may be done in a number of ways, and several assays are currently employed to provide this information.

In the following it is described how MHC multimers as described in the present invention can be used to detect specific T cell receptors (TCRs) and thereby antigen specific T cells in a variety of methods and assays. In the present invention detection includes detection of the presence of antigen specific T cell receptors/T cells in a sample, detection of and isolation of cells or entities with antigen specific T cell receptor from a sample and detection and enrichment of cells or entities with antigen specific T cell receptor in a sample.

The sample may be a biologic sample including solid tissue, solid tissue section or a fluid such as, but not limited to, whole blood, serum, plasma, nasal secretions, sputum, urine, sweat, saliva, transdermal exudates, pharyngeal exudates, bronchoalveolar lavage, tracheal aspirations, cerebrospinal fluid, synovial fluid, fluid from joints, vitreous fluid, vaginal or urethral secretions, or the like. Herein, disaggregated cellular tissues such as, for example, hair, skin, synovial tissue, tissue biopsies and nail scrapings are also considered as biological samples.

Many of the assays are particularly useful for assaying T-cells in blood samples. Blood samples are whole blood samples or blood processed to remove erythrocytes and platelets (e.g., by Ficoll density centrifugation or other such methods known to one of skill in the art) and the remaining PBMC sample, which includes the T-cells of interest, as well as B-cells, macrophages and dendritic cells, is used directly.

In order to be able to measure detection of specific T cells by MHC multimers, labels and marker molecules can be used.

Marker Molecules

Marker molecules are molecules or complexes of molecules that bind to other molecules. Marker molecules thus may bind to molecules on entities, including the desired entities as well as undesired entities. Labeling molecules are molecules that may be detected in a certain analysis, i.e. the labeling molecules provide a signal detectable by the used method. Marker molecules, linked to labeling molecules, constitute detection molecules. Likewise labeling molecules linked to MHC multimers also constitute detection molecules but in contrast to detection molecules made up of marker and labeling molecule labeled MHC multimers are specific for TCR.

Sometimes a marker molecule in itself provides a detectable signal, wherefore attachment to a labeling molecule is not necessary.

Marker molecules are typically antibodies or antibody fragments but can also be aptamers, proteins, peptides, small organic molecules, natural compounds (e.g. steroids), non-peptide polymers, or any other molecules that specifically and efficiently bind to other molecules are also marker molecules.

Labelling Molecules

Labelling molecules are molecules that can be detected in a certain analysis, i.e. the labelling molecules provide a signal detectable by the used method. The amount of labelling molecules can be quantified.

The labelling molecule is preferably such which is directly or indirectly detectable.

The labelling molecule may be any labelling molecule suitable for direct or indirect detection. By the term "direct" is meant that the labelling molecule can be detected per se without the need for a secondary molecule, i.e. is a "primary" labelling molecule. By the term "indirect" is meant that the labelling molecule can be detected by using one or more "secondary" molecules, i.e. the detection is performed by the detection of the binding of the secondary molecule(s) to the primary molecule.

The labelling molecule may further be attached via a suitable linker. Linkers suitable for attachment to labelling molecules would be readily known by the person skilled in the art and as described elsewhere herein for attachment of MHC molecules to multimerisation domains.

Examples of such suitable labelling compounds are fluorescent labels, enzyme labels, radioisotopes, chemiluminescent labels, bioluminescent labels, polymers, metal particles, haptens, antibodies, and dyes.

The labelling compound may suitably be selected: from fluorescent labels such as 5-(and 6)-carboxyfluorescein, 5- or 6-carboxyfluorescein, 6-(fluorescein)-5-(and 6)-carboxamido hexanoic acid, fluorescein isothiocyanate (FITC), rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, Green fluorescent protein (GFP) and analogues thereof, and conjugates of R-phycoerythrin or allophycoerythrin and e.g. Cy5 or Texas Red, and inorganic fluorescent labels based on semiconductor nanocrystals (like quantum dot and Qdot™ nanocrystals), and time-resolved fluorescent labels based on lanthanides like Eu3+ and Sm3+, from haptens such as DNP, biotin, and digoxiginin, from enzymic labels such as horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase and glucose oxidase (GO), from luminescence labels such as luminol, isoluminol, acridinium esters, 1,2-dioxetanes and pyridopyridazines, and from radioactivity labels such as incorporated isotopes of iodide, cobalt, selenium, tritium, and phosphor.

Radioactive labels may in particular be interesting in connection with labelling of the peptides harboured by the MHC multimeres.

Different principles of labelling and detection exist, based on the specific property of the labelling molecule. Examples of different types of labelling are emission of radioactive radiation (radionuclide, isotopes), absorption of light (e.g. dyes, chromophores), emission of light after excitation (fluorescence from fluorochromes), NMR (nuclear magnetic resonance form paramagnetic molecules) and reflection of light (scatter from e.g. such as gold-, plastic- or glass-beads/particles of various sizes and shapes). Alternatively, the labelling molecules can have an enzymatic activity, by which they catalyze a reaction between chemicals in the near environment of the labelling molecules, producing a signal, which include production of light (chemi-luminescence), precipitation of chromophor dyes, or precipitates that can be detected by an additional layer of detection molecules. The enzymatic product can deposit at the location of the enzyme or, in a cell based analysis system, react with the membrane of the cell or diffuse into the cell to which it is attached. Examples of labelling molecules and associated detection principles are shown in table 2 below.

TABLE 2

Examples of labelling molecules and associated detection principles.

| Labelling substance | Effect | Assay-principle |
|---|---|---|
| Fluorochromes | emission of light having a specific spectra | □Photometry, Microscopy, spectroscopy PMT, photographic film, CCD's (Color-Capture Device or Charge-coupled device). |
| Radionuclide | irradiation, α, β or gamma rays | Scintillation counting, GM-tube, photographic film, excitation of phosphor-imager screen |
| Enzyme; HRP, (horse reddish peroxidase), | catalysis of $H_2O_2$ reduction using luminol as Oxygen acceptor, resulting | □Photometry, Microscopy, spectroscopy PMT, photographic |

TABLE 2-continued

Examples of labelling molecules and associated detection principles.

| Labelling substance | Effect | Assay-principle |
|---|---|---|
| peroxidases in general | in oxidized luminal + light catalysis of $H_2O_2$ reduction using a soluble dye, or molecule containing a hapten, such as a biotin residue as Oxygen acceptor, resulting in precipitation. The habten can be recognized by a detection molecule. | film, CCD's (Colour-Capture Device or Charge-coupled device), Secondary label linked antibody |
| Particles; gold, polystyrene beads, pollen and other particles | Change of scatter, reflection and transparency of the associated entity | Microscopy, cytometry, electron microscopy PMT's, light detecting devices, flowcytometry scatter |
| AP (Alkaline Phosphatase) | Catalyze a chemical conversion of a non-detectable to a precipitated detectable molecule, such as a dye or a hapten | □Photometry, Microscopy, spectroscopy Secondary label linked antibody |
| Ionophores or chelating chemical compounds binding to specific ions, e.g. $Ca^{2+}$ | Change in absorption and emission spectrums when binding. Change in intensity | □Photometry, Cytometry, spectroscopy |
| Lanthanides | Fluorescence Phosphorescence | □photometry, cytometry, spectroscopy |
|  | Paramagnetic | NMR (Nuclear magnetic resonance) |
| DNA fluorescing stains | Propidium iodide Hoechst stain DAPI AMC DraQ5 ™ Acridine orange 7-AAD | □Photometry, cytometry, spectroscopy |

□Photometry; is to be understood as any method that can be applied to detect the intensity, analyze the wavelength spectra, and or measure the accumulation of light derived form a source emitting light of one or multiple wavelength or spectra.

Labelling molecules can be used to label MHC multimers as well as other reagents used together with MHC multimers, e.g. antibodies, aptamers or other proteins or molecules able to bind specific structures in another protein, in sugars, in DNA or in other molecules. In the following molecules able to bind a specific structure in another molecule are named a marker. Labelling molecules can be attached to a given MHC multimer or any other protein marker by covalent linkage as described for attachment of MHC multimeres to multimerization domains elsewhere herein. The attachment can be directly between reactive groups in the labelling molecule and reactive groups in the marker molecule or the attachment can be through a linker covalently attached to labelling molecule and marker, both as described elsewhere herein. When labelling MHC multimers the label can be attached either to the MHC complex (heavy chain, β2m or peptide) or to the multimerization domain.

In particular, one or more labelling molecules may be attached to the carrier molecule, or one or more labelling molecules may be attached to one or more of the scaffolds, or one or more labelling compounds may be attached to one or more of the MHC complexes, or one or more labelling compounds may be attached to the carrier molecule and/or one or more of the scaffolds and/or one or more of the MHC complexes, or one or more labelling compounds may be attached to the peptide harboured by the MHC molecule.

A single labelling molecule on a marker does not always generate sufficient signal intensity. The signal intensity can be improved by assembling single label molecules into large multi-labelling compounds, containing two or more label molecule residues. Generation of multi-label compounds can be achieved by covalent or non-covalent, association of labelling molecules with a major structural molecule. Examples of such structures are synthetic or natural polymers (e.g. dextramers), proteins (e.g. streptavidin), or polymers. The labelling molecules in a multi-labelling compound can all be of the same type or can be a mixture of different labelling molecules.

In some applications, it may be advantageous to apply different MHC complexes, either as a combination or in individual steps. Such different MHC multimeres can be differently labelled (i.e. by labelling with different labelling compounds) enabling visualisation of different target MHC recognising cells. Thus, if several different MHC multimeres with different labelling compounds are present, it is possible simultaneously to identify more than one specific receptor, if each of the MHC multimeres present a different peptide.

Detection principles, such as listed in Table 2, can be applied to flow cytometry, stationary cytometry, and batch-based analysis. Most batch-based approaches can use any of the labelling substances depending on the purpose of the assay. Flow cytometry primarily employs fluorescence, whereas stationary cytometry primarily employs light absorption, e.g. dyes or chromophore deposit from enzymatic activity. In the following section, principles involving fluorescence detection will be exemplified for flow cytometry, and principles involving chromophore detection will be exemplified in the context of stationary cytometry. However, the labelling molecules can be applied to any of the analyses described in this invention.

Labelling molecules of particular utility in Flow Cytometry:

In flow cytometry the typical label is detected by its fluorescence. Most often a positive detection is based on the presents of light from a single fluorochrome, but in other techniques the signal is detected by a shift in wavelength of emitted light; as in FRET based techniques, where the exited fluorochrome transfer its energy to an adjacent bound fluorochrome that emits light, or when using $Ca^{2+}$ chelating fluorescent props, which change the emission (and absorption) spectra upon binding to calcium.

Preferably labelling molecules employed in flow cytometry are illustrated in Table 3 and 4 and described in the following.

Simple fluorescent labels:
Fluor dyes, Pacific Blue™, Pacific Orange™, Cascade Yellow™,
AlexaFluor® (AF);
AF405, AF488, AF500, AF514, AF532, AF546, AF555, AF568, AF594, AF610, AF633, AF635, AF647, AF680, AF700, AF710, AF750, AF800
Quantum Dot based dyes, QDot® Nanocrystals (Invitrogen, MolecularProbs)
Qdot®525, Qdot®565, Qdot®585, Qdot®605, Qdot®655, Qdot®705, Qdot®800

DyLight™ Dyes (Pierce) (DL);
DL549, DL649, DL680, DL800
Fluorescein (Flu) or any derivate of that, ex. FITC
Cy-Dyes
Cy2, Cy3, Cy3.5, Cy5, Cy5.5, Cy7
Fluorescent Proteins;
RPE, PerCp, APC
Green fluorescent proteins;
GFP and GFP derivated mutant proteins; BFP, CFP, YFP, DsRed, T1, Dimer2, mRFP1, MBanana, mOrange, dTomato, tdTomato, mTangerine, mStrawberry, mCherry
Tandem dyes:
RPE-Cy5, RPE-Cy5.5, RPE-Cy7, RPE-AlexaFluor® tandem conjugates; RPE-Alexa610, RPE-TxRed
APC-Aleca600, APC-Alexa610, APC-Alexa750, APC-Cy5, APC-Cy5.5
Ionophors; ion chelating fluorescent props
Props that change wavelength when binding a specific ion, such as Calcium Props that change intensity when binding to a specific ion, such as Calcium
Combinations of fluorochromes on the same marker. Thus, the marker is not identified by a single fluorochrome but by a code of identification being a specific combination of fluorochromes, as well as inter related ratio of intensities.
Example: Antibody Ab1 and Ab2, are conjugated to both. FITC and BP but Ab1 have 1 FITC to 1 BP whereas Ab2 have 2 FITC to 1 BP. Each antibody may then be identified individually by the relative intensity of each fluorochrome. Any such combinations of n fluorochromes with m different ratios can be generated.

TABLE 3

Examples of preferable fluorochromes

| Fluorofor/Fluorochrome | Excitation nm | Emission nm |
|---|---|---|
| 2-(4'-maleimidylanilino)naphthalene-6-sulfonic acid, sodium salt | 322 | 417 |
| 5-((((2-iodoacetyl)amino)ethyl)amino) naphthalene-1-sulfonic acid | 336 | 490 |
| Pyrene-1-butanoic acid | 340 | 376 |
| AlexaFluor 350 (7-amino-6-sulfonic acid-4-methyl coumarin-3-acetic acid) | 346 | 442 |
| AMCA (7-amino-4-methyl coumarin-3-acetic acid) | 353 | 442 |
| 7-hydroxy-4-methyl coumarin-3-acetic acid | 360 | 455 |
| Marina Blue (6,8-difluoro-7-hydroxy-4-methyl coumarin-3-acetic acid) | 362 | 459 |
| 7-dimethylamino-coumarin-4-acetic acid | 370 | 459 |
| Fluorescamin-N-butyl amine adduct | 380 | 464 |
| 7-hydroxy-coumarine-3-carboxylic acid | 386 | 448 |
| CascadeBlue (pyrene-trisulphonic acid acetyl azide) | 396 | 410 |
| Cascade Yellow | 409 | 558 |
| Pacific Blue (6,8 difluoro-7-hydroxy coumarin-3-carboxylic acid) | 416 | 451 |
| 7-diethylamino-coumarin-3-carboxylic acid | 420 | 468 |
| N-(((4-azidobenzoyl)amino)ethyl)-4-amino-3,6-disulfo-1,8-naphthalimide, dipotassium salt | 426 | 534 |
| Alexa Fluor 430 | 434 | 539 |
| 3-perylenedodecanoic acid | 440 | 448 |
| 8-hydroxypyrene-1,3,6-trisulfonic acid, trisodium salt | 454 | 511 |
| 12-(N-(7-nitrobenz-2-oxa-1,3-diazol-4-yl)amino)dodecanoic acid | 467 | 536 |
| N,N'-dimethyl-N-(iodoacetyl)-N'-(7-nitrobenz-2-oxa-1,3-diazol-4-yl)ethylenediamine | 478 | 541 |
| Oregon Green 488 (difluoro carboxy fluorescein) | 488 | 518 |
| 5-iodoacetamidofluorescein | 492 | 515 |
| propidium iodide-DNA adduct | 493 | 636 |
| Carboxy fluorescein | 495 | 519 |

TABLE 4

Examples of preferable fluorochrome families

| Fluorochrome family | Example fluorochrome |
|---|---|
| AlexaFluor ®(AF) | AF ®350, AF405, AF430, AF488, AF500, AF514, AF532, AF546, AF555, AF568, AF594, AF610, AF633, AF635, AF647, AF680, AF700, AF710, AF750, AF800 |
| Quantum Dot (Qdot ®) based dyes | Qdot ®525, Qdot ®565, Qdot ®585, Qdot ®605, Qdot ®655, Qdot ®705, Qdot ®800 |
| DyLight ™ Dyes (DL) | DL549, DL649, DL680, DL800 |
| Small fluorescing dyes | FITC, Pacific Blue ™, Pacific Orange ™, Cascade Yellow ™, Marina blue ™, DSred, DSred-2, 7-AAD, TO-Pro-3, |
| Cy-Dyes | Cy2, Cy3, Cy3.5, Cy5, Cy5.5, Cy7 |
| Phycobili Proteins: | R-Phycoerythrin (RPE), PerCP, Allophycocyanin (APC), B-Phycoerythrin, C-Phycocyanin |
| Fluorescent Proteins | (E)GFP and GFP ((enhanced) green fluorescent protein) derived mutant proteins; BFP, CFP, YFP, DsRed, Ti, Dimer2, mRFP1,MBanana, mOrange, dTomato, tdTomato, mTangerine, mStrawberry, mCherry |
| Tandem dyes with RPE | RPE-Cy5, RPE-Cy5.5, RPE-Cy7, RPE-AlexaFluor ® tandem conjugates; RPE-Alexa610, RPE-TxRed |
| Tandem dyes with APC | APC-Aleca600, APC-Alexa610, APC-Alexa750, APC-Cy5, APC-Cy5.5 |
| Calcium dyes | Indo-1-Ca2+ Indo-2-Ca2+ |

Preferably Labelling Molecules Employed in Stationary Cytometry and IHC

Enzymatic labelling, as exemplified in Table 5:

Horse radish peroxidase; reduces peroxides ($H_2O_2$), and the signal is generated by the Oxygen acceptor when being oxidized.

Precipitating dyes; Dyes that when they are reduced they are soluble, and precipitate when oxidized, generating a coloured deposit at the site of the reaction.

Precipitating agent, carrying a chemical residue, a hapten, for second layer binding of marker molecules, for amplification of the primary signal.

Luminol reaction, generating a light signal at the site of reaction.

Other enzymes, such as Alkaline Phosphatase, capable of converting a chemical compound from a non-detectable molecule to a precipitated detectable molecule, which can be coloured, or carries a hapten as described above.

Fluorescent labels, as exemplified in Table 3 and 4; as those described for Flow cytometry are likewise important for used in stationary cytometry, such as in fluorescent microscopy.

TABLE 5

Examples of preferable labels for stationary cytometry

| Label | Enzyme substrate, Oxygen acceptor Chromogen/ precipitating agent | Precipitate or Residue, hapten* for secondary detection layer | Binding partner to hapten |
|---|---|---|---|
| HRP | diaminobenzidine (DAB) | Colored precipitate | — |
| HRP | 3-amino-9-ethyl-carbazole (AEC+) | Colored precipitate | — |
| AP | Fast red dye | Red precipitate | — |
| HRP | biotinyl tyramide | Exposed Biotin residue | Streptavidin, avidine |
| HRP | fluorescein tyramide | Exposed Fluorescein residue | Anti-Fluorecein Antibody |
| "Enzyme" | Substrate that when reacted precipitate | Primary label; being a dye, chemiluminescence's , or exposure of a hapten | Secondary label in case the primary label is a hapten |

Detection Methods and Principles

Detection of TCRs with multimers may be direct or indirect.

Direct Detection

Direct detection of TCRs is detection directly of the binding interaction between the specific T cell receptor and the MHC multimer. Direct detection includes detection of TCR when TCR is attached to lipid bilayer, when TCR is attached to or in a solid medium or when TCR is in solution.

Direct Detection of TCR Attached to Lipid Bilayer

One type of TCRs to detect and measure are TCRs attached to lipid bilayer including but is not limited to naturally occurring T cells (from blood, spleen, lymphnode, brain or any other tissue containing T cells), TCR transfected cells, T cell hybridomas, TCRs embedded in liposomes or any other membrane structure. In the following methods for direct detection of entities of TCRs attached to lipid bilayer will be described and any entity consisting of TCR attached to lipid bilayer will be referred to as T cells.

T cells can be directly detected either when in a fluid solution or when immobilized to a support.

Direct Detection of T Cells in Fluid Sample.

T cells can be detected in fluid samples as described elsewhere herein and in suspension of disrupted tissue, in culture media, in buffers or in other liquids. T cells in fluid samples can be detected individually or detected as populations of T cells. In the following different methods for direct detection of T cells in fluid samples are shown.

Direct Detection of Individual T Cells

Direct Detection of Individual T Cells Using Flow Cytometry.

A suspension of T cells are added MHC multimers, the sample washed and then the amount of MHC multimer bound to each cell are measured. Bound MHC multimers may be labelled directly or measured through addition of labelled marker molecules. The sample is analyzed using a flow cytometer, able to detect and count individual cells passing in a stream through a laser beam. For identification of specific T cells using MHC multimers, cells are stained with fluorescently labeled MHC multimer by incubating cells with MHC multimer and then forcing the cells with a large volume of liquid through a nozzle creating a stream of spaced cells. Each cell passes through a laser beam and any fluorochrome bound to the cell is excited and thereby fluoresces. Sensitive photomultipliers detect emitted fluorescence, providing information about the amount of MHC multimer bound to the cell. By this method MHC multimers can be used to identify specific T cell populations in liquid samples such as synovial fluid or blood.

When analyzing blood samples whole blood can be used with or without lysis of red blood cells. Alternatively lymphocytes can be purified before flow cytometry analysis using standard procedures like a Ficoll-Hypaque gradient. Another possibility is to isolate T cells from the blood sample for example by binding to antibody coated plastic surfaces, followed by elution of bound cells. This purified T cell population can then be used for flow cytometry analysis together with MHC multimers. Instead of actively isolating T cells unwanted cells like B cells and NK cells can be removed prior to the analysis. One way to do this is by affinity chromatography using columns coated with antibodies specific for the unwanted cells. Alternatively, specific antibodies can be added to the blood sample together with complement, thereby killing cells recognized by the antibodies.

Various gating reagents can be included in the analysis. Gating reagents here means labeled antibodies or other labeled markers identifying subsets of cells by binding to unique surface proteins. Preferred gating reagents when using MHC multimers are antibodies directed against CD3, CD4, and CD8 identifying major subsets of T cells. Other preferred gating reagents are antibodies against CD14, CD15, CD19, CD25, CD56, CD27, CD28, CD45, CD45RA, CD45RO, CCR7, CCR5, CD62L, Foxp3 recognizing specific proteins unique for different lymphocytes of the immune system. Following labelling with MHC multimers and before analysis on a flow cytometer stained cells can be treated with a fixation reagent like formaldehyde to cross-link bound MHC multimer to the cell surface. Stained cells can also be analyzed directly without fixation.

The number of cells in a sample can vary. When the target cells are rare, it is preferable to analyze large amounts of cells. In contrast, fewer cells are required when looking at T cell lines or samples containing many cells of the target cell type.

The flow cytometer can be equipped to separate and collect particular types of cells. This is called cell sorting. MHC multimers in combination with sorting on a flow cytometer can be used to isolate specific T cell populations. Isolated specific T cell populations can then be expanded in vitro. This can be useful in autologous cancer therapy.

Direct determination of the concentration of MHC-peptide specific T cells in a sample can be obtained by staining blood cells or other cell samples with MHC multimers and relevant gating reagents followed by addition of an exact amount of counting beads of known concentration. Counting beads is here to be understood as any fluorescent bead with a size that can be visualized by flow cytometry in a sample containing T cells. The beads could be made of polystyrene with a size of about 1-10 μm. They could also be made of agarose, polyacrylamide, silica, or any other material, and have any size between 0.1 μm and 100 m. The counting beads are used as reference population to measure the exact volume of analyzed sample. The sample are analyzed on a flow cytometer and the amount of MHC-specific T cell determined using a predefined gating strategy and then correlating this number to the number of counted counting beads in the same sample using the following equation: Amounts of MHC-peptide specific T cells in a blood sample can be determined by flow cytometry by calculating the amount of MHC'mer labeled cells in a given volume of sample with a given cell density and then back calculate. Exact enumeration of specific T cells is better achieved by staining with MHC'mers together with an exact amount of counting beads followed by flow cytometry analysis. The amount of T cells detected can then be correlated with the amount of counting beads in the same volume of the sample and an exact number of MHC-peptide specific T cells determined:

Concentration of MHC-specific *T*-cell in sample= (number of MHC-peptide specific *T* cells counted/number of counting beads counted)× concentration of counting beads in sample Direct Detection of Individual T Cells in Fluid Sample by Microscopy A suspension of T cells are added MHC multimers, the sample washed and then the amount of MHC multimer bound to each cell are measured. Bound MHC multimers may be labelled directly or measured through addition of labelled marker molecules. The sample is then spread out on a slide or similar in a thin layer able to distinguish individual cells and labelled cells identified using a microscope. Depending on the type of label different types of microscopes may be used, e.g. if fluorescent labels are used a fluorescent microscope is used for the analysis. For example MHC multimers can be labeled with a fluorochrome or bound MHC multimer detected with a fluorescent antibody. Cells with bound fluorescent MHC multimers can then be visualized using an immunofluorescence microscope or a confocal fluorescence microscope.

Direct Detection of Individual T Cells in Fluid Sample by Capture on Solid Support Followed by Elution.

MHC multimers are immobilized to a support e.g. beads, immunotubes, wells of a microtiterplate, CD, microchip or similar and as described elsewhere herein, then a suspension of T cells are added allowing specific T cells to bind MHC multimer molecules. Following washing bound T cells are recovered/eluted (e.g. using acid or competition with a competitor molecules) and counted.

Direct Detection of Populations of T Cells

Cell suspensions are added labeled MHC multimer, samples are washed and then total signal from label are measured. The MHC multimers may be labeled themselves or detected through a labeled marker molecule.

Cell suspensions are added labeled MHC multimer, samples are washed and then signal from label are amplified and then total signal from label and/or amplifier are measured.

Direct Detection of Immobilized T Cells.

T cells may be immobilized and then detected directly. Immobilization can be on solid support, in solid tissue or in fixator (e.g. paraffin, a sugar matrix or another medium fixing the T cells).

Direct Detection of T Cells Immobilized on Solid Support.

In a number of applications, it may be advantageous immobilise the T cell onto a solid or semi-solid support. Such support may be any which is suited for immobilisation, separation etc. Non-limiting examples include particles, beads, biodegradable particles, sheets, gels, filters, membranes (e.g. nylon membranes), fibres, capillaries, needles, microtitre strips, tubes, plates or wells, combs, pipette tips, micro arrays, chips, slides, or indeed any solid surface material. The solid or semi-solid support may be labelled, if this is desired. The support may also have scattering properties or sizes, which enable discrimination among supports of the same nature, e.g. particles of different sizes or scattering properties, colour or intensities.

Conveniently the support may be made of glass, silica, latex, plastic or any polymeric material. The support may also be made from a biodegradable material.

Generally speaking, the nature of the support is not critical and a variety of materials may be used. The surface of support may be hydrophobic or hydrophilic.

Preferred are materials presenting a high surface area for binding of the T cells. Such supports may be for example be porous or particulate e.g. particles, beads, fibres, webs, sinters or sieves.

Particulate materials like particles and beads are generally preferred due to their greater binding capacity. Particularly polymeric beads and particles may be of interest.

Conveniently, a particulate support (e.g. beads or particles) may be substantially spherical. The size of the particulate support is not critical, but it may for example have a diameter of at least 1 µm and preferably at least 2 µm, and have a maximum diameter of preferably not more than 10 µm and more preferably not more than 6 µm. For example, particulate supports having diameters of 2.8 µm and 4.5 µm will work well.

An example of a particulate support is monodisperse particles, i.e. such which are substantially uniform in size (e.g. size having a diameter standard deviation of less than 5%). Such have the advantage that they provide very uniform reproducibility of reaction. Monodisperse particles, e.g. made of a polymeric material, produced by the technique described in U.S. Pat. No. 4,336,173 (ref. 25) are especially suitable.

Non-magnetic polymer beads may also be applicable. Such are available from a wide range of manufactures, e.g. Dynal Particles AS, Qiagen, Amersham Biosciences, Serotec, Seradyne, Merck, Nippon Paint, Chemagen, Promega, Prolabo, Polysciences, Agowa, and Bangs Laboratories.

Another example of a suitable support is magnetic beads or particles. The term "magnetic" as used everywhere herein is intended to mean that the support is capable of having a magnetic moment imparted to it when placed in a magnetic field, and thus is displaceable under the action of that magnetic field. In other words, a support comprising magnetic beads or particles may readily be removed by magnetic aggregation, which provides a quick, simple and efficient way of separating out the beads or particles from a solution. Magnetic beads and particles may suitably be paramagnetic or superparamagnetic. Superparamagnetic beads and particles are e.g. described in EP 0 106 873 (Sintef, ref. 26). Magnetic beads and particles are available from several manufacturers, e.g. Dynal Biotech ASA (Oslo, Norway, previously Dynal AS, e.g. Dynabeads®).

The support may suitably have a functionalised surface. Different types of functionalisation include making the surface of the support positively or negatively charged, or hydrophilic or hydrophobic. This applies in particular to beads and particles. Various methods therefore are e.g. described in U.S. Pat. No. 4,336,173 (ref. 25), U.S. Pat. No. 4,459,378 (ref. 27) and U.S. Pat. No. 4,654,267 (ref. 28).

Immobilized T cells may be detected in several ways including:

Direct Detection of T Cells Directly Immobilized on Solid Support.

T cells may be directly immobilized on solid support e.g. by non-specifically adhesion. Then MHC multimers are added to the immobilized T cells thereby allowing specific T cells to bind the MHC multimers. Bound MHC multimer may be measured through label directly attached to the multimer or through labeled marker molecules. Individual T cells may be detected if the method for analysis is able to distinguish individual labeled cells, e.g. cells are immobilized in a monolayer on a cell culture well or a glass slide. Following staining with labeled multimer a digital picture is taken and labeled cells identified and counted.

Alternatively a population of T cells is detected by measurement of total signal from all labeled T cells, e.g. cells are plated to wells of a microtiter plate, stained with labeled MHC multimer and total signal from each well are measured.

Direct Detection of T Cells Immobilized on Solid Support Through Linker Molecule T cell can also be immobilized to solid support through a linker molecule. The linker molecule can be an antibody specific for the T cell, the linker can be MHC multimer or the linker can be any molecule able to bind the T cells. In any case the linker may be attached directly to the solid support, the linker may be attached to the solid support through another linker or the linker is embedded in a matrix, e.g. a sugar matrix.

Then MHC multimers are added to the immobilized T cells thereby allowing specific T cells to bind the MHC multimers. Bound MHC multimer may be measured through label directly attached to the multimer or through labeled marker molecules. Individual T cells may be detected if the method for analysis is able to distinguish individual labeled cells, e.g. a digital picture is taken and labeled cells identified and counted. Alternatively a population of T cells is detected by measurement of total signal from all labeled T cells.

Phenotyping T Cell Sample Using MHC Multimer Beads.

Different MHC multimers are immobilized to different beads with different characteristics (e.g. different size, different fluorescence's or different fluorescence intensities) where each kind of bead has a specific type of MHC multimer molecule immobilized. The immobilization may be direct or through a linker molecule as described above. The amount of bound T cells to a specific populations of beads can be analyzed, thereby, phenotyping the sample. The TCR on the T cell is defined by the bead to which it binds.

Direct Detection of T Cells Immobilized to Solid Support in a Defined Pattern.

Different MHC multimers are immobilized to a support to form a spatial array in a defined pattern, where the position specifies the identity of the MHC multimer immobilized at this position. The immobilization may be direct or through a linker molecule as described above. Then a suspension of labeled T cells are added or passed over the array of MHC multimers and specific T cells will bind the immobilized MHC multimer molecules. The label will thus be located at specific regions of the array, which will allow identification of the MHC multimers that bind the cells, and thus, allows the identification of T cells with recognition specificity for the immobilized MHC multimers. Alternatively, the cells can be labelled after they have been bound to the MHC multimers. The label can be specific for the type of cell that is expected to bind the MHC multimer (e.g. anti-CD4 for the labelling of T-helper cells in general, where some of the T-helper cells can be specific for a Class II MHC complex), or the label can stain cells in general (e.g. a label that binds DNA).

In this way T cells bound to the defined areas of the support are analyzed, thereby, phenotyping the sample. Each individual T cell is defined by the TCR it expose and depending on these TCRs each entity will bind to different types of MHC multimer molecules immobilized at defined positions on the solid support.

Direct Detection of Immobilized T Cells Followed by Sorting

T cells immobilized to solid support in either of the ways described above can following washing be eluted from the solid support and treated further. This is a method to sort out specific T cells from a population of different T cells. Specific T-cells can e.g. be isolated through the use of bead-based MHC multimers. Bead-based MHC multimers are beads whereto monomer MHC-peptide complexes or MHC multimers are immobilized. After the cells have been isolated they can be manipulated in many different ways. The isolated cells can be activated (to differentiate or proliferate), they can undergo induced apoptosis, or undesired cells of the isolated cell population can be removed. Then, the manipulated cell population can be re-introduced into the patient, or can be introduced into another patient.

A typical cell sorting experiment, based on bead-based MHC multimers, would follow some of the steps of the general procedure outlined in general terms in the following:

Acquire the sample, e.g. a cell sample from the bone marrow of a cancer patient.

Block the sample with a protein solution, e.g. BSA or skim milk.

Block the beads coated with MHC complexes, with BSA or skim milk.

Mix MHC-coated beads and the cell sample, and incubate.

Wash the beads with washing buffer, to remove unbound cells and non-specifically bound cells.

Isolate the immobilized cells, by either cleavage of the linker that connects MHC complex and bead; or alternatively, release the cells by a change in pH, salt-concentration addition of competitive binder or the like. Preferably, the cells are released under conditions that do not disrupt the integrity of the cells.

Manipulate the isolated cells (induce apoptosis, proliferation or differentiation)

Direct Detection of T Cells in Solid Tissue.

Direct Detection of T Cells in Solid Tissue In Vitro.

For in vitro methods of the present invention solid tissue includes tissue, tissue biopsies, frozen tissue or tissue biopsies, paraffin embedded tissue or tissue biopsies and sections of either of the above mentioned. In a preferred method of this invention sections of fixed or frozen tissues are incubated with MHC multimer, allowing MHC multimer to bind to specific T cells in the tissue section. The MHC multimer may be labeled directly or through a labeled marker molecule. As an example, the MHC multimer can be labeled with a tag that can be recognized by e.g. a secondary antibody, optionally labeled with HRP or another label. The bound MHC multimer is then detected by its fluorescence or absorbance (for fluorophore or chromophore), or by addition of an enzyme-labeled antibody directed against this tag, or another component of the MHC multimer (e.g. one of the protein chains, a label on the multimerization domain). The enzyme can be Horse Raddish Peroxidase (HRP) or Alkaline Phosphatase (AP), both of which convert a colorless substrate into a colored reaction product in situ. This colored deposit identifies the binding site of the MHC multimer, and can be visualized under a light microscope. The MHC multimer can also be directly labeled with e.g. HRP or AP, and used in IHC without an additional antibody.

The tissue sections may derive from blocks of tissue or tissue biopsies embedded in paraffin, and tissue sections from this paraffin-tissue block fixed in formalin before staining. This procedure may influence the structure of the TCR in the fixed T cells and thereby influence the ability to recognize specific MHC complexes. In this case, the native structure of TCR needs to be at least partly preserved in the fixed tissue. Fixation of tissue therefore should be gentle. Alternatively, the staining is performed on frozen tissue sections, and the fixation is done after MHC multimer staining.

Direct Detection of T Cells in Solid Tissue In Vivo

For in vivo detection of T cells labeled MHC multimers are injected in to the body of the individual to be investigated. The MHC multimers may be labeled with e.g. a paramagnetic isotope. Using a magnetic resonance imaging (MRI) scanner or electron spin resonance (ESR) scanner MHC multimer binding T cells can then be measured and localized. In general, any conventional method for diagnostic imaging visualization can be utilized. Usually gamma and positron emitting radioisotopes are used for camera and paramagnetic isotopes for MRI.

The methods described above for direct detection of TCR embedded in lipid bilayers collectively called T cells using MHC multimers also applies to detection of TCR in solution and detection of TCR attached to or in a solid medium. Though detection of individual TCRs may not be possible when TCR is in solution.

Indirect Detection of TCR

Indirect detection of TCR is primarily useful for detection of TCRs embedded in lipid bilayer, preferably natural occurring T cells, T cell hybridomas or transfected T cells. In indirect detection, the number or activity of T cells are measured, by detection of events that are the result of TCR-MHC-peptide complex interaction. Interaction between MHC multimer and T cell may stimulate the T cell resulting in activation of T cells, in cell division and proliferation of T cell populations or alternatively result in inactivation of T cells. All these mechanism can be measured using various detection methods.

Indirect Detection of T Cells by Measurement of Activation.

MHC multimers, e.g. antigen presenting cells, can stimulate T cells resulting in activation of the stimulated T cells. Activation of T cell can be detected by measurement of secretion of specific soluble factor from the stimulated T cell, e.g. secretion of cytokines like INFγ and IL2.

Stimulation of T cells can also be detected by measurement of changes in expression of specific surface receptors, or by measurement of T cell effector functions.

Measurement of activation of T cells involves the following steps:

a) To a sample of T cells, preferably a suspension of cells, is added MHC multimer to induce either secretion of soluble factor, up- or down-regulation of surface receptor or other changes in the T cell.

Alternatively, a sample of T cells containing antigen presenting cells is added antigenic peptide or protein/protein fragments that can be processed into antigenic peptides by the antigen presenting cell and that are able to bind MHC I or MHC II molecules expressed by the antigen presenting cells thereby generating a cell based MHC multimer in the sample. Several different peptides and proteins be added to the sample. The peptide-loaded antigen presenting cells can then stimulate specific T cells, and thereby induce the secretion of soluble factor, up- or down-regulation of surface receptors, or mediate other changes in the T cell, e.g. enhancing effector functions.

Optionally a second soluble factor, e.g. cytokine and/or growth factor(s) may be added to facilitate continued activation and expansion of T cell population.

b) Detect the presence of soluble factor, the presence/absence of surface receptor or detect effector function c) Correlate the measured result with presence of T cells. The measured signal/response indicate the presence of specific T cells that have been stimulated with particular MHC multimer.

The signal/response of a T lymphocyte population is a measure of the overall response. The frequency of specific T cells able to respond to a given MHC multimer can be determined by including a limiting-dilution culture in the assay also called a Limiting dilution assay.

The limiting-dilution culture method involves the following steps:
a) Sample of T cells in suspension are plated into culture wells at increasing dilutions
b) MHC multimers are added to stimulate specific T cells. Alternatively antigen presenting cells are provided in the sample and then antigenic peptide I added to the sample as described above.
Optionally growth factors, cytokines or other factors helping T cells to proliferate are added.
c) Cells are allowed to grow and proliferate (½-several days). Each well that initially contained a specific T cell will make a response to the MHC multimer and divide.
d) Wells are tested for a specific response e.g. secretion of soluble factors, cell proliferation, cytotoxicity or other effector function.

The assay is replicated with different numbers of T cells in the sample, and each well that originally contained a specific T cell will make a response to the MHC multimer. The frequency of specific T cells in the sample equals the reciprocal of the number of cells added to each well when 37% of the wells are negative, because due to Poisson distribution each well then on average contained one specific T cell at the beginning of the culture.

In the following various methods to measure secretion of specific soluble factor, expression of surface receptors, effector functions or proliferation is described.

Indirect Detection of T Cells by Measurement of Secretion of Soluble Factors.

Indirect Detection of T Cells by Measurement of Extracellular Secreted Soluble Factors.

Secreted soluble factors can be measured directly in fluid suspension, captured by immobilization on solid support and then detected or an effect of the secreted soluble factor can be detected.

Indirect Detection of T Cells by Measurement of Extracellular Secreted Soluble Factor Directly in Fluid Sample.

A sample of T cells are added MHC multimer or antigenic peptide as described above to induce secretion of soluble factors from antigen specific T cells. The secreted soluble factors can be measured directly in the supernatant using e.g. mass spectrometry.

Indirect Detection of T Cells by Capture of Extracellular Secreted Soluble Factor on Solid Support.

A sample of T cells are added MHC multimer or antigenic peptide as described above to induce secretion of soluble factors from antigen specific T cells. Secreted soluble factors in the supernatant are then immobilized on a solid support either directly or through a linker as described for immobilization of T cells elsewhere herein. Then immobilized soluble factors can be detected using labeled marker molecules.

Soluble factors secreted from individual T cells can be detected by capturing of the secreted soluble factors locally by marker molecules, e.g antibodies specific for the soluble factor. Soluble factor recognising marker molecules are then immobilised on a solid support together with T cells and soluble factors secreted by individual T cells are thereby captured in the proximity of each T cell. Bound soluble factor can be measured using labelled marker molecule specific for the captured soluble factor. The number of T cells that has given rise to labelled spots on solid support can then be enumerated and these spots indicate the presence of specific T cells that may be stimulated with particular MHC multimer.

Soluble factors secreted from a population of T cells are detected by capture and detection of soluble factor secreted from the entire population of specific T cells. In this case soluble factor do not have to be captured locally close to each T cell but the secreted soluble factors my be captured and detected in the same well as where the T cells are or transferred to another solid support with marker molecules for capture and detection e.g. beads or wells of ELISA plate.

Indirect Detection of T Cells Immobilized to Solid Support in a Defined Pattern.

Different MHC multimers of MHC-peptide complexes are immobilized to a support to form a spatial array in a defined pattern, where the position specifies the identity of the MHC multimer/MHC-peptide complex immobilized at this position. Marker molecules able to bind T cell secreted soluble factors are co-spotted together with MHC multimer/MHC-peptide complex. Such marker molecules can e.g. be antibodies specific for cytokines like INFγ or IL-2. The immobilization may be direct or through a linker molecule as described above. Then a suspension of labeled T cells are added or passed over the array of MHC multimers/MHC-peptide complexes and specific T cells will bind to the immobilized MHC multimers/MHC-peptide complexes and upon binding be stimulated to secrete soluble factors e.g. cytokines like INFγ ord IL-2. Soluble factors secreted by individual T cells are then captured in the proximity of each T cell and bound soluble factor can be measured using labelled marker molecule specific for the soluble factor. The number and position of different specific T cells that has given rise to labelled spots on solid support can then be identified and enumerated. In this way T cells bound to defined areas of the support are analyzed, thereby, phenotyping the sample. Each individual T cell is defined by the TCR it expose and depending on these TCRs each entity will bind to different types of MHC multimers/MHC-peptide complexes immobilized at defined positions on the solid support.

Indirect Detection of T Cells by Measurement of Effect of Extracellular Secreted Soluble Factor.

Secreted soluble factors can be measured and quantified indirectly by measurement of the effect of the soluble factor on other cell systems. Briefly, a sample of T cells are added MHC multimer or antigenic peptide as described above to induce secretion of soluble factors from antigen specific T cells. The supernatant containing secreted soluble factor are transferred to another cell system and the effect measured. The soluble factor may induce proliferation, secretion of other soluble factors, expression/downregulation of receptors, or the soluble factor may have cytotoxic effects on these other cells. All effects can be measured as described elsewhere herein.

Indirect Detection of T Cells by Measurement of Intracellular Secreted Soluble Factors Soluble factor production by stimulated T cells can be also be measured intracellular by e.g. flow cytometry. This can be done using block of secretion of soluble factor (e.g. by monensin), permeabilization of cell (by e.g. saponine) followed by immunofluorescent staining. The method involves the following steps: 1) Stimulation of T cells by binding specific MHC multimers, e.g. antigen presenting cells loaded with antigenic peptide. An reagent able to block extracellular secretion of cytokine is added, e.g. monensin that interrupt intracellular transport processes leading to accumulation of produced soluble factor, e.g. cytokine in the Golgi complex. During stimulation other soluble factors may be added to the T cell sample during stimulation to enhance activation and/or expansion. This other soluble factor can be cytokine and or growth factors. 2) addition of one or more labelled marker able to detect special surface receptors (e.g. CD8, CD4, CD3, CD27, CD28, CD2). 3) Fixation of cell membrane using mild fixator followed by permeabilization of cell membrane by. e.g. saponine. 4) Addition of labelled marker specific for the produced soluble factor to be determined, e.g. INFγ, IL-2, IL-4, IL-10. 5) Measurement of labelled cells using a flow cytometer.

An alternative to this procedure is to trap secreted soluble factors on the surface of the secreting T cell as described by Manz, R. et al., Proc. Natl. Acad. Sci. USA 92:1921 (1995).

Indirect Detection of T Cells by Measurement of Expression of Receptors

Activation of T cells can be detected by measurement of expression and/or down regulation of specific surface receptors. The method includes the following steps. A sample of T cells are added MHC multimer or antigenic peptide as described above to induce expression or downregulation of specific surface receptors on antigen specific T cells. These receptors include but are not limited to CD28, CD27, CCR7, CD45RO, CD45RA, IL2-receptor, CD62L, CCR5. Their expression level can be detected by addition of labelled marker specific for the desired receptor and then measure the amount of label using flow cytometry, microscopy, immobilization of activated T cell on solid support or any other method like those described for direct detection of TCR in lipid bilayer.

Indirect Detection of T Cells by Measurement of Effector Function

Activation of T cells can be detected indirectly by measurement of effector functions. A sample of T cells are added MHC multimer or antigenic peptide as described above to induce the T cell to be able to do effector function. The effector function is then measured. E.g. activation of antigen specific CD8 positive T cells can be measured in a cytotoxicity assay.

Indirect Detection of T Cells by Measurement of Proliferation

T cells can be stimulated to proliferate upon binding specific MHC multimers. Proliferation of T cells can be measured several ways including but not limited to:

Detection of mRNA

Proliferation of T cells can be detected by measurement of mRNA inside cell. Cell division and proliferation requires production of new protein in each cell which as an initial step requires production of mRNA encoding the proteins to be synthesized.

A sample of T cells are added MHC multimer or antigenic peptide as described above to induce proliferation of antigen specific T cells. Detection of levels of mRNA inside the proliferating T cells can be done by quantitative PCR and indirectly measure activation of a T cell population as a result of interaction with MHC multimer. An example is measurement of cytokine mRNA by in sity hybridization.

Detection of Incorporation of Thymidine

The proliferative capacity of T cells in response to stimulation by MHC multimer can be determined by a radioactive assay based on incorporation of [$^3$H]thymidine ([$^3$H]TdR) into newly generated DNA followed by measurement of radioactive signal.

Detection of Incorporation of BrdU

T cell proliferation can also be detected by of incorporation of bromo-2'-deoxyuridine (BrdU) followed by measurement of incorporated BrdU using a labeled anti-BrdU antibody in an ELISA based analysis.

Viability of cells may be measured by measurement ATP in a cell culture.

Indirect Detection of T Cells by Measurement of Inactivation

Not all MHC multimers will lead to activation of the T cells they bind. Under certain circumstances some MHC multimers may rather inactivate the T cells they bind to.

Indirect Detection of T Cells by Measurement of Effect of Blockade of TCR

Inactivation of T cells by MHC multimers may be measured be measuring the effect of blocking TCR on antigen specific T cells. MHC multimers, e.g. MHC-peptide complexes coupled to IgG scaffold can block the TCR of an antigen specific T cell by binding the TCR, thereby prevent the blocked T cell receptor interacting with e.g. antigen presenting cells. Blockade of TCRs of a T cell can be detected in any of the above described methods for detection of TCR by addition of an unlabeled blocking MHC multimer together with the labelled MHC multimer and then measuring the effect of the blockade on the readout.

Indirect Detection of T Cells by Measurement of Induction of Apoptosis

Inactivation of T cells by MHC multimers may be measured be measuring apoptosis of the antigen specific T cell. Binding of some MHC multimers to specific T cells may lead to induction of apoptosis. Inactivation of T cells by binding MHC multimer may therefore be detected by measuring apoptosis in the T cell population. Methods to measure apoptosis in T cells include but are not limited to measurement of the following:

DNA fragmentation

Alterations in membrane asymmetry (phosphatidylserine translocation)

Activation of apoptotic caspases

Release of cytochrome C and AIF from mitochondria into the cytoplasm

Positive Control Experiments for the Use of MHC Multimers in Flow Cytometry and Related Techniques When performing flow cytometry experiments, or when using similar technologies, it is important to include appropriate positive and negative controls. In addition to establishing proper conditions for the experiments, positive and negative control reagents can also be used to evaluate the quality (e.g. specificity and affinity) and stability (e.g. shelf life) of produced MHC multimers.

The quality and stability of a given MHC multimer can be tested in a number of different ways, including:

- Measurement of specific MHC multimer binding to beads, other types of solid support, or micelles and liposomes, to which TCR's have been immobilized. Other kinds of molecules that recognize specifically the MHC-peptide complex can be immobilized and used as well. Depending on the nature of the solid support or membrane structure to which the TCR is immobilized, the TCR can be full-length (i.e. comprise the intracellular- and intra-membrane domains), or can be truncated (e.g. only comprise the extracellular domains). Likewise, the TCR can be recombinant, and can be chemically or enzymatically modified.
- Measurement of MHC multimer binding to beads, other types of solid support, or micelles and liposomes, to which aptamers, antibodies or other kinds of molecules that recognize correctly folded MHC-peptide complexes have been immobilized.
- Measurement of specific MHC multimer binding to specific cell lines (e.g. T-cell lines) displaying MHC multimer-binding molecules, e.g. displaying TCRs with appropriate specificity and affinity for the MHC multimer in question.
- Measurement of specific MHC multimer binding to cells in blood samples, preparations of purified lymphocytes (HPBMCs), or other bodily fluids that contain cells carrying receptor molecules specific for the MHC multimer in question.
- Measurement of specific MHC multimer binding to soluble TCRs, aptamers, antibodies, or other soluble MHC-peptide complex-binding molecules, by density-gradient centrifugation (e.g. in CsCl) or by size exclusion chromatography, PAGE or other type of chromatographic method.
- Measurement of specific MHC binding to TCRs, aptamers, antibodies, streptavidin, or other MHC-peptide complex-binding molecules immobilized on a solid surface (e.g. a microtiter plate). The degree of MHC multimer binding can be visualized with a secondary component that binds the MHC multimer, e.g. a biotinylated fluorophore in cases where the MHC multimer contains streptavidin proteins, not fully loaded with biotin. Alternatively, the secondary component is unlabelled, and a labelled second component-specific compound is employed (e.g. EnVision System, Dako) for visualization. This solid surface can be beads, immunotubes, microtiterplates act. The principle for purification are basically the same I.e. T cells are added to the solid with immobilized MHC'mer, non-binding T cells are washed away and MHC-peptide specific T cells can be retrieved by elution with mild acid or a competitive binding reagent.
  - Measurement of specific MHC multimer binding to TCRs, aptamers, antibodies, streptavidin, or other MHC-peptide complex-binding molecules immobilized on a solid surface (e.g. a microtiter plate) visualized with a secondary component specific to MHC multimer (e.g. TCRs, aptamers, antibodies, streptavidin, or other MHC-peptide binding complex-binding molecules). Alternatively the secondary receptor is unlabelled, and a labelled second receptor-specific compound is employed (e.g. EnVision System, Dako) before visualization.

In the above mentioned approaches, positive control reagents include MHC multimers comprising correctly folded MHC, complexed with an appropriate peptide that allows the MHC multimer to interact specifically and efficiently with its cognate TCR. Negative control reagents include empty MHC multimers, or correctly folded MHC multimers complexed with so-called nonsense peptides that support a correct conformation of the MHC-peptide complex, but that do not efficiently bind TCRs through the peptide-binding site of the MHC complex.

Negative Control Reagents and Negative Control Experiments for the Use of MHC Multimers in Flow Cytometry and Related Techniques Experiments with MHC multimers require a negative control in order to determine background staining with MHC multimer. Background staining can be due to unwanted binding of any of the individual components of the MHC multimer, e.g., MHC complex or individual components of the MHC complex, multimerization domain or label molecules. The unwanted binding can be to any surface or intracellular protein or other cellular structure of any cell in the test sample, e.g. undesired binding to B cells, NK cells or T cells. Unwanted binding to certain cells or certain components on cells can normally be corrected for during the analysis, by staining with antibodies that bind to unique surface markers of these specific cells, and thus identifies these as false positives, or alternatively, that bind to other components of the target cells, and thus identifies these cells as true positives. A negative control reagent can be used in any experiment involving MHC multimers, e.g. flow cytometry analysis, other cytometric methods, immunohistochemistry (IHC) and ELISA. Negative control reagents include the following:

- MHC complexes or MHC multimers comprising MHC complexes carrying nonsense peptides. A nonsense peptide is here to be understood as a peptide that binds the MHC protein efficiently, but that does not support binding of the resultant MHC-peptide complex to the desired TCR. An example nonsense peptide is a peptide with an amino acid sequence different from the linear sequence of any peptide derived from any known protein. When choosing an appropriate nonsense peptide the following points are taken into consideration. The peptide should ideally have appropriate amino acids at relevant positions that can anchor the peptide to the peptide-binding groove of the MHC. The remaining amino acids should ideally be chosen in such a way that possible binding to TCR (through interactions with the peptide or peptide-binding site of MHC) are minimized. The peptide should ideally be soluble in water to make proper folding with MHC alpha chain and β2m possible in aqueous buffer. The length of the peptide should ideally match the type and allele of MHC complex. The final peptide sequence should ideally be taken through a blast search or similar analysis, to ensure that it is not identical with any peptide sequence found in any known naturally occurring proteins.
- MHC complexes or MHC multimers comprising MHC complexes carrying a chemically modified peptide in the peptide-binding groove. The modification should ideally allow proper conformation of the MHC-peptide structure, yet should not allow efficient interaction of the peptide or peptide-binding site of MHC with the TCR.

MHC complexes or MHC multimers comprising MHC complexes carrying a naturally occurring peptide different from the peptide used for analysis of specific T cells in the sample. When choosing the appropriate natural peptide the following should be taken into consideration. The peptide in complex with the MHC protein should ideally not be likely to bind a TCR of any T cell in the sample with such an affinity that it can be detected with the applied analysis method. The peptide should ideally be soluble in water to make proper folding with MHC alpha chain and β2m possible in aqueous buffer. The length of the peptide should match the type and allele of MHC complex.

Empty MHC complexes or MHC multimers comprising empty MHC complexes, meaning any correctly folded MHC complex without a peptide in the peptide-binding groove.

MHC heavy chain or MHC multimers comprising MHC heavy chain, where MHC heavy chain should be understood as full-length MHC I or MHC II heavy chain or any truncated version of MHC I or MHC II heavy chain. The MHC heavy chains can be either folded or unfolded. Of special interest is MHC I alpha chains containing the α3 domain that binds CD8 molecules on cytotoxic T cells. Another embodiment of special interest is MHC II β chains containing the β2 domain that binds CD4 on the surface of helper T cells.

Beta2microglobulin or subunits of beta2microglobulin, or MHC multimers comprising Beta2microglobulin or subunits of beta2microglobulin, folded or unfolded.

MHC-like complexes or MHC multimers comprising MHC-like complexes, folded or unfolded. An example could be CD1 molecules that are able to bind peptides in a peptide-binding groove that can be recognized by T cells (Russano et al. (2007). CD1-restricted recognition of exogenous and self-lipid antigens by duodenal gammadelta+ T lymphocytes. J. Immunol. 178(6): 3620-6)

Multimerization domains without MHC or MHC-like molecules, e.g. dextran, streptavidin, IgG, coiled-coil-domain liposomes.

Labels, e.g. FITC, PE, APC, pacific blue, cascade yellow, or any other label listed elsewhere herein.

Negative controls 1-4 can provide information about potentially undesired binding of the MHC multimer, through interaction of a surface of the MHC-peptide complex different from the peptide-binding groove and its surroundings. Negative control 5 and 6 can provide information about binding through interactions through the MHC I or MHC II proteins (in the absence of peptide). Negative control 7 can provide information about binding through surfaces of the MHC complex that is not unique to the MHC complex. Negative controls 8 and 9 provide information about potential undesired interactions between non-MHC-peptide complex components of the MHC multimer and cell constituents.

Minimization of Undesired Binding of the MHC Multimer

Identification of MHC-peptide specific T cells can give rise to background signals due to unwanted binding to cells that do not carry TCRs. This undesired binding can result from binding to cells or other material, by various components of the MHC multimer, e.g. the dextran in a MHC dextramer construct, the labelling molecule (e.g. FITC), or surface regions of the MHC-peptide complex that do not include the peptide and the peptide-binding cleft. MHC-peptide complexes bind to specific T cells through interaction with at least two receptors in the cell membrane of the T-cell. These two receptors are the T-cell receptor (TCR) and CD8 for MHC I-peptide complexes and TCR and CD4 receptor protein for MHC II-peptide complexes. Therefore, a particularly interesting example of undesired binding of a MHC multimer is its binding to the CD8 or CD4 molecules of T cells that do not carry a TCR specific for the actual MHC-peptide complex. The interaction of CD8 or CD4 molecules with the MHC is not very strong; however, because of the avidity gained from the binding of several MHC complexes of a MHC multimer, the interaction between the MHC multimer and several CD8 or CD4 receptors potentially can result in undesired but efficient binding of the MHC multimer to these T cells. In an analytical experiment this would give rise to an unwanted background signal; in a cell sorting experiment undesired cells might become isolated.

Other particular interesting examples of undesired binding is binding to lymphoid cells different from T cells, e.g. NK-cells, B-cells, monocytes, dendritic cells, and granulocytes like eosinophils, neutrophils and basophiles.

Apart from the MHC complex, other components in the MHC multimer can give rise to unspecific binding. Of special interest are the multimerization domain, multimerization domain molecules, and labelling molecules.

One way to overcome the problem with unwanted binding is to include negative controls in the experiment and subtract this signal from signals derived from the analyzed sample, as described elsewhere in the invention.

Alternatively, unwanted binding could be minimized or eliminated during the experiment. Methods to minimize or eliminate background signals include:

Mutations in areas of the MHC complex responsible for binding to unwanted cells can be introduced. Mutations here mean substitution, insertion, or deletion of natural or non-natural amino acids. Sub-domains in the MHC complex can be responsible for unwanted binding of the MHC multimer to cells without a TCR specific for the MHC-peptide complex contained in the MHC multimer. One example of special interest is a small region in the α3-domain of the α-chain of MHC I molecules that is responsible for binding to CD8 on all cytotoxic T cells. Mutations in this area can alter or completely abolish the interaction between CD8 on cytotoxic T cells and MHC multimer (Neveu et al. (2006) Int Immunol. 18, 1139-45). Similarly a sub domain in the β2 domain of the β-chain of MHC II molecules is responsible for binding CD4 molecules on all CD4 positive T cells. Mutations in this sub domain can alter or completely abolish the interaction between MHC 11 and CD4.

Another embodiment is to mutate other areas of MHC I/MHC II complexes that are involved in interactions with T cell surface receptors different from TCR, CD8 and CD4, or that bind surface receptors on B cells, NK cells, Eosiniophils, Neutrophils, Basophiles, Dendritic cells or monocytes.

Chemical alterations in areas of the MHC complex responsible for binding to unwanted cells can be employed in order to minimize unwanted binding of MHC multimer to irrelevant cells. Chemical alteration here means any chemical modification of one or more amino acids. Regions in MHC complexes that are of special interest are as mentioned above the α3 domain of the α-chain in MHC I molecules and β2 domains in the β-chain of MHC II molecules. Other regions in MHC I/MHC II molecules that can be chemically modified to decrease the extent of undesired binding are regions involved in interaction with T cell surface receptors different from TCR, CD8 and CD4, or that bind surface receptors on B cells, NK cells, Eosiniophils, Neutrophils, Basophiles, Dendritic cells or monocytes.

Another method to minimize undesired binding involves the addition of one or more components of a MHC multimer, predicted to be responsible for the unwanted binding. The added component is not labeled, or carries a label different from the label of the MHC multimer used for analysis. Of special interest is addition of MHC multimers that contain nonsense peptides, i.e. peptides that interact efficiently with the MHC protein, but that expectably do not support specific binding of the MHC multimer to the TCR in question. Another example of interest is addition of soluble MHC complexes not coupled to a multimerization domain, and with or without peptide bound in the peptide binding cleft. In another embodiment, individual components of the MHC complex can be added to the sample, e.g. I $\alpha$-chain or subunits of MHC I $\alpha$-chain either folded or unfolded, beta2microglobulin or subunits thereof either folded or unfolded, $\alpha/\beta$-chain of MHC II or subunits thereof either folded or unfolded. Any of the above mentioned individual components can also be attached to a multimerization domain identical or different from the one used in the MHC multimer employed in the analysis.

Of special interest is also addition of multimerization domain similar or identical to the multimerization domain used in the MHC multimer or individual components of the multimerization domain.

Reagents able to identify specific cell types either by selection or exclusion can be included in the analysis to help identify the population of T cells of interest, and in this way deselect the signal arising from binding of the MHC multimer to undesired cells.

Of special interest is the use of appropriate gating reagents in flow cytometry experiments. Thus, fluorescent antibodies directed against specific surface markers can be used for identification of specific subpopulations of cells, and in this way help to deselect signals resulting from MHC-multimers binding to undesired cells.

Gating reagents of special interest that helps identify the subset of T cells of interest when using MHC I multimers are reagents binding to CD3 and CD8 identifying all cytotoxic T cells. These reagents are preferably antibodies but can be any labeled molecule capable of binding CD3 or CD8. Gating reagents directed against CD3 and CD8 are preferably used together. As they stain overlapping cell populations they are preferably labeled with distinct fluorochromes. However, they can also be used individually in separate samples. In experiments with MHC II multimers reagents binding to CD3 and CD4 identifying T helper cells can be used. These reagents are preferably antibodies but can be any labeled molecule capable of binding CD3 or CD4. Gating reagents directed against CD3 and CD4 are preferable used together. As they stain overlapping cell populations they are preferably labeled with distinct fluorochromes. However, they can also be used individually in separate samples.

Other gating reagents of special interest in experiments with any MHC multimer, are reagents binding to the cell surface markers CD2, CD27, CD28, CD45RA, CD45RO, CD62L and CCR7. These surface markers are unique to T cells in various differentiation states. Co staining with either of these reagents or combinations thereof together with MHC multimers helps to select MHC multimer binding T cells expressing a correct TCR. These reagents can also be combined with reagents directed against CD3, CD4 and/or CD8.

Another flow cytometric method of special interest to remove signals from MHC multimer stained cells not expressing the specific TCR, is to introduce an exclusion gate. Antibodies or other reagents specific for surface markers unique to the unwanted cells are labeled with a fluorochrome and added to the test sample together with the MHC multimer. The number of antibodies or surface marker specific reagents are not limited to one but can be two, three, four, five, six, seven, eight, nine, ten or more individual reagents recognizing different surface markers, all of which are unique to the unwanted cells. During or after collection of data all events representing cells labeled with these antibodies are dumped in the same gate and removed from the dataset. This is possible because all the antibodies/reagents that bind to the wrong cells are labeled with the same fluorochrome.

Reagents of special interest that exclude irrelevant cells include reagents against CD45 expressed on red blood cells, CD19 expressed on B cells, CD56 expressed on NK cells, CD4 expressed on T helper cells and CD8 expressed on cytotoxic T cells, CD14 expressed on monocytes and CD15 expressed on granulocytes and monocytes.

Vaccine Treatment

For the purpose of making cancer vaccines or other types of vaccines it can be desirable to employ MHC multimers that comprise a polymer such as dextran, or that are cell-based (e.g. specialized dendritic cells such as described by Banchereau and Palucka, Nature Reviews, Immunology, 2005, vol. 5, p. 296-306).

Preventive vaccination leading to prophylaxis/sterile immunity by inducing memory in the immune system may be obtained by immunizing/vaccinating an individual or animal with MHC alone, or with MHC in combination with other molecules as mentioned elsewhere in the patent.

Vaccine antigens can be administered alone

Vaccine can be administered in combination with adjuvant(s).

Adjuvant can be mixed with vaccine component or administered alone, simultaneously or in any order.

Adjuvant can be administered by the same route as the other vaccine components

Vaccine administered more than once may change composition from $1^{st}$ administration to the $2^{nd}$, $3^{rd}$, etc.

Vaccine administered more than once can be administered by alternating routes

Vaccine components can be administered alone or in combinations by the same route or by alternating/mixed routes Vaccine can be administered by the following routes
Cutaneously
Subcutaneously (SC)
Intramuscular (IM)
Intravenous (IV)
Per-oral (PO)
Inter peritoneally
Pulmonally
Vaginally
Rectally Therapeutic vaccination i.e. vaccination "teaching" the immune system to fight an existing infection or disease, may be obtained by immunizing/vaccinating an individual or animal with MHC alone, or with MHC in combination with other molecules as mentioned elsewhere in the patent.

Vaccine antigens can be administered alone

Vaccine can be administered in combination with adjuvant(s).
- Adjuvant can be mixed with vaccine component or administered alone, simultaneously or in any order.
- Adjuvant can be administered by the same route as the other vaccine components Vaccine administered more than once may change composition from $1^{st}$ administration to the $2^{nd}$, $3^{rd}$, etc.

Vaccine administered more than once can be administered by alternating routes

Vaccine components can be administered alone or in combinations by the same route or by alternating/mixed routes Vaccine can be administered by the following routes
- Cutaneously
- Subcutaneously (SC)
- Intramuscular (IM)
- Intravenous (IV)
- Per-oral (PO)
- Inter peritoneally
- Pulmonally
- Vaginally
- Rectally Therapeutic Treatment Therapeutic treatment includes the use of MHC molecules alone or in any molecular combination mentioned elsewhere in the patent application for the purpose of treating a disease in any state. Treatment may be in the form of
- Per-orally intake
  - Pills
  - Capsules
- Injections
  - Systemic
  - Local
- Jet-infusion (micro-drops, micro-spheres, micro-beads) through skin
- Drinking solution, suspension or gel
- Inhalation
- Nose-drops
- Eye-drops
- Ear-drops
- Skin application as ointment, gel or creme
- Vaginal application as ointment, gel, crème or washing
- Gastro-Intestinal flushing
- Rectal washings or by use of suppositories Treatment can be performed as
- Single intake, injection, application, washing
- Multiple intake, injection, application, washing
  - On single day basis
  - Over prolonged time as days, month, years Treatment dose and regimen can be modified during the course Personalized Medicine Takes Advantage of the Large Diversity of Peptide Epitopes that May be Generated from a Given Antigen.

The immune system is very complex. Each individual has a very large repertoire of specific T cells (on the order of $10^6$-$10^9$ different T cell specificities), which again is only a small subset of the total T cell repertoire of a population of individuals. It is estimated that the Caucasian population represents a T cell diversity of $10^{10}$-$10^{12}$. MHC allele diversity combined with large variation among individuals' proteolytic metabolism further enhances the variation among different individuals' immune responses. As a result, each individual has its own characteristic immune response profile.

This is important when designing a MHC multimer-based immune monitoring reagent or immunotherapeutic agent. If an agent is sought that should be as generally applicable as possible, one should try to identify peptide epitopes and MHC alleles that are common for the majority of individuals of a population. As described elsewhere in this application, such peptide epitopes can be identified through computerized search algorithms developed for that same purpose, and may be further strengthened by experimental testing of a large set of individuals.

This approach will be advantageous in many cases, but because of the variability among immune responses of different individuals, is likely to be inefficient or inactive in certain individuals, because of these individuals' non-average profile. In these latter cases one may have to turn to personalized medicine. In the case of immune monitoring and immunotherapy, this may involve testing a large number of different epitopes from a given antigen, in order to find peptide epitopes that may provide MHC multimers with efficiency for a given individual.

Thus, personalized medicine takes advantage of the wealth of peptide epitopes that may be generated from a given antigen. A large number of the e.g. 8-, 9-, 10-, and 11-mer epitopes that may be generated from a given antigen to be included in a class 1 MHC multimer reagent, for use in immune monitoring or immunotherapy, are therefore of relevance in personalized medicine. Only in the case where one wants to generate a therapeutic agent or diagnostic reagent that is applicable to the majority of individuals of a population can the large majority of epitope sequences be said to be irrelevant, and only those identified by computerized search algorithms and experimental testing be said to be of value. For the odd individual with the odd immune response these disregarded peptide epitopes may be the epitopes that provide an efficient diagnostic reagent or cures that individual from a deadly disease.

Antigenic Peptides

The present invention relates to one or more MHC multimers and/or one or more MHC complexes comprising one or more antigenic peptides such as the antigenic peptides listed in table A, B, C, D, E, F, G, H, I, J, K, L, M, N, O, P, Q, R, S, T, U, V, X and Y.

The one or more antigenic peptides can in one embodiment comprise a fragment of one or more cancer antigens.

The one or more cancer antigens can be selected from Table A.

TABLE A

Protein designation and accession numbers for the four selected cancer antigens Bcl-2, BclX(L), Survivin and Mcl-1. The amino acid sequence of each protein is displayed.

| Protein and accession number | Cancer antigen |
|---|---|
| AAH27258.1<br>B-cell CLL/lymphoma 2,<br>Bcl-2 [Homo sapiens] | MAHAGRTGYDNREIVMKYIHYKLSQRGYEWDAGDVGAAPPGAAPAP<br>GIFSSQPGHTPHPAASRDPVARTSPLQTPAAPGAAAGPALSPVPPV<br>VHLTLRQAGDDFSRRYRRDFAEMSSQLHLTPFTARGRFATVVEELF<br>RDGVNWGRIVAFFEFGGVMCVESVNREMSPLVDNIALWMTEYLNRH<br>LHTWIQDNGGWDAFVELYGPSMRPLFDFSWLSLKTLLSLALVGACI<br>TLGAYLGHK |
| NP_612815.1<br>Bcl-X(L)<br>(BCL2-like 1 isoform 1)<br>[Homo sapiens] | MSQSNRELVVDFLSYKLSQKGYSWSQFSDVEENRTEAPEGTESEME<br>TPSAINGNPSWHLADSPAVNGATGHSSSLDAREVIPMAAVKQALRE<br>AGDEFELRYRRAFSDLTSQLHITPGTAYQSFEQVVNELFRDGVNWG<br>RIVAFFSFGGALCVESVDKEMQVLVSRIAAWMATYLNDHLEPWIQE<br>NGGWDTFVELYGNNAAAESRKGQERFNRWFLTGMTVAGVVLLGSLF<br>SRK |
| AAC51660.1<br>apoptosis inhibitor<br>survivin [Homo sapiens] | MGAPTLPPAWQPFLKDHRISTFKNWPFLEGCACTPERMAEAGFIHC<br>PTENEPDLAQCFFCFKELEGWEPDDDPIEEHKKHSSGCAFLSVKKQ<br>FEELTLGEFLKLDRERAKNKIAKETNNKKKEFEETAKKVRRAIEQL<br>AAMD |
| AAF64255.1<br>Mcl-1 [Homo sapiens] | MFGLKRNAVIGLNLYCGGAGLGAGSGGATRPGGRLLATEKEASARR<br>EIGGGEAGAVIGGSAGASPPSTLTPDSRRVARPPPIGAEVPDVTAT<br>PARLLFFAPTRRAAPLEEMEAPAADAIMSPEEELDGYEPEPLGKRP<br>AVLPLLELVGESGNNTSTDGSLPSTPPPAEEEEDDLYRQSLEIISR<br>YLREQATGAKDTKPMGRSGATSRKALETLRRVGDGVQRNHETAFQG<br>MLRKLDIKNEDDVKSLSRVMIHVFSDGVTNWGRIVTLISFGAFVAK<br>HLKTINQESCIEPLAESITDVLVRTKRDWLVKQRGWDGFVEFFHVE<br>DLEGGIRNVLLAFAGVAGVGAGLAYLIR |

SEQ ID NOS: 44889-44892

The one or more antigenic peptides can in one embodiment comprise one or more fragments from one or more cancer antigens capable of interacting with one or more MHC class 1 molecules.

The one or more antigenic peptides can in another embodiment comprise one or more fragments from one or more cancer antigens capable of interacting with one or more MHC class 2 molecules.

The one or more antigenic peptides can in one embodiment comprise one or more fragments from BclX(L).

The one or more antigenic peptides can in one embodiment comprise one or more fragments from Bcl-2.

The one or more antigenic peptides can in one embodiment comprise one or more fragments from Survivin.

The one or more antigenic peptides can in one embodiment comprise one or more fragments from Mcl-1.

Preferred fragments of BclX(L) capable of interacting with one or more MHC class 1 molecules are listed in table B.

TABLE B

Prediction of cancer antigen BclX(L) specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 8-mers | | | | | | |
| 57 | HLADSPAV | 0.691 | 28 | SB | Sequence | A0201 |
| 213 | FLTGMTVA | 0.687 | 29 | SB | Sequence | A0201 |
| 166 | AAWMATYL | 0.477 | 285 | WB | Sequence | A0201 |
| 160 | VLVSRIAA | 0.463 | 333 | WB | Sequence | A0201 |
| 119 | YQSFEQVV | 0.436 | 448 | WB | Sequence | A0201 |
| 147 | GALCVESV | 0.431 | 472 | WB | Sequence | A0201 |
| 223 | VLLGSLFS | 0.427 | 494 | WB | Sequence | A0201 |
| 213 | FLTGMTVA | 0.777 | 11 | SB | Sequence | A0202 |
| 57 | HLADSPAV | 0.771 | 11 | SB | Sequence | A0202 |
| 119 | YQSFEQVV | 0.590 | 84 | WB | Sequence | A0202 |
| 218 | TVAGVVLL | 0.565 | 110 | WB | Sequence | A0202 |
| 11 | FLSYKLSQ | 0.545 | 137 | WB | Sequence | A0202 |
| 82 | MAAVKQAL | 0.512 | 195 | WB | Sequence | A0202 |
| 73 | SLDAREVI | 0.475 | 294 | WB | Sequence | A0202 |
| 192 | ELYGNNAA | 0.444 | 410 | WB | Sequence | A0202 |
| 217 | MTVAGVVL | 0.440 | 425 | WB | Sequence | A0202 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 160 | VLVSRIAA | 0.434 | 454 | WB | Sequence | A0202 |
| 1 | SQSNRELV | 0.434 | 457 | WB | Sequence | A0202 |
| 213 | FLTGMTVA | 0.852 | 4 | SB | Sequence | A0203 |
| 57 | HLADSPAV | 0.831 | 6 | SB | Sequence | A0203 |
| 160 | VLVSRIAA | 0.642 | 48 | SB | Sequence | A0203 |
| 158 | MQVLVSRI | 0.602 | 74 | WB | Sequence | A0203 |
| 11 | FLSYKLSQ | 0.582 | 92 | WB | Sequence | A0203 |
| 133 | GVNWGRIV | 0.581 | 92 | WB | Sequence | A0203 |
| 216 | GMTVAGVV | 0.579 | 94 | WB | Sequence | A0203 |
| 119 | YQSFEQVV | 0.578 | 96 | WB | Sequence | A0203 |
| 164 | RIAAWMAT | 0.573 | 101 | WB | Sequence | A0203 |
| 78 | EVIPMAAV | 0.486 | 261 | WB | Sequence | A0203 |
| 1 | SQSNRELV | 0.481 | 274 | WB | Sequence | A0203 |
| 217 | MTVAGVVL | 0.467 | 318 | WB | Sequence | A0203 |
| 147 | GALCVESV | 0.464 | 328 | WB | Sequence | A0203 |
| 221 | GVVLLGSL | 0.443 | 412 | WB | Sequence | A0203 |
| 218 | TVAGVVLL | 0.440 | 429 | WB | Sequence | A0203 |
| 57 | HLADSPAV | 0.555 | 122 | WB | Sequence | A0204 |
| 153 | SVDKEMQV | 0.431 | 469 | WB | Sequence | A0204 |
| 57 | HLADSPAV | 0.780 | 10 | SB | Sequence | A0206 |
| 158 | MQVLVSRI | 0.733 | 18 | SB | Sequence | A0206 |
| 213 | FLTGMTVA | 0.682 | 31 | SB | Sequence | A0206 |
| 1 | SQSNRELV | 0.677 | 32 | SB | Sequence | A0206 |
| 119 | YQSFEQVV | 0.677 | 33 | SB | Sequence | A0206 |
| 138 | RIVAFFSF | 0.653 | 42 | SB | Sequence | A0206 |
| 164 | RIAAWMAT | 0.575 | 99 | WB | Sequence | A0206 |
| 147 | GALCVESV | 0.568 | 106 | WB | Sequence | A0206 |
| 166 | AAWMATYL | 0.567 | 108 | WB | Sequence | A0206 |
| 217 | MTVAGVVL | 0.563 | 112 | WB | Sequence | A0206 |
| 160 | VLVSRIAA | 0.517 | 185 | WB | Sequence | A0206 |
| 42 | SEMETPSA | 0.514 | 191 | WB | Sequence | A0206 |
| 78 | EVIPMAAV | 0.496 | 233 | WB | Sequence | A0206 |
| 153 | SVDKEMQV | 0.493 | 240 | WB | Sequence | A0206 |
| 57 | HLADSPAV | 0.955 | 1 | SB | Sequence | A0211 |
| 153 | SVDKEMQV | 0.898 | 3 | SB | Sequence | A0211 |
| 213 | FLTGMTVA | 0.893 | 3 | SB | Sequence | A0211 |
| 73 | SLDAREVI | 0.877 | 3 | SB | Sequence | A0211 |
| 192 | ELYGNNAA | 0.834 | 6 | SB | Sequence | A0211 |
| 218 | TVAGVVLL | 0.797 | 8 | SB | Sequence | A0211 |
| 172 | YLNDHLEP | 0.751 | 14 | SB | Sequence | A0211 |
| 78 | EVIPMAAV | 0.739 | 16 | SB | Sequence | A0211 |
| 216 | GMTVAGVV | 0.718 | 21 | SB | Sequence | A0211 |
| 160 | VLVSRIAA | 0.684 | 30 | SB | Sequence | A0211 |
| 223 | VLLGSLFS | 0.683 | 30 | SB | Sequence | A0211 |
| 133 | GVNWGRIV | 0.668 | 36 | SB | Sequence | A0211 |
| 212 | WFLTGMTV | 0.668 | 36 | SB | Sequence | A0211 |
| 144 | SFGGALCV | 0.591 | 83 | WB | Sequence | A0211 |
| 72 | SSLDAREV | 0.590 | 84 | WB | Sequence | A0211 |
| 106 | DLTSQLHI | 0.564 | 111 | WB | Sequence | A0211 |
| 119 | YQSFEQVV | 0.545 | 136 | WB | Sequence | A0211 |
| 81 | PMAAVKQA | 0.532 | 158 | WB | Sequence | A0211 |
| 11 | FLSYKLSQ | 0.511 | 198 | WB | Sequence | A0211 |
| 166 | AAWMATYL | 0.456 | 360 | WB | Sequence | A0211 |
| 1 | SQSNRELV | 0.439 | 431 | WB | Sequence | A0211 |
| 147 | GALCVESV | 0.439 | 434 | WB | Sequence | A0211 |
| 57 | HLADSPAV | 0.915 | 2 | SB | Sequence | A0212 |
| 192 | ELYGNNAA | 0.813 | 7 | SB | Sequence | A0212 |
| 213 | FLTGMTVA | 0.801 | 8 | SB | Sequence | A0212 |
| 153 | SVDKEMQV | 0.732 | 18 | SB | Sequence | A0212 |
| 73 | SLDAREVI | 0.714 | 22 | SB | Sequence | A0212 |
| 160 | VLVSRIAA | 0.662 | 38 | SB | Sequence | A0212 |
| 172 | YLNDHLEP | 0.662 | 38 | SB | Sequence | A0212 |
| 119 | YQSFEQVV | 0.586 | 88 | WB | Sequence | A0212 |
| 78 | EVIPMAAV | 0.585 | 88 | WB | Sequence | A0212 |
| 223 | VLLGSLFS | 0.582 | 92 | WB | Sequence | A0212 |
| 11 | FLSYKLSQ | 0.573 | 101 | WB | Sequence | A0212 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 212 | WFLTGMTV | 0.541 | 142 | WB | Sequence | A0212 |
| 216 | GMTVAGVV | 0.466 | 321 | WB | Sequence | A0212 |
| 57 | HLADSPAV | 0.892 | 3 | SB | Sequence | A0216 |
| 153 | SVDKEMQV | 0.817 | 7 | SB | Sequence | A0216 |
| 213 | FLTGMTVA | 0.761 | 13 | SB | Sequence | A0216 |
| 192 | ELYGNNAA | 0.715 | 21 | SB | Sequence | A0216 |
| 78 | EVIPMAAV | 0.666 | 37 | SB | Sequence | A0216 |
| 218 | TVAGVVLL | 0.657 | 41 | SB | Sequence | A0216 |
| 73 | SLDAREVI | 0.640 | 49 | SB | Sequence | A0216 |
| 144 | SFGGALCV | 0.630 | 54 | WB | Sequence | A0216 |
| 216 | GMTVAGVV | 0.613 | 65 | WB | Sequence | A0216 |
| 166 | AAWMATYL | 0.603 | 73 | WB | Sequence | A0216 |
| 160 | VLVSRIAA | 0.583 | 91 | WB | Sequence | A0216 |
| 212 | WFLTGMTV | 0.565 | 110 | WB | Sequence | A0216 |
| 11 | FLSYKLSQ | 0.488 | 255 | WB | Sequence | A0216 |
| 106 | DLTSQLHI | 0.487 | 258 | WB | Sequence | A0216 |
| 133 | GVNWGRIV | 0.470 | 308 | WB | Sequence | A0216 |
| 81 | PMAAVKQA | 0.469 | 311 | WB | Sequence | A0216 |
| 118 | AYQSFEQV | 0.461 | 342 | WB | Sequence | A0216 |
| 223 | VLLGSLFS | 0.442 | 417 | WB | Sequence | A0216 |
| 147 | GALCVESV | 0.438 | 436 | WB | Sequence | A0216 |
| 57 | HLADSPAV | 0.924 | 2 | SB | Sequence | A0219 |
| 213 | FLTGMTVA | 0.668 | 36 | SB | Sequence | A0219 |
| 153 | SVDKEMQV | 0.597 | 78 | WB | Sequence | A0219 |
| 73 | SLDAREVI | 0.576 | 98 | WB | Sequence | A0219 |
| 218 | TVAGVVLL | 0.517 | 185 | WB | Sequence | A0219 |
| 192 | ELYGNNAA | 0.486 | 259 | WB | Sequence | A0219 |
| 212 | WFLTGMTV | 0.458 | 352 | WB | Sequence | A0219 |
| 166 | AAWMATYL | 0.455 | 362 | WB | Sequence | A0219 |
| 106 | DLTSQLHI | 0.448 | 390 | WB | Sequence | A0219 |
| 223 | VLLGSLFS | 0.431 | 471 | WB | Sequence | A0219 |
| 12 | LSYKLSQK | 0.761 | 13 | SB | Sequence | A0301 |
| 8 | VVDFLSYK | 0.551 | 128 | WB | Sequence | A0301 |
| 224 | LLGSLFSR | 0.487 | 257 | WB | Sequence | A0301 |
| 8 | VVDFLSYK | 0.751 | 14 | SB | Sequence | A1101 |
| 12 | LSYKLSQK | 0.721 | 20 | SB | Sequence | A1101 |
| 79 | VIPMAAVK | 0.509 | 203 | WB | Sequence | A1101 |
| 124 | QVVNELFR | 0.472 | 302 | WB | Sequence | A1101 |
| 7 | LVVDFLSY | 0.457 | 355 | WB | Sequence | A1101 |
| 197 | NAAAESRK | 0.455 | 363 | WB | Sequence | A1101 |
| 135 | NWGRIVAF | 0.600 | 75 | WB | Sequence | A2301 |
| 138 | RIVAFFSF | 0.466 | 321 | WB | Sequence | A2301 |
| 222 | VVLLGSLF | 0.461 | 339 | WB | Sequence | A2301 |
| 135 | NWGRIVAF | 0.617 | 62 | WB | Sequence | A2402 |
| 118 | AYQSFEQV | 0.569 | 105 | WB | Sequence | A2403 |
| 78 | EVIPMAAV | 0.598 | 77 | WB | Sequence | A2601 |
| 7 | LVVDFLSY | 0.541 | 144 | WB | Sequence | A2601 |
| 78 | EVIPMAAV | 0.862 | 4 | SB | Sequence | A2602 |
| 7 | LVVDFLSY | 0.797 | 9 | SB | Sequence | A2602 |
| 112 | HITPGTAY | 0.755 | 14 | SB | Sequence | A2602 |
| 97 | ELRYRRAF | 0.589 | 85 | WB | Sequence | A2602 |
| 138 | RIVAFFSF | 0.529 | 164 | WB | Sequence | A2602 |
| 112 | HITPGTAY | 0.597 | 78 | WB | Sequence | A2902 |
| 7 | LVVDFLSY | 0.480 | 276 | WB | Sequence | A2902 |
| 204 | KGQERFNR | 0.743 | 16 | SB | Sequence | A3101 |
| 224 | LLGSLFSR | 0.697 | 26 | SB | Sequence | A3101 |
| 157 | EMQVLVSR | 0.583 | 90 | WB | Sequence | A3101 |
| 70 | HSSSLDAR | 0.577 | 97 | WB | Sequence | A3101 |
| 83 | AAVKQALR | 0.539 | 146 | WB | Sequence | A3101 |
| 95 | EFELRYRR | 0.509 | 201 | WB | Sequence | A3101 |
| 124 | QVVNELFR | 0.453 | 369 | WB | Sequence | A3101 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 12 | LSYKLSQK | 0.447 | 397 | WB | Sequence | A3101 |
| | | | | | | |
| 95 | EFELRYRR | 0.823 | 6 | SB | Sequence | A3301 |
| 157 | EMQVLVSR | 0.738 | 16 | SB | Sequence | A3301 |
| 94 | DEFELRYR | 0.650 | 43 | SB | Sequence | A3301 |
| 201 | ESRKGQER | 0.606 | 71 | WB | Sequence | A3301 |
| 224 | LLGSLFSR | 0.538 | 148 | WB | Sequence | A3301 |
| 70 | HSSSLDAR | 0.463 | 332 | WB | Sequence | A3301 |
| | | | | | | |
| 124 | QVVNELFR | 0.803 | 8 | SB | Sequence | A6801 |
| 70 | HSSSLDAR | 0.775 | 11 | SB | Sequence | A6801 |
| 197 | NAAAESRK | 0.681 | 31 | SB | Sequence | A6801 |
| 12 | LSYKLSQK | 0.647 | 45 | SB | Sequence | A6801 |
| 157 | EMQVLVSR | 0.599 | 76 | WB | Sequence | A6801 |
| 196 | NNAAAESR | 0.585 | 88 | WB | Sequence | A6801 |
| 83 | AAVKQALR | 0.535 | 153 | WB | Sequence | A6801 |
| 201 | ESRKGQER | 0.532 | 158 | WB | Sequence | A6801 |
| 165 | IAAWMATY | 0.532 | 158 | WB | Sequence | A6801 |
| 95 | EFELRYRR | 0.511 | 198 | WB | Sequence | A6801 |
| 117 | TAYQSFEQ | 0.507 | 208 | WB | Sequence | A6801 |
| 8 | VVDFLSYK | 0.481 | 273 | WB | Sequence | A6801 |
| 94 | DEFELRYR | 0.457 | 357 | WB | Sequence | A6801 |
| 26 | FSDVEENR | 0.442 | 418 | WB | Sequence | A6801 |
| 224 | LLGSLFSR | 0.430 | 476 | WB | Sequence | A6801 |
| | | | | | | |
| 78 | EVIPMAAV | 0.888 | 3 | SB | Sequence | A6802 |
| 218 | TVAGVVLL | 0.790 | 9 | SB | Sequence | A6802 |
| 215 | TGMTVAGV | 0.742 | 16 | SB | Sequence | A6802 |
| 217 | MTVAGVVL | 0.697 | 26 | SB | Sequence | A6802 |
| 82 | MAAVKQAL | 0.633 | 52 | WB | Sequence | A6802 |
| 57 | HLADSPAV | 0.549 | 131 | WB | Sequence | A6802 |
| 207 | ERFNRWFL | 0.481 | 273 | WB | Sequence | A6802 |
| 60 | DSPAVNGA | 0.473 | 300 | WB | Sequence | A6802 |
| 192 | ELYGNNAA | 0.447 | 395 | WB | Sequence | A6802 |
| 91 | EAGDEFEL | 0.436 | 444 | WB | Sequence | A6802 |
| | | | | | | |
| 78 | EVIPMAAV | 0.812 | 7 | SB | Sequence | A6901 |
| 57 | HLADSPAV | 0.740 | 16 | SB | Sequence | A6901 |
| 192 | ELYGNNAA | 0.570 | 104 | WB | Sequence | A6901 |
| 217 | MTVAGVVL | 0.544 | 138 | WB | Sequence | A6901 |
| 218 | TVAGVVLL | 0.507 | 206 | WB | Sequence | A6901 |
| 91 | EAGDEFEL | 0.489 | 252 | WB | Sequence | A6901 |
| 153 | SVDKEMQV | 0.437 | 441 | WB | Sequence | A6901 |
| 212 | WFLTGMTV | 0.436 | 445 | WB | Sequence | A6901 |
| | | | | | | |
| 61 | SPAVNGAT | 0.657 | 41 | SB | Sequence | B0702 |
| 82 | MAAVKQAL | 0.468 | 316 | WB | Sequence | B0702 |
| 166 | AAWMATYL | 0.430 | 477 | WB | Sequence | B0702 |
| | | | | | | |
| 97 | ELRYRRAF | 0.589 | 85 | WB | Sequence | B0801 |
| | | | | | | |
| 7 | LVVDFLSY | 0.511 | 198 | WB | Sequence | B1501 |
| 138 | RIVAFFSF | 0.493 | 240 | WB | Sequence | B1501 |
| 112 | HITPGTAY | 0.492 | 243 | WB | Sequence | B1501 |
| 165 | IAAWMATY | 0.473 | 300 | WB | Sequence | B1501 |
| 97 | ELRYRRAF | 0.439 | 430 | WB | Sequence | B1501 |
| 222 | VVLLGSLF | 0.433 | 461 | WB | Sequence | B1501 |
| | | | | | | |
| 206 | QERFNRWF | 0.528 | 165 | WB | Sequence | B1801 |
| 5 | RELVVDFL | 0.517 | 185 | WB | Sequence | B1801 |
| 122 | FEQVVNEL | 0.508 | 205 | WB | Sequence | B1801 |
| | | | | | | |
| 210 | NRWFLTGM | 0.510 | 200 | WB | Sequence | B2705 |
| | | | | | | |
| 165 | IAAWMATY | 0.806 | 8 | SB | Sequence | B3501 |
| 7 | LVVDFLSY | 0.629 | 55 | WB | Sequence | B3501 |
| 82 | MAAVKQAL | 0.591 | 83 | WB | Sequence | B3501 |
| 112 | HITPGTAY | 0.543 | 140 | WB | Sequence | B3501 |
| 75 | DAREVIPM | 0.516 | 187 | WB | Sequence | B3501 |
| 142 | FFSFGGAL | 0.499 | 226 | WB | Sequence | B3501 |
| 61 | SPAVNGAT | 0.478 | 283 | WB | Sequence | B3501 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 166 | AAWMATYL | 0.476 | 289 | WB | Sequence | B3501 |
| 217 | MTVAGVVL | 0.470 | 307 | WB | Sequence | B3501 |
| 5 | RELVVDFL | 0.624 | 58 | WB | Sequence | B4001 |
| 122 | FEQVVNEL | 0.618 | 62 | WB | Sequence | B4001 |
| 5 | RELVVDFL | 0.442 | 420 | WB | Sequence | B4002 |
| 156 | KEMQVLVS | 0.430 | 478 | WB | Sequence | B4403 |
| 77 | REVIPMAA | 0.434 | 456 | WB | Sequence | B4501 |
| 161 | LVSRIAAW | 0.626 | 57 | WB | Sequence | B5801 |
| 165 | IAAWMATY | 0.593 | 81 | WB | Sequence | B5801 |
| 16 | LSQKGYSW | 0.586 | 88 | WB | Sequence | B5801 |
| 19 | KGYSWSQF | 0.543 | 141 | WB | Sequence | B5801 |
| 138 | RIVAFFSF | 0.467 | 320 | WB | Sequence | B5801 |
| 49 | AINGNPSW | 0.447 | 394 | WB | Sequence | B5801 |

9.mers

| pos | peptide | logscore | affinity (nM) | Bind Level | Protein Name | Allele |
|---|---|---|---|---|---|---|
| 104 | FSDLTSQLH | 0.482 | 270 | WB | Sequence | A0101 |
| 143 | FSFGGALCV | 0.518 | 183 | WB | Sequence | A0201 |
| 217 | MTVAGVVLL | 0.478 | 282 | WB | Sequence | A0201 |
| 172 | YLNDHLEPW | 0.739 | 16 | SB | Sequence | A0202 |
| 217 | MTVAGVVLL | 0.604 | 72 | WB | Sequence | A0202 |
| 165 | IAAWMATYL | 0.568 | 107 | WB | Sequence | A0202 |
| 213 | FLTGMTVAG | 0.564 | 111 | WB | Sequence | A0202 |
| 11 | FLSYKLSQK | 0.520 | 179 | WB | Sequence | A0202 |
| 161 | LVSRIAAWM | 0.450 | 382 | WB | Sequence | A0202 |
| 8 | VVDFLSYKL | 0.449 | 387 | WB | Sequence | A0202 |
| 192 | ELYGNNAAA | 0.447 | 394 | WB | Sequence | A0202 |
| 81 | PMAAVKQAL | 0.437 | 441 | WB | Sequence | A0202 |
| 216 | GMTVAGVVL | 0.436 | 448 | WB | Sequence | A0202 |
| 214 | LTGMTVAGV | 0.691 | 28 | SB | Sequence | A0203 |
| 217 | MTVAGVVLL | 0.609 | 69 | WB | Sequence | A0203 |
| 165 | IAAWMATYL | 0.530 | 161 | WB | Sequence | A0203 |
| 84 | AVKQALREA | 0.518 | 183 | WB | Sequence | A0203 |
| 110 | QLHITPGTA | 0.507 | 206 | WB | Sequence | A0203 |
| 172 | YLNDHLEPW | 0.493 | 240 | WB | Sequence | A0203 |
| 117 | TAYQSFEQV | 0.473 | 300 | WB | Sequence | A0203 |
| 11 | FLSYKLSQK | 0.447 | 396 | WB | Sequence | A0203 |
| 214 | LTGMTVAGV | 0.504 | 213 | WB | Sequence | A0204 |
| 217 | MTVAGVVLL | 0.475 | 291 | WB | Sequence | A0204 |
| 109 | SQLHITPGT | 0.712 | 22 | SB | Sequence | A0206 |
| 217 | MTVAGVVLL | 0.675 | 33 | SB | Sequence | A0206 |
| 117 | TAYQSFEQV | 0.650 | 43 | SB | Sequence | A0206 |
| 1 | SQSNRELVV | 0.648 | 45 | SB | Sequence | A0206 |
| 143 | FSFGGALCV | 0.584 | 90 | WB | Sequence | A0206 |
| 77 | REVIPMAAV | 0.572 | 103 | WB | Sequence | A0206 |
| 165 | IAAWMATYL | 0.551 | 128 | WB | Sequence | A0206 |
| 158 | MQVLVSRIA | 0.544 | 138 | WB | Sequence | A0206 |
| 214 | LTGMTVAGV | 0.492 | 244 | WB | Sequence | A0206 |
| 172 | YLNDHLEPW | 0.464 | 331 | WB | Sequence | A0206 |
| 42 | SEMETPSAI | 0.440 | 426 | WB | Sequence | A0206 |
| 192 | ELYGNNAAA | 0.863 | 4 | SB | Sequence | A0211 |
| 143 | FSFGGALCV | 0.797 | 8 | SB | Sequence | A0211 |
| 81 | PMAAVKQAL | 0.794 | 9 | SB | Sequence | A0211 |
| 172 | YLNDHLEPW | 0.715 | 21 | SB | Sequence | A0211 |
| 153 | SVDKEMQVL | 0.703 | 24 | SB | Sequence | A0211 |
| 8 | VVDFLSYKL | 0.696 | 26 | SB | Sequence | A0211 |
| 217 | MTVAGVVLL | 0.634 | 52 | WB | Sequence | A0211 |
| 112 | HITPGTAYQ | 0.618 | 62 | WB | Sequence | A0211 |
| 117 | TAYQSFEQV | 0.617 | 63 | WB | Sequence | A0211 |
| 223 | VLLGSLFSR | 0.581 | 93 | WB | Sequence | A0211 |
| 213 | FLTGMTVAG | 0.581 | 93 | WB | Sequence | A0211 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 133 | GVNWGRIVA | 0.575 | 99 | WB | Sequence | A0211 |
| 216 | GMTVAGVVL | 0.553 | 126 | WB | Sequence | A0211 |
| 185 | GGWDTFVEL | 0.550 | 130 | WB | Sequence | A0211 |
| 103 | AFSDLTSQL | 0.472 | 302 | WB | Sequence | A0211 |
| 176 | HLEPWIQEN | 0.427 | 493 | WB | Sequence | A0211 |
| 192 | ELYGNNAAA | 0.845 | 5 | SB | Sequence | A0212 |
| 81 | PMAAVKQAL | 0.789 | 9 | SB | Sequence | A0212 |
| 143 | FSFGGALCV | 0.702 | 25 | SB | Sequence | A0212 |
| 172 | YLNDHLEPW | 0.673 | 34 | SB | Sequence | A0212 |
| 223 | VLLGSLFSR | 0.573 | 101 | WB | Sequence | A0212 |
| 8 | VVDFLSYKL | 0.561 | 115 | WB | Sequence | A0212 |
| 153 | SVDKEMQVL | 0.535 | 153 | WB | Sequence | A0212 |
| 213 | FLTGMTVAG | 0.521 | 178 | WB | Sequence | A0212 |
| 118 | AYQSFEQVV | 0.476 | 290 | WB | Sequence | A0212 |
| 192 | ELYGNNAAA | 0.741 | 16 | SB | Sequence | A0216 |
| 81 | PMAAVKQAL | 0.710 | 22 | SB | Sequence | A0216 |
| 143 | FSFGGALCV | 0.652 | 42 | SB | Sequence | A0216 |
| 117 | TAYQSFEQV | 0.593 | 81 | WB | Sequence | A0216 |
| 112 | HITPGTAYQ | 0.512 | 196 | WB | Sequence | A0216 |
| 216 | GMTVAGVVL | 0.430 | 479 | WB | Sequence | A0216 |
| 81 | PMAAVKQAL | 0.675 | 33 | SB | Sequence | A0219 |
| 143 | FSFGGALCV | 0.652 | 43 | SB | Sequence | A0219 |
| 192 | ELYGNNAAA | 0.541 | 142 | WB | Sequence | A0219 |
| 117 | TAYQSFEQV | 0.497 | 232 | WB | Sequence | A0219 |
| 172 | YLNDHLEPW | 0.459 | 348 | WB | Sequence | A0219 |
| 223 | VLLGSLFSR | 0.456 | 361 | WB | Sequence | A0219 |
| 214 | LTGMTVAGV | 0.450 | 384 | WB | Sequence | A0219 |
| 224 | LLGSLFSRK | 0.762 | 13 | SB | Sequence | A0301 |
| 11 | FLSYKLSQK | 0.710 | 23 | SB | Sequence | A0301 |
| 164 | RIAAWMATY | 0.698 | 26 | SB | Sequence | A0301 |
| 223 | VLLGSLFSR | 0.615 | 64 | WB | Sequence | A0301 |
| 7 | LVVDFLSYK | 0.497 | 231 | WB | Sequence | A0301 |
| 7 | LVVDFLSYK | 0.767 | 12 | SB | Sequence | A1101 |
| 224 | LLGSLFSRK | 0.612 | 66 | WB | Sequence | A1101 |
| 223 | VLLGSLFSR | 0.595 | 79 | WB | Sequence | A1101 |
| 164 | RIAAWMATY | 0.575 | 99 | WB | Sequence | A1101 |
| 148 | ALCVESVDK | 0.529 | 163 | WB | Sequence | A1101 |
| 78 | EVIPMAAVK | 0.509 | 201 | WB | Sequence | A1101 |
| 11 | FLSYKLSQK | 0.430 | 477 | WB | Sequence | A1101 |
| 99 | RYRRAFSDL | 0.690 | 28 | SB | Sequence | A2301 |
| 135 | NWGRIVAFF | 0.644 | 47 | SB | Sequence | A2301 |
| 137 | GRIVAFFSF | 0.459 | 346 | WB | Sequence | A2301 |
| 135 | NWGRIVAFF | 0.739 | 16 | SB | Sequence | A2402 |
| 99 | RYRRAFSDL | 0.550 | 129 | WB | Sequence | A2402 |
| 99 | RYRRAFSDL | 0.748 | 15 | SB | Sequence | A2403 |
| 121 | SFEQVVNEL | 0.557 | 120 | WB | Sequence | A2403 |
| 118 | AYQSFEQVV | 0.487 | 256 | WB | Sequence | A2403 |
| 6 | ELVVDFLSY | 0.532 | 158 | WB | Sequence | A2601 |
| 164 | RIAAWMATY | 0.495 | 235 | WB | Sequence | A2601 |
| 164 | RIAAWMATY | 0.923 | 2 | SB | Sequence | A2602 |
| 6 | ELVVDFLSY | 0.873 | 3 | SB | Sequence | A2602 |
| 161 | LVSRIAAWM | 0.677 | 32 | SB | Sequence | A2602 |
| 153 | SVDKEMQVL | 0.639 | 49 | SB | Sequence | A2602 |
| 78 | EVIPMAAVK | 0.496 | 234 | WB | Sequence | A2602 |
| 217 | MTVAGVVLL | 0.481 | 273 | WB | Sequence | A2602 |
| 111 | LHITPGTAY | 0.553 | 125 | WB | Sequence | A2902 |
| 6 | ELVVDFLSY | 0.539 | 146 | WB | Sequence | A2902 |
| 164 | RIAAWMATY | 0.463 | 334 | WB | Sequence | A3002 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 82 | MAAVKQALR | 0.766 | 12 | SB | Sequence | A3101 |
| 223 | VLLGSLFSR | 0.686 | 30 | SB | Sequence | A3101 |
| 7 | LVVDFLSYK | 0.573 | 101 | WB | Sequence | A3101 |
| 156 | KEMQVLVSR | 0.474 | 296 | WB | Sequence | A3101 |
| 94 | DEFELRYRR | 0.721 | 20 | SB | Sequence | A3301 |
| 82 | MAAVKQALR | 0.665 | 37 | SB | Sequence | A3301 |
| 97 | ELRYRRAFS | 0.614 | 65 | WB | Sequence | A3301 |
| 223 | VLLGSLFSR | 0.581 | 92 | WB | Sequence | A3301 |
| 91 | EAGDEFELR | 0.532 | 157 | WB | Sequence | A3301 |
| 25 | QFSDVEENR | 0.531 | 159 | WB | Sequence | A3301 |
| 78 | EVIPMAAVK | 0.848 | 5 | SB | Sequence | A6801 |
| 82 | MAAVKQALR | 0.813 | 7 | SB | Sequence | A6801 |
| 7 | LVVDFLSYK | 0.786 | 10 | SB | Sequence | A6801 |
| 91 | EAGDEFELR | 0.710 | 23 | SB | Sequence | A6801 |
| 123 | EQVVNELFR | 0.635 | 51 | WB | Sequence | A6801 |
| 11 | FLSYKLSQK | 0.558 | 119 | WB | Sequence | A6801 |
| 94 | DEFELRYRR | 0.544 | 139 | WB | Sequence | A6801 |
| 25 | QFSDVEENR | 0.540 | 145 | WB | Sequence | A6801 |
| 196 | NNAAAESRK | 0.474 | 295 | WB | Sequence | A6801 |
| 223 | VLLGSLFSR | 0.430 | 477 | WB | Sequence | A6801 |
| 217 | MTVAGVVLL | 0.796 | 9 | SB | Sequence | A6802 |
| 117 | TAYQSFEQV | 0.729 | 18 | SB | Sequence | A6802 |
| 215 | TGMTVAGVV | 0.654 | 42 | SB | Sequence | A6802 |
| 0 | MSQSNRELV | 0.587 | 86 | WB | Sequence | A6802 |
| 21 | YSWSQFSDV | 0.549 | 131 | WB | Sequence | A6802 |
| 143 | FSFGGALCV | 0.526 | 169 | WB | Sequence | A6802 |
| 152 | ESVDKEMQV | 0.525 | 171 | WB | Sequence | A6802 |
| 169 | MATYLNDHL | 0.520 | 180 | WB | Sequence | A6802 |
| 192 | ELYGNNAAA | 0.509 | 202 | WB | Sequence | A6802 |
| 140 | VAFFSFGGA | 0.500 | 222 | WB | Sequence | A6802 |
| 214 | LTGMTVAGV | 0.464 | 330 | WB | Sequence | A6802 |
| 165 | IAAWMATYL | 0.451 | 378 | WB | Sequence | A6802 |
| 217 | MTVAGVVLL | 0.705 | 24 | SB | Sequence | A6901 |
| 117 | TAYQSFEQV | 0.623 | 58 | WB | Sequence | A6901 |
| 192 | ELYGNNAAA | 0.604 | 72 | WB | Sequence | A6901 |
| 143 | FSFGGALCV | 0.589 | 85 | WB | Sequence | A6901 |
| 214 | LTGMTVAGV | 0.557 | 120 | WB | Sequence | A6901 |
| 21 | YSWSQFSDV | 0.489 | 252 | WB | Sequence | A6901 |
| 36 | APEGTESEM | 0.519 | 181 | WB | Sequence | B0702 |
| 61 | SPAVNGATG | 0.454 | 369 | WB | Sequence | B0702 |
| 114 | TPGTAYQSF | 0.450 | 382 | WB | Sequence | B0702 |
| 96 | FELRYRRAF | 0.497 | 229 | WB | Sequence | B0801 |
| 164 | RIAAWMATY | 0.586 | 87 | WB | Sequence | B1501 |
| 88 | ALREAGDEF | 0.520 | 180 | WB | Sequence | B1501 |
| 96 | FELRYRRAF | 0.752 | 14 | SB | Sequence | B1801 |
| 206 | QERFNRWFL | 0.592 | 82 | WB | Sequence | B1801 |
| 122 | FEQVVNELF | 0.523 | 174 | WB | Sequence | B1801 |
| 182 | QENGGWDTF | 0.476 | 290 | WB | Sequence | B1801 |
| 137 | GRIVAFFSF | 0.554 | 124 | WB | Sequence | B2705 |
| 101 | RRAFSDLTS | 0.434 | 459 | WB | Sequence | B2705 |
| 114 | TPGTAYQSF | 0.705 | 24 | SB | Sequence | B3501 |
| 165 | IAAWMATYL | 0.649 | 44 | SB | Sequence | B3501 |
| 36 | APEGTESEM | 0.540 | 144 | WB | Sequence | B3501 |
| 6 | ELVVDFLSY | 0.531 | 159 | WB | Sequence | B3501 |
| 111 | LHITPGTAY | 0.437 | 441 | WB | Sequence | B3501 |
| 53 | NPSWHLADS | 0.429 | 480 | WB | Sequence | B3501 |
| 164 | RIAAWMATY | 0.428 | 485 | WB | Sequence | B3501 |
| 90 | REAGDEFEL | 0.788 | 9 | SB | Sequence | B4001 |
| 206 | QERFNRWFL | 0.597 | 78 | WB | Sequence | B4001 |
| 182 | QENGGWDTF | 0.525 | 170 | WB | Sequence | B4001 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 122 | FEQVVNELF | 0.453 | 370 | WB | Sequence | B4001 |
| 96 | FELRYRRAF | 0.446 | 399 | WB | Sequence | B4001 |
| 42 | SEMETPSAI | 0.504 | 215 | WB | Sequence | B4002 |
| 96 | FELRYRRAF | 0.473 | 299 | WB | Sequence | B4002 |
| 182 | QENGGWDTF | 0.434 | 455 | WB | Sequence | B4402 |
| 42 | SEMETPSAI | 0.467 | 319 | WB | Sequence | B4403 |
| 5 | RELVVDFLS | 0.444 | 407 | WB | Sequence | B4403 |
| 77 | REVIPMAAV | 0.438 | 438 | WB | Sequence | B4501 |
| 165 | IAAWMATYL | 0.442 | 416 | WB | Sequence | B5301 |
| 80 | IPMAAVKQA | 0.716 | 21 | SB | Sequence | B5401 |
| 48 | SAINGNPSW | 0.641 | 48 | SB | Sequence | B5801 |
| 15 | KLSQKGYSW | 0.596 | 79 | WB | Sequence | B5801 |
| 165 | IAAWMATYL | 0.559 | 118 | WB | Sequence | B5801 |
| 172 | YLNDHLEPW | 0.506 | 208 | WB | Sequence | B5801 |
| | | | 10-mers | | | |
| 104 | FSDLTSQLHI | 0.427 | 492 | WB | Sequence | A0101 |
| 172 | YLNDHLEPWI | 0.866 | 4 | SB | Sequence | A0201 |
| 213 | FLTGMTVAGV | 0.841 | 5 | SB | Sequence | A0201 |
| 164 | RIAAWMATYL | 0.651 | 43 | SB | Sequence | A0201 |
| 168 | WMATYLNDHL | 0.573 | 101 | WB | Sequence | A0201 |
| 7 | LVVDFLSYKL | 0.524 | 173 | WB | Sequence | A0201 |
| 73 | SLDAREVIPM | 0.491 | 246 | WB | Sequence | A0201 |
| 160 | VLVSRIAAWM | 0.486 | 259 | WB | Sequence | A0201 |
| 153 | SVDKEMQVLV | 0.473 | 298 | WB | Sequence | A0201 |
| 216 | GMTVAGVVLL | 0.444 | 411 | WB | Sequence | A0201 |
| 213 | FLTGMTVAGV | 0.811 | 7 | SB | Sequence | A0202 |
| 168 | WMATYLNDHL | 0.772 | 11 | SB | Sequence | A0202 |
| 164 | RIAAWMATYL | 0.763 | 13 | SB | Sequence | A0202 |
| 7 | LVVDFLSYKL | 0.651 | 43 | SB | Sequence | A0202 |
| 102 | RAFSDLTSQL | 0.617 | 63 | WB | Sequence | A0202 |
| 73 | SLDAREVIPM | 0.616 | 63 | WB | Sequence | A0202 |
| 172 | YLNDHLEPWI | 0.587 | 87 | WB | Sequence | A0202 |
| 216 | GMTVAGVVLL | 0.496 | 233 | WB | Sequence | A0202 |
| 145 | FGGALCVESV | 0.480 | 276 | WB | Sequence | A0202 |
| 160 | VLVSRIAAWM | 0.430 | 476 | WB | Sequence | A0202 |
| 213 | FLTGMTVAGV | 0.936 | 2 | SB | Sequence | A0203 |
| 172 | YLNDHLEPWI | 0.891 | 3 | SB | Sequence | A0203 |
| 164 | RIAAWMATYL | 0.837 | 5 | SB | Sequence | A0203 |
| 168 | WMATYLNDHL | 0.647 | 45 | SB | Sequence | A0203 |
| 160 | VLVSRIAAWM | 0.613 | 66 | WB | Sequence | A0203 |
| 139 | IVAFFSFGGA | 0.596 | 79 | WB | Sequence | A0203 |
| 7 | LVVDFLSYKL | 0.581 | 92 | WB | Sequence | A0203 |
| 125 | VVNELFRDGV | 0.570 | 105 | WB | Sequence | A0203 |
| 216 | GMTVAGVVLL | 0.476 | 289 | WB | Sequence | A0203 |
| 102 | RAFSDLTSQL | 0.470 | 308 | WB | Sequence | A0203 |
| 214 | LTGMTVAGVV | 0.468 | 315 | WB | Sequence | A0203 |
| 116 | GTAYQSFEQV | 0.463 | 335 | WB | Sequence | A0203 |
| 213 | FLTGMTVAGV | 0.697 | 26 | SB | Sequence | A0204 |
| 172 | YLNDHLEPWI | 0.664 | 37 | SB | Sequence | A0204 |
| 73 | SLDAREVIPM | 0.477 | 287 | WB | Sequence | A0204 |
| 164 | RIAAWMATYL | 0.476 | 290 | WB | Sequence | A0204 |
| 7 | LVVDFLSYKL | 0.468 | 317 | WB | Sequence | A0204 |
| 49 | AINGNPSWHL | 0.452 | 374 | WB | Sequence | A0204 |
| 213 | FLTGMTVAGV | 0.869 | 4 | SB | Sequence | A0206 |
| 164 | RIAAWMATYL | 0.809 | 7 | SB | Sequence | A0206 |
| 172 | YLNDHLEPWI | 0.722 | 20 | SB | Sequence | A0206 |
| 158 | MQVLVSRIAA | 0.689 | 28 | SB | Sequence | A0206 |
| 7 | LVVDFLSYKL | 0.684 | 30 | SB | Sequence | A0206 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 168 | WMATYLNDHL | 0.680 | 31 | SB | Sequence | A0206 |
| 109 | SQLHITPGTA | 0.652 | 43 | SB | Sequence | A0206 |
| 116 | GTAYQSFEQV | 0.572 | 102 | WB | Sequence | A0206 |
| 153 | SVDKEMQVLV | 0.558 | 119 | WB | Sequence | A0206 |
| 102 | RAFSDLTSQL | 0.543 | 140 | WB | Sequence | A0206 |
| 156 | KEMQVLVSRI | 0.508 | 204 | WB | Sequence | A0206 |
| 181 | IQENGGWDTF | 0.508 | 205 | WB | Sequence | A0206 |
| 139 | IVAFFSFGGA | 0.495 | 235 | WB | Sequence | A0206 |
| 125 | VVNELFRDGV | 0.483 | 269 | WB | Sequence | A0206 |
| 117 | TAYQSFEQVV | 0.450 | 383 | WB | Sequence | A0206 |
| 213 | FLTGMTVAGV | 0.966 | 1 | SB | Sequence | A0211 |
| 172 | YLNDHLEPWI | 0.951 | 1 | SB | Sequence | A0211 |
| 153 | SVDKEMQVLV | 0.905 | 2 | SB | Sequence | A0211 |
| 73 | SLDAREVIPM | 0.826 | 6 | SB | Sequence | A0211 |
| 216 | GMTVAGVVLL | 0.737 | 17 | SB | Sequence | A0211 |
| 7 | LVVDFLSYKL | 0.730 | 18 | SB | Sequence | A0211 |
| 164 | RIAAWMATYL | 0.711 | 22 | SB | Sequence | A0211 |
| 125 | VVNELFRDGV | 0.687 | 29 | SB | Sequence | A0211 |
| 49 | AINGNPSWHL | 0.686 | 29 | SB | Sequence | A0211 |
| 168 | WMATYLNDHL | 0.685 | 30 | SB | Sequence | A0211 |
| 117 | TAYQSFEQVV | 0.633 | 52 | WB | Sequence | A0211 |
| 160 | VLVSRIAAWM | 0.632 | 53 | WB | Sequence | A0211 |
| 142 | FFSFGGALCV | 0.567 | 107 | WB | Sequence | A0211 |
| 223 | VLLGSLFSRK | 0.498 | 228 | WB | Sequence | A0211 |
| 102 | RAFSDLTSQL | 0.453 | 372 | WB | Sequence | A0211 |
| 116 | GTAYQSFEQV | 0.429 | 481 | WB | Sequence | A0211 |
| 213 | FLTGMTVAGV | 0.932 | 2 | SB | Sequence | A0212 |
| 172 | YLNDHLEPWI | 0.916 | 2 | SB | Sequence | A0212 |
| 153 | SVDKEMQVLV | 0.742 | 16 | SB | Sequence | A0212 |
| 168 | WMATYLNDHL | 0.697 | 26 | SB | Sequence | A0212 |
| 125 | VVNELFRDGV | 0.695 | 27 | SB | Sequence | A0212 |
| 7 | LVVDFLSYKL | 0.648 | 45 | SB | Sequence | A0212 |
| 160 | VLVSRIAAWM | 0.604 | 72 | WB | Sequence | A0212 |
| 73 | SLDAREVIPM | 0.594 | 80 | WB | Sequence | A0212 |
| 49 | AINGNPSWHL | 0.570 | 104 | WB | Sequence | A0212 |
| 164 | RIAAWMATYL | 0.550 | 129 | WB | Sequence | A0212 |
| 142 | FFSFGGALCV | 0.494 | 238 | WB | Sequence | A0212 |
| 223 | VLLGSLFSRK | 0.487 | 258 | WB | Sequence | A0212 |
| 117 | TAYQSFEQVV | 0.482 | 270 | WB | Sequence | A0212 |
| 192 | ELYGNNAAAE | 0.475 | 293 | WB | Sequence | A0212 |
| 216 | GMTVAGVVLL | 0.440 | 426 | WB | Sequence | A0212 |
| 213 | FLTGMTVAGV | 0.911 | 2 | SB | Sequence | A0216 |
| 172 | YLNDHLEPWI | 0.869 | 4 | SB | Sequence | A0216 |
| 153 | SVDKEMQVLV | 0.772 | 11 | SB | Sequence | A0216 |
| 168 | WMATYLNDHL | 0.696 | 26 | SB | Sequence | A0216 |
| 164 | RIAAWMATYL | 0.695 | 27 | SB | Sequence | A0216 |
| 49 | AINGNPSWHL | 0.680 | 31 | SB | Sequence | A0216 |
| 160 | VLVSRIAAWM | 0.657 | 41 | SB | Sequence | A0216 |
| 7 | LVVDFLSYKL | 0.643 | 47 | SB | Sequence | A0216 |
| 73 | SLDAREVIPM | 0.617 | 62 | WB | Sequence | A0216 |
| 216 | GMTVAGVVLL | 0.588 | 85 | WB | Sequence | A0216 |
| 117 | TAYQSFEQVV | 0.530 | 161 | WB | Sequence | A0216 |
| 142 | FFSFGGALCV | 0.487 | 256 | WB | Sequence | A0216 |
| 116 | GTAYQSFEQV | 0.444 | 408 | WB | Sequence | A0216 |
| 213 | FLTGMTVAGV | 0.927 | 2 | SB | Sequence | A0219 |
| 172 | YLNDHLEPWI | 0.884 | 3 | SB | Sequence | A0219 |
| 168 | WMATYLNDHL | 0.611 | 67 | WB | Sequence | A0219 |
| 49 | AINGNPSWHL | 0.543 | 140 | WB | Sequence | A0219 |
| 7 | LVVDFLSYKL | 0.539 | 146 | WB | Sequence | A0219 |
| 153 | SVDKEMQVLV | 0.533 | 156 | WB | Sequence | A0219 |
| 164 | RIAAWMATYL | 0.449 | 387 | WB | Sequence | A0219 |
| 73 | SLDAREVIPM | 0.445 | 404 | WB | Sequence | A0219 |
| 160 | VLVSRIAAWM | 0.441 | 421 | WB | Sequence | A0219 |
| 223 | VLLGSLFSRK | 0.767 | 12 | SB | Sequence | A0301 |
| 6 | ELVVDFLSYK | 0.504 | 213 | WB | Sequence | A0301 |
| 147 | GALCVESVDK | 0.488 | 253 | WB | Sequence | A0301 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 222 | VVLLGSLFSR | 0.457 | 356 | WB | Sequence | A0301 |
| 77 | REVIPMAAVK | 0.453 | 372 | WB | Sequence | A0301 |
| 223 | VLLGSLFSRK | 0.742 | 16 | SB | Sequence | A1101 |
| 222 | VVLLGSLFSR | 0.681 | 31 | SB | Sequence | A1101 |
| 147 | GALCVESVDK | 0.515 | 190 | WB | Sequence | A1101 |
| 24 | SQFSDVEENR | 0.470 | 310 | WB | Sequence | A1101 |
| 121 | SFEQVVNELF | 0.581 | 92 | WB | Sequence | A2301 |
| 171 | TYLNDHLEPW | 0.547 | 134 | WB | Sequence | A2301 |
| 121 | SFEQVVNELF | 0.528 | 165 | WB | Sequence | A2402 |
| 171 | TYLNDHLEPW | 0.520 | 180 | WB | Sequence | A2402 |
| 113 | ITPGTAYQSF | 0.460 | 343 | WB | Sequence | A2402 |
| 171 | TYLNDHLEPW | 0.739 | 16 | SB | Sequence | A2403 |
| 121 | SFEQVVNELF | 0.546 | 136 | WB | Sequence | A2403 |
| 113 | ITPGTAYQSF | 0.508 | 204 | WB | Sequence | A2403 |
| 35 | EAPEGTESEM | 0.448 | 390 | WB | Sequence | A2601 |
| 164 | RIAAWMATYL | 0.626 | 57 | WB | Sequence | A2602 |
| 113 | ITPGTAYQSF | 0.581 | 92 | WB | Sequence | A2602 |
| 160 | VLVSRIAAWM | 0.553 | 126 | WB | Sequence | A2602 |
| 35 | EAPEGTESEM | 0.507 | 207 | WB | Sequence | A2602 |
| 152 | ESVDKEMQVL | 0.490 | 249 | WB | Sequence | A2602 |
| 95 | EFELRYRRAF | 0.483 | 268 | WB | Sequence | A2602 |
| 110 | QLHITPGTAY | 0.506 | 209 | WB | Sequence | A2902 |
| 222 | VVLLGSLFSR | 0.683 | 30 | SB | Sequence | A3101 |
| 129 | LFRDGVNWGR | 0.667 | 36 | SB | Sequence | A3101 |
| 202 | SRKGQERFNR | 0.608 | 69 | WB | Sequence | A3101 |
| 81 | PMAAVKQALR | 0.521 | 177 | WB | Sequence | A3101 |
| 222 | VVLLGSLFSR | 0.572 | 103 | WB | Sequence | A3301 |
| 129 | LFRDGVNWGR | 0.553 | 126 | WB | Sequence | A3301 |
| 10 | DFLSYKLSQK | 0.470 | 308 | WB | Sequence | A3301 |
| 6 | ELVVDFLSYK | 0.702 | 25 | SB | Sequence | A6801 |
| 24 | SQFSDVEENR | 0.532 | 158 | WB | Sequence | A6801 |
| 222 | VVLLGSLFSR | 0.516 | 188 | WB | Sequence | A6801 |
| 194 | YGNNAAAESR | 0.493 | 240 | WB | Sequence | A6801 |
| 78 | EVIPMAAVKQ | 0.454 | 368 | WB | Sequence | A6801 |
| 169 | MATYLNDHLE | 0.448 | 394 | WB | Sequence | A6801 |
| 139 | IVAFFSFGGA | 0.742 | 16 | SB | Sequence | A6802 |
| 116 | GTAYQSFEQV | 0.673 | 34 | SB | Sequence | A6802 |
| 7 | LVVDFLSYKL | 0.659 | 39 | SB | Sequence | A6802 |
| 120 | QSFEQVVNEL | 0.618 | 62 | WB | Sequence | A6802 |
| 213 | FLTGMTVAGV | 0.577 | 96 | WB | Sequence | A6802 |
| 117 | TAYQSFEQVV | 0.561 | 115 | WB | Sequence | A6802 |
| 164 | RIAAWMATYL | 0.519 | 182 | WB | Sequence | A6802 |
| 65 | NGATGHSSSL | 0.496 | 234 | WB | Sequence | A6802 |
| 218 | TVAGVVLLGS | 0.491 | 246 | WB | Sequence | A6802 |
| 145 | FGGALCVESV | 0.474 | 294 | WB | Sequence | A6802 |
| 125 | VVNELFRDGV | 0.465 | 328 | WB | Sequence | A6802 |
| 161 | LVSRIAAWMA | 0.451 | 380 | WB | Sequence | A6802 |
| 215 | TGMTVAGVVL | 0.450 | 382 | WB | Sequence | A6802 |
| 153 | SVDKEMQVLV | 0.534 | 155 | WB | Sequence | A6901 |
| 213 | FLTGMTVAGV | 0.527 | 166 | WB | Sequence | A6901 |
| 117 | TAYQSFEQVV | 0.466 | 324 | WB | Sequence | A6901 |
| 7 | LVVDFLSYKL | 0.451 | 378 | WB | Sequence | A6901 |
| 164 | RIAAWMATYL | 0.443 | 412 | WB | Sequence | A6901 |
| 116 | GTAYQSFEQV | 0.427 | 493 | WB | Sequence | A6901 |
| 80 | IPMAAVKQAL | 0.704 | 24 | SB | Sequence | B0702 |
| 17 | SQKGYSWSQF | 0.572 | 102 | WB | Sequence | B1501 |
| 110 | QLHITPGTAY | 0.557 | 121 | WB | Sequence | B1501 |
| 133 | GVNWGRIVAF | 0.548 | 132 | WB | Sequence | B1501 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 181 | IQENGGWDTF | 0.522 | 175 | WB | Sequence | B1501 |
| 12 | LSYKLSQKGY | 0.455 | 364 | WB | Sequence | B1501 |
| 5 | RELVVDFLSY | 0.759 | 13 | SB | Sequence | B1801 |
| 163 | SRIAAWMATY | 0.588 | 86 | WB | Sequence | B2705 |
| 101 | RRAFSDLTSQ | 0.461 | 340 | WB | Sequence | B2705 |
| 80 | IPMAAVKQAL | 0.609 | 69 | WB | Sequence | B3501 |
| 178 | EPWIQENGGW | 0.604 | 72 | WB | Sequence | B3501 |
| 91 | EAGDEFELRY | 0.566 | 109 | WB | Sequence | B3501 |
| 35 | EAPEGTESEM | 0.563 | 112 | WB | Sequence | B3501 |
| 87 | QALREAGDEF | 0.508 | 206 | WB | Sequence | B3501 |
| 61 | SPAVNGATGH | 0.490 | 249 | WB | Sequence | B3501 |
| 46 | TPSAINGNPS | 0.483 | 269 | WB | Sequence | B3501 |
| 133 | GVNWGRIVAF | 0.455 | 362 | WB | Sequence | B3501 |
| 140 | VAFFSFGGAL | 0.454 | 367 | WB | Sequence | B3501 |
| 190 | FVELYGNNAA | 0.439 | 430 | WB | Sequence | B3501 |
| 200 | AESRKGQERF | 0.453 | 370 | WB | Sequence | B4501 |
| 178 | EPWIQENGGW | 0.603 | 73 | WB | Sequence | B5301 |
| 2 | QSNRELVVDF | 0.474 | 295 | WB | Sequence | B5801 |
| 159 | QVLVSRIAAW | 0.467 | 320 | WB | Sequence | B5801 |
| 47 | PSAINGNPSW | 0.437 | 444 | WB | Sequence | B5801 |
| | | | 11-mers | | | |
| 213 | FLTGMTVAGVV | 0.627 | 56 | WB | Sequence | A0201 |
| 73 | SLDAREVIPMA | 0.561 | 115 | WB | Sequence | A0201 |
| 160 | VLVSRIAAWMA | 0.547 | 135 | WB | Sequence | A0201 |
| 57 | HLADSPAVNGA | 0.539 | 147 | WB | Sequence | A0201 |
| 172 | YLNDHLEPWIQ | 0.480 | 278 | WB | Sequence | A0201 |
| 88 | ALREAGDEFEL | 0.470 | 309 | WB | Sequence | A0201 |
| 119 | YQSFEQVVNEL | 0.426 | 497 | WB | Sequence | A0201 |
| 57 | HLADSPAVNGA | 0.763 | 12 | SB | Sequence | A0202 |
| 213 | FLTGMTVAGVV | 0.754 | 14 | SB | Sequence | A0202 |
| 119 | YQSFEQVVNEL | 0.734 | 17 | SB | Sequence | A0202 |
| 88 | ALREAGDEFEL | 0.679 | 32 | SB | Sequence | A0202 |
| 172 | YLNDHLEPWIQ | 0.611 | 67 | WB | Sequence | A0202 |
| 139 | IVAFFSFGGAL | 0.558 | 119 | WB | Sequence | A0202 |
| 218 | TVAGVVLLGSL | 0.537 | 149 | WB | Sequence | A0202 |
| 160 | VLVSRIAAWMA | 0.525 | 170 | WB | Sequence | A0202 |
| 15 | KLSQKGYSWSQ | 0.450 | 382 | WB | Sequence | A0202 |
| 6 | ELVVDFLSYKL | 0.449 | 387 | WB | Sequence | A0202 |
| 73 | SLDAREVIPMA | 0.446 | 401 | WB | Sequence | A0202 |
| 213 | FLTGMTVAGVV | 0.864 | 4 | SB | Sequence | A0203 |
| 57 | HLADSPAVNGA | 0.844 | 5 | SB | Sequence | A0203 |
| 138 | RIVAFFSFGGA | 0.752 | 14 | SB | Sequence | A0203 |
| 160 | VLVSRIAAWMA | 0.649 | 44 | SB | Sequence | A0203 |
| 218 | TVAGVVLLGSL | 0.619 | 61 | WB | Sequence | A0203 |
| 88 | ALREAGDEFEL | 0.604 | 72 | WB | Sequence | A0203 |
| 119 | YQSFEQVVNEL | 0.567 | 108 | WB | Sequence | A0203 |
| 172 | YLNDHLEPWIQ | 0.565 | 110 | WB | Sequence | A0203 |
| 49 | AINGNPSWHLA | 0.562 | 114 | WB | Sequence | A0203 |
| 209 | FNRWFLTGMTV | 0.494 | 239 | WB | Sequence | A0203 |
| 139 | IVAFFSFGGAL | 0.487 | 257 | WB | Sequence | A0203 |
| 73 | SLDAREVIPMA | 0.480 | 276 | WB | Sequence | A0203 |
| 82 | MAAVKQALREA | 0.430 | 477 | WB | Sequence | A0203 |
| 124 | QVVNELFRDGV | 0.426 | 496 | WB | Sequence | A0203 |
| 213 | FLTGMTVAGVV | 0.584 | 90 | WB | Sequence | A0204 |
| 88 | ALREAGDEFEL | 0.526 | 168 | WB | Sequence | A0204 |
| 160 | VLVSRIAAWMA | 0.517 | 185 | WB | Sequence | A0204 |
| 172 | YLNDHLEPWIQ | 0.517 | 186 | WB | Sequence | A0204 |
| 73 | SLDAREVIPMA | 0.485 | 263 | WB | Sequence | A0204 |
| 213 | FLTGMTVAGVV | 0.746 | 15 | SB | Sequence | A0206 |
| 138 | RIVAFFSFGGA | 0.725 | 19 | SB | Sequence | A0206 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 181 | IQENGGWDTFV | 0.704 | 24 | SB | Sequence | A0206 |
| 119 | YQSFEQVVNEL | 0.671 | 35 | SB | Sequence | A0206 |
| 48 | SAINGNPSWHL | 0.664 | 38 | SB | Sequence | A0206 |
| 124 | QVVNELFRDGV | 0.619 | 62 | WB | Sequence | A0206 |
| 160 | VLVSRIAAWMA | 0.584 | 90 | WB | Sequence | A0206 |
| 86 | KQALREAGDEF | 0.547 | 134 | WB | Sequence | A0206 |
| 57 | HLADSPAVNGA | 0.509 | 201 | WB | Sequence | A0206 |
| 218 | TVAGVVLLGSL | 0.456 | 358 | WB | Sequence | A0206 |
| 88 | ALREAGDEFEL | 0.442 | 420 | WB | Sequence | A0206 |
| 109 | SQLHITPGTAY | 0.441 | 422 | WB | Sequence | A0206 |
| 213 | FLTGMTVAGVV | 0.943 | 1 | SB | Sequence | A0211 |
| 73 | SLDAREVIPMA | 0.876 | 3 | SB | Sequence | A0211 |
| 172 | YLNDHLEPWIQ | 0.852 | 4 | SB | Sequence | A0211 |
| 88 | ALREAGDEFEL | 0.799 | 8 | SB | Sequence | A0211 |
| 57 | HLADSPAVNGA | 0.787 | 10 | SB | Sequence | A0211 |
| 160 | VLVSRIAAWMA | 0.759 | 13 | SB | Sequence | A0211 |
| 15 | KLSQKGYSWSQ | 0.743 | 16 | SB | Sequence | A0211 |
| 6 | ELVVDFLSYKL | 0.682 | 31 | SB | Sequence | A0211 |
| 218 | TVAGVVLLGSL | 0.628 | 55 | WB | Sequence | A0211 |
| 49 | AINGNPSWHLA | 0.612 | 66 | WB | Sequence | A0211 |
| 212 | WFLTGMTVAGV | 0.577 | 97 | WB | Sequence | A0211 |
| 141 | AFFSFGGALCV | 0.571 | 103 | WB | Sequence | A0211 |
| 144 | SFGGALCVESV | 0.569 | 105 | WB | Sequence | A0211 |
| 79 | VIPMAAVKQAL | 0.568 | 107 | WB | Sequence | A0211 |
| 124 | QVVNELFRDGV | 0.535 | 152 | WB | Sequence | A0211 |
| 130 | FRDGVNWGRIV | 0.516 | 187 | WB | Sequence | A0211 |
| 48 | SAINGNPSWHL | 0.515 | 189 | WB | Sequence | A0211 |
| 192 | ELYGNNAAAES | 0.504 | 214 | WB | Sequence | A0211 |
| 150 | CVESVDKEMQV | 0.489 | 252 | WB | Sequence | A0211 |
| 116 | GTAYQSFEQVV | 0.452 | 376 | WB | Sequence | A0211 |
| 139 | IVAFFSFGGAL | 0.444 | 411 | WB | Sequence | A0211 |
| 213 | FLTGMTVAGVV | 0.824 | 6 | SB | Sequence | A0212 |
| 172 | YLNDHLEPWIQ | 0.812 | 7 | SB | Sequence | A0212 |
| 88 | ALREAGDEFEL | 0.779 | 10 | SB | Sequence | A0212 |
| 73 | SLDAREVIPMA | 0.745 | 15 | SB | Sequence | A0212 |
| 57 | HLADSPAVNGA | 0.714 | 22 | SB | Sequence | A0212 |
| 160 | VLVSRIAAWMA | 0.681 | 31 | SB | Sequence | A0212 |
| 79 | VIPMAAVKQAL | 0.604 | 72 | WB | Sequence | A0212 |
| 15 | KLSQKGYSWSQ | 0.568 | 107 | WB | Sequence | A0212 |
| 212 | WFLTGMTVAGV | 0.504 | 213 | WB | Sequence | A0212 |
| 6 | ELVVDFLSYKL | 0.451 | 380 | WB | Sequence | A0212 |
| 130 | FRDGVNWGRIV | 0.431 | 473 | WB | Sequence | A0212 |
| 213 | FLTGMTVAGVV | 0.862 | 4 | SB | Sequence | A0216 |
| 88 | ALREAGDEFEL | 0.821 | 6 | SB | Sequence | A0216 |
| 73 | SLDAREVIPMA | 0.744 | 16 | SB | Sequence | A0216 |
| 160 | VLVSRIAAWMA | 0.649 | 44 | SB | Sequence | A0216 |
| 150 | CVESVDKEMQV | 0.641 | 48 | SB | Sequence | A0216 |
| 57 | HLADSPAVNGA | 0.595 | 79 | WB | Sequence | A0216 |
| 144 | SFGGALCVESV | 0.591 | 83 | WB | Sequence | A0216 |
| 172 | YLNDHLEPWIQ | 0.581 | 92 | WB | Sequence | A0216 |
| 15 | KLSQKGYSWSQ | 0.561 | 115 | WB | Sequence | A0216 |
| 6 | ELVVDFLSYKL | 0.544 | 138 | WB | Sequence | A0216 |
| 218 | TVAGVVLLGSL | 0.534 | 154 | WB | Sequence | A0216 |
| 141 | AFFSFGGALCV | 0.526 | 168 | WB | Sequence | A0216 |
| 181 | IQENGGWDTFV | 0.497 | 231 | WB | Sequence | A0216 |
| 124 | QVVNELFRDGV | 0.490 | 249 | WB | Sequence | A0216 |
| 79 | VIPMAAVKQAL | 0.487 | 257 | WB | Sequence | A0216 |
| 192 | ELYGNNAAAES | 0.478 | 283 | WB | Sequence | A0216 |
| 48 | SAINGNPSWHL | 0.468 | 315 | WB | Sequence | A0216 |
| 212 | WFLTGMTVAGV | 0.437 | 441 | WB | Sequence | A0216 |
| 49 | AINGNPSWHLA | 0.436 | 447 | WB | Sequence | A0216 |
| 213 | FLTGMTVAGVV | 0.781 | 10 | SB | Sequence | A0219 |
| 57 | HLADSPAVNGA | 0.730 | 18 | SB | Sequence | A0219 |
| 172 | YLNDHLEPWIQ | 0.695 | 27 | SB | Sequence | A0219 |
| 73 | SLDAREVIPMA | 0.609 | 68 | WB | Sequence | A0219 |
| 88 | ALREAGDEFEL | 0.549 | 131 | WB | Sequence | A0219 |
| 212 | WFLTGMTVAGV | 0.524 | 172 | WB | Sequence | A0219 |
| 160 | VLVSRIAAWMA | 0.499 | 225 | WB | Sequence | A0219 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 222 | VVLLGSLFSRK | 0.688 | 29 | SB | Sequence | A0301 |
| 222 | VVLLGSLFSRK | 0.786 | 10 | SB | Sequence | A1101 |
| 221 | GVVLLGSLFSR | 0.596 | 78 | WB | Sequence | A1101 |
| 67 | ATGHSSSLDAR | 0.505 | 212 | WB | Sequence | A1101 |
| 5 | RELVVDFLSYK | 0.428 | 489 | WB | Sequence | A1101 |
| 135 | NWGRIVAFFSF | 0.695 | 26 | SB | Sequence | A2301 |
| 171 | TYLNDHLEPWI | 0.576 | 98 | WB | Sequence | A2301 |
| 167 | AWMATYLNDHL | 0.534 | 154 | WB | Sequence | A2301 |
| 13 | SYKLSQKGYSW | 0.531 | 159 | WB | Sequence | A2301 |
| 135 | NWGRIVAFFSF | 0.746 | 15 | SB | Sequence | A2402 |
| 171 | TYLNDHLEPWI | 0.746 | 15 | SB | Sequence | A2402 |
| 167 | AWMATYLNDHL | 0.520 | 180 | WB | Sequence | A2402 |
| 171 | TYLNDHLEPWI | 0.660 | 39 | SB | Sequence | A2403 |
| 167 | AWMATYLNDHL | 0.523 | 174 | WB | Sequence | A2403 |
| 13 | SYKLSQKGYSW | 0.523 | 174 | WB | Sequence | A2403 |
| 112 | HITPGTAYQSF | 0.431 | 473 | WB | Sequence | A2403 |
| 159 | QVLVSRIAAWM | 0.640 | 49 | SB | Sequence | A2602 |
| 112 | HITPGTAYQSF | 0.573 | 101 | WB | Sequence | A2602 |
| 180 | WIQENGGWDTF | 0.518 | 183 | WB | Sequence | A2602 |
| 11 | FLSYKLSQKGY | 0.516 | 188 | WB | Sequence | A2602 |
| 132 | DGVNWGRIVAF | 0.462 | 336 | WB | Sequence | A2602 |
| 218 | TVAGVVLLGSL | 0.443 | 415 | WB | Sequence | A2602 |
| 109 | SQLHITPGTAY | 0.516 | 188 | WB | Sequence | A2902 |
| 222 | VVLLGSLFSRK | 0.435 | 453 | WB | Sequence | A3001 |
| 99 | RYRRAFSDLTS | 0.428 | 486 | WB | Sequence | A3001 |
| 221 | GVVLLGSLFSR | 0.598 | 77 | WB | Sequence | A3101 |
| 121 | SFEQVVNELFR | 0.552 | 127 | WB | Sequence | A3101 |
| 201 | ESRKGQERFNR | 0.511 | 198 | WB | Sequence | A3101 |
| 67 | ATGHSSSLDAR | 0.475 | 292 | WB | Sequence | A3101 |
| 5 | RELVVDFLSYK | 0.442 | 417 | WB | Sequence | A3101 |
| 193 | LYGNNAAAESR | 0.435 | 449 | WB | Sequence | A3101 |
| 201 | ESRKGQERFNR | 0.690 | 28 | SB | Sequence | A3301 |
| 128 | ELFRDGVNWGR | 0.634 | 52 | WB | Sequence | A3301 |
| 91 | EAGDEFELRYR | 0.538 | 148 | WB | Sequence | A3301 |
| 121 | SFEQVVNELFR | 0.472 | 303 | WB | Sequence | A3301 |
| 221 | GVVLLGSLFSR | 0.447 | 396 | WB | Sequence | A3301 |
| 95 | EFELRYRRAFS | 0.435 | 449 | WB | Sequence | A3301 |
| 128 | ELFRDGVNWGR | 0.739 | 16 | SB | Sequence | A6801 |
| 23 | WSQFSDVEENR | 0.667 | 36 | SB | Sequence | A6801 |
| 201 | ESRKGQERFNR | 0.666 | 36 | SB | Sequence | A6801 |
| 91 | EAGDEFELRYR | 0.643 | 47 | SB | Sequence | A6801 |
| 221 | GVVLLGSLFSR | 0.638 | 49 | SB | Sequence | A6801 |
| 80 | IPMAAVKQALR | 0.566 | 109 | WB | Sequence | A6801 |
| 121 | SFEQVVNELFR | 0.536 | 151 | WB | Sequence | A6801 |
| 218 | TVAGVVLLGSL | 0.796 | 9 | SB | Sequence | A6802 |
| 124 | QVVNELFRDGV | 0.712 | 22 | SB | Sequence | A6802 |
| 139 | IVAFFSFGGAL | 0.684 | 30 | SB | Sequence | A6802 |
| 152 | ESVDKEMQVLV | 0.613 | 65 | WB | Sequence | A6802 |
| 215 | TGMTVAGVVLL | 0.561 | 116 | WB | Sequence | A6802 |
| 6 | ELVVDFLSYKL | 0.551 | 129 | WB | Sequence | A6802 |
| 138 | RIVAFFSFGGA | 0.548 | 132 | WB | Sequence | A6802 |
| 188 | DTFVELYGNNA | 0.530 | 161 | WB | Sequence | A6802 |
| 78 | EVIPMAAVKQA | 0.516 | 188 | WB | Sequence | A6802 |
| 116 | GTAYQSFEQVV | 0.514 | 191 | WB | Sequence | A6802 |
| 75 | DAREVIPMAAV | 0.509 | 203 | WB | Sequence | A6802 |
| 57 | HLADSPAVNGA | 0.508 | 206 | WB | Sequence | A6802 |
| 217 | MTVAGVVLLGS | 0.480 | 277 | WB | Sequence | A6802 |
| 45 | ETPSAINGNPS | 0.479 | 279 | WB | Sequence | A6802 |
| 213 | FLTGMTVAGVV | 0.470 | 308 | WB | Sequence | A6802 |
| 70 | HSSSLDAREVI | 0.447 | 397 | WB | Sequence | A6802 |

TABLE B-continued

Prediction of cancer antigen BclX(L) specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 48 | SAINGNPSWHL | 0.541 | 143 | WB | Sequence | A6901 |
| 75 | DAREVIPMAAV | 0.527 | 166 | WB | Sequence | A6901 |
| 152 | ESVDKEMQVLV | 0.511 | 199 | WB | Sequence | A6901 |
| 57 | HLADSPAVNGA | 0.485 | 263 | WB | Sequence | A6901 |
| 54 | PSWHLADSPAV | 0.469 | 312 | WB | Sequence | A6901 |
| 212 | WFLTGMTVAGV | 0.453 | 369 | WB | Sequence | A6901 |
| 78 | EVIPMAAVKQA | 0.442 | 417 | WB | Sequence | A6901 |
| 6 | ELVVDFLSYKL | 0.442 | 417 | WB | Sequence | A6901 |
| 218 | TVAGVVLLGSL | 0.430 | 475 | WB | Sequence | A6901 |
| 188 | DTFVELYGNNA | 0.427 | 494 | WB | Sequence | A6901 |
| 139 | IVAFFSFGGAL | 0.518 | 183 | WB | Sequence | B0702 |
| 53 | NPSWHLADSPA | 0.499 | 224 | WB | Sequence | B0702 |
| 61 | SPAVNGATGHS | 0.457 | 355 | WB | Sequence | B0702 |
| 109 | SQLHITPGTAY | 0.605 | 72 | WB | Sequence | B1501 |
| 86 | KQALREAGDEF | 0.567 | 108 | WB | Sequence | B1501 |
| 1 | SQSNRELVVDF | 0.540 | 144 | WB | Sequence | B1501 |
| 119 | YQSFEQVVNEL | 0.515 | 189 | WB | Sequence | B1501 |
| 158 | MQVLVSRIAAW | 0.512 | 196 | WB | Sequence | B1501 |
| 162 | VSRIAAWMATY | 0.477 | 285 | WB | Sequence | B1501 |
| 11 | FLSYKLSQKGY | 0.474 | 294 | WB | Sequence | B1501 |
| 180 | WIQENGGWDTF | 0.473 | 299 | WB | Sequence | B1501 |
| 120 | QSFEQVVNELF | 0.450 | 386 | WB | Sequence | B1501 |
| 112 | HITPGTAYQSF | 0.447 | 394 | WB | Sequence | B1501 |
| 133 | GVNWGRIVAFF | 0.433 | 463 | WB | Sequence | B1501 |
| 94 | DEFELRYRRAF | 0.829 | 6 | SB | Sequence | B1801 |
| 90 | REAGDEFELRY | 0.560 | 116 | WB | Sequence | B1801 |
| 109 | SQLHITPGTAY | 0.539 | 146 | WB | Sequence | B1801 |
| 151 | VESVDKEMQVL | 0.476 | 288 | WB | Sequence | B1801 |
| 177 | LEPWIQENGGW | 0.466 | 321 | WB | Sequence | B1801 |
| 209 | FNRWFLTGMTV | 0.444 | 409 | WB | Sequence | B1801 |
| 101 | RRAFSDLTSQL | 0.563 | 113 | WB | Sequence | B2705 |
| 163 | SRIAAWMATYL | 0.470 | 310 | WB | Sequence | B2705 |
| 53 | NPSWHLADSPA | 0.623 | 59 | WB | Sequence | B3501 |
| 46 | TPSAINGNPSW | 0.485 | 263 | WB | Sequence | B3501 |
| 180 | WIQENGGWDTF | 0.474 | 297 | WB | Sequence | B3501 |
| 132 | DGVNWGRIVAF | 0.442 | 419 | WB | Sequence | B3501 |
| 119 | YQSFEQVVNEL | 0.610 | 68 | WB | Sequence | B3901 |
| 151 | VESVDKEMQVL | 0.492 | 243 | WB | Sequence | B4001 |
| 40 | TESEMETPSAI | 0.446 | 402 | WB | Sequence | B4002 |
| 30 | EENRTEAPEGT | 0.498 | 228 | WB | Sequence | B4501 |
| 46 | TPSAINGNPSW | 0.772 | 11 | SB | Sequence | B5301 |
| 53 | NPSWHLADSPA | 0.430 | 474 | WB | Sequence | B5401 |
| 170 | ATYLNDHLEPW | 0.540 | 145 | WB | Sequence | B5701 |
| 170 | ATYLNDHLEPW | 0.537 | 150 | WB | Sequence | B5801 |
| 120 | QSFEQVVNELF | 0.495 | 235 | WB | Sequence | B5801 |

SEQ ID NOS.: 45801-46593

Preferred fragments of Bcl-2 capable of interacting with one or more MHC class 1 molecules are listed in table C below.

TABLE C

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 8-mer | | | | | | |
| 84 | ALSPVPPV | 0.783 | 10 | SB | Sequence | A0201 |
| 218 | TLLSLALV | 0.723 | 20 | SB | Sequence | A0201 |
| 173 | ALWMTEYL | 0.682 | 31 | SB | Sequence | A0201 |
| 154 | GVMCVESV | 0.630 | 54 | WB | Sequence | A0201 |
| 207 | PLFDFSWL | 0.488 | 253 | WB | Sequence | A0201 |
| 215 | SLKTLLSL | 0.449 | 387 | WB | Sequence | A0201 |
| 84 | ALSPVPPV | 0.710 | 23 | SB | Sequence | A0202 |
| 213 | WLSLKTLL | 0.709 | 23 | SB | Sequence | A0202 |
| 215 | SLKTLLSL | 0.661 | 39 | SB | Sequence | A0202 |
| 207 | PLFDFSWL | 0.653 | 42 | SB | Sequence | A0202 |
| 173 | ALWMTEYL | 0.631 | 54 | WB | Sequence | A0202 |
| 154 | GVMCVESV | 0.630 | 55 | WB | Sequence | A0202 |
| 218 | TLLSLALV | 0.610 | 68 | WB | Sequence | A0202 |
| 113 | EMSSQLHL | 0.570 | 105 | WB | Sequence | A0202 |
| 224 | LVGACITL | 0.534 | 154 | WB | Sequence | A0202 |
| 129 | FATVVEEL | 0.512 | 195 | WB | Sequence | A0202 |
| 167 | PLVDNIAL | 0.508 | 204 | WB | Sequence | A0202 |
| 179 | YLNRHLHT | 0.435 | 453 | WB | Sequence | A0202 |
| 209 | FDFSWLSL | 0.432 | 464 | WB | Sequence | A0202 |
| 84 | ALSPVPPV | 0.909 | 2 | SB | Sequence | A0203 |
| 215 | SLKTLLSL | 0.853 | 4 | SB | Sequence | A0203 |
| 154 | GVMCVESV | 0.754 | 14 | SB | Sequence | A0203 |
| 179 | YLNRHLHT | 0.682 | 31 | SB | Sequence | A0203 |
| 218 | TLLSLALV | 0.673 | 34 | SB | Sequence | A0203 |
| 213 | WLSLKTLL | 0.665 | 37 | SB | Sequence | A0203 |
| 140 | GVNWGRIV | 0.581 | 92 | WB | Sequence | A0203 |
| 123 | FTARGRFA | 0.523 | 174 | WB | Sequence | A0203 |
| 173 | ALWMTEYL | 0.497 | 229 | WB | Sequence | A0203 |
| 207 | PLFDFSWL | 0.478 | 284 | WB | Sequence | A0203 |
| 84 | ALSPVPPV | 0.763 | 13 | SB | Sequence | A0204 |
| 173 | ALWMTEYL | 0.541 | 144 | WB | Sequence | A0204 |
| 218 | TLLSLALV | 0.526 | 168 | WB | Sequence | A0204 |
| 154 | GVMCVESV | 0.478 | 283 | WB | Sequence | A0204 |
| 224 | LVGACITL | 0.451 | 381 | WB | Sequence | A0204 |
| 84 | ALSPVPPV | 0.764 | 12 | SB | Sequence | A0206 |
| 154 | GVMCVESV | 0.743 | 16 | SB | Sequence | A0206 |
| 116 | SQLHLTPF | 0.737 | 17 | SB | Sequence | A0206 |
| 218 | TLLSLALV | 0.714 | 21 | SB | Sequence | A0206 |
| 145 | RIVAFFEF | 0.623 | 58 | WB | Sequence | A0206 |
| 217 | KTLLSLAL | 0.574 | 100 | WB | Sequence | A0206 |
| 173 | ALWMTEYL | 0.538 | 148 | WB | Sequence | A0206 |
| 224 | LVGACITL | 0.463 | 334 | WB | Sequence | A0206 |
| 123 | FTARGRFA | 0.462 | 335 | WB | Sequence | A0206 |
| 213 | WLSLKTLL | 0.451 | 378 | WB | Sequence | A0206 |
| 129 | FATVVEEL | 0.450 | 383 | WB | Sequence | A0206 |
| 97 | RQAGDDFS | 0.436 | 445 | WB | Sequence | A0206 |
| 84 | ALSPVPPV | 0.956 | 1 | SB | Sequence | A0211 |
| 218 | TLLSLALV | 0.954 | 1 | SB | Sequence | A0211 |
| 173 | ALWMTEYL | 0.935 | 2 | SB | Sequence | A0211 |
| 207 | PLFDFSWL | 0.934 | 2 | SB | Sequence | A0211 |
| 167 | PLVDNIAL | 0.888 | 3 | SB | Sequence | A0211 |
| 215 | SLKTLLSL | 0.819 | 7 | SB | Sequence | A0211 |
| 213 | WLSLKTLL | 0.780 | 10 | SB | Sequence | A0211 |
| 179 | YLNRHLHT | 0.716 | 21 | SB | Sequence | A0211 |
| 113 | EMSSQLHL | 0.686 | 29 | SB | Sequence | A0211 |
| 140 | GVNWGRIV | 0.668 | 36 | SB | Sequence | A0211 |
| 154 | GVMCVESV | 0.578 | 95 | WB | Sequence | A0211 |
| 148 | AFFEFGGV | 0.534 | 154 | WB | Sequence | A0211 |
| 87 | PVPPVVHL | 0.512 | 197 | WB | Sequence | A0211 |
| 228 | CITLGAYL | 0.500 | 223 | WB | Sequence | A0211 |
| 224 | LVGACITL | 0.500 | 223 | WB | Sequence | A0211 |
| 223 | ALVGACIT | 0.479 | 281 | WB | Sequence | A0211 |
| 27 | YEWDAGDV | 0.472 | 303 | WB | Sequence | A0211 |
| 151 | EFGGVMCV | 0.452 | 377 | WB | Sequence | A0211 |
| 221 | SLALVGAC | 0.445 | 405 | WB | Sequence | A0211 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 84 | ALSPVPPV | 0.874 | 3 | SB | Sequence | A0212 |
| 173 | ALWMTEYL | 0.860 | 4 | SB | Sequence | A0212 |
| 218 | TLLSLALV | 0.857 | 4 | SB | Sequence | A0212 |
| 207 | PLFDFSWL | 0.836 | 5 | SB | Sequence | A0212 |
| 167 | PLVDNIAL | 0.787 | 9 | SB | Sequence | A0212 |
| 215 | SLKTLLSL | 0.756 | 13 | SB | Sequence | A0212 |
| 179 | YLNRHLHT | 0.720 | 20 | SB | Sequence | A0212 |
| 113 | EMSSQLHL | 0.594 | 80 | WB | Sequence | A0212 |
| 213 | WLSLKTLL | 0.564 | 112 | WB | Sequence | A0212 |
| 27 | YEWDAGDV | 0.477 | 288 | WB | Sequence | A0212 |
| 154 | GVMCVESV | 0.460 | 344 | WB | Sequence | A0212 |
| 84 | ALSPVPPV | 0.926 | 2 | SB | Sequence | A0216 |
| 173 | ALWMTEYL | 0.916 | 2 | SB | Sequence | A0216 |
| 218 | TLLSLALV | 0.902 | 2 | SB | Sequence | A0216 |
| 207 | PLFDFSWL | 0.889 | 3 | SB | Sequence | A0216 |
| 167 | PLVDNIAL | 0.767 | 12 | SB | Sequence | A0216 |
| 215 | SLKTLLSL | 0.723 | 20 | SB | Sequence | A0216 |
| 213 | WLSLKTLL | 0.718 | 21 | SB | Sequence | A0216 |
| 113 | EMSSQLHL | 0.665 | 37 | SB | Sequence | A0216 |
| 154 | GVMCVESV | 0.646 | 46 | SB | Sequence | A0216 |
| 179 | YLNRHLHT | 0.631 | 53 | WB | Sequence | A0216 |
| 223 | ALVGACIT | 0.591 | 83 | WB | Sequence | A0216 |
| 224 | LVGACITL | 0.531 | 159 | WB | Sequence | A0216 |
| 87 | PVPPVVHL | 0.526 | 168 | WB | Sequence | A0216 |
| 151 | EFGGVMCV | 0.524 | 173 | WB | Sequence | A0216 |
| 228 | CITLGAYL | 0.522 | 176 | WB | Sequence | A0216 |
| 140 | GVNWGRIV | 0.470 | 308 | WB | Sequence | A0216 |
| 84 | ALSPVPPV | 0.898 | 3 | SB | Sequence | A0219 |
| 173 | ALWMTEYL | 0.871 | 4 | SB | Sequence | A0219 |
| 218 | TLLSLALV | 0.847 | 5 | SB | Sequence | A0219 |
| 207 | PLFDFSWL | 0.785 | 10 | SB | Sequence | A0219 |
| 167 | PLVDNIAL | 0.713 | 22 | SB | Sequence | A0219 |
| 113 | EMSSQLHL | 0.613 | 65 | WB | Sequence | A0219 |
| 213 | WLSLKTLL | 0.599 | 76 | WB | Sequence | A0219 |
| 154 | GVMCVESV | 0.468 | 317 | WB | Sequence | A0219 |
| 215 | SLKTLLSL | 0.466 | 322 | WB | Sequence | A0219 |
| 27 | YEWDAGDV | 0.437 | 440 | WB | Sequence | A0219 |
| 179 | YLNRHLHT | 0.436 | 447 | WB | Sequence | A0219 |
| 14 | VMKYIHYK | 0.629 | 55 | WB | Sequence | A0301 |
| 13 | IVMKYIHY | 0.514 | 193 | WB | Sequence | A0301 |
| 119 | HLTPFTAR | 0.467 | 319 | WB | Sequence | A0301 |
| 199 | ELYGPSMR | 0.456 | 360 | WB | Sequence | A0301 |
| 14 | VMKYIHYK | 0.645 | 46 | SB | Sequence | A1101 |
| 131 | TVVEELFR | 0.616 | 63 | WB | Sequence | A1101 |
| 13 | IVMKYIHY | 0.577 | 97 | WB | Sequence | A1101 |
| 142 | NWGRIVAF | 0.600 | 75 | WB | Sequence | A2301 |
| 145 | RIVAFFEF | 0.518 | 184 | WB | Sequence | A2301 |
| 204 | SMRPLFDF | 0.469 | 312 | WB | Sequence | A2301 |
| 122 | PFTARGRF | 0.441 | 424 | WB | Sequence | A2301 |
| 142 | NWGRIVAF | 0.617 | 62 | WB | Sequence | A2402 |
| 212 | SWLSLKTL | 0.459 | 349 | WB | Sequence | A2402 |
| 204 | SMRPLFDF | 0.547 | 135 | WB | Sequence | A2403 |
| 145 | RIVAFFEF | 0.437 | 441 | WB | Sequence | A2403 |
| 13 | IVMKYIHY | 0.638 | 50 | WB | Sequence | A2602 |
| 113 | EMSSQLHL | 0.445 | 406 | WB | Sequence | A2602 |
| 145 | RIVAFFEF | 0.436 | 445 | WB | Sequence | A2602 |
| 12 | EIVMKYIH | 0.430 | 478 | WB | Sequence | A2602 |
| 130 | ATVVEELF | 0.428 | 489 | WB | Sequence | A2602 |
| 13 | IVMKYIHY | 0.603 | 73 | WB | Sequence | A2902 |
| 227 | ACITLGAY | 0.449 | 387 | WB | Sequence | A2902 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 14 | VMKYIHYK | 0.593 | 81 | WB | Sequence | A3001 |
| 60 | ASRDPVAR | 0.498 | 229 | WB | Sequence | A3001 |
| 126 | RGRFATVV | 0.480 | 276 | WB | Sequence | A3001 |
| 113 | EMSSQLHL | 0.446 | 401 | WB | Sequence | A3002 |
| 204 | SMRPLFDF | 0.444 | 410 | WB | Sequence | A3002 |
| 14 | VMKYIHYK | 0.842 | 5 | SB | Sequence | A3101 |
| 119 | HLTPFTAR | 0.709 | 23 | SB | Sequence | A3101 |
| 60 | ASRDPVAR | 0.692 | 28 | SB | Sequence | A3101 |
| 102 | DFSRRYRR | 0.622 | 59 | WB | Sequence | A3101 |
| 175 | WMTEYLNR | 0.564 | 112 | WB | Sequence | A3101 |
| 131 | TVVEELFR | 0.458 | 351 | WB | Sequence | A3101 |
| 102 | DFSRRYRR | 0.883 | 3 | SB | Sequence | A3301 |
| 119 | HLTPFTAR | 0.746 | 15 | SB | Sequence | A3301 |
| 210 | DFSWLSLK | 0.672 | 34 | SB | Sequence | A3301 |
| 101 | DDFSRRYR | 0.622 | 60 | WB | Sequence | A3301 |
| 199 | ELYGPSMR | 0.615 | 64 | WB | Sequence | A3301 |
| 131 | TVVEELFR | 0.546 | 136 | WB | Sequence | A3301 |
| 14 | VMKYIHYK | 0.510 | 199 | WB | Sequence | A3301 |
| 131 | TVVEELFR | 0.843 | 5 | SB | Sequence | A6801 |
| 199 | ELYGPSMR | 0.792 | 9 | SB | Sequence | A6801 |
| 119 | HLTPFTAR | 0.733 | 18 | SB | Sequence | A6801 |
| 210 | DFSWLSLK | 0.637 | 50 | WB | Sequence | A6801 |
| 121 | TPFTARGR | 0.625 | 58 | WB | Sequence | A6801 |
| 55 | TPHPAASR | 0.581 | 93 | WB | Sequence | A6801 |
| 101 | DDFSRRYR | 0.526 | 168 | WB | Sequence | A6801 |
| 14 | VMKYIHYK | 0.524 | 171 | WB | Sequence | A6801 |
| 98 | QAGDDFSR | 0.522 | 176 | WB | Sequence | A6801 |
| 175 | WMTEYLNR | 0.505 | 211 | WB | Sequence | A6801 |
| 156 | MCVESVNR | 0.502 | 219 | WB | Sequence | A6801 |
| 102 | DFSRRYRR | 0.491 | 247 | WB | Sequence | A6801 |
| 90 | PVVHLTLR | 0.456 | 358 | WB | Sequence | A6801 |
| 154 | GVMCVESV | 0.630 | 54 | WB | Sequence | A6802 |
| 165 | MSPLVDNI | 0.606 | 70 | WB | Sequence | A6802 |
| 123 | FTARGRFA | 0.594 | 80 | WB | Sequence | A6802 |
| 129 | FATVVEEL | 0.501 | 220 | WB | Sequence | A6802 |
| 72 | QTPAAPGA | 0.474 | 297 | WB | Sequence | A6802 |
| 218 | TLLSLALV | 0.607 | 70 | WB | Sequence | A6901 |
| 123 | FTARGRFA | 0.486 | 261 | WB | Sequence | A6901 |
| 113 | EMSSQLHL | 0.470 | 309 | WB | Sequence | A6901 |
| 84 | ALSPVPPV | 0.444 | 409 | WB | Sequence | A6901 |
| 202 | GPSMRPLF | 0.599 | 76 | WB | Sequence | B0702 |
| 73 | TPAAPGAA | 0.598 | 77 | WB | Sequence | B0702 |
| 69 | SPLQTPAA | 0.539 | 146 | WB | Sequence | B0702 |
| 89 | PPVVHLTL | 0.503 | 216 | WB | Sequence | B0702 |
| 206 | RPLFDFSW | 0.445 | 403 | WB | Sequence | B0702 |
| 116 | SQLHLTPF | 0.583 | 91 | WB | Sequence | B1501 |
| 204 | SMRPLFDF | 0.523 | 173 | WB | Sequence | B1501 |
| 13 | IVMKYIHY | 0.492 | 243 | WB | Sequence | B1501 |
| 145 | RIVAFFEF | 0.447 | 397 | WB | Sequence | B1501 |
| 198 | VELYGPSM | 0.595 | 80 | WB | Sequence | B1801 |
| 177 | TEYLNRHL | 0.498 | 228 | WB | Sequence | B1801 |
| 172 | IALWMTEY | 0.475 | 292 | WB | Sequence | B1801 |
| 116 | SQLHLTPF | 0.464 | 328 | WB | Sequence | B1801 |
| 150 | FEFGGVMC | 0.452 | 375 | WB | Sequence | B1801 |
| 172 | IALWMTEY | 0.767 | 12 | SB | Sequence | B3501 |
| 149 | FFEFGGVM | 0.548 | 132 | WB | Sequence | B3501 |
| 69 | SPLQTPAA | 0.503 | 215 | WB | Sequence | B3501 |
| 111 | FAEMSSQL | 0.488 | 253 | WB | Sequence | B3501 |
| 86 | SPVPPVVH | 0.443 | 413 | WB | Sequence | B3501 |
| 73 | TPAAPGAA | 0.435 | 452 | WB | Sequence | B3501 |
| 129 | FATVVEEL | 0.430 | 475 | WB | Sequence | B3501 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 177 | TEYLNRHL | 0.547 | 133 | WB | Sequence | B4001 |
| 11 | REIVMKYI | 0.513 | 194 | WB | Sequence | B4001 |
| 150 | FEFGGVMC | 0.466 | 324 | WB | Sequence | B4001 |
| 11 | REIVMKYI | 0.497 | 231 | WB | Sequence | B4002 |
| 112 | AEMSSQLH | 0.471 | 305 | WB | Sequence | B4501 |
| 134 | EELFRDGV | 0.465 | 326 | WB | Sequence | B4501 |
| 11 | REIVMKYI | 0.435 | 450 | WB | Sequence | B4501 |
| 222 | LALVGACI | 0.470 | 308 | WB | Sequence | B5101 |
| 89 | PPVVHLTL | 0.448 | 391 | WB | Sequence | B5101 |
| 206 | RPLFDFSW | 0.768 | 12 | SB | Sequence | B5301 |
| 202 | GPSMRPLF | 0.430 | 474 | WB | Sequence | B5301 |
| 73 | TPAAPGAA | 0.677 | 32 | SB | Sequence | B5401 |
| 69 | SPLQTPAA | 0.605 | 71 | WB | Sequence | B5401 |
| 37 | APPGAAPA | 0.557 | 120 | WB | Sequence | B5401 |
| 166 | SPLVDNIA | 0.470 | 309 | WB | Sequence | B5401 |
| 88 | VPPVVHLT | 0.450 | 382 | WB | Sequence | B5401 |
| 22 | LSQRGYEW | 0.648 | 45 | SB | Sequence | B5801 |
| 145 | RIVAFFEF | 0.512 | 196 | WB | Sequence | B5801 |
| 168 | LVDNIALW | 0.475 | 292 | WB | Sequence | B5801 |
| 172 | IALWMTEY | 0.460 | 345 | WB | Sequence | B5801 |
| | | | 9-mer | | | |
| 171 | NIALWMTEY | 0.497 | 230 | WB | Sequence | A0101 |
| 84 | ALSPVPPVV | 0.676 | 33 | SB | Sequence | A0201 |
| 223 | ALVGACITL | 0.631 | 54 | WB | Sequence | A0201 |
| 217 | KTLLSLALV | 0.613 | 65 | WB | Sequence | A0201 |
| 219 | LLSLALVGA | 0.542 | 141 | WB | Sequence | A0201 |
| 172 | IALWMTEYL | 0.487 | 258 | WB | Sequence | A0201 |
| 219 | LLSLALVGA | 0.824 | 6 | SB | Sequence | A0202 |
| 14 | VMKYIHYKL | 0.705 | 24 | SB | Sequence | A0202 |
| 223 | ALVGACITL | 0.654 | 42 | SB | Sequence | A0202 |
| 215 | SLKTLLSLA | 0.635 | 52 | WB | Sequence | A0202 |
| 160 | SVNREMSPL | 0.619 | 61 | WB | Sequence | A0202 |
| 80 | AAGPALSPV | 0.617 | 62 | WB | Sequence | A0202 |
| 84 | ALSPVPPVV | 0.593 | 81 | WB | Sequence | A0202 |
| 164 | EMSPLVDNI | 0.582 | 91 | WB | Sequence | A0202 |
| 221 | SLALVGACI | 0.579 | 94 | WB | Sequence | A0202 |
| 67 | RTSPLQTPA | 0.554 | 124 | WB | Sequence | A0202 |
| 204 | SMRPLFDFS | 0.495 | 234 | WB | Sequence | A0202 |
| 179 | YLNRHLHTW | 0.479 | 280 | WB | Sequence | A0202 |
| 172 | IALWMTEYL | 0.459 | 346 | WB | Sequence | A0202 |
| 217 | KTLLSLALV | 0.443 | 414 | WB | Sequence | A0202 |
| 113 | EMSSQLHLT | 0.432 | 464 | WB | Sequence | A0202 |
| 215 | SLKTLLSLA | 0.875 | 3 | SB | Sequence | A0203 |
| 84 | ALSPVPPVV | 0.842 | 5 | SB | Sequence | A0203 |
| 219 | LLSLALVGA | 0.839 | 5 | SB | Sequence | A0203 |
| 80 | AAGPALSPV | 0.770 | 11 | SB | Sequence | A0203 |
| 160 | SVNREMSPL | 0.699 | 26 | SB | Sequence | A0203 |
| 124 | TARGRFATV | 0.666 | 37 | SB | Sequence | A0203 |
| 14 | VMKYIHYKL | 0.642 | 48 | SB | Sequence | A0203 |
| 223 | ALVGACITL | 0.629 | 55 | WB | Sequence | A0203 |
| 221 | SLALVGACI | 0.605 | 71 | WB | Sequence | A0203 |
| 217 | KTLLSLALV | 0.584 | 90 | WB | Sequence | A0203 |
| 67 | RTSPLQTPA | 0.539 | 146 | WB | Sequence | A0203 |
| 147 | VAFFEFGGV | 0.520 | 180 | WB | Sequence | A0203 |
| 164 | EMSPLVDNI | 0.516 | 187 | WB | Sequence | A0203 |
| 117 | QLHLTPFTA | 0.490 | 249 | WB | Sequence | A0203 |
| 204 | SMRPLFDFS | 0.441 | 425 | WB | Sequence | A0203 |
| 179 | YLNRHLHTW | 0.432 | 468 | WB | Sequence | A0203 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 84 | ALSPVPPVV | 0.766 | 12 | SB | Sequence | A0204 |
| 223 | ALVGACITL | 0.571 | 103 | WB | Sequence | A0204 |
| 80 | AAGPALSPV | 0.454 | 366 | WB | Sequence | A0204 |
| 217 | KTLLSLALV | 0.742 | 16 | SB | Sequence | A0206 |
| 80 | AAGPALSPV | 0.729 | 18 | SB | Sequence | A0206 |
| 116 | SQLHLTPFT | 0.684 | 30 | SB | Sequence | A0206 |
| 71 | LQTPAAPGA | 0.676 | 33 | SB | Sequence | A0206 |
| 150 | FEFGGVMCV | 0.650 | 44 | SB | Sequence | A0206 |
| 223 | ALVGACITL | 0.635 | 52 | WB | Sequence | A0206 |
| 219 | LLSLALVGA | 0.624 | 58 | WB | Sequence | A0206 |
| 84 | ALSPVPPVV | 0.621 | 60 | WB | Sequence | A0206 |
| 123 | FTARGRFAT | 0.598 | 77 | WB | Sequence | A0206 |
| 188 | IQDNGGWDA | 0.594 | 80 | WB | Sequence | A0206 |
| 172 | IALWMTEYL | 0.589 | 85 | WB | Sequence | A0206 |
| 36 | AAPPGAAPA | 0.569 | 106 | WB | Sequence | A0206 |
| 124 | TARGRFATV | 0.543 | 140 | WB | Sequence | A0206 |
| 147 | VAFFEFGGV | 0.511 | 198 | WB | Sequence | A0206 |
| 67 | RTSPLQTPA | 0.462 | 336 | WB | Sequence | A0206 |
| 84 | ALSPVPPVV | 0.951 | 1 | SB | Sequence | A0211 |
| 223 | ALVGACITL | 0.929 | 2 | SB | Sequence | A0211 |
| 207 | PLFDFSWLS | 0.902 | 2 | SB | Sequence | A0211 |
| 150 | FEFGGVMCV | 0.812 | 7 | SB | Sequence | A0211 |
| 179 | YLNRHLHTW | 0.742 | 16 | SB | Sequence | A0211 |
| 221 | SLALVGACI | 0.715 | 21 | SB | Sequence | A0211 |
| 219 | LLSLALVGA | 0.627 | 56 | WB | Sequence | A0211 |
| 164 | EMSPLVDNI | 0.626 | 57 | WB | Sequence | A0211 |
| 117 | QLHLTPFTA | 0.626 | 57 | WB | Sequence | A0211 |
| 215 | SLKTLLSLA | 0.620 | 61 | WB | Sequence | A0211 |
| 168 | LVDNIALWM | 0.592 | 82 | WB | Sequence | A0211 |
| 217 | KTLLSLALV | 0.581 | 93 | WB | Sequence | A0211 |
| 140 | GVNWGRIVA | 0.575 | 99 | WB | Sequence | A0211 |
| 14 | VMKYIHYKL | 0.561 | 115 | WB | Sequence | A0211 |
| 80 | AAGPALSPV | 0.551 | 128 | WB | Sequence | A0211 |
| 113 | EMSSQLHLT | 0.531 | 159 | WB | Sequence | A0211 |
| 6 | TGYDNREIV | 0.513 | 194 | WB | Sequence | A0211 |
| 119 | HLTPFTARG | 0.505 | 211 | WB | Sequence | A0211 |
| 199 | ELYGPSMRP | 0.504 | 213 | WB | Sequence | A0211 |
| 192 | GGWDAFVEL | 0.503 | 216 | WB | Sequence | A0211 |
| 172 | IALWMTEYL | 0.462 | 337 | WB | Sequence | A0211 |
| 173 | ALWMTEYLN | 0.459 | 347 | WB | Sequence | A0211 |
| 36 | AAPPGAAPA | 0.432 | 467 | WB | Sequence | A0211 |
| 84 | ALSPVPPVV | 0.914 | 2 | SB | Sequence | A0212 |
| 223 | ALVGACITL | 0.760 | 13 | SB | Sequence | A0212 |
| 179 | YLNRHLHTW | 0.739 | 16 | SB | Sequence | A0212 |
| 150 | FEFGGVMCV | 0.735 | 17 | SB | Sequence | A0212 |
| 207 | PLFDFSWLS | 0.676 | 33 | SB | Sequence | A0212 |
| 14 | VMKYIHYKL | 0.596 | 79 | WB | Sequence | A0212 |
| 219 | LLSLALVGA | 0.587 | 87 | WB | Sequence | A0212 |
| 221 | SLALVGACI | 0.529 | 162 | WB | Sequence | A0212 |
| 164 | EMSPLVDNI | 0.520 | 180 | WB | Sequence | A0212 |
| 117 | QLHLTPFTA | 0.476 | 290 | WB | Sequence | A0212 |
| 123 | FTARGRFAT | 0.464 | 328 | WB | Sequence | A0212 |
| 84 | ALSPVPPVV | 0.915 | 2 | SB | Sequence | A0216 |
| 223 | ALVGACITL | 0.909 | 2 | SB | Sequence | A0216 |
| 80 | AAGPALSPV | 0.699 | 25 | SB | Sequence | A0216 |
| 150 | FEFGGVMCV | 0.640 | 49 | SB | Sequence | A0216 |
| 221 | SLALVGACI | 0.630 | 54 | WB | Sequence | A0216 |
| 14 | VMKYIHYKL | 0.570 | 104 | WB | Sequence | A0216 |
| 207 | PLFDFSWLS | 0.530 | 162 | WB | Sequence | A0216 |
| 117 | QLHLTPFTA | 0.490 | 250 | WB | Sequence | A0216 |
| 215 | SLKTLLSLA | 0.489 | 251 | WB | Sequence | A0216 |
| 179 | YLNRHLHTW | 0.461 | 340 | WB | Sequence | A0216 |
| 124 | TARGRFATV | 0.448 | 393 | WB | Sequence | A0216 |
| 84 | ALSPVPPVV | 0.899 | 2 | SB | Sequence | A0219 |
| 150 | FEFGGVMCV | 0.686 | 29 | SB | Sequence | A0219 |
| 223 | ALVGACITL | 0.683 | 30 | SB | Sequence | A0219 |
| 80 | AAGPALSPV | 0.557 | 120 | WB | Sequence | A0219 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 219 | LLSLALVGA | 0.542 | 142 | WB | Sequence | A0219 |
| 83 | PALSPVPPV | 0.498 | 229 | WB | Sequence | A0219 |
| 164 | EMSPLVDNI | 0.460 | 345 | WB | Sequence | A0219 |
| 113 | EMSSQLHLT | 0.437 | 443 | WB | Sequence | A0219 |
| 179 | YLNRHLHTW | 0.428 | 485 | WB | Sequence | A0219 |
| 13 | IVMKYIHYK | 0.758 | 13 | SB | Sequence | A0301 |
| 230 | TLGAYLGHK | 0.655 | 41 | SB | Sequence | A0301 |
| 209 | FDFSWLSLK | 0.457 | 357 | WB | Sequence | A0301 |
| 13 | IVMKYIHYK | 0.834 | 6 | SB | Sequence | A1101 |
| 230 | TLGAYLGHK | 0.708 | 23 | SB | Sequence | A1101 |
| 130 | ATVVEELFR | 0.574 | 100 | WB | Sequence | A1101 |
| 142 | NWGRIVAFF | 0.644 | 47 | SB | Sequence | A2301 |
| 203 | PSMRPLFDF | 0.530 | 161 | WB | Sequence | A2301 |
| 144 | GRIVAFFEF | 0.530 | 162 | WB | Sequence | A2301 |
| 13 | IVMKYIHYK | 0.499 | 226 | WB | Sequence | A2301 |
| 106 | RYRRDFAEM | 0.467 | 321 | WB | Sequence | A2301 |
| 128 | RFATVVEEL | 0.454 | 366 | WB | Sequence | A2301 |
| 142 | NWGRIVAFF | 0.739 | 16 | SB | Sequence | A2402 |
| 128 | RFATVVEEL | 0.568 | 107 | WB | Sequence | A2402 |
| 212 | SWLSLKTLL | 0.536 | 151 | WB | Sequence | A2402 |
| 106 | RYRRDFAEM | 0.669 | 35 | SB | Sequence | A2403 |
| 128 | RFATVVEEL | 0.626 | 57 | WB | Sequence | A2403 |
| 200 | LYGPSMRPL | 0.553 | 125 | WB | Sequence | A2403 |
| 12 | EIVMKYIHY | 0.628 | 55 | WB | Sequence | A2601 |
| 171 | NIALWMTEY | 0.622 | 60 | WB | Sequence | A2601 |
| 12 | EIVMKYIHY | 0.935 | 2 | SB | Sequence | A2602 |
| 171 | NIALWMTEY | 0.866 | 4 | SB | Sequence | A2602 |
| 160 | SVNREMSPL | 0.849 | 5 | SB | Sequence | A2602 |
| 179 | YLNRHLHTW | 0.538 | 148 | WB | Sequence | A2602 |
| 197 | FVELYGPSM | 0.520 | 180 | WB | Sequence | A2602 |
| 168 | LVDNIALWM | 0.432 | 464 | WB | Sequence | A2602 |
| 171 | NIALWMTEY | 0.586 | 88 | WB | Sequence | A2902 |
| 12 | EIVMKYIHY | 0.516 | 188 | WB | Sequence | A2902 |
| 13 | IVMKYIHYK | 0.758 | 13 | SB | Sequence | A3001 |
| 0 | MAHAGRTGY | 0.487 | 258 | WB | Sequence | A3001 |
| 230 | TLGAYLGHK | 0.475 | 293 | WB | Sequence | A3001 |
| 171 | NIALWMTEY | 0.427 | 491 | WB | Sequence | A3002 |
| 13 | IVMKYIHYK | 0.797 | 8 | SB | Sequence | A3101 |
| 17 | YIHYKLSQR | 0.715 | 21 | SB | Sequence | A3101 |
| 155 | VMCVESVNR | 0.631 | 54 | WB | Sequence | A3101 |
| 97 | RQAGDDFSR | 0.588 | 85 | WB | Sequence | A3101 |
| 14 | VMKYIHYKL | 0.497 | 230 | WB | Sequence | A3101 |
| 130 | ATVVEELFR | 0.471 | 307 | WB | Sequence | A3101 |
| 101 | DDFSRRYRR | 0.698 | 26 | SB | Sequence | A3301 |
| 17 | YIHYKLSQR | 0.649 | 44 | SB | Sequence | A3301 |
| 54 | HTPHPAASR | 0.476 | 290 | WB | Sequence | A3301 |
| 13 | IVMKYIHYK | 0.427 | 493 | WB | Sequence | A3301 |
| 13 | IVMKYIHYK | 0.790 | 9 | SB | Sequence | A6801 |
| 17 | YIHYKLSQR | 0.747 | 15 | SB | Sequence | A6801 |
| 54 | HTPHPAASR | 0.729 | 18 | SB | Sequence | A6801 |
| 120 | LTPFTARGR | 0.703 | 24 | SB | Sequence | A6801 |
| 130 | ATVVEELFR | 0.655 | 41 | SB | Sequence | A6801 |
| 101 | DDFSRRYRR | 0.571 | 103 | WB | Sequence | A6801 |
| 209 | FDFSWLSLK | 0.540 | 145 | WB | Sequence | A6801 |
| 98 | QAGDDFSRR | 0.529 | 163 | WB | Sequence | A6801 |
| 171 | NIALWMTEY | 0.477 | 288 | WB | Sequence | A6801 |
| 230 | TLGAYLGHK | 0.449 | 388 | WB | Sequence | A6801 |
| 0 | MAHAGRTGY | 0.447 | 398 | WB | Sequence | A6801 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 123 | FTARGRFAT | 0.692 | 27 | SB | Sequence | A6802 |
| 147 | VAFFEFGGV | 0.641 | 48 | SB | Sequence | A6802 |
| 57 | HPAASRDPV | 0.627 | 56 | WB | Sequence | A6802 |
| 72 | QTPAAPGAA | 0.604 | 72 | WB | Sequence | A6802 |
| 160 | SVNREMSPL | 0.570 | 104 | WB | Sequence | A6802 |
| 124 | TARGRFATV | 0.531 | 160 | WB | Sequence | A6802 |
| 6 | TGYDNREIV | 0.513 | 193 | WB | Sequence | A6802 |
| 164 | EMSPLVDNI | 0.512 | 196 | WB | Sequence | A6802 |
| 67 | RTSPLQTPA | 0.488 | 254 | WB | Sequence | A6802 |
| 225 | VGACITLGA | 0.472 | 303 | WB | Sequence | A6802 |
| 165 | MSPLVDNIA | 0.466 | 322 | WB | Sequence | A6802 |
| 150 | FEFGGVMCV | 0.449 | 388 | WB | Sequence | A6802 |
| 83 | PALSPVPPV | 0.726 | 19 | SB | Sequence | A6901 |
| 33 | DVGAAPPGA | 0.535 | 152 | WB | Sequence | A6901 |
| 57 | HPAASRDPV | 0.495 | 235 | WB | Sequence | A6901 |
| 164 | EMSPLVDNI | 0.485 | 262 | WB | Sequence | A6901 |
| 123 | FTARGRFAT | 0.483 | 267 | WB | Sequence | A6901 |
| 217 | KTLLSLALV | 0.460 | 344 | WB | Sequence | A6901 |
| 73 | TPAAPGAAA | 0.460 | 344 | WB | Sequence | A6901 |
| 172 | IALWMTEYL | 0.426 | 497 | WB | Sequence | A6901 |
| 57 | HPAASRDPV | 0.770 | 12 | SB | Sequence | B0702 |
| 63 | DPVARTSPL | 0.750 | 14 | SB | Sequence | B0702 |
| 166 | SPLVDNIAL | 0.674 | 33 | SB | Sequence | B0702 |
| 73 | TPAAPGAAA | 0.652 | 43 | SB | Sequence | B0702 |
| 206 | RPLFDFSWL | 0.627 | 56 | WB | Sequence | B0702 |
| 86 | SPVPPVVHL | 0.606 | 71 | WB | Sequence | B0702 |
| 76 | APGAAAGPA | 0.573 | 101 | WB | Sequence | B0702 |
| 88 | VPPVVHLTL | 0.542 | 142 | WB | Sequence | B0702 |
| 121 | TPFTARGRF | 0.505 | 210 | WB | Sequence | B0702 |
| 124 | TARGRFATV | 0.449 | 389 | WB | Sequence | B0702 |
| 0 | MAHAGRTGY | 0.532 | 158 | WB | Sequence | B1501 |
| 115 | SSQLHLTPF | 0.427 | 490 | WB | Sequence | B1501 |
| 150 | FEFGGVMCV | 0.633 | 53 | WB | Sequence | B1801 |
| 9 | DNREIVMKY | 0.541 | 143 | WB | Sequence | B1801 |
| 172 | IALWMTEYL | 0.505 | 211 | WB | Sequence | B1801 |
| 144 | GRIVAFFEF | 0.456 | 360 | WB | Sequence | B2705 |
| 105 | RRYRRDFAE | 0.456 | 361 | WB | Sequence | B2705 |
| 166 | SPLVDNIAL | 0.680 | 31 | SB | Sequence | B3501 |
| 0 | MAHAGRTGY | 0.658 | 40 | SB | Sequence | B3501 |
| 197 | FVELYGPSM | 0.628 | 55 | WB | Sequence | B3501 |
| 121 | TPFTARGRF | 0.610 | 67 | WB | Sequence | B3501 |
| 172 | IALWMTEYL | 0.584 | 90 | WB | Sequence | B3501 |
| 63 | DPVARTSPL | 0.584 | 90 | WB | Sequence | B3501 |
| 129 | FATVVEELF | 0.562 | 113 | WB | Sequence | B3501 |
| 73 | TPAAPGAAA | 0.551 | 128 | WB | Sequence | B3501 |
| 171 | NIALWMTEY | 0.523 | 174 | WB | Sequence | B3501 |
| 111 | FAEMSSQLH | 0.460 | 343 | WB | Sequence | B3501 |
| 112 | AEMSSQLHL | 0.740 | 16 | SB | Sequence | B4001 |
| 150 | FEFGGVMCV | 0.588 | 86 | WB | Sequence | B4001 |
| 112 | AEMSSQLHL | 0.554 | 124 | WB | Sequence | B4002 |
| 150 | FEFGGVMCV | 0.466 | 323 | WB | Sequence | B4002 |
| 112 | AEMSSQLHL | 0.454 | 368 | WB | Sequence | B4402 |
| 112 | AEMSSQLHL | 0.533 | 157 | WB | Sequence | B4403 |
| 112 | AEMSSQLHL | 0.587 | 87 | WB | Sequence | B4501 |
| 88 | VPPVVHLTL | 0.548 | 132 | WB | Sequence | B5101 |
| 206 | RPLFDFSWL | 0.470 | 307 | WB | Sequence | B5301 |
| 166 | SPLVDNIAL | 0.459 | 348 | WB | Sequence | B5301 |
| 172 | IALWMTEYL | 0.450 | 382 | WB | Sequence | B5301 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pospeptide | logscore | affinity (nM) | Bind Level | Protein Name | Allele |
|---|---|---|---|---|---|
| 73 TPAAPGAAA | 0.715 | 21 | SB | Sequence | B5401 |
| 57 HPAASRDPV | 0.684 | 30 | SB | Sequence | B5401 |
| 76 APGAAAGPA | 0.625 | 57 | WB | Sequence | B5401 |
| 51 QPGHTPHPA | 0.515 | 189 | WB | Sequence | B5401 |
| 179 YLNRHLHTW | 0.682 | 31 | SB | Sequence | B5801 |
| 21 KLSQRGYEW | 0.649 | 44 | SB | Sequence | B5801 |
| 129 FATVVEELF | 0.547 | 134 | WB | Sequence | B5801 |
| 40 GAAPAPGIF | 0.483 | 268 | WB | Sequence | B5801 |

10-mer

| pospeptide | logscore | affinity (nM) | Bind Level | Protein Name | Allele |
|---|---|---|---|---|---|
| 179 YLNRHLHTWI | 0.735 | 17 | SB | Sequence | A0201 |
| 13 IVMKYIHYKL | 0.638 | 50 | WB | Sequence | A0201 |
| 218 TLLSLALVGA | 0.571 | 103 | WB | Sequence | A0201 |
| 207 PLFDFSWLSL | 0.536 | 151 | WB | Sequence | A0201 |
| 213 WLSLKTLLSL | 0.530 | 161 | WB | Sequence | A0201 |
| 123 FTARGRFATV | 0.522 | 175 | WB | Sequence | A0201 |
| 171 NIALWMTEYL | 0.521 | 178 | WB | Sequence | A0201 |
| 175 WMTEYLNRHL | 0.486 | 260 | WB | Sequence | A0201 |
| 218 TLLSLALVGA | 0.731 | 18 | SB | Sequence | A0202 |
| 171 NIALWMTEYL | 0.727 | 19 | SB | Sequence | A0202 |
| 213 WLSLKTLLSL | 0.700 | 25 | SB | Sequence | A0202 |
| 215 SLKTLLSLAL | 0.646 | 46 | SB | Sequence | A0202 |
| 175 WMTEYLNRHL | 0.642 | 47 | SB | Sequence | A0202 |
| 207 PLFDFSWLSL | 0.637 | 50 | WB | Sequence | A0202 |
| 79 AAAGPALSPV | 0.588 | 86 | WB | Sequence | A0202 |
| 13 IVMKYIHYKL | 0.569 | 106 | WB | Sequence | A0202 |
| 123 FTARGRFATV | 0.568 | 106 | WB | Sequence | A0202 |
| 199 ELYGPSMRPL | 0.541 | 143 | WB | Sequence | A0202 |
| 179 YLNRHLHTWI | 0.540 | 145 | WB | Sequence | A0202 |
| 224 LVGACITLGA | 0.483 | 267 | WB | Sequence | A0202 |
| 146 IVAFFEFGGV | 0.439 | 431 | WB | Sequence | A0202 |
| 179 YLNRHLHTWI | 0.933 | 2 | SB | Sequence | A0203 |
| 123 FTARGRFATV | 0.821 | 6 | SB | Sequence | A0203 |
| 213 WLSLKTLLSL | 0.782 | 10 | SB | Sequence | A0203 |
| 215 SLKTLLSLAL | 0.773 | 11 | SB | Sequence | A0203 |
| 171 NIALWMTEYL | 0.682 | 31 | SB | Sequence | A0203 |
| 160 SVNREMSPLV | 0.680 | 31 | SB | Sequence | A0203 |
| 146 IVAFFEFGGV | 0.667 | 36 | SB | Sequence | A0203 |
| 79 AAAGPALSPV | 0.606 | 71 | WB | Sequence | A0203 |
| 175 WMTEYLNRHL | 0.569 | 106 | WB | Sequence | A0203 |
| 218 TLLSLALVGA | 0.545 | 137 | WB | Sequence | A0203 |
| 13 IVMKYIHYKL | 0.532 | 157 | WB | Sequence | A0203 |
| 224 LVGACITLGA | 0.532 | 158 | WB | Sequence | A0203 |
| 199 ELYGPSMRPL | 0.519 | 182 | WB | Sequence | A0203 |
| 50 SQPGHTPHPA | 0.447 | 398 | WB | Sequence | A0203 |
| 219 LLSLALVGAC | 0.444 | 410 | WB | Sequence | A0203 |
| 124 TARGRFATVV | 0.428 | 489 | WB | Sequence | A0203 |
| 179 YLNRHLHTWI | 0.655 | 41 | SB | Sequence | A0204 |
| 123 FTARGRFATV | 0.613 | 66 | WB | Sequence | A0204 |
| 13 IVMKYIHYKL | 0.509 | 203 | WB | Sequence | A0204 |
| 79 AAAGPALSPV | 0.474 | 296 | WB | Sequence | A0204 |
| 160 SVNREMSPLV | 0.450 | 384 | WB | Sequence | A0204 |
| 123 FTARGRFATV | 0.867 | 4 | SB | Sequence | A0206 |
| 116 SQLHLTPFTA | 0.776 | 11 | SB | Sequence | A0206 |
| 188 IQDNGGWDAF | 0.673 | 34 | SB | Sequence | A0206 |
| 213 WLSLKTLLSL | 0.667 | 36 | SB | Sequence | A0206 |
| 50 SQPGHTPHPA | 0.621 | 60 | WB | Sequence | A0206 |
| 179 YLNRHLHTWI | 0.619 | 61 | WB | Sequence | A0206 |
| 79 AAAGPALSPV | 0.602 | 74 | WB | Sequence | A0206 |
| 175 WMTEYLNRHL | 0.600 | 75 | WB | Sequence | A0206 |
| 160 SVNREMSPLV | 0.567 | 108 | WB | Sequence | A0206 |
| 171 NIALWMTEYL | 0.562 | 114 | WB | Sequence | A0206 |
| 218 TLLSLALVGA | 0.560 | 116 | WB | Sequence | A0206 |
| 146 IVAFFEFGGV | 0.553 | 125 | WB | Sequence | A0206 |
| 71 LQTPAAPGAA | 0.546 | 135 | WB | Sequence | A0206 |
| 13 IVMKYIHYKL | 0.525 | 171 | WB | Sequence | A0206 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 27 | YEWDAGDVGA | 0.511 | 199 | WB | Sequence | A0206 |
| 207 | PLFDFSWLSL | 0.486 | 260 | WB | Sequence | A0206 |
| 67 | RTSPLQTPAA | 0.477 | 286 | WB | Sequence | A0206 |
| 224 | LVGACITLGA | 0.471 | 304 | WB | Sequence | A0206 |
| 207 | PLFDFSWLSL | 0.935 | 2 | SB | Sequence | A0211 |
| 179 | YLNRHLHTWI | 0.925 | 2 | SB | Sequence | A0211 |
| 199 | ELYGPSMRPL | 0.888 | 3 | SB | Sequence | A0211 |
| 213 | WLSLKTLLSL | 0.835 | 5 | SB | Sequence | A0211 |
| 218 | TLLSLALVGA | 0.829 | 6 | SB | Sequence | A0211 |
| 123 | FTARGRFATV | 0.823 | 6 | SB | Sequence | A0211 |
| 167 | PLVDNIALWM | 0.802 | 8 | SB | Sequence | A0211 |
| 215 | SLKTLLSLAL | 0.799 | 8 | SB | Sequence | A0211 |
| 175 | WMTEYLNRHL | 0.796 | 9 | SB | Sequence | A0211 |
| 160 | SVNREMSPLV | 0.788 | 9 | SB | Sequence | A0211 |
| 87 | PVPPVVHLTL | 0.705 | 24 | SB | Sequence | A0211 |
| 79 | AAAGPALSPV | 0.635 | 51 | WB | Sequence | A0211 |
| 13 | IVMKYIHYKL | 0.601 | 74 | WB | Sequence | A0211 |
| 146 | IVAFFEFGGV | 0.568 | 107 | WB | Sequence | A0211 |
| 132 | VVEELFRDGV | 0.549 | 131 | WB | Sequence | A0211 |
| 171 | NIALWMTEYL | 0.547 | 133 | WB | Sequence | A0211 |
| 164 | EMSPLVDNIA | 0.488 | 254 | WB | Sequence | A0211 |
| 168 | LVDNIALWMT | 0.484 | 266 | WB | Sequence | A0211 |
| 149 | FFEFGGVMCV | 0.475 | 292 | WB | Sequence | A0211 |
| 221 | SLALVGACIT | 0.462 | 336 | WB | Sequence | A0211 |
| 187 | WIQDNGGWDA | 0.453 | 370 | WB | Sequence | A0211 |
| 179 | YLNRHLHTWI | 0.878 | 3 | SB | Sequence | A0212 |
| 207 | PLFDFSWLSL | 0.859 | 4 | SB | Sequence | A0212 |
| 123 | FTARGRFATV | 0.849 | 5 | SB | Sequence | A0212 |
| 215 | SLKTLLSLAL | 0.730 | 18 | SB | Sequence | A0212 |
| 199 | ELYGPSMRPL | 0.726 | 19 | SB | Sequence | A0212 |
| 175 | WMTEYLNRHL | 0.716 | 21 | SB | Sequence | A0212 |
| 213 | WLSLKTLLSL | 0.697 | 26 | SB | Sequence | A0212 |
| 218 | TLLSLALVGA | 0.692 | 27 | SB | Sequence | A0212 |
| 132 | VVEELFRDGV | 0.601 | 74 | WB | Sequence | A0212 |
| 167 | PLVDNIALWM | 0.560 | 116 | WB | Sequence | A0212 |
| 13 | IVMKYIHYKL | 0.533 | 156 | WB | Sequence | A0212 |
| 160 | SVNREMSPLV | 0.509 | 202 | WB | Sequence | A0212 |
| 187 | WIQDNGGWDA | 0.479 | 280 | WB | Sequence | A0212 |
| 146 | IVAFFEFGGV | 0.476 | 288 | WB | Sequence | A0212 |
| 87 | PVPPVVHLTL | 0.475 | 294 | WB | Sequence | A0212 |
| 27 | YEWDAGDVGA | 0.467 | 321 | WB | Sequence | A0212 |
| 179 | YLNRHLHTWI | 0.854 | 4 | SB | Sequence | A0216 |
| 207 | PLFDFSWLSL | 0.849 | 5 | SB | Sequence | A0216 |
| 123 | FTARGRFATV | 0.812 | 7 | SB | Sequence | A0216 |
| 199 | ELYGPSMRPL | 0.767 | 12 | SB | Sequence | A0216 |
| 213 | WLSLKTLLSL | 0.745 | 15 | SB | Sequence | A0216 |
| 167 | PLVDNIALWM | 0.702 | 25 | SB | Sequence | A0216 |
| 160 | SVNREMSPLV | 0.685 | 30 | SB | Sequence | A0216 |
| 13 | IVMKYIHYKL | 0.676 | 33 | SB | Sequence | A0216 |
| 175 | WMTEYLNRHL | 0.675 | 33 | SB | Sequence | A0216 |
| 79 | AAAGPALSPV | 0.661 | 39 | SB | Sequence | A0216 |
| 87 | PVPPVVHLTL | 0.638 | 50 | WB | Sequence | A0216 |
| 215 | SLKTLLSLAL | 0.634 | 52 | WB | Sequence | A0216 |
| 218 | TLLSLALVGA | 0.574 | 100 | WB | Sequence | A0216 |
| 171 | NIALWMTEYL | 0.557 | 120 | WB | Sequence | A0216 |
| 221 | SLALVGACIT | 0.472 | 301 | WB | Sequence | A0216 |
| 146 | IVAFFEFGGV | 0.429 | 483 | WB | Sequence | A0216 |
| 207 | PLFDFSWLSL | 0.805 | 8 | SB | Sequence | A0219 |
| 179 | YLNRHLHTWI | 0.789 | 9 | SB | Sequence | A0219 |
| 213 | WLSLKTLLSL | 0.766 | 12 | SB | Sequence | A0219 |
| 123 | FTARGRFATV | 0.703 | 24 | SB | Sequence | A0219 |
| 199 | ELYGPSMRPL | 0.585 | 88 | WB | Sequence | A0219 |
| 167 | PLVDNIALWM | 0.574 | 100 | WB | Sequence | A0219 |
| 79 | AAAGPALSPV | 0.563 | 112 | WB | Sequence | A0219 |
| 218 | TLLSLALVGA | 0.551 | 129 | WB | Sequence | A0219 |
| 175 | WMTEYLNRHL | 0.521 | 178 | WB | Sequence | A0219 |
| 83 | PALSPVPPVV | 0.486 | 259 | WB | Sequence | A0219 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pospeptide | logscore | affinity (nM) | Bind Level | Protein Name | Allele |
|---|---|---|---|---|---|
| 13 IVMKYIHYKL | 0.461 | 341 | WB | Sequence | A0219 |
| 171 NIALWMTEYL | 0.446 | 401 | WB | Sequence | A0219 |
| 229 ITLGAYLGHK | 0.760 | 13 | SB | Sequence | A0301 |
| 208 LFDFSWLSLK | 0.497 | 232 | WB | Sequence | A0301 |
| 12 EIVMKYIHYK | 0.475 | 292 | WB | Sequence | A0301 |
| 154 GVMCVESVNR | 0.444 | 411 | WB | Sequence | A0301 |
| 173 ALWMTEYLNR | 0.429 | 480 | WB | Sequence | A0301 |
| 229 ITLGAYLGHK | 0.752 | 14 | SB | Sequence | A1101 |
| 154 GVMCVESVNR | 0.637 | 50 | WB | Sequence | A1101 |
| 12 EIVMKYIHYK | 0.540 | 145 | WB | Sequence | A1101 |
| 173 ALWMTEYLNR | 0.455 | 363 | WB | Sequence | A1101 |
| 208 LFDFSWLSLK | 0.435 | 453 | WB | Sequence | A1101 |
| 178 EYLNRHLHTW | 0.686 | 29 | SB | Sequence | A2301 |
| 200 LYGPSMRPLF | 0.686 | 29 | SB | Sequence | A2301 |
| 128 RFATVVEELF | 0.620 | 60 | WB | Sequence | A2301 |
| 7 GYDNREIVMK | 0.595 | 80 | WB | Sequence | A2301 |
| 102 DFSRRYRRDF | 0.499 | 226 | WB | Sequence | A2301 |
| 13 IVMKYIHYKL | 0.451 | 381 | WB | Sequence | A2301 |
| 94 LTLRQAGDDF | 0.437 | 441 | WB | Sequence | A2301 |
| 128 RFATVVEELF | 0.764 | 12 | SB | Sequence | A2402 |
| 200 LYGPSMRPLF | 0.733 | 17 | SB | Sequence | A2402 |
| 178 EYLNRHLHTW | 0.715 | 21 | SB | Sequence | A2402 |
| 178 EYLNRHLHTW | 0.718 | 21 | SB | Sequence | A2403 |
| 128 RFATVVEELF | 0.657 | 41 | SB | Sequence | A2403 |
| 200 LYGPSMRPLF | 0.636 | 51 | WB | Sequence | A2403 |
| 170 DNIALWMTEY | 0.478 | 283 | WB | Sequence | A2601 |
| 159 ESVNREMSPL | 0.621 | 60 | WB | Sequence | A2602 |
| 199 ELYGPSMRPL | 0.595 | 79 | WB | Sequence | A2602 |
| 171 NIALWMTEYL | 0.549 | 131 | WB | Sequence | A2602 |
| 170 DNIALWMTEY | 0.487 | 258 | WB | Sequence | A2602 |
| 229 ITLGAYLGHK | 0.718 | 21 | SB | Sequence | A3001 |
| 16 KYIHYKLSQR | 0.837 | 5 | SB | Sequence | A3101 |
| 136 LFRDGVNWGR | 0.667 | 36 | SB | Sequence | A3101 |
| 154 GVMCVESVNR | 0.576 | 98 | WB | Sequence | A3101 |
| 119 HLTPFTARGR | 0.573 | 101 | WB | Sequence | A3101 |
| 173 ALWMTEYLNR | 0.509 | 203 | WB | Sequence | A3101 |
| 99 AGDDFSRRYR | 0.507 | 207 | WB | Sequence | A3101 |
| 129 FATVVEELFR | 0.493 | 241 | WB | Sequence | A3101 |
| 117 QLHLTPFTAR | 0.431 | 471 | WB | Sequence | A3101 |
| 136 LFRDGVNWGR | 0.553 | 126 | WB | Sequence | A3301 |
| 16 KYIHYKLSQR | 0.520 | 180 | WB | Sequence | A3301 |
| 129 FATVVEELFR | 0.516 | 188 | WB | Sequence | A3301 |
| 173 ALWMTEYLNR | 0.441 | 423 | WB | Sequence | A3301 |
| 129 FATVVEELFR | 0.829 | 6 | SB | Sequence | A6801 |
| 12 EIVMKYIHYK | 0.780 | 10 | SB | Sequence | A6801 |
| 119 HLTPFTARGR | 0.721 | 20 | SB | Sequence | A6801 |
| 197 FVELYGPSMR | 0.688 | 29 | SB | Sequence | A6801 |
| 154 GVMCVESVNR | 0.646 | 46 | SB | Sequence | A6801 |
| 229 ITLGAYLGHK | 0.568 | 106 | WB | Sequence | A6801 |
| 176 MTEYLNRHLH | 0.485 | 262 | WB | Sequence | A6801 |
| 117 QLHLTPFTAR | 0.466 | 322 | WB | Sequence | A6801 |
| 2 HAGRTGYDNR | 0.446 | 399 | WB | Sequence | A6801 |
| 123 FTARGRFATV | 0.861 | 4 | SB | Sequence | A6802 |
| 146 IVAFFEFGGV | 0.809 | 7 | SB | Sequence | A6802 |
| 171 NIALWMTEYL | 0.728 | 18 | SB | Sequence | A6802 |
| 13 IVMKYIHYKL | 0.680 | 31 | SB | Sequence | A6802 |
| 79 AAAGPALSPV | 0.644 | 47 | SB | Sequence | A6802 |
| 72 QTPAAPGAAA | 0.617 | 63 | WB | Sequence | A6802 |
| 165 MSPLVDNIAL | 0.591 | 83 | WB | Sequence | A6802 |
| 199 ELYGPSMRPL | 0.582 | 92 | WB | Sequence | A6802 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 159 | ESVNREMSPL | 0.550 | 129 | WB | Sequence | A6802 |
| 205 | MRPLFDFSWL | 0.522 | 175 | WB | Sequence | A6802 |
| 160 | SVNREMSPLV | 0.471 | 306 | WB | Sequence | A6802 |
| 124 | TARGRFATVV | 0.441 | 421 | WB | Sequence | A6802 |
| 123 | FTARGRFATV | 0.792 | 9 | SB | Sequence | A6901 |
| 199 | ELYGPSMRPL | 0.714 | 22 | SB | Sequence | A6901 |
| 83 | PALSPVPPVV | 0.580 | 94 | WB | Sequence | A6901 |
| 171 | NIALWMTEYL | 0.558 | 119 | WB | Sequence | A6901 |
| 160 | SVNREMSPLV | 0.537 | 149 | WB | Sequence | A6901 |
| 79 | AAAGPALSPV | 0.502 | 219 | WB | Sequence | A6901 |
| 33 | DVGAAPPGAA | 0.489 | 251 | WB | Sequence | A6901 |
| 146 | IVAFFEFGGV | 0.464 | 330 | WB | Sequence | A6901 |
| 13 | IVMKYIHYKL | 0.441 | 422 | WB | Sequence | A6901 |
| 76 | APGAAAGPAL | 0.708 | 23 | SB | Sequence | B0702 |
| 82 | GPALSPVPPV | 0.604 | 72 | WB | Sequence | B0702 |
| 57 | HPAASRDPVA | 0.536 | 152 | WB | Sequence | B0702 |
| 202 | GPSMRPLFDF | 0.468 | 317 | WB | Sequence | B0702 |
| 124 | TARGRFATVV | 0.465 | 327 | WB | Sequence | B0702 |
| 42 | APAPGIFSSQ | 0.451 | 378 | WB | Sequence | B0702 |
| 140 | GVNWGRIVAF | 0.548 | 132 | WB | Sequence | B1501 |
| 114 | MSSQLHLTPF | 0.504 | 214 | WB | Sequence | B1501 |
| 188 | IQDNGGWDAF | 0.490 | 249 | WB | Sequence | B1501 |
| 11 | REIVMKYIHY | 0.603 | 73 | WB | Sequence | B1801 |
| 105 | RRYRRDFAEM | 0.622 | 59 | WB | Sequence | B2705 |
| 127 | GRFATVVEEL | 0.493 | 241 | WB | Sequence | B2705 |
| 114 | MSSQLHLTPF | 0.582 | 91 | WB | Sequence | B3501 |
| 147 | VAFFEFGGVM | 0.561 | 115 | WB | Sequence | B3501 |
| 76 | APGAAAGPAL | 0.526 | 168 | WB | Sequence | B3501 |
| 222 | LALVGACITL | 0.473 | 297 | WB | Sequence | B3501 |
| 156 | MCVESVNREM | 0.473 | 299 | WB | Sequence | B3501 |
| 98 | QAGDDFSRRY | 0.461 | 340 | WB | Sequence | B3501 |
| 73 | TPAAPGAAAG | 0.459 | 346 | WB | Sequence | B3501 |
| 140 | GVNWGRIVAF | 0.455 | 362 | WB | Sequence | B3501 |
| 166 | SPLVDNIALW | 0.453 | 371 | WB | Sequence | B3501 |
| 11 | REIVMKYIHY | 0.502 | 218 | WB | Sequence | B4002 |
| 112 | AEMSSQLHLT | 0.472 | 303 | WB | Sequence | B4002 |
| 11 | REIVMKYIHY | 0.476 | 289 | WB | Sequence | B4402 |
| 11 | REIVMKYIHY | 0.481 | 273 | WB | Sequence | B4403 |
| 134 | EELFRDGVNW | 0.473 | 300 | WB | Sequence | B4403 |
| 112 | AEMSSQLHLT | 0.523 | 175 | WB | Sequence | B4501 |
| 11 | REIVMKYIHY | 0.438 | 437 | WB | Sequence | B4501 |
| 134 | EELFRDGVNW | 0.367 | 946 | | Sequence | B4501 |
| 222 | LALVGACITL | 0.480 | 277 | WB | Sequence | B5101 |
| 38 | PPGAAPAPGI | 0.427 | 490 | WB | Sequence | B5101 |
| 166 | SPLVDNIALW | 0.744 | 15 | SB | Sequence | B5301 |
| 57 | HPAASRDPVA | 0.665 | 37 | SB | Sequence | B5401 |
| 121 | TPFTARGRFA | 0.661 | 39 | SB | Sequence | B5401 |
| 51 | QPGHTPHPAA | 0.476 | 289 | WB | Sequence | B5401 |
| 82 | GPALSPVPPV | 0.461 | 340 | WB | Sequence | B5401 |
| 86 | SPVPPVVHLT | 0.434 | 456 | WB | Sequence | B5401 |
| 185 | HTWIQDNGGW | 0.427 | 491 | WB | Sequence | B5701 |
| 114 | MSSQLHLTPF | 0.611 | 67 | WB | Sequence | B5801 |
| 185 | HTWIQDNGGW | 0.580 | 94 | WB | Sequence | B5801 |
| 204 | SMRPLFDFSW | 0.474 | 294 | WB | Sequence | B5801 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| | | | 11-mer | | | |
| 223 | ALVGACITLGA | 0.632 | 53 | WB | Sequence | A0201 |
| 84 | ALSPVPPVVHL | 0.586 | 88 | WB | Sequence | A0201 |
| 215 | SLKTLLSLALV | 0.543 | 141 | WB | Sequence | A0201 |
| 188 | IQDNGGWDAFV | 0.504 | 215 | WB | Sequence | A0201 |
| 219 | LLSLALVGACI | 0.481 | 275 | WB | Sequence | A0201 |
| 221 | SLALVGACITL | 0.473 | 299 | WB | Sequence | A0201 |
| 145 | RIVAFFEFGGV | 0.453 | 373 | WB | Sequence | A0201 |
| 21 | KLSQRGYEWDA | 0.449 | 388 | WB | Sequence | A0201 |
| 204 | SMRPLFDFSWL | 0.772 | 11 | SB | Sequence | A0202 |
| 215 | SLKTLLSLALV | 0.763 | 12 | SB | Sequence | A0202 |
| 221 | SLALVGACITL | 0.710 | 23 | SB | Sequence | A0202 |
| 84 | ALSPVPPVVHL | 0.708 | 23 | SB | Sequence | A0202 |
| 219 | LLSLALVGACI | 0.692 | 28 | SB | Sequence | A0202 |
| 164 | EMSPLVDNIAL | 0.657 | 41 | SB | Sequence | A0202 |
| 223 | ALVGACITLGA | 0.630 | 54 | WB | Sequence | A0202 |
| 213 | WLSLKTLLSLA | 0.616 | 63 | WB | Sequence | A0202 |
| 123 | FTARGRFATVV | 0.602 | 74 | WB | Sequence | A0202 |
| 78 | GAAAGPALSPV | 0.597 | 78 | WB | Sequence | A0202 |
| 145 | RIVAFFEFGGV | 0.569 | 105 | WB | Sequence | A0202 |
| 179 | YLNRHLHTWIQ | 0.529 | 163 | WB | Sequence | A0202 |
| 21 | KLSQRGYEWDA | 0.499 | 226 | WB | Sequence | A0202 |
| 131 | TVVEELFRDGV | 0.478 | 284 | WB | Sequence | A0202 |
| 225 | VGACITLGAYL | 0.469 | 312 | WB | Sequence | A0202 |
| 215 | SLKTLLSLALV | 0.899 | 2 | SB | Sequence | A0203 |
| 204 | SMRPLFDFSWL | 0.853 | 4 | SB | Sequence | A0203 |
| 145 | RIVAFFEFGGV | 0.813 | 7 | SB | Sequence | A0203 |
| 78 | GAAAGPALSPV | 0.774 | 11 | SB | Sequence | A0203 |
| 213 | WLSLKTLLSLA | 0.765 | 12 | SB | Sequence | A0203 |
| 84 | ALSPVPPVVHL | 0.765 | 12 | SB | Sequence | A0203 |
| 223 | ALVGACITLGA | 0.751 | 14 | SB | Sequence | A0203 |
| 219 | LLSLALVGACI | 0.707 | 23 | SB | Sequence | A0203 |
| 123 | FTARGRFATVV | 0.672 | 34 | SB | Sequence | A0203 |
| 221 | SLALVGACITL | 0.617 | 63 | WB | Sequence | A0203 |
| 179 | YLNRHLHTWIQ | 0.565 | 110 | WB | Sequence | A0203 |
| 131 | TVVEELFRDGV | 0.507 | 206 | WB | Sequence | A0203 |
| 21 | KLSQRGYEWDA | 0.476 | 291 | WB | Sequence | A0203 |
| 84 | ALSPVPPVVHL | 0.633 | 53 | WB | Sequence | A0204 |
| 221 | SLALVGACITL | 0.593 | 82 | WB | Sequence | A0204 |
| 123 | FTARGRFATVV | 0.587 | 87 | WB | Sequence | A0204 |
| 78 | GAAAGPALSPV | 0.495 | 235 | WB | Sequence | A0204 |
| 21 | KLSQRGYEWDA | 0.488 | 255 | WB | Sequence | A0204 |
| 179 | YLNRHLHTWIQ | 0.461 | 340 | WB | Sequence | A0204 |
| 145 | RIVAFFEFGGV | 0.868 | 4 | SB | Sequence | A0206 |
| 188 | IQDNGGWDAFV | 0.822 | 6 | SB | Sequence | A0206 |
| 123 | FTARGRFATVV | 0.729 | 18 | SB | Sequence | A0206 |
| 131 | TVVEELFRDGV | 0.725 | 19 | SB | Sequence | A0206 |
| 223 | ALVGACITLGA | 0.670 | 35 | SB | Sequence | A0206 |
| 50 | SQPGHTPHPAA | 0.659 | 40 | SB | Sequence | A0206 |
| 71 | LQTPAAPGAAA | 0.657 | 40 | SB | Sequence | A0206 |
| 78 | GAAAGPALSPV | 0.598 | 77 | WB | Sequence | A0206 |
| 217 | KTLLSLALVGA | 0.537 | 149 | WB | Sequence | A0206 |
| 84 | ALSPVPPVVHL | 0.533 | 157 | WB | Sequence | A0206 |
| 204 | SMRPLFDFSWL | 0.494 | 239 | WB | Sequence | A0206 |
| 215 | SLKTLLSLALV | 0.477 | 286 | WB | Sequence | A0206 |
| 213 | WLSLKTLLSLA | 0.475 | 293 | WB | Sequence | A0206 |
| 27 | YEWDAGDVGAA | 0.474 | 295 | WB | Sequence | A0206 |
| 21 | KLSQRGYEWDA | 0.453 | 373 | WB | Sequence | A0206 |
| 84 | ALSPVPPVVHL | 0.906 | 2 | SB | Sequence | A0211 |
| 215 | SLKTLLSLALV | 0.896 | 3 | SB | Sequence | A0211 |
| 221 | SLALVGACITL | 0.892 | 3 | SB | Sequence | A0211 |
| 179 | YLNRHLHTWIQ | 0.853 | 4 | SB | Sequence | A0211 |
| 164 | EMSPLVDNIAL | 0.832 | 6 | SB | Sequence | A0211 |
| 204 | SMRPLFDFSWL | 0.813 | 7 | SB | Sequence | A0211 |
| 223 | ALVGACITLGA | 0.803 | 8 | SB | Sequence | A0211 |
| 123 | FTARGRFATVV | 0.782 | 10 | SB | Sequence | A0211 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 188 | IQDNGGWDAFV | 0.746 | 15 | SB | Sequence | A0211 |
| 148 | AFFEFGGVMCV | 0.730 | 18 | SB | Sequence | A0211 |
| 207 | PLFDFSWLSLK | 0.720 | 20 | SB | Sequence | A0211 |
| 131 | TVVEELFRDGV | 0.717 | 21 | SB | Sequence | A0211 |
| 167 | PLVDNIALWMT | 0.706 | 24 | SB | Sequence | A0211 |
| 21 | KLSQRGYEWDA | 0.702 | 25 | SB | Sequence | A0211 |
| 213 | WLSLKTLLSLA | 0.655 | 41 | SB | Sequence | A0211 |
| 145 | RIVAFFEFGGV | 0.634 | 52 | WB | Sequence | A0211 |
| 199 | ELYGPSMRPLF | 0.626 | 56 | WB | Sequence | A0211 |
| 219 | LLSLALVGACI | 0.581 | 92 | WB | Sequence | A0211 |
| 78 | GAAAGPALSPV | 0.533 | 156 | WB | Sequence | A0211 |
| 137 | FRDGVNWGRIV | 0.516 | 187 | WB | Sequence | A0211 |
| 218 | TLLSLALVGAC | 0.500 | 223 | WB | Sequence | A0211 |
| 119 | HLTPFTARGRF | 0.462 | 335 | WB | Sequence | A0211 |
| 175 | WMTEYLNRHLH | 0.458 | 352 | WB | Sequence | A0211 |
| 84 | ALSPVPPVVHL | 0.817 | 7 | SB | Sequence | A0212 |
| 179 | YLNRHLHTWIQ | 0.794 | 9 | SB | Sequence | A0212 |
| 123 | FTARGRFATVV | 0.784 | 10 | SB | Sequence | A0212 |
| 204 | SMRPLFDFSWL | 0.781 | 10 | SB | Sequence | A0212 |
| 215 | SLKTLLSLALV | 0.719 | 20 | SB | Sequence | A0212 |
| 221 | SLALVGACITL | 0.719 | 20 | SB | Sequence | A0212 |
| 164 | EMSPLVDNIAL | 0.714 | 22 | SB | Sequence | A0212 |
| 21 | KLSQRGYEWDA | 0.616 | 63 | WB | Sequence | A0212 |
| 223 | ALVGACITLGA | 0.604 | 72 | WB | Sequence | A0212 |
| 131 | TVVEELFRDGV | 0.602 | 74 | WB | Sequence | A0212 |
| 188 | IQDNGGWDAFV | 0.569 | 106 | WB | Sequence | A0212 |
| 148 | AFFEFGGVMCV | 0.548 | 133 | WB | Sequence | A0212 |
| 145 | RIVAFFEFGGV | 0.511 | 198 | WB | Sequence | A0212 |
| 219 | LLSLALVGACI | 0.504 | 213 | WB | Sequence | A0212 |
| 167 | PLVDNIALWMT | 0.483 | 269 | WB | Sequence | A0212 |
| 207 | PLFDFSWLSLK | 0.472 | 301 | WB | Sequence | A0212 |
| 137 | FRDGVNWGRIV | 0.431 | 473 | WB | Sequence | A0212 |
| 84 | ALSPVPPVVHL | 0.878 | 3 | SB | Sequence | A0216 |
| 221 | SLALVGACITL | 0.855 | 4 | SB | Sequence | A0216 |
| 215 | SLKTLLSLALV | 0.806 | 8 | SB | Sequence | A0216 |
| 204 | SMRPLFDFSWL | 0.753 | 14 | SB | Sequence | A0216 |
| 123 | FTARGRFATVV | 0.739 | 16 | SB | Sequence | A0216 |
| 223 | ALVGACITLGA | 0.697 | 26 | SB | Sequence | A0216 |
| 188 | IQDNGGWDAFV | 0.637 | 50 | WB | Sequence | A0216 |
| 164 | EMSPLVDNIAL | 0.625 | 57 | WB | Sequence | A0216 |
| 179 | YLNRHLHTWIQ | 0.613 | 65 | WB | Sequence | A0216 |
| 131 | TVVEELFRDGV | 0.586 | 88 | WB | Sequence | A0216 |
| 78 | GAAAGPALSPV | 0.571 | 103 | WB | Sequence | A0216 |
| 148 | AFFEFGGVMCV | 0.563 | 112 | WB | Sequence | A0216 |
| 167 | PLVDNIALWMT | 0.535 | 153 | WB | Sequence | A0216 |
| 145 | RIVAFFEFGGV | 0.503 | 216 | WB | Sequence | A0216 |
| 151 | EFGGVMCVESV | 0.502 | 217 | WB | Sequence | A0216 |
| 213 | WLSLKTLLSLA | 0.493 | 241 | WB | Sequence | A0216 |
| 21 | KLSQRGYEWDA | 0.490 | 248 | WB | Sequence | A0216 |
| 219 | LLSLALVGACI | 0.478 | 285 | WB | Sequence | A0216 |
| 207 | PLFDFSWLSLK | 0.436 | 445 | WB | Sequence | A0216 |
| 84 | ALSPVPPVVHL | 0.786 | 10 | SB | Sequence | A0219 |
| 188 | IQDNGGWDAFV | 0.605 | 71 | WB | Sequence | A0219 |
| 123 | FTARGRFATVV | 0.594 | 81 | WB | Sequence | A0219 |
| 164 | EMSPLVDNIAL | 0.584 | 89 | WB | Sequence | A0219 |
| 179 | YLNRHLHTWIQ | 0.574 | 100 | WB | Sequence | A0219 |
| 221 | SLALVGACITL | 0.561 | 115 | WB | Sequence | A0219 |
| 219 | LLSLALVGACI | 0.551 | 128 | WB | Sequence | A0219 |
| 167 | PLVDNIALWMT | 0.537 | 149 | WB | Sequence | A0219 |
| 78 | GAAAGPALSPV | 0.496 | 233 | WB | Sequence | A0219 |
| 215 | SLKTLLSLALV | 0.490 | 248 | WB | Sequence | A0219 |
| 204 | SMRPLFDFSWL | 0.486 | 259 | WB | Sequence | A0219 |
| 223 | ALVGACITLGA | 0.467 | 320 | WB | Sequence | A0219 |
| 207 | PLFDFSWLSLK | 0.604 | 72 | WB | Sequence | A0301 |
| 228 | CITLGAYLGHK | 0.462 | 339 | WB | Sequence | A0301 |
| 207 | PLFDFSWLSLK | 0.626 | 57 | WB | Sequence | A1101 |
| 116 | SQLHLTPFTAR | 0.586 | 88 | WB | Sequence | A1101 |

TABLE C-continued

Prediction of cancer antigen Bcl-2 specific MHC class1, 8-,
9-, 10-, 11-mer peptide binders for 42 MHC class 1 alleles
(see FIG. 11) using the www.cbs.dtu.dk/services/
NetMHC/ database. The MHC class 1 molecules for which
no binders were found are not listed.

| pos | peptide | logscore | affinity (nM) | Bind Level | Protein Name | Allele |
|---|---|---|---|---|---|---|
| 228 | CITLGAYLGHK | 0.580 | 94 | WB | Sequence | A1101 |
| 172 | IALWMTEYLNR | 0.524 | 172 | WB | Sequence | A1101 |
| 6 | TGYDNREIVMK | 0.437 | 439 | WB | Sequence | A1101 |
| 142 | NWGRIVAFFEF | 0.733 | 18 | SB | Sequence | A2301 |
| 178 | EYLNRHLHTWI | 0.592 | 82 | WB | Sequence | A2301 |
| 19 | HYKLSQRGYEW | 0.563 | 112 | WB | Sequence | A2301 |
| 174 | LWMTEYLNRHL | 0.457 | 355 | WB | Sequence | A2301 |
| 212 | SWLSLKTLLSL | 0.439 | 431 | WB | Sequence | A2301 |
| 178 | EYLNRHLHTWI | 0.794 | 9 | SB | Sequence | A2402 |
| 142 | NWGRIVAFFEF | 0.744 | 15 | SB | Sequence | A2402 |
| 212 | SWLSLKTLLSL | 0.514 | 192 | WB | Sequence | A2402 |
| 174 | LWMTEYLNRHL | 0.497 | 230 | WB | Sequence | A2402 |
| 178 | EYLNRHLHTWI | 0.599 | 76 | WB | Sequence | A2403 |
| 19 | HYKLSQRGYEW | 0.573 | 101 | WB | Sequence | A2403 |
| 142 | NWGRIVAFFEF | 0.486 | 260 | WB | Sequence | A2403 |
| 17 | YIHYKLSQRGY | 0.524 | 172 | WB | Sequence | A2601 |
| 113 | EMSSQLHLTPF | 0.866 | 4 | SB | Sequence | A2602 |
| 17 | YIHYKLSQRGY | 0.817 | 7 | SB | Sequence | A2602 |
| 12 | EIVMKYIHYKL | 0.760 | 13 | SB | Sequence | A2602 |
| 187 | WIQDNGGWDAF | 0.631 | 54 | WB | Sequence | A2602 |
| 199 | ELYGPSMRPLF | 0.568 | 106 | WB | Sequence | A2602 |
| 224 | LVGACITLGAY | 0.545 | 137 | WB | Sequence | A2602 |
| 139 | DGVNWGRIVAF | 0.462 | 336 | WB | Sequence | A2602 |
| 207 | PLFDFSWLSLK | 0.456 | 359 | WB | Sequence | A3001 |
| 11 | REIVMKYIHYK | 0.439 | 434 | WB | Sequence | A3001 |
| 113 | EMSSQLHLTPF | 0.533 | 156 | WB | Sequence | A3002 |
| 128 | RFATVVEELFR | 0.765 | 12 | SB | Sequence | A3101 |
| 116 | SQLHLTPFTAR | 0.741 | 16 | SB | Sequence | A3101 |
| 196 | AFVELYGPSMR | 0.640 | 48 | SB | Sequence | A3101 |
| 172 | IALWMTEYLNR | 0.614 | 64 | WB | Sequence | A3101 |
| 11 | REIVMKYIHYK | 0.571 | 104 | WB | Sequence | A3101 |
| 15 | MKYIHYKLSQR | 0.500 | 224 | WB | Sequence | A3101 |
| 98 | QAGDDFSRRYR | 0.483 | 269 | WB | Sequence | A3101 |
| 135 | ELFRDGVNWGR | 0.634 | 52 | WB | Sequence | A3301 |
| 128 | RFATVVEELFR | 0.492 | 244 | WB | Sequence | A3301 |
| 172 | IALWMTEYLNR | 0.481 | 273 | WB | Sequence | A3301 |
| 196 | AFVELYGPSMR | 0.467 | 318 | WB | Sequence | A3301 |
| 135 | ELFRDGVNWGR | 0.739 | 16 | SB | Sequence | A6801 |
| 228 | CITLGAYLGHK | 0.618 | 62 | WB | Sequence | A6801 |
| 172 | IALWMTEYLNR | 0.593 | 81 | WB | Sequence | A6801 |
| 57 | HPAASRDPVAR | 0.579 | 95 | WB | Sequence | A6801 |
| 15 | MKYIHYKLSQR | 0.540 | 145 | WB | Sequence | A6801 |
| 98 | QAGDDFSRRYR | 0.525 | 170 | WB | Sequence | A6801 |
| 6 | TGYDNREIVMK | 0.515 | 190 | WB | Sequence | A6801 |
| 128 | RFATVVEELFR | 0.507 | 207 | WB | Sequence | A6801 |
| 95 | TLRQAGDDFSR | 0.490 | 249 | WB | Sequence | A6801 |
| 207 | PLFDFSWLSLK | 0.470 | 308 | WB | Sequence | A6801 |
| 123 | FTARGRFATVV | 0.809 | 7 | SB | Sequence | A6802 |
| 131 | TVVEELFRDGV | 0.784 | 10 | SB | Sequence | A6802 |
| 145 | RIVAFFEFGGV | 0.727 | 19 | SB | Sequence | A6802 |
| 12 | EIVMKYIHYKL | 0.592 | 83 | WB | Sequence | A6802 |
| 78 | GAAAGPALSPV | 0.560 | 116 | WB | Sequence | A6802 |
| 164 | EMSPLVDNIAL | 0.520 | 179 | WB | Sequence | A6802 |
| 159 | ESVNREMSPLV | 0.488 | 254 | WB | Sequence | A6802 |
| 225 | VGACITLGAYL | 0.459 | 349 | WB | Sequence | A6802 |
| 55 | TPHPAASRDPV | 0.435 | 453 | WB | Sequence | A6802 |
| 123 | FTARGRFATVV | 0.710 | 23 | SB | Sequence | A6901 |
| 164 | EMSPLVDNIAL | 0.541 | 144 | WB | Sequence | A6901 |
| 131 | TVVEELFRDGV | 0.510 | 201 | WB | Sequence | A6901 |
| 159 | ESVNREMSPLV | 0.485 | 263 | WB | Sequence | A6901 |

TABLE C-continued

Prediction of cancer antigen Bcl-2 specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 206 | RPLFDFSWLSL | 0.747 | 15 | SB | Sequence | B0702 |
| 86 | SPVPPVVHLTL | 0.717 | 21 | SB | Sequence | B0702 |
| 55 | TPHPAASRDPV | 0.567 | 108 | WB | Sequence | B0702 |
| 82 | GPALSPVPPVV | 0.559 | 118 | WB | Sequence | B0702 |
| 166 | SPLVDNIALWM | 0.469 | 312 | WB | Sequence | B0702 |
| 126 | RGRFATVVEEL | 0.463 | 332 | WB | Sequence | B0702 |
| 121 | TPFTARGRFAT | 0.443 | 416 | WB | Sequence | B0702 |
| 97 | RQAGDDFSRRY | 0.600 | 75 | WB | Sequence | B1501 |
| 187 | WIQDNGGWDAF | 0.499 | 226 | WB | Sequence | B1501 |
| 224 | LVGACITLGAY | 0.491 | 245 | WB | Sequence | B1501 |
| 17 | YIHYKLSQRGY | 0.476 | 290 | WB | Sequence | B1501 |
| 113 | EMSSQLHLTPF | 0.433 | 461 | WB | Sequence | B1501 |
| 140 | GVNWGRIVAFF | 0.433 | 463 | WB | Sequence | B1501 |
| 177 | TEYLNRHLHTW | 0.585 | 89 | WB | Sequence | B1801 |
| 198 | VELYGPSMRPL | 0.558 | 119 | WB | Sequence | B1801 |
| 158 | VESVNREMSPL | 0.514 | 191 | WB | Sequence | B1801 |
| 133 | VEELFRDGVNW | 0.459 | 348 | WB | Sequence | B1801 |
| 127 | GRFATVVEELF | 0.512 | 196 | WB | Sequence | B2705 |
| 108 | RRDFAEMSSQL | 0.481 | 273 | WB | Sequence | B2705 |
| 97 | RQAGDDFSRRY | 0.445 | 405 | WB | Sequence | B2705 |
| 166 | SPLVDNIALWM | 0.573 | 101 | WB | Sequence | B3501 |
| 187 | WIQDNGGWDAF | 0.544 | 139 | WB | Sequence | B3501 |
| 195 | DAFVELYGPSM | 0.543 | 140 | WB | Sequence | B3501 |
| 113 | EMSSQLHLTPF | 0.543 | 140 | WB | Sequence | B3501 |
| 121 | TPFTARGRFAT | 0.503 | 217 | WB | Sequence | B3501 |
| 224 | LVGACITLGAY | 0.502 | 218 | WB | Sequence | B3501 |
| 146 | IVAFFEFGGVM | 0.500 | 222 | WB | Sequence | B3501 |
| 86 | SPVPPVVHLTL | 0.443 | 416 | WB | Sequence | B3501 |
| 139 | DGVNWGRIVAF | 0.442 | 419 | WB | Sequence | B3501 |
| 61 | SRDPVARTSPL | 0.500 | 223 | WB | Sequence | B3901 |
| 198 | VELYGPSMRPL | 0.547 | 134 | WB | Sequence | B4001 |
| 158 | VESVNREMSPL | 0.471 | 306 | WB | Sequence | B4001 |
| 177 | TEYLNRHLHTW | 0.520 | 180 | WB | Sequence | B4402 |
| 112 | AEMSSQLHLTP | 0.529 | 163 | WB | Sequence | B4501 |
| 37 | APPGAAPAPGI | 0.507 | 207 | WB | Sequence | B5101 |
| 82 | GPALSPVPPVV | 0.465 | 326 | WB | Sequence | B5101 |
| 86 | SPVPPVVHLTL | 0.433 | 461 | WB | Sequence | B5101 |
| 166 | SPLVDNIALWM | 0.453 | 373 | WB | Sequence | B5301 |
| 206 | RPLFDFSWLSL | 0.436 | 448 | WB | Sequence | B5301 |
| 121 | TPFTARGRFAT | 0.638 | 50 | WB | Sequence | B5401 |
| 69 | SPLQTPAAPGA | 0.557 | 121 | WB | Sequence | B5401 |
| 89 | PPVVHLTLRQA | 0.501 | 220 | WB | Sequence | B5401 |
| 55 | TPHPAASRDPV | 0.428 | 489 | WB | Sequence | B5401 |
| 165 | MSPLVDNIALW | 0.462 | 335 | WB | Sequence | B5701 |
| 203 | PSMRPLFDFSW | 0.635 | 51 | WB | Sequence | B5801 |

SEQ ID NOS: 44893-45800

Preferred fragments of BclX(L) capable of interacting with one or more MHC class 2 molecules are listed in table D.

TABLE D

Prediction of cancer antigen BclX(L) specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0101 | 212 RWFLTGMTVAGV-VLL | LTGMTVAGV | 0.8028 | 8 | SB | BclX(L) |
| DRB1_0101 | 209 RFNRWFLTGMT-VAGV | FLTGMTVAG | 0.7932 | 9 | SB | BclX(L) |
| DRB1_0101 | 210 FNRWFLTGMT-VAGVV | LTGMTVAGV | 0.7940 | 9 | SB | BclX(L) |
| DRB1_0101 | 211 NRWFLTGMT-VAGVVL | LTGMTVAGV | 0.7970 | 9 | SB | BclX(L) |
| DRB1_0101 | 213 WFLTGMTVAGVV-LLG | LTGMTVAGV | 0.7753 | 11 | SB | BclX(L) |
| DRB1_0101 | 76 DAREVIP-MAAVKQAL | VIPMAAVKQ | 0.7755 | 11 | SB | BclX(L) |
| DRB1_0101 | 77 AREVIP-MAAVKQALR | VIPMAAVKQ | 0.7788 | 11 | SB | BclX(L) |
| DRB1_0101 | 78 REVIP-MAAVKQALRE | VIPMAAVKQ | 0.7772 | 11 | SB | BclX(L) |
| DRB1_0101 | 75 LDAREVIP-MAAVKQA | VIPMAAVKQ | 0.7730 | 12 | SB | BclX(L) |
| DRB1_0101 | 157 KEMQVLVSRI-AAWMA | MQVLVSRIA | 0.7458 | 16 | SB | BclX(L) |
| DRB1_0101 | 108 LTSQLHITPG-TAYQS | LHITPGTAY | 0.7338 | 18 | SB | BclX(L) |
| DRB1_0101 | 109 TSQLHITPGTAY-QSF | ITPGTAYQS | 0.7313 | 18 | SB | BclX(L) |
| DRB1_0101 | 74 SLDAREVIP-MAAVKQ | AREVIPMAA | 0.7348 | 18 | SB | BclX(L) |
| DRB1_0101 | 110 SQLHITPGTAY-QSFE | ITPGTAYQS | 0.7287 | 19 | SB | BclX(L) |
| DRB1_0101 | 214 FLTGMTVAGVV-LLGS | LTGMTVAGV | 0.7282 | 19 | SB | BclX(L) |
| DRB1_0101 | 156 DKEMQVLVSRI-AAWM | MQVLVSRIA | 0.7226 | 20 | SB | BclX(L) |
| DRB1_0101 | 111 QLHITPGTAYQS-FEQ | ITPGTAYQS | 0.7202 | 21 | SB | BclX(L) |
| DRB1_0101 | 112 LHITPGTAYQS-FEQV | ITPGTAYQS | 0.7189 | 21 | SB | BclX(L) |
| DRB1_0101 | 154 SVDKEMQVLVS-RIAA | MQVLVSRIA | 0.7165 | 21 | SB | BclX(L) |
| DRB1_0101 | 79 EVIPMAAVKQAL-REA | IPMAAVKQA | 0.7208 | 21 | SB | BclX(L) |
| DRB1_0101 | 153 ESVDKEMQVLVS-RIA | VDKEMQVLV | 0.7145 | 22 | SB | BclX(L) |
| DRB1_0101 | 155 VDKEMQVLVSRI-AAW | MQVLVSRIA | 0.7141 | 22 | SB | BclX(L) |
| DRB1_0101 | 215 LTGMTVAGVV-LLGSL | LTGMTVAGV | 0.7090 | 23 | SB | BclX(L) |
| DRB1_0101 | 208 ERFNRWFLTGMT-VAG | FNRWFLTGM | 0.7077 | 24 | SB | BclX(L) |
| DRB1_0101 | 46 ETPSAING-NPSWHLA | INGNPSWHL | 0.7051 | 24 | SB | BclX(L) |
| DRB1_0101 | 47 TPSAING-NPSWHLAD | INGNPSWHL | 0.7051 | 24 | SB | BclX(L) |
| DRB1_0101 | 48 PSAING-NPSWHLADS | INGNPSWHL | 0.7076 | 24 | SB | BclX(L) |
| DRB1_0101 | 49 SAING-NPSWHLADSP | INGNPSWHL | 0.7072 | 24 | SB | BclX(L) |
| DRB1_0101 | 45 METPSAING-NPSWHL | PSAINGNPS | 0.7034 | 25 | SB | BclX(L) |
| DRB1_0101 | 158 EMQVLVSRIAAW-MAT | MQVLVSRIA | 0.6845 | 30 | SB | BclX(L) |
| DRB1_0101 | 80 VIPMAAVKQAL-REAG | VIPMAAVKQ | 0.6856 | 30 | SB | BclX(L) |
| DRB1_0101 | 159 MQVLVSRIAAW-MATY | MQVLVSRIA | 0.6834 | 31 | SB | BclX(L) |
| DRB1_0101 | 161 VLVSRIAAW-MATYLN | IAAWMATYL | 0.6838 | 31 | SB | BclX(L) |
| DRB1_0101 | 217 GMTVAGVVLLG-SLFS | MTVAGVVLL | 0.6800 | 32 | SB | BclX(L) |
| DRB1_0101 | 218 MTVAGVVLLG-SLFSR | VVLLGSLFS | 0.6800 | 32 | SB | BclX(L) |
| DRB1_0101 | 51 INGNPSWHLAD-SPAV | INGNPSWHL | 0.6778 | 33 | SB | BclX(L) |
| DRB1_0101 | 192 VELYGNNAAAES-RKG | YGNNAAAES | 0.6693 | 36 | SB | BclX(L) |
| DRB1_0101 | 219 TVAGVVLLGSLF-SRK | VVLLGSLFS | 0.6677 | 36 | SB | BclX(L) |
| DRB1_0101 | 160 QVLVSRIAAW-MATYL | VSRIAAWMA | 0.6652 | 37 | SB | BclX(L) |

TABLE D-continued

Prediction of cancer antigen BclX(L) specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0101 | 191 FVELYGN-NAAAESRK | YGNNAAAES | 0.6658 | 37 | SB | BclX(L) |
| DRB1_0101 | 193 ELYGNNAAAES-RKGQ | YGNNAAAES | 0.6661 | 37 | SB | BclX(L) |
| DRB1_0101 | 99 LRYRRAF-SDLTSQLH | YRRAFSDLT | 0.6657 | 37 | SB | BclX(L) |
| DRB1_0101 | 162 LVSRIAAW-MATYLND | IAAWMATYL | 0.6627 | 38 | SB | BclX(L) |
| DRB1_0101 | 190 TFVELYGN-NAAAESR | YGNNAAAES | 0.6628 | 38 | SB | BclX(L) |
| DRB1_0101 | 189 DTFVELYGN-NAAAES | FVELYGNNA | 0.6613 | 39 | SB | BclX(L) |
| DRB1_0101 | 54 NPSWHLAD-SPAVNGA | WHLADSPAV | 0.6617 | 39 | SB | BclX(L) |
| DRB1_0101 | 55 PSWHLADSPAVN-GAT | WHLADSPAV | 0.6611 | 39 | SB | BclX(L) |
| DRB1_0101 | 216 TGMTVAGVVLLG-SLF | MTVAGVVLL | 0.6543 | 42 | SB | BclX(L) |
| DRB1_0101 | 163 VSRIAAW-MATYLNDH | IAAWMATYL | 0.6531 | 43 | SB | BclX(L) |
| DRB1_0101 | 53 GNPSWHLAD-SPAVNG | WHLADSPAV | 0.6532 | 43 | SB | BclX(L) |
| DRB1_0101 | 59 LADSPAVNGAT-GHSS | LADSPAVNG | 0.6361 | 51 | WB | BclX(L) |
| DRB1_0101 | 98 ELRYRRAF-SDLTSQL | YRRAFSDLT | 0.6357 | 51 | WB | BclX(L) |
| DRB1_0101 | 164 SRIAAW-MATYLNDHL | IAAWMATYL | 0.6357 | 52 | WB | BclX(L) |
| DRB1_0101 | 97 FELRYRRAF-SDLTSQ | YRRAFSDLT | 0.6337 | 53 | WB | BclX(L) |
| DRB1_0101 | 96 EFELRYRRAF-SDLTS | YRRAFSDLT | 0.6321 | 54 | WB | BclX(L) |
| DRB1_0101 | 95 DEFELRYRRAF-SDLT | LRYRRAFSD | 0.6294 | 55 | WB | BclX(L) |
| DRB1_0101 | 140 IVAFFSFGGAL-CVES | FSFGGALCV | 0.6203 | 61 | WB | BclX(L) |
| DRB1_0101 | 56 SWHLADSPAVN-GATG | LADSPAVNG | 0.6196 | 61 | WB | BclX(L) |
| DRB1_0101 | 61 DSPAVNGAT-GHSSSL | VNGATGHSS | 0.6197 | 61 | WB | BclX(L) |
| DRB1_0101 | 62 SPAVNGAT-GHSSSLD | VNGATGHSS | 0.6205 | 61 | WB | BclX(L) |
| DRB1_0101 | 141 VAFFSFGGAL-CVESV | FSFGGALCV | 0.6191 | 62 | WB | BclX(L) |
| DRB1_0101 | 60 ADSPAVNGAT-GHSSS | VNGATGHSS | 0.6174 | 63 | WB | BclX(L) |
| DRB1_0101 | 142 AFFSFGGAL-CVESVD | FSFGGALCV | 0.6153 | 64 | WB | BclX(L) |
| DRB1_0101 | 57 WHLADSPAVN-GATGH | LADSPAVNG | 0.6162 | 64 | WB | BclX(L) |
| DRB1_0101 | 113 HITPGTAYQS-FEQVV | ITPGTAYQS | 0.6121 | 66 | WB | BclX(L) |
| DRB1_0101 | 114 ITPGTAYQS-FEQVVN | ITPGTAYQS | 0.6131 | 66 | WB | BclX(L) |
| DRB1_0101 | 50 AINGNPSWHLAD-SPA | INGNPSWHL | 0.6133 | 66 | WB | BclX(L) |
| DRB1_0101 | 63 PAVNGAT-GHSSSLDA | VNGATGHSS | 0.6078 | 70 | WB | BclX(L) |
| DRB1_0101 | 100 RYRRAF-SDLTSQLHI | YRRAFSDLT | 0.6026 | 74 | WB | BclX(L) |
| DRB1_0101 | 101 YRRAFSDLTSQL-HIT | YRRAFSDLT | 0.6021 | 74 | WB | BclX(L) |
| DRB1_0101 | 52 NGNPSWHLAD-SPAVN | WHLADSPAV | 0.6004 | 75 | WB | BclX(L) |
| DRB1_0101 | 138 GRIVAFFSFG-GALCV | IVAFFSFGG | 0.5864 | 88 | WB | BclX(L) |
| DRB1_0101 | 194 LYGNNAAAESRK-GQE | YGNNAAAES | 0.5808 | 93 | WB | BclX(L) |
| DRB1_0101 | 165 RIAAWMATYLND-HLE | AAWMATYLN | 0.5762 | 98 | WB | BclX(L) |
| DRB1_0101 | 195 YGNNAAAESRK-GQER | YGNNAAAES | 0.5731 | 101 | WB | BclX(L) |
| DRB1_0101 | 139 RIVAFFSFGGAL-CVE | FSFGGALCV | 0.5729 | 102 | WB | BclX(L) |
| DRB1_0101 | 131 FRDGVN-WGRIVAFFS | VNWGRIVAF | 0.5627 | 114 | WB | BclX(L) |
| DRB1_0101 | 143 FFSFGGALCVES-VDK | FSFGGALCV | 0.5613 | 115 | WB | BclX(L) |

TABLE D-continued

Prediction of cancer antigen BclX(L) specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0101 | 144 FSFGGALCVES-VDKE | FSFGGALCV | 0.5583 | 119 | WB | BclX(L) |
| DRB1_0101 | 132 RDGVN-WGRIVAFFSF | VNWGRIVAF | 0.5561 | 122 | WB | BclX(L) |
| DRB1_0101 | 133 DGVN-WGRIVAFFSFG | VNWGRIVAF | 0.5558 | 122 | WB | BclX(L) |
| DRB1_0101 | 81 IPMAAVKQAL-REAGD | IPMAAVKQA | 0.5527 | 126 | WB | BclX(L) |
| DRB1_0101 | 102 RRAFSDLTSQL-HITP | FSDLTSQLH | 0.5334 | 156 | WB | BclX(L) |
| DRB1_0101 | 103 RAFSDLTSQL-HITPG | FSDLTSQLH | 0.5314 | 159 | WB | BclX(L) |
| DRB1_0101 | 58 HLADSPAVNGAT-GHS | LADSPAVNG | 0.5293 | 163 | WB | BclX(L) |
| DRB1_0101 | 134 GVN-WGRIVAFFSFGG | VNWGRIVAF | 0.5282 | 165 | WB | BclX(L) |
| DRB1_0101 | 166 IAAWMATYLNDH-LEP | IAAWMATYL | 0.5271 | 167 | WB | BclX(L) |
| DRB1_0101 | 64 AVNGAT-GHSSSLDAR | VNGATGHSS | 0.5266 | 168 | WB | BclX(L) |
| DRB1_0101 | 135 VNWGRIVAFFSF-GGA | VNWGRIVAF | 0.5248 | 171 | WB | BclX(L) |
| DRB1_0101 | 7 ELVVDFL-SYKLSQKG | VVDFLSYKL | 0.5243 | 172 | WB | BclX(L) |
| DRB1_0101 | 129 ELFRDGVN-WGRIVAF | FRDGVNWGR | 0.5154 | 189 | WB | BclX(L) |
| DRB1_0101 | 65 VNGAT-GHSSSLDARE | VNGATGHSS | 0.5156 | 189 | WB | BclX(L) |
| DRB1_0101 | 130 LFRDGVN-WGRIVAFF | VNWGRIVAF | 0.5023 | 218 | WB | BclX(L) |
| DRB1_0101 | 8 LVVDFL-SYKLSQKGY | LSYKLSQKG | 0.4921 | 244 | WB | BclX(L) |
| DRB1_0101 | 9 VVDFLSYKLSQK-GYS | LSYKLSQKG | 0.4892 | 251 | WB | BclX(L) |
| DRB1_0101 | 207 QERFNRWFLTG-MTVA | FNRWFLTGM | 0.4845 | 264 | WB | BclX(L) |
| DRB1_0101 | 42 ESEMETPSAING-NPS | METPSAING | 0.4626 | 335 | WB | BclX(L) |
| DRB1_0101 | 40 GTESEMETP-SAINGN | METPSAING | 0.4622 | 337 | WB | BclX(L) |
| DRB1_0101 | 107 DLTSQLHITPG-TAYQ | LHITPGTAY | 0.4593 | 347 | WB | BclX(L) |
| DRB1_0101 | 39 EGTESEMETPSA-ING | ESEMETPSA | 0.4591 | 348 | WB | BclX(L) |
| DRB1_0101 | 43 SEMETPSAING-NPSW | METPSAING | 0.4590 | 348 | WB | BclX(L) |
| DRB1_0101 | 106 SDLTSQLHITPG-TAY | SQLHITPGT | 0.4569 | 356 | WB | BclX(L) |
| DRB1_0101 | 10 VDFLSYKLSQK-GYSW | LSYKLSQKG | 0.4565 | 358 | WB | BclX(L) |
| DRB1_0101 | 41 TESEMETP-SAINGNP | METPSAING | 0.4564 | 358 | WB | BclX(L) |
| DRB1_0101 | 167 AAWMATYLND-HLEPW | AAWMATYLN | 0.4556 | 361 | WB | BclX(L) |
| DRB1_0101 | 11 DFLSYKLSQK-GYSWS | LSYKLSQKG | 0.4515 | 378 | WB | BclX(L) |
| DRB1_0101 | 104 AFSDLTSQLHIT-PGT | FSDLTSQLH | 0.4453 | 404 | WB | BclX(L) |
| DRB1_0101 | 105 FSDLTSQLHIT-PGTA | FSDLTSQLH | 0.4451 | 405 | WB | BclX(L) |
| DRB1_0101 | 137 WGRIVAFFSFG-GALC | IVAFFSFGG | 0.4311 | 471 | WB | BclX(L) |
| DRB1_0101 | 206 GQERFNRWFLTG-MTV | FNRWFLTGM | 0.4277 | 489 | WB | BclX(L) |
| DRB1_0401 | 99 LRYRRAF-SDLTSQLH | YRRAFSDLT | 0.5618 | 115 | WB | BclX(L) |
| DRB1_0401 | 97 FELRYRRAF-SDLTSQ | YRRAFSDLT | 0.5300 | 162 | WB | BclX(L) |
| DRB1_0401 | 96 EFELRYRRAF-SDLTS | YRRAFSDLT | 0.5284 | 164 | WB | BclX(L) |
| DRB1_0401 | 95 DEFELRYRRAF-SDLT | DEFELRYRR | 0.5275 | 166 | WB | BclX(L) |
| DRB1_0401 | 98 ELRYRRAF-SDLTSQL | YRRAFSDLT | 0.5259 | 169 | WB | BclX(L) |
| DRB1_0401 | 185 NGGWDTFVELYG-NNA | WDTFVELYG | 0.5189 | 182 | WB | BclX(L) |

TABLE D-continued

Prediction of cancer antigen BclX(L) specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0401 | 186 GGWDTFVELYGN-NAA | FVELYGNNA | 0.5180 | 184 | WB | BclX(L) |
| DRB1_0401 | 188 WDTFVELYGN-NAAAE | FVELYGNNA | 0.5159 | 188 | WB | BclX(L) |
| DRB1_0401 | 187 GWDTFVELYGN-NAAA | FVELYGNNA | 0.5157 | 189 | WB | BclX(L) |
| DRB1_0401 | 189 DTFVELYGN-NAAAES | FVELYGNNA | 0.5154 | 189 | WB | BclX(L) |
| DRB1_0401 | 100 RYRRAF-SDLTSQLHI | YRRAFSDLT | 0.4844 | 265 | WB | BclX(L) |
| DRB1_0401 | 101 YRRAFSDLTSQL-HIT | YRRAFSDLT | 0.4813 | 274 | WB | BclX(L) |
| DRB1_0401 | 153 ESVDKEMQVLVS-RIA | KEMQVLVSR | 0.4561 | 360 | WB | BclX(L) |
| DRB1_0401 | 155 VDKEMQVLVSRI-AAW | MQVLVSRIA | 0.4519 | 376 | WB | BclX(L) |
| DRB1_0401 | 208 ERFNRWFLTGMT-VAG | WFLTGMTVA | 0.4512 | 379 | WB | BclX(L) |
| DRB1_0401 | 154 SVDKEMQVLVS-RIAA | MQVLVSRIA | 0.4495 | 386 | WB | BclX(L) |
| DRB1_0401 | 209 RFNRWFLTGMT-VAGV | FLTGMTVAG | 0.4467 | 398 | WB | BclX(L) |
| DRB1_0401 | 210 FNRWFLTGMT-VAGVV | FLTGMTVAG | 0.4427 | 416 | WB | BclX(L) |
| DRB1_0401 | 157 KEMQVLVSRI-AAWMA | MQVLVSRIA | 0.4419 | 419 | WB | BclX(L) |
| DRB1_0401 | 156 DKEMQVLVSRI-AAWM | MQVLVSRIA | 0.4413 | 422 | WB | BclX(L) |
| DRB1_0401 | 211 NRWFLTGMT-VAGVVL | FLTGMTVAG | 0.4327 | 463 | WB | BclX(L) |
| DRB1_0404 | 167 AAWMATYLND-HLEPW | WMATYLNDH | 0.5484 | 132 | WB | BclX(L) |
| DRB1_0404 | 164 SRIAAW-MATYLNDHL | WMATYLNDH | 0.5424 | 141 | WB | BclX(L) |
| DRB1_0404 | 165 RIAAWMATYLND-HLE | WMATYLNDH | 0.5417 | 142 | WB | BclX(L) |
| DRB1_0404 | 166 IAAWMATYLNDH-LEP | WMATYLNDH | 0.5330 | 156 | WB | BclX(L) |
| DRB1_0404 | 163 VSRIAAW-MATYLNDH | AAWMATYLN | 0.5217 | 177 | WB | BclX(L) |
| DRB1_0404 | 219 TVAGVVLLGSLF-SRK | VVLLGSLFS | 0.5094 | 202 | WB | BclX(L) |
| DRB1_0404 | 209 RFNRWFLTGMT-VAGV | FLTGMTVAG | 0.4902 | 249 | WB | BclX(L) |
| DRB1_0404 | 210 FNRWFLTGMT-VAGVV | FLTGMTVAG | 0.4853 | 262 | WB | BclX(L) |
| DRB1_0404 | 211 NRWFLTGMT-VAGVVL | FLTGMTVAG | 0.4826 | 270 | WB | BclX(L) |
| DRB1_0404 | 208 ERFNRWFLTGMT-VAG | WFLTGMTVA | 0.4761 | 290 | WB | BclX(L) |
| DRB1_0404 | 168 AWMATYLND-HLEPWI | WMATYLNDH | 0.4694 | 311 | WB | BclX(L) |
| DRB1_0404 | 212 RWFLTGMTVAGV-VLL | FLTGMTVAG | 0.4547 | 365 | WB | BclX(L) |
| DRB1_0404 | 189 DTFVELYGN-NAAAES | FVELYGNNA | 0.4505 | 382 | WB | BclX(L) |
| DRB1_0404 | 187 GWDTFVELYGN-NAAA | FVELYGNNA | 0.4498 | 385 | WB | BclX(L) |
| DRB1_0404 | 169 WMATYLNDHLEP-WIQ | WMATYLNDH | 0.4478 | 393 | WB | BclX(L) |
| DRB1_0404 | 188 WDTFVELYGN-NAAAE | FVELYGNNA | 0.4462 | 400 | WB | BclX(L) |
| DRB1_0404 | 186 GGWDTFVELYGN-NAA | FVELYGNNA | 0.4437 | 411 | WB | BclX(L) |
| DRB1_0404 | 185 NGGWDTFVELYG-NNA | GWDTFVELY | 0.4388 | 434 | WB | BclX(L) |
| DRB1_0405 | 118 TAYQSFEQV-VNELFR | YQSFEQVVN | 0.5794 | 95 | WB | BclX(L) |
| DRB1_0405 | 117 GTAYQSFEQV-VNELF | YQSFEQVVN | 0.5772 | 97 | WB | BclX(L) |
| DRB1_0405 | 115 TPGTAYQSFEQV-VNE | YQSFEQVVN | 0.5541 | 124 | WB | BclX(L) |
| DRB1_0405 | 116 PGTAYQSFEQV-VNEL | YQSFEQVVN | 0.5538 | 125 | WB | BclX(L) |
| DRB1_0405 | 114 ITPGTAYQS-FEQVVN | AYQSFEQVV | 0.5505 | 129 | WB | BclX(L) |

TABLE D-continued

Prediction of cancer antigen BclX(L) specific MHC class 2, 15-mer
peptide binders for 14 MHC class 2 alleles (see FIG. 11) using the
www.cbs.dtu.dk/services/NetMHCII/ database. The MHC class 2
molecules for which no binders were found are not listed.

| Allele | pospeptide | core | 1-log50k(aff) | affinity (nM) | Bind Level | Identity |
|---|---|---|---|---|---|---|
| DRB1_0405 | 163 VSRIAAW-MATYLNDH | AAWMATYLN | 0.5510 | 129 | WB | BclX(L) |
| DRB1_0405 | 162 LVSRIAAW-MATYLND | AAWMATYLN | 0.5473 | 134 | WB | BclX(L) |
| DRB1_0405 | 161 VLVSRIAAW-MATYLN | IAAWMATYL | 0.5442 | 139 | WB | BclX(L) |
| DRB1_0405 | 164 SRIAAW-MATYLNDHL | AAWMATYLN | 0.5402 | 145 | WB | BclX(L) |
| DRB1_0405 | 99 LRYRRAF-SDLTSQLH | YRRAFSDLT | 0.5100 | 201 | WB | BclX(L) |
| DRB1_0405 | 97 FELRYRRAF-SDLTSQ | YRRAFSDLT | 0.5085 | 204 | WB | BclX(L) |
| DRB1_0405 | 96 EFELRYRRAF-SDLTS | YRRAFSDLT | 0.5069 | 208 | WB | BclX(L) |
| DRB1_0405 | 165 RIAAWMATYLND-HLE | AAWMATYLN | 0.5055 | 211 | WB | BclX(L) |
| DRB1_0405 | 119 AYQSFEQVVNEL-FRD | YQSFEQVVN | 0.4974 | 230 | WB | BclX(L) |
| DRB1_0405 | 120 YQSFEQVVNEL-FRDG | YQSFEQVVN | 0.4968 | 231 | WB | BclX(L) |
| DRB1_0405 | 98 ELRYRRAF-SDLTSQL | YRRAFSDLT | 0.4923 | 243 | WB | BclX(L) |
| DRB1_0405 | 18 SQKGYSWSQFSD-VEE | GYSWSQFSD | 0.4575 | 354 | WB | BclX(L) |
| DRB1_0405 | 95 DEFELRYRRAF-SDLT | LRYRRAFSD | 0.4574 | 355 | WB | BclX(L) |
| DRB1_0405 | 19 QKGYSWSQFSD-VEEN | WSQFSDVEE | 0.4562 | 359 | WB | BclX(L) |
| DRB1_0405 | 100 RYRRAF-SDLTSQLHI | YRRAFSDLT | 0.4475 | 395 | WB | BclX(L) |
| DRB1_0405 | 20 KGYSWSQFSD-VEENR | WSQFSDVEE | 0.4430 | 414 | WB | BclX(L) |
| DRB1_0405 | 166 IAAWMATYLNDH-LEP | AAWMATYLN | 0.4423 | 418 | WB | BclX(L) |
| DRB1_0405 | 21 GYSWSQFSD-VEENRT | WSQFSDVEE | 0.4353 | 450 | WB | BclX(L) |
| DRB1_0701 | 157 KEMQVLVSRI-AAWMA | VLVSRIAAW | 0.5228 | 175 | WB | BclX(L) |
| DRB1_0701 | 159 MQVLVSRIAAW-MATY | VLVSRIAAW | 0.5194 | 181 | WB | BclX(L) |
| DRB1_0701 | 158 EMQVLVSRIAAW-MAT | VLVSRIAAW | 0.5191 | 182 | WB | BclX(L) |
| DRB1_0701 | 156 DKEMQVLVSRI-AAWM | VLVSRIAAW | 0.4971 | 231 | WB | BclX(L) |
| DRB1_0701 | 160 QVLVSRIAAW-MATYL | VLVSRIAAW | 0.4833 | 268 | WB | BclX(L) |
| DRB1_0701 | 46 ETPSAING-NPSWHLA | INGNPSWHL | 0.4783 | 283 | WB | BclX(L) |
| DRB1_0701 | 45 METPSAING-NPSWHL | AINGNPSWH | 0.4779 | 284 | WB | BclX(L) |
| DRB1_0701 | 155 VDKEMQVLVSRI-AAW | MQVLVSRIA | 0.4772 | 286 | WB | BclX(L) |
| DRB1_0701 | 47 TPSAING-NPSWHLAD | INGNPSWHL | 0.4774 | 286 | WB | BclX(L) |
| DRB1_0701 | 48 PSAING-NPSWHLADS | INGNPSWHL | 0.4764 | 289 | WB | BclX(L) |
| DRB1_0701 | 161 VLVSRIAAW-MATYLN | VLVSRIAAW | 0.4745 | 295 | WB | BclX(L) |
| DRB1_0701 | 49 SAING-NPSWHLADSP | INGNPSWHL | 0.4718 | 303 | WB | BclX(L) |
| DRB1_0701 | 99 LRYRRAF-SDLTSQLH | YRRAFSDLT | 0.4627 | 335 | WB | BclX(L) |
| DRB1_0701 | 100 RYRRAF-SDLTSQLHI | FSDLTSQLH | 0.4416 | 420 | WB | BclX(L) |
| DRB1_0701 | 101 YRRAFSDLTSQL-HIT | FSDLTSQLH | 0.4344 | 455 | WB | BclX(L) |
| DRB1_0701 | 51 INGNPSWHLAD-SPAV | INGNPSWHL | 0.4291 | 481 | WB | BclX(L) |
| DRB1_0901 | 55 PSWHLADSPAVN-GAT | WHLADSPAV | 0.5482 | 133 | WB | BclX(L) |
| DRB1_0901 | 54 NPSWHLAD-SPAVNGA | WHLADSPAV | 0.5414 | 143 | WB | BclX(L) |
| DRB1_0901 | 53 GNPSWHLAD-SPAVNG | WHLADSPAV | 0.5408 | 144 | WB | BclX(L) |
| DRB1_0901 | 51 INGNPSWHLAD-SPAV | SWHLADSPA | 0.5289 | 164 | WB | BclX(L) |

TABLE D-continued

Prediction of cancer antigen BclX(L) specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0901 | 52 NGNPSWHLADSPAVN | WHLADSPAV | 0.5284 | 164 | WB | BclX(L) |
| DRB1_0901 | 56 SWHLADSPAVNGATG | WHLADSPAV | 0.4678 | 317 | WB | BclX(L) |
| DRB1_0901 | 57 WHLADSPAVNGATGH | WHLADSPAV | 0.4636 | 331 | WB | BclX(L) |
| DRB1_0901 | 212 RWFLTGMTVAGVVLL | FLTGMTVAG | 0.4483 | 391 | WB | BclX(L) |
| DRB1_0901 | 213 WFLTGMTVAGVVLLG | MTVAGVVLL | 0.4445 | 408 | WB | BclX(L) |
| DRB1_0901 | 214 FLTGMTVAGVVLLGS | MTVAGVVLL | 0.4327 | 463 | WB | BclX(L) |
| DRB1_1101 | 157 KEMQVLVSRIAAWMA | MQVLVSRIA | 0.4319 | 467 | WB | BclX(L) |
| DRB1_1101 | 131 FRDGVNWGRIVAFFS | GVNWGRIVA | 0.4310 | 472 | WB | BclX(L) |
| DRB1_1101 | 156 DKEMQVLVSRIAAWM | MQVLVSRIA | 0.4308 | 473 | WB | BclX(L) |
| DRB1_1101 | 155 VDKEMQVLVSRIAAW | MQVLVSRIA | 0.4292 | 481 | WB | BclX(L) |
| DRB1_1101 | 132 RDGVNWGRIVAFFSF | GVNWGRIVA | 0.4283 | 486 | WB | BclX(L) |
| DRB1_1101 | 154 SVDKEMQVLVSRIAA | MQVLVSRIA | 0.4267 | 494 | WB | BclX(L) |
| DRB1_1302 | 218 MTVAGVVLLGSLFSR | VVLLGSLFS | 0.4945 | 237 | WB | BclX(L) |
| DRB1_1302 | 216 TGMTVAGVVLLGSLF | MTVAGVVLL | 0.4855 | 262 | WB | BclX(L) |
| DRB1_1302 | 214 FLTGMTVAGVVLLGS | MTVAGVVLL | 0.4842 | 265 | WB | BclX(L) |
| DRB1_1302 | 217 GMTVAGVVLLGSLFS | MTVAGVVLL | 0.4840 | 266 | WB | BclX(L) |
| DRB1_1302 | 212 RWFLTGMTVAGVVLL | FLTGMTVAG | 0.4832 | 268 | WB | BclX(L) |
| DRB1_1302 | 215 LTGMTVAGVVLLGSL | MTVAGVVLL | 0.4775 | 285 | WB | BclX(L) |
| DRB1_1302 | 213 WFLTGMTVAGVVLLG | MTVAGVVLL | 0.4716 | 304 | WB | BclX(L) |
| DRB1_1302 | 189 DTFVELYGNNAAAES | VELYGNNAA | 0.4688 | 313 | WB | BclX(L) |
| DRB1_1302 | 190 TFVELYGNNAAAESR | YGNNAAAES | 0.4615 | 339 | WB | BclX(L) |
| DRB1_1302 | 191 FVELYGNNAAAESRK | YGNNAAAES | 0.4526 | 373 | WB | BclX(L) |
| DRB1_1302 | 192 VELYGNNAAAESRKG | YGNNAAAES | 0.4415 | 421 | WB | BclX(L) |
| DRB1_1302 | 219 TVAGVVLLGSLFSRK | VVLLGSLFS | 0.4384 | 436 | WB | BclX(L) |
| DRB1_1302 | 193 ELYGNNAAAESRKGQ | YGNNAAAES | 0.4275 | 490 | WB | BclX(L) |
| DRB1_1501 | 219 TVAGVVLLGSLFSRK | VLLGSLFSR | 0.6681 | 36 | SB | BclX(L) |
| DRB1_1501 | 218 MTVAGVVLLGSLFSR | VVLLGSLFS | 0.6441 | 47 | SB | BclX(L) |
| DRB1_1501 | 6 RELVVDFLSYKLSQK | LVVDFLSYK | 0.5208 | 179 | WB | BclX(L) |
| DRB1_1501 | 7 ELVVDFLSYKLSQKG | FLSYKLSQK | 0.5009 | 221 | WB | BclX(L) |
| DRB1_1501 | 157 KEMQVLVSRIAAWMA | MQVLVSRIA | 0.4968 | 231 | WB | BclX(L) |
| DRB1_1501 | 156 DKEMQVLVSRIAAWM | MQVLVSRIA | 0.4965 | 232 | WB | BclX(L) |
| DRB1_1501 | 209 RFNRWFLTGMTVAGV | FNRWFLTGM | 0.4870 | 257 | WB | BclX(L) |
| DRB1_1501 | 164 SRIAAWMATYLNDHL | WMATYLNDH | 0.4849 | 263 | WB | BclX(L) |
| DRB1_1501 | 210 FNRWFLTGMTVAGVV | LTGMTVAGV | 0.4836 | 267 | WB | BclX(L) |
| DRB1_1501 | 8 LVVDFLSYKLSQKGY | FLSYKLSQK | 0.4778 | 284 | WB | BclX(L) |
| DRB1_1501 | 5 NRELVVDFLSYKLSQ | LVVDFLSYK | 0.4777 | 285 | WB | BclX(L) |
| DRB1_1501 | 135 VNWGRIVAFFSFGGA | IVAFFSFGG | 0.4756 | 291 | WB | BclX(L) |

TABLE D-continued

Prediction of cancer antigen BclX(L) specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_1501 | 4 SNRELVVDFL-SYKLS | LVVDFLSYK | 0.4755 | 291 | WB | BclX(L) |
| DRB1_1501 | 159 MQVLVSRIAAW-MATY | LVSRIAAWM | 0.4693 | 312 | WB | BclX(L) |
| DRB1_1501 | 163 VSRIAAW-MATYLNDH | IAAWMATYL | 0.4691 | 312 | WB | BclX(L) |
| DRB1_1501 | 158 EMQVLVSRIAAW-MAT | VLVSRIAAW | 0.4683 | 315 | WB | BclX(L) |
| DRB1_1501 | 165 RIAAWMATYLND-HLE | WMATYLNDH | 0.4685 | 315 | WB | BclX(L) |
| DRB1_1501 | 128 NELFRDGVN-WGRIVA | LFRDGVNWG | 0.4675 | 318 | WB | BclX(L) |
| DRB1_1501 | 125 QVVNELFRDGVN-WGR | LFRDGVNWG | 0.4668 | 320 | WB | BclX(L) |
| DRB1_1501 | 126 VVNELFRDGVN-WGRI | LFRDGVNWG | 0.4668 | 320 | WB | BclX(L) |
| DRB1_1501 | 166 IAAWMATYLNDH-LEP | WMATYLNDH | 0.4649 | 327 | WB | BclX(L) |
| DRB1_1501 | 137 WGRIVAFFSFG-GALC | IVAFFSFGG | 0.4643 | 329 | WB | BclX(L) |
| DRB1_1501 | 136 NWGRIVAFFSFG-GAL | IVAFFSFGG | 0.4638 | 331 | WB | BclX(L) |
| DRB1_1501 | 207 QERFNRWFLTG-MTVA | FNRWFLTGM | 0.4608 | 342 | WB | BclX(L) |
| DRB1_1501 | 208 ERFNRWFLTGMT-VAG | FNRWFLTGM | 0.4602 | 344 | WB | BclX(L) |
| DRB1_1501 | 138 GRIVAFFSFG-GALCV | IVAFFSFGG | 0.4587 | 350 | WB | BclX(L) |
| DRB1_1501 | 9 VVDFLSYKLSQK-GYS | FLSYKLSQK | 0.4584 | 351 | WB | BclX(L) |
| DRB1_1501 | 155 VDKEMQVLVSRI-AAW | MQVLVSRIA | 0.4570 | 356 | WB | BclX(L) |
| DRB1_1501 | 167 AAWMATYLND-HLEPW | WMATYLNDH | 0.4551 | 364 | WB | BclX(L) |
| DRB1_1501 | 3 QSNRELVVDFL-SYKL | LVVDFLSYK | 0.4543 | 367 | WB | BclX(L) |
| DRB1_1501 | 127 VNELFRDGVN-WGRIV | LFRDGVNWG | 0.4431 | 414 | WB | BclX(L) |
| DRB1_1501 | 134 GVN-WGRIVAFFSFGG | VNWGRIVAF | 0.4391 | 432 | WB | BclX(L) |
| DRB1_1501 | 129 ELFRDGVN-WGRIVAF | LFRDGVNWG | 0.4390 | 433 | WB | BclX(L) |
| DRB1_1501 | 217 GMTVAGVVLLG-SLFS | VAGVVLLGS | 0.4377 | 439 | WB | BclX(L) |
| DRB1_1501 | 124 EQVVNEL-FRDGVNWG | VVNELFRDG | 0.4373 | 441 | WB | BclX(L) |
| DRB1_1501 | 139 RIVAFFSFGGAL-CVE | IVAFFSFGG | 0.4300 | 477 | WB | BclX(L) |
| DRB1_1501 | 211 NRWFLTGMT-VAGVVL | LTGMTVAGV | 0.4264 | 496 | WB | BclX(L) |
| DRB4_0101 | 99 LRYRRAF-SDLTSQLH | YRRAFSDLT | 0.4654 | 325 | WB | BclX(L) |
| DRB4_0101 | 100 RYRRAF-SDLTSQLHI | FSDLTSQLH | 0.4328 | 463 | WB | BclX(L) |

SEQ ID NOS: 47134-47645

Preferred fragments of Bcl-2 capable of interacting with one or more MHC class 2 molecules are listed in table E.

TABLE E

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0101 | 211 DFSWLSLK-TLLSLAL | WLSLKTLLS | 0.8912 | 3 | SB | Bcl-2 |
| DRB1_0101 | 212 FSWLSLK-TLLSLALV | LKTLLSLAL | 0.8917 | 3 | SB | Bcl-2 |

TABLE E-continued

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | affinity 1-log50k(aff) | (nM) | Bind Level | Identity |
|---|---|---|---|---|---|---|
| DRB1_0101 | 214 WLSLKTLLSLA-LVGA | LKTLLSLAL | 0.8933 | 3 | SB | Bcl-2 |
| DRB1_0101 | 215 LSLKTLLSLALV-GAC | LKTLLSLAL | 0.8867 | 3 | SB | Bcl-2 |
| DRB1_0101 | 213 SWLSLKTLLSLA-LVG | LKTLLSLAL | 0.8776 | 4 | SB | Bcl-2 |
| DRB1_0101 | 216 SLKTLLSLALV-GACI | LKTLLSLAL | 0.8024 | 8 | SB | Bcl-2 |
| DRB1_0101 | 217 LKTLLSLALV-GACIT | LKTLLSLAL | 0.8038 | 8 | SB | Bcl-2 |
| DRB1_0101 | 68 RTSPLQTPAAP-GAAA | LQTPAAPGA | 0.7623 | 13 | SB | Bcl-2 |
| DRB1_0101 | 69 TSPLQTPAAP-GAAAG | LQTPAAPGA | 0.7650 | 13 | SB | Bcl-2 |
| DRB1_0101 | 70 SPLQTPAAP-GAAAGP | LQTPAAPGA | 0.7631 | 13 | SB | Bcl-2 |
| DRB1_0101 | 66 VARTSPLQT-PAAPGA | TSPLQTPAA | 0.7565 | 14 | SB | Bcl-2 |
| DRB1_0101 | 67 ARTSPLQTPAAP-GAA | LQTPAAPGA | 0.7584 | 14 | SB | Bcl-2 |
| DRB1_0101 | 209 LFDFSWLSLK-TLLSL | WLSLKTLLS | 0.7419 | 16 | SB | Bcl-2 |
| DRB1_0101 | 208 PLFDFSWLSLK-TLLS | FSWLSLKTL | 0.7389 | 17 | SB | Bcl-2 |
| DRB1_0101 | 210 FDFSWLSLK-TLLSLA | WLSLKTLLS | 0.7403 | 17 | SB | Bcl-2 |
| DRB1_0101 | 219 TLLSLALVGAC-ITLG | LLSLALVGA | 0.7270 | 19 | SB | Bcl-2 |
| DRB1_0101 | 220 LLSLALVGAC-ITLGA | LVGACITLG | 0.7299 | 19 | SB | Bcl-2 |
| DRB1_0101 | 223 LALVGACITL-GAYLG | LVGACITLG | 0.7079 | 24 | SB | Bcl-2 |
| DRB1_0101 | 221 LSLALVGACITL-GAY | LVGACITLG | 0.7021 | 25 | SB | Bcl-2 |
| DRB1_0101 | 222 SLALVGACITL-GAYL | LVGACITLG | 0.7016 | 25 | SB | Bcl-2 |
| DRB1_0101 | 106 RRYRRD-FAEMSSQLH | YRRDFAEMS | 0.6774 | 33 | SB | Bcl-2 |
| DRB1_0101 | 72 LQTPAAP-GAAAGPAL | LQTPAAPGA | 0.6778 | 33 | SB | Bcl-2 |
| DRB1_0101 | 71 PLQTPAAP-GAAAGPA | LQTPAAPGA | 0.6750 | 34 | SB | Bcl-2 |
| DRB1_0101 | 108 YRRDFAEMSSQL-HLT | FAEMSSQLH | 0.6686 | 36 | SB | Bcl-2 |
| DRB1_0101 | 107 RYRRD-FAEMSSQLHL | FAEMSSQLH | 0.6670 | 37 | SB | Bcl-2 |
| DRB1_0101 | 218 KTLLSLALVGAC-ITL | LLSLALVGA | 0.6642 | 38 | SB | Bcl-2 |
| DRB1_0101 | 109 RRDFAEMSSQL-HLTP | FAEMSSQLH | 0.6615 | 39 | SB | Bcl-2 |
| DRB1_0101 | 110 RDFAEMSSQL-HLTPF | FAEMSSQLH | 0.6572 | 41 | SB | Bcl-2 |
| DRB1_0101 | 31 DAGDVGAAPP-GAAPA | VGAAPPGAA | 0.6561 | 41 | SB | Bcl-2 |
| DRB1_0101 | 32 AGDVGAAPPGAA-PAP | VGAAPPGAA | 0.6565 | 41 | SB | Bcl-2 |
| DRB1_0101 | 29 EWDAGDVGAAPP-GAA | DVGAAPPGA | 0.6512 | 44 | SB | Bcl-2 |
| DRB1_0101 | 30 WDAGDVGAAPP-GAAP | VGAAPPGAA | 0.6504 | 44 | SB | Bcl-2 |
| DRB1_0101 | 33 GDVGAAPPGAA-PAPG | VGAAPPGAA | 0.6438 | 47 | SB | Bcl-2 |
| DRB1_0101 | 207 RPLFDFSWLSLK-TLL | FSWLSLKTL | 0.6332 | 53 | WB | Bcl-2 |
| DRB1_0101 | 224 ALVGACITLGAY-LGH | LVGACITLG | 0.6316 | 54 | WB | Bcl-2 |
| DRB1_0101 | 206 MRPLFDF-SWLSLKTL | DFSWLSLKT | 0.6303 | 55 | WB | Bcl-2 |
| DRB1_0101 | 225 LVGACITLGAYL-GHK | LVGACITLG | 0.6212 | 60 | WB | Bcl-2 |
| DRB1_0101 | 13 EIVMKYI-HYKLSQRG | MKYIHYKLS | 0.6124 | 66 | WB | Bcl-2 |
| DRB1_0101 | 14 IVMKYI-HYKLSQRGY | IHYKLSQRG | 0.6114 | 67 | WB | Bcl-2 |
| DRB1_0101 | 15 VMKYIHYKLSQR-GYE | IHYKLSQRG | 0.6087 | 69 | WB | Bcl-2 |
| DRB1_0101 | 16 MKYIHYKLSQR-GYEW | IHYKLSQRG | 0.6059 | 71 | WB | Bcl-2 |

TABLE E-continued

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | affinity 1-log50k(aff) | (nM) | Bind Level | Identity |
|---|---|---|---|---|---|---|
| DRB1_0101 | 17 KYIHYKLSQR-GYEWD | IHYKLSQRG | 0.6042 | 72 | WB | Bcl-2 |
| DRB1_0101 | 164 REMSPLVDNIAL-WMT | LVDNIALWM | 0.5967 | 79 | WB | Bcl-2 |
| DRB1_0101 | 165 EMSPLVDNIALW-MTE | VDNIALWMT | 0.5914 | 83 | WB | Bcl-2 |
| DRB1_0101 | 167 SPLVDNIALW-MTEYL | VDNIALWMT | 0.5912 | 83 | WB | Bcl-2 |
| DRB1_0101 | 166 MSPLVDNIALW-MTEY | VDNIALWMT | 0.5908 | 84 | WB | Bcl-2 |
| DRB1_0101 | 63 RDPVARTSPLQT-PAA | VARTSPLQT | 0.5908 | 84 | WB | Bcl-2 |
| DRB1_0101 | 64 DPVARTSPLQT-PAAP | VARTSPLQT | 0.5876 | 87 | WB | Bcl-2 |
| DRB1_0101 | 168 PLVDNIALW-MTEYLN | VDNIALWMT | 0.5794 | 95 | WB | Bcl-2 |
| DRB1_0101 | 196 DAFVELYGPSMR-PLF | FVELYGPSM | 0.5684 | 107 | WB | Bcl-2 |
| DRB1_0101 | 34 DVGAAPPGAA-PAPGI | VGAAPPGAA | 0.5672 | 108 | WB | Bcl-2 |
| DRB1_0101 | 62 SRDP-VARTSPLQTPA | VARTSPLQT | 0.5669 | 108 | WB | Bcl-2 |
| DRB1_0101 | 195 WDAFVELYGPSM-RPL | FVELYGPSM | 0.5666 | 109 | WB | Bcl-2 |
| DRB1_0101 | 61 ASRDP-VARTSPLQTP | VARTSPLQT | 0.5637 | 112 | WB | Bcl-2 |
| DRB1_0101 | 86 LSPVPPVVHLTL-RQA | LSPVPPVVH | 0.5639 | 112 | WB | Bcl-2 |
| DRB1_0101 | 111 DFAEMSSQLHLT-PFT | FAEMSSQLH | 0.5615 | 115 | WB | Bcl-2 |
| DRB1_0101 | 89 VPPVVHLTL-RQAGDD | VVHLTLRQA | 0.5593 | 118 | WB | Bcl-2 |
| DRB1_0101 | 87 SPVPPVVHLTL-RQAG | VVHLTLRQA | 0.5579 | 119 | WB | Bcl-2 |
| DRB1_0101 | 88 PVPPVVHLTL-RQAGD | VVHLTLRQA | 0.5581 | 119 | WB | Bcl-2 |
| DRB1_0101 | 112 FAEMSSQLHLTP-FTA | FAEMSSQLH | 0.5577 | 120 | WB | Bcl-2 |
| DRB1_0101 | 35 VGAAPPGAAPAP-GIF | VGAAPPGAA | 0.5569 | 121 | WB | Bcl-2 |
| DRB1_0101 | 90 PPVVHLTL-RQAGDDF | VVHLTLRQA | 0.5563 | 122 | WB | Bcl-2 |
| DRB1_0101 | 80 AAAGPALSPVP-PVVH | AAAGPALSP | 0.5545 | 124 | WB | Bcl-2 |
| DRB1_0101 | 160 ESVNREMSPLVD-NIA | VNREMSPLV | 0.5523 | 127 | WB | Bcl-2 |
| DRB1_0101 | 60 AASRDP-VARTSPLQT | SRDPVARTS | 0.5524 | 127 | WB | Bcl-2 |
| DRB1_0101 | 117 SQLHLTPFTAR-GRFA | LTPFTARGR | 0.5480 | 133 | WB | Bcl-2 |
| DRB1_0101 | 115 MSSQLHLTPF-TARGR | LHLTPFTAR | 0.5456 | 137 | WB | Bcl-2 |
| DRB1_0101 | 116 SSQLHLTPFTAR-GRF | LTPFTARGR | 0.5418 | 142 | WB | Bcl-2 |
| DRB1_0101 | 81 AAGPALSPVPPV-VHL | LSPVPPVVH | 0.5390 | 147 | WB | Bcl-2 |
| DRB1_0101 | 118 QLHLTPFTARGR-FAT | LTPFTARGR | 0.5379 | 148 | WB | Bcl-2 |
| DRB1_0101 | 197 AFVELYGPSMR-PLFD | LYGPSMRPL | 0.5381 | 148 | WB | Bcl-2 |
| DRB1_0101 | 156 VMCVESVNREM-SPLV | VMCVESVNR | 0.5366 | 151 | WB | Bcl-2 |
| DRB1_0101 | 158 CVESVNREM-SPLVDN | VNREMSPLV | 0.5360 | 151 | WB | Bcl-2 |
| DRB1_0101 | 159 VESVNREM-SPLVDNI | VNREMSPLV | 0.5364 | 151 | WB | Bcl-2 |
| DRB1_0101 | 198 FVELYGPSMR-PLFDF | LYGPSMRPL | 0.5345 | 154 | WB | Bcl-2 |
| DRB1_0101 | 157 MCVESVNREM-SPLVD | VNREMSPLV | 0.5315 | 159 | WB | Bcl-2 |
| DRB1_0101 | 119 LHLTPFTARGR-FATV | LTPFTARGR | 0.5307 | 160 | WB | Bcl-2 |
| DRB1_0101 | 82 AGPALSPVPPV-VHLT | LSPVPPVVH | 0.5312 | 160 | WB | Bcl-2 |
| DRB1_0101 | 83 GPALSPVPPV-VHLTL | LSPVPPVVH | 0.5307 | 160 | WB | Bcl-2 |
| DRB1_0101 | 148 VAFFEFGGVM-CVESV | FEFGGVMCV | 0.5291 | 163 | WB | Bcl-2 |

TABLE E-continued

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0101 | 149 AFFEFGGVMCVESVN | FEFGGVMCV | 0.5288 | 164 | WB | Bcl-2 |
| DRB1_0101 | 46 PGIFSSQPGHTPHPA | FSSQPGHTP | 0.5270 | 167 | WB | Bcl-2 |
| DRB1_0101 | 170 VDNIALWMTEYLNRH | VDNIALWMT | 0.5265 | 168 | WB | Bcl-2 |
| DRB1_0101 | 43 APAPGIFSSQPGHTP | IFSSQPGHT | 0.5223 | 176 | WB | Bcl-2 |
| DRB1_0101 | 84 PALSPVPPVVHLTLR | LSPVPPVVH | 0.5195 | 181 | WB | Bcl-2 |
| DRB1_0101 | 147 IVAFFEFGGVMCVES | FEFGGVMCV | 0.5190 | 182 | WB | Bcl-2 |
| DRB1_0101 | 65 PVARTSPLQTPAAPG | VARTSPLQT | 0.5190 | 182 | WB | Bcl-2 |
| DRB1_0101 | 45 APGIFSSQPGHTPHP | FSSQPGHTP | 0.5186 | 183 | WB | Bcl-2 |
| DRB1_0101 | 120 HLTPFTARGRFATVV | LTPFTARGR | 0.5178 | 184 | WB | Bcl-2 |
| DRB1_0101 | 121 LTPFTARGRFATVVE | ARGRFATVV | 0.5182 | 184 | WB | Bcl-2 |
| DRB1_0101 | 136 ELFRDGVNWGRIVAF | FRDGVNWGR | 0.5154 | 189 | WB | Bcl-2 |
| DRB1_0101 | 44 PAPGIFSSQPGHTPH | FSSQPGHTP | 0.5142 | 192 | WB | Bcl-2 |
| DRB1_0101 | 138 FRDGVNWGRIVAFFE | VNWGRIVAF | 0.5122 | 196 | WB | Bcl-2 |
| DRB1_0101 | 169 LVDNIALWMTEYLNR | VDNIALWMT | 0.5062 | 209 | WB | Bcl-2 |
| DRB1_0101 | 18 YIHYKLSQRGYEWDA | IHYKLSQRG | 0.5057 | 210 | WB | Bcl-2 |
| DRB1_0101 | 137 LFRDGVNWGRIVAFF | VNWGRIVAF | 0.5023 | 218 | WB | Bcl-2 |
| DRB1_0101 | 19 IHYKLSQRGYEWDAG | IHYKLSQRG | 0.5022 | 218 | WB | Bcl-2 |
| DRB1_0101 | 47 GIFSSQPGHTPHPAA | FSSQPGHTP | 0.5023 | 218 | WB | Bcl-2 |
| DRB1_0101 | 76 AAPGAAAGPALSPVP | AAAGPALSP | 0.5005 | 222 | WB | Bcl-2 |
| DRB1_0101 | 139 RDGVNWGRIVAFFEF | VNWGRIVAF | 0.4998 | 224 | WB | Bcl-2 |
| DRB1_0101 | 74 TPAAPGAAAGPALSP | GAAAGPALS | 0.4991 | 226 | WB | Bcl-2 |
| DRB1_0101 | 194 GWDAFVELYGPSMRP | FVELYGPSM | 0.4987 | 227 | WB | Bcl-2 |
| DRB1_0101 | 75 PAAPGAAAGPALSPV | AAAGPALSP | 0.4981 | 228 | WB | Bcl-2 |
| DRB1_0101 | 77 APGAAAGPALSPVPP | AAAGPALSP | 0.4980 | 229 | WB | Bcl-2 |
| DRB1_0101 | 140 DGVNWGRIVAFFEFG | VNWGRIVAF | 0.4959 | 234 | WB | Bcl-2 |
| DRB1_0101 | 105 SRRYRRDFAEMSSQL | YRRDFAEMS | 0.4945 | 237 | WB | Bcl-2 |
| DRB1_0101 | 91 PVVHLTLRQAGDDFS | VVHLTLRQA | 0.4935 | 240 | WB | Bcl-2 |
| DRB1_0101 | 199 VELYGPSMRPLFDFS | LYGPSMRPL | 0.4895 | 251 | WB | Bcl-2 |
| DRB1_0101 | 92 VVHLTLRQAGDDFSR | VVHLTLRQA | 0.4870 | 257 | WB | Bcl-2 |
| DRB1_0101 | 104 FSRRYRRDFAEMSSQ | YRRDFAEMS | 0.4851 | 263 | WB | Bcl-2 |
| DRB1_0101 | 103 DFSRRYRRDFAEMSS | YRRDFAEMS | 0.4834 | 268 | WB | Bcl-2 |
| DRB1_0101 | 102 DDFSRRYRRDFAEMS | RYRRDFAEM | 0.4800 | 278 | WB | Bcl-2 |
| DRB1_0101 | 145 GRIVAFFEFGGVMCV | FFEFGGVMC | 0.4796 | 279 | WB | Bcl-2 |
| DRB1_0101 | 146 RIVAFFEFGGVMCVE | FEFGGVMCV | 0.4791 | 280 | WB | Bcl-2 |
| DRB1_0101 | 78 PGAAAGPALSPVPPV | AAAGPALSP | 0.4771 | 286 | WB | Bcl-2 |
| DRB1_0101 | 161 SVNREMSPLVDNIAL | VNREMSPLV | 0.4763 | 289 | WB | Bcl-2 |
| DRB1_0101 | 150 FFEFGGVMCVESVNR | FEFGGVMCV | 0.4737 | 297 | WB | Bcl-2 |
| DRB1_0101 | 162 VNREMSPLVDNIALW | VNREMSPLV | 0.4734 | 298 | WB | Bcl-2 |
| DRB1_0101 | 151 FEFGGVMCVESVNRE | FEFGGVMCV | 0.4731 | 299 | WB | Bcl-2 |

TABLE E-continued

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | affinity 1-log50k(aff) | (nM) | Bind Level | Identity |
|---|---|---|---|---|---|---|
| DRB1_0101 | 114 EMSSQLHLTPF-TARG | LHLTPFTAR | 0.4711 | 306 | WB | Bcl-2 |
| DRB1_0101 | 122 TPFTARGRFATV-VEE | ARGRFATVV | 0.4638 | 331 | WB | Bcl-2 |
| DRB1_0101 | 73 QTPAAPGAAAG-PALS | APGAAAGPA | 0.4635 | 332 | WB | Bcl-2 |
| DRB1_0101 | 49 FSSQPGHTPH-PAASR | FSSQPGHTP | 0.4615 | 339 | WB | Bcl-2 |
| DRB1_0101 | 48 IFSSQPGHTPH-PAAS | FSSQPGHTP | 0.4531 | 371 | WB | Bcl-2 |
| DRB1_0101 | 36 GAAPPGAAPAP-GIFS | PGAAPAPGI | 0.4518 | 376 | WB | Bcl-2 |
| DRB1_0101 | 123 PFTARGRFATV-VEEL | ARGRFATVV | 0.4516 | 377 | WB | Bcl-2 |
| DRB1_0101 | 124 FTARGRFATV-VEELF | ARGRFATVV | 0.4490 | 388 | WB | Bcl-2 |
| DRB1_0101 | 174 ALWMTEYLN-RHLHTW | WMTEYLNRH | 0.4444 | 408 | WB | Bcl-2 |
| DRB1_0101 | 85 ALSPVPPV-VHLTLRQ | LSPVPPVVH | 0.4436 | 411 | WB | Bcl-2 |
| DRB1_0101 | 113 AEMSSQLHLTPF-TAR | SQLHLTPFT | 0.4430 | 414 | WB | Bcl-2 |
| DRB1_0101 | 171 DNIALWMTEYLN-RHL | WMTEYLNRH | 0.4414 | 421 | WB | Bcl-2 |
| DRB1_0101 | 193 GGWDAFVE-LYGPSMR | FVELYGPSM | 0.4396 | 430 | WB | Bcl-2 |
| DRB1_0101 | 200 ELYGPSMRPLFD-FSW | LYGPSMRPL | 0.4395 | 430 | WB | Bcl-2 |
| DRB1_0101 | 37 AAPPGAAPAP-GIFSS | AAPAPGIFS | 0.4393 | 431 | WB | Bcl-2 |
| DRB1_0101 | 79 GAAAGPALSPVP-PVV | AAAGPALSP | 0.4394 | 431 | WB | Bcl-2 |
| DRB1_0101 | 172 NIALWMTEYLN-RHLH | WMTEYLNRH | 0.4279 | 488 | WB | Bcl-2 |
| DRB1_0101 | 28 YEWDAGDVGAAP-PGA | WDAGDVGAA | 0.4274 | 490 | WB | Bcl-2 |
| DRB1_0101 | 42 AAPAPGIF-SSQPGHT | AAPAPGIFS | 0.4268 | 494 | WB | Bcl-2 |
| DRB1_0101 | 163 NREMSPLVD-NIALWM | MSPLVDNIA | 0.4266 | 495 | WB | Bcl-2 |
| DRB1_0401 | 208 PLFDFSWLSLK-TLLS | DFSWLSLKT | 0.5448 | 138 | WB | Bcl-2 |
| DRB1_0401 | 211 DFSWLSLK-TLLSLAL | WLSLKTLLS | 0.5436 | 139 | WB | Bcl-2 |
| DRB1_0401 | 212 FSWLSLK-TLLSLALV | WLSLKTLLS | 0.5395 | 146 | WB | Bcl-2 |
| DRB1_0401 | 209 LFDFSWLSLK-TLLSL | WLSLKTLLS | 0.5358 | 152 | WB | Bcl-2 |
| DRB1_0401 | 210 FDFSWLSLK-TLLSLA | WLSLKTLLS | 0.5305 | 161 | WB | Bcl-2 |
| DRB1_0401 | 156 VMCVESVNREM-SPLV | MCVESVNRE | 0.4924 | 243 | WB | Bcl-2 |
| DRB1_0401 | 158 CVESVNREM-SPLVDN | VNREMSPLV | 0.4915 | 245 | WB | Bcl-2 |
| DRB1_0401 | 157 MCVESVNREM-SPLVD | VNREMSPLV | 0.4907 | 247 | WB | Bcl-2 |
| DRB1_0401 | 160 ESVNREMSPLVD-NIA | VNREMSPLV | 0.4909 | 247 | WB | Bcl-2 |
| DRB1_0401 | 159 VESVNREM-SPLVDNI | VNREMSPLV | 0.4870 | 257 | WB | Bcl-2 |
| DRB1_0401 | 214 WLSLKTLLSLA-LVGA | WLSLKTLLS | 0.4662 | 322 | WB | Bcl-2 |
| DRB1_0401 | 213 SWLSLKTLLSLA-LVG | WLSLKTLLS | 0.4661 | 323 | WB | Bcl-2 |
| DRB1_0401 | 106 RRYRRD-FAEMSSQLH | YRRDFAEMS | 0.4563 | 359 | WB | Bcl-2 |
| DRB1_0401 | 170 VDNIALWMTEYL-NRH | NIALWMTEY | 0.4319 | 467 | WB | Bcl-2 |
| DRB1_0404 | 174 ALWMTEYLN-RHLHTW | WMTEYLNRH | 0.5813 | 93 | WB | Bcl-2 |
| DRB1_0404 | 170 VDNIALWMTEYL-NRH | IALWMTEYL | 0.5418 | 142 | WB | Bcl-2 |
| DRB1_0404 | 171 DNIALWMTEYLN-RHL | WMTEYLNRH | 0.5422 | 142 | WB | Bcl-2 |
| DRB1_0404 | 172 NIALWMTEYLN-RHLH | WMTEYLNRH | 0.5371 | 150 | WB | Bcl-2 |

TABLE E-continued

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0404 | 173 IALWMTEYLNRHLHT | WMTEYLNRH | 0.5341 | 155 | WB | Bcl-2 |
| DRB1_0404 | 175 LWMTEYLNRHLHTWI | WMTEYLNRH | 0.5171 | 186 | WB | Bcl-2 |
| DRB1_0404 | 115 MSSQLHLTPFTARGR | HLTPFTARG | 0.5121 | 196 | WB | Bcl-2 |
| DRB1_0404 | 114 EMSSQLHLTPFTARG | LHLTPFTAR | 0.5118 | 197 | WB | Bcl-2 |
| DRB1_0404 | 176 WMTEYLNRHLHTWIQ | WMTEYLNRH | 0.5110 | 199 | WB | Bcl-2 |
| DRB1_0404 | 116 SSQLHLTPFTARGRF | HLTPFTARG | 0.5043 | 213 | WB | Bcl-2 |
| DRB1_0404 | 117 SQLHLTPFTARGRFA | HLTPFTARG | 0.5004 | 223 | WB | Bcl-2 |
| DRB1_0404 | 118 QLHLTPFTARGRFAT | HLTPFTARG | 0.4918 | 244 | WB | Bcl-2 |
| DRB1_0404 | 45 APGIFSSQPGHTPHP | FSSQPGHTP | 0.4688 | 313 | WB | Bcl-2 |
| DRB1_0404 | 46 PGIFSSQPGHTPHPA | FSSQPGHTP | 0.4665 | 321 | WB | Bcl-2 |
| DRB1_0404 | 47 GIFSSQPGHTPHPAA | SQPGHTPHP | 0.4485 | 390 | WB | Bcl-2 |
| DRB1_0404 | 109 RRDFAEMSSQLHLTP | FAEMSSQLH | 0.4422 | 418 | WB | Bcl-2 |
| DRB1_0404 | 210 FDFSWLSLKTLLSLA | WLSLKTLLS | 0.4405 | 426 | WB | Bcl-2 |
| DRB1_0404 | 110 RDFAEMSSQLHLTPF | FAEMSSQLH | 0.4393 | 431 | WB | Bcl-2 |
| DRB1_0404 | 211 DFSWLSLKTLLSLAL | WLSLKTLLS | 0.4316 | 469 | WB | Bcl-2 |
| DRB1_0404 | 212 FSWLSLKTLLSLALV | WLSLKTLLS | 0.4313 | 470 | WB | Bcl-2 |
| DRB1_0405 | 208 PLFDFSWLSLKTLLS | FSWLSLKTL | 0.6517 | 43 | SB | Bcl-2 |
| DRB1_0405 | 209 LFDFSWLSLKTLLSL | WLSLKTLLS | 0.6415 | 48 | SB | Bcl-2 |
| DRB1_0405 | 210 FDFSWLSLKTLLSLA | WLSLKTLLS | 0.6398 | 49 | SB | Bcl-2 |
| DRB1_0405 | 211 DFSWLSLKTLLSLAL | WLSLKTLLS | 0.6392 | 50 | WB | Bcl-2 |
| DRB1_0405 | 212 FSWLSLKTLLSLALV | WLSLKTLLS | 0.6381 | 50 | WB | Bcl-2 |
| DRB1_0405 | 213 SWLSLKTLLSLALVG | WLSLKTLLS | 0.5584 | 119 | WB | Bcl-2 |
| DRB1_0405 | 214 WLSLKTLLSLALVGA | WLSLKTLLS | 0.5575 | 120 | WB | Bcl-2 |
| DRB1_0405 | 160 ESVNREMSPLVDNIA | NREMSPLVD | 0.5021 | 219 | WB | Bcl-2 |
| DRB1_0405 | 158 CVESVNREMSPLVDN | NREMSPLVD | 0.4974 | 230 | WB | Bcl-2 |
| DRB1_0405 | 159 VESVNREMSPLVDNI | NREMSPLVD | 0.4930 | 241 | WB | Bcl-2 |
| DRB1_0405 | 170 VDNIALWMTEYLNRH | IALWMTEYL | 0.4903 | 248 | WB | Bcl-2 |
| DRB1_0405 | 168 PLVDNIALWMTEYLN | IALWMTEYL | 0.4841 | 266 | WB | Bcl-2 |
| DRB1_0405 | 171 DNIALWMTEYLNRHL | IALWMTEYL | 0.4841 | 266 | WB | Bcl-2 |
| DRB1_0405 | 169 LVDNIALWMTEYLNR | IALWMTEYL | 0.4812 | 274 | WB | Bcl-2 |
| DRB1_0405 | 157 MCVESVNREMSPLVD | VNREMSPLV | 0.4756 | 291 | WB | Bcl-2 |
| DRB1_0405 | 167 SPLVDNIALWMTEYL | NIALWMTEY | 0.4744 | 295 | WB | Bcl-2 |
| DRB1_0405 | 161 SVNREMSPLVDNIAL | NREMSPLVD | 0.4718 | 303 | WB | Bcl-2 |
| DRB1_0405 | 106 RRYRRDFAEMSSQLH | YRRDFAEMS | 0.4486 | 390 | WB | Bcl-2 |
| DRB1_0405 | 162 VNREMSPLVDNIALW | NREMSPLVD | 0.4294 | 480 | WB | Bcl-2 |
| DRB1_0701 | 83 GPALSPVPPVVHLTL | LSPVPPVVH | 0.5316 | 159 | WB | Bcl-2 |
| DRB1_0701 | 82 AGPALSPVPPVVHLT | LSPVPPVVH | 0.5286 | 164 | WB | Bcl-2 |
| DRB1_0701 | 81 AAGPALSPVPPVVHL | LSPVPPVVH | 0.5256 | 169 | WB | Bcl-2 |

TABLE E-continued

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_0701 | 84 PALSPVPPV-VHLTLR | LSPVPPVH | 0.5210 | 178 | WB | Bcl-2 |
| DRB1_0701 | 80 AAAGPALSPVP-PVVH | ALSPVPVV | 0.5179 | 184 | WB | Bcl-2 |
| DRB1_0701 | 85 ALSPVPPV-VHLTLRQ | LSPVPPVH | 0.4370 | 442 | WB | Bcl-2 |
| DRB1_0701 | 86 LSPVPPVVHLTL-RQA | LSPVPPVH | 0.4291 | 482 | WB | Bcl-2 |
| DRB1_0901 | 196 DAFVELYGPSMR-PLF | VELYGPSMR | 0.4599 | 345 | WB | Bcl-2 |
| DRB1_0901 | 197 AFVELYGPSMR-PLFD | YGPSMRPLF | 0.4582 | 352 | WB | Bcl-2 |
| DRB1_0901 | 198 FVELYGPSMR-PLFDF | YGPSMRPLF | 0.4429 | 415 | WB | Bcl-2 |
| DRB1_0901 | 199 VELYGPSMR-PLFDFS | YGPSMRPLF | 0.4428 | 415 | WB | Bcl-2 |
| DRB1_1302 | 212 FSWLSLK-TLLSLALV | WLSLKTLLS | 0.5351 | 153 | WB | Bcl-2 |
| DRB1_1302 | 211 DFSWLSLK-TLLSLAL | WLSLKTLLS | 0.5323 | 158 | WB | Bcl-2 |
| DRB1_1302 | 209 LFDFSWLSLK-TLLSL | WLSLKTLLS | 0.4963 | 233 | WB | Bcl-2 |
| DRB1_1302 | 210 FDFSWLSLK-TLLSLA | WLSLKTLLS | 0.4951 | 236 | WB | Bcl-2 |
| DRB1_1302 | 208 PLFDFSWLSLK-TLLS | FSWLSLKTL | 0.4783 | 283 | WB | Bcl-2 |
| DRB1_1302 | 213 SWLSLKTLLSLA-LVG | WLSLKTLLS | 0.4770 | 287 | WB | Bcl-2 |
| DRB1_1302 | 214 WLSLKTLLSLA-LVGA | WLSLKTLLS | 0.4769 | 287 | WB | Bcl-2 |
| DRB1_1302 | 196 DAFVELYGPSMR-PLF | VELYGPSMR | 0.4640 | 330 | WB | Bcl-2 |
| DRB1_1302 | 197 AFVELYGPSMR-PLFD | VELYGPSMR | 0.4607 | 342 | WB | Bcl-2 |
| DRB1_1302 | 167 SPLVDNIALW-MTEYL | VDNIALWMT | 0.4494 | 387 | WB | Bcl-2 |
| DRB1_1302 | 168 PLVDNIALW-MTEYLN | VDNIALWMT | 0.4385 | 435 | WB | Bcl-2 |
| DRB1_1501 | 13 EIVMKYI-HYKLSQRG | YIHYKLSQR | 0.6338 | 53 | WB | Bcl-2 |
| DRB1_1501 | 14 IVMKYI-HYKLSQRGY | YIHYKLSQR | 0.6318 | 54 | WB | Bcl-2 |
| DRB1_1501 | 15 VMKYIHYKLSQR-GYE | YIHYKLSQR | 0.6170 | 63 | WB | Bcl-2 |
| DRB1_1501 | 16 MKYIHYKLSQR-GYEW | YIHYKLSQR | 0.6121 | 66 | WB | Bcl-2 |
| DRB1_1501 | 12 REIVMKYI-HYKLSQR | IVMKYIHYK | 0.6057 | 71 | WB | Bcl-2 |
| DRB1_1501 | 17 KYIHYKLSQR-GYEWD | YIHYKLSQR | 0.5372 | 150 | WB | Bcl-2 |
| DRB1_1501 | 115 MSSQLHLTPF-TARGR | LHLTPFTAR | 0.5174 | 185 | WB | Bcl-2 |
| DRB1_1501 | 116 SSQLHLTPFTAR-GRF | LHLTPFTAR | 0.5162 | 188 | WB | Bcl-2 |
| DRB1_1501 | 18 YIHYKLSQR-GYEWDA | YIHYKLSQR | 0.5136 | 193 | WB | Bcl-2 |
| DRB1_1501 | 117 SQLHLTPFTAR-GRFA | LHLTPFTAR | 0.5054 | 211 | WB | Bcl-2 |
| DRB1_1501 | 119 LHLTPFTARGR-FATV | LTPFTARGR | 0.4756 | 291 | WB | Bcl-2 |
| DRB1_1501 | 135 EELFRDGVN-WGRIVA | LFRDGVNWG | 0.4694 | 311 | WB | Bcl-2 |
| DRB1_1501 | 212 FSWLSLK-TLLSLALV | WLSLKTLLS | 0.4694 | 312 | WB | Bcl-2 |
| DRB1_1501 | 211 DFSWLSLK-TLLSLAL | WLSLKTLLS | 0.4655 | 325 | WB | Bcl-2 |
| DRB1_1501 | 118 QLHLTPFTARGR-FAT | LHLTPFTAR | 0.4592 | 348 | WB | Bcl-2 |
| DRB1_1501 | 87 SPVPPVVHLTL-RQAG | VVHLTLRQA | 0.4553 | 363 | WB | Bcl-2 |
| DRB1_1501 | 88 PVPPVVHLTL-RQAGD | VVHLTLRQA | 0.4528 | 373 | WB | Bcl-2 |
| DRB1_1501 | 214 WLSLKTLLSLA-LVGA | LKTLLSLAL | 0.4517 | 377 | WB | Bcl-2 |

TABLE E-continued

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | affinity (nM) | Bind Level | Identity |
|---|---|---|---|---|---|---|
| DRB1_1501 | 209 LFDFSWLSLK-TLLSL | WLSLKTLLS | 0.4495 | 386 | WB | Bcl-2 |
| DRB1_1501 | 156 VMCVESVNREM-SPLV | VMCVESVNR | 0.4490 | 388 | WB | Bcl-2 |
| DRB1_1501 | 193 GGWDAFVE-LYGPSMR | FVELYGPSM | 0.4489 | 389 | WB | Bcl-2 |
| DRB1_1501 | 195 WDAFVELYGPSM-RPL | VELYGPSMR | 0.4483 | 391 | WB | Bcl-2 |
| DRB1_1501 | 196 DAFVELYGPSMR-PLF | FVELYGPSM | 0.4482 | 392 | WB | Bcl-2 |
| DRB1_1501 | 132 TVVEELFRDGVN-WGR | LFRDGVNWG | 0.4470 | 397 | WB | Bcl-2 |
| DRB1_1501 | 133 VVEELFRDGVN-WGRI | LFRDGVNWG | 0.4467 | 398 | WB | Bcl-2 |
| DRB1_1501 | 194 GWDAFVE-LYGPSMRP | VELYGPSMR | 0.4467 | 398 | WB | Bcl-2 |
| DRB1_1501 | 174 ALWMTEYLN-RHLHTW | WMTEYLNRH | 0.4463 | 400 | WB | Bcl-2 |
| DRB1_1501 | 208 PLFDFSWLSLK-TLLS | LFDFSWLSL | 0.4459 | 401 | WB | Bcl-2 |
| DRB1_1501 | 172 NIALWMTEYLN-RHLH | WMTEYLNRH | 0.4448 | 406 | WB | Bcl-2 |
| DRB1_1501 | 173 IALWMTEYLN-RHLHT | WMTEYLNRH | 0.4448 | 407 | WB | Bcl-2 |
| DRB1_1501 | 134 VEELFRDGVN-WGRIV | LFRDGVNWG | 0.4431 | 414 | WB | Bcl-2 |
| DRB1_1501 | 171 DNIALWMTEYLN-RHL | WMTEYLNRH | 0.4431 | 414 | WB | Bcl-2 |
| DRB1_1501 | 89 VPPVVHLTL-RQAGDD | VVHLTLRQA | 0.4422 | 418 | WB | Bcl-2 |
| DRB1_1501 | 210 FDFSWLSLK-TLLSLA | WLSLKTLLS | 0.4399 | 429 | WB | Bcl-2 |
| DRB1_1501 | 136 ELFRDGVN-WGRIVAF | LFRDGVNWG | 0.4390 | 433 | WB | Bcl-2 |
| DRB1_1501 | 86 LSPVPPVVHLTL-RQA | PPVVHLTLR | 0.4378 | 438 | WB | Bcl-2 |
| DRB1_1501 | 213 SWLSLKTLLSLA-LVG | LKTLLSLAL | 0.4330 | 461 | WB | Bcl-2 |
| DRB1_1501 | 90 PPVVHLTL-RQAGDDF | VVHLTLRQA | 0.4313 | 470 | WB | Bcl-2 |
| DRB4_0101 | 196 DAFVELYGPSMR-PLF | VELYGPSMR | 0.5364 | 151 | WB | Bcl-2 |
| DRB4_0101 | 197 AFVELYGPSMR-PLFD | VELYGPSMR | 0.5361 | 151 | WB | Bcl-2 |
| DRB4_0101 | 195 WDAFVELYGPSM-RPL | VELYGPSMR | 0.5323 | 158 | WB | Bcl-2 |
| DRB4_0101 | 193 GGWDAFVE-LYGPSMR | FVELYGPSM | 0.4796 | 279 | WB | Bcl-2 |
| DRB4_0101 | 194 GWDAFVE-LYGPSMRP | VELYGPSMR | 0.4785 | 282 | WB | Bcl-2 |
| DRB4_0101 | 198 FVELYGPSMR-PLFDF | VELYGPSMR | 0.4761 | 289 | WB | Bcl-2 |
| DRB4_0101 | 199 VELYGPSMR-PLFDFS | VELYGPSMR | 0.4763 | 289 | WB | Bcl-2 |
| DRB4_0101 | 81 AAGPALSPVPPV-VHL | LSPVPPVVH | 0.4638 | 331 | WB | Bcl-2 |
| DRB4_0101 | 80 AAAGPALSPVP-PVVH | ALSPVPPVV | 0.4614 | 339 | WB | Bcl-2 |
| DRB4_0101 | 170 VDNIALWMTEYL-NRH | IALWMTEYL | 0.4593 | 347 | WB | Bcl-2 |
| DRB4_0101 | 83 GPALSPVPPV-VHLTL | LSPVPPVVH | 0.4589 | 349 | WB | Bcl-2 |
| DRB4_0101 | 82 AGPALSPVPPV-VHLT | LSPVPPVVH | 0.4574 | 354 | WB | Bcl-2 |
| DRB4_0101 | 84 PALSPVPPV-VHLTLR | LSPVPPVVH | 0.4565 | 358 | WB | Bcl-2 |
| DRB4_0101 | 171 DNIALWMTEYLN-RHL | WMTEYLNRH | 0.4552 | 363 | WB | Bcl-2 |
| DRB4_0101 | 172 NIALWMTEYLN-RHLH | LWMTEYLNR | 0.4326 | 464 | WB | Bcl-2 |
| DRB4_0101 | 173 IALWMTEYLN-RHLHT | WMTEYLNRH | 0.4273 | 491 | WB | Bcl-2 |

TABLE E-continued

Prediction of cancer antigen Bcl-2 specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | affinity 1-log50k(aff) | (nM) | Bind Level | Identity |
|---|---|---|---|---|---|---|
| DRB5_0101 | 16 MKYIHYKLSQR-GYEW | YIHYKLSQR | 0.4394 | 431 | WB | Bcl-2 |
| DRB5_0101 | 15 VMKYIHYKLSQR-GYE | YIHYKLSQR | 0.4386 | 435 | WB | Bcl-2 |

SEQ ID NOS: 46594-47133

Preferred fragments of Survivin capable of interacting with one or more MHC class 1 molecules are listed in table F.

TABLE F

Prediction of cancer antigen Survivin specific MHC class 1 peptide sequences. Prediction of 8-, 9-, 10-, 11-mers using the program displayed in FIG. 2.

8 mers:

MGAPTLPP; GAPTLPPA; APTLPPAW; PTLPPAWQ; TLPPAWQP; LPPAWQPF;
PPAWQPFL; PAWQPFLK; AWQPFLKD; WQPFLKDH; QPFLKDHR; PFLKDHRI;
FLKDHRIS; LKDHRIST; KDHRISTF; DHRISTFK; HRISTFKN; RISTFKNW;
ISTFKNWP; STFKNWPF; TFKNWPFL; FKNWPFLE; KNWPFLEG; NWPFLEGC;
WPFLEGCA; PFLEGCAC; FLEGCACT; LEGCACTP; EGCACTPE; GCACTPER;
CACTPERM; ACTPERMA; CTPERMAE; TPERMAEA; PERMAEAG; ERMAEAGF;
RMAEAGFI; MAEAGFIH; AEAGFIHC; EAGFIHCP; AGFIHCPT; GFIHCPTE;
FIHCPTEN; IHCPTENE; HCPTENEP; CPTENEPD; PTENEPDL; TENEPDLA;
ENEPDLAQ; NEPDLAQC; EPDLAQCF; PDLAQCFF; DLAQCFFC; LAQCFFCF;
AQCFFCFK; QCFFCFKE; CFFCFKEL; FFCFKELE; FCFKELEG; CFKELEGW;
FKELEGWE; KELEGWEP; ELEGWEPD; LEGWEPDD; EGWEPDDD; GWEPDDDP;
WEPDDDPI; EPDDDPIE; PDDDPIEE; DDDPIEEH; DDPIEEHK; DPIEEHKK;
PIEEHKKH; IEEHKKHS; EEHKKHSS; EHKKHSSG; HKKHSSGC; KKHSSGCA;
KHSSGCAF; HSSGCAFL; SSGCAFLS; SGCAFLSV; GCAFLSVK; CAFLSVKK;
AFLSVKKQ; FLSVKKQF; LSVKKQFE; SVKKQFEE; VKKQFEEL; KKQFEELT;
KQFEELTL; QFEELTLG; FEELTLGE; EELTLGEF; ELTLGEFL; LTLGEFLK;
TLGEFLKL; LGEFLKLD; GEFLKLDR; EFLKLDRE; FLKLDRER; LKLDRERA;
KLDRERAK; LDRERAKN; DRERAKNK; RERAKNKI; ERAKNKIA; RAKNKIAK;
AKNKIAKE; KNKIAKET; NKIAKETN; KIAKETNN; IAKETNNK; AKETNNKK;
KETNNKKK; ETNNKKKE; TNNKKKEF; NNKKKEFE; NKKKEFEE; KKKEFEET;
KKEFEETA; KEFEETAK; EFEETAKK; FEETAKKV; EETAKKVR; ETAKKVRR;
TAKKVRRA; AKKVRRAI; KKVRRAIE; KVRRAIEQ; VRRAIEQL; RRAIEQLA;
RAIEQLAA; AIEQLAAM; IEQLAAMD; EQLAAMD☐

9 mers:

MGAPTLPPA; GAPTLPPAW; APTLPPAWQ; PTLPPAWQP; TLPPAWQPF; LPPAWQPFL;
PPAWQPFLK; PAWQPFLKD; AWQPFLKDH; WQPFLKDHR; QPFLKDHRI; PFLKDHRIS;
FLKDHRIST; LKDHRISTF; KDHRISTFK; DHRISTFKN; HRISTFKNW; RISTFKNWP;
ISTFKNWPF; STFKNWPFL; TFKNWPFLE; FKNWPFLEG; KNWPFLEGC; NWPFLEGCA;
WPFLEGCAC; PFLEGCACT; FLEGCACTP; LEGCACTPE; EGCACTPER; GCACTPERM;
CACTPERMA; ACTPERMAE; CTPERMAEA; TPERMAEAG; PERMAEAGF; ERMAEAGFI;
RMAEAGFIH; MAEAGFIHC; AEAGFIHCP; EAGFIHCPT; AGFIHCPTE; GFIHCPTEN;
FIHCPTENE; IHCPTENEP; HCPTENEPD; CPTENEPDL; PTENEPDLA; TENEPDLAQ;
ENEPDLAQC; NEPDLAQCF; EPDLAQCFF; PDLAQCFFC; DLAQCFFCF; LAQCFFCFK;
AQCFFCFKE; QCFFCFKEL; CFFCFKELE; FFCFKELEG; FCFKELEGW; CFKELEGWE;
FKELEGWEP; KELEGWEPD; ELEGWEPDD; LEGWEPDDD; EGWEPDDDP; GWEPDDDPI;
WEPDDDPIE; EPDDDPIEE; PDDDPIEEH; DDDPIEEHK; DDPIEEHKK; DPIEEHKKH;
PIEEHKKHS; IEEHKKHSS; EEHKKHSSG; EHKKHSSGC; HKKHSSGCA; KKHSSGCAF;
KHSSGCAFL; HSSGCAFLS; SSGCAFLSV; SGCAFLSVK; GCAFLSVKK; CAFLSVKKQ;
AFLSVKKQF; FLSVKKQFE; LSVKKQFEE; SVKKQFEEL; VKKQFEELT; KKQFEELTL;
KQFEELTLG; QFEELTLGE; FEELTLGEF; EELTLGEFL; ELTLGEFLK; LTLGEFLKL;
TLGEFLKLD; LGEFLKLDR; GEFLKLDRE; EFLKLDRER; FLKLDRERA; LKLDRERAK;
KLDRERAKN; LDRERAKNK; DRERAKNKI; RERAKNKIA; ERAKNKIAK; RAKNKIAKE;
AKNKIAKET; KNKIAKETN; NKIAKETNN; KIAKETNNK; IAKETNNKK; AKETNNKKK;
KETNNKKKE; ETNNKKKEF; TNNKKKEFE; NNKKKEFEE; NKKKEFEET; KKKEFEETA;
KKEFEETAK; KEFEETAKK; EFEETAKKV; FEETAKKVR; EETAKKVRR; ETAKKVRRA;
TAKKVRRAI; AKKVRRAIE; KKVRRAIEQ; KVRRAIEQL; VRRAIEQLA; RRAIEQLAA;
RAIEQLAAM; AIEQLAAMD; ☐

TABLE F-continued

Prediction of cancer antigen Survivin specific MHC class 1 peptide sequences. Prediction of 8-, 9-, 10-, 11-mers using the program displayed in FIG. 2.

10 mers:

MGAPTLPPAW; GAPTLPPAWQ; APTLPPAWQP; PTLPPAWQPF; TLPPAWQPFL;
LPPAWQPFLK; PPAWQPFLKD; PAWQPFLKDH; AWQPFLKDHR; WQPFLKDHRI;
QPFLKDHRIS; PFLKDHRIST; FLKDHRISTF; LKDHRISTFK; KDHRISTFKN;
DHRISTFKNW; HRISTFKNWP; RISTFKNWPF; ISTFKNWPFL; STFKNWPFLE;
TFKNWPFLEG; FKNWPFLEGC; KNWPFLEGCA; NWPFLEGCAC; WPFLEGCACT;
PFLEGCACTP; FLEGCACTPE; LEGCACTPER; EGCACTPERM; GCACTPERMA;
CACTPERMAE; ACTPERMAEA; CTPERMAEAG; TPERMAEAGF; PERMAEAGFI;
ERMAEAGFIH; RMAEAGFIHC; MAEAGFIHCP; AEAGFIHCPT; EAGFIHCPTE;
AGFIHCPTEN; GFIHCPTENE; FIHCPTENEP; IHCPTENEPD; HCPTENEPDL;
CPTENEPDLA; PTENEPDLAQ; TENEPDLAQC; ENEPDLAQCF; NEPDLAQCFF;
EPDLAQCFFC; PDLAQCFFCF; DLAQCFFCFK; LAQCFFCFKE; AQCFFCFKEL;
QCFFCFKELE; CFFCFKELEG; FFCFKELEGW; FCFKELEGWE; CFKELEGWEP;
FKELEGWEPD; KELEGWEPDD; ELEGWEPDDD; LEGWEPDDDP; EGWEPDDDPI;
GWEPDDDPIE; WEPDDDPIEE; EPDDDPIEEH; PDDDPIEEHK; DDDPIEEHKK;
DDPIEEHKKH; DPIEEHKKHS; PIEEHKKHSS; IEEHKKHSSG; EEHKKHSSGC;
EHKKHSSGCA; HKKHSSGCAF; KKHSSGCAFL; KHSSGCAFLS; HSSGCAFLSV;
SSGCAFLSVK; SGCAFLSVKK; GCAFLSVKKQ; CAFLSVKKQF; AFLSVKKQFE;
FLSVKKQFEE; LSVKKQFEEL; SVKKQFEELT; VKKQFEELTL; KKQFEELTLG;
KQFEELTLGE; QFEELTLGEF; FEELTLGEFL; EELTLGEFLK; ELTLGEFLKL;
LTLGEFLKLD; TLGEFLKLDR; LGEFLKLDRE; GEFLKLDRER; EFLKLDRERA;
FLKLDRERAK; LKLDRERAKN; KLDRERAKNK; LDRERAKNKI; DRERAKNKIA;
RERAKNKIAK; ERAKNKIAKE; RAKNKIAKET; AKNKIAKETN; KNKIAKETNN;
NKIAKETNNK; KIAKETNNKK; IAKETNNKKK; AKETNNKKKE; KETNNKKKEF;
ETNNKKKEFE; TNNKKKEFEE; NNKKKEFEET; NKKKEFEETA; KKKEFEETAK;
KKEFEETAKK; KEFEETAKKV; EFEETAKKVR; FEETAKKVRR; EETAKKVRRA;
ETAKKVRRAI; TAKKVRRAIE; AKKVRRAIEQ; KKVRRAIEQL; KVRRAIEQLA;
VRRAIEQLAA; RRAIEQLAAM; RAIEQLAAMD;

11 mers:

MGAPTLPPAWQ; GAPTLPPAWQP; APTLPPAWQPF; PTLPPAWQPFL; TLPPAWQPFLK;
LPPAWQPFLKD; PPAWQPFLKDH; PAWQPFLKDHR; AWQPFLKDHRI; WQPFLKDHRIS;
QPFLKDHRIST; PFLKDHRISTF; FLKDHRISTFK; LKDHRISTFKN; KDHRISTFKNW;
DHRISTFKNWP; HRISTFKNWPF; RISTFKNWPFL; ISTFKNWPFLE; STFKNWPFLEG;
TFKNWPFLEGC; FKNWPFLEGCA; KNWPFLEGCAC; NWPFLEGCACT; WPFLEGCACTP;
PFLEGCACTPE; FLEGCACTPER; LEGCACTPERM; EGCACTPERMA; GCACTPERMAE;
CACTPERMAEA; ACTPERMAEAG; CTPERMAEAGF; TPERMAEAGFI; PERMAEAGFIH;
ERMAEAGFIHC; RMAEAGFIHCP; MAEAGFIHCPT; AEAGFIHCPTE; EAGFIHCPTEN;
AGFIHCPTENE; GFIHCPTENEP; FIHCPTENEPD; IHCPTENEPDL; HCPTENEPDLA;
CPTENEPDLAQ; PTENEPDLAQC; TENEPDLAQCF; ENEPDLAQCFF; NEPDLAQCFFC;
EPDLAQCFFCF; PDLAQCFFCFK; DLAQCFFCFKE; LAQCFFCFKEL; AQCFFCFKELE;
QCFFCFKELEG; CFFCFKELEGW; FFCFKELEGWE; FCFKELEGWEP; CFKELEGWEPD;
FKELEGWEPDD; KELEGWEPDDD; ELEGWEPDDDP; LEGWEPDDDPI; EGWEPDDDPIE;
GWEPDDDPIEE; WEPDDDPIEEH; EPDDDPIEEHK; PDDDPIEEHKK; DDDPIEEHKKH;
DDPIEEHKKHS; DPIEEHKKHSS; PIEEHKKHSSG; IEEHKKHSSGC; EEHKKHSSGCA;
EHKKHSSGCAF; HKKHSSGCAFL; KKHSSGCAFLS; KHSSGCAFLSV; HSSGCAFLSVK;
SSGCAFLSVKK; SGCAFLSVKKQ; GCAFLSVKKQF; CAFLSVKKQFE; AFLSVKKQFEE;
FLSVKKQFEEL; LSVKKQFEELT; SVKKQFEELTL; VKKQFEELTLG; KKQFEELTLGE;
KQFEELTLGEF; QFEELTLGEFL; FEELTLGEFLK; EELTLGEFLKL; ELTLGEFLKLD;
LTLGEFLKLDR; TLGEFLKLDRE; LGEFLKLDRER; GEFLKLDRERA; EFLKLDRERAK;
FLKLDRERAKN; LKLDRERAKNK; KLDRERAKNKI; LDRERAKNKIA; DRERAKNKIAK;
RERAKNKIAKE; ERAKNKIAKET; RAKNKIAKETN; AKNKIAKETNN; KNKIAKETNNK;
NKIAKETNNKK; KIAKETNNKKK; IAKETNNKKKE; AKETNNKKKEF; KETNNKKKEFE;
ETNNKKKEFEE; TNNKKKEFEET; NNKKKEFEETA; NKKKEFEETAK; KKKEFEETAKK;
KKEFEETAKKV; KEFEETAKKVR; EFEETAKKVRR; FEETAKKVRRA; EETAKKVRRAI;
ETAKKVRRAIE; TAKKVRRAIEQ; AKKVRRAIEQL; KKVRRAIEQLA; KVRRAIEQLAA;
VRRAIEQLAAM; RRAIEQLAAMD

SEQ ID NOS: 47646-48180

Preferred fragments of Mcl-1 capable of interacting with one or more MHC class 2 molecules are listed in table G.

TABLE G

Prediction of cancer antigen Mcl-1 specific MHC class 2 peptide sequences. Prediction of 13-, 14-, 15-, 16-mers using the program displayed in FIG. 2.;

13 mers:

MFGLKRNAVIGLN; FGLKRNAVIGLNL; GLKRNAVIGLNLY; LKRNAVIGLNLYC;
KRNAVIGLNLYCG; RNAVIGLNLYCGG; NAVIGLNLYCGGA; AVIGLNLYCGGAG;
VIGLNLYCGGAGL; IGLNLYCGGAGLG; GLNLYCGGAGLGA; LNLYCGGAGLGAG;
NLYCGGAGLGAGS; LYCGGAGLGAGSG; YCGGAGLGAGSGG; CGGAGLGAGSGGA;
GGAGLGAGSGGAT; GAGLGAGSGGATR; AGLGAGSGGATRP; GLGAGSGGATRPG;
LGAGSGGATRPGG; GAGSGGATRPGGR; AGSGGATRPGGRL; GSGGATRPGGRLL;
SGGATRPGGRLLA; GGATRPGGRLLAT; GATRPGGRLLATE; ATRPGGRLLATEK;
TRPGGRLLATEKE; RPGGRLLATEKEA; PGGRLLATEKEAS; GGRLLATEKEASA;
GRLLATEKEASAR; RLLATEKEASARR; LLATEKEASARRE; LATEKEASARREI;
ATEKEASARREIG; TEKEASARREIGG; EKEASARREIGGG; KEASARREIGGGE;
EASARREIGGGEA; ASARREIGGGEAG; SARREIGGGEAGA; ARREIGGGEAGAV;
RREIGGGEAGAVI; REIGGGEAGAVIG; EIGGGEAGAVIGG; IGGGEAGAVIGGS;
GGGEAGAVIGGSA; GGEAGAVIGGSAG; GEAGAVIGGSAGA; EAGAVIGGSAGAS;
AGAVIGGSAGASP; GAVIGGSAGASPP; AVIGGSAGASPPS; VIGGSAGASPPST;
IGGSAGASPPSTL; GGSAGASPPSTLT; GSAGASPPSTLTP; SAGASPPSTLTPD;
AGASPPSTLTPDS; GASPPSTLTPDSR; ASPPSTLTPDSRR; SPPSTLTPDSRRV;
PPSTLTPDSRRVA; PSTLTPDSRRVAR; STLTPDSRRVARP; TLTPDSRRVARPP;
LTPDSRRVARPPP; TPDSRRVARPPPI; PDSRRVARPPPIG; DSRRVARPPPIGA;
SRRVARPPPIGAE; RRVARPPPIGAEV; RVARPPPIGAEVP; VARPPPIGAEVPD;
ARPPPIGAEVPDV; RPPPIGAEVPDVT; PPPIGAEVPDVTA; PPIGAEVPDVTAT;
PIGAEVPDVTATP; IGAEVPDVTATPA; GAEVPDVTATPAR; AEVPDVTATPARL;
EVPDVTATPARLL; VPDVTATPARLLF; PDVTATPARLLFF; DVTATPARLLFFA;
VTATPARLLFFAP; TATPARLLFFAPT; ATPARLLFFAPTR; TPARLLFFAPTRR;
PARLLFFAPTRRA; ARLLFFAPTRRAA; RLLFFAPTRRAAP; LLFFAPTRRAAPL;
LFFAPTRRAAPLE; FFAPTRRAAPLEE; FAPTRRAAPLEEM; APTRRAAPLEEME;
PTRRAAPLEEMEA; TRRAAPLEEMEAP; RRAAPLEEMEAPA; RAAPLEEMEAPAA;
AAPLEEMEAPAAD; APLEEMEAPAADA; PLEEMEAPAADAI; LEEMEAPAADAIM;
EEMEAPAADAIMS; EMEAPAADAIMSP; MEAPAADAIMSPE; EAPAADAIMSPEE;
APAADAIMSPEEE; PAADAIMSPEEEL; AADAIMSPEEELD; ADAIMSPEEELDG;
DAIMSPEEELDGY; AIMSPEEELDGYE; IMSPEEELDGYEP; MSPEEELDGYEPE;
SPEEELDGYEPEP; PEEELDGYEPEPL; EEELDGYEPEPLG; EELDGYEPEPLGK;
ELDGYEPEPLGKR; LDGYEPEPLGKRP; DGYEPEPLGKRPA; GYEPEPLGKRPAV;
YEPEPLGKRPAVL; EPEPLGKRPAVLP; PEPLGKRPAVLPL; EPLGKRPAVLPLL;
PLGKRPAVLPLLE; LGKRPAVLPLLEL; GKRPAVLPLLELV; KRPAVLPLLELVG;
RPAVLPLLELVGE; PAVLPLLELVGES; AVLPLLELVGESG; VLPLLELVGESGN;
LPLLELVGESGNN; PLLELVGESGNNT; LLELVGESGNNTS; LELVGESGNNTST;
ELVGESGNNTSTD; LVGESGNNTSTDG; VGESGNNTSTDGS; GESGNNTSTDGSL;
ESGNNTSTDGSLP; SGNNTSTDGSLPS; GNNTSTDGSLPST; NNTSTDGSLPSTP;
NTSTDGSLPSTPP; TSTDGSLPSTPPP; STDGSLPSTPPPA; TDGSLPSTPPPAE;
DGSLPSTPPPAEE; GSLPSTPPPAEEE; SLPSTPPPAEEEE; LPSTPPPAEEEED;
PSTPPPAEEEEDD; STPPPAEEEEDDL; TPPPAEEEEDDLY; PPPAEEEEDDLYR;
PPAEEEEDDLYRQ; PAEEEEDDLYRQS; AEEEEDDLYRQSL; EEEEDDLYRQSLE;
EEEDDLYRQSLEI; EEDDLYRQSLEII; EDDLYRQSLEIIS; DDLYRQSLEIISR;
DLYRQSLEIISRY; LYRQSLEIISRYL; YRQSLEIISRYLR; RQSLEIISRYLRE;
QSLEIISRYLREQ; SLEIISRYLREQA; LEIISRYLREQAT; EIISRYLREQATG;
IISRYLREQATGA; ISRYLREQATGAK; SRYLREQATGAKD; RYLREQATGAKDT;
YLREQATGAKDTK; LREQATGAKDTKP; REQATGAKDTKPM; EQATGAKDTKPMG;
QATGAKDTKPMGR; ATGAKDTKPMGRS; TGAKDTKPMGRSG; GAKDTKPMGRSGA;
AKDTKPMGRSGAT; KDTKPMGRSGATS; DTKPMGRSGATSR; TKPMGRSGATSRK;
KPMGRSGATSRKA; PMGRSGATSRKAL; MGRSGATSRKALE; GRSGATSRKALET;
RSGATSRKALETL; SGATSRKALETLR; GATSRKALETLRR; ATSRKALETLRRV;
TSRKALETLRRVG; SRKALETLRRVGD; RKALETLRRVGDG; KALETLRRVGDGV;
ALETLRRVGDGVQ; LETLRRVGDGVQR; ETLRRVGDGVQRN; TLRRVGDGVQRNH;
LRRVGDGVQRNHE; RRVGDGVQRNHET; RVGDGVQRNHETA; VGDGVQRNHETAF;
GDGVQRNHETAFQ; DGVQRNHETAFQG; GVQRNHETAFQGM; VQRNHETAFQGML;
QRNHETAFQGMLR; RNHETAFQGMLRK; NHETAFQGMLRKL; HETAFQGMLRKLD;
ETAFQGMLRKLDI; TAFQGMLRKLDIK; AFQGMLRKLDIKN; FQGMLRKLDIKNE;
QGMLRKLDIKNED; GMLRKLDIKNEDD; MLRKLDIKNEDDV; LRKLDIKNEDDVK;
RKLDIKNEDDVKS; KLDIKNEDDVKSL; LDIKNEDDVKSLS; DIKNEDDVKSLSR;
IKNEDDVKSLSRV; KNEDDVKSLSRVM; NEDDVKSLSRVMI; EDDVKSLSRVMIH;
DDVKSLSRVMIHV; DVKSLSRVMIHVF; VKSLSRVMIHVFS; KSLSRVMIHVFSD;
SLSRVMIHVFSDG; LSRVMIHVFSDGV; SRVMIHVFSDGVT; RVMIHVFSDGVTN;
VMIHVFSDGVTNW; MIHVFSDGVTNWG; IHVFSDGVTNWGR; HVFSDGVTNWGRI;
VFSDGVTNWGRIV; FSDGVTNWGRIVT; SDGVTNWGRIVTL; DGVTNWGRIVTLI;
GVTNWGRIVTLIS; VTNWGRIVTLISF; TNWGRIVTLISFG; NWGRIVTLISFGA;
WGRIVTLISFGAF; GRIVTLISFGAFV; RIVTLISFGAFVA; IVTLISFGAFVAK;
VTLISFGAFVAKH; TLISFGAFVAKHL; LISFGAFVAKHLK; ISFGAFVAKHLKT;
SFGAFVAKHLKTI; FGAFVAKHLKTIN; GAFVAKHLKTINQ; AFVAKHLKTINQE;
FVAKHLKTINQES; VAKHLKTINQESC; AKHLKTINQESCI; KHLKTINQESCIE;
HLKTINQESCIEP; LKTINQESCIEPL; KTINQESCIEPLA; TINQESCIEPLAE;
INQESCIEPLAES; NQESCIEPLAESI; QESCIEPLAESIT; ESCIEPLAESITD;

TABLE G-continued

Prediction of cancer antigen Mcl-1 specific MHC class 2 peptide sequences. Prediction of 13-, 14-, 15-, 16-mers using the program displayed in FIG. 2.;

SCIEPLAESITDV; CIEPLAESITDVL; IEPLAESITDVLV; EPLAESITDVLVR;
PLAESITDVLVRT; LAESITDVLVRTK; AESITDVLVRTKR; ESITDVLVRTKRD;
SITDVLVRTKRDW; ITDVLVRTKRDWL; TDVLVRTKRDWLV; DVLVRTKRDWLVK;
VLVRTKRDWLVKQ; LVRTKRDWLVKQR; VRTKRDWLVKQRG; RTKRDWLVKQRGW;
TKRDWLVKQRGWD; KRDWLVKQRGWDG; RDWLVKQRGWDGF; DWLVKQRGWDGFV;
WLVKQRGWDGFVE; LVKQRGWDGFVEF; VKQRGWDGFVEFF; KQRGWDGFVEFFH;
QRGWDGFVEFFHV; RGWDGFVEFFHVE; GWDGFVEFFHVED; WDGFVEFFHVEDL;
DGFVEFFHVEDLE; GFVEFFHVEDLEG; FVEFFHVEDLEGG; VEFFHVEDLEGGI;
EFFHVEDLEGGIR; FFHVEDLEGGIRN; FHVEDLEGGIRNV; HVEDLEGGIRNVL;
VEDLEGGIRNVLL; EDLEGGIRNVLLA; DLEGGIRNVLLAF; LEGGIRNVLLAFA;
EGGIRNVLLAFAG; GGIRNVLLAFAGV; GIRNVLLAFAGVA; IRNVLLAFAGVAG;
RNVLLAFAGVAGV; NVLLAFAGVAGVG; VLLAFAGVAGVGA; LLAFAGVAGVGAG;
LAFAGVAGVGAGL; AFAGVAGVGAGLA; FAGVAGVGAGLAY; AGVAGVGAGLAYL;
GVAGVGAGLAYLI; VAGVGAGLAYLIR 14 mers:

MFGLKRNAVIGLNL; FGLKRNAVIGLNLY; GLKRNAVIGLNLYC; LKRNAVIGLNLYCG;
KRNAVIGLNLYCGG; RNAVIGLNLYCGGA; NAVIGLNLYCGGAG; AVIGLNLYCGGAGL;
VIGLNLYCGGAGLG; IGLNLYCGGAGLGA; GLNLYCGGAGLGAG; LNLYCGGAGLGAGS;
NLYCGGAGLGAGSG; LYCGGAGLGAGSGG; YCGGAGLGAGSGGA; CGGAGLGAGSGGAT;
GGAGLGAGSGGATR; GAGLGAGSGGATRP; AGLGAGSGGATRPG; GLGAGSGGATRPGG;
LGAGSGGATRPGGR; GAGSGGATRPGGRL; AGSGGATRPGGRLL; GSGGATRPGGRLLA;
SGGATRPGGRLLAT; GGATRPGGRLLATE; GATRPGGRLLATEK; ATRPGGRLLATEKE;
TRPGGRLLATEKEA; RPGGRLLATEKEAS; PGGRLLATEKEASA; GGRLLATEKEASAR;
GRLLATEKEASARR; RLLATEKEASARRE; LLATEKEASARREI; LATEKEASARREIG;
ATEKEASARREIGG; TEKEASARREIGGG; EKEASARREIGGGE; KEASARREIGGGEA;
EASARREIGGGEAG; ASARREIGGGEAGA; SARREIGGGEAGAV; ARREIGGGEAGAVI;
RREIGGGEAGAVIG; REIGGGEAGAVIGG; EIGGGEAGAVIGGS; IGGGEAGAVIGGSA;
GGGEAGAVIGGSAG; GGEAGAVIGGSAGA; GEAGAVIGGSAGAS; EAGAVIGGSAGASP;
AGAVIGGSAGASPP; GAVIGGSAGASPPS; AVIGGSAGASPPST; VIGGSAGASPPSTL;
IGGSAGASPPSTLT; GGSAGASPPSTLTP; GSAGASPPSTLTPD; SAGASPPSTLTPDS;
AGASPPSTLTPDSR; GASPPSTLTPDSRR; ASPPSTLTPDSRRV; SPPSTLTPDSRRVA;
PPSTLTPDSRRVAR; PSTLTPDSRRVARP; STLTPDSRRVARPP; TLTPDSRRVARPPP;
LTPDSRRVARPPPI; TPDSRRVARPPPIG; PDSRRVARPPPIGA; DSRRVARPPPIGAE;
SRRVARPPPIGAEV; RRVARPPPIGAEVP; RVARPPPIGAEVPD; VARPPPIGAEVPDV;
ARPPPIGAEVPDVT; RPPPIGAEVPDVTA; PPPIGAEVPDVTAT; PPIGAEVPDVTATP;
PIGAEVPDVTATPA; IGAEVPDVTATPAR; GAEVPDVTATPARL; AEVPDVTATPARLL;
EVPDVTATPARLLF; VPDVTATPARLLFF; PDVTATPARLLFFA; DVTATPARLLFFAP;
VTATPARLLFFAPT; TATPARLLFFAPTR; ATPARLLFFAPTRR; TPARLLFFAPTRRA;
PARLLFFAPTRRAA; ARLLFFAPTRRAAP; RLLFFAPTRRAAPL; LLFFAPTRRAAPLE;
LFFAPTRRAAPLEE; FFAPTRRAAPLEEM; FAPTRRAAPLEEME; APTRRAAPLEEMEA;
PTRRAAPLEEMEAP; TRRAAPLEEMEAPA; RRAAPLEEMEAPAA; RAAPLEEMEAPAAD;
AAPLEEMEAPAADA; APLEEMEAPAADAI; PLEEMEAPAADAIM; LEEMEAPAADAIMS;
EEMEAPAADAIMSP; EMEAPAADAIMSPE; MEAPAADAIMSPEE; EAPAADAIMSPEEE;
APAADAIMSPEEEL; PAADAIMSPEEELD; AADAIMSPEEELDG; ADAIMSPEEELDGY;
DAIMSPEEELDGYE; AIMSPEEELDGYEP; IMSPEEELDGYEPE; MSPEEELDGYEPEP;
SPEEELDGYEPEPL; PEEELDGYEPEPLG; EEELDGYEPEPLGK; EELDGYEPEPLGKR;
ELDGYEPEPLGKRP; LDGYEPEPLGKRPA; DGYEPEPLGKRPAV; GYEPEPLGKRPAVL;
YEPEPLGKRPAVLP; EPEPLGKRPAVLPL; PEPLGKRPAVLPLL; EPLGKRPAVLPLLE;
PLGKRPAVLPLLEL; LGKRPAVLPLLELV; GKRPAVLPLLELVG; KRPAVLPLLELVGE;
RPAVLPLLELVGES; PAVLPLLELVGESG; AVLPLLELVGESGN; VLPLLELVGESGNN;
LPLLELVGESGNNT; PLLELVGESGNNTS; LLELVGESGNNTST; LELVGESGNNTSTD;
ELVGESGNNTSTDG; LVGESGNNTSTDGS; VGESGNNTSTDGSL; GESGNNTSTDGSLP;
ESGNNTSTDGSLPS; SGNNTSTDGSLPST; GNNTSTDGSLPSTP; NNTSTDGSLPSTPP;
NTSTDGSLPSTPPP; TSTDGSLPSTPPPA; STDGSLPSTPPPAE; TDGSLPSTPPPAEE;
DGSLPSTPPPAEEE; GSLPSTPPPAEEEE; SLPSTPPPAEEEED; LPSTPPPAEEEEDD;
PSTPPPAEEEEDDL; STPPPAEEEEDDLY; TPPPAEEEEDDLYR; PPPAEEEEDDLYRQ;
PPAEEEEDDLYRQS; PAEEEEDDLYRQSL; AEEEEDDLYRQSLE; EEEEDDLYRQSLEI;
EEEDDLYRQSLEII; EEDDLYRQSLEIIS; EDDLYRQSLEIISR; DDLYRQSLEIISRY;
DLYRQSLEIISRYL; LYRQSLEIISRYLR; YRQSLEIISRYLRE; RQSLEIISRYLREQ;
QSLEIISRYLREQA; SLEIISRYLREQAT; LEIISRYLREQATG; EIISRYLREQATGA;
IISRYLREQATGAK; ISRYLREQATGAKD; SRYLREQATGAKDT; RYLREQATGAKDTK;
YLREQATGAKDTKP; LREQATGAKDTKPM; REQATGAKDTKPMG; EQATGAKDTKPMGR;
QATGAKDTKPMGRS; ATGAKDTKPMGRSG; TGAKDTKPMGRSGA; GAKDTKPMGRSGAT;
AKDTKPMGRSGATS; KDTKPMGRSGATSR; DTKPMGRSGATSRK; TKPMGRSGATSRKA;
KPMGRSGATSRKAL; PMGRSGATSRKALE; MGRSGATSRKALET; GRSGATSRKALETL;
RSGATSRKALETLR; SGATSRKALETLRR; GATSRKALETLRRV; ATSRKALETLRRVG;
TSRKALETLRRVGD; SRKALETLRRVGDG; RKALETLRRVGDGV; KALETLRRVGDGVQ;
ALETLRRVGDGVQR; LETLRRVGDGVQRN; ETLRRVGDGVQRNH; TLRRVGDGVQRNHE;
LRRVGDGVQRNHET; RRVGDGVQRNHETA; RVGDGVQRNHETAF; VGDGVQRNHETAFQ;
GDGVQRNHETAFQG; DGVQRNHETAFQGM; GVQRNHETAFQGML; VQRNHETAFQGMLR;
QRNHETAFQGMLRK; RNHETAFQGMLRKL; NHETAFQGMLRKLD; HETAFQGMLRKLDI;
ETAFQGMLRKLDIK; TAFQGMLRKLDIKN; AFQGMLRKLDIKNE; FQGMLRKLDIKNED;
QGMLRKLDIKNEDD; GMLRKLDIKNEDDV; MLRKLDIKNEDDVK; LRKLDIKNEDDVKS;
RKLDIKNEDDVKSL; KLDIKNEDDVKSLS; LDIKNEDDVKSLSR; DIKNEDDVKSLSRV;

TABLE G-continued

Prediction of cancer antigen Mcl-1 specific MHC class 2 peptide sequences. Prediction of 13-, 14-, 15-, 16-mers using the program displayed in FIG. 2.;

IKNEDDVKSLSRVM; KNEDDVKSLSRVMI; NEDDVKSLSRVMIH; EDDVKSLSRVMIHV;
DDVKSLSRVMIHVF; DVKSLSRVMIHVFS; VKSLSRVMIHVFSD; KSLSRVMIHVFSDG;
SLSRVMIHVFSDGV; LSRVMIHVFSDGVT; SRVMIHVFSDGVTN; RVMIHVFSDGVTNW;
VMIHVFSDGVTNWG; MIHVFSDGVTNWGR; IHVFSDGVTNWGRI; HVFSDGVTNWGRIV;
VFSDGVTNWGRIVT; FSDGVTNWGRIVTL; SDGVTNWGRIVTLI; DGVTNWGRIVTLIS;
GVTNWGRIVTLISF; VTNWGRIVTLISFG; TNWGRIVTLISFGA; NWGRIVTLISFGAF;
WGRIVTLISFGAFV; GRIVTLISFGAFVA; RIVTLISFGAFVAK; IVTLISFGAFVAKH;
VTLISFGAFVAKHL; TLISFGAFVAKHLK; LISFGAFVAKHLKT; ISFGAFVAKHLKTI;
SFGAFVAKHLKTIN; FGAFVAKHLKTINQ; GAFVAKHLKTINQE; AFVAKHLKTINQES;
FVAKHLKTINQESC; VAKHLKTINQESCI; AKHLKTINQESCIE; KHLKTINQESCIEP;
HLKTINQESCIEPL; LKTINQESCIEPLA; KTINQESCIEPLAE; TINQESCIEPLAES;
INQESCIEPLAESI; NQESCIEPLAESIT; QESCIEPLAESITD; ESCIEPLAESITDV;
SCIEPLAESITDVL; CIEPLAESITDVLV; IEPLAESITDVLVR; EPLAESITDVLVRT;
PLAESITDVLVRTK; LAESITDVLVRTKR; AESITDVLVRTKRD; ESITDVLVRTKRDW;
SITDVLVRTKRDWL; ITDVLVRTKRDWLV; TDVLVRTKRDWLVK; DVLVRTKRDWLVKQ;
VLVRTKRDWLVKQR; LVRTKRDWLVKQRG; VRTKRDWLVKQRGW; RTKRDWLVKQRGWD;
TKRDWLVKQRGWDG; KRDWLVKQRGWDGF; RDWLVKQRGWDGFV; DWLVKQRGWDGFVE;
WLVKQRGWDGFVEF; LVKQRGWDGFVEFF; VKQRGWDGFVEFFH; KQRGWDGFVEFFHV;
QRGWDGFVEFFHVE; RGWDGFVEFFHVED; GWDGFVEFFHVEDL; WDGFVEFFHVEDLE;
DGFVEFFHVEDLEG; GFVEFFHVEDLEGG; FVEFFHVEDLEGGI; VEFFHVEDLEGGIR;
EFFHVEDLEGGIRN; FFHVEDLEGGIRNV; FHVEDLEGGIRNVL; HVEDLEGGIRNVLL;
VEDLEGGIRNVLLA; EDLEGGIRNVLLAF; DLEGGIRNVLLAFA; LEGGIRNVLLAFAG;
EGGIRNVLLAFAGV; GGIRNVLLAFAGVA; GIRNVLLAFAGVAG; IRNVLLAFAGVAGV;
RNVLLAFAGVAGVG; NVLLAFAGVAGVGA; VLLAFAGVAGVGAG; LLAFAGVAGVGAGL;
LAFAGVAGVGAGLA; AFAGVAGVGAGLAY; FAGVAGVGAGLAYL; AGVAGVGAGLAYLI;
GVAGVGAGLAYLIR 15 mers:

MFGLKRNAVIGLNLY; FGLKRNAVIGLNLYC; GLKRNAVIGLNLYCG;
LKRNAVIGLNLYCGG; KRNAVIGLNLYCGGA; RNAVIGLNLYCGGAG;
NAVIGLNLYCGGAGL; AVIGLNLYCGGAGLG; VIGLNLYCGGAGLGA;
IGLNLYCGGAGLGAG; GLNLYCGGAGLGAGS; LNLYCGGAGLGAGSG;
NLYCGGAGLGAGSGG; LYCGGAGLGAGSGGA; YCGGAGLGAGSGGAT;
CGGAGLGAGSGGATR; GGAGLGAGSGGATRP; GAGLGAGSGGATRPG;
AGLGAGSGGATRPGG; GLGAGSGGATRPGGR; LGAGSGGATRPGGRL;
GAGSGGATRPGGRLL; AGSGGATRPGGRLLA; GSGGATRPGGRLLAT;
SGGATRPGGRLLATE; GGATRPGGRLLATEK; GATRPGGRLLATEKE;
ATRPGGRLLATEKEA; TRPGGRLLATEKEAS; RPGGRLLATEKEASA;
PGGRLLATEKEASAR; GGRLLATEKEASARR; GRLLATEKEASARRE;
RLLATEKEASARREI; LLATEKEASARREIG; LATEKEASARREIGG;
ATEKEASARREIGGG; TEKEASARREIGGGE; EKEASARREIGGGEA;
KEASARREIGGGEAG; EASARREIGGGEAGA; ASARREIGGGEAGAV;
SARREIGGGEAGAVI; ARREIGGGEAGAVIG; RREIGGGEAGAVIGG;
REIGGGEAGAVIGGS; EIGGGEAGAVIGGSA; IGGGEAGAVIGGSAG;
GGGEAGAVIGGSAGA; GGEAGAVIGGSAGAS; GEAGAVIGGSAGASP;
EAGAVIGGSAGASPP; AGAVIGGSAGASPPS; GAVIGGSAGASPPST;
AVIGGSAGASPPSTL; VIGGSAGASPPSTLT; IGGSAGASPPSTLTP;
GGSAGASPPSTLTPD; GSAGASPPSTLTPDS; SAGASPPSTLTPDSR;
AGASPPSTLTPDSRR; GASPPSTLTPDSRRV; ASPPSTLTPDSRRVA;
SPPSTLTPDSRRVAR; PPSTLTPDSRRVARP; PSTLTPDSRRVARPP;
STLTPDSRRVARPPP; TLTPDSRRVARPPPI; LTPDSRRVARPPPIG;
TPDSRRVARPPPIGA; PDSRRVARPPPIGAE; DSRRVARPPPIGAEV;
SRRVARPPPIGAEVP; RRVARPPPIGAEVPD; RVARPPPIGAEVPDV;
VARPPPIGAEVPDVT; ARPPPIGAEVPDVTA; RPPPIGAEVPDVTAT;
PPPIGAEVPDVTATP; PPIGAEVPDVTATPA; PIGAEVPDVTATPAR;
IGAEVPDVTATPARL; GAEVPDVTATPARLL; AEVPDVTATPARLLF;
EVPDVTATPARLLFF; VPDVTATPARLLFFA; PDVTATPARLLFFAP;
DVTATPARLLFFAPT; VTATPARLLFFAPTR; TATPARLLFFAPTRR;
ATPARLLFFAPTRRA; TPARLLFFAPTRRAA; PARLLFFAPTRRAAP;
ARLLFFAPTRRAAPL; RLLFFAPTRRAAPLE; LLFFAPTRRAAPLEE;
LFFAPTRRAAPLEEM; FFAPTRRAAPLEEME; FAPTRRAAPLEEMEA;
APTRRAAPLEEMEAP; PTRRAAPLEEMEAPA; TRRAAPLEEMEAPAA;
RRAAPLEEMEAPAAD; RAAPLEEMEAPAADA; AAPLEEMEAPAADAI;
APLEEMEAPAADAIM; PLEEMEAPAADAIMS; LEEMEAPAADAIMSP;
EEMEAPAADAIMSPE; EMEAPAADAIMSPEE; MEAPAADAIMSPEEE;
EAPAADAIMSPEEEL; APAADAIMSPEEELD; PAADAIMSPEEELDG;
AADAIMSPEEELDGY; ADAIMSPEEELDGYE; DAIMSPEEELDGYEP;
AIMSPEEELDGYEPE; IMSPEEELDGYEPEP; MSPEEELDGYEPEPL;
SPEEELDGYEPEPLG; PEEELDGYEPEPLGK; EEELDGYEPEPLGKR;
EELDGYEPEPLGKRP; ELDGYEPEPLGKRPA; LDGYEPEPLGKRPAV;
DGYEPEPLGKRPAVL; GYEPEPLGKRPAVLP; YEPEPLGKRPAVLPL;
EPEPLGKRPAVLPLL; PEPLGKRPAVLPLLE; EPLGKRPAVLPLLEL;
PLGKRPAVLPLLELV; LGKRPAVLPLLELVG; GKRPAVLPLLELVGE;
KRPAVLPLLELVGES; RPAVLPLLELVGESG; PAVLPLLELVGESGN;
AVLPLLELVGESGNN; VLPLLELVGESGNNT; LPLLELVGESGNNTS;

TABLE G-continued

Prediction of cancer antigen Mcl-1 specific MHC class 2 peptide sequences. Prediction of 13-, 14-, 15-, 16-mers using the program displayed in FIG. 2.;

PLLELVGESGNNTST; LLELVGESGNNTSTD; LELVGESGNNTSTDG;
ELVGESGNNTSTDGS; LVGESGNNTSTDGSL; VGESGNNTSTDGSLP;
GESGNNTSTDGSLPS; ESGNNTSTDGSLPST; SGNNTSTDGSLPSTP;
GNNTSTDGSLPSTPP; NNTSTDGSLPSTPPP; NTSTDGSLPSTPPPA;
TSTDGSLPSTPPPAE; STDGSLPSTPPPAEE; TDGSLPSTPPPAEEE;
DGSLPSTPPPAEEEE; GSLPSTPPPAEEEED; SLPSTPPPAEEEEDD;
LPSTPPPAEEEEDDL; PSTPPPAEEEEDDLY; STPPPAEEEEDDLYR;
TPPPAEEEEDDLYRQ; PPPAEEEEDDLYRQS; PPAEEEEDDLYRQSL;
PAEEEEDDLYRQSLE; AEEEEDDLYRQSLEI; EEEEDDLYRQSLEII;
EEEDDLYRQSLEIIS; EEDDLYRQSLEIISR; EDDLYRQSLEIISRY;
DDLYRQSLEIISRYL; DLYRQSLEIISRYLR; LYRQSLEIISRYLRE;
YRQSLEIISRYLREQ; RQSLEIISRYLREQA; QSLEIISRYLREQAT;
SLEIISRYLREQATG; LEIISRYLREQATGA; EIISRYLREQATGAK;
IISRYLREQATGAKD; ISRYLREQATGAKDT; SRYLREQATGAKDTK;
RYLREQATGAKDTKP; YLREQATGAKDTKPM; LREQATGAKDTKPMG;
REQATGAKDTKPMGR; EQATGAKDTKPMGRS; QATGAKDTKPMGRSG;
ATGAKDTKPMGRSGA; TGAKDTKPMGRSGAT; GAKDTKPMGRSGATS;
AKDTKPMGRSGATSR; KDTKPMGRSGATSRK; DTKPMGRSGATSRKA;
TKPMGRSGATSRKAL; KPMGRSGATSRKALE; PMGRSGATSRKALET;
MGRSGATSRKALETL; GRSGATSRKALETLR; RSGATSRKALETLRR;
SGATSRKALETLRRV; GATSRKALETLRRVG; ATSRKALETLRRVGD;
TSRKALETLRRVGDG; SRKALETLRRVGDGV; RKALETLRRVGDGVQ;
KALETLRRVGDGVQR; ALETLRRVGDGVQRN; LETLRRVGDGVQRNH;
ETLRRVGDGVQRNHE; TLRRVGDGVQRNHET; LRRVGDGVQRNHETA;
RRVGDGVQRNHETAF; RVGDGVQRNHETAFQ; VGDGVQRNHETAFQG;
GDGVQRNHETAFQGM; DGVQRNHETAFQGML; GVQRNHETAFQGMLR;
VQRNHETAFQGMLRK; QRNHETAFQGMLRKL; RNHETAFQGMLRKLD;
NHETAFQGMLRKLDI; HETAFQGMLRKLDIK; ETAFQGMLRKLDIKN;
TAFQGMLRKLDIKNE; AFQGMLRKLDIKNED; FQGMLRKLDIKNEDD;
QGMLRKLDIKNEDDV; GMLRKLDIKNEDDVK; MLRKLDIKNEDDVKS;
LRKLDIKNEDDVKSL; RKLDIKNEDDVKSLS; KLDIKNEDDVKSLSR;
LDIKNEDDVKSLSRV; DIKNEDDVKSLSRVM; IKNEDDVKSLSRVMI;
KNEDDVKSLSRVMIH; NEDDVKSLSRVMIHV; EDDVKSLSRVMIHVF;
DDVKSLSRVMIHVFS; DVKSLSRVMIHVFSD; VKSLSRVMIHVFSDG;
KSLSRVMIHVFSDGV; SLSRVMIHVFSDGVT; LSRVMIHVFSDGVTN;
SRVMIHVFSDGVTNW; RVMIHVFSDGVTNWG; VMIHVFSDGVTNWGR;
MIHVFSDGVTNWGRI; IHVFSDGVTNWGRIV; HVFSDGVTNWGRIVT;
VFSDGVTNWGRIVTL; FSDGVTNWGRIVTLI; SDGVTNWGRIVTLIS;
DGVTNWGRIVTLISF; GVTNWGRIVTLISFG; VTNWGRIVTLISFGA;
TNWGRIVTLISFGAF; NWGRIVTLISFGAFV; WGRIVTLISFGAFVA;
GRIVTLISFGAFVAK; RIVTLISFGAFVAKH; IVTLISFGAFVAKHL;
VTLISFGAFVAKHLK; TLISFGAFVAKHLKT; LISFGAFVAKHLKTI;
ISFGAFVAKHLKTIN; SFGAFVAKHLKTINQ; FGAFVAKHLKTINQE;
GAFVAKHLKTINQES; AFVAKHLKTINQESC; FVAKHLKTINQESCI;
VAKHLKTINQESCIE; AKHLKTINQESCIEP; KHLKTINQESCIEPL;
HLKTINQESCIEPLA; LKTINQESCIEPLAE; KTINQESCIEPLAES;
TINQESCIEPLAESI; INQESCIEPLAESIT; NQESCIEPLAESITD;
QESCIEPLAESITDV; ESCIEPLAESITDVL; SCIEPLAESITDVLV;
CIEPLAESITDVLVR; IEPLAESITDVLVRT; EPLAESITDVLVRTK;
PLAESITDVLVRTKR; LAESITDVLVRTKRD; AESITDVLVRTKRDW;
ESITDVLVRTKRDWL; SITDVLVRTKRDWLV; ITDVLVRTKRDWLVK;
TDVLVRTKRDWLVKQ; DVLVRTKRDWLVKQR; VLVRTKRDWLVKQRG;
LVRTKRDWLVKQRGW; VRTKRDWLVKQRGWD; RTKRDWLVKQRGWDG;
TKRDWLVKQRGWDGF; KRDWLVKQRGWDGFV; RDWLVKQRGWDGFVE;
DWLVKQRGWDGFVEF; WLVKQRGWDGFVEFF; LVKQRGWDGFVEFFH;
VKQRGWDGFVEFFHV; KQRGWDGFVEFFHVE; QRGWDGFVEFFHVED;
RGWDGFVEFFHVEDL; GWDGFVEFFHVEDLE; WDGFVEFFHVEDLEG;
DGFVEFFHVEDLEGG; GFVEFFHVEDLEGGI; FVEFFHVEDLEGGIR;
VEFFHVEDLEGGIRN; EFFHVEDLEGGIRNV; FFHVEDLEGGIRNVL;
FHVEDLEGGIRNVLL; HVEDLEGGIRNVLLA; VEDLEGGIRNVLLAF;
EDLEGGIRNVLLAFA; DLEGGIRNVLLAFAG; LEGGIRNVLLAFAGV;
EGGIRNVLLAFAGVA; GGIRNVLLAFAGVAG; GIRNVLLAFAGVAGV;
IRNVLLAFAGVAGVG; RNVLLAFAGVAGVGA; NVLLAFAGVAGVGAG;
VLLAFAGVAGVGAGL; LLAFAGVAGVGAGLA; LAFAGVAGVGAGLAY;
AFAGVAGVGAGLAYL; FAGVAGVGAGLAYLI; AGVAGVGAGLAYLIR 16 mers:

MFGLKRNAVIGLNLYC; FGLKRNAVIGLNLYCG; GLKRNAVIGLNLYCGG;
LKRNAVIGLNLYCGGA; KRNAVIGLNLYCGGAG; RNAVIGLNLYCGGAGL;
NAVIGLNLYCGGAGLG; AVIGLNLYCGGAGLGA; VIGLNLYCGGAGLGAG;
IGLNLYCGGAGLGAGS; GLNLYCGGAGLGAGSG; LNLYCGGAGLGAGSGG;
NLYCGGAGLGAGSGGA; LYCGGAGLGAGSGGAT; YCGGAGLGAGSGGATR;
CGGAGLGAGSGGATRP; GGAGLGAGSGGATRPG; GAGLGAGSGGATRPGG;
AGLGAGSGGATRPGGR; GLGAGSGGATRPGGRL; LGAGSGGATRPGGRLL;
GAGSGGATRPGGRLLA; AGSGGATRPGGRLLAT; GSGGATRPGGRLLATE;

TABLE G-continued

Prediction of cancer antigen Mcl-1 specific MHC class 2 peptide sequences. Prediction of 13-, 14-, 15-, 16-mers using the program displayed in FIG. 2.;

SGGATRPGGRLLATEK; GGATRPGGRLLATEKE; GATRPGGRLLATEKEA;
ATRPGGRLLATEKEAS; TRPGGRLLATEKEASA; RPGGRLLATEKEASAR;
PGGRLLATEKEASARR; GGRLLATEKEASARRE; GRLLATEKEASARREI;
RLLATEKEASARREIG; LLATEKEASARREIGG; LATEKEASARREIGGG;
ATEKEASARREIGGGE; TEKEASARREIGGGEA; EKEASARREIGGGEAG;
KEASARREIGGGEAGA; EASARREIGGGEAGAV; ASARREIGGGEAGAVI;
SARREIGGGEAGAVIG; ARREIGGGEAGAVIGG; RREIGGGEAGAVIGGS;
REIGGGEAGAVIGGSA; EIGGGEAGAVIGGSAG; IGGGEAGAVIGGSAGA;
GGGEAGAVIGGSAGAS; GGEAGAVIGGSAGASP; GEAGAVIGGSAGASPP;
EAGAVIGGSAGASPPS; AGAVIGGSAGASPPST; GAVIGGSAGASPPSTL;
AVIGGSAGASPPSTLT; VIGGSAGASPPSTLTP; IGGSAGASPPSTLTPD;
GGSAGASPPSTLTPDS; GSAGASPPSTLTPDSR; SAGASPPSTLTPDSRR;
AGASPPSTLTPDSRRV; GASPPSTLTPDSRRVA; ASPPSTLTPDSRRVAR;
SPPSTLTPDSRRVARP; PPSTLTPDSRRVARPP; PSTLTPDSRRVARPPP;
STLTPDSRRVARPPPI; TLTPDSRRVARPPPIG; LTPDSRRVARPPPIGA;
TPDSRRVARPPPIGAE; PDSRRVARPPPIGAEV; DSRRVARPPPIGAEVP;
SRRVARPPPIGAEVPD; RRVARPPPIGAEVPDV; RVARPPPIGAEVPDVT;
VARPPPIGAEVPDVTA; ARPPPIGAEVPDVTAT; RPPPIGAEVPDVTATP;
PPPIGAEVPDVTATPA; PPIGAEVPDVTATPAR; PIGAEVPDVTATPARL;
IGAEVPDVTATPARLL; GAEVPDVTATPARLLF; AEVPDVTATPARLLFF;
EVPDVTATPARLLFFA; VPDVTATPARLLFFAP; PDVTATPARLLFFAPT;
DVTATPARLLFFAPTR; VTATPARLLFFAPTRR; TATPARLLFFAPTRRA;
ATPARLLFFAPTRRAA; TPARLLFFAPTRRAAP; PARLLFFAPTRRAAPL;
ARLLFFAPTRRAAPLE; RLLFFAPTRRAAPLEE; LLFFAPTRRAAPLEEM;
LFFAPTRRAAPLEEME; FFAPTRRAAPLEEMEA; FAPTRRAAPLEEMEAP;
APTRRAAPLEEMEAPA; PTRRAAPLEEMEAPAA; TRRAAPLEEMEAPAAD;
RRAAPLEEMEAPAADA; RAAPLEEMEAPAADAI; AAPLEEMEAPAADAIM;
APLEEMEAPAADAIMS; PLEEMEAPAADAIMSP; LEEMEAPAADAIMSPE;
EEMEAPAADAIMSPEE; EMEAPAADAIMSPEEE; MEAPAADAIMSPEEEL;
EAPAADAIMSPEEELD; APAADAIMSPEEELDG; PAADAIMSPEEELDGY;
AADAIMSPEEELDGYE; ADAIMSPEEELDGYEP; DAIMSPEEELDGYEPE;
AIMSPEEELDGYEPEP; IMSPEEELDGYEPEPL; MSPEEELDGYEPEPLG;
SPEEELDGYEPEPLGK; PEEELDGYEPEPLGKR; EEELDGYEPEPLGKRP;
EELDGYEPEPLGKRPA; ELDGYEPEPLGKRPAV; LDGYEPEPLGKRPAVL;
DGYEPEPLGKRPAVLP; GYEPEPLGKRPAVLPL; YEPEPLGKRPAVLPLL;
EPEPLGKRPAVLPLLE; PEPLGKRPAVLPLLEL; EPLGKRPAVLPLLELV;
PLGKRPAVLPLLELVG; LGKRPAVLPLLELVGE; GKRPAVLPLLELVGES;
KRPAVLPLLELVGESG; RPAVLPLLELVGESGN; PAVLPLLELVGESGNN;
AVLPLLELVGESGNNT; VLPLLELVGESGNNTS; LPLLELVGESGNNTST;
PLLELVGESGNNTSTD; LLELVGESGNNTSTDG; LELVGESGNNTSTDGS;
ELVGESGNNTSTDGSL; LVGESGNNTSTDGSLP; VGESGNNTSTDGSLPS;
GESGNNTSTDGSLPST; ESGNNTSTDGSLPSTP; SGNNTSTDGSLPSTPP;
GNNTSTDGSLPSTPPP; NNTSTDGSLPSTPPPA; NTSTDGSLPSTPPPAE;
TSTDGSLPSTPPPAEE; STDGSLPSTPPPAEEE; TDGSLPSTPPPAEEEE;
DGSLPSTPPPAEEEED; GSLPSTPPPAEEEEDD; SLPSTPPPAEEEEDDL;
LPSTPPPAEEEEDDLY; PSTPPPAEEEEDDLYR; STPPPAEEEEDDLYRQ;
TPPPAEEEEDDLYRQS; PPPAEEEEDDLYRQSL; PPAEEEEDDLYRQSLE;
PAEEEEDDLYRQSLEI; AEEEEDDLYRQSLEII; EEEEDDLYRQSLEIIS;
EEEDDLYRQSLEIISR; EEDDLYRQSLEIISRY; EDDLYRQSLEIISRYL;
DDLYRQSLEIISRYLR; DLYRQSLEIISRYLRE; LYRQSLEIISRYLREQ;
YRQSLEIISRYLREQA; RQSLEIISRYLREQAT; QSLEIISRYLREQATG;
SLEIISRYLREQATGA; LEIISRYLREQATGAK; EIISRYLREQATGAKD;
IISRYLREQATGAKDT; ISRYLREQATGAKDTK; SRYLREQATGAKDTKP;
RYLREQATGAKDTKPM; YLREQATGAKDTKPMG; LREQATGAKDTKPMGR;
REQATGAKDTKPMGRS; EQATGAKDTKPMGRSG; QATGAKDTKPMGRSGA;
ATGAKDTKPMGRSGAT; TGAKDTKPMGRSGATS; GAKDTKPMGRSGATSR;
AKDTKPMGRSGATSRK; KDTKPMGRSGATSRKA; DTKPMGRSGATSRKAL;
TKPMGRSGATSRKALE; KPMGRSGATSRKALET; PMGRSGATSRKALETL;
MGRSGATSRKALETLR; GRSGATSRKALETLRR; RSGATSRKALETLRRV;
SGATSRKALETLRRVG; GATSRKALETLRRVGD; ATSRKALETLRRVGDG;
TSRKALETLRRVGDGV; SRKALETLRRVGDGVQ; RKALETLRRVGDGVQR;
KALETLRRVGDGVQRN; ALETLRRVGDGVQRNH; LETLRRVGDGVQRNHE;
ETLRRVGDGVQRNHET; TLRRVGDGVQRNHETA; LRRVGDGVQRNHETAF;
RRVGDGVQRNHETAFQ; RVGDGVQRNHETAFQG; VGDGVQRNHETAFQGM;
GDGVQRNHETAFQGML; DGVQRNHETAFQGMLR; GVQRNHETAFQGMLRK;
VQRNHETAFQGMLRKL; QRNHETAFQGMLRKLD; RNHETAFQGMLRKLDI;
NHETAFQGMLRKLDIK; HETAFQGMLRKLDIKN; ETAFQGMLRKLDIKNE;
TAFQGMLRKLDIKNED; AFQGMLRKLDIKNEDD; FQGMLRKLDIKNEDDV;
QGMLRKLDIKNEDDVK; GMLRKLDIKNEDDVKS; MLRKLDIKNEDDVKSL;
LRKLDIKNEDDVKSLS; RKLDIKNEDDVKSLSR; KLDIKNEDDVKSLSRV;
LDIKNEDDVKSLSRVM; DIKNEDDVKSLSRVMI; IKNEDDVKSLSRVMIH;
KNEDDVKSLSRVMIHV; NEDDVKSLSRVMIHVF; EDDVKSLSRVMIHVFS;
DDVKSLSRVMIHVFSD; DVKSLSRVMIHVFSDG; VKSLSRVMIHVFSDGV;
KSLSRVMIHVFSDGVT; SLSRVMIHVFSDGVTN; LSRVMIHVFSDGVTNW;
SRVMIHVFSDGVTNWG; RVMIHVFSDGVTNWGR; VMIHVFSDGVTNWGRI;
MIHVFSDGVTNWGRIV; IHVFSDGVTNWGRIVT; HVFSDGVTNWGRIVTL;

TABLE G-continued

Prediction of cancer antigen Mcl-1 specific MHC class 2
peptide sequences. Prediction of 13-, 14-, 15-, 16-mers using
the program displayed in FIG. 2.;

VFSDGVTNWGRIVTLI; FSDGVTNWGRIVTLIS; SDGVTNWGRIVTLISF;
DGVTNWGRIVTLISFG; GVTNWGRIVTLISFGA; VTNWGRIVTLISFGAF;
TNWGRIVTLISFGAFV; NWGRIVTLISFGAFVA; WGRIVTLISFGAFVAK;
GRIVTLISFGAFVAKH; RIVTLISFGAFVAKHL; IVTLISFGAFVAKHLK;
VTLISFGAFVAKHLKT; TLISFGAFVAKHLKTI; LISFGAFVAKHLKTIN;
ISFGAFVAKHLKTINQ; SFGAFVAKHLKTINQE; FGAFVAKHLKTINQES;
GAFVAKHLKTINQESC; AFVAKHLKTINQESCI; FVAKHLKTINQESCIE;
VAKHLKTINQESCIEP; AKHLKTINQESCIEPL; KHLKTINQESCIEPLA;
HLKTINQESCIEPLAE; LKTINQESCIEPLAES; KTINQESCIEPLAESI;
TINQESCIEPLAESIT; INQESCIEPLAESITD; NQESCIEPLAESITDV;
QESCIEPLAESITDVL; ESCIEPLAESITDVLV; SCIEPLAESITDVLVR;
CIEPLAESITDVLVRT; IEPLAESITDVLVRTK; EPLAESITDVLVRTKR;
PLAESITDVLVRTKRD; LAESITDVLVRTKRDW; AESITDVLVRTKRDWL;
ESITDVLVRTKRDWLV; SITDVLVRTKRDWLVK; ITDVLVRTKRDWLVKQ;
TDVLVRTKRDWLVKQR; DVLVRTKRDWLVKQRG; VLVRTKRDWLVKQRGW;
LVRTKRDWLVKQRGWD; VRTKRDWLVKQRGWDG; RTKRDWLVKQRGWDGF;
TKRDWLVKQRGWDGFV; KRDWLVKQRGWDGFVE; RDWLVKQRGWDGFVEF;
DWLVKQRGWDGFVEFF; WLVKQRGWDGFVEFFH; LVKQRGWDGFVEFFHV;
VKQRGWDGFVEFFHVE; KQRGWDGFVEFFHVED; QRGWDGFVEFFHVEDL;
RGWDGFVEFFHVEDLE; GWDGFVEFFHVEDLEG; WDGFVEFFHVEDLEGG;
DGFVEFFHVEDLEGGI; GFVEFFHVEDLEGGIR; FVEFFHVEDLEGGIRN;
VEFFHVEDLEGGIRNV; EFFHVEDLEGGIRNVL; FFHVEDLEGGIRNVLL;
FHVEDLEGGIRNVLLA; HVEDLEGGIRNVLLAF; VEDLEGGIRNVLLAFA;
EDLEGGIRNVLLAFAG; DLEGGIRNVLLAFAGV; LEGGIRNVLLAFAGVA;
EGGIRNVLLAFAGVAG; GGIRNVLLAFAGVAGV; GIRNVLLAFAGVAGVG;
IRNVLLAFAGVAGVGA; RNVLLAFAGVAGVGAG; NVLLAFAGVAGVGAGL;
VLLAFAGVAGVGAGLA; LLAFAGVAGVGAGLAY; LAFAGVAGVGAGLAYL;
AFAGVAGVGAGLAYLI; FAGVAGVGAGLAYLIR

SEQ ID NOS: 48181-49526

The one or more antigenic peptides can in one embodiment comprise a fragment of one or more BK virus antigens.

The one or more BK virus antigens can be selected from Table H.

TABLE H

Protein designation and accession numbers for the proteins encoded by the
BK virus genome. The amino acid sequence of each protein is displayed.

| BK virus protein accession data | Amino acid sequence |
|---|---|
| >gi\|118752\|sp\|P14998\|DNBI_POVBA DNA-binding protein (Agnoprotein) | MFCEPKNLVVLRQLSRQASVKVGKTWTGTKKRAQRIFIFILELL LEFCRGEDSVDGKNKSTTALPAVKDSVKDS |
| >gi\|135313\|sp\|P15000\|TASM_POVBA Small T antigen | MDKVLNREESMELMDLLGLERAAWGNLPLMRKAYLKKCKEFHPD KGGDEDKMKRMNTLYKKMEQDVKVAHQPDFGTWNSSEVCADFPL CPDTLYCKEWPICSKKPSVHCPCMLCQLRLRHLNRKFLRKEPLV WIDCYCIDCFTQWFGLDLTEETLQWWVQIIGETPFRDLKL |
| >gi\|135279\|sp\|P14999\|TALA_POVBA Large T antigen | MDKVLNREESMELMDLLGLERAAWGNLPLMRKAYLKKCKEFHPD KGGDEDKMKRMNTLYKKMEQDVKVAHQPDFGTWNSSEVPTYGTE EWESWWSSFNEKWDEDLFCHEDMFASDEEATADSQHSTPPKKKR KVEDPKDFPSDLHQFLSQAVFSNRTLACFAVYTTKEKAQILYKK LMEKYSVTFISRHMCAGHNIIFFLTPHRHRVSAINNFCQKLCTF SFLICKGVNKEYLLYSALTRDPYHIIEESIQGGLKEHDFNPEEP EETKQVSWKLITEYAVETKCEDVFLLLGMYLEFQYNVEECKKCQ KKDQPYHFKYHEKHFANAIIFAESKNQKSICQQAVDTVLAKKRV DTLHMTREEMLTERFNHILDKMDLIFGAHGNAVLEQYMAGVAWL HCLLPKMDSVIFDFLHCVVFNVPKRRYWLFKGPIDSGKTTLAAG LLDLCGGKALNVNLPMERLTFELGVAIDQYMVVFEDVKGTGAES KDLPSGHGINNLDSLRDYLDGSVKVNLEKKHLNKRTQIFPPGLV TMNEYPVPKTLQARFVRQIDFRPKIYLRKSLQNSEFLLEKRILQ SGMTLLLLLIWFRPVADFSKDIQSRIVEWKERLDSEISMYTFSR MKYNICMGKCILDITREEDSETEDSGHGSSTESQSQCSSQVSDT SAPDSENPHSQELHLCKGFQCFKRPKTPPPK |
| >gi\|116622\|sp\|P14996\|COA1_POVBA Coat protein VP1 | MAPTKRKGECPGAAPKKPKEPVQVPKLLIKGGVEVLEVKTGVDA ITEVECFLNPEMGDPDDNLRGYSQHLSAENAFESDSPDRKMLPC YSTARIPLPNLNEDLTCGNLLMWEAVTVKTEVIGITSMLNLHAG SQKVHENGGGKPVQGSNFHFFAVGGDPLEMQGVLMNYRTKYPQG TITPKNPTAQSQVMNTDHKAYLDKNNAYPVECWIPDPSRNENTR |

TABLE H-continued

Protein designation and accession numbers for the proteins encoded by the BK virus genome. The amino acid sequence of each protein is displayed.

| BK virus protein accession data | Amino acid sequence |
|---|---|
| | YFGTYTGGENVPPVLHVTNTATTVLLDEQGVGPLCKADSLYVSA ADICGLFTNSSGTQQWRGLARYFKIRLRKRSVKNPYPISFLLSD LINRRTQKVDGQPMYGMESQVEEVRVFDGTEQLPGDPDMIRYID RQGQLQTKMV |
| >gi\|116641\|sp\|P14997\|COA2_POVBA Coat protein VP2/VP3 | MGAALALLGDLVASVSEAAAATGFSVAEIAAGEAAAAIEVQIAS LATVEGITTTSEAIAAIGLTPQTYAVIAGAPGAIAGFAALIQTV TGISSLAQVGYRFFSDWDHKVSTVGLYQQSGMALELFNPDEYYD ILFPGVNTFVNNIQYLDPRHWGPSLFATISQALWHVIRDDIPAI TSQELQRRTERFFRDSLARFLEETTWTIVNAPINFYNYIQDYYS NLSPIRPSMVRQVAEREGTHVNFGHTYSIDNADSIEEVTQRMDL RNKESVHSGEFIEKTIAPGGANQRTAPQWMLPLLLGLYGTVTPA LEAYEDGPNQKKRRVSRGSSQKAKGTRASAKTTNKRRSRSSRS MAHAGRTGYDNREIVMKYIHYKLSQRGYEWDAGDVGAAPPGAAP APGIFSSQPGHTPHPAASRDPVARTS PLQTPAAPGAAAGPALSPVPPVVHLTLRQAGDDFSRRYRRDFAE MSSQLHLTPFTARGRFATVVEELFRD GVNWGRIVAFFEFGGVMCVESVNREMSPLVDNIALWMTEYLNRH LHTWIQDNGGWDAFVELYGPSMRPLF DFSWLSLKTLLSLALVGACITLGAYLGHK |

SEQ ID NOS: 1-6

Preferred BK virus fragments capable of interacting with one or more MHC class 1 molecules are listed in Table I.

TABLE I

Predicted MHC class 1 BK virus peptide sequences. Prediction of 8-, 9-, 10-, 11-mers from all 6 reading frames of the genome (access no #V01108) obtained using the program displayed in FIG. 2.

BK virus reading frame 1

8 mers:

FCKNCKRI; CKNCKRIG; KNCKRIGI; NCKRIGIS; CKRIGISP; KRIGISPN; RIGISPNS; IGISPNSF; GISPNSFA; ISPNSFAR; SPNSFARP; PNSFARPQ; NSFARPQK; SFARPQKK; FARPQKKP; ARPQKKPP; RPQKKPPH; PQKKPPHP; QKKPPHPY; KKPPHPYY; KPPHPYYL; PPHPYYLR; PHPYYLRE; HPYYLRER; PYYLRERV; YYLRERVE; YLRERVEA; LRERVEAE; RERVEAEA; ERVEAEAA; RVEAEAAS; VEAEAASA; EAEAASAS; AEAASASY; EAASASYI; AASASYIL; KKRPQGGA; KRPQGGAA; RPQGGAAY; PQGGAAYP; QGGAAYPW; GGAAYPWN; GAAYPWNA; AAYPWNAA; AYPWNAAK; YPWNAAKP; PQEGKCMT; QEGKCMTH; EGKCMTHR; GKCMTHRG; KCMTHRGM; CMTHRGMQ; MTHRGMQP; THRGMQPN; HRGMQPNH; RGMQPNHD; GMQPNHDL; MQPNHDLR; QPNHDLRK; PNHDLRKE; NHDLRKES; HDLRKESA; LTGRSCLP; TGRSCLPM; GRSCLPME; RSCLPMEC; SCLPMECS; CLPMECSQ; LPMECSQT; PMECSQTM; MECSQTMT; ECSQTMTS; CSQTMTSG; SQTMTSGR; QTMTSGRK; TMTSGRKV; MTSGRKVH; TSGRKVHD; SGRKVHDR; GRKVHDRH; RKVHDRHV; KVHDRHVL; VHDRHVLR; HDRHVLRA; ESWPCPQL; SWPCPQLN; WPCPQLNW; PCPQLNWT; CPQLNWTK; PQLNWTKA; QLNWTKAM; LNWTKAMV; NWTKAMVL; WTKAMVLR; TKAMVLRQ; KAMVLRQL; AMVLRQLS; MVLRQLSR; VLRQLSRQ; LRQLSRQA; RQLSRQAS; QLSRQASV; LSRQASVK; SRQASVKV; RQASVKVG; QASVKVGK; ASVKVGKT; SVKVGKTW; VKVGKTWT; KVGKTWTG; VGKTWTGT; GKTWTGTK; KTWTGTKK; TWTGTKKR; WTGTKKRA; TGTKKRAQ; GTKKRAQR; TKKRAQRI; KKRAQRIF; KRAQRIFI; RAQRIFIF; AQRIFIFI; QRIFIFIL; RIFIFILE; IFIFILEL; FIFILELL; IFILELLL; FILELLLE; ILELLLEF; LELLLEFC; ELLLEFCR; LLLEFCRG; LLEFCRGE; LEFCRGED; EFCRGEDS; FCRGEDSV; CRGEDSVD; RGEDSVDG; GEDSVDGK; EDSVDGKN; DSVDGKNK; SVDGKNKS; VDGKNKST; DGKNKSTT; GKNKSTTA; KNKSTTAL; NKSTTALP; KSTTALPA; STTALPAV; TTALPAVK; TALPAVKD; ALPAVKDS; LPAVKDSV; PAVKDSVK; AVKDSVKD; VKDSVKDS; VSNPFFFV; SNPFFFVF; NPFFFVFP; PFFFVFPG; FFFVFPGS; FFVFPGSW; FVFPGSWV; VFPGSWVL; FPGSWVLL; LPVYLRLL; PVYLRLLL; VYLRLLLP; YLRLLLPQ; LRLLLPQD; RLLLPQDF; LLLPQDFQ; LLPQDFQW; LPQDFQWL; PQDFQWLK; QDFQWLKL; DFQWLKLL; FQWLKLLL; QWLKLLLG; WLKLLLGR; LKLLLGRL; KLLLGRLL; LLLGRLLL; LLGRLLLL; KFKLHPLL; FKLHPLLL; LLVLLGLL; LVLLGLLL; VLLGLLLG; LLGLLLGL; LGLLLGLL; GLLLGLLL; FKLLVVLV; KLLVVLVP; GISSLMIG; ISSLMIGI; SSLMIGIT; SLMIGITK; LMIGITKF; MIGITKFP; IGITKFPL; ASISNQAW; SISNQAWL; ISNQAWLW; SNQAWLWN; NQAWLWNC; QAWLWNCL; AWLWNCLT; WLWNCLTQ; LWNCLTQM; WNCLTQMS; NCLTQMST; CLTQMSTM; LTQMSTMI; TQMSTMIF; QMSTMIFC; MSTMIFCF; STMIFCFL; TMIFCFLV; ILLLIIFN; LLLIIFNT; LLIIFNTL; LIIFNTLI; IIFNTLIL; IFNTLILG; FNTLILGI; NTLILGIG; TLILGIGV; LILGIGVL; ILGIGVLL; LGIGVLLC; GIGVLLCL; IGVLLCLL; GVLLCLLL; VLLCLLLF; LLCLLLFP; LCLLLFPR; CLLLFPRL; LLLFPRLC; LLFPRLCG; LFPRLCGM; FPRLCGML; PRLCGMLL; RLCGMLLG; LCGMLLGM; CGMLLGMI; GMLLGMIY; MLLGMIYL; LLGMIYLL; PHRNCREE; HRNCREEQ; RNCREEQK;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

NCREEQKD; CREEQKDF; REEQKDFL; EEQKDFLE; EQKDFLET; QKDFLETP; KDFLETPW;
DFLETPWL; FLETPWLD; LETPWLDF; ETPWLDFW; TPWLDFWR; PWLDFWRK; WLDFWRKL;
LDFWRKLP; DFWRKLPG; FWRKLPGQ; WRKLPGQL; TFIIIFNN; FIIIFNNI; IIIFNNII;
IIFNNIIL; IFNNIILI; FNNIILIF; NNIILIFP; NIILIFPL; IILIFPLL; ILIFPLLG;
LIFPLLGP; IFPLLGPQ; FPLLGPQW; PLLGPQWL; LLGPQWLD; LGPQWLDK; LGKVPVY;
KGKVPVYI; GKVPVYIL; KVPVYILA; VPVYILAI; PVYILAIL; VYILAILI; YILAILIV;
KKLHKEWT; EINKVYIQ; INKVYIQE; NKVYIQES; KVYIQESL; KKLLPQEV; KLLPQEVL;
LLPQEVLI; LPQEVLIK; PQEVLIKE; QEVLIKEL; EVLIKELL; VLIKELLL; LIKELLLN;
IKELLLNG; KELLLNGC; ELLLNGCC; LLLNGCCL; LLNGCCLY; LNGCCLYF; HLLLKHMK;
LLLKHMKM; LLKHMKMA; LKHMKMAP; KHMKMAPT; HMKMAPTK; MKMAPTKR; KMAPTKRK;
MAPTKRKG; APTKRKGE; PTKRKGEC; TKRKGECP; KRKGECPG; RKGECPGA; KGECPGAA;
GECPGAAP; ECPGAAPK; CPGAAPKK; PGAAPKKP; GAAPKKPK; AAPKKPKE; APKKPKEP;
PKKPKEPV; KKPKEPVQ; KPKEPVQV; PKEPVQVP; KEPVQVPK; EPVQVPKL; PVQVPKLL;
VQVPKLLI; QVPKLLIK; VPKLLIKG; PKLLIKGG; KLLIKGGV; LLIKGGVE; LIKGGVEV;
IKGGVEVL; KGGVEVLE; GGVEVLEV; GVEVLEVK; VEVLEVKT; EVLEVKTG; VLEVKTGV;
LEVKTGVD; EVKTGVDA; VKTGVDAI; KTGVDAIT; TGVDAITE; GVDAITEV; VDAITEVE;
DAITEVEC; AITEVECF; ITEVECFL; TEVECFLN; EVECFLNP; VECFLNPE; ECFLNPEM;
CFLNPEMG; FLNPEMGD; LNPEMGDP; NPEMGDPD; PEMGDPDE; EMGDPDEN; MGDPDENL;
GDPDENLR; DPDENLRG; PDENLRGF; DENLRGFS; ENLRGFSL; NLRGFSLK; LRGFSLKL;
RGFSLKLS; GFSLKLSA; FSLKLSAE; SLKLSAEN; LKLSAEND; KLSAENDF; LSAENDFS;
SAENDFSS; AENDFSSD; ENDFSSDS; NDFSSDSP; DFSSDSPE; FSSDSPER; SSDSPERK;
SDSPERKM; DSPERKML; SPERKMLP; PERKMLPC; ERKMLPCY; RKMLPCYS; KMLPCYST;
MLPCYSTA; LPCYSTAR; PCYSTARI; CYSTARIP; YSTARIPL; STARIPLP; TARIPLPN;
ARIPLPNL; RIPLPNLN; IPLPNLNE; PLPNLNED; LPNLNEDL; PNLNEDLT; NLNEDLTC;
LNEDLTCG; NEDLTCGN; EDLTCGNL; DLTCGNLL; LTCGNLLM; TCGNLLMW; CGNLLMWE;
GNLLMWEA; NLLMWEAV; LLMWEAVT; LMWEAVTV; MWEAVTVQ; WEAVTVQT; EAVTVQTE;
AVTVQTEV; VTVQTEVI; TVQTEVIG; VQTEVIGI; QTEVIGIT; TEVIGITS; EVIGITSM;
VIGITSML; IGITSMLN; GITSMLNL; ITSMLNLH; TSMLNLHA; SMLNLHAG; MLNLHAGS;
LNLHAGSQ; NLHAGSQK; LHAGSQKV; HAGSQKVH; AGSQKVHE; GSQKVHEH; SQKVHEHG;
QKVHEHGG; KVHEHGGG; VHEHGGGK; HEHGGGKP; EHGGGKPI; HGGGKPIQ; GGGKPIQG;
GGKPIQGS; GKPIQGSN; KPIQGSNF; PIQGSNFH; IQGSNFHF; QGSNFHFF; GSNFHFFA;
SNFHFFAV; NFHFFAVG; FHFFAVGG; HFFAVGGE; FFAVGGEP; FAVGGEPL; AVGGEPLE;
VGGEPLEM; GGEPLEMQ; GEPLEMQG; EPLEMQGV; PLEMQGVL; LEMQGVLM; EMQGVLMN;
MQGVLMNY; QGVLMNYR; GVLMNYRS; VLMNYRSK; LMNYRSKY; MNYRSKYP; NYRSKYPD;
YRSKYPDG; RSKYPDGT; SKYPDGTI; KYPDGTIT; YPDGTITP; PDGTITPK; DGTITPKN;
GTITPKNP; TITPKNPT; ITPKNPTA; TPKNPTAQ; PKNPTAQS; KNPTAQSQ; NPTAQSQV;
PTAQSQVM; TAQSQVMN; AQSQVMNT; QSQVMNTD; SQVMNTDH; QVMNTDHK; VMNTDHKA;
MNTDHKAY; NTDHKAYL; TDHKAYLD; DHKAYLDK; HKAYLDKN; KAYLDKNN; AYLDKNNA;
YLDKNNAY; LDKNNAYP; DKNNAYPV; KNNAYPVE; NNAYPVEC; NAYPVECW; AYPVECWV;
YPVECWVP; PVECWVPD; VECWVPDP; ECWVPDPS; CWVPDPSR; WVPDPSRN; VPDPSRNE;
PDPSRNEN; DPSRNENA; PSRNENAR; SRNENARY; RNENARYF; NENARYFG; ENARYFGT;
NARYFGTF; ARYFGTFT; RYFGTFTG; YFGTFTGG; FGTFTGGE; GTFTGGEN; TFTGGENV;
FTGGENVP; TGGENVPP; GGENVPPV; GENVPPVL; ENVPPVLH; NVPPVLHV; VPPVLHVT;
PPVLHVTN; PVLHVTNT; VLHVTNTA; LHVTNTAT; HVTNTATT; VTNTATTV; TNTATTVL;
NTATTVLL; TATTVLLD; ATTVLLDE; TTVLLDEQ; TVLLDEQG; VLLDEQGV; LLDEQGVG;
LDEQGVGP; DEQGVGPL; EQGVGPLC; QGVGPLCK; GVGPLCKA; VGPLCKAD; GPLCKADS;
PLCKADSL; LCKADSLY; CKADSLYV; KADSLYVS; ADSLYVSA; DSLYVSAA; SLYVSAAD;
LYVSAADI; YVSAADIC; VSAADICG; SAADICGL; AADICGLF; ADICGLFT; DICGLFTN;
ICGLFTNS; CGLFTNSS; GLFTNSSG; LFTNSSGT; FTNSSGTQ; TNSSGTQQ; NSSGTQQW;
SSGTQQWR; SGTQQWRG; GTQQWRGL; TQQWRGLA; QQWRGLAR; QWRGLARY; WRGLARYF;
RGLARYFK; GLARYFKI; LARYFKIR; ARYFKIRL; RYFKIRLR; YFKIRLRK; FKIRLRKR;
KIRLRKRS; IRLRKRSV; RLRKRSVK; LRKRSVKN; RKRSVKNP; KRSVKNPY; RSVKNPYP;
SVKNPYPI; VKNPYPIS; KNPYPISF; NPYPISFL; PYPISFLL; YPISFLLS; PISFLLSD;
ISFLLSDL; SFLLSDLI; FLLSDLIN; LLSDLINR; LSDLINRR; SDLINRRT; DLINRRTQ;
LINRRTQR; INRRTQRV; NRRTQRVD; RRTQRVDG; RTQRVDGQ; TQRVDGQP; QRVDGQPM;
RVDGQPMY; VDGQPMYG; DGQPMYGM; GQPMYGME; QPMYGMES; PMYGMESQ; MYGMESQV;
YGMESQVE; GMESQVEE; MESQVEEV; ESQVEEVR; SQVEEVRV; QVEEVRVF; VEEVRVFD;
EEVRVFDG; EVRVFDGT; VRVFDGTE; RVFDGTER; VFDGTERL; FDGTERLP; DGTERLPG;
GTERLPGD; TERLPGDP; ERLPGDPD; RLPGDPDM; LPGDPDMI; PGDPDMIR; GDPDMIRY;
DPDMIRYI; PDMIRYID; DMIRYIDK; MIRYIDKQ; IRYIDKQG; RYIDKQGQ; YIDKQGQL;
IDKQGQLQ; DKQGQLQT; KQGQLQTK; QGQLQTKM; GQLQTKML; TGAFIVHI; GAFIVHIH;
AFIVHIHL; FIVHIHLI; IVHIHLIN; VHIHLINA; HIHLINAA; IHLINAAF; HLINAAFV;
ATFKLVLF; TFKLVLFW; FKLVLFWG; KLVLFWGW; LVLFWGWC; VLFWGWCF; LFWGWCFR;
FWGWCFRP; WGWCFRPF; GWCFRPFK; WCFRPFKT; CFRPFKTL; FRPFKTLK; RPFKTLKA;
PFKTLKAF; FKTLKAFT; KTLKAFTQ; TLKAFTQM; LKAFTQMQ; KAFTQMQL; AFTQMQLL;
FTQMQLLT; TQMQLLTM; QMQLLTMG; MQLLTMGV; PLGIFSRG; SMSRVFSF; ILFSCNIK;
LFSCNIKN; FSCNIKNT; SCNIKNTF; CNIKNTFP; NIKNTFPH; IKNTFPHA; KNTFPHAY;
NTFPHAYI; TFPHAYII; FPHAYIIF; PHAYIIFH; HAYIIFHP; KSIHTYLR; SIHTYLRI;
IHTYLRIQ; HTYLRIQP; TYLRIQPF; YLRIQPFL; LRIQPFLP; RIQPFLPF; IQPFLPFN;
QPFLPFNN; PFLPFNNS; FLPFNNSR; LPFNNSRL; PFNNSRLY; FNNSRLYI; NNSRLYIS;
NSRLYISC; SRLYISCK; RLYISCKI; LYISCKIS; YISCKISY; ISCKISYR; SCKISYRP;
CKISYRPK; KISYRPKP; ISYRPKPN; IYFGPKIY; YFGPKIYL; FGPKIYLS; GPKIYLSY;
PKIYLSYK; KIYLSYKS; IYLSYKSS; YLSYKSSL; LSYKSSLQ; SYKSSLQG; YKSSLQGF;
KSSLQGFR; SSLQGFRD; SLQGFRDR; LQGFRDRI; QGFRDRIL; GFRDRILI; FRDRILIH;
RDRILIHC; DRILIHCN; RILIHCNQ; ILIHCNQA; LIHCNQAW; IHCNQAWW; HCNQAWWK;
CNQAWWKY; NQAWWKYL; QAWWKYLG; AWWKYLGS; WWKYLGSF; WKYLGSFV; FSSCPFYI;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

SSCPFYIF; SCPFYIFK; CPFYIFKN; PFYIFKNN; FYIFKNNH; YIFKNNHV; IFKNNHVL;
FKNNHVLI; KNNHVLIY; NNHVLIYS; NHVLIYSY; HVLIYSYT; CCFSTING; CFSTINGT;
FSTINGTF; STINGTFK; PVSSFRYI; VSSFRYIE; SSFRYIEN; SFRYIENN; FRYIENNT;
RYIENNTV; YIENNTVQ; IENNTVQK; ENNTVQKI; NNTVQKIK; NTVQKIKY; TVQKIKYY;
VQKIKYYR; QKIKYYRI; KIKYYRIH; IKYYRIHF; KYYRIHFR; QTVQPSNT; TVQPSNTC;
VQPSNTCH; QPSNTCHI; PSNTCHIL; SNTCHILF; YSISMSSK; SISMSSKY; HFFPGHMK;
FFPGHMKG; FPGHMKGI; PGHMKGIY; GHMKGIYS; HMKGIYSF; MKGIYSFF; KGIYSFFS;
NCIYCLLT; CIYCLLTN; IYCLLTNT; YCLLTNTF; CLLTNTFL; LLTNTFLI; LTNTFLIF;
TNTFLIFT; NTFLIFTF; TFLIFTFC; FLIFTFCK; LIFTFCKN; IFTFCKNN; FTFCKNNS;
TFCKNNSI; FCKNNSIC; CKNNSICK; KNNSICKV; NNSICKVL; NSICKVLF; SICKVLFM;
ICKVLFMI; CKVLFMIL; KVLFMILK; VLFMILKV; LFMILKVI; FMILKVIR; MILKVIRL;
ILKVIRLV; LKVIRLVF; KVIRLVFF; VIRLVFFL; IRLVFFLT; RLVFFLTL; LVFFLTLF;
VFFLTLFT; FFLTLFTL; FLTLFTLL; LTLFTLLY; TLFTLLYI; FTLLYIVL;
TLLYIVLK; LLYIVLKF; KHILTLCL; HILTLCLY; ILTLCLYC; LTLCLYCI; TLCLYCIL;
LCLYCILS; CLYCILSN; FPRHLLCF; PRHLLCFF; RHLLCFFR; HLLCFFRL; LLCFFRLF;
LCFFRLFW; CFFRLFWA; FFRLFWAK; FRLFWAKI; RLFWAKIM; LFWAKIML; FWAKIMLL;
APLNAFFY; PLNAFFYS; LNAFFYSM; NAFFYSMV; AFFYSMVW; FFYSMVWI; FYSMVWIS;
YSMVWISS; VFLINTLT; FLINTLTN; KTKGTQLL; TKGTQLLT; KGTQLLTE; GTQLLTEI;
TQLLTEII; QLLTEIIN; LLTEIINC; LTEIINCR; TEIINCRN; EIINCRNS; IINCRNSM;
INCRNSMS; NCRNSMSM; CRNSMSMW; RNSMSMWS; KEYNIMPS; EYNIMPST; YNIMPSTH;
NIMPSTHV; IMPSTHVS; MPSTHVST; PSTHVSTN; STHVSTNK; THVSTNKS; HVSTNKSY;
VSTNKSYR; STNKSYRI; TNKSYRIF; NKSYRIFF; KSYRIFFH; SYRIFFHK; YRIFFHKF;
RIFFHKFF; IFFHKFFI; FFHKFFIQ; PHKFFIQN; HKFFIQNL; KFFIQNLS; FFIQNLSF;
FIQNLSFF; IQNLSFFF; QNLSFFFS; NLSFFFSS; LSFFFSSI; SFFFSSIH; FFFSSIHS;
FFSSIHSK; FSSIHSKA; SSIHSKAG; SIHSKAGK; IHSKAGKG; HSKAGKGS; SKAGKGSI;
KAGKGSIT; AGKGSITK; GKGSITKY; KGSITKYS; GSITKYSL; SITKYSLT; ITKYSLTK;
TKYSLTKK; KYSLTKKL; YSLTKKLV; IRGKVFRV; RGKVFRVF; GKVFRVFY; KVFRVFYL;
VFRVFYLS; FRVFYLSF; RVFYLSFF; VFYLSFFF; FYLSFFFG; YLSFFFGW; LSFFFGWC;
VLRICCCF; LRICCCFF; RICCCFFI; ICCCFFIT; CCCFFITG; CCFFITGK; CFFITGKH;
FFITGKHI; FITGKHIF; ITGKHIFM; TGKHIFMA; GKHIFMAK; IPIPFFIK; FIPFFIKG;
IPFFIKGT; PFFIKGTP; FFIKGTPP; FIKGTPPG; IKGTPPGL; KGTPPGLP; GTPPGLPL;
TPPGLPLF; PPGLPLFC; PGLPLFCS; GLPLFCSI; LPLFCSIG; PLFCSIGW; LFCSIGWH;
FCSIGWHL; YPIIYLNI; FIIYLNIS; SFRSLKGV; FRSLKGVS; RSLKGVSP; SLKGVSPI;
LKGVSPII; KGVSPIIW; GVSPIIWT; VSPIIWTH; SPIIWTHH; PIIWTHHC; IIWTHHCV;
IWTHHCRV; WTHHCRVS; THHCRVSS; HHCRVSSV; HCRVSSVR; CRVSSVRS; RVSSVRSK;
VSSVRSKP; SSVRSKPN; SVRSKPNH; VRSKPNHC; RSKPNHCV; SKPNHCVK; KPNHCVKQ;
PNHCVKQS; NHCVKQSM; HCVKQSMQ; QSIQTKGS; SIQTKGSF; IQTKGSFL; QTKGSFLK;
TKGSFLKN; KGSFLKNF; GSFLKNFL; SFLKNFLF; FLKNFLFK; LKNFLFKC; KNFLFKCL;
NFLFKCLN; FLFKCLNL; LFKCLNLS; HSMQGCT; SMQGCTE; MQGCTEG; QGCTEGF;
GQCTEGFL; QCTEGFLE; CTEGFLEQ; TEGFLEQI; EGFLEQIG; GFLEQIGH; FLEQIGHS;
LEQIGHSL; EQIGHSLQ; QIGHSLQY; IGHSLQYR; GHSLQYRV; HSLQYRVS; SLQYRVSG;
LQYRVSGQ; QYRVSGQR; YRVSGQRG; RVSGQRGK; VSGQRGKS; SGQRGKSA; GQRGKSAQ;
QRGKSAQT; RGKSAQTS; GKSAQTSE; KSAQTSEL; SAQTSELL; AQTSELLQ; QTSELLQV;
TSELLQVP; SELLQVPK; ELLQVPKS; LLQVPKSG; ATFTSCSI; TFTSCSIF; FTSCSIFL;
TSCSIFLY; SCSIFLYK; CSIFLYKV; SIFLYKVF; IFLYKVFI; FLYKVFIL; LYKVFILF;
YKVFILFI; KVFILFIL; VFILFILS; FILFILSS; ILFILSSS; LFILSSSP; FILSSSPP;
ILSSSPPL; LSSSPPLS; SSSPPLSG; AFLIKGRF; FLIKGRFP; LIKGRFPQ; IKGRFPQA;
KGRFPQAA; GRFPQAAL; RFPQAALS; FPQAALSR; PQAALSRP; QAALSRPK; AALSRPKR;
ALSRPKRS; LSRPKRSM; SRPKRSMS; RPKRSMSS; PKRSMSSM; KRSMSSMD; RSMSSMDS;
SMSSMDSS; MSSMDSSL; SSMDSSLL; SMDSSLLR; MDSSLLRT; DSSLLRTL; SSLLRTLS 9 mers:

FCKNCKRIG; CKNCKRIGI; KNCKRIGIS; NCKRIGISP; CKRIGISPN; KRIGISPNS;
RIGISPNSF; IGISPNSFA; GISPNSFAR; ISPNSFARP; SPNSFARPQ; PNSFARPQK;
NSFARPQKK; SFARPQKKP; FARPQKKPP; ARPQKKPPH; RPQKKPPHP; PQKKPPHPY;
QKKPPHPYY; KKPPHPYYL; KPPHPYYLR; PPHPYYLRE; PHPYYLRER; HPYYLRERV;
PYYLRERVE; YYLRERVEA; YLRERVEAE; LRERVEAEA; RERVEAEAA; ERVEAEAAS;
RVEAEAASA; VEAEAASAS; EAEAASASY; AEAASASYI; EAASASYIL; KKRPQGGAA;
KRPQGGAAY; RPQGGAAYP; PQGGAAYPW; QGGAAYPWN; GGAAYPWNA; GAAYPWNAA;
AAYPWNAAK; AYPWNAAKP; PQEGKCMTH; QEGKCMTHR; EGKCMTHRG; GKCMTHRGM;
KCMTHRGMQ; CMTHRGMQP; MTHRGMQPN; THRGMQPNH; HRGMQPNHD; RGMQPNHDL;
GMQPNHDLR; MQPNHDLRK; QPNHDLRKE; PNHDLRKES; NHDLRKESA; LTGRSCLPM;
TGRSCLPME; GRSCLPMEC; RSCLPMECS; SCLPMECSQ; CLPMECSQT; LPMECSQTM;
PMECSQTMT; MECSQTMTS; ECSQTMTSG; CSQTMTSGR; SQTMTSGRK; QTMTSGRKV;
TMTSGRKVH; MTSGRKVHD; TSGRKVHDR; SGRKVHDRH; GRKVHDRHV; RKVHDRHVL;
KVHDRHVLR; VHDRHVLRA; ESWPCPQLN; SWPCPQLNW; WPCPQLNWT; PCPQLNWTK;
CPQLNWTKA; PQLNWTKAM; QLNWTKAMV; LNWTKAMVL; NWTKAMVLR; WTKAMVLRQ;
TKAMVLRQL; KAMVLRQLS; AMVLRQLSR; MVLRQLSRQ; VLRQLSRQA; LRQLSRQAS;
RQLSRQASV; QLSRQASVK; LSRQASVKV; SRQASVKVG; RQASVKVGK; QASVKVGKT;
ASVKVGKTW; SVKVGKTWT; VKVGKTWTG; KVGKTWTGT; VGKTWTGTK; GKTWTGTKK;
KTWTGTKKR; TWTGTKKRA; WTGTKKRAQ; TGTKKRAQR; GTKKRAQRI; TKKRAQRIF;
KKRAQRIFI; KRAQRIFIF; RAQRIFIFI; AQRIFIFIL; QRIFIFILE; RIFIFILEL;
IFIFILELL; FIFILELLL; IFILELLLE; FILELLLEF; ILELLLEFC; LELLLEFCR;
ELLLEFCRG; LLLEFCRGE; LLEFCRGED; LEFCRGEDS; EFCRGEDSV; FCRGEDSVD;
CRGEDSVDG; RGEDSVDGK; GEDSVDGKN; EDSVDGKNK; DSVDGKNKS; SVDGKNKST;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

VDGKNKSTT; DGKNKSTTA; GKNKSTTAL; KNKSTTALP; NKSTTALPA; KSTTALPAV;
STTALPAVK; TTALPAVKD; TALPAVKDS; ALPAVKDSV; LPAVKDSVK; PAVKDSVKD;
AVKDSVKDS; VSNPFFFVF; SNPFFFVFP; NPFFFVFPG; PFFFVFPGS; FFFVFPGSW;
FFVFPGSWV; FVFPGSWVL; VFPGSWVLL; LPVYLRLLL; PVYLRLLLP; VYLRLLLPQ;
YLRLLLPQD; LRLLLPQDF; RLLLPQDFQ; LLLPQDFQW; LLPQDFQWL; LPQDFQWLK;
PQDFQWLKL; QDFQWLKLL; DFQWLKLLL; FQWLKLLLG; QWLKLLLGR; WLKLLLGRL;
LKLLLGRLL; KLLLGRLLL; LLLGRLLLL; KFKLHPLLL; LLVLLGLLL; LVLLGLLLG;
VLLGLLLGL; LLGLLLGLL; LGLLLGLLL; FKLLVVLVP; GISSLMIGI; ISSLMIGIT;
SSLMIGITK; SLMIGITKF; LMIGITKFP; MIGITKFPL; ASISNQAWL; SISNQAWLW;
ISNQAWLWN; SNQAWLWNC; NQAWLWNCL; QAWLWNCLT; AWLWNCLTQ; WLWNCLTQM;
LWNCLTQMS; WNCLTQMST; NCLTQMSTM; CLTQMSTMI; LTQMSTMIF; TQMSTMIFC;
QMSTMIFCF; MSTMIFCFL; STMIFCFLV; ILLLIIFNT; LLLIIFNTL; LLIIFNTLI;
LIIFNTLIL; IIFNTLILG; IFNTLILGI; FNTLILGIG; NTLILGIGV; TLILGIGVL;
LILGIGVLL; ILGIGVLLC; LGIGVLLCL; GIGVLLCLL; IGVLLCLLL; GVLLCLLLF;
VLLCLLLFP; LLCLLLFPR; LCLLLFPRL; CLLLFPRLC; LLLFPRLCG; LLFPRLCGM;
LFPRLCGML; FPRLCGMLL; PRLCGMLLG; RLCGMLLGM; LCGMLLGMI; CGMLLGMIY;
GMLLGMIYL; MLLGMIYLL; PHRNCREEQ; HRNCREEQK; RNCREEQKD; NCREEQKDF;
CREEQKDFL; REEQKDFLE; EEQKDFLET; EQKDFLETP; QKDFLETPW; KDFLETPWL;
DFLETPWLD; FLETPWLDF; LETPWLDFW; ETPWLDFWR; TPWLDFWRK; PWLDFWRKL;
WLDFWRKLP; LDFWRKLPG; DFWRKLPGQ; FWRKLPGQL; TFIIIFNNI; FIIIFNNII;
IIIFNNIIL; IIFNNIILI; IFNNIILIF; FNNIILIFP; NNIILIFPL; NIILIFPLL;
IILIFPLLG; ILIFPLLGP; LIFPLLGPQ; IFPLLGPQW; FPLLGPQWL; PLLGPQWLD;
LLGPQWLDK; LKGKVPVYI; KGKVPVYIL; GKVPVYILA; KVPVYILAI; VPVYILAIL;
PVYILAILI; VYILAILIV; EINKVYIQE; INKVYIQES; NKVYIQESL; KKLLPQEVL;
KLLPQEVLI; LLPQEVLIK; LPQEVLIKE; PQEVLIKEL; QEVLIKELL; EVLIKELLL;
VLIKELLLN; LIKELLLNG; IKELLLNGC; KELLLNGCC; ELLLNGCCL; LLLNGCCLY;
LLNGCCLYF; HLLLKHMKM; LLLKHMKMA; LLKHMKMAP; LKHMKMAPT; KHMKMAPTK;
HMKMAPTKR; MKMAPTKRK; KMAPTKRKG; MAPTKRKGE; APTKRKGEC; PTKRKGECP;
TKRKGECPG; KRKGECPGA; RKGECPGAA; KGECPGAAP; GECPGAAPK; ECPGAAPKK;
CPGAAPKKP; PGAAPKKPK; GAAPKKPKE; AAPKKPKEP; APKKPKEPV; PKKPKEPVQ;
KKPKEPVQV; KPKEPVQVP; PKEPVQVPK; KEPVQVPKL; EPVQVPKLL; PVQVPKLLI;
VQVPKLLIK; QVPKLLIKG; VPKLLIKGG; PKLLIKGGV; KLLIKGGVE; LLIKGGVEV;
LIKGGVEVL; IKGGVEVLE; KGGVEVLEV; GGVEVLEVK; GVEVLEVKT; VEVLEVKTG;
EVLEVKTGV; VLEVKTGVD; LEVKTGVDA; EVKTGVDAI; VKTGVDAIT; KTGVDAITE;
TGVDAITEV; GVDAITEVE; VDAITEVEC; DAITEVECF; AITEVECFL; ITEVECFLN;
TEVECFLNP; EVECFLNPE; VECFLNPEM; ECFLNPEMG; CFLNPEMGD; FLNPEMGDP;
LNPEMGDPD; NPEMGDPDE; PEMGDPDEN; EMGDPDENL; MGDPDENLR; GDPDENLRG;
DPDENLRGF; PDENLRGFS; DENLRGFSL; ENLRGFSLK; NLRGFSLKL; LRGFSLKLS;
RGFSLKLSA; GFSLKLSAE; FSLKLSAEN; SLKLSAEND; LKLSAENDF; KLSAENDFS;
LSAENDFSS; SAENDFSSD; AENDFSSDS; ENDFSSDSP; NDFSSDSPE; DFSSDSPER;
FSSDSPERK; SSDSPERKM; SDSPERKML; DSPERKMLP; SPERKMLPC; PERKMLPCY;
ERKMLPCYS; RKMLPCYST; KMLPCYSTA; MLPCYSTAR; LPCYSTARI; PCYSTARIP;
CYSTARIPL; YSTARIPLP; STARIPLPN; TARIPLPNL; ARIPLPNLN; RIPLPNLNE;
IPLPNLNED; PLPNLNEDL; LPNLNEDLT; PNLNEDLTC; NLNEDLTCG; LNEDLTCGN;
NEDLTCGNL; EDLTCGNLL; DLTCGNLLM; LTCGNLLMW; TCGNLLMWE; CGNLLMWEA;
GNLLMWEAV; NLLMWEAVT; LLMWEAVTV; LMWEAVTVQ; MWEAVTVQT; WEAVTVQTE;
EAVTVQTEV; AVTVQTEVI; VTVQTEVIG; TVQTEVIGI; VQTEVIGIT; QTEVIGITS;
TEVIGITSM; EVIGITSML; VIGITSMLN; IGITSMLNL; GITSMLNLH; ITSMLNLHA;
TSMLNLHAG; SMLNLHAGS; MLNLHAGSQ; LNLHAGSQK; NLHAGSQKV; LHAGSQKVH;
HAGSQKVHE; AGSQKVHEH; GSQKVHEHG; SQKVHEHGG; QKVHEHGGG; KVHEHGGGK;
VHEHGGGKP; HEHGGGKPI; EHGGGKPIQ; HGGGKPIQG; GGGKPIQGS; GGKPIQGSN;
GKPIQGSNF; KPIQGSNFH; PIQGSNFHF; IQGSNFHFF; QGSNFHFFA; GSNFHFFAV;
SNFHFFAVG; NFHFFAVGG; FHFFAVGGE; HFFAVGGEP; FFAVGGEPL; FAVGGEPLE;
AVGGEPLEM; VGGEPLEMQ; GGEPLEMQG; GEPLEMQGV; EPLEMQGVL; PLEMQGVLM;
LEMQGVLMN; EMQGVLMNY; MQGVLMNYR; QGVLMNYRS; GVLMNYRSK; VLMNYRSKY;
LMNYRSKYP; MNYRSKYPD; NYRSKYPDG; YRSKYPDGT; RSKYPDGTI; SKYPDGTIT;
KYPDGTITP; YPDGTITPK; PDGTITPKN; DGTITPKNP; GTITPKNPT; TITPKNPTA;
ITPKNPTAQ; TPKNPTAQS; PKNPTAQSQ; KNPTAQSQV; NPTAQSQVM; PTAQSQVMN;
TAQSQVMNT; AQSQVMNTD; QSQVMNTDH; SQVMNTDHK; QVMNTDHKA; VMNTDHKAY;
MNTDHKAYL; NTDHKAYLD; TDHKAYLDK; DHKAYLDKN; HKAYLDKNN; KAYLDKNNA;
AYLDKNNAY; YLDKNNAYP; LDKNNAYPV; DKNNAYPVE; KNNAYPVEC; NNAYPVECW;
NAYPVECWV; AYPVECWVP; YPVECWVPD; PVECWVPDP; VECWVPDPS; ECWVPDPSR;
CWVPDPSRN; WVPDPSRNE; VPDPSRNEN; PDPSRNENA; DPSRNENAR; PSRNENARY;
SRNENARYF; RNENARYFG; NENARYFGT; ENARYFGTF; NARYFGTFT; ARYFGTFTG;
RYFGTFTGG; YFGTFTGGE; FGTFTGGEN; GTFTGGENV; TFTGGENVP; FTGGENVPP;
TGGENVPPV; GGENVPPVL; GENVPPVLH; ENVPPVLHV; NVPPVLHVT; VPPVLHVTN;
PPVLHVTNT; PVLHVTNTA; VLHVTNTAT; LHVTNTATT; HVTNTATTV; VTNTATTVL;
TNTATTVLL; NTATTVLLD; TATTVLLDE; ATTVLLDEQ; TTVLLDEQG; TVLLDEQGV;
VLLDEQGVG; LLDEQGVGP; LDEQGVGPL; DEQGVGPLC; EQGVGPLCK; QGVGPLCKA;
GVGPLCKAD; VGPLCKADS; GPLCKADSL; PLCKADSLY; LCKADSLYV; CKADSLYVS;
KADSLYVSA; ADSLYVSAA; DSLYVSAAD; SLYVSAADI; LYVSAADIC; YVSAADICG;
VSAADICGL; SAADICGLF; AADICGLFT; ADICGLFTN; DICGLFTNS; ICGLFTNSS;
CGLFTNSSG; GLFTNSSGT; LFTNSSGTQ; FTNSSGTQQ; TNSSGTQQW; NSSGTQQWR;
SSGTQQWRG; SGTQQWRGL; GTQQWRGLA; TQQWRGLAR; QQWRGLARY; QWRGLARYF;
WRGLARYFK; RGLARYFKI; GLARYFKIR; LARYFKIRL; ARYFKIRLR; RYFKIRLRK;
YFKIRLRKR; FKIRLRKRS; KIRLRKRSV; IRLRKRSVK; RLRKRSVKN; LRKRSVKNP;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

RKRSVKNPY; KRSVKNPYP; RSVKNPYPI; SVKNPYPIS; VKNPYPISF; KNPYPISFL;
NPYPISFLL; PYPISFLLS; YPISFLLSD; PISFLLSDL; ISFLLSDLI; SFLLSDLIN;
FLLSDLINR; LLSDLINRR; LSDLINRRT; SDLINRRTQ; DLINRRTQR; LINRRTQRV;
INRRTQRVD; NRRTQRVDG; RRTQRVDGQ; RTQRVDGQP; TQRVDGQPM; QRVDGQPMY;
RVDGQPMYG; VDGQPMYGM; DGQPMYGME; GQPMYGMES; QPMYGMESQ; PMYGMESQV;
MYGMESQVE; YGMESQVEE; GMESQVEEV; MESQVEEVR; ESQVEEVRV; SQVEEVRVF;
QVEEVRVFD; VEEVRVFDG; EEVRVFDGT; EVRVFDGTE; VRVFDGTER; RVFDGTERL;
VFDGTERLP; FDGTERLPG; DGTERLPGD; GTERLPGDP; TERLPGDPD; ERLPGDPDM;
RLPGDPDMI; LPGDPDMIR; PGDPDMIRY; GDPDMIRYI; DPDMIRYID; PDMIRYIDK;
DMIRYIDKQ; MIRYIDKQG; IRYIDKQGQ; RYIDKQGQL; YIDKQGQLQ; IDKQGQLQT;
DKQGQLQTK; KQGQLQTKM; QGQLQTKML; TGAFIVHIH; GAFIVHIHL; AFIVHIHLI;
FIVHIHLIN; IVHIHLINA; VHIHLINAA; HIHLINAAF; IHLINAAFV; ATFKLVLFW;
TFKLVLFWG; FKLVLFWGW; KLVLFWGWC; LVLFWGWCF; VLFWGWCFR; LFWGWCFRP;
FWGWCFRPF; WGWCFRPFK; GWCFRPFKT; WCFRPFKTL; CFRPFKTLK; FRPFKTLKA;
RPFKTLKAF; PFKTLKAFT; FKTLKAFTQ; KTLKAFTQM; TLKAFTQMQ; LKAFTQMQL;
KAFTQMQLL; AFTQMQLLT; FTQMQLLTM; TQMQLLTMG; QMQLLTMGV; ILFSCNIKN;
LFSCNIKNT; FSCNIKNTF; SCNIKNTFP; CNIKNTFPH; NIKNTFPHA; IKNTFPHAY;
KNTFPHAYI; NTFPHAYII; TFPHAYIIF; FPHAYIIFH; PHAYIIFHP; KSIHTYLRI;
SIHTYLRIQ; IHTYLRIQP; HTYLRIQPF; TYLRIQPFL; YLRIQPFLP; LRIQPFLPF;
RIQPFLPFN; IQPFLPFNN; QPFLPFNNS; PFLPFNNSR; FLPFNNSRL; LPFNNSRLY;
PFNNSRLYI; FNNSRLYIS; NNSRLYISC; NSRLYISCK; SRLYISCKI; RLYISCKIS;
LYISCKISY; YISCKISYR; ISCKISYRP; SCKISYRPK; CKISYRPKP; KISYRPKPN;
IYFGPKIYL; YFGPKIYLS; FGPKIYLSY; GPKIYLSYK; PKIYLSYKS; KIYLSYKSS;
IYLSYKSSL; YLSYKSSLQ; LSYKSSLQG; SYKSSLQGF; YKSSLQGFR; KSSLQGFRD;
SSLQGFRDR; SLQGFRDRI; LQGFRDRIL; QGFRDRILI; GFRDRILIH; FRDRILIHC;
RDRILIHCN; DRILIHCNQ; RILIHCNQA; ILIHCNQAW; LIHCNQAWW; IHCNQAWWK;
HCNQAWWKY; CNQAWWKYL; NQAWWKYLG; QAWWKYLGS; AWWKYLGSF; WWKYLGSFV;
FSSCPFYIF; SSCPFYIFK; SCPFYIFKN; CPFYIFKNN; PFYIFKNNH; FYIFKNNHV;
YIFKNNHVL; IFKNNHVLI; FKNNHVLIY; KNNHVLIYS; NNHVLIYSY; NHVLIYSYT;
CCFSTINGT; CFSTINGTF; FSTINGTFK; PVSSFRYIE; VSSFRYIEN; SSFRYIENN;
SFRYIENNT; FRYIENNTV; RYIENNTVQ; YIENNTVQK; IENNTVQKI; ENNTVQKIK;
NNTVQKIKY; NTVQKIKYY; TVQKIKYYR; VQKIKYYRI; QKIKYYRIH; KIKYYRIHF;
IKYYRIHFR; QTVQPSNTC; TVQPSNTCH; VQPSNTCHI; QPSNTCHIL; PSNTCHILF;
YSISMSSKY; HFFPGHMKG; FFPGHMKGI; FPGHMKGIY; PGHMKGIYS; GHMKGIYSF;
HMKGIYSFF; MKGIYSFFS; NCIYCLLTN; CIYCLLTNT; IYCLLTNTF; YCLLTNTFL;
CLLTNTFLI; LLTNTFLIF; LTNTFLIFT; TNTFLIFTF; NTFLIFTFC; TFLIFTFCK;
FLIFTFCKN; LIFTFCKNN; IFTFCKNNS; FTFCKNNSI; TFCKNNSIC; FCKNNSICK;
CKNNSICKV; KNNSICKVL; NNSICKVLF; NSICKVLFM; SICKVLFMI; ICKVLFMIL;
CKVLFMILK; KVLFMILKV; VLFMILKVI; LFMILKVIR; FMILKVIRL; MILKVIRLV;
ILKVIRLVF; LKVIRLVFF; KVIRLVFFL; VIRLVFFLT; IRLVFFLTL; RLVFFLTLF;
LVFFLTLFT; VFFLTLFTL; FFLTLFTLL; FLTLFTLLY; LTLFTLLYI; TLFTLLYIV;
LFTLLYIVL; FTLLYIVLK; TLLYIVLKF; KHILTLCLY; HILTLCLYC; ILTLCLYCI;
LTLCLYCIL; TLCLYCILS; LCLYCILSN; FPRHLLCFF; PRHLLCFFR; RHLLCFFRL;
HLLCFFRLF; LLCFFRLFW; LCFFRLFWA; CFFRLFWAK; FFRLFWAKI; FRLFWAKIM;
RLFWAKIML; LFWAKIMLL; APLNAFFYS; PLNAFFYSM; LNAFFYSMV; NAFFYSMVW;
AFFYSMVWI; FFYSMVWIS; FYSMVWISS; VFLINTLTN; KTKGTQLLT; TKGTQLLTE;
KGTQLLTEI; GTQLLTEII; TQLLTEIIN; QLLTEIINC; LLTEIINCR; LTEIINCRN;
TEIINCRNS; EIINCRNSM; IINCRNSMS; INCRNSMSM; NCRNSMSMW; CRNSMSMWS;
KEYNIMPST; EYNIMPSTH; YNIMPSTHV; NIMPSTHVS; IMPSTHVST; MPSTHVSTN;
PSTHVSTNK; STHVSTNKS; THVSTNKSY; HVSTNKSYR; VSTNKSYRI; STNKSYRIF;
TNKSYRIFF; NKSYRIFFH; KSYRIFFHK; SYRIFFHKF; YRIFFHKFF; RIFFHKFFI;
IFFHKFFIQ; FFHKFFIQN; FHKFFIQNL; HKFFIQNLS; KFFIQNLSF; FFIQNLSFF;
FIQNLSFFF; IQNLSFFFS; QNLSFFFSS; NLSFFFSSI; LSFFFSSIH; SFFFSSIHS;
FFFSSIHSK; FFSSIHSKA; FSSIHSKAG; SSIHSKAGK; SIHSKAGKG; IHSKAGKGS;
HSKAGKGSI; SKAGKGSIT; KAGKGSITK; AGKGSITKY; GKGSITKYS; KGSITKYSL;
GSITKYSLT; SITKYSLTK; ITKYSLTKK; TKYSLTKKL; KYSLTKKLV; IRGKVFRVF;
RGKVFRVFY; GKVFRVFYL; KVFRVFYLS; VFRVFYLSF; FRVFYLSFF; RVFYLSFFF;
VFYLSFFFG; FYLSFFFGW; YLSFFFGWC; VLRICCCFF; LRICCCFFI; RICCCFFIT;
ICCCFFITG; CCCFFITGK; CCFFITGKH; CFFITGKHI; FFITGKHIF; FITGKHIFM;
ITGKHIFMA; TGKHIFMAK; IFIPPFIKG; FIPPFIKGT; IPPFIKGTP; PPFIKGTPP;
FFIKGTPPG; FIKGTPPGL; IKGTPPGLP; KGTPPGLPL; GTPPGLPLF; TPPGLPLFC;
PPGLPLFCS; PGLPLFCSI; GLPLFCSIG; LPLFCSIGW; PLFCSIGWH; LFCSIGWHL;
YPIIYLNIS; SFRSLKGVS; FRSLKGVSP; RSLKGVSPI; SLKGVSPII; LKGVSPIIW;
KGVSPIIWT; GVSPIIWTH; VSPIIWTHH; SPIIWTHHC; PIIWTHHCR; IIWTHHCRV;
IWTHHCRVS; WTHHCRVSS; THHCRVSSV; HHCRVSSVR; HCRVSSVRS; CRVSSVRSK;
RVSSVRSKP; VSSVRSKPN; SSVRSKPNH; SVRSKPNHC; VRSKPNHCV; RSKPNHCVK;
SKPNHCVKQ; KPNHCVKQS; PNHCVKQSM; NHCVKQSMV; QSIQTKGSF; SIQTKGSFL;
IQTKGSFLK; QTKGSFLKN; TKGSFLKNF; KGSFLKNFL; GSFLKNFLF; SFLKNFLFK;
FLKNFLFKC; LKNFLFKCL; KNFLFKCLN; NFLFKCLNL; FLFKCLNLS; HSMQGQCTE;
SMQGQCTEG; MQGQCTEGF; QGQCTEGFL; GQCTEGFLE; QCTEGFLEQ; CTEGFLEQI;
TEGFLEQIG; EGFLEQIGH; GFLEQIGHS; FLEQIGHSL; LEQIGHSLQ; EQIGHSLQY;
QIGHSLQYR; IGHSLQYRV; GHSLQYRVS; HSLQYRVSG; SLQYRVSGQ; LQYRVSGQR;
QYRVSGQRG; YRVSGQRGK; RVSGQRGKS; VSGQRGKSA; SGQRGKSAQ; GQRGKSAQT;
QRGKSAQTS; RGKSAQTSE; GKSAQTSEL; KSAQTSELL; SAQTSELLQ; AQTSELLQV;
QTSELLQVP; TSELLQVPK; SELLQVPKS; ELLQVPKSG; ATFTSCSIF; TFTSCSIFL;
FTSCSIFLY; TSCSIFLYK; SCSIFLYKV; CSIFLYKVF; SIFLYKVFI; IFLYKVFIL;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

FLYKVFILF; LYKVFILFI; YKVFILFIL; KVFILFILS; VFILFILSS; FILFILSSS;
ILFILSSSP; LFILSSSPP; FILSSSPPL; ILSSSPPLS; LSSSPPLSG; AFLIKGRFP;
FLIKGRFPQ; LIKGRFPQA; IKGRFPQAA; KGRFPQAAL; GRFPQAALS; RFPQAALSR;
FPQAALSRP; PQAALSRPK; QAALSRPKR; AALSRPKRS; ALSRPKRSM; LSRPKRSMS;
SRPKRSMSS; RPKRSMSSM; PKRSMSSMD; KRSMSSMDS; RSMSSMDSS; SMSSMDSSL;
MSSMDSSLL; SSMDSSLLR; SMDSSLLRT; MDSSLLRTL; DSSLLRTLS 10 mers:

FCKNCKRIGI; CKNCKRIGIS; KNCKRIGISP; NCKRIGISPN; CKRIGISPNS;
KRIGISPNSF; RIGISPNSFA; IGISPNSFAR; GISPNSFARP; ISPNSFARPQ;
SPNSFARPQK; PNSFARPQKK; NSFARPQKKP; SFARPQKKPP; FARPQKKPPH;
ARPQKKPPHP; RPQKKPPHPY; PQKKPPHPYY; QKKPPHPYYL; KKPPHPYYLR;
KPPHPYYLRE; PPHPYYLRER; PHPYYLRERV; HPYYLRERVE; PYYLRERVEA;
YYLRERVEAE; YLRERVEAEA; LRERVEAEAA; RERVEAEAAS; ERVEAEAASA;
RVEAEAASAS; VEAEAASASY; EAEAASASYI; AEAASASYIL; KKRPQGGAAY;
KRPQGGAAYP; RPQGGAAYPW; PQGGAAYPWN; QGGAAYPWNA; GGAAYPWNAAK;
GAAYPWNAAK; AAYPWNAAKP; PQEGKCMTHR; QEGKCMTHRG; EGKCMTHRGM;
GKCMTHRGMQ; KCMTHRGMQP; CMTHRGMQPN; MTHRGMQPNH; THRGMQPNHD;
HRGMQPNHDL; RGMQPNHDLR; GMQPNHDLRK; MQPNHDLRKE; QPNHDLRKES;
PNHDLRKESA; LTGRSCLPME; TGRSCLPMEC; GRSCLPMECS; RSCLPMECSQ;
SCLPMECSQT; CLPMECSQTM; LPMECSQTMT; PMECSQTMTS; MECSQTMTSG;
ECSQTMTSGR; CSQTMTSGRK; SQTMTSGRKV; QTMTSGRKVH; TMTSGRKVHD;
MTSGRKVHDR; TSGRKVHDRH; SGRKVHDRHV; GRKVHDRHVL; RKVHDRHVLR;
KVHDRHVLRA; ESWPCPQLNW; SWPCPQLNWT; WPCPQLNWTK; PCPQLNWTKA;
CPQLNWTKAM; PQLNWTKAMV; QLNWTKAMVL; LNWTKAMVLR; NWTKAMVLRQ;
WTKAMVLRQL; TKAMVLRQLS; KAMVLRQLSR; AMVLRQLSRQ; MVLRQLSRQA;
VLRQLSRQAS; LRQLSRQASV; RQLSRQASVK; QLSRQASVKV; LSRQASVKVG;
SRQASVKVGK; RQASVKVGKT; QASVKVGKTW; ASVKVGKTWT; SVKVGKTWTG;
VKVGKTWTGT; KVGKTWTGTK; VGKTWTGTKK; GKTWTGTKKR; KTWTGTKKRA;
TWTGTKKRAQ; WTGTKKRAQR; TGTKKRAQRI; GTKKRAQRIF; TKKRAQRIFI;
KKRAQRIFIF; KRAQRIFIFI; RAQRIFIFIL; AQRIFIFILE; QRIFIFILEL;
RIFIFILELL; IFIFILELLL; FIFILELLLE; IFILELLLEF; FILELLLEFC;
ILELLLEFCR; LELLLEFCRG; ELLLEFCRGE; LLLEFCRGED; LLEFCRGEDS;
LEFCRGEDSV; EFCRGEDSVD; FCRGEDSVDG; CRGEDSVDGK; RGEDSVDGKN;
GEDSVDGKNK; EDSVDGKNKS; DSVDGKNKST; SVDGKNKSTT; VDGKNKSTTA;
DGKNKSTTAL; GKNKSTTALP; KNKSTTALPA; NKSTTALPAV; KSTTALPAVK;
STTALPAVKD; TTALPAVKDS; TALPAVKDSV; ALPAVKDSVK; LPAVKDSVKD;
PAVKDSVKDS; VSNPFFFVFP; SNPFFFVFPG; NPFFFVFPGS; PFFFVFPGSW;
FFFVFPGSWV; FFVFPGSWVL; FVFPGSWVLL; LPVYLRLLLP; PVYLRLLLPQ;
VYLRLLLPQD; YLRLLLPQDF; LRLLLPQDFQ; RLLLPQDFQW; LLLPQDFQWL;
LLPQDFQWLK; LPQDFQWLKL; PQDFQWLKLL; QDFQWLKLLL; DFQWLKLLLG;
FQWLKLLLGR; QWLKLLLGRL; WLKLLLGRLL; LKLLLGRLLL; KLLLGRLLLL;
LLVLLGLLLG; LVLLGLLLGL; VLLGLLLGLL; LLGLLLGLLL; GISSLMIGIT;
ISSLMIGITK; SSLMIGITKF; SLMIGITKFP; LMIGITKFPL; ASISNQAWLW;
SISNQAWLWN; ISNQAWLWNC; SNQAWLWNCL; NQAWLWNCLT; QAWLWNCLTQ;
AWLWNCLTQM; WLWNCLTQMS; LWNCLTQMST; WNCLTQMSTM; NCLTQMSTMI;
CLTQMSTMIF; LTQMSTMIFC; TQMSTMIFCF; QMSTMIFCFL; MSTMIFCFLV;
ILLLIIFNTL; LLLIIFNTLI; LLIIFNTLIL; LIIFNTLILG; IIFNTLILGI;
IFNTLILGIG; FNTLILGIGV; NTLILGIGVL; TLILGIGVLL; LILGIGVLLC;
ILGIGVLLCL; LGIGVLLCLL; GIGVLLCLLL; IGVLLCLLLF; GVLLCLLLFP;
VLLCLLLFPR; LLCLLLFPRL; LCLLLFPRLC; CLLLFPRLCG; LLLFPRLCGM;
LLFPRLCGML; LFPRLCGMLL; FPRLCGMLLG; PRLCGMLLGM; RLCGMLLGMI;
LCGMLLGMIY; CGMLLGMIYL; GMLLGMIYLL; PHRNCREEQK; HRNCREEQKD;
RNCREEQKDF; NCREEQKDFL; CREEQKDFLE; REEQKDFLET; EEQKDFLETP;
EQKDFLETPW; QKDFLETPWL; KDFLETPWLD; DFLETPWLDF; FLETPWLDFW;
LETPWLDFWR; ETPWLDFWRK; TPWLDFWRKL; PWLDFWRKLP; WLDFWRKLPG;
LDFWRKLPGQ; DFWRKLPGQL; TFIIIFNNII; FIIIFNNIIL; IIIFNNIILI;
IIFNNIILIF; IFNNIILIFP; FNNIILIFPL; NNIILIFPLL; NIILIFPLLG;
IILIFPLLGP; ILIFPLLGPQ; LIFPLLGPQW; IFPLLGPQWL; FPLLGPQWLD;
PLLGPQWLDK; LKGKVPVYIL; KGKVPVYILA; GKVPVYILAI; KVPVYILAIL;
VPVYILAILI; PVYILAILIV; EINKVYIQES; INKVYIQESL; KKLLPQEVLI;
KLLPQEVLIK; LLPQEVLIKE; LPQEVLIKEL; PQEVLIKELL; QEVLIKELLL;
EVLIKELLLN; VLIKELLLNG; LIKELLLNGC; IKELLLNGCC; KELLLNGCCL;
ELLLNGCCLY; LLLNGCCLYF; HLLLKHMKMA; LLLKHMKMAP; LLKHMKMAPT;
LKHMKMAPTK; KHMKMAPTKR; HMKMAPTKRK; MKMAPTKRKG; KMAPTKRKGE;
MAPTKRKGEC; APTKRKGECP; PTKRKGECPG; TKRKGECPGA; KRKGECPGAA;
RKGECPGAAP; KGECPGAAPK; GECPGAAPKK; ECPGAAPKKP; CPGAAPKKPK;
PGAAPKKPKE; GAAPKKPKEP; AAPKKPKEPV; APKKPKEPVQ; PKKPKEPVQV;
KKPKEPVQVP; KPKEPVQVPK; PKEPVQVPKL; KEPVQVPKLL; EPVQVPKLLI;
PVQVPKLLIK; VQVPKLLIKG; QVPKLLIKGG; VPKLLIKGGV; PKLLIKGGVE;
KLLIKGGVEV; LLIKGGVEVL; LIKGGVEVLE; IKGGVEVLEV; KGGVEVLEVK;
GGVEVLEVKT; GVEVLEVKTG; VEVLEVKTGV; EVLEVKTGVD; VLEVKTGVDA;
LEVKTGVDAI; EVKTGVDAIT; VKTGVDAITE; KTGVDAITEV; TGVDAITEVE;
GVDAITEVEC; VDAITEVECF; DAITEVECFL; AITEVECFLN; ITEVECFLNP;
TEVECFLNPE; EVECFLNPEM; VECFLNPEMG; ECFLNPEMGD; CFLNPEMGDP;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

FLNPEMGDPD; LNPEMGDPDE; NPEMGDPDEN; PEMGDPDENL; EMGDPDENLR;
MGDPDENLRG; GDPDENLRGF; DPDENLRGFS; PDENLRGFSL; DENLRGFSLK;
ENLRGFSLKL; NLRGFSLKLS; LRGFSLKLSA; RGFSLKLSAE; GFSLKLSAEN;
FSLKLSAEND; SLKLSAENDF; LKLSAENDFS; KLSAENDFSS; LSAENDFSSD;
SAENDFSSDS; AENDFSSDSP; ENDFSSDSPE; NDFSSDSPER; DFSSDSPERK;
FSSDSPERKM; SSDSPERKML; SDSPERKMLP; DSPERKMLPC; SPERKMLPCY;
PERKMLPCYS; ERKMLPCYST; RKMLPCYSTA; KMLPCYSTAR; MLPCYSTARI;
LPCYSTARIP; PCYSTARIPL; CYSTARIPLP; YSTARIPLPN; STARIPLPNL;
TARIPLPNLN; ARIPLPNLNE; RIPLPNLNED; IPLPNLNEDL; PLPNLNEDLT;
LPNLNEDLTC; PNLNEDLTCG; NLNEDLTCGN; LNEDLTCGNL; NEDLTCGNLL;
EDLTCGNLLM; DLTCGNLLMW; LTCGNLLMWE; TCGNLLMWEA; CGNLLMWEAV;
GNLLMWEAVT; NLLMWEAVTV; LLMWEAVTVQ; LMWEAVTVQT; MWEAVTVQTE;
WEAVTVQTEV; EAVTVQTEVI; AVTVQTEVIG; VTVQTEVIGI; TVQTEVIGIT;
VQTEVIGITS; QTEVIGITSM; TEVIGITSML; EVIGITSMLN; VIGITSMLNL;
IGITSMLNLH; GITSMLNLHA; ITSMLNLHAG; TSMLNLHAGS; SMLNLHAGSQ;
MLNLHAGSQK; LNLHAGSQKV; NLHAGSQKVH; LHAGSQKVHE; HAGSQKVHEH;
AGSQKVHEHG; GSQKVHEHGG; SQKVHEHGGG; QKVHEHGGGK; KVHEHGGGKP;
VHEHGGGKPI; HEHGGGKPIQ; EHGGGKPIQG; HGGGKPIQGS; GGGKPIQGSN;
GGKPIQGSNF; GKPIQGSNFH; KPIQGSNFHF; PIQGSNFHFF; IQGSNFHFFA;
QGSNFHFFAV; GSNFHFFAVG; SNFHFFAVGG; NFHFFAVGGE; FHFFAVGGEP;
HFFAVGGEPL; FFAVGGEPLE; FAVGGEPLEM; AVGGEPLEMQ; VGGEPLEMQG;
GGEPLEMQGV; GEPLEMQGVL; EPLEMQGVLM; PLEMQGVLMN; LEMQGVLMNY;
EMQGVLMNYR; MQGVLMNYRS; QGVLMNYRSK; GVLMNYRSKY; VLMNYRSKYP;
LMNYRSKYPD; MNYRSKYPDG; NYRSKYPDGT; YRSKYPDGTI; RSKYPDGTIT;
SKYPDGTITP; KYPDGTITPK; YPDGTITPKN; PDGTITPKNP; DGTITPKNPT;
GTITPKNPTA; TITPKNPTAQ; ITPKNPTAQS; TPKNPTAQSQ; PKNPTAQSQV;
KNPTAQSQVM; NPTAQSQVMN; PTAQSQVMNT; TAQSQVMNTD; AQSQVMNTDH;
QSQVMNTDHK; SQVMNTDHKA; QVMNTDHKAY; VMNTDHKAYL; MNTDHKAYLD;
NTDHKAYLDK; TDHKAYLDKN; DHKAYLDKNN; HKAYLDKNNA; KAYLDKNNAY;
AYLDKNNAYP; YLDKNNAYPV; LDKNNAYPVE; DKNNAYPVEC; KNNAYPVECW;
NNAYPVECWV; NAYPVECWVP; AYPVECWVPD; YPVECWVPDP; PVECWVPDPS;
VECWVPDPSR; ECWVPDPSRN; CWVPDPSRNE; WVPDPSRNEN; VPDPSRNENA;
PDPSRNENAR; DPSRNENARY; PSRNENARYF; SRNENARYFG; RNENARYFGT;
NENARYFGTF; ENARYFGTFT; NARYFGTFTG; ARYFGTFTGG; RYFGTFTGGE;
YFGTFTGGEN; FGTFTGGENV; GTFTGGENVP; TFTGGENVPP; FTGGENVPPV;
TGGENVPPVL; GGENVPPVLH; GENVPPVLHV; ENVPPVLHVT; NVPPVLHVTN;
VPPVLHVTNT; PPVLHVTNTA; PVLHVTNTAT; VLHVTNTATT; LHVTNTATTV;
HVTNTATTVL; VTNTATTVLL; TNTATTVLLD; NTATTVLLDE; TATTVLLDEQ;
ATTVLLDEQG; TTVLLDEQGV; TVLLDEQGVG; VLLDEQGVGP; LLDEQGVGPL;
LDEQGVGPLC; DEQGVGPLCK; EQGVGPLCKA; QGVGPLCKAD; GVGPLCKADS;
VGPLCKADSL; GPLCKADSLY; PLCKADSLYV; LCKADSLYVS; CKADSLYVSA;
KADSLYVSAA; ADSLYVSAAD; DSLYVSAADI; SLYVSAADIC; LYVSAADICG;
YVSAADICGL; VSAADICGLF; SAADICGLFT; AADICGLFTN; ADICGLFTNS;
DICGLFTNSS; ICGLFTNSSG; CGLFTNSSGT; GLFTNSSGTQ; LFTNSSGTQQ;
FTNSSGTQQW; TNSSGTQQWR; NSSGTQQWRG; SSGTQQWRGL; SGTQQWRGLA;
GTQQWRGLAR; TQQWRGLARY; QQWRGLARYF; QWRGLARYFK; WRGLARYFKI;
RGLARYFKIR; GLARYFKIRL; LARYFKIRLR; ARYFKIRLRK; RYFKIRLRKR;
YFKIRLRKRS; FKIRLRKRSV; KIRLRKRSVK; IRLRKRSVKN; RLRKRSVKNP;
LRKRSVKNPY; RKRSVKNPYP; KRSVKNPYPI; RSVKNPYPIS; SVKNPYPISF;
VKNPYPISFL; KNPYPISFLL; NPYPISFLLS; PYPISFLLSD; YPISFLLSDL;
PISFLLSDLI; ISFLLSDLIN; SFLLSDLINR; FLLSDLINRR; LLSDLINRRT;
LSDLINRRTQ; SDLINRRTQR; DLINRRTQRV; LINRRTQRVD; INRRTQRVDG;
NRRTQRVDGQ; RRTQRVDGQP; RTQRVDGQPM; TQRVDGQPMY; QRVDGQPMYG;
RVDGQPMYGM; VDGQPMYGME; DGQPMYGMES; GQPMYGMESQ; QPMYGMESQV;
PMYGMESQVE; MYGMESQVEE; YGMESQVEEV; GMESQVEEVR; MESQVEEVRV;
ESQVEEVRVF; SQVEEVRVFD; QVEEVRVFDG; VEEVRVFDGT; EEVRVFDGTE;
EVRVFDGTER; VRVFDGTERL; RVFDGTERLP; VFDGTERLPG; FDGTERLPGD;
DGTERLPGDP; GTERLPGDPD; TERLPGDPDM; ERLPGDPDMI; RLPGDPDMIR;
LPGDPDMIRY; PGDPDMIRYI; GDPDMIRYID; DPDMIRYIDK; PDMIRYIDKQ;
DMIRYIDKQG; MIRYIDKQGQ; IRYIDKQGQL; RYIDKQGQLQ; YIDKQGQLQT;
IDKQGQLQTK; DKQGQLQTKM; KQGQLQTKML; TGAFIVHIHL; GAFIVHIHLI;
AFIVHIHLIN; FIVHIHLINA; IVHIHLINAA; VHIHLINAAF; HIHLINAAFV;
ATFKLVLFWG; TFKLVLFWGW; FKLVLFWGWC; KLVLFWGWCF; LVLFWGWCFR;
VLFWGWCFRP; LFWGWCFRPF; FWGWCFRPFK; WGWCFRPFKT; GWCFRPFKTL;
WCFRPFKTLK; CFRPFKTLKA; FRPFKTLKAF; RPFKTLKAFT; PFKTLKAFTQ;
FKTLKAFTQM; KTLKAFTQMQ; TLKAFTQMQL; LKAFTQMQLL; KAFTQMQLLT;
AFTQMQLLTM; FTQMQLLTMG; TQMQLLTMGV; ILFSCNIKNT; LFSCNIKNTF;
FSCNIKNTFP; SCNIKNTFPH; CNIKNTFPHA; NIKNTFPHAY; IKNTFPHAYI;
KNTFPHAYII; NTFPHAYIIF; TFPHAYIIFH; FPHAYIIFHP; KSIHTYLRIQ;
SIHTYLRIQP; IHTYLRIQPF; HTYLRIQPFL; TYLRIQPFLP; YLRIQPFLPF;
LRIQPFLPFN; RIQPFLPFNN; IQPFLPFNNS; QPFLPFNNSR; PFLPFNNSRL;
FLPFNNSRLY; LPFNNSRLYI; PFNNSRLYIS; FNNSRLYISC; NNSRLYISCK;
NSRLYISCKI; SRLYISCKIS; RLYISCKISY; LYISCKISYR; YISCKISYRP;
ISCKISYRPK; SCKISYRPKP; CKISYRPKPN; IYFGPKIYLS; YFGPKIYLSY;
FGPKIYLSYK; GPKIYLSYKS; PKIYLSYKSS; KIYLSYKSSL; IYLSYKSSLQ;
YLSYKSSLQG; LSYKSSLQGF; SYKSSLQGFR; YKSSLQGFRD; KSSLQGFRDR;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

SSLQGFRDRI; SLQGFRDRIL; LQGFRDRILI; QGFRDRILIH; GFRDRILIHC;
FRDRILIHCN; RDRILIHCNQ; DRILIHCNQA; RILIHCNQAW; ILIHCNQAWW;
LIHCNQAWWK; IHCNQAWWKY; HCNQAWWKYL; CNQAWWKYLG; NQAWWKYLGS;
QAWWKYLGSF; AWWKYLGSFV; FSSCPFYIFK; SSCPFYIFKN; SCPFYIFKNN;
CPFYIFKNNH; PFYIFKNNHV; FYIFKNNHVL; YIFKNNHVLI; IFKNNHVLIY;
FKNNHVLIYS; KNNHVLIYSY; NNHVLIYSYT; CCFSTINGTF; CFSTINGTFK;
PVSSFRYIEN; VSSFRYIENN; SSFRYIENNT; SFRYIENNTV; FRYIENNTVQ;
RYIENNTVQK; YIENNTVQKI; IENNTVQKIK; ENNTVQKIKY; NNTVQKIKYY;
NTVQKIKYYR; TVQKIKYYRI; VQKIKYYRIH; QKIKYYRIHF; KIKYYRIHFR;
QTVQPSNTCH; TVQPSNTCHI; VQPSNTCHIL; QPSNTCHILF; HFFPGHMKGI;
FFPGHMKGIY; FPGHMKGIYS; PGHMKGIYSF; GHMKGIYSFF; HMKGIYSFFS;
NCIYCLLTNT; CIYCLLTNTF; IYCLLTNTFL; YCLLTNTFLI; CLLTNTFLIF;
LLTNTFLIFT; LTNTFLIFTF; TNTFLIFTFC; NTFLIFTFCK; TFLIFTFCKN;
FLIFTFCKNN; LIFTFCKNNS; IFTFCKNNSI; FTFCKNNSIC; TFCKNNSICK;
FCKNNSICKV; CKNNSICKVL; KNNSICKVLF; NNSICKVLFM; NSICKVLFMI;
SICKVLFMIL; ICKVLFMILK; CKVLFMILKV; KVLFMILKVI; VLFMILKVIR;
LFMILKVIRL; FMILKVIRLV; MILKVIRLVF; ILKVIRLVFF; LKVIRLVFFL;
KVIRLVFFLT; VIRLVFFLTL; IRLVFFLTLF; RLVFFLTLFT; LVFFLTLFTL;
VFFLTLFTLL; FFLTLFTLLY; FLTLFTLLYI; LTLFTLLYIV; TLFTLLYIVL;
LFTLLYIVLK; FTLLYIVLKF; KHILTLCLYC; HILTLCLYCI; ILTLCLYCIL;
LTLCLYCILS; TLCLYCILSN; FPRHLLCFFR; PRHLLCFFRL; RHLLCFFRLF;
HLLCFFRLFW; LLCFFRLFWA; LCFFRLFWAK; CFFRLFWAKI; FFRLFWAKIM;
FRLFWAKIML; RLFWAKIMLL; APLNAFFYSM; PLNAFFYSMV; LNAFFYSMVW;
NAFFYSMVWI; AFFYSMVWIS; FFYSMVWISS; KTKGTQLLTE; TKGTQLLTEI;
KGTQLLTEII; GTQLLTEIIN; TQLLTEIINC; QLLTEIINCR; LLTEIINCRN;
LTEIINCRNS; TEIINCRNSM; EIINCRNSMS; IINCRNSMSM; INCRNSMSMW;
NCRNSMSMWS; KEYNIMPSTH; EYNIMPSTHV; YNIMPSTHVS; NIMPSTHVST;
IMPSTHVSTN; MPSTHVSTNK; PSTHVSTNKS; STHVSTNKSY; THVSTNKSYR;
HVSTNKSYRI; VSTNKSYRIF; STNKSYRIFF; TNKSYRIFFH; NKSYRIFFHK;
KSYRIFFHKF; SYRIFFHKFF; YRIFFHKFFI; RIFFHKFFIQ; IFFHKFFIQN;
FFHKFFIQNL; FHKFFIQNLS; HKFFIQNLSF; KFFIQNLSFF; FFIQNLSFFF;
FIQNLSFFFS; IQNLSFFFSS; QNLSFFFSSI; NLSFFFSSIH; LSFFFSSIHS;
SFFFSSIHSK; FFFSSIHSKA; FFSSIHSKAG; FSSIHSKAGK; SSIHSKAGKG;
SIHSKAGKGS; IHSKAGKGSI; HSKAGKGSIT; SKAGKGSITK; KAGKGSITKY;
AGKGSITKYS; GKGSITKYSL; KGSITKYSLT; GSITKYSLTK; SITKYSLTKK;
ITKYSLTKKL; TKYSLTKKLV; IRGKVFRVFY; RGKVFRVFYL; GKVFRVFYLS;
KVFRVFYLSF; VFRVFYLSFF; FRVFYLSFFF; RVFYLSFFFG; VFYLSFFFGW;
FYLSFFFGWC; VLRICCCFFI; LRICCCFFIT; RICCCFFITG; ICCCFFITGK;
CCCFFITGKH; CCFFITGKHI; CFFITGKHIF; FFITGKHIFM; FITGKHIFMA;
ITGKHIFMAK; IFIPFFIKGT; FIPFFIKGTP; IPFFIKGTPP; PFFIKGTPPG;
FFIKGTPPGL; FIKGTPPGLP; IKGTPPGLPL; KGTPPGLPLF; GTPPGLPLFC;
TPPGLPLFCS; PPGLPLFCSI; PGLPLFCSIG; GLPLFCSIGW; LPLFCSIGWH;
PLFCSIGWHL; SFRSLKGVSP; FRSLKGVSPI; RSLKGVSPII; SLKGVSPIIW;
LKGVSPIIWT; KGVSPIIWTH; GVSPIIWTHH; VSPIIWTHHC; SPIIWTHHCR;
PIIWTHHCRV; IIWTHHCRVS; IWTHHCRVSS; WTHHCRVSSV; THHCRVSSVR;
HHCRVSSVRS; HCRVSSVRSK; CRVSSVRSKP; RVSSVRSKPN; VSSVRSKPNH;
SSVRSKPNHC; SVRSKPNHCV; VRSKPNHCVK; RSKPNHCVKQ; SKPNHCVKQS;
KPNHCVKQSM; PNHCVKQSMQ; QSIQTKGSFL; SIQTKGSFLK; IQTKGSFLKN;
QTKGSFLKNF; TKGSFLKNFL; KGSFLKNFLF; GSFLKNFLFK; SFLKNFLFKC;
FLKNFLFKCL; LKNFLFKCLN; KNFLFKCLNL; NFLFKCLNLS; HSMQGQCTEG;
SMQGQCTEGF; MQGQCTEGFL; QGQCTEGFLE; GQCTEGFLEQ; QCTEGFLEQI;
CTEGFLEQIG; TEGFLEQIGH; EGFLEQIGHS; GFLEQIGHSL; FLEQIGHSLQ;
LEQIGHSLQY; EQIGHSLQYR; QIGHSLQYRV; IGHSLQYRVS; GHSLQYRVSG;
HSLQYRVSGQ; SLQYRVSGQR; LQYRVSGQRG; QYRVSGQRGK; YRVSGQRGKS;
RVSGQRGKSA; VSGQRGKSAQ; SGQRGKSAQT; GQRGKSAQTS; QRGKSAQTSE;
RGKSAQTSEL; GKSAQTSELL; KSAQTSELLQ; SAQTSELLQV; AQTSELLQVP;
QTSELLQVPK; TSELLQVPKS; SELLQVPKSG; ATFTSCSIFL; TFTSCSIFLY;
FTSCSIFLYK; TSCSIFLYKV; SCSIFLYKVF; CSIFLYKVFI; SIFLYKVFIL;
IFLYKVFILF; FLYKVFILFI; LYKVFILFIL; YKVFILFILS; KVFILFILSS;
VFILFILSSS; FILFILSSSP; ILFILSSSPP; LFILSSSPPL; FILSSSPPLS;
ILSSSPPLSG; AFLIKGRFPQ; FLIKGRFPQA; LIKGRFPQAA; IKGRFPQAAL;
KGRFPQAALS; GRFPQAALSR; RFPQAALSRP; FPQAALSRPK; PQAALSRPKR;
QAALSRPKRS; AALSRPKRSM; ALSRPKRSMS; LSRPKRSMSS; SRPKRSMSSM;
RPKRSMSSMD; PKRSMSSMDS; KRSMSSMDSS; RSMSSMDSSL; SMSSMDSSLL;
MSSMDSSLLR; SSMDSSLLRT; SMDSSLLRTL; MDSSLLRTLS 11 mers:

FCKNCKRIGIS; CKNCKRIGISP; KNCKRIGISPN; NCKRIGISPNS; CKRIGISPNSF;
KRIGISPNSFA; RIGISPNSFAR; IGISPNSFARP; GISPNSFARPQ; ISPNSFARPQK;
SPNSFARPQKK; PNSFARPQKKP; NSFARPQKKPP; SFARPQKKPPH; FARPQKKPPHP;
ARPQKKPPHPY; RPQKKPPHPYY; PQKKPPHPYYL; QKKPPHPYYLR; KKPPHPYYLRE;
KPPHPYYLRER; PPHPYYLRERV; PHPYYLRERVE; HPYYLRERVEA; PYYLRERVEAE;
YYLRERVEAEA; YLRERVEAEAA; LRERVEAEAAS; RERVEAEAASA; ERVEAEAASAS;
RVEAEAASASY; VEAEAASASYI; EAEAASASYIL; KKRPQGGAAYP; KRPQGGAAYPW;
RPQGGAAYPWN; PQGGAAYPWNA; QGGAAYPWNAA; GGAAYPWNAAK; GAAYPWNAAKP;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

PQEGKCMTHRG; QEGKCMTHRGM; EGKCMTHRGMQ; GKCMTHRGMQP; KCMTHRGMQPN;
CMTHRGMQPNH; MTHRGMQPNHD; THRGMQPNHDL; HRGMQPNHDLR; RGMQPNHDLRK;
GMQPNHDLRKE; MQPNHDLRKES; QPNHDLRKESA; LTGRSCLPMEC; TGRSCLPMECS;
GRSCLPMECSQ; RSCLPMECSQT; SCLPMECSQTM; CLPMECSQTMT; LPMECSQTMTS;
PMECSQTMTSG; MECSQTMTSGR; ECSQTMTSGRK; CSQTMTSGRKV; SQTMTSGRKVH;
QTMTSGRKVHD; TMTSGRKVHDR; MTSGRKVHDRH; TSGRKVHDRHV; SGRKVHDRHVL;
GRKVHDRHVLR; RKVHDRHVLRA; ESWPCPQLNWT; SWPCPQLNWTK; WPCPQLNWTKA;
PCPQLNWTKAM; CPQLNWTKAMV; PQLNWTKAMVL; QLNWTKAMVLR; LNWTKAMVLRQ;
NWTKAMVLRQL; WTKAMVLRQLS; TKAMVLRQLSR; KAMVLRQLSRQ; AMVLRQLSRQA;
MVLRQLSRQAS; VLRQLSRQASV; LRQLSRQASVK; RQLSRQASVKV; QLSRQASVKVG;
LSRQASVKVGK; SRQASVKVGKT; RQASVKVGKTW; QASVKVGKTWT; ASVKVGKTWTG;
SVKVGKTWTGT; VKVGKTWTGTK; KVGKTWTGTKK; VGKTWTGTKKR; GKTWTGTKKRA;
KTWTGTKKRAQ; TWTGTKKRAQR; WTGTKKRAQRI; TGTKKRAQRIF; GTKKRAQRIFI;
TKKRAQRIFIF; KKRAQRIFIFI; KRAQRIFIFIL; RAQRIFIFILE; AQRIFIFILEL;
QRIFIFILELL; RIFIFILELLL; IFIFILELLLE; FIFILELLLEF; IFILELLLEFC;
FILELLLEFCR; ILELLLEFCRG; LELLLEFCRGE; ELLLEFCRGED; LLLEFCRGEDS;
LLEFCRGEDSV; LEFCRGEDSVD; EFCRGEDSVDG; FCRGEDSVDGK; CRGEDSVDGKN;
RGEDSVDGKNK; GEDSVDGKNKS; EDSVDGKNKST; DSVDGKNKSTT; SVDGKNKSTTA;
VDGKNKSTTAL; DGKNKSTTALP; GKNKSTTALPA; KNKSTTALPAV; NKSTTALPAVK;
KSTTALPAVKD; STTALPAVKDS; TTALPAVKDSV; TALPAVKDSVK; ALPAVKDSVKD;
LPAVKDSVKDS; VSNPFFVFPG; SNPFFVFPGS; NPFFFVFPGSW; PFFFVFPGSWV;
FFFVFPGSWVL; FFVFPGSWVLL; LPVYLRLLLPQ; PVYLRLLLPQD; VYLRLLLPQDF;
YLRLLLPQDFQ; LRLLLPQDFQW; RLLLPQDFQWL; LLLPQDFQWLK; LLPQDFQWLKL;
LPQDFQWLKLL; PQDFQWLKLLL; QDFQWLKLLLG; DFQWLKLLLGR; FQWLKLLLGRL;
QWLKLLLGRLL; WLKLLLGRLLL; LKLLLGRLLLL; LLLGLLLGLL; VLLGLLLGLLL;
VLLGLLLGLLL; GISSLMIGITK; ISSLMIGITKF; SSLMIGITKFP; SLMIGITKFPL;
ASISNQAWLWN; SISNQAWLWNC; ISNQAWLWNCL; SNQAWLWNCLT; NQAWLWNCLTQ;
QAWLWNCLTQM; AWLWNCLTQMS; WLWNCLTQMST; LWNCLTQMSTM; WNCLTQMSTMI;
NCLTQMSTMIF; CLTQMSTMIFC; LTQMSTMIFCF; TQMSTMIFCFL; QMSTMIFCFLV;
ILLLIIFNTLI; LLLIIFNTLIL; LLIIFNTLILG; LIIFNTLILGI; IIFNTLILGIG;
IFNTLILGIGV; FNTLILGIGVL; NTLILGIGVLL; TLILGIGVLLC; LILGIGVLLCL;
ILGIGVLLCLL; LGIGVLLCLLL; GIGVLLCLLLF; IGVLLCLLLFP; GVLLCLLLFPR;
VLLCLLLFPRL; LLCLLLFPRLC; LCLLLFPRLCG; CLLLFPRLCGM; LLLFPRLCGML;
LLFPRLCGMLL; LFPRLCGMLLG; FPRLCGMLLGM; PRLCGMLLGMI; RLCGMLLGMIY;
LCGMLLGMIYL; CGMLLGMIYLL; PHRNCREEQKD; HRNCREEQKDF; RNCREEQKDFL;
NCREEQKDFLE; CREEQKDFLET; REEQKDFLETP; EEQKDFLETPW; EQKDFLETPWL;
QKDFLETPWLD; KDFLETPWLDF; DFLETPWLDFW; FLETPWLDFWR; LETPWLDFWRK;
ETPWLDFWRKL; TPWLDFWRKLP; PWLDFWRKLPG; WLDFWRKLPGQ; LDFWRKLPGQL;
TFIIIFNNIIL; FIIIFNNIILI; IIIFNNIILIF; IIFNNIILIFP; IFNNIILIFPL;
FNNIILIFPLL; NNIILIFPLLG; NIILIFPLLGP; IILIFPLLGPQ; ILIFPLLGPQW;
LIFPLLGPQWL; IFPLLGPQWLD; FPLLGPQWLDK; LKGKVPVYILA; KGKVPVYILAI;
GKVPVYILAIL; KVPVYILAILI; VPVYILAILIV; EINKVYIQESL; KKLLPQEVLIK;
KLLPQEVLIKE; LLPQEVLIKEL; LPQEVLIKELL; PQEVLIKELLL; QEVLIKELLLN;
EVLIKELLLNG; VLIKELLLNGC; LIKELLLNGCC; IKELLLNGCCL; KELLLNGCCLY;
ELLLNGCCLYF; HLLLKHMKMAP; LLLKHMKMAPT; LLKHMKMAPTK; LKHMKMAPTKR;
KHMKMAPTKRK; HMKMAPTKRKG; MKMAPTKRKGE; KMAPTKRKGEC; MAPTKRKGECP;
APTKRKGECPG; PTKRKGECPGA; TKRKGECPGAA; KRKGECPGAAP; RKGECPGAAPK;
KGECPGAAPKK; GECPGAAPKKP; ECPGAAPKKPK; CPGAAPKKPKE; PGAAPKKPKEP;
GAAPKKPKEPV; AAPKKPKEPVQ; APKKPKEPVQV; PKKPKEPVQVP; KKPKEPVQVPK;
KPKEPVQVPKL; PKEPVQVPKLL; KEPVQVPKLLI; EPVQVPKLLIK; PVQVPKLLIKG;
VQVPKLLIKGG; QVPKLLIKGGV; VPKLLIKGGVE; PKLLIKGGVEV; KLLIKGGVEVL;
LLIKGGVEVLE; LIKGGVEVLEV; IKGGVEVLEVK; KGGVEVLEVKT; GGVEVLEVKTG;
GVEVLEVKTGV; VEVLEVKTGVD; EVLEVKTGVDA; VLEVKTGVDAI; LEVKTGVDAIT;
EVKTGVDAITE; VKTGVDAITEV; KTGVDAITEVE; TGVDAITEVEC; GVDAITEVECF;
VDAITEVECFL; DAITEVECFLN; AITEVECFLNP; ITEVECFLNPE; TEVECFLNPEM;
EVECFLNPEMG; VECFLNPEMGD; ECFLNPEMGDP; CFLNPEMGDPD; FLNPEMGDPDE;
LNPEMGDPDEN; NPEMGDPDENL; PEMGDPDENLR; EMGDPDENLRG; MGDPDENLRGF;
GDPDENLRGFS; DPDENLRGFSL; PDENLRGFSLK; DENLRGFSLKL; ENLRGFSLKLS;
NLRGFSLKLSA; LRGFSLKLSAE; RGFSLKLSAEN; GFSLKLSAEND; FSLKLSAENDF;
SLKLSAENDFS; LKLSAENDFSS; KLSAENDFSSD; LSAENDFSSDS; SAENDFSSDSP;
AENDFSSDSPE; ENDFSSDSPER; NDFSSDSPERK; DFSSDSPERKM; FSSDSPERKML;
SSDSPERKMLP; SDSPERKMLPC; DSPERKMLPCY; SPERKMLPCYS; PERKMLPCYST;
ERKMLPCYSTA; RKMLPCYSTAR; KMLPCYSTARI; MLPCYSTARIP; LPCYSTARIPL;
PCYSTARIPLP; CYSTARIPLPN; YSTARIPLPNL; STARIPLPNLN; TARIPLPNLNE;
ARIPLPNLNED; RIPLPNLNEDL; IPLPNLNEDLT; PLPNLNEDLTC; LPNLNEDLTCG;
PNLNEDLTCGN; NLNEDLTCGNL; LNEDLTCGNLL; NEDLTCGNLLM; EDLTCGNLLMW;
DLTCGNLLMWE; LTCGNLLMWEA; TCGNLLMWEAV; CGNLLMWEAVT; GNLLMWEAVTV;
NLLMWEAVTVQ; LLMWEAVTVQT; LMWEAVTVQTE; MWEAVTVQTEV; WEAVTVQTEVI;
EAVTVQTEVIG; AVTVQTEVIGI; VTVQTEVIGIT; TVQTEVIGITS; VQTEVIGITSM;
QTEVIGITSML; TEVIGITSMLN; EVIGITSMLNL; VIGITSMLNLH; IGITSMLNLHA;
GITSMLNLHAG; ITSMLNLHAGS; TSMLNLHAGSQ; SMLNLHAGSQK; MLNLHAGSQKV;
LNLHAGSQKVH; NLHAGSQKVHE; LHAGSQKVHEH; HAGSQKVHEHG; AGSQKVHEHGG;
GSQKVHEHGGG; SQKVHEHGGGK; QKVHEHGGGKP; KVHEHGGGKPI; VHEHGGGKPIQ;
HEHGGGKPIQG; EHGGGKPIQGS; HGGGKPIQGSN; GGGKPIQGSNF; GGKPIQGSNFH;
GKPIQGSNFHF; KPIQGSNFHFF; PIQGSNFHFFA; IQGSNFHFFAV; QGSNFHFFAVG;
GSNFHFFAVGG; SNFHFFAVGGE; NFHFFAVGGEP; FHFFAVGGEPL; HFFAVGGEPLE;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

FFAVGGEPLEM; FAVGGEPLEMQ; AVGGEPLEMQG; VGGEPLEMQGV; GGEPLEMQGVL;
GEPLEMQGVLM; EPLEMQGVLMN; PLEMQGVLMNY; LEMQGVLMNYR; EMQGVLMNYRS;
MQGVLMNYRSK; QGVLMNYRSKY; GVLMNYRSKYP; VLMNYRSKYPD; LMNYRSKYPDG;
MNYRSKYPDGT; NYRSKYPDGTI; YRSKYPDGTIT; RSKYPDGTITP; SKYPDGTITPK;
KYPDGTITPKN; YPDGTITPKNP; PDGTITPKNPT; DGTITPKNPTA; GTITPKNPTAQ;
TITPKNPTAQS; ITPKNPTAQSQ; TPKNPTAQSQV; PKNPTAQSQVM; KNPTAQSQVMN;
NPTAQSQVMNT; PTAQSQVMNTD; TAQSQVMNTDH; AQSQVMNTDHK; QSQVMNTDHKA;
SQVMNTDHKAY; QVMNTDHKAYL; VMNTDHKAYLD; MNTDHKAYLDK; NTDHKAYLDKN;
TDHKAYLDKNN; DHKAYLDKNNA; HKAYLDKNNAY; KAYLDKNNAYP; AYLDKNNAYPV;
YLDKNNAYPVE; LDKNNAYPVEC; DKNNAYPVECW; KNNAYPVECWV; NNAYPVECWVP;
NAYPVECWVPD; AYPVECWVPDP; YPVECWVPDPS; PVECWVPDPSR; VECWVPDPSRN;
ECWVPDPSRNE; CWVPDPSRNEN; WVPDPSRNENA; VPDPSRNENAR; PDPSRNENARY;
DPSRNENARYF; PSRNENARYFG; SRNENARYFGT; RNENARYFGTF; NENARYFGTFT;
ENARYFGTFTG; NARYFGTFTGG; ARYFGTFTGGE; RYFGTFTGGEN; YFGTFTGGENV;
FGTFTGGENVP; GTFTGGENVPP; TFTGGENVPPV; FTGGENVPPVL; TGGENVPPVLH;
GGENVPPVLHV; GENVPPVLHVT; ENVPPVLHVTN; NVPPVLHVTNT; VPPVLHVTNTA;
PPVLHVTNTAT; PVLHVTNTATT; VLHVTNTATTV; LHVTNTATTVL; HVTNTATTVLL;
VTNTATTVLLD; TNTATTVLLDE; NTATTVLLDEQ; TATTVLLDEQG; ATTVLLDEQGV;
TTVLLDEQGVG; TVLLDEQGVGP; VLLDEQGVGPL; LLDEQGVGPLC; LDEQGVGPLCK;
DEQGVGPLCKA; EQGVGPLCKAD; QGVGPLCKADS; GVGPLCKADSL; VGPLCKADSLY;
GPLCKADSLYV; PLCKADSLYVS; LCKADSLYVSA; CKADSLYVSAA; KADSLYVSAAD;
ADSLYVSAADI; DSLYVSAADIC; SLYVSAADICG; LYVSAADICGL; YVSAADICGLF;
VSAADICGLFT; SAADICGLFTN; AADICGLFTNS; ADICGLFTNSS; DICGLFTNSSG;
ICGLFTNSSGT; CGLFTNSSGTQ; GLFTNSSGTQQ; LFTNSSGTQQW; FTNSSGTQQWR;
TNSSGTQQWRG; NSSGTQQWRGL; SSGTQQWRGLA; SGTQQWRGLAR; GTQQWRGLARY;
TQQWRGLARYF; QQWRGLARYFK; QWRGLARYFKI; WRGLARYFKIR; RGLARYFKIRL;
GLARYFKIRLR; LARYFKIRLRK; ARYFKIRLRKR; RYFKIRLRKRS; YFKIRLRKRSV;
FKIRLRKRSVK; KIRLRKRSVKN; IRLRKRSVKNP; RLRKRSVKNPY; LRKRSVKNPYP;
RKRSVKNPYPI; KRSVKNPYPIS; RSVKNPYPISF; SVKNPYPISFL; VKNPYPISFLL;
KNPYPISFLLS; NPYPISFLLSD; PYPISFLLSDL; YPISFLLSDLI; PISFLLSDLIN;
ISFLLSDLINR; SFLLSDLINRR; FLLSDLINRRT; LLSDLINRRTQ; LSDLINRRTQR;
SDLINRRTQRV; DLINRRTQRVD; LINRRTQRVDG; INRRTQRVDGQ; NRRTQRVDGQP;
RRTQRVDGQPM; RTQRVDGQPMY; TQRVDGQPMYG; QRVDGQPMYGM; RVDGQPMYGME;
VDGQPMYGMES; DGQPMYGMESQ; GQPMYGMESQV; QPMYGMESQVE; PMYGMESQVEE;
MYGMESQVEEV; YGMESQVEEVR; GMESQVEEVRV; MESQVEEVRVF; ESQVEEVRVFD;
SQVEEVRVFDG; QVEEVRVFDGT; VEEVRVFDGTE; EEVRVFDGTER; EVRVFDGTERL;
VRVFDGTERLP; RVFDGTERLPG; VFDGTERLPGD; FDGTERLPGDP; DGTERLPGDPD;
GTERLPGDPDM; TERLPGDPDMI; ERLPGDPDMIR; RLPGDPDMIRY; LPGDPDMIRYI;
PGDPDMIRYID; GDPDMIRYIDK; DPDMIRYIDKQ; PDMIRYIDKQG; DMIRYIDKQGQ;
MIRYIDKQGQL; IRYIDKQGQLQ; RYIDKQGQLQT; YIDKQGQLQTK; IDKQGQLQTKM;
DKQGQLQTKML; TGAFIVIHLI; GAFIVIHLIN; AFIVIHLINA; FIVIHLINAA;
IVIHLINAAF; VIHLINAAFV; ATFKLVLFWGW; TFKLVLFWGWC; FKLVLFWGWCF;
KLVLFWGWCFR; LVLFWGWCFRP; VLFWGWCFRPF; LFWGWCFRPFK; FWGWCFRPFKT;
WGWCFRPFKTL; GWCFRPFKTLK; WCFRPFKTLKA; CFRPFKTLKAF; FRPFKTLKAFT;
RPFKTLKAFTQ; PFKTLKAFTQM; FKTLKAFTQMQ; KTLKAFTQMQL; TLKAFTQMQLL;
LKAFTQMQLLT; KAFTQMQLLTM; AFTQMQLLTMG; FTQMQLLTMGV; ILFSCNIKNTF;
LFSCNIKNTFP; FSCNIKNTFPH; SCNIKNTFPHA; CNIKNTFPHAY; NIKNTFPHAYI;
IKNTFPHAYII; KNTFPHAYIIF; NTFPHAYIIPH; TFPHAYIIFHP; KSIHTYLRIQP;
SIHTYLRIQPF; IHTYLRIQPFL; HTYLRIQPFLP; TYLRIQPFLPF; YLRIQPFLPFN;
LRIQPFLPFNN; RIQPFLPFNNS; IQPFLPFNNSR; QPFLPFNNSRL; PFLPFNNSRLY;
FLPFNNSRLYI; LPFNNSRLYIS; PFNNSRLYISC; FNNSRLYISCK; NNSRLYISCKI;
NSRLYISCKIS; SRLYISCKISY; RLYISCKISYR; LYISCKISYRP; YISCKISYRPK;
ISCKISYRPKP; SCKISYRPKPN; IYFGPKIYLSY; YFGPKIYLSYK; FGPKIYLSYKS;
GPKIYLSYKSS; PKIYLSYKSSL; KIYLSYKSSLQ; IYLSYKSSLQG; YLSYKSSLQGF;
LSYKSSLQGFR; SYKSSLQGFRD; YKSSLQGFRDR; KSSLQGFRDRI; SSLQGFRDRIL;
SLQGFRDRILI; LQGFRDRILIH; QGFRDRILIHC; GFRDRILIHCN; FRDRILIHCNQ;
RDRILIHCNQA; DRILIHCNQAW; RILIHCNQAWW; ILIHCNQAWWK; LIHCNQAWWKY;
IHCNQAWWKYL; HCNQAWWKYLG; CNQAWWKYLGS; NQAWWKYLGSF; QAWWKYLGSFV;
FSSCPFYIFKN; SSCPFYIFKNN; SCPFYIFKNNH; CPFYIFKNNHV; PFYIFKNNHVL;
FYIFKNNHVLI; YIFKNNHVLIY; IFKNNHVLIYS; FKNNHVLIYST; KNNHVLIYSYT;
CCFSTINGTFK; PVSSFRYIENN; VSSFRYIENNT; SSFRYIENNTV; SFRYIENNTVQ;
FRYIENNTVQK; RYIENNTVQKI; YIENNTVQKIK; IENNTVQKIKY; ENNTVQKIKYY;
NNTVQKIKYYR; NTVQKIKYYRI; TVQKIKYYRIH; VQKIKYYRIHF; QKIKYYRIHFR;
QTVQPSNTCHI; TVQPSNTCHIL; VQPSNTCHILF; HFFPGHMKGIY; FFPGHMKGIYS;
FPGHMKGIYSF; PGHMKGIYSFF; GHMKGIYSFFS; NCIYCLLTNTF; CIYCLLTNTFL;
IYCLLTNTFLI; YCLLTNTFLIF; CLLTNTFLIFT; LLTNTFLIFTF; LTNTFLIFTFC;
TNTFLIFTFCK; NTFLIFTFCKN; TFLIFTFCKNS; FLIFTFCKNNS; LIFTFCKNNSI;
IFTFCKNNSIC; FTFCKNNSICK; TFCKNNSICKV; FCKNNSICKVL; CKNNSICKVLF;
KNNSICKVLFM; NNSICKVLFMI; NSICKVLFMIL; SICKVLFMILK; ICKVLFMILKV;
CKVLFMILKVI; KVLFMILKVIR; VLFMILKVIRL; LFMILKVIRLV; FMILKVIRLVF;
MILKVIRLVFF; ILKVIRLVFFL; LKVIRLVFFLT; KVIRLVFFLTL; VIRLVFFLTLF;
IRLVFFLTLFT; RLVFFLTLFTL; LVFFLTLFTLL; VFFLTLFTLLY; FFLTLFTLLYI;
FLTLFTLLYIV; LTLFTLLYIVL; TLFTLLYIVLK; LFTLLYIVLKF; KHILTLCLYCI;
HILTLCLYCIL; ILTLCLYCILS; LTLCLYCILSN; FPRHLLCFFRL; PRHLLCFFRLF;
RHLLCFFRLFW; HLLCFFRLFWA; LLCFFRLFWAK; LCFFRLFWAKI; CFFRLFWAKIM;
FFRLFWAKIML; FRLFWAKIMLL; APLNAFFYSMV; PLNAFFYSMVW; LNAFFYSMVWI;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

NAFFYSMVWIS; AFFYSMVWISS; KTKGTQLLTEI; TKGTQLLTEII; KGTQLLTEIIN;
GTQLLTEIINC; TQLLTEIINCR; QLLTEIINCRN; LLTEIINCRNS; LTEIINCRNSM;
TEIINCRNSMS; EIINCRNSMSM; IINCRNSMSMW; INCRNSMSMWS; KEYNIMPSTHV;
EYNIMPSTHVS; YNIMPSTHVST; NIMPSTHVSTN; IMPSTHVSTNK; MPSTHVSTNKS;
PSTHVSTNKSY; STHVSTNKSYR; THVSTNKSYRI; HVSTNKSYRIF; VSTNKSYRIFF;
STNKSYRIFFH; TNKSYRIFFHK; NKSYRIFFHKF; KSYRIFFHKFF; SYRIFFHKFFI;
YRIFFHKFFIQ; RIFFHKFFIQN; IFFHKFFIQNL; FFHKFFIQNLS; FHKFFIQNLSF;
HKFFIQNLSFF; KFFIQNLSFFF; FFIQNLSFFFS; FIQNLSFFFSS; IQNLSFFFSSI;
QNLSFFFSSIH; NLSFFFSSIHS; LSFFFSSIHSK; SFFFSSIHSKA; FFFSSIHSKAG;
FFSSIHSKAGK; FSSIHSKAGKG; SSIHSKAGKGS; SIHSKAGKGSI; IHSKAGKGSIT;
HSKAGKGSITK; SKAGKGSITKY; KAGKGSITKYS; AGKGSITKYSL; GKGSITKYSLT;
KGSITKYSLTK; GSITKYSLTKK; SITKYSLTKKL; ITKYSLTKKLV; IRGKVFRVFYL;
RGKVFRVFYLS; GKVFRVFYLSF; KVFRVFYLSFF; VFRVFYLSFFF; FRVFYLSFFFG;
RVFYLSFFFGW; VFYLSFFFGWC; VLRICCCFFIT; LRICCCFFITG; RICCCFFITGK;
ICCCFFITGKH; CCCFFITGKHI; CCFFITGKHIF; CFFITGKHIFM; FFITGKHIFMA;
FITGKHIFMAK; IFIPFFIKGTP; FIPFFIKGTPP; IPFFIKGTPPG; PFFIKGTPPGL;
FFIKGTPPGLP; FIKGTPPGLPL; IKGTPPGLPLF; KGTPPGLPLFC; GTPPGLPLFCS;
TPPGLPLFCSI; PPGLPLFCSIG; PGLPLFCSIGW; GLPLFCSIGWH; LPLFCSIGWHL;
SFRSLKGVSPI; FRSLKGVSPII; RSLKGVSPIIW; SLKGVSPIIWT; LKGVSPIIWTH;
KGVSPIIWTHH; GVSPIIWTHHC; VSPIIWTHHCR; SPIIWTHHCRV; PIIWTHHCRVS;
IIWTHHCRVSS; IWTHHCRVSSV; WTHHCRVSSVR; THHCRVSSVRS; HHCRVSSVRSK;
HCRVSSVRSKP; CRVSSVRSKPN; RVSSVRSKPNH; VSSVRSKPNHC; SSVRSKPNHCV;
SVRSKPNHCVK; VRSKPNHCVKQ; RSKPNHCVKQS; SKPNHCVKQSM; KPNHCVKQSMQ;
QSIQTKGSFLK; SIQTKGSFLKN; IQTKGSFLKNF; QTKGSFLKNFL; TKGSFLKNFLF;
KGSFLKNFLFK; GSFLKNFLFKC; SFLKNFLFKCL; FLKNFLFKCLN; LKNFLFKCLNL;
KNFLFKCLNLS; HSMQGQCTEGF; SMQGQCTEGFL; MQGQCTEGFLE; QGQCTEGFLEQ;
GQCTEGFLEQI; QCTEGFLEQIG; CTEGFLEQIGH; TEGFLEQIGHS; EGFLEQIGHSL;
GFLEQIGHSLQ; FLEQIGHSLQY; LEQIGHSLQYR; EQIGHSLQYRV; QIGHSLQYRVS;
IGHSLQYRVSG; GHSLQYRVSGQ; HSLQYRVSGQR; SLQYRVSGQRG; LQYRVSGQRGK;
QYRVSGQRGKS; YRVSGQRGKSA; RVSGQRGKSAQ; VSGQRGKSAQT; SGQRGKSAQTS;
GQRGKSAQTSE; QRGKSAQTSEL; RGKSAQTSELL; GKSAQTSELLQ; KSAQTSELLQV;
SAQTSELLQVP; AQTSELLQVPK; QTSELLQVPKS; TSELLQVPKSG; ATFTSCSIFLY;
TFTSCSIFLYK; FTSCSIFLYKV; TSCSIFLYKVF; SCSIFLYKVFI; CSIFLYKVFIL;
SIFLYKVFILF; IFLYKVFILFI; FLYKVFILFIL; LYKVFILFILS; YKVFILFILSS;
KVFILFILSSS; VFILFILSSSP; FILFILSSSPP; ILFILSSSPPL; LFILSSSPPLS;
FILSSSPPLSG; AFLIKGRFPQA; FLIKGRFPQAA; LIKGRFPQAAL; IKGRFPQAALS;
KGRFPQAALSR; GRFPQAALSRP; RFPQAALSRPK; FPQAALSRPKR; PQAALSRPKRS;
QAALSRPKRSM; AALSRPKRSMS; ALSRPKRSMSS; LSRPKRSMSSM; SRPKRSMSSMD;
RPKRSMSSMDS; PKRSMSSMDSS; KRSMSSMDSSL; RSMSSMDSSLL; SMSSMDSSLLR;
MSSMDSSLLRT; SSMDSSLLRTL; SMDSSLLRTLS

| BK virus reading frame 2 |
|---|

8 mers:

GFPQIVLL; FPQIVLLG; PQIVLLGL; QIVLLGLR; IVLLGLRK; VLLGLRKS; LLGLRKSL;
LGLRKSLH; GLRKSLHT; LRKSLHTL; RKSLHTLT; KSLHTLTT; EKGWRQRR; KGWRQRRP;
GWRQRRPR; WRQRRPRP; RQRRPRPL; QRRPRPLI; RRPRPLIY; RPRPLIYY; PRPLIYYK;
RPLIYYKK; PLIYYKKK; LIYYKKKG; IYYKKKGH; YYKKKGHR; YKKKGHRE; KKKGHREE;
KKGHREEL; KGHREELL; GHREELLT; HREELLTH; REELLTHG; EELLTHGM; ELLTHGMQ;
LLTHGMQP; LTHGMQPN; THGMQPNH; HGMQPNHD; GMQPNHDL; MQPNHDLR; QPNHDLRK;
PNHDLRKE; NHDLRKES; HDLRKESA; LTGECSQT; TGECSQTM; GECSQTMT; ECSQTMTS;
CSQTMTSG; SQTMTSGR; QTMTSGRK; TMTSGRKV; MTSGRKVH; TSGRKVHD; SGRKVHDS;
GRKVHDSQ; RKVHDSQG; KVHDSQGG; VHDSQGGA; HDSQGGAA; DSQGGAAY; SQGGAAYP;
QGGAAYPW; GGAAYPWN; GAAYPWNA; AAYPWNAA; AYPWNAAK; YPWNAAKP; PQEGKCMT;
QEGKCMTD; EGKCMTDM; GKCMTDMF; KCMTDMFC; CMTDMFCE; MTDMFCEP; TDMFCEPR;
DMFCEPRN; MFCEPRNL; FCEPRNLG; CEPRNLGL; EPRNLGLV; PRNLGLVP; RNLGLVPS;
TGQRPWFC; GQRPWFCA; QRPWFCAS; RPWFCASC; PWFCASCH; WFCASCHD; FCASCHDK;
CASCHDKL; ASCHDKLQ; KLVKPGLE; LVKPGLEQ; VKPGLEQK; KPGLEQKK; PGLEQKKE;
GLEQKKEL; LEQKKELR; EQKKELRG; QKKELRGF; KKELRGFL; KELRGFLF; ELRGFLFL;
LRGFLFLF; SFCWNFVE; FCWNFVEV; CWNFVEVK; WNFVEVKT; NFVEVKTV; TGKTKVPL;
GKTKVPLL; KTKVPLLY; TKVPLLYL; KVPLLYLL; VPLLYLLQ; PLLYLLQF; LLYLLQFF;
FFLYFQVH; FLYFQVHG; LYFQVHGC; YFQVHGCC; FQVHGCCS; QVHGCCSS; VHGCCSST;
HGCCSSTF; GCCSSTFG; CCSSTFGG; CSSTFGGP; SSTFGGPS; STFGGPSC; TFGGPSCQ;
FGGPSCQC; GGPSCQCI; GCCCHRIF; CCCHRIFS; CCHRIFSG; NCCWGGCC; CCWGGCCC;
CWGGCCCY; WGGCCCYR; GGCCCYRS; GCCCYRSS; CCCYRSSN; CCYRSSNC; CYRSSNCI;
YRSSNCIP; RSSNCIPC; SSNCIPCY; SNCIPCYC; NCIPCYCR; CIPCYCRG; IPCYCRGH;
PCYCRGHN; CYCRGHNK; YCRGHNKY; CRGHNKYL; RGHNKYLR; GHNKYLRG; HNKYLRGY;
NKYLRGYS; KYLRGYSC; YLRGYSCY; LRGYSCYR; RGYSCYRP; GYSCYRPN; YSCYRPNS;
SCYRPNSS; CYRPNSSN; YRPNSSNI; RPNSSNIC; PNSSNICC; NSSNICCN; SSNICCNC;
SNICCNCW; NICCNCWC; ICCNCWCS; CCNCWCSW; CNCWCSWG; NCWCSWGY; CWCSWGYC;
WCSWGYCW; CSWGYCWV; SWGYCWVC; WGYCWVCC; GYCWVCCF; YCWVCCFN; CWVCCFNS;
WVCCFNSN; VCCFNSNC; LGSQSFHC; GSQSFHCR; SQSFHCRP; QSFHCRPL; SFHCRPLS;
FHCRPLSA; HCRPLSAI; CRPLSAIR; RPLSAIRH; PLSAIRHG; LSAIRHGF; SAIRHGFG;
AIRHGFGI; IRHGFGIV; YSVSWCKY; SVSWCKYF; VSWCKYFC; ALGSFFVC; LGSFFVCY;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

GSFFVCYY; SFFVCYYF; FFVCYYFP; FVCYYFPG; VCYYFPGF; CYYFPGFV; YYFPGFVA;
YFPGFVAC; FPGFVACY; YTFYNLTG; TFYNLTGI; FYNLTGIA; YNLTGIAE; NLTGIAEK;
LTGIAEKN; TGIAEKNR; GIAEKNRK; IAEKNRKI; AEKNRKIF; IFGGNYLD; FGGNYLDN;
GGNYLDNC; GNYLDNCK; NYLDNCKC; YLDNCKCP; LDNCKCPY; DNCKCPYK; NCKCPYKL;
CKCPYKLL; KGRYPCTF; GRYPCTFW; RYPCTFWP; YPCTFWPY; PCTFWPYL; QYRRSYTK;
YRRSYTKN; RRSYTKNG; RSYTKNGL; SYTKNGLK; YTKNGLKK; TKNGLKKS; KNGLKKST;
NGLKKSTK; GLKKSTKC; LKKSTKCT; KKSTKCTF; KSTKCTFR; STKCTFRR; TKCTFRRV;
KCTFRRVY; CTFRRVYR; TFRRVYRK; FRRVYRKN; RRVYRKNY; RVYRKNYC; VYRKNYCP;
YRKNYCPR; RKNYCPRR; KNYCPRRC; SKNCSSMD; KNCSSMDV; NCSSMDVA; CSSMDVAF;
SSMDVAFT; SMDVAFTS; MDVAFTSR; DVAFTSRP; VAFTSRPV; AFTSRPVR; FTSRPVRD;
TSRPVRDC; SRPVRDCN; RPVRDCNT; PVRDCNTC; VRDCNTCS; RWPQPKEK; WPQPKEKE;
PQPKEKES; QPKEKESV; PKEKESVQ; KEKESVQG; EKESVQGQ; KESVQGQL; ESVQGQLP;
SVQGQLPK; VQGQLPKS; QGQLPKSQ; GQLPKSQR; QLPKSQRN; LPKSQRNP; PKSQRNPC;
KSQRNPCK; SQRNPCKC; QRNPCKCQ; RNPCKCQN; NPCKCQNY; TQKWGIQM; QKWGIQMK;
KWGIQMKT; WGIQMKTL; GIQMKTLG; IQMKTLGA; QMKTLGAL; MKTLGALV; VLKMTLAV;
LKMTLAVI; KMTLAVIA; MTLAVIAQ; TLAVIAQR; LAVIAQRE; AVIAQREK; VIAQREKC;
IAQREKCF; AQREKCFP; QREKCFPV; REKCFPVT; EKCFPVTA; KCFPVTAQ; CFPVTAQQ;
FPVTAQQE; PVTAQQEF; VTAQQEFP; TAQQEFPS; AQQEFPSP; QQEFPSPI; LYKQRLLE;
LACLTFMQ; ACLTFMQG; CLTFMQGH; LTFMQGHK; TFMQGHKK; FMQGHKKC; MQGHKKCM;
QGHKKCMS; GHKKCMSM; HKKCMSMV; KKCMSMVE; KCMSMVEE; CMSMVEEN; MSMVEENL;
SMVEENLF; MVEENLFK; VEENLFKA; EENLFKAV; ENLFKAVI; LFKAVIST; FKAVISTS;
FKAVISTS; KAVISTSL; AVISTSLL; VENPWKCR; ENPWKCRE; NPWKCREC; ITGQSTLM;
TGQSTLMV; GQSTLMVL; PLKTQQPS; LKTQQPSP; KTQQPSPR; ILTIRPIW; LTIRPIWT;
TIRPIWTK; IRPIWTKT; RPIWTKTM; PIWTKTML; IWTKTMLI; WTKTMLIQ; TKTMLIQL;
KTMLIQLS; TMLIQLSA; MLIQLSAG; LIQLSAGY; IQLSAGYL; QLSAGYLI; LSAGYLIP;
SAGYLIPV; AGYLIPVE; GYLIPVEM; YLIPVEMK; LIPVEMKM; IPVEMKML; PVEMKMLG;
VEMKMLGI; EMKMLGIL; MKMLGILG; KMLGILGL; MLGILGLS; LGILGLSQ; GILGLSQE;
ILGLSQEG; LGLSQEGK; GLSQEGKM; LSQEGKMF; SQEGKMFP; QEGKMFPQ; EGKMFPQY;
GKMFPQYF; KMFPQYFM; PTQLPQCC; MNRVWGLF; NRVWGLFV; RVWGLFVK; VWGLFVKL;
WGLFVKLI; GLFVKLIA; LFVKLIAC; FVKLIACM; VKLIACMF; KLIACMFQ; LIACMFQL;
IACMFQLL; ACMFQLLI; CMFQLLIF; MFQLLIFV; FQLLIFVA; QLLIFVAC; LLIFVACL;
LIFVACLL; IFVACLLT; FVACLLTA; VACLLTAL; ACLLTALE; CLLTALEH; LLTALEHN;
LTALEHNS; TALEHNSG; ALEHNSGE; LEHNSGEA; EHNSGEAL; HNSGEALQ; NSGEALQD;
SGEALQDI; GEALQDIL; EALQDILR; ALQDILRS; LQDILRSA; RILTQFPF; ILTQFPFC;
TGEPREWM; GEPREWMG; EPREWMGS; PREWMGSL; REWMGSLC; EWMGSLCM; WMGSLCMV;
MGSLCMVW; GSLCMVWN; SLCMVWNP; LCMVWNPR; KRLGCLMA; RLGCLMAQ; LGCLMAQK;
GCLMAQKD; CLMAQKDF; LMAQKDFQ; MAQKDFQG; AQKDFQGT; QKDFQGTQ; KDFQGTQI;
DILTNRDN; ILTNRDNC; LTNRDNCK; TNRDNCKP; NRDNCKPK; RDNCKPKC; DNCKPKCF;
NCKPKCFK; CKPKCFKQ; KPKCFKQV; PKCFKQVL; KCFKQVLL; CFKQVLLL; FKQVLLLY;
KQVLLLYI; QVLLLYIY; VLLLYIYI; MLLLYKPL; LLLYKPLL; LLYKPLLS; LYKPLLSL;
YKPLLSLC; KPLLSLCY; PLLSLCYF; LLSLCYFG; LSLCYFGG; SLCYFGGG; LCYFGGGV;
CYFGGGVL; YFGGGVLG; FGGGVLGL; GGGVLGLL; GGVLGLLK; GVLGLLKH; KPLHKCNS;
LWGSDLWE; WGSDLWES; GSDLWESS; SDLWESSA; DLWESSAG; LWESSAGA; WESSAGAE;
ESSAGAEV; SSAGAEVS; SAGAEVSE; AGAEVSET; GAEVSETW; AEVSETWE; EVSETWEE;
VSETWEEH; SETWEEHC; ETWEEHCD; TWEEHCDW; WEEHCDWD; EEHCDWDS; EHCDWDSV;
HCDWDSVL; CDWDSVLD; DWDSVLDP; WDSVLDPC; DSVLDPCP; SVLDPCPE; VLDPCPES;
LDPCPESS; DPCPESSV; PCPESSVS; CPESSVSE; PESSVSES; ESSVSESS; SSVSESSS;
SVSESSSL; VSESSSLV; SESSSLVI; ESSSLVIS; SSSLVISR; SSLVISRI; SLVISRIH;
LVISRIHF; VISRIHFP; ISRIHFPM; SRIHFPMH; RIHFPMHI; IHFPMHIL; HFPMHILY;
FPMHILYF; PMHILYFI; MHILYFIL; HILYFILE; ILYFILEK; LYFILEKV; YFILEKVY;
FILEKVYI; ILEKVYIL; LEKVYILI; EKVYILIS; KVYILISE; VYILISES; YILISESS;
ILISESSL; LISESSLS; ISESSLSF; SESSLSPH; ESSLSPHS; SSLSFHST; SLSFHSTI;
LSFHSTIL; SFHSTILD; FHSTILDC; HSTILDCI; STILDCIS; TILDCISV; ILDCISVA;
LDCISVAK; DCISVAKS; CISVAKSA; ISVAKSAT; SVAKSATG; VAKSATGL; AKSATGLN;
KSATGLNQ; SATGLNQI; ATGLNQIS; TGLNQISS; GLNQISSS; LNQISSSN; NQISSSNK;
QISSSNKV; ISSSNKVI; SSSNKVIP; SSNKVIPL; SNKVIPLC; NKVIPLCK; KVIPLCKI;
VIPLCKIL; IPLCKILF; PLCKILFS; LCKILFSS; CKILFSSK; KILFSSKN; ILFSSKNS;
LFSSKNSE; FSSKNSEF; SSKNSEFC; SKNSEFCK; KNSEFCKD; NSEFCKDF; SEFCKDPL;
EFCKDFLK; FCKDFLKY; CKDFLKYI; KDFLKYIL; DFLKYILG; FLKYILGL; LKYILGLK;
KYILGLKS; YILGLKSI; ILGLKSIC; LGLKSICL; GLKSICLT; LKSICLTN; KSICLTNL;
SICLTNLA; ICLTNLAC; CLTNLACR; LTNLACRV; TNLACRVL; NLACRVLG; LACRVLGT;
ACRVLGTG; CRVLGTGY; RVLGTGYS; VLGTGYSF; LGTGYSFI; GTGYSFIV; TGYSFIVT;
GYSFIVTK; YSFIVTKP; SFIVTKPG; FIVTKPGG; IVTKPGGN; VTKPGGNI; TKPGGNIW;
KPGGNIWV; PGGNIWVL; GGNIWVLL; GNIWVLLF; NIWVLLFK; IWVLLFKC; WVLLFKCF;
VLLFKCFF; LLFKCFFS; LFKCFFSK; FKCFFSKF; KCFFSKFT; CFFSKFTL; FFSKFTLT;
FSKFTLTL; SKFTLTLP; KFTLTLPS; FTLTLPSK; SLKLSKLF; LKLSKLFI; KLSKLFIP;
LSKLFIPC; SKLFIPCP; KLFIPCPE; LFIPCPEG; FIPCPEGK; IPCPEGKS; PCPEGKSF;
CPEGKSFD; PEGKSFDS; EGKSFDSA; GKSFDSAP; KSFDSAPV; SFDSAPVP; FDSAPVPF;
DSAPVPFT; SAPVPFTS; APVPFTSS; PVPFTSSK; VPFTSSKT; PFTSSKTT; FTSSKTTM;
TSSKTTMY; SIATPSSK; IATPSSKV; ATPSSKVS; TPSSKVSL; PSSKVSLS; SSKVSLSM;
SKVSLSMG; KVSLSMGR; VSLSMGRF; SLSMGRFT; LSMGRFTF; SMGRFTFK; MGRFTFKA;
GRFTFKAL; RFTFKALP; FTFKALPP; TFKALPPH; FKALPPHK; KALPPHKS; ALPPHKSN;
LPPHKSNN; PPHKSNNP; PHKSNNPA; HKSNNPAA; KSNNPAAS; SNNPAASV; NNPAASVV;
NPAASVVF; PAASVVFP; AASVVFPL; ASVVFPLS; SVVFPLSM; VVFPLSMG; VFPLSMGP;
FPLSMGPL; PLSMGPLN; LSMGPLNN; SMGPLNNQ; MGPLNNQY; GPLNNQYL; PLNNQYLL;
LNNQYLLL; NNQYLLLG; NQYLLLGT; QYLLLGTL; YLLLGTLK; LLLGTLKT; LLGTLKTI;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

LGTLKTIQ; GTLKTIQC; TLKTIQCK; LKTIQCKK; KTIQCKKS; TIQCKKSN; IQCKKSNI;
QCKKSNIT; CKKSNITE; KKSNITES; KSNITESI; SNITESIL; NITESILG; ITESILGS;
TESILGSK; ESILGSKQ; SILGSKQC; ILGSKQCS; LGSKQCSQ; GSKQCSQA; SKQCSQAT;
KQCSQATP; QCSQATPA; CSQATPAI; SQATPAIY; QATPAIYC; ATPAIYCS; TPAIYCSS;
PAIYCSST; AIYCSSTA; IYCSSTAF; YCSSTAFP; APNIKSIL; PNIKSILS; NIKSILSN;
IKSILSNI; LNLSVSIS; NLSVSISS; LSVSISSL; SVSISSLV; VSISSLVI; RVSTLFLA;
VSTLFLAK; STLFLAKT; TLFLAKTV; LFLAKTVS; FLAKTVST; LAKTVSTA; AKTVSTAC;
FLLSAKII; LLSAKIIA; LSAKIIAF; SAKIIAFA; AKIIAFAK; KIIAFAKC; IIAFAKCF;
IAFAKCFS; HPFLHSSTL; FLHSSTLY; NSKYIPNN; SKYIPNNK; KYIPNNKN; YIPNNKNT;
IPNNKNTS; PNNKNTSS; NNKNTSSH; NKNTSSHF; KNTSSHFV; NTSSHFVS; TSSHFVST;
SSHFVSTA; SHFVSTAY; HFVSTAYS; FVSTAYSV; VSTAYSVI; STAYSVIN; TAYSVINF;
AYSVINFQ; YSVINFQD; SVINFQDT; VINFQDTC; INFQDTCF; NFQDTCFV; FQDTCFVS;
QDTCFVSS; DTCFVSSG; TCFVSSGS; CFVSSGSS; VSSGSSGL; SSGSSGLK;
SGSSGLKS; GSSGLKSC; SSGLKSCS; SGLKSCSF; GLKSCSFK; LKSCSFKP; KSCSFKPP;
MLSSIVWY; LSSIVWYG; SSIVWYGS; SIVWYGSL; IVWYGSLV; VWYGSLVK; WYGSLVKA;
YGSLVKAL; GSLVKALY; SLVKALYS; LVKALYSK; VKALYSKY; KALYSKYS; ALYSKYSL;
LYSKYSLL; YSKYSLLT; SKYSLLTP; KYSLLTPL; YSLLTPLQ; SLLTPLQI; LLTPLQIK;
LTPLQIKK; TPLQIKKL; PLQIKKLK; LQIKKLKV; QIKKLKVH; IKKLKVHS; KKLKVHSF;
QKLLIAET; KLLIAETL; LLIAETLC; LIAETLCL; IAETLCLC; AETLCLCG; ETLCLCGV;
TLCLCGVK; LCLCGVKK; CLCGVKKN; LCGVKKNI; CGVKKNII; GVKKNIIL; VKKNIILC;
KNIILCP; KNIILCPA; NIILCPAH; IILCPAHM; ILCPAHMC; LCPAHMCL; CPAHMCLL;
PAHMCLLI; AHMCLLIK; HMCLLIKV; MCLLIKVT; CLLIKVTE; LLIKVTEY; LIKVTEYF;
IKVTEYFS; KVTEYFSI; VTEYFSIS; TEYFSISF; EYFSISFL; YFSISFLY; FSISFLYR;
SISFLYRI; AFSLVVYT; FSLVVYTA; SLVVYTAK; LVVYTAKQ; VVYTAKQA; VYTAKQAR;
YTAKQARV; TAKQARVL; AKQARVLL; KQARVLLL; QARVLLLN; ARVLLLNT; RVLLLNTA;
LRNWCRSE; RNWCRSEG; NWCRSEGK; WCRSEGKS; CRSEGKSL; RSEGKSLG; SEGKSLGS;
EGKSLGSS; GKSLGSST; KSLGSSTF; SLGSSTFL; LGSSTFLF; GSSTFLFF; SSTFLFFL;
STFLFFLG; TFLFFLGG; FLFFLGGV; LFFLGGVE; FFLGGVEC; ESAVASSS; SAVASSSL;
AVASSSLA; VASSSLAN; ASSSLANI; SSSLANIS; SSLANISS; SLANISSW; LANISSWQ;
ANISSWQN; NISSWQNK; ISSWQNKS; SSWQNKSS; SWQNKSSH; WQNKSSHF; QNKSSHF;
NKSSSHFS; KSSSHFSL; SSSHFSLK; SSHFSLKE; SHFSLKEL; HFSLKELH; FSLKELHQ;
SLKELHQD; LKELHQDS; KELHQDSH; ELHQDSHS; LHQDSHSS; HQDSHSSV; QDSHSSVP;
VGTYKKNN; GTYKKNNY; TYKKNNYL; YKKNNYLG; KKNNYLGP; KNNYLGPF; NNYLGPFN;
NYLGPFNI; YLGPFNIL; LGPFNILL; GPFNILLF; PFNILLFI; VSYLKALD; SYLKALDL;
REFLQLFG; EFLQLFGP; FLQLFGPT; LQLFGPTI; QLFGPTIA; LFGPTIAE; FGPTIAEF;
GPTIAEFL; PTIAEFLQ; TIAEFLQL; IAEFLQLG; AEFLQLGL; EFLQLGLS; FLQLGLSQ;
LQLGLSQT; QLGLSQTT; LGLSQTTV; SSQCSSNL; SQCSSNLS; QCSSNLSK; CSSNLSKP;
SSNLSKPR; SNLSKPRA; NLSKPRAL; LSKPRALF; SKPRALFL; KPRALFLK; PRALFLKI;
RALFLKIF; ALFLKIFY; LFLKIFYL; FLKIFYLN; LKIFYLNA; KIFYLNAL; IFYLNALI;
ADIACKGS; DIACKGSA; IACKGSAQ; ACKGSAQK; CKGSAQKA; KGSAQKAF; GSAQKAFW;
SAQKAFWN; AQKAFWNK; AIPCSTGY; IPCSTGYL; PCSTGYLG; CSTGYLGK; STGYLGKE;
TGYLGKEE; GYLGKEEN; YLGKEENQ; LGKEENQH; GKEENQHK; KEENQHKP; EENQHKPL;
ENQHKPLS; NQHKPLSY; QHKPLSYS; HKPLSYSR; KPLSYSRF; PLSYSRFQ; LSYSRFQN;
SYSRFQNQ; YSRFQNQA; SRFQNQAD; RFQNQADE; FQNQADEL; QNQADELP; NQADELPL;
QADELPLH; ADELPLHP; DELPLHPA; ELPLHPAP; LPLHPAPF; PLHPAPFF; LHPAPFFY;
HPAPFFYT; PAPFFYTK; APFFYTKY; PFFYTKYS; FFYTKYSF; FTKYSFS; YTKYSFSS;
TKYSFSSF; KYSFSSFY; YSFSSFYP; SFSSFYPR; FSSFYPRR; SSFYPRRP; SFYPRRPL;
FYPRRPLC; YPRRPLCQ; PRRPLCQG; RRPLCQGE; RPLCQGEI; PLCQGEIP; LCQGEIPY;
CQGEIPYT; QGEIPYTS; GEIPYTSL; EIPYTSLN; IPYTSLNK; PYTSLNKL; YTSLNKLF;
TSLNKLFS; SLNKLFSL; LNKLFSLR; NKLFSLRE; KLFSLRED; LFSLREDF; FSLREDFP;
SLREDFPR; LREDFPRQ; REDFPRQL; EDFPRQLF; DFPRQLFQ; FPRQLFQG; PRQLFQGL;
RQLFQGLK; QLFQGLKG; LFQGLKGP 9 mers:

GFPQIVLLG; FPQIVLLGL; PQIVLLGLR; QIVLLGLRK; IVLLGLRKS; VLLGLRKSL;
LLGLRKSLH; LGLRKSLHT; GLRKSLHTL; LRKSLHTLT; RKSLHTLTT; EKGWRQRRP;
KGWRQRRPR; GWRQRRPRP; WRQRRPRPL; RQRRPRPLI; QRRPRPLIY; RRPRPLIYY;
RPRPLIYYK; PRPLIYYKK; RPLIYYKKG; PLIYYKKKG; LIYYKKKGH; IYYKKKGHR;
YYKKKGHRE; YKKKGHREE; KKKGHREEL; KKGHREELL; KGHREELLT; GHREELLTH;
HREELLTHG; REELLTHGM; EELLTHGMQ; ELLTHGMQP; LLTHGMQPN; LTHGMQPNH;
THGMQPNHD; HGMQPNHDL; GMQPNHDLR; MQPNHDLRK; QPNHDLRKE; PNHDLRKES;
NHDLRKESA; LTGECSQTM; TGECSQTMT; GECSQTMTS; ECSQTMTSG; CSQTMTSGR;
SQTMTSGRK; QTMTSGRKV; TMTSGRKVH; MTSGRKVHD; TSGRKVHDS; SGRKVHDSQ;
GRKVHDSQG; RKVHDSQGG; KVHDSQGGA; VHDSQGGAA; HDSQGGAAY; DSQGGAAYP;
SQGGAAYPW; QGGAAYPWN; GGAAYPWNA; GAAYPWNAA; AAYPWNAAK; AYPWNAAKP;
PQEGKCMTD; QEGKCMTDM; EGKCMTDMF; GKCMTDMFC; KCMTDMFCE; CMTDMFCEP;
MTDMFCEPR; TDMFCEPRN; DMFCEPRNL; MFCEPRNLG; FCEPRNLGL; CEPRNLGLV;
EPRNLGLVP; PRNLGLVPS; TGQRPWFCA; GQRPWFCAS; QRPWFCASC; RPWFCASCH;
PWFCASCHD; WFCASCHDK; FCASCHDKL; CASCHDKLQ; KLVKPGLEQ; LVKPGLEQK;
VKPGLEQKK; KPGLEQKKE; PGLEQKKEL; GLEQKKELR; LEQKKELRG; EQKKELRGF;
QKKELRGFL; KKELRGFLF; KELRGFLFL; ELRGFLFLF; SFCWNFVEV; FCWNFVEVK;
CWNFVEVKT; WNFVEVKTV; TGKTKVPLL; GKTKVPLLY; KTKVPLLYL; TKVPLLYLL;
VIPFFLYFQ; IPFFLYFQV; PFFLYFQVH; FFLYFQVHG; FLYFQVHGC; LYFQVHGCC;
YFQVHGCCS; FQVHGCCSS; QVHGCCSST; VHGCCSSTF; HGCCSSTFG; GCCSSTFGG;
CCSSTFGGP; CSSTFGGPS; SSTFGGPSC; STFGGPSCQ; TFGGPSCQC; FGGPSCQCI;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

GCCCHRIFS; CCCHRIFSG; NCCWGGCCC; CCWGGCCCY; CWGGCCCYR; WGGCCCYRS;
GGCCCYRSS; GCCCYRSSN; CCCYRSSNC; CCYRSSNCI; CYRSSNCIP; YRSSNCIPC;
RSSNCIPCY; SSNCIPCYC; SNCIPCYCR; NCIPCYCRG; CIPCYCRGH; IPCYCRGHN;
PCYCRGHNK; CYCRGHNKY; YCRGHNKYL; CRGHNKYLR; RGHNKYLRG; GHNKYLRGY;
HNKYLRGYS; NKYLRGYSC; KYLRGYSCY; YLRGYSCYR; LRGYSCYRP; RGYSCYRPN;
GYSCYRPNS; YSCYRPNSS; SCYRPNSSN; CYRPNSSNI; YRPNSSNIC; RPNSSNICC;
PNSSNICCN; NSSNICCNC; SSNICCNCW; SNICCNCWC; NICCNCWCS; ICCNCWCSW;
CCNCWCSWG; CNCWCSWGY; NCWCSWGYC; CWCSWGYCW; WCSWGYCWV; CSWGYCWVC;
SWGYCWVCC; WGYCWVCCF; GYCWVCCFN; YCWVCCFNS; CWVCCFNSN; WVCCFNSNC;
LGSQSFHCR; GSQSFHCRP; SQSFHCRPL; QSFHCRPLS; SFHCRPLSA; FHCRPLSAI;
HCRPLSAIR; CRPLSAIRH; RPLSAIRHG; PLSAIRHGF; LSAIRHGFG; SAIRHGFGI;
AIRHGFGIV; YSVSWCKYF; SVSWCKYFC; ALGSFFVCY; LGSFFVCYY; GSFFVCYYF;
SFFVCYYFP; FFVCYYFPG; FVCYYFPGF; VCYYFPGFV; CYYFPGFVA; YYFPGFVAC;
YFPGFVACY; YTFYNLTGI; TFYNLTGIA; FYNLTGIAE; YNLTGIAEK; NLTGIAEKN;
LTGIAEKNR; TGIAEKNRK; GIAEKNRKI; IAEKNRKIF; IFGGNYLDN; FGGNYLDNC;
GGNYLDNCK; GNYLDNCKC; NYLDNCKCP; YLDNCKCPY; LDNCKCPYK; DNCKCPYKL;
NCKCPYKLL; KGRYPCTFW; GRYPCTFWP; RYPCTFWPY; YPCTFWPYL; QYRRSYTKN;
YRRSYTKNG; RRSYTKNGL; RSYTKNGLK; SYTKNGLKK; YTKNGLKKS; TKNGLKKST;
KNGLKKSTK; NGLKKSTKC; GLKKSTKCT; LKKSTKCTF; KKSTKCTFR; KSTKCTFRR;
STKCTFRRV; TKCTFRRVY; KCTFRRVYR; CTFRRVYRK; TFRRVYRKN; FRRVYRKNY;
RRVYRKNYC; RVYRKNYCP; VYRKNYCPR; YRKNYCPRR; RKNYCPRRC; SKNCSSMDV;
KNCSSMDVA; NCSSMDVAF; CSSMDVAFT; SSMDVAFTS; SMDVAFTSR; MDVAFTSRP;
DVAFTSRPV; VAFTSRPVR; AFTSRPVRD; FTSRPVRDC; TSRPVRDCN; SRPVRDCNT;
RPVRDCNTC; PVRDCNTCS; RWPQPKEKE; WPQPKEKES; PQPKEKESV; QPKEKESVQ;
PKEKESVQG; KEKESVQGQ; EKESVQGQL; KESVQGQLP; ESVQGQLPK; SVQGQLPKS;
VQGQLPKSQ; QGQLPKSQR; GQLPKSQRN; QLPKSQRNP; LPKSQRNPC; PKSQRNPCK;
KSQRNPCKC; SQRNPCKCQ; QRNPCKCQN; RNPCKCQNY; TQKWGIQMK; QKWGIQMKT;
KWGIQMKTL; WGIQMKTLG; GIQMKTLGA; IQMKTLGAL; QMKTLGALV; VLKMTLAVI;
LKMTLAVIA; KMTLAVIAQ; MTLAVIAQR; TLAVIAQRE; LAVIAQREK; AVIAQREKC;
VIAQREKCF; IAQREKCFP; AQREKCFPV; QREKCFPVT; REKCFPVTA; EKCFPVTAQ;
KCFPVTAQQ; CFPVTAQQE; FPVTAQQEF; PVTAQQEFP; VTAQQEFPS; TAQQEFPSP;
AQQEFPSPI; LACLTFMQG; ACLTFMQGH; CLTFMQGHK; LTFMQGHKK; TFMQGHKKC;
FMQGHKKCM; MQGHKKCMS; QGHKKCMSM; GHKKCMSMV; HKKCMSMVE; KKCMSMVEE;
KCMSMVEEN; CMSMVEENL; MSMVEENLF; SMVEENLFK; MVEENLFKA; VEENLFKAV;
EENLFKAVI; ENLFKAVIS; NLFKAVIST; LFKAVISTS; FKAVISTSL; KAVISTSLL;
VENPWKCRE; ENPWKCREC; ITGQSTLMV; TGQSTLMVL; PLKTQQPSP; LKTQQPSPR;
ILTIRPIWT; LTIRPIWTK; TIRPIWTKT; IRPIWTKTM; RPIWTKTML; PIWTKTMLI;
IWTKTMLIQ; WTKTMLIQL; TKTMLIQLS; KTMLIQLSA; TMLIQLSAG; MLIQLSAGY;
LIQLSAGYL; IQLSAGYLI; QLSAGYLIP; LSAGYLIPV; SAGYLIPVE; AGYLIPVEM;
GYLIPVEMK; YLIPVEMKM; LIPVEMKML; IPVEMKMLG; PVEMKMLGI; VEMKMLGIL;
EMKMLGILG; MKMLGILGL; KMLGILGLS; MLGILGLSQ; LGILGLSQE; GILGLSQEG;
ILGLSQEGK; LGLSQEGKM; GLSQEGKMF; LSQEGKMFP; SQEGKMFPQ; QEGKMFPQY;
EGKMFPQYF; GKMFPQYFM; MNRVWGLFV; NRVWGLFVK; RVWGLFVKL; VWGLFVKLI;
WGLFVKLIA; GLFVKLIAC; LFVKLIACM; FVKLIACMF; VKLIACMFQ; KLIACMFQL;
LIACMFQLL; IACMFQLLI; ACMFQLLIF; CMFQLLIFV; MFQLLIFVA; FQLLIFVAC;
QLLIFVACL; LLIFVACLL; LIFVACLLT; IFVACLLTA; FVACLLTAL; VACLLTALE;
ACLLTALEH; CLLTALEHN; LLTALEHNS; LTALEHNSG; TALEHNSGE; ALEHNSGEA;
LEHNSGEAL; EHNSGEALQ; HNSGEALQD; NSGEALQDI; SGEALQDIL; GEALQDILR;
EALQDILRS; ALQDILRSA; RILTQFPFC; TGEPREWMG; GEPREWMGS; EPREWMGSL;
PREWMGSLC; REWMGSLCM; EWMGSLCMV; WMGSLCMVW; MGSLCMVWN; GSLCMVWNP;
SLCMVWNPR; KRLGCLMAQ; RLGCLMAQK; LGCLMAQKD; GCLMAQKDF; CLMAQKDFQ;
LMAQKDFQG; MAQKDFQGT; AQKDFQGTQ; QKDFQGTQI; DILTNRDNC; ILTNRDNCK;
LTNRDNCKP; TNRDNCKPK; NRDNCKPKC; RDNCKPKCF; DNCKPKCFK; NCKPKCFKQ;
CKPKCFKQV; KPKCFKQVL; PKCFKQVLL; KCFKQVLLL; CFKQVLLLY; FKQVLLLYI;
KQVLLLYIY; QVLLLYIYI; MLLLYKPLL; LLLYKPLLS; LLYKPLLSL; LYKPLLSLC;
YKPLLSLCY; KPLLSLCYF; PLLSLCYFG; LLSLCYFGG; LSLCYFGGG; SLCYFGGGV;
LCYFGGGVL; CYFGGGVLG; YFGGGVLGL; FGGGVLGLL; GGGVLGLLK; GGVLGLLKH;
LWGSDLWES; WGSDLWESS; GSDLWESSA; SDLWESSAG; DLWESSAGA; LWESSAGAE;
WESSAGAEV; ESSAGAEVS; SSAGAEVSE; SAGAEVSET; AGAEVSETW; GAEVSETWE;
AEVSETWEE; EVSETWEEH; VSETWEEHC; SETWEEHCD; ETWEEHCDW; TWEEHCDWD;
WEEHCDWDS; EEHCDWDSV; EHCDWDSVL; HCDWDSVLD; CDWDSVLDP; DWDSVLDPC;
WDSVLDPCP; DSVLDPCPE; SVLDPCPES; VLDPCPESS; LDPCPESSV; DPCPESSVS;
PCPESSVSE; CPESSVSES; PESSVSESS; ESSVSESSS; SSVSESSSL; SVSESSSLV;
VSESSSLVI; SESSSLVIS; ESSSLVISR; SSSLVISRI; SSLVISRIH; SLVISRIHF;
LVISRIHFP; VISRIHFPM; ISRIHFPMH; SRIHFPMHI; RIHFPMHIL; IHFPMHILY;
HFPMHILYF; FPMHILYFI; PMHILYFIL; MHILYFILE; HILYFILEK; ILYFILEKV;
LYFILEKVY; YFILEKVYI; FILEKVYIL; ILEKVYILI; LEKVYILIS; EKVYILISE;
KVYILISES; VYILISESS; YILISESSL; ILISESSLS; LISESSLSF; ISESSLSFH;
SESSLSFHS; ESSLSFHST; SSLSFHSTI; SLSFHSTIL; LSFHSTILD; SFHSTILDC;
FHSTILDCI; HSTILDCIS; STILDCISV; TILDCISVA; ILDCISVAK; LDCISVAKS;
DCISVAKSA; CISVAKSAT; ISVAKSATG; SVAKSATGL; VAKSATGLN; AKSATGLNQ;
KSATGLNQI; SATGLNQIS; ATGLNQISS; TGLNQISSS; GLNQISSSN; LNQISSSNK;
NQISSSNKV; QISSSNKVI; ISSSNKVIP; SSSNKVIPL; SSNKVIPLC; SNKVIPLCK;
NKVIPLCKI; KVIPLCKIL; VIPLCKILF; IPLCKILFS; PLCKILFSS; LCKILFSSK;
CKILFSSKN; KILFSSKNS; ILFSSKNSE; LFSSKNSEF; FSSKNSEFC; SSKNSEFCK;
SKNSEFCKD; KNSEFCKDF; NSEFCKDFL; SEFCKDFLK; EFCKDFLKY; FCKDFLKYI;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

CKDFLKYIL; KDFLKYILG; DFLKYILGL; FLKYILGLK; LKYILGLKS; KYILGLKSI;
YILGLKSIC; ILGLKSICL; LGLKSICLT; GLKSICLTN; LKSICLTNL; KSICLTNLA;
SICLTNLAC; ICLTNLACR; CLTNLACRV; LTNLACRVL; TNLACRVLG; NLACRVLGT;
LACRVLGTG; ACRVLGTGY; CRVLGTGYS; RVLGTGYSF; VLGTGYSFI; LGTGYSFIV;
GTGYSFIVT; TGYSFIVTK; GYSFIVTKP; YSFIVTKPG; SFIVTKPGG; FIVTKPGGN;
IVTKPGGNI; VTKPGGNIW; TKPGGNIWV; KPGGNIWVL; PGGNIWVLL; GGNIWVLLF;
GNIWVLLFK; NIWVLLFKC; IWVLLFKCF; WVLLFKCFF; VLLFKCFFS; LLFKCFFSK;
LFKCFFSKF; FKCFFSKFT; KCFFSKFTL; CFFSKFTLT; FFSKFTLTL; FSKFTLTLP;
SKFTLTLPS; KFTLTLPSK; SLKLSKLFI; LKLSKLFIP; KLSKLFIPC; LSKLFIPCP;
SKLFIPCPE; KLFIPCPEG; LFIPCPEGK; FIPCPEGKS; IPCPEGKSF; PCPEGKSFD;
CPEGKSFDS; PEGKSFDSA; EGKSFDSAP; GKSFDSAPV; KSFDSAPVP; SFDSAPVPF;
FDSAPVPFT; DSAPVPFTS; SAPVPFTSS; APVPFTSSK; PVPFTSSKT; VPFTSSKTT;
PFTSSKTTM; FTSSKTTMY; SIATPSSKV; IATPSSKVS; ATPSSKVSL; TPSSKVSLS;
PSSKVSLSM; SSKVSLSMG; SKVSLSMGR; KVSLSMGRF; VSLSMGRFT; SLSMGRFTF;
LSMGRFTFK; SMGRFTFKA; MGRFTFKAL; GRFTFKALP; RFTFKALPP; FTFKALPPH;
TFKALPPHK; FKALPPHKS; KALPPHKSN; ALPPHKSNN; LPPHKSNNP; PPHKSNNPA;
PHKSNNPAA; HKSNNPAAS; KSNNPAASV; SNNPAASVV; NNPAASVVF; NPAASVVFP;
PAASVVFPL; AASVVFPLS; ASVVFPLSM; SVVFPLSMG; VVFPLSMGP; VFPLSMGPL;
FPLSMGPLN; PLSMGPLNN; LSMGPLNNQ; SMGPLNNQY; MGPLNNQYL; GPLNNQYLL;
PLNNQYLLL; LNNQYLLLG; NNQYLLLGT; NQYLLLGTL; QYLLLGTLK; YLLLGTLKT;
LLLGTLKTI; LLGTLKTIQ; LGTLKTIQC; GTLKTIQCK; TLKTIQCKK; LKTIQCKKS;
KTIQCKKSN; TIQCKKSNI; IQCKKSNIT; QCKKSNITE; CKKSNITES; KKSNITESI;
KSNITESIL; SNITESILG; NITESILGS; ITESILGSK; TESILGSKQ; ESILGSKQC;
SILGSKQCS; ILGSKQCSQ; LGSKQCSQA; GSKQCSQAT; SKQCSQATP; KQCSQATPA;
QCSQATPAI; CSQATPAIY; SQATPAIYC; QATPAIYCS; ATPAIYCSS; TPAIYCSST;
PAIYCSSTA; AIYCSSTAF; IYCSSTAFP; APNIKSILS; PNIKSILSN; NIKSILSNI;
LNLSVSISS; NLSVSISSL; LSVSISSLV; SVSISSLVI; RVSTLFLAK; VSTLFLAKT;
STLFLAKTV; TLFLAKTVS; LFLAKTVST; FLAKTVSTA; LAKTVSTAC; FLLSAKIIA;
LLSAKIIAF; LSAKIIAFA; SAKIIAFAK; AKIIAFAKC; KIIAFAKCF; IIAFAKCFS;
HFLHSSTLY; NSKYIPNNK; SKYIPNNKN; KYIPNNKNT; YIPNNKNTS; IPNNKNTSS;
PNNKNTSSH; NNKNTSSHF; NKNTSSHFV; KNTSSHFVS; NTSSHFVST; TSSHFVSTA;
SSHFVSTAY; SHFVSTAYS; HFVSTAYSV; FVSTAYSVI; VSTAYSVIN; STAYSVINF;
TAYSVINFQ; AYSVINFQD; YSVINFQDT; SVINFQDTC; VINFQDTCF; INFQDTCFV;
NFQDTCFVS; FQDTCFVSS; QDTCFVSSG; DTCFVSSGS; TCFVSSGSS; CFVSSGSSG;
FVSSGSSGL; VSSGSSGLK; SSGSSGLKS; SGSSGLKSC; GSSGLKSCS; SSGLKSCSF;
SGLKSCSFK; GLKSCSFKP; LKSCSFKPP; MLSSIVWYG; LSSIVWYGS; SSIVWYGSL;
SIVWYGSLV; IVWYGSLVK; VWYGSLVKA; WYGSLVKAL; YGSLVKALY; GSLVKALYS;
SLVKALYSK; LVKALYSKY; VKALYSKYS; KALYSKYSL; ALYSKYSLL; LYSKYSLLT;
YSKYSLLTP; SKYSLLTPL; KYSLLTPLQ; YSLLTPLQI; SLLTPLQIK; LLTPLQIKK;
LTPLQIKKL; TPLQIKKLK; PLQIKKLKV; LQIKKLKVH; QIKKLKVHS; IKKLKVHSF;
QKLLIAETL; KLLIAETLC; LLIAETLCL; LIAETLCLC; IAETLCLCG; AETLCLCGV;
ETLCLCGVK; TLCLCGVKK; LCLCGVKKN; CLCGVKKNI; LCGVKKNII; CGVKKNIIL;
GVKKNIILC; VKKNIILCP; KKNIILCPA; KNIILCPAH; NIILCPAHM; IILCPAHMC;
ILCPAHMCL; LCPAHMCLL; CPAHMCLLI; PAHMCLLIK; AHMCLLIKV; HMCLLIKVT;
MCLLIKVTE; CLLIKVTEY; LLIKVTEYF; LIKVTEYFS; IKVTEYFSI; KVTEYFSIS;
VTEYFSISF; TEYFSISFL; EYFSISFLY; YFSISFLYR; FSISFLYRI; APSLVVYTA;
FSLVVYTAK; SLVVYTAKQ; LVVYTAKQA; VVYTAKQAR; VYTAKQARV; YTAKQARVL;
TAKQARVLL; AKQARVLLL; KQARVLLLN; QARVLLLNT; ARVLLLNTA; LRNWCRSEG;
RNWCRSEGK; NWCRSEGKS; WCRSEGKSL; CRSEGKSLG; RSEGKSLGS; SEGKSLGSS;
EGKSLGSST; GKSLGSSTF; KSLGSSTFL; SLGSSTFLF; LGSSTFLFF; GSSTFLFFL;
SSTFLFFLG; STFLFFLGG; TFLFFLGGV; FLFFLGGVE; LFFLGGVEC; ESAVASSSL;
SAVASSSLA; AVASSSLAN; VASSSLANI; ASSSLANIS; SSSLANISS; SSLANISSW;
SLANISSWQ; LANISSWQN; ANISSWQNK; NISSWQNKS; ISSWQNKSS; SSWQNKSSS;
SWQNKSSSH; WQNKSSSHF; QNKSSSHFS; NKSSSHFSL; KSSSHFSLK; SSSHFSLKE;
SSHFSLKEL; SHFSLKELH; HFSLKELHQ; FSLKELHQD; SLKELHQDS; LKELHQDSH;
KELHQDSHS; ELHQDSHSS; LHQDSHSSV; HQDSHSSVP; VGTYKKNNY; GTYKKNNYL;
TYKKNNYLG; YKKNNYLGP; KKNNYLGPF; KNNYLGPFN; NNYLGPFNI; NYLGPFNIL;
YLGPFNILL; LGPFNILLF; GPFNILLFI; VSYLKALDL; REFLQLFGP; EFLQLFGPT;
FLQLFGPTI; LQLFGPTIA; QLFGPTIAE; LFGPTIAEF; FGPTIAEFL; GPTIAEFLQ;
PTIAEFLQL; TIAEFLQLG; IAEFLQLGL; AEFLQLGLS; EFLQLGLSQ; FLQLGLSQT;
LQLGLSQTT; QLGLSQTTV; SSQCSSNLS; SQCSSNLSK; QCSSNLSKP; CSSNLSKPR;
SSNLSKPRA; SNLSKPRAL; NLSKPRALF; LSKPRALFL; SKPRALFLK; KPRALFLKI;
PRALFLKIF; RALFLKIFY; ALFLKIFYL; LFLKIFYLN; FLKIFYLNA; LKIFYLNAL;
KIFYLNALI; ADIACKGSA; DIACKGSAQ; IACKGSAQK; ACKGSAQKA; CKGSAQKAF;
KGSAQKAFW; GSAQKAFWN; SAQKAFWNK; AIPCSTGYL; IPCSTGYLG; PCSTGYLGK;
CSTGYLGKE; STGYLGKEE; TGYLGKEEN; GYLGKEENQ; YLGKEENQH; LGKEENQHK;
GKEENQHKP; KEENQHKPL; EENQHKPLS; ENQHKPLSY; NQHKPLSYS; QHKPLSYSR;
HKPLSYSRF; KPLSYSRFQ; PLSYSRFQN; LSYSRFQNQ; SYSRFQNQA; YSRFQNQAD;
SRFQNQADE; RFQNQADEL; FQNQADELP; QNQADELPL; NQADELPLH; QADELPLHP;
ADELPLHPA; DELPLHPAP; ELPLHPAPF; LPLHPAPFF; PLHPAPFFY; LHPAPFFYT;
HPAPFFYTK; PAPFFYTKY; APFFYTKYS; PFFYTKYSF; FFYTKYSFS; FYTKYSFSS;
YTKYSFSSF; TKYSFSSFY; KYSFSSFYP; YSFSSFYPR; SFSSFYPRR; FSSFYPRRP;
SSFYPRRPL; SFYPRRPLC; FYPRRPLCQ; YPRRPLCQG; PRRPLCQGE; RRPLCQGEI;
RPLCQGEIP; PLCQGEIPY; LCQGEIPYT; CQGEIPYTS; QGEIPYTSL; GEIPYTSLN;
EIPYTSLNK; IPYTSLNKL; PYTSLNKLF; YTSLNKLFS; TSLNKLFSL; SLNKLFSLR;
LNKLFSLRE; NKLFSLRED; KLFSLREDF; LFSLREDFP; FSLREDFPR; SLREDFPRQ;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

LREDFPRQL; REDFPRQLF; EDFPRQLFQ; DFPRQLFQG; FPRQLFQGL; PRQLFQGLK; RQLFQGLKG; QLFQGLKGP 10 mers:

GFPQIVLLGL; FPQIVLLGLR; PQIVLLGLRK; QIVLLGLRKS; IVLLGLRKSL; VLLGLRKSLH; LLGLRKSLHT; LGLRKSLHTL; GLRKSLHTLT; LRKSLHTLTT; EKGWRQRRPR; KGWRQRRPRP; GWRQRRPRPL; WRQRRPRPLI; RQRRPRPLIY; QRRPRPLIYY; RRPRPLIYYK; RPRPLIYYKK; PRPLIYYKKG; RPLIYYKKKG; PLIYYKKKGH; LIYYKKKGHR; IYYKKKGHRE; YYKKKGHREE; YKKKGHREEL; KKKGHREELL; KKGHREELLT; KGHREELLTH; GHREELLTHG; HREELLTHGM; REELLTHGMQ; EELLTHGMQP; ELLTHGMQPN; LLTHGMQPNH; LTHGMQPNHD; THGMQPNHDL; HGMQPNHDLR; GMQPNHDLRK; MQPNHDLRKE; QPNHDLRKES; PNHDLRKESA; LTGECSQTMT; TGECSQTMTS; GECSQTMTSG; ECSQTMTSGR; CSQTMTSGRK; SQTMTSGRKV; QTMTSGRKVH; TMTSGRKVHD; MTSGRKVHDS; TSGRKVHDSQ; SGRKVHDSQG; GRKVHDSQGG; RKVHDSQGGA; KVHDSQGGAA; VHDSQGGAAY; HDSQGGAAYP; DSQGGAAYPW; SQGGAAYPWN; QGGAAYPWNA; GGAAYPWNAA; GAAYPWNAAK; AAYPWNAAKP; PQEGKCMTDM; QEGKCMTDMF; EGKCMTDMFC; GKCMTDMFCE; KCMTDMFCEP; CMTDMFCEPR; MTDMFCEPRN; TDMFCEPRNL; DMFCEPRNLG; MFCEPRNLGL; FCEPRNLGLV; CEPRNLGLVP; EPRNLGLVPS; TGQRPWFCAS; GQRPWFCASC; QRPWFCASCH; RPWFCASCHD; PWFCASCHDK; WFCASCHDKL; FCASCHDKLQ; KLVKPGLEQK; LVKPGLEQKK; VKPGLEQKKE; KPGLEQKKEL; PGLEQKKELR; GLEQKKELRG; LEQKKELRGF; EQKKELRGFL; QKKELRGFLF; KKELRGFLFL; KELRGFLFLF; SFCWNFVEVK; FCWNFVEVKT; CWNFVEVKTV; TGKTKVPLLY; GKTKVPLLYL; KTKVPLLYLL; VIPFFLYFQV; IPFFLYFQVH; PFFLYFQVHG; FFLYFQVHGC; FLYFQVHGCC; LYFQVHGCCS; YFQVHGCCSS; FQVHGCCSST; QVHGCCSSTF; VHGCCSSTFG; HGCCSSTFGG; GCCSSTFGGP; CCSSTFGGPS; CSSTFGGPSC; SSTFGGPSCQ; STFGGPSCQC; TFGGPSCQCI; GCCCHRIFSG; NCCWGGCCCY; CCWGGCCCYR; CWGGCCCYRS; WGGCCCYRSS; GGCCCYRSSN; GCCCYRSSNC; CCCYRSSNCI; CCYRSSNCIP; CYRSSNCIPC; YRSSNCIPCY; RSSNCIPCYC; SSNCIPCYCR; SNCIPCYCRG; NCIPCYCRGH; CIPCYCRGHN; IPCYCRGHNK; PCYCRGHNKY; CYCRGHNKYL; YCRGHNKYLR; CRGHNKYLRG; RGHNKYLRGY; GHNKYLRGYS; HNKYLRGYSC; NKYLRGYSCY; KYLRGYSCYR; YLRGYSCYRP; LRGYSCYRPN; RGYSCYRPNS; GYSCYRPNSS; YSCYRPNSSN; SCYRPNSSNI; CYRPNSSNIC; YRPNSSNICC; RPNSSNICCN; PNSSNICCNC; NSSNICCNCW; SSNICCNCWC; SNICCNCWCS; NICCNCWCSW; ICCNCWCSWG; CCNCWCSWGY; CNCWCSWGYC; NCWCSWGYCW; CWCSWGYCWV; WCSWGYCWVC; CSWGYCWVCC; SWGYCWVCCF; WGYCWVCCFN; GYCWVCCFNS; YCWVCCFNSN; CWVCCFNSNC; LGSQSFHCRP; GSQSFHCRPL; SQSFHCRPLS; QSFHCRPLSA; SFHCRPLSAI; FHCRPLSAIR; HCRPLSAIRH; CRPLSAIRHG; RPLSAIRHGF; PLSAIRHGFG; LSAIRHGFGI; SAIRHGFGIV; YSVSWCKYFC; ALGSFFVCYY; LGSFFVCYYF; GSFFVCYYFP; SFFVCYYFPG; FFVCYYFPGF; FVCYYFPGFV; VCYYFPGFVA; CYYFPGFVAC; YYFPGFVACY; YTFYNLTGIA; TFYNLTGIAE; FYNLTGIAEK; YNLTGIAEKN; NLTGIAEKNR; LTGIAEKNRK; TGIAEKNRKI; GIAEKNRKIF; IFGGNYLDNC; FGGNYLDNCK; GGNYLDNCKC; GNYLDNCKCP; NYLDNCKCPY; YLDNCKCPYK; LDNCKCPYKL; DNCKCPYKLL; KGRYPCTFWP; GRYPCTFWPY; RYPCTFWPYL; QYRRSYTKNG; YRRSYTKNGL; RRSYTKNGLK; RSYTKNGLKK; SYTKNGLKKS; YTKNGLKKST; TKNGLKKSTK; KNGLKKSTKC; NGLKKSTKCT; GLKKSTKCTF; LKKSTKCTFR; KKSTKCTFRR; KSTKCTFRRV; STKCTFRRVY; TKCTFRRVYR; KCTFRRVYRK; CTFRRVYRKN; TFRRVYRKNY; FRRVYRKNYC; RRVYRKNYCP; RVYRKNYCPR; VYRKNYCPRR; YRKNYCPRRC; SKNCSSMDVA; KNCSSMDVAF; NCSSMDVAFT; CSSMDVAFTS; SSMDVAFTSR; SMDVAFTSRP; MDVAFTSRPV; DVAFTSRPVR; VAFTSRPVRD; AFTSRPVRDC; FTSRPVRDCN; TSRPVRDCNT; SRPVRDCNTC; RPVRDCNTCS; RWPQPKEKES; WPQPKEKESV; PQPKEKESVQ; QPKEKESVQG; PKEKESVQGQ; KEKESVQGQL; EKESVQGQLP; KESVQGQLPK; ESVQGQLPKS; SVQGQLPKSQ; VQGQLPKSQR; QGQLPKSQRN; GQLPKSQRNP; QLPKSQRNPC; LPKSQRNPCK; PKSQRNPCKC; KSQRNPCKCQ; SQRNPCKCQN; QRNPCKCQNY; TQKWGIQMKT; QKWGIQMKTL; KWGIQMKTLG; WGIQMKTLGA; GIQMKTLGAL; IQMKTLGALV; VLKMTLAVIA; LKMTLAVIAQ; KMTLAVIAQR; MTLAVIAQRE; TLAVIAQREK; LAVIAQREKC; AVIAQREKCF; VIAQREKCFP; IAQREKCFPV; AQREKCFPVT; QREKCFPVTA; REKCFPVTAQ; EKCFPVTAQQ; KCFPVTAQQE; CFPVTAQQEF; FPVTAQQEFP; PVTAQQEFPS; VTAQQEFPSP; TAQQEFPSPI; LACLTFMQGH; ACLTFMQGHK; CLTFMQGHKK; LTFMQGHKKC; TFMQGHKKCM; FMQGHKKCMS; MQGHKKCMSM; QGHKKCMSMV; GHKKCMSMVE; HKKCMSMVEE; KKCMSMVEEN; KCMSMVEENL; CMSMVEENLF; MSMVEENLFK; SMVEENLFKA; MVEENLFKAV; VEENLFKAVI; EENLFKAVIS; ENLFKAVIST; NLFKAVISTS; LFKAVISTSL; FKAVISTSLL; VENPWKCREC; ITGQSTLMVL; PLKTQQPSPR; ILTIRPIWTK; LTIRPIWTKT; TIRPIWTKTM; IRPIWTKTML; RPIWTKTMLI; PIWTKTMLIQ; IWTKTMLIQL; WTKTMLIQLS; TKTMLIQLSA; KTMLIQLSAG; TMLIQLSAGY; MLIQLSAGYL; LIQLSAGYLI; IQLSAGYLIP; QLSAGYLIPV; LSAGYLIPVE; SAGYLIPVEM; AGYLIPVEMK; GYLIPVEMKM; YLIPVEMKML; LIPVEMKMLG; IPVEMKMLGI; PVEMKMLGIL; VEMKMLGILG; EMKMLGILGL; MKMLGILGLS; KMLGILGLSQ; MLGILGLSQE; LGILGLSQEG; GILGLSQEGK; ILGLSQEGKM; LGLSQEGKMF; GLSQEGKMFP; LSQEGKMFPQ; SQEGKMFPQY; QEGKMFPQYF; EGKMFPQYFM; MNRVWGLFVK; NRVWGLFVKL;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

RVWGLFVKLI; VWGLFVKLIA; WGLFVKLIAC; GLFVKLIACM; LFVKLIACMF;
FVKLIACMFQ; VKLIACMFQL; KLIACMFQLL; LIACMFQLLI; IACMFQLLIF;
ACMFQLLIFV; CMFQLLIFVA; MFQLLIFVAC; FQLLIFVACL; QLLIFVACLL;
LLIFVACLLT; LIFVACLLTA; IFVACLLTAL; FVACLLTALE; VACLLTALEH;
ACLLTALEHN; CLLTALEHNS; LLTALEHNSG; LTALEHNSGE; TALEHNSGEA;
ALEHNSGEAL; LEHNSGEALQ; EHNSGEALQD; HNSGEALQDI; NSGEALQDIL;
SGEALQDILR; GEALQDILRS; EALQDILRSA; TGEPREWMGS; GEPREWMGSL;
EPREWMGSLC; PREWMGSLCM; REWMGSLCMV; EWMGSLCMVW; WMGSLCMVWN;
MGSLCMVWNP; GSLCMVWNPR; KRLGCLMAQK; RLGCLMAQKD; LGCLMAQKDF;
GCLMAQKDFQ; CLMAQKDFQG; LMAQKDFQGT; MAQKDFQGTQ; AQKDFQGTQI;
DILTNRDNCK; ILTNRDNCKP; LTNRDNCKPK; TNRDNCKPKC; NRDNCKPKCF;
RDNCKPKCFK; DNCKPKCFKQ; NCKPKCFKQV; CKPKCFKQVL; KPKCFKQVLL;
PKCFKQVLLL; KCFKQVLLLY; CFKQVLLLYI; FKQVLLLYIY; KQVLLLYIYI;
MLLLYKPLLS; LLLYKPLLSL; LLYKPLLSLC; LYKPLLSLCY; YKPLLSLCYF;
KPLLSLCYFG; PLLSLCYFGG; LLSLCYFGGG; LSLCYFGGGV; SLCYFGGGVL;
LCYFGGGVLG; CYFGGGVLGL; YFGGGVLGLL; FGGGVLGLLK; GGGVLGLLKH;
LWGSDLWESS; WGSDLWESSA; GSDLWESSAG; SDLWESSAGA; DLWESSAGAE;
LWESSAGAEV; WESSAGAEVS; ESSAGAEVSE; SSAGAEVSET; SAGAEVSETW;
AGAEVSETWE; GAEVSETWEE; AEVSETWEEH; EVSETWEEHC; VSETWEEHCD;
SETWEEHCDW; ETWEEHCDWD; TWEEHCDWDS; WEEHCDWDSV; EEHCDWDSVL;
EHCDWDSVLD; HCDWDSVLDP; CDWDSVLDPC; DWDSVLDPCP; WDSVLDPCPE;
DSVLDPCPES; SVLDPCPESS; VLDPCPESSV; LDPCPESSVS; DPCPESSVSE;
PCPESSVSES; CPESSVSESS; PESSVSESSS; ESSVSESSSL; SSVSESSSLV;
SVSESSSLVI; VSESSSLVIS; SESSSLVISR; ESSSLVISRI; SSSLVISRIH;
SSLVISRIHF; SLVISRIHFP; LVISRIHFPM; VISRIHFPMH; ISRIHFPMHI;
SRIHFPMHIL; RIHFPMHILY; IHFPMHILYF; HFPMHILYFI; FPMHILYFIL;
PMHILYFILE; MHILYFILEK; HILYFILEKV; ILYFILEKVY; LYFILEKVYI;
YFILEKVYIL; FILEKVYILI; ILEKVYILIS; LEKVYILISE; EKVYILISES;
KVYILISESS; VYILISESSL; YILISESSLS; ILISESSLSF; LISESSLSFH;
ISESSLSFHS; SESSLSFHST; ESSLSFHSTI; SSLSFHSTIL; SLSFHSTILD;
LSFHSTILDC; SFHSTILDCI; FHSTILDCIS; HSTILDCISV; STILDCISVA;
TILDCISVAK; ILDCISVAKS; LDCISVAKSA; DCISVAKSAT; CISVAKSATG;
ISVAKSATGL; SVAKSATGLN; VAKSATGLNQ; AKSATGLNQI; KSATGLNQIS;
SATGLNQISS; ATGLNQISSS; TGLNQISSSN; GLNQISSSNK; LNQISSSNKV;
NQISSSNKVI; QISSSNKVIP; ISSSNKVIPL; SSSNKVIPLC; SSNKVIPLCK;
SNKVIPLCKI; NKVIPLCKIL; KVIPLCKILF; VIPLCKILFS; IPLCKILFSS;
PLCKILFSSK; LCKILFSSKN; CKILFSSKNS; KILFSSKNSE; ILFSSKNSEF;
LFSSKNSEFC; FSSKNSEFCK; SSKNSEFCKD; SKNSEFCKDF; KNSEFCKDFL;
NSEFCKDFLK; SEFCKDFLKY; EFCKDFLKYI; FCKDFLKYIL; CKDFLKYILG;
KDFLKYILGL; DFLKYILGLK; FLKYILGLKS; LKYILGLKSI; KYILGLKSIC;
YILGLKSICL; ILGLKSICLT; LGLKSICLTN; GLKSICLTNL; LKSICLTNLA;
KSICLTNLAC; SICLTNLACR; ICLTNLACRV; CLTNLACRVL; LTNLACRVLG;
TNLACRVLGT; NLACRVLGTG; LACRVLGTGY; ACRVLGTGYS; CRVLGTGYSF;
RVLGTGYSFI; VLGTGYSFIV; LGTGYSFIVT; GTGYSFIVTK; TGYSFIVTKP;
GYSFIVTKPG; YSFIVTKPGG; SFIVTKPGGN; FIVTKPGGNI; IVTKPGGNIW;
VTKPGGNIWV; TKPGGNIWVL; KPGGNIWVLL; PGGNIWVLLF; GGNIWVLLFK;
GNIWVLLFKC; NIWVLLFKCF; IWVLLFKCFF; WVLLFKCFFS; VLLFKCFFSK;
LLFKCFFSKF; LFKCFFSKFT; FKCFFSKFTL; KCFFSKFTLT; CFFSKFTLTL;
FFSKFTLTLP; FSKFTLTLPS; SKFTLTLPSK; SLKLSKLFIP; LKLSKLFIPC;
KLSKLFIPCP; LSKLFIPCPE; SKLFIPCPEG; KLFIPCPEGK; LFIPCPEGKS;
FIPCPEGKSF; IPCPEGKSFD; PCPEGKSFDS; CPEGKSFDSA; PEGKSFDSAP;
EGKSFDSAPV; GKSFDSAPVP; KSFDSAPVPF; SFDSAPVPFT; FDSAPVPFTS;
DSAPVPFTSS; SAPVPFTSSK; APVPFTSSKT; PVPFTSSKTT; VPFTSSKTTM;
PFTSSKTTMY; SIATPSSKVS; IATPSSKVSL; ATPSSKVSLS; TPSSKVSLSM;
PSSKVSLSMG; SSKVSLSMGR; SKVSLSMGRF; KVSLSMGRFT; VSLSMGRFTF;
SLSMGRFTFK; LSMGRFTFKA; SMGRFTFKAL; MGRFTFKALP; GRFTFKALPP;
RFTFKALPPH; FTFKALPPHK; TFKALPPHKS; FKALPPHKSN; KALPPHKSNN;
ALPPHKSNNP; LPPHKSNNPA; PPHKSNNPAA; PHKSNNPAAS; HKSNNPAASV;
KSNNPAASVV; SNNPAASVVF; NNPAASVVFP; NPAASVVFPL; PAASVVFPLS;
AASVVFPLSM; ASVVFPLSMG; SVVFPLSMGP; VVFPLSMGPL; VFPLSMGPLN;
FPLSMGPLNN; PLSMGPLNNQ; LSMGPLNNQY; SMGPLNNQYL; MGPLNNQYLL;
GPLNNQYLLL; PLNNQYLLLG; LNNQYLLLGT; NNQYLLLGTL; NQYLLLGTLK;
QYLLLGTLKT; YLLLGTLKTI; LLLGTLKTIQ; LLGTLKTIQC; LGTLKTIQCK;
GTLKTIQCKK; TLKTIQCKKS; LKTIQCKKSN; KTIQCKKSNI; TIQCKKSNIT;
IQCKKSNITE; QCKKSNITES; CKKSNITESI; KKSNITESIL; KSNITESILG;
SNITESILGS; NITESILGSK; ITESILGSKQ; TESILGSKQC; ESILGSKQCS;
SILGSKQCSQ; ILGSKQCSQA; LGSKQCSQAT; GSKQCSQATP; SKQCSQATPA;
KQCSQATPAI; QCSQATPAIY; CSQATPAIYC; SQATPAIYCS; QATPAIYCSS;
ATPAIYCSST; TPAIYCSSTA; PAIYCSSTAF; AIYCSSTAFP; APNIKSILSN;
PNIKSILSNI; LNLSVSISSL; NLSVSISSLV; LSVSISSLVI; RVSTLFLAKT;
VSTLFLAKTV; STLFLAKTVS; TLFLAKTVST; LFLAKTVSTA; FLAKTVSTAC;
FLLSAKIIAF; LLSAKIIAFA; LSAKIIAFAK; SAKIIAFAKC; AKIIAFAKCF;
KIIAFAKCFS; NSKYIPNNKN; SKYIPNNKNT; KYIPNNKNTS; YIPNNKNTSS;
IPNNKNTSSH; PNNKNTSSHF; NNKNTSSHFV; NKNTSSHFVS; KNTSSHFVST;
NTSSHFVSTA; TSSHFVSTAY; SSHFVSTAYS; SHFVSTAYSV; HFVSTAYSVI;
FVSTAYSVIN; VSTAYSVINF; STAYSVINFQ; TAYSVINFQD; AYSVINFQDT;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

YSVINFQDTC; SVINFQDTCF; VINFQDTCFV; INFQDTCFVS; NFQDTCFVSS;
FQDTCFVSSG; QDTCFVSSGS; DTCFVSSGSS; TCFVSSGSSG; CFVSSGSSGL;
FVSSGSSGLK; VSSGSSGLKS; SSGSSGLKSC; SGSSGLKSCS; GSSGLKSCSF;
SSGLKSCSFK; SGLKSCSFKP; GLKSCSFKPP; MLSSIVWYGS; LSSIVWYGSL;
SSIVWYGSLV; SIVWYGSLVK; IVWYGSLVKA; VWYGSLVKAL; WYGSLVKALY;
YGSLVKALYS; GSLVKALYSK; SLVKALYSKY; LVKALYSKYS; VKALYSKYSL;
KALYSKYSLL; ALYSKYSLLT; LYSKYSLLTP; YSKYSLLTPL; SKYSLLTPLQ;
KYSLLTPLQI; YSLLTPLQIK; SLLTPLQIKK; LLTPLQIKKL; LTPLQIKKLK;
TPLQIKKLKV; PLQIKKLKVH; LQIKKLKVHS; QIKKLKVHSF; QKLLIAETLC;
KLLIAETLCL; LLIAETLCLC; LIAETLCLCG; IAETLCLCGV; AETLCLCGVK;
ETLCLCGVKK; TLCLCGVKKN; LCLCGVKKNI; CLCGVKKNII; LCGVKKNIIL;
CGVKKNIILC; GVKKNIILCP; VKKNIILCPA; KKNIILCPAH; KNIILCPAHM;
NIILCPAHMC; IILCPAHMCL; ILCPAHMCLL; LCPAHMCLLI; CPAHMCLLIK;
PAHMCLLIKV; AHMCLLIKVT; HMCLLIKVTE; MCLLIKVTEY; CLLIKVTEYF;
LLIKVTEYFS; LIKVTEYFSI; IKVTEYFSIS; KVTEYFSISF; VTEYFSISFL;
TEYFSISFLY; EYFSISFLYR; YFSISFLYRI; AFSLVVYTAK; FSLVVYTAKQ;
SLVVYTAKQA; LVVYTAKQAR; VVYTAKQARV; VYTAKQARVL; YTAKQARVLL;
TAKQARVLLL; AKQARVLLLN; KQARVLLLNT; QARVLLLNTA; LRNWCRSEGK;
RNWCRSEGKS; NWCRSEGKSL; WCRSEGKSLG; CRSEGKSLGS; RSEGKSLGSS;
SEGKSLGSST; EGKSLGSSTF; GKSLGSSTFL; KSLGSSTFLF; SLGSSTFLFF;
LGSSTFLFFL; GSSTFLFFLG; SSTFLFFLGG; STFLFFLGGV; TFLFFLGGVE;
FLFFLGGVEC; ESAVASSSLA; SAVASSSLAN; AVASSSLANI; VASSSLANIS;
ASSSLANISS; SSSLANISSW; SSLANISSWQ; SLANISSWQN; LANISSWQNK;
ANISSWQNKS; NISSWQNKSS; ISSWQNKSSS; SSWQNKSSSH; SWQNKSSSHF;
WQNKSSSHFS; QNKSSSHFSL; NKSSSHFSLK; KSSSHFSLKE; SSSHFSLKEL;
SSHFSLKELH; SHFSLKELHQ; HFSLKELHQD; FSLKELHQDS; SLKELHQDSH;
LKELHQDSHS; KELHQDSHSS; ELHQDSHSSV; LHQDSHSSVP; VGTYKKNNYL;
GTYKKNNYLG; TYKKNNYLGP; YKKNNYLGPF; KKNNYLGPFN; KNNYLGPFNI;
NNYLGPFNIL; NYLGPFNILL; YLGPFNILLF; LGPFNILLFI; REFLQLFGPT;
EFLQLFGPTI; FLQLFGPTIA; LQLFGPTIAE; QLFGPTIAEF; LFGPTIAEFL;
FGPTIAEFLQ; GPTIAEFLQL; PTIAEFLQLG; TIAEFLQLGL; IAEFLQLGLS;
AEFLQLGLSQ; EFLQLGLSQT; FLQLGLSQTT; LQLGLSQTTV; SSQCSSNLSK;
SQCSSNLSKP; QCSSNLSKPR; CSSNLSKPRA; SSNLSKPRAL; SNLSKPRALF;
NLSKPRALFL; LSKPRALFLK; SKPRALFLKI; KPRALFLKIF; PRALFLKIFY;
RALFLKIFYL; ALFLKIFYLN; LFLKIFYLNA; FLKIFYLNAL; LKIFYLNALI;
ADIACKGSAQ; DIACKGSAQK; IACKGSAQKA; ACKGSAQKAF; CKGSAQKAFW;
KGSAQKAFWN; GSAQKAFWNK; AIPCSTGYLG; IPCSTGYLGK; PCSTGYLGKE;
CSTGYLGKEE; STGYLGKEEN; TGYLGKEENQ; GYLGKEENQH; YLGKEENQHK;
LGKEENQHKP; GKEENQHKPL; KEENQHKPLS; EENQHKPLSY; ENQHKPLSYS;
NQHKPLSYSR; QHKPLSYSRF; HKPLSYSRFQ; KPLSYSRFQN; PLSYSRFQNQ;
LSYSRFQNQA; SYSRFQNQAD; YSRFQNQADE; SRFQNQADEL; RFQNQADELP;
FQNQADELPL; QNQADELPLH; NQADELPLHP; QADELPLHPA; ADELPLHPAP;
DELPLHPAPF; ELPLHPAPFF; LPLHPAPFFY; PLHPAPFFYT; LHPAPFFYTK;
HPAPFFYTKY; PAPFFYTKYS; APFFYTKYSF; PFFYTKYSFS; FFYTKYSFSS;
FYTKYSFSSF; YTKYSFSSFY; TKYSFSSFYP; KYSFSSFYPR; YSFSSFYPRR;
SFSSFYPRRP; FSSFYPRRPL; SSFYPRRPLC; SFYPRRPLCQ; FYPRRPLCQG;
YPRRPLCQGE; PRRPLCQGEI; RRPLCQGEIP; RPLCQGEIPY; PLCQGEIPYT;
LCQGEIPYTS; CQGEIPYTSL; QGEIPYTSLN; GEIPYTSLNK; EIPYTSLNKL;
IPYTSLNKLF; PYTSLNKLFS; YTSLNKLFSL; TSLNKLFSLR; SLNKLFSLRE;
LNKLFSLRED; NKLFSLREDF; KLFSLREDFP; LFSLREDFPR; FSLREDFPRQ;
SLREDFPRQL; LREDFPRQLF; REDFPRQLFQ; EDFPRQLFQG; DFPRQLFQGL;
FPRQLFQGLK; PRQLFQGLKG; RQLFQGLKGP 11 mers:

GFPQIVLLGLR; FPQIVLLGLRK; PQIVLLGLRKS; QIVLLGLRKSL; IVLLGLRKSLH;
VLLGLRKSLHT; LLGLRKSLHTL; LGLRKSLHTLT; GLRKSLHTLTT; EKGWRQRRPRP;
KGWRQRRPRPL; GWRQRRPRPLI; WRQRRPRPLIY; RQRRPRPLIYY; QRRPRPLIYYK;
RRPRPLIYYKK; RPRPLIYYKKK; PRPLIYYKKKG; RPLIYYKKKGH; PLIYYKKKGHR;
LIYYKKKGHRE; IYYKKKGHREE; YYKKKGHREEL; YKKKGHREELL; KKKGHREELLT;
KKGHREELLTH; KGHREELLTHG; GHREELLTHGM; HREELLTHGMQ; REELLTHGMQP;
EELLTHGMQPN; ELLTHGMQPNH; LLTHGMQPNHD; LTHGMQPNHDL; THGMQPNHDLR;
HGMQPNHDLRK; GMQPNHDLRKE; MQPNHDLRKES; QPNHDLRKESA; LTGECSQTMTS;
TGECSQTMTSG; GECSQTMTSGR; ECSQTMTSGRK; CSQTMTSGRKV; SQTMTSGRKVH;
QTMTSGRKVHD; TMTSGRKVHDS; MTSGRKVHDSQ; TSGRKVHDSQG; SGRKVHDSQGG;
GRKVHDSQGGA; RKVHDSQGGAA; KVHDSQGGAAY; VHDSQGGAAYP; HDSQGGAAYPW;
DSQGGAAYPWN; SQGGAAYPWNA; QGGAAYPWNAA; GGAAYPWNAAK; GAAYPWNAAKP;
PQEGKCMTDMF; QEGKCMTDMFC; EGKCMTDMFCE; GKCMTDMFCEP; KCMTDMFCEPR;
CMTDMFCEPRN; MTDMFCEPRNL; TDMFCEPRNLG; DMFCEPRNLGL; MFCEPRNLGLV;
FCEPRNLGLVP; CEPRNLGLVPS; TGQRPWFCASC; GQRPWFCASCH; QRPWFCASCHD;
RPWFCASCHDK; PWFCASCHDKL; WFCASCHDKLQ; KLVKPGLEQKK; LVKPGLEQKKE;
VKPGLEQKKEL; KPGLEQKKELR; PGLEQKKELRG; GLEQKKELRGF; LEQKKELRGFL;
EQKKELRGFLF; QKKELRGFLFL; KKELRGFLFLF; SFCWNFVEVKT; FCWNFVEVKTV;
TGKTKVPLLYL; GKTKVPLLYLL; VIPFFLYFQVH; IPFFLYFQVHG; PFFLYFQVHGC;
FFLYFQVHGCC; FLYFQVHGCCS; LYFQVHGCCSS; YFQVHGCCSST; FQVHGCCSSTF;
QVHGCCSSTFG; VHGCCSSTFGG; HGCCSSTFGGP; GCCSSTFGGPS; CCSSTFGGPSC;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

CSSTFGGPSCQ; SSTFGGPSCQC; STFGGPSCQCI; NCCWGGCCCYR; CCWGGCCCYRS;
CWGGCCCYRSS; WGGCCCYRSSN; GGCCCYRSSNC; GCCCYRSSNCI; CCCYRSSNCIP;
CCYRSSNCIPC; CYRSSNCIPCY; YRSSNCIPCYC; RSSNCIPCYCR; SSNCIPCYCRG;
SNCIPCYCRGH; NCIPCYCRGHN; CIPCYCRGHNK; IPCYCRGHNKY; PCYCRGHNKYL;
CYCRGHNKYLR; YCRGHNKYLRG; CRGHNKYLRGY; RGHNKYLRGYS; GHNKYLRGYSC;
HNKYLRGYSCY; NKYLRGYSCYR; KYLRGYSCYRP; YLRGYSCYRPN; LRGYSCYRPNS;
RGYSCYRPNSS; GYSCYRPNSSN; YSCYRPNSSNI; SCYRPNSSNIC; CYRPNSSNICC;
YRPNSSNICCN; RPNSSNICCNC; PNSSNICCNCW; NSSNICCNCWC; SSNICCNCWCS;
SNICCNCWCSW; NICCNCWCSWG; ICCNCWCSWGY; CCNCWCSWGYC; CNCWCSWGYCW;
NCWCSWGYCWV; CWCSWGYCWVC; WCSWGYCWVCC; CSWGYCWVCCF; SWGYCWVCCFN;
WGYCWVCCFNS; GYCWVCCFNSN; YCWVCCFNSNC; LGSQSFHCRPL; GSQSFHCRPLS;
SQSFHCRPLSA; QSFHCRPLSAI; SFHCRPLSAIR; FHCRPLSAIRH; HCRPLSAIRHG;
CRPLSAIRHGF; RPLSAIRHGFG; PLSAIRHGFGI; LSAIRHGFGIV; ALGSFFVCYYF;
LGSFFVCYYFP; GSFFVCYYFPG; SFFVCYYFPGF; FFVCYYFPGFV; FVCYYFPGFVA;
VCYYFPGFVAC; CYYFPGFVACY; YTFYNLTGIAE; TFYNLTGIAEK; FYNLTGIAEKN;
YNLTGIAEKNR; NLTGIAEKNRK; LTGIAEKNRKI; TGIAEKNRKIF; IFGGNYLDNCK;
FGGNYLDNCKC; GGNYLDNCKCP; GNYLDNCKCPY; NYLDNCKCPYK; YLDNCKCPYKL;
LDNCKCPYKLL; KGRYPCTFWPY; GRYPCTFWPYL; QYRRSYTKNGL; YRRSYTKNGLK;
RRSYTKNGLKK; RSYTKNGLKKS; SYTKNGLKKST; YTKNGLKKSTK; TKNGLKKSTKC;
KNGLKKSTKCT; NGLKKSTKCTF; GLKKSTKCTFR; LKKSTKCTFRR; KKSTKCTFRRV;
KSTKCTFRRVY; STKCTFRRVYR; TKCTFRRVYRK; KCTFRRVYRKN; CTFRRVYRKNY;
TFRRVYRKNYC; FRRVYRKNYCP; RRVYRKNYCPR; RVYRKNYCPRR; VYRKNYCPRRC;
SKNCSSMDVAF; KNCSSMDVAFT; NCSSMDVAFTS; CSSMDVAFTSR; SSMDVAFTSRP;
SMDVAFTSRPV; MDVAFTSRPVR; DVAFTSRPVRD; VAFTSRPVRDC; AFTSRPVRDCN;
FTSRPVRDCNT; TSRPVRDCNTC; SRPVRDCNTCS; RWPQPKEKESV; WPQPKEKESVQ;
PQPKEKESVQG; QPKEKESVQGQ; PKEKESVQGQL; KEKESVQGQLP; EKESVQGQLPK;
KESVQGQLPKS; ESVQGQLPKSQ; SVQGQLPKSQR; VQGQLPKSQRN; QGQLPKSQRNP;
GQLPKSQRNPC; QLPKSQRNPCK; LPKSQRNPCKC; PKSQRNPCKCQ; KSQRNPCKCQN;
SQRNPCKCQNY; TQKWGIQMKTL; QKWGIQMKTLG; KWGIQMKTLGA; WGIQMKTLGAL;
GIQMKTLGALV; VLKMTLAVIAQ; LKMTLAVIAQR; KMTLAVIAQRE; MTLAVIAQREK;
TLAVIAQREKC; LAVIAQREKCF; AVIAQREKCFP; VIAQREKCFPV; IAQREKCFPVT;
AQREKCFPVTA; QREKCFPVTAQ; REKCFPVTAQQ; EKCFPVTAQQE; KCFPVTAQQEF;
CFPVTAQQEFP; FPVTAQQEFPS; PVTAQQEFPSP; VTAQQEFPSPI; LACLTFMQGHK;
ACLTFMQGHKK; CLTFMQGHKKC; LTFMQGHKKCM; TFMQGHKKCMS; FMQGHKKCMSM;
MQGHKKCMSMV; QGHKKCMSMVE; GHKKCMSMVEE; HKKCMSMVEEN; KKCMSMVEENL;
KCMSMVEENLF; CMSMVEENLFK; MSMVEENLFKA; SMVEENLFKAV; MVEENLFKAVI;
VEENLFKAVIS; EENLFKAVIST; ENLFKAVISTS; NLFKAVISTSL; LFKAVISTSLL;
ILTIRPIWTKT; LTIRPIWTKTM; TIRPIWTKTML; IRPIWTKTMLI; RPIWTKTMLIQ;
PIWTKTMLIQL; IWTKTMLIQLS; WTKTMLIQLSA; TKTMLIQLSAG; KTMLIQLSAGY;
TMLIQLSAGYL; MLIQLSAGYLI; LIQLSAGYLIP; IQLSAGYLIPV; QLSAGYLIPVE;
LSAGYLIPVEM; SAGYLIPVEMK; AGYLIPVEMKM; GYLIPVEMKML; YLIPVEMKMLG;
LIPVEMKMLGI; IPVEMKMLGIL; PVEMKMLGILG; VEMKMLGILGL; EMKMLGILGLS;
MKMLGILGLSQ; KMLGILGLSQE; MLGILGLSQEG; LGILGLSQEGK; GILGLSQEGKM;
ILGLSQEGKMF; LGLSQEGKMFP; GLSQEGKMFPQ; LSQEGKMFPQY; SQEGKMFPQYF;
QEGKMFPQYFM; MNRVWGLFVKL; NRVWGLFVKLI; RVWGLFVKLIA; VWGLFVKLIAC;
WGLFVKLIACM; GLFVKLIACMF; LFVKLIACMFQ; FVKLIACMFQL; VKLIACMFQLL;
KLIACMFQLLI; LIACMFQLLIF; IACMFQLLIFV; ACMFQLLIFVA; CMFQLLIFVAC;
MFQLLIFVACL; FQLLIFVACLL; QLLIFVACLLT; LLIFVACLLTA; LIFVACLLTAL;
IFVACLLTALE; FVACLLTALEH; VACLLTALEHN; ACLLTALEHNS; CLLTALEHNSG;
LLTALEHNSGE; LTALEHNSGEA; TALEHNSGEAL; ALEHNSGEALQ; LEHNSGEALQD;
EHNSGEALQDI; HNSGEALQDIL; NSGEALQDILR; SGEALQDILRS; GEALQDILRSA;
TGEPREWMGSL; GEPREWMGSLC; EPREWMGSLCM; PREWMGSLCMV; REWMGSLCMVW;
EWMGSLCMVWN; WMGSLCMVWNP; MGSLCMVWNPR; KRLGCLMAQKD; RLGCLMAQKDF;
LGCLMAQKDFQ; GCLMAQKDFQG; CLMAQKDFQGT; LMAQKDFQGTQ; MAQKDFQGTQI;
DILTNRDNCKP; ILTNRDNCKPK; LTNRDNCKPKC; TNRDNCKPKCF; NRDNCKPKCFK;
RDNCKPKCFKQ; DNCKPKCFKQV; NCKPKCFKQVL; CKPKCFKQVLL; KPKCFKQVLLL;
PKCFKQVLLLY; KCFKQVLLLYI; CFKQVLLLYIY; FKQVLLLYIYI; MLLLYKPLLSL;
LLLYKPLLSLC; LLYKPLLSLCY; LYKPLLSLCYF; YKPLLSLCYFG; KPLLSLCYFGG;
PLLSLCYFGGG; LLSLCYFGGGV; LSLCYFGGGVL; SLCYFGGGVLG; LCYFGGGVLGL;
CYFGGGVLGLL; YFGGGVLGLLK; FGGGVLGLLKH; LWGSDLWESSA; WGSDLWESSAG;
GSDLWESSAGA; SDLWESSAGAE; DLWESSAGAEV; LWESSAGAEVS; WESSAGAEVSE;
ESSAGAEVSET; SSAGAEVSETW; SAGAEVSETWE; AGAEVSETWEE; GAEVSETWEEH;
AEVSETWEEHC; EVSETWEEHCD; VSETWEEHCDW; SETWEEHCDWD; ETWEEHCDWDS;
TWEEHCDWDSV; WEEHCDWDSVL; EEHCDWDSVLD; EHCDWDSVLDP; HCDWDSVLDPC;
CDWDSVLDPCP; DWDSVLDPCPE; WDSVLDPCPES; DSVLDPCPESS; SVLDPCPESSV;
VLDPCPESSVS; LDPCPESSVSE; DPCPESSVSES; PCPESSVSESS; CPESSVSESSS;
PESSVSESSSL; ESSVSESSSLV; SSVSESSSLVI; SVSESSSLVIS; VSESSSLVISR;
SESSSLVISRI; ESSSLVISRIH; SSSLVISRIHF; SSLVISRIHFP; SLVISRIHFPM;
LVISRIHFPMH; VISRIHFPMHI; ISRIHFPMHIL; SRIHFPMHILY; RIHFPMHILYF;
IHFPMHILYFI; HFPMHILYFIL; FPMHILYFILE; PMHILYFILEK; MHILYFILEKV;
HILYFILEKVY; ILYFILEKVYI; LYFILEKVYIL; YFILEKVYILI; FILEKVYILIS;
ILEKVYILISE; LEKVYILISES; EKVYILISESS; KVYILISESSL; VYILISESSLS;
YILISESSLSF; ILISESSLSFH; LISESSLSFHS; ISESSLSFHST; SESSLSFHSTI;
ESSLSFHSTIL; SSLSFHSTILD; SLSFHSTILDC; LSFHSTILDCI; SFHSTILDCIS;
FHSTILDCISV; HSTILDCISVA; STILDCISVAK; TILDCISVAKS; ILDCISVAKSA;
LDCISVAKSAT; DCISVAKSATG; CISVAKSATGL; ISVAKSATGLN; SVAKSATGLNQ;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

VAKSATGLNQI; AKSATGLNQIS; KSATGLNQISS; SATGLNQISSS; ATGLNQISSSN;
TGLNQISSSNK; GLNQISSSNKV; LNQISSSNKVI; NQISSSNKVIP; QISSSNKVIPL;
ISSSNKVIPLC; SSSNKVIPLCK; SSNKVIPLCKI; SNKVIPLCKIL; NKVIPLCKILF;
KVIPLCKILFS; VIPLCKILFSS; IPLCKILFSSK; PLCKILFSSKN; LCKILFSSKNS;
CKILFSSKNSE; KILFSSKNSEF; ILFSSKNSEFC; LFSSKNSEFCK; FSSKNSEFCKD;
SSKNSEFCKDF; SKNSEFCKDFL; KNSEFCKDFLK; NSEFCKDFLKY; SEFCKDFLKYI;
EFCKDFLKYIL; FCKDFLKYILG; CKDFLKYILGL; KDFLKYILGLK; DFLKYILGLKS;
FLKYILGLKSI; LKYILGLKSIC; KYILGLKSICL; YILGLKSICLT; ILGLKSICLTN;
LGLKSICLTNL; GLKSICLTNLA; LKSICLTNLAC; KSICLTNLACR; SICLTNLACRV;
ICLTNLACRVL; CLTNLACRVLG; LTNLACRVLGT; TNLACRVLGTG; NLACRVLGTGY;
LACRVLGTGYS; ACRVLGTGYSF; CRVLGTGYSFI; RVLGTGYSFIV; VLGTGYSFIVT;
LGTGYSFIVTK; GTGYSFIVTKP; TGYSFIVTKPG; GYSFIVTKPGG; YSFIVTKPGGN;
SFIVTKPGGNI; FIVTKPGGNIW; IVTKPGGNIWV; VTKPGGNIWVL; TKPGGNIWVLL;
KPGGNIWVLLF; PGGNIWVLLFK; GGNIWVLLFKC; GNIWVLLFKCF; NIWVLLFKCFF;
IWVLLFKCFFS; WVLLFKCFFSK; VLLFKCFFSKF; LLFKCFFSKFT; LFKCFFSKFTL;
FKCFFSKFTLT; KCFFSKFTLTL; CFFSKFTLTLP; FFSKFTLTLPS; FSKFTLTLPSK;
SLKLSKLFIPC; LKLSKLFIPCP; KLSKLFIPCPE; LSKLFIPCPEG; SKLFIPCPEGK;
KLFIPCPEGKS; LFIPCPEGKSF; FIPCPEGKSFD; IPCPEGKSFDS; PCPEGKSFDSA;
CPEGKSFDSAP; PEGKSFDSAPV; EGKSFDSAPVP; GKSFDSAPVPF; KSFDSAPVPFT;
SFDSAPVPFTS; FDSAPVPFTSS; DSAPVPFTSSK; SAPVPFTSSKT; APVPFTSSKTT;
PVPFTSSKTTM; VPFTSSKTTMY; SIATPSSKVSL; IATPSSKVSLS; ATPSSKVSLSM;
TPSSKVSLSMG; PSSKVSLSMGR; SSKVSLSMGRF; SKVSLSMGRFT; KVSLSMGRFTF;
VSLSMGRFTFK; SLSMGRFTFKA; LSMGRFTFKAL; SMGRFTFKALP; MGRFTFKALPP;
GRFTFKALPPH; RFTFKALPPHK; FTFKALPPHKS; TFKALPPHKSN; FKALPPHKSNN;
KALPPHKSNNP; ALPPHKSNNPA; LPPHKSNNPAA; PPHKSNNPAAS; PHKSNNPAASV;
HKSNNPAASVV; KSNNPAASVVF; SNNPAASVVFP; NNPAASVVFPL; NPAASVVFPLS;
PAASVVFPLSM; AASVVFPLSMG; ASVVFPLSMGP; SVVFPLSMGPL; VVFPLSMGPLN;
VFPLSMGPLNN; FPLSMGPLNNQ; PLSMGPLNNQY; LSMGPLNNQYL; SMGPLNNQYLL;
MGPLNNQYLLL; GPLNNQYLLLG; PLNNQYLLLGT; LNNQYLLLGTL; NNQYLLLGTLK;
NQYLLLGTLKT; QYLLLGTLKTI; YLLLGTLKTIQ; LLLGTLKTIQC; LLGTLKTIQCK;
LGTLKTIQCKK; GTLKTIQCKKS; TLKTIQCKKSN; LKTIQCKKSNI; KTIQCKKSNIT;
TIQCKKSNITE; IQCKKSNITES; QCKKSNITESI; CKKSNITESIL; KKSNITESILG;
KSNITESILGS; SNITESILGSK; NITESILGSKQ; ITESILGSKQC; TESILGSKQCS;
ESILGSKQCSQ; SILGSKQCSQA; ILGSKQCSQAT; LGSKQCSQATP; GSKQCSQATPA;
SKQCSQATPAI; KQCSQATPAIY; QCSQATPAIYC; CSQATPAIYCS; SQATPAIYCSS;
QATPAIYCSST; ATPAIYCSSTA; TPAIYCSSTAF; PAIYCSSTAFP; APNIKSILSNI;
LNLSVSISSLV; NLSVSISSLVI; RVSTLFLAKTV; VSTLFLAKTVS; STLFLAKTVST;
TLFLAKTVSTA; LFLAKTVSTAC; FLLSAKIIAFA; LLSAKIIAFAK; LSAKIIAFAKC;
SAKIIAFAKCF; AKIIAFAKCFS; NSKYIPNNKNT; SKYIPNNKNTS; KYIPNNKNTSS;
YIPNNKNTSSH; IPNNKNTSSHF; PNNKNTSSHFV; NNKNTSSHFVS; NKNTSSHFVST;
KNTSSHFVSTA; NTSSHFVSTAY; TSSHFVSTAYS; SSHFVSTAYSV; SHFVSTAYSVI;
HFVSTAYSVIN; FVSTAYSVINF; VSTAYSVINFQ; STAYSVINFQD; TAYSVINFQDT;
AYSVINFQDTC; YSVINFQDTCF; SVINFQDTCFV; VINFQDTCFVS; INFQDTCFVSS;
NFQDTCFVSSG; FQDTCFVSSGS; QDTCFVSSGSS; DTCFVSSGSSG; TCFVSSGSSGL;
CFVSSGSSGLK; FVSSGSSGLKS; VSSGSSGLKSC; SSGSSGLKSCS; SGSSGLKSCSF;
GSSGLKSCSFK; SSGLKSCSFKP; SGLKSCSFKPP; MLSSIVWYGSL; LSSIVWYGSLV;
SSIVWYGSLVK; SIVWYGSLVKA; IVWYGSLVKAL; VWYGSLVKALY; WYGSLVKALYS;
YGSLVKALYSK; GSLVKALYSKY; SLVKALYSKYS; LVKALYSKYSL; VKALYSKYSLL;
KALYSKYSLLT; ALYSKYSLLTP; LYSKYSLLTPL; YSKYSLLTPLQ; SKYSLLTPLQI;
KYSLLTPLQIK; YSLLTPLQIKK; SLLTPLQIKKL; LLTPLQIKKLK; LTPLQIKKLKV;
TPLQIKKLKVH; PLQIKKLKVHS; LQIKKLKVHSF; QKLLIAETLCL; KLLIAETLCLC;
LLIAETLCLCG; LIAETLCLCGV; IAETLCLCGVK; AETLCLCGVKK; ETLCLCGVKKN;
TLCLCGVKKNI; LCLCGVKKNII; CLCGVKKNIIL; LCGVKKNIILC; CGVKKNIILCP;
GVKKNIILCPA; VKKNIILCPAH; KKNIILCPAHM; KNIILCPAHMC; NIILCPAHMCL;
IILCPAHMCLL; ILCPAHMCLLI; LCPAHMCLLIK; CPAHMCLLIKV; PAHMCLLIKVT;
AHMCLLIKVTE; HMCLLIKVTEY; MCLLIKVTEYF; CLLIKVTEYFS; LLIKVTEYFSI;
LIKVTEYFSIS; IKVTEYFSISF; KVTEYFSISFL; VTEYFSISFLY; TEYFSISFLYR;
EYFSISFLYRI; AFSLVVYTAKQ; FSLVVYTAKQA; SLVVYTAKQAR; LVVYTAKQARV;
VVYTAKQARVL; VYTAKQARVLL; YTAKQARVLLL; TAKQARVLLLN; AKQARVLLLNT;
KQARVLLLNTA; LRNWCRSEGKS; RNWCRSEGKSL; NWCRSEGKSLG; WCRSEGKSLGS;
CRSEGKSLGSS; RSEGKSLGSST; SEGKSLGSSTF; EGKSLGSSTFL; GKSLGSSTFLF;
KSLGSSTFLFF; SLGSSTFLFFL; LGSSTFLFFLG; GSSTFLFFLGG; SSTFLFFLGGV;
STFLFFLGGVE; TFLFFLGGVEC; ESAVASSSLAN; SAVASSSLANI; AVASSSLANIS;
VASSSLANISS; ASSSLANISSW; SSSLANISSWQ; SSLANISSWQN; SLANISSWQNK;
LANISSWQNKS; ANISSWQNKSS; NISSWQNKSSS; ISSWQNKSSSH; SSWQNKSSSHF;
SWQNKSSSHFS; WQNKSSSHFSL; QNKSSSHFSLK; NKSSSHFSLKE; KSSSHFSLKEL;
SSSHFSLKELH; SSHFSLKELHQ; SHFSLKELHQD; HFSLKELHQDS; FSLKELHQDSH;
SLKELHQDSHS; LKELHQDSHSS; KELHQDSHSSV; ELHQDSHSSVP; VGTYKKNNYLG;
GTYKKNNYLGP; TYKKNNYLGPF; YKKNNYLGPFN; KKNNYLGPFNI; KNNYLGPFNIL;
NNYLGPFNILL; NYLGPFNILLF; YLGPFNILLFI; REFLQLFGPTI; EFLQLFGPTIA;
FLQLFGPTIAE; LQLFGPTIAEF; QLFGPTIAEFL; LFGPTIAEFLQ; FGPTIAEFLQL;
GPTIAEFLQLG; PTIAEFLQLGL; TIAEFLQLGLS; IAEFLQLGLSQ; AEFLQLGLSQT;
EFLQLGLSQTT; FLQLGLSQTTV; SSQCSSNLSKP; SQCSSNLSKPR; QCSSNLSKPRA;
CSSNLSKPRAL; SSNLSKPRALF; SNLSKPRALFL; NLSKPRALFLK; LSKPRALFLKI;
SKPRALFLKIF; KPRALFLKIFY; PRALFLKIFYL; RALFLKIFYLN; ALFLKIFYLNA;
LFLKIFYLNAL; FLKIFYLNALI; ADIACKGSAQK; DIACKGSAQKA; IACKGSAQKAF;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

ACKGSAQKAFW; CKGSAQKAFWN; KGSAQKAFWNK; AIPCSTGYLGK; IPCSTGYLGKE;
PCSTGYLGKEE; CSTGYLGKEEN; STGYLGKEENQ; TGYLGKEENQH; GYLGKEENQHK;
YLGKEENQHKP; LGKEENQHKPL; GKEENQHKPLS; KEENQHKPLSY; EENQHKPLSYS;
ENQHKPLSYSR; NQHKPLSYSRF; QHKPLSYSRFQ; HKPLSYSRFQN; KPLSYSRFQNQ;
PLSYSRFQNQA; LSYSRFQNQAD; SYSRFQNQADE; YSRFQNQADEL; SRFQNQADELP;
RFQNQADELPL; FQNQADELPLH; QNQADELPLHP; NQADELPLHPA; QADELPLHPAP;
ADELPLHPAPF; DELPLHPAPFF; ELPLHPAPFFY; LPLHPAPFFYT; PLHPAPFFYTK;
LHPAPFFYTKY; HPAPFFYTKYS; PAPFFYTKYSF; APFFYTKYSFS; PFFYTKYSFSS;
FFYTKYSFSSF; FYTKYSFSSFY; YTKYSFSSFYP; TKYSFSSFYPR; KYSFSSFYPRR;
YSFSSFYPRRP; SFSSFYPRRPL; FSSFYPRRPLC; SSFYPRRPLCQ; SFYPRRPLCQG;
FYPRRPLCQGE; YPRRPLCQGEI; PRRPLCQGEIP; RRPLCQGEIPY; RPLCQGEIPYT;
PLCQGEIPYTS; LCQGEIPYTSL; CQGEIPYTSLN; QGEIPYTSLNK; GEIPYTSLNKL;
EIPYTSLNKLF; IPYTSLNKLFS; PYTSLNKLFSL; YTSLNKLFSLR; TSLNKLFSLRE;
SLNKLFSLRED; LNKLFSLREDF; NKLFSLREDFP; KLFSLREDFPR; LFSLREDFPRQ;
FSLREDFPRQL; SLREDFPRQLF; LREDFPRQLFQ; REDFPRQLFQG; EDFPRQLFQGL;
DFPRQLFQGLK; FPRQLFQGLKG; PRQLFQGLKGP

BK reading frame 3

8 mers:

LQKLQKNR; QKLQKNRD; KLQKNRDF; LQKNRDFP; QKNRDFPK; ASEKASTP; SEKASTPL;
EKASTPLL; KASTPLLL; ASTPLLLE; STPLLLER; TPLLLERK; PLLLERKG; LLLERKGG;
LLERKGGR; LERKGGGR; ERKGGGRG; RKGGGRGG; KGGGRGGL; GGGRGGLG; GGRGGLGL;
GRGGLGLL; RGGLGLLY; GGLGLLYI; GLGLLYII; LGLLYIIK; GLLYIIKK; LLYIIKKK;
LYIIKKKA; YIIKKKAT; IIKKKATG; IKKKATGR; KKKATGRS; KKATGRSC; KATGRSCL;
ATGRSCLP; TGRSCLPM; GRSCLPME; RSCLPMEC; SCLPMECS; CLPMECSQ; LPMECSQT;
PMECSQTM; MECSQTMT; ECSQTMTS; CSQTMTSG; SQTMTSGR; QTMTSGRK; TMTSGRKV;
MTSGRKVH; TSGRKVHD; SGRKVHDS; GRKVHDSQ; RKVHDSQG; KVHDSQGN; VHDSQGNA;
HDSQGNAA; DSQGNAAK; SQGNAAKP; PQEGKCMT; QEGKCMTH; EGKCMTHR; GKCMTHRE;
KCMTHREE; CMTHREEL; MTHREELL; THREELLT; HREELLTH; REELLTHG; EELLTHGM;
ELLTHGMQ; LLTHGMQP; LTHGMQPN; THGMQPNH; HGMQPNHD; GMQPNHDL; MQPNHDLR;
QPNHDLRK; PNHDLRKE; NHDLRKES; HDLRKESA; DLRKESAL; LRKESALG; RKESALGI;
KESALGIL; ESALGILA; SALGILAL; ALGILALS; LGILALSP; GILALSPV; ILALSPVK; LALSPVKL;
ALSPVKLD; LSPVKLDK; SPVKLDKG; PVKLDKGH; VKLDKGHG; KLDKGHGS; LDKGHGSA;
DKGHGSAP; KGHGSAPA; GHGSAPAV; HGSAPAVT; GSAPAVTT; SAPAVTTS; APAVTTSF;
PAVTTSFS; AVTTSFSE; VTTSFSES; TTSFSESW; NLDWNKKK; LDWNKKKS; DWNKKKSS;
WNKKKSSE; NKKKSSED; KKKSSEDF; KKSSEDFY; KSSEDFYF; SSEDFYFY; SEDFYFYF;
EDFYFYFR; DFYFYFRA; FYFYFRAF; YFYFRAFA; FYFRAFAG; YFRAFAGI; FRAFAGIL;
RQCRREKQ; QCRREKQK; CRREKQKY; RREKQKYH; REKQKYHC; EKQKYHCF; KQKYHCFT;
QKYHCFTC; KYHCFTCC; YHCFTCCK; HCFTCCKR; CFTCCKRL; FTCCKRLC; TCCKRLCK;
CCKRLCKR; CKRLCKRL; KRLCKRLL; RLCKRLLG; LCKRLLGK; SLFFCISR; LFFCISRF;
FFCISRFM; FCISRFMG; CISRFMGA; ISRFMGAA; SRFMGAAL; RFMGAALA; FMGAALAL;
MGAALALL; GAALALLG; AALALLGD; ALALLGDL; LALLGDLV; ALLGDLVA; LLGDLVAS;
LGDLVASV; GDLVASVS; DLVASVSE; LVASVSEA; VASVSEAA; ASVSEAAA; SVSEAAAA;
VSEAAAAT; SEAAAATG; EAAAATGF; AAAATGFS; AAATGFSV; AATGFSVA; ATGFSVAE;
TGFSVAEI; GFSVAEIA; FSVAEIAA; SVAEIAAG; VAEIAAGE; AEIAAGEA; EIAAGEAA;
IAAGEAAA; AAGEAAAA; AGEAAAAI; GEAAAAIE; EAAAAIEV; AAAAIEVQ; AAAIEVQI;
AAIEVQIA; AIEVQIAS; IEVQIASL; EVQIASLA; VQIASLAT; QIASLATV; IASLATVE;
ASLATVEG; SLATVEGI; LATVEGIT; ATVEGITS; TVEGITST; VEGITSTS; EGITSTSE;
GITSTSEA; ITSTSEAI; TSTSEAIA; STSEAIAA; TSEAIAAI; SEAIAAIG; EAIAAIGL;
AIAAIGLT; IAAIGLTP; AAIGLTPQ; AIGLTPQT; IGLTPQTY; GLTPQTYA; LTPQTYAV;
TPQTYAVI; PQTYAVIA; QTYAVIAG; TYAVIAGA; YAVIAGAP; AVIAGAPG; VIAGAPGA;
IAGAPGAI; AGAPGAIA; GAPGAIAG; APGAIAGF; PGAIAGFA; GAIAGFAA; AIAGFAAL;
IAGFAALI; AGFAALIQ; GFAALIQT; FAALIQTV; AALIQTVS; ALIQTVSG; LIQTVSGI;
IQTVSGIS; QTVSGISS; TVSGISSL; VSGISSLA; SGISSLAQ; GISSLAQV; ISSLAQVG;
SSLAQVGY; SLAQVGYK; LAQVGYKF; AQVGYKFF; QVGYKFFD; VGYKFFDD; GYKFFDDW;
YKFFDDWD; KFFDDWDH; FFDDWDHK; FDDWDHKV; DDWDHKVS; DWDHKVST; WDHKVSTV;
DHKVSTVG; HKVSTVGL; KVSTVGLY; VSTVGLYQ; STVGLYQQ; TVGLYQQS; VGLYQQSG;
GLYQQSGM; LYQQSGMA; YQQSGMAL; QQSGMALE; QSGMALEL; SGMALELF; GMALELFN;
MALELFNP; ALELFNPD; LELFNPDE; ELFNPDEY; LFNPDEYY; FNPDEYYD; NPDEYYDI;
PDEYYDIL; DEYYDILF; EYYDILFP; YYDILFPG; YDILFPGV; DILFPGVN; ILFPGVNT;
LFPGVNTF; FPGVNTFV; PGVNTFVN; GVNTFVNN; VNTFVNNI; NTFVNNIQ; TFVNNIQY;
FVNNIQYL; VNNIQYLD; NNIQYLDP; NIQYLDPR; IQYLDPRH; QYLDPRHW; YLDPRHWG;
LDPRHWGP; DPRHWGPS; PRHWGPSL; RHWGPSLF; HWGPSLFA; WGPSLFAT; GPSLFATI;
PSLFATIS; SLFATISQ; LFATISQA; FATISQAL; ATISQALW; TISQALWH; ISQALWHV;
SQALWHVI; QALWHVIR; ALWHVIRD; LWHVIRDD; WHVIRDDI; HVIRDDIP; VIRDDIPS;
IRDDIPSI; RDDIPSIT; DDIPSITS; DIPSITSQ; IPSITSQE; PSITSQEL; SITSQELQ;
ITSQELQR; TSQELQRR; SQELQRRT; QELQRRTE; ELQRRTER; LQRRTERF; QRRTERFF;
RRTERFFR; RTERFFRD; TERFFRDS; ERFFRDSL; RFFRDSLA; FFRDSLAR; FRDSLARF;
RDSLARFL; DSLARFLE; SLARFLEE; LARFLEET; ARFLEETT; RFLEETTW; FLEETTWT;
LEETTWTI; EETTWTIV; ETTWTIVN; TTWTIVNA; TWTIVNAP; WTIVNAPI; TIVNAPIN;
IVNAPINF; VNAPINFY; NAPINFYN; APINFYNY; PINFYNYI; INFYNYIQ; NFYNYIQQ;
FYNYIQQY; YNYIQQYY; NYIQQYYS; YIQQYYSD; IQQYYSDL; QQYYSDLS; QYYSDLSP;
YYSDLSPI; YSDLSPIR; SDLSPIRP; DLSPIRPS; LSPIRPSM; SPIRPSMV; PIRPSMVR;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

IRPSMVRQ; RPSMVRQV; PSMVRQVA; SMVRQVAE; MVRQVAER; VRQVAERE; RQVAEREG; QVAEREGT; VAEREGTR; AEREGTRV; EREGTRVH; REGTRVHF; EGTRVHFG; GTRVHFGH; TRVHFGHT; RVHFGHTY; VHFGHTYS; HFGHTYSI; FGHTYSID; GHTYSIDD; HTYSIDDA; TYSIDDAD; YSIDDADS; SIDDADSI; IDDADSIE; DDADSIEE; DADSIEEV; ADSIEEVT; DSIEEVTQ; SIEEVTQR; IEEVTQRM; EEVTQRMD; EVTQRMDL; VTQRMDLR; TQRMDLRN; QRMDLRNQ; RMDLRNQQ; MDLRNQQS; DLRNQQSV; LRNQQSVH; RNQQSVHS; NQQSVHSG; QQSVHSGE; QSVHSGEF; SVHSGEFI; VHSGEFIE; HSGEFIEK; SGEFIEKT; GEFIEKTI; EFIEKTIA; FIEKTIAP; IEKTIAPG; EKTIAPGG; KTIAPGGA; TIAPGGAN; IAPGGANQ; APGGANQR; PGGANQRT; GGANQRTA; GANQRTAP; ANQRTAPQ; NQRTAPQW; QRTAPQWM; RTAPQWML; TAPQWMLP; APQWMLPL; PQWMLPLL; QWMLPLLL; WMLPLLLG; MLPLLLGL; LPLLLGLY; PLLLGLYG; LLLGLYGT; LLGLYGTV; LGLYGTVT; GLYGTVTP; LYGTVTPA; YGTVTPAL; GTVTPALE; TVTPALEA; VTPALEAY; TPALEAYE; PALEAYED; ALEAYEDG; LEAYEDGP; EAYEDGPN; AYEDGPNQ; YEDGPNQK; EDGPNQKK; DGPNQKKR; GPNQKKRR; PNQKKRRV; NQKKRRVS; QKKRRVSR; KKRRVSRG; KRRVSRGS; RRVSRGSS; RVSRGSSQ; VSRGSSQK; SRGSSQKA; RGSSQKAK; GSSQKAKG; SSQKAKGT; SQKAKGTR; QKAKGTRA; KAKGTRAS; AKGTRASA; KGTRASAK; GTRASAKT; TRASAKTT; RASAKTTN; ASAKTTNK; SAKTTNKR; AKTTNKRR; KTTNKRRS; TTNKRRSR; TNKRRSRS; NKRRSRSS; KRRSRSSR; RRSRSSRS; NWGRCYYR; WGRCYYRG; GRCYYRGR; RCYYRGRM; CYYRGRML; YYRGRMLP; YRGRMLPK; RGRMLPKP; GRMLPKPR; RMLPKPRN; MLPKPRNG; LPKPRNGG; PKPRNGGS; KPRNGGSR; PREKNASL; REKNASLL; EKNASLLQ; KNASLLQH; NASLLQHS; ASLLQHSK; SLLQHSKN; LLQHSKNS; LQHSKNSP; QHSKNSPP; HSKNSPPQ; SKNSPPQF; KNSPPQFK; GPNLWKST; PNLWKSTD; NLWKSTDV; LWKSTDVG; WKSTDVGG; KSTDVGGC; STDVGGCN; TDVGGCNC; DVGGCNCT; VGGCNCTN; GGCNCTNR; GCNCTNRG; CNCTNRGY; NCTNRGYW; CTNRGYWN; TNRGYWNN; PSCRVTKS; SCRVTKSA; AWWRKTYS; WWRKTYSR; WRKTYSRQ; FPLLCCRW; PLLCCRWR; LLCCRWRT; LCCRWRTL; CCRWRTLG; CRWRTLGN; RWRTLGNA; WRTLGNAG; RTLGNAGS; TLGNAGSA; LGNAGSAN; GNAGSANE; NAGSANEL; AGSANELQ; GSANELQV; SANELQVK; ANELQVKV; NELQVKVP; KPNSPVPG; PNSPVPGN; NSPVPGNE; SPVPGNEY; GLFGQKQC; LFGQKQCL; FGQKQCLS; GQKQCLSS; VFWDFHRR; FWDFHRRG; WDFHRRGK; DFHRRGKC; FHRRGKCS; HRRGKCSP; RRGKCSPS; RGKCSPST; GKCSPSTS; KCSPSTSC; CSPSTSCD; SPSTSCDQ; PSTSCDQH; STSCDQHS; TSCDQHSY; SCDQHSYH; CDQHSYHS; DQHSYHSV; QHSYHSVA; HSYHSVAR; QLWNTTVE; LWNTTVER; WNTTVERP; NTTVERPC; TTVERPCK; TVERPCKI; VERPCKIF; DPPEKKIC; PPEKKICK; PEKKICKE; EKKICKES; KKICKESL; KICKESLP; ICKESLPN; CKESLPNF; KESLPNFL; ESLPNFLF; SLPNFLFA; LPNFLFAK; PYKQENPE; YKQENPES; KQENPESG; QENPESGW; ENPESGWA; NPESGWAA; PESGWAAY; ESGWAAYV; SGWAAYVW; GWAAYVWY; WAAYVWYG; AAYVWYGI; AYVWYGIP; YVWYGIPG; VWYGIPGR; WYGIPGRR; YGIPGRRG; WHRKTSRG; HRKTSRGP; RKTSRGPR; KTSRGPRY; TSRGPRYD; SRGPRYDK; RGPRYDKI; GPRYDKIY; QTGTIANQ; TGTIANQN; GTIANQNA; TIANQNAL; IANQNALN; ANQNALNR; NQNALNRC; QNALNRCF; NALNRCFY; ALNRCFYC; LNRCFYCT; NRCFYCTY; RCFYCTYT; CFYCTYTF; FYCTYTFN; YCTYTFNK; CTYTFNKC; TYTFNKCC; YTFNKCCF; TFNKCCFC; FNKCCFCI; NKCCFCIS; KCCFCISH; CCFCISHF; ACVILGVV; CVILGVVF; NTESLYTN; TESLYTNA; ESLYTNAT; SLYTNATL; LYTNATLD; YTNATLDY; TNATLDYG; NATLDYGG; ATLDYGGL; TLDYGGLT; LDYGGLTF; DYGGLTFG; YGGLTFGN; GGLTFGNL; GLTFGNLQ; LTFGNLQQ; TFGNLQQG; FGNLQQGL; GNLQQGLK; NLQQGLKY; LQQGLKYL; QQGLKYLR; QGLKYLRL; GLKYLRLG; LKYLRLGK; KYLRLGKS; YLRLGKSI; LRLGKSIV; RLGKSIVI; LGKSIVIG; GKSIVIGI; KSIVIGIQ; SIVIGIQC; IVIGIQCL; VIGIQCLI; IGIQCLIH; GIQCLIHV; IQCLIHVQ; QCLIHVQS; CLIHVQSL; LIHVQSLQ; IHVQSLQF; HVQSLQFL; VQSLQFLN; QSLQFLNP; SLQFLNPL; LQFLNPLL; QFLNPLLL; YQEYISPC; QEYISPCI; EYISPCIY; YISPCIYY; ISPCIYYI; SPCIYYIS; PCIYYISS; CIYYISSL; IYYISSLK; YYISSLKK; YISSLKKY; ISSLKKYT; SSLKKYTY; SLKKYTYL; LKKYTYLS; KKYTYLSQ; KYTYLSQN; YTYLSQNP; TYLSQNPA; YLSQNPAF; LSQNPAFP; SQNPAFPS; QNPAFPSI; NPAFPSIQ; PAFPSIQQ; AFPSIQQF; IVYQLQNQ; VYQLQNQL; YQLQNQLQ; QLQNQLQA; TKLAVATR; KLAVATRS; LAVATRSF; AVATRSFH; VATRSFHF; ATRSFHFV; TRSFHFVK; RSFHFVKF; SFHFVKFF; FHFVKFFF; HFVKFFFQ; FVKFFFQV; VKFFFQVR; KFFFQVRT; FFFQVRTL; FFQVRTLS; FQVRTLSF; QVRTLSFV; VRTLSFVR; RTLSFVRI; TLSFVRIF; LSFVRIFL; SFVRIFLN; FVRIFLNI; VRIFLNIF; RIFLNIFW; IFLNIFWA; PSLVEIFG; SLVEIFGF; LVEIFGFF; VEIFGFFC; EIFGFFCL; IFGFFCLN; FGFFCLNV; GFFCLNVS; FFCLNVSF; FCLNVSFL; CLNVSFLN; LNVSFLNL; NVSFLNLP; HFHLNNLS; FHLNNLSN; HLNNLSNC; LNNLSNCL; NNLSNCLN; NLSNCLNC; LSNCLNCL; SNCLNCLF; NCLNCLFH; CLNCLFHV; LNCLFHVL; NCLFHVLK; CLFHVLKA; LFHVLKAN; FHVLKANP; HVLKANPL; VLKANPLI; LKANPLIQ; KANPLIQL; ANPLIQLL; NPLIQLLS; PLIQLLSL; LIQLLSLL; IQLLSLLH; QLLSLLHL; LLSLLHLQ; LSLLHLQK; SLLHLQKQ; LLHLQKQP; LHLQKQPC; HLQKQPCT; LQKQPCTD; QKQPCTDL; LHLAQRLA; HLAQRLAF; LAQRLAFP; AQRLAFPW; QRLAFPWV; RLAFPWVG; LAFPWVGL; AFPWVGLH; FPWVGLHL; PWVGLHLR; WVGLHLRL; VGLHLRLY; GLHLRLYH; LHLRLYHH; HLRLYHHT; LRLYHHTN; RLYHHTNL; LYHHTNLI; YHHTNLIT; HHTNLITL; HTNLITLQ; TNLITLQL; NLITLQLV; LITLQLVL; ITLQLVLF; TLQLVLFF; LQLVLFFH; QLVLFFHY; LVLFFHYQ; VLFFHYQW; LFFHYQWD; FFHYQWDK; KQYSAKNQ; QYSAKNQI; YSAKNQIL; SAKNQILQ; AKNQILQN; KNQILQNP; NQILQNPF; VANSAAKQ; ANSAAKQH; NSAAKQHL; SAAKQHLP; AAKQHLPY; AKQHLPYI; KQHLPYIV; QHLPYIVL; HLPYIVLV; LPYIVLVQ; PYIVLVQH; YIVLVQHF; IVLVQHFH; VLVQHFHE; LVQHFHEL; VQHFHELQ; QHFHELQI; HFHELQIL; FHELQILN; HELQILNP; ELQILNPF; LQILNPFY; QILNPFYL; ILNPFYLI; LNPFYLIY; NPFYLIYD; IFLLAFLP; FLLAFLPW; LLAFLPWS; LAFLPWSY; AFLPWSYE; FLPWSYEG; LPWSYEGY; PWSYEGYL; WSYEGYLL; SYEGYLLF; YEGYLLFF; LKLYLLLA; KLYLLLAD; LYLLLADK; YLLLADKY; LLLADKYF; LLADKYFF; LADKYFFD; ADKYFFDF; DKYFFDFY; KYFFDFYF; YFFDFYFL; FFDFYFLQ; FDFYFLQK; HLQSAFHD; LQSAFHDT; SDKAGLFS; DKAGLFSD; KAGLFSDT; AGLFSDTF; GLFSDTFY; LFSDTFYT;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

FSDTFYTP; SDTFYTPL; DTFYTPLH; TFYTPLHC; FYTPLHCI; YTPLHCIE; TPLHCIEI; PLHCIEIL; LHCIEILN; HCIEILNT; CIEILNTY; IEILNTYL; EILNTYLI; ILNTYLII; LNTYLIIK; NTYLIIKT; TYLIIKTH; YLIIKTHP; LIIKTHPH; IIKTHPHT; IKTHPHTL; KTHPHTLS; THPHTLSL; HPHTLSLL; PHTLSLLH; HTLSLLHT; TLSLLHTQ; LSLLHTQP (wait)

FSDTFYTP; SDTFYTPL; DTFYTPLH; TFYTPLHC; FYTPLHCI; YTPLHCIE; TPLHCIEI;
PLHCIEIL; LHCIEILN; HCIEILNT; CIEILNTY; IEILNTYL; EILNTYLI; ILNTYLII;
LNTYLIIK; NTYLIIKT; TYLIIKTH; YLIIKTHP; LIIKTHPH; IIKTHPHT; IKTHPHTL;
KTHPHTLS; THPHTLSL; HPHTLSLL; PHTLSLLH; HTLSLLHT; TLSLLHTQ; LISKTPAL;
ISKTPALF; SKTPALFL; KTPALFLQ; TPALFLQA; PALFLQAL; ALFLQALL; LFLQALLG;
NHAPLSPL; HAPLSPLE; APLSPLEC; PLSPLECF; LSPLECFL; SPLECFLL; LRHYIVSI;
RHYIVSIP; HYIVSIPY; RYTAFDRN; YTAFDRNY; LQKLYVYV; QKLYVYVE; KLYVYVEL;
LYVYVELK; YVYVELKR; VYVELKRI; YYAQHTCV; YAQHTCVY; VFYTEFEL; FYTEFELF;
YTEFELFL; YTQQSRQG; TQQSRQGF; QQSRQGFY; QSRQGFYY; ETGVDQRE; TGVDQRES;
GVDQRESL; GLLPFFFF; LLPFFFFW; LPFFFFWV; PFFFFWVV; FFFFWVVL; FFFWVVLS;
FFWVVLSV; FWVVLSVE; WVVLSVEN; VVLSVENL; VLSVENLL; LSVENLLL; SVENLLLL;
VENLLLLL; ENLLLLLH; NLLLLLHH; LLLLLHHW; LLLLHHWQ; LLLHHWQT; LLHHWQTY;
LHHWQTYL; HHWQTYLH; HWQTYLHG; WQTYLHGK; QTYLHGKI; TYLHGKIN; YLHGKINL;
LHGKINLH; HGKINLHP; GKINLHPI; KINLHPIF; INLHPIFH; RNSTRTPT; NSTRTPTL;
STRTPTLL; TRTPTLLF; RTPTLLFH; TPTLLFHR; PTLLFHRL; TLLFHRLA; LLFHRLAP;
LFHRLAPI; FHRLAPIK; HRLAPIKK; RLAPIKKI; LAPIKKII; APIKKIIT; GLLIFYYL;
LLIFYYLS; LIFYYLSK; IFYYLSKY; FYYLSKYK; YYLSKYKL; YLSKYKLV; LSKYKLVT;
SKYKLVTL; KYKLVTLK; YKLVTLKL; ISEGSFSN; SEGSFSNY; EGSFSNYL; GSFSNYLD;
SFSNYLDP; FSNYLDPP; SNYLDPPL; NYLDPPLQ; YLDPPLQS; LDPPLQSF; DPPLQSFF;
PPLQSFFS; AKPLCEAV; KPLCEAVN; PLCEAVNA; LCEAVNAV; CEAVNAVA; EAVNAVAI;
AVNAVAIY; VNAVAIYP; NAVAIYPN; AVAIYPNQ; VAIYPNQG; AIYPNQGL; IYPNQGLF;
YPNQGLFS; HARAVHRR; ARAVHRRL; RAVHRRLF; AVHRRLFG; VHRRLFGT; HRRLFGTN;
RRLFGTNR; RLFGTNRP; LFGTNRPF; FGTNRPFL; GTNRPFLA; TNRPFLAV; NRPFLAVQ;
RPFLAVQG; PFLAVQGI; FLAVQGIW; LAVQGIWA; AVQGIWAK; VQGIWAKR; QGIWAKRK;
GIWAKRKI; IWAKRKIS; WAKRKIST; AKRKISTN; KRKISTNL; ATPGSKIR; TPGSKIRL;
PGSKIRLM; GSKIRLMS; SKIRLMSY; KIRLMSYL; IRLMSYLY; RLMSYLYI; LMSYLYIL;
MSYLYILL; SYLYILLH; YLYILLHF; LYILLHFF; YILLHFFI; ILLHFFIQ; LLHFFIQS;
LHFFIQSI; HFFIQSIH; FFIQSIHS; FIQSIHSL; IQSIHSLH; QSIHSLHF; SIHSLHFI;
IHSLHFIL; HSLHFILV; SLHFILVA; LHFILVAP; HFILVAPF; FILVAPFV; ILVAPFVR;
LVAPFVRV; VAPFVRVK; APFVRVKF; PFVRVKFL; FVRVKFLT; VRVKFLTL; RVKFLTLP;
GKISPGSS; KISPGSSF; ISPGSSFK; SPGSSFKA; KVHELHGF; VHELHGFF; HELHGFFP;
ELHGFFPV; LHGFFPVK; HGFFPVKN; GFFPVKNF; FFPVKNFI; FPVKNFIH 9 mers:

LQKLQKNRD; QKLQKNRDF; KLQKNRDFP; LQKNRDFPK; ASEKASTPL; SEKASTPLL;
EKASTPLLL; KASTPLLLE; ASTPLLLER; STPLLLERK; TPLLLERKG; PLLLERKGG;
LLLERKGGG; LLERKGGGR; LERKGGGRG; ERKGGGRGG; RKGGGRGGL; KGGGRGGLG;
GGGRGGLGL; GGRGGLGLL; GRGGLGLLY; RGGLGLLYI; GGLGLLYII; GLGLLYIIK;
LGLLYIIKK; GLLYIIKKK; LLYIIKKKA; LYIIKKKAT; YIIKKKATG; IIKKKATGR;
IKKKATGRS; KKKATGRSC; KKATGRSCL; KATGRSCLP; ATGRSCLPM; TGRSCLPME;
GRSCLPMEC; RSCLPMECS; SCLPMECSQ; CLPMECSQT; LPMECSQTM; PMECSQTMT;
MECSQTMTS; ECSQTMTSG; CSQTMTSGR; SQTMTSGRK; QTMTSGRKV; TMTSGRKVH;
MTSGRKVHD; TSGRKVHDS; SGRKVHDSQ; GRKVHDSQG; RKVHDSQGN; KVHDSQGNA;
VHDSQGNAA; HDSQGNAAK; DSQGNAAKP; PQEGKCMTH; QEGKCMTHR; EGKCMTHRE;
GKCMTHREE; KCMTHREEL; CMTHREELL; MTHREELLT; THREELLTH; HREELLTHG;
REELLTHGM; EELLTHGMQ; ELLTHGMQP; LLTHGMQPN; LTHGMQPNH; THGMQPNHD;
HGMQPNHDL; GMQPNHDLR; MQPNHDLRK; QPNHDLRKE; PNHDLRKES; NHDLRKESA;
QTCFASLGI; TCFASLGIL; CFASLGILA; FASLGILAL; ASLGILALS; SLGILALSP;
LGILALSPV; GILALSPVK; ILALSPVKL; LALSPVKLD; ALSPVKLDK; LSPVKLDKG;
SPVKLDKGH; PVKLDKGHG; VKLDKGHGS; KLDKGHGSA; LDKGHGSAP; DKGHGSAPA;
KGHGSAPAV; GHGSAPAVT; HGSAPAVTT; GSAPAVTTS; SAPAVTTSF; APAVTTSFS;
PAVTTSFSE; AVTTSFSES; VTTSFSESW; NLDWNKKKS; LDWNKKKSS; DWNKKKSSE;
WNKKKSSED; NKKKSSEDF; KKKSSEDFY; KKSSEDFYF; KSSEDFYFY; SSEDFYFYF;
SEDFYFYFR; EDFYFYFRA; DFYFYFRAF; FYFYFRAFA; YFYFRAFAG; FYFRAFAGI;
YFRAFAGIL; RQCRREKQK; QCRREKQKY; CRREKQKYH; RREKQKYHC; REKQKYHCF;
EKQKYHCFT; KQKYHCFTC; QKYHCFTCC; KYHCFTCCK; YHCFTCCKR; HCFTCCKRL;
CFTCCKRLC; FTCCKRLCK; TCCKRLCKR; CCKRLCKRL; CKRLCKRLL; KRLCKRLLG;
RLCKRLLGK; SLFFCISRF; LFFCISRFM; FFCISRFMG; FCISRFMGA; CISRFMGAA;
ISRFMGAAL; SRFMGAALA; RFMGAALAL; FMGAALALL; MGAALALLG; GAALALLGD;
AALALLGDL; ALALLGDLV; LALLGDLVA; ALLGDLVAS; LLGDLVASV; LGDLVASVS;
GDLVASVSE; DLVASVSEA; LVASVSEAA; VASVSEAAA; ASVSEAAAA; SVSEAAAAT;
VSEAAAATG; SEAAAATGF; EAAAATGFS; AAAATGFSV; AAATGFSVA; AATGFSVAE;
ATGFSVAEI; TGFSVAEIA; GFSVAEIAA; FSVAEIAAG; SVAEIAAGE; VAEIAAGEA;
AEIAAGEAA; EIAAGEAAA; IAAGEAAAI; AAGEAAAIE; AGEAAAIEV; GEAAAIEVQ;
EAAAIEVQ; AAAAIEVQI; AAAIEVQIA; AAIEVQIAS; AIEVQIASL; IEVQIASLA;
EVQIASLAT; VQIASLATV; QIASLATVE; IASLATVEG; ASLATVEGI; SLATVEGIT;
LATVEGITS; ATVEGITST; TVEGITSTS; VEGITSTSE; EGITSTSEA; GITSTSEAI;
ITSTSEAIA; TSTSEAIAA; STSEAIAAI; TSEAIAAIG; SEAIAAIGL; EAIAAIGLT;
AIAAIGLTP; IAAIGLTPQ; AAIGLTPQT; AIGLTPQTY; IGLTPQTYA; GLTPQTYAV;
LTPQTYAVI; TPQTYAVIA; PQTYAVIAG; QTYAVIAGA; TYAVIAGAP; YAVIAGAPG;
AVIAGAPGA; VIAGAPGAI; IAGAPGAIA; AGAPGAIAG; GAPGAIAGF; APGAIAGFA;
PGAIAGFAA; GAIAGFAAL; AIAGFAALI; IAGFAALIQ; AGFAALIQT; GFAALIQTV;
FAALIQTVS; AALIQTVSG; ALIQTVSGI; LIQTVSGIS; IQTVSGISS; QTVSGISSL;
TVSGISSLA; VSGISSLAQ; SGISSLAQV; GISSLAQVG; ISSLAQVGY; SSLAQVGYK;
SLAQVGYKF; LAQVGYKFF; AQVGYKFFD; QVGYKFFDD; VGYKFFDDW; GYKFFDDWD;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

YKFFDDWDH; KFFDDWDHK; FFDDWDHKV; FDDWDHKVS; DDWDHKVST; DWDHKVSTV;
WDHKVSTVG; DHKVSTVGL; HKVSTVGLY; KVSTVGLYQ; VSTVGLYQQ; STVGLYQQS;
TVGLYQQSG; VGLYQQSGM; GLYQQSGMA; LYQQSGMAL; YQQSGMALE; QQSGMALEL;
QSGMALELF; SGMALELFN; GMALELFNP; MALELFNPD; ALELFNPDE; LELFNPDEY;
ELFNPDEYY; LFNPDEYYD; FNPDEYYDI; NPDEYYDIL; PDEYYDILF; DEYYDILFP;
EYYDILFPG; YYDILFPGV; YDILFPGVN; DILFPGVNT; ILFPGVNTF; LFPGVNTFV;
FPGVNTFVN; PGVNTFVNN; GVNTFVNNI; VNTFVNNIQ; NTFVNNIQY; TFVNNIQYL;
FVNNIQYLD; VNNIQYLDP; NNIQYLDPR; NIQYLDPRH; IQYLDPRHW; QYLDPRHWG;
YLDPRHWGP; LDPRHWGPS; DPRHWGPSL; PRHWGPSLF; RHWGPSLFA; HWGPSLFAT;
WGPSLFATI; GPSLFATIS; PSLFATISQ; SLFATISQA; LFATISQAL; FATISQALW;
ATISQALWH; TISQALWHV; ISQALWHVI; SQALWHVIR; QALWHVIRD; ALWHVIRDD;
LWHVIRDDI; WHVIRDDIP; HVIRDDIPS; VIRDDIPSI; IRDDIPSIT; RDDIPSITS;
DDIPSITSQ; DIPSITSQE; IPSITSQEL; PSITSQELQ; SITSQELQR; ITSQELQRR;
TSQELQRRT; SQELQRRTE; QELQRRTER; ELQRRTERF; LQRRTERFF; QRRTERFFR;
RRTERFFRD; RTERFFRDS; TERFFRDSL; ERFFRDSLA; RFFRDSLAR; FFRDSLARF;
FRDSLARFL; RDSLARFLE; DSLARFLEE; SLARFLEET; LARFLEETT; ARFLEETTW;
RFLEETTWT; FLEETTWTI; LEETTWTIV; EETTWTIVN; ETTWTIVNA; TTWTIVNAP;
TWTIVNAPI; WTIVNAPIN; TIVNAPINF; IVNAPINFY; VNAPINFYN; NAPINFYNY;
APINFYNYI; PINFYNYIQ; INFYNYIQQ; NFYNYIQQY; FYNYIQQYY; YNYIQQYYS;
NYIQQYYSD; YIQQYYSDL; IQQYYSDLS; QQYYSDLSP; QYYSDLSPI; YYSDLSPIR;
YSDLSPIRP; SDLSPIRPS; DLSPIRPSM; LSPIRPSMV; SPIRPSMVR; PIRPSMVRQ;
IRPSMVRQV; RPSMVRQVA; PSMVRQVAE; SMVRQVAER; MVRQVAERE; VRQVAEREG;
RQVAEREGT; QVAEREGTR; VAEREGTRV; AEREGTRVH; EREGTRVHF; REGTRVHFG;
EGTRVHFGH; GTRVHFGHT; TRVHFGHTY; RVHFGHTYS; VHFGHTYSI; HFGHTYSID;
FGHTYSIDD; GHTYSIDDA; HTYSIDDAD; TYSIDDADS; YSIDDADSI; SIDDADSIE;
IDDADSIEE; DDADSIEEV; DADSIEEVT; ADSIEEVTQ; DSIEEVTQR; SIEEVTQRM;
IEEVTQRMD; EEVTQRMDL; EVTQRMDLR; VTQRMDLRN; TQRMDLRNQ; QRMDLRNQQ;
RMDLRNQQS; MDLRNQQSV; DLRNQQSVH; LRNQQSVHS; RNQQSVHSG; NQQSVHSGE;
QQSVHSGEF; QSVHSGEFI; SVHSGEFIE; VHSGEFIEK; HSGEFIEKT; SGEFIEKTI;
GEFIEKTIA; EFIEKTIAP; FIEKTIAPG; IEKTIAPGG; EKTIAPGGA; KTIAPGGAN;
TIAPGGANQ; IAPGGANQR; APGGANQRT; PGGANQRTA; GGANQRTAP; GANQRTAPQ;
ANQRTAPQW; NQRTAPQWM; QRTAPQWML; RTAPQWMLP; TAPQWMLPL; APQWMLPLL;
PQWMLPLLL; QWMLPLLLG; WMLPLLLGL; MLPLLLGLY; LPLLLGLYG; PLLLGLYGT;
LLLGLYGTV; LLGLYGTVT; LGLYGTVTP; GLYGTVTPA; LYGTVTPAL; YGTVTPALE;
GTVTPALEA; TVTPALEAY; VTPALEAYE; TPALEAYED; PALEAYEDG; ALEAYEDGP;
LEAYEDGPN; EAYEDGPNQ; AYEDGPNQK; YEDGPNQKK; EDGPNQKKR; DGPNQKKRR;
GPNQKKRRV; PNQKKRRVS; NQKKRRVSR; QKKRRVSRG; KKRRVSRGS; KRRVSRGSS;
RRVSRGSSQ; RVSRGSSQK; VSRGSSQKA; SRGSSQKAK; RGSSQKAKG; GSSQKAKGT;
SSQKAKGTR; SQKAKGTRA; QKAKGTRAS; KAKGTRASA; AKGTRASAK; KGTRASAKT;
GTRASAKTT; TRASAKTTN; RASAKTTNK; ASAKTTNKR; SAKTTNKRR; AKTTNKRRS;
KTTNKRRSR; TTNKRRSRS; TNKRRSRSS; NKRRSRSSR; KRRSRSSRS; NWGRCYYRG;
WGRCYYRGR; GRCYYRGRM; RCYYRGRML; CYYRGRMLP; YYRGRMLPK; YRGRMLPKP;
RGRMLPKPR; GRMLPKPRN; RMLPKPRNG; MLPKPRNGG; LPKPRNGGS; PKPRNGGSR;
PREKNASLL; REKNASLLQ; EKNASLLQH; KNASLLQHS; NASLLQHSK; ASLLQHSKN;
SLLQHSKNS; LLQHSKNSP; LQHSKNSPP; QHSKNSPPQ; HSKNSPPQF; SKNSPPQFK;
GPNLWKSTD; PNLWKSTDV; NLWKSTDVG; LWKSTDVGG; WKSTDVGGC; KSTDVGGCN;
STDVGGCNC; TDVGGCNCT; DVGGCNCTN; VGGCNCTNR; GGCNCTNRG; GCNCTNRGY;
CNCTNRGYW; NCTNRGYWN; CTNRGYWNN; PSCRVTKSA; AWWRKTYSR; WWRKTYSRQ;
FPLLCCRWR; PLLCCRWRT; LLCCRWRTL; LCCRWRTLG; CCRWRTLGN; CRWRTLGNA;
RWRTLGNAG; WRTLGNAGS; RTLGNAGSA; TLGNAGSAN; LGNAGSANE; GNAGSANEL;
NAGSANELQ; AGSANELQV; GSANELQVK; SANELQVKV; ANELQVKVP; KPNSPVPGN;
PNSPVPGNE; NSPVPGNEY; GLFGQKQCL; LFGQKQCLS; FGQKQCLSS; VFWDFHRRG;
FWDFHRRGK; WDFHRRGKC; DFHRRGKCS; FHRRGKCSP; HRRGKCSPS; RRGKCSPST;
RGKCSPSTS; GKCSPSTSC; KCSPSTSCD; CSPSTSCDQ; SPSTSCDQH; PSTSCDQHS;
STSCDQHSY; TSCDQHSYH; SCDQHSYHS; CDQHSYHSV; DQHSYHSVA; QHSYHSVAR;
QLWNTTVER; LWNTTVERP; WNTTVERPC; NTTVERPCK; TTVERPCKI; TVERPCKIF;
DPPEKKICK; PPEKKICKE; PEKKICKES; EKKICKESL; KKICKESLP; KICKESLPN;
ICKESLPNF; CKESLPNFL; KESLPNFLF; ESLPNFLFA; SLPNFLFAK; PYKQENPES;
YKQENPESG; KQENPESGW; QENPESGWA; ENPESGWAA; NPESGWAAY; PESGWAAYV;
ESGWAAYVW; SGWAAYVWY; GWAAYVWYG; WAAYVWYGI; AAYVWYGIP; AYVWYGIPG;
YVWYGIPGR; VWYGIPGRR; WYGIPGRRG; WHRKTSRGP; HRKTSRGPR; RKTSRGPRY;
KTSRGPRYD; TSRGPRYDK; SRGPRYDKI; RGPRYDKIY; QTGTIANQN; TGTIANQNA;
GTIANQNAL; TIANQNALN; IANQNALNR; ANQNALNRC; NQNALNRCF; QNALNRCFY;
NALNRCFYC; ALNRCFYCT; LNRCFYCTY; NRCFYCTYT; RCFYCTYTF; CFYCTYTFN;
FYCTYTFNK; YCTYTFNKC; CTYTFNKCC; TYTFNKCCF; YTFNKCCFC; TFNKCCFCI;
FNKCCFCIS; NKCCFCISH; KCCFCISHF; ACVILGVVF; NTESLYTNA; TESLYTNAT;
ESLYTNATL; SLYTNATLD; LYTNATLDY; YTNATLDYG; TNATLDYGG; NATLDYGGL;
ATLDYGGLT; TLDYGGLTF; LDYGGLTFG; DYGGLTFGN; YGGLTFGNL; GGLTFGNLQ;
GLTFGNLQQ; LTFGNLQQG; TFGNLQQGL; FGNLQQGLK; GNLQQGLKY; NLQQGLKYL;
LQQGLKYLR; QQGLKYLRL; QGLKYLRLG; GLKYLRLGK; LKYLRLGKS; KYLRLGKSI;
YLRLGKSIV; LRLGKSIVI; RLGKSIVIG; LGKSIVIGI; GKSIVIGIQ; KSIVIGIQC;
SIVIGIQCL; IVIGIQCLI; VIGIQCLIH; IGIQCLIHV; GIQCLIHVQ; IQCLIHVQS;
QCLIHVQSL; CLIHVQSLQ; LIHVQSLQF; IHVQSLQFL; HVQSLQFLN; VQSLQFLNP;
QSLQFLNPL; SLQFLNPLL; LQFLNPLLL; YQEYISPCI; QEYISPCIY; EYISPCIYY;
YISPCIYYI; ISPCIYYIS; SPCIYYISS; PCIYYISSL; CIYYISSLK; IYYISSLKK;
YYISSLKKY; YISSLKKYT; ISSLKKYTY; SSLKKYTYL; SLKKYTYLS; LKKYTYLSQ;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

KKYTYLSQN; KYTYLSQNP; YTYLSQNPA; TYLSQNPAF; YLSQNPAFP; LSQNPAFPS;
SQNPAFPSI; QNPAFPSIQ; NPAFPSIQQ; PAFPSIQQF; IVYQLQNQL; VYQLQNQLQ;
YQLQNQLQA; TKLAVATRS; KLAVATRSF; LAVATRSFH; AVATRSFHF; VATRSFHFV;
ATRSFHFVK; TRSFHFVKF; RSFHFVKFF; SFHFVKFFF; FHFVKFFFQ; HFVKFFFQV;
FVKFFFQVR; VKFFFQVRT; KFFFQVRTL; FFFQVRTLS; FFQVRTLSF; FQVRTLSFV;
QVRTLSFVR; VRTLSFVRI; RTLSFVRIF; TLSFVRIFL; LSFVRIFLN; SFVRIFLNI;
FVRIFLNIF; VRIFLNIFW; RIFLNIFWA; PSLVEIFGF; SLVEIFGFF; LVEIFGFFC;
VEIFGFFCL; EIFGFFCLN; IFGFFCLNV; FGFFCLNVS; GFFCLNVSF; FFCLNVSFL;
FCLNVSFLN; CLNVSFLNL; LNVSFLNLP; HFHLNNLSN; FHLNNLSNC; HLNNLSNCL;
LNNLSNCLN; NNLSNCLNC; NLSNCLNCL; LSNCLNCLF; SNCLNCLFH; NCLNCLFHV;
CLNCLFHVL; LNCLFHVLK; NCLFHVLKA; CLFHVLKAN; LFHVLKANP; FHVLKANPL;
HVLKANPLI; VLKANPLIQ; LKANPLIQL; KANPLIQLL; ANPLIQLLS; NPLIQLLSL;
PLIQLLSLL; LIQLLSLLH; IQLLSLLHL; QLLSLLHLQ; LLSLLHLQK; LSLLHLQKQ;
SLLHLQKQP; LLHLQKQPC; LHLQKQPCT; HLQKQPCTD; LQKQPCTDL; LHLAQRLAF;
HLAQRLAFP; LAQRLAFPW; AQRLAFPWV; QRLAFPWVG; RLAFPWVGL; LAFPWVGLH;
AFPWVGLHL; FPWVGLHLR; PWVGLHLRL; WVGLHLRLY; VGLHLRLYH; GLHLRLYHH;
LHLRLYHHT; HLRLYHHTN; LRLYHHTNL; RLYHHTNLI; LYHHTNLIT; YHHTNLITL;
HHTNLITLQ; HTNLITLQL; TNLITLQLV; NLITLQLVL; LITLQLVLF; ITLQLVLFF;
TLQLVLFFH; LQLVLFFHY; QLVLFFHYQ; LVLFFHYQW; VLFFHYQWD; LFFHYQWDL;
KQYSAKNQI; QYSAKNQIL; YSAKNQILQ; SAKNQILQN; AKNQILQNP; KNQILQNPF;
VANSAAKQH; ANSAAKQHL; NSAAKQHLP; SAAKQHLPY; AAKQHLPYI; AKQHLPYIV;
KQHLPYIVL; QHLPYIVLV; HLPYIVLVQ; LPYIVLVQH; PYIVLVQHF; YIVLVQHFH;
IVLVQHFHE; VLVQHFHEL; LVQHFHELQ; VQHFHELQI; QHFHELQIL; HFHELQILN;
FHELQILNP; HELQILNPF; ELQILNPFY; LQILNPFYL; QILNPFYLI; ILNPFYLIY;
LNPFYLIYD; IFLLAFLPW; FLLAFLPWS; LLAFLPWSY; LAFLPWSYE; AFLPWSYEG;
FLPWSYEGY; LPWSYEGYL; PWSYEGYLL; WSYEGYLLF; SYEGYLLFF; LKLYLLLAD;
KLYLLLADK; LYLLLADKY; YLLLADKYF; LLLADKYFF; LLADKYFFD; LADKYFFDF;
ADKYFFDFY; DKYFFDFYF; KYFFDFYFL; YFFDFYFLQ; FFDFYFLQK; HLQSAFHDT;
SDKAGLFSD; DKAGLFSDT; KAGLFSDTF; AGLFSDTFY; GLFSDTFYT; LFSDTFYTP;
FSDTFYTPL; SDTFYTPLH; DTFYTPLHC; TFYTPLHCI; FYTPLHCIE; YTPLHCIEI;
TPLHCIEIL; PLHCIEILN; LHCIEILNT; HCIEILNTY; CIEILNTYL; IEILNTYLI;
EILNTYLII; ILNTYLIIK; LNTYLIIKT; NTYLIIKTH; TYLIIKTHP; YLIIKTHPH;
LIIKTHPHT; IIKTHPHTL; IKTHPHTLS; KTHPHTLSL; THPHTLSLL; HPHTLSLLH;
PHTLSLLHT; HTLSLLHTQ; LISKTPALF; ISKTPALFL; SKTPALFLQ; KTPALFLQA;
TPALFLQAL; PALFLQALL; ALFLQALLG; NHAPLSPLE; HAPLSPLEC; APLSPLECF;
PLSPLECFL; LSPLECFLL; LRHYIVSIP; RHYIVSIPY; RYTAFDRNY; LQKLYVYVE;
QKLYVYVEL; KLYVYVELK; LYVYVELKR; YVYVELKRI; YYAQHTCVY; VFYTEFELF;
FYTEFELFL; YTQQSRQGF; TQQSRQGFY; QQSRQGFYY; ETGVDQRES; TGVDQRESL;
GLLPFFFFW; LLPFFFFWV; LPFFFFWVV; PFFFFWVVL; FFFFWVVLS; FFFWVVLSV;
FFWVVLSVE; FWVVLSVEN; WVVLSVENL; VVLSVENLL; VLSVENLLL; LSVENLLLL;
SVENLLLLL; VENLLLLLH; ENLLLLLHH; NLLLLLHHW; LLLLLHHWQ; LLLLHHWQT;
LLLHHWQTY; LLHHWQTYL; LHHWQTYLH; HHWQTYLHG; HWQTYLHGK; WQTYLHGKI;
QTYLHGKIN; TYLHGKINL; YLHGKINLH; LHGKINLHP; HGKINLHPI; GKINLHPIF;
KINLHPIFH; RNSTRTPTL; NSTRTPTLL; STRTPTLLF; TRTPTLLFH; RTPTLLFHR;
TPTLLFHRL; PTLLFHRLA; TLLFHRLAP; LLFHRLAPI; LFHRLAPIK; FHRLAPIKK;
HRLAPIKKI; RLAPIKKII; LAPIKKIIT; GLLIFYYLS; LLIFYYLSK; LIFYYLSKY;
IFYYLSKYK; FYYLSKYKL; YYLSKYKLV; YLSKYKLVT; LSKYKLVTL; SKYKLVTLK;
KYKLVTLKL; ISEGSFSNY; SEGSFSNYL; EGSFSNYLD; GSFSNYLDP; SFSNYLDPP;
FSNYLDPPL; SNYLDPPLQ; NYLDPPLQS; YLDPPLQSF; LDPPLQSFF; DPPLQSFFS;
AKPLCEAVN; KPLCEAVNA; PLCEAVNAV; LCEAVNAVA; CEAVNAVAI; EAVNAVAIY;
AVNAVAIYP; VNAVAIYPN; NAVAIYPNQ; AVAIYPNQG; VAIYPNQGL; AIYPNQGLF;
IYPNQGLFS; HARAVHRRL; ARAVHRRLF; RAVHRRLFG; AVHRRLFGT; VHRRLFGTN;
HRRLFGTNR; RRLFGTNRP; RLFGTNRPF; LFGTNRPFL; FGTNRPFLA; GTNRPFLAV;
TNRPFLAVQ; NRPFLAVQG; RPFLAVQGI; PFLAVQGIW; FLAVQGIWA; LAVQGIWAK;
AVQGIWAKR; VQGIWAKRK; QGIWAKRKI; GIWAKRKIS; IWAKRKIST; WAKRKISTN;
AKRKISTNL; ATPGSKIRL; TPGSKIRLM; PGSKIRLMS; GSKIRLMSY; SKIRLMSYL;
KIRLMSYLY; IRLMSYLYI; RLMSYLYIL; LMSYLYILL; MSYLYILLH; SYLYILLHF;
YLYILLHFF; LYILLHFFI; YILLHFFIQ; ILLHFFIQS; LLHFFIQSI; LHFFIQSIH;
HFFIQSIHS; FFIQSIHSL; FIQSIHSLH; IQSIHSLHF; QSIHSLHFI; SIHSLHFIL;
IHSLHFILV; HSLHFILVA; SLHFILVAP; LHFILVAPF; HFILVAPFV; FILVAPFVR;
ILVAPFVRV; LVAPFVRVK; VAPFVRVKF; APFVRVKFL; PFVRVKFLT; FVRVKFLTL;
VRVKFLTLP; GKISPGSSF; KISPGSSFK; ISPGSSFKA; KVHELHGFF; VHELHGFFP;
HELHGFFPV; ELHGFFPVK; LHGFFPVKN; HGFFPVKNF; GFFPVKNFI; FFPVKNFIH 10 mers:

LQKLQKNRDF; QKLQKNRDFP; KLQKNRDFPK; ASEKASTPLL; SEKASTPLLL;
EKASTPLLLE; KASTPLLLER; ASTPLLLERK; STPLLLERKG; TPLLLERKGG;
PLLLERKGGG; LLLERKGGGR; LLERKGGGRG; LERKGGGRGG; ERKGGGRGGL;
RKGGGRGGLG; KGGGRGGLGL; GGGRGGLGLL; GGRGGLGLLY; GRGGLGLLYI;
RGGLGLLYII; GGLGLLYIIK; GLGLLYIIKK; LGLLYIIKKK; GLLYIIKKKA;
LLYIIKKKAT; LYIIKKKATG; YIIKKKATGR; IIKKKATGRS; IKKKATGRSC;
KKKATGRSCL; KKATGRSCLP; KATGRSCLPM; ATGRSCLPME; TGRSCLPMEC;
GRSCLPMECS; RSCLPMECSQ; SCLPMECSQT; CLPMECSQTM; LPMECSQTMT;
PMECSQTMTS; MECSQTMTSG; ECSQTMTSGR; CSQTMTSGRK; SQTMTSGRKV;
QTMTSGRKVH; TMTSGRKVHD; MTSGRKVHDS; TSGRKVHDSQ; SGRKVHDSQG;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

GRKVHDSQGN; RKVHDSQGNA; KVHDSQGNAA; VHDSQGNAAK; HDSQGNAAKP;
PQEGKCMTHR; QEGKCMTHRE; EGKCMTHREE; GKCMTHREEL; KCMTHREELL;
CMTHREELLT; MTHREELLTH; THREELLTHG; HREELLTHGM; REELLTHGMQ;
EELLTHGMQP; ELLTHGMQPN; LLTHGMQPNH; LTHGMQPNHD; THGMQPNHDL;
HGMQPNHDLR; GMQPNHDLRK; MQPNHDLRKE; QPNHDLRKES; PNHDLRKESA;
QTCFASLGIL; TCFASLGILA; CFASLGILAL; FASLGILALS; ASLGILALSP;
SLGILALSPV; LGILALSPVK; GILALSPVKL; ILALSPVKLD; LALSPVKLDK;
ALSPVKLDKG; LSPVKLDKGH; SPVKLDKGHG; PVKLDKGHGS; VKLDKGHGSA;
KLDKGHGSAP; LDKGHGSAPA; DKGHGSAPAV; KGHGSAPAVT; GHGSAPAVTT;
HGSAPAVTTS; GSAPAVTTSF; SAPAVTTSFS; APAVTTSFSE; PAVTTSFSES;
AVTTSFSESW; NLDWNKKKSS; LDWNKKKSSE; DWNKKKSSED; WNKKKSSEDF;
NKKKSSEDFY; KKKSSEDFYF; KKSSEDFYFY; KSSEDFYFYF; SSEDFYFYFR;
SEDFYFYFRA; EDFYFYFRAF; DFYFYFRAFA; FYFYFRAFAG; YFYFRAFAGI;
FYFRAFAGIL; RQCRREKQKY; QCRREKQKYH; CRREKQKYHC; RREKQKYHCF;
REKQKYHCFT; EKQKYHCFTC; KQKYHCFTCC; QKYHCFTCCK; KYHCFTCCKR;
YHCFTCCKRL; HCFTCCKRLC; CFTCCKRLCK; FTCCKRLCKR; TCCKRLCKRL;
CCKRLCKRLL; CKRLCKRLLG; KRLCKRLLGK; RLCKRLLGKS; LFFCISRFM;
FFCISRFMGA; FCISRFMGAA; CISRFMGAAL; ISRFMGAALA; SRFMGAALAL;
RFMGAALALL; FMGAALALLG; MGAALALLGD; GAALALLGDL; AALALLGDLV;
ALALLGDLVA; LALLGDLVAS; ALLGDLVASV; LLGDLVASVS; LGDLVASVSE;
GDLVASVSEA; DLVASVSEAA; LVASVSEAAA; VASVSEAAAA; ASVSEAAAAT;
SVSEAAAATG; VSEAAAATGF; SEAAAATGFS; EAAAATGFSV; AAAATGFSVA;
AAATGFSVAE; AATGFSVAEI; ATGFSVAEIA; TGFSVAEIAA; GFSVAEIAAG;
FSVAEIAAGE; SVAEIAAGEA; VAEIAAGEAA; AEIAAGEAAA; EIAAGEAAAA;
IAAGEAAAAI; AAGEAAAAIE; AGEAAAAIEV; GEAAAAIEVQ; EAAAAIEVQI;
AAAAIEVQIA; AAAIEVQIAS; AAIEVQIASL; AIEVQIASLA; IEVQIASLAT;
EVQIASLATV; VQIASLATVE; QIASLATVEG; IASLATVEGI; ASLATVEGIT;
SLATVEGITS; LATVEGITST; ATVEGITSTS; TVEGITSTSE; VEGITSTSEA;
EGITSTSEAI; GITSTSEAIA; ITSTSEAIAA; TSTSEAIAAI; STSEAIAAIG;
TSEAIAAIGL; SEAIAAIGLT; EAIAAIGLTP; AIAAIGLTPQ; IAAIGLTPQT;
AAIGLTPQTY; AIGLTPQTYA; IGLTPQTYAV; GLTPQTYAVI; LTPQTYAVIA;
TPQTYAVIAG; PQTYAVIAGA; QTYAVIAGAP; TYAVIAGAPG; YAVIAGAPGA;
AVIAGAPGAI; VIAGAPGAIA; IAGAPGAIAG; AGAPGAIAGF; GAPGAIAGFA;
APGAIAGFAA; PGAIAGFAAL; GAIAGFAALI; AIAGFAALIQ; IAGFAALIQT;
AGFAALIQTV; GFAALIQTVS; FAALIQTVSG; AALIQTVSGI; ALIQTVSGIS;
LIQTVSGISS; IQTVSGISSL; QTVSGISSLA; TVSGISSLAQ; VSGISSLAQV;
SGISSLAQVG; GISSLAQVGY; ISSLAQVGYK; SSLAQVGYKF; SLAQVGYKFF;
LAQVGYKFFD; AQVGYKFFDD; QVGYKFFDDW; VGYKFFDDWD; GYKFFDDWDH;
YKFFDDWDHK; KFFDDWDHKV; FFDDWDHKVS; FDDWDHKVST; DDWDHKVSTV;
DWDHKVSTVG; WDHKVSTVGL; DHKVSTVGLY; HKVSTVGLYQ; KVSTVGLYQQ;
VSTVGLYQQS; STVGLYQQSG; TVGLYQQSGM; VGLYQQSGMA; GLYQQSGMAL;
LYQQSGMALE; YQQSGMALEL; QQSGMALELF; QSGMALELFN; SGMALELFNP;
GMALELFNPD; MALELFNPDE; ALELFNPDEY; LELFNPDEYY; ELFNPDEYYD;
LFNPDEYYDI; FNPDEYYDIL; NPDEYYDILF; PDEYYDILFP; DEYYDILFPG;
EYYDILFPGV; YYDILFPGVN; YDILFPGVNT; DILFPGVNTF; ILFPGVNTFV;
LFPGVNTFVN; FPGVNTFVNN; PGVNTFVNNI; GVNTFVNNIQ; VNTFVNNIQY;
NTFVNNIQYL; TFVNNIQYLD; FVNNIQYLDP; VNNIQYLDPR; NNIQYLDPRH;
NIQYLDPRHW; IQYLDPRHWG; QYLDPRHWGP; YLDPRHWGPS; LDPRHWGPSL;
DPRHWGPSLF; PRHWGPSLFA; RHWGPSLFAT; HWGPSLFATI; WGPSLFATIS;
GPSLFATISQ; PSLFATISQA; SLFATISQAL; LFATISQALW; FATISQALWH;
ATISQALWHV; TISQALWHVI; ISQALWHVIR; SQALWHVIRD; QALWHVIRDD;
ALWHVIRDDI; LWHVIRDDIP; WHVIRDDIPS; HVIRDDIPSI; VIRDDIPSIT;
IRDDIPSITS; RDDIPSITSQ; DDIPSITSQE; DIPSITSQEL; IPSITSQELQ;
PSITSQELQR; SITSQELQRR; ITSQELQRRT; TSQELQRRTE; SQELQRRTEF;
QELQRRTERF; ELQRRTERFF; LQRRTERFFR; QRRTERFFRD; RRTERFFRDS;
RTERFFRDSL; TERFFRDSLA; ERFFRDSLAR; RFFRDSLARF; FFRDSLARFL;
FRDSLARFLE; RDSLARFLEE; DSLARFLEET; SLARFLEETT; LARFLEETTW;
ARFLEETTWT; RFLEETTWTI; FLEETTWTIV; LEETTWTIVN; EETTWTIVNA;
ETTWTIVNAP; TTWTIVNAPI; TWTIVNAPIN; WTIVNAPINF; TIVNAPINFY;
IVNAPINFYN; VNAPINFYNY; NAPINFYNYI; APINFYNYIQ; PINFYNYIQQ;
INFYNYIQQY; NFYNYIQQYY; FYNYIQQYYS; YNYIQQYYSD; NYIQQYYSDL;
YIQQYYSDLS; IQQYYSDLSP; QQYYSDLSPI; QYYSDLSPIR; YYSDLSPIRP;
YSDLSPIRPS; SDLSPIRPSM; DLSPIRPSMV; LSPIRPSMVR; SPIRPSMVRQ;
PIRPSMVRQV; IRPSMVRQVA; RPSMVRQVAE; PSMVRQVAER; SMVRQVAERE;
MVRQVAEREG; VRQVAEREGT; RQVAEREGTR; QVAEREGTRV; VAEREGTRVH;
AEREGTRVHF; EREGTRVHFG; REGTRVHFGH; EGTRVHFGHT; GTRVHFGHTY;
TRVHFGHTYS; RVHFGHTYSI; VHFGHTYSID; HFGHTYSIDD; FGHTYSIDDA;
GHTYSIDDAD; HTYSIDDADS; TYSIDDADSI; YSIDDADSIE; SIDDADSIEE;
IDDADSIEEV; DDADSIEEVT; DADSIEEVTQ; ADSIEEVTQR; DSIEEVTQRM;
SIEEVTQRMD; IEEVTQRMDL; EEVTQRMDLR; EVTQRMDLRN; VTQRMDLRNQ;
TQRMDLRNQQ; QRMDLRNQQS; RMDLRNQQSV; MDLRNQQSVH; DLRNQQSVHS;
LRNQQSVHSG; RNQQSVHSGE; NQQSVHSGEF; QQSVHSGEFI; QSVHSGEFIE;
SVHSGEFIEK; VHSGEFIEKT; HSGEFIEKTI; SGEFIEKTIA; GEFIEKTIAP;
EFIEKTIAPG; FIEKTIAPGG; IEKTIAPGGA; EKTIAPGGAN; KTIAPGGANQ;
TIAPGGANQR; IAPGGANQRT; APGGANQRTA; PGGANQRTAP; GGANQRTAPQ;
GANQRTAPQW; ANQRTAPQWM; NQRTAPQWML; QRTAPQWMLP; RTAPQWMLPL;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

TAPQWMLPLL; APQWMLPLLL; PQWMLPLLLG; QWMLPLLLGL; WMLPLLLGLY;
MLPLLLGLYG; LPLLLGLYGT; PLLLGLYGTV; LLLGLYGTVT; LLGLYGTVTP;
LGLYGTVTPA; GLYGTVTPAL; LYGTVTPALE; YGTVTPALEA; GTVTPALEAY;
TVTPALEAYE; VTPALEAYED; TPALEAYEDG; PALEAYEDGP; ALEAYEDGPN;
LEAYEDGPNQ; EAYEDGPNQK; AYEDGPNQKK; YEDGPNQKKR; EDGPNQKKRR;
DGPNQKKRRV; GPNQKKRRVS; PNQKKRRVSR; NQKKRRVSRG; QKKRRVSRGS;
KKRRVSRGSS; KRRVSRGSSQ; RRVSRGSSQK; RVSRGSSQKA; VSRGSSQKAK;
SRGSSQKAKG; RGSSQKAKGT; GSSQKAKGTR; SSQKAKGTRA; SQKAKGTRAS;
QKAKGTRASA; KAKGTRASAK; AKGTRASAKT; KGTRASAKTT; GTRASAKTTN;
TRASAKTTNK; RASAKTTNKR; ASAKTTNKRR; SAKTTNKRRS; AKTTNKRRSR;
KTTNKRRSRS; TTNKRRSRSS; TNKRRSRSSR; NKRRSRSSRS; NWGRCYYRGR;
WGRCYYRGRM; GRCYYRGRML; RCYYRGRMLP; CYYRGRMLPK; YYRGRMLPKP;
YRGRMLPKPR; RGRMLPKPRN; GRMLPKPRNG; RMLPKPRNGG; MLPKPRNGGS;
LPKPRNGGSR; PREKNASLLQ; REKNASLLQH; EKNASLLQHS; KNASLLQHSK;
NASLLQHSKN; ASLLQHSKNS; SLLQHSKNSP; LLQHSKNSPP; LQHSKNSPPQ;
QHSKNSPPQF; HSKNSPPQFK; GPNLWKSTDV; PNLWKSTDVG; NLWKSTDVGG;
LWKSTDVGGC; WKSTDVGGCN; KSTDVGGCNC; STDVGGCNCT; TDVGGCNCTN;
DVGGCNCTNR; VGGCNCTNRG; GGCNCTNRGY; GCNCTNRGYW; CNCTNRGYWN;
NCTNRGYWNN; AWWRKTYSRQ; FPLLCCRWRT; PLLCCRWRTL; LLCCRWRTLG;
LCCRWRTLGN; CCRWRTLGNA; CRWRTLGNAG; RWRTLGNAGS; WRTLGNAGSA;
RTLGNAGSAN; TLGNAGSANE; LGNAGSANEL; GNAGSANELQ; NAGSANELQV;
AGSANELQVK; GSANELQVKV; SANELQVKVP; KPNSPVPGNE; PNSPVPGNEY;
GLFGQKQCLS; LFGQKQCLSS; VFWDFHRRGK; FWDFHRRGKC; WDFHRRGKCS;
DFHRRGKCSP; FHRRGKCSPS; HRRGKCSPST; RRGKCSPSTS; RGKCSPSTSC;
GKCSPSTSCD; KCSPSTSCDQ; CSPSTSCDQH; SPSTSCDQHS; PSTSCDQHSY;
STSCDQHSYH; TSCDQHSYHS; SCDQHSYHSV; CDQHSYHSVA; DQHSYHSVAR;
QLWNTTVERP; LWNTTVERPC; WNTTVERPCK; NTTVERPCKI; TTVERPCKIF;
DPPEKKICKE; PPEKKICKES; PEKKICKESL; EKKICKESLP; KKICKESLPN;
KICKESLPNF; ICKESLPNFL; CKESLPNFLF; KESLPNFLFA; ESLPNFLFAK;
PYKQENPESG; YKQENPESGW; KQENPESGWA; QENPESGWAA; ENPESGWAAY;
NPESGWAAYV; PESGWAAYVW; ESGWAAYVWY; SGWAAYVWYG; GWAAYVWYGI;
WAAYVWYGIP; AAYVWYGIPG; AYVWYGIPGR; YVWYGIPGRR; VWYGIPGRRG;
WHRKTSRGPR; HRKTSRGPRY; RKTSRGPRYD; KTSRGPRYDK; TSRGPRYDKI;
SRGPRYDKIY; QTGTIANQNA; TGTIANQNAL; GTIANQNALN; TIANQNALNR;
IANQNALNRC; ANQNALNRCF; NQNALNRCFY; QNALNRCFYC; NALNRCFYCT;
ALNRCFYCTY; LNRCFYCTYT; NRCFYCTYTF; RCFYCTYTFN; CFYCTYTFNK;
FYCTYTFNKC; YCTYTFNKCC; CTYTFNKCCF; TYTFNKCCFC; YTFNKCCFCI;
TFNKCCFCIS; FNKCCFCISH; NKCCFCISHF; KCCFCISHFT; CCFCISHFTE;
ESLYTNATLD; SLYTNATLDY; LYTNATLDYG; YTNATLDYGG; TNATLDYGGL;
NATLDYGGLT; ATLDYGGLTF; TLDYGGLTFG; LDYGGLTFGN; DYGGLTFGNL;
YGGLTFGNLQ; GGLTFGNLQQ; GLTFGNLQQG; LTFGNLQQGL; TFGNLQQGLK;
FGNLQQGLKY; GNLQQGLKYL; NLQQGLKYLR; LQQGLKYLRL; QQGLKYLRLG;
QGLKYLRLGK; GLKYLRLGKS; LKYLRLGKSI; KYLRLGKSIV; YLRLGKSIVI;
LRLGKSIVIG; RLGKSIVIGI; LGKSIVIGIQ; GKSIVIGIQC; KSIVIGIQCL;
SIVIGIQCLI; IVIGIQCLIH; VIGIQCLIHV; IGIQCLIHVQ; GIQCLIHVQS;
IQCLIHVQSL; QCLIHVQSLQ; CLIHVQSLQF; LIHVQSLQFL; IHVQSLQFLN;
HVQSLQFLNP; VQSLQFLNPL; QSLQFLNPLL; SLQFLNPLLL; YQEYISPCIY;
QEYISPCIYY; EYISPCIYYI; YISPCIYYIS; ISPCIYYISS; SPCIYYISSL;
PCIYYISSLK; CIYYISSLKK; IYYISSLKKY; YYISSLKKYT; YISSLKKYTY;
ISSLKKYTYL; SSLKKYTYLS; SLKKYTYLSQ; LKKYTYLSQN; KKYTYLSQNP;
KYTYLSQNPA; YTYLSQNPAF; TYLSQNPAFP; YLSQNPAFPS; LSQNPAFPSI;
SQNPAFPSIQ; QNPAFPSIQQ; NPAFPSIQQF; IVYQLQNQLQ; VYQLQNQLQA;
TKLAVATRSF; KLAVATRSFH; LAVATRSFHF; AVATRSFHFV; VATRSFHFVK;
ATRSFHFVKF; TRSFHFVKFF; RSFHFVKFFF; SFHFVKFFFQ; FHFVKFFFQV;
HFVKFFFQVR; FVKFFFQVRT; VKFFFQVRTL; KFFFQVRTLS; FFFQVRTLSF;
FFQVRTLSFV; FQVRTLSFVR; QVRTLSFVRI; VRTLSFVRIF; RTLSFVRIFL;
TLSFVRIFLN; LSFVRIFLNI; SFVRIFLNIF; FVRIFLNIFW; VRIFLNIFWA;
PSLVEIFGFF; SLVEIFGFFC; LVEIFGFFCL; VEIFGFFCLN; EIFGFFCLNV;
IFGFFCLNVS; FGFFCLNVSF; GFFCLNVSFL; FFCLNVSFLN; FCLNVSFLNL;
CLNVSFLNLP; HFHLNNLSNC; FHLNNLSNCL; HLNNLSNCLN; LNNLSNCLNC;
NNLSNCLNCL; NLSNCLNCLF; LSNCLNCLFH; SNCLNCLFHV; NCLNCLFHVL;
CLNCLFHVLK; LNCLFHVLKA; NCLFHVLKAN; CLFHVLKANP; LFHVLKANPL;
FHVLKANPLI; HVLKANPLIQ; VLKANPLIQL; LKANPLIQLL; KANPLIQLLS;
ANPLIQLLSL; NPLIQLLSLL; PLIQLLSLLH; LIQLLSLLHL; IQLLSLLHLQ;
QLLSLLHLQK; LLSLLHLQKQ; LSLLHLQKQP; SLLHLQKQPC; LLHLQKQPCT;
LHLQKQPCTD; HLQKQPCTDL; LHLAQRLAFP; HLAQRLAFPW; LAQRLAFPWV;
AQRLAFPWVG; QRLAFPWVGL; RLAFPWVGLH; LAFPWVGLHL; AFPWVGLHLR;
FPWVGLHLRL; PWVGLHLRLY; WVGLHLRLYH; VGLHLRLYHH; GLHLRLYHHT;
LHLRLYHHTN; HLRLYHHTNL; LRLYHHTNLI; RLYHHTNLIT; LYHHTNLITL;
YHHTNLITLQ; HHTNLITLQL; HTNLITLQLV; TNLITLQLVL; NLITLQLVLF;
LITLQLVLFF; ITLQLVLFFH; TLQLVLFFHY; LQLVLFFHYQ; QLVLFFHYQW;
LVLFFHYQWD; VLFFHYQWDL; KQYSAKNQIL; QYSAKNQILQ; YSAKNQILQN;
SAKNQILQNP; AKNQILQNPF; VANSAAKQHL; ANSAAKQHLP; NSAAKQHLPY;
SAAKQHLPYI; AAKQHLPYIV; AKQHLPYIVL; KQHLPYIVLV; QHLPYIVLVQ;
HLPYIVLVQH; LPYIVLVQHF; PYIVLVQHFH; YIVLVQHFHE; IVLVQHFHEL;
VLVQHFHELQ; LVQHFHELQI; VQHFHELQIL; QHFHELQILN; HFHELQILNP;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

FHELQILNPF; HELQILNPFY; ELQILNPFYL; LQILNPFYLI; QILNPFYLIY;
ILNPFYLIYD; IFLLAFLPWS; FLLAFLPWSY; LLAFLPWSYE; LAFLPWSYEG;
AFLPWSYEGY; FLPWSYEGYL; LPWSYEGYLL; PWSYEGYLLF; WSYEGYLLFF;
LKLYLLLADK; KLYLLLADKY; LYLLLADKYF; YLLLADKYFF; LLLADKYFFD;
LLADKYFFDF; LADKYFFDFY; ADKYFFDFYF; DKYFFDFYFL; KYFFDFYFLQ;
YFFDFYFLQK; SDKAGLFSDT; DKAGLFSDTF; KAGLFSDTFY; AGLFSDTFYT;
GLFSDTFYTP; LFSDTFYTPL; FSDTFYTPLH; SDTFYTPLHC; DTFYTPLHCI;
TFYTPLHCIE; FYTPLHCIEI; YTPLHCIEIL; TPLHCIEILN; PLHCIEILNT;
LHCIEILNTY; HCIEILNTYL; CIEILNTYLI; IEILNTYLII; EILNTYLIIK;
ILNTYLIIKT; LNTYLIIKTH; NTYLIIKTHP; TYLIIKTHPH; YLIIKTHPHT;
LIIKTHPHTL; IIKTHPHTLS; IKTHPHTLSL; KTHPHTLSLL; THPHTLSLLH;
HPHTLSLLHT; PHTLSLLHTQ; LISKTPALFL; ISKTPALFLQ; SKTPALFLQA;
KTPALFLQAL; TPALFLQALL; PALFLQALLG; NHAPLSPLEC; HAPLSPLECF;
APLSPLECFL; PLSPLECFLL; LRHYIVSIPY; LQKLYVYVEL; QKLYVYVELK;
KLYVYVELKR; LYVYVELKRI; VFYTEFELFL; YTQQSRQGFY; TQQSRQGFYY;
ETGVDQRESL; GLLPFFFFWV; LLPFFFFWVV; LPFFFFWVVL; PFFFFWVVLS;
FFFFWVVLSV; FFFWVVLSVE; FFWVVLSVEN; FWVVLSVENL; WVVLSVENLL;
VVLSVENLLL; VLSVENLLLL; LSVENLLLLL; SVENLLLLLH; VENLLLLLHH;
ENLLLLLHHW; NLLLLLHHWQ; LLLLLHHWQT; LLLLHHWQTY; LLLHHWQTYL;
LLHHWQTYLH; LHHWQTYLHG; HHWQTYLHGK; HWQTYLHGKI; WQTYLHGKIN;
QTYLHGKINL; TYLHGKINLH; YLHGKINLHP; LHGKINLHPI; HGKINLHPIF;
GKINLHPIFH; RNSTRTPTLL; NSTRTPTLLF; STRTPTLLFH; TRTPTLLFHR;
RTPTLLFHRL; TPTLLFHRLA; PTLLFHRLAP; TLLFHRLAPI; LLFHRLAPIK;
LFHRLAPIKK; FHRLAPIKKI; HRLAPIKKII; RLAPIKKIIT; GLLIFYYLSK;
LLIFYYLSKY; LIFYYLSKYK; IFYYLSKYKL; FYYLSKYKLV; YYLSKYKLVT;
YLSKYKLVTL; LSKYKLVTLK; SKYKLVTLKL; ISEGSFSNYL; SEGSFSNYLD;
EGSFSNYLDP; GSFSNYLDPP; SFSNYLDPPL; FSNYLDPPLQ; SNYLDPPLQS;
NYLDPPLQSF; YLDPPLQSFF; LDPPLQSFFS; AKPLCEAVNA; KPLCEAVNAV;
PLCEAVNAVA; LCEAVNAVAI; CEAVNAVAIY; EAVNAVAIYP; AVNAVAIYPN;
VNAVAIYPNQ; NAVAIYPNQG; AVAIYPNQGL; VAIYPNQGLF; AIYPNQGLFS;
HARAVHRRLF; ARAVHRRLFG; RAVHRRLFGT; AVHRRLFGTN; VHRRLFGTNR;
HRRLFGTNRP; RRLFGTNRPF; RLFGTNRPFL; LFGTNRPFLA; FGTNRPFLAV;
GTNRPFLAVQ; TNRPFLAVQG; NRPFLAVQGI; RPFLAVQGIW; PFLAVQGIWA;
FLAVQGIWAK; LAVQGIWAKR; AVQGIWAKRK; VQGIWAKRKI; QGIWAKRKIS;
GIWAKRKIST; IWAKRKISTN; WAKRKISTNL; ATPGSKIRLM; TPGSKIRLMS;
PGSKIRLMSY; GSKIRLMSYL; SKIRLMSYLY; KIRLMSYLYI; IRLMSYLYIL;
RLMSYLYILL; LMSYLYILLH; MSYLYILLHF; SYLYILLHFF; YLYILLHFFI;
LYILLHFFIQ; YILLHFFIQS; ILLHFFIQSI; LLHFFIQSIH; LHFFIQSIHS;
HFFIQSIHSL; FFIQSIHSLH; FIQSIHSLHF; IQSIHSLHFI; QSIHSLHFIL;
SIHSLHFILV; IHSLHFILVA; HSLHFILVAP; SLHFILVAPF; LHFILVAPFV;
HFILVAPFVR; FILVAPFVRV; ILVAPFVRVK; LVAPFVRVKF; VAPFVRVKFL;
APFVRVKFLT; PFVRVKFLTL; FVRVKFLTLP; GKISPGSSFK; KISPGSSFKA;
KVHELHGFFP; VHELHGFFPV; HELHGFFPVK; ELHGFFPVKN; LHGFFPVKNF;
HGFFPVKNFI; GFFPVKNFIH 11 mers:

LQKLQKNRDFP; QKLQKNRDFPK; ASEKASTPLLL; SEKASTPLLLE; EKASTPLLLER;
KASTPLLLERK; ASTPLLLERKG; STPLLLERKGG; TPLLLERKGGG; PLLLERKGGGR;
LLLERKGGGRG; LLERKGGGRGG; LERKGGGRGGL; ERKGGGRGGLG; RKGGGRGGLGL;
KGGGRGGLGLL; GGGRGGLGLLY; GGRGGLGLLYI; GRGGLGLLYII; RGGLGLLYIIK;
GGLGLLYIIKK; GLGLLYIIKKK; LGLLYIIKKKA; GLLYIIKKKAT; LLYIIKKKATG;
LYIIKKKATGR; YIIKKKATGRS; IIKKKATGRSC; IKKKATGRSCL; KKKATGRSCLP;
KKATGRSCLPM; KATGRSCLPME; ATGRSCLPMEC; TGRSCLPMECS; GRSCLPMECSQ;
RSCLPMECSQT; SCLPMECSQTM; CLPMECSQTMT; LPMECSQTMTS; PMECSQTMTSG;
MECSQTMTSGR; ECSQTMTSGRK; CSQTMTSGRKV; SQTMTSGRKVH; QTMTSGRKVHD;
TMTSGRKVHDS; MTSGRKVHDSQ; TSGRKVHDSQG; SGRKVHDSQGN; GRKVHDSQGNA;
RKVHDSQGNAA; KVHDSQGNAAK; VHDSQGNAAKP; PQEGKCMTHRE; QEGKCMTHREE;
EGKCMTHREEL; GKCMTHREELL; KCMTHREELLT; CMTHREELLTH; MTHREELLTHG;
THREELLTHGM; HREELLTHGMQ; REELLTHGMQP; EELLTHGMQPN; ELLTHGMQPNH;
LLTHGMQPNHD; LTHGMQPNHDL; THGMQPNHDLR; HGMQPNHDLRK; GMQPNHDLRKE;
MQPNHDLRKES; QPNHDLRKESA; QTCFASLGILA; TCFASLGILAL; CFASLGILALS;
FASLGILALSP; ASLGILALSPV; SLGILALSPVK; LGILALSPVKL; GILALSPVKLD;
ILALSPVKLDK; LALSPVKLDKG; ALSPVKLDKGH; LSPVKLDKGHG; SPVKLDKGHGS;
PVKLDKGHGSA; VKLDKGHGSAP; KLDKGHGSAPA; LDKGHGSAPAV; DKGHGSAPAVT;
KGHGSAPAVTT; GHGSAPAVTTS; HGSAPAVTTSF; GSAPAVTTSFS; SAPAVTTSFSE;
APAVTTSFSES; PAVTTSFSESW; NLDWNKKKSSE; LDWNKKKSSED; DWNKKKSSEDF;
WNKKKSSEDFY; NKKKSSEDFYF; KKKSSEDFYFY; KKSSEDFYFYF; KSSEDFYFYFR;
SSEDFYFYFRA; SEDFYFYFRAF; EDFYFYFRAFA; DFYFYFRAFAG; FYFYFRAFAGI;
YFYFRAFAGIL; RQCRREKQKYH; QCRREKQKYHC; CRREKQKYHCF; RREKQKYHCFT;
REKQKYHCFTC; EKQKYHCFTCC; KQKYHCFTCCK; QKYHCFTCCKR; KYHCFTCCKRL;
YHCFTCCKRLC; HCFTCCKRLCK; CFTCCKRLCKR; FTCCKRLCKRL; TCCKRLCKRLL;
CCKRLCKRLLG; CKRLCKRLLGK; SLFFCISRFMG; LFFCISRFMGA; FFCISRFMGAA;
FCISRFMGAAL; CISRFMGAALA; ISRFMGAALAL; SRFMGAALALL; RFMGAALALLG;
FMGAALALLGD; MGAALALLGDL; GAALALLGDLV; AALALLGDLVA; ALALLGDLVAS;
LALLGDLVASV; ALLGDLVASVS; LLGDLVASVSE; LGDLVASVSEA; GDLVASVSEAA;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

DLVASVSEAAA; LVASVSEAAAA; VASVSEAAAAT; ASVSEAAAATG; SVSEAAAATGF;
VSEAAAATGFS; SEAAAATGFSV; EAAAATGFSVA; AAAATGFSVAE; AAATGFSVAEI;
AATGFSVAEIA; ATGFSVAEIAA; TGFSVAEIAAG; GFSVAEIAAGE; FSVAEIAAGEA;
SVAEIAAGEAA; VAEIAAGEAAA; AEIAAGEAAAA; EIAAGEAAAAI; IAAGEAAAAIE;
AAGEAAAAIEV; AGEAAAAIEVQ; GEAAAAIEVQI; EAAAAIEVQIA; AAAAIEVQIAS;
AAAIEVQIASL; AAIEVQIASLA; AIEVQIASLAT; IEVQIASLATV; EVQIASLATVE;
VQIASLATVEG; QIASLATVEGI; IASLATVEGIT; ASLATVEGITS; SLATVEGITST;
LATVEGITSTS; ATVEGITSTSE; TVEGITSTSEA; VEGITSTSEAI; EGITSTSEAIA;
GITSTSEAIAA; ITSTSEAIAAI; TSTSEAIAAIG; STSEAIAAIGL; TSEAIAAIGLT;
SEAIAAIGLTP; EAIAAIGLTPQ; AIAAIGLTPQT; IAAIGLTPQTY; AAIGLTPQTYA;
AIGLTPQTYAV; IGLTPQTYAVI; GLTPQTYAVIA; LTPQTYAVIAG; TPQTYAVIAGA;
PQTYAVIAGAP; QTYAVIAGAPG; TYAVIAGAPGA; YAVIAGAPGAI; AVIAGAPGAIA;
VIAGAPGAIAG; IAGAPGAIAGF; AGAPGAIAGFA; GAPGAIAGFAA; APGAIAGFAAL;
PGAIAGFAALI; GAIAGFAALIQ; AIAGFAALIQT; IAGFAALIQTV; AGFAALIQTVS;
GFAALIQTVSG; FAALIQTVSGI; AALIQTVSGIS; ALIQTVSGISS; LIQTVSGISSL;
IQTVSGISSLA; QTVSGISSLAQ; TVSGISSLAQV; VSGISSLAQVG; SGISSLAQVGY;
GISSLAQVGYK; ISSLAQVGYKF; SSLAQVGYKFF; SLAQVGYKFFD; LAQVGYKFFDD;
AQVGYKFFDDW; QVGYKFFDDWD; VGYKFFDDWDH; GYKFFDDWDHK; YKFFDDWDHKV;
KFFDDWDHKVS; FFDDWDHKVST; FDDWDHKVSTV; DDWDHKVSTVG; DWDHKVSTVGL;
WDHKVSTVGLY; DHKVSTVGLYQ; HKVSTVGLYQQ; KVSTVGLYQQS; VSTVGLYQQSG;
STVGLYQQSGM; TVGLYQQSGMA; VGLYQQSGMAL; GLYQQSGMALE; LYQQSGMALEL;
YQQSGMALELF; QQSGMALELFN; QSGMALELFNP; SGMALELFNPD; GMALELFNPDE;
MALELFNPDEY; ALELFNPDEYY; LELFNPDEYYD; ELFNPDEYYDI; LFNPDEYYDIL;
FNPDEYYDILF; NPDEYYDILFP; PDEYYDILFPG; DEYYDILFPGV; EYYDILFPGVN;
YYDILFPGVNT; YDILFPGVNTF; DILFPGVNTFV; ILFPGVNTFVN; LFPGVNTFVNN;
FPGVNTFVNNI; PGVNTFVNNIQ; GVNTFVNNIQY; VNTFVNNIQYL; NTFVNNIQYLD;
TFVNNIQYLDP; FVNNIQYLDPR; VNNIQYLDPRH; NNIQYLDPRHW; NIQYLDPRHWG;
IQYLDPRHWGP; QYLDPRHWGPS; YLDPRHWGPSL; LDPRHWGPSLF; DPRHWGPSLFA;
PRHWGPSLFAT; RHWGPSLFATI; HWGPSLFATIS; WGPSLFATISQ; GPSLFATISQA;
PSLFATISQAL; SLFATISQALW; LFATISQALWH; FATISQALWHV; ATISQALWHVI;
TISQALWHVIR; ISQALWHVIRD; SQALWHVIRDD; QALWHVIRDDI; ALWHVIRDDIP;
LWHVIRDDIPS; WHVIRDDIPSI; HVIRDDIPSIT; VIRDDIPSITS; IRDDIPSITSQ;
RDDIPSITSQE; DDIPSITSQEL; DIPSITSQELQ; IPSITSQELQR; PSITSQELQRR;
SITSQELQRRT; ITSQELQRRTE; TSQELQRRTER; SQELQRRTERF; QELQRRTERFF;
ELQRRTERFFR; LQRRTERFFRD; QRRTERFFRDS; RRTERFFRDSL; RTERFFRDSLA;
TERFFRDSLAR; ERFFRDSLARF; RFFRDSLARFL; FFRDSLARFLE; FRDSLARFLEE;
RDSLARFLEET; DSLARFLEETT; SLARFLEETTW; LARFLEETTWT; ARFLEETTWTI;
RFLEETTWTIV; FLEETTWTIVN; LEETTWTIVNA; EETTWTIVNAP; ETTWTIVNAPI;
TTWTIVNAPIN; TWTIVNAPINF; WTIVNAPINFY; TIVNAPINFYN; IVNAPINFYNY;
VNAPINFYNYI; NAPINFYNYIQ; APINFYNYIQQ; PINFYNYIQQY; INFYNYIQQYY;
NFYNYIQQYYS; FYNYIQQYYSD; YNYIQQYYSDL; NYIQQYYSDLS; YIQQYYSDLSP;
IQQYYSDLSPI; QQYYSDLSPIR; QYYSDLSPIRP; YYSDLSPIRPS; YSDLSPIRPSM;
SDLSPIRPSMV; DLSPIRPSMVR; LSPIRPSMVRQ; SPIRPSMVRQV; PIRPSMVRQVA;
IRPSMVRQVAE; RPSMVRQVAER; PSMVRQVAERE; SMVRQVAEREG; MVRQVAEREGT;
VRQVAEREGTR; RQVAEREGTRV; QVAEREGTRVH; VAEREGTRVHF; AEREGTRVHFG;
EREGTRVHFGH; REGTRVHFGHT; EGTRVHFGHTY; GTRVHFGHTYS; TRVHFGHTYSI;
RVHFGHTYSID; VHFGHTYSIDD; HFGHTYSIDDA; FGHTYSIDDAD; GHTYSIDDADS;
HTYSIDDADSI; TYSIDDADSIE; YSIDDADSIEE; SIDDADSIEEV; IDDADSIEEVT;
DDADSIEEVTQ; DADSIEEVTQR; ADSIEEVTQRM; DSIEEVTQRMD; SIEEVTQRMDL;
IEEVTQRMDLR; EEVTQRMDLRN; EVTQRMDLRNQ; VTQRMDLRNQQ; TQRMDLRNQQS;
QRMDLRNQQSV; RMDLRNQQSVH; MDLRNQQSVHS; DLRNQQSVHSG; LRNQQSVHSGE;
RNQQSVHSGEF; NQQSVHSGEFI; QQSVHSGEFIE; QSVHSGEFIEK; SVHSGEFIEKT;
VHSGEFIEKTI; HSGEFIEKTIA; SGEFIEKTIAP; GEFIEKTIAPG; EFIEKTIAPGG;
FIEKTIAPGGA; IEKTIAPGGAN; EKTIAPGGANQ; KTIAPGGANQR; TIAPGGANQRT;
IAPGGANQRTA; APGGANQRTAP; PGGANQRTAPQ; GGANQRTAPQW; GANQRTAPQWM;
ANQRTAPQWML; NQRTAPQWMLP; QRTAPQWMLPL; RTAPQWMLPLL; TAPQWMLPLLL;
APQWMLPLLLG; PQWMLPLLLGL; QWMLPLLLGLY; WMLPLLLGLYG; MLPLLLGLYGT;
LPLLLGLYGTV; PLLLGLYGTVT; LLLGLYGTVTP; LLGLYGTVTPA; LGLYGTVTPAL;
GLYGTVTPALE; LYGTVTPALEA; YGTVTPALEAY; GTVTPALEAYE; TVTPALEAYED;
VTPALEAYEDG; TPALEAYEDGP; PALEAYEDGPN; ALEAYEDGPNQ; LEAYEDGPNQK;
EAYEDGPNQKK; AYEDGPNQKKR; YEDGPNQKKRR; EDGPNQKKRRV; DGPNQKKRRVS;
GPNQKKRRVSR; PNQKKRRVSRG; NQKKRRVSRGS; QKKRRVSRGSS; KKRRVSRGSSQ;
KRRVSRGSSQK; RRVSRGSSQKA; RVSRGSSQKAK; VSRGSSQKAKG; SRGSSQKAKGT;
RGSSQKAKGTR; GSSQKAKGTRA; SSQKAKGTRAS; SQKAKGTRASA; QKAKGTRASAK;
KAKGTRASAKT; AKGTRASAKTT; KGTRASAKTTN; GTRASAKTTNK; TRASAKTTNKR;
RASAKTTNKRR; ASAKTTNKRRS; SAKTTNKRRSR; AKTTNKRRSRS; KTTNKRRSRSS;
TTNKRRSRSSR; TNKRRSRSSRS; NWGRCYYRGRM; WGRCYYRGRML; GRCYYRGRMLP;
RCYYRGRMLPK; CYYRGRMLPKP; YYRGRMLPKPR; YRGRMLPKPRN; RGRMLPKPRNG;
GRMLPKPRNGG; RMLPKPRNGGS; MLPKPRNGGSR; PREKNASLLQH; REKNASLLQHS;
EKNASLLQHSK; KNASLLQHSKN; NASLLQHSKNS; ASLLQHSKNSP; SLLQHSKNSPP;
LLQHSKNSPPQ; LQHSKNSPPQF; QHSKNSPPQFK; GPNLWKSTDVG; PNLWKSTDVGG;
NLWKSTDVGGC; LWKSTDVGGCN; WKSTDVGGCNC; KSTDVGGCNCT; STDVGGCNCTN;
TDVGGCNCTNR; DVGGCNCTNRG; VGGCNCTNRGY; GGCNCTNRGYW; GCNCTNRGYWN;
CNCTNRGYWNN; FPLLCCRWRTL; PLLCCRWRTLG; LLCCRWRTLGN; LCCRWRTLGNA;
CCRWRTLGNAG; CRWRTLGNAGS; RWRTLGNAGSA; WRTLGNAGSAN; RTLGNAGSANE;
TLGNAGSANEL; LGNAGSANELQ; GNAGSANELQV; NAGSANELQVK; AGSANELQVKV;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

GSANELQVKVP; KPNSPVPGNEY; GLFGQKQCLSS; VFWDFHRRGKC; FWDFHRRGKCS;
WDFHRRGKCSP; DFHRRGKCSPS; FHRRGKCSPST; HRRGKCSPSTS; RRGKCSPSTSC;
RGKCSPSTSCD; GKCSPSTSCDQ; KCSPSTSCDQH; CSPSTSCDQHS; SPSTSCDQHSY;
PSTSCDQHSYH; STSCDQHSYHS; TSCDQHSYHSV; SCDQHSYHSVA; CDQHSYHSVAR;
QLWNTTVERPC; LWNTTVERPCK; WNTTVERPCKI; NTTVERPCKIF; DPPEKKICKES;
PPEKKICKESL; PEKKICKESLP; EKKICKESLPN; KKICKESLPNF; KICKESLPNFL;
ICKESLPNFLF; CKESLPNFLFA; KESLPNFLFAK; PYKQENPESGW; YKQENPESGWA;
KQENPESGWAA; QENPESGWAAY; ENPESGWAAYV; NPESGWAAYVW; PESGWAAYVWY;
ESGWAAYVWYG; SGWAAYVWYGI; GWAAYVWYGIP; WAAYVWYGIPG; AAYVWYGIPGR;
AYVWYGIPGRR; YVWYGIPGRRG; WHRKTSRGPRY; HRKTSRGPRYD; RKTSRGPRYDK;
KTSRGPRYDKI; TSRGPRYDKIY; QTGTIANQNAL; TGTIANQNALN; GTIANQNALNR;
TIANQNALNRC; IANQNALNRCF; ANQNALNRCFY; NQNALNRCFYC; QNALNRCFYCT;
NALNRCFYCTY; ALNRCFYCTYT; LNRCFYCTYTF; NRCFYCTYTFN; RCFYCTYTFNK;
CFYCTYTFNKC; FYCTYTFNKCC; YCTYTFNKCCF; CTYTFNKCCFC; TYTFNKCCFCI;
YTFNKCCFCIS; TFNKCCFCISH; FNKCCFCISHF; NTESLYTNATL; TESLYTNATLD;
ESLYTNATLDY; SLYTNATLDYG; LYTNATLDYGG; YTNATLDYGGL; TNATLDYGGLT;
NATLDYGGLTF; ATLDYGGLTFG; TLDYGGLTFGN; LDYGGLTFGNL; DYGGLTFGNLQ;
YGGLTFGNLQQ; GGLTFGNLQQG; GLTFGNLQQGL; LTFGNLQQGLK; TFGNLQQGLKY;
FGNLQQGLKYL; GNLQQGLKYLR; NLQQGLKYLRL; LQQGLKYLRLG; QQGLKYLRLGK;
QGLKYLRLGKS; GLKYLRLGKSI; LKYLRLGKSIV; KYLRLGKSIVI; YLRLGKSIVIG;
LRLGKSIVIGI; RLGKSIVIGIQ; LGKSIVIGIQC; GKSIVIGIQCL; KSIVIGIQCLI;
SIVIGIQCLIH; IVIGIQCLIHV; VIGIQCLIHVQ; IGIQCLIHVQS; GIQCLIHVQSL;
IQCLIHVQSLQ; QCLIHVQSLQF; CLIHVQSLQFL; LIHVQSLQFLN; IHVQSLQFLNP;
HVQSLQFLNPL; VQSLQFLNPLL; QSLQFLNPLLL; YQEYISPCIYY; QEYISPCIYYI;
EYISPCIYYIS; YISPCIYYISS; ISPCIYYISSL; SPCIYYISSLK; PCIYYISSLKK;
CIYYISSLKKY; IYYISSLKKYT; YYISSLKKYTY; YISSLKKYTYL; ISSLKKYTYLS;
SSLKKYTYLSQ; SLKKYTYLSQN; LKKYTYLSQNP; KKYTYLSQNPA; KYTYLSQNPAF;
YTYLSQNPAFP; TYLSQNPAFPS; YLSQNPAFPSI; LSQNPAFPSIQ; SQNPAFPSIQQ;
QNPAFPSIQQF; IVYQLQNQLQA; TKLAVATRSFH; KLAVATRSFHF; LAVATRSFHFV;
AVATRSFHFVK; VATRSFHFVKF; ATRSFHFVKFF; TRSFHFVKFFF; RSFHFVKFFFQ;
SFHFVKFFFQV; FHFVKFFFQVR; HFVKFFFQVRT; FVKFFFQVRTL; VKFFFQVRTLS;
KFFFQVRTLSF; FFFQVRTLSFV; FFQVRTLSFVR; FQVRTLSFVRI; QVRTLSFVRIF;
VRTLSFVRIFL; RTLSFVRIFLN; TLSFVRIFLNI; LSFVRIFLNIF; SFVRIFLNIFW;
FVRIFLNIFWA; PSLVEIFGFFC; SLVEIFGFFCL; LVEIFGFFCLN; VEIFGFFCLNV;
EIFGFFCLNVS; IFGFFCLNVSF; FGFFCLNVSFL; GFFCLNVSFLN; FFCLNVSFLNL;
FCLNVSFLNLP; HFHLNNLSNCL; PHLNNLSNCLN; HLNNLSNCLNC; LNNLSNCLNCL;
NNLSNCLNCLF; NLSNCLNCLFH; LSNCLNCLFHV; SNCLNCLFHVL; NCLNCLFHVLK;
CLNCLFHVLKA; LNCLFHVLKAN; NCLFHVLKANP; CLFHVLKANPL; LFHVLKANPLI;
FHVLKANPLIQ; HVLKANPLIQL; VLKANPLIQLL; LKANPLIQLLS; KANPLIQLLSL;
ANPLIQLLSLL; NPLIQLLSLLH; PLIQLLSLLHL; LIQLLSLLHLQ; IQLLSLLHLQK;
QLLSLLHLQKQ; LLSLLHLQKQP; LSLLHLQKQPC; SLLHLQKQPCT; LLHLQKQPCTD;
LHLQKQPCTDL; HLAQRLAFPW; HLAQRLAFPWV; LAQRLAFPWVG; AQRLAFPWVGL;
QRLAFPWVGLH; RLAFPWVGLHL; LAFPWVGLHLR; AFPWVGLHLRL; FPWVGLHLRLY;
PWVGLHLRLYH; WVGLHLRLYHH; VGLHLRLYHHT; GLHLRLYHHTN; LHLRLYHHTNL;
HLRLYHHTNLI; LRLYHHTNLIT; RLYHHTNLITL; LYHHTNLITLQ; YHHTNLITLQL;
HHTNLITLQLV; HTNLITLQLVL; TNLITLQLVLF; NLITLQLVLFF; LITLQLVLFFH;
ITLQLVLFFHY; TLQLVLFFHYQ; LQLVLFFHYQW; QLVLFFHYQWD; LVLFFHYQWDL;
KQYSAKNQILQ; QYSAKNQILQN; YSAKNQILQNP; SAKNQILQNPF; VANSAAKQHLP;
ANSAAKQHLPY; NSAAKQHLPYI; SAAKQHLPYIV; AAKQHLPYIVL; AKQHLPYIVLV;
KQHLPYIVLVQ; QHLPYIVLVQH; HLPYIVLVQHF; LPYIVLVQHFE; PYIVLVQHFEL;
YIVLVQHFHEL; IVLVQHFHELQ; VLVQHFHELQI; LVQHFHELQIL; VQHFHELQILN;
QHFHELQILNP; HFHELQILNPF; FHELQILNPFY; HELQILNPFYL; ELQILNPFYLI;
LQILNPFYLIY; QILNPFYLIYD; IFLLAFLPWSY; FLLAFLPWSYE; LLAFLPWSYEG;
LAFLPWSYEGY; AFLPWSYEGYL; FLPWSYEGYLL; LPWSYEGYLLF; PWSYEGYLLFF;
LKLYLLLADKY; KLYLLLADKYF; LYLLLADKYFF; YLLLADKYFFD; LLLADKYFFDF;
LLADKYFFDFY; LADKYFFDFYF; ADKYFFDFYFL; DKYFFDFYFLQ; KYFFDFYFLQK;
SDKAGLFSDTF; DKAGLFSDTFY; KAGLFSDTFYT; AGLFSDTFYTP; GLFSDTFYTPL;
LFSDTFYTPLH; FSDTFYTPLHC; SDTFYTPLHCI; DTFYTPLHCIE; TFYTPLHCIEI;
FYTPLHCIEIL; YTPLHCIEILN; TPLHCIEILNT; PLHCIEILNTY; LHCIEILNTYL;
HCIEILNTYLI; CIEILNTYLII; IEILNTYLIIK; EILNTYLIIKT; ILNTYLIIKTH;
LNTYLIIKTHP; NTYLIIKTHPH; TYLIIKTHPHT; YLIIKTHPHTL; LIIKTHPHTLS;
IIKTHPHTLSL; IKTHPHTLSLL; KTHPHTLSLLH; THPHTLSLLHT; HPHTLSLLHTQ;
LISKTPALFLQ; ISKTPALFLQA; SKTPALFLQAL; KTPALFLQALL; TPALFLQALLG;
NHAPLSPLECF; HAPLSPLECFL; APLSPLECFLL; LQKLYVYVELK; QKLYVYVELKR;
KLYVYVELKRI; YTQQSRQGFYY; GLLPFFFFWVV; LLPFFFFWVVL; LPFFFFWVVLS;
PFFFFWVVLSV; FFFFWVVLSVE; FFFWVVLSVEN; FFWVVLSVENL; FWVVLSVENLL;
WVVLSVENLLL; VVLSVENLLLL; VLSVENLLLLL; LSVENLLLLLH; SVENLLLLLHH;
VENLLLLLHHW; ENLLLLLHHWQ; NLLLLLHHWQT; LLLLLHHWQTY; LLLLHHWQTYL;
LLLHHWQTYLH; LLHHWQTYLHG; LHHWQTYLHGK; HHWQTYLHGKI; HWQTYLHGKIN;
WQTYLHGKINL; QTYLHGKINLH; TYLHGKINLHP; YLHGKINLHPI; LHGKINLHPIF;
HGKINLHPIFH; RNSTRTPTLLF; NSTRTPTLLFH; STRTPTLLFHR; TRTPTLLFHRL;
RTPTLLFHRLA; TPTLLFHRLAP; PTLLFHRLAPI; TLLFHRLAPIK; LLFHRLAPIKK;
LFHRLAPIKKI; FHRLAPIKKII; HRLAPIKKIIT; GLLIFYYLSKY; LLIFYYLSKYK;
LIFYYLSKYKL; IFYYLSKYKLV; FYYLSKYKLVT; YYLSKYKLVTL; YLSKYKLVTLK;
LSKYKLVTLKL; ISEGSFSNYLD; SEGSFSNYLDP; EGSFSNYLDPP; GSFSNYLDPPL;
SFSNYLDPPLQ; FSNYLDPPLQS; SNYLDPPLQSF; NYLDPPLQSFF; YLDPPLQSFFS;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

AKPLCEAVNAV; KPLCEAVNAVA; PLCEAVNAVAI; LCEAVNAVAIY; CEAVNAVAIYP;
EAVNAVAIYPN; AVNAVAIYPNQ; VNAVAIYPNQG; NAVAIYPNQGL; AVAIYPNQGLF;
VAIYPNQGLFS; HARAVHRRLFG; ARAVHRRLFGT; RAVHRRLFGTN; AVHRRLFGTNR;
VHRRLFGTNRP; HRRLFGTNRPF; RRLFGTNRPFL; RLFGTNRPFLA; LFGTNRPFLAV;
FGTNRPFLAVQ; GTNRPFLAVQG; TNRPFLAVQGI; NRPFLAVQGIW; RPFLAVQGIWA;
PFLAVQGIWAK; FLAVQGIWAKR; LAVQGIWAKRK; AVQGIWAKRKI; VQGIWAKRKIS;
QGIWAKRKIST; GIWAKRKISTN; IWAKRKISTNL; ATPGSKIRLMS; TPGSKIRLMSY;
PGSKIRLMSYL; GSKIRLMSYLY; SKIRLMSYLYI; KIRLMSYLYIL; IRLMSYLYILL;
RLMSYLYILLH; LMSYLYILLHF; MSYLYILLHFF; SYLYILLHFFI; YLYILLHFFIQ;
LYILLHFFIQS; YILLHFFIQSI; ILLHFFIQSIH; LLHFFIQSIHS; LHFFIQSIHSL;
HFFIQSIHSLH; FFIQSIHSLHF; FIQSIHSLHFI; IQSIHSLHFIL; QSIHSLHFILV;
SIHSLHFILVA; IHSLHFILVAP; HSLHFILVAPF; SLHFILVAPFV; LHFILVAPFVR;
HFILVAPFVRV; FILVAPFVRVK; ILVAPFVRVKF; LVAPFVRVKFL; VAPFVRVKFLT;
APFVRVKFLTL; PFVRVKFLTLP; GKISPGSSFKA; KVHELHGFFPV; VHELHGFFPVK;
HELHGFFPVKN; ELHGFFPVKNF; LHGFFPVKNFI; HGFFPVKNFIH

BK virus complementary reading frame 1

8 mers:

MDKVLNRE; DKVLNREE; KVLNREES; VLNREESM; LNREESME; NREESMEL; REESMELM;
EESMELMD; ESMELMDL; SMELMDLL; MELMDLLG; ELMDLLGL; LMDLLGLE; MDLLGLER;
DLLGLERA; LLGLERAA; LGLERAAW; GLERAAWG; LERAAWGN; ERAAWGNL; RAAWGNLP;
AAWGNLPL; AWGNLPLM; WGNLPLMR; GNLPLMRK; NLPLMRKA; LPLMRKAY; PLMRKAYL;
LMRKAYLR; MRKAYLRK; RKAYLRKC; KAYLRKCK; AYLRKCKE; YLRKCKEF; LRKCKEFH;
RKCKEFHP; KCKEFHPD; CKEFHPDK; KEFHPDKG; EFHPDKGG; FHPDKGGD; HPDKGGDE;
PDKGGDED; DKGGDEDK; KGGDEDKM; GGDEDKMK; GDEDKMKR; DEDKMKRM; EDKMKRMN;
DKMKRMNT; KMKRMNTL; MKRMNTLY; KRMNTLYK; RMNTLYKK; MNTLYKKM; NTLYKKME;
TLYKKMEQ; LYKKMEQD; YKKMEQDV; KKMEQDVK; KMEQDVKV; MEQDVKVA; EQDVKVAH;
QDVKVAHQ; DVKVAHQP; VKVAHQPD; KVAHQPDF; VAHQPDFG; AHQPDFGT; HQPDFGTW;
QPDFGTWS; PDFGTWSS; DFGTWSSS; FGTWSSSE; GTWSSSEV; TWSSSEVC; WSSSEVCA;
SSSEVCAD; SSEVCADF; SEVCADFP; EVCADFPL; VCADFPLC; CADFPLCP; ADFPLCPD;
DFPLCPDT; FPLCPDTL; PLCPDTLY; LCPDTLYC; CPDTLYCK; PDTLYCKE; DTLYCKEW;
TLYCKEWP; LYCKEWPI; YCKEWPIC; CKEWPICS; KEWPICSK; EWPICSKK; WPICSKKP;
PICSKKPS; ICSKKPSV; CSKKPSVH; SKKPSVHC; KKPSVHCP; KPSVHCPC; PSVHCPCM;
SVHCPCML; VHCPCMLC; HCPCMLCQ; CPCMLCQL; PCMLCQLR; CMLCQLRL; MLCQLRLR;
LCQLRLRH; CQLRLRHL; QLRLRHLN; LRLRHLNR; RLRHLNRK; LRHLNRKF; RHLNRKFL;
HLNRKFLR; LNRKFLRK; NRKFLRKE; RKFLRKEP; KFLRKEPL; FLRKEPLV; LRKEPLVW;
RKEPLVWI; KEPLVWID; EPLVWIDC; PLVWIDCY; LVWIDCYC; VWIDCYCI; WIDCYCID;
IDCYCIDC; DCYCIDCF; CYCIDCFT; YCIDCFTQ; CIDCFTQW; IDCFTQWF; DCFTQWFG;
CFTQWFGL; FTQWFGLD; TQWFGLDL; QWFGLDLT; WFGLDLTE; FGLDLTEE; GLDLTEET;
LDLTEETL; DLTEETLQ; LTEETLQW; TEETLQWW; EETLQWWV; ETLQWWVQ; TLQWWVQI;
LQWWVQII; QWWVQIIG; WWVQIIGE; WVQIIGET; VQIIGETP; QIIGETPF; IIGETPFR;
IGETPFRD; GETPFRDL; ETPFRDLK; TPFRDLKL; KALSNYFF; ALSNYFFY; LSNYFFYR;
SNYFFYRC; NYFFYRCQ; YFFYRCQP; FFYRCQPM; FYRCQPME; YRCQPMEQ; RCQPMEQK;
CQPMEQKS; QPMEQKSG; PMEQKSGS; MEQKSGSP; EQKSGSPG; QKSGSPGG; KSGSPGGV;
SGSPGGVP; GSPGGVPL; SPGGVPLM; PGGVPLMK; GGVPLMKN; GVPLMKNG; VPLMKNGM;
PLMKNGMK; LMKNGMKI; MKNGMKIY; KNGMKIYF; NGMKIYFA; GMKIYFAM; MKIYFAMK;
KIYFAMKI; IYFAMKIC; YFAMKICL; FAMKICLP; AMKICLPV; MKICLPVM; KICLPVMK;
ICLPVMKK; CLPVMKKQ; LPVMKKQQ; PVMKKQQQ; VMKKQQQI; MKKQQQIL; KKQQQILN;
KQQQILNT; QQQILNTQ; QQILNTQH; QILNTQHH; ILNTQHHP; LNTQHHPK; NTQHHPKK;
TQHHPKKK; QHHPKKKE; HHPKKKER; KTLKTFPL; TLKTFPLI; LKTFPLIY; KTFPLIYT;
TFPLIYTS; FPLIYTSF; PLIYTSFL; LIYTSFLV; IYTSFLVK; YTSFLVKL; TSFLVKLY;
SFLVKLYL; FLVKLYLV; LVKLYLVI; VKLYLVIE; KLYLVIEP; LYLVIEPL; YLVIEPLP;
LVIEPLPA; VIEPLPAL; IEPLPALL; EPLPALLC; PLPALLCI; LPALLCIL; PALLCILL;
ALLCILLK; LLCILLKK; LCILLKKK; CILLKKKL; ILLKKKLK; LLKKKLKF; LKKKLKFC;
KKKLKFCI; KKLKFCIK; KLKFCIKN; LKFCIKNL; KFCIKNLW; FCIKNLWK; CIKNLWKN;
IKNLWKNI; KNLWKNIL; LLLVDTCV; LLVDTCVL; LVDTCVLG; VDTCVLGI; DTCVLGII;
TCVLGIIL; CVLGIILY; VLGIILYS; LGIILYSF; LHIDIEFL; HIDIEFLQ; IDIEFLQL;
DIEFLQLI; IEFLQLII; EFLQLIIS; FLQLIISV; LQLIISVK; QLIISVKS; LIISVKSC;
IISVKSCV; ISVKSCVP; SVKSCVPL; VKSCVPLV; KSCVPLVF; FVRVLIRN; VRVLIRNT;
RVLIRNTY; VLIRNTYY; LIRNTYYI; IRNTYYIV; RNTYYIVP; RSMILAQK; SMILAQKS;
MILAQKSL; ILAQKSLK; LAQKSLKK; AQKSLKKQ; QKSLKKQS; KSLKKQSR; SLKKQSRC;
LKKQSRCL; KKQSRCLG; KQSRCLGN; RQSVRMCF; QSVRMCFY; SVRMCFYY; RSVKSVRK;
SVKSVRKK; VKSVRKKT; KSVRKKTS; SVRKKTSL; VRKKTSLI; RKKTSLIT; KKTSLITL;
KTSLITLS; TSLITLSI; SLITLSIM; LITLSIMK; ITLSIMKS; TLSIMKST; LSIMKSTL;
SIMKSTLQ; IMKSTLQM; MKSTLQML; KSTLQMLL; STLQMLLF; TLQMLLFL; LQMLLFLQ;
QMLLFLQK; MLLFLQKV; LLFLQKVK; LFLQKVKI; FLQKVKIK; LQKVKIKK; QKVKIKKV;
KVKIKKVF; VKIKKVFV; KIKKVFVS; IKKVFVSK; KKVFVSKQ; YLELMEML; LELMEMLY;
NNIWQVLL; NIWQVLLG; IWQVLLGC; WQVLLGCT; QVLLGCTV; VLLGCTVC; LLGCTVCY;
LGCTVCYL; GCTVCYLK; CTVCYLKW; TVCYLKWI; VCYLKWIL; YLIFCTVL; LIFCTVLF;
IFCTVLFS; FCTVLFSM; CTVLFSMY; TVLFSMYL; VLFSMYLK; LFSMYLKE; FSMYLKED;
SMYLKEDT; MYLKEDTG; YLKEDTGY; LKEDTGYL; KEDTGYLK; EDTGYLKV; DTGYLKVP;
TGYLKVPL; GYLKVPLI; YLKVPLIV; LKVPLIVE; KVPLIVEK; VPLIVEKQ; PLIVEKQH;
ISTWLFLK; STWLFLKM; KGQELNQR; GQELNQRI; QELNQRIC; ELNQRICL; LNQRICLQ;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

NQRICLQD; QRICLQDM; RICLQDME; TKEPKYFH; KEPKYFHQ; EPKYFHQA; PKYFHQAW;
KYFHQAWL; YFHQAWLQ; MSILSLKP; SILSLKPC; ILSLKPCK; LSLKPCKL; SLKPCKLD;
LKPCKLDL; ENPYKTQS; NPYKTQSS; PYKTQSSY; YKTQSSYL; KTQSSYLK; TQSSYLKK;
QSSYLKKE; SSYLKKEF; SYLKKEFY; YLKKEFYK; LKKEFYKV; KKEFYKVE; LILQLIYN;
ILQLIYNL; LQLIYNLE; QLIYNLEL; LIYNLELL; IYNLELLN; YNLELLNG; NLELLNGR;
LELLNGRK; ELLNGRKG; LLNGRKGW; LNGRKGWI; NGRKGWIL; GRKGWILR; NIIYAWGN;
IIYAWGNV; IYAWGNVF; YAWGNVFL; AWGNVFLI; WGNVFLIL; GNVFLILQ; NVFLILQE;
VFLILQEK; FLILQEKR; LILQEKRI; ILQEKRIQ; LQEKRIQK; QEKRIQKL; EKRIQKLK;
KRIQKLKT; RIQKLKTL; IQKLKTLD; QKLKTLDM; KLKTLDMD; LKTLDMDQ; KTLDMDQA;
TLDMDQAL; LDMDQALN; DMDQALNP; MDQALNPN; DQALNPNH; QALNPNHN; ALNPNHNA;
LNPNHNAL; NPNHNALP; PNHNALPK; NHNALPKS; HNALPKSQ; NALPKSQI; ALPKSQIL;
LPKSQILQ; PKSQILQP; KSQILQPL; SQILQPLL; QILQPLLK; ILQPLLKI; LQPLLKIP;
QPLLKIPK; PLLKIPKG; LLKIPKGQ; LKIPKGQT; KIPKGQTP; IPKGQTPI; PKGQTPIV;
KGQTPIVK; GQTPIVKS; QTPIVKSC; TPIVKSCI; PIVKSCIC; IVKSCICV; VKSCICVK;
KSCICVKA; SCICVKAF; CICVKAFS; ICVKAFSV; CVKAFSVL; VKAFSVLK; KAFSVLKG;
AFSVLKGL; FSVLKGLK; SVLKGLKH; VLKGLKHH; LKGLKHHP; KGLKHHPQ; GLKHHPQN;
LKHHPQNN; KHHPQNNT; HHPQNNTS; HPQNNTSL; PQNNTSLK; QNNTSLKV; NNTSLKVA;
NTSLKVAY; TSLKVAYT; SLKVAYTK; LKVAYTKA; KVAYTKAA; VAYTKAAF; AYTKAAFI;
YTKAAFIK; TKAAFIKC; KAAFIKCI; AAFIKCIC; AFIKCICT; FIKCICTI; IKCICTIK;
KCICTIKA; CICTIKAP; ICTIKAPV; SILVCNCP; ILVCNCPC; LVCNCPCL; VCNCPCLS;
CNCPCLSI; NCPCLSIY; CPCLSIYL; PCLSIYLI; CLSIYLII; LSIYLIIS; SIYLIISG;
IYLIISGS; YLIISGSP; LIISGSPG; IISGSPGS; ISGSPGSL; SGSPGSLS; GSPGSLSV;
SPGSLSVP; PGSLSVPS; GSLSVPSN; SLSVPSNT; LSVPSNTL; SVPSNTLT; VPSNTLTS;
PSNTLTSS; SNTLTSST; NTLTSSTW; TLTSSTWD; LTSSTWDS; TSSTWDSI; SSTWDSIP;
STWDSIPY; TWDSIPYI; WDSIPYIG; DSIPYIGC; SIPYIGCP; IPYIGCPS; PYIGCPST;
YIGCPSTL; IGCPSTLW; GCPSTLWV; CPSTLWVL; PSTLWVLL; STLWVLLF; TLWVLLFI;
LWVLLFIR; WVLLFIRS; VLLFIRSL; LLFIRSLS; LFIRSLSK; FIRSLSKK; IRSLSKKE;
RSLSKKEI; SLSKKEIG; GFFTDLFL; FFTDLFLR; FTDLFLRR; TDLFLRRI; DLFLRRIL;
LFLRRILK; FLRRILKY; LRRILKYL; RRILKYLA; RILKYLAR; ILKYLARP; LKYLARPL;
KYLARPLH; YLARPLHC; LARPLHCC; ARPLHCCV; RPLHCCVP; PLHCCVPE; LHCCVPEL;
HCCVPELL; CCVPELLV; CVPELLVN; VPELLVNR; PELLVNRP; ELLVNRPQ; LLVNRPQI;
LVNRPQIS; VNRPQISA; NRPQISAA; RPQISAAE; PQISAAET; QISAAETY; ISAAETYR;
SAAETYRL; AAETYRLS; AETYRLSA; ETYRLSAL; TYRLSALQ; YRLSALQR; RLSALQRG;
LSALQRGP; SALQRGPT; ALQRGPTP; LQRGPTPC; QRGPTPCS; RGPTPCSS; GPTPCSSS;
PTPCSSSN; TPCSSSNT; PCSSSNTV; CSSSNTVV; SSSNTVVA; SSNTVVAV; SNTVVAVL;
NTVVAVLV; TVVAVLVT; STGGTFSP; TGGTFSPP; GGTFSPPV; GTFSPPVK; TFSPPVKV;
FSPPVKVP; SPPVKVPK; PPVKVPKY; PVKVPKYL; VKVPKYLA; KVPKYLAF; VPKYLAFS;
PKYLAFSF; KYLAFSFL; YLAFSFLL; LAFSFLLG; AFSFLLGS; FSFLLGSG; SFLLGSGT;
FLLGSGTQ; LLGSGTQH; LGSGTQHS; GSGTQHST; SGTQHSTG; ALWSVFIT; LWSVFITW;
WSVFITWD; SVFITWDW; VFITWDWA; FITWDWAV; ITWDWAVG; TWDWAVGF; WDWAVGFL;
DWAVGFLG; WAVGFLGV; AVGFLGVI; VGFLGVIV; GFLGVIVP; FLGVIVPS; LGVIVPSG;
GVIVPSGY; VIVPSGYF; IVPSGYFD; VPSGYFDL; FISTPCIS; ISTPCISK; STPCISKG;
TPCISKGS; PCISKGSP; CISKGSPP; ISKGSPPT; SKGSPPTA; KGSPPTAK; GSPPTAKK;
SPPTAKKW; PPTAKKWK; PTAKKWKL; TAKKWKLL; AKKWKLLP; IGFPPPCS; GFPPPCSC;
FPPPCSCT; PPPCSCTF; PPCSCTFC; PCSCTFCD; CSCTFCDP; SCTFCDPA; RLSMLVIP;
LSMLVIPI; SMLVIPIT; MLVIPITS; LVIPITSV; VIPITSVC; IPITSVCT; PITSVCTV;
ITSVCTVT; TSVCTVTA; SVCTVTAS; VCTVTASH; CTVTASHI; TVTASHIS; VTASHISR;
TASHISRF; ASHISRFP; SHISRFPQ; HISRFPQV; ISRFPQVR; SRFPQVRS; RFPQVRSS;
FPQVRSSF; PQVRSSFK; QVRSSFKL; VRSSFKLG; RSSFKLGR; SSFKLGRG; SFKLGRGI;
FKLGRGIL; KLGRGILA; LGRGILAV; GRGILAVL; QGSIFLSG; GSIFLSGL; SIFLSGLS;
IFLSGLSL; FLSGLSLL; LSGLSLLK; SGLSLLKS; GLSLLKSF; LSLLKSFS; SLLKSFSA;
LLKSFSAL; LKSFSALS; KSFSALSF; SFSALSFR; FSALSFRL; SALSFRLK; ALSFRLKP;
LSFRLKPL; SFRLKPLR; FRLKPLRF; RLKPLRFS; LKPLRFSS; KPLRFSSG; PLRFSSGS;
LRFSSGSP; RFSSGSPI; FSSGSPIS; SSGSPISG; SGSPISGF; GSPISGFR; SPISGFRK;
PISGFRKH; ISGFRKHS; SGFRKHST; GFRKHSTS; FRKHSTSV; RKHSTSVI; KHSTSVIA;
HSTSVIAS; STSVIAST; TSVIASTP; SVIASTPV; VIASTPVL; IASTPVLT; ASTPVLTS;
STPVLTSR; TPVLTSRT; PVLTSRTS; VLTSRTST; LTSRTSTP; TSRTSTPP; SRTSTPPF;
RTSTPPFI; TSTPPFIS; STPPFISS; TPPFISSF; PPFISSFG; PFISSFGT; FISSFGTC;
ISSFGTCT; SSFGTCTG; SFGTCTGS; FGTCTGSF; GTCTGSFG; TCTGSFGF; CTGSFGFL;
TGSFGFLG; GSFGFLGA; SFGFLGAA; FGFLGAAP; GFLGAAPG; FLGAAPGH; LGAAPGHS;
GAAPGHSP; AAPGHSPF; APGHSPFL; PGHSPFLL; GHSPFLLV; HSPFLLVG; SPFLLVGA;
PFLLVGAI; FLLVGAIF; LLVGAIFI; LVGAIFIC; VGAIFICF; GAIFICFK; AIFICFKS;
IFICFKSR; FICFKSRC; ICFKSRCY; CFKSRCYS; FKSRCYSP; KSRCYSPV; SRCYSPVQ;
RCYSPVQA; RQHPLRSS; QHPLRSSS; HPLRSSSL; PLRSSSLI; LRSSSLIS; RSSSLIST;
SSSLISTS; SSLISTSW; SLISTSWG; LISTSWGN; ISTSWGNS; STSWGNSF; TSWGNSFF;
SWGNSFFY; WGNSFFYK; GNSFFYKL; NSFFYKLS; VHSLCNFF; HSLCNFFY; SLCNFFYT;
LCNFFYTV; CNFFYTVS; NFFYTVSI; FFYTVSII; FYTVSIIY; YTVSIIYT; TVSIIYTI;
VSIIYTIS; SIIYTISM; IIYTISMA; IYTISMAK; YTISMAKM; TISMAKMY; ISMAKMYT;
SMAKMYTG; MAKMYTGT; AKMYTGTF; KMYTGTFP; MYTGTFPF; YTGTFPPS; TGTFPFSY;
GTFPFSYL; TFPFSYLS; FPFSYLSN; PFSYLSNH; GPNRGKIR; PNRGKIRI; NRGKIRII;
RGKIRIIL; GKIRIILL; KIRIILLN; IRIILLNI; RIILLNII; IILLNIII; ILLNIIIK;
LLNIIIKV; LNIIIKVY; NIIIKVYR; IIIKVYRG; IIKVYRGI; IKVYRGIY; KVYRGIYN;
VYRGIYNC; YRGIYNCP; RGIYNCPG; GIYNCPGS; IYNCPGSF; YNCPGSFL; NCPGSFLQ;
CPGSFLQK; PGSFLQKS; GSFLQKSS; SFLQKSSQ; FLQKSSQG; LQKSSQGV; QKSSQGVS;
KSSQGVSK; SSQGVSKK; SQGVSKKS; QGVSKKSF; GVSKKSFC; VSKKSFCS; SKKSFCSS;
KKSFCSSL; KSFCSSLQ; SFCSSLQF; FCSSLQFL; GYRRYIIP; YRRYIIPN; RRYIIPNN;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

RYIIPNNM; YIIPNNMP; IIPNNMPQ; IPNNMPQS; PNNMPQSL; NNMPQSLG; NMPQSLGN;
MPQSLGNS; PQSLGNSS; QSLGNSSK; SLGNSSKQ; LGNSSKQR; GNSSKQRR; NSSKQRRT;
SSKQRRTP; SKQRRTPM; KQRRTPMP; QRRTPMPR; RRTPMPRI; RTPMPRIK; TPMPRIKV;
PMPRIKVL; MPRIKVLN; PRIKVLNI; RIKVLNII; IKVLNIIN; KVLNIINK; VLNIINKS;
LNIINKSI; NIINKSIY; IINKSIYT; INKSIYTR; NKSIYTRK; KSIYTRKQ; SIYTRKQN;
IYTRKQNI; YTRKQNII; TRKQNIIV; RKQNIIVL; KQNIIVLI; QNIIVLIW; NIIVLIWV;
IIVLIWVK; IVLIWVKQ; VLIWVKQF; LIWVKQFQ; IWVKQFQS; WVKQFQSH; VKQFQSHA;
LLIEAYSG; LIEAYSGN; IEAYSGNF; EAYSGNFV; AYSGNFVI; YSGNFVIP; SGNFVIPI;
GNFVIPII; NFVIPIIK; FVIPIIKE; VIPIIKEL; IPIIKELI; PIIKELIP; IIKELIPY;
IKELIPYL; KELIPYLS; GTNTTNSL; TNTTNSLN; SSKPSNSP; SKPSNSPR; KPSNSPRS;
PSNSPRST; SNSPRSTS; NSPRSTSN; SPRSTSNY; PRSTSNYS; RSTSNYSI; STSNYSIC;
TSNYSICL; SNYSICLR; NYSICLRS; GTCYALYS; TCYALYSS; CYALYSSK; YALYSSKG;
ALYSSKGC; LYSSKGCN; YSSKGCNL; SSKGCNLN; SKGCNLNF; KGCNLNFY; GCNLNFYS;
CNLNFYSS; NLNFYSSS; LNFYSSSS; NFYSSSSL; FYSSSSLP; YSSSSLPS; SSSSLPSS;
SSSLPSSN; SSLPSSNF; SLPSSNFS; LPSSNFSH; KSCGSSSL; SCGSSSLR; CGSSSLRY;
GSSSLRYT; SSSLRYTG; SSLRYTGN; SSTHEPGN; STHEPGNT; THEPGNTK; HEPGNTKK;
EPGNTKKK; PGNTKKKG; GNTKKKGL; NTKKKGLL; TKKKGLLT; ESFTESFT; SFTESFTA;
FTESFTAG; TESFTAGK; ESFTAGKA; SFTAGKAV; FTAGKAVV; TAGKAVVL; AGKAVVLL;
GKAVVLLF; KAVVLLFF; AVVLLFFP; VVLLFFPS; VLLFFPST; LLFFPSTL; LFFPSTLS;
FFPSTLSS; FPSTLSSP; PSTLSSPL; STLSSPLQ; TLSSPLQN; LSSPLQNS; SSPLQNSS;
SPLQNSSK; PLQNSSKS; LQNSSKSS; QNSSKSSK; NSSKSSKI; SSKSSKIK; SKSSKIKI;
KSSKIKIK; SSKIKIKI; SKIKIKIL; ALFFVPVQ; LFFVPVQV; FFVPVQVL; FVPVQVLP;
VPVQVLPT; PVQVLPTF; VQVLPTFT; QVLPTFTE; VLPTFTEA; LPTFTEAC; PTFTEACR;
TFTEACRD; FTEACRDS; TEACRDSW; EACRDSWR; ACRDSWRR; CRDSWRRT; RDSWRRTM;
DSWRRTMA; SWRRTMAF; WRRTMAFV; RRTMAFVQ; RTMAFVQF; TMAFVQFN; MAFVQFNW;
AFVQFNWG; FVQFNWGQ; VQFNWGQG; QFNWGQGQ; FNWGQGQD; NWGQGQDS; ARKTCLSC;
RKTCLSCT; KTCLSCTF; TCLSCTFL; CLSCTFLP; LSCTFLPE; SCTFLPEV; CTFLPEVM;
TFLPEVMV; FLPEVMVW; LPEVMVWL; PEVMVWLH; EVMVWLHS; VMVWLHSM; MVWLHSMG;
VWLHSMGK; WLHSMGKQ; LHSMGKQL; HSMGKQLL; SMGKQLLP; MGKQLLPV; GKQLLPVS;
KQLLPVSH; QLLPVSHA; LLPVSHAL; LPVSHALS; PVSHALSF; VSHALSFL; SHALSFLR;
HALSFLRS; ALSFLRSW; LSFLRSWF; SFLRSWFG; FLRSWFGC; LRSWFGCI; RSWFGCIP;
SWFGCIPL; GHGLAAFH; HGLAAFHG; AAPPCGLF; APPCGLFF; PPCGLFFY; PCGLFFYN;
CGLFFYNI; EAEAASAS; AEAASAST; EAASASTL; AASASTLS; ASASTLSL; SASTLSLK;
GLAKLFGE; LAKLFGEI; AKLFGEIP; KLFGEIPI; LFGEIPIL; FGEIPILL; GEIPILLQ;
EIPILLQF; IPILLQFL; PILLQFLQ

---

9 mers:

MDKVLNREE; DKVLNREES; KVLNREESM; VLNREESME; LNREESMEL; NREESMELM;
REESMELMD; EESMELMDL; ESMELMDLL; SMELMDLLG; MELMDLLGL; ELMDLLGLE;
LMDLLGLER; MDLLGLERA; DLLGLERAA; LLGLERAAW; LGLERAAWG; GLERAAWGN;
LERAAWGNL; ERAAWGNLP; RAAWGNLPL; AAWGNLPLM; AWGNLPLMR; WGNLPLMRK;
GNLPLMRKA; NLPLMRKAY; LPLMRKAYL; PLMRKAYLR; LMRKAYLRK; MRKAYLRKC;
RKAYLRKCK; KAYLRKCKE; AYLRKCKEF; YLRKCKEFH; LRKCKEFHP; RKCKEFHPD;
KCKEFHPDK; CKEFHPDKG; KEFHPDKGG; EFHPDKGGD; FHPDKGGDE; HPDKGGDED;
PDKGGDEDK; DKGGDEDKM; KGGDEDKMK; GGDEDKMKR; GDEDKMKRM; DEDKMKRMN;
EDKMKRMNT; DKMKRMNTL; KMKRMNTLY; MKRMNTLYK; KRMNTLYKK; RMNTLYKKM;
MNTLYKKME; NTLYKKMEQ; TLYKKMEQD; LYKKMEQDV; YKKMEQDVK; KKMEQDVKV;
KMEQDVKVA; MEQDVKVAH; EQDVKVAHQ; QDVKVAHQP; DVKVAHQPD; VKVAHQPDF;
KVAHQPDFG; VAHQPDFGT; AHQPDFGTW; HQPDFGTWS; QPDFGTWSS; PDFGTWSSS;
DFGTWSSSE; FGTWSSSEV; GTWSSSEVC; TWSSSEVCA; WSSSEVCAD; SSSEVCADF;
SSEVCADFP; SEVCADFPL; EVCADFPLC; VCADFPLCP; CADFPLCPD; ADFPLCPDT;
DFPLCPDTL; FPLCPDTLY; PLCPDTLYC; LCPDTLYCK; CPDTLYCKE; PDTLYCKEW;
DTLYCKEWP; TLYCKEWPI; LYCKEWPIC; YCKEWPICS; CKEWPICSK; KEWPICSKK;
EWPICSKKP; WPICSKKPS; PICSKKPSV; ICSKKPSVH; CSKKPSVHC; SKKPSVHCP;
KKPSVHCPC; KPSVHCPCM; PSVHCPCML; SVHCPCMLC; VHCPCMLCQ; HCPCMLCQL;
CPCMLCQLR; PCMLCQLRL; CMLCQLRLR; MLCQLRLRH; LCQLRLRHL; CQLRLRHLN;
QLRLRHLNR; LRLRHLNRK; RLRHLNRKF; LRHLNRKFL; RHLNRKFLR; HLNRKFLRK;
LNRKFLRKE; NRKFLRKEP; RKFLRKEPL; KFLRKEPLV; FLRKEPLVW; LRKEPLVWI;
RKEPLVWID; KEPLVWIDC; EPLVWIDCY; PLVWIDCYC; LVWIDCYCI; VWIDCYCID;
WIDCYCIDC; IDCYCIDCF; DCYCIDCFT; CYCIDCFTQ; YCIDCFTQW; CIDCFTQWF;
IDCFTQWFG; DCFTQWFGL; CFTQWFGLD; FTQWFGLDL; TQWFGLDLT; QWFGLDLTE;
WFGLDLTEE; FGLDLTEET; GLDLTEETL; LDLTEETLQ; DLTEETLQW; LTEETLQWW;
TEETLQWWV; EETLQWWVQ; ETLQWWVQI; TLQWWVQII; LQWWVQIIG; QWWVQIIGE;
WWVQIIGET; WVQIIGETP; VQIIGETPF; QIIGETPFR; IIGETPFRD; IGETPFRDL;
GETPFRDLK; ETPFRDLKL; KALSNYFFY; ALSNYFFYR; LSNYFFYRC; SNYFFYRCQ;
NYFFYRCQP; YFFYRCQPM; FFYRCQPME; FYRCQPMEQ; YRCQPMEQK; RCQPMEQKS;
CQPMEQKSG; QPMEQKSGS; PMEQKSGSP; MEQKSGSPG; EQKSGSPGG; QKSGSPGGV;
KSGSPGGVP; SGSPGGVPL; GSPGGVPLM; SPGGVPLMK; PGGVPLMKN; GGVPLMKNG;
GVPLMKNGM; VPLMKNGMK; PLMKNGMKI; LMKNGMKIY; MKNGMKIYF; KNGMKIYFA;
NGMKIYFAM; GMKIYFAMK; MKIYFAMKI; KIYFAMKIC; IYFAMKICL; YFAMKICLP;
FAMKICLPV; AMKICLPVM; MKICLPVMK; KICLPVMKK; ICLPVMKKQ; CLPVMKKQQ;
LPVMKKQQQ; PVMKKQQQI; VMKKQQQIL; MKKQQQILN; KKQQQILNT; KQQQILNTQ;
QQQILNTQH; QQILNTQHH; QILNTQHHP; ILNTQHHPK; LNTQHHPKK; NTQHHPKKK;
TQHHPKKKE; QHHPKKKER; KTLKTFPLI; TLKTFPLIY; LKTFPLIYT; KTFPLIYTS;
TFPLIYTSF; FPLIYTSFL; PLIYTSFLV; LIYTSFLVK; IYTSFLVKL; YTSFLVKLY;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

TSFLVKLYL; SFLVKLYLV; FLVKLYLVI; LVKLYLVIE; VKLYLVIEP; KLYLVIEPL;
LYLVIEPLP; YLVIEPLPA; LVIEPLPAL; VIEPLPALL; IEPLPALLC; EPLPALLCI;
PLPALLCIL; LPALLCILL; PALLCILLK; ALLCILLKK; LLCILLKKK; LCILLKKKL;
CILLKKKLK; ILLKKKLKF; LLKKKLKFC; LKKKLKFCI; KKKLKFCIK; KKLKFCIKN;
KLKFCIKNL; LKFCIKNLW; KFCIKNLWK; FCIKNLWKN; CIKNLWKNI; IKNLWKNIL;
LLLVDTCVL; LLVDTCVLG; LVDTCVLGI; VDTCVLGII; DTCVLGIIL; TCVLGIILY;
CVLGIILYS; VLGIILYSF; LHIDIEFLQ; HIDIEFLQL; IDIEFLQLI; DIEFLQLII;
IEFLQLIIS; EFLQLIISV; FLQLIISVK; LQLIISVKS; QLIISVKSC; LIISVKSCV;
IISVKSCVP; ISVKSCVPL; SVKSCVPLV; VKSCVPLVF; FVRVLIRNT; VRVLIRNTY;
RVLIRNTYY; VLIRNTYYI; LIRNTYYIV; IRNTYYIVP; RSMILAQKS; SMILAQKSL;
MILAQKSLK; ILAQKSLKK; LAQKSLKKQ; AQKSLKKQS; QKSLKKQSR; KSLKKQSRC;
SLKKQSRCL; LKKQSRCLG; KKQSRCLGN; RQSVRMCFY; QSVRMCFYY; RSVKSVRKK;
SVKSVRKKT; VKSVRKKTS; KSVRKKTSL; SVRKKTSLI; VRKKTSLIT; RKKTSLITL;
KKTSLITLS; KTSLITLSI; TSLITLSIM; SLITLSIMK; LITLSIMKS; ITLSIMKST;
TLSIMKSTL; LSIMKSTLQ; SIMKSTLQM; IMKSTLQML; MKSTLQMLL; KSTLQMLLF;
STLQMLLFL; TLQMLLFLQ; LQMLLFLQK; QMLLFLQKV; MLLFLQKVK; LLFLQKVKI;
LFLQKVKIK; FLQKVKIKK; LQKVKIKKV; QKVKIKKVF; KVKIKKVFV; VKIKKVFVS;
KIKKVFVSK; IKKVFVSKQ; YLELMEMLY; NNIWQVLLG; NIWQVLLGC; IWQVLLGCT;
WQVLLGCTV; QVLLGCTVC; VLLGCTVCY; LLGCTVCYL; LGCTVCYLK; GCTVCYLKW;
CTVCYLKWI; TVCYLKWIL; YLIFCTVLF; LIFCTVLFS; IFCTVLFSM; FCTVLFSMY;
CTVLFSMYL; TVLFSMYLK; VLFSMYLKE; LFSMYLKED; FSMYLKEDT; SMYLKEDTG;
MYLKEDTGY; YLKEDTGYL; LKEDTGYLK; KEDTGYLKV; EDTGYLKVP; DTGYLKVPL;
TGYLKVPLI; GYLKVPLIV; YLKVPLIVE; LKVPLIVEK; KVPLIVEKQ; VPLIVEKQH;
ISTWLFLKM; KGQELNQRI; GQELNQRIC; QELNQRICL; ELNQRICLQ; LNQRICLQD;
NQRICLQDM; QRICLQDME; TKEPKYFHQ; KEPKYFHQA; EPKYFHQAW; PKYFHQAWL;
KYFHQAWLQ; MSILSLKPC; SILSLKPCK; ILSLKPCKL; LSLKPCKLD; SLKPCKLDL;
ENPYKTQSS; NPYKTQSSY; PYKTQSSYL; YKTQSSYLK; KTQSSYLKK; TQSSYLKKE;
QSSYLKKEF; SSYLKKEFY; SYLKKEFYK; YLKKEFYKV; LKKEFYKVE; LILQLIYNL;
ILQLIYNLE; LQLIYNLEL; QLIYNLELL; LIYNLELLN; IYNLELLNG; YNLELLNGR;
NLELLNGRK; LELLNGRKG; ELLNGRKGW; LLNGRKGWI; LNGRKGWIL; NGRKGWILR;
NIIYAWGNV; IIYAWGNVF; IYAWGNVFL; YAWGNVFLI; AWGNVFLIL; WGNVFLILQ;
GNVFLILQE; NVFLILQEK; VFLILQEKR; FLILQEKRI; LILQEKRIQ; ILQEKRIQK;
LQEKRIQKL; QEKRIQKLK; EKRIQKLKT; KRIQKLKTL; RIQKLKTLD; IQKLKTLDM;
QKLKTLDMD; KLKTLDMDQ; LKTLDMDQA; KTLDMDQAL; TLDMDQALN; LDMDQALNP;
DMDQALNPN; MDQALNPNH; DQALNPNHN; QALNPNHNA; ALNPNHNAL; LNPNHNALP;
NPNHNALPK; PNHNALPKS; NHNALPKSQ; HNALPKSQI; NALPKSQIL; ALPKSQILQ;
LPKSQILQP; PKSQILQPL; KSQILQPLL; SQILQPLLK; QILQPLLKI; ILQPLLKIP;
LQPLLKIPK; QPLLKIPKG; PLLKIPKGQ; LLKIPKGQT; LKIPKGQTP; KIPKGQTPI;
IPKGQTPIV; PKGQTPIVK; KGQTPIVKS; GQTPIVKSC; QTPIVKSCI; TPIVKSCIC;
PIVKSCICV; IVKSCICVK; VKSCICVKA; KSCICVKAF; SCICVKAFS; CICVKAFSV;
ICVKAFSVL; CVKAFSVLK; VKAFSVLKG; KAFSVLKGL; AFSVLKGLK; FSVLKGLKH;
SVLKGLKHH; VLKGLKHHP; LKGLKHHPQ; KGLKHHPQN; GLKHHPQNN; LKHHPQNNT;
KHHPQNNTS; HHPQNNTSL; HPQNNTSLK; PQNNTSLKV; QNNTSLKVA; NNTSLKVAY;
NTSLKVAYT; TSLKVAYTK; SLKVAYTKA; LKVAYTKAA; KVAYTKAAF; VAYTKAAFI;
AYTKAAFIK; YTKAAFIKC; TKAAFIKCI; KAAFIKCIC; AAFIKCICT; AFIKCICTI;
FIKCICTIK; IKCICTIKA; KCICTIKAP; CICTIKAPV; ICTIKAPVS; ILVCNCPCL;
LVCNCPCLS; VCNCPCLSI; CNCPCLSIY; NCPCLSIYL; CPCLSIYLI; PCLSIYLII;
CLSIYLIIS; LSIYLIISG; SIYLIISGS; IYLIISGSP; YLIISGSPG; LIISGSPGS;
IISGSPGSL; ISGSPGSLS; SGSPGSLSV; GSPGSLSVP; SPGSLSVPS; PGSLSVPSN;
GSLSVPSNT; SLSVPSNTL; LSVPSNTLT; SVPSNTLTS; VPSNTLTSS; PSNTLTSST;
SNTLTSSTW; NTLTSSTWD; TLTSSTWDS; LTSSTWDSI; TSSTWDSIP; SSTWDSIPY;
STWDSIPYI; TWDSIPYIG; WDSIPYIGC; DSIPYIGCP; SIPYIGCPS; IPYIGCPST;
PYIGCPSTL; YIGCPSTLW; IGCPSTLWV; GCPSTLWVL; CPSTLWVLL; PSTLWVLLF;
STLWVLLFI; TLWVLLFIR; LWVLLFIRS; WVLLFIRSL; VLLFIRSLS; LLFIRSLSK;
LFIRSLSKK; FIRSLSKKE; IRSLSKKEI; RSLSKKEIG; GFFTDLFLR; FFTDLFLRR;
FTDLFLRRI; TDLFLRRIL; DLFLRRILK; LFLRRILKY; FLRRILKYL; LRRILKYLA;
RRILKYLAR; RILKYLARP; ILKYLARPL; LKYLARPLH; KYLARPLHC; YLARPLHCC;
LARPLHCCV; ARPLHCCVP; RPLHCCVPE; PLHCCVPEL; LHCCVPELL; HCCVPELLV;
CCVPELLVN; CVPELLVNR; VPELLVNRP; PELLVNRPQ; ELLVNRPQI; LLVNRPQIS;
LVNRPQISA; VNRPQISAA; NRPQISAAE; RPQISAAET; PQISAAETY; QISAAETYR;
ISAAETYRL; SAAETYRLS; AAETYRLSA; AETYRLSAL; ETYRLSALQ; TYRLSALQR;
YRLSALQRG; RLSALQRGP; LSALQRGPT; SALQRGPTP; ALQRGPTPC; LQRGPTPCS;
QRGPTPCSS; RGPTPCSSS; GPTPCSSSN; PTPCSSSNT; TPCSSSNTV; PCSSSNTVV;
CSSSNTVVA; SSSNTVVAV; SSNTVVAVL; SNTVVAVLV; NTVVAVLVT; STGGTFSPP;
TGGTFSPPV; GGTFSPPVK; GTFSPPVKV; TFSPPVKVP; FSPPVKVPK; SPPVKVPKY;
PPVKVPKYL; PVKVPKYLA; VKVPKYLAF; KVPKYLAFS; VPKYLAFSF; PKYLAFSFL;
KYLAFSFLL; YLAFSFLLG; LAFSFLLGS; AFSFLLGSG; FSFLLGSGT; SFLLGSGTQ;
FLLGSGTQH; LLGSGTQHS; LGSGTQHST; GSGTQHSTG; ALWSVFITW; LWSVFITWD;
WSVFITWDW; SVFITWDWA; VFITWDWAV; FITWDWAVG; ITWDWAVGF; TWDWAVGFL;
WDWAVGFLG; DWAVGFLGV; WAVGFLGVI; AVGFLGVIV; VGFLGVIVP; GFLGVIVPS;
FLGVIVPSG; LGVIVPSGY; GVIVPSGYF; VIVPSGYFD; IVPSGYFDL; FISTPCISK;
ISTPCISKG; STPCISKGS; TPCISKGSP; PCISKGSPP; CISKGSPPT; ISKGSPPTA;
SKGSPPTAK; KGSPPTAKK; GSPPTAKKW; SPPTAKKWK; PPTAKKWKL; PTAKKWKLL;
TAKKWKLLP; IGFPPPCSC; GFPPPCSCT; FPPPCSCTF; PPPCSCTFC; PPCSCTFCD;
PCSCTFCDP; CSCTFCDPA; RLSMLVIPI; LSMLVIPIT; SMLVIPITS; MLVIPITSV;
LVIPITSVC; VIPITSVCT; IPITSVCTV; PITSVCTVT; ITSVCTVTA; TSVCTVTAS;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

SVCTVTASH; VCTVTASHI; CTVTASHIS; TVTASHISR; VTASHISRF; TASHISRFP;
ASHISRFPQ; SHISRFPQV; HISRFPQVR; ISRFPQVRS; SRFPQVRSS; RFPQVRSSF;
FPQVRSSFK; PQVRSSFKL; QVRSSFKLG; VRSSFKLGR; RSSFKLGRG; SSFKLGRGI;
SFKLGRGIL; FKLGRGILA; KLGRGILAV; LGRGILAVL; QGSIFLSGL; GSIFLSGLS;
SIFLSGLSL; IFLSGLSLL; FLSGLSLLK; LSGLSLLKS; SGLSLLKSF; GLSLLKSFS;
LSLLKSFSA; SLLKSFSAL; LLKSFSALS; LKSFSALSF; KSFSALSFR; SFSALSFRL;
FSALSFRLK; SALSFRLKP; ALSFRLKPL; LSFRLKPLR; SFRLKPLRF; FRLKPLRFS;
RLKPLRFSS; LKPLRFSSG; KPLRFSSGS; PLRFSSGSP; LRFSSGSPI; RFSSGSPIS;
FSSGSPISG; SSGSPISGF; SGSPISGFR; GSPISGFRK; SPISGFRKH; PISGFRKHS;
ISGFRKHST; SGFRKHSTS; GFRKHSTSV; FRKHSTSVI; RKHSTSVIA; KHSTSVIAS;
HSTSVIAST; STSVIASTP; TSVIASTPV; SVIASTPVL; VIASTPVLT; IASTPVLTS;
ASTPVLTSR; STPVLTSRT; TPVLTSRTS; PVLTSRTST; VLTSRTSTP; LTSRTSTPP;
TSRTSTPPF; SRTSTPPFI; RTSTPPFIS; TSTPPFISS; STPPFISSF; TPPFISSFG;
PPFISSFGT; PFISSFGTC; FISSFGTCT; ISSFGTCTG; SSFGTCTGS; SFGTCTGSF;
FGTCTGSFG; GTCTGSFGF; TCTGSFGFL; CTGSFGFLG; TGSFGFLGA; GSFGFLGAA;
SFGFLGAAP; FGFLGAAPG; GFLGAAPGH; FLGAAPGHS; LGAAPGHSP; GAAPGHSPF;
AAPGHSPFL; APGHSPFLL; PGHSPFLLV; GHSPFLLVG; HSPFLLVGA; SPFLLVGAI;
PFLLVGAIF; FLLVGAIFI; LLVGAIFIC; LVGAIFICF; VGAIFICFK; GAIFICFKS;
AIFICFKSR; IFICFKSRC; FICFKSRCY; ICFKSRCYS; CFKSRCYSP; FKSRCYSPV;
KSRCYSPVQ; SRCYSPVQA; RQHPLRSSS; QHPLRSSSL; HPLRSSSLI; PLRSSSLIS;
LRSSSLIST; RSSSLISTS; SSSLISTSW; SSLISTSWG; SLISTSWGN; LISTSWGNS;
ISTSWGNSF; STSWGNSFF; TSWGNSFFY; SWGNSFFYK; WGNSFFYKL; GNSFFYKLS;
VHSLCNFFY; HSLCNFFYT; SLCNFFYTV; LCNFFYTVS; CNFFYTVSI; NFFYTVSII;
FFYTVSIIY; FYTVSIIYT; YTVSIIYTI; TVSIIYTIS; VSIIYTISM; SIIYTISMA;
IIYTISMAK; IYTISMAKM; YTISMAKMY; TISMAKMYT; ISMAKMYTG; SMAKMYTGT;
MAKMYTGTF; AKMYTGTFP; KMYTGTFPF; MYTGTFPFS; YTGTFPFSY; TGTFPFSYL;
GTFPFSYLS; TFPFSYLSN; FPFSYLSNH; GPNRGKIRI; PNRGKIRII; NRGKIRIIL;
RGKIRIILL; GKIRIILLN; KIRIILLNI; IRIILLNII; RIILLNIII; IILLNIIIK;
ILLNIIIKV; LLNIIIKVY; LNIIIKVYR; NIIIKVYRG; IIIKVYRGI; IIKVYRGIY;
IKVYRGIYN; KVYRGIYNC; VYRGIYNCP; YRGIYNCPG; RGIYNCPGS; GIYNCPGSF;
IYNCPGSFL; YNCPGSFLQ; NCPGSFLQK; CPGSFLQKS; PGSFLQKSS; GSFLQKSSQ;
SFLQKSSQG; FLQKSSQGV; LQKSSQGVS; QKSSQGVSK; KSSQGVSKK; SSQGVSKKS;
SQGVSKKSF; QGVSKKSFC; GVSKKSFCS; VSKKSFCSS; SKKSFCSSL; KKSFCSSLQ;
KSFCSSLQF; SFCSSLQFL; GYRRYIIPN; YRRYIIPNN; RRYIIPNNM; RYIIPNNMP;
YIIPNNMPQ; IIPNNMPQS; IPNNMPQSL; PNNMPQSLG; NNMPQSLGN; NMPQSLGNS;
MPQSLGNSS; PQSLGNSSK; QSLGNSSKQ; SLGNSSKQR; LGNSSKQRR; GNSSKQRRT;
NSSKQRRTP; SSKQRRTPM; SKQRRTPMP; KQRRTPMPR; QRRTPMPRI; RRTPMPRIK;
RTPMPRIKV; TPMPRIKVL; PMPRIKVLN; MPRIKVLNI; PRIKVLNII; RIKVLNIIN;
IKVLNIINK; KVLNIINKS; VLNIINKSI; LNIINKSIY; NIINKSIYT; IINKSIYTR;
INKSIYTRK; NKSIYTRKQ; KSIYTRKQN; SIYTRKQNI; IYTRKQNII; YTRKQNIIV;
TRKQNIIVL; RKQNIIVLI; KQNIIVLIW; QNIIVLIWV; NIIVLIWVK; IIVLIWVKQ;
IVLIWVKQF; VLIWVKQFQ; LIWVKQFQS; IWVKQFQSH; WVKQFQSHA; LLIEAYSGN;
LIEAYSGNF; IEAYSGNFV; EAYSGNFVI; AYSGNFVIP; YSGNFVIPI; SGNFVIPII;
GNFVIPIIK; NFVIPIIKE; FVIPIIKEL; VIPIIKELI; IPIIKELIP; PIIKELIPY;
IIKELIPYL; IKELIPYLS; GTNTTNSLN; SSKPSNSPR; SKPSNSPRS; KPSNSPRST;
PSNSPRSTS; SNSPRSTSN; NSPRSTSNY; SPRSTSNYS; PRSTSNYSI; RSTSNYSIC;
STSNYSICL; TSNYSICLR; SNYSICLRS; GTCYALYSS; TCYALYSSK; CYALYSSKG;
YALYSSKGC; ALYSSKGCN; LYSSKGCNL; YSSKGCNLN; SSKGCNLNF; SKGCNLNFY;
KGCNLNFYS; GCNLNFYSS; CNLNFYSSS; NLNFYSSSS; LNFYSSSSL; NFYSSSSLP;
FYSSSSLPS; YSSSSLPSS; SSSSLPSSN; SSSLPSSNF; SSLPSSNFS; SLPSSNFSH;
KSCGSSSLR; SCGSSSLRY; CGSSSLRYT; GSSSLRYTG; SSSLRYTGN; SSTHEPGNT;
STHEPGNTK; THEPGNTKK; HEPGNTKKK; EPGNTKKKG; PGNTKKKGL; GNTKKKGLL;
NTKKKGLLT; ESFTESFTA; SFTESFTAG; FTESFTAGK; TESFTAGKA; ESFTAGKAV;
SFTAGKAVV; FTAGKAVVL; TAGKAVVLL; AGKAVVLLF; GKAVVLLFF; KAVVLLFFP;
AVVLLFFPS; VVLLFFPST; VLLFFPSTL; LLFFPSTLS; LFFPSTLSS; FFPSTLSSP;
FPSTLSSPL; PSTLSSPLQ; STLSSPLQN; TLSSPLQNS; LSSPLQNSS; SSPLQNSSK;
SPLQNSSKS; PLQNSSKSS; LQNSSKSSK; QNSSKSSKI; NSSKSSKIK; SSKSSKIKI;
SKSSKIKIK; KSSKIKIKI; SSKIKIKIL; ALFFVPVQV; LFFVPVQVL; FFVPVQVLP;
FVPVQVLPT; VPVQVLPTF; PVQVLPTFT; VQVLPTFTE; QVLPTFTEA; VLPTFTEAC;
LPTFTEACR; PTFTEACRD; TFTEACRDS; FTEACRDSW; TEACRDSWR; EACRDSWRR;
ACRDSWRRT; CRDSWRRTM; RDSWRRTMA; DSWRRTMAF; SWRRTMAFV; WRRTMAFVQ;
RRTMAFVQF; RTMAFVQFN; TMAFVQFNW; MAFVQFNWG; AFVQFNWGQ; FVQFNWGQG;
VQFNWGQGQ; QFNWGQGQD; FNWGQGQDS; ARKTCLSCT; RKTCLSCTF; KTCLSCTFL;
TCLSCTFLP; CLSCTFLPE; LSCTFLPEV; SCTFLPEVM; CTFLPEVMV; TFLPEVMVW;
FLPEVMVWL; LPEVMVWLH; PEVMVWLHS; EVMVWLHSM; VMVWLHSMG; MVWLHSMGK;
VWLHSMGKQ; WLHSMGKQL; LHSMGKQLL; HSMGKQLLP; SMGKQLLPV; MGKQLLPVS;
GKQLLPVSH; KQLLPVSHA; QLLPVSHAL; LLPVSHALS; LPVSHALSF; PVSHALSFL;
VSHALSFLR; SHALSFLRS; HALSFLRSW; ALSFLRSWF; LSFLRSWFG; SFLRSWFGC;
FLRSWFGCI; LRSWFGCIP; RSWFGCIPL; GHGLAAFHG; AAPPCGLFF; APPCGLFFY;
PPCGLFFYN; PCGLFFYNI; EAEAASAST; AEAASASTL; EAASASTLS; AASASTLSL;
ASASTLSLK; GLAKLFGEI; LAKLFGEIP; AKLFGEIPI; KLFGEIPIL; LFGEIPILL;
FGEIPILLQ; GEIPILLQF; EIPILLQFL; IPILLQFLQ

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

10 mers:

MDKVLNREES; DKVLNREESM; KVLNREESME; VLNREESMEL; LNREESMELM;
NREESMELMD; REESMELMDL; EESMELMDLL; ESMELMDLLG; SMELMDLLGL;
MELMDLLGLE; ELMDLLGLER; LMDLLGLERA; MDLLGLERAA; DLLGLERAAW;
LLGLERAAWG; LGLERAAWGN; GLERAAWGNL; LERAAWGNLP; ERAAWGNLPL;
RAAWGNLPLM; AAWGNLPLMR; AWGNLPLMRK; WGNLPLMRKA; GNLPLMRKAY;
NLPLMRKAYL; LPLMRKAYLR; PLMRKAYLRK; LMRKAYLRKC; MRKAYLRKCK;
RKAYLRKCKE; KAYLRKCKEF; AYLRKCKEFH; YLRKCKEFHP; LRKCKEFHPD;
RKCKEFHPDK; KCKEFHPDKG; CKEFHPDKGG; KEFHPDKGGD; EFHPDKGGDE;
FHPDKGGDED; HPDKGGDEDK; PDKGGDEDKM; DKGGDEDKMK; KGGDEDKMKR;
GGDEDKMKRM; GDEDKMKRMN; DEDKMKRMNT; EDKMKRMNTL; DKMKRMNTLY;
KMKRMNTLYK; MKRMNTLYKK; KRMNTLYKKM; RMNTLYKKME; MNTLYKKMEQ;
NTLYKKMEQD; TLYKKMEQDV; LYKKMEQDVK; YKKMEQDVKV; KKMEQDVKVA;
KMEQDVKVAH; MEQDVKVAHQ; EQDVKVAHQP; QDVKVAHQPD; DVKVAHQPDF;
VKVAHQPDFG; KVAHQPDFGT; VAHQPDFGTW; AHQPDFGTWS; HQPDFGTWSS;
QPDFGTWSSS; PDFGTWSSSE; DFGTWSSSEV; FGTWSSSEVC; GTWSSSEVCA;
TWSSSEVCAD; WSSSEVCADF; SSSEVCADFP; SSEVCADFPL; SEVCADFPLC;
EVCADFPLCP; VCADFPLCPD; CADFPLCPDT; ADFPLCPDTL; DFPLCPDTLY;
FPLCPDTLYC; PLCPDTLYCK; LCPDTLYCKE; CPDTLYCKEW; PDTLYCKEWP;
DTLYCKEWPI; TLYCKEWPIC; LYCKEWPICS; YCKEWPICSK; CKEWPICSKK;
KEWPICSKKP; EWPICSKKPS; WPICSKKPSV; PICSKKPSVH; ICSKKPSVHC;
CSKKPSVHCP; SKKPSVHCPC; KKPSVHCPCM; KPSVHCPCML; PSVHCPCMLC;
SVHCPCMLCQ; VHCPCMLCQL; HCPCMLCQLR; CPCMLCQLRL; PCMLCQLRLR;
CMLCQLRLRH; MLCQLRLRHL; LCQLRLRHLN; CQLRLRHLNR; QLRLRHLNRK;
LRLRHLNRKF; RLRHLNRKFL; LRHLNRKFLR; RHLNRKFLRK; HLNRKFLRKE;
LNRKFLRKEP; NRKFLRKEPL; RKFLRKEPLV; KFLRKEPLVW; FLRKEPLVWI;
LRKEPLVWID; RKEPLVWIDC; KEPLVWIDCY; EPLVWIDCYC; PLVWIDCYCI;
LVWIDCYCID; VWIDCYCIDC; WIDCYCIDCF; IDCYCIDCFT; DCYCIDCFTQ;
CYCIDCFTQW; YCIDCFTQWF; CIDCFTQWFG; IDCFTQWFGL; DCFTQWFGLD;
CFTQWFGLDL; FTQWFGLDLT; TQWFGLDLTE; QWFGLDLTEE; WFGLDLTEET;
FGLDLTEETL; GLDLTEETLQ; LDLTEETLQW; DLTEETLQWW; LTEETLQWWV;
TEETLQWWVQ; EETLQWWVQI; ETLQWWVQII; TLQWWVQIIG; LQWWVQIIGE;
QWWVQIIGET; WWVQIIGETP; WVQIIGETPF; VQIIGETPFR; QIIGETPFRD;
IIGETPFRDL; IGETPFRDLK; GETPFRDLKL; KALSNYFFYR; ALSNYFFYRC;
LSNYFFYRCQ; SNYFFYRCQP; NYFFYRCQPM; YFFYRCQPME; FFYRCQPMEQ;
FYRCQPMEQK; YRCQPMEQKS; RCQPMEQKSG; CQPMEQKSGS; QPMEQKSGSP;
PMEQKSGSPG; MEQKSGSPGG; EQKSGSPGGV; QKSGSPGGVP; KSGSPGGVPL;
SGSPGGVPLM; GSPGGVPLMK; SPGGVPLMKN; PGGVPLMKNG; GGVPLMKNGM;
GVPLMKNGMK; VPLMKNGMKI; PLMKNGMKIY; LMKNGMKIYF; MKNGMKIYFA;
KNGMKIYFAM; NGMKIYFAMK; GMKIYFAMKI; MKIYFAMKIC; KIYFAMKICL;
IYFAMKICLP; YFAMKICLPV; FAMKICLPVM; AMKICLPVMK; MKICLPVMKK;
KICLPVMKKQ; ICLPVMKKQQ; CLPVMKKQQQ; LPVMKKQQQI; PVMKKQQQIL;
VMKKQQQILN; MKKQQQILNT; KKQQQILNTQ; KQQQILNTQH; QQQILNTQHH;
QQILNTQHHP; QILNTQHHPK; ILNTQHHPKK; LNTQHHPKKE; NTQHHPKKER;
TQHHPKKKER; KTLKTFPLIY; TLKTFPLIYT; LKTFPLIYTS; KTFPLIYTSF;
TFPLIYTSFL; FPLIYTSFLV; PLIYTSFLVK; LIYTSFLVKL; IYTSFLVKLY;
YTSFLVKLYL; TSFLVKLYLV; SFLVKLYLVI; FLVKLYLVIE; LVKLYLVIEP;
VKLYLVIEPL; KLYLVIEPLP; LYLVIEPLPA; YLVIEPLPAL; LVIEPLPALL;
VIEPLPALLC; IEPLPALLCI; EPLPALLCIL; PLPALLCILL; LPALLCILLK;
PALLCILLKK; ALLCILLKKK; LLCILLKKKL; LCILLKKKLK; CILLKKKLKF;
ILLKKKLKFC; LLKKKLKFCI; LKKKLKFCIK; KKKLKFCIKN; KKLKFCIKNL;
KLKFCIKNLW; LKFCIKNLWK; KFCIKNLWKN; FCIKNLWKNI; CIKNLWKNIL;
LLLVDTCVLG; LLVDTCVLGI; LVDTCVLGII; VDTCVLGIIL; DTCVLGIILY;
TCVLGIILYS; CVLGIILYSF; LHIDIEFLQL; HIDIEFLQLI; IDIEFLQLII;
DIEFLQLIIS; IEFLQLIISV; EFLQLIISVK; FLQLIISVKS; LQLIISVKSC;
QLIISVKSCV; LIISVKSCVP; IISVKSCVPL; ISVKSCVPLV; SVKSCVPLVF;
FVRVLIRNTY; VRVLIRNTYY; RVLIRNTYYI; VLIRNTYYIV; LIRNTYYIVP;
RSMILAQKSL; SMILAQKSLK; MILAQKSLKK; ILAQKSLKKQ; LAQKSLKKQS;
AQKSLKKQSR; QKSLKKQSRC; KSLKKQSRCL; SLKKQSRCLG; LKKQSRCLGN;
RQSVRMCFYY; RSVKSVRKKT; SVKSVRKKTS; VKSVRKKTSL; KSVRKKTSLI;
SVRKKTSLIT; VRKKTSLITL; RKKTSLITLS; KKTSLITLSI; KTSLITLSIM;
TSLITLSIMK; SLITLSIMKS; LITLSIMKST; ITLSIMKSTL; TLSIMKSTLQ;
LSIMKSTLQM; SIMKSTLQML; IMKSTLQMLL; MKSTLQMLLF; KSTLQMLLFL;
STLQMLLFLQ; TLQMLLFLQK; LQMLLFLQKV; QMLLFLQKVK; MLLFLQKVKI;
LLFLQKVKIK; LFLQKVKIKK; FLQKVKIKKV; LQKVKIKKVF; QKVKIKKVFV;
KVKIKKVFVS; VKIKKVFVSK; KIKKVFVSKQ; NNIWQVLLGC; NIWQVLLGCT;
IWQVLLGCTV; WQVLLGCTVC; QVLLGCTVCY; VLLGCTVCYL; LLGCTVCYLK;
LGCTVCYLKW; GCTVCYLKWI; CTVCYLKWIL; YLIFCTVLFS; LIFCTVLFSM;
IFCTVLFSMY; FCTVLFSMYL; CTVLFSMYLK; TVLFSMYLKE; VLFSMYLKED;
LFSMYLKEDT; FSMYLKEDTG; SMYLKEDTGY; MYLKEDTGYL; YLKEDTGYLK;
LKEDTGYLKV; KEDTGYLKVP; EDTGYLKVPL; DTGYLKVPLI; TGYLKVPLIV;
GYLKVPLIVE; YLKVPLIVEK; LKVPLIVEKQ; KVPLIVEKQH; KGQELNQRIC;
GQELNQRICL; QELNQRICLQ; ELNQRICLQD; LNQRICLQDM; NQRICLQDME;
TKEPKYFHQA; KEPKYFHQAW; EPKYFHQAWL; PKYFHQAWLQ; MSILSLKPCK;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

SILSLKPCKL; ILSLKPCKLD; LSLKPCKLDL; ENPYKTQSSY; NPYKTQSSYL;
PYKTQSSYLK; YKTQSSYLKK; KTQSSYLKKE; TQSSYLKKEF; QSSYLKKEFY;
SSYLKKEFYK; SYLKKEFYKV; YLKKEFYKVE; LILQLIYNLE; ILQLIYNLEL;
LQLIYNLELL; QLIYNLELLN; LIYNLELLNG; IYNLELLNGR; YNLELLNGRK;
NLELLNGRKG; LELLNGRKGW; ELLNGRKGWI; LLNGRKGWIL; LNGRKGWILR;
NIIYAWGNVF; IIYAWGNVFL; IYAWGNVFLI; YAWGNVFLIL; AWGNVFLILQ;
WGNVFLILQE; GNVFLILQEK; NVFLILQEKR; VFLILQEKRI; FLILQEKRIQ;
LILQEKRIQK; ILQEKRIQKL; LQEKRIQKLK; QEKRIQKLKT; EKRIQKLKTL;
KRIQKLKTLD; RIQKLKTLDM; IQKLKTLDMD; QKLKTLDMDQ; KLKTLDMDQA;
LKTLDMDQAL; KTLDMDQALN; TLDMDQALNP; LDMDQALNPN; DMDQALNPNH;
MDQALNPNHN; DQALNPNHNA; QALNPNHNAL; ALNPNHNALP; LNPNHNALPK;
NPNHNALPKS; PNHNALPKSQ; NHNALPKSQI; HNALPKSQIL; NALPKSQILQ;
ALPKSQILQP; LPKSQILQPL; PKSQILQPLL; KSQILQPLLK; SQILQPLLKI;
QILQPLLKIP; ILQPLLKIPK; LQPLLKIPKG; QPLLKIPKGQ; PLLKIPKGQT;
LLKIPKGQTP; LKIPKGQTPI; KIPKGQTPIV; IPKGQTPIVK; PKGQTPIVKS;
KGQTPIVKSC; GQTPIVKSCI; QTPIVKSCIC; TPIVKSCICV; PIVKSCICVK;
IVKSCICVKA; VKSCICVKAF; KSCICVKAFS; SCICVKAFSV; CICVKAFSVL;
ICVKAFSVLK; CVKAFSVLKG; VKAFSVLKGL; KAFSVLKGLK; AFSVLKGLKH;
FSVLKGLKHH; SVLKGLKHHP; VLKGLKHHPQ; LKGLKHHPQN; KGLKHHPQNN;
GLKHHPQNNT; LKHHPQNNTS; KHHPQNNTSL; HHPQNNTSLK; HPQNNTSLKV;
PQNNTSLKVA; QNNTSLKVAY; NNTSLKVAYT; NTSLKVAYTK; TSLKVAYTKA;
SLKVAYTKAA; LKVAYTKAAF; KVAYTKAAFI; VAYTKAAFIK; AYTKAAFIKC;
YTKAAFIKCI; TKAAFIKCIC; KAAFIKCICT; AAFIKCICTI; AFIKCICTIK;
FIKCICTIKA; IKCICTIKAP; KCICTIKAPV; SILVCNCPCL; ILVCNCPCLS;
LVCNCPCLSI; VCNCPCLSIY; CNCPCLSIYL; NCPCLSIYLI; CPCLSIYLII;
PCLSIYLIIS; CLSIYLIISG; LSIYLIISGS; SIYLIISGSP; IYLIISGSPG;
YLIISGSPGS; LIISGSPGSL; IISGSPGSLS; ISGSPGSLSV; SGSPGSLSVP;
GSPGSLSVPS; SPGSLSVPSN; PGSLSVPSNT; GSLSVPSNTL; SLSVPSNTLT;
LSVPSNTLTS; SVPSNTLTSS; VPSNTLTSST; PSNTLTSSTW; SNTLTSSTWD;
NTLTSSTWDS; TLTSSTWDSI; LTSSTWDSIP; TSSTWDSIPY; SSTWDSIPYI;
STWDSIPYIG; TWDSIPYIGC; WDSIPYIGCP; DSIPYIGCPS; SIPYIGCPST;
IPYIGCPSTL; PYIGCPSTLW; YIGCPSTLWV; IGCPSTLWVL; GCPSTLWVLL;
CPSTLWVLLF; PSTLWVLLFI; STLWVLLFIR; TLWVLLFIRS; LWVLLFIRSL;
WVLLFIRSLS; VLLFIRSLSK; LLFIRSLSKK; LFIRSLSKKE; FIRSLSKKEI;
IRSLSKKEIG; GFFTDLFLRR; FFTDLFLRRI; FTDLFLRRIL; TDLFLRRILK;
DLFLRRILKY; LFLRRILKYL; FLRRILKYLA; LRRILKYLAR; RRILKYLARP;
RILKYLARPL; ILKYLARPLH; LKYLARPLHC; KYLARPLHCC; YLARPLHCCV;
LARPLHCCVP; ARPLHCCVPE; RPLHCCVPEL; PLHCCVPELL; LHCCVPELLV;
HCCVPELLVN; CCVPELLVNR; CVPELLVNRP; VPELLVNRPQ; PELLVNRPQI;
ELLVNRPQIS; LLVNRPQISA; LVNRPQISAA; VNRPQISAAE; NRPQISAAET;
RPQISAAETY; PQISAAETYR; QISAAETYRL; ISAAETYRLS; SAAETYRLSA;
AAETYRLSAL; AETYRLSALQ; ETYRLSALQR; TYRLSALQRG; YRLSALQRGP;
RLSALQRGPT; LSALQRGPTP; SALQRGPTPC; ALQRGPTPCS; LQRGPTPCSS;
QRGPTPCSSS; RGPTPCSSSN; GPTPCSSSNT; PTPCSSSNTV; TPCSSSNTVV;
PCSSSNTVVA; CSSSNTVVAV; SSSNTVVAVL; SSNTVVAVLV; SNTVVAVLVT;
STGGTFSPPV; TGGTFSPPVK; GGTFSPPVKV; GTFSPPVKVP; TFSPPVKVPK;
FSPPVKVPKY; SPPVKVPKYL; PPVKVPKYLA; PVKVPKYLAF; VKVPKYLAFS;
KVPKYLAFSF; VPKYLAFSFL; PKYLAFSFLL; KYLAFSFLLG; YLAFSFLLGS;
LAFSFLLGSG; AFSFLLGSGT; FSFLLGSGTQ; SFLLGSGTQH; FLLGSGTQHS;
LLGSGTQHST; LGSGTQHSTG; ALWSVFITWD; LWSVFITWDW; WSVFITWDWA;
SVFITWDWAV; VFITWDWAVG; FITWDWAVGF; ITWDWAVGFL; TWDWAVGFLG;
WDWAVGFLGV; DWAVGFLGVI; WAVGFLGVIV; AVGFLGVIVP; VGFLGVIVPS;
GFLGVIVPSG; FLGVIVPSGY; LGVIVPSGYF; GVIVPSGYFD; VIVPSGYFDL;
FISTPCISKG; ISTPCISKGS; STPCISKGSP; TPCISKGSPP; PCISKGSPPT;
CISKGSPPTA; ISKGSPPTAK; SKGSPPTAKK; KGSPPTAKKW; GSPPTAKKWK;
SPPTAKKWKL; PPTAKKWKLL; PTAKKWKLLP; IGFPPPCSCT; GFPPPCSCTF;
FPPPCSCTFC; PPPCSCTFCD; PPCSCTFCDP; PCSCTFCDPA; RLSMLVIPIT;
LSMLVIPITS; SMLVIPITSV; MLVIPITSVC; LVIPITSVCT; VIPITSVCTV;
IPITSVCTVT; PITSVCTVTA; ITSVCTVTAS; TSVCTVTASH; SVCTVTASHI;
VCTVTASHIS; CTVTASHISR; TVTASHISRF; VTASHISRFP; TASHISRFPQ;
ASHISRFPQV; SHISRFPQVR; HISRFPQVRS; ISRFPQVRSS; SRFPQVRSSF;
RFPQVRSSFK; FPQVRSSFKL; PQVRSSFKLG; QVRSSFKLGR; VRSSFKLGRG;
RSSFKLGRGI; SSFKLGRGIL; SFKLGRGILA; FKLGRGILAV; KLGRGILAVL;
QGSIFLSGLS; GSIFLSGLSL; SIFLSGLSLL; IFLSGLSLLK; FLSGLSLLKS;
LSGLSLLKSF; SGLSLLKSFS; GLSLLKSFSA; LSLLKSFSAL; SLLKSFSALS;
LLKSFSALSF; LKSFSALSFR; KSFSALSFRL; SFSALSFRLK; FSALSFRLKP;
SALSFRLKPL; ALSFRLKPLR; LSFRLKPLRF; SFRLKPLRFS; FRLKPLRFSS;
RLKPLRFSSG; LKPLRFSSGS; KPLRFSSGSP; PLRFSSGSPI; LRFSSGSPIS;
RFSSGSPISG; FSSGSPISGF; SSGSPISGFR; SGSPISGFRK; GSPISGFRKH;
SPISGFRKHS; PISGFRKHST; ISGFRKHSTS; SGFRKHSTSV; GFRKHSTSVI;
FRKHSTSVIA; RKHSTSVIAS; KHSTSVIAST; HSTSVIASTP; STSVIASTPV;
TSVIASTPVL; SVIASTPVLT; VIASTPVLTS; IASTPVLTSR; ASTPVLTSRT;
STPVLTSRTS; TPVLTSRTST; PVLTSRTSTP; VLTSRTSTPP; LTSRTSTPPF;
TSRTSTPPFI; SRTSTPPFIS; RTSTPPFISS; TSTPPFISSF; STPPFISSFG;
TPPFISSFGT; PPFISSFGTC; PFISSFGTCT; FISSFGTCTG; ISSFGTCTGS;
SSFGTCTGSF; SFGTCTGSFG; FGTCTGSFGF; GTCTGSFGFL; TCTGSFGFLG;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

CTGSFGFLGA; TGSFGFLGAA; GSFGFLGAAP; SFGFLGAAPG; FGFLGAAPGH;
GFLGAAPGHS; FLGAAPGHSP; LGAAPGHSPF; GAAPGHSPFL; AAPGHSPFLL;
APGHSPFLLV; PGHSPFLLVG; GHSPFLLVGA; HSPFLLVGAI; SPFLLVGAIF;
PFLLVGAIFI; FLLVGAIFIC; LLVGAIFICF; LVGAIFICFK; VGAIFICFKS;
GAIFICFKSR; AIFICFKSRC; IFICFKSRCY; FICFKSRCYS; ICFKSRCYSP;
CFKSRCYSPV; FKSRCYSPVQ; KSRCYSPVQA; RQHPLRSSSL; QHPLRSSSLI;
HPLRSSSLIS; PLRSSSLIST; LRSSSLISTS; RSSSLISTSW; SSSLISTSWG;
SSLISTSWGN; SLISTSWGNS; LISTSWGNSF; ISTSWGNSFF; STSWGNSFFY;
TSWGNSFFYK; SWGNSFFYKL; WGNSFFYKLS; VHSLCNFFYT; HSLCNFFYTV;
SLCNFFYTVS; LCNFFYTVSI; CNFFYTVSII; NFFYTVSIIY; FFYTVSIIYT;
FYTVSIIYTI; YTVSIIYTIS; TVSIIYTISM; VSIIYTISMA; SIIYTISMAK;
IIYTISMAKM; IYTISMAKMY; YTISMAKMYT; TISMAKMYTG; ISMAKMYTGT;
SMAKMYTGTF; MAKMYTGTFP; AKMYTGTFPF; KMYTGTFPFS; MYTGTFPFSY;
YTGTFPFSYL; TGTFPFSYLS; GTFPFSYLSN; TFPFSYLSNH; GPNRGKIRII;
PNRGKIRIIL; NRGKIRIILL; RGKIRIILLN; GKIRIILLNI; KIRIILLNII;
IRIILLNIII; RIILLNIIIK; IILLNIIIKV; ILLNIIIKVY; LLNIIIKVYR;
LNIIIKVYRG; NIIIKVYRGI; IIIKVYRGIY; IIKVYRGIYN; IKVYRGIYNC;
KVYRGIYNCP; VYRGIYNCPG; YRGIYNCPGS; RGIYNCPGSF; GIYNCPGSFL;
IYNCPGSFLQ; YNCPGSFLQK; NCPGSFLQKS; CPGSFLQKSS; PGSFLQKSSQ;
GSFLQKSSQG; SFLQKSSQGV; FLQKSSQGVS; LQKSSQGVSK; QKSSQGVSKK;
KSSQGVSKKS; SSQGVSKKSF; SQGVSKKSFC; QGVSKKSFCS; GVSKKSFCSS;
VSKKSFCSSL; SKKSFCSSLQ; KKSFCSSLQF; KSFCSSLQFL; GYRRYIIPNN;
YRRYIIPNNM; RRYIIPNNMP; RYIIPNNMPQ; YIIPNNMPQS; IIPNNMPQSL;
IPNNMPQSLG; PNNMPQSLGN; NNMPQSLGNS; NMPQSLGNSS; MPQSLGNSSK;
PQSLGNSSKQ; QSLGNSSKQR; SLGNSSKQRR; LGNSSKQRRT; GNSSKQRRTP;
NSSKQRRTPM; SSKQRRTPMP; SKQRRTPMPR; KQRRTPMPRI; QRRTPMPRIK;
RRTPMPRIKV; RTPMPRIKVL; TPMPRIKVLN; PMPRIKVLNI; MPRIKVLNII;
PRIKVLNIIN; RIKVLNIINK; IKVLNIINKS; KVLNIINKSI; VLNIINKSIY;
LNIINKSIYT; NIINKSIYTR; IINKSIYTRK; INKSIYTRKQ; NKSIYTRKQN;
KSIYTRKQNI; SIYTRKQNII; IYTRKQNIIV; YTRKQNIIVL; TRKQNIIVLI;
RKQNIIVLIW; KQNIIVLIWV; QNIIVLIWVK; NIIVLIWVKQ; IIVLIWVKQF;
IVLIWVKQFQ; VLIWVKQFQS; LIWVKQFQSH; IWVKQFQSHA; LLIEAYSGNF;
LIEAYSGNFV; IEAYSGNFVI; EAYSGNFVIP; AYSGNFVIPI; YSGNFVIPII;
SGNFVIPIIK; GNFVIPIIKE; NFVIPIIKEL; FVIPIIKELI; VIPIIKELIP;
IPIIKELIPY; PIIKELIPYL; IIKELIPYLS; SSKPSNSPRS; SKPSNSPRST;
KPSNSPRSTS; PSNSPRSTSN; SNSPRSTSNY; NSPRSTSNYS; SPRSTSNYSI;
PRSTSNYSIC; RSTSNYSICL; STSNYSICLR; TSNYSICLRS; GTCYALYSSK;
TCYALYSSKG; CYALYSSKGC; YALYSSKGCN; ALYSSKGCNL; LYSSKGCNLN;
YSSKGCNLNF; SSKGCNLNFY; SKGCNLNFYS; KGCNLNFYSS; GCNLNFYSSS;
CNLNFYSSSS; NLNFYSSSSL; LNFYSSSSLP; NFYSSSSLPS; FYSSSSLPSS;
YSSSSLPSSN; SSSSLPSSNF; SSSLPSSNFS; SSLPSSNFSH; KSCGSSSLRY;
SCGSSSLRYT; CGSSSLRYTG; GSSSLRYTGN; SSTHEPGNTK; STHEPGNTKK;
THEPGNTKKK; HEPGNTKKKG; EPGNTKKKGL; PGNTKKKGLL; GNTKKKGLLT;
ESFTESFTAG; SFTESFTAGK; FTESFTAGKA; TESFTAGKAV; ESFTAGKAVV;
SFTAGKAVVL; FTAGKAVVLL; TAGKAVVLLF; AGKAVVLLFF; GKAVVLLFFP;
KAVVLLFFPS; AVVLLFFPST; VVLLFFPSTL; VLLFFPSTLS; LLFFPSTLSS;
LFFPSTLSSP; FFPSTLSSPL; FPSTLSSPLQ; PSTLSSPLQN; STLSSPLQNS;
TLSSPLQNSS; LSSPLQNSSK; SSPLQNSSKS; SPLQNSSKSS; PLQNSSKSSK;
LQNSSKSSKI; QNSSKSSKIK; NSSKSSKIKI; SSKSSKIKIK; SKSSKIKIKI;
KSSKIKIKIL; ALFFVPVQVL; LFFVPVQVLP; FFVPVQVLPT; FVPVQVLPTF;
VPVQVLPTFT; PVQVLPTFTE; VQVLPTFTEA; QVLPTFTEAC; VLPTFTEACR;
LPTFTEACRD; PTFTEACRDS; TFTEACRDSW; FTEACRDSWR; TEACRDSWRR;
EACRDSWRRT; ACRDSWRRTM; CRDSWRRTMA; RDSWRRTMAF; DSWRRTMAFV;
SWRRTMAFVQ; WRRTMAFVQF; RRTMAFVQFN; RTMAFVQFNW; TMAFVQFNWG;
MAFVQFNWGQ; AFVQFNWGQG; FVQFNWGQGQ; VQFNWGQGQD; QFNWGQGQDS;
ARKTCLSCTF; RKTCLSCTFL; KTCLSCTFLP; TCLSCTFLPE; CLSCTFLPEV;
LSCTFLPEVM; SCTFLPEVMV; CTFLPEVMVW; TFLPEVMVWL; FLPEVMVWLH;
LPEVMVWLHS; PEVMVWLHSM; EVMVWLHSMG; VMVWLHSMGK; MVWLHSMGKQ;
VWLHSMGKQL; WLHSMGKQLL; LHSMGKQLLP; HSMGKQLLPV; SMGKQLLPVS;
MGKQLLPVSH; GKQLLPVSHA; KQLLPVSHAL; QLLPVSHALS; LLPVSHALSF;
LPVSHALSFL; PVSHALSFLR; VSHALSFLRS; SHALSFLRSW; HALSFLRSWF;
ALSFLRSWFG; LSFLRSWFGC; SFLRSWFGCI; FLRSWFGCIP; LRSWFGCIPL;
AAPPCGLFFY; APPCGLFFYN; PPCGLFFYNI; EAEAASASTL; AEAASASTLS;
EAASASTLSL; AASASTLSLK; GLAKLFGEIP; LAKLFGEIPI; AKLFGEIPIL;
KLFGEIPILL; LFGEIPILLQ; FGEIPILLQF; GEIPILLQFL; EIPILLQFLQ 11 mers:

MDKVLNREESM; DKVLNREESME; KVLNREESMEL; VLNREESMELM; LNREESMELMD;
NREESMELMDL; REESMELMDLL; EESMELMDLLG; ESMELMDLLGL; SMELMDLLGLE;
MELMDLLGLER; ELMDLLGLERA; LMDLLGLERAA; MDLLGLERAAW; DLLGLERAAWG;
LLGLERAAWGN; LGLERAAWGNL; GLERAAWGNLP; LERAAWGNLPL; ERAAWGNLPLM;
RAAWGNLPLMR; AAWGNLPLMRK; AWGNLPLMRKA; WGNLPLMRKAY; GNLPLMRKAYL;
NLPLMRKAYLR; LPLMRKAYLRK; PLMRKAYLRKC; LMRKAYLRKCK; MRKAYLRKCKE;
RKAYLRKCKEF; KAYLRKCKEFH; AYLRKCKEFHP; YLRKCKEFHPD; LRKCKEFHPDK;
RKCKEFHPDKG; KCKEFHPDKGG; CKEFHPDKGGD; KEFHPDKGGDE; EFHPDKGGDED;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

FHPDKGGDEDK; HPDKGGDEDKM; PDKGGDEDKMK; DKGGDEDKMKR; KGGDEDKMKRM;
GGDEDKMKRMN; GDEDKMKRMNT; DEDKMKRMNTL; EDKMKRMNTLY; DKMKRMNTLYK;
KMKRMNTLYKK; MKRMNTLYKKM; KRMNTLYKKME; RMNTLYKKMEQ; MNTLYKKMEQD;
NTLYKKMEQDV; TLYKKMEQDVK; LYKKMEQDVKV; YKKMEQDVKVA; KKMEQDVKVAH;
KMEQDVKVAHQ; MEQDVKVAHQP; EQDVKVAHQPD; QDVKVAHQPDF; DVKVAHQPDFG;
VKVAHQPDFGT; KVAHQPDFGTW; VAHQPDFGTWS; AHQPDFGTWSS; HQPDFGTWSSS;
QPDFGTWSSSE; PDFGTWSSSEV; DFGTWSSSEVC; FGTWSSSEVCA; GTWSSSEVCAD;
TWSSSEVCADF; WSSSEVCADFP; SSSEVCADFPL; SSEVCADFPLC; SEVCADFPLCP;
EVCADFPLCPD; VCADFPLCPDT; CADFPLCPDTL; ADFPLCPDTLY; DFPLCPDTLYC;
FPLCPDTLYCK; PLCPDTLYCKE; LCPDTLYCKEW; CPDTLYCKEWP; PDTLYCKEWPI;
DTLYCKEWPIC; TLYCKEWPICS; LYCKEWPICSK; YCKEWPICSKK; CKEWPICSKKP;
KEWPICSKKPS; EWPICSKKPSV; WPICSKKPSVH; PICSKKPSVHC; ICSKKPSVHCP;
CSKKPSVHCPC; SKKPSVHCPCM; KKPSVHCPCML; KPSVHCPCMLQ; PSVHCPCMLCQ;
SVHCPCMLCQL; VHCPCMLCQLR; HCPCMLCQLRL; CPCMLCQLRLR; PCMLCQLRLRH;
CMLCQLRLRHL; MLCQLRLRHLN; LCQLRLRHLNR; CQLRLRHLNRK; QLRLRHLNRKF;
LRLRHLNRKFL; RLRHLNRKFLR; LRHLNRKFLRK; RHLNRKFLRKE; HLNRKFLRKEP;
LNRKFLRKEPL; NRKFLRKEPLV; RKFLRKEPLVW; KFLRKEPLVWI; FLRKEPLVWID;
LRKEPLVWIDC; RKEPLVWIDCY; KEPLVWIDCYC; EPLVWIDCYCI; PLVWIDCYCID;
LVWIDCYCIDC; VWIDCYCIDCF; WIDCYCIDCFT; IDCYCIDCFTQ; DCYCIDCFTQW;
CYCIDCFTQWF; YCIDCFTQWFG; CIDCFTQWFGL; IDCFTQWFGLD; DCFTQWFGLDL;
CFTQWFGLDLT; FTQWFGLDLTE; TQWFGLDLTEE; QWFGLDLTEET; WFGLDLTEETL;
FGLDLTEETLQ; GLDLTEETLQW; LDLTEETLQWW; DLTEETLQWWV; LTEETLQWWVQ;
TEETLQWWVQI; EETLQWWVQII; ETLQWWVQIIG; TLQWWVQIIGE; LQWWVQIIGET;
QWWVQIIGETP; WWVQIIGETPF; WVQIIGETPFR; VQIIGETPFRD; QIIGETPFRDL;
IIGETPFRDLK; IGETPFRDLKL; KALSNYFFYRC; ALSNYFFYRCQ; LSNYFFYRCQP;
SNYFFYRCQPM; NYFFYRCQPME; YFFYRCQPMEQ; FFYRCQPMEQK; FYRCQPMEQKS;
YRCQPMEQKSG; RCQPMEQKSGS; CQPMEQKSGSP; QPMEQKSGSPG; PMEQKSGSPGG;
MEQKSGSPGGV; EQKSGSPGGVP; QKSGSPGGVPL; KSGSPGGVPLM; SGSPGGVPLMK;
GSPGGVPLMKN; SPGGVPLMKNG; PGGVPLMKNGM; GGVPLMKNGMK; GVPLMKNGMKI;
VPLMKNGMKIY; PLMKNGMKIYF; LMKNGMKIYFA; MKNGMKIYFAM; KNGMKIYFAMK;
NGMKIYFAMKI; GMKIYFAMKIC; MKIYFAMKICL; KIYFAMKICLP; IYFAMKICLPV;
YFAMKICLPVM; FAMKICLPVMK; AMKICLPVMKK; MKICLPVMKKQ; KICLPVMKKQQ;
ICLPVMKKQQQ; CLPVMKKQQQI; LPVMKKQQQIL; PVMKKQQQILN; VMKKQQQILNT;
MKKQQQILNTQ; KKQQQILNTQH; KQQQILNTQHH; QQQILNTQHHP; QQILNTQHHPK;
QILNTQHHPKK; ILNTQHHPKKK; LNTQHHPKKKE; NTQHHPKKKER; KTLKTFPLIYT;
TLKTFPLIYTS; LKTFPLIYTSF; KTFPLIYTSFL; TFPLIYTSFLV; FPLIYTSFLVK;
PLIYTSFLVKL; LIYTSFLVKLY; IYTSFLVKLYL; YTSFLVKLYLV; TSFLVKLYLVI;
SFLVKLYLVIE; FLVKLYLVIEP; LVKLYLVIEPL; VKLYLVIEPLP; KLYLVIEPLPA;
LYLVIEPLPAL; YLVIEPLPALL; LVIEPLPALLC; VIEPLPALLCI; IEPLPALLCIL;
EPLPALLCILL; PLPALLCILLK; LPALLCILLKK; PALLCILLKKK; ALLCILLKKKL;
LLCILLKKKLK; LCILLKKKLKF; CILLKKKLKFC; ILLKKKLKFCI; LLKKKLKFCIK;
LKKKLKFCIKN; KKKLKFCIKNL; KKLKFCIKNLW; KLKFCIKNLWK; LKFCIKNLWKN;
KFCIKNLWKNI; FCIKNLWKNIL; LLLVDTCVLGI; LLVDTCVLGII; LVDTCVLGIIL;
VDTCVLGIILY; DTCVLGIILYS; TCVLGIILYSF; LHIDIEFLQLI; HIDIEFLQLII;
IDIEFLQLIIS; DIEFLQLIISV; IEFLQLIISVK; EFLQLIISVKS; FLQLIISVKSC;
LQLIISVKSCV; QLIISVKSCVP; LIISVKSCVPL; IISVKSCVPLV; ISVKSCVPLVF;
FVRVLIRNTYY; VRVLIRNTYYI; RVLIRNTYYIV; VLIRNTYYIVP; RSMILAQKSLK;
SMILAQKSLKK; MILAQKSLKKQ; ILAQKSLKKQS; LAQKSLKKQSR; AQKSLKKQSRC;
QKSLKKQSRCL; KSLKKQSRCLG; SLKKQSRCLGN; RSVKSVRKKTS; SVKSVRKKTSL;
VKSVRKKTSLI; KSVRKKTSLIT; SVRKKTSLITL; VRKKTSLITLS; RKKTSLITLSI;
KKTSLITLSIM; KTSLITLSIMK; TSLITLSIMKS; SLITLSIMKST; LITLSIMKSTL;
ITLSIMKSTLQ; TLSIMKSTLQM; LSIMKSTLQML; SIMKSTLQMLL; IMKSTLQMLLF;
MKSTLQMLLFL; KSTLQMLLFLQ; STLQMLLFLQK; TLQMLLFLQKV; LQMLLFLQKVK;
QMLLFLQKVKI; MLLFLQKVKIK; LLFLQKVKIKK; LFLQKVKIKKV; FLQKVKIKKVF;
LQKVKIKKVFV; QKVKIKKVFVS; KVKIKKVFVSK; VKIKKVFVSKQ; NNIWQVLLGCT;
NIWQVLLGCTV; IWQVLLGCTVC; WQVLLGCTVCY; QVLLGCTVCYL; VLLGCTVCYLK;
LLGCTVCYLKW; LGCTVCYLKWI; GCTVCYLKWIL; YLIFCTVLFSM; LIFCTVLFSMY;
IFCTVLFSMYL; FCTVLFSMYLK; CTVLFSMYLKE; TVLFSMYLKED; VLFSMYLKEDT;
LFSMYLKEDTG; FSMYLKEDTGY; SMYLKEDTGYL; MYLKEDTGYLK; YLKEDTGYLKV;
LKEDTGYLKVP; KEDTGYLKVPL; EDTGYLKVPLI; DTGYLKVPLIV; TGYLKVPLIVE;
GYLKVPLIVEK; YLKVPLIVEKQ; LKVPLIVEKQH; KGQELNQRICL; GQELNQRICLQ;
QELNQRICLQD; ELNQRICLQDM; LNQRICLQDME; TKEPKYFHQAW; KEPKYFHQAWL;
EPKYFHQAWLQ; MSILSLKPCKL; SILSLKPCKLD; ILSLKPCKLDL; ENPYKTQSSYL;
NPYKTQSSYLK; PYKTQSSYLKK; YKTQSSYLKKE; KTQSSYLKKEF; TQSSYLKKEFY;
QSSYLKKEFYK; SSYLKKEFYKV; SYLKKEFYKVE; LILQLIYNLEL; ILQLIYNLELL;
LQLIYNLELLN; QLIYNLELLNG; LIYNLELLNGR; IYNLELLNGRK; YNLELLNGRKG;
NLELLNGRKGW; LELLNGRKGWI; ELLNGRKGWIL; LLNGRKGWILR; NIIYAWGNVFL;
IIYAWGNVFLI; IYAWGNVFLIL; YAWGNVFLILQ; AWGNVFLILQE; WGNVFLILQEK;
GNVFLILQEKR; NVFLILQEKRI; VFLILQEKRIQ; FLILQEKRIQK; LILQEKRIQKL;
ILQEKRIQKLK; LQEKRIQKLKT; QEKRIQKLKTL; EKRIQKLKTLD; KRIQKLKTLDM;
RIQKLKTLDMD; IQKLKTLDMDQ; QKLKTLDMDQA; KLKTLDMDQAL; LKTLDMDQALN;
KTLDMDQALNP; TLDMDQALNPN; LDMDQALNPNH; DMDQALNPNHN; MDQALNPNHNA;
DQALNPNHNAL; QALNPNHNALP; ALNPNHNALPK; LNPNHNALPKS; NPNHNALPKSQ;
PNHNALPKSQI; NHNALPKSQIL; HNALPKSQILQ; NALPKSQILQP; ALPKSQILQPL;
LPKSQILQPLL; PKSQILQPLLK; KSQILQPLLKI; SQILQPLLKIP; QILQPLLKIPK;
ILQPLLKIPKG; LQPLLKIPKGQ; QPLLKIPKGQT; PLLKIPKGQTP; LLKIPKGQTPI;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

LKIPKGQTPIV; KIPKGQTPIVK; IPKGQTPIVKS; PKGQTPIVKSC; KGQTPIVKSCI;
GQTPIVKSCIC; QTPIVKSCICV; TPIVKSCICVK; PIVKSCICVKA; IVKSCICVKAF;
VKSCICVKAFS; KSCICVKAFSV; SCICVKAFSVL; CICVKAFSVLK; ICVKAFSVLKG;
CVKAFSVLKGL; VKAFSVLKGLK; KAFSVLKGLKH; AFSVLKGLKHH; FSVLKGLKHHP;
SVLKGLKHHPQ; VLKGLKHHPQN; LKGLKHHPQNN; KGLKHHPQNNT; GLKHHPQNNTS;
LKHHPQNNTSL; KHHPQNNTSLK; HHPQNNTSLKV; HPQNNTSLKVA; PQNNTSLKVAY;
QNNTSLKVAYT; NNTSLKVAYTK; NTSLKVAYTKA; TSLKVAYTKAA; SLKVAYTKAAF;
LKVAYTKAAFI; KVAYTKAAFIK; VAYTKAAFIKC; AYTKAAFIKCI; YTKAAFIKCIC;
TKAAFIKCICT; KAAFIKCICTI; AAFIKCICTIK; AFIKCICTIKA; FIKCICTIKAP;
IKCICTIKAPV; SILVCNCPCLS; ILVCNCPCLSI; LVCNCPCLSIY; VCNCPCLSIYL;
CNCPCLSIYLI; NCPCLSIYLII; CPCLSIYLIIS; PCLSIYLIISG; CLSIYLIISGS;
LSIYLIISGSP; SIYLIISGSPG; IYLIISGSPGS; YLIISGSPGSL; LIISGSPGSLS;
IISGSPGSLSV; ISGSPGSLSVP; SGSPGSLSVPS; GSPGSLSVPSN; SPGSLSVPSNT;
PGSLSVPSNTL; GSLSVPSNTLT; SLSVPSNTLTS; LSVPSNTLTSS; SVPSNTLTSST;
VPSNTLTSSTW; PSNTLTSSTWD; SNTLTSSTWDS; NTLTSSTWDSI; TLTSSTWDSIP;
LTSSTWDSIPY; TSSTWDSIPYI; SSTWDSIPYIG; STWDSIPYIGC; TWDSIPYIGCP;
WDSIPYIGCPS; DSIPYIGCPST; SIPYIGCPSTL; IPYIGCPSTLW; PYIGCPSTLWV;
YIGCPSTLWVL; IGCPSTLWVLL; GCPSTLWVLLF; CPSTLWVLLFI; PSTLWVLLFIR;
STLWVLLFIRS; TLWVLLFIRSL; LWVLLFIRSLS; WVLLFIRSLSK; VLLFIRSLSKK;
LLFIRSLSKKE; LFIRSLSKKEI; FIRSLSKKEIG; GFFTDLFLRRI; FFTDLFLRRIL;
FTDLFLRRILK; TDLFLRRILKY; DLFLRRILKYL; LFLRRILKYLA; FLRRILKYLAR;
LRRILKYLARP; RRILKYLARPL; RILKYLARPLH; ILKYLARPLHC; LKYLARPLHCC;
KYLARPLHCCV; YLARPLHCCVP; LARPLHCCVPE; ARPLHCCVPEL; RPLHCCVPELL;
PLHCCVPELLV; LHCCVPELLVN; HCCVPELLVNR; CCVPELLVNRP; CVPELLVNRPQ;
VPELLVNRPQI; PELLVNRPQIS; ELLVNRPQISA; LLVNRPQISAA; LVNRPQISAAE;
VNRPQISAAET; NRPQISAAETY; RPQISAAETYR; PQISAAETYRL; QISAAETYRLS;
ISAAETYRLSA; SAAETYRLSAL; AAETYRLSALQ; AETYRLSALQR; ETYRLSALQRG;
TYRLSALQRGP; YRLSALQRGPT; RLSALQRGPTP; LSALQRGPTPC; SALQRGPTPCS;
ALQRGPTPCSS; LQRGPTPCSSS; QRGPTPCSSSN; RGPTPCSSSNT; GPTPCSSSNTV;
PTPCSSSNTVV; TPCSSSNTVVA; PCSSSNTVVAV; CSSSNTVVAVL; SSSNTVVAVLV;
SSNTVVAVLVT; STGGTFSPPVK; TGGTFSPPVKV; GGTFSPPVKVP; GTFSPPVKVPK;
TFSPPVKVPKY; FSPPVKVPKYL; SPPVKVPKYLA; PPVKVPKYLAF; PVKVPKYLAFS;
VKVPKYLAFSF; KVPKYLAFSFL; VPKYLAFSFLL; PKYLAFSFLLG; KYLAFSFLLGS;
YLAFSFLLGSG; LAFSFLLGSGT; AFSFLLGSGTQ; FSFLLGSGTQH; SFLLGSGTQHS;
FLLGSGTQHST; LLGSGTQHSTG; ALWSVFITWDW; LWSVFITWDWA; WSVFITWDWAV;
SVFITWDWAVG; VFITWDWAVGF; FITWDWAVGFL; ITWDWAVGFLG; TWDWAVGFLGV;
WDWAVGFLGVI; DWAVGFLGVIV; WAVGFLGVIVP; AVGFLGVIVPS; VGFLGVIVPSG;
GFLGVIVPSGY; FLGVIVPSGYF; LGVIVPSGYFD; GVIVPSGYFDL; FISTPCISKGS;
ISTPCISKGSP; STPCISKGSPP; TPCISKGSPPT; PCISKGSPPTA; CISKGSPPTAK;
ISKGSPPTAKK; SKGSPPTAKKW; KGSPPTAKKWK; GSPPTAKKWKL; SPPTAKKWKLL;
PPTAKKWKLLP; IGFPPPCSCTF; GFPPPCSCTFC; FPPPCSCTFCD; PPPCSCTFCDP;
PPCSCTFCDPA; RLSMLVIPITS; LSMLVIPITSV; SMLVIPITSVC; MLVIPITSVCT;
LVIPITSVCTV; VIPITSVCTVT; IPITSVCTVTA; PITSVCTVTAS; ITSVCTVTASH;
TSVCTVTASHI; SVCTVTASHIS; VCTVTASHISR; CTVTASHISRF; TVTASHISRFP;
VTASHISRFPQ; TASHISRFPQV; ASHISRFPQVR; SHISRFPQVRS; HISRFPQVRSS;
ISRFPQVRSSF; SRFPQVRSSFK; RFPQVRSSFKL; FPQVRSSFKLG; PQVRSSFKLGR;
QVRSSFKLGRG; VRSSFKLGRGI; RSSFKLGRGIL; SSFKLGRGILA; SFKLGRGILAV;
FKLGRGILAVL; QGSIFLSGLSL; GSIFLSGLSLL; SIFLSGLSLLK; IFLSGLSLLKS;
FLSGLSLLKSF; LSGLSLLKSFS; SGLSLLKSFSA; GLSLLKSFSAL; LSLLKSFSALS;
SLLKSFSALSF; LLKSFSALSFR; LKSFSALSFRL; KSFSALSFRLK; SFSALSFRLKP;
FSALSFRLKPL; SALSFRLKPLR; ALSFRLKPLRF; LSFRLKPLRFS; SFRLKPLRFSS;
FRLKPLRFSSG; RLKPLRFSSGS; LKPLRFSSGSP; KPLRFSSGSPI; PLRFSSGSPIS;
LRFSSGSPISG; RFSSGSPISGF; FSSGSPISGFR; SSGSPISGFRK; SGSPISGFRKH;
GSPISGFRKHS; SPISGFRKHST; PISGFRKHSTS; ISGFRKHSTSV; SGFRKHSTSVI;
GFRKHSTSVIA; FRKHSTSVIAS; RKHSTSVIAST; KHSTSVIASTP; HSTSVIASTPV;
STSVIASTPVL; TSVIASTPVLT; SVIASTPVLTS; VIASTPVLTSR; IASTPVLTSRT;
ASTPVLTSRTS; STPVLTSRTST; TPVLTSRTSTP; PVLTSRTSTPP; VLTSRTSTPPF;
LTSRTSTPPFI; TSRTSTPPFIS; SRTSTPPFISS; RTSTPPFISSF; TSTPPFISSFG;
STPPFISSFGT; TPPFISSFGTC; PPFISSFGTCT; PFISSFGTCTG; FISSFGTCTGS;
ISSFGTCTGSF; SSFGTCTGSFG; SFGTCTGSFGF; FGTCTGSFGFL; GTCTGSFGFLG;
TCTGSFGFLGA; CTGSFGFLGAA; TGSFGFLGAAP; GSFGFLGAAPG; SFGFLGAAPGH;
FGFLGAAPGHS; GFLGAAPGHSP; FLGAAPGHSPF; LGAAPGHSPFL; GAAPGHSPFLL;
AAPGHSPFLLV; APGHSPFLLVG; PGHSPFLLVGA; GHSPFLLVGAI; HSPFLLVGAIF;
SPFLLVGAIFI; PFLLVGAIFIC; FLLVGAIFICF; LLVGAIFICFK; LVGAIFICFKS;
VGAIFICFKSR; GAIFICFKSRC; AIFICFKSRCY; IFICFKSRCYS; FICFKSRCYSP;
ICFKSRCYSPV; CFKSRCYSPVQ; FKSRCYSPVQA; RQHPLRSSSLI; QHPLRSSSLIS;
HPLRSSSLIST; PLRSSSLISTS; LRSSSLISTSW; RSSSLISTSWG; SSSLISTSWGN;
SSLISTSWGNS; SLISTSWGNSF; LISTSWGNSFF; ISTSWGNSFFY; STSWGNSFFYK;
TSWGNSFFYKL; SWGNSFFYKLS; VHSLCNFFYTV; HSLCNFFYTVS; SLCNFFYTVSI;
LCNFFYTVSII; CNFFYTVSIIY; NFFYTVSIIYT; FFYTVSIIYTI; FYTVSIIYTIS;
YTVSIIYTISM; TVSIIYTISMA; VSIIYTISMAK; IIYTISMAKMY;
IYTISMAKMYT; YTISMAKMYTG; TISMAKMYTGT; ISMAKMYTGTF; SMAKMYTGTFP;
MAKMYTGTFPF; AKMYTGTFPFS; KMYTGTFPFSY; MYTGTFPFSYL; YTGTFPFSYLS;
TGTFPFSYLSN; GTFPFSYLSNH; GPNRGKIRIIL; PNRGKIRIILL; NRGKIRIILLN;
RGKIRIILLNI; GKIRIILLNII; KIRIILLNIII; IRIILLNIIIK; RIILLNIIIKV;
IILLNIIIKVY; ILLNIIIKVYR; LLNIIIKVYRG; LNIIIKVYRGI; NIIIKVYRGIY;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

IIIKVYRGIYN; IIKVYRGIYNC; IKVYRGIYNCP; KVYRGIYNCPG; VYRGIYNCPGS;
YRGIYNCPGSF; RGIYNCPGSFL; GIYNCPGSFLQ; IYNCPGSFLQK; YNCPGSFLQKS;
NCPGSFLQKSS; CPGSFLQKSSQ; PGSFLQKSSQG; GSFLQKSSQGV; SFLQKSSQGVS;
FLQKSSQGVSK; LQKSSQGVSKK; QKSSQGVSKKS; KSSQGVSKKSF; SSQGVSKKSFC;
SQGVSKKSFCS; QGVSKKSFCSS; GVSKKSFCSSL; VSKKSFCSSLQ; SKKSFCSSLQF;
KKSFCSSLQFL; GYRRYIIPNNM; YRRYIIPNNMP; RRYIIPNNMPQ; RYIIPNNMPQS;
YIIPNNMPQSL; IIPNNMPQSLG; IPNNMPQSLGN; PNNMPQSLGNS; NNMPQSLGNSS;
NMPQSLGNSSK; MPQSLGNSSKQ; PQSLGNSSKQR; QSLGNSSKQRR; SLGNSSKQRRT;
LGNSSKQRRTP; GNSSKQRRTPM; NSSKQRRTPMP; SSKQRRTPMPR; SKQRRTPMPRI;
KQRRTPMPRIK; QRRTPMPRIKV; RRTPMPRIKVL; RTPMPRIKVLN; TPMPRIKVLNI;
PMPRIKVLNII; MPRIKVLNIIN; PRIKVLNIINK; RIKVLNIINKS; IKVLNIINKSI;
KVLNIINKSIY; VLNIINKSIYT; LNIINKSIYTR; NIINKSIYTRK; IINKSIYTRKQ;
INKSIYTRKQN; NKSIYTRKQNI; KSIYTRKQNII; SIYTRKQNIIV; IYTRKQNIIVL;
YTRKQNIIVLI; TRKQNIIVLIW; RKQNIIVLIWV; KQNIIVLIWVK; QNIIVLIWVKQ;
NIIVLIWVKQF; IIVLIWVKQFQ; IVLIWVKQFQS; VLIWVKQFQSH; LIWVKQFQSHA;
LLIEAYSGNFV; LIEAYSGNFVI; IEAYSGNFVIP; EAYSGNFVIPI; AYSGNFVIPII;
YSGNFVIPIIK; SGNFVIPIIKE; GNFVIPIIKEL; NFVIPIIKELI; FVIPIIKELIP;
VIPIIKELIPY; IPIIKELIPYL; PIIKELIPYLS; SSKPSNSPRST; SKPSNSPRSTS;
KPSNSPRSTSN; PSNSPRSTSNY; SNSPRSTSNYS; NSPRSTSNYSI; SPRSTSNYSIC;
PRSTSNYSICL; RSTSNYSICLR; STSNYSICLRS; GTCYALYSSKG; TCYALYSSKGC;
CYALYSSKGCN; YALYSSKGCNL; ALYSSKGCNLN; LYSSKGCNLNF; YSSKGCNLNFY;
SSKGCNLNFYS; SKGCNLNFYSS; KGCNLNFYSSS; GCNLNFYSSSS; CNLNFYSSSSL;
NLNFYSSSSLP; LNFYSSSSLPS; NFYSSSSLPSS; FYSSSSLPSSN; YSSSSLPSSNF;
SSSSLPSSNFS; SSSLPSSNFSH; KSCGSSSLRYT; SCGSSSLRYTG; CGSSSLRYTGN;
SSTHEPGNTKK; STHEPGNTKKK; THEPGNTKKKG; HEPGNTKKKGL; EPGNTKKKGLL;
PGNTKKKGLLT; ESFTESFTAGK; SFTESFTAGKA; FTESFTAGKAV; TESFTAGKAVV;
ESFTAGKAVVL; SFTAGKAVVLL; FTAGKAVVLLF; TAGKAVVLLFF; AGKAVVLLFFP;
GKAVVLLFFPS; KAVVLLFFPST; AVVLLFFPSTL; VVLLFFPSTLS; VLLFFPSTLSS;
LLFFPSTLSSP; LFFPSTLSSPL; FFPSTLSSPLQ; FPSTLSSPLQN; PSTLSSPLQNS;
STLSSPLQNSS; TLSSPLQNSSK; LSSPLQNSSKS; SSPLQNSSKSS; SPLQNSSKSSK;
PLQNSSKSSKI; LQNSSKSSKIK; QNSSKSSKIKI; NSSKSSKIKIK; SSKSSKIKIKI;
SKSSKIKIKIL; ALFFVPVQVLP; LFFVPVQVLPT; FFVPVQVLPTF; FVPVQVLPTFT;
VPVQVLPTFTE; PVQVLPTFTEA; VQVLPTFTEAC; QVLPTFTEACR; VLPTFTEACRD;
LPTFTEACRDS; PTFTEACRDSW; TFTEACRDSWR; FTEACRDSWRR; TEACRDSWRRT;
EACRDSWRRTM; ACRDSWRRTMA; CRDSWRRTMAF; RDSWRRTMAFV; DSWRRTMAFVQ;
SWRRTMAFVQF; WRRTMAFVQFN; RRTMAFVQFNW; RTMAFVQFNWG; TMAFVQFNWGQ;
MAFVQFNWGQG; AFVQFNWGQGQ; FVQFNWGQGQD; VQFNWGQGQDS; ARKTCLSCTFL;
RKTCLSCTFLP; KTCLSCTFLPE; TCLSCTFLPEV; CLSCTFLPEVM; LSCTFLPEVMV;
SCTFLPEVMVW; CTFLPEVMVWL; TFLPEVMVWLH; FLPEVMVWLHS; LPEVMVWLHSM;
PEVMVWLHSMG; EVMVWLHSMGK; VMVWLHSMGKQ; MVWLHSMGKQL; VWLHSMGKQLL;
WLHSMGKQLLP; LHSMGKQLLPV; HSMGKQLLPVS; SMGKQLLPVSH; MGKQLLPVSHA;
GKQLLPVSHAL; KQLLPVSHALS; QLLPVSHALSF; LLPVSHALSFL; LPVSHALSFLR;
PVSHALSFLRS; VSHALSFLRSW; SHALSFLRSWF; HALSFLRSWFG; ALSFLRSWFGC;
LSFLRSWFGCI; SFLRSWFGCIP; FLRSWFGCIPL; AAPPCGLFFYN; APPCGLFFYNI;
EAEAASASTLS; AEAASASTLSL; EAASASTLSLK; GLAKLFGEIPI; LAKLFGEIPIL;
AKLFGEIPILL; KLFGEIPILLQ; LFGEIPILLQF; FGEIPILLQFL; GEIPILLQFLQ

BK virus complementary reading frame 2

8 mers:

WIKFLTGK; IKFLTGKN; KFLTGKNP; FLTGKNPW; LTGKNPWS; TGKNPWSS; GKNPWSSW;
KNPWSSWT; NPWSSWTF; ALKELPGE; LKELPGEI; KELPGEIF; ELPGEIFP; GSVRNFTL;
SVRNFTLT; VRNFTLTK; RNFTLTKG; NFTLTKGA; FTLTKGAT; TLTKGATR; LTKGATRI;
TKGATRIK; ILCIKKWS; LCIKKWSR; CIKKWSRM; LISLILEP; ISLILEPG; SLILEPGV;
LILEPGVA; ILEPGVAQ; LEPGVAQR; EPGVAQRF; PGVAQRFV; GVAQRFVL; VAQRFVLI;
AQRFVLIF; QRFVLIFL; RFVLIFLF; FVLIFLFA; VLIFLFAQ; LIFLFAQI; IFLFAQIP;
FLFAQIPC; LFAQIPCT; FAQIPCTA; AQIPCTAR; QIPCTARN; IPCTARNG; PCTARNGL;
CTARNGLF; TARNGLFV; ARNGLFVP; RNGLFVPK; NGLFVPKS; GLFVPKSL; LFVPKSLL;
FVPKSLLC; VPKSLLCT; PKSLLCTA; KSLLCTAL; SLLCTALA; LLCTALAC; LCTALACY;
CTALACYV; TALACYVS; ALACYVSL; LACYVSLD; IATALTAS; ATALTASH; TALTASHS;
ALTASHSG; LTASHSGL; TASHSGLA; LKKLCNGG; KLCNGGSK; LCNGGSKL; LEKLPSEI;
SFKVTNLY; FKVTNLYL; KVTNLYLD; VTNLYLDK; VIIFFIGA; IIFFIGAN; IFFIGANL;
FFIGANLW; FIGANLWN; IGANLWNR; GANLWNRR; ANLWNRRV; NLWNRRVG; LWNRRVGV;
WNRRVGVL; NRRVGVLV; RRVGVLVE; RVGVLVEF; VGVLVEFL; RSNSRFST; SNSRFSTL;
NSRFSTLN; SRFSTLNT; RFSTLNTT; FSTLNTTQ; STLNTTQK; TLNTTQKK; LNTTQKKK;
NTTQKKKK; TTQKKKKG; TQKKKKGR; QKKKKGRR; KKKKGRRP; NPCLLCCV; PCLLCCVY;
CLLCCVYY; KTYGKIFC; TYGKIFCN; YGKIFCNF; GKIFCNFY; YYILFNST; FLSKAVYL;
RSIPYYRR; SIPYYRRK; IPYYRRKH; PYYRRKHS; YYRRKHSR; YRRKHSRG; RRKHSRGL;
RKHSRGLK; KHSRGLKG; HSRGLKGA; RNKAGVLE; NKAGVLEI; KAGVLEIN; AGVLEINY;
GCVFIIRY; CVFIIRYV; VFIIRYVF; FIIRYVFR; IIRYVFRI; IRYVFRIS; RYVFRISI;
YVFRISIQ; VFRISIQC; FRISIQCR; RISIQCRG; ISIQCRGV; KVSEKRPA; VSEKRPAL;
SEKRPALS; EKRPALSL; KALCKCYY; ALCKCYYF; LCKCYYFC; CKCYYFCR; KCYYFCRK;
KSKKYLSA; SKKYLSAS; KKYLSASS; KYLSASSR; YLSASSRY; LSASSRYS; SASSRYSF;
ASSRYSFS; KKSRYPSY; KSRYPSYD; SRYPSYDQ; RYPSYDQG; YPSYDQGR; PSYDQGRN;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

SYDQGRNA; YDQGRNAN; DQGRNANR; QGRNANRK; GRNANRKI; RNANRKIQ; NANRKIQS;
ANRKIQSY; NRKIQSYI; RKIQSYIR; NGFNIWSS; GFNIWSSW; FNIWSSWK; NIWSSWKC;
IWSSWKCC; WSSWKCCT; SSWKCCTR; SWKCCTRT; WKCCTRTI; KCCTRTIY; CCTRTIYG;
CTRTIYGR; TRTIYGRC; RTIYGRCC; TIYGRCCL; IYGRCCLA; YGRCCLAA; GRCCLAAL;
RCCLAALF; CCLAALFA; CLAALFAT; FFALYCFQ; FALYCFQC; ALYCFQCT; WKNNTSCR;
KNNTSCRV; NNTSCRVI; NTSCRVIR; TSCRVIRF; SCRVIRFV; CRVIRFVW; RVIRFVWW;
SLKCKPTH; LKCKPTHG; KCKPTHGK; CKPTHGKA; KPTHGKAN; PTHGKANL; ARCSYRSV;
RCSYRSVH; CSYRSVHG; SYRSVHGC; YRSVHGCF; IKGFAFRT; KGFAFRTW; GFAFRTWN;
FAFRTWNK; APRTWNKQ; FRTWNKQF; RTWNKQFR; TWNKQFRQ; WNKQFRQF; NKQFRQFE;
KQFRQFER; QFRQFERL; FRQFERLF; RQFERLFR; QFERLFRW; FERLFRWK; ERLFRWKC;
GKFRKETF; KFRKETFK; FRKETFKQ; RKETFKQK; KETFKQKN; ETFKQKNP; TFKQKNPN;
FKQKNPNI; KQKNPNIS; QKNPNIST; KNPNISTR; NPNISTRL; PNISTRLG; NISTRLGY;
ISTRLGYN; STRLGYNE; AQNIFKKI; QNIFKKIL; NIFKKILT; IFKKILTK; FKKILTKL;
KKILTKLR; KILTKLRV; ILTKLRVL; LTKLRVLT; KKNFTKWN; KNFTKWND; NFTKWNDL;
FTKWNDLV; TKWNDLVA; KWNDLVAT; WNDLVATA; NDLVATAN; DLVATANL; LVATANLV;
DKYVYFFK; KYVYFFKD; YVYFFKDE; VYFFKDEI; YMHGEMYS; YYKRRGFR; YKRRGFRN;
RLWTWIKH; IPITMLFP; PITMLFPS; ITMLFPSL; TMLFPSLR; MLFPSLRY; LFPSLRYF;
FPSLRYFS; PSLRYFSP; SLRYFSPC; RFPKVRPP; NTTPKITQ; TTPKITQA; KWLIQKQH;
WLIQKQHL; LIQKQHLL; IQKQHLLN; QKQHLLNV; KQHLLNVY; QHLLNVYV; HLLNVYVQ;
KHLFKAFW; HLFKAFWF; LFKAFWFA; FKAFWFAI; KAFWFAIV; AFWFAIVP; FWFAIVPV;
WFAIVPVC; FAIVPVCQ; AIVPVCQY; IVPVCQYI; VPVCQYIL; PVCQYILS; VCQYILSY;
CQYILSYL; QYILSYLG; YILSYLGP; ILSYLGPL; LSYLGPLE; SYLGPLEV; YLGPLEVF;
LGPLEVFL; GPLEVFLC; PLEVFLCH; LEVFLCHQ; EVFLCHQT; VFLCHQTP; PLLPGIPY;
LLPGIPYH; LPGIPYHT; AAHPLSGF; AHPLSGFS; HPLSGFSC; PLSGFSCL; GHLAKRKL;
HLAKRKLG; LAKRKLGK; AKRKLGKD; KRKLGKDS; RKLGKDSL; KLGKDSLQ; LGKDSLQI;
GKDSLQIF; KDSLQIFF; DSLQIFFS; SLQIFFSG; LQIFFSGG; QIFFSGGS; NILQGLST;
ILQGLSTV; LQGLSTVV; QGLSTVVF; GLSTVVFQ; LSTVVFQS; STVVFQSC; TGHKYQQL;
GHKYQQLK; HKYQQLKH; KYQQLKHT; YQQLKHTG; QQLKHTGY; QLKHTGYQ; LKHTGYQL;
KHTGYQLY; HTGYQLYK; TGYQLYKE; GYQLYKEA; YQLYKEAP; QLYKEAPH; LYKEAPHP;
YKEAPHPV; KEAPHPVH; EAPHPVHL; APHPVHLA; PHPVHLAT; HPVHLATL; PVHLATLW;
LCWSHEVL; CWSHEVLG; WSHEVLGE; SHEVLGEH; HEVLGEHF; EVLGEHFP; VLGEHFPL;
LGEHFPLL; HFHFYWDQ; FHFYWDQV; HFYWDQVP; FYWDQVPS; YWDQVPST; WDQVPSTQ;
DQVPSTQL; QVPSTQLD; VPSTQLDK; PSTQLDKH; STQLDKHC; TQLDKHCF; QLDKHCFC;
LDKHCFCP; DKHCFCPN; KHCFCPNR; HCFCPNRP; CFCPNRPY; FCPNRPYG; CPNRPYGQ;
PNRPYGQY; NRPYGQYS; RPYGQYSL; PYGQYSLP; YGQYSLPG; GQYSLPGT; QYSLPGTG;
YSLPGTGL; SLPGTGLL; LPGTGLLG; PGTGLLGF; YHQGTLTC; HQGTLTCN; QGTLTCNS;
GTLTCNSL; TLTCNSLA; LTCNSLAL; TCNSLALP; CNSLALPA; NSLALPAF; SLALPAFP;
LALPAFPR; ALPAFPRV; LPAFPRVL; PAFPRVLH; FPRVLHLQ; PRVLHLQQ;
RVLHLQQR; VLHLQQRS; LHLQQRSG; HLQQRSGN; LQQRSGNY; QQRSGNYC; QRSGNYCL;
RSGNYCLE; VFLHHAHA; FLHHAHAL; LHHAHALF; HHAHALFV; HAHALFVT; AHALFVTL;
HALFVTLH; ALFVTLHE; LFVTLHEG; PLFVQLQP; LFVQLQPP; FVQLQPPT; VQLQPPTS;
QLQPPTSV; LQPPTSVD; QPPTSVDF; PPTSVDFH; PTSVDFHR; TSVDFHRL; SVDFHRLG;
VDFHRLGP; DFHRLGPH; FHRLGPHL; HRLGPHLN; RLGPHLNW; LGPHLNWG; GPHLNWGG;
PHLNWGGE; HLNWGGEF; LNWGGEFL; NWGGEFLL; WGGEFLLC; GGEFLLCC; GEFLLCCN;
EFLLCCNR; FLLCCNRE; LLCCNREA; LCCNREAF; CCNREAFF; CNREAFFS; NREAFFSL;
REAFFSLG; EAFFSLGY; AFFSLGYH; FFSLGYHC; SHFQHLAL; HFQHLALD; FQHLALDP;
FHLDPPFL; HLDPPFLG; LDPPFLGL; DPPFLGLG; PPFLGLGS; PFLGLGSI; FLGLGSIL;
LGLGSILP; GLGSILPL; LLELLLLL; LELLLLLL; ELLLLLLL; LLLLLLLV; LLLLLLVV;
LLLLLVVL; LLLLVVLA; LLLVVLAL; LLVVLALA; LVVLALAR; VVLALARV; VLALARVP;
LALARVPL; ALARVPLA; LARVPLAF; ARVPLAFW; RVPLAFWE; VPLAFWEL; PLAFWELP;
LAFWELPL; AFWELPLD; FWELPLDT; WELPLDTL; ELPLDTLL; LPLDTLLF; PLDTLLFF;
LDTLLFFW; DTLLFFWL; TLLFFWLG; LLFFWLGP; LFFWLGPS; FFWLGPSS; FWLGPSSY;
WLGPSSYA; LGPSSYAS; GPSSYASR; PSSYASRA; SSYASRAG; SYASRAGV; YASRAGVT;
ASRAGVTV; SRAGVTVP; RAGVTVPY; AGVTVPYR; GVTVPYRP; VTVPYRPR; TVPYRPRS;
VPYRPRSK; PYRPRSKG; YRPRSKGN; RPRSKGNI; PRSKGNIH; LAPPGAIV; APPGAIVF;
PPGAIVFS; PGAIVFSI; GAIVFSIN; AIVFSINS; IVFSINSP; VFSINSPE; FSINSPEC;
SINSPECT; INSPECTL; NSPECTLC; FLKSILCV; LKSILCVT; KSILCVTS; SILCVTSS;
ILCVTSSI; LCVTSSIL; CVTSSILS; VTSSILSA; TSSILSAS; SSILSASS; SILSASSI;
ILSASSIL; VWPKCTRV; WPKCTRVP; PKCTRVPS; CTRVPSLS; TRVPSLSA;
RVPSLSAT; VPSLSATC; PSLSATCL; SLSATCLT; LSATCLTI; SATCLTIE; ATCLTIEG;
TCLTIEGL; CLTIEGLI; LTIEGLIG; TIEGLIGE; IEGLIGER; EGLIGERS; GLIGERSE;
KFIGAFTI; FIGAFTIV; IGAFTIVQ; GAFTIVQV; AFTIVQVV; FTIVQVVS; TIVQVVSS;
IVQVVSSK; VQVVSSKN; QVVSSKNL; VVSSKNLA; VSSKNLAK; SSKNLAKE; SKNLAKES;
KNLAKESL; NLAKESLK; LAKESLKN; AKESLKNL; KESLKNLS; ESLKNLSV; SLKNLSVL;
LKNLSVLL; KNLSVLLC; NLSVLLCN; LSVLLCNS; SVLLCNSC; VLLCNSCE; LLCNSCEV;
LCNSCEVI; CNSCEVIE; NSCEVIEG; SCEVIEGI; CEVIEGIS; EVIEGISS; VIEGISSL;
IEGISSLI; EGISSLIT; GISSLITC; ISSLITCH; SSLITCHK; SLITCHKA; LITCHKAW;
ITCHKAWE; TCHKAWEI; CHKAWEIV; HKAWEIVA; KAWEIVAN; AWEIVANK; WEIVANKE;
EIVANKEG; IVANKEGP; VANKEGPQ; ANKEGPQC; NKEGPQCL; KEGPQCLG; EGPQCLGS;
GPQCLGSR; PQCLGSRY; ILLTKVFT; LLTKVFTP; LTKVFTPG; TKVFTPGN; KVFTPGNR;
VFTPGNRI; FTPGNRIS; YSSGLNNS; SSGLNNSK; SGLNNSKA; GLNNSKAM; LNNSKAMP;
NNSKAMPD; NSKAMPDC; SQSSKNLY; QSSKNLYP; SSKNLYPT; AKELIPLT; KELIPLTV;
IKAANPAI; KAANPAIA; AANPAIAP; ANPAIAPG; NPAIAPGA; PAIAPGAP; AIAPGAPA;
IAPGAPAI; APGAPAIT; PGAPAITA; GAPAITAY; APAITAYV; GVRPIAAI; VRPIAAIA;
RPIAAIAS; PIAAIASE; IAAIASEV; AAIASEVL; AIASEVLV; IASEVLVM; ASEVLVMP;
SEVLVMPS; EVLVMPST; VLVMPSTV; LVMPSTVA; VMPSTVAR; MPSTVARD; PSTVARDA;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

STVARDAI; TSIAAAAS; SIAAAASP; IAAAASPA; AAAASPAA; AASPAAI; ASPAAIS;
ASPAAISA; SPAAISAT; PAAISATE; AAISATEN; AISATENP; ISATENPV; SATENPVA;
ATENPVAA; TENPVAAA; ENPVAAAA; NPVAAAAS; PVAAAASD; VAAAASDT; AAAASDTL;
AAASDTLA; AASDTLAT; ASDTLATR; SDTLATRS; DTLATRSP; TLATRSPK; LATRSPKS;
ATRSPKSA; TRSPKSAR; RSPKSARA; SPKSARAA; PKSARAAP; KSARAAPM; SARAAPMN;
ARAAPMNL; RAAPMNLE; AAPMNLEI; APMNLEIQ; PMNLEIQK; MNLEIQKK; NLEIQKKR;
LEIQKKRD; EIQKKRDY; IQKKRDYL; QKKRDYLP; KKRDYLPR; KRDYLPRS; RDYLPRSL;
DYLPRSLL; YLPRSLLQ; LPRSLLQS; PRSLLQSL; RSLLQSLL; SLLQSLLQ; LLQSLLQQ;
LQSLLQQV; QSLLQQVK; SLLQQVKQ; LLQQVKQW; LQQVKQWY; QVKQWYF; QVKQWYFC;
VKQWYFCF; KQWYFCFS; QWYFCFSR; WYFCFSRL; YFCFSRLH; FCFSRLHC; CFSRLHCL;
FSRLHCLH; SRLHCLHL; RLHCLHLY; LHCLHLYK; HCLHLYKI; CLHLYKIP; LHLYKIPA;
HLYKIPAK; LYKIPAKA; YKIPAKAL; KIPAKALK; KSSELFFL; SSELFFLF; SELFFLFQ;
ELFFLFQS; LFFLFQSR; FFLFQSRF; FLFQSRFY; LFQSRFYQ; FQSRFYQL; QSRFYQLS;
SRFYQLSL; RFYQLSLK; FYQLSLKL; YQLSLKLV; QLSLKLVV; LSLKLVVT; SLKLVVTA;
LKLVVTAG; KLVVTAGA; LVVTAGAE; VVTAGAEP; VTAGAEPW; TAGAEPWP; AGAEPWPL;
GAEPWPLS; AEPWPLSS; EPWPLSSL; PWPLSSLT; WPLSSLTG; PLSSLTGD; LSSLTGDK;
SSLTGDKA; SLTGDKAK; LTGDKAKI; TGDKAKIP; GDKAKIPR; DKAKIPRL; KAKIPRLA;
AKIPRLAK; KIPRLAKH; IPRLAKHV; PRLAKHVC; RLAKHVCH; LAKHVCHA; AKHVCHAL;
KHVCHALS; HVCHALSF; VCHALSFL; CHALSFLR; HALSFLRS; ALSFLRSW; LSFLRSWF;
SFLRSWFG; FLRSWFGC; LRSWFGCI; RSWFGCIP; SWFGCIPW; WFGCIPWV; FGCIPWVS;
GCIPWVSS; CIPWVSSS; IPWVSSSS; PWVSSSSL; GHGLAAFP; HGLAAFPC; GLAAFPCE;
LAAFPCES; AAFPCESC; AFPCESCT; FPCESCTF; PCESCTFL; CESCTFLP; ESCTFLPE;
SCTFLPEV; CTFLPEVM; TFLPEVMV; FLPEVMVW; LPEVMVWL; PEVMVWLH; EVMVWLHS;
VMVWLHSM; MVWLHSMG; VWLHSMGK; WLHSMGKQ; LHSMGKQL; HSMGKQLL; SMGKQLLP;
MGKQLLPV; GKQLLPVA; KQLLPVAF; QLLPVAFF; LLPVAFFF; LPVAFFFI; PVAFFFII;
VAFFFIIY; AFFFIIYK; FFFIIYKR; FFIIYKRP; FIIYKRPR; IIYKRPRP; IYKRPRPP;
YKRPRPPL; KRPRPPLP; RPRPPLPP; PRPPLPPP; RPPLPPPF; PPLPPPFL; PLPPPFLS;
LPPPFLSS; PPPFLSSS; PPFLSSSK; PFLSSSKG; FLSSSKGV; LSSSKGVE; SSSKGVEA;
SSKGVEAF; SKGVEAFS; KGVEAFSE; GVEAFSEA; QNYLGKSL; NYLGKSLF; YLGKSLFF;
LGKSLFFC; GKSLFFCN; KSLFFCNF; SLFFCNFC; LFFCNFCK 9 mers:

WIKFLTGKN; IKFLTGKNP; KFLTGKNPW; FLTGKNPWS; LTGKNPWSS; TGKNPWSSW;
GKNPWSSWT; KNPWSSWTF; ALKELPGEI; LKELPGEIF; KELPGEIFP; GSVRNFTLT;
SVRNFTLTK; VRNFTLTKG; RNFTLTKGA; NFTLTKGAT; FTLTKGATR; TLTKGATRI;
LTKGATRIK; ILCIKKWSR; LCIKKWSRM; LISLILEPG; ISLILEPGV; SLILEPGVA;
LILEPGVAQ; ILEPGVAQR; LEPGVAQRF; EPGVAQRFV; PGVAQRFVL; GVAQRFVLI;
VAQRFVLIF; AQRFVLIFL; QRFVLIFLF; RFVLIFLFA; FVLIFLFAQ; VLIFLFAQI;
LIFLFAQIP; IFLFAQIPC; FLFAQIPCT; LFAQIPCTA; FAQIPCTAR; AQIPCTARN;
QIPCTARNG; IPCTARNGL; PCTARNGLF; CTARNGLFV; TARNGLFVP; ARNGLFVPK;
RNGLFVPKS; NGLFVPKSL; GLFVPKSLL; LFVPKSLLC; FVPKSLLCT; VPKSLLCTA;
PKSLLCTAL; KSLLCTALA; SLLCTALAC; LLCTALACY; LCTALACYV; CTALACYVS;
TALACYVSL; ALACYVSLD; IATALTASH; ATALTASHS; TALTASHSG; ALTASHSGL;
LTASHSGLA; LKKLCNGGS; KKLCNGGSK; SFKVTNLYL; FKVTNLYLD; KVTNLYLDK;
VIIFFIGAN; IIFFIGANL; IFFIGANLW; FFIGANLWN; FIGANLWNR; IGANLWNRR;
GANLWNRRV; ANLWNRRVG; NLWNRRVGV; LWNRRVGVL; WNRRVGVLV; NRRVGVLVE;
RRVGVLVEF; RVGVLVEFL; RSNSRFSTL; SNSRFSTLN; NSRFSTLNT; SRFSTLNTT;
RFSTLNTTQ; FSTLNTTQK; STLNTTQKK; TLNTTQKKK; LNTTQKKKK; NTTQKKKKG;
TTQKKKKGR; TQKKKKGRR; QKKKKGRRP; NPCLLCCVY; PCLLCCVYY; KTYGKIFCN;
TYGKIFCNF; YGKIFCNFY; RSIPYYRRK; SIPYYRRKH; IPYYRRKHS; PYYRRKHSR;
YYRRKHSRG; YRRKHSRGL; RRKHSRGLK; RKHSRGLKG; KHSRGLKGA; RNKAGVLEI;
NKAGVLEIN; KAGVLEINY; GCVFIIRYV; CVFIIRYVF; VFIIRYVFR; FIIRYVFRI;
IIRYVFRIS; IRYVFRISI; RYVFRISIQ; YVFRISIQC; VFRISIQCR; FRISIQCRG;
RISIQCRGV; KVSEKRPAL; VSEKRPALS; SEKRPALSL; KALCKCYYF; ALCKCYYFC;
LCKCYYFCR; CKCYYFCRK; KSKKYLSAS; SKKYLSASS; KKYLSASSR; KYLSASSRY;
YLSASSRYS; LSASSRYSF; SASSRYSFS; KKSRYPSYD; KSRYPSYDQ; SRYPSYDQG;
RYPSYDQGR; YPSYDQGRN; PSYDQGRNA; SYDQGRNAN; YDQGRNANR; DQGRNANRK;
QGRNANRKI; GRNANRKIQ; RNANRKIQS; NANRKIQSY; ANRKIQSYI; NRKIQSYIR;
NGFNIWSSW; GFNIWSSWK; FNIWSSWKC; NIWSSWKCC; IWSSWKCCT; WSSWKCCTR;
SSWKCCTRT; SWKCCTRTI; WKCCTRTIY; KCCTRTIYG; CCTRTIYGR; CTRTIYGRC;
TRTIYGRCC; RTIYGRCCL; TIYGRCCLA; IYGRCCLAA; YGRCCLAAL; GRCCLAALF;
RCCLAALFA; CCLAALFAT; FFALYCFQC; FALYCFQCT; WKNNTSCRV; KNNTSCRVI;
NNTSCRVIR; NTSCRVIRF; TSCRVIRFV; SCRVIRFVW; CRVIRFVWW; SLKCKPTHG;
LKCKPTHGK; KCKPTHGKA; CKPTHGKAN; KPTHGKANL; ARCSYRSVH; RCSYRSVHG;
CSYRSVHGC; SYRSVHGCF; IKGFAFRTW; KGFAFRTWN; GFAFRTWNK; FAFRTWNKQ;
AFRTWNKQF; FRTWNKQFR; RTWNKQFRQ; TWNKQFRQF; WNKQFRQFE; NKQFRQFER;
KQFRQFERL; QFRQFERLF; FRQFERLFR; RQFERLFRW; QFERLFRWK; FERLFRWKC;
GKFRKETFK; KFRKETFKQ; FRKETFKQK; RKETFKQKN; KETFKQKNP; ETFKQKNPN;
TFKQKNPNI; FKQKNPNIS; KQKNPNIST; QKNPNISTR; KNPNISTRL; NPNISTRLG;
PNISTRLGY; NISTRLGYN; ISTRLGYNE; AQNIFKKIL; QNIFKKILT; NIFKKILTK;
IFKKILTKL; FKKILTKLR; KKILTKLRV; KILTKLRVL; ILTKLRVLT; KKNFTKWND;
KNFTKWNDL; NFTKWNDLV; FTKWNDLVA; TKWNDLVAT; KWNDLVATA; WNDLVATAN;
NDLVATANL; DLVATANLV; DKYVYFFKD; KYVYFFKDE; YVYFFKDEI; YYKRRGFRN;
IPITMLFPS; PITMLFPSL; ITMLFPSLR; TMLFPSLRY; MLFPSLRYF; LFPSLRYFS;
FPSLRYFSP; PSLRYFSPC; NTTPKITQA; KWLIQKQHL; WLIQKQHLL; LIQKQHLLN;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

IQKQHLLNV; QKQHLLNVY; KQHLLNVYV; QHLLNVYVQ; KHLFKAFWF; HLFKAFWFA;
LFKAFWFAI; FKAFWFAIV; KAFWFAIVP; AFWFAIVPV; FWFAIVPVC; WFAIVPVCQ;
FAIVPVCQY; AIVPVCQYI; IVPVCQYIL; VPVCQYILS; PVCQYILSY; VCQYILSYL;
CQYILSYLG; QYILSYLGP; YILSYLGPL; ILSYLGPLE; LSYLGPLEV; SYLGPLEVF;
YLGPLEVFL; LGPLEVFLC; GPLEVFLCH; PLEVFLCHQ; LEVFLCHQT; EVFLCHQTP;
PLLPGIPYH; LLPGIPYHT; AAHPLSGFS; AHPLSGFSC; HPLSGFSCL; GHLAKRKLG;
HLAKRKLGK; LAKRKLGKD; AKRKLGKDS; KRKLGKDSL; RKLGKDSLQ; KLGKDSLQI;
LGKDSLQIF; GKDSLQIFF; KDSLQIFFS; DSLQIFFSG; SLQIFFSGG; LQIFFSGGS;
NILQGLSTV; ILQGLSTVV; LQGLSTVVF; QGLSTVVFQ; GLSTVVFQS; LSTVVFQSC;
TGHKYQQLK; GHKYQQLKH; HKYQQLKHT; KYQQLKHTG; YQQLKHTGY; QQLKHTGYQ;
QLKHTGYQL; LKHTGYQLY; KHTGYQLYK; HTGYQLYKE; TGYQLYKEA; GYQLYKEAP;
YQLYKEAPH; QLYKEAPHP; LYKEAPHPV; YKEAPHPVH; KEAPHPVHL; EAPHPVHLA;
APHPVHLAT; PHPVHLATL; HPVHLATLW; LCWSHEVLG; CWSHEVLGE; WSHEVLGEH;
SHEVLGEHF; HEVLGEHFP; EVLGEHFPL; VLGEHFPLL; HFHFYWDQV; FHFYWDQVP;
HFYWDQVPS; FYWDQVPST; YWDQVPSTQ; WDQVPSTQL; DQVPSTQLD; QVPSTQLDK;
VPSTQLDKH; PSTQLDKHC; STQLDKHCF; TQLDKHCFC; QLDKHCFCP; LDKHCFCPN;
DKHCFCPNR; KHCFCPNRP; HCFCPNRPY; CFCPNRPYG; FCPNRPYGQ; CPNRPYGQY;
PNRPYGQYS; NRPYGQYSL; RPYGQYSLP; PYGQYSLPG; YGQYSLPGT; GQYSLPGTG;
QYSLPGTGL; YSLPGTGLL; SLPGTGLLG; LPGTGLLGF; YHQGTLTCN; HQGTLTCNS;
QGTLTCNSL; GTLTCNSLA; TLTCNSLAL; LTCNSLALP; TCNSLALPA; CNSLALPAF;
NSLALPAFP; SLALPAFPR; LALPAFPRV; ALPAFPRVL; LPAFPRVLH; PAFPRVLHL;
AFPRVLHLQ; FPRVLHLQQ; PRVLHLQQR; RVLHLQQRS; VLHLQQRSG; LHLQQRSGN;
HLQQRSGNY; LQQRSGNYC; QQRSGNYCL; QRSGNYCLE; VFLHHAHAL; FLHHAHALF;
LHHAHALFV; HHAHALFVT; HAHALFVTL; AHALFVTLH; HALFVTLHE; ALFVTLHEG;
PLFVQLQPP; LFVQLQPPT; FVQLQPPTS; VQLQPPTSV; QLQPPTSVD; LQPPTSVDF;
QPPTSVDFH; PPTSVDFHR; PTSVDFHRL; TSVDFHRLG; SVDFHRLGP; VDFHRLGPH;
DFHRLGPHL; FHRLGPHLN; HRLGPHLNW; RLGPHLNWG; LGPHLNWGG; GPHLNWGGE;
PHLNWGGEF; HLNWGGEFL; LNWGGEFLL; NWGGEFLLC; WGGEFLLCC; GGEFLLCCN;
GEFLLCCNR; EFLLCCNRE; FLLCCNREA; LLCCNREAF; LCCNREAFF; CCNREAFFS;
CNREAFFSL; NREAFFSLG; REAFFSLGY; EAFFSLGYH; AFFSLGYHC; SHFQHLALD;
GFHLDPPFL; FHLDPPFLG; HLDPPFLGL; LDPPFLGLG; DPPFLGLGS; PPFLGLGSI;
PFLGLGSIL; FLGLGSILP; LGLGSILPL; LLELLLLLL; LELLLLLLV; ELLLLLLLV;
LLLLLLLVV; LLLLLLVVL; LLLLLVVLA; LLLVVLAL; LLVVLALA; LLVVLALAR;
LVVLALARV; VVLALARVP; VLALARVPL; LALARVPLA; ALARVPLAF; LARVPLAFW;
ARVPLAFWE; RVPLAFWEL; VPLAFWELP; PLAFWELPL; LAFWELPLD; AFWELPLDT;
FWELPLDTL; WELPLDTLL; ELPLDTLLF; LPLDTLLFF; PLDTLLFFW; LDTLLFFWL;
DTLLFFWLG; TLLFFWLGP; LLFFWLGPS; LFFWLGPSS; FFWLGPSSY; FWLGPSSYA;
WLGPSSYAS; LGPSSYASR; GPSSYASRA; PSSYASRAG; SSYASRAGV; SYASRAGVT;
YASRAGVTV; ASRAGVTVP; SRAGVTVPY; RAGVTVPYR; AGVTVPYRP; GVTVPYRPR;
VTVPYRPRS; TVPYRPRSK; VPYRPRSKG; PYRPRSKGN; YRPRSKGNI; RPRSKGNIH;
LAPPGAIVF; APPGAIVFS; PPGAIVFSI; PGAIVFSIN; GAIVFSINS; AIVFSINSP;
IVFSINSPE; VFSINSPEC; FSINSPECT; SINSPECTL; INSPECTLC; FLKSILCVT;
LKSILCVTS; KSILCVTSS; SILCVTSSI; ILCVTSSIL; LCVTSSILS; CVTSSILSA;
VTSSILSAS; TSSILSASS; SSILSASSI; SILSASSIL; VWPKCTRVP; WPKCTRVPS;
PKCTRVPSL; KCTRVPSLS; CTRVPSLSA; TRVPSLSAT; RVPSLSATC; VPSLSATCL;
PSLSATCLT; SLSATCLTI; LSATCLTIE; SATCLTIEG; ATCLTIEGL; TCLTIEGLI;
CLTIEGLIG; LTIEGLIGE; TIEGLIGER; IEGLIGERS; EGLIGERSE; KFIGAFTIV;
FIGAFTIVQ; IGAFTIVQV; GAFTIVQVV; AFTIVQVVS; FTIVQVVSS; TIVQVVSSK;
IVQVVSSKN; VQVVSSKNL; QVVSSKNLA; VVSSKNLAK; VSSKNLAKE; SSKNLAKES;
SKNLAKESL; KNLAKESLK; NLAKESLKN; LAKESLKNL; AKESLKNLS; KESLKNLSV;
ESLKNLSVL; SLKNLSVLL; LKNLSVLLC; KNLSVLLCN; NLSVLLCNS; LSVLLCNSC;
SVLLCNSCE; VLLCNSCEV; LLCNSCEVI; LCNSCEVIE; CNSCEVIEG; NSCEVIEGI;
SCEVIEGIS; CEVIEGISS; EVIEGISSL; VIEGISSLI; IEGISSLIT; EGISSLITC;
GISSLITCH; ISSLITCHK; SSLITCHKA; SLITCHKAW; LITCHKAWE; ITCHKAWEI;
TCHKAWEIV; CHKAWEIVA; HKAWEIVAN; KAWEIVANK; AWEIVANKE; WEIVANKEG;
EIVANKEGP; IVANKEGPQ; VANKEGPQC; ANKEGPQCL; NKEGPQCLG; KEGPQCLGS;
EGPQCLGSR; GPQCLGSRY; ILLTKVFTP; LLTKVFTPG; LTKVFTPGN; TKVFTPGNR;
KVFTPGNRI; VFTPGNRIS; YSSGLNNSK; SSGLNNSKA; SGLNNSKAM; GLNNSKAMP;
LNNSKAMPD; NNSKAMPDC; SQSSKNLYP; QSSKNLYPT; AKELIPLTV; IKAANPAIA;
KAANPAIAP; AANPAIAPG; ANPAIAPGA; NPAIAPGAP; PAIAPGAPA; AIAPGAPAI;
IAPGAPAIT; APGAPAITA; PGAPAITAY; GAPAITAYV; GVRPIAAIA; VRPIAAIAS;
RPIAAIASE; PIAAIASEV; IAAIASEVL; AAIASEVLV; AIASEVLVM; IASEVLVMP;
ASEVLVMPS; SEVLVMPST; EVLVMPSTV; VLVMPSTVA; LVMPSTVAR; VMPSTVARD;
MPSTVARDA; PSTVARDAI; TSIAAAASP; SIAAAASPA; IAAAASPAA; AAAASPAAI;
AAASPAAIS; AASPAAISA; ASPAAISAT; SPAAISATE; PAAISATEN; AAISATENP;
AISATENPV; ISATENPVA; SATENPVAA; ATENPVAAA; TENPVAAAA; ENPVAAAAS;
NPVAAAASD; PVAAAASDT; VAAAASDTL; AAAASDTLA; AAASDTLAT; AASDTLATR;
ASDTLATRS; SDTLATRSP; DTLATRSPK; TLATRSPKS; LATRSPKSA; ATRSPKSAR;
TRSPKSARA; RSPKSARAA; SPKSARAAP; PKSARAAPM; KSARAAPMN; SARAAPMNL;
ARAAPMNLE; RAAPMNLEI; AAPMNLEIQ; APMNLEIQK; PMNLEIQKK; MNLEIQKKR;
NLEIQKKRD; LEIQKKRDY; EIQKKRDYL; IQKKRDYLP; QKKRDYLPR; KKRDYLPRS;
KRDYLPRSL; RDYLPRSLL; DYLPRSLLQ; YLPRSLLQS; LPRSLLQSL; PRSLLQSLL;
RSLLQSLLQ; SLLQSLLQQ; LLQSLLQQV; LQSLLQQVK; QSLLQQVKQ; SLLQQVKQW;
LLQQVKQWY; LQQVKQWYF; QQVKQWYFC; QVKQWYFCF; VKQWYFCFS; KQWYFCFSR;
QWYFCFSRL; WYFCFSRLH; YFCFSRLHC; FCFSRLHCL; CFSRLHCLH; FSRLHCLHL;
SRLHCLHLY; RLHCLHLYK; LHCLHLYKI; HCLHLYKIP; CLHLYKIPA; LHLYKIPAK;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

HLYKIPAKA; LYKIPAKAL; YKIPAKALK; KSSELFFLF; SSELFFLFQ; SELFFLFQS;
ELFFLFQSR; LFFLFQSRF; FFLFQSRFY; FLFQSRFYQ; LFQSRFYQL; FQSRFYQLS;
QSRFYQLSL; SRFYQLSLK; RFYQLSLKL; FYQLSLKLV; YQLSLKLVV; QLSLKLVVT;
LSLKLVVTA; SLKLVVTAG; LKLVVTAGA; KLVVTAGAE; LVVTAGAEP; VVTAGAEPW;
VTAGAEPWP; TAGAEPWPL; AGAEPWPLS; GAEPWPLSS; AEPWPLSSL; EPWPLSSLT;
PWPLSSLTG; WPLSSLTGD; PLSSLTGDK; LSSLTGDKA; SSLTGDKAK; SLTGDKAKI;
LTGDKAKIP; TGDKAKIPR; GDKAKIPRL; DKAKIPRLA; KAKIPRLAK; AKIPRLAKH;
KIPRLAKHV; IPRLAKHVC; PRLAKHVCH; RLAKHVCHA; LAKHVCHAL; AKHVCHALS;
KHVCHALSF; HVCHALSFL; VCHALSFLR; CHALSFLRS; HALSFLRSW; ALSFLRSWF;
LSFLRSWFG; SFLRSWFGC; FLRSWFGCI; LRSWFGCIP; RSWFGCIPW; SWFGCIPWV;
WFGCIPWVS; FGCIPWVSS; GCIPWVSSS; CIPWVSSSS; IPWVSSSSL; GHGLAAFPC;
HGLAAFPCE; GLAAFPCES; LAAFPCESC; AAFPCESCT; AFPCESCTF; FPCESCTFL;
PCESCTFLP; CESCTFLPE; ESCTFLPEV; SCTFLPEVM; CTFLPEVMV; TFLPEVMVW;
FLPEVMVWL; LPEVMVWLH; PEVMVWLHS; EVMVWLHSM; VMVWLHSMG; MVWLHSMGK;
VWLHSMGKQ; WLHSMGKQL; LHSMGKQLL; HSMGKQLLP; SMGKQLLPV; MGKQLLPVA;
GKQLLPVAF; KQLLPVAFF; QLLPVAFFF; LLPVAFFFI; LPVAFFFII; PVAFFFIIY;
VAFFFIIYK; AFFFIIYKR; FFFIIYKRP; FFIIYKRPR; FIIYKRPRP; IIYKRPRPP;
IYKRPRPPL; YKRPRPPLP; KRPRPPLPP; RPRPPLPPP; PRPPLPPPF; RPPLPPPFL;
PPLPPPFLS; PLPPPFLSS; LPPPFLSSS; PPPFLSSSK; PPFLSSSKG; PFLSSSKGV;
FLSSSKGVE; LSSSKGVEA; SSSKGVEAF; SSKGVEAFS; SKGVEAFSE; KGVEAFSEA;
QNYLGKSLF; NYLGKSLFF; YLGKSLFFC; LGKSLFFCN; GKSLFFCNF; KSLFFCNFC;
SLFFCNFCK 10 mers:

WIKFLTGKNP; IKFLTGKNPW; KFLTGKNPWS; FLTGKNPWSS; LTGKNPWSSW;
TGKNPWSSWT; GKNPWSSWTF; ALKELPGEIF; LKELPGEIFP; GSVRNFTLTK;
SVRNFTLTKG; VRNFTLTKGA; RNFTLTKGAT; NFTLTKGATR; FTLTKGATRI;
TLTKGATRIK; ILCIKKWSRM; LISLILEPGV; ISLILEPGVA; SLILEPGVAQ;
LILEPGVAQR; ILEPGVAQRF; LEPGVAQRFV; EPGVAQRFVL; PGVAQRFVLI;
GVAQRFVLIF; VAQRFVLIFL; AQRFVLIFLF; QRFVLIFLFA; RFVLIFLFAQ;
FVLIFLFAQI; VLIFLFAQIP; LIFLFAQIPC; IFLFAQIPCT; FLFAQIPCTA;
LFAQIPCTAR; FAQIPCTARN; AQIPCTARNG; QIPCTARNGL; IPCTARNGLF;
PCTARNGLFV; CTARNGLFVP; TARNGLFVPK; ARNGLFVPKS; RNGLFVPKSL;
NGLFVPKSLL; GLFVPKSLLC; LFVPKSLLCT; FVPKSLLCTA; VPKSLLCTAL;
PKSLLCTALA; KSLLCTALAC; SLLCTALACY; LLCTALACYV; LCTALACYVS;
CTALACYVSL; TALACYVSLD; IATALTASHS; ATALTASHSG; TALTASHSGL;
ALTASHSGLA; LKKLCNGGSK; SFKVTNLYLD; FKVTNLYLDK; VIIFFIGANL;
IIFFIGANLW; IFFIGANLWN; FFIGANLWNR; FIGANLWNRR; IGANLWNRRV;
GANLWNRRVG; ANLWNRRVGV; NLWNRRVGVL; LWNRRVGVLV; WNRRVGVLVE;
NRRVGVLVEF; RRVGVLVEFL; RSNSRFSTLN; SNSRFSTLNT; NSRFSTLNTT;
SRFSTLNTTQ; RFSTLNTTQK; FSTLNTTQKK; STLNTTQKKK; TLNTTQKKKK;
LNTTQKKKKG; NTTQKKKKGR; TTQKKKKGRR; TQKKKKGRRP; NPCLLCCVYY;
KTYGKIFCNF; TYGKIFCNFY; RSIPYYRRKH; SIPYYRRKHS; IPYYRRKHSR;
PYYRRKHSRG; YYRRKHSRGL; YRRKHSRGLK; RRKHSRGLKG; RKHSRGLKGA;
RNKAGVLEIN; NKAGVLEINY; GCVFIIRYVF; CVFIIRYVFR; VFIIRYVFRI;
FIIRYVFRIS; IIRYVFRISI; IRYVFRISIQ; RYVFRISIQC; YVFRISIQCR;
VFRISIQCRG; FRISIQCRGV; KVSEKRPALS; VSEKRPALSL; KALCKCYYFC;
ALCKCYYFCR; LCKCYYFCRK; KSKKYLSASS; SKKYLSASSR; KKYLSASSRY;
KYLSASSRYS; YLSASSRYSF; LSASSRYSFS; KKSRYPSYDQ; KSRYPSYDQG;
SRYPSYDQGR; RYPSYDQGRN; YPSYDQGRNA; PSYDQGRNAN; SYDQGRNANR;
YDQGRNANRK; DQGRNANRKI; QGRNANRKIQ; GRNANRKIQS; RNANRKIQSY;
NANRKIQSYI; ANRKIQSYIR; NGFNIWSSWK; GFNIWSSWKC; FNIWSSWKCC;
NIWSSWKCCT; IWSSWKCCTR; WSSWKCCTRT; SSWKCCTRTI; SWKCCTRTIY;
WKCCTRTIYG; KCCTRTIYGR; CCTRTIYGRC; CTRTIYGRCC; TRTIYGRCCL;
RTIYGRCCLA; TIYGRCCLAA; IYGRCCLAAL; YGRCCLAALF; GRCCLAALFA;
RCCLAALFAT; FFALYCFQCT; WKNNTSCRVI; KNNTSCRVIR; NNTSCRVIRF;
NTSCRVIRFV; TSCRVIRFVW; SCRVIRFVWW; SLKCKPTHGK; LKCKPTHGKA;
KCKPTHGKAN; CKPTHGKANL; ARCSYRSVHG; RCSYRSVHGC; CSYRSVHGCF;
IKGFAFRTWN; KGFAFRTWNK; GFAFRTWNKQ; FAFRTWNKQF; AFRTWNKQFR;
FRTWNKQFRQ; RTWNKQFRQF; TWNKQFRQFE; WNKQFRQFER; NKQFRQFERL;
KQFRQFERLF; QFRQFERLFR; FRQFERLFRW; RQFERLFRWK; QFERLFRWKC;
GKFRKETFKQ; KFRKETFKQK; FRKETFKQKN; RKETFKQKNP; KETFKQKNPN;
ETFKQKNPNI; TFKQKNPNIS; FKQKNPNIST; KQKNPNISTR; QKNPNISTRL;
KNPNISTRLG; NPNISTRLGY; PNISTRLGYN; NISTRLGYNE; AQNIFKKILT;
QNIFKKILTK; NIFKKILTKL; IFKKILTKLR; FKKILTKLRV; KKILTKLRVL;
KILTKLRVLT; KKNFTKWNDL; KNFTKWNDLV; NFTKWNDLVA; FTKWNDLVAT;
TKWNDLVATA; KWNDLVATAN; WNDLVATANL; NDLVATANLV; DKYVYFFKDE;
KYVYFFKDEI; IPITMLFPSL; PITMLFPSLR; ITMLFPSLRY; TMLFPSLRYF;
MLFPSLRYFS; LFPSLRYFSP; FPSLRYFSPC; KWLIQKQHLL; WLIQKQHLLN;
LIQKQHLLNV; IQKQHLLNVY; QKQHLLNVYV; KQHLLNVYVQ; HLFKAFWFA;
HLFKAFWFAI; LFKAFWFAIV; FKAFWFAIVP; KAFWFAIVPV; AFWFAIVPVC;
FWFAIVPVCQ; WFAIVPVCQY; FAIVPVCQYI; AIVPVCQYIL; IVPVCQYILS;
VPVCQYILSY; PVCQYILSYL; VCQYILSYLG; CQYILSYLGP; QYILSYLGPL;
YILSYLGPLE; ILSYLGPLEV; LSYLGPLEVF; SYLGPLEVFL; YLGPLEVFLC;
LGPLEVFLCH; GPLEVFLCHQ; PLEVFLCHQT; LEVFLCHQTP; PLPGIPYHT;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

AAHPLSGFSC; AHPLSGFSCL; GHLAKRKLGK; HLAKRKLGKD; LAKRKLGKDS;
AKRKLGKDSL; KRKLGKDSLQ; RKLGKDSLQI; KLGKDSLQIF; LGKDSLQIFF;
GKDSLQIFFS; KDSLQIFFSG; DSLQIFFSGG; SLQIFFSGGS; NILQGLSTVV;
ILQGLSTVVF; LQGLSTVVFQ; QGLSTVVFQS; GLSTVVFQSC; TGHKYQQLKH;
GHKYQQLKHT; HKYQQLKHTG; KYQQLKHTGY; YQQLKHTGYQ; QQLKHTGYQL;
QLKHTGYQLY; LKHTGYQLYK; KHTGYQLYKE; HTGYQLYKEA; TGYQLYKEAP;
GYQLYKEAPH; YQLYKEAPHP; QLYKEAPHPV; LYKEAPHPVH; YKEAPHPVHL;
KEAPHPVHLA; EAPHPVHLAT; APHPVHLATL; PHPVHLATLW; LCWSHEVLGE;
CWSHEVLGEH; WSHEVLGEHF; SHEVLGEHFP; HEVLGEHFPL; EVLGEHFPLL;
HFHFYWDQVP; FHFYWDQVPS; HFYWDQVPST; FYWDQVPSTQ; YWDQVPSTQL;
WDQVPSTQLD; DQVPSTQLDK; QVPSTQLDKH; VPSTQLDKHC; PSTQLDKHCF;
STQLDKHCFC; TQLDKHCFCP; QLDKHCFCPN; LDKHCFCPNR; DKHCFCPNRP;
KHCFCPNRPY; HCFCPNRPYG; CFCPNRPYGQ; FCPNRPYGQY; CPNRPYGQYS;
PNRPYGQYSL; NRPYGQYSLP; RPYGQYSLPG; PYGQYSLPGT; YGQYSLPGTG;
GQYSLPGTGL; QYSLPGTGLL; YSLPGTGLLG; SLPGTGLLGF; YHQGTLTCNS;
HQGTLTCNSL; QGTLTCNSLA; GTLTCNSLAL; TLTCNSLALP; LTCNSLALPA;
TCNSLALPAF; CNSLALPAFP; NSLALPAFPR; SLALPAFPRV; LALPAFPRVL;
ALPAFPRVLH; LPAFPRVLHL; PAFPRVLHLQ; AFPRVLHLQQ; FPRVLHLQQR;
PRVLHLQQRS; RVLHLQQRSG; VLHLQQRSGN; LHLQQRSGNY; HLQQRSGNYC;
LQQRSGNYCL; QQRSGNYCLE; VFLHHAHALF; FLHHAHALFV; LHHAHALFVT;
HHAHALFVTL; HAHALFVTLH; AHALFVTLHE; HALFVTLHEG; PLFVQLQPPT;
LFVQLQPPTS; FVQLQPPTSV; VQLQPPTSVD; QLQPPTSVDF; LQPPTSVDFH;
QPPTSVDFHR; PPTSVDFHRL; PTSVDFHRLG; TSVDFHRLGP; SVDFHRLGPH;
VDFHRLGPHL; DFHRLGPHLN; FHRLGPHLNW; HRLGPHLNWG; RLGPHLNWGG;
LGPHLNWGGE; GPHLNWGGEF; PHLNWGGEFL; HLNWGGEFLL; LNWGGEFLLC;
NWGGEFLLCC; WGGEFLLCCN; GGEFLLCCNR; GEFLLCCNRE; EFLLCCNREA;
FLLCCNREAF; LLCCNREAFF; LCCNREAFFS; CCNREAFFSL; CNREAFFSLG;
NREAFFSLGY; REAFFSLGYH; EAFFSLGYHC; GFHLDPPFLG; FHLDPPFLGL;
HLDPPFLGLG; LDPPFLGLGS; DPPFLGLGSI; PPFLGLGSIL; PFLGLGSILP;
FLGLGSILPL; LLELLLLLLL; LELLLLLLLV; ELLLLLLLVV; LLLLLLLVVL;
LLLLLLVVLA; LLLLLVVLAL; LLLLVVLALA; LLLVVLALAR; LLVVLALARV;
LVVLALARVP; VVLALARVPL; VLALARVPLA; LALARVPLAF; ALARVPLAFW;
LARVPLAFWE; ARVPLAFWEL; RVPLAFWELP; VPLAFWELPL; PLAFWELPLD;
LAFWELPLDT; AFWELPLDTL; FWELPLDTLL; WELPLDTLLF; ELPLDTLLFF;
LPLDTLLFFW; PLDTLLFFWL; LDTLLFFWLG; DTLLFFWLGP; TLLFFWLGPS;
LLFFWLGPSS; LFFWLGPSSY; FFWLGPSSYA; FWLGPSSYAS; WLGPSSYASR;
LGPSSYASRA; GPSSYASRAG; PSSYASRAGV; SSYASRAGVT; SYASRAGVTV;
YASRAGVTVP; ASRAGVTVPY; SRAGVTVPYR; RAGVTVPYRP; AGVTVPYRPR;
GVTVPYRPRS; VTVPYRPRSK; TVPYRPRSKG; VPYRPRSKGN; PYRPRSKGNI;
YRPRSKGNIH; LAPPGAIVFS; APPGAIVFSI; PPGAIVFSIN; PGAIVFSINS;
GAIVFSINSP; AIVFSINSPE; IVFSINSPEC; VFSINSPECT; FSINSPECTL;
SINSPECTLC; FLKSILCVTS; LKSILCVTSS; KSILCVTSSI; SILCVTSSIL;
ILCVTSSILS; LCVTSSILSA; CVTSSILSAS; VTSSILSASS; TSSILSASSI;
SSILSASSIL; VWPKCTRVPS; WPKCTRVPSL; PKCTRVPSLS; KCTRVPSLSA;
CTRVPSLSAT; TRVPSLSATC; RVPSLSATCL; VPSLSATCLT; PSLSATCLTI;
SLSATCLTIE; LSATCLTIEG; SATCLTIEGL; ATCLTIEGLI; TCLTIEGLIG;
CLTIEGLIGE; LTIEGLIGER; TIEGLIGERS; IEGLIGERSE; KFIGAFTIVQ;
FIGAFTIVQV; IGAFTIVQVV; GAFTIVQVVS; AFTIVQVVSS; FTIVQVVSSK;
TIVQVVSSKN; IVQVVSSKNL; VQVVSSKNLA; QVVSSKNLAK; VVSSKNLAKE;
VSSKNLAKES; SSKNLAKESL; SKNLAKESLK; KNLAKESLKN; NLAKESLKNL;
LAKESLKNLS; AKESLKNLSV; KESLKNLSVL; ESLKNLSVLL; SLKNLSVLLC;
LKNLSVLLCN; KNLSVLLCNS; NLSVLLCNSC; LSVLLCNSCE; SVLLCNSCEV;
VLLCNSCEVI; LLCNSCEVIE; LCNSCEVIEG; CNSCEVIEGI; NSCEVIEGIS;
SCEVIEGISS; CEVIEGISSL; EVIEGISSLI; VIEGISSLIT; IEGISSLITC;
EGISSLITCH; GISSLITCHK; ISSLITCHKA; SSLITCHKAW; SLITCHKAWE;
LITCHKAWEI; ITCHKAWEIV; TCHKAWEIVA; CHKAWEIVAN; HKAWEIVANK;
KAWEIVANKE; AWEIVANKEG; WEIVANKEGP; EIVANKEGPQ; IVANKEGPQC;
VANKEGPQCL; ANKEGPQCLG; NKEGPQCLGS; KEGPQCLGSR; EGPQCLGSRY;
ILLTKVFTPG; LLTKVFTPGN; LTKVFTPGNR; TKVFTPGNRI; KVFTPGNRIS;
YSSGLNNSKA; SSGLNNSKAM; SGLNNSKAMP; GLNNSKAMPD; LNNSKAMPDC;
SQSSKNLYPT; IKAANPAIAP; KAANPAIAPG; AANPAIAPGA; ANPAIAPGAP;
NPAIAPGAPA; PAIAPGAPAI; AIAPGAPAIT; IAPGAPAITA; APGAPAITAY;
PGAPAITAYV; GVRPIAAIAS; VRPIAAIASE; RPIAAIASEV; PIAAIASEVL;
IAAIASEVLV; AAIASEVLVM; AIASEVLVMP; IASEVLVMPS; ASEVLVMPST;
SEVLVMPSTV; EVLVMPSTVA; VLVMPSTVAR; LVMPSTVARD; VMPSTVARDA;
MPSTVARDAI; TSIAAAASPA; SIAAAASPAA; IAAAASPAAI; AAAASPAAIS;
AAASPAAISA; AASPAAISAT; ASPAAISATE; SPAAISATEN; PAAISATENP;
AAISATENPV; AISATENPVA; ISATENPVAA; SATENPVAAA; ATENPVAAAA;
TENPVAAAAS; ENPVAAAASD; NPVAAAASDT; PVAAAASDTL; VAAAASDTLA;
AAAASDTLAT; AAASDTLATR; AASDTLATRS; ASDTLATRSP; SDTLATRSPK;
DTLATRSPKS; TLATRSPKSA; LATRSPKSAR; ATRSPKSARA; TRSPKSARAA;
RSPKSARAAP; SPKSARAAPM; PKSARAAPMN; KSARAAPMNL; SARAAPMNLE;
ARAAPMNLEI; RAAPMNLEIQ; AAPMNLEIQK; APMNLEIQKK; PMNLEIQKKR;
MNLEIQKKRD; NLEIQKKRDY; LEIQKKRDYL; EIQKKRDYLP; IQKKRDYLPR;
QKKRDYLPRS; KKRDYLPRSL; KRDYLPRSLL; RDYLPRSLLQ; DYLPRSLLQS;
YLPRSLLQSL; LPRSLLQSLL; PRSLLQSLLQ; RSLLQSLLQQ; SLLQSLLQQV;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

LLQSLLQQVK; LQSLLQQVKQ; QSLLQQVKQW; SLLQQVKQWY; LLQQVKQWYF;
LQQVKQWYFC; QQVKQWYFCF; QVKQWYFCFS; VKQWYFCFSR; KQWYFCFSRL;
QWYFCFSRLH; WYFCFSRLHC; YFCFSRLHCL; FCFSRLHCLH; CFSRLHCLHL;
FSRLHCLHLY; SRLHCLHLYK; RLHCLHLYKI; LHCLHLYKIP; HCLHLYKIPA;
CLHLYKIPAK; LHLYKIPAKA; HLYKIPAKAL; LYKIPAKALK; KSSELFFLFQ;
SSELFFLFQS; SELFFLFQSR; ELFFLFQSRF; LFFLFQSRFY; FFLFQSRFYQ;
FLFQSRFYQL; LFQSRFYQLS; FQSRFYQLSL; QSRFYQLSLK; SRFYQLSLKL;
RFYQLSLKLV; FYQLSLKLVV; YQLSLKLVVT; QLSLKLVVTA; LSLKLVVTAG;
SLKLVVTAGA; LKLVVTAGAE; KLVVTAGAEP; LVVTAGAEPW; VVTAGAEPWP;
VTAGAEPWPL; TAGAEPWPLS; AGAEPWPLSS; GAEPWPLSSL; AEPWPLSSLT;
EPWPLSSLTG; PWPLSSLTGD; WPLSSLTGDK; PLSSLTGDKA; LSSLTGDKAK;
SSLTGDKAKI; SLTGDKAKIP; LTGDKAKIPR; TGDKAKIPRL; GDKAKIPRLA;
DKAKIPRLAK; KAKIPRLAKH; AKIPRLAKHV; KIPRLAKHVC; IPRLAKHVCH;
PRLAKHVCHA; RLAKHVCHAL; LAKHVCHALS; AKHVCHALSF; KHVCHALSFL;
HVCHALSFLR; VCHALSFLRS; CHALSFLRSW; HALSFLRSWF; ALSFLRSWFG;
LSFLRSWFGC; SFLRSWFGCI; FLRSWFGCIP; LRSWFGCIPW; RSWFGCIPWV;
SWFGCIPWVS; WFGCIPWVSS; FGCIPWVSSS; GCIPWVSSSL; CIPWVSSSLL;
GHGLAAFPCE; HGLAAFPCES; GLAAFPCESC; LAAFPCESCT; AAFPCESCTF;
AFPCESCTFL; FPCESCTFLP; PCESCTFLPE; CESCTFLPEV; ESCTFLPEVM;
SCTFLPEVMV; CTFLPEVMVW; TFLPEVMVWL; FLPEVMVWLH; LPEVMVWLHS;
PEVMVWLHSM; EVMVWLHSMG; VMVWLHSMGK; MVWLHSMGKQ; VWLHSMGKQL;
WLHSMGKQLL; LHSMGKQLLP; HSMGKQLLPV; SMGKQLLPVA; MGKQLLPVAF;
GKQLLPVAFF; KQLLPVAFFF; QLLPVAFFFI; LLPVAFFFII; LPVAFFFIIY;
PVAFFFIIYK; VAFFFIIYKR; AFFFIIYKRP; FFFIIYKRPR; FFIIYKRPRP;
FIIYKRPRPP; IIYKRPRPPL; IYKRPRPPLP; YKRPRPPLPP; KRPRPPLPPP;
RPRPPLPPPF; PRPPLPPPFL; RPPLPPPFLS; PPLPPPFLSS; PLPPPFLSSS;
LPPPFLSSSK; PPPFLSSSKG; PPFLSSSKGV; PFLSSSKGVE; FLSSSKGVEA;
LSSSKGVEAF; SSSKGVEAFS; SSKGVEAFSE; SKGVEAFSEA; QNYLGKSLFF;
NYLGKSLFFC; YLGKSLFFCN; LGKSLFFCNF; GKSLFFCNFC; KSLFFCNFCK 11 mers:

WIKFLTGKNPW; IKFLTGKNPWS; KFLTGKNPWSS; FLTGKNPWSSW; LTGKNPWSSWT;
TGKNPWSSWTF; ALKELPGEIFP; GSVRNFTLTKG; SVRNFTLTKGA; VRNFTLTKGAT;
RNFTLTKGATR; NFTLTKGATRI; FTLTKGATRIK; LISLILEPGVA; ISLILEPGVAQ;
SLILEPGVAQR; LILEPGVAQRF; ILEPGVAQRFV; LEPGVAQRFVL; EPGVAQRFVLI;
PGVAQRFVLIF; GVAQRFVLIFL; VAQRFVLIFLF; AQRFVLIFLFA; QRFVLIFLFAQ;
RFVLIFLFAQI; FVLIFLFAQIP; VLIFLFAQIPC; LIFLFAQIPCT; IFLFAQIPCTA;
FLFAQIPCTAR; LFAQIPCTARN; FAQIPCTARNG; AQIPCTARNGL; QIPCTARNGLF;
IPCTARNGLFV; PCTARNGLFVP; CTARNGLFVPK; TARNGLFVPKS; ARNGLFVPKSL;
RNGLFVPKSLL; NGLFVPKSLLC; GLFVPKSLLCT; LFVPKSLLCTA; FVPKSLLCTAL;
VPKSLLCTALA; PKSLLCTALAC; KSLLCTALACY; SLLCTALACYV; LLCTALACYVS;
LCTALACYVSL; CTALACYVSLD; IATALTASHSG; ATALTASHSGL; TALTASHSGLA;
SPKVTNLYLDK; VIIFFIGANLW; IIFFIGANLWN; IFFIGANLWNR; FFIGANLWNRR;
FIGANLWNRRV; IGANLWNRRVG; GANLWNRRVGV; ANLWNRRVGVL; NLWNRRVGVLV;
LWNRRVGVLVE; WNRRVGVLVEF; NRRVGVLVEFL; RSNSRFSTLNT; SNSRFSTLNTT;
NSRFSTLNTTQ; SRFSTLNTTQK; RFSTLNTTQKK; FSTLNTTQKKK; STLNTTQKKKK;
TLNTTQKKKKG; LNTTQKKKKGR; NTTQKKKKGRR; TTQKKKKGRRP; KTYGKIFCNFY;
RSIPYYRRKHS; SIPYYRRKHSR; IPYYRRKHSRG; PYYRRKHSRGL; YYRRKHSRGLK;
YRRKHSRGLKG; RRKHSRGLKGA; RNKAGVLEINY; GCVFIIRYVFR; CVFIIRYVFRI;
VFIIRYVFRIS; FIIRYVFRISI; IIRYVFRISIQ; IRYVFRISIQC; RYVFRISIQCR;
YVFRISIQCRG; VFRISIQCRGV; KVSEKRPALSL; KALCKCYYFCR; ALCKCYYFCRK;
KSKKYLSASSR; SKKYLSASSRY; KKYLSASSRYS; KYLSASSRYSF; YLSASSRYSFS;
KKSRYPSYDQG; KSRYPSYDQGR; SRYPSYDQGRN; RYPSYDQGRNA; YPSYDQGRNAN;
PSYDQGRNANR; SYDQGRNANRK; YDQGRNANRKI; DQGRNANRKIQ; QGRNANRKIQS;
GRNANRKIQSY; RNANRKIQSYI; NANRKIQSYIR; NGFNIWSSWKC; GFNIWSSWKCC;
FNIWSSWKCCT; NIWSSWKCCTR; IWSSWKCCTRT; WSSWKCCTRTI; SSWKCCTRTIY;
SWKCCTRTIYG; WKCCTRTIYGR; KCCTRTIYGRC; CCTRTIYGRCC; CTRTIYGRCCL;
TRTIYGRCCLA; RTIYGRCCLAA; TIYGRCCLAAL; IYGRCCLAALF; YGRCCLAALFA;
GRCCLAALFAT; WKNNTSCRVIR; KNNTSCRVIRF; NNTSCRVIRFV; NTSCRVIRFVW;
TSCRVIRFVWW; SLKCKPTHGKA; LCKCKPTHGKAN; KCKPTHGKANL; ARCSYRSVHGC;
RCSYRSVHGCF; IKGFAFRTWNK; KGFAFRTWNKQ; GFAFRTWNKQF; FAFRTWNKQFR;
APRTWNKQFRQ; FRTWNKQFRQF; RTWNKQFRQFE; TWNKQFRQFER; WNKQFRQFERL;
NKQFRQFERLF; KQFRQFERLFR; QFRQFERLFRW; FRQFERLFRWK; RQFERLFRWKC;
GKFRKETFKQK; KFRKETFKQKN; FRKETFKQKNP; RKETFKQKNPN; KETFKQKNPNI;
ETFKQKNPNIS; TFKQKNPNIST; FKQKNPNISTR; KQKNPNISTRL; QKNPNISTRLG;
KNPNISTRLGY; NPNISTRLGYN; PNISTRLGYNE; AQNIFKKILTK; QNIFKKILTKL;
NIFKKILTKLR; IFKKILTKLRV; FKKILTKLRVL; KKILTKLRVLT; KKNFTKWNDLV;
KNFTKWNDLVA; NFTKWNDLVAT; FTKWNDLVATA; TKWNDLVATAN; KWNDLVATANL;
WNDLVATANLV; DKYVYFFKDEI; IPITMLFPSLR; PITMLFPSLRY; ITMLFPSLRYF;
TMLFPSLRYFS; MLFPSLRYFSP; LFPSLRYFSPC; KWLIQKQHLLN; WLIQKQHLLNV;
LIQKQHLLNVY; IQKQHLLNVYV; QKQHLLNVYVQ; KHLFKAFWFAI; HLFKAFWFAIV;
LFKAFWFAIVP; FKAFWFAIVPV; KAFWFAIVPVC; AFWFAIVPVCQ; FWFAIVPVCQY;
WFAIVPVCQYI; FAIVPVCQYIL; AIVPVCQYILS; IVPVCQYILSY; VPVCQYILSYL;
PVCQYILSYLG; VCQYILSYLGP; CQYILSYLGPL; QYILSYLGPLE; YILSYLGPLEV;
ILSYLGPLEVF; LSYLGPLEVFL; SYLGPLEVFLC; YLGPLEVFLCH; LGPLEVFLCHQ;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

GPLEVFLCHQT; PLEVFLCHQTP; AAHPLSGFSCL; GHLAKRKLGKD; HLAKRKLGKDS;
LAKRKLGKDSL; AKRKLGKDSLQ; KRKLGKDSLQI; RKLGKDSLQIF; KLGKDSLQIFF;
LGKDSLQIFFS; GKDSLQIFFSG; KDSLQIFFSGG; DSLQIFFSGGS; NILQGLSTVVF;
ILQGLSTVVFQ; LQGLSTVVFQS; QGLSTVVFQSC; TGHKYQQLKHT; GHKYQQLKHTG;
HKYQQLKHTGY; KYQQLKHTGYQ; YQQLKHTGYQL; QQLKHTGYQLY; QLKHTGYQLYK;
LKHTGYQLYKE; KHTGYQLYKEA; HTGYQLYKEAP; TGYQLYKEAPH; GYQLYKEAPHP;
YQLYKEAPHPV; QLYKEAPHPVH; LYKEAPHPVHL; YKEAPHPVHLA; KEAPHPVHLAT;
EAPHPVHLATL; APHPVHLATLW; LCWSHEVLGEH; CWSHEVLGEHF; WSHEVLGEHFP;
SHEVLGEHFPL; HEVLGEHFPLL; HFHFYWDQVPS; FHFYWDQVPST; HFYWDQVPSTQ;
FYWDQVPSTQL; YWDQVPSTQLD; WDQVPSTQLDK; DQVPSTQLDKH; QVPSTQLDKHC;
VPSTQLDKHCF; PSTQLDKHCFC; STQLDKHCFCP; TQLDKHCFCPN; QLDKHCFCPNR;
LDKHCFCPNRP; DKHCFCPNRPY; KHCFCPNRPYG; HCFCPNRPYGQ; CFCPNRPYGQY;
FCPNRPYGQYS; CPNRPYGQYSL; PNRPYGQYSLP; NRPYGQYSLPG; RPYGQYSLPGT;
PYGQYSLPGTG; YGQYSLPGTGL; GQYSLPGTGLL; QYSLPGTGLLG; YSLPGTGLLGF;
YHQGTLTCNSL; HQGTLTCNSLA; QGTLTCNSLAL; GTLTCNSLALP; TLTCNSLALPA;
LTCNSLALPAF; TCNSLALPAFP; CNSLALPAFPR; NSLALPAFPRV; SLALPAFPRVL;
LALPAFPRVLH; ALPAFPRVLHL; LPAFPRVLHLQ; PAFPRVLHLQQ; AFPRVLHLQQR;
FPRVLHLQQRS; PRVLHLQQRSG; RVLHLQQRSGN; VLHLQQRSGNY; LHLQQRSGNYC;
HLQQRSGNYCL; LQQRSGNYCLE; VFLHHAHALFV; FLHHAHALFVT; LHHAHALFVTL;
HHAHALFVTLH; HAHALFVTLHE; AHALFVTLHEG; PLFVQLQPPTS; LFVQLQPPTSV;
FVQLQPPTSVD; VQLQPPTSVDF; QLQPPTSVDFH; LQPPTSVDFHR; QPPTSVDFHRL;
PPTSVDFHRLG; PTSVDFHRLGP; TSVDFHRLGPH; SVDFHRLGPHL; VDFHRLGPHLN;
DFHRLGPHLNW; FHRLGPHLNWG; HRLGPHLNWGG; RLGPHLNWGGE; LGPHLNWGGEF;
GPHLNWGGEFL; PHLNWGGEFLL; HLNWGGEFLLC; LNWGGEFLLCC; NWGGEFLLCCN;
WGGEFLLCCNR; GGEFLLCCNRE; GEFLLCCNREA; EFLLCCNREAF; FLLCCNREAFF;
LLCCNREAFFS; LCCNREAFFSL; CCNREAFFSLG; CNREAFFSLGY; NREAFFSLGYH;
REAFFSLGYHC; GFHLDPPFLGL; FHLDPPFLGLG; HLDPPFLGLGS; LDPPFLGLGSI;
DPPFLGLGSIL; PPFLGLGSILP; PFLGLGSILPL; LLELLLLLLLV; LELLLLLLVV;
ELLLLLLLVVL; LLLLLLLVVLA; LLLLLLVVLAL; LLLLLVVLALA; LLLLVVLALAR;
LLLVVLALARV; LLVVLALARVP; LVVLALARVPL; VVLALARVPLA; VLALARVPLAF;
LALARVPLAFW; ALARVPLAFWE; LARVPLAFWEL; ARVPLAFWELP; RVPLAFWELPL;
VPLAFWELPLD; PLAFWELPLDT; LAFWELPLDTL; AFWELPLDTLL; FWELPLDTLLF;
WELPLDTLLFF; ELPLDTLLFFW; LPLDTLLFFWL; PLDTLLFFWLG; LDTLLFFWLGP;
DTLLFFWLGPS; TLLFFWLGPSS; LLFFWLGPSSY; LFFWLGPSSYA; FFWLGPSSYAS;
FWLGPSSYASR; WLGPSSYASRA; LGPSSYASRAG; GPSSYASRAGV; PSSYASRAGVT;
SSYASRAGVTV; SYASRAGVTVP; YASRAGVTVPY; ASRAGVTVPYR; SRAGVTVPYRP;
RAGVTVPYRPR; AGVTVPYRPRS; GVTVPYRPRSK; VTVPYRPRSKG; TVPYRPRSKGN;
VPYRPRSKGNI; PYRPRSKGNIH; LAPPGAIVFSI; APPGAIVFSIN; PGAIVFSINS;
PGAIVFSINSP; GAIVFSINSPE; AIVFSINSPEC; IVFSINSPECT; VFSINSPECTL;
FSINSPECTLC; FLKSILCVTSS; LKSILCVTSSI; KSILCVTSSIL; SILCVTSSILS;
ILCVTSSILSA; LCVTSSILSAS; CVTSSILSASS; VTSSILSASSI; TSSILSASSIL;
VWPKCTRVPSL; WPKCTRVPSLS; PKCTRVPSLSA; KCTRVPSLSAT; CTRVPSLSATC;
TRVPSLSATCL; RVPSLSATCLT; VPSLSATCLTI; PSLSATCLTIE; SLSATCLTIEG;
LSATCLTIEGL; SATCLTIEGLI; ATCLTIEGLIG; TCLTIEGLIGE; CLTIEGLIGER;
LTIEGLIGERS; TIEGLIGERSE; KFIGAFTIVQV; FIGAFTIVQVV; IGAFTIVQVVS;
GAFTIVQVVSS; AFTIVQVVSSK; FTIVQVVSSKN; TIVQVVSSKNL; IVQVVSSKNLA;
VQVVSSKNLAK; QVVSSKNLAKE; VVSSKNLAKES; VSSKNLAKESL; SSKNLAKESLK;
SKNLAKESLKN; KNLAKESLKNL; NLAKESLKNLS; LAKESLKNLSV; AKESLKNLSVL;
KESLKNLSVLL; ESLKNLSVLLC; SLKNLSVLLCN; LKNLSVLLCNS; KNLSVLLCNSC;
NLSVLLCNSCE; LSVLLCNSCEV; SVLLCNSCEVI; VLLCNSCEVIG; LLCNSCEVIEG;
LCNSCEVIEGI; CNSCEVIEGIS; NSCEVIEGISS; SCEVIEGISSL; CEVIEGISSLI;
EVIEGISSLIT; VIEGISSLITC; IEGISSLITCH; EGISSLITCHK; GISSLITCHKA;
ISSLITCHKAW; SSLITCHKAWE; SLITCHKAWEI; LITCHKAWEIV; ITCHKAWEIVA;
TCHKAWEIVAN; CHKAWEIVANK; HKAWEIVANKE; KAWEIVANKEG; AWEIVANKEGP;
WEIVANKEGPQ; EIVANKEGPQC; IVANKEGPQCL; VANKEGPQCLG; ANKEGPQCLGS;
NKEGPQCLGSR; KEGPQCLGSRY; ILLTKVFTPGN; LLTKVFTPGNR; LTKVFTPGNRI;
TKVFTPGNRIS; YSSGLNNSKAM; SSGLNNSKAMP; SGLNNSKAMPD; GLNNSKAMPDC;
IKAANPAIAPG; KAANPAIAPGA; AANPAIAPGAP; ANPAIAPGAPA; NPAIAPGAPAI;
PAIAPGAPAIT; AIAPGAPAITA; IAPGAPAITAY; APGAPAITAYV; GVRPIAAIASE;
VRPIAAIASEV; RPIAAIASEVL; PIAAIASEVLV; IAAIASEVLVM; AAIASEVLVMP;
AIASEVLVMPS; IASEVLVMPST; ASEVLVMPSTV; SEVLVMPSTVA; EVLVMPSTVAR;
VLVMPSTVARD; LVMPSTVARDA; VMPSTVARDAI; TSIAAAASPAA; SIAAAASPAAI;
IAAAASPAAIS; AAAASPAAISA; AAASPAAISAT; AASPAAISATE; ASPAAISATEN;
SPAAISATENP; PAAISATENPV; AAISATENPVA; AISATENPVAA; ISATENPVAAA;
SATENPVAAAA; ATENPVAAAAS; TENPVAAAASD; ENPVAAAASDT; NPVAAAASDTL;
PVAAAASDTLA; VAAAASDTLAT; AAAASDTLATR; AAASDTLATRS; AASDTLATRSP;
ASDTLATRSPK; SDTLATRSPKS; DTLATRSPKSA; TLATRSPKSAR; LATRSPKSARA;
ATRSPKSARAA; TRSPKSARAAP; RSPKSARAAPM; SPKSARAAPMN; PKSARAAPMNL;
KSARAAPMNLE; SARAAPMNLEI; ARAAPMNLEIQ; RAAPMNLEIQK; AAPMNLEIQKK;
APMNLEIQKKR; PMNLEIQKKRD; MNLEIQKKRDY; NLEIQKKRDYL; LEIQKKRDYLP;
EIQKKRDYLPR; IQKKRDYLPRS; QKKRDYLPRSL; KKRDYLPRSLL; KRDYLPRSLLQ;
RDYLPRSLLQS; DYLPRSLLQSL; YLPRSLLQSLL; LPRSLLQSLLQ; PRSLLQSLLQQ;
RSLLQSLLQQV; SLLQSLLQQVK; LLQSLLQQVKQ; LQSLLQQVKQW; QSLLQQVKQWY;
SLLQQVKQWYF; LLQQVKQWYFC; LQQVKQWYFCF; QQVKQWYFCFS; QVKQWYFCFSR;
VKQWYFCFSRL; KQWYFCFSRLH; QWYFCFSRLHC; WYFCFSRLHCL; YFCFSRLHCLH;
FCFSRLHCLHL; CFSRLHCLHLY; FSRLHCLHLYK; SRLHCLHLYKI; RLHCLHLYKIP;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

LHCLHLYKIPA; HCLHLYKIPAK; CLHLYKIPAKA; LHLYKIPAKAL; HLYKIPAKALK;
KSSELFFLFQS; SSELFFLFQSR; SELFFLFQSRF; ELFFLFQSRFY; LFFLFQSRFYQ;
FFLFQSRFYQL; FLFQSRFYQLS; LFQSRFYQLSL; FQSRFYQLSLK; QSRFYQLSLKL;
SRFYQLSLKLV; RFYQLSLKLVV; FYQLSLKLVVT; YQLSLKLVVTA; QLSLKLVVTAG;
LSLKLVVTAGA; SLKLVVTAGAE; LKLVVTAGAEP; KLVVTAGAEPW; LVVTAGAEPWP;
VVTAGAEPWPL; VTAGAEPWPLS; TAGAEPWPLSS; AGAEPWPLSSL; GAEPWPLSSLT;
AEPWPLSSLTG; EPWPLSSLTGD; PWPLSSLTGDK; WPLSSLTGDKA; PLSSLTGDKAK;
LSSLTGDKAKI; SSLTGDKAKIP; SLTGDKAKIPR; LTGDKAKIPRL; TGDKAKIPRLA;
GDKAKIPRLAK; DKAKIPRLAKH; KAKIPRLAKHV; AKIPRLAKHVC; KIPRLAKHVCH;
IPRLAKHVCHA; PRLAKHVCHAL; RLAKHVCHALS; LAKHVCHALSF; AKHVCHALSFL;
KHVCHALSFLR; HVCHALSFLRS; VCHALSFLRSW; CHALSFLRSWF; HALSFLRSWFG;
ALSFLRSWFGC; LSFLRSWFGCI; SFLRSWFGCIP; FLRSWFGCIPW; LRSWFGCIPWV;
RSWFGCIPWVS; SWFGCIPWVSS; WFGCIPWVSSS; FGCIPWVSSSL; GCIPWVSSSLS;
GHGLAAFPCES; HGLAAFPCESC; GLAAFPCESCT; LAAFPCESCTF; AAFPCESCTFL;
APFCESCTFLP; FPCESCTFLPE; PCESCTFLPEV; CESCTFLPEVM; ESCTFLPEVMV;
SCTFLPEVMVW; CTFLPEVMVWL; TFLPEVMVWLH; FLPEVMVWLHS; LPEVMVWLHSM;
PEVMVWLHSMG; EVMVWLHSMGK; VMVWLHSMGKQ; MVWLHSMGKQL; VWLHSMGKQLL;
WLHSMGKQLLP; LHSMGKQLLPV; HSMGKQLLPVA; SMGKQLLPVAF; MGKQLLPVAFF;
GKQLLPVAFFF; KQLLPVAFFFI; QLLPVAFFFII; LLPVAFFFIIY; LPVAFFFIIYK;
PVAFFFIIYKR; VAFFFIIYKRP; AFFFIIYKRPR; FFFIIYKRPRP; FFIIYKRPRPP;
FIIYKRPRPPL; IIYKRPRPPLP; IYKRPRPPLPP; YKRPRPPLPPP; KRPRPPLPPPF;
RPRPPLPPPFL; PRPPLPPPFLS; RPPLPPPFLSS; PPLPPPFLSSS; PLPPPFLSSSK;
LPPPFLSSSKG; PPPFLSSSKGV; PPFLSSSKGVE; PFLSSSKGVEA; FLSSSKGVEAF;
LSSSKGVEAFS; SSSKGVEAFSE; SSKGVEAFSEA; QNYLGKSLFFC; NYLGKSLFFCN;
YLGKSLFFCNF; LGKSLFFCNFC; GKSLFFCNFCK

BK virus complementary reading frame 3

8 mers:

QGRIHGAH; GRIHGAHG; RIHGAHGP; IHGAHGPF; HGAHGPFR; GAHGPFRP; KSCLGKSS;
SCLGKSSL; CLGKSSLN; LGKSSLNE; GKSSLNEK; KSSLNEKS; SSLNEKSL; SLNEKSLF;
LNEKSLFK; NEKSLFKE; EKSLFKEV; NEENEYFV; KNGAGCKG; NGAGCKGS; GAGCKGSS;
AGCKGSSS; GCKGSSSA; FSSLPRYP; SSLPRYPV; SLPRYPVL; LPRYPVLQ; PRYPVLQG;
RYPVLQGM; YPVLQGMA; PVLQGMAY; VLQGMAYL; LQGMAYLF; QGMAYLFQ; GMAYLFQK;
MAYLFQKA; AYLFQKAF; YLFQKAFC; LFQKAFCA; FQKAFCAL; QKAFCALP; KAFCALPL;
AFCALPLH; FCALPLHA; CALPLHAM; ALPLHAMS; LPLHAMSA; PLHAMSAI; KIFKKRAL; FKKRALGL;
FKKRALGL; KKRALGLD; KRALGLDR; RALGLDRL; ALGLDRLL; LGLDRLLL; GLDRLLLH;
LLHTVVWL; LHTVVWLR; HTVVWLRP; TVVWLRPN; RNSAMVGP; NSAMVGPN; SAMVGPNN;
AMVGPNNW; MVGPNNWR; VGPNNWRN; GPNNWRNS; PNNWRNSL; NNWRNSLQ; NWRNSLQR;
WRNSLQRS; RNSLQRSK; NSLQRSKA; SLQRSKAL; LQRSKALR; INNKILKG; NNKILKGP;
NKILKGPK; VPTYGTEE; PTYGTEEW; TYGTEEWE; YGTEEWES; GTEEWESW; TEEWESWW;
EEWESWWS; EWESWWSS; WESWWSSF; ESWWSSFN; SWWSSFNE; WWSSFNEK; WSSFNEKW;
SSFNEKWD; SFNEKWDE; FNEKWDED; NEKWDEDL; EKWDEDLF; KWDEDLFC; WDEDLFCH;
DEDLFCHE; EDLFCHED; DLFCHEDM; LFCHEDMF; FCHEDMFA; CHEDMFAS; HEDMFASD;
EDMFASDE; DMFASDEE; MFASDEEA; FASDEEAT; ASDEEATA; SDEEATAD; DEEATADS;
EEATADSQ; EATADSQH; ATADSQHS; TADSQHST; ADSQHSTP; DSQHSTPP; SQHSTPPK;
QHSTPPKK; HSTPPKKK; STPPKKKR; TPPKKKRK; PPKKKRKV; PKKKRKVE; KKKRKVED;
KKRKVEDP; KRKVEDPK; RKVEDPKD; KVEDPKDF; VEDPKDFP; EDPKDFPS; DPKDFPSD;
PKDFPSDL; KDFPSDLH; DFPSDLHQ; FPSDLHQF; PSDLHQFL; SDLHQFLS; DLHQFLSQ;
LHQFLSQA; HQFLSQAV; QFLSQAVF; FLSQAVFS; LSQAVFSN; SQAVFSNR; QAVFSNRT;
AVFSNRTL; VFSNRTLA; FSNRTLAC; SNRTLACF; NRTLACFA; RTLACFAV; TLACFAVY;
LACFAVYT; ACFAVYTT; CFAVYTTK; FAVYTTKE; AVYTTKEK; VYTTKEKA; YTTKEKAQ;
TTKEKAQI; TKEKAQIL; KEKAQILY; EKAQILYK; KAQILYKK; AQILYKKL; QILYKKLM;
ILYKKLME; LYKKLMEK; YKKLMEKY; KKLMEKYS; KLMEKYSV; LMEKYSVT; MEKYSVTF;
EKYSVTFI; KYSVTFIS; YSVTFISR; SVTFISRH; VTFISRHM; TFISRHMC; FISRHMCA;
ISRHMCAG; SRHMCAGH; RHMCAGHN; HMCAGHNI; MCAGHNII; CAGHNIIF; AGHNIIFF;
GHNIIFFL; HNIIFFLT; NIIFFLTP; IIFFLTPH; IFFLTPHR; FFLTPHRH; FLTPHRHR;
LTPHRHRV; TPHRHRVS; PHRHRVSA; HRHRVSAI; RHRVSAIN; HRVSAINN; RVSAINNF;
VSAINNFC; SAINNFCQ; AINNFCQK; INNFCQKL; NNFCQKLC; NFCQKLCT; FCQKLCTF;
CQKLCTFS; QKLCTFSF; KLCTFSFL; LCTFSFLI; CTFSFLIC; TFSFLICK; FSFLICKG;
SFLICKGV; FLICKGVN; LICKGVNK; ICKGVNKE; CKGVNKEY; KGVNKEYL; GVNKEYLL;
VNKEYLLY; NKEYLLYS; KEYLLYSA; EYLLYSAL; YLLYSALT; LLYSALTR; LYSALTRD;
YSALTRDP; SALTRDPY; ALTRDPYH; LTRDPYHT; TRDPYHTI; RDPYHTIE; DPYHTIEE;
PYHTIEES; YHTIEESI; HTIEESIQ; TIEESIQG; IEESIQGG; EESIQGGL; ESIQGGLK;
SIQGGLKE; IQGGLKEH; QGGLKEHD; GGLKEHDF; GLKEHDFS; LKEHDFSP; KEHDFSPE;
EHDFSPEE; HDFSPEEP; DFSPEEPE; FSPEEPEE; SPEEPEET; PEEPEETK; EEPEETKQ;
EPEETKQV; PEETKQVS; EETKQVSW; ETKQVSWK; TKQVSWKL; KQVSWKLI; QVSWKLIT;
VSWKLITE; SWKLITEY; WKLITEYA; KLITEYAV; LITEYAVE; ITEYAVET; TEYAVETK;
EYAVETKC; YAVETKCE; AVETKCED; VETKCEDV; ETKCEDVF; TKCEDVFL; KCEDVFLL;
CEDVFLLL; EDVFLLLG; DVFLLLGM; VFLLLGMY; FLLLGMYL; LLLGMYLE; LLGMYLEF;
LGMYLEFQ; GMYLEFQY; MYLEFQYN; YLEFQYNV; LEFQYNVE; EFQYNVEE; FQYNVEEC;
QYNVEECK; YNVEECKK; NVEECKKC; VEECKKCQ; EECKKCQK; ECKKCQKK; CKKCQKKD;
KKCQKKDQ; KCQKKDQP; CQKKDQPY; QKKDQPYH; KKDQPYHF; KDQPYHFK; DQPYHFKY;
QPYHFKYH; PYHFKYHE; YHFKYHEK; HFKYHEKH; FKYHEKHF; KYHEKHFA; YHEKHFAN;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

HEKHFANA; EKHFANAI; KHFANAII; HFANAIIF; FANAIIFA; ANAIIFAE; NAIIFAES;
AIIFAESK; IIFAESKN; IFAESKNQ; FAESKNQK; AESKNQKS; ESKNQKSI; SKNQKSIC;
KNQKSICQ; NQKSICQQ; QKSICQQA; KSICQQAV; SICQQAVD; ICQQAVDT; CQQAVDTV;
QQAVDTVL; QAVDTVLA; AVDTVLAK; VDTVLAKK; DTVLAKKR; TVLAKKRV; VLAKKRVD;
LAKKRVDT; AKKRVDTL; KKRVDTLH; KRVDTLHM; RVDTLHMT; VDTLHMTR; DTLHMTRE;
TLHMTREE; LHMTREEM; HMTREEML; MTREEMLT; TREEMLTE; REEMLTER; EEMLTERF;
EMLTERFN; MLTERFNH; LTERFNHI; TERFNHIL; ERFNHILD; RFNHILDK; FNHILDKM;
NHILDKMD; HILDKMDL; ILDKMDLI; LDKMDLIF; DKMDLIFG; KMDLIFGA; MDLIFGAH;
DLIFGAHG; LIFGAHGN; IFGAHGNA; FGAHGNAV; GAHGNAVL; AHGNAVLE; HGNAVLEQ;
GNAVLEQY; NAVLEQYM; AVLEQYMA; VLEQYMAG; LEQYMAGV; EQYMAGVA; QYMAGVAW;
YMAGVAWL; MAGVAWLH; AGVAWLHC; GVAWLHCL; VAWLHCLL; AWLHCLLP; WLHCLLPK;
LHCLLPKM; HCLLPKMD; CLLPKMDS; LLPKMDSV; LPKMDSVI; PKMDSVIF; KMDSVIFD;
MDSVIFDF; DSVIFDFL; SVIFDFLH; VIFDFLHC; IFDFLHCI; FDFLHCIV; DFLHCIVF;
FLHCIVFN; LHCIVFNV; HCIVFNVP; CIVFNVPK; IVFNVPKR; VFNVPKRR; FNVPKRRY;
NVPKRRYW; VPKRRYWL; PKRRYWLF; KRRYWLFK; RRYWLFKG; RYWLFKGP; YWLFKGPI;
WLFKGPID; LFKGPIDS; FKGPIDSG; KGPIDSGK; GPIDSGKT; PIDSGKTT; IDSGKTTL;
DSGKTTLA; SGKTTLAA; GKTTLAAG; KTTLAAGL; TTLAAGLL; TLAAGLLD; LAAGLLDL;
AAGLLDLC; AGLLDLCG; GLLDLCGG; LLDLCGGK; LDLCGGKA; DLCGGKAL; LCGGKALN;
CGGKALNV; GGKALNVN; GKALNVNL; KALNVNLP; ALNVNLPM; LNVNLPME; NVNLPMER;
VNLPMERL; NLPMERLT; LPMERLTF; PMERLTFE; MERLTFEL; ERLTFELG; RLTFELGV;
LTFELGVA; TFELGVAI; FELGVAID; ELGVAIDQ; LGVAIDQY; GVAIDQYM; VAIDQYMV;
AIDQYMVV; IDQYMVVF; DQYMVVFE; QYMVVFED; YMVVFEDV; MVVFEDVK; VVFEDVKG;
VFEDVKGT; FEDVKGTG; EDVKGTGA; DVKGTGAE; VKGTGAES; KGTGAESK; GTGAESKD;
TGAESKDL; GAESKDLP; AESKDLPS; ESKDLPSG; SKDLPSGH; KDLPSGHG; DLPSGHGI;
LPSGHGIN; PSGHGINN; SGHGINNL; GHGINNLD; HGINNLDS; GINNLDSL; INNLDSLR;
NNLDSLRD; NLDSLRDY; LDSLRDYL; DSLRDYLD; SLRDYLDG; LRDYLDGS; RDYLDGSV;
DYLDGSVK; YLDGSVKV; LDGSVKVN; DGSVKVNL; GSVKVNLE; SVKVNLEK; VKVNLEKK;
KVNLEKKH; VNLEKKHL; NLEKKHLN; LEKKHLNK; EKKHLNKR; KKHLNKRT; KHLNKRTQ;
HLNKRTQI; LNKRTQIF; NKRTQIFP; KRTQIFPP; RTQIFPPG; TQIFPPGL; QIFPPGLV;
IFPPGLVT; FPPGLVTM; PPGLVTMN; PGLVTMNE; GLVTMNEY; LVTMNEYP; VTMNEYPV;
TMNEYPVP; MNEYPVPK; NEYPVPKT; EYPVPKTL; YPVPKTLQ; PVPKTLQA; VPKTLQAR;
PKTLQARF; KTLQARFV; TLQARFVR; LQARFVRQ; QARFVRQI; ARFVRQID; RFVRQIDF;
FVRQIDFR; VRQIDFRP; RQIDFRPK; QIDFRPKI; IDFRPKIY; DFRPKIYL; FRPKIYLR;
RPKIYLRK; PKIYLRKS; KIYLRKSL; IYLRKSLQ; YLRKSLQN; LRKSLQNS; RKSLQNSE;
KSLQNSEF; SLQNSEFL; LQNSEFLL; QNSEFLLE; NSEFLLEK; SEFLLEKR; EFLLEKRI;
FLLEKRIL; LLEKRILQ; LEKRILQS; EKRILQSG; KRILQSGM; RILQSGMT; ILQSGMTL;
LQSGMTLL; QSGMTLLL; SGMTLLLL; GMTLLLLL; MTLLLLLI; TLLLLLIW; LLLLLIWF;
LLLLIWFR; LLLIWFRP; LLIWFRPV; LIWFRPVA; IWFRPVAD; WFRPVADF; FRPVADFA;
RPVADFAT; PVADFATD; VADFATDI; ADFATDIQ; DFATDIQS; FATDIQSR; ATDIQSRI;
TDIQSRIV; DIQSRIVE; IQSRIVEW; QSRIVEWK; SRIVEWKE; RIVEWKER; IVEWKERL;
VEWKERLD; EWKERLDS; WKERLDSE; KERLDSEI; ERLDSEIS; RLDSEISM; LDSEISMY;
DSEISMYT; SEISMYTF; EISMYTFS; ISMYTFSR; SMYTFSRM; MYTFSRMK; YTFSRMKY;
TFSRMKYN; FSRMKYNI; SRMKYNIC; RMKYNICM; MKYNICMG; KYNICMGK; YNICMGKC;
NICMGKCI; ICMGKCIL; CMGKCILD; MGKCILDI; GKCILDIT; KCILDITR; CILDITRE;
ILDITREE; LDITREED; DITREEDS; ITREEDSE; TREEDSET; REEDSETE; EEDSETED;
EDSETEDS; DSETEDSG; SETEDSGH; ETEDSGHG; TEDSGHGS; EDSGHGSS; DSGHGSST;
SGHGSSTE; GHGSSTES; HGSSTESQ; GSSTESQS; SSTESQSQ; STESQSQC; TESQSQCS;
ESQSQCSS; SQSQCSSQ; QSQCSSQV; SQCSSQVS; QCSSQVSD; CSSQVSDT; SSQVSDTS;
SQVSDTSA; QVSDTSAP; VSDTSAPA; SDTSAPAE; DTSAPAED; TSAPAEDS; SAPAEDSQ;
APAEDSQR; PAEDSQRS; AEDSQRSD; EDSQRSDP; DSQRSDPH; SQRSDPHS; QRSDPHSQ;
RSDPHSQE; SDPHSQEL; DPHSQELH; PHSQELHL; HSQELHLC; SQELHLCK; QELHLCKG;
ELHLCKGF; LHLCKGFQ; HLCKGFQC; LCKGFQCF; CKGFQCFK; KGFQCFKR; GFQCFKRP;
FQCFKRPK; QCFKRPKT; CFKRPKTP; FKRPKTPP; KRPKTPPP; RPKTPPPK; HKLKSGLY;
KLKSGLYK; LKSGLYKS; KSGLYKSS; SGLYKSSI; GLYKSSIY; MYMYNKST; YMYNKSTC;
MYNKSTCL; YNKSTCLK; NKSTCLKH; KSTCLKHF; STCLKHFG; TCLKHFGL; CLKHFGLQ;
LKHFGLQL; KHFGLQLS; HFGLQLSL; FGLQLSLF; GLQLSLFV; LQLSLFVN; QLSLFVNI;
LSLFVNIS; SLFVNISY; LFVNISYH; FVNISYHI; VNISYHIW; NISYHIWV; ISYHIWVP;
SYHIWVPW; YHIWVPWK; HIWVPWKS; IWVPWKSF; WVPWKSFC; VPWKSFCA; PWKSFCAI;
WKSFCAIK; KSFCAIKH; SFCAIKHP; FCAIKHPN; CAIKHPNL; AIKHPNLF; IKHPNLFY;
KHPNLFYL; HPNLFYLG; PNLFYLGF; NLFYLGFH; LFYLGFHT; FYLGFHTI; YLGFHTIH;
LGFHTIHR; GFHTIHRL; FHTIHRLP; HTIHRLPI; TIHRLPIH; IHRLPIHS; HRLPIHSL;
RLPIHSLG; LPIHSLGS; PIHSLGSP; IHSLGSPV; HSLGSPVY; SLGSPVYK; LGSPVYKV;
GSPVYKVT; QKGNWVRI; KGNWVRIL; GNWVRILY; NWVRILYR; WVRILYRS; VRILYRSF;
RILYRSFS; ILYRSFSQ; LYRSFSQA; YRSFSQAD; RSFSQADL; SFSQADLK; FSQADLKI;
SQADLKIS; QADLKISC; ADLKISCK; DLKISCKA; LKISCKAS; KISCKASP; ISCKASPL;
SCKASPLL; CKASPLLC; KASPLLCS; ASPLLCSR; SPLLCSRA; PLLCSRAV; LLCSRAVS;
LCSRAVSK; CSRAVSKQ; SRAVSKQA; RAVSKQAT; AVSKQATN; VSKQATNI; SKQATNIS;
KQATNISS; NIQAISFT; IQAISFTK; QAISFTKR; AISFTKRP; ISFTKRPH; SFTKRPHT;
FTKRPHTL; TKRPHTLF; KRPHTLFI; QHCGSCVG; HCGSCVGH; CGSCVGHM; GSCVGHMK;
SCVGHMKY; CVGHMKYW; VGHMKYWG; GHMKYWGN; HMKYWGNI; MKYWGNIF; KYWGNIFP;
YWGNIFPS; WGNIFPSC; GNIFPSCE; NIFPSCES; IFPSCESP; FPSCESPK; PSCESPKI;
SCESPKIP; CESPKIPS; ESPKIPSI; SPKIPSIF; PKIPSIFI; KIPSIFIS; IPSIFIST;
PSIFISTG; SIFISTGI; IFISTGIR; FISTGIRY; ISTGIRYP; STGIRYPA; TGIRYPAL;
GIRYPALN; IRYPALNW; RYPALNWI; YPALNWIS; PALNWISI; ALNWISIV; LNWISIVF;
NWISIVFV; WISIVFVQ; ISIVFVQI; SIVFVQIG; IVFVQIGL; VFVQIGLM; FVQIGLMV;
VQIGLMVS; QIGLMVSI; IGLMVSIH; GLMVSIHY; LMVSIHYL; MVSIHYLG; VSIHYLGL;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

SIHYLGLG; IHYLGLGC; HYLGLGCW; YLGLGCWV; LGLGCWVF; GLGCWVFR; LGCWVFRG;
GCWVFRGY; CWVFRGYS; WVFRGYST; VFRGYSTI; FRGYSTIR; RGYSTIRV; GYSTIRVL;
HSLHFQGF; SLHFQGFS; LHFQGFST; HFQGFSTY; FQGFSTYS; QGFSTYSK; GFSTYSKE;
FSTYSKEV; STYSKEVE; TYSKEVEI; YSKEVEIT; SKEVEITA; KEVEITAL; EVEITALN;
VEITALNR; EITALNRF; ITALNRFS; TALNRFSS; ALNRFSST; LNRFSSTM; NRFSSTML;
RFSSTMLM; FSSTMLMH; SSTMLMHF; STMLMHFL; PCMKVKHA; CMKVKHAS; MKVKHASY;
KVKHASYS; VKHASYSN; KHASYSNN; HASYSNNL; ASYSNNLC; SYSNNLCL; YSNNLCLY;
SNNLCLYS; NNLCLYSY; NLCLYSYS; LCLYSYSL; CLYSYSLP; LYSYSLPH; YSYSLPHQ;
IGEGNSCC; GEGNSCCA; EGNSCCAV; GNSCCAVT; NSCCAVTG; SCCAVTGK; CCAVTGKH;
CAVTGKHF; AVTGKHFS; VTGKHFSL; TGKHFSLW; GKHFSLWA; KHFSLWAI; HFSLWAIT;
FSLWAITA; SLWAITAK; LWAITAKV; WAITAKVI; AITAKVIF; ITAKVIFS; TAKVIFST;
TKAPKVFI; KAPKVFIW; APKVFIWI; PKVFIWIP; KVFIWIPH; VFIWIPHF; FIWIPHFW;
IWIPHFWV; EAFYLCNS; AFYLCNSI; FYLCNSIY; YLCNSIYP; LCNSIYPS; CNSIYPSF;
NSIYPSFN; SIYPSFNF; FWHLHGFL; WHLHGFLW; HLHGFLWL; LHGFLWLF; HGFLWLFG;
GFLWLFGS; FLWLFGSC; LWLFGSCP; WLFGSCPW; LFGSCPWT; FGSCPWTL; GSCPWTLS;
SCPWTLSF; CPWTLSFS; PWTLSFSF; WTLSFSFG; TLSFSFGW; LSFSFGWG; SFSFGWGH;
FSFGWGHL; SFGWGHLH; FGWGHLHM; GWGHLHML; WGHLHMLQ; GHLHMLQE; HLHMLQEQ;
LHMLQEQV; HMLQEQVL; MLQEQVLQ; LQEQVLQS; QEQVLQSR; EQVLQSRT; QVLQSRTG;
VLQSRTGL; LQSRTGLE; QSRTGLEV; SRTGLEVK; RTGLEVKA; TGLEVKAT; GLEVKATS;
LEVKATSI; EVKATSIE; VKATSIEE; KATSIEEQ; ATSIEEQF; TSIEEQFF; SIEEQFFD;
TLLNVHFV; LLNVHFVD; LNVHFVDF; NVHFVDFL; VHFVDFLS; HFVDFLSP; FVDFLSPF;
VDFLSPFF; DFLSPFFV; LLLYCQHH; LLYCQHHL; LYCQHHLY; YCQHHLYY; CQHHLYYK;
QHHLYYKY; HHLYYKYG; HLYYKYGQ; LYYKYGQN; YYKYGQNV; YKYGQNVH; KYGQNVHG;
YGQNVHGY; GQNVHGYL; QNVHGYLP; NVHGYLPF; VHGYLPFQ; HGYLPFQL; GYLPFQLL;
YLPFQLLV; GKDQNNIV; KDQNNIVE; DQNNIVEY; QNNIVEYN; NNIVEYNY; NIVEYNYK;
IVEYNYKS; VEYNYKSL; KIFLFFSA; IFLFFSAI; FLFFSAIP; LFFSAIPV; FFSAIPVR;
FSAIPVRL; QTKKDPNA; QKYLHQET; KYLHQETE; YLHQETEY; LHQETEYH; HQETEYHS;
QETEYHST; ETEYHSTH; TEYHSTHL; EYHSTHLG; TIPKPCLI; IPKPCLIA; PKPCLIAD;
KPCLIADR; PCLIADRG; CLIADRGL; LIADRGLQ; IADRGLQW; ADRGLQWK; DRGLQWKL;
RGLQWKLC; GLQWKLCD; LQWKLCDP; QWKLCDPN; WKLCDPNH; KLCDPNHQ; LCDPNHQR;
CDPNHQRT; DPNHQRTY; PNHQRTYT; NHQRTYTL; HQRTYTLL; QRTYTLLE; RTYTLLEL;
TYTLLELR; YTLLELRN; QFELKQQT; FELKQQTQ; ELKQQTQQ; PQEHQQLQ; QEHQQLQH;
EHQQLQHM; HQQLQHMF; QQLQHMFE; QLQHMFEE; LQHMFEEL; QHMFEELG; HMFEELGL;
PLRYLLCP; LRYLLCPL; RYLLCPLQ; QGMQFELL; QGMQFELLQ; QGMQFELLQQ; QPPQQQFQ;
PPQQQFQP; PQQQFQPL; QQQFQPLK; QQFQPLKI; QFQPLKIL; FQPLKILW; QPLKILWQ;
PLKILWQQ; LKILWQQQ; KILWQQQP; ILWQQQPQ; LWQQQPQI; WQQQPQIH; QQQPQIHW;
QQPQIHWQ; QPQIHWQL; PQIHWQLG; QIHWQLGP; IHWQLGPP; HWQLGPPK; WQLGPPKV;
QLGPPKVL; LGPPKVLE; GPPKVLEQ; PPKVLEQH; PKVLEQHP; TWKYKKKG; WKYKKKGI;
KYKKKGIT; YKKKGITY; KKKGITYL; KKGITYLG; KGITYLGV; GITYLGVF; ITYLGVFY;
TYLGVFYR; YLGVFYRV; LGVFYRVF; GVFYRVFY; VFYRVFYS; FYRVFYSR; SSGTFVFP;
SGTFVFPV; GTFVFPVY; TFVFPVYT; FVFPVYTV; VFPVYTVF; FPVYTVFT; PVYTVFTS;
VYTVFTST; YTVFTSTK; TVFTSTKF; VFTSTKFQ; FTSTKFQQ; TSTKFQQK; STKFQQKL;
NKNKNPLS; KNKNPLSS; NKNPLSSF; KNPLSSFF; NPLSSFFC; PLSSFFCS; LSSFFCSS;
SSFFCSSP; SFFCSSPG; FFCSSPGF; FCSSPGFT; CSSPGFTN; SSPGFTNF; SPGFTNFH;
QLAQNHGL; LAQNHGLC; AQNHGLCP; QNHGLCPV; LGTRPRFL; GTRPRFLG; TRPRFLGS;
RPRFLGSQ; PRFLGSQN; RFLGSQNM; FLGSQNMS; LGSQNMSV; GSQNMSVM; SQNMSVMH;
QNMSVMHF; NMSVMHFP; MSVMHFPS; GHGLAAFH; HGLAAFHG; AAPPCESC; APPCESCT;
PPCESCTF; PCESCTFL; CESCTFLP; ESCTFLPE; SCTFLPEV; CTFLPEVM; TFLPEVMV;
FLPEVMVW; LPEVMVWL; PEVMVWLH; EVMVWLHS; VMVWLHSP; MVWLHSPV; VWLHSPVS;
WLHSPVSH; LHSPVSHA; HSPVSHAL; SPVSHALS; PVSHALSF; VSHALSFL; SHALSFLR;
HALSFLRS; ALSFLRSW; LSFLRSWF; SFLRSWFG; FLRSWFGC; LRSWFGCI; RSWFGCIP;
SWFGCIPW; WFGCIPWV; FGCIPWVS; GCIPWVSS; CIPWVSSS; IPWVSSSS; PWVSSSSL;
WVSSSSLW; VSSSSLWP; SSSSLWPF; SSSLWPFF; SSLWPFFL; YIRGRGRL; IRGRGRLC;
RGRGRLCL; GRGRLCLH; RGRLCLHP; GRLCLHPF; RLCLHPFS; LCLHPFSQ; CLHPFSQV;
LHPFSQVV; HPFSQVVR; PFSQVVRV; FSQVVRVW; SQVVRVWR; QVVRVWRL; VVRVWRLF;
VRVWRLFL; RVWRLFLR; VWRLFLRP; WRLFLRPS; RLFLRPSK; LFLRPSKT; FLRPSKTI;
LRPSKTIW; RPSKTIWG; PSKTIWGN; SKTIWGNP; KTIWGNPY; TIWGNPYS; IWGNPYSF;
WGNPYSFA; GNPYSFAI; NPYSFAIF; PYSFAIFA; YSFAIFAK 9 mers:

QGRIHGAHG; GRIHGAHGP; RIHGAHGPF; IHGAHGPFR; HGAHGPFRP; KSCLGKSSL;
SCLGKSSLN; CLGKSSLNE; LGKSSLNEK; GKSSLNEKS; KSSLNEKSL; SSLNEKSLF;
SLNEKSLFK; LNEKSLFKE; NEKSLFKEV; KNGAGCKGS; NGAGCKGSS; GAGCKGSSS;
AGCKGSSSA; FSSLPRYPV; SSLPRYPVL; SLPRYPVLQ; LPRYPVLQG; PRYPVLQGM;
RYPVLQGMA; YPVLQGMAY; PVLQGMAYL; VLQGMAYLF; LQGMAYLFQ; QGMAYLFQK;
GMAYLFQKA; MAYLFQKAF; AYLFQKAFC; YLFQKAFCA; LFQKAFCAL; FQKAFCALP;
QKAFCALPL; KAFCALPLH; AFCALPLHA; FCALPLHAM; CALPLHAMS; ALPLHAMSA;
KIFKKRALG; IFKKRALGL; FKKRALGLD; KKRALGLDR; KRALGLDRL; RALGLDRLL;
ALGLDRLLL; LGLDRLLLH; LLHTVVWLR; LHTVVWLRP; HTVVWLRPN; RNSAMVGPN;
NSAMVGPNN; SAMVGPNNW; AMVGPNNWR; MVGPNNWRN; VGPNNWRNS; GPNNWRNSL;
PNNWRNSLQ; NNWRNSLQR; NWRNSLQRS; WRNSLQRSK; RNSLQRSKA; NSLQRSKAL;
SLQRSKALR; INNKILKGP; NNKILKGPK; VPTYGTEEW; PTYGTEEWE; TYGTEEWES;
YGTEEWESW; GTEEWESWW; TEEWESWWS; EEWESWWSS; EWESWWSSF; WESWWSSFN;
ESWWSSFNE; SWWSSFNEK; WWSSFNEKW; WSSFNEKWD; SSFNEKWDE; SFNEKWDED;
FNEKWDEDL; NEKWDEDLF; EKWDEDLFC; KWDEDLFCH; WDEDLFCHE; DEDLFCHED;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

EDLFCHEDM; DLFCHEDMF; LFCHEDMFA; FCHEDMFAS; CHEDMFASD; HEDMFASDE;
EDMFASDEE; DMFASDEEA; MFASDEEAT; FASDEEATA; ASDEEATAD; SDEEATADS;
DEEATADSQ; EEATADSQH; EATADSQHS; ATADSQHST; TADSQHSTP; ADSQHSTPP;
DSQHSTPPK; SQHSTPPKK; QHSTPPKKK; HSTPPKKKR; STPPKKKRK; TPPKKKRKV;
PPKKKRKVE; PKKKRKVED; KKKRKVEDP; KKRKVEDPK; KRKVEDPKD; RKVEDPKDF;
KVEDPKDFP; VEDPKDFPS; EDPKDFPSD; DPKDFPSDL; PKDFPSDLH; KDFPSDLHQ;
DFPSDLHQF; FPSDLHQFL; PSDLHQFLS; SDLHQFLSQ; DLHQFLSQA; LHQFLSQAV;
HQFLSQAVF; QFLSQAVFS; FLSQAVFSN; LSQAVFSNR; SQAVFSNRT; QAVFSNRTL;
AVFSNRTLA; VFSNRTLAC; FSNRTLACF; SNRTLACFA; NRTLACFAV; RTLACFAVY;
TLACFAVYT; LACFAVYTT; ACFAVYTTK; CFAVYTTKE; FAVYTTKEK; AVYTTKEKA;
VYTTKEKAQ; YTTKEKAQI; TTKEKAQIL; TKEKAQILY; KEKAQILYK; EKAQILYKK;
KAQILYKKL; AQILYKKLM; QILYKKLME; ILYKKLMEK; LYKKLMEKY; YKKLMEKYS;
KKLMEKYSV; KLMEKYSVT; LMEKYSVTF; MEKYSVTFI; EKYSVTFIS; KYSVTFISR;
YSVTFISRH; SVTFISRHM; VTFISRHMC; TFISRHMCA; FISRHMCAG; ISRHMCAGH;
SRHMCAGHN; RHMCAGHNI; HMCAGHNII; MCAGHNIIF; CAGHNIIFF; AGHNIIFFL;
GHNIIFFLT; HNIIFFLTP; NIIFFLTPH; IIFFLTPHR; IFFLTPHRH; FFLTPHRHR;
FLTPHRHRV; LTPHRHRVS; TPHRHRVSA; PHRHRVSAI; HRHRVSAIN; RHRVSAINN;
HRVSAINNF; RVSAINNFC; VSAINNFCQ; SAINNFCQK; AINNFCQKL; INNFCQKLC;
NNFCQKLCT; NFCQKLCTF; FCQKLCTFS; CQKLCTFSF; QKLCTFSFL; KLCTFSFLI;
LCTFSFLIC; CTFSFLICK; TFSFLICKG; FSFLICKGV; SFLICKGVN; FLICKGVNK;
LICKGVNKE; ICKGVNKEY; CKGVNKEYL; KGVNKEYLL; GVNKEYLLY; VNKEYLLYS;
NKEYLLYSA; KEYLLYSAL; EYLLYSALT; YLLYSALTR; LLYSALTRD; LYSALTRDP;
YSALTRDPY; SALTRDPYH; ALTRDPYHT; LTRDPYHTI; TRDPYHTIE; RDPYHTIEE;
DPYHTIEES; PYHTIEESI; YHTIEESIQ; HTIEESIQG; TIEESIQGG; IEESIQGGL;
EESIQGGLK; ESIQGGLKE; SIQGGLKEH; IQGGLKEHD; QGGLKEHDF; GGLKEHDFS;
GLKEHDFSP; LKEHDFSPE; KEHDFSPEE; EHDFSPEEP; HDFSPEEPE; DFSPEEPEE;
FSPEEPEET; SPEEPEETK; PEEPEETKQ; EEPEETKQV; EPEETKQVS; PEETKQVSW;
EETKQVSWK; ETKQVSWKL; TKQVSWKLI; KQVSWKLIT; QVSWKLITE; VSWKLITEY;
SWKLITEYA; WKLITEYAV; KLITEYAVE; LITEYAVET; ITEYAVETK; TEYAVETKC;
EYAVETKCE; YAVETKCED; AVETKCEDV; VETKCEDVF; ETKCEDVFL; TKCEDVFLL;
KCEDVFLLL; CEDVFLLLG; EDVFLLLGM; DVFLLLGMY; VFLLLGMYL; FLLLGMYLE;
LLLGMYLEF; LLGMYLEFQ; LGMYLEFQY; GMYLEFQYN; MYLEFQYNV; YLEFQYNVE;
LEFQYNVEE; EFQYNVEEC; FQYNVEECK; QYNVEECKK; YNVEECKKC; NVEECKKCQ;
VEECKKCQK; EECKKCQKK; ECKKCQKKD; CKKCQKKDQ; KKCQKKDQP; KCQKKDQPY;
CQKKDQPYH; QKKDQPYHF; KKDQPYHFK; KDQPYHFKY; DQPYHFKYH; QPYHFKYHE;
PYHFKYHEK; YHFKYHEKH; HFKYHEKHF; FKYHEKHFA; KYHEKHFAN; YHEKHFANA;
HEKHFANAI; EKHFANAII; KHFANAIIF; HFANAIIFA; FANAIIFAE; ANAIIFAES;
NAIIFAESK; AIIFAESKN; IIFAESKNQ; IFAESKNQK; FAESKNQKS; AESKNQKSI;
ESKNQKSIC; SKNQKSICQ; KNQKSICQQ; NQKSICQQA; QKSICQQAV; KSICQQAVD;
SICQQAVDT; ICQQAVDTV; CQQAVDTVL; QQAVDTVLA; QAVDTVLAK; AVDTVLAKK;
VDTVLAKKR; DTVLAKKRV; TVLAKKRVD; VLAKKRVDT; LAKKRVDTL; AKKRVDTLH;
KKRVDTLHM; KRVDTLHMT; RVDTLHMTR; VDTLHMTRE; DTLHMTREE; TLHMTREEM;
LHMTREEML; HMTREEMLT; MTREEMLTE; TREEMLTER; REEMLTERF; EEMLTERFN;
EMLTERFNH; MLTERFNHI; LTERFNHIL; TERFNHILD; ERFNHILDK; RFNHILDKM;
FNHILDKMD; NHILDKMDL; HILDKMDLI; ILDKMDLIF; LDKMDLIFG; DKMDLIFGA;
KMDLIFGAH; MDLIFGAHG; DLIFGAHGN; LIFGAHGNA; IFGAHGNAV; FGAHGNAVL;
GAHGNAVLE; AHGNAVLEQ; HGNAVLEQY; GNAVLEQYM; NAVLEQYMA; AVLEQYMAG;
VLEQYMAGV; LEQYMAGVA; EQYMAGVAW; QYMAGVAWL; YMAGVAWLH; MAGVAWLHC;
AGVAWLHCL; GVAWLHCLL; VAWLHCLLP; AWLHCLLPK; WLHCLLPKM; LHCLLPKMD;
HCLLPKMDS; CLLPKMDSV; LLPKMDSVI; LPKMDSVIF; PKMDSVIFD; KMDSVIFDF;
MDSVIFDFL; DSVIFDFLH; SVIFDFLHC; VIFDFLHCI; IFDFLHCIV; FDFLHCIVF;
DFLHCIVFN; FLHCIVFNV; LHCIVFNVP; HCIVFNVPK; CIVFNVPKR; IVFNVPKRR;
VFNVPKRRY; FNVPKRRYW; NVPKRRYWL; VPKRRYWLF; PKRRYWLFK; KRRYWLFKG;
RRYWLFKGP; RYWLFKGPI; YWLFKGPID; WLFKGPIDS; LFKGPIDSG; FKGPIDSGK;
KGPIDSGKT; GPIDSGKTT; PIDSGKTTL; IDSGKTTLA; DSGKTTLAA; SGKTTLAAG;
GKTTLAAGL; KTTLAAGLL; TTLAAGLLD; TLAAGLLDL; LAAGLLDLC; AAGLLDLCG;
AGLLDLCGG; GLLDLCGGK; LLDLCGGKA; LDLCGGKAL; DLCGGKALN; LCGGKALNV;
CGGKALNVN; GGKALNVNL; GKALNVNLP; KALNVNLPM; ALNVNLPME; LNVNLPMER;
NVNLPMERL; VNLPMERLT; NLPMERLTF; LPMERLTFE; PMERLTFEL; MERLTFELG;
ERLTFELGV; RLTFELGVA; LTFELGVAI; TFELGVAID; FELGVAIDQ; ELGVAIDQY;
LGVAIDQYM; GVAIDQYMV; VAIDQYMVV; AIDQYMVVF; IDQYMVVFE; DQYMVVFED;
QYMVVFEDV; YMVVFEDVK; MVVFEDVKG; VVFEDVKGT; VFEDVKGTG; FEDVKGTGA;
EDVKGTGAE; DVKGTGAES; VKGTGAESK; KGTGAESKD; GTGAESKDL; TGAESKDLP;
GAESKDLPS; AESKDLPSG; ESKDLPSGH; SKDLPSGHG; KDLPSGHGI; DLPSGHGIN;
LPSGHGINN; PSGHGINNL; SGHGINNLD; GHGINNLDS; HGINNLDSL; GINNLDSLR;
INNLDSLRD; NNLDSLRDY; NLDSLRDYL; LDSLRDYLD; DSLRDYLDG; SLRDYLDGS;
LRDYLDGSV; RDYLDGSVK; DYLDGSVKV; YLDGSVKVN; LDGSVKVNL; DGSVKVNLE;
GSVKVNLEK; SVKVNLEKK; VKVNLEKKH; KVNLEKKHL; VNLEKKHLN; NLEKKHLNK;
LEKKHLNKR; EKKHLNKRT; KKHLNKRTQ; KHLNKRTQI; HLNKRTQIF; LNKRTQIFP;
NKRTQIFPP; KRTQIFPPG; RTQIFPPGL; TQIFPPGLV; QIFPPGLVT; IFPPGLVTM;
FPPGLVTMN; PPGLVTMNE; PGLVTMNEY; GLVTMNEYP; LVTMNEYPV; VTMNEYPVP;
TMNEYPVPK; MNEYPVPKT; NEYPVPKTL; EYPVPKTLQ; YPVPKTLQA; PVPKTLQAR;
VPKTLQARF; PKTLQARFV; KTLQARFVR; TLQARFVRQ; LQARFVRQI; QARFVRQID;
ARFVRQIDF; RFVRQIDFR; FVRQIDFRP; VRQIDFRPK; RQIDFRPKI; QIDFRPKIY;
IDFRPKIYL; DFRPKIYLR; FRPKIYLRK; RPKIYLRKS; PKIYLRKSL; KIYLRKSLQ;
IYLRKSLQN; YLRKSLQNS; LRKSLQNSE; RKSLQNSEF; KSLQNSEFL; SLQNSEFLL;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

LQNSEFLLE; QNSEFLLEK; NSEFLLEKR; SEFLLEKRI; EFLLEKRIL; FLLEKRILQ;
LLEKRILQS; LEKRILQSG; EKRILQSGM; KRILQSGMT; RILQSGMTL; ILQSGMTLL;
LQSGMTLLL; QSGMTLLLL; SGMTLLLLL; GMTLLLLLI; MTLLLLLIW; TLLLLLIWF;
LLLLLIWFR; LLLLIWFRP; LLLIWFRPV; LLIWFRPVA; LIWFRPVAD; IWFRPVADF;
WFRPVADFA; FRPVADFAT; RPVADFATD; PVADFATDI; VADFATDIQ; ADFATDIQS;
DFATDIQSR; FATDIQSRI; ATDIQSRIV; TDIQSRIVE; DIQSRIVEW; IQSRIVEWK;
QSRIVEWKE; SRIVEWKER; RIVEWKERL; IVEWKERLD; VEWKERLDS; EWKERLDSE;
WKERLDSEI; KERLDSEIS; ERLDSEISM; RLDSEISMY; LDSEISMYT; DSEISMYTF;
SEISMYTFS; EISMYTFSR; ISMYTFSRM; SMYTFSRMK; MYTFSRMKY; YTFSRMKYN;
TFSRMKYNI; FSRMKYNIC; SRMKYNICM; RMKYNICMG; MKYNICMGK; KYNICMGKC;
YNICMGKCI; NICMGKCIL; ICMGKCILD; CMGKCILDI; MGKCILDIT; GKCILDITR;
KCILDITRE; CILDITREE; ILDITREED; LDITREEDS; DITREEDSE; ITREEDSET;
TREEDSETE; REEDSETED; EEDSETEDS; EDSETEDSG; DSETEDSGH; SETEDSGHG;
ETEDSGHGS; TEDSGHGSS; EDSGHGSST; DSGHGSSTE; SGHGSSTES; GHGSSTESQ;
HGSSTESQS; GSSTESQSQ; SSTESQSQC; STESQSQCS; TESQSQCSS; ESQSQCSSQ;
SQSQCSSQV; QSQCSSQVS; SQCSSQVSD; QCSSQVSDT; CSSQVSDTS; SSQVSDTSA;
SQVSDTSAP; QVSDTSAPA; VSDTSAPAE; SDTSAPAED; DTSAPAEDS; TSAPAEDSQ;
SAPAEDSQR; APAEDSQRS; PAEDSQRSD; AEDSQRSDP; EDSQRSDPH; DSQRSDPHS;
SQRSDPHSQ; QRSDPHSQE; RSDPHSQEL; SDPHSQELH; DPHSQELHL; PHSQELHLC;
HSQELHLCK; SQELHLCKG; QELHLCKGF; ELHLCKGFQ; LHLCKGFQC; HLCKGFQCF;
LCKGFQCFK; CKGFQCFKR; KGFQCFKRP; GFQCFKRPK; FQCFKRPKT; QCFKRPKTP;
CFKRPKTPP; FKRPKTPPP; KRPKTPPPK; HKLKSGLYK; KLKSGLYKS; LKSGLYKSS;
KSGLYKSSI; SGLYKSSIY; MYMYNKSTC; YMYNKSTCL; MYNKSTCLK; YNKSTCLKH;
NKSTCLKHF; KSTCLKHFG; STCLKHFGL; TCLKHFGLQ; CLKHFGLQL; LKHFGLQLS;
KHFGLQLSL; HFGLQLSLF; FGLQLSLFV; GLQLSLFVN; LQLSLFVNI; QLSLFVNIS;
LSLFVNISY; SLFVNISYH; LFVNISYHI; FVNISYHIW; VNISYHIWV; NISYHIWVP;
ISYHIWVPW; SYHIWVPWK; YHIWVPWKS; HIWVPWKSF; IWVPWKSFC; WVPWKSFCA;
VPWKSFCAI; PWKSFCAIK; WKSFCAIKH; KSFCAIKHP; SFCAIKHPN; FCAIKHPNL;
CAIKHPNLF; AIKHPNLFY; IKHPNLFYL; KHPNLFYLG; HPNLFYLGF; PNLFYLGFH;
NLFYLGFHT; LFYLGFHTI; FYLGFHTIH; YLGFHTIHR; LGFHTIHRL; GFHTIHRLP;
FHTIHRLPI; HTIHRLPIH; TIHRLPIHS; IHRLPIHSL; HRLPIHSLG; RLPIHSLGS;
LPIHSLGSP; PIHSLGSPV; IHSLGSPVY; HSLGSPVYK; SLGSPVYKV; LGSPVYKVT;
QKGNWVRIL; KGNWVRILY; GNWVRILYR; NWVRILYRS; WVRILYRSF; VRILYRSFS;
RILYRSFSQ; ILYRSFSQA; LYRSFSQAD; YRSFSQADL; RSFSQADLK; SFSQADLKI;
FSQADLKIS; SQADLKISC; QADLKISCK; ADLKISCKA; DLKISCKAS; LKISCKASP;
KISCKASPL; ISCKASPLL; SCKASPLLC; CKASPLLCS; KASPLLCSR; ASPLLCSRA;
SPLLCSRAV; PLLCSRAVS; LLCSRAVSK; LCSRAVSKQ; CSRAVSKQA; SRAVSKQAT;
RAVSKQATN; AVSKQATNI; VSKQATNIS; SKQATNISS; NIQAISFTK; IQAISFTKR;
QAISFTKRP; AISFTKRPH; ISFTKRPHT; SFTKRPHTL; FTKRPHTLF; TKRPHTLFI;
QHCGSCVGH; HCGSCVGHM; CGSCVGHMK; GSCVGHMKY; SCVGHMKYW; CVGHMKYWG;
VGHMKYWGN; GHMKYWGNI; HMKYWGNIF; MKYWGNIFP; KYWGNIFPS; YWGNIFPSC;
WGNIFPSCE; GNIFPSCES; NIFPSCESP; IFPSCESPK; FPSCESPKI; PSCESPKIP;
SCESPKIPS; CESPKIPSI; ESPKIPSIF; SPKIPSIFI; PKIPSIFIS; KIPSIFIST;
IPSIFISTG; PSIFISTGI; SIFISTGIR; IFISTGIRY; FISTGIRYP; ISTGIRYPA;
STGIRYPAL; TGIRYPALN; GIRYPALNW; IRYPALNWI; RYPALNWIS; YPALNWISI;
PALNWISIV; ALNWISIVF; LNWISIVFV; NWISIVFVQ; WISIVFVQI; ISIVFVQIG;
SIVFVQIGL; IVFVQIGLM; VFVQIGLMV; FVQIGLMVS; VQIGLMVSI; QIGLMVSIH;
IGLMVSIHY; GLMVSIHYL; LMVSIHYLG; MVSIHYLGL; VSIHYLGLG; SIHYLGLGC;
IHYLGLGCW; HYLGLGCWV; YLGLGCWVF; LGLGCWVFR; GLGCWVFRG; LGCWVFRGY;
GCWVFRGYS; CWVFRGYST; WVFRGYSTI; VFRGYSTIR; FRGYSTIRV; RGYSTIRVL;
HSLHFQGFS; SLHFQGFST; LHFQGFSTY; HFQGFSTYS; FQGFSTYSK; QGFSTYSKE;
GFSTYSKEV; FSTYSKEVE; STYSKEVEI; TYSKEVEIT; YSKEVEITA; SKEVEITAL;
KEVEITALN; EVEITALNR; VEITALNRF; EITALNRFS; ITALNRFSS; TALNRFSST;
ALNRFSSTM; LNRFSSTML; NRFSSTMLM; RFSSTMLMH; FSSTMLMHF; SSTMLMHFL;
PCMKVKHAS; CMKVKHASY; MKVKHASYS; KVKHASYSN; VKHASYSNN; KHASYSNNL;
HASYSNNLC; ASYSNNLCL; SYSNNLCLY; YSNNLCLYS; SNNLCLYSY; NNLCLYSYS;
NLCLYSYSL; LCLYSYSLP; CLYSYSLPH; LYSYSLPHQ; IGEGNSCCA; GEGNSCCAV;
EGNSCCAVT; GNSCCAVTG; NSCCAVTGK; SCCAVTGKH; CCAVTGKHF; CAVTGKHFS;
AVTGKHFSL; VTGKHFSLW; TGKHFSLWA; GKHFSLWAI; KHFSLWAIT; HFSLWAITA;
FSLWAITAK; SLWAITAKV; LWAITAKVI; WAITAKVIF; AITAKVIFS; ITAKVIFST;
TKAPKVPIW; KAPKVPIWI; APKVPIWIP; PKVPIWIPH; KVPIWIPHF; VPIWIPHFW;
FIWIPHFWV; EAFYLCNSI; AFYLCNSIY; FYLCNSIYP; YLCNSIYPS; LCNSIYPSF;
CNSIYPSFN; NSIYPSFNF; FWHLHGFLW; WHLHGFLWL; HLHGFLWLF; LHGFLWLFG;
HGFLWLFGS; GFLWLFGSC; FLWLFGSCP; LWLFGSCPW; WLFGSCPWT; LFGSCPWTL;
FGSCPWTLS; GSCPWTLSF; SCPWTLSFS; CPWTLSFSF; PWTLSFSFG; WTLSFSFGW;
TLSFSFGWG; LSFSFGWGH; SFSFGWGHL; FSFGWGHLH; SFGWGHLHM; FGWGHLHML;
GWGHLHMLQ; WGHLHMLQE; GHLHMLQEQ; HLHMLQEQV; LHMLQEQVL; HMLQEQVLQ;
MLQEQVLQS; LQEQVLQSR; QEQVLQSRT; EQVLQSRTG; QVLQSRTGL; VLQSRTGLE;
LQSRTGLEV; QSRTGLEVK; SRTGLEVKA; RTGLEVKAT; TGLEVKATS; GLEVKATSI;
LEVKATSIE; EVKATSIEE; VKATSIEEQ; KATSIEEQF; ATSIEEQFF; TSIEEQFFD;
TLLNVHFVD; LLNVHFVDF; LNVHFVDFL; NVHFVDFLS; VHFVDFLSP; HFVDFLSPF;
FVDFLSPFF; VDFLSPFFV; LLLYCQHHL; LLYCQHHLY; LYCQHHLYY; YCQHHLYYK;
CQHHLYYKY; QHHLYYKYG; HHLYYKYGQ; HLYYKYGQN; LYYKYGQNV; YYKYGQNVH;
YKYGQNVHG; KYGQNVHGY; YGQNVHGYL; GQNVHGYLP; QNVHGYLPF; NVHGYLPFQ;
VHGYLPFQL; HGYLPFQLL; GYLPFQLLV; GKDQNNIVE; KDQNNIVEY; DQNNIVEYN;
QNNIVEYNY; NNIVEYNYK; NIVEYNYKS; IVEYNYKSL; KIFLFFSAI; IFLFFSAIP;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

FLFFSAIPV; LFFSAIPVR; FFSAIPVRL; QKYLHQETE; KYLHQETEY; YLHQETEYH;
LHQETEYHS; HQETEYHST; QETEYHSTH; ETEYHSTHL; TEYHSTHLG; TIPKPCLIA;
IPKPCLIAD; PKPCLIADR; KPCLIADRG; PCLIADRGL; CLIADRGLQ; LIADRGLQW;
IADRGLQWK; ADRGLQWKL; DRGLQWKLC; RGLQWKLCD; GLQWKLCDP; LQWKLCDPN;
QWKLCDPNH; WKLCDPNHQ; KLCDPNHQR; LCDPNHQRT; CDPNHQRTY; DPNHQRTYT;
PNHQRTYTL; NHQRTYTLL; HQRTYTLLE; QRTYTLLEL; RTYTLLELR; TYTLLELRN;
QFELKQQTQ; FELKQQTQQ; PQEHQQLQH; QEHQQLQHM; EHQQLQHMF; HQQLQHMFE;
QQLQHMFEE; QLQHMFEEL; LQHMFEELG; QHMFEELGL; PLRYLLCPL; LRYLLCPLQ;
QQQPPQQQF; QQPPQQQFQ; QPPQQQFQP; PPQQQFQPL; PQQQFQPLK; QQQFQPLKI;
QQFQPLKIL; QFQPLKILW; FQPLKILWQ; QPLKILWQQ; PLKILWQQQ; LKILWQQQP;
KILWQQQPQ; ILWQQQPQI; LWQQQPQIH; WQQQPQIHW; QQQPQIHWQ; QQPQIHWQL;
QPQIHWQLG; PQIHWQLGP; QIHWQLGPP; IHWQLGPPK; HWQLGPPKV; WQLGPPKVL;
QLGPPKVLE; LGPPKVLEQ; GPPKVLEQH; PPKVLEQHP; TWKYKKKGI; WKYKKKGIT;
KYKKKGITY; YKKKGITYL; KKKGITYLG; KKGITYLGV; KGITYLGVF; GITYLGVFY;
ITYLGVFYR; TYLGVFYRV; YLGVFYRVF; LGVFYRVFY; GVFYRVFYS; VFYRVFYSR;
SSGTFVPPV; SGTFVPPVY; GTFVPPVYT; TFVPPVYTV; FVPPVYTVF; VPPVYTVFT;
FPVYTVFTS; PVYTVFTST; VYTVFTSTK; YTVFTSTKF; TVFTSTKFQ; VFTSTKFQQ;
FTSTKFQQK; TSTKFQQKL; NKNKNPLSS; KNKNPLSSF; NKNPLSSFF; KNPLSSFFC;
NPLSSFFCS; PLSSFFCSS; LSSFFCSSP; SSFFCSSPG; SFFCSSPGF; FFCSSPGFT;
FCSSPGFTN; CSSPGFTNF; SSPGFTNFH; QLAQNHGLC; LAQNHGLCP; AQNHGLCPV;
LGTRPRFLG; GTRPRFLGS; TRPRFLGSQ; RPRFLGSQN; PRFLGSQNM; RFLGSQNMS;
FLGSQNMSV; LGSQNMSVM; GSQNMSVMH; SQNMSVMHF; QNMSVMHFP; NMSVMHFPS;
GHGLAAFHG; AAPPCESCT; APPCESCTF; PPCESCTFL; PCESCTFLP; CESCTFLPE;
ESCTFLPEV; SCTFLPEVM; CTFLPEVMV; TFLPEVMVW; FLPEVMVWL; LPEVMVWLH;
PEVMVWLHS; EVMVWLHSP; VMVWLHSPV; MVWLHSPVS; VWLHSPVSH; WLHSPVSHA;
LHSPVSHAL; HSPVSHALS; SPVSHALSF; PVSHALSFL; VSHALSFLR; SHALSFLRS;
HALSFLRSW; ALSFLRSWF; LSFLRSWFG; SFLRSWFGC; FLRSWFGCI; LRSWFGCIP;
RSWFGCIPW; SWFGCIPWV; WFGCIPWVS; FGCIPWVSS; GCIPWVSSS; CIPWVSSSS;
IPWVSSSSL; PWVSSSSLW; WVSSSSLWP; VSSSSLWPF; SSSSLWPFF; SSSLWPFFL;
YIRGRGRLC; IRGRGRLCL; RGRGRLCLH; GRGRLCLHP; RGRLCLHPF; GRLCLHPFS;
RLCLHPFSQ; LCLHPFSQV; CLHPFSQVV; LHPFSQVVR; HPFSQVVRV; PFSQVVRVW;
FSQVVRVWR; SQVVRVWRL; QVVRVWRLF; VVRVWRLFL; VRVWRLFLR; RVWRLFLRP;
VWRLFLRPS; WRLFLRPSK; RLFLRPSKT; LFLRPSKTI; FLRPSKTIW; LRPSKTIWG;
RPSKTIWGN; PSKTIWGNP; SKTIWGNPY; KTIWGNPYS; TIWGNPYSF; IWGNPYSFA;
WGNPYSFAI; GNPYSFAIF; NPYSFAIFA; PYSFAIFAK 10 mers:

QGRIHGAHGP; GRIHGAHGPF; RIHGAHGPFR; IHGAHGPFRP; KSCLGKSSLN;
SCLGKSSLNE; CLGKSSLNEK; LGKSSLNEKS; GKSSLNEKSL; KSSLNEKSLF;
SSLNEKSLFK; SLNEKSLFKE; LNEKSLFKEV; KNGAGCKGSS; NGAGCKGSSS;
GAGCKGSSSA; FSSLPRYPVL; SSLPRYPVLQ; SLPRYPVLQG; LPRYPVLQGM;
PRYPVLQGMA; RYPVLQGMAY; YPVLQGMAYL; PVLQGMAYLF; VLQGMAYLFQ;
LQGMAYLFQK; QGMAYLFQKA; GMAYLFQKAF; MAYLFQKAFC; AYLFQKAFCA;
YLFQKAFCAL; LFQKAFCALP; FQKAFCALPL; QKAFCALPLH; KAFCALPLHA;
AFCALPLHAM; FCALPLHAMS; CALPLHAMSA; KIFKKRALGL; IFKKRALGLD;
FKKRALGLDR; KKRALGLDRL; KRALGLDRLL; RALGLDRLLL; ALGLDRLLLH;
LLHTVVWLRP; LHTVVWLRPN; RNSAMVGPNN; NSAMVGPNNW; SAMVGPNNWR;
AMVGPNNWRN; MVGPNNWRNS; VGPNNWRNSL; GPNNWRNSLQ; PNNWRNSLQR;
NNWRNSLQRS; NWRNSLQRSK; WRNSLQRSKA; RNSLQRSKAL; NSLQRSKALR;
INNKILKGPK; VPTYGTEEWE; PTYGTEEWES; TYGTEEWESW; YGTEEWESWW;
GTEEWESWWS; TEEWESWWSS; EEWESWWSSF; EWESWWSSFN; WESWWSSFNE;
ESWWSSFNEK; SWWSSFNEKW; WWSSFNEKWD; WSSFNEKWDE; SSFNEKWDED;
SFNEKWDEDL; FNEKWDEDLF; NEKWDEDLFC; EKWDEDLFCH; KWDEDLFCHE;
WDEDLFCHED; DEDLFCHEDM; EDLFCHEDMF; DLFCHEDMFA; LFCHEDMFAS;
FCHEDMFASD; CHEDMFASDE; HEDMFASDEE; EDMFASDEEA; DMFASDEEAT;
MFASDEEATA; FASDEEATAD; ASDEEATADS; SDEEATADSQ; DEEATADSQH;
EEATADSQHS; EATADSQHST; ATADSQHSTP; TADSQHSTPP; ADSQHSTPPK;
DSQHSTPPKK; SQHSTPPKKK; QHSTPPKKKR; HSTPPKKKRK; STPPKKKRKV;
TPPKKKRKVE; PPKKKRKVED; PKKKRKVEDP; KKKRKVEDPK; KKRKVEDPKD;
KRKVEDPKDF; RKVEDPKDFP; KVEDPKDFPS; VEDPKDFPSD; EDPKDFPSDL;
DPKDFPSDLH; PKDFPSDLHQ; KDFPSDLHQF; DFPSDLHQFL; FPSDLHQFLS;
PSDLHQFLSQ; SDLHQFLSQA; DLHQFLSQAV; LHQFLSQAVF; HQFLSQAVFS;
QFLSQAVFSN; FLSQAVFSNR; LSQAVFSNRT; SQAVFSNRTL; QAVFSNRTLA;
AVFSNRTLAC; VFSNRTLACF; FSNRTLACFA; SNRTLACFAV; NRTLACFAVY;
RTLACFAVYT; TLACFAVYTT; LACFAVYTTK; ACFAVYTTKE; CFAVYTTKEK;
FAVYTTKEKA; AVYTTKEKAQ; VYTTKEKAQI; YTTKEKAQIL; TTKEKAQILY;
TKEKAQILYK; KEKAQILYKK; EKAQILYKKL; KAQILYKKLM; AQILYKKLME;
QILYKKLMEK; ILYKKLMEKY; LYKKLMEKYS; YKKLMEKYSV; KKLMEKYSVT;
KLMEKYSVTF; LMEKYSVTFI; MEKYSVTFIS; EKYSVTFISR; KYSVTFISRH;
YSVTFISRHM; SVTFISRHMC; VTFISRHMCA; TFISRHMCAG; FISRHMCAGH;
ISRHMCAGHN; SRHMCAGHNI; RHMCAGHNII; HMCAGHNIIF; MCAGHNIIFF;
CAGHNIIFFL; AGHNIIFFLT; GHNIIFFLTP; HNIIFFLTPH; NIIFFLTPHR;
IIFFLTPHRH; IFFLTPHRHR; FFLTPHRHRV; FLTPHRHRVS; LTPHRHRVSA;
TPHRHRVSAI; PHRHRVSAIN; HRHRVSAINN; RHRVSAINNF; HRVSAINNFC;
RVSAINNFCQ; VSAINNFCQK; SAINNFCQKL; AINNFCQKLC; INNFCQKLCT;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

NNFCQKLCTF; NFCQKLCTFS; FCQKLCTFSF; CQKLCTFSFL; QKLCTFSFLI;
KLCTFSFLIC; LCTFSFLICK; CTFSFLICKG; TFSFLICKGV; FSFLICKGVN;
SFLICKGVNK; FLICKGVNKE; LICKGVNKEY; ICKGVNKEYL; CKGVNKEYLL;
KGVNKEYLLY; GVNKEYLLYS; VNKEYLLYSA; NKEYLLYSAL; KEYLLYSALT;
EYLLYSALTR; YLLYSALTRD; LLYSALTRDP; LYSALTRDPY; YSALTRDPYH;
SALTRDPYHT; ALTRDPYHTI; LTRDPYHTIE; TRDPYHTIEE; RDPYHTIEES;
DPYHTIEESI; PYHTIEESIQ; YHTIEESIQG; HTIEESIQGG; TIEESIQGGL;
IEESIQGGLK; EESIQGGLKE; ESIQGGLKEH; SIQGGLKEHD; IQGGLKEHDF;
QGGLKEHDFS; GGLKEHDFSP; GLKEHDFSPE; LKEHDFSPEE; KEHDFSPEEP;
EHDFSPEEPE; HDFSPEEPEE; DFSPEEPEET; FSPEEPEETK; SPEEPEETKQ;
PEEPEETKQV; EEPEETKQVS; EPEETKQVSW; PEETKQVSWK; EETKQVSWKL;
ETKQVSWKLI; TKQVSWKLIT; KQVSWKLITE; QVSWKLITEY; VSWKLITEYA;
SWKLITEYAV; WKLITEYAVE; KLITEYAVET; LITEYAVETK; ITEYAVETKC;
TEYAVETKCE; EYAVETKCED; YAVETKCEDV; AVETKCEDVF; VETKCEDVFL;
ETKCEDVFLL; TKCEDVFLLL; KCEDVFLLLG; CEDVFLLLGM; EDVFLLLGMY;
DVFLLLGMYL; VFLLLGMYLE; FLLLGMYLEF; LLLGMYLEFQ; LLGMYLEFQY;
LGMYLEFQYN; GMYLEFQYNV; MYLEFQYNVE; YLEFQYNVEE; LEFQYNVEEC;
EFQYNVEECK; FQYNVEECKK; QYNVEECKKC; YNVEECKKCQ; NVEECKKCQK;
VEECKKCQKK; EECKKCQKKD; ECKKCQKKDQ; CKKCQKKDQP; KKCQKKDQPY;
KCQKKDQPYH; CQKKDQPYHF; QKKDQPYHFK; KKDQPYHFKY; KDQPYHFKYH;
DQPYHFKYHE; QPYHFKYHEK; PYHFKYHEKH; YHFKYHEKHF; HFKYHEKHFA;
FKYHEKHFAN; KYHEKHFANA; YHEKHFANAI; HEKHFANAII; EKHFANAIIF;
KHFANAIIFA; HFANAIIFAE; FANAIIFAES; ANAIIFAESK; NAIIFAESKN;
AIIFAESKNQ; IIFAESKNQQ; IFAESKNQQK; FAESKNQKSI; AESKNQKSIC;
ESKNQKSICQ; SKNQKSICQQ; KNQKSICQQA; NQKSICQQAV; QKSICQQAVD;
KSICQQAVDT; SICQQAVDTV; ICQQAVDTVL; CQQAVDTVLA; QQAVDTVLAK;
QAVDTVLAKK; AVDTVLAKKR; VDTVLAKKRV; DTVLAKKRVD; TVLAKKRVDT;
VLAKKRVDTL; LAKKRVDTLH; AKKRVDTLHM; KKRVDTLHMT; KRVDTLHMTR;
RVDTLHMTRE; VDTLHMTREE; DTLHMTREEM; TLHMTREEML; LHMTREEMLT;
HMTREEMLTE; MTREEMLTER; TREEMLTERF; REEMLTERFN; EEMLTERFNH;
EMLTERFNHI; MLTERFNHIL; LTERFNHILD; TERFNHILDK; ERFNHILDKM;
RFNHILDKMD; FNHILDKMDL; NHILDKMDLI; HILDKMDLIF; ILDKMDLIFG;
LDKMDLIFGA; DKMDLIFGAH; KMDLIFGAHG; MDLIFGAHGN; DLIFGAHGNA;
LIFGAHGNAV; IFGAHGNAVL; FGAHGNAVLE; GAHGNAVLEQ; AHGNAVLEQY;
HGNAVLEQYM; GNAVLEQYMA; NAVLEQYMAG; AVLEQYMAGV; VLEQYMAGVA;
LEQYMAGVAW; EQYMAGVAWL; QYMAGVAWLH; YMAGVAWLHC; MAGVAWLHCL;
AGVAWLHCLL; GVAWLHCLLP; VAWLHCLLPK; AWLHCLLPKM; WLHCLLPKMD;
LHCLLPKMDS; HCLLPKMDSV; CLLPKMDSVI; LLPKMDSVIF; LPKMDSVIFD;
PKMDSVIFDF; KMDSVIFDFL; MDSVIFDFLH; DSVIFDFLHC; SVIFDFLHCI;
VIFDFLHCIV; IFDFLHCIVF; FDFLHCIVFN; DFLHCIVFNV; FLHCIVFNVP;
LHCIVFNVPK; HCIVFNVPKR; CIVFNVPKRR; IVFNVPKRRY; VFNVPKRRYW;
FNVPKRRYWL; NVPKRRYWLF; VPKRRYWLFK; PKRRYWLFKG; KRRYWLFKGP;
RRYWLFKGPI; RYWLFKGPID; YWLFKGPIDS; WLFKGPIDSG; LFKGPIDSGK;
FKGPIDSGKT; KGPIDSGKTT; GPIDSGKTTL; PIDSGKTTLA; IDSGKTTLAA;
DSGKTTLAAG; SGKTTLAAGL; GKTTLAAGLL; KTTLAAGLLD; TTLAAGLLDL;
TLAAGLLDLC; LAAGLLDLCG; AAGLLDLCGG; AGLLDLCGGK; GLLDLCGGKA;
LLDLCGGKAL; LDLCGGKALN; DLCGGKALNV; LCGGKALNVN; CGGKALNVNL;
GGKALNVNLP; GKALNVNLPM; KALNVNLPME; ALNVNLPMER; LNVNLPMERL;
NVNLPMERLT; VNLPMERLTF; NLPMERLTFE; LPMERLTFEL; PMERLTFELG;
MERLTFELGV; ERLTFELGVA; RLTFELGVAI; LTFELGVAID; TFELGVAIDQ;
FELGVAIDQY; ELGVAIDQYM; LGVAIDQYMV; GVAIDQYMVV; VAIDQYMVVF;
AIDQYMVVFE; IDQYMVVFED; DQYMVVFEDV; QYMVVFEDVK; YMVVFEDVKG;
MVVFEDVKGT; VVFEDVKGTG; VFEDVKGTGA; FEDVKGTGAE; EDVKGTGAES;
DVKGTGAESK; VKGTGAESKD; KGTGAESKDL; GTGAESKDLP; TGAESKDLPS;
GAESKDLPSG; AESKDLPSGH; ESKDLPSGHG; SKDLPSGHGI; KDLPSGHGIN;
DLPSGHGINN; LPSGHGINNL; PSGHGINNLD; SGHGINNLDS; GHGINNLDSL;
HGINNLDSLR; GINNLDSLRD; INNLDSLRDY; NNLDSLRDYL; NLDSLRDYLD;
LDSLRDYLDG; DSLRDYLDGS; SLRDYLDGSV; LRDYLDGSVK; RDYLDGSVKV;
DYLDGSVKVN; YLDGSVKVNL; LDGSVKVNLE; DGSVKVNLEK; GSVKVNLEKK;
SVKVNLEKKH; VKVNLEKKHL; KVNLEKKHLN; VNLEKKHLNK; NLEKKHLNKR;
LEKKHLNKRT; EKKHLNKRTQ; KKHLNKRTQI; KHLNKRTQIF; HLNKRTQIFP;
LNKRTQIFPP; NKRTQIFPPG; KRTQIFPPGL; RTQIFPPGLV; TQIFPPGLVT;
QIFPPGLVTM; IFPPGLVTMN; FPPGLVTMNE; PPGLVTMNEY; PGLVTMNEYP;
GLVTMNEYPV; LVTMNEYPVP; VTMNEYPVPK; TMNEYPVPKT; MNEYPVPKTL;
NEYPVPKTLQ; EYPVPKTLQA; YPVPKTLQAR; PVPKTLQARF; VPKTLQARFV;
PKTLQARFVR; KTLQARFVRQ; TLQARFVRQI; LQARFVRQID; QARFVRQIDF;
ARFVRQIDFR; RFVRQIDFRP; FVRQIDFRPK; VRQIDFRPKI; RQIDFRPKIY;
QIDFRPKIYL; IDFRPKIYLR; DFRPKIYLRK; FRPKIYLRKS; RPKIYLRKSL;
PKIYLRKSLQ; KIYLRKSLQN; IYLRKSLQNS; YLRKSLQNSE; LRKSLQNSEF;
RKSLQNSEFL; KSLQNSEFLL; SLQNSEFLLE; LQNSEFLLEK; QNSEFLLEKR;
NSEFLLEKRI; SEFLLEKRIL; EFLLEKRILQ; FLLEKRILQS; LLEKRILQSG;
LEKRILQSGM; EKRILQSGMT; KRILQSGMTL; RILQSGMTLL; ILQSGMTLLL;
LQSGMTLLLL; QSGMTLLLLL; SGMTLLLLLI; GMTLLLLLIW; MTLLLLLIWF;
TLLLLLIWFR; LLLLLIWFRP; LLLLIWFRPV; LLLIWFRPVA; LLIWFRPVAD;
LIWFRPVADF; IWFRPVADFA; WFRPVADFAT; FRPVADFATD; RPVADFATDI;
PVADFATDIQ; VADFATDIQS; ADFATDIQSR; DFATDIQSRI; FATDIQSRIV;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

ATDIQSRIVE; TDIQSRIVEW; DIQSRIVEWK; IQSRIVEWKE; QSRIVEWKER;
SRIVEWKERL; RIVEWKERLD; IVEWKERLDS; VEWKERLDSE; EWKERLDSEI;
WKERLDSEIS; KERLDSEISM; ERLDSEISMY; RLDSEISMYT; LDSEISMYTF;
DSEISMYTFS; SEISMYTFSR; EISMYTFSRM; ISMYTFSRMK; SMYTFSRMKY;
MYTFSRMKYN; YTFSRMKYNI; TFSRMKYNIC; FSRMKYNICM; SRMKYNICMG;
RMKYNICMGK; MKYNICMGKC; KYNICMGKCI; YNICMGKCIL; NICMGKCILD;
ICMGKCILDI; CMGKCILDIT; MGKCILDITR; GKCILDITRE; KCILDITREE;
CILDITREED; ILDITREEDS; LDITREEDSE; DITREEDSET; ITREEDSETE;
TREEDSETED; REEDSETEDS; EEDSETEDSG; EDSETEDSGH; DSETEDSGHG;
SETEDSGHGS; ETEDSGHGSS; TEDSGHGSST; EDSGHGSSTE; DSGHGSSTES;
SGHGSSTESQ; GHGSSTESQS; HGSSTESQSQ; GSSTESQSQC; SSTESQSQCS;
STESQSQCSS; TESQSQCSSQ; ESQSQCSSQV; SQSQCSSQVS; QSQCSSQVSD;
SQCSSQVSDT; QCSSQVSDTS; CSSQVSDTSA; SSQVSDTSAP; SQVSDTSAPA;
QVSDTSAPAE; VSDTSAPAED; SDTSAPAEDS; DTSAPAEDSQ; TSAPAEDSQR;
SAPAEDSQRS; APAEDSQRSD; PAEDSQRSDP; AEDSQRSDPH; EDSQRSDPHS;
DSQRSDPHSQ; SQRSDPHSQE; QRSDPHSQEL; RSDPHSQELH; SDPHSQELHL;
DPHSQELHLC; PHSQELHLCK; HSQELHLCKG; SQELHLCKGF; QELHLCKGFQ;
ELHLCKGFQC; LHLCKGFQCF; HLCKGFQCFK; LCKGFQCFKR; CKGFQCFKRP;
KGFQCFKRPK; GFQCFKRPKT; FQCFKRPKTP; QCFKRPKTPP; CFKRPKTPPP;
FKRPKTPPPK; HKLKSGLYKS; KLKSGLYKSS; LKSGLYKSSI; KSGLYKSSIY;
MYMYNKSTCL; YMYNKSTCLK; MYNKSTCLKH; YNKSTCLKHF; NKSTCLKHFG;
KSTCLKHFGL; STCLKHFGLQ; TCLKHFGLQL; CLKHFGLQLS; LKHFGLQLSL;
KHFGLQLSLF; HFGLQLSLFV; FGLQLSLFVN; GLQLSLFVNI; LQLSLFVNIS;
QLSLFVNISY; LSLFVNISYH; SLFVNISYHI; LFVNISYHIW; FVNISYHIWV;
VNISYHIWVP; NISYHIWVPW; ISYHIWVPWK; SYHIWVPWKS; YHIWVPWKSF;
HIWVPWKSFC; IWVPWKSFCA; WVPWKSFCAI; VPWKSFCAIK; PWKSFCAIKH;
WKSFCAIKHP; KSFCAIKHPN; SFCAIKHPNL; FCAIKHPNLF; CAIKHPNLFY;
AIKHPNLFYL; IKHPNLFYLG; KHPNLFYLGF; HPNLFYLGFH; PNLFYLGFHT;
NLFYLGFHTI; LFYLGFHTIH; FYLGFHTIHR; YLGFHTIHRL; LGFHTIHRLP;
GFHTIHRLPI; FHTIHRLPIH; HTIHRLPIHS; TIHRLPIHSL; IHRLPIHSLG;
HRLPIHSLGS; RLPIHSLGSP; LPIHSLGSPV; PIHSLGSPVY; IHSLGSPVYK;
HSLGSPVYKV; SLGSPVYKVT; QKGNWVRILY; KGNWVRILYR; GNWVRILYRS;
NWVRILYRSF; WVRILYRSFS; VRILYRSFSQ; RILYRSFSQA; ILYRSFSQAD;
LYRSFSQADL; YRSFSQADLK; RSFSQADLKI; SFSQADLKIS; FSQADLKISC;
SQADLKISCK; QADLKISCKA; ADLKISCKAS; DLKISCKASP; LKISCKASPL;
KISCKASPLL; ISCKASPLLC; SCKASPLLCS; CKASPLLCSR; KASPLLCSRA;
ASPLLCSRAV; SPLLCSRAVS; PLLCSRAVSK; LLCSRAVSKQ; LCSRAVSKQA;
CSRAVSKQAT; SRAVSKQATN; RAVSKQATNI; AVSKQATNIS; VSKQATNISS;
NIQAISFTKR; IQAISFTKRP; QAISFTKRPH; AISFTKRPHT; ISFTKRPHTL;
SFTKRPHTLF; FTKRPHTLFI; QHCGSCVGHM; HCGSCVGHMK; CGSCVGHMKY;
GSCVGHMKYW; SCVGHMKYWG; CVGHMKYWGN; VGHMKYWGNI; GHMKYWGNIF;
HMKYWGNIFP; MKYWGNIFPS; KYWGNIFPSC; YWGNIFPSCE; WGNIFPSCES;
GNIFPSCESP; NIFPSCESPK; IFPSCESPKI; FPSCESPKIP; PSCESPKIPS;
SCESPKIPSI; CESPKIPSIF; ESPKIPSIFI; SPKIPSIFIS; PKIPSIFIST;
KIPSIFISTG; IPSIFISTGI; PSIFISTGIR; SIFISTGIRY; IFISTGIRYP;
FISTGIRYPA; ISTGIRYPAL; STGIRYPALN; TGIRYPALNW; GIRYPALNWI;
IRYPALNWIS; RYPALNWISI; YPALNWISIV; PALNWISIVF; ALNWISIVFV;
LNWISIVFVQ; NWISIVFVQI; WISIVFVQIG; ISIVFVQIGL; SIVFVQIGLM;
IVFVQIGLMV; VFVQIGLMVS; FVQIGLMVSI; VQIGLMVSIH; QIGLMVSIHY;
IGLMVSIHYL; GLMVSIHYLG; LMVSIHYLGL; MVSIHYLGLG; VSIHYLGLGC;
SIHYLGLGCW; IHYLGLGCWV; HYLGLGCWVF; YLGLGCWVFR; LGLGCWVFRG;
GLGCWVFRGY; LGCWVFRGYS; GCWVFRGYST; CWVFRGYSTI; WVFRGYSTIR;
VFRGYSTIRV; FRGYSTIRVL; HSLHFQGFST; SLHFQGFSTY; LHFQGFSTYS;
HFQGFSTYSK; FQGFSTYSKE; QGFSTYSKEV; GFSTYSKEVE; FSTYSKEVEI;
STYSKEVEIT; TYSKEVEITA; YSKEVEITAL; SKEVEITALN; KEVEITALNR;
EVEITALNRF; VEITALNRFS; EITALNRFSS; ITALNRFSST; TALNRFSSTM;
ALNRFSSTML; LNRFSSTMLM; NRFSSTMLMH; RFSSTMLMHF; FSSTMLMHFL;
PCMKVKHASY; CMKVKHASYS; MKVKHASYSN; KVKHASYSNN; VKHASYSNNL;
KHASYSNNLC; HASYSNNLCL; ASYSNNLCLY; SYSNNLCLYS; YSNNLCLYSY;
SNNLCLYSYS; NNLCLYSYSL; NLCLYSYSLP; LCLYSYSLPH; CLYSYSLPHQ;
IGEGNSCCAV; GEGNSCCAVT; EGNSCCAVTG; GNSCCAVTGK; NSCCAVTGKH;
SCCAVTGKHF; CCAVTGKHFS; CAVTGKHFSL; AVTGKHFSLW; VTGKHFSLWA;
TGKHFSLWAI; GKHFSLWAIT; KHFSLWAITA; HFSLWAITAK; FSLWAITAKV;
SLWAITAKVI; LWAITAKVIF; WAITAKVIFS; AITAKVIFST; TKAPKVFIWI;
KAPKVFIWIP; APKVFIWIPH; PKVFIWIPHF; KVFIWIPHFW; VFIWIPHFWV;
EAFYLCNSIY; AFYLCNSIYP; FYLCNSIYPS; YLCNSIYPSF; LCNSIYPSFN;
CNSIYPSFNF; FWHLHGFLWL; WHLHGFLWLF; HLHGFLWLFG; LHGFLWLFGS;
HGFLWLFGSC; GFLWLFGSCP; FLWLFGSCPW; LWLFGSCPWT; WLFGSCPWTL;
LFGSCPWTLS; FGSCPWTLSF; GSCPWTLSFS; SCPWTLSFSF; CPWTLSFSFG;
PWTLSFSFGW; WTLSFSFGWG; TLSFSFGWGH; LSFSFGWGHL; SFSFGWGHLH;
FSFGWGHLHM; SFGWGHLHML; FGWGHLHMLQ; GWGHLHMLQE; WGHLHMLQEQ;
GHLHMLQEQV; HLHMLQEQVL; LHMLQEQVLQ; HMLQEQVLQS; MLQEQVLQSR;
LQEQVLQSRT; QEQVLQSRTG; EQVLQSRTGL; QVLQSRTGLE; VLQSRTGLEV;
LQSRTGLEVK; QSRTGLEVKA; SRTGLEVKAT; RTGLEVKATS; TGLEVKATSI;
GLEVKATSIE; LEVKATSIEE; EVKATSIEEQ; VKATSIEEQF; KATSIEEQFF;
ATSIEEQFFD; TLLNVHFVDF; LLNVHFVDFL; LNVHFVDFLS; NVHFVDFLSP;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

VHFVDFLSPF; HFVDFLSPFF; FVDFLSPFFV; LLLYCQHHLY; LLYCQHHLYY;
LYCQHHLYYK; YCQHHLYYKY; CQHHLYYKYG; QHHLYYKYGQ; HHLYYKYGQN;
HLYYKYGQNV; LYYKYGQNVH; YYKYGQNVHG; YKYGQNVHGY; KYGQNVHGYL;
YGQNVHGYLP; GQNVHGYLPF; QNVHGYLPFQ; NVHGYLPFQL; VHGYLPFQLL;
HGYLPFQLLV; GKDQNNIVEY; KDQNNIVEYN; DQNNIVEYNY; QNNIVEYNYK;
NNIVEYNYKS; NIVEYNYKSL; KIFLFFSAIP; IFLFFSAIPV; FLFFSAIPVR;
LFFSAIPVRL; QKYLHQETEY; KYLHQETEYH; YLHQETEYHS; LHQETEYHST;
HQETEYHSTH; QETEYHSTHL; ETEYHSTHLG; TIPKPCLIAD; IPKPCLIADR;
PKPCLIADRG; KPCLIADRGL; PCLIADRGLQ; CLIADRGLQW; LIADRGLQWK;
IADRGLQWKL; ADRGLQWKLC; DRGLQWKLCD; RGLQWKLCDP; GLQWKLCDPN;
LQWKLCDPNH; QWKLCDPNHQ; WKLCDPNHQR; KLCDPNHQRT; LCDPNHQRTY;
CDPNHQRTYT; DPNHQRTYTL; PNHQRTYTLL; NHQRTYTLLE; HQRTYTLLEL;
QRTYTLLELR; RTYTLLELRN; QFELKQQTQQ; PQEHQQLQHM; QEHQQLQHMF;
EHQQLQHMFE; HQQLQHMFEE; QQLQHMFEEL; QLQHMFEELG; LQHMFEELGL;
PLRYLLCPLQ; QQQPPQQQFQ; QQPPQQQFQP; PPQQQFQPL; PPQQQFQPLK;
PQQQFQPLKI; QQQFQPLKIL; QQFQPLKILW; QFQPLKILWQ; FQPLKILWQQ;
QPLKILWQQQ; PLKILWQQQP; LKILWQQQPQ; KILWQQQPQI; ILWQQQPQIH;
LWQQQPQIHW; WQQQPQIHWQ; QQQPQIHWQL; QQPQIHWQLG; QPQIHWQLGP;
PQIHWQLGPP; QIHWQLGPPK; IHWQLGPPKV; HWQLGPPKVL; WQLGPPKVLE;
QLGPPKVLEQ; LGPPKVLEQH; GPPKVLEQHP; TWKYKKKGIT; WKYKKKGITY;
KYKKKGITYL; YKKKGITYLG; KKKGITYLGV; KKGITYLGVF; KGITYLGVFY;
GITYLGVFYR; ITYLGVFYRV; TYLGVFYRVF; YLGVFYRVFY; LGVFYRVFYS;
GVFYRVFYSR; SSGTFVFPVY; SGTFVFPVYT; GTFVFPVYTV; TFVFPVYTVF;
FVFPVYTVFT; VFPVYTVFTS; FPVYTVFTST; PVYTVFTSTK; VYTVFTSTKF;
YTVFTSTKFQ; TVFTSTKFQQ; VFTSTKFQQK; FTSTKFQQKL; NKNKNPLSSF;
KNKNPLSSFF; NKNPLSSFFC; KNPLSSFFCS; NPLSSFFCSS; PLSSFFCSSP;
LSSFFCSSPG; SSFFCSSPGF; SFFCSSPGFT; FFCSSPGFTN; FCSSPGFTNF;
CSSPGFTNFH; QLAQNHGLCP; LAQNHGLCPV; LGTRPRFLGS; GTRPRFLGSQ;
TRPRFLGSQN; RPRFLGSQNM; PRFLGSQNMS; RFLGSQNMSV; FLGSQNMSVM;
LGSQNMSVMH; GSQNMSVMHF; SQNMSVMHFP; QNMSVMHFPS; AAPPCESCTF;
APPCESCTFL; PPCESCTFLP; PCESCTFLPE; CESCTFLPEV; ESCTFLPEVM;
SCTFLPEVMV; CTFLPEVMVW; TFLPEVMVWL; FLPEVMVWLH; LPEVMVWLHS;
PEVMVWLHSP; EVMVWLHSPV; VMWLHSPVS; MVWLHSPVSH; VWLHSPVSHA;
WLHSPVSHAL; LHSPVSHALS; HSPVSHALSF; SPVSHALSFL; PVSHALSFLR;
VSHALSFLRS; SHALSFLRSW; HALSFLRSWF; ALSFLRSWFG; LSFLRSWFGC;
SFLRSWFGCI; FLRSWFGCIP; LRSWFGCIPW; RSWFGCIPWV; SWFGCIPWVS;
WFGCIPWVSS; FGCIPWVSSS; GCIPWVSSSS; CIPWVSSSSL; IPWVSSSSLW;
PWVSSSSLWP; WVSSSSLWPF; VSSSSLWPFF; SSSSLWPFFL; YIRGRGRLCL;
IRGRGRLCLH; RGRGRLCLHP; GRGRLCLHPF; RGRLCLHPFS; GRLCLHPFSQ;
RLCLHPFSQV; LCLHPFSQVV; CLHPFSQVVR; LHPFSQVVRV; HPFSQVVRVW;
PFSQVVRVWR; FSQVVRVWRL; SQVVRVWRLF; QVVRVWRLFL; VVRVWRLFLR;
VRVWRLFLRP; RVWRLFLRPS; VWRLFLRPSK; WRLFLRPSKT; RLFLRPSKTI;
LFLRPSKTIW; FLRPSKTIWG; LRPSKTIWGN; RPSKTIWGNP; PSKTIWGNPY;
SKTIWGNPYS; KTIWGNPYSF; TIWGNPYSFA; IWGNPYSFAI; WGNPYSFAIF;
GNPYSFAIFA; NPYSFAIFAK 11 mers:

QGRIHGAHGPF; GRIHGAHGPFR; RIHGAHGPFRP; KSCLGKSSLNE; SCLGKSSLNEK;
CLGKSSLNEKS; LGKSSLNEKSL; GKSSLNEKSLF; KSSLNEKSLFK; SSLNEKSLFKE;
SLNEKSLFKEV; KNGAGCKGSSS; NGAGCKGSSSA; FSSLPRYPVLQ; SSLPRYPVLQG;
SLPRYPVLQGM; LPRYPVLQGMA; PRYPVLQGMAY; RYPVLQGMAYL; YPVLQGMAYLF;
PVLQGMAYLFQ; VLQGMAYLFQK; LQGMAYLFQKA; QGMAYLFQKAF; GMAYLFQKAFC;
MAYLFQKAFCA; AYLFQKAFCAL; YLFQKAFCALP; LFQKAFCALPL; FQKAFCALPLH;
QKAFCALPLHA; KAFCALPLHAM; AFCALPLHAMS; FCALPLHAMSA; KIFKKRALGLD;
IFKKRALGLDR; FKKRALGLDRL; KKRALGLDRLL; KRALGLDRLLL; RALGLDRLLLH;
LLHTVVWLRPN; RNSAMVGPNNW; NSAMVGPNNWR; SAMVGPNNWRN; AMVGPNNWRNS;
MVGPNNWRNSL; VGPNNWRNSLQ; GPNNWRNSLQR; PNNWRNSLQRS; NNWRNSLQRSK;
NWRNSLQRSKA; WRNSLQRSKAL; RNSLQRSKALR; VPTYGTEEWES; PTYGTEEWESW;
TYGTEEWESWW; YGTEEWESWWS; GTEEWESWWSS; TEEWESWWSSF; EEWESWWSSFN;
EWESWWSSFNE; WESWWSSFNEK; ESWWSSFNEKW; SWWSSFNEKWD; WWSSFNEKWDE;
WSSFNEKWDED; SSFNEKWDEDL; SFNEKWDEDLF; FNEKWDEDLFC; NEKWDEDLFCH;
EKWDEDLFCHE; KWDEDLFCHED; WDEDLFCHEDM; DEDLFCHEDMF; EDLFCHEDMFA;
DLFCHEDMFAS; LFCHEDMFASD; FCHEDMFASDE; CHEDMFASDEE; HEDMFASDEEA;
EDMFASDEEAT; DMFASDEEATA; MFASDEEATAD; FASDEEATADS; ASDEEATADSQ;
SDEEATADSQH; DEEATADSQHS; EEATADSQHST; EATADSQHSTP; ATADSQHSTPP;
TADSQHSTPPK; ADSQHSTPPKK; DSQHSTPPKKK; SQHSTPPKKKR; QHSTPPKKKRK;
HSTPPKKKRKV; STPPKKKRKVE; TPPKKKRKVED; PPKKKRKVEDP; PKKKRKVEDPK;
KKKRKVEDPKD; KKRKVEDPKDF; KRKVEDPKDFP; RKVEDPKDFPS; KVEDPKDFPSD;
VEDPKDFPSDL; EDPKDFPSDLH; DPKDFPSDLHQ; PKDFPSDLHQF; KDFPSDLHQFL;
DFPSDLHQFLS; FPSDLHQFLSQ; PSDLHQFLSQA; SDLHQFLSQAV; DLHQFLSQAVF;
LHQFLSQAVFS; HQFLSQAVFSN; QFLSQAVFSNR; FLSQAVFSNRT; LSQAVFSNRTL;
SQAVFSNRTLA; QAVFSNRTLAC; AVFSNRTLACF; VFSNRTLACFA; FSNRTLACFAV;
SNRTLACFAVY; NRTLACFAVYT; RTLACFAVYTT; TLACFAVYTTK; LACFAVYTTKE;
ACFAVYTTKEK; CFAVYTTKEKA; FAVYTTKEKAQ; AVYTTKEKAQI; VYTTKEKAQIL;
YTTKEKAQILY; TTKEKAQILYK; TKEKAQILYKK; KEKAQILYKKL; EKAQILYKKLM;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

KAQILYKKLME; AQILYKKLMEK; QILYKKLMEKY; ILYKKLMEKYS; LYKKLMEKYSV;
YKKLMEKYSVT; KKLMEKYSVTF; KLMEKYSVTFI; LMEKYSVTFIS; MEKYSVTFISR;
EKYSVTFISRH; KYSVTFISRHM; YSVTFISRHMC; SVTFISRHMCA; VTFISRHMCAG;
TFISRHMCAGH; FISRHMCAGHN; ISRHMCAGHNI; SRHMCAGHNII; RHMCAGHNIIF;
HMCAGHNIIFF; MCAGHNIIFFL; CAGHNIIFFLT; AGHNIIFFLTP; GHNIIFFLTPH;
HNIIFFLTPHR; NIIFFLTPHRH; IIFFLTPHRHR; IFFLTPHRHRV; FFLTPHRHRVS;
FLTPHRHRVSA; LTPHRHRVSAI; TPHRHRVSAIN; PHRHRVSAINN; HRHRVSAINNF;
RHRVSAINNFC; HRVSAINNFCQ; RVSAINNFCQK; VSAINNFCQKL; SAINNFCQKLC;
AINNFCQKLCT; INNFCQKLCTF; NNFCQKLCTFS; NFCQKLCTFSF; FCQKLCTFSFL;
CQKLCTFSFLI; QKLCTFSFLIC; KLCTFSFLICK; LCTFSFLICKG; CTFSFLICKGV;
TFSFLICKGVN; FSFLICKGVNK; SFLICKGVNKE; FLICKGVNKEY; LICKGVNKEYL;
ICKGVNKEYLL; CKGVNKEYLLY; KGVNKEYLLYS; GVNKEYLLYSA; VNKEYLLYSAL;
NKEYLLYSALT; KEYLLYSALTR; EYLLYSALTRD; YLLYSALTRDP; LLYSALTRDPY;
LYSALTRDPYH; YSALTRDPYHT; SALTRDPYHTI; ALTRDPYHTIE; LTRDPYHTIEE;
TRDPYHTIEES; RDPYHTIEESI; DPYHTIEESIQ; PYHTIEESIQG; YHTIEESIQGG;
HTIEESIQGGL; TIEESIQGGLK; IEESIQGGLKE; EESIQGGLKEH; ESIQGGLKEHD;
SIQGGLKEHDF; IQGGLKEHDFS; QGGLKEHDFSP; GGLKEHDFSPE; GLKEHDFSPEE;
LKEHDFSPEEP; KEHDFSPEEPE; EHDFSPEEPEE; HDFSPEEPEET; DFSPEEPEETK;
FSPEEPEETKQ; SPEEPEETKQV; PEEPEETKQVS; EEPEETKQVSW; EPEETKQVSWK;
PEETKQVSWKL; EETKQVSWKLI; ETKQVSWKLIT; TKQVSWKLITE; KQVSWKLITEY;
QVSWKLITEYA; VSWKLITEYAV; SWKLITEYAVE; WKLITEYAVET; KLITEYAVETK;
LITEYAVETKC; ITEYAVETKCE; TEYAVETKCED; EYAVETKCEDV; YAVETKCEDVF;
AVETKCEDVFL; VETKCEDVFLL; ETKCEDVFLLL; TKCEDVFLLLG; KCEDVFLLLGM;
CEDVFLLLGMY; EDVFLLLGMYL; DVFLLLGMYLE; VFLLLGMYLEF; FLLLGMYLEFQ;
LLLGMYLEFQY; LLGMYLEFQYN; LGMYLEFQYNV; GMYLEFQYNVE; MYLEFQYNVEE;
YLEFQYNVEEC; LEFQYNVEECK; EFQYNVEECKK; FQYNVEECKKC; QYNVEECKKCQ;
YNVEECKKCQK; NVEECKKCQKK; VEECKKCQKKD; EECKKCQKKDQ; ECKKCQKKDQP;
CKKCQKKDQPY; KKCQKKDQPYH; KCQKKDQPYHF; CQKKDQPYHFK; QKKDQPYHFKY;
KKDQPYHFKYH; KDQPYHFKYHE; DQPYHFKYHEK; QPYHFKYHEKH; PYHFKYHEKHF;
YHFKYHEKHFA; HFKYHEKHFAN; FKYHEKHFANA; KYHEKHFANAI; YHEKHFANAII;
HEKHFANAIIF; EKHFANAIIFA; KHFANAIIFAE; HFANAIIFAES; FANAIIFAESK;
ANAIIFAESKN; NAIIFAESKNQ; AIIFAESKNQK; IIFAESKNQKS; IFAESKNQKSI;
FAESKNQKSIC; AESKNQKSICQ; ESKNQKSICQQ; SKNQKSICQQA; KNQKSICQQAV;
NQKSICQQAVD; QKSICQQAVDT; KSICQQAVDTV; SICQQAVDTVL; ICQQAVDTVLA;
CQQAVDTVLAK; QQAVDTVLAKK; QAVDTVLAKKR; AVDTVLAKKRV; VDTVLAKKRVD;
DTVLAKKRVDT; TVLAKKRVDTL; VLAKKRVDTLH; LAKKRVDTLHM; AKKRVDTLHMT;
KKRVDTLHMTR; KRVDTLHMTRE; RVDTLHMTREE; VDTLHMTREEM; DTLHMTREEML;
TLHMTREEMLT; LHMTREEMLTE; HMTREEMLTER; MTREEMLTERF; TREEMLTERFN;
REEMLTERFNH; EEMLTERFNHI; EMLTERFNHIL; MLTERFNHILD; LTERFNHILDK;
TERFNHILDKM; ERFNHILDKMD; RFNHILDKMDL; FNHILDKMDLI; NHILDKMDLIF;
HILDKMDLIFG; ILDKMDLIFGA; LDKMDLIFGAH; DKMDLIFGAHG; KMDLIFGAHGN;
MDLIFGAHGNA; DLIFGAHGNAV; LIFGAHGNAVL; IFGAHGNAVLE; FGAHGNAVLEQ;
GAHGNAVLEQY; AHGNAVLEQYM; HGNAVLEQYMA; GNAVLEQYMAG; NAVLEQYMAGV;
AVLEQYMAGVA; VLEQYMAGVAW; LEQYMAGVAWL; EQYMAGVAWLH; QYMAGVAWLHC;
YMAGVAWLHCL; MAGVAWLHCLL; AGVAWLHCLLP; GVAWLHCLLPK; VAWLHCLLPKM;
AWLHCLLPKMD; WLHCLLPKMDS; LHCLLPKMDSV; HCLLPKMDSVI; CLLPKMDSVIF;
LLPKMDSVIFD; LPKMDSVIFDF; PKMDSVIFDFL; KMDSVIFDFLH; MDSVIFDFLHC;
DSVIFDFLHCI; SVIFDFLHCIV; VIFDFLHCIVF; IFDFLHCIVFN; FDFLHCIVFNV;
DFLHCIVFNVP; FLHCIVFNVPK; LHCIVFNVPKR; HCIVFNVPKRR; CIVFNVPKRRY;
IVFNVPKRRYW; VFNVPKRRYWL; FNVPKRRYWLF; NVPKRRYWLFK; VPKRRYWLFKG;
PKRRYWLFKGP; KRRYWLFKGPI; RRYWLFKGPID; RYWLFKGPIDS; YWLFKGPIDSG;
WLFKGPIDSGK; LFKGPIDSGKT; FKGPIDSGKTT; KGPIDSGKTTL; GPIDSGKTTLA;
PIDSGKTTLAA; IDSGKTTLAAG; DSGKTTLAAGL; SGKTTLAAGLL; GKTTLAAGLLD;
KTTLAAGLLDL; TTLAAGLLDLC; TLAAGLLDLCG; LAAGLLDLCGG; AAGLLDLCGGK;
AGLLDLCGGKA; GLLDLCGGKAL; LLDLCGGKALN; LDLCGGKALNV; DLCGGKALNVN;
LCGGKALNVNL; CGGKALNVNLP; GGKALNVNLPM; GKALNVNLPME; KALNVNLPMER;
ALNVNLPMERL; LNVNLPMERLT; NVNLPMERLTF; VNLPMERLTFE; NLPMERLTFEL;
LPMERLTFELG; PMERLTFELGV; MERLTFELGVA; ERLTFELGVAI; RLTFELGVAID;
LTFELGVAIDQ; TFELGVAIDQY; FELGVAIDQYM; ELGVAIDQYMV; LGVAIDQYMVV;
GVAIDQYMVVF; VAIDQYMVVFE; AIDQYMVVFED; IDQYMVVFEDV; DQYMVVFEDVK;
QYMVVFEDVKG; YMVVFEDVKGT; MVVFEDVKGTG; VVFEDVKGTGA; VFEDVKGTGAE;
FEDVKGTGAES; EDVKGTGAESK; DVKGTGAESKD; VKGTGAESKDL; KGTGAESKDLP;
GTGAESKDLPS; TGAESKDLPSG; GAESKDLPSGH; AESKDLPSGHI; ESKDLPSGHIG;
SKDLPSGHGIN; KDLPSGHGINN; DLPSGHGINNL; LPSGHGINNLD; PSGHGINNLDS;
SGHGINNLDSL; GHGINNLDSLR; HGINNLDSLRD; GINNLDSLRDY; INNLDSLRDYL;
NNLDSLRDYLD; NLDSLRDYLDG; LDSLRDYLDGS; DSLRDYLDGSV; SLRDYLDGSVK;
LRDYLDGSVKV; RDYLDGSVKVN; DYLDGSVKVNL; YLDGSVKVNLE; LDGSVKVNLEK;
DGSVKVNLEKK; GSVKVNLEKKH; SVKVNLEKKHL; VKVNLEKKHLN; KVNLEKKHLNK;
VNLEKKHLNKR; NLEKKHLNKRT; LEKKHLNKRTQ; EKKHLNKRTQI; KKHLNKRTQIF;
KHLNKRTQIFP; HLNKRTQIFPP; LNKRTQIFPPP; NKRTQIFPPGL; KRTQIFPPGLV;
RTQIFPPGLVT; TQIFPPGLVTM; QIFPPGLVTMN; IFPPGLVTMNE; FPPGLVTMNEY;
PPGLVTMNEYP; PGLVTMNEYPV; GLVTMNEYPVP; LVTMNEYPVPK; VTMNEYPVPKT;
TMNEYPVPKTL; MNEYPVPKTLQ; NEYPVPKTLQA; EYPVPKTLQAR; YPVPKTLQARF;
PVPKTLQARFV; VPKTLQARFVR; PKTLQARFVRQ; KTLQARFVRQI; TLQARFVRQID;
LQARFVRQIDF; QARFVRQIDFR; ARFVRQIDFRP; RFVRQIDFRPK; FVRQIDFRPKI;
VRQIDFRPKIY; RQIDFRPKIYL; QIDFRPKIYLR; IDFRPKIYLRK; DFRPKIYLRKS;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

FRPKIYLRKSL; RPKIYLRKSLQ; PKIYLRKSLQN; KIYLRKSLQNS; IYLRKSLQNSE;
YLRKSLQNSEF; LRKSLQNSEFL; RKSLQNSEFLL; KSLQNSEFLLE; SLQNSEFLLEK;
LQNSEFLLEKR; QNSEFLLEKRI; NSEFLLEKRIL; SEFLLEKRILQ; EFLLEKRILQS;
FLLEKRILQSG; LLEKRILQSGM; LEKRILQSGMT; EKRILQSGMTL; KRILQSGMTLL;
RILQSGMTLLL; ILQSGMTLLLL; LQSGMTLLLLL; QSGMTLLLLLI; SGMTLLLLLIW;
GMTLLLLLIWF; MTLLLLLIWFR; TLLLLLIWFRP; LLLLLIWFRPV; LLLLIWFRPVA;
LLLIWFRPVAD; LLIWFRPVADF; LIWFRPVADFA; IWFRPVADFAT; WFRPVADFATD;
FRPVADFATDI; RPVADFATDIQ; PVADFATDIQS; VADFATDIQSR; ADFATDIQSRI;
DFATDIQSRIV; FATDIQSRIVE; ATDIQSRIVEW; TDIQSRIVEWK; DIQSRIVEWKE;
IQSRIVEWKER; QSRIVEWKERL; SRIVEWKERLD; RIVEWKERLDS; IVEWKERLDSE;
VEWKERLDSEI; EWKERLDSEIS; WKERLDSEISM; KERLDSEISMY; ERLDSEISMYT;
RLDSEISMYTF; LDSEISMYTFS; DSEISMYTFSR; SEISMYTFSRM; EISMYTFSRMK;
ISMYTFSRMKY; SMYTFSRMKYN; MYTFSRMKYNI; YTFSRMKYNIC; TFSRMKYNICM;
FSRMKYNICMG; SRMKYNICMGK; RMKYNICMGKC; MKYNICMGKCI; KYNICMGKCIL;
YNICMGKCILD; NICMGKCILDI; ICMGKCILDIT; CMGKCILDITR; MGKCILDITRE;
GKCILDITREE; KCILDITREED; CILDITREEDS; ILDITREEDSE; LDITREEDSET;
DITREEDSETE; ITREEDSETED; TREEDSETEDS; REEDSETEDSG; EEDSETEDSGH;
EDSETEDSGHG; DSETEDSGHGS; SETEDSGHGSS; ETEDSGHGSST; TEDSGHGSSTE;
EDSGHGSSTES; DSGHGSSTESQ; SGHGSSTESQS; GHGSSTESQSQ; HGSSTESQSQC;
GSSTESQSQCS; SSTESQSQCSS; STESQSQCSSQ; TESQSQCSSQV; ESQSQCSSQVS;
SQSQCSSQVSD; QSQCSSQVSDT; SQCSSQVSDTS; QCSSQVSDTSA; CSSQVSDTSAP;
SSQVSDTSAPA; SQVSDTSAPAE; QVSDTSAPAED; VSDTSAPAEDS; SDTSAPAEDSQ;
DTSAPAEDSQR; TSAPAEDSQRS; SAPAEDSQRSD; APAEDSQRSDP; PAEDSQRSDPH;
AEDSQRSDPHS; EDSQRSDPHSQ; DSQRSDPHSQE; SQRSDPHSQEL; QRSDPHSQELH;
RSDPHSQELHL; SDPHSQELHLC; DPHSQELHLCK; PHSQELHLCKG; HSQELHLCKGF;
SQELHLCKGFQ; QELHLCKGFQC; ELHLCKGFQCF; LHLCKGFQCFK; HLCKGFQCFKR;
LCKGFQCFKRP; CKGFQCFKRPK; KGFQCFKRPKT; GFQCFKRPKTP; FQCFKRPKTPP;
QCFKRPKTPPP; CFKRPKTPPPK; HKLKSGLYKSS; KLKSGLYKSSI; LKSGLYKSSIY;
MYMYNKSTCLK; YMYNKSTCLKH; MYNKSTCLKHF; YNKSTCLKHFG; NKSTCLKHFGL;
KSTCLKHFGLQ; STCLKHFGLQL; TCLKHFGLQLS; CLKHFGLQLSL; LKHFGLQLSLF;
KHFGLQLSLFV; HFGLQLSLFVN; FGLQLSLFVNI; GLQLSLFVNIS; LQLSLFVNISY;
QLSLFVNISYH; LSLFVNISYHI; SLFVNISYHIW; LFVNISYHIWV; FVNISYHIWVP;
VNISYHIWVPW; NISYHIWVPWK; ISYHIWVPWKS; SYHIWVPWKSF; YHIWVPWKSFC;
HIWVPWKSFCA; IWVPWKSFCAI; WVPWKSFCAIK; VPWKSFCAIKH; PWKSFCAIKHP;
WKSFCAIKHPN; KSFCAIKHPNL; SFCAIKHPNLF; FCAIKHPNLFY; CAIKHPNLFYL;
AIKHPNLFYLG; IKHPNLFYLGF; KHPNLFYLGFH; HPNLFYLGFHT; PNLFYLGFHTI;
NLFYLGFHTIH; LFYLGFHTIHR; FYLGFHTIHRL; YLGFHTIHRLP; LGFHTIHRLPI;
GFHTIHRLPIH; FHTIHRLPIHS; HTIHRLPIHSL; TIHRLPIHSLG; IHRLPIHSLGS;
HRLPIHSLGSP; RLPIHSLGSPV; LPIHSLGSPVY; PIHSLGSPVYK; IHSLGSPVYKV;
HSLGSPVYKVT; QKGNWVRILYR; KGNWVRILYRS; GNWVRILYRSF; NWVRILYRSFS;
WVRILYRSFSQ; VRILYRSFSQA; RILYRSFSQAD; ILYRSFSQADL; LYRSFSQADLK;
YRSFSQADLKI; RSFSQADLKIS; SFSQADLKISC; FSQADLKISCK; SQADLKISCKA;
QADLKISCKAS; ADLKISCKASP; DLKISCKASPL; LKISCKASPLL; KISCKASPLLC;
ISCKASPLLCS; SCKASPLLCSR; CKASPLLCSRA; KASPLLCSRAV; ASPLLCSRAVS;
SPLLCSRAVSK; PLLCSRAVSKQ; LLCSRAVSKQA; LCSRAVSKQAT; CSRAVSKQATN;
SRAVSKQATNI; RAVSKQATNIS; AVSKQATNISS; NIQAISFTKRP; IQAISFTKRPH;
QAISFTKRPHT; AISFTKRPHTL; ISFTKRPHTLF; SFTKRPHTLFI; QHCGSCVGHMK;
HCGSCVGHMKY; CGSCVGHMKYW; GSCVGHMKYWG; SCVGHMKYWGN; CVGHMKYWGNI;
VGHMKYWGNIF; GHMKYWGNIFP; HMKYWGNIFPS; MKYWGNIFPSC; KYWGNIFPSCE;
YWGNIFPSCES; WGNIFPSCESP; GNIFPSCESPK; NIFPSCESPKI; IFPSCESPKIP;
FPSCESPKIPS; PSCESPKIPSI; SCESPKIPSIF; CESPKIPSIFI; ESPKIPSIFIS;
SPKIPSIFIST; PKIPSIFISTG; KIPSIFISTGI; IPSIFISTGIR; PSIFISTGIRY;
SIFISTGIRYP; IFISTGIRYPA; FISTGIRYPAL; ISTGIRYPALN; STGIRYPALNW;
TGIRYPALNWI; GIRYPALNWIS; IRYPALNWISI; RYPALNWISIV; YPALNWISIVF;
PALNWISIVFV; ALNWISIVFVQ; LNWISIVFVQI; NWISIVFVQIG; WISIVFVQIGL;
ISIVFVQIGLM; SIVFVQIGLMV; IVFVQIGLMVS; VFVQIGLMVSI; FVQIGLMVSIH;
VQIGLMVSIHY; QIGLMVSIHYL; IGLMVSIHYLG; GLMVSIHYLGL; LMVSIHYLGLG;
MVSIHYLGLGC; VSIHYLGLGCW; SIHYLGLGCWV; IHYLGLGCWVF; HYLGLGCWVFR;
YLGLGCWVFRG; LGLGCWVFRGY; GLGCWVFRGYS; LGCWVFRGYST; GCWVFRGYSTI;
CWVFRGYSTIR; WVFRGYSTIRV; VFRGYSTIRVL; HSLHFQGFSTY; SLHFQGFSTYS;
LHFQGFSTYSK; HFQGFSTYSKE; FQGFSTYSKEV; QGFSTYSKEVE; GFSTYSKEVEI;
FSTYSKEVEIT; STYSKEVEITA; TYSKEVEITAL; YSKEVEITALN; SKEVEITALNR;
KEVEITALNRF; EVEITALNRFS; VEITALNRFSS; EITALNRFSST; ITALNRFSSTM;
TALNRFSSTML; ALNRFSSTMLM; LNRFSSTMLMH; NRFSSTMLMHF; RFSSTMLMHFL;
PCMKVKHASYS; CMKVKHASYSN; MKVKHASYSNN; KVKHASYSNNL; VKHASYSNNLC;
KHASYSNNLCL; HASYSNNLCLY; ASYSNNLCLYS; SYSNNLCLYSY; YSNNLCLYSYS;
SNNLCLYSYSL; NNLCLYSYSLP; NLCLYSYSLPH; LCLYSYSLPHQ; IGEGNSCCAVT;
GEGNSCCAVTG; EGNSCCAVTGK; GNSCCAVTGKH; NSCCAVTGKHF; SCCAVTGKHFS;
CCAVTGKHFSL; CAVTGKHFSLW; AVTGKHFSLWA; VTGKHFSLWAI; TGKHFSLWAIT;
GKHFSLWAITA; KHFSLWAITAK; HFSLWAITAKV; FSLWAITAKVI; SLWAITAKVIF;
LWAITAKVIFS; WAITAKVIFST; TKAPKVFIWIP; KAPKVFIWIPH; APKVFIWIPHF;
PKVFIWIPHFW; KVFIWIPHFWV; EAFYLCNSIYP; AFYLCNSIYPS; FYLCNSIYPSF;
YLCNSIYPSFN; LCNSIYPSFNF; FWHLHGFLWLF; WHLHGFLWLFG; HLHGFLWLFGS;
LHGFLWLFGSC; HGFLWLFGSCP; GFLWLFGSCPW; FLWLFGSCPWT; LWLFGSCPWTL;
WLFGSCPWTLS; LFGSCPWTLSF; FGSCPWTLSFS; GSCPWTLSFSF; SCPWTLSFSFG;
CPWTLSFSFGW; PWTLSFSFGWG; WTLSFSFGWGH; TLSFSFGWGHL; LSFSFGWGHLH;

TABLE I-continued

Predicted MHC class 1 BK virus peptide sequences. Prediction of 8-, 9-, 10-, 11-mers from all 6 reading frames of the genome (access no #V01108) obtained using the program displayed in FIG. 2.

SFSFGWGHLHM; FSFGWGHLHML; SFGWGHLHMLQ; FGWGHLHMLQE; GWGHLHMLQEQ;
WGHLHMLQEQV; GHLHMLQEQVL; HLHMLQEQVLQ; LHMLQEQVLQS; HMLQEQVLQSR;
MLQEQVLQSRT; LQEQVLQSRTG; QEQVLQSRTGL; EQVLQSRTGLE; QVLQSRTGLEV;
VLQSRTGLEVK; LQSRTGLEVKA; QSRTGLEVKAT; SRTGLEVKATS; RTGLEVKATSI;
TGLEVKATSIE; GLEVKATSIEE; LEVKATSIEEQ; EVKATSIEEQF; VKATSIEEQFF;
KATSIEEQFFD; TLLNVHFVDFL; LLNVHFVDFLS; LNVHFVDFLSP; NVHFVDFLSPF;
VHFVDFLSPFF; HFVDFLSPFFV; LLLYCQHHLYY; LLYCQHHLYYK; LYCQHHLYYKY;
YCQHHLYYKYG; CQHHLYYKYGQ; QHHLYYKYGQN; HHLYYKYGQNV; HLYYKYGQNVH;
LYYKYGQNVHG; YYKYGQNVHGY; YKYGQNVHGYL; KYGQNVHGYLP; YGQNVHGYLPF;
GQNVHGYLPFQ; QNVHGYLPFQL; NVHGYLPFQLL; VHGYLPFQLLV; GKDQNNIVEYN;
KDQNNIVEYNY; DQNNIVEYNYK; QNNIVEYNYKS; NNIVEYNYKSL; KIFLFFSAIPV;
IFLFFSAIPVR; FLFFSAIPVRL; QKYLHQETEYH; KYLHQETEYHS; YLHQETEYHST;
LHQETEYHSTH; HQETEYHSTHL; QETEYHSTHLG; TIPKPCLIADR; IPKPCLIADRG;
PKPCLIADRGL; KPCLIADRGLQ; PCLIADRGLQW; CLIADRGLQWK; LIADRGLQWKL;
IADRGLQWKLC; ADRGLQWKLCD; DRGLQWKLCDP; RGLQWKLCDPN; GLQWKLCDPNH;
LQWKLCDPNHQ; QWKLCDPNHQR; WKLCDPNHQRT; KLCDPNHQRTY; LCDPNHQRTYT;
CDPNHQRTYTL; DPNHQRTYTLL; PNHQRTYTLLE; NHQRTYTLLEL; HQRTYTLLELR;
QRTYTLLELRN; PQEHQQLQHMF; QEHQQLQHMFE; EHQQLQHMFEE; HQQLQHMFEEL;
QQLQHMFEELG; QLQHMFEELGL; QQQPPQQQFQP; QQPPQQQFQPL; QPPQQQFQPLK;
PPQQQFQPLKI; PQQQFQPLKIL; QQQFQPLKILW; QQFQPLKILWQ; QFQPLKILWQQ;
FQPLKILWQQQ; QPLKILWQQQP; PLKILWQQQPQ; LKILWQQQPQI; KILWQQQPQIH;
ILWQQQPQIHW; LWQQQPQIHWQ; WQQQPQIHWQL; QQQPQIHWQLG; QQPQIHWQLGP;
QPQIHWQLGPP; PQIHWQLGPPK; QIHWQLGPPKV; IHWQLGPPKVL; HWQLGPPKVLE;
WQLGPPKVLEQ; QLGPPKVLEQH; LGPPKVLEQHP; TWKYKKKGITY; WKYKKKGITYL;
KYKKKGITYLG; YKKKGITYLGV; KKKGITYLGVF; KKGITYLGVFY; KGITYLGVFYR;
GITYLGVFYRV; ITYLGVFYRVF; TYLGVFYRVFY; YLGVFYRVFYS; LGVFYRVFYSR;
SSGTFVFPVYT; SGTFVFPVYTV; GTFVFPVYTVF; TFVFPVYTVFT; FVFPVYTVFTS;
VFPVYTVFTST; FPVYTVFTSTK; PVYTVFTSTKF; VYTVFTSTKFQ; YTVFTSTKFQQ;
TVFTSTKFQQK; VFTSTKFQQKL; NKNKNPLSSFF; KNKNPLSSFFC; NKNPLSSFFCS;
KNPLSSFFCSS; NPLSSFFCSSP; PLSSFFCSSPG; LSSFFCSSPGF; SSFFCSSPGFT;
SFFCSSPGFTN; FFCSSPGFTNF; FCSSPGFTNFH; QLAQNHGLCPV; LGTRPRFLGSQ;
GTRPRFLGSQN; TRPRFLGSQNM; RPRFLGSQNMS; PRFLGSQNMSV; RFLGSQNMSVM;
FLGSQNMSVMH; LGSQNMSVMHF; GSQNMSVMHFP; SQNMSVMHFPS; AAPPCESCTFL;
APPCESCTFLP; PPCESCTFLPE; PCESCTFLPEV; CESCTFLPEVM; ESCTFLPEVMV;
SCTFLPEVMVW; CTFLPEVMVWL; TFLPEVMVWLH; FLPEVMVWLHS; LPEVMVWLHSP;
PEVMVWLHSPV; EVMVWLHSPVS; VMVWLHSPVSH; MVWLHSPVSHA; VWLHSPVSHAL;
WLHSPVSHALS; LHSPVSHALSF; HSPVSHALSFL; SPVSHALSFLR; PVSHALSFLRS;
VSHALSFLRSW; SHALSFLRSWF; HALSFLRSWFG; ALSFLRSWFGC; LSFLRSWFGCI;
SFLRSWFGCIP; FLRSWFGCIPW; LRSWFGCIPWV; RSWFGCIPWVS; SWFGCIPWVSS;
WFGCIPWVSSS; FGCIPWVSSSS; GCIPWVSSSSL; CIPWVSSSSLW; IPWVSSSSLWP;
PWVSSSSLWPF; WVSSSSLWPFF; VSSSSLWPFFL; YIRGRGRLCLH; IRGRGRLCLHP;
RGRGRLCLHPF; GRGRLCLHPFS; RGRLCLHPFSQ; GRLCLHPFSQV; RLCLHPFSQVV;
LCLHPFSQVVR; CLHPFSQVVRV; LHPFSQVVRVW; HPFSQVVRVWR; PFSQVVRVWRL;
FSQVVRVWRLF; SQVVRVWRLFL; QVVRVWRLFLR; VVRVWRLFLRP; VRVWRLFLRPS;
RVWRLFLRPSK; VWRLFLRPSKT; WRLFLRPSKTI; RLFLRPSKTIW; LFLRPSKTIWG;
FLRPSKTIWGN; LRPSKTIWGNP; RPSKTIWGNPY; PSKTIWGNPYS; SKTIWGNPYSF;
KTIWGNPYSFA; TIWGNPYSFAI; IWGNPYSFAIF; WGNPYSFAIFA; GNPYSFAIFAK

SEQ ID NOS.: 7-24956

Preferred BK virus fragments of VP2-3 capable of interacting with one or more MHC class 1 molecules are listed in Table J.

TABLE J

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| | | | 8-mers | | | |
| 107 | KVSTVGLY | 0.435 | 454 | WB | VP2-3 | A0101 |
| 140 | FVNNIQYL | 0.674 | 33 | SB | VP2-3 | A0201 |
| 80 | FAALIQTV | 0.581 | 93 | WB | VP2-3 | A0201 |
| 195 | FLEETTWT | 0.576 | 98 | WB | VP2-3 | A0201 |
| 5 | ALLGDLVA | 0.564 | 111 | WB | VP2-3 | A0201 |
| 43 | SLATVEGI | 0.559 | 118 | WB | VP2-3 | A0201 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 293 | MLPLLLGL | 0.552 | 127 | WB | VP2-3 | A0201 |
| 40 | QIASLATV | 0.533 | 155 | WB | VP2-3 | A0201 |
| 61 | GLTPQTYA | 0.533 | 155 | WB | VP2-3 | A0201 |
| 296 | LLLGLYGT | 0.529 | 163 | WB | VP2-3 | A0201 |
| 76 | AIAGFAAL | 0.469 | 311 | WB | VP2-3 | A0201 |
| 89 | GISSLAQV | 0.456 | 358 | WB | VP2-3 | A0201 |
| 297 | LLGLYGTV | 0.439 | 433 | WB | VP2-3 | A0201 |
| 132 | ILFPGVNT | 0.434 | 457 | WB | VP2-3 | A0201 |
| 140 | FVNNIQYL | 0.869 | 4 | SB | VP2-3 | A0202 |
| 293 | MLPLLLGL | 0.799 | 8 | SB | VP2-3 | A0202 |
| 80 | FAALIQTV | 0.745 | 15 | SB | VP2-3 | A0202 |
| 43 | SLATVEGI | 0.730 | 18 | SB | VP2-3 | A0202 |
| 61 | GLTPQTYA | 0.709 | 23 | SB | VP2-3 | A0202 |
| 195 | FLEETTWT | 0.686 | 29 | SB | VP2-3 | A0202 |
| 76 | AIAGFAAL | 0.667 | 36 | SB | VP2-3 | A0202 |
| 89 | GISSLAQV | 0.640 | 49 | SB | VP2-3 | A0202 |
| 3 | ALALLGDL | 0.630 | 54 | WB | VP2-3 | A0202 |
| 297 | LLGLYGTV | 0.607 | 69 | WB | VP2-3 | A0202 |
| 40 | QIASLATV | 0.606 | 71 | WB | VP2-3 | A0202 |
| 0 | MGAALALL | 0.581 | 92 | WB | VP2-3 | A0202 |
| 112 | GLYQQSGM | 0.575 | 99 | WB | VP2-3 | A0202 |
| 287 | RTAPQWML | 0.543 | 139 | WB | VP2-3 | A0202 |
| 6 | LLGDLVAS | 0.539 | 146 | WB | VP2-3 | A0202 |
| 157 | FATISQAL | 0.530 | 162 | WB | VP2-3 | A0202 |
| 10 | LVASVSEA | 0.524 | 173 | WB | VP2-3 | A0202 |
| 296 | LLLGLYGT | 0.477 | 287 | WB | VP2-3 | A0202 |
| 155 | SLFATISQ | 0.473 | 298 | WB | VP2-3 | A0202 |
| 86 | TVTGISSL | 0.461 | 341 | WB | VP2-3 | A0202 |
| 62 | LTPQTYAV | 0.458 | 352 | WB | VP2-3 | A0202 |
| 114 | YQQSGMAL | 0.445 | 405 | WB | VP2-3 | A0202 |
| 13 | SVSEAAAA | 0.433 | 461 | WB | VP2-3 | A0202 |
| 18 | AAATGFSV | 0.427 | 490 | WB | VP2-3 | A0202 |
| 132 | ILFPGVNT | 0.427 | 491 | WB | VP2-3 | A0202 |
| 43 | SLATVEGI | 0.798 | 8 | SB | VP2-3 | A0203 |
| 140 | FVNNIQYL | 0.775 | 11 | SB | VP2-3 | A0203 |
| 297 | LLGLYGTV | 0.773 | 11 | SB | VP2-3 | A0203 |
| 40 | QIASLATV | 0.748 | 15 | SB | VP2-3 | A0203 |
| 80 | FAALIQTV | 0.730 | 18 | SB | VP2-3 | A0203 |
| 61 | GLTPQTYA | 0.706 | 24 | SB | VP2-3 | A0203 |
| 89 | GISSLAQV | 0.701 | 25 | SB | VP2-3 | A0203 |
| 76 | AIAGFAAL | 0.701 | 25 | SB | VP2-3 | A0203 |
| 83 | LIQTVTGI | 0.666 | 37 | SB | VP2-3 | A0203 |
| 18 | AAATGFSV | 0.649 | 44 | SB | VP2-3 | A0203 |
| 3 | ALALLGDL | 0.643 | 47 | SB | VP2-3 | A0203 |
| 112 | GLYQQSGM | 0.624 | 58 | WB | VP2-3 | A0203 |
| 10 | LVASVSEA | 0.604 | 72 | WB | VP2-3 | A0203 |
| 114 | YQQSGMAL | 0.558 | 119 | WB | VP2-3 | A0203 |
| 296 | LLLGLYGT | 0.552 | 127 | WB | VP2-3 | A0203 |
| 195 | FLEETTWT | 0.540 | 144 | WB | VP2-3 | A0203 |
| 132 | ILFPGVNT | 0.534 | 154 | WB | VP2-3 | A0203 |
| 62 | LTPQTYAV | 0.523 | 175 | WB | VP2-3 | A0203 |
| 69 | VIAGAPGA | 0.516 | 187 | WB | VP2-3 | A0203 |
| 161 | SQALWHVI | 0.493 | 241 | WB | VP2-3 | A0203 |
| 86 | TVTGISSL | 0.464 | 330 | WB | VP2-3 | A0203 |
| 5 | ALLGDLVA | 0.455 | 364 | WB | VP2-3 | A0203 |
| 13 | SVSEAAAA | 0.454 | 368 | WB | VP2-3 | A0203 |
| 268 | SVHSGEFI | 0.440 | 426 | WB | VP2-3 | A0203 |
| 167 | VIRDDIPA | 0.435 | 450 | WB | VP2-3 | A0203 |
| 297 | LLGLYGTV | 0.613 | 66 | WB | VP2-3 | A0204 |
| 43 | SLATVEGI | 0.584 | 90 | WB | VP2-3 | A0204 |
| 140 | FVNNIQYL | 0.522 | 175 | WB | VP2-3 | A0204 |
| 80 | FAALIQTV | 0.522 | 176 | WB | VP2-3 | A0204 |
| 287 | RTAPQWML | 0.509 | 203 | WB | VP2-3 | A0204 |
| 114 | YQQSGMAL | 0.793 | 9 | SB | VP2-3 | A0206 |
| 80 | FAALIQTV | 0.748 | 15 | SB | VP2-3 | A0206 |
| 18 | AAATGFSV | 0.743 | 16 | SB | VP2-3 | A0206 |
| 140 | FVNNIQYL | 0.719 | 20 | SB | VP2-3 | A0206 |

TABLE J-continued

Prediction of BK virus VP2-3 protein specific MHC
class1, 8-, 9-, 10-, 11-mer peptide binders for
42 MHC class 1 alleles (see FIG. 11) using the
www.cbs.dtu.dk/services/NetMHC/ database.
The MHC class 1 molecules for which no binders were
found are not listed.

| pos | peptide | logscore | affinity(nM) | Bind Level | Protein Name | Allele |
|---|---|---|---|---|---|---|
| 39 | VQIASLAT | 0.713 | 22 | SB | VP2-3 | A0206 |
| 161 | SQALWHVI | 0.700 | 25 | SB | VP2-3 | A0206 |
| 40 | QIASLATV | 0.665 | 37 | SB | VP2-3 | A0206 |
| 75 | GAIAGFAA | 0.665 | 37 | SB | VP2-3 | A0206 |
| 76 | AIAGFAAL | 0.657 | 40 | SB | VP2-3 | A0206 |
| 293 | MLPLLLGL | 0.644 | 47 | SB | VP2-3 | A0206 |
| 94 | AQVGYRFF | 0.637 | 50 | WB | VP2-3 | A0206 |
| 62 | LTPQTYAV | 0.598 | 77 | WB | VP2-3 | A0206 |
| 214 | IQDYYSNL | 0.578 | 96 | WB | VP2-3 | A0206 |
| 201 | WTIVNAPI | 0.563 | 112 | WB | VP2-3 | A0206 |
| 195 | FLEETTWT | 0.551 | 129 | WB | VP2-3 | A0206 |
| 296 | LLGLYGT | 0.550 | 129 | WB | VP2-3 | A0206 |
| 89 | GISSLAQV | 0.537 | 149 | WB | VP2-3 | A0206 |
| 5 | ALLGDLVA | 0.535 | 153 | WB | VP2-3 | A0206 |
| 157 | FATISQAL | 0.507 | 207 | WB | VP2-3 | A0206 |
| 13 | SVSEAAAA | 0.502 | 217 | WB | VP2-3 | A0206 |
| 287 | RTAPQWML | 0.501 | 221 | WB | VP2-3 | A0206 |
| 61 | GLTPQTYA | 0.499 | 226 | WB | VP2-3 | A0206 |
| 23 | FSVAEIAA | 0.479 | 279 | WB | VP2-3 | A0206 |
| 297 | LLGLYGTV | 0.477 | 286 | WB | VP2-3 | A0206 |
| 45 | ATVEGITT | 0.475 | 292 | WB | VP2-3 | A0206 |
| 4 | LALLGDLV | 0.460 | 346 | WB | VP2-3 | A0206 |
| 101 | FSDWDHKV | 0.454 | 366 | WB | VP2-3 | A0206 |
| 10 | LVASVSEA | 0.443 | 412 | WB | VP2-3 | A0206 |
| 132 | ILFPGVNT | 0.441 | 425 | WB | VP2-3 | A0206 |
| 247 | SIDNADSI | 0.437 | 440 | WB | VP2-3 | A0206 |
| 303 | TVTPALEA | 0.437 | 443 | WB | VP2-3 | A0206 |
| 43 | SLATVEGI | 0.433 | 463 | WB | VP2-3 | A0206 |
| 35 | AAIEVQIA | 0.427 | 493 | WB | VP2-3 | A0206 |
| 5 | ALLGDLVA | 0.884 | 3 | SB | VP2-3 | A0211 |
| 293 | MLPLLLGL | 0.861 | 4 | SB | VP2-3 | A0211 |
| 61 | GLTPQTYA | 0.856 | 4 | SB | VP2-3 | A0211 |
| 297 | LLGLYGTV | 0.852 | 4 | SB | VP2-3 | A0211 |
| 146 | YLDPRHWG | 0.842 | 5 | SB | VP2-3 | A0211 |
| 89 | GISSLAQV | 0.841 | 5 | SB | VP2-3 | A0211 |
| 155 | SLFATISQ | 0.823 | 6 | SB | VP2-3 | A0211 |
| 76 | AIAGFAAL | 0.819 | 7 | SB | VP2-3 | A0211 |
| 43 | SLATVEGI | 0.812 | 7 | SB | VP2-3 | A0211 |
| 40 | QIASLATV | 0.801 | 8 | SB | VP2-3 | A0211 |
| 296 | LLGLYGT | 0.762 | 13 | SB | VP2-3 | A0211 |
| 140 | FVNNIQYL | 0.727 | 19 | SB | VP2-3 | A0211 |
| 132 | ILFPGVNT | 0.718 | 21 | SB | VP2-3 | A0211 |
| 80 | FAALIQTV | 0.692 | 27 | SB | VP2-3 | A0211 |
| 195 | FLEETTWT | 0.687 | 29 | SB | VP2-3 | A0211 |
| 86 | TVTGISSL | 0.686 | 29 | SB | VP2-3 | A0211 |
| 101 | FSDWDHKV | 0.685 | 30 | SB | VP2-3 | A0211 |
| 62 | LTPQTYAV | 0.680 | 32 | SB | VP2-3 | A0211 |
| 18 | AAATGFSV | 0.673 | 34 | SB | VP2-3 | A0211 |
| 112 | GLYQQSGM | 0.663 | 38 | SB | VP2-3 | A0211 |
| 287 | RTAPQWML | 0.657 | 40 | SB | VP2-3 | A0211 |
| 247 | SIDNADSI | 0.657 | 40 | SB | VP2-3 | A0211 |
| 250 | NADSIEEV | 0.652 | 43 | SB | VP2-3 | A0211 |
| 262 | DLRNKESV | 0.628 | 56 | WB | VP2-3 | A0211 |
| 299 | GLYGTVTP | 0.595 | 79 | WB | VP2-3 | A0211 |
| 6 | LLGDLVAS | 0.595 | 79 | WB | VP2-3 | A0211 |
| 292 | WMLPLLLG | 0.555 | 123 | WB | VP2-3 | A0211 |
| 268 | SVHSGEFI | 0.540 | 145 | WB | VP2-3 | A0211 |
| 303 | TVTPALEA | 0.519 | 182 | WB | VP2-3 | A0211 |
| 3 | ALALLGDL | 0.514 | 191 | WB | VP2-3 | A0211 |
| 32 | EAAAAIEV | 0.514 | 192 | WB | VP2-3 | A0211 |
| 191 | SLARFLEE | 0.502 | 217 | WB | VP2-3 | A0211 |
| 13 | SVSEAAAA | 0.493 | 240 | WB | VP2-3 | A0211 |
| 69 | VIAGAPGA | 0.467 | 317 | WB | VP2-3 | A0211 |
| 4 | LALLGDLV | 0.450 | 382 | WB | VP2-3 | A0211 |
| 167 | VIRDDIPA | 0.450 | 384 | WB | VP2-3 | A0211 |
| 293 | MLPLLLGL | 0.799 | 8 | SB | VP2-3 | A0212 |
| 297 | LLGLYGTV | 0.778 | 11 | SB | VP2-3 | A0212 |
| 5 | ALLGDLVA | 0.772 | 11 | SB | VP2-3 | A0212 |
| 76 | AIAGFAAL | 0.741 | 16 | SB | VP2-3 | A0212 |

TABLE J-continued

Prediction of BK virus VP2-3 protein specific MHC
class1, 8-, 9-, 10-, 11-mer peptide binders for
42 MHC class 1 alleles (see FIG. 11) using the
www.cbs.dtu.dk/services/NetMHC/ database.
The MHC class 1 molecules for which no binders were
found are not listed.

| pos | peptide | logscore | affinity(nM) | Bind Level | Protein Name | Allele |
|---|---|---|---|---|---|---|
| 146 | YLDPRHWG | 0.731 | 18 | SB | VP2-3 | A0212 |
| 43 | SLATVEGI | 0.730 | 18 | SB | VP2-3 | A0212 |
| 296 | LLLGLYGT | 0.725 | 19 | SB | VP2-3 | A0212 |
| 140 | FVNNIQYL | 0.685 | 30 | SB | VP2-3 | A0212 |
| 40 | QIASLATV | 0.664 | 37 | SB | VP2-3 | A0212 |
| 112 | GLYQQSGM | 0.661 | 39 | SB | VP2-3 | A0212 |
| 132 | ILFPGVNT | 0.661 | 39 | SB | VP2-3 | A0212 |
| 80 | FAALIQTV | 0.654 | 42 | SB | VP2-3 | A0212 |
| 155 | SLFATISQ | 0.649 | 44 | SB | VP2-3 | A0212 |
| 62 | LTPQTYAV | 0.635 | 51 | WB | VP2-3 | A0212 |
| 61 | GLTPQTYA | 0.635 | 51 | WB | VP2-3 | A0212 |
| 195 | FLEETTWT | 0.616 | 63 | WB | VP2-3 | A0212 |
| 89 | GISSLAQV | 0.615 | 64 | WB | VP2-3 | A0212 |
| 262 | DLRNKESV | 0.607 | 70 | WB | VP2-3 | A0212 |
| 6 | LLGDLVAS | 0.562 | 114 | WB | VP2-3 | A0212 |
| 114 | YQQSGMAL | 0.562 | 114 | WB | VP2-3 | A0212 |
| 69 | VIAGAPGA | 0.521 | 178 | WB | VP2-3 | A0212 |
| 101 | FSDWDHKV | 0.505 | 211 | WB | VP2-3 | A0212 |
| 18 | AAATGFSV | 0.490 | 249 | WB | VP2-3 | A0212 |
| 287 | RTAPQWML | 0.482 | 270 | WB | VP2-3 | A0212 |
| 299 | GLYGTVTP | 0.463 | 335 | WB | VP2-3 | A0212 |
| 3 | ALALLGDL | 0.450 | 383 | WB | VP2-3 | A0212 |
| 213 | YIQDYYSN | 0.440 | 430 | WB | VP2-3 | A0212 |
| 297 | LLGLYGTV | 0.869 | 4 | SB | VP2-3 | A0216 |
| 61 | GLTPQTYA | 0.801 | 8 | SB | VP2-3 | A0216 |
| 89 | GISSLAQV | 0.801 | 8 | SB | VP2-3 | A0216 |
| 40 | QIASLATV | 0.770 | 11 | SB | VP2-3 | A0216 |
| 262 | DLRNKESV | 0.743 | 16 | SB | VP2-3 | A0216 |
| 76 | AIAGFAAL | 0.723 | 20 | SB | VP2-3 | A0216 |
| 155 | SLFATISQ | 0.689 | 28 | SB | VP2-3 | A0216 |
| 140 | FVNNIQYL | 0.684 | 30 | SB | VP2-3 | A0216 |
| 293 | MLPLLLGL | 0.670 | 35 | SB | VP2-3 | A0216 |
| 5 | ALLGDLVA | 0.656 | 41 | SB | VP2-3 | A0216 |
| 80 | FAALIQTV | 0.647 | 45 | SB | VP2-3 | A0216 |
| 195 | FLEETTWT | 0.641 | 48 | SB | VP2-3 | A0216 |
| 43 | SLATVEGI | 0.614 | 64 | WB | VP2-3 | A0216 |
| 18 | AAATGFSV | 0.614 | 65 | WB | VP2-3 | A0216 |
| 86 | TVTGISSL | 0.612 | 66 | WB | VP2-3 | A0216 |
| 112 | GLYQQSGM | 0.597 | 78 | WB | VP2-3 | A0216 |
| 132 | ILFPGVNT | 0.596 | 79 | WB | VP2-3 | A0216 |
| 62 | LTPQTYAV | 0.580 | 93 | WB | VP2-3 | A0216 |
| 250 | NADSIEEV | 0.545 | 136 | WB | VP2-3 | A0216 |
| 296 | LLLGLYGT | 0.536 | 152 | WB | VP2-3 | A0216 |
| 146 | YLDPRHWG | 0.527 | 167 | WB | VP2-3 | A0216 |
| 32 | EAAAAIEV | 0.507 | 206 | WB | VP2-3 | A0216 |
| 247 | SIDNADSI | 0.502 | 219 | WB | VP2-3 | A0216 |
| 268 | SVHSGEFI | 0.451 | 380 | WB | VP2-3 | A0216 |
| 250 | NADSIEEV | 0.620 | 61 | WB | VP2-3 | A0219 |
| 40 | QIASLATV | 0.614 | 65 | WB | VP2-3 | A0219 |
| 18 | AAATGFSV | 0.612 | 66 | WB | VP2-3 | A0219 |
| 293 | MLPLLLGL | 0.609 | 68 | WB | VP2-3 | A0219 |
| 43 | SLATVEGI | 0.596 | 78 | WB | VP2-3 | A0219 |
| 146 | YLDPRHWG | 0.579 | 95 | WB | VP2-3 | A0219 |
| 80 | FAALIQTV | 0.579 | 95 | WB | VP2-3 | A0219 |
| 296 | LLLGLYGT | 0.567 | 108 | WB | VP2-3 | A0219 |
| 140 | FVNNIQYL | 0.565 | 110 | WB | VP2-3 | A0219 |
| 89 | GISSLAQV | 0.562 | 114 | WB | VP2-3 | A0219 |
| 297 | LLGLYGTV | 0.543 | 139 | WB | VP2-3 | A0219 |
| 61 | GLTPQTYA | 0.537 | 150 | WB | VP2-3 | A0219 |
| 76 | AIAGFAAL | 0.526 | 168 | WB | VP2-3 | A0219 |
| 5 | ALLGDLVA | 0.523 | 174 | WB | VP2-3 | A0219 |
| 62 | LTPQTYAV | 0.508 | 205 | WB | VP2-3 | A0219 |
| 86 | TVTGISSL | 0.502 | 220 | WB | VP2-3 | A0219 |
| 195 | FLEETTWT | 0.500 | 223 | WB | VP2-3 | A0219 |
| 32 | EAAAAIEV | 0.455 | 364 | WB | VP2-3 | A0219 |
| 132 | ILFPGVNT | 0.452 | 374 | WB | VP2-3 | A0219 |
| 114 | YQQSGMAL | 0.451 | 378 | WB | VP2-3 | A0219 |
| 262 | DLRNKESV | 0.442 | 418 | WB | VP2-3 | A0219 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 107 | KVSTVGLY | 0.604 | 72 | WB | VP2-3 | A0301 |
| 322 | VSRGSSQK | 0.592 | 83 | WB | VP2-3 | A0301 |
| 335 | ASAKTTNK | 0.580 | 93 | WB | VP2-3 | A0301 |
| 239 | HVNFGHTY | 0.472 | 302 | WB | VP2-3 | A0301 |
| 335 | ASAKTTNK | 0.732 | 18 | SB | VP2-3 | A1101 |
| 270 | HSGEFIEK | 0.611 | 67 | WB | VP2-3 | A1101 |
| 257 | VTQRMDLR | 0.584 | 90 | WB | VP2-3 | A1101 |
| 107 | KVSTVGLY | 0.575 | 98 | WB | VP2-3 | A1101 |
| 339 | TTNKRRSR | 0.528 | 165 | WB | VP2-3 | A1101 |
| 92 | SLAQVGYR | 0.509 | 202 | WB | VP2-3 | A1101 |
| 175 | ITSQELQR | 0.479 | 280 | WB | VP2-3 | A1101 |
| 91 | SSLAQVGY | 0.475 | 293 | WB | VP2-3 | A1101 |
| 322 | VSRGSSQK | 0.474 | 297 | WB | VP2-3 | A1101 |
| 176 | TSQELQRR | 0.469 | 312 | WB | VP2-3 | A1101 |
| 97 | GYRFFSDW | 0.582 | 91 | WB | VP2-3 | A2301 |
| 145 | QYLDPRHW | 0.515 | 190 | WB | VP2-3 | A2301 |
| 133 | LFPGVNTF | 0.508 | 205 | WB | VP2-3 | A2301 |
| 100 | FFSDWDHK | 0.478 | 283 | WB | VP2-3 | A2301 |
| 217 | YYSNLSPI | 0.443 | 412 | WB | VP2-3 | A2301 |
| 194 | RFLEETTW | 0.435 | 453 | WB | VP2-3 | A2301 |
| 217 | YYSNLSPI | 0.742 | 16 | SB | VP2-3 | A2402 |
| 133 | LFPGVNTF | 0.635 | 51 | WB | VP2-3 | A2402 |
| 291 | QWMLPLLL | 0.529 | 163 | WB | VP2-3 | A2402 |
| 97 | GYRFFSDW | 0.659 | 40 | SB | VP2-3 | A2403 |
| 194 | RFLEETTW | 0.644 | 47 | SB | VP2-3 | A2403 |
| 217 | YYSNLSPI | 0.636 | 51 | WB | VP2-3 | A2403 |
| 133 | LFPGVNTF | 0.624 | 58 | WB | VP2-3 | A2403 |
| 145 | QYLDPRHW | 0.611 | 67 | WB | VP2-3 | A2403 |
| 304 | VTPALEAY | 0.815 | 7 | SB | VP2-3 | A2602 |
| 256 | EVTQRMDL | 0.685 | 30 | SB | VP2-3 | A2602 |
| 122 | ELFNPDEY | 0.657 | 40 | SB | VP2-3 | A2602 |
| 287 | RTAPQWML | 0.612 | 66 | WB | VP2-3 | A2602 |
| 239 | HVNFGHTY | 0.607 | 69 | WB | VP2-3 | A2602 |
| 107 | KVSTVGLY | 0.569 | 105 | WB | VP2-3 | A2602 |
| 76 | AIAGFAAL | 0.544 | 138 | WB | VP2-3 | A2602 |
| 267 | ESVHSGEF | 0.496 | 232 | WB | VP2-3 | A2602 |
| 158 | ATISQALW | 0.474 | 296 | WB | VP2-3 | A2602 |
| 140 | FVNNIQYL | 0.465 | 324 | WB | VP2-3 | A2602 |
| 210 | FYNYIQDY | 0.674 | 34 | SB | VP2-3 | A2902 |
| 239 | HVNFGHTY | 0.663 | 38 | SB | VP2-3 | A2902 |
| 123 | LFNPDEYY | 0.588 | 86 | WB | VP2-3 | A2902 |
| 139 | TFVNNIQY | 0.582 | 91 | WB | VP2-3 | A2902 |
| 122 | ELFNPDEY | 0.546 | 136 | WB | VP2-3 | A2902 |
| 211 | YNYIQDYY | 0.522 | 177 | WB | VP2-3 | A2902 |
| 107 | KVSTVGLY | 0.502 | 219 | WB | VP2-3 | A2902 |
| 204 | VNAPINFY | 0.450 | 383 | WB | VP2-3 | A2902 |
| 322 | VSRGSSQK | 0.699 | 26 | SB | VP2-3 | A3001 |
| 331 | KGTRASAK | 0.573 | 101 | WB | VP2-3 | A3001 |
| 228 | MVRQVAER | 0.521 | 178 | WB | VP2-3 | A3001 |
| 342 | KRRSRSSR | 0.469 | 312 | WB | VP2-3 | A3001 |
| 335 | ASAKTTNK | 0.448 | 393 | WB | VP2-3 | A3001 |
| 324 | RGSSQKAK | 0.442 | 420 | WB | VP2-3 | A3001 |
| 107 | KVSTVGLY | 0.586 | 88 | WB | VP2-3 | A3002 |
| 210 | FYNYIQDY | 0.499 | 226 | WB | VP2-3 | A3002 |
| 339 | TTNKRRSR | 0.798 | 8 | SB | VP2-3 | A3101 |
| 228 | MVRQVAER | 0.756 | 13 | SB | VP2-3 | A3101 |
| 327 | SQKAKGTR | 0.755 | 14 | SB | VP2-3 | A3101 |
| 257 | VTQRMDLR | 0.637 | 50 | WB | VP2-3 | A3101 |
| 336 | SAKTTNKR | 0.631 | 53 | WB | VP2-3 | A3101 |
| 187 | FFRDSLAR | 0.594 | 80 | WB | VP2-3 | A3101 |
| 92 | SLAQVGYR | 0.593 | 81 | WB | VP2-3 | A3101 |
| 218 | YSNLSPIR | 0.579 | 95 | WB | VP2-3 | A3101 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 162 | QALWHVIR | 0.557 | 120 | WB | VP2-3 | A3101 |
| 176 | TSQELQRR | 0.511 | 198 | WB | VP2-3 | A3101 |
| 179 | ELQRRTER | 0.476 | 288 | WB | VP2-3 | A3101 |
| 182 | RRTERFFR | 0.473 | 299 | WB | VP2-3 | A3101 |
| 143 | NIQYLDPR | 0.430 | 474 | WB | VP2-3 | A3101 |
| 179 | ELQRRTER | 0.741 | 16 | SB | VP2-3 | A3301 |
| 228 | MVRQVAER | 0.701 | 25 | SB | VP2-3 | A3301 |
| 187 | FFRDSLAR | 0.688 | 29 | SB | VP2-3 | A3301 |
| 339 | TTNKRRSR | 0.662 | 38 | SB | VP2-3 | A3301 |
| 143 | NIQYLDPR | 0.508 | 205 | WB | VP2-3 | A3301 |
| 228 | MVRQVAER | 0.823 | 6 | SB | VP2-3 | A6801 |
| 339 | TTNKRRSR | 0.774 | 11 | SB | VP2-3 | A6801 |
| 175 | ITSQELQR | 0.722 | 20 | SB | VP2-3 | A6801 |
| 92 | SLAQVGYR | 0.704 | 24 | SB | VP2-3 | A6801 |
| 218 | YSNLSPIR | 0.701 | 25 | SB | VP2-3 | A6801 |
| 253 | SIEEVTQR | 0.642 | 48 | SB | VP2-3 | A6801 |
| 143 | NIQYLDPR | 0.634 | 52 | WB | VP2-3 | A6801 |
| 162 | QALWHVIR | 0.599 | 76 | WB | VP2-3 | A6801 |
| 179 | ELQRRTER | 0.592 | 82 | WB | VP2-3 | A6801 |
| 257 | VTQRMDLR | 0.581 | 92 | WB | VP2-3 | A6801 |
| 336 | SAKTTNKR | 0.571 | 103 | WB | VP2-3 | A6801 |
| 176 | TSQELQRR | 0.567 | 107 | WB | VP2-3 | A6801 |
| 270 | HSGEFIEK | 0.558 | 119 | WB | VP2-3 | A6801 |
| 239 | HVNFGHTY | 0.520 | 180 | WB | VP2-3 | A6801 |
| 138 | NTFVNNIQ | 0.471 | 305 | WB | VP2-3 | A6801 |
| 122 | ELFNPDEY | 0.441 | 425 | WB | VP2-3 | A6801 |
| 100 | FFSDWDHK | 0.434 | 458 | WB | VP2-3 | A6801 |
| 32 | EAAAAIEV | 0.852 | 4 | SB | VP2-3 | A6802 |
| 80 | FAALIQTV | 0.773 | 11 | SB | VP2-3 | A6802 |
| 86 | TVTGISSL | 0.765 | 12 | SB | VP2-3 | A6802 |
| 201 | WTIVNAPI | 0.749 | 15 | SB | VP2-3 | A6802 |
| 55 | EAIAAIGL | 0.732 | 18 | SB | VP2-3 | A6802 |
| 140 | FVNNIQYL | 0.714 | 22 | SB | VP2-3 | A6802 |
| 199 | TTWTIVNA | 0.686 | 29 | SB | VP2-3 | A6802 |
| 62 | LTPQTYAV | 0.667 | 36 | SB | VP2-3 | A6802 |
| 244 | HTYSIDNA | 0.652 | 43 | SB | VP2-3 | A6802 |
| 287 | RTAPQWML | 0.650 | 44 | SB | VP2-3 | A6802 |
| 40 | QIASLATV | 0.640 | 49 | SB | VP2-3 | A6802 |
| 0 | MGAALALL | 0.635 | 51 | WB | VP2-3 | A6802 |
| 52 | TTSEAIAA | 0.624 | 58 | WB | VP2-3 | A6802 |
| 27 | EIAAGEAA | 0.616 | 63 | WB | VP2-3 | A6802 |
| 21 | TGFSVAEI | 0.588 | 86 | WB | VP2-3 | A6802 |
| 10 | LVASVSEA | 0.583 | 90 | WB | VP2-3 | A6802 |
| 18 | AAATGFSV | 0.561 | 115 | WB | VP2-3 | A6802 |
| 76 | AIAGFAAL | 0.537 | 149 | WB | VP2-3 | A6802 |
| 53 | TSEAIAAI | 0.500 | 223 | WB | VP2-3 | A6802 |
| 303 | TVTPALEA | 0.475 | 293 | WB | VP2-3 | A6802 |
| 185 | ERFFRDSL | 0.472 | 301 | WB | VP2-3 | A6802 |
| 256 | EVTQRMDL | 0.455 | 363 | WB | VP2-3 | A6802 |
| 157 | FATISQAL | 0.452 | 375 | WB | VP2-3 | A6802 |
| 23 | FSVAEIAA | 0.451 | 380 | WB | VP2-3 | A6802 |
| 13 | SVSEAAAA | 0.446 | 400 | WB | VP2-3 | A6802 |
| 38 | EVQIASLA | 0.440 | 427 | WB | VP2-3 | A6802 |
| 43 | SLATVEGI | 0.440 | 430 | WB | VP2-3 | A6802 |
| 250 | NADSIEEV | 0.433 | 460 | WB | VP2-3 | A6802 |
| 32 | EAAAAIEV | 0.788 | 9 | SB | VP2-3 | A6901 |
| 199 | TTWTIVNA | 0.689 | 28 | SB | VP2-3 | A6901 |
| 201 | WTIVNAPI | 0.671 | 35 | SB | VP2-3 | A6901 |
| 40 | QIASLATV | 0.635 | 52 | WB | VP2-3 | A6901 |
| 55 | EAIAAIGL | 0.619 | 61 | WB | VP2-3 | A6901 |
| 134 | FPGVNTFV | 0.612 | 66 | WB | VP2-3 | A6901 |
| 80 | FAALIQTV | 0.611 | 67 | WB | VP2-3 | A6901 |
| 101 | FSDWDHKV | 0.563 | 112 | WB | VP2-3 | A6901 |
| 27 | EIAAGEAA | 0.546 | 135 | WB | VP2-3 | A6901 |
| 62 | LTPQTYAV | 0.541 | 143 | WB | VP2-3 | A6901 |
| 140 | FVNNIQYL | 0.534 | 154 | WB | VP2-3 | A6901 |
| 244 | HTYSIDNA | 0.533 | 156 | WB | VP2-3 | A6901 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 250 | NADSIEEV | 0.521 | 178 | WB | VP2-3 | A6901 |
| 52 | TTSEAIAA | 0.511 | 198 | WB | VP2-3 | A6901 |
| 18 | AAATGFSV | 0.493 | 241 | WB | VP2-3 | A6901 |
| 287 | RTAPQWML | 0.476 | 289 | WB | VP2-3 | A6901 |
| 222 | SPIRPSMV | 0.469 | 313 | WB | VP2-3 | A6901 |
| 289 | APQWMLPL | 0.773 | 11 | SB | VP2-3 | B0702 |
| 225 | RPSMVRQV | 0.705 | 24 | SB | VP2-3 | B0702 |
| 222 | SPIRPSMV | 0.604 | 72 | WB | VP2-3 | B0702 |
| 153 | GPSLFATI | 0.482 | 272 | WB | VP2-3 | B0702 |
| 134 | FPGVNTFV | 0.477 | 287 | WB | VP2-3 | B0702 |
| 63 | TPQTYAVI | 0.476 | 289 | WB | VP2-3 | B0702 |
| 73 | APGAIAGF | 0.460 | 343 | WB | VP2-3 | B0702 |
| 114 | YQQSGMAL | 0.579 | 94 | WB | VP2-3 | B1501 |
| 180 | LQRRTERF | 0.557 | 120 | WB | VP2-3 | B1501 |
| 94 | AQVGYRFF | 0.550 | 129 | WB | VP2-3 | B1501 |
| 239 | HVNFGHTY | 0.550 | 130 | WB | VP2-3 | B1501 |
| 203 | IVNAPINF | 0.498 | 228 | WB | VP2-3 | B1501 |
| 39 | VQIASLAT | 0.466 | 321 | WB | VP2-3 | B1501 |
| 107 | KVSTVGLY | 0.464 | 331 | WB | VP2-3 | B1501 |
| 161 | SQALWHVI | 0.446 | 400 | WB | VP2-3 | B1501 |
| 127 | DEYYDILF | 0.753 | 14 | SB | VP2-3 | B1801 |
| 37 | IEVQIASL | 0.745 | 15 | SB | VP2-3 | B1801 |
| 233 | AEREGTHV | 0.477 | 286 | WB | VP2-3 | B1801 |
| 182 | RRTERFFR | 0.519 | 182 | WB | VP2-3 | B2705 |
| 342 | KRRSRSSR | 0.514 | 192 | WB | VP2-3 | B2705 |
| 259 | QRMDLRNK | 0.511 | 197 | WB | VP2-3 | B2705 |
| 320 | RRVSRGSS | 0.459 | 349 | WB | VP2-3 | B2705 |
| 294 | LPLLLGLY | 0.729 | 18 | SB | VP2-3 | B3501 |
| 16 | EAAAATGF | 0.672 | 34 | SB | VP2-3 | B3501 |
| 239 | HVNFGHTY | 0.639 | 49 | SB | VP2-3 | B3501 |
| 206 | APINFYNY | 0.606 | 71 | WB | VP2-3 | B3501 |
| 157 | FATISQAL | 0.598 | 77 | WB | VP2-3 | B3501 |
| 289 | APQWMLPL | 0.579 | 95 | WB | VP2-3 | B3501 |
| 139 | TFVNNIQY | 0.501 | 221 | WB | VP2-3 | B3501 |
| 93 | LAQVGYRF | 0.486 | 261 | WB | VP2-3 | B3501 |
| 123 | LFNPDEYY | 0.476 | 289 | WB | VP2-3 | B3501 |
| 73 | APGAIAGF | 0.469 | 313 | WB | VP2-3 | B3501 |
| 114 | YQQSGMAL | 0.547 | 134 | WB | VP2-3 | B3901 |
| 37 | IEVQIASL | 0.623 | 59 | WB | VP2-3 | B4001 |
| 272 | GEFIEKTI | 0.558 | 118 | WB | VP2-3 | B4001 |
| 127 | DEYYDILF | 0.459 | 346 | WB | VP2-3 | B4001 |
| 235 | REGTHVNF | 0.445 | 404 | WB | VP2-3 | B4001 |
| 233 | AEREGTHV | 0.430 | 476 | WB | VP2-3 | B4001 |
| 235 | REGTHVNF | 0.564 | 111 | WB | VP2-3 | B4002 |
| 197 | EETTWTIV | 0.485 | 263 | WB | VP2-3 | B4002 |
| 272 | GEFIEKTI | 0.467 | 318 | WB | VP2-3 | B4002 |
| 26 | AEIAAGEA | 0.493 | 240 | WB | VP2-3 | B4403 |
| 235 | REGTHVNF | 0.426 | 497 | WB | VP2-3 | B4403 |
| 26 | AEIAAGEA | 0.624 | 58 | WB | VP2-3 | B4501 |
| 233 | AEREGTHV | 0.483 | 269 | WB | VP2-3 | B4501 |
| 197 | EETTWTIV | 0.443 | 413 | WB | VP2-3 | B4501 |
| 153 | GPSLFATI | 0.494 | 238 | WB | VP2-3 | B5101 |
| 63 | TPQTYAVI | 0.493 | 241 | WB | VP2-3 | B5101 |
| 294 | LPLLLGLY | 0.483 | 269 | WB | VP2-3 | B5101 |
| 134 | FPGVNTFV | 0.466 | 321 | WB | VP2-3 | B5101 |
| 222 | SPIRPSMV | 0.440 | 427 | WB | VP2-3 | B5101 |
| 206 | APINFYNY | 0.677 | 32 | SB | VP2-3 | B5301 |
| 134 | FPGVNTFV | 0.594 | 81 | WB | VP2-3 | B5301 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 63 | TPQTYAVI | 0.488 | 254 | WB | VP2-3 | B5301 |
| 153 | GPSLFATI | 0.467 | 320 | WB | VP2-3 | B5301 |
| 134 | FPGVNTFV | 0.703 | 24 | SB | VP2-3 | B5401 |
| 294 | LPLLLGLY | 0.526 | 168 | WB | VP2-3 | B5401 |
| 80 | FAALIQTV | 0.437 | 443 | WB | VP2-3 | B5401 |
| 158 | ATISQALW | 0.681 | 31 | SB | VP2-3 | B5801 |
| 194 | RFLEETTW | 0.580 | 93 | WB | VP2-3 | B5801 |
| 287 | RTAPQWML | 0.551 | 129 | WB | VP2-3 | B5801 |
| 203 | IVNAPINF | 0.463 | 332 | WB | VP2-3 | B5801 |

9-mers

| pos | peptide | logscore | affinity(nM) | Bind Level | Protein Name | Allele |
|---|---|---|---|---|---|---|
| 138 | NTFVNNIQY | 0.453 | 373 | WB | VP2-3 | A0101 |
| 195 | FLEETTWTI | 0.822 | 6 | SB | VP2-3 | A0201 |
| 6 | LLGDLVASV | 0.810 | 7 | SB | VP2-3 | A0201 |
| 292 | WMLPLLLGL | 0.786 | 10 | SB | VP2-3 | A0201 |
| 213 | YIQDYYSNL | 0.758 | 13 | SB | VP2-3 | A0201 |
| 61 | GLTPQTYAV | 0.678 | 32 | SB | VP2-3 | A0201 |
| 82 | ALIQTVTGI | 0.643 | 47 | SB | VP2-3 | A0201 |
| 299 | GLYGTVTPA | 0.622 | 59 | WB | VP2-3 | A0201 |
| 159 | TISQALWHV | 0.608 | 69 | WB | VP2-3 | A0201 |
| 39 | VQIASLATV | 0.593 | 81 | WB | VP2-3 | A0201 |
| 296 | LLLGLYGTV | 0.532 | 157 | WB | VP2-3 | A0201 |
| 155 | SLFATISQA | 0.509 | 203 | WB | VP2-3 | A0201 |
| 3 | ALALLGDLV | 0.509 | 203 | WB | VP2-3 | A0201 |
| 76 | AIAGFAALI | 0.477 | 288 | WB | VP2-3 | A0201 |
| 17 | AAAATGFSV | 0.471 | 307 | WB | VP2-3 | A0201 |
| 100 | FFSDWDHKV | 0.465 | 327 | WB | VP2-3 | A0201 |
| 191 | SLARFLEET | 0.427 | 492 | WB | VP2-3 | A0201 |
| 61 | GLTPQTYAV | 0.877 | 3 | SB | VP2-3 | A0202 |
| 6 | LLGDLVASV | 0.801 | 8 | SB | VP2-3 | A0202 |
| 195 | FLEETTWTI | 0.800 | 8 | SB | VP2-3 | A0202 |
| 3 | ALALLGDLV | 0.789 | 9 | SB | VP2-3 | A0202 |
| 213 | YIQDYYSNL | 0.759 | 13 | SB | VP2-3 | A0202 |
| 159 | TISQALWHV | 0.692 | 27 | SB | VP2-3 | A0202 |
| 155 | SLFATISQA | 0.675 | 33 | SB | VP2-3 | A0202 |
| 292 | WMLPLLLGL | 0.671 | 35 | SB | VP2-3 | A0202 |
| 299 | GLYGTVTPA | 0.656 | 41 | SB | VP2-3 | A0202 |
| 82 | ALIQTVTGI | 0.656 | 41 | SB | VP2-3 | A0202 |
| 191 | SLARFLEET | 0.649 | 44 | SB | VP2-3 | A0202 |
| 10 | LVASVSEAA | 0.578 | 96 | WB | VP2-3 | A0202 |
| 52 | TTSEAIAAI | 0.559 | 118 | WB | VP2-3 | A0202 |
| 76 | AIAGFAALI | 0.550 | 130 | WB | VP2-3 | A0202 |
| 296 | LLLGLYGTV | 0.537 | 149 | WB | VP2-3 | A0202 |
| 39 | VQIASLATV | 0.505 | 211 | WB | VP2-3 | A0202 |
| 33 | AAAAIEVQI | 0.497 | 231 | WB | VP2-3 | A0202 |
| 220 | NLSPIRPSM | 0.483 | 269 | WB | VP2-3 | A0202 |
| 80 | FAALIQTVT | 0.482 | 272 | WB | VP2-3 | A0202 |
| 112 | GLYQQSGMA | 0.457 | 356 | WB | VP2-3 | A0202 |
| 75 | GAIAGFAAL | 0.449 | 388 | WB | VP2-3 | A0202 |
| 17 | AAAATGFSV | 0.447 | 396 | WB | VP2-3 | A0202 |
| 65 | QTYAVIAGA | 0.445 | 405 | WB | VP2-3 | A0202 |
| 36 | AIEVQIASL | 0.443 | 413 | WB | VP2-3 | A0202 |
| 136 | GVNTFVNNI | 0.436 | 444 | WB | VP2-3 | A0202 |
| 132 | ILFPGVNTF | 0.435 | 454 | WB | VP2-3 | A0202 |
| 100 | FFSDWDHKV | 0.428 | 488 | WB | VP2-3 | A0202 |
| 6 | LLGDLVASV | 0.941 | 1 | SB | VP2-3 | A0203 |
| 299 | GLYGTVTPA | 0.900 | 2 | SB | VP2-3 | A0203 |
| 61 | GLTPQTYAV | 0.878 | 3 | SB | VP2-3 | A0203 |
| 82 | ALIQTVTGI | 0.870 | 4 | SB | VP2-3 | A0203 |
| 39 | VQIASLATV | 0.845 | 5 | SB | VP2-3 | A0203 |
| 213 | YIQDYYSNL | 0.840 | 5 | SB | VP2-3 | A0203 |
| 292 | WMLPLLLGL | 0.787 | 10 | SB | VP2-3 | A0203 |
| 296 | LLLGLYGTV | 0.779 | 10 | SB | VP2-3 | A0203 |
| 195 | FLEETTWTI | 0.757 | 13 | SB | VP2-3 | A0203 |
| 112 | GLYQQSGMA | 0.739 | 16 | SB | VP2-3 | A0203 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 155 | SLFATISQA | 0.730 | 18 | SB | VP2-3 | A0203 |
| 65 | QTYAVIAGA | 0.690 | 28 | SB | VP2-3 | A0203 |
| 3 | ALALLGDLV | 0.687 | 29 | SB | VP2-3 | A0203 |
| 69 | VIAGAPGAI | 0.670 | 35 | SB | VP2-3 | A0203 |
| 136 | GVNTFVNNI | 0.666 | 37 | SB | VP2-3 | A0203 |
| 76 | AIAGFAALI | 0.664 | 37 | SB | VP2-3 | A0203 |
| 191 | SLARFLEET | 0.663 | 38 | SB | VP2-3 | A0203 |
| 159 | TISQALWHV | 0.608 | 69 | WB | VP2-3 | A0203 |
| 85 | QTVTGISSL | 0.606 | 70 | WB | VP2-3 | A0203 |
| 52 | TTSEAIAAI | 0.586 | 88 | WB | VP2-3 | A0203 |
| 167 | VIRDDIPAI | 0.553 | 125 | WB | VP2-3 | A0203 |
| 17 | AAAATGFSV | 0.540 | 145 | WB | VP2-3 | A0203 |
| 75 | GAIAGFAAL | 0.515 | 190 | WB | VP2-3 | A0203 |
| 10 | LVASVSEAA | 0.487 | 258 | WB | VP2-3 | A0203 |
| 18 | AAATGFSVA | 0.483 | 269 | WB | VP2-3 | A0203 |
| 20 | ATGFSVAEI | 0.460 | 344 | WB | VP2-3 | A0203 |
| 79 | GFAALIQTV | 0.447 | 396 | WB | VP2-3 | A0203 |
| 220 | NLSPIRPSM | 0.428 | 485 | WB | VP2-3 | A0203 |
| 6 | LLGDLVASV | 0.693 | 27 | SB | VP2-3 | A0204 |
| 195 | FLEETTWTI | 0.675 | 33 | SB | VP2-3 | A0204 |
| 61 | GLTPQTYAV | 0.670 | 35 | SB | VP2-3 | A0204 |
| 82 | ALIQTVTGI | 0.615 | 64 | WB | VP2-3 | A0204 |
| 155 | SLFATISQA | 0.590 | 84 | WB | VP2-3 | A0204 |
| 296 | LLLGLYGTV | 0.582 | 91 | WB | VP2-3 | A0204 |
| 100 | FFSDWDHKV | 0.570 | 104 | WB | VP2-3 | A0204 |
| 17 | AAAATGFSV | 0.494 | 238 | WB | VP2-3 | A0204 |
| 292 | WMLPLLLGL | 0.493 | 241 | WB | VP2-3 | A0204 |
| 213 | YIQDYYSNL | 0.491 | 246 | WB | VP2-3 | A0204 |
| 299 | GLYGTVTPA | 0.468 | 317 | WB | VP2-3 | A0204 |
| 159 | TISQALWHV | 0.463 | 333 | WB | VP2-3 | A0204 |
| 191 | SLARFLEET | 0.455 | 365 | WB | VP2-3 | A0204 |
| 39 | VQIASLATV | 0.928 | 2 | SB | VP2-3 | A0206 |
| 292 | WMLPLLLGL | 0.907 | 2 | SB | VP2-3 | A0206 |
| 195 | FLEETTWTI | 0.894 | 3 | SB | VP2-3 | A0206 |
| 61 | GLTPQTYAV | 0.849 | 5 | SB | VP2-3 | A0206 |
| 159 | TISQALWHV | 0.830 | 6 | SB | VP2-3 | A0206 |
| 6 | LLGDLVASV | 0.811 | 7 | SB | VP2-3 | A0206 |
| 75 | GAIAGFAAL | 0.805 | 8 | SB | VP2-3 | A0206 |
| 68 | AVIAGAPGA | 0.768 | 12 | SB | VP2-3 | A0206 |
| 17 | AAAATGFSV | 0.719 | 20 | SB | VP2-3 | A0206 |
| 82 | ALIQTVTGI | 0.701 | 25 | SB | VP2-3 | A0206 |
| 296 | LLLGLYGTV | 0.688 | 29 | SB | VP2-3 | A0206 |
| 45 | ATVEGITTT | 0.678 | 32 | SB | VP2-3 | A0206 |
| 94 | AQVGYRFFS | 0.625 | 57 | WB | VP2-3 | A0206 |
| 146 | YLDPRHWGP | 0.622 | 59 | WB | VP2-3 | A0206 |
| 213 | YIQDYYSNL | 0.593 | 81 | WB | VP2-3 | A0206 |
| 52 | TTSEAIAAI | 0.579 | 94 | WB | VP2-3 | A0206 |
| 10 | LVASVSEAA | 0.547 | 133 | WB | VP2-3 | A0206 |
| 129 | YYDILFPGV | 0.545 | 137 | WB | VP2-3 | A0206 |
| 288 | TAPQWMLPL | 0.544 | 139 | WB | VP2-3 | A0206 |
| 114 | YQQSGMALE | 0.542 | 141 | WB | VP2-3 | A0206 |
| 246 | YSIDNADSI | 0.520 | 180 | WB | VP2-3 | A0206 |
| 18 | AAATGFSVA | 0.517 | 186 | WB | VP2-3 | A0206 |
| 299 | GLYGTVTPA | 0.516 | 189 | WB | VP2-3 | A0206 |
| 85 | QTVTGISSL | 0.511 | 198 | WB | VP2-3 | A0206 |
| 76 | AIAGFAALI | 0.511 | 198 | WB | VP2-3 | A0206 |
| 29 | AAGEAAAAI | 0.508 | 205 | WB | VP2-3 | A0206 |
| 132 | ILFPGVNTF | 0.505 | 210 | WB | VP2-3 | A0206 |
| 230 | RQVAEREGT | 0.497 | 230 | WB | VP2-3 | A0206 |
| 3 | ALALLGDLV | 0.496 | 234 | WB | VP2-3 | A0206 |
| 65 | QTYAVIAGA | 0.478 | 282 | WB | VP2-3 | A0206 |
| 5 | ALLGDLVAS | 0.462 | 337 | WB | VP2-3 | A0206 |
| 167 | VIRDDIPAI | 0.444 | 409 | WB | VP2-3 | A0206 |
| 115 | QQSGMALEL | 0.438 | 437 | WB | VP2-3 | A0206 |
| 61 | GLTPQTYAV | 0.969 | 1 | SB | VP2-3 | A0211 |
| 6 | LLGDLVASV | 0.968 | 1 | SB | VP2-3 | A0211 |
| 296 | LLLGLYGTV | 0.950 | 1 | SB | VP2-3 | A0211 |
| 292 | WMLPLLLGL | 0.944 | 1 | SB | VP2-3 | A0211 |
| 195 | FLEETTWTI | 0.936 | 2 | SB | VP2-3 | A0211 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 159 | TISQALWHV | 0.904 | 2 | SB | VP2-3 | A0211 |
| 155 | SLFATISQA | 0.891 | 3 | SB | VP2-3 | A0211 |
| 299 | GLYGTVTPA | 0.884 | 3 | SB | VP2-3 | A0211 |
| 100 | FFSDWDHKV | 0.872 | 4 | SB | VP2-3 | A0211 |
| 146 | YLDPRHWGP | 0.871 | 4 | SB | VP2-3 | A0211 |
| 3 | ALALLGDLV | 0.860 | 4 | SB | VP2-3 | A0211 |
| 213 | YIQDYYSNL | 0.850 | 5 | SB | VP2-3 | A0211 |
| 220 | NLSPIRPSM | 0.829 | 6 | SB | VP2-3 | A0211 |
| 132 | ILFPGVNTF | 0.826 | 6 | SB | VP2-3 | A0211 |
| 76 | AIAGFAALI | 0.816 | 7 | SB | VP2-3 | A0211 |
| 191 | SLARFLEET | 0.802 | 8 | SB | VP2-3 | A0211 |
| 82 | ALIQTVTGI | 0.775 | 11 | SB | VP2-3 | A0211 |
| 129 | YYDILFPGV | 0.734 | 17 | SB | VP2-3 | A0211 |
| 92 | SLAQVGYRF | 0.679 | 32 | SB | VP2-3 | A0211 |
| 79 | GFAALIQTV | 0.662 | 38 | SB | VP2-3 | A0211 |
| 5 | ALLGDLVAS | 0.660 | 39 | SB | VP2-3 | A0211 |
| 112 | GLYQQSGMA | 0.658 | 40 | SB | VP2-3 | A0211 |
| 17 | AAAATGFSV | 0.657 | 41 | SB | VP2-3 | A0211 |
| 295 | PLLLGLYGT | 0.632 | 53 | WB | VP2-3 | A0211 |
| 133 | LFPGVNTFV | 0.594 | 80 | WB | VP2-3 | A0211 |
| 167 | VIRDDIPAI | 0.594 | 81 | WB | VP2-3 | A0211 |
| 253 | SIEEVTQRM | 0.567 | 108 | WB | VP2-3 | A0211 |
| 86 | TVTGISSLA | 0.472 | 303 | WB | VP2-3 | A0211 |
| 288 | TAPQWMLPL | 0.472 | 304 | WB | VP2-3 | A0211 |
| 27 | EIAAGEAAA | 0.450 | 383 | WB | VP2-3 | A0211 |
| 6 | LLGDLVASV | 0.931 | 2 | SB | VP2-3 | A0212 |
| 61 | GLTPQTYAV | 0.924 | 2 | SB | VP2-3 | A0212 |
| 296 | LLLGLYGTV | 0.910 | 2 | SB | VP2-3 | A0212 |
| 292 | WMLPLLLGL | 0.910 | 2 | SB | VP2-3 | A0212 |
| 213 | YIQDYYSNL | 0.894 | 3 | SB | VP2-3 | A0212 |
| 195 | FLEETTWTI | 0.892 | 3 | SB | VP2-3 | A0212 |
| 146 | YLDPRHWGP | 0.842 | 5 | SB | VP2-3 | A0212 |
| 100 | FFSDWDHKV | 0.833 | 6 | SB | VP2-3 | A0212 |
| 299 | GLYGTVTPA | 0.769 | 12 | SB | VP2-3 | A0212 |
| 159 | TISQALWHV | 0.717 | 21 | SB | VP2-3 | A0212 |
| 132 | ILFPGVNTF | 0.716 | 21 | SB | VP2-3 | A0212 |
| 167 | VIRDDIPAI | 0.698 | 26 | SB | VP2-3 | A0212 |
| 155 | SLFATISQA | 0.679 | 32 | SB | VP2-3 | A0212 |
| 82 | ALIQTVTGI | 0.678 | 32 | SB | VP2-3 | A0212 |
| 191 | SLARFLEET | 0.662 | 38 | SB | VP2-3 | A0212 |
| 3 | ALALLGDLV | 0.654 | 42 | SB | VP2-3 | A0212 |
| 129 | YYDILFPGV | 0.650 | 43 | SB | VP2-3 | A0212 |
| 220 | NLSPIRPSM | 0.622 | 59 | WB | VP2-3 | A0212 |
| 5 | ALLGDLVAS | 0.593 | 82 | WB | VP2-3 | A0212 |
| 79 | GFAALIQTV | 0.532 | 157 | WB | VP2-3 | A0212 |
| 133 | LFPGVNTFV | 0.528 | 164 | WB | VP2-3 | A0212 |
| 295 | PLLLGLYGT | 0.485 | 261 | WB | VP2-3 | A0212 |
| 27 | EIAAGEAAA | 0.471 | 306 | WB | VP2-3 | A0212 |
| 17 | AAAATGFSV | 0.450 | 383 | WB | VP2-3 | A0212 |
| 76 | AIAGFAALI | 0.448 | 393 | WB | VP2-3 | A0212 |
| 253 | SIEEVTQRM | 0.430 | 475 | WB | VP2-3 | A0212 |
| 6 | LLGDLVASV | 0.934 | 2 | SB | VP2-3 | A0216 |
| 61 | GLTPQTYAV | 0.916 | 2 | SB | VP2-3 | A0216 |
| 296 | LLLGLYGTV | 0.886 | 3 | SB | VP2-3 | A0216 |
| 159 | TISQALWHV | 0.864 | 4 | SB | VP2-3 | A0216 |
| 195 | FLEETTWTI | 0.847 | 5 | SB | VP2-3 | A0216 |
| 155 | SLFATISQA | 0.847 | 5 | SB | VP2-3 | A0216 |
| 299 | GLYGTVTPA | 0.835 | 5 | SB | VP2-3 | A0216 |
| 213 | YIQDYYSNL | 0.801 | 8 | SB | VP2-3 | A0216 |
| 100 | FFSDWDHKV | 0.789 | 9 | SB | VP2-3 | A0216 |
| 133 | LFPGVNTFV | 0.782 | 10 | SB | VP2-3 | A0216 |
| 292 | WMLPLLLGL | 0.764 | 12 | SB | VP2-3 | A0216 |
| 3 | ALALLGDLV | 0.763 | 12 | SB | VP2-3 | A0216 |
| 191 | SLARFLEET | 0.721 | 20 | SB | VP2-3 | A0216 |
| 82 | ALIQTVTGI | 0.677 | 33 | SB | VP2-3 | A0216 |
| 220 | NLSPIRPSM | 0.650 | 44 | SB | VP2-3 | A0216 |
| 76 | AIAGFAALI | 0.635 | 51 | WB | VP2-3 | A0216 |
| 17 | AAAATGFSV | 0.610 | 67 | WB | VP2-3 | A0216 |
| 132 | ILFPGVNTF | 0.584 | 90 | WB | VP2-3 | A0216 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 112 | GLYQQSGMA | 0.570 | 104 | WB | VP2-3 | A0216 |
| 92 | SLAQVGYRF | 0.552 | 127 | WB | VP2-3 | A0216 |
| 79 | GFAALIQTV | 0.522 | 176 | WB | VP2-3 | A0216 |
| 6 | LLGDLVASV | 0.930 | 2 | SB | VP2-3 | A0219 |
| 292 | WMLPLLLGL | 0.899 | 2 | SB | VP2-3 | A0219 |
| 61 | GLTPQTYAV | 0.888 | 3 | SB | VP2-3 | A0219 |
| 195 | FLEETTWTI | 0.848 | 5 | SB | VP2-3 | A0219 |
| 159 | TISQALWHV | 0.840 | 5 | SB | VP2-3 | A0219 |
| 100 | FFSDWDHKV | 0.782 | 10 | SB | VP2-3 | A0219 |
| 213 | YIQDYYSNL | 0.736 | 17 | SB | VP2-3 | A0219 |
| 296 | LLLGLYGTV | 0.726 | 19 | SB | VP2-3 | A0219 |
| 146 | YLDPRHWGP | 0.682 | 31 | SB | VP2-3 | A0219 |
| 82 | ALIQTVTGI | 0.643 | 47 | SB | VP2-3 | A0219 |
| 17 | AAAATGFSV | 0.629 | 55 | WB | VP2-3 | A0219 |
| 155 | SLFATISQA | 0.603 | 73 | WB | VP2-3 | A0219 |
| 299 | GLYGTVTPA | 0.564 | 111 | WB | VP2-3 | A0219 |
| 295 | PLLLGLYGT | 0.553 | 125 | WB | VP2-3 | A0219 |
| 129 | YYDILFPGV | 0.529 | 163 | WB | VP2-3 | A0219 |
| 220 | NLSPIRPSM | 0.528 | 164 | WB | VP2-3 | A0219 |
| 167 | VIRDDIPAI | 0.507 | 208 | WB | VP2-3 | A0219 |
| 132 | ILFPGVNTF | 0.504 | 214 | WB | VP2-3 | A0219 |
| 3 | ALALLGDLV | 0.475 | 291 | WB | VP2-3 | A0219 |
| 321 | RVSRGSSQK | 0.719 | 20 | SB | VP2-3 | A0301 |
| 334 | RASAKTTNK | 0.651 | 43 | SB | VP2-3 | A0301 |
| 203 | IVNAPINFY | 0.555 | 123 | WB | VP2-3 | A0301 |
| 293 | MLPLLLGLY | 0.473 | 299 | WB | VP2-3 | A0301 |
| 334 | RASAKTTNK | 0.729 | 18 | SB | VP2-3 | A1101 |
| 321 | RVSRGSSQK | 0.724 | 19 | SB | VP2-3 | A1101 |
| 91 | SSLAQVGYR | 0.688 | 29 | SB | VP2-3 | A1101 |
| 203 | IVNAPINFY | 0.666 | 37 | SB | VP2-3 | A1101 |
| 99 | RFFSDWDHK | 0.496 | 234 | WB | VP2-3 | A1101 |
| 158 | ATISQALWH | 0.460 | 345 | WB | VP2-3 | A1101 |
| 161 | SQALWHVIR | 0.457 | 356 | WB | VP2-3 | A1101 |
| 174 | AITSQELQR | 0.448 | 392 | WB | VP2-3 | A1101 |
| 139 | TFVNNIQYL | 0.584 | 90 | WB | VP2-3 | A2301 |
| 187 | FFRDSLARF | 0.577 | 97 | WB | VP2-3 | A2301 |
| 113 | LYQQSGMAL | 0.564 | 111 | WB | VP2-3 | A2301 |
| 132 | ILFPGVNTF | 0.521 | 178 | WB | VP2-3 | A2301 |
| 300 | LYGTVTPAL | 0.518 | 183 | WB | VP2-3 | A2301 |
| 216 | DYYSNLSPI | 0.482 | 271 | WB | VP2-3 | A2301 |
| 310 | AYEDGPNQK | 0.478 | 283 | WB | VP2-3 | A2301 |
| 202 | TIVNAPINF | 0.466 | 322 | WB | VP2-3 | A2301 |
| 99 | RFFSDWDHK | 0.466 | 323 | WB | VP2-3 | A2301 |
| 92 | SLAQVGYRF | 0.459 | 348 | WB | VP2-3 | A2301 |
| 300 | LYGTVTPAL | 0.661 | 39 | SB | VP2-3 | A2402 |
| 216 | DYYSNLSPI | 0.637 | 50 | WB | VP2-3 | A2402 |
| 156 | LFATISQAL | 0.560 | 116 | WB | VP2-3 | A2402 |
| 113 | LYQQSGMAL | 0.530 | 160 | WB | VP2-3 | A2402 |
| 200 | TWTIVNAPI | 0.452 | 374 | WB | VP2-3 | A2402 |
| 113 | LYQQSGMAL | 0.743 | 16 | SB | VP2-3 | A2403 |
| 139 | TFVNNIQYL | 0.591 | 83 | WB | VP2-3 | A2403 |
| 187 | FFRDSLARF | 0.572 | 102 | WB | VP2-3 | A2403 |
| 300 | LYGTVTPAL | 0.502 | 218 | WB | VP2-3 | A2403 |
| 292 | WMLPLLLGL | 0.426 | 498 | WB | VP2-3 | A2403 |
| 122 | ELFNPDEYY | 0.557 | 120 | WB | VP2-3 | A2601 |
| 303 | TVTPALEAY | 0.843 | 5 | SB | VP2-3 | A2602 |
| 203 | IVNAPINFY | 0.823 | 6 | SB | VP2-3 | A2602 |
| 122 | ELFNPDEYY | 0.792 | 9 | SB | VP2-3 | A2602 |
| 85 | QTVTGISSL | 0.778 | 11 | SB | VP2-3 | A2602 |
| 213 | YIQDYYSNL | 0.629 | 55 | WB | VP2-3 | A2602 |
| 293 | MLPLLLGLY | 0.578 | 96 | WB | VP2-3 | A2602 |
| 179 | ELQRRTERF | 0.551 | 128 | WB | VP2-3 | A2602 |
| 36 | AIEVQIASL | 0.518 | 183 | WB | VP2-3 | A2602 |
| 138 | NTFVNNIQY | 0.503 | 215 | WB | VP2-3 | A2602 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 187 | FFRDSLARF | 0.468 | 316 | WB | VP2-3 | A2602 |
| 202 | TIVNAPINF | 0.447 | 398 | WB | VP2-3 | A2602 |
| 62 | LTPQTYAVI | 0.442 | 416 | WB | VP2-3 | A2602 |
| 210 | FYNYIQDYY | 0.765 | 12 | SB | VP2-3 | A2902 |
| 122 | ELFNPDEYY | 0.716 | 21 | SB | VP2-3 | A2902 |
| 138 | NTFVNNIQY | 0.580 | 94 | WB | VP2-3 | A2902 |
| 203 | IVNAPINFY | 0.465 | 327 | WB | VP2-3 | A2902 |
| 209 | NFYNYIQDY | 0.457 | 357 | WB | VP2-3 | A2902 |
| 293 | MLPLLLGLY | 0.446 | 402 | WB | VP2-3 | A2902 |
| 99 | RFFSDWDHK | 0.765 | 12 | SB | VP2-3 | A3001 |
| 321 | RVSRGSSQK | 0.639 | 49 | SB | VP2-3 | A3001 |
| 334 | RASAKTTNK | 0.593 | 81 | WB | VP2-3 | A3001 |
| 186 | RFFRDSLAR | 0.501 | 222 | WB | VP2-3 | A3001 |
| 329 | KAKGTRASA | 0.446 | 401 | WB | VP2-3 | A3001 |
| 210 | FYNYIQDYY | 0.594 | 80 | WB | VP2-3 | A3002 |
| 203 | IVNAPINFY | 0.508 | 205 | WB | VP2-3 | A3002 |
| 293 | MLPLLLGLY | 0.466 | 321 | WB | VP2-3 | A3002 |
| 338 | KTTNKRRSR | 0.829 | 6 | SB | VP2-3 | A3101 |
| 316 | NQKKRRVSR | 0.804 | 8 | SB | VP2-3 | A3101 |
| 227 | SMVRQVAER | 0.772 | 11 | SB | VP2-3 | A3101 |
| 186 | RFFRDSLAR | 0.765 | 12 | SB | VP2-3 | A3101 |
| 91 | SSLAQVGYR | 0.756 | 13 | SB | VP2-3 | A3101 |
| 161 | SQALWHVIR | 0.641 | 48 | SB | VP2-3 | A3101 |
| 326 | SSQKAKGTR | 0.632 | 53 | WB | VP2-3 | A3101 |
| 334 | RASAKTTNK | 0.583 | 91 | WB | VP2-3 | A3101 |
| 217 | YYSNLSPIR | 0.570 | 105 | WB | VP2-3 | A3101 |
| 336 | SAKTTNKRR | 0.537 | 149 | WB | VP2-3 | A3101 |
| 99 | RFFSDWDHK | 0.504 | 214 | WB | VP2-3 | A3101 |
| 335 | ASAKTTNKR | 0.479 | 280 | WB | VP2-3 | A3101 |
| 321 | RVSRGSSQK | 0.435 | 453 | WB | VP2-3 | A3101 |
| 256 | EVTQRMDLR | 0.709 | 23 | SB | VP2-3 | A3301 |
| 316 | NQKKRRVSR | 0.703 | 24 | SB | VP2-3 | A3301 |
| 252 | DSIEEVTQR | 0.585 | 89 | WB | VP2-3 | A3301 |
| 341 | NKRRSRSSR | 0.463 | 333 | WB | VP2-3 | A3301 |
| 256 | EVTQRMDLR | 0.844 | 5 | SB | VP2-3 | A6801 |
| 252 | DSIEEVTQR | 0.787 | 10 | SB | VP2-3 | A6801 |
| 138 | NTFVNNIQY | 0.711 | 22 | SB | VP2-3 | A6801 |
| 175 | ITSQELQRR | 0.650 | 44 | SB | VP2-3 | A6801 |
| 279 | IAPGGANQR | 0.616 | 63 | WB | VP2-3 | A6801 |
| 217 | YYSNLSPIR | 0.607 | 70 | WB | VP2-3 | A6801 |
| 91 | SSLAQVGYR | 0.605 | 71 | WB | VP2-3 | A6801 |
| 227 | SMVRQVAER | 0.599 | 76 | WB | VP2-3 | A6801 |
| 335 | ASAKTTNKR | 0.531 | 160 | WB | VP2-3 | A6801 |
| 122 | ELFNPDEYY | 0.510 | 201 | WB | VP2-3 | A6801 |
| 210 | FYNYIQDYY | 0.503 | 217 | WB | VP2-3 | A6801 |
| 174 | AITSQELQR | 0.462 | 338 | WB | VP2-3 | A6801 |
| 142 | NNIQYLDPR | 0.461 | 341 | WB | VP2-3 | A6801 |
| 326 | SSQKAKGTR | 0.457 | 357 | WB | VP2-3 | A6801 |
| 321 | RVSRGSSQK | 0.456 | 360 | WB | VP2-3 | A6801 |
| 303 | TVTPALEAY | 0.454 | 367 | WB | VP2-3 | A6801 |
| 161 | SQALWHVIR | 0.451 | 379 | WB | VP2-3 | A6801 |
| 203 | IVNAPINFY | 0.449 | 388 | WB | VP2-3 | A6801 |
| 338 | KTTNKRRSR | 0.428 | 487 | WB | VP2-3 | A6801 |
| 336 | SAKTTNKRR | 0.427 | 493 | WB | VP2-3 | A6801 |
| 65 | QTYAVIAGA | 0.846 | 5 | SB | VP2-3 | A6802 |
| 52 | TTSEAIAAI | 0.827 | 6 | SB | VP2-3 | A6802 |
| 86 | TVTGISSLA | 0.764 | 12 | SB | VP2-3 | A6802 |
| 10 | LVASVSEAA | 0.709 | 23 | SB | VP2-3 | A6802 |
| 198 | ETTWTIVNA | 0.691 | 28 | SB | VP2-3 | A6802 |
| 85 | QTVTGISSL | 0.677 | 32 | SB | VP2-3 | A6802 |
| 16 | EAAAATGFS | 0.649 | 44 | SB | VP2-3 | A6802 |
| 267 | ESVHSGEFI | 0.602 | 73 | WB | VP2-3 | A6802 |
| 27 | EIAAGEAAA | 0.596 | 79 | WB | VP2-3 | A6802 |
| 17 | AAAATGFSV | 0.574 | 100 | WB | VP2-3 | A6802 |

TABLE J-continued

Prediction of BK virus VP2-3 protein specific MHC
class1, 8-, 9-, 10-, 11-mer peptide binders for
42 MHC class 1 alleles (see FIG. 11) using the
www.cbs.dtu.dk/services/NetMHC/ database.
The MHC class 1 molecules for which no binders were
found are not listed.

| pos | peptide | logscore | affinity(nM) | Bind Level | Protein Name | Allele |
|---|---|---|---|---|---|---|
| 249 | DNADSIEEV | 0.562 | 114 | WB | VP2-3 | A6802 |
| 166 | HVIRDDIPA | 0.561 | 115 | WB | VP2-3 | A6802 |
| 159 | TISQALWHV | 0.550 | 130 | WB | VP2-3 | A6802 |
| 88 | TGISSLAQV | 0.536 | 151 | WB | VP2-3 | A6802 |
| 48 | EGITTTSEA | 0.535 | 152 | WB | VP2-3 | A6802 |
| 246 | YSIDNADSI | 0.523 | 174 | WB | VP2-3 | A6802 |
| 76 | AIAGFAALI | 0.521 | 177 | WB | VP2-3 | A6802 |
| 55 | EAIAAIGLT | 0.484 | 267 | WB | VP2-3 | A6802 |
| 80 | FAALIQTVT | 0.481 | 273 | WB | VP2-3 | A6802 |
| 152 | WGPSLFATI | 0.478 | 284 | WB | VP2-3 | A6802 |
| 33 | AAAAIEVQI | 0.458 | 353 | WB | VP2-3 | A6802 |
| 288 | TAPQWMLPL | 0.443 | 416 | WB | VP2-3 | A6802 |
| 51 | TTTSEAIAA | 0.433 | 463 | WB | VP2-3 | A6802 |
| 65 | QTYAVIAGA | 0.710 | 23 | SB | VP2-3 | A6901 |
| 198 | ETTWTIVNA | 0.703 | 24 | SB | VP2-3 | A6901 |
| 52 | TTSEAIAAI | 0.684 | 30 | SB | VP2-3 | A6901 |
| 159 | TISQALWHV | 0.622 | 59 | WB | VP2-3 | A6901 |
| 292 | WMLPLLLGL | 0.604 | 72 | WB | VP2-3 | A6901 |
| 17 | AAAATGFSV | 0.601 | 74 | WB | VP2-3 | A6901 |
| 27 | EIAAGEAAA | 0.579 | 94 | WB | VP2-3 | A6901 |
| 195 | FLEETTWTI | 0.570 | 104 | WB | VP2-3 | A6901 |
| 288 | TAPQWMLPL | 0.545 | 137 | WB | VP2-3 | A6901 |
| 6 | LLGDLVASV | 0.506 | 209 | WB | VP2-3 | A6901 |
| 296 | LLLGLYGTV | 0.472 | 301 | WB | VP2-3 | A6901 |
| 100 | FFSDWDHKV | 0.429 | 484 | WB | VP2-3 | A6901 |
| 225 | RPSMVRQVA | 0.705 | 24 | SB | VP2-3 | B0702 |
| 172 | IPAITSQEL | 0.628 | 55 | WB | VP2-3 | B0702 |
| 148 | DPRHWGPSL | 0.610 | 67 | WB | VP2-3 | B0702 |
| 289 | APQWMLPLL | 0.598 | 77 | WB | VP2-3 | B0702 |
| 314 | GPNQKKRRV | 0.530 | 162 | WB | VP2-3 | B0702 |
| 206 | APINFYNYI | 0.475 | 294 | WB | VP2-3 | B0702 |
| 132 | ILFPGVNTF | 0.606 | 70 | WB | VP2-3 | B1501 |
| 203 | IVNAPINFY | 0.578 | 96 | WB | VP2-3 | B1501 |
| 180 | LQRRTERFF | 0.558 | 118 | WB | VP2-3 | B1501 |
| 115 | QQSGMALEL | 0.503 | 216 | WB | VP2-3 | B1501 |
| 39 | VQIASLATV | 0.477 | 287 | WB | VP2-3 | B1501 |
| 122 | ELFNPDEYY | 0.439 | 432 | WB | VP2-3 | B1501 |
| 92 | SLAQVGYRF | 0.428 | 489 | WB | VP2-3 | B1501 |
| 184 | TERFFRDSL | 0.622 | 59 | WB | VP2-3 | B1801 |
| 292 | WMLPLLLGL | 0.590 | 84 | WB | VP2-3 | B1801 |
| 148 | DPRHWGPSL | 0.584 | 90 | WB | VP2-3 | B1801 |
| 54 | SEAIAAIGL | 0.546 | 135 | WB | VP2-3 | B1801 |
| 255 | EEVTQRMDL | 0.451 | 380 | WB | VP2-3 | B1801 |
| 15 | SEAAATGF | 0.435 | 449 | WB | VP2-3 | B1801 |
| 320 | RRVSRGSSQ | 0.507 | 206 | WB | VP2-3 | B2705 |
| 303 | TVTPALEAY | 0.686 | 29 | SB | VP2-3 | B3501 |
| 172 | IPAITSQEL | 0.611 | 67 | WB | VP2-3 | B3501 |
| 125 | NPDEYYDIL | 0.606 | 71 | WB | VP2-3 | B3501 |
| 238 | THVNFGHTY | 0.550 | 130 | WB | VP2-3 | B3501 |
| 156 | LFATISQAL | 0.521 | 178 | WB | VP2-3 | B3501 |
| 67 | YAVIAGAPG | 0.510 | 199 | WB | VP2-3 | B3501 |
| 288 | TAPQWMLPL | 0.508 | 204 | WB | VP2-3 | B3501 |
| 289 | APQWMLPLL | 0.499 | 225 | WB | VP2-3 | B3501 |
| 132 | ILFPGVNTF | 0.484 | 265 | WB | VP2-3 | B3501 |
| 80 | FAALIQTVT | 0.470 | 310 | WB | VP2-3 | B3501 |
| 63 | TPQTYAVIA | 0.453 | 372 | WB | VP2-3 | B3501 |
| 28 | IAAGEAAAA | 0.446 | 400 | WB | VP2-3 | B3501 |
| 134 | FPGVNTFVN | 0.445 | 405 | WB | VP2-3 | B3501 |
| 205 | NAPINFYNY | 0.437 | 442 | WB | VP2-3 | B3501 |
| 13 | SVSEAAAAT | 0.433 | 461 | WB | VP2-3 | B3501 |
| 75 | GAIAGFAAL | 0.429 | 483 | WB | VP2-3 | B3501 |
| 54 | SEAIAAIGL | 0.703 | 24 | SB | VP2-3 | B4001 |
| 31 | GEAAAAIEV | 0.632 | 53 | WB | VP2-3 | B4001 |
| 255 | EEVTQRMDL | 0.542 | 141 | WB | VP2-3 | B4001 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 15 | SEAAAATGF | 0.509 | 202 | WB | VP2-3 | B4001 |
| 184 | TERFFRDSL | 0.467 | 319 | WB | VP2-3 | B4001 |
| | | | | | | |
| 266 | KESVHSGEF | 0.574 | 99 | WB | VP2-3 | B4002 |
| 255 | EEVTQRMDL | 0.532 | 158 | WB | VP2-3 | B4002 |
| 272 | GEFIEKTIA | 0.496 | 232 | WB | VP2-3 | B4002 |
| 15 | SEAAAATGF | 0.495 | 235 | WB | VP2-3 | B4002 |
| 54 | SEAIAAIGL | 0.445 | 405 | WB | VP2-3 | B4002 |
| | | | | | | |
| 54 | SEAIAAIGL | 0.492 | 243 | WB | VP2-3 | B4403 |
| 15 | SEAAAATGF | 0.476 | 288 | WB | VP2-3 | B4403 |
| 26 | AEIAAGEAA | 0.466 | 322 | WB | VP2-3 | B4403 |
| | | | | | | |
| 26 | AEIAAGEAA | 0.639 | 49 | SB | VP2-3 | B4501 |
| 255 | EEVTQRMDL | 0.521 | 178 | WB | VP2-3 | B4501 |
| 31 | GEAAAAIEV | 0.456 | 361 | WB | VP2-3 | B4501 |
| 197 | EETTWTIVN | 0.432 | 464 | WB | VP2-3 | B4501 |
| | | | | | | |
| 206 | APINFYNYI | 0.497 | 230 | WB | VP2-3 | B5101 |
| 294 | LPLLLGLYG | 0.451 | 381 | WB | VP2-3 | B5101 |
| | | | | | | |
| 206 | APINFYNYI | 0.608 | 69 | WB | VP2-3 | B5301 |
| 289 | APQWMLPLL | 0.545 | 136 | WB | VP2-3 | B5301 |
| 157 | FATISQALW | 0.522 | 176 | WB | VP2-3 | B5301 |
| | | | | | | |
| 206 | APINFYNYI | 0.614 | 64 | WB | VP2-3 | B5401 |
| 73 | APGAIAGFA | 0.573 | 100 | WB | VP2-3 | B5401 |
| 119 | MALELFNPD | 0.511 | 199 | WB | VP2-3 | B5401 |
| 134 | FPGVNTFVN | 0.502 | 218 | WB | VP2-3 | B5401 |
| 294 | LPLLLGLYG | 0.488 | 254 | WB | VP2-3 | B5401 |
| 63 | TPQTYAVIA | 0.478 | 282 | WB | VP2-3 | B5401 |
| 80 | FAALIQTVT | 0.464 | 329 | WB | VP2-3 | B5401 |
| | | | | | | |
| 157 | FATISQALW | 0.723 | 19 | SB | VP2-3 | B5801 |
| 90 | ISSLAQVGY | 0.546 | 136 | WB | VP2-3 | B5801 |
| 96 | VGYRFFSDW | 0.481 | 274 | WB | VP2-3 | B5801 |
| | | | 10-mers | | | |
| 237 | GTHVNFGHTY | 0.517 | 185 | WB | VP2-3 | A0101 |
| | | | | | | |
| 5 | ALLGDLVASV | 0.820 | 6 | SB | VP2-3 | A0201 |
| 132 | ILFPGVNTFV | 0.785 | 10 | SB | VP2-3 | A0201 |
| 299 | GLYGTVTPAL | 0.721 | 20 | SB | VP2-3 | A0201 |
| 195 | FLEETTWTIV | 0.703 | 24 | SB | VP2-3 | A0201 |
| 155 | SLFATISQAL | 0.632 | 53 | WB | VP2-3 | A0201 |
| 114 | YQQSGMALEL | 0.529 | 162 | WB | VP2-3 | A0201 |
| 158 | ATISQALWHV | 0.476 | 288 | WB | VP2-3 | A0201 |
| 199 | TTWTIVNAPI | 0.473 | 298 | WB | VP2-3 | A0201 |
| 61 | GLTPQTYAVI | 0.471 | 305 | WB | VP2-3 | A0201 |
| 112 | GLYQQSGMAL | 0.455 | 364 | WB | VP2-3 | A0201 |
| 260 | RMDLRNKESV | 0.442 | 418 | WB | VP2-3 | A0201 |
| 220 | NLSPIRPSMV | 0.436 | 445 | WB | VP2-3 | A0201 |
| 163 | ALWHVIRDDI | 0.430 | 476 | WB | VP2-3 | A0201 |
| | | | | | | |
| 132 | ILFPGVNTFV | 0.798 | 8 | SB | VP2-3 | A0202 |
| 5 | ALLGDLVASV | 0.785 | 10 | SB | VP2-3 | A0202 |
| 155 | SLFATISQAL | 0.742 | 16 | SB | VP2-3 | A0202 |
| 299 | GLYGTVTPAL | 0.680 | 32 | SB | VP2-3 | A0202 |
| 112 | GLYQQSGMAL | 0.654 | 42 | SB | VP2-3 | A0202 |
| 195 | FLEETTWTIV | 0.589 | 85 | WB | VP2-3 | A0202 |
| 3 | ALALLGDLVA | 0.583 | 91 | WB | VP2-3 | A0202 |
| 191 | SLARFLEETT | 0.557 | 120 | WB | VP2-3 | A0202 |
| 114 | YQQSGMALEL | 0.554 | 124 | WB | VP2-3 | A0202 |
| 296 | LLLGLYGTVT | 0.537 | 149 | WB | VP2-3 | A0202 |
| 138 | NTFVNNIQYL | 0.525 | 170 | WB | VP2-3 | A0202 |
| 220 | NLSPIRPSMV | 0.519 | 182 | WB | VP2-3 | A0202 |
| 158 | ATISQALWHV | 0.501 | 222 | WB | VP2-3 | A0202 |
| 10 | LVASVSEAAA | 0.479 | 280 | WB | VP2-3 | A0202 |
| 61 | GLTPQTYAVI | 0.466 | 322 | WB | VP2-3 | A0202 |
| 124 | FNPDEYYDIL | 0.461 | 342 | WB | VP2-3 | A0202 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 295 | PLLLGLYGTV | 0.450 | 382 | WB | VP2-3 | A0202 |
| 260 | RMDLRNKESV | 0.447 | 397 | WB | VP2-3 | A0202 |
| 293 | MLPLLLGLYG | 0.427 | 492 | WB | VP2-3 | A0202 |
| 2 | AALALLGDLV | 0.426 | 498 | WB | VP2-3 | A0202 |
| 132 | ILFPGVNTFV | 0.888 | 3 | SB | VP2-3 | A0203 |
| 5 | ALLGDLVASV | 0.868 | 4 | SB | VP2-3 | A0203 |
| 195 | FLEETTWTIV | 0.820 | 7 | SB | VP2-3 | A0203 |
| 299 | GLYGTVTPAL | 0.803 | 8 | SB | VP2-3 | A0203 |
| 220 | NLSPIRPSMV | 0.788 | 9 | SB | VP2-3 | A0203 |
| 112 | GLYQQSGMAL | 0.756 | 14 | SB | VP2-3 | A0203 |
| 61 | GLTPQTYAVI | 0.703 | 24 | SB | VP2-3 | A0203 |
| 155 | SLFATISQAL | 0.700 | 25 | SB | VP2-3 | A0203 |
| 239 | HVNFGHTYSI | 0.663 | 38 | SB | VP2-3 | A0203 |
| 287 | RTAPQWMLPL | 0.629 | 55 | WB | VP2-3 | A0203 |
| 260 | RMDLRNKESV | 0.533 | 156 | WB | VP2-3 | A0203 |
| 191 | SLARFLEETT | 0.530 | 161 | WB | VP2-3 | A0203 |
| 68 | AVIAGAPGAI | 0.529 | 163 | WB | VP2-3 | A0203 |
| 158 | ATISQALWHV | 0.516 | 187 | WB | VP2-3 | A0203 |
| 24 | SVAEIAAGEA | 0.513 | 193 | WB | VP2-3 | A0203 |
| 114 | YQQSGMALEL | 0.513 | 194 | WB | VP2-3 | A0203 |
| 35 | AAIEVQIASL | 0.509 | 203 | WB | VP2-3 | A0203 |
| 295 | PLLLGLYGTV | 0.503 | 217 | WB | VP2-3 | A0203 |
| 69 | VIAGAPGAIA | 0.490 | 248 | WB | VP2-3 | A0203 |
| 3 | ALALLGDLVA | 0.472 | 303 | WB | VP2-3 | A0203 |
| 10 | LVASVSEAAA | 0.471 | 304 | WB | VP2-3 | A0203 |
| 75 | GAIAGFAALI | 0.453 | 373 | WB | VP2-3 | A0203 |
| 85 | QTVTGISSLA | 0.440 | 425 | WB | VP2-3 | A0203 |
| 43 | SLATVEGITT | 0.431 | 473 | WB | VP2-3 | A0203 |
| 132 | ILFPGVNTFV | 0.738 | 17 | SB | VP2-3 | A0204 |
| 195 | FLEETTWTIV | 0.686 | 30 | SB | VP2-3 | A0204 |
| 5 | ALLGDLVASV | 0.678 | 32 | SB | VP2-3 | A0204 |
| 155 | SLFATISQAL | 0.630 | 54 | WB | VP2-3 | A0204 |
| 158 | ATISQALWHV | 0.567 | 108 | WB | VP2-3 | A0204 |
| 299 | GLYGTVTPAL | 0.485 | 263 | WB | VP2-3 | A0204 |
| 112 | GLYQQSGMAL | 0.468 | 317 | WB | VP2-3 | A0204 |
| 287 | RTAPQWMLPL | 0.457 | 356 | WB | VP2-3 | A0204 |
| 5 | ALLGDLVASV | 0.873 | 3 | SB | VP2-3 | A0206 |
| 195 | FLEETTWTIV | 0.869 | 4 | SB | VP2-3 | A0206 |
| 132 | ILFPGVNTFV | 0.865 | 4 | SB | VP2-3 | A0206 |
| 114 | YQQSGMALEL | 0.803 | 8 | SB | VP2-3 | A0206 |
| 158 | ATISQALWHV | 0.779 | 10 | SB | VP2-3 | A0206 |
| 35 | AAIEVQIASL | 0.711 | 22 | SB | VP2-3 | A0206 |
| 75 | GAIAGFAALI | 0.649 | 44 | SB | VP2-3 | A0206 |
| 287 | RTAPQWMLPL | 0.626 | 57 | WB | VP2-3 | A0206 |
| 299 | GLYGTVTPAL | 0.599 | 76 | WB | VP2-3 | A0206 |
| 68 | AVIAGAPGAI | 0.591 | 83 | WB | VP2-3 | A0206 |
| 67 | YAVIAGAPGA | 0.588 | 86 | WB | VP2-3 | A0206 |
| 84 | IQTVTGISSL | 0.569 | 105 | WB | VP2-3 | A0206 |
| 2 | AALALLGDLV | 0.550 | 129 | WB | VP2-3 | A0206 |
| 94 | AQVGYRFFSD | 0.537 | 150 | WB | VP2-3 | A0206 |
| 146 | YLDPRHWGPS | 0.525 | 169 | WB | VP2-3 | A0206 |
| 260 | RMDLRNKESV | 0.525 | 170 | WB | VP2-3 | A0206 |
| 166 | HVIRDDIPAI | 0.513 | 193 | WB | VP2-3 | A0206 |
| 288 | TAPQWMLPLL | 0.507 | 208 | WB | VP2-3 | A0206 |
| 155 | SLFATISQAL | 0.500 | 223 | WB | VP2-3 | A0206 |
| 39 | VQIASLATVE | 0.488 | 254 | WB | VP2-3 | A0206 |
| 24 | SVAEIAAGEA | 0.488 | 255 | WB | VP2-3 | A0206 |
| 194 | RFLEETTWTI | 0.480 | 276 | WB | VP2-3 | A0206 |
| 10 | LVASVSEAAA | 0.470 | 309 | WB | VP2-3 | A0206 |
| 112 | GLYQQSGMAL | 0.466 | 322 | WB | VP2-3 | A0206 |
| 220 | NLSPIRPSMV | 0.460 | 344 | WB | VP2-3 | A0206 |
| 159 | TISQALWHVI | 0.458 | 353 | WB | VP2-3 | A0206 |
| 17 | AAAATGFSVA | 0.457 | 354 | WB | VP2-3 | A0206 |
| 45 | ATVEGITTTS | 0.454 | 365 | WB | VP2-3 | A0206 |
| 231 | QVAEREGTHV | 0.453 | 371 | WB | VP2-3 | A0206 |
| 78 | AGFAALIQTV | 0.448 | 394 | WB | VP2-3 | A0206 |
| 115 | QQSGMALELF | 0.438 | 437 | WB | VP2-3 | A0206 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 81 | AALIQTVTGI | 0.433 | 460 | WB | VP2-3 | A0206 |
| 61 | GLTPQTYAVI | 0.432 | 466 | WB | VP2-3 | A0206 |
| 132 | ILFPGVNTFV | 0.975 | 1 | SB | VP2-3 | A0211 |
| 5 | ALLGDLVASV | 0.972 | 1 | SB | VP2-3 | A0211 |
| 155 | SLFATISQAL | 0.940 | 1 | SB | VP2-3 | A0211 |
| 299 | GLYGTVTPAL | 0.939 | 1 | SB | VP2-3 | A0211 |
| 195 | FLEETTWTIV | 0.931 | 2 | SB | VP2-3 | A0211 |
| 260 | RMDLRNKESV | 0.912 | 2 | SB | VP2-3 | A0211 |
| 220 | NLSPIRPSMV | 0.891 | 3 | SB | VP2-3 | A0211 |
| 295 | PLLLGLYGTV | 0.885 | 3 | SB | VP2-3 | A0211 |
| 112 | GLYQQSGMAL | 0.864 | 4 | SB | VP2-3 | A0211 |
| 61 | GLTPQTYAVI | 0.850 | 5 | SB | VP2-3 | A0211 |
| 146 | YLDPRHWGPS | 0.740 | 16 | SB | VP2-3 | A0211 |
| 191 | SLARFLEETT | 0.737 | 17 | SB | VP2-3 | A0211 |
| 128 | EYYDILFPGV | 0.731 | 18 | SB | VP2-3 | A0211 |
| 159 | TISQALWHVI | 0.674 | 34 | SB | VP2-3 | A0211 |
| 102 | SDWDHKVSTV | 0.641 | 48 | SB | VP2-3 | A0211 |
| 292 | WMLPLLLGLY | 0.638 | 50 | WB | VP2-3 | A0211 |
| 163 | ALWHVIRDDI | 0.620 | 60 | WB | VP2-3 | A0211 |
| 3 | ALALLGDLVA | 0.616 | 63 | WB | VP2-3 | A0211 |
| 92 | SLAQVGYRFF | 0.615 | 64 | WB | VP2-3 | A0211 |
| 158 | ATISQALWHV | 0.598 | 77 | WB | VP2-3 | A0211 |
| 99 | RFFSDWDHKV | 0.596 | 79 | WB | VP2-3 | A0211 |
| 287 | RTAPQWMLPL | 0.585 | 89 | WB | VP2-3 | A0211 |
| 78 | AGFAALIQTV | 0.570 | 105 | WB | VP2-3 | A0211 |
| 43 | SLATVEGITT | 0.568 | 107 | WB | VP2-3 | A0211 |
| 223 | PIRPSMVRQV | 0.566 | 109 | WB | VP2-3 | A0211 |
| 296 | LLLGLYGTVT | 0.548 | 133 | WB | VP2-3 | A0211 |
| 38 | EVQIASLATV | 0.532 | 158 | WB | VP2-3 | A0211 |
| 114 | YQQSGMALEL | 0.530 | 162 | WB | VP2-3 | A0211 |
| 194 | RFLEETTWTI | 0.518 | 184 | WB | VP2-3 | A0211 |
| 239 | HVNFGHTYSI | 0.510 | 199 | WB | VP2-3 | A0211 |
| 24 | SVAEIAAGEA | 0.497 | 230 | WB | VP2-3 | A0211 |
| 171 | DIPAITSQEL | 0.484 | 265 | WB | VP2-3 | A0211 |
| 231 | QVAEREGTHV | 0.484 | 265 | WB | VP2-3 | A0211 |
| 288 | TAPQWMLPLL | 0.470 | 310 | WB | VP2-3 | A0211 |
| 16 | EAAAATGFSV | 0.464 | 330 | WB | VP2-3 | A0211 |
| 87 | VTGISSLAQV | 0.454 | 366 | WB | VP2-3 | A0211 |
| 6 | LLGDLVASVS | 0.453 | 372 | WB | VP2-3 | A0211 |
| 35 | AAIEVQIASL | 0.437 | 439 | WB | VP2-3 | A0211 |
| 132 | ILFPGVNTFV | 0.943 | 1 | SB | VP2-3 | A0212 |
| 5 | ALLGDLVASV | 0.935 | 2 | SB | VP2-3 | A0212 |
| 195 | FLEETTWTIV | 0.906 | 2 | SB | VP2-3 | A0212 |
| 299 | GLYGTVTPAL | 0.904 | 2 | SB | VP2-3 | A0212 |
| 155 | SLFATISQAL | 0.880 | 3 | SB | VP2-3 | A0212 |
| 260 | RMDLRNKESV | 0.826 | 6 | SB | VP2-3 | A0212 |
| 220 | NLSPIRPSMV | 0.779 | 10 | SB | VP2-3 | A0212 |
| 112 | GLYQQSGMAL | 0.778 | 11 | SB | VP2-3 | A0212 |
| 295 | PLLLGLYGTV | 0.757 | 13 | SB | VP2-3 | A0212 |
| 191 | SLARFLEETT | 0.661 | 39 | SB | VP2-3 | A0212 |
| 61 | GLTPQTYAVI | 0.654 | 42 | SB | VP2-3 | A0212 |
| 163 | ALWHVIRDDI | 0.638 | 50 | WB | VP2-3 | A0212 |
| 128 | EYYDILFPGV | 0.616 | 63 | WB | VP2-3 | A0212 |
| 146 | YLDPRHWGPS | 0.615 | 64 | WB | VP2-3 | A0212 |
| 114 | YQQSGMALEL | 0.540 | 145 | WB | VP2-3 | A0212 |
| 296 | LLLGLYGTVT | 0.537 | 149 | WB | VP2-3 | A0212 |
| 102 | SDWDHKVSTV | 0.537 | 150 | WB | VP2-3 | A0212 |
| 231 | QVAEREGTHV | 0.480 | 278 | WB | VP2-3 | A0212 |
| 292 | WMLPLLLGLY | 0.456 | 358 | WB | VP2-3 | A0212 |
| 158 | ATISQALWHV | 0.442 | 419 | WB | VP2-3 | A0212 |
| 99 | RFFSDWDHKV | 0.441 | 423 | WB | VP2-3 | A0212 |
| 213 | YIQDYYSNLS | 0.431 | 472 | WB | VP2-3 | A0212 |
| 132 | ILFPGVNTFV | 0.955 | 1 | SB | VP2-3 | A0216 |
| 5 | ALLGDLVASV | 0.929 | 2 | SB | VP2-3 | A0216 |
| 299 | GLYGTVTPAL | 0.896 | 3 | SB | VP2-3 | A0216 |
| 195 | FLEETTWTIV | 0.888 | 3 | SB | VP2-3 | A0216 |
| 220 | NLSPIRPSMV | 0.866 | 4 | SB | VP2-3 | A0216 |
| 155 | SLFATISQAL | 0.857 | 4 | SB | VP2-3 | A0216 |

TABLE J-continued

Prediction of BK virus VP2-3 protein specific MHC
class1, 8-, 9-, 10-, 11-mer peptide binders for
42 MHC class 1 alleles (see FIG. 11) using the
www.cbs.dtu.dk/services/NetMHC/ database.
The MHC class 1 molecules for which no binders were
found are not listed.

| pos | peptide | logscore | affinity(nM) | Bind Level | Protein Name | Allele |
|---|---|---|---|---|---|---|
| 295 | PLLLGLYGTV | 0.819 | 7 | SB | VP2-3 | A0216 |
| 260 | RMDLRNKESV | 0.787 | 9 | SB | VP2-3 | A0216 |
| 112 | GLYQQSGMAL | 0.782 | 10 | SB | VP2-3 | A0216 |
| 61 | GLTPQTYAVI | 0.651 | 43 | SB | VP2-3 | A0216 |
| 191 | SLARFLEETT | 0.648 | 45 | SB | VP2-3 | A0216 |
| 158 | ATISQALWHV | 0.620 | 60 | WB | VP2-3 | A0216 |
| 102 | SDWDHKVSTV | 0.575 | 99 | WB | VP2-3 | A0216 |
| 163 | ALWHVIRDDI | 0.562 | 114 | WB | VP2-3 | A0216 |
| 231 | QVAEREGTHV | 0.553 | 125 | WB | VP2-3 | A0216 |
| 128 | EYYDILFPGV | 0.552 | 126 | WB | VP2-3 | A0216 |
| 38 | EVQIASLATV | 0.550 | 130 | WB | VP2-3 | A0216 |
| 223 | PIRPSMVRQV | 0.520 | 179 | WB | VP2-3 | A0216 |
| 43 | SLATVEGITT | 0.498 | 229 | WB | VP2-3 | A0216 |
| 99 | RFFSDWDHKV | 0.498 | 229 | WB | VP2-3 | A0216 |
| 171 | DIPAITSQEL | 0.485 | 262 | WB | VP2-3 | A0216 |
| 87 | VTGISSLAQV | 0.455 | 363 | WB | VP2-3 | A0216 |
| 16 | EAAAATGFSV | 0.451 | 379 | WB | VP2-3 | A0216 |
| 114 | YQQSGMALEL | 0.446 | 401 | WB | VP2-3 | A0216 |
| 78 | AGFAALIQTV | 0.438 | 434 | WB | VP2-3 | A0216 |
| 3 | ALALLGDLVA | 0.434 | 456 | WB | VP2-3 | A0216 |
| 59 | AIGLTPQTYA | 0.433 | 460 | WB | VP2-3 | A0216 |
| 296 | LLLGLYGTVT | 0.427 | 492 | WB | VP2-3 | A0216 |
| 5 | ALLGDLVASV | 0.918 | 2 | SB | VP2-3 | A0219 |
| 195 | FLEETTWTIV | 0.849 | 5 | SB | VP2-3 | A0219 |
| 299 | GLYGTVTPAL | 0.826 | 6 | SB | VP2-3 | A0219 |
| 220 | NLSPIRPSMV | 0.768 | 12 | SB | VP2-3 | A0219 |
| 155 | SLFATISQAL | 0.750 | 14 | SB | VP2-3 | A0219 |
| 260 | RMDLRNKESV | 0.698 | 26 | SB | VP2-3 | A0219 |
| 295 | PLLLGLYGTV | 0.664 | 37 | SB | VP2-3 | A0219 |
| 61 | GLTPQTYAVI | 0.545 | 137 | WB | VP2-3 | A0219 |
| 114 | YQQSGMALEL | 0.523 | 175 | WB | VP2-3 | A0219 |
| 128 | EYYDILFPGV | 0.521 | 177 | WB | VP2-3 | A0219 |
| 159 | TISQALWHVI | 0.498 | 228 | WB | VP2-3 | A0219 |
| 16 | EAAAATGFSV | 0.480 | 277 | WB | VP2-3 | A0219 |
| 112 | GLYQQSGMAL | 0.441 | 424 | WB | VP2-3 | A0219 |
| 158 | ATISQALWHV | 0.439 | 430 | WB | VP2-3 | A0219 |
| 268 | SVHSGEFIEK | 0.544 | 139 | WB | VP2-3 | A0301 |
| 329 | KAKGTRASAK | 0.506 | 208 | WB | VP2-3 | A0301 |
| 320 | RRVSRGSSQK | 0.471 | 306 | WB | VP2-3 | A0301 |
| 202 | TIVNAPINFY | 0.464 | 331 | WB | VP2-3 | A0301 |
| 292 | WMLPLLLGLY | 0.456 | 358 | WB | VP2-3 | A0301 |
| 268 | SVHSGEFIEK | 0.783 | 10 | SB | VP2-3 | A1101 |
| 257 | VTQRMDLRNK | 0.698 | 26 | SB | VP2-3 | A1101 |
| 160 | ISQALWHVIR | 0.561 | 115 | WB | VP2-3 | A1101 |
| 329 | KAKGTRASAK | 0.536 | 152 | WB | VP2-3 | A1101 |
| 202 | TIVNAPINFY | 0.497 | 230 | WB | VP2-3 | A1101 |
| 90 | ISSLAQVGYR | 0.464 | 329 | WB | VP2-3 | A1101 |
| 212 | NYIQDYYSNL | 0.652 | 43 | SB | VP2-3 | A2301 |
| 186 | RFFRDSLARF | 0.651 | 43 | SB | VP2-3 | A2301 |
| 194 | RFLEETTWTI | 0.548 | 132 | WB | VP2-3 | A2301 |
| 201 | WTIVNAPINF | 0.547 | 135 | WB | VP2-3 | A2301 |
| 310 | AYEDGPNQKK | 0.490 | 250 | WB | VP2-3 | A2301 |
| 245 | TYSIDNADSI | 0.489 | 252 | WB | VP2-3 | A2301 |
| 91 | SSLAQVGYRF | 0.461 | 340 | WB | VP2-3 | A2301 |
| 179 | ELQRRTERFF | 0.429 | 482 | WB | VP2-3 | A2301 |
| 212 | NYIQDYYSNL | 0.650 | 44 | SB | VP2-3 | A2402 |
| 194 | RFLEETTWTI | 0.609 | 69 | WB | VP2-3 | A2402 |
| 151 | HWGPSLFATI | 0.540 | 145 | WB | VP2-3 | A2402 |
| 245 | TYSIDNADSI | 0.529 | 162 | WB | VP2-3 | A2402 |
| 186 | RFFRDSLARF | 0.484 | 266 | WB | VP2-3 | A2402 |
| 156 | LFATISQALW | 0.476 | 290 | WB | VP2-3 | A2402 |
| 194 | RFLEETTWTI | 0.667 | 36 | SB | VP2-3 | A2403 |
| 186 | RFFRDSLARF | 0.659 | 39 | SB | VP2-3 | A2403 |
| 212 | NYIQDYYSNL | 0.619 | 62 | WB | VP2-3 | A2403 |

TABLE J-continued

Prediction of BK virus VP2-3 protein specific MHC
class1, 8-, 9-, 10-, 11-mer peptide binders for
42 MHC class 1 alleles (see FIG. 11) using the
www.cbs.dtu.dk/services/NetMHC/ database.
The MHC class 1 molecules for which no binders were
found are not listed.

| pos | peptide | logscore | affinity(nM) | Bind Level | Protein Name | Allele |
|---|---|---|---|---|---|---|
| 245 | TYSIDNADSI | 0.461 | 341 | WB | VP2-3 | A2403 |
| 291 | QWMLPLLLGL | 0.429 | 481 | WB | VP2-3 | A2403 |
| 202 | TIVNAPINFY | 0.620 | 60 | WB | VP2-3 | A2601 |
| 252 | DSIEEVTQRM | 0.617 | 63 | WB | VP2-3 | A2601 |
| 202 | TIVNAPINFY | 0.801 | 8 | SB | VP2-3 | A2602 |
| 302 | GTVTPALEAY | 0.771 | 11 | SB | VP2-3 | A2602 |
| 287 | RTAPQWMLPL | 0.760 | 13 | SB | VP2-3 | A2602 |
| 201 | WTIVNAPINF | 0.744 | 15 | SB | VP2-3 | A2602 |
| 179 | ELQRRTERFF | 0.735 | 17 | SB | VP2-3 | A2602 |
| 171 | DIPAITSQEL | 0.532 | 158 | WB | VP2-3 | A2602 |
| 166 | HVIRDDIPAI | 0.531 | 159 | WB | VP2-3 | A2602 |
| 131 | DILFPGVNTF | 0.488 | 253 | WB | VP2-3 | A2602 |
| 38 | EVQIASLATV | 0.471 | 304 | WB | VP2-3 | A2602 |
| 209 | NFYNYIQDYY | 0.572 | 102 | WB | VP2-3 | A2902 |
| 204 | VNAPINFYNY | 0.549 | 131 | WB | VP2-3 | A2902 |
| 292 | WMLPLLLGLY | 0.547 | 134 | WB | VP2-3 | A2902 |
| 329 | KAKGTRASAK | 0.783 | 10 | SB | VP2-3 | A3001 |
| 322 | VSRGSSQKAK | 0.757 | 13 | SB | VP2-3 | A3001 |
| 268 | SVHSGEFIEK | 0.678 | 32 | SB | VP2-3 | A3001 |
| 180 | LQRRTERFFR | 0.485 | 263 | WB | VP2-3 | A3001 |
| 237 | GTHVNFGHTY | 0.479 | 281 | WB | VP2-3 | A3001 |
| 89 | GISSLAQVGY | 0.518 | 184 | WB | VP2-3 | A3002 |
| 292 | WMLPLLLGLY | 0.511 | 198 | WB | VP2-3 | A3002 |
| 209 | NFYNYIQDYY | 0.475 | 292 | WB | VP2-3 | A3002 |
| 202 | TIVNAPINFY | 0.437 | 443 | WB | VP2-3 | A3002 |
| 180 | LQRRTERFFR | 0.756 | 14 | SB | VP2-3 | A3101 |
| 334 | RASAKTTNKR | 0.645 | 46 | SB | VP2-3 | A3101 |
| 337 | AKTTNKRRSR | 0.606 | 71 | WB | VP2-3 | A3101 |
| 160 | ISQALWHVIR | 0.591 | 83 | WB | VP2-3 | A3101 |
| 174 | AITSQELQRR | 0.577 | 97 | WB | VP2-3 | A3101 |
| 177 | SQELQRRTER | 0.543 | 140 | WB | VP2-3 | A3101 |
| 329 | KAKGTRASAK | 0.520 | 180 | WB | VP2-3 | A3101 |
| 90 | ISSLAQVGYR | 0.491 | 246 | WB | VP2-3 | A3101 |
| 340 | TNKRRSRSSR | 0.489 | 252 | WB | VP2-3 | A3101 |
| 226 | PSMVRQVAER | 0.471 | 305 | WB | VP2-3 | A3101 |
| 335 | ASAKTTNKRR | 0.455 | 363 | WB | VP2-3 | A3101 |
| 315 | PNQKKRRVSR | 0.448 | 393 | WB | VP2-3 | A3101 |
| 216 | DYYSNLSPIR | 0.588 | 86 | WB | VP2-3 | A3301 |
| 180 | LQRRTERFFR | 0.560 | 116 | WB | VP2-3 | A3301 |
| 160 | ISQALWHVIR | 0.507 | 206 | WB | VP2-3 | A3301 |
| 278 | TIAPGGANQR | 0.743 | 16 | SB | VP2-3 | A6801 |
| 309 | EAYEDGPNQK | 0.741 | 16 | SB | VP2-3 | A6801 |
| 90 | ISSLAQVGYR | 0.713 | 22 | SB | VP2-3 | A6801 |
| 216 | DYYSNLSPIR | 0.707 | 23 | SB | VP2-3 | A6801 |
| 268 | SVHSGEFIEK | 0.645 | 46 | SB | VP2-3 | A6801 |
| 185 | ERFFRDSLAR | 0.541 | 142 | WB | VP2-3 | A6801 |
| 334 | RASAKTTNKR | 0.535 | 152 | WB | VP2-3 | A6801 |
| 202 | TIVNAPINFY | 0.532 | 158 | WB | VP2-3 | A6801 |
| 160 | ISQALWHVIR | 0.498 | 228 | WB | VP2-3 | A6801 |
| 255 | EEVTQRMDLR | 0.495 | 237 | WB | VP2-3 | A6801 |
| 209 | NFYNYIQDYY | 0.464 | 329 | WB | VP2-3 | A6801 |
| 221 | LSPIRPSMVR | 0.439 | 434 | WB | VP2-3 | A6801 |
| 16 | EAAAATGFSV | 0.886 | 3 | SB | VP2-3 | A6802 |
| 199 | TTWTIVNAPI | 0.877 | 3 | SB | VP2-3 | A6802 |
| 32 | EAAAAIEVQI | 0.797 | 8 | SB | VP2-3 | A6802 |
| 138 | NTFVNNIQYL | 0.763 | 12 | SB | VP2-3 | A6802 |
| 239 | HVNFGHTYSI | 0.707 | 23 | SB | VP2-3 | A6802 |
| 287 | RTAPQWMLPL | 0.692 | 28 | SB | VP2-3 | A6802 |
| 24 | SVAEIAAGEA | 0.669 | 36 | SB | VP2-3 | A6802 |
| 51 | TTTSEAIAAI | 0.664 | 38 | SB | VP2-3 | A6802 |
| 205 | NAPINFYNYI | 0.663 | 38 | SB | VP2-3 | A6802 |
| 27 | EIAAGEAAAA | 0.642 | 47 | SB | VP2-3 | A6802 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 48 | EGITTTSEAI | 0.641 | 48 | SB | VP2-3 | A6802 |
| 85 | QTVTGISSLA | 0.637 | 50 | WB | VP2-3 | A6802 |
| 38 | EVQIASLATV | 0.608 | 69 | WB | VP2-3 | A6802 |
| 171 | DIPAITSQEL | 0.587 | 86 | WB | VP2-3 | A6802 |
| 10 | LVASVSEAAA | 0.570 | 105 | WB | VP2-3 | A6802 |
| 128 | EYYDILFPGV | 0.563 | 113 | WB | VP2-3 | A6802 |
| 220 | NLSPIRPSMV | 0.549 | 130 | WB | VP2-3 | A6802 |
| 132 | ILFPGVNTFV | 0.545 | 138 | WB | VP2-3 | A6802 |
| 166 | HVIRDDIPAI | 0.535 | 152 | WB | VP2-3 | A6802 |
| 155 | SLFATISQAL | 0.516 | 188 | WB | VP2-3 | A6802 |
| 159 | TISQALWHVI | 0.500 | 223 | WB | VP2-3 | A6802 |
| 28 | IAAGEAAAAI | 0.487 | 257 | WB | VP2-3 | A6802 |
| 231 | QVAEREGTHV | 0.474 | 296 | WB | VP2-3 | A6802 |
| 158 | ATISQALWHV | 0.457 | 357 | WB | VP2-3 | A6802 |
| 41 | IASLATVEGI | 0.435 | 450 | WB | VP2-3 | A6802 |
| 16 | EAAAATGFSV | 0.809 | 7 | SB | VP2-3 | A6901 |
| 199 | TTWTIVNAPI | 0.775 | 11 | SB | VP2-3 | A6901 |
| 128 | EYYDILFPGV | 0.674 | 34 | SB | VP2-3 | A6901 |
| 38 | EVQIASLATV | 0.655 | 41 | SB | VP2-3 | A6901 |
| 138 | NTFVNNIQYL | 0.647 | 45 | SB | VP2-3 | A6901 |
| 158 | ATISQALWHV | 0.607 | 69 | WB | VP2-3 | A6901 |
| 32 | EAAAAIEVQI | 0.603 | 73 | WB | VP2-3 | A6901 |
| 27 | EIAAGEAAAA | 0.569 | 105 | WB | VP2-3 | A6901 |
| 239 | HVNFGHTYSI | 0.516 | 187 | WB | VP2-3 | A6901 |
| 287 | RTAPQWMLPL | 0.511 | 198 | WB | VP2-3 | A6901 |
| 166 | HVIRDDIPAI | 0.505 | 210 | WB | VP2-3 | A6901 |
| 132 | ILFPGVNTFV | 0.497 | 229 | WB | VP2-3 | A6901 |
| 231 | QVAEREGTHV | 0.482 | 271 | WB | VP2-3 | A6901 |
| 5 | ALLGDLVASV | 0.460 | 346 | WB | VP2-3 | A6901 |
| 51 | TTTSEAIAAI | 0.451 | 381 | WB | VP2-3 | A6901 |
| 87 | VTGISSLAQV | 0.440 | 426 | WB | VP2-3 | A6901 |
| 288 | TAPQWMLPLL | 0.437 | 441 | WB | VP2-3 | A6901 |
| 24 | SVAEIAAGEA | 0.434 | 456 | WB | VP2-3 | A6901 |
| 289 | APQWMLPLLL | 0.641 | 48 | SB | VP2-3 | B0702 |
| 225 | RPSMVRQVAE | 0.621 | 60 | WB | VP2-3 | B0702 |
| 148 | DPRHWGPSLF | 0.517 | 185 | WB | VP2-3 | B0702 |
| 73 | APGAIAGFAA | 0.513 | 194 | WB | VP2-3 | B0702 |
| 292 | WMLPLLLGLY | 0.543 | 140 | WB | VP2-3 | B1501 |
| 115 | QQSGMALELF | 0.542 | 141 | WB | VP2-3 | B1501 |
| 114 | YQQSGMALEL | 0.537 | 150 | WB | VP2-3 | B1501 |
| 84 | IQTVTGISSL | 0.522 | 176 | WB | VP2-3 | B1501 |
| 155 | SLFATISQAL | 0.494 | 238 | WB | VP2-3 | B1501 |
| 230 | RQVAEREGTH | 0.480 | 276 | WB | VP2-3 | B1501 |
| 92 | SLAQVGYRFF | 0.475 | 291 | WB | VP2-3 | B1501 |
| 58 | AAIGLTPQTY | 0.469 | 311 | WB | VP2-3 | B1501 |
| 237 | GTHVNFGHTY | 0.447 | 398 | WB | VP2-3 | B1501 |
| 299 | GLYGTVTPAL | 0.434 | 457 | WB | VP2-3 | B1501 |
| 201 | WTIVNAPINF | 0.426 | 497 | WB | VP2-3 | B1501 |
| 233 | AEREGTHVNF | 0.711 | 22 | SB | VP2-3 | B1801 |
| 121 | LELFNPDEYY | 0.515 | 189 | WB | VP2-3 | B1801 |
| 178 | QELQRRTERF | 0.507 | 207 | WB | VP2-3 | B1801 |
| 37 | IEVQIASLAT | 0.487 | 257 | WB | VP2-3 | B1801 |
| 148 | DPRHWGPSLF | 0.482 | 273 | WB | VP2-3 | B1801 |
| 292 | WMLPLLLGLY | 0.445 | 407 | WB | VP2-3 | B1801 |
| 320 | RRVSRGSSQK | 0.631 | 54 | WB | VP2-3 | B2705 |
| 98 | YRFFSDWDHK | 0.450 | 383 | WB | VP2-3 | B2705 |
| 125 | NPDEYYDILF | 0.757 | 13 | SB | VP2-3 | B3501 |
| 58 | AAIGLTPQTY | 0.566 | 109 | WB | VP2-3 | B3501 |
| 148 | DPRHWGPSLF | 0.544 | 138 | WB | VP2-3 | B3501 |
| 28 | IAAGEAAAAI | 0.514 | 192 | WB | VP2-3 | B3501 |
| 202 | TIVNAPINFY | 0.476 | 289 | WB | VP2-3 | B3501 |
| 67 | YAVIAGAPGA | 0.456 | 358 | WB | VP2-3 | B3501 |
| 292 | WMLPLLLGLY | 0.447 | 397 | WB | VP2-3 | B3501 |
| 209 | NFYNYIQDYY | 0.429 | 480 | WB | VP2-3 | B3501 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 114 | YQQSGMALEL | 0.466 | 323 | WB | VP2-3 | B3901 |
| 233 | AEREGTHVNF | 0.508 | 204 | WB | VP2-3 | B4001 |
| 254 | IEEVTQRMDL | 0.497 | 230 | WB | VP2-3 | B4001 |
| 266 | KESVHSGEFI | 0.457 | 355 | WB | VP2-3 | B4002 |
| 233 | AEREGTHVNF | 0.450 | 382 | WB | VP2-3 | B4002 |
| 26 | AEIAAGEAAA | 0.461 | 340 | WB | VP2-3 | B4403 |
| 26 | AEIAAGEAAA | 0.637 | 50 | WB | VP2-3 | B4501 |
| 197 | EETTWTIVNA | 0.481 | 273 | WB | VP2-3 | B4501 |
| 233 | AEREGTHVNF | 0.474 | 297 | WB | VP2-3 | B4501 |
| 294 | LPLLLGLYGT | 0.583 | 91 | WB | VP2-3 | B5101 |
| 289 | APQWMLPLLL | 0.580 | 94 | WB | VP2-3 | B5301 |
| 125 | NPDEYYDILF | 0.476 | 289 | WB | VP2-3 | B5301 |
| 294 | LPLLLGLYGT | 0.816 | 7 | SB | VP2-3 | B5401 |
| 73 | APGAIAGFAA | 0.666 | 36 | SB | VP2-3 | B5401 |
| 134 | FPGVNTFVNN | 0.529 | 163 | WB | VP2-3 | B5401 |
| 192 | LARFLEETTW | 0.441 | 422 | WB | VP2-3 | B5701 |
| 283 | GANQRTAPQW | 0.661 | 39 | SB | VP2-3 | B5801 |
| 192 | LARFLEETTW | 0.570 | 105 | WB | VP2-3 | B5801 |
| 201 | WTIVNAPINF | 0.543 | 139 | WB | VP2-3 | B5801 |
| 156 | LFATISQALW | 0.490 | 247 | WB | VP2-3 | B5801 |
| 287 | RTAPQWMLPL | 0.462 | 337 | WB | VP2-3 | B5801 |
| 91 | SSLAQVGYRF | 0.439 | 432 | WB | VP2-3 | B5801 |
| 11-mers | | | | | | |
| 201 | WTIVNAPINFY | 0.505 | 212 | WB | VP2-3 | A0101 |
| 146 | YLDPRHWGPSL | 0.844 | 5 | SB | VP2-3 | A0201 |
| 247 | SIDNADSIEEV | 0.608 | 69 | WB | VP2-3 | A0201 |
| 157 | FATISQALWHV | 0.499 | 226 | WB | VP2-3 | A0201 |
| 297 | LLGLYGTVTPA | 0.443 | 413 | WB | VP2-3 | A0201 |
| 61 | GLTPQTYAVIA | 0.440 | 428 | WB | VP2-3 | A0201 |
| 80 | FAALIQTVTGI | 0.740 | 16 | SB | VP2-3 | A0202 |
| 146 | YLDPRHWGPSL | 0.686 | 29 | SB | VP2-3 | A0202 |
| 297 | LLGLYGTVTPA | 0.612 | 66 | WB | VP2-3 | A0202 |
| 293 | MLPLLLGLYGT | 0.607 | 69 | WB | VP2-3 | A0202 |
| 61 | GLTPQTYAVIA | 0.598 | 77 | WB | VP2-3 | A0202 |
| 24 | SVAEIAAGEAA | 0.577 | 96 | WB | VP2-3 | A0202 |
| 157 | FATISQALWHV | 0.572 | 102 | WB | VP2-3 | A0202 |
| 52 | TTSEAIAAIGL | 0.559 | 117 | WB | VP2-3 | A0202 |
| 40 | QIASLATVEGI | 0.554 | 124 | WB | VP2-3 | A0202 |
| 287 | RTAPQWMLPLL | 0.542 | 142 | WB | VP2-3 | A0202 |
| 247 | SIDNADSIEEV | 0.539 | 146 | WB | VP2-3 | A0202 |
| 92 | SLAQVGYRFFS | 0.525 | 170 | WB | VP2-3 | A0202 |
| 10 | LVASVSEAAAA | 0.525 | 170 | WB | VP2-3 | A0202 |
| 59 | AIGLTPQTYAV | 0.518 | 183 | WB | VP2-3 | A0202 |
| 86 | TVTGISSLAQV | 0.493 | 241 | WB | VP2-3 | A0202 |
| 43 | SLATVEGITTT | 0.487 | 258 | WB | VP2-3 | A0202 |
| 3 | ALALLGDLVAS | 0.480 | 278 | WB | VP2-3 | A0202 |
| 34 | AAAIEVQIASL | 0.471 | 305 | WB | VP2-3 | A0202 |
| 83 | LIQTVTGISSL | 0.467 | 318 | WB | VP2-3 | A0202 |
| 1 | GAALALLGDLV | 0.467 | 320 | WB | VP2-3 | A0202 |
| 244 | HTYSIDNADSI | 0.466 | 324 | WB | VP2-3 | A0202 |
| 155 | SLFATISQALW | 0.458 | 350 | WB | VP2-3 | A0202 |
| 274 | FIEKTIAPGGA | 0.427 | 490 | WB | VP2-3 | A0202 |
| 140 | FVNNIQYLDPR | 0.427 | 492 | WB | VP2-3 | A0202 |
| 146 | YLDPRHWGPSL | 0.801 | 8 | SB | VP2-3 | A0203 |
| 297 | LLGLYGTVTPA | 0.759 | 13 | SB | VP2-3 | A0203 |
| 83 | LIQTVTGISSL | 0.719 | 20 | SB | VP2-3 | A0203 |
| 293 | MLPLLLGLYGT | 0.711 | 22 | SB | VP2-3 | A0203 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 80 | FAALIQTVTGI | 0.669 | 36 | SB | VP2-3 | A0203 |
| 43 | SLATVEGITTT | 0.657 | 40 | SB | VP2-3 | A0203 |
| 59 | AIGLTPQTYAV | 0.639 | 49 | SB | VP2-3 | A0203 |
| 61 | GLTPQTYAVIA | 0.610 | 67 | WB | VP2-3 | A0203 |
| 18 | AAATGFSVAEI | 0.562 | 114 | WB | VP2-3 | A0203 |
| 40 | QIASLATVEGI | 0.559 | 118 | WB | VP2-3 | A0203 |
| 86 | TVTGISSLAQV | 0.542 | 141 | WB | VP2-3 | A0203 |
| 287 | RTAPQWMLPLL | 0.526 | 168 | WB | VP2-3 | A0203 |
| 274 | FIEKTIAPGGA | 0.518 | 183 | WB | VP2-3 | A0203 |
| 10 | LVASVSEAAAA | 0.513 | 193 | WB | VP2-3 | A0203 |
| 4 | LALLGDLVASV | 0.490 | 248 | WB | VP2-3 | A0203 |
| 24 | SVAEIAAGEAA | 0.488 | 253 | WB | VP2-3 | A0203 |
| 34 | AAAIEVQIASL | 0.478 | 283 | WB | VP2-3 | A0203 |
| 327 | SQKAKGTRASA | 0.474 | 294 | WB | VP2-3 | A0203 |
| 247 | SIDNADSIEEV | 0.455 | 365 | WB | VP2-3 | A0203 |
| 157 | FATISQALWHV | 0.447 | 396 | WB | VP2-3 | A0203 |
| 101 | FSDWDHKVSTV | 0.447 | 398 | WB | VP2-3 | A0203 |
| 67 | YAVIAGAPGAI | 0.430 | 477 | WB | VP2-3 | A0203 |
| 146 | YLDPRHWGPSL | 0.615 | 64 | WB | VP2-3 | A0204 |
| 29 | AAGEAAAAIEV | 0.520 | 180 | WB | VP2-3 | A0204 |
| 59 | AIGLTPQTYAV | 0.517 | 185 | WB | VP2-3 | A0204 |
| 297 | LLGLYGTVTPA | 0.495 | 236 | WB | VP2-3 | A0204 |
| 247 | SIDNADSIEEV | 0.488 | 255 | WB | VP2-3 | A0204 |
| 43 | SLATVEGITTT | 0.466 | 322 | WB | VP2-3 | A0204 |
| 146 | YLDPRHWGPSL | 0.882 | 3 | SB | VP2-3 | A0206 |
| 214 | IQDYYSNLSPI | 0.767 | 12 | SB | VP2-3 | A0206 |
| 230 | RQVAEREGTHV | 0.764 | 12 | SB | VP2-3 | A0206 |
| 157 | FATISQALWHV | 0.747 | 15 | SB | VP2-3 | A0206 |
| 114 | YQQSGMALELF | 0.741 | 16 | SB | VP2-3 | A0206 |
| 247 | SIDNADSIEEV | 0.659 | 40 | SB | VP2-3 | A0206 |
| 29 | AAGEAAAAIEV | 0.632 | 53 | WB | VP2-3 | A0206 |
| 287 | RTAPQWMLPLL | 0.614 | 64 | WB | VP2-3 | A0206 |
| 80 | FAALIQTVTGI | 0.614 | 65 | WB | VP2-3 | A0206 |
| 35 | AAIEVQIASLA | 0.587 | 86 | WB | VP2-3 | A0206 |
| 37 | IEVQIASLATV | 0.586 | 88 | WB | VP2-3 | A0206 |
| 24 | SVAEIAAGEAA | 0.580 | 93 | WB | VP2-3 | A0206 |
| 4 | LALLGDLVASV | 0.580 | 94 | WB | VP2-3 | A0206 |
| 101 | FSDWDHKVSTV | 0.577 | 97 | WB | VP2-3 | A0206 |
| 15 | SEAAAATGFSV | 0.572 | 102 | WB | VP2-3 | A0206 |
| 86 | TVTGISSLAQV | 0.557 | 120 | WB | VP2-3 | A0206 |
| 59 | AIGLTPQTYAV | 0.537 | 150 | WB | VP2-3 | A0206 |
| 293 | MLPLLLGLYGT | 0.536 | 151 | WB | VP2-3 | A0206 |
| 58 | AAIGLTPQTYA | 0.531 | 159 | WB | VP2-3 | A0206 |
| 10 | LVASVSEAAAA | 0.524 | 173 | WB | VP2-3 | A0206 |
| 18 | AAATGFSVAEI | 0.509 | 203 | WB | VP2-3 | A0206 |
| 68 | AVIAGAPGAIA | 0.503 | 215 | WB | VP2-3 | A0206 |
| 84 | IQTVTGISSLA | 0.500 | 223 | WB | VP2-3 | A0206 |
| 52 | TTSEAIAAIGL | 0.457 | 357 | WB | VP2-3 | A0206 |
| 1 | GAALALLGDLV | 0.454 | 366 | WB | VP2-3 | A0206 |
| 297 | LLGLYGTVTPA | 0.442 | 420 | WB | VP2-3 | A0206 |
| 13 | SVSEAAAATGF | 0.441 | 423 | WB | VP2-3 | A0206 |
| 45 | ATVEGITTTSE | 0.429 | 481 | WB | VP2-3 | A0206 |
| 146 | YLDPRHWGPSL | 0.969 | 1 | SB | VP2-3 | A0211 |
| 247 | SIDNADSIEEV | 0.903 | 2 | SB | VP2-3 | A0211 |
| 86 | TVTGISSLAQV | 0.868 | 4 | SB | VP2-3 | A0211 |
| 61 | GLTPQTYAVIA | 0.808 | 7 | SB | VP2-3 | A0211 |
| 92 | SLAQVGYRFFS | 0.759 | 13 | SB | VP2-3 | A0211 |
| 59 | AIGLTPQTYAV | 0.737 | 17 | SB | VP2-3 | A0211 |
| 122 | ELFNPDEYYDI | 0.669 | 35 | SB | VP2-3 | A0211 |
| 43 | SLATVEGITTT | 0.657 | 40 | SB | VP2-3 | A0211 |
| 29 | AAGEAAAAIEV | 0.644 | 46 | SB | VP2-3 | A0211 |
| 4 | LALLGDLVASV | 0.626 | 56 | WB | VP2-3 | A0211 |
| 287 | RTAPQWMLPLL | 0.626 | 57 | WB | VP2-3 | A0211 |
| 131 | DILFPGVNTFV | 0.620 | 60 | WB | VP2-3 | A0211 |
| 101 | FSDWDHKVSTV | 0.615 | 64 | WB | VP2-3 | A0211 |
| 157 | FATISQALWHV | 0.608 | 69 | WB | VP2-3 | A0211 |
| 293 | MLPLLLGLYGT | 0.597 | 78 | WB | VP2-3 | A0211 |
| 132 | ILFPGVNTFVN | 0.565 | 110 | WB | VP2-3 | A0211 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 297 | LLGLYGTVTPA | 0.547 | 134 | WB | VP2-3 | A0211 |
| 76 | AIAGFAALIQT | 0.537 | 150 | WB | VP2-3 | A0211 |
| 292 | WMLPLLLGLYG | 0.526 | 167 | WB | VP2-3 | A0211 |
| 24 | SVAEIAAGEAA | 0.526 | 168 | WB | VP2-3 | A0211 |
| 253 | SIEEVTQRMDL | 0.525 | 170 | WB | VP2-3 | A0211 |
| 296 | LLLGLYGTVTP | 0.523 | 174 | WB | VP2-3 | A0211 |
| 98 | YRFFSDWDHKV | 0.515 | 190 | WB | VP2-3 | A0211 |
| 6 | LLGDLVASVSE | 0.504 | 213 | WB | VP2-3 | A0211 |
| 27 | EIAAGEAAAAI | 0.496 | 234 | WB | VP2-3 | A0211 |
| 194 | RFLEETTWTIV | 0.476 | 288 | WB | VP2-3 | A0211 |
| 155 | SLFATISQALW | 0.468 | 315 | WB | VP2-3 | A0211 |
| 5 | ALLGDLVASVS | 0.465 | 325 | WB | VP2-3 | A0211 |
| 83 | LIQTVTGISSL | 0.454 | 369 | WB | VP2-3 | A0211 |
| 77 | IAGFAALIQTV | 0.449 | 386 | WB | VP2-3 | A0211 |
| 278 | TIAPGGANQRT | 0.438 | 437 | WB | VP2-3 | A0211 |
| 191 | SLARFLEETTW | 0.437 | 444 | WB | VP2-3 | A0211 |
| 299 | GLYGTVTPALE | 0.429 | 482 | WB | VP2-3 | A0211 |
| 146 | YLDPRHWGPSL | 0.942 | 1 | SB | VP2-3 | A0212 |
| 247 | SIDNADSIEEV | 0.724 | 19 | SB | VP2-3 | A0212 |
| 59 | AIGLTPQTYAV | 0.677 | 32 | SB | VP2-3 | A0212 |
| 61 | GLTPQTYAVIA | 0.591 | 83 | WB | VP2-3 | A0212 |
| 43 | SLATVEGITTT | 0.566 | 109 | WB | VP2-3 | A0212 |
| 122 | ELFNPDEYYDI | 0.556 | 121 | WB | VP2-3 | A0212 |
| 4 | LALLGDLVASV | 0.541 | 143 | WB | VP2-3 | A0212 |
| 293 | MLPLLLGLYGT | 0.513 | 194 | WB | VP2-3 | A0212 |
| 6 | LLGDLVASVSE | 0.507 | 207 | WB | VP2-3 | A0212 |
| 83 | LIQTVTGISSL | 0.499 | 226 | WB | VP2-3 | A0212 |
| 253 | SIEEVTQRMDL | 0.493 | 242 | WB | VP2-3 | A0212 |
| 292 | WMLPLLLGLYG | 0.489 | 251 | WB | VP2-3 | A0212 |
| 92 | SLAQVGYRFFS | 0.479 | 281 | WB | VP2-3 | A0212 |
| 86 | TVTGISSLAQV | 0.475 | 292 | WB | VP2-3 | A0212 |
| 157 | FATISQALWHV | 0.435 | 454 | WB | VP2-3 | A0212 |
| 132 | ILFPGVNTFVN | 0.434 | 457 | WB | VP2-3 | A0212 |
| 213 | YIQDYYSNLSP | 0.433 | 464 | WB | VP2-3 | A0212 |
| 98 | YRFFSDWDHKV | 0.432 | 468 | WB | VP2-3 | A0212 |
| 296 | LLLGLYGTVTP | 0.431 | 473 | WB | VP2-3 | A0212 |
| 146 | YLDPRHWGPSL | 0.908 | 2 | SB | VP2-3 | A0216 |
| 247 | SIDNADSIEEV | 0.852 | 4 | SB | VP2-3 | A0216 |
| 86 | TVTGISSLAQV | 0.811 | 7 | SB | VP2-3 | A0216 |
| 59 | AIGLTPQTYAV | 0.755 | 14 | SB | VP2-3 | A0216 |
| 29 | AAGEAAAAIEV | 0.714 | 22 | SB | VP2-3 | A0216 |
| 92 | SLAQVGYRFFS | 0.674 | 34 | SB | VP2-3 | A0216 |
| 131 | DILFPGVNTFV | 0.671 | 35 | SB | VP2-3 | A0216 |
| 43 | SLATVEGITTT | 0.635 | 52 | WB | VP2-3 | A0216 |
| 61 | GLTPQTYAVIA | 0.633 | 53 | WB | VP2-3 | A0216 |
| 297 | LLGLYGTVTPA | 0.621 | 60 | WB | VP2-3 | A0216 |
| 83 | LIQTVTGISSL | 0.526 | 169 | WB | VP2-3 | A0216 |
| 157 | FATISQALWHV | 0.524 | 172 | WB | VP2-3 | A0216 |
| 122 | ELFNPDEYYDI | 0.508 | 205 | WB | VP2-3 | A0216 |
| 4 | LALLGDLVASV | 0.499 | 225 | WB | VP2-3 | A0216 |
| 77 | IAGFAALIQTV | 0.459 | 350 | WB | VP2-3 | A0216 |
| 76 | AIAGFAALIQT | 0.458 | 351 | WB | VP2-3 | A0216 |
| 146 | YLDPRHWGPSL | 0.941 | 1 | SB | VP2-3 | A0219 |
| 247 | SIDNADSIEEV | 0.699 | 26 | SB | VP2-3 | A0219 |
| 86 | TVTGISSLAQV | 0.670 | 35 | SB | VP2-3 | A0219 |
| 59 | AIGLTPQTYAV | 0.566 | 109 | WB | VP2-3 | A0219 |
| 4 | LALLGDLVASV | 0.537 | 149 | WB | VP2-3 | A0219 |
| 157 | FATISQALWHV | 0.530 | 161 | WB | VP2-3 | A0219 |
| 83 | LIQTVTGISSL | 0.499 | 225 | WB | VP2-3 | A0219 |
| 332 | GTRASAKTTNK | 0.622 | 59 | WB | VP2-3 | A0301 |
| 321 | RVSRGSSQKAK | 0.580 | 93 | WB | VP2-3 | A0301 |
| 203 | IVNAPINFYNY | 0.501 | 220 | WB | VP2-3 | A0301 |
| 339 | TTNKRRSRSSR | 0.487 | 258 | WB | VP2-3 | A0301 |
| 203 | IVNAPINFYNY | 0.678 | 32 | SB | VP2-3 | A1101 |
| 339 | TTNKRRSRSSR | 0.651 | 43 | SB | VP2-3 | A1101 |
| 277 | KTIAPGGANQR | 0.634 | 52 | WB | VP2-3 | A1101 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 321 | RVSRGSSQKAK | 0.626 | 57 | WB | VP2-3 | A1101 |
| 332 | GTRASAKTTNK | 0.606 | 70 | WB | VP2-3 | A1101 |
| 89 | GISSLAQVGYR | 0.521 | 177 | WB | VP2-3 | A1101 |
| 136 | GVNTFVNNIQY | 0.517 | 185 | WB | VP2-3 | A1101 |
| 159 | TISQALWHVIR | 0.481 | 274 | WB | VP2-3 | A1101 |
| 176 | TSQELQRRTER | 0.476 | 289 | WB | VP2-3 | A1101 |
| 140 | FVNNIQYLDPR | 0.469 | 313 | WB | VP2-3 | A1101 |
| 267 | ESVHSGEFIEK | 0.437 | 442 | WB | VP2-3 | A1101 |
| 200 | TWTIVNAPINF | 0.630 | 54 | WB | VP2-3 | A2301 |
| 97 | GYRFFSDWDHK | 0.623 | 59 | WB | VP2-3 | A2301 |
| 113 | LYQQSGMALEL | 0.597 | 77 | WB | VP2-3 | A2301 |
| 186 | RFFRDSLARFL | 0.449 | 389 | WB | VP2-3 | A2301 |
| 200 | TWTIVNAPINF | 0.612 | 66 | WB | VP2-3 | A2402 |
| 113 | LYQQSGMALEL | 0.533 | 156 | WB | VP2-3 | A2402 |
| 113 | LYQQSGMALEL | 0.750 | 14 | SB | VP2-3 | A2403 |
| 186 | RFFRDSLARFL | 0.485 | 263 | WB | VP2-3 | A2403 |
| 91 | SSLAQVGYRFF | 0.459 | 347 | WB | VP2-3 | A2403 |
| 201 | WTIVNAPINFY | 0.672 | 34 | SB | VP2-3 | A2601 |
| 109 | STVGLYQQSGM | 0.619 | 61 | WB | VP2-3 | A2601 |
| 201 | WTIVNAPINFY | 0.930 | 2 | SB | VP2-3 | A2602 |
| 109 | STVGLYQQSGM | 0.769 | 12 | SB | VP2-3 | A2602 |
| 27 | EIAAGEAAAAI | 0.765 | 12 | SB | VP2-3 | A2602 |
| 287 | RTAPQWMLPLL | 0.678 | 32 | SB | VP2-3 | A2602 |
| 203 | IVNAPINFYNY | 0.672 | 34 | SB | VP2-3 | A2602 |
| 13 | SVSEAAAATGF | 0.566 | 109 | WB | VP2-3 | A2602 |
| 88 | TGISSLAQVGY | 0.498 | 228 | WB | VP2-3 | A2602 |
| 291 | QWMLPLLLGLY | 0.553 | 126 | WB | VP2-3 | A2902 |
| 203 | IVNAPINFYNY | 0.517 | 185 | WB | VP2-3 | A2902 |
| 236 | EGTHVNFGHTY | 0.485 | 262 | WB | VP2-3 | A2902 |
| 208 | INFYNYIQDYY | 0.471 | 304 | WB | VP2-3 | A2902 |
| 136 | GVNTFVNNIQY | 0.468 | 317 | WB | VP2-3 | A2902 |
| 319 | KRRVSRGSSQK | 0.802 | 8 | SB | VP2-3 | A3001 |
| 332 | GTRASAKTTNK | 0.790 | 9 | SB | VP2-3 | A3001 |
| 97 | GYRFFSDWDHK | 0.743 | 16 | SB | VP2-3 | A3001 |
| 321 | RVSRGSSQKAK | 0.684 | 30 | SB | VP2-3 | A3001 |
| 203 | IVNAPINFYNY | 0.460 | 345 | WB | VP2-3 | A3002 |
| 339 | TTNKRRSRSSR | 0.837 | 5 | SB | VP2-3 | A3101 |
| 277 | KTIAPGGANQR | 0.682 | 31 | SB | VP2-3 | A3101 |
| 334 | RASAKTTNKRR | 0.664 | 37 | SB | VP2-3 | A3101 |
| 336 | SAKTTNKRRSR | 0.656 | 41 | SB | VP2-3 | A3101 |
| 140 | FVNNIQYLDPR | 0.655 | 41 | SB | VP2-3 | A3101 |
| 176 | TSQELQRRTER | 0.645 | 46 | SB | VP2-3 | A3101 |
| 179 | ELQRRTERFFR | 0.636 | 51 | WB | VP2-3 | A3101 |
| 225 | RPSMVRQVAER | 0.580 | 94 | WB | VP2-3 | A3101 |
| 324 | RGSSQKAKGTR | 0.569 | 105 | WB | VP2-3 | A3101 |
| 89 | GISSLAQVGYR | 0.567 | 108 | WB | VP2-3 | A3101 |
| 159 | TISQALWHVIR | 0.483 | 268 | WB | VP2-3 | A3101 |
| 332 | GTRASAKTTNK | 0.446 | 401 | WB | VP2-3 | A3101 |
| 220 | NLSPIRPSMVR | 0.432 | 465 | WB | VP2-3 | A3101 |
| 179 | ELQRRTERFFR | 0.812 | 7 | SB | VP2-3 | A3301 |
| 339 | TTNKRRSRSSR | 0.738 | 17 | SB | VP2-3 | A3301 |
| 140 | FVNNIQYLDPR | 0.519 | 181 | WB | VP2-3 | A3301 |
| 176 | TSQELQRRTER | 0.516 | 188 | WB | VP2-3 | A3301 |
| 220 | NLSPIRPSMVR | 0.506 | 210 | WB | VP2-3 | A3301 |
| 159 | TISQALWHVIR | 0.465 | 326 | WB | VP2-3 | A3301 |
| 339 | TTNKRRSRSSR | 0.848 | 5 | SB | VP2-3 | A6801 |
| 140 | FVNNIQYLDPR | 0.795 | 9 | SB | VP2-3 | A6801 |
| 159 | TISQALWHVIR | 0.758 | 13 | SB | VP2-3 | A6801 |
| 256 | EVTQRMDLRNK | 0.719 | 20 | SB | VP2-3 | A6801 |
| 179 | ELQRRTERFFR | 0.714 | 22 | SB | VP2-3 | A6801 |
| 309 | EAYEDGPNQKK | 0.713 | 22 | SB | VP2-3 | A6801 |

TABLE J-continued

Prediction of BK virus VP2-3 protein specific MHC
class1, 8-, 9-, 10-, 11-mer peptide binders for
42 MHC class 1 alleles (see FIG. 11) using the
www.cbs.dtu.dk/services/NetMHC/ database.
The MHC class 1 molecules for which no binders were
found are not listed.

| pos | peptide | logscore | affinity(nM) | Bind Level | Protein Name | Allele |
|---|---|---|---|---|---|---|
| 267 | ESVHSGEFIEK | 0.706 | 24 | SB | VP2-3 | A6801 |
| 220 | NLSPIRPSMVR | 0.687 | 29 | SB | VP2-3 | A6801 |
| 250 | NADSIEEVTQR | 0.655 | 41 | SB | VP2-3 | A6801 |
| 176 | TSQELQRRTER | 0.647 | 45 | SB | VP2-3 | A6801 |
| 201 | WTIVNAPINFY | 0.600 | 75 | WB | VP2-3 | A6801 |
| 89 | GISSLAQVGYR | 0.591 | 83 | WB | VP2-3 | A6801 |
| 277 | KTIAPGGANQR | 0.588 | 86 | WB | VP2-3 | A6801 |
| 172 | IPAITSQELQR | 0.515 | 190 | WB | VP2-3 | A6801 |
| 225 | RPSMVRQVAER | 0.438 | 438 | WB | VP2-3 | A6801 |
| 215 | QDYYSNLSPIR | 0.437 | 444 | WB | VP2-3 | A6801 |
| 198 | ETTWTIVNAPI | 0.863 | 4 | SB | VP2-3 | A6802 |
| 86 | TVTGISSLAQV | 0.804 | 8 | SB | VP2-3 | A6802 |
| 16 | EAAAATGFSVA | 0.777 | 11 | SB | VP2-3 | A6802 |
| 80 | FAALIQTVTGI | 0.761 | 13 | SB | VP2-3 | A6802 |
| 27 | EIAAGEAAAAI | 0.759 | 13 | SB | VP2-3 | A6802 |
| 244 | HTYSIDNADSI | 0.756 | 13 | SB | VP2-3 | A6802 |
| 52 | TTSEAIAAIGL | 0.729 | 18 | SB | VP2-3 | A6802 |
| 24 | SVAEIAAGEAA | 0.724 | 19 | SB | VP2-3 | A6802 |
| 40 | QIASLATVEGI | 0.649 | 44 | SB | VP2-3 | A6802 |
| 32 | EAAAIEVQIA | 0.633 | 52 | WB | VP2-3 | A6802 |
| 10 | LVASVSEAAAA | 0.605 | 71 | WB | VP2-3 | A6802 |
| 131 | DILFPGVNTFV | 0.561 | 115 | WB | VP2-3 | A6802 |
| 287 | RTAPQWMLPLL | 0.551 | 129 | WB | VP2-3 | A6802 |
| 259 | QRMDLRNKESV | 0.550 | 129 | WB | VP2-3 | A6802 |
| 122 | ELFNPDEYYDI | 0.549 | 131 | WB | VP2-3 | A6802 |
| 46 | TVEGITTTSEA | 0.537 | 150 | WB | VP2-3 | A6802 |
| 157 | FATISQALWHV | 0.500 | 223 | WB | VP2-3 | A6802 |
| 109 | STVGLYQQSGM | 0.495 | 235 | WB | VP2-3 | A6802 |
| 204 | VNAPINFYNYI | 0.467 | 319 | WB | VP2-3 | A6802 |
| 18 | AAATGFSVAEI | 0.465 | 326 | WB | VP2-3 | A6802 |
| 23 | FSVAEIAAGEA | 0.463 | 333 | WB | VP2-3 | A6802 |
| 15 | SEAAAATGFSV | 0.457 | 356 | WB | VP2-3 | A6802 |
| 98 | YRFFSDWDHKV | 0.453 | 371 | WB | VP2-3 | A6802 |
| 50 | ITTTSEAIAAI | 0.442 | 419 | WB | VP2-3 | A6802 |
| 67 | YAVIAGAPGAI | 0.439 | 430 | WB | VP2-3 | A6802 |
| 0 | MGAALALLGDL | 0.426 | 497 | WB | VP2-3 | A6802 |
| 198 | ETTWTIVNAPI | 0.765 | 12 | SB | VP2-3 | A6901 |
| 27 | EIAAGEAAAAI | 0.722 | 20 | SB | VP2-3 | A6901 |
| 131 | DILFPGVNTFV | 0.706 | 23 | SB | VP2-3 | A6901 |
| 157 | FATISQALWHV | 0.625 | 58 | WB | VP2-3 | A6901 |
| 52 | TTSEAIAAIGL | 0.581 | 93 | WB | VP2-3 | A6901 |
| 244 | HTYSIDNADSI | 0.559 | 117 | WB | VP2-3 | A6901 |
| 86 | TVTGISSLAQV | 0.494 | 237 | WB | VP2-3 | A6901 |
| 24 | SVAEIAAGEAA | 0.491 | 245 | WB | VP2-3 | A6901 |
| 67 | YAVIAGAPGAI | 0.465 | 326 | WB | VP2-3 | A6901 |
| 146 | YLDPRHWGPSL | 0.462 | 338 | WB | VP2-3 | A6901 |
| 29 | AAGEAAAAIEV | 0.456 | 360 | WB | VP2-3 | A6901 |
| 101 | FSDWDHKVSTV | 0.443 | 416 | WB | VP2-3 | A6901 |
| 294 | LPLLLGLYGTV | 0.439 | 433 | WB | VP2-3 | A6901 |
| 40 | QIASLATVEGI | 0.436 | 448 | WB | VP2-3 | A6901 |
| 287 | RTAPQWMLPLL | 0.433 | 459 | WB | VP2-3 | A6901 |
| 73 | APGAIAGFAAL | 0.671 | 35 | SB | VP2-3 | B0702 |
| 222 | SPIRPSMVRQV | 0.530 | 162 | WB | VP2-3 | B0702 |
| 67 | YAVIAGAPGAI | 0.489 | 251 | WB | VP2-3 | B0702 |
| 114 | YQQSGMALELF | 0.567 | 108 | WB | VP2-3 | B1501 |
| 201 | WTIVNAPINFY | 0.536 | 151 | WB | VP2-3 | B1501 |
| 203 | IVNAPINFYNY | 0.501 | 221 | WB | VP2-3 | B1501 |
| 13 | SVSEAAAATGF | 0.500 | 223 | WB | VP2-3 | B1501 |

TABLE J-continued

Prediction of BK virus VP2-3 protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity(nM) | Bind Level | Protein Name | Allele |
|---|---|---|---|---|---|---|
| 264 | RNKESVHSGEF | 0.488 | 254 | WB | VP2-3 | B1501 |
| 57 | IAAIGLTPQTY | 0.455 | 361 | WB | VP2-3 | B1501 |
| 37 | IEVQIASLATV | 0.605 | 71 | WB | VP2-3 | B1801 |
| 127 | DEYYDILFPGV | 0.591 | 83 | WB | VP2-3 | B1801 |
| 178 | QELQRRTERFF | 0.466 | 323 | WB | VP2-3 | B1801 |
| 130 | YDILFPGVNTF | 0.426 | 495 | WB | VP2-3 | B1801 |
| 182 | RRTERFFRDSL | 0.564 | 111 | WB | VP2-3 | B2705 |
| 319 | KRRVSRGSSQK | 0.498 | 227 | WB | VP2-3 | B2705 |
| 320 | RRVSRGSSQKA | 0.461 | 342 | WB | VP2-3 | B2705 |
| 286 | QRTAPQWMLPL | 0.430 | 477 | WB | VP2-3 | B2705 |
| 119 | MALELFNPDEY | 0.799 | 8 | SB | VP2-3 | B3501 |
| 57 | IAAIGLTPQTY | 0.701 | 25 | SB | VP2-3 | B3501 |
| 67 | YAVIAGAPGAI | 0.605 | 71 | WB | VP2-3 | B3501 |
| 13 | SVSEAAAATGF | 0.558 | 119 | WB | VP2-3 | B3501 |
| 201 | WTIVNAPINFY | 0.508 | 204 | WB | VP2-3 | B3501 |
| 73 | APGAIAGFAAL | 0.500 | 224 | WB | VP2-3 | B3501 |
| 301 | YGTVTPALEAY | 0.466 | 322 | WB | VP2-3 | B3501 |
| 11 | VASVSEAAAAT | 0.445 | 404 | WB | VP2-3 | B3501 |
| 146 | YLDPRHWGPSL | 0.500 | 223 | WB | VP2-3 | B3901 |
| 211 | YNYIQDYYSNL | 0.445 | 405 | WB | VP2-3 | B3901 |
| 31 | GEAAAAIEVQI | 0.587 | 87 | WB | VP2-3 | B4001 |
| 15 | SEAAAATGFSV | 0.513 | 194 | WB | VP2-3 | B4001 |
| 37 | IEVQIASLATV | 0.477 | 287 | WB | VP2-3 | B4001 |
| 127 | DEYYDILFPGV | 0.451 | 380 | WB | VP2-3 | B4001 |
| 178 | QELQRRTERFF | 0.497 | 231 | WB | VP2-3 | B4002 |
| 26 | AEIAAGEAAAA | 0.428 | 489 | WB | VP2-3 | B4002 |
| 26 | AEIAAGEAAAA | 0.484 | 264 | WB | VP2-3 | B4403 |
| 26 | AEIAAGEAAAA | 0.620 | 61 | WB | VP2-3 | B4501 |
| 294 | LPLLLGLYGTV | 0.749 | 15 | SB | VP2-3 | B5101 |
| 134 | FPGVNTFVNNI | 0.632 | 53 | WB | VP2-3 | B5101 |
| 134 | FPGVNTFVNNI | 0.791 | 9 | SB | VP2-3 | B5301 |
| 294 | LPLLLGLYGTV | 0.479 | 281 | WB | VP2-3 | B5301 |
| 119 | MALELFNPDEY | 0.477 | 287 | WB | VP2-3 | B5301 |
| 294 | LPLLLGLYGTV | 0.839 | 5 | SB | VP2-3 | B5401 |
| 134 | FPGVNTFVNNI | 0.750 | 14 | SB | VP2-3 | B5401 |
| 63 | TPQTYAVIAGA | 0.491 | 245 | WB | VP2-3 | B5401 |
| 80 | FAALIQTVTGI | 0.454 | 369 | WB | VP2-3 | B5401 |
| 222 | SPIRPSMVRQV | 0.451 | 378 | WB | VP2-3 | B5401 |
| 90 | ISSLAQVGYRF | 0.685 | 30 | SB | VP2-3 | B5801 |
| 191 | SLARFLEETTW | 0.631 | 54 | WB | VP2-3 | B5801 |
| 155 | SLFATISQALW | 0.572 | 102 | WB | VP2-3 | B5801 |
| 57 | IAAIGLTPQTY | 0.539 | 145 | WB | VP2-3 | B5801 |
| 282 | GGANQRTAPQW | 0.529 | 162 | WB | VP2-3 | B5801 |
| 287 | RTAPQWMLPLL | 0.488 | 253 | WB | VP2-3 | B5801 |

SEQ ID NOS: 52253-53779

Preferred BK virus fragments of VP1 capable of interacting with one or more MHC class 1 molecules are listed in Table K.

TABLE K

Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 8-mers | | | | | | |
| 196 | YLDKNNAY | 0.756 | 14 | SB | VP1 | A0101 |
| 108 | LMWEAVTV | 0.819 | 7 | SB | VP1 | A0201 |
| 243 | VLLDEQGV | 0.703 | 24 | SB | VP1 | A0201 |
| 83 | KMLPCYST | 0.657 | 41 | SB | VP1 | A0201 |
| 40 | GVDAITEV | 0.595 | 79 | WB | VP1 | A0201 |
| 281 | GLARYFKI | 0.591 | 83 | WB | VP1 | A0201 |
| 106 | NLLMWEAV | 0.580 | 94 | WB | VP1 | A0201 |
| 84 | MLPCYSTA | 0.562 | 114 | WB | VP1 | A0201 |
| 107 | LLMWEAVT | 0.498 | 229 | WB | VP1 | A0201 |
| 281 | GLARYFKI | 0.717 | 21 | SB | VP1 | A0202 |
| 108 | LMWEAVTV | 0.668 | 36 | SB | VP1 | A0202 |
| 84 | MLPCYSTA | 0.666 | 37 | SB | VP1 | A0202 |
| 243 | VLLDEQGV | 0.663 | 38 | SB | VP1 | A0202 |
| 262 | SAADICGL | 0.662 | 38 | SB | VP1 | A0202 |
| 40 | GVDAITEV | 0.633 | 52 | WB | VP1 | A0202 |
| 34 | VLEVKTGV | 0.510 | 200 | WB | VP1 | A0202 |
| 152 | FAVGGDPL | 0.508 | 205 | WB | VP1 | A0202 |
| 121 | GITSMLNL | 0.475 | 291 | WB | VP1 | A0202 |
| 125 | MLNLHAGS | 0.470 | 310 | WB | VP1 | A0202 |
| 25 | KLLIKGGV | 0.457 | 354 | WB | VP1 | A0202 |
| 107 | LLMWEAVT | 0.451 | 379 | WB | VP1 | A0202 |
| 238 | NTATTVLL | 0.447 | 394 | WB | VP1 | A0202 |
| 84 | MLPCYSTA | 0.841 | 5 | SB | VP1 | A0203 |
| 108 | LMWEAVTV | 0.784 | 10 | SB | VP1 | A0203 |
| 27 | LIKGGVEV | 0.779 | 10 | SB | VP1 | A0203 |
| 281 | GLARYFKI | 0.762 | 13 | SB | VP1 | A0203 |
| 243 | VLLDEQGV | 0.746 | 15 | SB | VP1 | A0203 |
| 236 | VTNTATTV | 0.674 | 33 | SB | VP1 | A0203 |
| 25 | KLLIKGGV | 0.657 | 41 | SB | VP1 | A0203 |
| 106 | NLLMWEAV | 0.643 | 47 | SB | VP1 | A0203 |
| 34 | VLEVKTGV | 0.635 | 51 | WB | VP1 | A0203 |
| 233 | VLHVTNTA | 0.633 | 52 | WB | VP1 | A0203 |
| 107 | LLMWEAVT | 0.563 | 113 | WB | VP1 | A0203 |
| 262 | SAADICGL | 0.538 | 148 | WB | VP1 | A0203 |
| 188 | VMNTDHKA | 0.531 | 159 | WB | VP1 | A0203 |
| 83 | KMLPCYST | 0.509 | 203 | WB | VP1 | A0203 |
| 125 | MLNLHAGS | 0.509 | 203 | WB | VP1 | A0203 |
| 326 | SQVEEVRV | 0.501 | 221 | WB | VP1 | A0203 |
| 229 | NVPPVLHV | 0.492 | 244 | WB | VP1 | A0203 |
| 121 | GITSMLNL | 0.490 | 248 | WB | VP1 | A0203 |
| 40 | GVDAITEV | 0.488 | 255 | WB | VP1 | A0203 |
| 294 | SVKNPYPI | 0.470 | 308 | WB | VP1 | A0203 |
| 112 | AVTVKTEV | 0.456 | 358 | WB | VP1 | A0203 |
| 119 | VIGITSML | 0.439 | 433 | WB | VP1 | A0203 |
| 108 | LMWEAVTV | 0.780 | 10 | SB | VP1 | A0204 |
| 243 | VLLDEQGV | 0.740 | 16 | SB | VP1 | A0204 |
| 25 | KLLIKGGV | 0.582 | 91 | WB | VP1 | A0204 |
| 281 | GLARYFKI | 0.510 | 201 | WB | VP1 | A0204 |
| 34 | VLEVKTGV | 0.498 | 228 | WB | VP1 | A0204 |
| 236 | VTNTATTV | 0.489 | 253 | WB | VP1 | A0204 |
| 326 | SQVEEVRV | 0.453 | 371 | WB | VP1 | A0204 |
| 106 | NLLMWEAV | 0.441 | 423 | WB | VP1 | A0204 |
| 27 | LIKGGVEV | 0.432 | 465 | WB | VP1 | A0204 |
| 40 | GVDAITEV | 0.431 | 472 | WB | VP1 | A0204 |
| 108 | LMWEAVTV | 0.852 | 4 | SB | VP1 | A0206 |
| 326 | SQVEEVRV | 0.789 | 9 | SB | VP1 | A0206 |
| 106 | NLLMWEAV | 0.731 | 18 | SB | VP1 | A0206 |
| 152 | FAVGGDPL | 0.729 | 18 | SB | VP1 | A0206 |
| 243 | VLLDEQGV | 0.720 | 20 | SB | VP1 | A0206 |
| 40 | GVDAITEV | 0.691 | 28 | SB | VP1 | A0206 |
| 21 | VQVPKLLI | 0.685 | 30 | SB | VP1 | A0206 |
| 84 | MLPCYSTA | 0.624 | 58 | WB | VP1 | A0206 |
| 83 | KMLPCYST | 0.623 | 59 | WB | VP1 | A0206 |
| 354 | GQLQTKMV | 0.584 | 89 | WB | VP1 | A0206 |
| 229 | NVPPVLHV | 0.574 | 99 | WB | VP1 | A0206 |
| 25 | KLLIKGGV | 0.543 | 139 | WB | VP1 | A0206 |
| 262 | SAADICGL | 0.513 | 193 | WB | VP1 | A0206 |
| 236 | VTNTATTV | 0.506 | 208 | WB | VP1 | A0206 |
| 281 | GLARYFKI | 0.505 | 211 | WB | VP1 | A0206 |
| 144 | VQGSNFHF | 0.481 | 275 | WB | VP1 | A0206 |
| 112 | AVTVKTEV | 0.454 | 368 | WB | VP1 | A0206 |
| 276 | TQQWRGLA | 0.439 | 434 | WB | VP1 | A0206 |
| 184 | AQSQVMNT | 0.432 | 465 | WB | VP1 | A0206 |
| 147 | SNFHFFAV | 0.432 | 467 | WB | VP1 | A0206 |
| 108 | LMWEAVTV | 0.966 | 1 | SB | VP1 | A0211 |
| 243 | VLLDEQGV | 0.965 | 1 | SB | VP1 | A0211 |
| 106 | NLLMWEAV | 0.910 | 2 | SB | VP1 | A0211 |
| 40 | GVDAITEV | 0.856 | 4 | SB | VP1 | A0211 |
| 27 | LIKGGVEV | 0.838 | 5 | SB | VP1 | A0211 |
| 229 | NVPPVLHV | 0.830 | 6 | SB | VP1 | A0211 |
| 25 | KLLIKGGV | 0.823 | 6 | SB | VP1 | A0211 |
| 349 | YIDRQGQL | 0.819 | 7 | SB | VP1 | A0211 |
| 281 | GLARYFKI | 0.788 | 9 | SB | VP1 | A0211 |
| 84 | MLPCYSTA | 0.786 | 10 | SB | VP1 | A0211 |
| 196 | YLDKNNAY | 0.751 | 14 | SB | VP1 | A0211 |
| 83 | KMLPCYST | 0.746 | 15 | SB | VP1 | A0211 |
| 34 | VLEVKTGV | 0.731 | 18 | SB | VP1 | A0211 |
| 101 | DLTCGNLL | 0.639 | 49 | SB | VP1 | A0211 |
| 262 | SAADICGL | 0.614 | 65 | WB | VP1 | A0211 |
| 97 | NLNEDLTC | 0.603 | 73 | WB | VP1 | A0211 |
| 188 | VMNTDHKA | 0.602 | 74 | WB | VP1 | A0211 |
| 233 | VLHVTNTA | 0.594 | 80 | WB | VP1 | A0211 |
| 112 | AVTVKTEV | 0.578 | 96 | WB | VP1 | A0211 |
| 320 | PMYGMESQ | 0.573 | 102 | WB | VP1 | A0211 |
| 326 | SQVEEVRV | 0.548 | 133 | WB | VP1 | A0211 |
| 332 | RVFDGTEQ | 0.542 | 141 | WB | VP1 | A0211 |
| 333 | VFDGTEQL | 0.505 | 211 | WB | VP1 | A0211 |
| 254 | CKADSLYV | 0.500 | 224 | WB | VP1 | A0211 |
| 236 | VTNTATTV | 0.498 | 229 | WB | VP1 | A0211 |
| 124 | SMLNLHAG | 0.491 | 246 | WB | VP1 | A0211 |
| 121 | GITSMLNL | 0.481 | 276 | WB | VP1 | A0211 |
| 147 | SNFHFFAV | 0.471 | 305 | WB | VP1 | A0211 |
| 107 | LLMWEAVT | 0.456 | 358 | WB | VP1 | A0211 |
| 252 | PLCKADSL | 0.453 | 370 | WB | VP1 | A0211 |
| 223 | TYTGGENV | 0.451 | 378 | WB | VP1 | A0211 |
| 339 | QLPGDPDM | 0.440 | 428 | WB | VP1 | A0211 |
| 119 | VIGITSML | 0.437 | 439 | WB | VP1 | A0211 |
| 243 | VLLDEQGV | 0.938 | 1 | SB | VP1 | A0212 |
| 108 | LMWEAVTV | 0.932 | 2 | SB | VP1 | A0212 |
| 106 | NLLMWEAV | 0.866 | 4 | SB | VP1 | A0212 |
| 27 | LIKGGVEV | 0.758 | 13 | SB | VP1 | A0212 |
| 281 | GLARYFKI | 0.738 | 17 | SB | VP1 | A0212 |
| 34 | VLEVKTGV | 0.730 | 18 | SB | VP1 | A0212 |
| 196 | YLDKNNAY | 0.708 | 23 | SB | VP1 | A0212 |
| 25 | KLLIKGGV | 0.691 | 28 | SB | VP1 | A0212 |
| 349 | YIDRQGQL | 0.659 | 40 | SB | VP1 | A0212 |
| 84 | MLPCYSTA | 0.645 | 46 | SB | VP1 | A0212 |
| 40 | GVDAITEV | 0.626 | 57 | WB | VP1 | A0212 |
| 229 | NVPPVLHV | 0.625 | 57 | WB | VP1 | A0212 |
| 320 | PMYGMESQ | 0.570 | 104 | WB | VP1 | A0212 |
| 188 | VMNTDHKA | 0.557 | 120 | WB | VP1 | A0212 |
| 233 | VLHVTNTA | 0.537 | 149 | WB | VP1 | A0212 |

TABLE K-continued

Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 83 | KMLPCYST | 0.496 | 234 | WB | VP1 | A0212 |
| 339 | QLPGDPDM | 0.474 | 295 | WB | VP1 | A0212 |
| 107 | LLMWEAVT | 0.462 | 337 | WB | VP1 | A0212 |
| 124 | SMLNLHAG | 0.437 | 443 | WB | VP1 | A0212 |
| 50 | FLNPEMGD | 0.437 | 444 | WB | VP1 | A0212 |
| 236 | VTNTATTV | 0.435 | 450 | WB | VP1 | A0212 |
| 97 | NLNEDLTC | 0.431 | 469 | WB | VP1 | A0212 |
| 326 | SQVEEVRV | 0.429 | 483 | WB | VP1 | A0212 |
| 108 | LMWEAVTV | 0.930 | 2 | SB | VP1 | A0216 |
| 243 | VLLDEQGV | 0.867 | 4 | SB | VP1 | A0216 |
| 106 | NLLMWEAV | 0.829 | 6 | SB | VP1 | A0216 |
| 27 | LIKGGVEV | 0.816 | 7 | SB | VP1 | A0216 |
| 229 | NVPPVLHV | 0.794 | 9 | SB | VP1 | A0216 |
| 40 | GVDAITEV | 0.784 | 10 | SB | VP1 | A0216 |
| 281 | GLARYFKI | 0.745 | 15 | SB | VP1 | A0216 |
| 34 | VLEVKTGV | 0.709 | 23 | SB | VP1 | A0216 |
| 84 | MLPCYSTA | 0.699 | 26 | SB | VP1 | A0216 |
| 349 | YIDRQGQL | 0.698 | 26 | SB | VP1 | A0216 |
| 25 | KLLIKGGV | 0.668 | 36 | SB | VP1 | A0216 |
| 112 | AVTVKTEV | 0.647 | 45 | SB | VP1 | A0216 |
| 252 | PLCKADSL | 0.627 | 56 | WB | VP1 | A0216 |
| 101 | DLTCGNLL | 0.529 | 163 | WB | VP1 | A0216 |
| 233 | VLHVTNTA | 0.520 | 179 | WB | VP1 | A0216 |
| 119 | VIGITSML | 0.493 | 241 | WB | VP1 | A0216 |
| 83 | KMLPCYST | 0.490 | 250 | WB | VP1 | A0216 |
| 320 | PMYGMESQ | 0.474 | 296 | WB | VP1 | A0216 |
| 236 | VTNTATTV | 0.470 | 309 | WB | VP1 | A0216 |
| 196 | YLDKNNAY | 0.461 | 339 | WB | VP1 | A0216 |
| 321 | MYGMESQV | 0.456 | 360 | WB | VP1 | A0216 |
| 152 | FAVGGDPL | 0.438 | 439 | WB | VP1 | A0216 |
| 223 | TYTGGENV | 0.434 | 457 | WB | VP1 | A0216 |
| 108 | LMWEAVTV | 0.930 | 2 | SB | VP1 | A0219 |
| 243 | VLLDEQGV | 0.896 | 3 | SB | VP1 | A0219 |
| 106 | NLLMWEAV | 0.798 | 8 | SB | VP1 | A0219 |
| 40 | GVDAITEV | 0.662 | 38 | SB | VP1 | A0219 |
| 229 | NVPPVLHV | 0.606 | 70 | WB | VP1 | A0219 |
| 27 | LIKGGVEV | 0.540 | 144 | WB | VP1 | A0219 |
| 349 | YIDRQGQL | 0.526 | 168 | WB | VP1 | A0219 |
| 34 | VLEVKTGV | 0.485 | 262 | WB | VP1 | A0219 |
| 254 | CKADSLYV | 0.484 | 265 | WB | VP1 | A0219 |
| 196 | YLDKNNAY | 0.451 | 381 | WB | VP1 | A0219 |
| 236 | VTNTATTV | 0.446 | 399 | WB | VP1 | A0219 |
| 333 | VFDGTEQL | 0.439 | 432 | WB | VP1 | A0219 |
| 281 | GLARYFKI | 0.434 | 456 | WB | VP1 | A0219 |
| 101 | DLTCGNLL | 0.430 | 474 | WB | VP1 | A0219 |
| 289 | RLRKRSVK | 0.776 | 11 | SB | VP1 | A0301 |
| 308 | LINRRTQK | 0.697 | 26 | SB | VP1 | A0301 |
| 164 | VLMNYRTK | 0.693 | 27 | SB | VP1 | A0301 |
| 127 | NLHAGSQK | 0.656 | 41 | SB | VP1 | A0301 |
| 165 | LMNYRTKY | 0.467 | 318 | WB | VP1 | A0301 |
| 280 | RGLARYFK | 0.446 | 399 | WB | VP1 | A0301 |
| 352 | RQGQLQTK | 0.432 | 468 | WB | VP1 | A0301 |
| 187 | QVMNTDHK | 0.705 | 24 | SB | VP1 | A1101 |
| 164 | VLMNYRTK | 0.620 | 60 | WB | VP1 | A1101 |
| 308 | LINRRTQK | 0.613 | 65 | WB | VP1 | A1101 |
| 280 | RGLARYFK | 0.596 | 79 | WB | VP1 | A1101 |
| 22 | QVPKLLIK | 0.510 | 200 | WB | VP1 | A1101 |
| 31 | GVEVLEVK | 0.506 | 210 | WB | VP1 | A1101 |
| 11 | GAAPKKPK | 0.444 | 408 | WB | VP1 | A1101 |
| 352 | RQGQLQTK | 0.436 | 447 | WB | VP1 | A1101 |
| 298 | PYPISFLL | 0.570 | 104 | WB | VP1 | A2301 |
| 259 | LYVSAADI | 0.509 | 203 | WB | VP1 | A2301 |
| 144 | VQGSNFHF | 0.499 | 225 | WB | VP1 | A2301 |
| 109 | MWEAVTVK | 0.470 | 310 | WB | VP1 | A2301 |
| 284 | RYFKIRLR | 0.448 | 393 | WB | VP1 | A2301 |
| 298 | PYPISFLL | 0.771 | 11 | SB | VP1 | A2402 |
| 202 | AYPVECWI | 0.672 | 34 | SB | VP1 | A2402 |
| 259 | LYVSAADI | 0.538 | 148 | WB | VP1 | A2402 |
| 302 | SFLLSDLI | 0.533 | 156 | WB | VP1 | A2402 |
| 144 | VQGSNFHF | 0.441 | 422 | WB | VP1 | A2402 |
| 202 | AYPVECWI | 0.721 | 20 | SB | VP1 | A2403 |
| 298 | PYPISFLL | 0.614 | 65 | SB | VP1 | A2403 |
| 259 | LYVSAADI | 0.464 | 329 | WB | VP1 | A2403 |
| 118 | EVIGITSM | 0.834 | 6 | SB | VP1 | A2601 |
| 118 | EVIGITSM | 0.909 | 2 | SB | VP1 | A2602 |
| 315 | KVDGQPMY | 0.730 | 18 | SB | VP1 | A2602 |
| 196 | YLDKNNAY | 0.675 | 33 | SB | VP1 | A2602 |
| 182 | PTAQSQVM | 0.599 | 76 | WB | VP1 | A2602 |
| 217 | NTRYFGTY | 0.573 | 101 | WB | VP1 | A2602 |
| 349 | YIDRQGQL | 0.555 | 123 | WB | VP1 | A2602 |
| 327 | QVEEVRVF | 0.491 | 245 | WB | VP1 | A2602 |
| 190 | NTDHKAYL | 0.463 | 332 | WB | VP1 | A2602 |
| 238 | NTATTVLL | 0.462 | 338 | WB | VP1 | A2602 |
| 196 | YLDKNNAY | 0.550 | 130 | WB | VP1 | A2902 |
| 165 | LMNYRTKY | 0.498 | 228 | WB | VP1 | A2902 |
| 289 | RLRKRSVK | 0.873 | 3 | SB | VP1 | A3001 |
| 280 | RGLARYFK | 0.802 | 8 | SB | VP1 | A3001 |
| 187 | QVMNTDHK | 0.563 | 113 | WB | VP1 | A3001 |
| 308 | LINRRTQK | 0.535 | 153 | WB | VP1 | A3001 |
| 164 | VLMNYRTK | 0.534 | 153 | WB | VP1 | A3001 |
| 285 | YFKIRLRK | 0.497 | 231 | WB | VP1 | A3001 |
| 84 | RYFKIRLR | 0.452 | 377 | WB | VP1 | A3001 |
| 127 | NLHAGSQK | 0.426 | 497 | WB | VP1 | A3001 |
| 315 | KVDGQPMY | 0.436 | 447 | WB | VP1 | A3002 |
| 165 | LMNYRTKY | 0.431 | 473 | WB | VP1 | A3002 |
| 284 | RYFKIRLR | 0.898 | 3 | SB | VP1 | A3101 |
| 280 | RGLARYFK | 0.716 | 21 | SB | VP1 | A3101 |
| 289 | RLRKRSVK | 0.670 | 35 | SB | VP1 | A3101 |
| 282 | LARYFKIR | 0.663 | 38 | SB | VP1 | A3101 |
| 277 | QQWRGLAR | 0.643 | 47 | SB | VP1 | A3101 |
| 285 | YFKIRLRK | 0.581 | 93 | WB | VP1 | A3101 |
| 304 | LLSDLINR | 0.569 | 106 | WB | VP1 | A3101 |
| 308 | LINRRTQK | 0.542 | 141 | WB | VP1 | A3101 |
| 273 | SSGTQQWR | 0.503 | 215 | WB | VP1 | A3101 |
| 164 | VLMNYRTK | 0.434 | 458 | WB | VP1 | A3101 |
| 345 | DMIRYIDR | 0.767 | 12 | SB | VP1 | A3301 |
| 284 | RYFKIRLR | 0.631 | 54 | WB | VP1 | A3301 |
| 282 | LARYFKIR | 0.515 | 190 | WB | VP1 | A3301 |
| 285 | YFKIRLRK | 0.504 | 213 | WB | VP1 | A3301 |
| 277 | QQWRGLAR | 0.444 | 410 | WB | VP1 | A3301 |
| 187 | QVMNTDHK | 0.708 | 23 | SB | VP1 | A6801 |
| 345 | DMIRYIDR | 0.627 | 56 | WB | VP1 | A6801 |
| 325 | ESQVEEVR | 0.606 | 70 | WB | VP1 | A6801 |
| 85 | LPCYSTAR | 0.568 | 107 | WB | VP1 | A6801 |
| 127 | NLHAGSQK | 0.503 | 217 | WB | VP1 | A6801 |
| 304 | LLSDLINR | 0.497 | 230 | WB | VP1 | A6801 |
| 308 | LINRRTQK | 0.497 | 231 | WB | VP1 | A6801 |
| 284 | RYFKIRLR | 0.488 | 254 | WB | VP1 | A6801 |
| 162 | QGVLMNYR | 0.487 | 257 | WB | VP1 | A6801 |
| 305 | LSDLINRR | 0.439 | 431 | WB | VP1 | A6801 |
| 282 | LARYFKIR | 0.438 | 439 | WB | VP1 | A6801 |

TABLE K-continued

Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 238 | NTATTVLL | 0.723 | 19 | SB | VP1 | A6802 |
| 262 | SAADICGL | 0.718 | 21 | SB | VP1 | A6802 |
| 118 | EVIGITSM | 0.718 | 21 | SB | VP1 | A6802 |
| 147 | SNFHFFAV | 0.659 | 39 | SB | VP1 | A6802 |
| 229 | NVPPVLHV | 0.647 | 45 | SB | VP1 | A6802 |
| 297 | NPYPISFL | 0.515 | 191 | WB | VP1 | A6802 |
| 152 | FAVGGDPL | 0.506 | 210 | WB | VP1 | A6802 |
| 88 | YSTARIPL | 0.473 | 300 | WB | VP1 | A6802 |
| 294 | SVKNPYPI | 0.458 | 351 | WB | VP1 | A6802 |
| 254 | CKADSLYV | 0.441 | 421 | WB | VP1 | A6802 |
| 108 | LMWEAVTV | 0.730 | 18 | SB | VP1 | A6901 |
| 238 | NTATTVLL | 0.636 | 51 | WB | VP1 | A6901 |
| 157 | DPLEMQGV | 0.635 | 51 | WB | VP1 | A6901 |
| 297 | NPYPISFL | 0.557 | 120 | WB | VP1 | A6901 |
| 118 | EVIGITSM | 0.548 | 132 | WB | VP1 | A6901 |
| 229 | NVPPVLHV | 0.545 | 137 | WB | VP1 | A6901 |
| 106 | NLLMWEAV | 0.539 | 147 | WB | VP1 | A6901 |
| 262 | SAADICGL | 0.441 | 421 | WB | VP1 | A6901 |
| 19 | EPVQVPKL | 0.431 | 471 | WB | VP1 | A6901 |
| 142 | KPVQGSNF | 0.685 | 30 | SB | VP1 | B0702 |
| 297 | NPYPISFL | 0.489 | 251 | WB | VP1 | B0702 |
| 16 | KPKEPVQV | 0.433 | 462 | WB | VP1 | B0702 |
| 95 | LPNLNEDL | 0.428 | 488 | WB | VP1 | B0702 |
| 68 | HLSAENAF | 0.555 | 123 | WB | VP1 | B1501 |
| 165 | LMNYRTKY | 0.542 | 142 | WB | VP1 | B1501 |
| 161 | MQGVLMNY | 0.509 | 202 | WB | VP1 | B1501 |
| 144 | VQGSNFHF | 0.453 | 369 | WB | VP1 | B1501 |
| 196 | YLDKNNAY | 0.448 | 393 | WB | VP1 | B1501 |
| 246 | DEQGVGPL | 0.554 | 124 | WB | VP1 | B1801 |
| 324 | MESQVEEV | 0.449 | 389 | WB | VP1 | B1801 |
| 159 | LEMQGVLM | 0.439 | 432 | WB | VP1 | B1801 |
| 283 | ARYFKIRL | 0.453 | 371 | WB | VP1 | B2705 |
| 292 | KRSVKNPY | 0.436 | 446 | WB | VP1 | B2705 |
| 279 | WRGLARYF | 0.426 | 496 | WB | VP1 | B2705 |
| 152 | FAVGGDPL | 0.737 | 17 | SB | VP1 | B3501 |
| 142 | KPVQGSNF | 0.631 | 54 | WB | VP1 | B3501 |
| 19 | EPVQVPKL | 0.547 | 134 | WB | VP1 | B3501 |
| 196 | YLDKNNAY | 0.544 | 138 | WB | VP1 | B3501 |
| 118 | EVIGITSM | 0.533 | 157 | WB | VP1 | B3501 |
| 95 | LPNLNEDL | 0.482 | 270 | WB | VP1 | B3501 |
| 299 | YPISFLLS | 0.480 | 278 | WB | VP1 | B3501 |
| 68 | HLSAENAF | 0.472 | 304 | WB | VP1 | B3501 |
| 297 | NPYPISFL | 0.470 | 309 | WB | VP1 | B3501 |
| 227 | GENVPPVL | 0.576 | 98 | WB | VP1 | B4001 |
| 159 | LEMQGVLM | 0.513 | 194 | WB | VP1 | B4001 |
| 324 | MESQVEEV | 0.433 | 462 | WB | VP1 | B4001 |
| 246 | DEQGVGPL | 0.430 | 476 | WB | VP1 | B4001 |
| 227 | GENVPPVL | 0.457 | 357 | WB | VP1 | B4002 |
| 71 | AENAFESD | 0.469 | 312 | WB | VP1 | B4501 |
| 340 | LPGDPDMI | 0.621 | 60 | WB | VP1 | B5101 |
| 230 | VPPVLHVT | 0.446 | 401 | WB | VP1 | B5101 |
| 203 | YPVECWIP | 0.426 | 498 | WB | VP1 | B5101 |
| 297 | NPYPISFL | 0.568 | 107 | WB | VP1 | B5301 |
| 142 | KPVQGSNF | 0.533 | 156 | WB | VP1 | B5301 |
| 19 | EPVQVPKL | 0.525 | 171 | WB | VP1 | B5301 |
| 340 | LPGDPDMI | 0.522 | 176 | WB | VP1 | B5301 |
| 95 | LPNLNEDL | 0.434 | 456 | WB | VP1 | B5301 |
| 299 | YPISFLLS | 0.612 | 66 | WB | VP1 | B5401 |
| 203 | YPVECWIP | 0.524 | 172 | WB | VP1 | B5401 |
| 230 | VPPVLHVT | 0.521 | 178 | WB | VP1 | B5401 |
| 85 | LPCYSTAR | 0.450 | 382 | WB | VP1 | B5401 |
| 340 | LPGDPDMI | 0.436 | 448 | WB | VP1 | B5401 |
| 272 | NSSGTQQW | 0.527 | 166 | WB | VP1 | B5701 |
| 201 | NAYPVECW | 0.479 | 280 | WB | VP1 | B5701 |
| 201 | NAYPVECW | 0.691 | 28 | SB | VP1 | B5801 |
| 272 | NSSGTQQW | 0.675 | 33 | SB | VP1 | B5801 |

9-mers

| pos | peptide | logscore | affinity (nM) | Bind Level | Protein Name | Allele |
|---|---|---|---|---|---|---|
| 107 | LLMWEAVTV | 0.761 | 13 | SB | VP1 | A0201 |
| 83 | KMLPCYSTA | 0.724 | 19 | SB | VP1 | A0201 |
| 26 | LLIKGGVEV | 0.573 | 101 | WB | VP1 | A0201 |
| 323 | GMESQVEEV | 0.550 | 129 | WB | VP1 | A0201 |
| 332 | RVFDGTEQL | 0.550 | 130 | WB | VP1 | A0201 |
| 107 | LLMWEAVTV | 0.769 | 12 | SB | VP1 | A0202 |
| 332 | RVFDGTEQL | 0.681 | 31 | SB | VP1 | A0202 |
| 323 | GMESQVEEV | 0.678 | 32 | SB | VP1 | A0202 |
| 26 | LLIKGGVEV | 0.632 | 53 | WB | VP1 | A0202 |
| 83 | KMLPCYSTA | 0.540 | 145 | WB | VP1 | A0202 |
| 308 | LINRRTQKV | 0.539 | 146 | WB | VP1 | A0202 |
| 61 | NLRGYSQHL | 0.534 | 154 | WB | VP1 | A0202 |
| 127 | NLHAGSQKV | 0.529 | 163 | WB | VP1 | A0202 |
| 43 | AITEVECFL | 0.504 | 213 | WB | VP1 | A0202 |
| 118 | EVIGITSML | 0.480 | 277 | WB | VP1 | A0202 |
| 304 | LLSDLINRR | 0.474 | 295 | WB | VP1 | A0202 |
| 268 | GLFTNSSGT | 0.463 | 333 | WB | VP1 | A0202 |
| 339 | QLPGDPDMI | 0.455 | 363 | WB | VP1 | A0202 |
| 146 | GSNFHFFAV | 0.439 | 430 | WB | VP1 | A0202 |
| 236 | VTNTATTVL | 0.439 | 434 | WB | VP1 | A0202 |
| 107 | LLMWEAVTV | 0.839 | 5 | SB | VP1 | A0203 |
| 308 | LINRRTQKV | 0.820 | 6 | SB | VP1 | A0203 |
| 26 | LLIKGGVEV | 0.818 | 7 | SB | VP1 | A0203 |
| 127 | NLHAGSQKV | 0.786 | 10 | SB | VP1 | A0203 |
| 83 | KMLPCYSTA | 0.761 | 13 | SB | VP1 | A0203 |
| 27 | LIKGGVEVL | 0.623 | 59 | WB | VP1 | A0203 |
| 61 | NLRGYSQHL | 0.616 | 64 | WB | VP1 | A0203 |
| 332 | RVFDGTEQL | 0.609 | 68 | WB | VP1 | A0203 |
| 323 | GMESQVEEV | 0.604 | 72 | WB | VP1 | A0203 |
| 222 | GTYTGGENV | 0.586 | 88 | WB | VP1 | A0203 |
| 258 | SLYVSAADI | 0.570 | 104 | WB | VP1 | A0203 |
| 268 | GLFTNSSGT | 0.535 | 153 | WB | VP1 | A0203 |
| 235 | HVTNTATTV | 0.512 | 195 | WB | VP1 | A0203 |
| 320 | PMYGMESQV | 0.509 | 203 | WB | VP1 | A0203 |
| 125 | MLNLHAGSQ | 0.480 | 277 | WB | VP1 | A0203 |
| 114 | TVKTEVIGI | 0.476 | 288 | WB | VP1 | A0203 |
| 287 | KIRLRKRSV | 0.452 | 374 | WB | VP1 | A0203 |
| 236 | VTNTATTVL | 0.450 | 384 | WB | VP1 | A0203 |
| 107 | LLMWEAVTV | 0.751 | 14 | SB | VP1 | A0204 |
| 26 | LLIKGGVEV | 0.688 | 29 | SB | VP1 | A0204 |
| 323 | GMESQVEEV | 0.648 | 45 | SB | VP1 | A0204 |
| 127 | NLHAGSQKV | 0.613 | 65 | WB | VP1 | A0204 |
| 308 | LINRRTQKV | 0.547 | 133 | WB | VP1 | A0204 |
| 83 | KMLPCYSTA | 0.504 | 214 | WB | VP1 | A0204 |
| 33 | EVLVKTGV | 0.476 | 289 | WB | VP1 | A0204 |
| 43 | AITEVECFL | 0.428 | 488 | WB | VP1 | A0204 |
| 107 | LLMWEAVTV | 0.865 | 4 | SB | VP1 | A0206 |
| 26 | LLIKGGVEV | 0.808 | 7 | SB | VP1 | A0206 |
| 332 | RVFDGTEQL | 0.797 | 8 | SB | VP1 | A0206 |
| 83 | KMLPCYSTA | 0.723 | 20 | SB | VP1 | A0206 |

TABLE K-continued

Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 235 | HVTNTATTV | 0.591 | 83 | WB | VP1 | A0206 |
| 144 | VQGSNFHFF | 0.586 | 88 | WB | VP1 | A0206 |
| 146 | GSNFHFFAV | 0.555 | 123 | WB | VP1 | A0206 |
| 43 | AITEVECFL | 0.542 | 142 | WB | VP1 | A0206 |
| 326 | SQVEEVRVF | 0.472 | 303 | WB | VP1 | A0206 |
| 39 | TGVDAITEV | 0.460 | 344 | WB | VP1 | A0206 |
| 127 | NLHAGSQKV | 0.451 | 378 | WB | VP1 | A0206 |
| 107 | LLMWEAVTV | 0.952 | 1 | SB | VP1 | A0211 |
| 26 | LLIKGGVEV | 0.946 | 1 | SB | VP1 | A0211 |
| 127 | NLHAGSQKV | 0.943 | 1 | SB | VP1 | A0211 |
| 320 | PMYGMESQV | 0.941 | 1 | SB | VP1 | A0211 |
| 332 | RVFDGTEQL | 0.923 | 2 | SB | VP1 | A0211 |
| 83 | KMLPCYSTA | 0.869 | 4 | SB | VP1 | A0211 |
| 43 | AITEVECFL | 0.830 | 6 | SB | VP1 | A0211 |
| 33 | EVLEVKTGV | 0.818 | 7 | SB | VP1 | A0211 |
| 61 | NLRGYSQHL | 0.804 | 8 | SB | VP1 | A0211 |
| 323 | GMESQVEEV | 0.800 | 8 | SB | VP1 | A0211 |
| 308 | LINRRTQKV | 0.688 | 29 | SB | VP1 | A0211 |
| 235 | HVTNTATTV | 0.687 | 29 | SB | VP1 | A0211 |
| 242 | TVLLDEQGV | 0.669 | 35 | SB | VP1 | A0211 |
| 196 | YLDKNNAYP | 0.642 | 48 | SB | VP1 | A0211 |
| 339 | QLPGDPDMI | 0.623 | 59 | WB | VP1 | A0211 |
| 101 | DLTCGNLLM | 0.603 | 73 | WB | VP1 | A0211 |
| 54 | EMGDPDDNL | 0.589 | 85 | WB | VP1 | A0211 |
| 27 | LIKGGVEVL | 0.568 | 107 | WB | VP1 | A0211 |
| 258 | SLYVSAADI | 0.564 | 111 | WB | VP1 | A0211 |
| 176 | TITPKNPTA | 0.543 | 140 | WB | VP1 | A0211 |
| 349 | YIDRQGQLQ | 0.525 | 169 | WB | VP1 | A0211 |
| 222 | GTYTGGENV | 0.521 | 178 | WB | VP1 | A0211 |
| 124 | SMLNLHAGS | 0.494 | 238 | WB | VP1 | A0211 |
| 108 | LMWEAVTVK | 0.489 | 251 | WB | VP1 | A0211 |
| 39 | TGVDAITEV | 0.488 | 253 | WB | VP1 | A0211 |
| 94 | PLPNLNEDL | 0.487 | 256 | WB | VP1 | A0211 |
| 255 | KADSLYVSA | 0.475 | 292 | WB | VP1 | A0211 |
| 118 | EVIGITSML | 0.472 | 304 | WB | VP1 | A0211 |
| 201 | NAYPVECWI | 0.470 | 310 | WB | VP1 | A0211 |
| 106 | NLLMWEAVT | 0.467 | 320 | WB | VP1 | A0211 |
| 268 | GLFTNSSGT | 0.463 | 332 | WB | VP1 | A0211 |
| 244 | LLDEQGVGP | 0.443 | 415 | WB | VP1 | A0211 |
| 26 | LLIKGGVEV | 0.905 | 2 | SB | VP1 | A0212 |
| 107 | LLMWEAVTV | 0.903 | 2 | SB | VP1 | A0212 |
| 127 | NLHAGSQKV | 0.895 | 3 | SB | VP1 | A0212 |
| 320 | PMYGMESQV | 0.883 | 3 | SB | VP1 | A0212 |
| 61 | NLRGYSQHL | 0.837 | 5 | SB | VP1 | A0212 |
| 33 | EVLEVKTGV | 0.810 | 7 | SB | VP1 | A0212 |
| 332 | RVFDGTEQL | 0.768 | 12 | SB | VP1 | A0212 |
| 308 | LINRRTQKV | 0.710 | 23 | SB | VP1 | A0212 |
| 43 | AITEVECFL | 0.696 | 26 | SB | VP1 | A0212 |
| 323 | GMESQVEEV | 0.680 | 31 | SB | VP1 | A0212 |
| 242 | TVLLDEQGV | 0.643 | 47 | SB | VP1 | A0212 |
| 196 | YLDKNNAYP | 0.604 | 72 | WB | VP1 | A0212 |
| 54 | EMGDPDDNL | 0.597 | 78 | WB | VP1 | A0212 |
| 83 | KMLPCYSTA | 0.575 | 99 | WB | VP1 | A0212 |
| 339 | QLPGDPDMI | 0.548 | 132 | WB | VP1 | A0212 |
| 108 | LMWEAVTVK | 0.537 | 149 | WB | VP1 | A0212 |
| 268 | GLFTNSSGT | 0.534 | 155 | WB | VP1 | A0212 |
| 222 | GTYTGGENV | 0.527 | 166 | WB | VP1 | A0212 |
| 27 | LIKGGVEVL | 0.505 | 212 | WB | VP1 | A0212 |
| 124 | SMLNLHAGS | 0.492 | 243 | WB | VP1 | A0212 |
| 244 | LLDEQGVGP | 0.484 | 266 | WB | VP1 | A0212 |
| 164 | VLMNYRTKY | 0.481 | 274 | WB | VP1 | A0212 |
| 94 | PLPNLNEDL | 0.480 | 276 | WB | VP1 | A0212 |
| 235 | HVTNTATTV | 0.457 | 356 | WB | VP1 | A0212 |
| 304 | LLSDLINRR | 0.443 | 414 | WB | VP1 | A0212 |
| 258 | SLYVSAADI | 0.436 | 449 | WB | VP1 | A0212 |
| 349 | YIDRQGQLQ | 0.435 | 452 | WB | VP1 | A0212 |
| 201 | NAYPVECWI | 0.435 | 453 | WB | VP1 | A0212 |
| 26 | LLIKGGVEV | 0.935 | 2 | SB | VP1 | A0216 |
| 320 | PMYGMESQV | 0.926 | 2 | SB | VP1 | A0216 |
| 127 | NLHAGSQKV | 0.887 | 3 | SB | VP1 | A0216 |
| 107 | LLMWEAVTV | 0.872 | 3 | SB | VP1 | A0216 |
| 332 | RVFDGTEQL | 0.838 | 5 | SB | VP1 | A0216 |
| 61 | NLRGYSQHL | 0.835 | 5 | SB | VP1 | A0216 |
| 43 | AITEVECFL | 0.834 | 6 | SB | VP1 | A0216 |
| 323 | GMESQVEEV | 0.826 | 6 | SB | VP1 | A0216 |
| 235 | HVTNTATTV | 0.762 | 13 | SB | VP1 | A0216 |
| 33 | EVLEVKTGV | 0.742 | 16 | SB | VP1 | A0216 |
| 308 | LINRRTQKV | 0.701 | 25 | SB | VP1 | A0216 |
| 83 | KMLPCYSTA | 0.653 | 42 | SB | VP1 | A0216 |
| 54 | EMGDPDDNL | 0.649 | 44 | SB | VP1 | A0216 |
| 201 | NAYPVECWI | 0.593 | 81 | WB | VP1 | A0216 |
| 111 | EAVTVKTEV | 0.540 | 145 | WB | VP1 | A0216 |
| 39 | TGVDAITEV | 0.524 | 171 | WB | VP1 | A0216 |
| 118 | EVIGITSML | 0.513 | 194 | WB | VP1 | A0216 |
| 196 | YLDKNNAYP | 0.512 | 196 | WB | VP1 | A0216 |
| 339 | QLPGDPDMI | 0.491 | 245 | WB | VP1 | A0216 |
| 222 | GTYTGGENV | 0.485 | 262 | WB | VP1 | A0216 |
| 27 | LIKGGVEVL | 0.467 | 318 | WB | VP1 | A0216 |
| 176 | TITPKNPTA | 0.462 | 336 | WB | VP1 | A0216 |
| 94 | PLPNLNEDL | 0.426 | 496 | WB | VP1 | A0216 |
| 127 | NLHAGSQKV | 0.862 | 4 | SB | VP1 | A0219 |
| 107 | LLMWEAVTV | 0.811 | 7 | SB | VP1 | A0219 |
| 320 | PMYGMESQV | 0.786 | 10 | SB | VP1 | A0219 |
| 26 | LLIKGGVEV | 0.776 | 11 | SB | VP1 | A0219 |
| 332 | RVFDGTEQL | 0.762 | 13 | SB | VP1 | A0219 |
| 323 | GMESQVEEV | 0.643 | 47 | SB | VP1 | A0219 |
| 61 | NLRGYSQHL | 0.621 | 60 | WB | VP1 | A0219 |
| 54 | EMGDPDDNL | 0.581 | 93 | WB | VP1 | A0219 |
| 235 | HVTNTATTV | 0.537 | 150 | WB | VP1 | A0219 |
| 33 | EVLEVKTGV | 0.529 | 162 | WB | VP1 | A0219 |
| 308 | LINRRTQKV | 0.528 | 165 | WB | VP1 | A0219 |
| 39 | TGVDAITEV | 0.492 | 242 | WB | VP1 | A0219 |
| 108 | LMWEAVTVK | 0.442 | 417 | WB | VP1 | A0219 |
| 27 | LIKGGVEVL | 0.438 | 437 | WB | VP1 | A0219 |
| 284 | RYFKIRLRK | 0.643 | 47 | SB | VP1 | A0301 |
| 108 | LMWEAVTVK | 0.570 | 104 | WB | VP1 | A0301 |
| 134 | KVHENGGGK | 0.525 | 170 | WB | VP1 | A0301 |
| 164 | VLMNYRTKY | 0.453 | 370 | WB | VP1 | A0301 |
| 163 | GVLMNYRTK | 0.440 | 426 | WB | VP1 | A0301 |
| 163 | GVLMNYRTK | 0.621 | 60 | WB | VP1 | A1101 |
| 186 | SQVMNTDHK | 0.599 | 76 | WB | VP1 | A1101 |
| 284 | RYFKIRLRK | 0.586 | 88 | WB | VP1 | A1101 |
| 276 | TQQWRGLAR | 0.561 | 115 | WB | VP1 | A1101 |
| 134 | KVHENGGGK | 0.556 | 121 | WB | VP1 | A1101 |
| 284 | RYFKIRLRK | 0.724 | 19 | SB | VP1 | A2301 |
| 87 | CYSTARIPL | 0.572 | 102 | WB | VP1 | A2301 |
| 143 | PVQGSNFHF | 0.555 | 123 | WB | VP1 | A2301 |
| 348 | RYIDRQGQL | 0.538 | 147 | WB | VP1 | A2301 |
| 144 | VQGSNFHFF | 0.480 | 277 | WB | VP1 | A2301 |
| 144 | VQGSNFHFF | 0.521 | 178 | WB | VP1 | A2402 |
| 348 | RYIDRQGQL | 0.506 | 210 | WB | VP1 | A2402 |
| 348 | RYIDRQGQL | 0.602 | 73 | WB | VP1 | A2403 |
| 195 | AYLDKNNAY | 0.502 | 218 | WB | VP1 | A2403 |
| 278 | QWRGLARYF | 0.434 | 457 | WB | VP1 | A2403 |

TABLE K-continued

Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 118 | EVIGITSML | 0.663 | 38 | SB | VP1 | A2601 |
| 160 | EMQGVLMNY | 0.553 | 126 | WB | VP1 | A2601 |
| 118 | EVIGITSML | 0.898 | 3 | SB | VP1 | A2602 |
| 160 | EMQGVLMNY | 0.659 | 39 | SB | VP1 | A2602 |
| 36 | EVKTGVDAI | 0.584 | 90 | WB | VP1 | A2602 |
| 164 | VLMNYRTKY | 0.620 | 61 | WB | VP1 | A2902 |
| 188 | VMNTDHKAY | 0.535 | 153 | WB | VP1 | A2902 |
| 195 | AYLDKNNAY | 0.524 | 172 | WB | VP1 | A2902 |
| 284 | RYFKIRLRK | 0.812 | 7 | SB | VP1 | A3001 |
| 134 | KVHENGGGK | 0.791 | 9 | SB | VP1 | A3001 |
| 163 | GVLMNYRTK | 0.563 | 113 | WB | VP1 | A3001 |
| 291 | RKRSVKNPY | 0.543 | 141 | WB | VP1 | A3001 |
| 169 | RTKYPQGTI | 0.492 | 243 | WB | VP1 | A3001 |
| 191 | TDHKAYLDK | 0.436 | 444 | WB | VP1 | A3001 |
| 287 | KIRLRKRSV | 0.436 | 446 | WB | VP1 | A3001 |
| 289 | RLRKRSVKN | 0.436 | 447 | WB | VP1 | A3001 |
| 186 | SQVMNTDHK | 0.434 | 455 | WB | VP1 | A3001 |
| 161 | MQGVLMNYR | 0.811 | 7 | SB | VP1 | A3101 |
| 285 | YFKIRLRKR | 0.800 | 8 | SB | VP1 | A3101 |
| 284 | RYFKIRLRK | 0.762 | 13 | SB | VP1 | A3101 |
| 276 | TQQWRGLAR | 0.627 | 56 | WB | VP1 | A3101 |
| 84 | MLPCYSTAR | 0.578 | 95 | WB | VP1 | A3101 |
| 304 | LLSDLINRR | 0.573 | 101 | WB | VP1 | A3101 |
| 281 | GLARYFKIR | 0.520 | 180 | WB | VP1 | A3101 |
| 108 | LMWEAVTVK | 0.502 | 219 | WB | VP1 | A3101 |
| 303 | FLLSDLINR | 0.441 | 422 | WB | VP1 | A3101 |
| 285 | YFKIRLRKR | 0.782 | 10 | SB | VP1 | A3301 |
| 307 | DLINRRTQK | 0.659 | 39 | SB | VP1 | A3301 |
| 272 | NSSGTQQWR | 0.732 | 18 | SB | VP1 | A6801 |
| 84 | MLPCYSTAR | 0.720 | 20 | SB | VP1 | A6801 |
| 307 | DLINRRTQK | 0.593 | 81 | WB | VP1 | A6801 |
| 324 | MESQVEEVR | 0.548 | 132 | WB | VP1 | A6801 |
| 304 | LLSDLINRR | 0.543 | 140 | WB | VP1 | A6801 |
| 118 | EVIGITSML | 0.509 | 202 | WB | VP1 | A6801 |
| 161 | MQGVLMNYR | 0.437 | 442 | WB | VP1 | A6801 |
| 284 | RYFKIRLRK | 0.437 | 444 | WB | VP1 | A6801 |
| 118 | EVIGITSML | 0.903 | 2 | SB | VP1 | A6802 |
| 111 | EAVTVKTEV | 0.739 | 16 | SB | VP1 | A6802 |
| 33 | EVLEVKTGV | 0.728 | 18 | SB | VP1 | A6802 |
| 39 | TGVDAITEV | 0.683 | 30 | SB | VP1 | A6802 |
| 297 | NPYPISFLL | 0.632 | 53 | WB | VP1 | A6802 |
| 332 | RVFDGTEQL | 0.578 | 95 | WB | VP1 | A6802 |
| 145 | QGSNFHFFA | 0.563 | 113 | WB | VP1 | A6802 |
| 201 | NAYPVECWI | 0.556 | 121 | WB | VP1 | A6802 |
| 187 | QVMNTDHKA | 0.527 | 167 | WB | VP1 | A6802 |
| 146 | GSNFHFFAV | 0.497 | 231 | WB | VP1 | A6802 |
| 293 | RSVKNPYPI | 0.457 | 357 | WB | VP1 | A6802 |
| 261 | VSAADICGL | 0.455 | 364 | WB | VP1 | A6802 |
| 235 | HVTNTATTV | 0.444 | 410 | WB | VP1 | A6802 |
| 229 | NVPPVLHVT | 0.441 | 422 | WB | VP1 | A6802 |
| 297 | NPYPISFLL | 0.673 | 34 | SB | VP1 | A6901 |
| 118 | EVIGITSML | 0.636 | 51 | WB | VP1 | A6901 |
| 235 | HVTNTATTV | 0.546 | 136 | WB | VP1 | A6901 |
| 107 | LLMWEAVTV | 0.499 | 225 | WB | VP1 | A6901 |
| 201 | NAYPVECWI | 0.485 | 262 | WB | VP1 | A6901 |
| 111 | EAVTVKTEV | 0.483 | 268 | WB | VP1 | A6901 |
| 225 | TGGENVPPV | 0.469 | 311 | WB | VP1 | A6901 |
| 222 | GTYTGGENV | 0.437 | 440 | WB | VP1 | A6901 |
| 127 | NLHAGSQKV | 0.433 | 463 | WB | VP1 | A6901 |
| 332 | RVFDGTEQL | 0.430 | 474 | WB | VP1 | A6901 |
| 85 | LPCYSTARI | 0.692 | 28 | SB | VP1 | B0702 |
| 13 | APKKPKEPV | 0.688 | 29 | SB | VP1 | B0702 |
| 1 | APTKRKGEC | 0.619 | 61 | WB | VP1 | B0702 |
| 282 | LARYFKIRL | 0.535 | 153 | WB | VP1 | B0702 |
| 287 | KIRLRKRSV | 0.520 | 179 | WB | VP1 | B0702 |
| 181 | NPTAQSQVM | 0.498 | 227 | WB | VP1 | B0702 |
| 79 | SPDRKMLPC | 0.482 | 272 | WB | VP1 | B0702 |
| 19 | EPVQVPKLL | 0.474 | 295 | WB | VP1 | B0702 |
| 251 | GPLCKADSL | 0.455 | 364 | WB | VP1 | B0702 |
| 287 | KIRLRKRSV | 0.431 | 472 | WB | VP1 | B0801 |
| 326 | SQVEEVRVF | 0.598 | 77 | WB | VP1 | B1501 |
| 188 | VMNTDHKAY | 0.589 | 85 | WB | VP1 | B1501 |
| 313 | TQKVDGQPM | 0.566 | 108 | WB | VP1 | B1501 |
| 277 | QQWRGLARY | 0.543 | 140 | WB | VP1 | B1501 |
| 160 | EMQGVLMNY | 0.456 | 360 | WB | VP1 | B1501 |
| 295 | VKNPYPISF | 0.595 | 79 | WB | VP1 | B1801 |
| 117 | TEVIGITSM | 0.472 | 303 | WB | VP1 | B1801 |
| 288 | IRLRKRSVK | 0.523 | 174 | WB | VP1 | B2705 |
| 279 | WRGLARYFK | 0.486 | 259 | WB | VP1 | B2705 |
| 181 | NPTAQSQVM | 0.758 | 13 | SB | VP1 | B3501 |
| 57 | DPDDNLRGY | 0.613 | 65 | WB | VP1 | B3501 |
| 157 | DPLEMQGVL | 0.577 | 97 | WB | VP1 | B3501 |
| 142 | KPVQGSNFH | 0.574 | 99 | WB | VP1 | B3501 |
| 297 | NPYPISFLL | 0.568 | 107 | WB | VP1 | B3501 |
| 151 | FFAVGGDPL | 0.565 | 110 | WB | VP1 | B3501 |
| 67 | QHLSAENAF | 0.495 | 235 | WB | VP1 | B3501 |
| 203 | YPVECWIPD | 0.491 | 247 | WB | VP1 | B3501 |
| 19 | EPVQVPKLL | 0.475 | 292 | WB | VP1 | B3501 |
| 42 | DAITEVECF | 0.468 | 317 | WB | VP1 | B3501 |
| 95 | LPNLNEDLT | 0.441 | 424 | WB | VP1 | B3501 |
| 136 | HENGGGKPV | 0.448 | 391 | WB | VP1 | B4001 |
| 47 | VECFLNPEM | 0.431 | 469 | WB | VP1 | B4001 |
| 71 | AENAFESDS | 0.600 | 75 | WB | VP1 | B4501 |
| 85 | LPCYSTARI | 0.659 | 39 | SB | VP1 | B5101 |
| 19 | EPVQVPKLL | 0.475 | 292 | WB | VP1 | B5101 |
| 297 | NPYPISFLL | 0.459 | 350 | WB | VP1 | B5101 |
| 85 | LPCYSTARI | 0.655 | 41 | SB | VP1 | B5301 |
| 297 | NPYPISFLL | 0.623 | 59 | WB | VP1 | B5301 |
| 19 | EPVQVPKLL | 0.535 | 152 | WB | VP1 | B5301 |
| 95 | LPNLNEDLT | 0.636 | 51 | WB | VP1 | B5401 |
| 85 | LPCYSTARI | 0.591 | 83 | WB | VP1 | B5401 |
| 203 | YPVECWIPD | 0.481 | 273 | WB | VP1 | B5401 |
| 299 | YPISFLLSD | 0.435 | 452 | WB | VP1 | B5401 |
| 102 | LTCGNLLMW | 0.453 | 371 | WB | VP1 | B5701 |
| 102 | LTCGNLLMW | 0.624 | 58 | WB | VP1 | B5801 |

10-mers

| pos | peptide | logscore | affinity (nM) | Bind Level | Protein Name | Allele |
|---|---|---|---|---|---|---|
| 196 | YLDKNNAYPV | 0.866 | 4 | SB | VP1 | A0201 |
| 108 | LMWEAVTVKT | 0.691 | 28 | SB | VP1 | A0201 |
| 84 | MLPCYSTARI | 0.675 | 33 | SB | VP1 | A0201 |
| 106 | NLLMWEAVTV | 0.634 | 52 | WB | VP1 | A0201 |
| 224 | YTGGENVPPV | 0.608 | 69 | WB | VP1 | A0201 |
| 260 | YVSAADICGL | 0.589 | 85 | WB | VP1 | A0201 |
| 244 | LLDEQGVGPL | 0.537 | 150 | WB | VP1 | A0201 |
| 25 | KLLIKGGVEV | 0.517 | 185 | WB | VP1 | A0201 |
| 188 | VMNTDHKAYL | 0.504 | 214 | WB | VP1 | A0201 |
| 281 | GLARYFKIRL | 0.482 | 271 | WB | VP1 | A0201 |

TABLE K-continued

Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 322 | YGMESQVEEV | 0.465 | 325 | WB | VP1 | A0201 |
| 26 | LLIKGGVEVL | 0.465 | 328 | WB | VP1 | A0201 |
| 196 | YLDKNNAYPV | 0.722 | 20 | SB | VP1 | A0202 |
| 260 | YVSAADICGL | 0.676 | 33 | SB | VP1 | A0202 |
| 244 | LLDEQGVGPL | 0.652 | 43 | SB | VP1 | A0202 |
| 26 | LLIKGGVEVL | 0.621 | 60 | WB | VP1 | A0202 |
| 188 | VMNTDHKAYL | 0.613 | 66 | WB | VP1 | A0202 |
| 84 | MLPCYSTARI | 0.604 | 72 | WB | VP1 | A0202 |
| 106 | NLLMWEAVTV | 0.571 | 104 | WB | VP1 | A0202 |
| 224 | YTGGENVPPV | 0.554 | 124 | WB | VP1 | A0202 |
| 281 | GLARYFKIRL | 0.520 | 179 | WB | VP1 | A0202 |
| 303 | FLLSDLINRR | 0.495 | 236 | WB | VP1 | A0202 |
| 304 | LLSDLINRRT | 0.487 | 257 | WB | VP1 | A0202 |
| 322 | YGMESQVEEV | 0.470 | 308 | WB | VP1 | A0202 |
| 25 | KLLIKGGVEV | 0.462 | 338 | WB | VP1 | A0202 |
| 38 | KTGVDAITEV | 0.453 | 372 | WB | VP1 | A0202 |
| 255 | KADSLYVSAA | 0.442 | 419 | WB | VP1 | A0202 |
| 84 | MLPCYSTARI | 0.854 | 4 | SB | VP1 | A0203 |
| 196 | YLDKNNAYPV | 0.801 | 8 | SB | VP1 | A0203 |
| 244 | LLDEQGVGPL | 0.704 | 24 | SB | VP1 | A0203 |
| 188 | VMNTDHKAYL | 0.702 | 25 | SB | VP1 | A0203 |
| 26 | LLIKGGVEVL | 0.663 | 38 | SB | VP1 | A0203 |
| 106 | NLLMWEAVTV | 0.660 | 39 | SB | VP1 | A0203 |
| 224 | YTGGENVPPV | 0.611 | 67 | WB | VP1 | A0203 |
| 260 | YVSAADICGL | 0.606 | 70 | WB | VP1 | A0203 |
| 25 | KLLIKGGVEV | 0.596 | 79 | WB | VP1 | A0203 |
| 281 | GLARYFKIRL | 0.590 | 84 | WB | VP1 | A0203 |
| 304 | LLSDLINRRT | 0.530 | 162 | WB | VP1 | A0203 |
| 108 | LMWEAVTVKT | 0.467 | 319 | WB | VP1 | A0203 |
| 233 | VLHVTNTATT | 0.462 | 338 | WB | VP1 | A0203 |
| 352 | RQGQLQTKMV | 0.448 | 391 | WB | VP1 | A0203 |
| 236 | VTNTATTVLL | 0.446 | 399 | WB | VP1 | A0203 |
| 38 | KTGVDAITEV | 0.441 | 424 | WB | VP1 | A0203 |
| 307 | DLINRRTQKV | 0.438 | 437 | WB | VP1 | A0203 |
| 196 | YLDKNNAYPV | 0.658 | 40 | SB | VP1 | A0204 |
| 25 | KLLIKGGVEV | 0.650 | 44 | SB | VP1 | A0204 |
| 244 | LLDEQGVGPL | 0.598 | 77 | WB | VP1 | A0204 |
| 224 | YTGGENVPPV | 0.596 | 78 | WB | VP1 | A0204 |
| 108 | LMWEAVTVKT | 0.548 | 133 | WB | VP1 | A0204 |
| 106 | NLLMWEAVTV | 0.541 | 142 | WB | VP1 | A0204 |
| 38 | KTGVDAITEV | 0.517 | 185 | WB | VP1 | A0204 |
| 322 | YGMESQVEEV | 0.499 | 226 | WB | VP1 | A0204 |
| 188 | VMNTDHKAYL | 0.473 | 299 | WB | VP1 | A0204 |
| 26 | LLIKGGVEVL | 0.468 | 315 | WB | VP1 | A0204 |
| 89 | STARIPLPNL | 0.433 | 459 | WB | VP1 | A0204 |
| 196 | YLDKNNAYPV | 0.873 | 3 | SB | VP1 | A0206 |
| 144 | VQGSNFHFFA | 0.733 | 17 | SB | VP1 | A0206 |
| 106 | NLLMWEAVTV | 0.694 | 27 | SB | VP1 | A0206 |
| 260 | YVSAADICGL | 0.677 | 32 | SB | VP1 | A0206 |
| 84 | MLPCYSTARI | 0.671 | 35 | SB | VP1 | A0206 |
| 244 | LLDEQGVGPL | 0.637 | 50 | WB | VP1 | A0206 |
| 224 | YTGGENVPPV | 0.606 | 71 | WB | VP1 | A0206 |
| 38 | KTGVDAITEV | 0.590 | 84 | WB | VP1 | A0206 |
| 25 | KLLIKGGVEV | 0.588 | 86 | WB | VP1 | A0206 |
| 186 | SQVMNTDHKA | 0.588 | 86 | WB | VP1 | A0206 |
| 352 | RQGQLQTKMV | 0.559 | 118 | WB | VP1 | A0206 |
| 152 | FAVGGDPLEM | 0.550 | 129 | WB | VP1 | A0206 |
| 26 | LLIKGGVEVL | 0.549 | 131 | WB | VP1 | A0206 |
| 322 | YGMESQVEEV | 0.514 | 191 | WB | VP1 | A0206 |
| 277 | QQWRGLARYF | 0.509 | 202 | WB | VP1 | A0206 |
| 108 | LMWEAVTVKT | 0.503 | 216 | WB | VP1 | A0206 |
| 161 | MQGVLMNYRT | 0.428 | 486 | WB | VP1 | A0206 |
| 196 | YLDKNNAYPV | 0.976 | 1 | SB | VP1 | A0211 |
| 106 | NLLMWEAVTV | 0.926 | 2 | SB | VP1 | A0211 |
| 244 | LLDEQGVGPL | 0.906 | 2 | SB | VP1 | A0211 |
| 25 | KLLIKGGVEV | 0.849 | 5 | SB | VP1 | A0211 |
| 26 | LLIKGGVEVL | 0.843 | 5 | SB | VP1 | A0211 |
| 224 | YTGGENVPPV | 0.820 | 7 | SB | VP1 | A0211 |
| 281 | GLARYFKIRL | 0.817 | 7 | SB | VP1 | A0211 |
| 252 | PLCKADSLYV | 0.801 | 8 | SB | VP1 | A0211 |
| 188 | VMNTDHKAYL | 0.798 | 8 | SB | VP1 | A0211 |
| 84 | MLPCYSTARI | 0.773 | 11 | SB | VP1 | A0211 |
| 307 | DLINRRTQKV | 0.751 | 14 | SB | VP1 | A0211 |
| 108 | LMWEAVTVKT | 0.740 | 16 | SB | VP1 | A0211 |
| 260 | YVSAADICGL | 0.693 | 27 | SB | VP1 | A0211 |
| 349 | YIDRQGQLQT | 0.652 | 43 | SB | VP1 | A0211 |
| 304 | LLSDLINRRT | 0.628 | 55 | WB | VP1 | A0211 |
| 322 | YGMESQVEEV | 0.608 | 69 | WB | VP1 | A0211 |
| 155 | GGDPLEMQGV | 0.597 | 78 | WB | VP1 | A0211 |
| 315 | KVDGQPMYGM | 0.593 | 82 | WB | VP1 | A0211 |
| 124 | SMLNLHAGSQ | 0.578 | 96 | WB | VP1 | A0211 |
| 38 | KTGVDAITEV | 0.533 | 156 | WB | VP1 | A0211 |
| 268 | GLFTNSSGTQ | 0.499 | 226 | WB | VP1 | A0211 |
| 243 | VLLDEQGVGP | 0.427 | 494 | WB | VP1 | A0211 |
| 196 | YLDKNNAYPV | 0.940 | 1 | SB | VP1 | A0212 |
| 106 | NLLMWEAVTV | 0.863 | 4 | SB | VP1 | A0212 |
| 26 | LLIKGGVEVL | 0.799 | 8 | SB | VP1 | A0212 |
| 244 | LLDEQGVGPL | 0.763 | 12 | SB | VP1 | A0212 |
| 281 | GLARYFKIRL | 0.762 | 13 | SB | VP1 | A0212 |
| 224 | YTGGENVPPV | 0.734 | 17 | SB | VP1 | A0212 |
| 188 | VMNTDHKAYL | 0.728 | 19 | SB | VP1 | A0212 |
| 108 | LMWEAVTVKT | 0.718 | 21 | SB | VP1 | A0212 |
| 25 | KLLIKGGVEV | 0.705 | 24 | SB | VP1 | A0212 |
| 84 | MLPCYSTARI | 0.659 | 40 | SB | VP1 | A0212 |
| 260 | YVSAADICGL | 0.646 | 46 | SB | VP1 | A0212 |
| 307 | DLINRRTQKV | 0.625 | 57 | WB | VP1 | A0212 |
| 252 | PLCKADSLYV | 0.620 | 60 | WB | VP1 | A0212 |
| 304 | LLSDLINRRT | 0.541 | 143 | WB | VP1 | A0212 |
| 349 | YIDRQGQLQT | 0.533 | 157 | WB | VP1 | A0212 |
| 155 | GGDPLEMQGV | 0.513 | 195 | WB | VP1 | A0212 |
| 243 | VLLDEQGVGP | 0.504 | 213 | WB | VP1 | A0212 |
| 303 | FLLSDLINRR | 0.481 | 274 | WB | VP1 | A0212 |
| 322 | YGMESQVEEV | 0.474 | 297 | WB | VP1 | A0212 |
| 124 | SMLNLHAGSQ | 0.430 | 477 | WB | VP1 | A0212 |
| 196 | YLDKNNAYPV | 0.945 | 1 | SB | VP1 | A0216 |
| 106 | NLLMWEAVTV | 0.882 | 3 | SB | VP1 | A0216 |
| 252 | PLCKADSLYV | 0.866 | 4 | SB | VP1 | A0216 |
| 281 | GLARYFKIRL | 0.844 | 5 | SB | VP1 | A0216 |
| 307 | DLINRRTQKV | 0.820 | 7 | SB | VP1 | A0216 |
| 26 | LLIKGGVEVL | 0.800 | 8 | SB | VP1 | A0216 |
| 25 | KLLIKGGVEV | 0.779 | 10 | SB | VP1 | A0216 |
| 244 | LLDEQGVGPL | 0.740 | 16 | SB | VP1 | A0216 |
| 224 | YTGGENVPPV | 0.726 | 19 | SB | VP1 | A0216 |
| 84 | MLPCYSTARI | 0.723 | 19 | SB | VP1 | A0216 |
| 188 | VMNTDHKAYL | 0.662 | 38 | SB | VP1 | A0216 |
| 108 | LMWEAVTVKT | 0.606 | 70 | WB | VP1 | A0216 |
| 260 | YVSAADICGL | 0.545 | 136 | WB | VP1 | A0216 |
| 38 | KTGVDAITEV | 0.510 | 199 | WB | VP1 | A0216 |
| 304 | LLSDLINRRT | 0.477 | 285 | WB | VP1 | A0216 |
| 349 | YIDRQGQLQT | 0.470 | 309 | WB | VP1 | A0216 |
| 28 | IKGGVEVLEV | 0.430 | 478 | WB | VP1 | A0216 |
| 196 | YLDKNNAYPV | 0.940 | 1 | SB | VP1 | A0219 |
| 106 | NLLMWEAVTV | 0.763 | 12 | SB | VP1 | A0219 |
| 224 | YTGGENVPPV | 0.678 | 32 | SB | VP1 | A0219 |
| 26 | LLIKGGVEVL | 0.671 | 35 | SB | VP1 | A0219 |
| 260 | YVSAADICGL | 0.656 | 41 | SB | VP1 | A0219 |
| 244 | LLDEQGVGPL | 0.644 | 46 | SB | VP1 | A0219 |

TABLE K-continued

Prediction of BK virus VP1 protein specific MHC class1, 8-, 9-, 10-, 11-mer peptide binders for 42 MHC class TABLE K-continued Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 117 | TEVIGITSML | 0.570 | 104 | WB | VP1 | B4001 |
| 324 | MESQVEEVRV | 0.475 | 293 | WB | VP1 | B4001 |
| 53 | PEMGDPDDNL | 0.473 | 298 | WB | VP1 | B4001 |
| 99 | NEDLTCGNLL | 0.471 | 304 | WB | VP1 | B4001 |
| 110 | WEAVTVKTEV | 0.428 | 488 | WB | VP1 | B4001 |
| 215 | NENTRYFGTY | 0.430 | 476 | WB | VP1 | B4402 |
| 71 | AENAFESDSP | 0.495 | 235 | WB | VP1 | B4501 |
| 19 | EPVQVPKLLI | 0.654 | 42 | SB | VP1 | B5101 |
| 299 | YPISFLLSDL | 0.557 | 120 | WB | VP1 | B5101 |
| 19 | EPVQVPKLLI | 0.658 | 40 | SB | VP1 | B5301 |
| 299 | YPISFLLSDL | 0.604 | 72 | WB | VP1 | B5301 |
| 142 | KPVQGSNFHF | 0.531 | 159 | WB | VP1 | B5301 |
| 340 | LPGDPDMIRY | 0.523 | 174 | WB | VP1 | B5301 |
| 79 | SPDRKMLPCY | 0.468 | 315 | WB | VP1 | B5301 |
| 211 | DPSRNENTRY | 0.468 | 316 | WB | VP1 | B5301 |
| 23 | VPKLLIKGGV | 0.607 | 70 | WB | VP1 | B5401 |
| 231 | PPVLHVTNTA | 0.590 | 84 | WB | VP1 | B5401 |
| 85 | LPCYSTARIP | 0.533 | 157 | WB | VP1 | B5401 |
| 19 | EPVQVPKLLI | 0.463 | 332 | WB | VP1 | B5401 |
| 203 | YPVECWIPDP | 0.456 | 358 | WB | VP1 | B5401 |
| 270 | FTNSSGTQQW | 0.478 | 285 | WB | VP1 | B5701 |
| 270 | FTNSSGTQQW | 0.738 | 16 | SB | VP1 | B5801 |
| 199 | KNNAYPVECW | 0.634 | 52 | WB | VP1 | B5801 |
| 261 | VSAADICGLF | 0.458 | 351 | WB | VP1 | B5801 |

11-mers

| pos | peptide | logscore | affinity (nM) | Bind Level | Protein Name | Allele |
|---|---|---|---|---|---|---|
| 83 | KMLPCYSTARI | 0.778 | 11 | SB | VP1 | A0201 |
| 107 | LLMWEAVTVKT | 0.594 | 80 | WB | VP1 | A0201 |
| 243 | VLLDEQGVGPL | 0.577 | 97 | WB | VP1 | A0201 |
| 303 | FLLSDLINRRT | 0.551 | 129 | WB | VP1 | A0201 |
| 233 | VLHVTNTATTV | 0.497 | 230 | WB | VP1 | A0201 |
| 144 | VQGSNFHFFAV | 0.461 | 342 | WB | VP1 | A0201 |
| 125 | MLNLHAGSQKV | 0.459 | 348 | WB | VP1 | A0201 |
| 187 | QVMNTDHKAYL | 0.444 | 407 | WB | VP1 | A0201 |
| 323 | GMESQVEEVRV | 0.434 | 458 | WB | VP1 | A0201 |
| 125 | MLNLHAGSQKV | 0.757 | 13 | SB | VP1 | A0202 |
| 97 | NLNEDLTCGNL | 0.678 | 32 | SB | VP1 | A0202 |
| 243 | VLLDEQGVGPL | 0.618 | 62 | WB | VP1 | A0202 |
| 83 | KMLPCYSTARI | 0.597 | 78 | WB | VP1 | A0202 |
| 107 | LLMWEAVTVKT | 0.592 | 82 | WB | VP1 | A0202 |
| 323 | GMESQVEEVRV | 0.558 | 119 | WB | VP1 | A0202 |
| 144 | VQGSNFHFFAV | 0.548 | 133 | WB | VP1 | A0202 |
| 233 | VLHVTNTATTV | 0.506 | 209 | WB | VP1 | A0202 |
| 187 | QVMNTDHKAYL | 0.482 | 270 | WB | VP1 | A0202 |
| 303 | FLLSDLINRRT | 0.438 | 436 | WB | VP1 | A0202 |
| 125 | MLNLHAGSQKV | 0.897 | 3 | SB | VP1 | A0203 |
| 27 | LIKGGVEVLEV | 0.784 | 10 | SB | VP1 | A0203 |
| 83 | KMLPCYSTARI | 0.744 | 15 | SB | VP1 | A0203 |
| 233 | VLHVTNTATTV | 0.743 | 16 | SB | VP1 | A0203 |
| 97 | NLNEDLTCGNL | 0.709 | 23 | SB | VP1 | A0203 |
| 243 | VLLDEQGVGPL | 0.708 | 23 | SB | VP1 | A0203 |
| 61 | NLRGYSQHLSA | 0.693 | 27 | SB | VP1 | A0203 |
| 107 | LLMWEAVTVKT | 0.605 | 71 | WB | VP1 | A0203 |
| 134 | KVHENGGGKPV | 0.574 | 99 | WB | VP1 | A0203 |
| 144 | VQGSNFHFFAV | 0.520 | 180 | WB | VP1 | A0203 |
| 294 | SVKNPYPISFL | 0.475 | 292 | WB | VP1 | A0203 |
| 346 | MIRYIDRQGQL | 0.471 | 306 | WB | VP1 | A0203 |
| 323 | GMESQVEEVRV | 0.459 | 348 | WB | VP1 | A0203 |
| 303 | FLLSDLINRRT | 0.454 | 367 | WB | VP1 | A0203 |
| 125 | MLNLHAGSQKV | 0.687 | 29 | SB | VP1 | A0204 |
| 233 | VLHVTNTATTV | 0.655 | 41 | SB | VP1 | A0204 |
| 243 | VLLDEQGVGPL | 0.629 | 55 | WB | VP1 | A0204 |
| 134 | KVHENGGGKPV | 0.544 | 138 | WB | VP1 | A0204 |
| 323 | GMESQVEEVRV | 0.544 | 138 | WB | VP1 | A0204 |
| 83 | KMLPCYSTARI | 0.497 | 230 | WB | VP1 | A0204 |
| 144 | VQGSNFHFFAV | 0.476 | 290 | WB | VP1 | A0204 |
| 107 | LLMWEAVTVKT | 0.464 | 328 | WB | VP1 | A0204 |
| 195 | AYLDKNNAYPV | 0.460 | 345 | WB | VP1 | A0204 |
| 25 | KLLIKGGVEVL | 0.443 | 415 | WB | VP1 | A0204 |
| 224 | YTGGENVPPVL | 0.428 | 487 | WB | VP1 | A0204 |
| 144 | VQGSNFHFFAV | 0.865 | 4 | SB | VP1 | A0206 |
| 83 | KMLPCYSTARI | 0.720 | 20 | SB | VP1 | A0206 |
| 125 | MLNLHAGSQKV | 0.576 | 97 | WB | VP1 | A0206 |
| 243 | VLLDEQGVGPL | 0.571 | 103 | WB | VP1 | A0206 |
| 318 | GQPMYGMESQV | 0.519 | 181 | WB | VP1 | A0206 |
| 107 | LLMWEAVTVKT | 0.498 | 229 | WB | VP1 | A0206 |
| 187 | QVMNTDHKAYL | 0.485 | 261 | WB | VP1 | A0206 |
| 233 | VLHVTNTATTV | 0.435 | 450 | WB | VP1 | A0206 |
| 303 | FLLSDLINRRT | 0.433 | 462 | WB | VP1 | A0206 |
| 243 | VLLDEQGVGPL | 0.906 | 2 | SB | VP1 | A0211 |
| 233 | VLHVTNTATTV | 0.899 | 2 | SB | VP1 | A0211 |
| 125 | MLNLHAGSQKV | 0.897 | 3 | SB | VP1 | A0211 |
| 83 | KMLPCYSTARI | 0.831 | 6 | SB | VP1 | A0211 |
| 27 | LIKGGVEVLEV | 0.813 | 7 | SB | VP1 | A0211 |
| 323 | GMESQVEEVRV | 0.770 | 12 | SB | VP1 | A0211 |
| 244 | LLDEQGVGPLC | 0.735 | 17 | SB | VP1 | A0211 |
| 61 | NLRGYSQHLSA | 0.703 | 24 | SB | VP1 | A0211 |
| 304 | LLSDLINRRTQ | 0.696 | 26 | SB | VP1 | A0211 |
| 25 | KLLIKGGVEVL | 0.681 | 31 | SB | VP1 | A0211 |
| 134 | KVHENGGGKPV | 0.674 | 34 | SB | VP1 | A0211 |
| 97 | NLNEDLTCGNL | 0.669 | 35 | SB | VP1 | A0211 |
| 195 | AYLDKNNAYPV | 0.636 | 51 | WB | VP1 | A0211 |
| 303 | FLLSDLINRRT | 0.612 | 66 | WB | VP1 | A0211 |
| 164 | VLMNYRTKYPQ | 0.607 | 70 | WB | VP1 | A0211 |
| 223 | TYTGGENVPPV | 0.585 | 89 | WB | VP1 | A0211 |
| 196 | YLDKNNAYPVE | 0.560 | 116 | WB | VP1 | A0211 |
| 107 | LLMWEAVTVKT | 0.551 | 128 | WB | VP1 | A0211 |
| 235 | HVTNTATTVLL | 0.525 | 171 | WB | VP1 | A0211 |
| 22 | QVPKLLIKGGV | 0.523 | 174 | WB | VP1 | A0211 |
| 268 | GLFTNSSGTQQ | 0.506 | 209 | WB | VP1 | A0211 |
| 339 | QLPGDPDMIRY | 0.501 | 222 | WB | VP1 | A0211 |
| 144 | VQGSNFHFFAV | 0.500 | 224 | WB | VP1 | A0211 |
| 187 | QVMNTDHKAYL | 0.499 | 225 | WB | VP1 | A0211 |
| 11 | GAAPKKPKEPV | 0.474 | 297 | WB | VP1 | A0211 |
| 224 | YTGGENVPPVL | 0.472 | 302 | WB | VP1 | A0211 |
| 160 | EMQGVLMNYRT | 0.468 | 317 | WB | VP1 | A0211 |
| 349 | YIDRQGQLQTK | 0.450 | 385 | WB | VP1 | A0211 |
| 240 | ATTVLLDEQGV | 0.437 | 443 | WB | VP1 | A0211 |
| 233 | VLHVTNTATTV | 0.838 | 5 | SB | VP1 | A0212 |
| 243 | VLLDEQGVGPL | 0.823 | 6 | SB | VP1 | A0212 |
| 125 | MLNLHAGSQKV | 0.813 | 7 | SB | VP1 | A0212 |
| 323 | GMESQVEEVRV | 0.713 | 22 | SB | VP1 | A0212 |
| 27 | LIKGGVEVLEV | 0.697 | 26 | SB | VP1 | A0212 |
| 61 | NLRGYSQHLSA | 0.690 | 28 | SB | VP1 | A0212 |
| 144 | VQGSNFHFFAV | 0.652 | 42 | SB | VP1 | A0212 |
| 244 | LLDEQGVGPLC | 0.645 | 46 | SB | VP1 | A0212 |
| 304 | LLSDLINRRTQ | 0.599 | 76 | WB | VP1 | A0212 |
| 83 | KMLPCYSTARI | 0.596 | 79 | WB | VP1 | A0212 |
| 164 | VLMNYRTKYPQ | 0.576 | 98 | WB | VP1 | A0212 |
| 196 | YLDKNNAYPVE | 0.569 | 106 | WB | VP1 | A0212 |
| 303 | FLLSDLINRRT | 0.561 | 115 | WB | VP1 | A0212 |

TABLE K-continued

Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 224 | YTGGENVPPVL | 0.543 | 140 | WB | VP1 | A0212 |
| 25 | KLLIKGGVEVL | 0.530 | 161 | WB | VP1 | A0212 |
| 107 | LLMWEAVTVKT | 0.511 | 199 | WB | VP1 | A0212 |
| 97 | NLNEDLTCGNL | 0.491 | 247 | WB | VP1 | A0212 |
| 195 | AYLDKNNAYPV | 0.490 | 249 | WB | VP1 | A0212 |
| 349 | YIDRQGQLQTK | 0.465 | 325 | WB | VP1 | A0212 |
| 154 | VGGDPLEMQGV | 0.464 | 329 | WB | VP1 | A0212 |
| 160 | EMQGVLMNYRT | 0.460 | 345 | WB | VP1 | A0212 |
| 108 | LMWEAVTVKTE | 0.438 | 434 | WB | VP1 | A0212 |
| 233 | VLHVTNTATTV | 0.865 | 4 | SB | VP1 | A0216 |
| 125 | MLNLHAGSQKV | 0.827 | 6 | SB | VP1 | A0216 |
| 323 | GMESQVEEVRV | 0.804 | 8 | SB | VP1 | A0216 |
| 27 | LIKGGVEVLEV | 0.752 | 14 | SB | VP1 | A0216 |
| 243 | VLLDEQGVGPL | 0.724 | 19 | SB | VP1 | A0216 |
| 83 | KMLPCYSTARI | 0.660 | 39 | SB | VP1 | A0216 |
| 61 | NLRGYSQHLSA | 0.647 | 45 | SB | VP1 | A0216 |
| 187 | QVMNTDHKAYL | 0.643 | 47 | SB | VP1 | A0216 |
| 164 | VLMNYRTKYPQ | 0.619 | 61 | WB | VP1 | A0216 |
| 195 | AYLDKNNAYPV | 0.616 | 64 | WB | VP1 | A0216 |
| 11 | GAAPKKPKEPV | 0.542 | 142 | WB | VP1 | A0216 |
| 294 | SVKNPYPISFL | 0.530 | 162 | WB | VP1 | A0216 |
| 318 | GQPMYGMESQV | 0.525 | 170 | WB | VP1 | A0216 |
| 25 | KLLIKGGVEVL | 0.517 | 186 | WB | VP1 | A0216 |
| 223 | TYTGGENVPPV | 0.512 | 196 | WB | VP1 | A0216 |
| 268 | GLFTNSSGTQQ | 0.495 | 236 | WB | VP1 | A0216 |
| 97 | NLNEDLTCGNL | 0.481 | 274 | WB | VP1 | A0216 |
| 22 | QVPKLLIKGGV | 0.478 | 284 | WB | VP1 | A0216 |
| 304 | LLSDLINRRTQ | 0.474 | 295 | WB | VP1 | A0216 |
| 160 | EMQGVLMNYRT | 0.464 | 329 | WB | VP1 | A0216 |
| 31 | GVEVLEVKTGV | 0.459 | 348 | WB | VP1 | A0216 |
| 144 | VQGSNFHFFAV | 0.456 | 361 | WB | VP1 | A0216 |
| 235 | HVTNTATTVLL | 0.454 | 368 | WB | VP1 | A0216 |
| 303 | FLLSDLINRRT | 0.453 | 372 | WB | VP1 | A0216 |
| 249 | GVGPLCKADSL | 0.450 | 383 | WB | VP1 | A0216 |
| 220 | YFGTYTGGENV | 0.447 | 394 | WB | VP1 | A0216 |
| 37 | VKTGVDAITEV | 0.439 | 433 | WB | VP1 | A0216 |
| 134 | KVHENGGGKPV | 0.434 | 454 | WB | VP1 | A0216 |
| 233 | VLHVTNTATTV | 0.703 | 24 | SB | VP1 | A0219 |
| 125 | MLNLHAGSQKV | 0.697 | 26 | SB | VP1 | A0219 |
| 243 | VLLDEQGVGPL | 0.673 | 34 | SB | VP1 | A0219 |
| 27 | LIKGGVEVLEV | 0.581 | 93 | WB | VP1 | A0219 |
| 144 | VQGSNFHFFAV | 0.546 | 135 | WB | VP1 | A0219 |
| 323 | GMESQVEEVRV | 0.511 | 198 | WB | VP1 | A0219 |
| 83 | KMLPCYSTARI | 0.501 | 221 | WB | VP1 | A0219 |
| 223 | TYTGGENVPPV | 0.457 | 357 | WB | VP1 | A0219 |
| 154 | VGGDPLEMQGV | 0.443 | 413 | WB | VP1 | A0219 |
| 224 | YTGGENVPPVL | 0.428 | 485 | WB | VP1 | A0219 |
| 124 | SMLNLHAGSQK | 0.698 | 26 | SB | VP1 | A0301 |
| 289 | RLRKRSVKNPY | 0.560 | 117 | WB | VP1 | A0301 |
| 281 | GLARYFKIRLR | 0.520 | 180 | WB | VP1 | A0301 |
| 106 | NLLMWEAVTVK | 0.478 | 285 | WB | VP1 | A0301 |
| 270 | FTNSSGTQQWR | 0.447 | 395 | WB | VP1 | A0301 |
| 124 | SMLNLHAGSQK | 0.754 | 14 | SB | VP1 | A1101 |
| 184 | AQSQVMNTDHK | 0.640 | 49 | SB | VP1 | A1101 |
| 301 | ISFLLSDLINR | 0.631 | 54 | WB | VP1 | A1101 |
| 277 | QQWRGLARYFK | 0.573 | 101 | WB | VP1 | A1101 |
| 73 | NAFESDSPDRK | 0.538 | 148 | WB | VP1 | A1101 |
| 275 | GTQQWRGLARY | 0.477 | 288 | WB | VP1 | A1101 |
| 106 | NLLMWEAVTVK | 0.462 | 336 | WB | VP1 | A1101 |
| 161 | MQGVLMNYRTK | 0.448 | 390 | WB | VP1 | A1101 |
| 312 | RTQKVDGQPMY | 0.441 | 421 | WB | VP1 | A1101 |
| 282 | LARYFKIRLRK | 0.432 | 467 | WB | VP1 | A1101 |
| 305 | LSDLINRRTQK | 0.431 | 473 | WB | VP1 | A1101 |
| 259 | LYVSAADICGL | 0.573 | 102 | WB | VP1 | A2301 |
| 298 | PYPISFLLSDL | 0.474 | 295 | WB | VP1 | A2301 |
| 298 | PYPISFLLSDL | 0.564 | 111 | WB | VP1 | A2402 |
| 167 | NYRTKYPQGTI | 0.552 | 128 | WB | VP1 | A2402 |
| 278 | QWRGLARYFKI | 0.438 | 439 | WB | VP1 | A2402 |
| 65 | YSQHLSAENAF | 0.655 | 41 | SB | VP1 | A2403 |
| 298 | PYPISFLLSDL | 0.628 | 56 | WB | VP1 | A2403 |
| 259 | LYVSAADICGL | 0.536 | 151 | WB | VP1 | A2403 |
| 269 | LFTNSSGTQQW | 0.434 | 458 | WB | VP1 | A2403 |
| 118 | EVIGITSMLNL | 0.705 | 24 | SB | VP1 | A2601 |
| 78 | DSPDRKMLPCY | 0.602 | 74 | WB | VP1 | A2601 |
| 118 | EVIGITSMLNL | 0.894 | 3 | SB | VP1 | A2602 |
| 294 | SVKNPYPISFL | 0.778 | 11 | SB | VP1 | A2602 |
| 78 | DSPDRKMLPCY | 0.715 | 21 | SB | VP1 | A2602 |
| 260 | YVSAADICGLF | 0.691 | 28 | SB | VP1 | A2602 |
| 339 | QLPGDPDMIRY | 0.669 | 35 | SB | VP1 | A2602 |
| 187 | QVMNTDHKAYL | 0.618 | 62 | WB | VP1 | A2602 |
| 275 | GTQQWRGLARY | 0.593 | 81 | WB | VP1 | A2602 |
| 312 | RTQKVDGQPMY | 0.482 | 273 | WB | VP1 | A2602 |
| 289 | RLRKRSVKNPY | 0.805 | 8 | SB | VP1 | A3001 |
| 282 | LARYFKIRLRK | 0.787 | 10 | SB | VP1 | A3001 |
| 6 | KGECPGAAPKK | 0.656 | 41 | SB | VP1 | A3001 |
| 134 | KVHENGGGKPV | 0.525 | 169 | WB | VP1 | A3001 |
| 132 | SQKVHENGGGK | 0.508 | 205 | WB | VP1 | A3001 |
| 312 | RTQKVDGQPMY | 0.498 | 227 | WB | VP1 | A3001 |
| 277 | QQWRGLARYFK | 0.477 | 286 | WB | VP1 | A3001 |
| 161 | MQGVLMNYRTK | 0.455 | 362 | WB | VP1 | A3001 |
| 291 | RKRSVKNPYPI | 0.432 | 468 | WB | VP1 | A3001 |
| 312 | RTQKVDGQPMY | 0.474 | 295 | WB | VP1 | A3002 |
| 277 | QQWRGLARYFK | 0.695 | 27 | SB | VP1 | A3101 |
| 301 | ISFLLSDLINR | 0.646 | 46 | SB | VP1 | A3101 |
| 302 | SFLLSDLINRR | 0.634 | 52 | WB | VP1 | A3101 |
| 270 | FTNSSGTQQWR | 0.615 | 64 | WB | VP1 | A3101 |
| 124 | SMLNLHAGSQK | 0.602 | 74 | WB | VP1 | A3101 |
| 281 | GLARYFKIRLR | 0.598 | 77 | WB | VP1 | A3101 |
| 282 | LARYFKIRLRK | 0.457 | 355 | WB | VP1 | A3101 |
| 161 | MQGVLMNYRTK | 0.453 | 371 | WB | VP1 | A3101 |
| 82 | RKMLPCYSTAR | 0.428 | 486 | WB | VP1 | A3101 |
| 301 | ISFLLSDLINR | 0.516 | 187 | WB | VP1 | A3301 |
| 302 | SFLLSDLINRR | 0.486 | 259 | WB | VP1 | A3301 |
| 270 | FTNSSGTQQWR | 0.792 | 9 | SB | VP1 | A6801 |
| 301 | ISFLLSDLINR | 0.717 | 21 | SB | VP1 | A6801 |
| 73 | NAFESDSPDRK | 0.709 | 23 | SB | VP1 | A6801 |
| 72 | ENAFESDSPDR | 0.595 | 80 | WB | VP1 | A6801 |
| 322 | YGMESQVEEVR | 0.478 | 284 | WB | VP1 | A6801 |
| 282 | LARYFKIRLRK | 0.478 | 284 | WB | VP1 | A6801 |
| 118 | EVIGITSMLNL | 0.811 | 7 | SB | VP1 | A6802 |
| 187 | QVMNTDHKAYL | 0.666 | 36 | SB | VP1 | A6802 |
| 22 | QVPKLLIKGGV | 0.649 | 44 | SB | VP1 | A6802 |
| 235 | HVTNTATTVLL | 0.487 | 257 | WB | VP1 | A6802 |
| 330 | EVRVFDGTEQL | 0.471 | 306 | WB | VP1 | A6802 |
| 103 | TCGNLLMWEAV | 0.457 | 354 | WB | VP1 | A6802 |
| 118 | EVIGITSMLNL | 0.681 | 31 | SB | VP1 | A6901 |
| 33 | EVLEVKTGVDA | 0.574 | 99 | WB | VP1 | A6901 |
| 187 | QVMNTDHKAYL | 0.533 | 155 | WB | VP1 | A6901 |

TABLE K-continued

Prediction of BK virus VP1 protein specific MHC class1, 8-, 9-, 10-, 11-mer peptide binders for 42 MHC class 1 alleles (see FIG. 11) using the //www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 99 | YPISFLLSDLI | 0.456 | 361 | WB | VP1 | A6901 |
| 224 | YTGGENVPPVL | 0.454 | 366 | WB | VP1 | A6901 |
| 235 | HVTNTATTVLL | 0.449 | 389 | WB | VP1 | A6901 |
| 85 | LPCYSTARIPL | 0.805 | 8 | SB | VP1 | B0702 |
| 142 | KPVQGSNFHFF | 0.686 | 29 | SB | VP1 | B0702 |
| 13 | APKKPKEPVQV | 0.564 | 112 | WB | VP1 | B0702 |
| 1 | APTKRKGECPG | 0.493 | 242 | WB | VP1 | B0702 |
| 16 | KPKEPVQVPKL | 0.491 | 245 | WB | VP1 | B0702 |
| 178 | TPKNPTAQSQV | 0.486 | 259 | WB | VP1 | B0702 |
| 299 | YPISFLLSDLI | 0.435 | 452 | WB | VP1 | B0702 |
| 285 | YFKIRLRKRSV | 0.492 | 244 | WB | VP1 | B0801 |
| 276 | TQQWRGLARYF | 0.585 | 89 | WB | VP1 | B1501 |
| 289 | RLRKRSVKNPY | 0.578 | 96 | WB | VP1 | B1501 |
| 186 | SQVMNTDHKAY | 0.565 | 110 | WB | VP1 | B1501 |
| 65 | YSQHLSAENAF | 0.559 | 118 | WB | VP1 | B1501 |
| 60 | YVSAADICGLF | 0.550 | 130 | WB | VP1 | B1501 |
| 312 | RTQKVDGQPMY | 0.427 | 492 | WB | VP1 | B1501 |
| 324 | MESQVEEVRVF | 0.678 | 32 | SB | VP1 | B1801 |
| 45 | TEVECFLNPEM | 0.554 | 124 | WB | VP1 | B1801 |
| 75 | FESDSPDRKML | 0.525 | 171 | WB | VP1 | B1801 |
| 110 | WEAVTVKTEVI | 0.483 | 267 | WB | VP1 | B1801 |
| 311 | RRTQKVDGQPM | 0.521 | 177 | WB | VP1 | B2705 |
| 277 | QQWRGLARYFK | 0.429 | 480 | WB | VP1 | B2705 |
| 142 | KPVQGSNFHFF | 0.739 | 16 | SB | VP1 | B3501 |
| 203 | YPVECWIPDPS | 0.712 | 22 | SB | VP1 | B3501 |
| 85 | LPCYSTARIPL | 0.676 | 33 | SB | VP1 | B3501 |
| 211 | DPSRNENTRYF | 0.625 | 57 | WB | VP1 | B3501 |
| 65 | YSQHLSAENAF | 0.609 | 68 | WB | VP1 | B3501 |
| 151 | FFAVGGDPLEM | 0.579 | 95 | WB | VP1 | B3501 |
| 260 | YVSAADICGLF | 0.578 | 96 | WB | VP1 | B3501 |
| 299 | YPISFLLSDLI | 0.498 | 227 | WB | VP1 | B3501 |
| 52 | NPEMGDPDDNL | 0.470 | 310 | WB | VP1 | B3501 |
| 193 | HKAYLDKNNAY | 0.461 | 342 | WB | VP1 | B3501 |
| 149 | FHFFAVGGDPL | 0.586 | 88 | WB | VP1 | B3901 |
| 234 | LHVTNTATTVL | 0.579 | 94 | WB | VP1 | B3901 |
| 224 | YTGGENVPPVL | 0.498 | 227 | WB | VP1 | B3901 |
| 75 | FESDSPDRKML | 0.556 | 121 | WB | VP1 | B4001 |
| 45 | TEVECFLNPEM | 0.446 | 402 | WB | VP1 | B4001 |
| 45 | TEVECFLNPEM | 0.451 | 379 | WB | VP1 | B4002 |
| 45 | TEVECFLNPEM | 0.477 | 287 | WB | VP1 | B4403 |
| 71 | AENAFESDSPD | 0.487 | 257 | WB | VP1 | B4501 |
| 299 | YPISFLLSDLI | 0.706 | 24 | SB | VP1 | B5101 |
| 340 | LPGDPDMIRYI | 0.600 | 75 | WB | VP1 | B5101 |
| 30 | VPPVLHVTNTA | 0.508 | 206 | WB | VP1 | B5101 |
| 85 | LPCYSTARIPL | 0.492 | 243 | WB | VP1 | B5101 |
| 299 | YPISFLLSDLI | 0.735 | 17 | SB | VP1 | B5301 |
| 340 | LPGDPDMIRYI | 0.564 | 112 | WB | VP1 | B5301 |
| 142 | KPVQGSNFHFF | 0.534 | 154 | WB | VP1 | B5301 |
| 85 | LPCYSTARIPL | 0.434 | 455 | WB | VP1 | B5301 |
| 299 | YPISFLLSDLI | 0.778 | 11 | SB | VP1 | B5401 |
| 230 | VPPVLHVTNTA | 0.720 | 20 | SB | VP1 | B5401 |
| 203 | YPVECWIPDPS | 0.657 | 40 | SB | VP1 | B5401 |
| 93 | IPLPNLNEDLT | 0.542 | 142 | WB | VP1 | B5401 |
| 85 | LPCYSTARIPL | 0.510 | 200 | WB | VP1 | B5401 |
| 340 | LPGDPDMIRYI | 0.458 | 350 | WB | VP1 | B5401 |
| 293 | RSVKNPYPISF | 0.691 | 28 | SB | VP1 | B5801 |

SEQ ID NOS.: 53780-54917

Preferred BK virus fragments of small T antigen capable of interacting with one or more MHC class 1 molecules are listed in Table L.

TABLE L

Prediction of BK virus small t protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 8-mers | | | | | | |
| 124 | FLRKEPLV | 0.663 | 38 | SB | Small t | A0201 |
| 11 | ELMDLLGL | 0.599 | 76 | WB | Small t | A0201 |
| 153 | TLQWWVQI | 0.543 | 141 | WB | Small t | A0201 |
| 74 | GTWNSSEV | 0.542 | 141 | WB | Small t | A0201 |
| 154 | LQWWVQII | 0.520 | 179 | WB | Small t | A0201 |
| 110 | CMLCQLRL | 0.509 | 202 | WB | Small t | A0201 |
| 21 | AAWGNLPL | 0.473 | 297 | WB | Small t | A0201 |
| 60 | KMEQDVKV | 0.452 | 375 | WB | Small t | A0201 |
| 11 | ELMDLLGL | 0.762 | 13 | SB | Small t | A0202 |
| 124 | FLRKEPLV | 0.715 | 21 | SB | Small t | A0202 |
| 9 | SMELMDLL | 0.628 | 56 | WB | Small t | A0202 |
| 50 | KMKRMNTL | 0.586 | 88 | WB | Small t | A0202 |
| 60 | KMEQDVKV | 0.505 | 211 | WB | Small t | A0202 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 27 | PLMRKAYL | 0.488 | 254 | WB | Small t | A0202 |
| 110 | CMLCQLRL | 0.475 | 292 | WB | Small t | A0202 |
| 124 | FLRKEPLV | 0.863 | 4 | SB | Small t | A0203 |
| 50 | KMKRMNTL | 0.758 | 13 | SB | Small t | A0203 |
| 11 | ELMDLLGL | 0.712 | 22 | SB | Small t | A0203 |
| 153 | TLQWWVQI | 0.690 | 28 | SB | Small t | A0203 |
| 110 | CMLCQLRL | 0.515 | 189 | WB | Small t | A0203 |
| 105 | SVHCPCML | 0.430 | 474 | WB | Small t | A0203 |
| 60 | KMEQDVKV | 0.429 | 484 | WB | Small t | A0203 |
| 60 | KMEQDVKV | 0.615 | 64 | WB | Small t | A0204 |
| 124 | FLRKEPLV | 0.573 | 100 | WB | Small t | A0204 |
| 153 | TLQWWVQI | 0.524 | 172 | WB | Small t | A0204 |
| 11 | ELMDLLGL | 0.521 | 178 | WB | Small t | A0204 |
| 50 | KMKRMNTL | 0.443 | 412 | WB | Small t | A0204 |
| 154 | LQWWVQII | 0.679 | 32 | SB | Small t | A0206 |
| 74 | GTWNSSEV | 0.645 | 46 | SB | Small t | A0206 |
| 11 | ELMDLLGL | 0.594 | 80 | WB | Small t | A0206 |
| 124 | FLRKEPLV | 0.581 | 92 | WB | Small t | A0206 |
| 21 | AAWGNLPL | 0.571 | 104 | WB | Small t | A0206 |
| 110 | CMLCQLRL | 0.496 | 233 | WB | Small t | A0206 |
| 142 | TQWFGLDL | 0.494 | 239 | WB | Small t | A0206 |
| 153 | TLQWWVQI | 0.468 | 315 | WB | Small t | A0206 |
| 60 | KMEQDVKV | 0.427 | 490 | WB | Small t | A0206 |
| 11 | ELMDLLGL | 0.904 | 2 | SB | Small t | A0211 |
| 124 | FLRKEPLV | 0.865 | 4 | SB | Small t | A0211 |
| 153 | TLQWWVQI | 0.861 | 4 | SB | Small t | A0211 |
| 60 | KMEQDVKV | 0.845 | 5 | SB | Small t | A0211 |
| 14 | DLLGLERA | 0.725 | 19 | SB | Small t | A0211 |
| 74 | GTWNSSEV | 0.720 | 20 | SB | Small t | A0211 |
| 110 | CMLCQLRL | 0.666 | 37 | SB | Small t | A0211 |
| 27 | PLMRKAYL | 0.666 | 37 | SB | Small t | A0211 |
| 21 | AAWGNLPL | 0.638 | 50 | WB | Small t | A0211 |
| 9 | SMELMDLL | 0.635 | 51 | WB | Small t | A0211 |
| 56 | TLYKKMEQ | 0.625 | 57 | WB | Small t | A0211 |
| 50 | KMKRMNTL | 0.582 | 92 | WB | Small t | A0211 |
| 146 | GLDLTEET | 0.563 | 113 | WB | Small t | A0211 |
| 3 | VLNREESM | 0.494 | 239 | WB | Small t | A0211 |
| 105 | SVHCPCML | 0.430 | 474 | WB | Small t | A0211 |
| 148 | DLTEETLQ | 0.428 | 487 | WB | Small t | A0211 |
| 124 | FLRKEPLV | 0.884 | 3 | SB | Small t | A0212 |
| 11 | ELMDLLGL | 0.842 | 5 | SB | Small t | A0212 |
| 153 | TLQWWVQI | 0.692 | 28 | SB | Small t | A0212 |
| 60 | KMEQDVKV | 0.666 | 37 | SB | Small t | A0212 |
| 3 | VLNREESM | 0.639 | 49 | SB | Small t | A0212 |
| 27 | PLMRKAYL | 0.597 | 78 | WB | Small t | A0212 |
| 110 | CMLCQLRL | 0.580 | 94 | WB | Small t | A0212 |
| 50 | KMKRMNTL | 0.579 | 94 | WB | Small t | A0212 |
| 14 | DLLGLERA | 0.523 | 174 | WB | Small t | A0212 |
| 74 | GTWNSSEV | 0.521 | 178 | WB | Small t | A0212 |
| 56 | TLYKKMEQ | 0.520 | 180 | WB | Small t | A0212 |
| 21 | AAWGNLPL | 0.511 | 197 | WB | Small t | A0212 |
| 9 | SMELMDLL | 0.426 | 495 | WB | Small t | A0212 |
| 124 | FLRKEPLV | 0.876 | 3 | SB | Small t | A0216 |
| 27 | PLMRKAYL | 0.829 | 6 | SB | Small t | A0216 |
| 11 | ELMDLLGL | 0.740 | 16 | SB | Small t | A0216 |
| 74 | GTWNSSEV | 0.734 | 17 | SB | Small t | A0216 |
| 60 | KMEQDVKV | 0.732 | 18 | SB | Small t | A0216 |
| 153 | TLQWWVQI | 0.684 | 30 | SB | Small t | A0216 |
| 56 | TLYKKMEQ | 0.662 | 38 | SB | Small t | A0216 |
| 50 | KMKRMNTL | 0.651 | 43 | SB | Small t | A0216 |
| 21 | AAWGNLPL | 0.600 | 75 | WB | Small t | A0216 |
| 110 | CMLCQLRL | 0.577 | 97 | WB | Small t | A0216 |
| 14 | DLLGLERA | 0.566 | 109 | WB | Small t | A0216 |
| 9 | SMELMDLL | 0.532 | 158 | WB | Small t | A0216 |
| 146 | GLDLTEET | 0.453 | 370 | WB | Small t | A0216 |
| 3 | VLNREESM | 0.429 | 482 | WB | Small t | A0216 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 11 | ELMDLLGL | 0.807 | 8 | SB | Small t | A0219 |
| 124 | FLRKEPLV | 0.736 | 17 | SB | Small t | A0219 |
| 21 | AAWGNLPL | 0.637 | 51 | WB | Small t | A0219 |
| 153 | TLQWWVQI | 0.608 | 69 | WB | Small t | A0219 |
| 27 | PLMRKAYL | 0.589 | 85 | WB | Small t | A0219 |
| 110 | CMLCQLRL | 0.548 | 133 | WB | Small t | A0219 |
| 74 | GTWNSSEV | 0.540 | 145 | WB | Small t | A0219 |
| 116 | RLRHLNRK | 0.728 | 19 | SB | Small t | A0301 |
| 53 | RMNTLYKK | 0.719 | 20 | SB | Small t | A0301 |
| 119 | HLNRKFLR | 0.676 | 33 | SB | Small t | A0301 |
| 28 | LMRKAYLK | 0.671 | 35 | SB | Small t | A0301 |
| 31 | KAYLKKCK | 0.506 | 210 | WB | Small t | A0301 |
| 53 | RMNTLYKK | 0.727 | 19 | SB | Small t | A1101 |
| 31 | KAYLKKCK | 0.639 | 49 | SB | Small t | A1101 |
| 52 | KRMNTLYK | 0.454 | 367 | WB | Small t | A1101 |
| 119 | HLNRKFLR | 0.443 | 415 | WB | Small t | A1101 |
| 160 | IIGETPFR | 0.438 | 436 | WB | Small t | A1101 |
| 28 | LMRKAYLK | 0.435 | 452 | WB | Small t | A1101 |
| 131 | VWIDCYCI | 0.479 | 280 | WB | Small t | A2301 |
| 92 | LYCKEWPI | 0.458 | 351 | WB | Small t | A2301 |
| 131 | VWIDCYCI | 0.675 | 33 | SB | Small t | A2402 |
| 92 | LYCKEWPI | 0.622 | 60 | WB | Small t | A2402 |
| 11 | ELMDLLGL | 0.486 | 259 | WB | Small t | A2601 |
| 159 | QIIGETPF | 0.823 | 6 | SB | Small t | A2602 |
| 80 | EVCADFPL | 0.594 | 80 | WB | Small t | A2602 |
| 66 | KVAHQPDF | 0.563 | 112 | WB | Small t | A2602 |
| 11 | ELMDLLGL | 0.500 | 224 | WB | Small t | A2602 |
| 86 | PLCPDTLY | 0.515 | 189 | WB | Small t | A2902 |
| 116 | RLRHLNRK | 0.810 | 7 | SB | Small t | A3001 |
| 28 | LMRKAYLK | 0.805 | 8 | SB | Small t | A3001 |
| 53 | RMNTLYKK | 0.672 | 34 | SB | Small t | A3001 |
| 31 | KAYLKKCK | 0.628 | 55 | WB | Small t | A3001 |
| 52 | KRMNTLYK | 0.620 | 60 | WB | Small t | A3001 |
| 29 | MRKAYLKK | 0.612 | 66 | WB | Small t | A3001 |
| 120 | LNRKFLRK | 0.571 | 104 | WB | Small t | A3001 |
| 119 | HLNRKFLR | 0.850 | 5 | SB | Small t | A3101 |
| 53 | RMNTLYKK | 0.816 | 7 | SB | Small t | A3101 |
| 111 | MLCQLRLR | 0.684 | 30 | SB | Small t | A3101 |
| 28 | LMRKAYLK | 0.646 | 46 | SB | Small t | A3101 |
| 116 | RLRHLNRK | 0.541 | 142 | WB | Small t | A3101 |
| 160 | IIGETPFR | 0.540 | 145 | WB | Small t | A3101 |
| 31 | KAYLKKCK | 0.504 | 214 | WB | Small t | A3101 |
| 119 | HLNRKFLR | 0.745 | 15 | SB | Small t | A3301 |
| 111 | MLCQLRLR | 0.521 | 177 | WB | Small t | A3301 |
| 160 | IIGETPFR | 0.469 | 313 | WB | Small t | A3301 |
| 163 | ETPFRDLK | 0.799 | 8 | SB | Small t | A6801 |
| 111 | MLCQLRLR | 0.725 | 19 | SB | Small t | A6801 |
| 119 | HLNRKFLR | 0.654 | 42 | SB | Small t | A6801 |
| 160 | IIGETPFR | 0.568 | 107 | WB | Small t | A6801 |
| 80 | EVCADFPL | 0.773 | 11 | SB | Small t | A6802 |
| 11 | ELMDLLGL | 0.583 | 90 | WB | Small t | A6802 |
| 8 | ESMELMDL | 0.563 | 113 | WB | Small t | A6802 |
| 105 | SVHCPCML | 0.510 | 200 | WB | Small t | A6802 |
| 19 | ERAAWGNL | 0.434 | 456 | WB | Small t | A6802 |
| 11 | ELMDLLGL | 0.667 | 36 | SB | Small t | A6901 |
| 80 | EVCADFPL | 0.549 | 131 | WB | Small t | A6901 |
| 74 | GTWNSSEV | 0.545 | 137 | WB | Small t | A6901 |
| 85 | FPLCPDTL | 0.537 | 150 | WB | Small t | A6901 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 21 | AAWGNLPL | 0.513 | 193 | WB | Small t | A6901 |
| 8 | ESMELMDL | 0.453 | 372 | WB | Small t | A6901 |
| 103 | KPSVHCPC | 0.540 | 145 | WB | Small t | B0702 |
| 21 | AAWGNLPL | 0.482 | 270 | WB | Small t | B0702 |
| 26 | LPLMRKAY | 0.431 | 472 | WB | Small t | B0702 |
| 50 | KMKRMNTL | 0.479 | 282 | WB | Small t | B0801 |
| 33 | YLKKCKEF | 0.446 | 401 | WB | Small t | B0801 |
| 159 | QIIGETPF | 0.529 | 163 | WB | Small t | B1501 |
| 33 | YLKKCKEF | 0.496 | 232 | WB | Small t | B1501 |
| 50 | KMKRMNTL | 0.474 | 294 | WB | Small t | B1501 |
| 52 | KRMNTLYK | 0.623 | 58 | WB | Small t | B2705 |
| 29 | MRKAYLKK | 0.430 | 477 | WB | Small t | B2705 |
| 26 | LPLMRKAY | 0.749 | 15 | SB | Small t | B3501 |
| 85 | FPLCPDTL | 0.706 | 24 | SB | Small t | B3501 |
| 21 | AAWGNLPL | 0.509 | 203 | WB | Small t | B3501 |
| 159 | QIIGETPF | 0.457 | 355 | WB | Small t | B3501 |
| 5 | NREESMEL | 0.555 | 123 | WB | Small t | B3901 |
| 162 | GETPFRDL | 0.607 | 69 | WB | Small t | B4001 |
| 6 | REESMELM | 0.511 | 197 | WB | Small t | B4001 |
| 6 | REESMELM | 0.433 | 463 | WB | Small t | B4002 |
| 151 | EETLQWWV | 0.428 | 488 | WB | Small t | B4002 |
| 150 | TEETLQWW | 0.443 | 414 | WB | Small t | B4402 |
| 151 | EETLQWWV | 0.426 | 497 | WB | Small t | B4403 |
| 151 | EETLQWWV | 0.447 | 397 | WB | Small t | B4501 |
| 85 | FPLCPDTL | 0.509 | 202 | WB | Small t | B5101 |
| 108 | CPCMLCQL | 0.480 | 276 | WB | Small t | B5101 |
| 26 | LPLMRKAY | 0.636 | 51 | WB | Small t | B5301 |
| 85 | FPLCPDTL | 0.559 | 117 | WB | Small t | B5301 |
| 26 | LPLMRKAY | 0.482 | 271 | WB | Small t | B5401 |
| 149 | LTEETLQW | 0.602 | 74 | WB | Small t | B5701 |
| 149 | LTEETLQW | 0.555 | 123 | WB | Small t | B5801 |
| 66 | KVAHQPDF | 0.491 | 246 | WB | Small t | B5801 |
| 16 | LGLERAAW | 0.439 | 430 | WB | Small t | B5801 |

9-mers

| pos | peptide | logscore | affinity (nM) | Bind Level | Protein Name | Allele |
|---|---|---|---|---|---|---|
| 91 | TLYCKEWPI | 0.629 | 55 | WB | Small t | A0201 |
| 153 | TLQWWVQII | 0.605 | 71 | WB | Small t | A0201 |
| 130 | LVWIDCYCI | 0.509 | 201 | WB | Small t | A0201 |
| 91 | TLYCKEWPI | 0.697 | 26 | SB | Small t | A0202 |
| 146 | GLDLTEETL | 0.429 | 483 | WB | Small t | A0202 |
| 153 | TLQWWVQII | 0.838 | 5 | SB | Small t | A0203 |
| 91 | TLYCKEWPI | 0.728 | 18 | SB | Small t | A0203 |
| 20 | RAAWGNLPL | 0.491 | 246 | WB | Small t | A0203 |
| 53 | RMNTLYKKM | 0.490 | 249 | WB | Small t | A0203 |
| 153 | TLQWWVQII | 0.535 | 152 | WB | Small t | A0204 |
| 91 | TLYCKEWPI | 0.525 | 170 | WB | Small t | A0204 |
| 59 | KKMEQDVKV | 0.514 | 191 | WB | Small t | A0204 |
| 158 | VQIIGETPF | 0.700 | 25 | SB | Small t | A0206 |
| 142 | TQWFGLDLT | 0.667 | 36 | SB | Small t | A0206 |
| 91 | TLYCKEWPI | 0.660 | 39 | SB | Small t | A0206 |
| 20 | RAAWGNLPL | 0.634 | 52 | WB | Small t | A0206 |
| 79 | SEVCADFPL | 0.515 | 189 | WB | Small t | A0206 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pospeptide | logscore | affinity (nM) | Bind Level | Protein Name | Allele |
|---|---|---|---|---|---|
| 10 MELMDLLGL | 0.496 | 233 | WB | Small t | A0206 |
| 21 AAWGNLPLM | 0.457 | 357 | WB | Small t | A0206 |
| 146 GLDLTEETL | 0.857 | 4 | SB | Small t | A0211 |
| 91 TLYCKEWPI | 0.856 | 4 | SB | Small t | A0211 |
| 153 TLQWWVQII | 0.797 | 8 | SB | Small t | A0211 |
| 20 RAAWGNLPL | 0.620 | 61 | WB | Small t | A0211 |
| 14 DLLGLERAA | 0.614 | 65 | WB | Small t | A0211 |
| 86 PLCPDTLYC | 0.564 | 111 | WB | Small t | A0211 |
| 130 LVWIDCYCI | 0.505 | 210 | WB | Small t | A0211 |
| 73 FGTWNSSEV | 0.481 | 274 | WB | Small t | A0211 |
| 21 AAWGNLPLM | 0.448 | 394 | WB | Small t | A0211 |
| 152 ETLQWWVQI | 0.445 | 404 | WB | Small t | A0211 |
| 98 PICSKKPSV | 0.436 | 448 | WB | Small t | A0211 |
| 129 PLVWIDCYC | 0.432 | 465 | WB | Small t | A0211 |
| 146 GLDLTEETL | 0.773 | 11 | SB | Small t | A0212 |
| 91 TLYCKEWPI | 0.751 | 14 | SB | Small t | A0212 |
| 153 TLQWWVQII | 0.666 | 37 | SB | Small t | A0212 |
| 14 DLLGLERAA | 0.548 | 133 | WB | Small t | A0212 |
| 141 FTQWFGLDL | 0.521 | 178 | WB | Small t | A0212 |
| 98 PICSKKPSV | 0.430 | 474 | WB | Small t | A0212 |
| 146 GLDLTEETL | 0.773 | 11 | SB | Small t | A0216 |
| 91 TLYCKEWPI | 0.720 | 20 | SB | Small t | A0216 |
| 98 PICSKKPSV | 0.617 | 62 | WB | Small t | A0216 |
| 153 TLQWWVQII | 0.518 | 184 | WB | Small t | A0216 |
| 129 PLVWIDCYC | 0.472 | 302 | WB | Small t | A0216 |
| 146 GLDLTEETL | 0.704 | 24 | SB | Small t | A0219 |
| 153 TLQWWVQII | 0.531 | 160 | WB | Small t | A0219 |
| 21 AAWGNLPLM | 0.506 | 209 | WB | Small t | A0219 |
| 91 TLYCKEWPI | 0.505 | 211 | WB | Small t | A0219 |
| 119 HLNRKFLRK | 0.834 | 6 | SB | Small t | A0301 |
| 28 LMRKAYLKK | 0.703 | 24 | SB | Small t | A0301 |
| 50 KMKRMNTLY | 0.654 | 42 | SB | Small t | A0301 |
| 27 PLMRKAYLK | 0.578 | 96 | WB | Small t | A0301 |
| 114 QLRLRHLNR | 0.447 | 397 | WB | Small t | A0301 |
| 119 HLNRKFLRK | 0.694 | 27 | SB | Small t | A1101 |
| 27 PLMRKAYLK | 0.576 | 98 | WB | Small t | A1101 |
| 159 QIIGETPFR | 0.516 | 187 | WB | Small t | A1101 |
| 32 AYLKKCKEF | 0.708 | 23 | SB | Small t | A2301 |
| 32 AYLKKCKEF | 0.523 | 174 | WB | Small t | A2402 |
| 32 AYLKKCKEF | 0.859 | 4 | SB | Small t | A2403 |
| 68 AHQPDFGTW | 0.542 | 142 | WB | Small t | A2403 |
| 8 ESMELMDLL | 0.463 | 335 | WB | Small t | A2601 |
| 163 ETPFRDLKL | 0.795 | 9 | SB | Small t | A2602 |
| 152 ETLQWWVQI | 0.499 | 225 | WB | Small t | A2602 |
| 8 ESMELMDLL | 0.476 | 290 | WB | Small t | A2602 |
| 50 KMKRMNTLY | 0.576 | 98 | WB | Small t | A2902 |
| 85 FPLCPDTLY | 0.475 | 291 | WB | Small t | A2902 |
| 28 LMRKAYLKK | 0.830 | 6 | SB | Small t | A3001 |
| 51 MKRMNTLYK | 0.827 | 6 | SB | Small t | A3001 |
| 36 KCKEFHPDK | 0.817 | 7 | SB | Small t | A3001 |
| 114 QLRLRHLNR | 0.516 | 187 | WB | Small t | A3001 |
| 50 KMKRMNTLY | 0.501 | 220 | WB | Small t | A3001 |
| 119 HLNRKFLRK | 0.445 | 405 | WB | Small t | A3001 |
| 27 PLMRKAYLK | 0.439 | 431 | WB | Small t | A3001 |
| 52 KRMNTLYKK | 0.435 | 453 | WB | Small t | A3001 |
| 50 KMKRMNTLY | 0.561 | 115 | WB | Small t | A3002 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 118 | RHLNRKFLR | 0.820 | 7 | SB | Small t | A3101 |
| 110 | CMLCQLRLR | 0.649 | 44 | SB | Small t | A3101 |
| 114 | QLRLRHLNR | 0.628 | 56 | WB | Small t | A3101 |
| 50 | KMKRMNTLY | 0.540 | 144 | WB | Small t | A3101 |
| 119 | HLNRKFLRK | 0.514 | 191 | WB | Small t | A3101 |
| 28 | LMRKAYLKK | 0.436 | 447 | WB | Small t | A3101 |
| 114 | QLRLRHLNR | 0.699 | 25 | SB | Small t | A3301 |
| 159 | QIIGETPFR | 0.822 | 6 | SB | Small t | A6801 |
| 108 | CPCMLCQLR | 0.553 | 125 | WB | Small t | A6801 |
| 8 | ESMELMDLL | 0.767 | 12 | SB | Small t | A6802 |
| 139 | DCFTQWFGL | 0.659 | 40 | SB | Small t | A6802 |
| 73 | FGTWNSSEV | 0.580 | 94 | WB | Small t | A6802 |
| 152 | ETLQWWVQI | 0.522 | 175 | WB | Small t | A6802 |
| 134 | DCYCIDCFT | 0.491 | 247 | WB | Small t | A6802 |
| 163 | ETPFRDLKL | 0.490 | 247 | WB | Small t | A6802 |
| 152 | ETLQWWVQI | 0.832 | 6 | SB | Small t | A6901 |
| 8 | ESMELMDLL | 0.609 | 68 | WB | Small t | A6901 |
| 91 | TLYCKEWPI | 0.506 | 210 | WB | Small t | A6901 |
| 130 | LVWIDCYCI | 0.492 | 244 | WB | Small t | A6901 |
| 21 | AAWGNLPLM | 0.483 | 267 | WB | Small t | A6901 |
| 20 | RAAWGNLPL | 0.721 | 20 | SB | Small t | B0702 |
| 26 | LPLMRKAYL | 0.719 | 20 | SB | Small t | B0702 |
| 103 | KPSVHCPCM | 0.431 | 472 | WB | Small t | B0702 |
| 158 | VQIIGETPF | 0.615 | 64 | WB | Small t | B1501 |
| 50 | KMKRMNTLY | 0.561 | 115 | WB | Small t | B1501 |
| 116 | RLRHLNRKF | 0.503 | 216 | WB | Small t | B1501 |
| 20 | RAAWGNLPL | 0.444 | 411 | WB | Small t | B1501 |
| 10 | MELMDLLGL | 0.722 | 20 | SB | Small t | B1801 |
| 150 | TEETLQWWV | 0.497 | 230 | WB | Small t | B1801 |
| 79 | SEVCADFPL | 0.470 | 308 | WB | Small t | B1801 |
| 52 | KRMNTLYKK | 0.656 | 41 | SB | Small t | B2705 |
| 85 | FPLCPDTLY | 0.805 | 8 | SB | Small t | B3501 |
| 128 | EPLVWIDCY | 0.750 | 14 | SB | Small t | B3501 |
| 20 | RAAWGNLPL | 0.618 | 62 | WB | Small t | B3501 |
| 21 | AAWGNLPLM | 0.545 | 137 | WB | Small t | B3501 |
| 103 | KPSVHCPCM | 0.451 | 377 | WB | Small t | B3501 |
| 10 | MELMDLLGL | 0.751 | 14 | SB | Small t | B4001 |
| 79 | SEVCADFPL | 0.738 | 16 | SB | Small t | B4001 |
| 7 | EESMELMDL | 0.561 | 115 | WB | Small t | B4001 |
| 18 | LERAAWGNL | 0.497 | 231 | WB | Small t | B4001 |
| 79 | SEVCADFPL | 0.455 | 365 | WB | Small t | B4002 |
| 79 | SEVCADFPL | 0.591 | 83 | WB | Small t | B4403 |
| 151 | EETLQWWVQ | 0.463 | 334 | WB | Small t | B4403 |
| 85 | FPLCPDTLY | 0.710 | 23 | SB | Small t | B5301 |
| 128 | EPLVWIDCY | 0.651 | 43 | SB | Small t | B5301 |
| 26 | LPLMRKAYL | 0.625 | 57 | WB | Small t | B5301 |
| 97 | WPICSKKPS | 0.548 | 132 | WB | Small t | B5401 |
| 149 | LTEETLQWW | 0.564 | 112 | WB | Small t | B5701 |
| 124 | FLRKEPLVW | 0.534 | 154 | WB | Small t | B5801 |
| 20 | RAAWGNLPL | 0.460 | 344 | WB | Small t | B5801 |

10-mers

| 124 | FLRKEPLVWI | 0.574 | 100 | WB | Small t | A0201 |
|---|---|---|---|---|---|---|
| 56 | TLYKKMEQDV | 0.485 | 263 | WB | Small t | A0201 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 12 | LMDLLGLERA | 0.456 | 361 | WB | Small t | A0201 |
| 3 | VLNREESMEL | 0.434 | 454 | WB | Small t | A0201 |
| 111 | MLCQLRLRHL | 0.647 | 45 | SB | Small t | A0202 |
| 124 | FLRKEPLVWI | 0.608 | 69 | WB | Small t | A0202 |
| 12 | LMDLLGLERA | 0.607 | 70 | WB | Small t | A0202 |
| 3 | VLNREESMEL | 0.562 | 114 | WB | Small t | A0202 |
| 56 | TLYKKMEQDV | 0.516 | 187 | WB | Small t | A0202 |
| 145 | FGLDLTEETL | 0.516 | 188 | WB | Small t | A0202 |
| 9 | SMELMDLLGL | 0.507 | 206 | WB | Small t | A0202 |
| 25 | NLPLMRKAYL | 0.483 | 269 | WB | Small t | A0202 |
| 124 | FLRKEPLVWI | 0.870 | 4 | SB | Small t | A0203 |
| 56 | TLYKKMEQDV | 0.707 | 23 | SB | Small t | A0203 |
| 3 | VLNREESMEL | 0.666 | 37 | SB | Small t | A0203 |
| 111 | MLCQLRLRHL | 0.549 | 131 | WB | Small t | A0203 |
| 12 | LMDLLGLERA | 0.468 | 314 | WB | Small t | A0203 |
| 9 | SMELMDLLGL | 0.462 | 338 | WB | Small t | A0203 |
| 116 | RLRHLNRKFL | 0.429 | 484 | WB | Small t | A0203 |
| 149 | LTEETLQWWV | 0.571 | 104 | WB | Small t | A0204 |
| 3 | VLNREESMEL | 0.557 | 120 | WB | Small t | A0204 |
| 124 | FLRKEPLVWI | 0.500 | 223 | WB | Small t | A0204 |
| 149 | LTEETLQWWV | 0.581 | 93 | WB | Small t | A0206 |
| 154 | LQWWVQIIGE | 0.521 | 177 | WB | Small t | A0206 |
| 20 | RAAWGNLPLM | 0.518 | 184 | WB | Small t | A0206 |
| 142 | TQWFGLDLTE | 0.463 | 334 | WB | Small t | A0206 |
| 124 | FLRKEPLVWI | 0.430 | 474 | WB | Small t | A0206 |
| 56 | TLYKKMEQDV | 0.875 | 3 | SB | Small t | A0211 |
| 3 | VLNREESMEL | 0.824 | 6 | SB | Small t | A0211 |
| 149 | LTEETLQWWV | 0.779 | 10 | SB | Small t | A0211 |
| 12 | LMDLLGLERA | 0.757 | 13 | SB | Small t | A0211 |
| 124 | FLRKEPLVWI | 0.715 | 21 | SB | Small t | A0211 |
| 9 | SMELMDLLGL | 0.706 | 24 | SB | Small t | A0211 |
| 111 | MLCQLRLRHL | 0.689 | 28 | SB | Small t | A0211 |
| 25 | NLPLMRKAYL | 0.682 | 31 | SB | Small t | A0211 |
| 129 | PLVWIDCYCI | 0.681 | 31 | SB | Small t | A0211 |
| 116 | RLRHLNRKFL | 0.554 | 124 | WB | Small t | A0211 |
| 146 | GLDLTEETLQ | 0.516 | 188 | WB | Small t | A0211 |
| 17 | GLERAAWGNL | 0.502 | 219 | WB | Small t | A0211 |
| 145 | FGLDLTEETL | 0.451 | 381 | WB | Small t | A0211 |
| 56 | TLYKKMEQDV | 0.893 | 3 | SB | Small t | A0212 |
| 3 | VLNREESMEL | 0.788 | 9 | SB | Small t | A0212 |
| 124 | FLRKEPLVWI | 0.756 | 13 | SB | Small t | A0212 |
| 149 | LTEETLQWWV | 0.727 | 19 | SB | Small t | A0212 |
| 12 | LMDLLGLERA | 0.604 | 72 | WB | Small t | A0212 |
| 111 | MLCQLRLRHL | 0.584 | 90 | WB | Small t | A0212 |
| 9 | SMELMDLLGL | 0.579 | 95 | WB | Small t | A0212 |
| 145 | FGLDLTEETL | 0.484 | 264 | WB | Small t | A0212 |
| 25 | NLPLMRKAYL | 0.477 | 287 | WB | Small t | A0212 |
| 116 | RLRHLNRKFL | 0.449 | 386 | WB | Small t | A0212 |
| 17 | GLERAAWGNL | 0.430 | 474 | WB | Small t | A0212 |
| 56 | TLYKKMEQDV | 0.842 | 5 | SB | Small t | A0216 |
| 3 | VLNREESMEL | 0.768 | 12 | SB | Small t | A0216 |
| 25 | NLPLMRKAYL | 0.703 | 24 | SB | Small t | A0216 |
| 124 | FLRKEPLVWI | 0.687 | 29 | SB | Small t | A0216 |
| 149 | LTEETLQWWV | 0.632 | 53 | WB | Small t | A0216 |
| 111 | MLCQLRLRHL | 0.627 | 56 | WB | Small t | A0216 |
| 116 | RLRHLNRKFL | 0.566 | 110 | WB | Small t | A0216 |
| 17 | GLERAAWGNL | 0.545 | 137 | WB | Small t | A0216 |
| 129 | PLVWIDCYCI | 0.522 | 175 | WB | Small t | A0216 |
| 12 | LMDLLGLERA | 0.484 | 265 | WB | Small t | A0216 |
| 9 | SMELMDLLGL | 0.468 | 316 | WB | Small t | A0216 |
| 149 | LTEETLQWWV | 0.627 | 56 | WB | Small t | A0219 |
| 3 | VLNREESMEL | 0.573 | 101 | WB | Small t | A0219 |
| 56 | TLYKKMEQDV | 0.570 | 104 | WB | Small t | A0219 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 124 | FLRKEPLVWI | 0.551 | 128 | WB | Small t | A0219 |
| 12 | LMDLLGLERA | 0.486 | 260 | WB | Small t | A0219 |
| 50 | KMKRMNTLYK | 0.754 | 14 | SB | Small t | A0301 |
| 118 | RHLNRKFLRK | 0.678 | 32 | SB | Small t | A0301 |
| 27 | PLMRKAYLKK | 0.663 | 38 | SB | Small t | A0301 |
| 114 | QLRLRHLNRK | 0.562 | 114 | WB | Small t | A0301 |
| 22 | AWGNLPLMRK | 0.533 | 156 | WB | Small t | A0301 |
| 26 | LPLMRKAYLK | 0.500 | 222 | WB | Small t | A0301 |
| 50 | KMKRMNTLYK | 0.700 | 25 | SB | Small t | A1101 |
| 27 | PLMRKAYLKK | 0.478 | 284 | WB | Small t | A1101 |
| 21 | AAWGNLPLMR | 0.475 | 293 | WB | Small t | A1101 |
| 22 | AWGNLPLMRK | 0.449 | 387 | WB | Small t | A1101 |
| 86 | PLCPDTLYCK | 0.444 | 410 | WB | Small t | A1101 |
| 135 | CYCIDCFTQW | 0.623 | 58 | WB | Small t | A2301 |
| 57 | LYKKMEQDVK | 0.531 | 160 | WB | Small t | A2301 |
| 136 | YCIDCFTQWF | 0.433 | 463 | WB | Small t | A2301 |
| 135 | CYCIDCFTQW | 0.616 | 63 | WB | Small t | A2403 |
| 123 | KFLRKEPLVW | 0.549 | 132 | WB | Small t | A2403 |
| 64 | DVKVAHQPDF | 0.665 | 37 | SB | Small t | A2602 |
| 152 | ETLQWWVQII | 0.483 | 269 | WB | Small t | A2602 |
| 84 | DFPLCPDTLY | 0.458 | 353 | WB | Small t | A2902 |
| 50 | KMKRMNTLYK | 0.848 | 5 | SB | Small t | A3001 |
| 114 | QLRLRHLNRK | 0.729 | 18 | SB | Small t | A3001 |
| 51 | MKRMNTLYKK | 0.685 | 30 | SB | Small t | A3001 |
| 27 | PLMRKAYLKK | 0.500 | 224 | WB | Small t | A3001 |
| 116 | RLRHLNRKFL | 0.497 | 231 | WB | Small t | A3001 |
| 29 | MRKAYLKKCK | 0.488 | 255 | WB | Small t | A3001 |
| 117 | LRHLNRKFLR | 0.676 | 33 | SB | Small t | A3101 |
| 113 | CQLRLRHLNR | 0.674 | 34 | SB | Small t | A3101 |
| 50 | KMKRMNTLYK | 0.640 | 49 | SB | Small t | A3101 |
| 51 | MKRMNTLYKK | 0.468 | 316 | WB | Small t | A3101 |
| 118 | RHLNRKFLRK | 0.446 | 400 | WB | Small t | A3101 |
| 11 | ELMDLLGLER | 0.512 | 196 | WB | Small t | A3301 |
| 117 | LRHLNRKFLR | 0.430 | 476 | WB | Small t | A3301 |
| 11 | ELMDLLGLER | 0.720 | 20 | SB | Small t | A6801 |
| 90 | DTLYCKEWPI | 0.574 | 99 | WB | Small t | A6802 |
| 152 | ETLQWWVQII | 0.456 | 358 | WB | Small t | A6802 |
| 19 | ERAAWGNLPL | 0.452 | 375 | WB | Small t | A6802 |
| 152 | ETLQWWVQII | 0.795 | 9 | SB | Small t | A6901 |
| 90 | DTLYCKEWPI | 0.586 | 88 | WB | Small t | A6901 |
| 149 | LTEETLQWWV | 0.575 | 98 | WB | Small t | A6901 |
| 97 | WPICSKKPSV | 0.518 | 184 | WB | Small t | A6901 |
| 103 | KPSVHCPCML | 0.703 | 24 | SB | Small t | B0702 |
| 97 | WPICSKKPSV | 0.563 | 113 | WB | Small t | B0702 |
| 116 | RLRHLNRKFL | 0.471 | 304 | WB | Small t | B0702 |
| 157 | WVQIIGETPF | 0.540 | 145 | WB | Small t | B1501 |
| 52 | KRMNTLYKKM | 0.591 | 83 | WB | Small t | B2705 |
| 157 | WVQIIGETPF | 0.638 | 50 | WB | Small t | B3501 |
| 20 | RAAWGNLPLM | 0.595 | 80 | WB | Small t | B3501 |
| 136 | YCIDCFTQWF | 0.429 | 483 | WB | Small t | B3501 |
| 19 | ERAAWGNLPL | 0.539 | 147 | WB | Small t | B3901 |
| 6 | REESMELMDL | 0.707 | 23 | SB | Small t | B4001 |
| 162 | GETPFRDLKL | 0.618 | 62 | WB | Small t | B4001 |
| 7 | EESMELMDLL | 0.488 | 253 | WB | Small t | B4001 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 7 | EESMELMDLL | 0.482 | 271 | WB | Small t | B4002 |
| 127 | KEPLVWIDCY | 0.429 | 481 | WB | Small t | B4402 |
| 151 | EETLQWWVQI | 0.495 | 235 | WB | Small t | B4403 |
| 127 | KEPLVWIDCY | 0.434 | 456 | WB | Small t | B4403 |
| 97 | WPICSKKPSV | 0.434 | 454 | WB | Small t | B5101 |
| 97 | WPICSKKPSV | 0.735 | 17 | SB | Small t | B5401 |
| 26 | LPLMRKAYLK | 0.511 | 197 | WB | Small t | B5401 |
| 67 | VAHQPDFGTW | 0.448 | 393 | WB | Small t | B5701 |
| 123 | KFLRKEPLVW | 0.620 | 60 | WB | Small t | B5801 |
| 67 | VAHQPDFGTW | 0.537 | 149 | WB | Small t | B5801 |
| 20 | RAAWGNLPLM | 0.485 | 263 | WB | Small t | B5801 |
| 31 | KAYLKKCKEF | 0.431 | 473 | WB | Small t | B5801 |
| | | | 11-mers | | | |
| 11 | ELMDLLGLERA | 0.458 | 351 | WB | Small t | A0201 |
| 2 | KVLNREESMEL | 0.432 | 467 | WB | Small t | A0201 |
| 11 | ELMDLLGLERA | 0.582 | 92 | WB | Small t | A0202 |
| 137 | CIDCFTQWFGL | 0.516 | 187 | WB | Small t | A0202 |
| 3 | VLNREESMELM | 0.491 | 245 | WB | Small t | A0202 |
| 148 | DLTEETLQWWV | 0.445 | 404 | WB | Small t | A0202 |
| 11 | ELMDLLGLERA | 0.652 | 42 | SB | Small t | A0203 |
| 110 | CMLCQLRLRHL | 0.520 | 180 | WB | Small t | A0203 |
| 3 | VLNREESMELM | 0.473 | 298 | WB | Small t | A0203 |
| 105 | SVHCPCMLCQL | 0.449 | 389 | WB | Small t | A0203 |
| 2 | KVLNREESMEL | 0.525 | 170 | WB | Small t | A0204 |
| 148 | DLTEETLQWWV | 0.453 | 372 | WB | Small t | A0204 |
| 105 | SVHCPCMLCQL | 0.450 | 384 | WB | Small t | A0204 |
| 2 | KVLNREESMEL | 0.620 | 61 | WB | Small t | A0206 |
| 154 | LQWWVQIIGET | 0.600 | 75 | WB | Small t | A0206 |
| 137 | CIDCFTQWFGL | 0.565 | 110 | WB | Small t | A0206 |
| 142 | TQWFGLDLTEE | 0.519 | 182 | WB | Small t | A0206 |
| 132 | WIDCYCIDCFT | 0.435 | 452 | WB | Small t | A0206 |
| 148 | DLTEETLQWWV | 0.957 | 1 | SB | Small t | A0211 |
| 11 | ELMDLLGLERA | 0.815 | 7 | SB | Small t | A0211 |
| 137 | CIDCFTQWFGL | 0.698 | 26 | SB | Small t | A0211 |
| 12 | LMDLLGLERAA | 0.669 | 35 | SB | Small t | A0211 |
| 2 | KVLNREESMEL | 0.597 | 77 | WB | Small t | A0211 |
| 105 | SVHCPCMLCQL | 0.539 | 146 | WB | Small t | A0211 |
| 3 | VLNREESMELM | 0.535 | 153 | WB | Small t | A0211 |
| 148 | DLTEETLQWWV | 0.806 | 8 | SB | Small t | A0212 |
| 11 | ELMDLLGLERA | 0.654 | 42 | SB | Small t | A0212 |
| 12 | LMDLLGLERAA | 0.577 | 96 | WB | Small t | A0212 |
| 137 | CIDCFTQWFGL | 0.551 | 128 | WB | Small t | A0212 |
| 3 | VLNREESMELM | 0.514 | 192 | WB | Small t | A0212 |
| 2 | KVLNREESMEL | 0.481 | 273 | WB | Small t | A0212 |
| 148 | DLTEETLQWWV | 0.886 | 3 | SB | Small t | A0216 |
| 11 | ELMDLLGLERA | 0.650 | 43 | SB | Small t | A0216 |
| 2 | KVLNREESMEL | 0.514 | 191 | WB | Small t | A0216 |
| 105 | SVHCPCMLCQL | 0.496 | 233 | WB | Small t | A0216 |
| 137 | CIDCFTQWFGL | 0.440 | 427 | WB | Small t | A0216 |
| 148 | DLTEETLQWWV | 0.849 | 5 | SB | Small t | A0219 |
| 11 | ELMDLLGLERA | 0.602 | 73 | WB | Small t | A0219 |
| 137 | CIDCFTQWFGL | 0.566 | 109 | WB | Small t | A0219 |
| 50 | KMKRMNTLYKK | 0.667 | 36 | SB | Small t | A0301 |
| 116 | RLRHLNRKFLR | 0.645 | 46 | SB | Small t | A0301 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 56 | TLYKKMEQDVK | 0.645 | 46 | SB | Small t | A0301 |
| 21 | AAWGNLPLMRK | 0.508 | 205 | WB | Small t | A0301 |
| 28 | LMRKAYLKKCK | 0.454 | 369 | WB | Small t | A0301 |
| 160 | IIGETPFRDLK | 0.432 | 464 | WB | Small t | A0301 |
| 21 | AAWGNLPLMRK | 0.742 | 16 | SB | Small t | A1101 |
| 56 | TLYKKMEQDVK | 0.640 | 49 | SB | Small t | A1101 |
| 50 | KMKRMNTLYKK | 0.634 | 52 | WB | Small t | A1101 |
| 160 | IIGETPFRDLK | 0.632 | 53 | WB | Small t | A1101 |
| 113 | CQLRLRHLNRK | 0.537 | 149 | WB | Small t | A1101 |
| 20 | RAAWGNLPLMR | 0.531 | 160 | WB | Small t | A1101 |
| 135 | CYCIDCFTQWF | 0.785 | 10 | SB | Small t | A2301 |
| 131 | VWIDCYCIDCF | 0.697 | 26 | SB | Small t | A2301 |
| 92 | LYCKEWPICSK | 0.544 | 139 | WB | Small t | A2301 |
| 156 | WWVQIIGETPF | 0.530 | 161 | WB | Small t | A2301 |
| 75 | TWNSSEVCADF | 0.493 | 240 | WB | Small t | A2301 |
| 131 | VWIDCYCIDCF | 0.708 | 23 | SB | Small t | A2402 |
| 135 | CYCIDCFTQWF | 0.672 | 34 | SB | Small t | A2402 |
| 156 | WWVQIIGETPF | 0.515 | 190 | WB | Small t | A2402 |
| 123 | KFLRKEPLVWI | 0.489 | 251 | WB | Small t | A2402 |
| 75 | TWNSSEVCADF | 0.462 | 339 | WB | Small t | A2402 |
| 135 | CYCIDCFTQWF | 0.775 | 11 | SB | Small t | A2403 |
| 123 | KFLRKEPLVWI | 0.525 | 170 | WB | Small t | A2403 |
| 75 | TWNSSEVCADF | 0.428 | 485 | WB | Small t | A2403 |
| 8 | ESMELMDLLGL | 0.474 | 297 | WB | Small t | A2601 |
| 159 | QIIGETPFRDL | 0.618 | 62 | WB | Small t | A2602 |
| 8 | ESMELMDLLGL | 0.433 | 462 | WB | Small t | A2602 |
| 50 | KMKRMNTLYKK | 0.760 | 13 | SB | Small t | A3001 |
| 28 | LMRKAYLKKCK | 0.745 | 15 | SB | Small t | A3001 |
| 116 | RLRHLNRKFLR | 0.667 | 36 | SB | Small t | A3001 |
| 117 | LRHLNRKFLRK | 0.531 | 160 | WB | Small t | A3001 |
| 34 | LKKCKEFHPDK | 0.429 | 482 | WB | Small t | A3001 |
| 116 | RLRHLNRKFLR | 0.853 | 4 | SB | Small t | A3101 |
| 50 | KMKRMNTLYKK | 0.838 | 5 | SB | Small t | A3101 |
| 20 | RAAWGNLPLMR | 0.617 | 63 | WB | Small t | A3101 |
| 157 | WVQIIGETPFR | 0.496 | 232 | WB | Small t | A3101 |
| 112 | LCQLRLRHLNR | 0.451 | 380 | WB | Small t | A3101 |
| 31 | KAYLKKCKEFH | 0.448 | 392 | WB | Small t | A3101 |
| 113 | CQLRLRHLNRK | 0.434 | 458 | WB | Small t | A3101 |
| 28 | LMRKAYLKKCK | 0.433 | 461 | WB | Small t | A3101 |
| 116 | RLRHLNRKFLR | 0.594 | 80 | WB | Small t | A3301 |
| 157 | WVQIIGETPFR | 0.716 | 21 | SB | Small t | A6801 |
| 20 | RAAWGNLPLMR | 0.562 | 114 | WB | Small t | A6801 |
| 56 | TLYKKMEQDVK | 0.549 | 131 | WB | Small t | A6801 |
| 25 | NLPLMRKAYLK | 0.482 | 272 | WB | Small t | A6801 |
| 108 | CPCMLCQLRLR | 0.467 | 319 | WB | Small t | A6801 |
| 8 | ESMELMDLLGL | 0.653 | 42 | SB | Small t | A6802 |
| 77 | NSSEVCADFPL | 0.649 | 44 | SB | Small t | A6802 |
| 11 | ELMDLLGLERA | 0.570 | 105 | WB | Small t | A6802 |
| 105 | SVHCPCMLCQL | 0.506 | 209 | WB | Small t | A6802 |
| 137 | CIDCFTQWFGL | 0.468 | 315 | WB | Small t | A6802 |
| 128 | EPLVWIDCYCI | 0.606 | 71 | WB | Small t | A6901 |
| 8 | ESMELMDLLGL | 0.560 | 116 | WB | Small t | A6901 |
| 11 | ELMDLLGLERA | 0.539 | 145 | WB | Small t | A6901 |
| 148 | DLTEETLQWWV | 0.482 | 273 | WB | Small t | A6901 |
| 55 | NTLYKKMEQDV | 0.432 | 464 | WB | Small t | A6901 |
| 114 | QLRLRHLNRKF | 0.463 | 333 | WB | Small t | B0801 |
| 114 | QLRLRHLNRKF | 0.473 | 298 | WB | Small t | B1501 |
| 18 | LERAAWGNLPL | 0.572 | 102 | WB | Small t | B1801 |

TABLE L-continued

Prediction of BK virus small t protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 41 | HPDKGGDEDKM | 0.545 | 136 | WB | Small t | B3501 |
| 97 | WPICSKKPSVH | 0.529 | 164 | WB | Small t | B3501 |
| 156 | WWVQIIGETPF | 0.482 | 270 | WB | Small t | B3501 |
| 6 | REESMELMDLL | 0.673 | 34 | SB | Small t | B4001 |
| 18 | LERAAWGNLPL | 0.630 | 54 | WB | Small t | B4001 |
| 47 | DEDKMKRMNTL | 0.434 | 458 | WB | Small t | B4001 |
| 6 | REESMELMDLL | 0.511 | 198 | WB | Small t | B4002 |
| 151 | EETLQWWVQII | 0.500 | 224 | WB | Small t | B4002 |
| 128 | EPLVWIDCYCI | 0.605 | 72 | WB | Small t | B5101 |
| 128 | EPLVWIDCYCI | 0.529 | 163 | WB | Small t | B5301 |
| 85 | FPLCPDTLYCK | 0.471 | 304 | WB | Small t | B5401 |
| 66 | KVAHQPDFGTW | 0.658 | 40 | SB | Small t | B5801 |
| 122 | RKFLRKEPLVW | 0.499 | 225 | WB | Small t | B5801 |

SEQ ID NOS.: 54918-55453

Preferred BK virus fragments of large T antigen capable of interacting with one or more MHC class 1 molecules are listed in Table M.

TABLE M

Prediction of BK virus Large T protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| | | | 8-mers | | | |
| 77 | NSSEVPTY | 0.514 | 193 | WB | Large T | A0101 |
| 611 | YTFSRMKY | 0.480 | 276 | WB | Large T | A0101 |
| 175 | KLMEKYSV | 0.847 | 5 | SB | Large T | A0201 |
| 388 | YMAGVAWL | 0.833 | 6 | SB | Large T | A0201 |
| 287 | FLLLGMYL | 0.807 | 8 | SB | Large T | A0201 |
| 501 | YLDGSVKV | 0.800 | 8 | SB | Large T | A0201 |
| 272 | KLITEYAV | 0.733 | 18 | SB | Large T | A0201 |
| 469 | YMVVFEDV | 0.711 | 22 | SB | Large T | A0201 |
| 579 | LLIWFRPV | 0.705 | 24 | SB | Large T | A0201 |
| 372 | KMDLIFGA | 0.695 | 27 | SB | Large T | A0201 |
| 155 | RTLACFAV | 0.663 | 38 | SB | Large T | A0201 |
| 293 | YLEFQYNV | 0.656 | 41 | SB | Large T | A0201 |
| 527 | VTMNEYPV | 0.629 | 55 | WB | Large T | A0201 |
| 563 | FLLEKRIL | 0.620 | 61 | WB | Large T | A0201 |
| 322 | FANAIIFA | 0.612 | 66 | WB | Large T | A0201 |
| 231 | YLLYSALT | 0.611 | 67 | WB | Large T | A0201 |
| 557 | SLQNSEFL | 0.608 | 69 | WB | Large T | A0201 |
| 11 | ELMDLLGL | 0.599 | 76 | WB | Large T | A0201 |
| 215 | KLCTFSFL | 0.590 | 84 | WB | Large T | A0201 |
| 457 | RLTFELGV | 0.587 | 86 | WB | Large T | A0201 |
| 398 | LLPKMDSV | 0.582 | 91 | WB | Large T | A0201 |
| 465 | AIDQYMVV | 0.565 | 111 | WB | Large T | A0201 |
| 369 | ILDKMDLI | 0.551 | 128 | WB | Large T | A0201 |
| 74 | GTWNSSEV | 0.542 | 141 | WB | Large T | A0201 |
| 603 | RLDSEISM | 0.535 | 153 | WB | Large T | A0201 |
| 569 | ILQSGMTL | 0.529 | 164 | WB | Large T | A0201 |
| 573 | GMTLLLLL | 0.519 | 181 | WB | Large T | A0201 |
| 146 | FLSQAVFS | 0.495 | 234 | WB | Large T | A0201 |
| 21 | AAWGNLPL | 0.473 | 297 | WB | Large T | A0201 |
| 448 | ALNVNLPM | 0.468 | 316 | WB | Large T | A0201 |
| 609 | SMYTFSRM | 0.459 | 347 | WB | Large T | A0201 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 574 | MTLLLLLI | 0.458 | 350 | WB | Large T | A0201 |
| 60 | KMEQDVKV | 0.452 | 375 | WB | Large T | A0201 |
| 388 | YMAGVAWL | 0.861 | 4 | SB | Large T | A0202 |
| 175 | KLMEKYSV | 0.858 | 4 | SB | Large T | A0202 |
| 293 | YLEFQYNV | 0.811 | 7 | SB | Large T | A0202 |
| 287 | FLLLGMYL | 0.800 | 8 | SB | Large T | A0202 |
| 272 | KLITEYAV | 0.772 | 11 | SB | Large T | A0202 |
| 11 | ELMDLLGL | 0.762 | 13 | SB | Large T | A0202 |
| 146 | FLSQAVFS | 0.740 | 16 | SB | Large T | A0202 |
| 322 | FANAIIFA | 0.740 | 16 | SB | Large T | A0202 |
| 215 | KLCTFSFL | 0.732 | 18 | SB | Large T | A0202 |
| 398 | LLPKMDSV | 0.721 | 20 | SB | Large T | A0202 |
| 501 | YLDGSVKV | 0.716 | 21 | SB | Large T | A0202 |
| 557 | SLQNSEFL | 0.712 | 22 | SB | Large T | A0202 |
| 570 | LQSGMTLL | 0.696 | 26 | SB | Large T | A0202 |
| 372 | KMDLIFGA | 0.672 | 34 | SB | Large T | A0202 |
| 457 | RLTFELGV | 0.666 | 37 | SB | Large T | A0202 |
| 573 | GMTLLLLL | 0.655 | 41 | SB | Large T | A0202 |
| 579 | LLIWFRPV | 0.643 | 47 | SB | Large T | A0202 |
| 9 | SMELMDLL | 0.628 | 56 | WB | Large T | A0202 |
| 469 | YMVVFEDV | 0.606 | 70 | WB | Large T | A0202 |
| 558 | LQNSEFLL | 0.596 | 78 | WB | Large T | A0202 |
| 563 | FLLEKRIL | 0.593 | 81 | WB | Large T | A0202 |
| 50 | KMKRMNTL | 0.586 | 88 | WB | Large T | A0202 |
| 369 | ILDKMDLI | 0.585 | 89 | WB | Large T | A0202 |
| 391 | GVAWLHCL | 0.577 | 96 | WB | Large T | A0202 |
| 491 | GINNLDSL | 0.576 | 98 | WB | Large T | A0202 |
| 184 | FISRHMCA | 0.571 | 103 | WB | Large T | A0202 |
| 514 | HLNKRTQI | 0.561 | 115 | WB | Large T | A0202 |
| 377 | FGAHGNAV | 0.549 | 131 | WB | Large T | A0202 |
| 569 | ILQSGMTL | 0.546 | 135 | WB | Large T | A0202 |
| 527 | VTMNEYPV | 0.533 | 156 | WB | Large T | A0202 |
| 226 | GVNKEYLL | 0.525 | 171 | WB | Large T | A0202 |
| 448 | ALNVNLPM | 0.512 | 196 | WB | Large T | A0202 |
| 355 | HMTREEML | 0.510 | 200 | WB | Large T | A0202 |
| 60 | KMEQDVKV | 0.505 | 211 | WB | Large T | A0202 |
| 27 | PLMRKAYL | 0.488 | 254 | WB | Large T | A0202 |
| 603 | RLDSEISM | 0.481 | 276 | WB | Large T | A0202 |
| 144 | HQFLSQAV | 0.472 | 301 | WB | Large T | A0202 |
| 465 | AIDQYMVV | 0.458 | 353 | WB | Large T | A0202 |
| 155 | RTLACFAV | 0.443 | 412 | WB | Large T | A0202 |
| 609 | SMYTFSRM | 0.442 | 419 | WB | Large T | A0202 |
| 464 | VAIDQYMV | 0.429 | 483 | WB | Large T | A0202 |
| 388 | YMAGVAWL | 0.893 | 3 | SB | Large T | A0203 |
| 579 | LLIWFRPV | 0.884 | 3 | SB | Large T | A0203 |
| 175 | KLMEKYSV | 0.870 | 4 | SB | Large T | A0203 |
| 501 | YLDGSVKV | 0.811 | 7 | SB | Large T | A0203 |
| 457 | RLTFELGV | 0.781 | 10 | SB | Large T | A0203 |
| 287 | FLLLGMYL | 0.780 | 10 | SB | Large T | A0203 |
| 272 | KLITEYAV | 0.779 | 10 | SB | Large T | A0203 |
| 398 | LLPKMDSV | 0.777 | 11 | SB | Large T | A0203 |
| 293 | YLEFQYNV | 0.769 | 12 | SB | Large T | A0203 |
| 50 | KMKRMNTL | 0.758 | 13 | SB | Large T | A0203 |
| 469 | YMVVFEDV | 0.736 | 17 | SB | Large T | A0203 |
| 11 | ELMDLLGL | 0.712 | 22 | SB | Large T | A0203 |
| 569 | ILQSGMTL | 0.711 | 22 | SB | Large T | A0203 |
| 322 | FANAIIFA | 0.697 | 26 | SB | Large T | A0203 |
| 184 | FISRHMCA | 0.689 | 28 | SB | Large T | A0203 |
| 514 | HLNKRTQI | 0.680 | 31 | SB | Large T | A0203 |
| 609 | SMYTFSRM | 0.642 | 48 | SB | Large T | A0203 |
| 563 | FLLEKRIL | 0.628 | 55 | WB | Large T | A0203 |
| 372 | KMDLIFGA | 0.622 | 59 | WB | Large T | A0203 |
| 570 | LQSGMTLL | 0.608 | 69 | WB | Large T | A0203 |
| 215 | KLCTFSFL | 0.607 | 70 | WB | Large T | A0203 |
| 391 | GVAWLHCL | 0.570 | 104 | WB | Large T | A0203 |
| 448 | ALNVNLPM | 0.556 | 122 | WB | Large T | A0203 |
| 188 | HMCAGHNI | 0.551 | 128 | WB | Large T | A0203 |
| 527 | VTMNEYPV | 0.548 | 132 | WB | Large T | A0203 |
| 573 | GMTLLLLL | 0.535 | 153 | WB | Large T | A0203 |
| 520 | QIFPPGLV | 0.531 | 159 | WB | Large T | A0203 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 146 | FLSQAVFS | 0.528 | 165 | WB | Large T | A0203 |
| 144 | HQFLSQAV | 0.527 | 166 | WB | Large T | A0203 |
| 491 | GINNLDSL | 0.526 | 168 | WB | Large T | A0203 |
| 557 | SLQNSEFL | 0.517 | 186 | WB | Large T | A0203 |
| 465 | AIDQYMVV | 0.513 | 193 | WB | Large T | A0203 |
| 155 | RTLACFAV | 0.509 | 202 | WB | Large T | A0203 |
| 464 | VAIDQYMV | 0.497 | 232 | WB | Large T | A0203 |
| 551 | KIYLRKSL | 0.489 | 252 | WB | Large T | A0203 |
| 369 | ILDKMDLI | 0.466 | 321 | WB | Large T | A0203 |
| 654 | SQVSDTSA | 0.462 | 338 | WB | Large T | A0203 |
| 231 | YLLYSALT | 0.453 | 372 | WB | Large T | A0203 |
| 199 | LTPHRHRV | 0.447 | 394 | WB | Large T | A0203 |
| 60 | KMEQDVKV | 0.429 | 484 | WB | Large T | A0203 |
| 615 | RMKYNICM | 0.427 | 490 | WB | Large T | A0203 |
| 175 | KLMEKYSV | 0.762 | 13 | SB | Large T | A0204 |
| 388 | YMAGVAWL | 0.708 | 23 | SB | Large T | A0204 |
| 272 | KLITEYAV | 0.652 | 43 | SB | Large T | A0204 |
| 527 | VTMNEYPV | 0.635 | 52 | WB | Large T | A0204 |
| 579 | LLIWFRPV | 0.627 | 56 | WB | Large T | A0204 |
| 60 | KMEQDVKV | 0.615 | 64 | WB | Large T | A0204 |
| 287 | FLLLGMYL | 0.601 | 75 | WB | Large T | A0204 |
| 569 | ILQSGMTL | 0.572 | 102 | WB | Large T | A0204 |
| 501 | YLDGSVKV | 0.571 | 104 | WB | Large T | A0204 |
| 557 | SLQNSEFL | 0.565 | 110 | WB | Large T | A0204 |
| 563 | FLLEKRIL | 0.554 | 124 | WB | Large T | A0204 |
| 293 | YLEFQYNV | 0.537 | 149 | WB | Large T | A0204 |
| 215 | KLCTFSFL | 0.534 | 154 | WB | Large T | A0204 |
| 11 | ELMDLLGL | 0.521 | 178 | WB | Large T | A0204 |
| 469 | YMVVFEDV | 0.512 | 195 | WB | Large T | A0204 |
| 464 | VAIDQYMV | 0.512 | 196 | WB | Large T | A0204 |
| 536 | KTLQARFV | 0.494 | 239 | WB | Large T | A0204 |
| 155 | RTLACFAV | 0.475 | 293 | WB | Large T | A0204 |
| 398 | LLPKMDSV | 0.460 | 345 | WB | Large T | A0204 |
| 465 | AIDQYMVV | 0.459 | 349 | WB | Large T | A0204 |
| 457 | RLTFELGV | 0.448 | 393 | WB | Large T | A0204 |
| 50 | KMKRMNTL | 0.443 | 412 | WB | Large T | A0204 |
| 175 | KLMEKYSV | 0.879 | 3 | SB | Large T | A0206 |
| 155 | RTLACFAV | 0.822 | 6 | SB | Large T | A0206 |
| 272 | KLITEYAV | 0.820 | 6 | SB | Large T | A0206 |
| 579 | LLIWFRPV | 0.813 | 7 | SB | Large T | A0206 |
| 287 | FLLLGMYL | 0.784 | 10 | SB | Large T | A0206 |
| 654 | SQVSDTSA | 0.782 | 10 | SB | Large T | A0206 |
| 501 | YLDGSVKV | 0.771 | 11 | SB | Large T | A0206 |
| 388 | YMAGVAWL | 0.737 | 17 | SB | Large T | A0206 |
| 469 | YMVVFEDV | 0.730 | 18 | SB | Large T | A0206 |
| 267 | KQVSWKLI | 0.720 | 20 | SB | Large T | A0206 |
| 144 | HQFLSQAV | 0.705 | 24 | SB | Large T | A0206 |
| 372 | KMDLIFGA | 0.695 | 27 | SB | Large T | A0206 |
| 570 | LQSGMTLL | 0.694 | 27 | SB | Large T | A0206 |
| 296 | FQYNVEEC | 0.688 | 29 | SB | Large T | A0206 |
| 457 | RLTFELGV | 0.678 | 32 | SB | Large T | A0206 |
| 398 | LLPKMDSV | 0.673 | 34 | SB | Large T | A0206 |
| 558 | LQNSEFLL | 0.665 | 37 | SB | Large T | A0206 |
| 338 | CQQAVDTV | 0.654 | 42 | SB | Large T | A0206 |
| 322 | FANAIIFA | 0.648 | 45 | SB | Large T | A0206 |
| 465 | AIDQYMVV | 0.646 | 45 | SB | Large T | A0206 |
| 74 | GTWNSSEV | 0.645 | 46 | SB | Large T | A0206 |
| 527 | VTMNEYPV | 0.615 | 64 | WB | Large T | A0206 |
| 293 | YLEFQYNV | 0.613 | 65 | WB | Large T | A0206 |
| 11 | ELMDLLGL | 0.594 | 80 | WB | Large T | A0206 |
| 536 | KTLQARFV | 0.593 | 81 | WB | Large T | A0206 |
| 464 | VAIDQYMV | 0.572 | 102 | WB | Large T | A0206 |
| 21 | AAWGNLPL | 0.571 | 104 | WB | Large T | A0206 |
| 383 | AVLEQYMA | 0.539 | 146 | WB | Large T | A0206 |
| 563 | FLLEKRIL | 0.534 | 155 | WB | Large T | A0206 |
| 574 | MTLLLLLI | 0.517 | 185 | WB | Large T | A0206 |
| 215 | KLCTFSFL | 0.512 | 195 | WB | Large T | A0206 |
| 184 | FISRHMCA | 0.511 | 197 | WB | Large T | A0206 |
| 519 | TQIFPPGL | 0.505 | 210 | WB | Large T | A0206 |
| 377 | FGAHGNAV | 0.470 | 308 | WB | Large T | A0206 |

TABLE M-continued

Prediction of BK virus Large T protein specific MHC class1,
8-, 9-, 10-, 11-mer peptide binders for 42 MHC class 1 alleles
(see FIG. 11) using the www.cbs.dtu.dk/services/
NetMHC/ database. The MHC class 1 molecules for which
no binders were found are not listed.

| pos | peptide | logscore | affinity (nM) | Bind Level | Protein Name | Allele |
|---|---|---|---|---|---|---|
| 335 | KSICQQAV | 0.469 | 311 | WB | Large T | A0206 |
| 369 | ILDKMDLI | 0.464 | 328 | WB | Large T | A0206 |
| 520 | QIFPPGLV | 0.458 | 352 | WB | Large T | A0206 |
| 391 | GVAWLHCL | 0.457 | 355 | WB | Large T | A0206 |
| 231 | YLLYSALT | 0.451 | 380 | WB | Large T | A0206 |
| 569 | ILQSGMTL | 0.445 | 406 | WB | Large T | A0206 |
| 339 | QQAVDTVL | 0.443 | 414 | WB | Large T | A0206 |
| 146 | FLSQAVFS | 0.438 | 436 | WB | Large T | A0206 |
| 169 | AQILYKKL | 0.435 | 453 | WB | Large T | A0206 |
| 60 | KMEQDVKV | 0.427 | 490 | WB | Large T | A0206 |
| 501 | YLDGSVKV | 0.977 | 1 | SB | Large T | A0211 |
| 388 | YMAGVAWL | 0.963 | 1 | SB | Large T | A0211 |
| 175 | KLMEKYSV | 0.945 | 1 | SB | Large T | A0211 |
| 287 | FLLLGMYL | 0.937 | 1 | SB | Large T | A0211 |
| 579 | LLIWFRPV | 0.922 | 2 | SB | Large T | A0211 |
| 465 | AIDQYMVV | 0.919 | 2 | SB | Large T | A0211 |
| 272 | KLITEYAV | 0.906 | 2 | SB | Large T | A0211 |
| 11 | ELMDLLGL | 0.904 | 2 | SB | Large T | A0211 |
| 398 | LLPKMDSV | 0.900 | 2 | SB | Large T | A0211 |
| 457 | RLTFELGV | 0.899 | 2 | SB | Large T | A0211 |
| 293 | YLEFQYNV | 0.897 | 3 | SB | Large T | A0211 |
| 557 | SLQNSEFL | 0.882 | 3 | SB | Large T | A0211 |
| 569 | ILQSGMTL | 0.870 | 4 | SB | Large T | A0211 |
| 469 | YMVVFEDV | 0.866 | 4 | SB | Large T | A0211 |
| 563 | FLLEKRIL | 0.862 | 4 | SB | Large T | A0211 |
| 603 | RLDSEISM | 0.848 | 5 | SB | Large T | A0211 |
| 60 | KMEQDVKV | 0.845 | 5 | SB | Large T | A0211 |
| 369 | ILDKMDLI | 0.828 | 6 | SB | Large T | A0211 |
| 573 | GMTLLLLL | 0.824 | 6 | SB | Large T | A0211 |
| 215 | KLCTFSFL | 0.821 | 6 | SB | Large T | A0211 |
| 520 | QIFPPGLV | 0.811 | 7 | SB | Large T | A0211 |
| 609 | SMYTFSRM | 0.780 | 10 | SB | Large T | A0211 |
| 372 | KMDLIFGA | 0.777 | 11 | SB | Large T | A0211 |
| 464 | VAIDQYMV | 0.743 | 16 | SB | Large T | A0211 |
| 14 | DLLGLERA | 0.725 | 19 | SB | Large T | A0211 |
| 74 | GTWNSSEV | 0.720 | 20 | SB | Large T | A0211 |
| 391 | GVAWLHCL | 0.719 | 20 | SB | Large T | A0211 |
| 485 | DLPSGHGI | 0.719 | 21 | SB | Large T | A0211 |
| 155 | RTLACFAV | 0.693 | 27 | SB | Large T | A0211 |
| 442 | DLCGGKAL | 0.686 | 29 | SB | Large T | A0211 |
| 231 | YLLYSALT | 0.682 | 31 | SB | Large T | A0211 |
| 536 | KTLQARFV | 0.668 | 36 | SB | Large T | A0211 |
| 355 | HMTREEML | 0.667 | 36 | SB | Large T | A0211 |
| 27 | PLMRKAYL | 0.666 | 37 | SB | Large T | A0211 |
| 406 | IFDFLHCV | 0.646 | 46 | SB | Large T | A0211 |
| 514 | HLNKRTQI | 0.642 | 48 | SB | Large T | A0211 |
| 21 | AAWGNLPL | 0.638 | 50 | WB | Large T | A0211 |
| 9 | SMELMDLL | 0.635 | 51 | WB | Large T | A0211 |
| 56 | TLYKKMEQ | 0.625 | 57 | WB | Large T | A0211 |
| 188 | HMCAGHNI | 0.618 | 62 | WB | Large T | A0211 |
| 576 | LLLLLIWF | 0.614 | 64 | WB | Large T | A0211 |
| 146 | FLSQAVFS | 0.597 | 78 | WB | Large T | A0211 |
| 383 | AVLEQYMA | 0.594 | 81 | WB | Large T | A0211 |
| 405 | VIFDFLHC | 0.587 | 87 | WB | Large T | A0211 |
| 344 | TVLAKKRV | 0.583 | 91 | WB | Large T | A0211 |
| 50 | KMKRMNTL | 0.582 | 92 | WB | Large T | A0211 |
| 288 | LLLGMYLE | 0.577 | 96 | WB | Large T | A0211 |
| 448 | ALNVNLPM | 0.573 | 100 | WB | Large T | A0211 |
| 368 | HILDKMDL | 0.570 | 104 | WB | Large T | A0211 |
| 527 | VTMNEYPV | 0.561 | 115 | WB | Large T | A0211 |
| 150 | AVFSNRTL | 0.555 | 122 | WB | Large T | A0211 |
| 184 | FISRHMCA | 0.545 | 137 | WB | Large T | A0211 |
| 199 | LTPHRHRV | 0.543 | 140 | WB | Large T | A0211 |
| 551 | KIYLRKSL | 0.523 | 173 | WB | Large T | A0211 |
| 3 | VLNREESM | 0.494 | 239 | WB | Large T | A0211 |
| 491 | GINNLDSL | 0.485 | 262 | WB | Large T | A0211 |
| 291 | GMYLEFQY | 0.468 | 315 | WB | Large T | A0211 |
| 350 | RVDTLHMT | 0.466 | 322 | WB | Large T | A0211 |
| 142 | DLHQFLSQ | 0.459 | 348 | WB | Large T | A0211 |
| 401 | KMDSVIFD | 0.458 | 350 | WB | Large T | A0211 |
| 673 | HLCKGFQC | 0.458 | 350 | WB | Large T | A0211 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 289 | LLGMYLEF | 0.450 | 383 | WB | Large T | A0211 |
| 577 | LLLLIWFR | 0.450 | 384 | WB | Large T | A0211 |
| 439 | GLLDLCGG | 0.448 | 390 | WB | Large T | A0211 |
| 501 | YLDGSVKV | 0.940 | 1 | SB | Large T | A0212 |
| 388 | YMAGVAWL | 0.924 | 2 | SB | Large T | A0212 |
| 175 | KLMEKYSV | 0.912 | 2 | SB | Large T | A0212 |
| 287 | FLLLGMYL | 0.903 | 2 | SB | Large T | A0212 |
| 398 | LLPKMDSV | 0.879 | 3 | SB | Large T | A0212 |
| 469 | YMVVFEDV | 0.878 | 3 | SB | Large T | A0212 |
| 293 | YLEFQYNV | 0.872 | 4 | SB | Large T | A0212 |
| 579 | LLIWFRPV | 0.853 | 4 | SB | Large T | A0212 |
| 563 | FLLEKRIL | 0.852 | 4 | SB | Large T | A0212 |
| 272 | KLITEYAV | 0.852 | 4 | SB | Large T | A0212 |
| 465 | AIDQYMVV | 0.843 | 5 | SB | Large T | A0212 |
| 11 | ELMDLLGL | 0.842 | 5 | SB | Large T | A0212 |
| 569 | ILQSGMTL | 0.821 | 6 | SB | Large T | A0212 |
| 457 | RLTFELGV | 0.787 | 10 | SB | Large T | A0212 |
| 557 | SLQNSEFL | 0.757 | 13 | SB | Large T | A0212 |
| 609 | SMYTFSRM | 0.711 | 22 | SB | Large T | A0212 |
| 464 | VAIDQYMV | 0.698 | 26 | SB | Large T | A0212 |
| 60 | KMEQDVKV | 0.666 | 37 | SB | Large T | A0212 |
| 355 | HMTREEML | 0.663 | 38 | SB | Large T | A0212 |
| 603 | RLDSEISM | 0.662 | 38 | SB | Large T | A0212 |
| 368 | HILDKMDL | 0.659 | 39 | SB | Large T | A0212 |
| 3 | VLNREESM | 0.639 | 49 | SB | Large T | A0212 |
| 184 | FISRHMCA | 0.635 | 52 | WB | Large T | A0212 |
| 405 | VIFDFLHC | 0.629 | 55 | WB | Large T | A0212 |
| 215 | KLCTFSFL | 0.615 | 64 | WB | Large T | A0212 |
| 369 | ILDKMDLI | 0.609 | 68 | WB | Large T | A0212 |
| 27 | PLMRKAYL | 0.597 | 78 | WB | Large T | A0212 |
| 372 | KMDLIFGA | 0.588 | 86 | WB | Large T | A0212 |
| 50 | KMKRMNTL | 0.579 | 94 | WB | Large T | A0212 |
| 520 | QIFPPGLV | 0.577 | 96 | WB | Large T | A0212 |
| 573 | GMTLLLLL | 0.577 | 96 | WB | Large T | A0212 |
| 527 | VTMNEYPV | 0.571 | 104 | WB | Large T | A0212 |
| 188 | HMCAGHNI | 0.546 | 135 | WB | Large T | A0212 |
| 14 | DLLGLERA | 0.523 | 174 | WB | Large T | A0212 |
| 442 | DLCGGKAL | 0.521 | 178 | WB | Large T | A0212 |
| 74 | GTWNSSEV | 0.521 | 178 | WB | Large T | A0212 |
| 56 | TLYKKMEQ | 0.520 | 180 | WB | Large T | A0212 |
| 485 | DLPSGHGI | 0.518 | 183 | WB | Large T | A0212 |
| 21 | AAWGNLPL | 0.511 | 197 | WB | Large T | A0212 |
| 391 | GVAWLHCL | 0.511 | 199 | WB | Large T | A0212 |
| 231 | YLLYSALT | 0.504 | 213 | WB | Large T | A0212 |
| 288 | LLLGMYLE | 0.486 | 259 | WB | Large T | A0212 |
| 514 | HLNKRTQI | 0.480 | 276 | WB | Large T | A0212 |
| 199 | LTPHRHRV | 0.477 | 285 | WB | Large T | A0212 |
| 155 | RTLACFAV | 0.476 | 290 | WB | Large T | A0212 |
| 377 | FGAHGNAV | 0.461 | 340 | WB | Large T | A0212 |
| 146 | FLSQAVFS | 0.442 | 418 | WB | Large T | A0212 |
| 9 | SMELMDLL | 0.426 | 495 | WB | Large T | A0212 |
| 501 | YLDGSVKV | 0.928 | 2 | SB | Large T | A0216 |
| 388 | YMAGVAWL | 0.917 | 2 | SB | Large T | A0216 |
| 175 | KLMEKYSV | 0.905 | 2 | SB | Large T | A0216 |
| 398 | LLPKMDSV | 0.895 | 3 | SB | Large T | A0216 |
| 287 | FLLLGMYL | 0.891 | 3 | SB | Large T | A0216 |
| 293 | YLEFQYNV | 0.849 | 5 | SB | Large T | A0216 |
| 557 | SLQNSEFL | 0.846 | 5 | SB | Large T | A0216 |
| 569 | ILQSGMTL | 0.836 | 5 | SB | Large T | A0216 |
| 272 | KLITEYAV | 0.832 | 6 | SB | Large T | A0216 |
| 465 | AIDQYMVV | 0.829 | 6 | SB | Large T | A0216 |
| 27 | PLMRKAYL | 0.829 | 6 | SB | Large T | A0216 |
| 579 | LLIWFRPV | 0.804 | 8 | SB | Large T | A0216 |
| 215 | KLCTFSFL | 0.784 | 10 | SB | Large T | A0216 |
| 11 | ELMDLLGL | 0.740 | 16 | SB | Large T | A0216 |
| 74 | GTWNSSEV | 0.734 | 17 | SB | Large T | A0216 |
| 60 | KMEQDVKV | 0.732 | 18 | SB | Large T | A0216 |
| 457 | RLTFELGV | 0.727 | 19 | SB | Large T | A0216 |
| 469 | YMVVFEDV | 0.718 | 21 | SB | Large T | A0216 |
| 563 | FLLEKRIL | 0.709 | 23 | SB | Large T | A0216 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 520 | QIFPPGLV | 0.701 | 25 | SB | Large T | A0216 |
| 514 | HLNKRTQI | 0.689 | 29 | SB | Large T | A0216 |
| 369 | ILDKMDLI | 0.673 | 34 | SB | Large T | A0216 |
| 56 | TLYKKMEQ | 0.662 | 38 | SB | Large T | A0216 |
| 50 | KMKRMNTL | 0.651 | 43 | SB | Large T | A0216 |
| 609 | SMYTFSRM | 0.647 | 45 | SB | Large T | A0216 |
| 603 | RLDSEISM | 0.626 | 56 | WB | Large T | A0216 |
| 355 | HMTREEML | 0.623 | 58 | WB | Large T | A0216 |
| 21 | AAWGNLPL | 0.600 | 75 | WB | Large T | A0216 |
| 442 | DLCGGKAL | 0.597 | 78 | WB | Large T | A0216 |
| 573 | GMTLLLLL | 0.595 | 79 | WB | Large T | A0216 |
| 464 | VAIDQYMV | 0.593 | 82 | WB | Large T | A0216 |
| 344 | TVLAKKRV | 0.583 | 91 | WB | Large T | A0216 |
| 199 | LTPHRHRV | 0.568 | 106 | WB | Large T | A0216 |
| 14 | DLLGLERA | 0.566 | 109 | WB | Large T | A0216 |
| 485 | DLPSGHGI | 0.550 | 130 | WB | Large T | A0216 |
| 536 | KTLQARFV | 0.548 | 132 | WB | Large T | A0216 |
| 9 | SMELMDLL | 0.532 | 158 | WB | Large T | A0216 |
| 391 | GVAWLHCL | 0.522 | 176 | WB | Large T | A0216 |
| 150 | AVFSNRTL | 0.516 | 187 | WB | Large T | A0216 |
| 188 | HMCAGHNI | 0.512 | 195 | WB | Large T | A0216 |
| 527 | VTMNEYPV | 0.506 | 210 | WB | Large T | A0216 |
| 146 | FLSQAVFS | 0.504 | 213 | WB | Large T | A0216 |
| 231 | YLLYSALT | 0.501 | 220 | WB | Large T | A0216 |
| 491 | GINNLDSL | 0.476 | 290 | WB | Large T | A0216 |
| 184 | FISRHMCA | 0.474 | 296 | WB | Large T | A0216 |
| 551 | KIYLRKSL | 0.468 | 315 | WB | Large T | A0216 |
| 155 | RTLACFAV | 0.465 | 327 | WB | Large T | A0216 |
| 673 | HLCKGFQC | 0.463 | 334 | WB | Large T | A0216 |
| 448 | ALNVNLPM | 0.442 | 418 | WB | Large T | A0216 |
| 372 | KMDLIFGA | 0.442 | 419 | WB | Large T | A0216 |
| 406 | IFDFLHCV | 0.433 | 460 | WB | Large T | A0216 |
| 3 | VLNREESM | 0.429 | 482 | WB | Large T | A0216 |
| 501 | YLDGSVKV | 0.939 | 1 | SB | Large T | A0219 |
| 388 | YMAGVAWL | 0.930 | 2 | SB | Large T | A0219 |
| 287 | FLLLGMYL | 0.835 | 5 | SB | Large T | A0219 |
| 11 | ELMDLLGL | 0.807 | 8 | SB | Large T | A0219 |
| 175 | KLMEKYSV | 0.800 | 8 | SB | Large T | A0219 |
| 569 | ILQSGMTL | 0.780 | 10 | SB | Large T | A0219 |
| 398 | LLPKMDSV | 0.713 | 22 | SB | Large T | A0219 |
| 293 | YLEFQYNV | 0.711 | 22 | SB | Large T | A0219 |
| 557 | SLQNSEFL | 0.660 | 39 | SB | Large T | A0219 |
| 465 | AIDQYMVV | 0.659 | 39 | SB | Large T | A0219 |
| 272 | KLITEYAV | 0.651 | 43 | SB | Large T | A0219 |
| 21 | AAWGNLPL | 0.637 | 51 | WB | Large T | A0219 |
| 457 | RLTFELGV | 0.599 | 76 | WB | Large T | A0219 |
| 27 | PLMRKAYL | 0.589 | 85 | WB | Large T | A0219 |
| 603 | RLDSEISM | 0.574 | 100 | WB | Large T | A0219 |
| 369 | ILDKMDLI | 0.567 | 108 | WB | Large T | A0219 |
| 469 | YMVVFEDV | 0.565 | 111 | WB | Large T | A0219 |
| 579 | LLIWFRPV | 0.564 | 112 | WB | Large T | A0219 |
| 563 | FLLEKRIL | 0.555 | 123 | WB | Large T | A0219 |
| 485 | DLPSGHGI | 0.542 | 142 | WB | Large T | A0219 |
| 74 | GTWNSSEV | 0.540 | 145 | WB | Large T | A0219 |
| 464 | VAIDQYMV | 0.507 | 208 | WB | Large T | A0219 |
| 355 | HMTREEML | 0.497 | 230 | WB | Large T | A0219 |
| 372 | KMDLIFGA | 0.431 | 469 | WB | Large T | A0219 |
| 406 | IFDFLHCV | 0.429 | 482 | WB | Large T | A0219 |
| 573 | GMTLLLLL | 0.426 | 497 | WB | Large T | A0219 |
| 53 | RMNTLYKK | 0.719 | 20 | SB | Large T | A0301 |
| 232 | LLYSALTR | 0.673 | 34 | SB | Large T | A0301 |
| 28 | LMRKAYLK | 0.671 | 35 | SB | Large T | A0301 |
| 394 | WLHCLLPK | 0.536 | 150 | WB | Large T | A0301 |
| 208 | AINNFCQK | 0.529 | 162 | WB | Large T | A0301 |
| 161 | AVYTTKEK | 0.526 | 169 | WB | Large T | A0301 |
| 577 | LLLLIWFR | 0.513 | 193 | WB | Large T | A0301 |
| 365 | RFNHILDK | 0.512 | 196 | WB | Large T | A0301 |
| 291 | GMYLEFQY | 0.507 | 207 | WB | Large T | A0301 |
| 31 | KAYLKKCK | 0.506 | 210 | WB | Large T | A0301 |
| 608 | ISMYTFSR | 0.489 | 252 | WB | Large T | A0301 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pospeptide | logscore | affinity (nM) | Bind Level | Protein Name | Allele |
|---|---|---|---|---|---|
| 413 VVFNVPKR | 0.483 | 270 | WB | Large T | A0301 |
| 121 SQHSTPPK | 0.481 | 274 | WB | Large T | A0301 |
| 156 TLACFAVY | 0.475 | 294 | WB | Large T | A0301 |
| 222 LICKGVNK | 0.438 | 435 | WB | Large T | A0301 |
| 195 IIFFLTPH | 0.434 | 456 | WB | Large T | A0301 |
| 412 CVVFNVPK | 0.428 | 486 | WB | Large T | A0301 |
|  |  |  |  |  |  |
| 208 AINNFCQK | 0.764 | 12 | SB | Large T | A1101 |
| 161 AVYTTKEK | 0.761 | 13 | SB | Large T | A1101 |
| 121 SQHSTPPK | 0.746 | 15 | SB | Large T | A1101 |
| 325 AIIFAESK | 0.737 | 17 | SB | Large T | A1101 |
| 341 AVDTVLAK | 0.732 | 18 | SB | Large T | A1101 |
| 53 RMNTLYKK | 0.727 | 19 | SB | Large T | A1101 |
| 608 ISMYTFSR | 0.721 | 20 | SB | Large T | A1101 |
| 544 RQIDFRPK | 0.709 | 23 | SB | Large T | A1101 |
| 505 SVKVNLEK | 0.695 | 27 | SB | Large T | A1101 |
| 168 KAQILYKK | 0.672 | 34 | SB | Large T | A1101 |
| 412 CVVFNVPK | 0.665 | 37 | SB | Large T | A1101 |
| 669 SQELHLCK | 0.657 | 40 | SB | Large T | A1101 |
| 31 KAYLKKCK | 0.639 | 49 | SB | Large T | A1101 |
| 218 TFSFLICK | 0.626 | 57 | WB | Large T | A1101 |
| 413 VVFNVPKR | 0.613 | 65 | WB | Large T | A1101 |
| 537 TLQARFVR | 0.609 | 68 | WB | Large T | A1101 |
| 470 MVVFEDVK | 0.604 | 72 | WB | Large T | A1101 |
| 404 SVIFDPLH | 0.596 | 79 | WB | Large T | A1101 |
| 222 LICKGVNK | 0.581 | 93 | WB | Large T | A1101 |
| 560 NSEFLLEK | 0.574 | 100 | WB | Large T | A1101 |
| 611 YTFSRMKY | 0.568 | 107 | WB | Large T | A1101 |
| 148 SQAVFSNR | 0.553 | 125 | WB | Large T | A1101 |
| 450 NVNLPMER | 0.526 | 168 | WB | Large T | A1101 |
| 394 WLHCLLPK | 0.499 | 226 | WB | Large T | A1101 |
| 291 GMYLEFQY | 0.497 | 231 | WB | Large T | A1101 |
| 617 KYNICMGK | 0.464 | 328 | WB | Large T | A1101 |
| 247 ESIQGGLK | 0.464 | 331 | WB | Large T | A1101 |
| 577 LLLLIWFR | 0.462 | 338 | WB | Large T | A1101 |
| 52 KRMNTLYK | 0.454 | 367 | WB | Large T | A1101 |
| 678 FQCFKRPK | 0.440 | 426 | WB | Large T | A1101 |
| 28 LMRKAYLK | 0.435 | 452 | WB | Large T | A1101 |
| 365 RFNHILDK | 0.427 | 494 | WB | Large T | A1101 |
|  |  |  |  |  |  |
| 408 DFLHCVVF | 0.671 | 35 | SB | Large T | A2301 |
| 541 RFVRQIDF | 0.664 | 37 | SB | Large T | A2301 |
| 610 MYTFSRMK | 0.660 | 39 | SB | Large T | A2301 |
| 321 HFANAIIF | 0.633 | 53 | WB | Large T | A2301 |
| 172 LYKKLMEK | 0.626 | 57 | WB | Large T | A2301 |
| 104 LFCHEDMF | 0.617 | 63 | WB | Large T | A2301 |
| 500 DYLDGSVK | 0.609 | 68 | WB | Large T | A2301 |
| 582 WFRPVADF | 0.608 | 69 | WB | Large T | A2301 |
| 230 EYLLYSAL | 0.601 | 75 | WB | Large T | A2301 |
| 617 KYNICMGK | 0.599 | 76 | WB | Large T | A2301 |
| 205 RVSAINNF | 0.504 | 214 | WB | Large T | A2301 |
| 387 QYMAGVAW | 0.502 | 219 | WB | Large T | A2301 |
| 576 LLLLLIWF | 0.493 | 241 | WB | Large T | A2301 |
| 92 WWSSFNEK | 0.492 | 243 | WB | Large T | A2301 |
| 145 QFLSQAVF | 0.489 | 252 | WB | Large T | A2301 |
| 365 RFNHILDK | 0.475 | 292 | WB | Large T | A2301 |
| 556 KSLQNSEF | 0.460 | 343 | WB | Large T | A2301 |
| 159 CFAVYTTK | 0.441 | 423 | WB | Large T | A2301 |
|  |  |  |  |  |  |
| 230 EYLLYSAL | 0.680 | 32 | SB | Large T | A2402 |
| 145 QFLSQAVF | 0.522 | 176 | WB | Large T | A2402 |
| 408 DFLHCVVF | 0.519 | 182 | WB | Large T | A2402 |
| 531 EYPVPKTL | 0.510 | 199 | WB | Large T | A2402 |
| 321 HFANAIIF | 0.507 | 206 | WB | Large T | A2402 |
| 422 YWLFKGPI | 0.506 | 210 | WB | Large T | A2402 |
| 541 RFVRQIDF | 0.460 | 344 | WB | Large T | A2402 |
| 387 QYMAGVAW | 0.445 | 405 | WB | Large T | A2402 |
|  |  |  |  |  |  |
| 387 QYMAGVAW | 0.768 | 12 | SB | Large T | A2403 |
| 582 WFRPVADF | 0.765 | 12 | SB | Large T | A2403 |
| 145 QFLSQAVF | 0.713 | 22 | SB | Large T | A2403 |
| 541 RFVRQIDF | 0.706 | 24 | SB | Large T | A2403 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 321 | HFANAIIF | 0.691 | 28 | SB | Large T | A2403 |
| 230 | EYLLYSAL | 0.591 | 83 | WB | Large T | A2403 |
| 408 | DFLHCVVF | 0.567 | 108 | WB | Large T | A2403 |
| 556 | KSLQNSEF | 0.546 | 135 | WB | Large T | A2403 |
| 104 | LFCHEDMF | 0.497 | 230 | WB | Large T | A2403 |
| 531 | EYPVPKTL | 0.496 | 233 | WB | Large T | A2403 |
| 611 | YTFSRMKY | 0.680 | 31 | SB | Large T | A2601 |
| 285 | DVFLLLGM | 0.588 | 86 | WB | Large T | A2601 |
| 11 | ELMDLLGL | 0.486 | 259 | WB | Large T | A2601 |
| 611 | YTFSRMKY | 0.903 | 2 | SB | Large T | A2602 |
| 285 | DVFLLLGM | 0.810 | 7 | SB | Large T | A2602 |
| 280 | ETKCEDVF | 0.737 | 17 | SB | Large T | A2602 |
| 66 | KVAHQPDF | 0.563 | 112 | WB | Large T | A2602 |
| 11 | ELMDLLGL | 0.500 | 224 | WB | Large T | A2602 |
| 463 | GVAIDQYM | 0.486 | 261 | WB | Large T | A2602 |
| 80 | EVPTYGTE | 0.485 | 262 | WB | Large T | A2602 |
| 291 | GMYLEFQY | 0.680 | 31 | SB | Large T | A2902 |
| 286 | VFLLLGMY | 0.624 | 58 | WB | Large T | A2902 |
| 611 | YTFSRMKY | 0.617 | 63 | WB | Large T | A2902 |
| 156 | TLACFAVY | 0.552 | 127 | WB | Large T | A2902 |
| 270 | SWKLITEY | 0.500 | 223 | WB | Large T | A2902 |
| 121 | SQHSTPPK | 0.836 | 5 | SB | Large T | A3001 |
| 419 | KRRYWLFK | 0.811 | 7 | SB | Large T | A3001 |
| 28 | LMRKAYLK | 0.805 | 8 | SB | Large T | A3001 |
| 544 | RQIDFRPK | 0.771 | 11 | SB | Large T | A3001 |
| 683 | RPKTPPPK | 0.740 | 16 | SB | Large T | A3001 |
| 505 | SVKVNLEK | 0.732 | 18 | SB | Large T | A3001 |
| 53 | RMNTLYKK | 0.672 | 34 | SB | Large T | A3001 |
| 394 | WLHCLLPK | 0.669 | 36 | SB | Large T | A3001 |
| 309 | KDQPYHFK | 0.647 | 45 | SB | Large T | A3001 |
| 31 | KAYLKKCK | 0.628 | 55 | WB | Large T | A3001 |
| 52 | KRMNTLYK | 0.620 | 60 | WB | Large T | A3001 |
| 161 | AVYTTKEK | 0.613 | 65 | WB | Large T | A3001 |
| 29 | MRKAYLKK | 0.612 | 66 | WB | Large T | A3001 |
| 594 | QSRIVEWK | 0.594 | 80 | WB | Large T | A3001 |
| 168 | KAQILYKK | 0.583 | 91 | WB | Large T | A3001 |
| 549 | RPKIYLRK | 0.571 | 103 | WB | Large T | A3001 |
| 172 | LYKKLMEK | 0.566 | 109 | WB | Large T | A3001 |
| 130 | KRKVEDPK | 0.560 | 116 | WB | Large T | A3001 |
| 617 | KYNICMGK | 0.549 | 131 | WB | Large T | A3001 |
| 610 | MYTFSRMK | 0.541 | 142 | WB | Large T | A3001 |
| 365 | RFNHILDK | 0.516 | 188 | WB | Large T | A3001 |
| 196 | IFFLTPHR | 0.458 | 350 | WB | Large T | A3001 |
| 208 | AINNFCQK | 0.450 | 382 | WB | Large T | A3001 |
| 237 | LTRDPYHI | 0.443 | 416 | WB | Large T | A3001 |
| 205 | RVSAINNF | 0.506 | 210 | WB | Large T | A3002 |
| 611 | YTFSRMKY | 0.440 | 428 | WB | Large T | A3002 |
| 577 | LLLLIWFR | 0.818 | 7 | SB | Large T | A3101 |
| 53 | RMNTLYKK | 0.816 | 7 | SB | Large T | A3101 |
| 608 | ISMYTFSR | 0.791 | 9 | SB | Large T | A3101 |
| 537 | TLQARFVR | 0.773 | 11 | SB | Large T | A3101 |
| 196 | IFFLTPHR | 0.772 | 11 | SB | Large T | A3101 |
| 414 | VFNVPKRR | 0.682 | 31 | SB | Large T | A3101 |
| 148 | SQAVFSNR | 0.678 | 32 | SB | Large T | A3101 |
| 180 | YSVTFISR | 0.672 | 34 | SB | Large T | A3101 |
| 676 | KGFQCFKR | 0.671 | 35 | SB | Large T | A3101 |
| 413 | VVFNVPKR | 0.665 | 37 | SB | Large T | A3101 |
| 617 | KYNICMGK | 0.648 | 45 | SB | Large T | A3101 |
| 28 | LMRKAYLK | 0.646 | 46 | SB | Large T | A3101 |
| 544 | RQIDFRPK | 0.646 | 46 | SB | Large T | A3101 |
| 232 | LLYSALTR | 0.630 | 55 | WB | Large T | A3101 |
| 168 | KAQILYKK | 0.618 | 62 | WB | Large T | A3101 |
| 542 | FVRQIDFR | 0.590 | 84 | WB | Large T | A3101 |
| 589 | FSKDIQSR | 0.590 | 84 | WB | Large T | A3101 |
| 596 | RIVEWKER | 0.580 | 93 | WB | Large T | A3101 |
| 198 | FLTPHRHR | 0.569 | 106 | WB | Large T | A3101 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 172 | LYKKLMEK | 0.550 | 129 | WB | Large T | A3101 |
| 365 | RFNHILDK | 0.540 | 145 | WB | Large T | A3101 |
| 610 | MYTFSRMK | 0.532 | 157 | WB | Large T | A3101 |
| 450 | NVNLPMER | 0.515 | 189 | WB | Large T | A3101 |
| 31 | KAYLKKCK | 0.504 | 214 | WB | Large T | A3101 |
| 208 | AINNFCQK | 0.461 | 339 | WB | Large T | A3101 |
| 155 | RTLACFAV | 0.460 | 345 | WB | Large T | A3101 |
| 121 | SQHSTPPK | 0.452 | 376 | WB | Large T | A3101 |
| 577 | LLLLIWFR | 0.795 | 9 | SB | Large T | A3301 |
| 196 | IFFLTPHR | 0.758 | 13 | SB | Large T | A3301 |
| 608 | ISMYTFSR | 0.631 | 54 | WB | Large T | A3301 |
| 450 | NVNLPMER | 0.631 | 54 | WB | Large T | A3301 |
| 542 | FVRQIDFR | 0.628 | 55 | WB | Large T | A3301 |
| 537 | TLQARFVR | 0.608 | 69 | WB | Large T | A3301 |
| 343 | DTVLAKKR | 0.575 | 99 | WB | Large T | A3301 |
| 180 | YSVTFISR | 0.574 | 100 | WB | Large T | A3301 |
| 589 | FSKDIQSR | 0.535 | 152 | WB | Large T | A3301 |
| 547 | DFRPKIYL | 0.526 | 169 | WB | Large T | A3301 |
| 500 | DYLDGSVK | 0.521 | 178 | WB | Large T | A3301 |
| 198 | FLTPHRHR | 0.504 | 215 | WB | Large T | A3301 |
| 265 | ETKQVSWK | 0.447 | 397 | WB | Large T | A3301 |
| 265 | ETKQVSWK | 0.836 | 5 | SB | Large T | A6801 |
| 608 | ISMYTFSR | 0.827 | 6 | SB | Large T | A6801 |
| 470 | MVVFEDVK | 0.812 | 7 | SB | Large T | A6801 |
| 180 | YSVTFISR | 0.805 | 8 | SB | Large T | A6801 |
| 343 | DTVLAKKR | 0.798 | 8 | SB | Large T | A6801 |
| 412 | CVVFNVPK | 0.772 | 11 | SB | Large T | A6801 |
| 450 | NVNLPMER | 0.771 | 11 | SB | Large T | A6801 |
| 542 | FVRQIDFR | 0.764 | 12 | SB | Large T | A6801 |
| 611 | YTFSRMKY | 0.753 | 14 | SB | Large T | A6801 |
| 610 | MYTFSRMK | 0.746 | 15 | SB | Large T | A6801 |
| 413 | VVFNVPKR | 0.728 | 19 | SB | Large T | A6801 |
| 247 | ESIQGGLK | 0.662 | 38 | SB | Large T | A6801 |
| 232 | LLYSALTR | 0.652 | 43 | SB | Large T | A6801 |
| 589 | FSKDIQSR | 0.648 | 44 | SB | Large T | A6801 |
| 537 | TLQARFVR | 0.632 | 53 | WB | Large T | A6801 |
| 196 | IFFLTPHR | 0.626 | 57 | WB | Large T | A6801 |
| 577 | LLLLIWFR | 0.606 | 71 | WB | Large T | A6801 |
| 218 | TFSFLICK | 0.597 | 78 | WB | Large T | A6801 |
| 560 | NSEFLLEK | 0.575 | 99 | WB | Large T | A6801 |
| 325 | AIIFAESK | 0.570 | 105 | WB | Large T | A6801 |
| 198 | FLTPHRHR | 0.567 | 108 | WB | Large T | A6801 |
| 505 | SVKVNLEK | 0.553 | 126 | WB | Large T | A6801 |
| 167 | EKAQILYK | 0.548 | 132 | WB | Large T | A6801 |
| 148 | SQAVFSNR | 0.536 | 151 | WB | Large T | A6801 |
| 159 | CFAVYTTK | 0.531 | 159 | WB | Large T | A6801 |
| 161 | AVYTTKEK | 0.529 | 163 | WB | Large T | A6801 |
| 208 | AINNFCQK | 0.516 | 188 | WB | Large T | A6801 |
| 328 | FAESKNQK | 0.505 | 212 | WB | Large T | A6801 |
| 596 | RIVEWKER | 0.471 | 306 | WB | Large T | A6801 |
| 492 | INNLDSLR | 0.464 | 329 | WB | Large T | A6801 |
| 156 | TLACFAVY | 0.458 | 351 | WB | Large T | A6801 |
| 124 | STPPKKKR | 0.453 | 371 | WB | Large T | A6801 |
| 275 | TEYAVETK | 0.432 | 465 | WB | Large T | A6801 |
| 123 | HSTPPKKK | 0.429 | 482 | WB | Large T | A6801 |
| 404 | SVIFDFLH | 0.427 | 492 | WB | Large T | A6801 |
| 313 | YHFKYHEK | 0.426 | 496 | WB | Large T | A6801 |
| 322 | FANAIIFA | 0.703 | 24 | SB | Large T | A6802 |
| 520 | QIFPPGLV | 0.669 | 35 | SB | Large T | A6802 |
| 155 | RTLACFAV | 0.653 | 42 | SB | Large T | A6802 |
| 377 | FGAHGNAV | 0.634 | 52 | WB | Large T | A6802 |
| 527 | VTMNEYPV | 0.617 | 63 | WB | Large T | A6802 |
| 403 | DSVIFDFL | 0.603 | 73 | WB | Large T | A6802 |
| 11 | ELMDLLGL | 0.583 | 90 | WB | Large T | A6802 |
| 189 | MCAGHNII | 0.575 | 99 | WB | Large T | A6802 |
| 8 | ESMELMDL | 0.563 | 113 | WB | Large T | A6802 |
| 199 | LTPHRHRV | 0.555 | 123 | WB | Large T | A6802 |
| 178 | EKYSVTFI | 0.531 | 160 | WB | Large T | A6802 |
| 388 | YMAGVAWL | 0.523 | 174 | WB | Large T | A6802 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pospeptide | logscore | affinity (nM) | Bind Level | Protein Name | Allele |
|---|---|---|---|---|---|
| 574 MTLLLLLI | 0.480 | 278 | WB | Large T | A6802 |
| 464 VAIDQYMV | 0.479 | 281 | WB | Large T | A6802 |
| 579 LLIWFRPV | 0.477 | 286 | WB | Large T | A6802 |
| 649 QSQCSSQV | 0.455 | 365 | WB | Large T | A6802 |
| 19 ERAAWGNL | 0.434 | 456 | WB | Large T | A6802 |
| 434 TTLAAGLL | 0.431 | 470 | WB | Large T | A6802 |
| 216 LCTFSFLI | 0.428 | 489 | WB | Large T | A6802 |
| 520 QIFPPGLV | 0.711 | 22 | SB | Large T | A6901 |
| 11 ELMDLLGL | 0.667 | 36 | SB | Large T | A6901 |
| 155 RTLACFAV | 0.636 | 51 | WB | Large T | A6901 |
| 574 MTLLLLLI | 0.613 | 66 | WB | Large T | A6901 |
| 527 VTMNEYPV | 0.575 | 99 | WB | Large T | A6901 |
| 434 TTLAAGLL | 0.571 | 103 | WB | Large T | A6901 |
| 501 YLDGSVKV | 0.546 | 135 | WB | Large T | A6901 |
| 74 GTWNSSEV | 0.545 | 137 | WB | Large T | A6901 |
| 464 VAIDQYMV | 0.523 | 175 | WB | Large T | A6901 |
| 322 FANAIIFA | 0.514 | 192 | WB | Large T | A6901 |
| 21 AAWGNLPL | 0.513 | 193 | WB | Large T | A6901 |
| 579 LLIWFRPV | 0.508 | 205 | WB | Large T | A6901 |
| 287 FLLLGMYL | 0.504 | 214 | WB | Large T | A6901 |
| 388 YMAGVAWL | 0.494 | 238 | WB | Large T | A6901 |
| 340 QAVDTVLA | 0.464 | 328 | WB | Large T | A6901 |
| 8 ESMELMDL | 0.453 | 372 | WB | Large T | A6901 |
| 458 LTFELGVA | 0.433 | 462 | WB | Large T | A6901 |
| 377 FGAHGNAV | 0.431 | 472 | WB | Large T | A6901 |
| 383 AVLEQYMA | 0.426 | 499 | WB | Large T | A6901 |
| 453 LPMERLTF | 0.735 | 17 | SB | Large T | B0702 |
| 417 VPKRRYWL | 0.608 | 69 | WB | Large T | B0702 |
| 399 LPKMDSVI | 0.500 | 223 | WB | Large T | B0702 |
| 21 AAWGNLPL | 0.482 | 270 | WB | Large T | B0702 |
| 139 FPSDLHQF | 0.479 | 281 | WB | Large T | B0702 |
| 26 LPLMRKAY | 0.431 | 472 | WB | Large T | B0702 |
| 417 VPKRRYWL | 0.555 | 123 | WB | Large T | B0801 |
| 50 KMKRMNTL | 0.479 | 282 | WB | Large T | B0801 |
| 33 YLKKCKEF | 0.446 | 401 | WB | Large T | B0801 |
| 205 RVSAINNF | 0.544 | 139 | WB | Large T | B1501 |
| 306 CQKKDQPY | 0.511 | 199 | WB | Large T | B1501 |
| 339 QQAVDTVL | 0.504 | 214 | WB | Large T | B1501 |
| 615 RMKYNICM | 0.498 | 228 | WB | Large T | B1501 |
| 33 YLKKCKEF | 0.496 | 232 | WB | Large T | B1501 |
| 388 YMAGVAWL | 0.493 | 240 | WB | Large T | B1501 |
| 611 YTFSRMKY | 0.492 | 244 | WB | Large T | B1501 |
| 291 GMYLEFQY | 0.486 | 261 | WB | Large T | B1501 |
| 144 HQFLSQAV | 0.476 | 288 | WB | Large T | B1501 |
| 50 KMKRMNTL | 0.474 | 294 | WB | Large T | B1501 |
| 156 TLACFAVY | 0.469 | 311 | WB | Large T | B1501 |
| 570 LQSGMTLL | 0.441 | 424 | WB | Large T | B1501 |
| 89 WESWWSSF | 0.814 | 7 | SB | Large T | B1801 |
| 455 MERLTFEL | 0.686 | 29 | SB | Large T | B1801 |
| 606 SEISMYTF | 0.646 | 45 | SB | Large T | B1801 |
| 177 MEKYSVTF | 0.627 | 56 | WB | Large T | B1801 |
| 363 TERFNHIL | 0.449 | 388 | WB | Large T | B1801 |
| 86 TEEWESWW | 0.434 | 458 | WB | Large T | B1801 |
| 52 KRMNTLYK | 0.623 | 58 | WB | Large T | B2705 |
| 567 KRILQSGM | 0.555 | 122 | WB | Large T | B2705 |
| 544 RQIDFRPK | 0.533 | 155 | WB | Large T | B2705 |
| 419 KRRYWLFK | 0.506 | 209 | WB | Large T | B2705 |
| 349 KRVDTLHM | 0.461 | 341 | WB | Large T | B2705 |
| 29 MRKAYLKK | 0.430 | 477 | WB | Large T | B2705 |
| 139 FPSDLHQF | 0.796 | 9 | SB | Large T | B3501 |
| 522 FPPGLVTM | 0.773 | 11 | SB | Large T | B3501 |
| 453 LPMERLTF | 0.752 | 14 | SB | Large T | B3501 |
| 26 LPLMRKAY | 0.749 | 15 | SB | Large T | B3501 |
| 235 SALTRDPY | 0.599 | 76 | WB | Large T | B3501 |
| 382 NAVLEQYM | 0.558 | 119 | WB | Large T | B3501 |

TABLE M-continued

Prediction of BK virus Large T protein specific MHC class1,
8-, 9-, 10-, 11-mer peptide binders for 42 MHC class 1 alleles
(see FIG. 11) using the www.cbs.dtu.dk/services/
NetMHC/ database. The MHC class 1 molecules for which
no binders were found are not listed.

| pos | peptide | logscore | affinity (nM) | Bind Level | Protein Name | Allele |
|---|---|---|---|---|---|---|
| 111 | FASDEEAT | 0.538 | 148 | WB | Large T | B3501 |
| 156 | TLACFAVY | 0.533 | 156 | WB | Large T | B3501 |
| 321 | HFANAIIF | 0.513 | 193 | WB | Large T | B3501 |
| 21 | AAWGNLPL | 0.509 | 203 | WB | Large T | B3501 |
| 77 | NSSEVPTY | 0.502 | 218 | WB | Large T | B3501 |
| 98 | EKWDEDLF | 0.451 | 381 | WB | Large T | B3501 |
| 145 | QFLSQAVF | 0.450 | 384 | WB | Large T | B3501 |
| 89 | WESWWSSF | 0.445 | 407 | WB | Large T | B3501 |
| 5 | NREESMEL | 0.555 | 123 | WB | Large T | B3901 |
| 339 | QQAVDTVL | 0.464 | 330 | WB | Large T | B3901 |
| 388 | YMAGVAWL | 0.429 | 483 | WB | Large T | B3901 |
| 455 | MERLTFEL | 0.676 | 33 | SB | Large T | B4001 |
| 363 | TERFNHIL | 0.626 | 57 | WB | Large T | B4001 |
| 283 | CEDVFLLL | 0.595 | 80 | WB | Large T | B4001 |
| 606 | SEISMYTF | 0.593 | 81 | WB | Large T | B4001 |
| 6 | REESMELM | 0.511 | 197 | WB | Large T | B4001 |
| 177 | MEKYSVTF | 0.487 | 257 | WB | Large T | B4001 |
| 246 | EESIQGGL | 0.432 | 465 | WB | Large T | B4001 |
| 606 | SEISMYTF | 0.568 | 107 | WB | Large T | B4002 |
| 89 | WESWWSSF | 0.495 | 237 | WB | Large T | B4002 |
| 166 | KEKAQILY | 0.489 | 250 | WB | Large T | B4002 |
| 359 | EEMLTERF | 0.489 | 251 | WB | Large T | B4002 |
| 246 | EESIQGGL | 0.464 | 328 | WB | Large T | B4002 |
| 177 | MEKYSVTF | 0.454 | 367 | WB | Large T | B4002 |
| 264 | EETKQVSW | 0.446 | 403 | WB | Large T | B4002 |
| 6 | REESMELM | 0.433 | 463 | WB | Large T | B4002 |
| 264 | EETKQVSW | 0.514 | 193 | WB | Large T | B4402 |
| 606 | SEISMYTF | 0.472 | 303 | WB | Large T | B4402 |
| 86 | TEEWESWW | 0.464 | 329 | WB | Large T | B4402 |
| 166 | KEKAQILY | 0.461 | 342 | WB | Large T | B4402 |
| 359 | EEMLTERF | 0.449 | 388 | WB | Large T | B4402 |
| 606 | SEISMYTF | 0.549 | 131 | WB | Large T | B4403 |
| 359 | EEMLTERF | 0.526 | 167 | WB | Large T | B4403 |
| 359 | EEMLTERF | 0.512 | 196 | WB | Large T | B4501 |
| 329 | AESKNQKS | 0.443 | 415 | WB | Large T | B4501 |
| 246 | EESIQGGL | 0.433 | 460 | WB | Large T | B4501 |
| 481 | AESKDLPS | 0.431 | 470 | WB | Large T | B4501 |
| 522 | FPPGLVTM | 0.629 | 55 | WB | Large T | B5101 |
| 453 | LPMERLTF | 0.621 | 60 | WB | Large T | B5101 |
| 399 | LPKMDSVI | 0.598 | 77 | WB | Large T | B5101 |
| 453 | LPMERLTF | 0.755 | 14 | SB | Large T | B5301 |
| 139 | FPSDLHQF | 0.729 | 18 | SB | Large T | B5301 |
| 26 | LPLMRKAY | 0.636 | 51 | WB | Large T | B5301 |
| 399 | LPKMDSVI | 0.632 | 53 | WB | Large T | B5301 |
| 522 | FPPGLVTM | 0.582 | 91 | WB | Large T | B5301 |
| 522 | FPPGLVTM | 0.577 | 97 | WB | Large T | B5401 |
| 322 | FANAIIFA | 0.511 | 198 | WB | Large T | B5401 |
| 26 | LPLMRKAY | 0.482 | 271 | WB | Large T | B5401 |
| 82 | PTYGTEEW | 0.517 | 186 | WB | Large T | B5701 |
| 93 | WSSFNEKW | 0.678 | 32 | SB | Large T | B5801 |
| 556 | KSLQNSEF | 0.602 | 74 | WB | Large T | B5801 |
| 593 | IQSRIVEW | 0.573 | 101 | WB | Large T | B5801 |
| 205 | RVSAINNF | 0.525 | 169 | WB | Large T | B5801 |
| 82 | PTYGTEEW | 0.504 | 215 | WB | Large T | B5801 |
| 66 | KVAHQPDF | 0.491 | 246 | WB | Large T | B5801 |
| 16 | LGLERAAW | 0.439 | 430 | WB | Large T | B5801 |
| 77 | NSSEVPTY | 0.431 | 469 | WB | Large T | B5801 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| | | | 9-mers | | | |
| 603 | RLDSEISMY | 0.648 | 44 | SB | Large T | A0101 |
| 226 | GVNKEYLLY | 0.477 | 286 | WB | Large T | A0101 |
| 234 | YSALTRDPY | 0.471 | 304 | WB | Large T | A0101 |
| | | | | | | |
| 409 | FLHCVVFNV | 0.891 | 3 | SB | Large T | A0201 |
| 405 | VIFDFLHCV | 0.842 | 5 | SB | Large T | A0201 |
| 215 | KLCTFSFLI | 0.747 | 15 | SB | Large T | A0201 |
| 198 | FLTPHRHRV | 0.693 | 27 | SB | Large T | A0201 |
| 578 | LLLIWFRPV | 0.690 | 28 | SB | Large T | A0201 |
| 384 | VLEQYMAGV | 0.680 | 31 | SB | Large T | A0201 |
| 557 | SLQNSEFLL | 0.658 | 40 | SB | Large T | A0201 |
| 397 | CLLPKMDSV | 0.639 | 49 | SB | Large T | A0201 |
| 569 | ILQSGMTLL | 0.614 | 64 | WB | Large T | A0201 |
| 175 | KLMEKYSVT | 0.580 | 94 | WB | Large T | A0201 |
| 435 | TLAAGLLDL | 0.578 | 95 | WB | Large T | A0201 |
| 361 | MLTERFNHI | 0.562 | 114 | WB | Large T | A0201 |
| 579 | LLIWFRPVA | 0.505 | 212 | WB | Large T | A0201 |
| 573 | GMTLLLLLI | 0.494 | 237 | WB | Large T | A0201 |
| 368 | HILDKMDLI | 0.488 | 254 | WB | Large T | A0201 |
| 621 | CMGKCILDI | 0.465 | 327 | WB | Large T | A0201 |
| 394 | WLHCLLPKM | 0.443 | 412 | WB | Large T | A0201 |
| 156 | TLACFAVYT | 0.437 | 440 | WB | Large T | A0201 |
| | | | | | | |
| 409 | FLHCVVFNV | 0.885 | 3 | SB | Large T | A0202 |
| 198 | FLTPHRHRV | 0.824 | 6 | SB | Large T | A0202 |
| 361 | MLTERFNHI | 0.774 | 11 | SB | Large T | A0202 |
| 569 | ILQSGMTLL | 0.765 | 12 | SB | Large T | A0202 |
| 405 | VIFDFLHCV | 0.742 | 16 | SB | Large T | A0202 |
| 384 | VLEQYMAGV | 0.728 | 19 | SB | Large T | A0202 |
| 494 | NLDSLRDYL | 0.687 | 29 | SB | Large T | A0202 |
| 557 | SLQNSEFLL | 0.676 | 33 | SB | Large T | A0202 |
| 570 | LQSGMTLLL | 0.676 | 33 | SB | Large T | A0202 |
| 397 | CLLPKMDSV | 0.658 | 40 | SB | Large T | A0202 |
| 402 | MDSVIFDFL | 0.642 | 48 | SB | Large T | A0202 |
| 215 | KLCTFSFLI | 0.640 | 49 | SB | Large T | A0202 |
| 497 | SLRDYLDGS | 0.630 | 54 | WB | Large T | A0202 |
| 463 | GVAIDQYMV | 0.614 | 65 | WB | Large T | A0202 |
| 435 | TLAAGLLDL | 0.605 | 71 | WB | Large T | A0202 |
| 175 | KLMEKYSVT | 0.560 | 116 | WB | Large T | A0202 |
| 573 | GMTLLLLLI | 0.558 | 119 | WB | Large T | A0202 |
| 156 | TLACFAVYT | 0.554 | 124 | WB | Large T | A0202 |
| 289 | LLGMYLEFQ | 0.542 | 142 | WB | Large T | A0202 |
| 648 | SQSQCSSQV | 0.542 | 142 | WB | Large T | A0202 |
| 391 | GVAWLHCLL | 0.529 | 163 | WB | Large T | A0202 |
| 219 | FSFLICKGV | 0.528 | 165 | WB | Large T | A0202 |
| 208 | AINNFCQKL | 0.524 | 173 | WB | Large T | A0202 |
| 191 | AGHNIIFFL | 0.514 | 191 | WB | Large T | A0202 |
| 111 | FASDEEATA | 0.506 | 208 | WB | Large T | A0202 |
| 139 | FPSDLHQFL | 0.505 | 211 | WB | Large T | A0202 |
| 236 | ALTRDPYHI | 0.501 | 220 | WB | Large T | A0202 |
| 589 | FSKDIQSRI | 0.499 | 226 | WB | Large T | A0202 |
| 526 | LVTMNEYPV | 0.493 | 240 | WB | Large T | A0202 |
| 146 | FLSQAVFSN | 0.480 | 278 | WB | Large T | A0202 |
| 578 | LLLIWFRPV | 0.466 | 321 | WB | Large T | A0202 |
| 377 | FGAHGNAVL | 0.465 | 327 | WB | Large T | A0202 |
| 458 | LTFELGVAI | 0.452 | 376 | WB | Large T | A0202 |
| 572 | SGMTLLLLL | 0.450 | 385 | WB | Large T | A0202 |
| 398 | LLPKMDSVI | 0.448 | 392 | WB | Large T | A0202 |
| 368 | HILDKMDLI | 0.438 | 438 | WB | Large T | A0202 |
| | | | | | | |
| 409 | FLHCVVFNV | 0.911 | 2 | SB | Large T | A0203 |
| 198 | FLTPHRHRV | 0.891 | 3 | SB | Large T | A0203 |
| 361 | MLTERFNHI | 0.884 | 3 | SB | Large T | A0203 |
| 384 | VLEQYMAGV | 0.838 | 5 | SB | Large T | A0203 |
| 578 | LLLIWFRPV | 0.819 | 7 | SB | Large T | A0203 |
| 397 | CLLPKMDSV | 0.815 | 7 | SB | Large T | A0203 |
| 569 | ILQSGMTLL | 0.803 | 8 | SB | Large T | A0203 |
| 405 | VIFDFLHCV | 0.796 | 9 | SB | Large T | A0203 |
| 435 | TLAAGLLDL | 0.744 | 16 | SB | Large T | A0203 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 175 | KLMEKYSVT | 0.694 | 27 | SB | Large T | A0203 |
| 457 | RLTFELGVA | 0.683 | 30 | SB | Large T | A0203 |
| 497 | SLRDYLDGS | 0.596 | 79 | WB | Large T | A0203 |
| 579 | LLIWFRPVA | 0.575 | 99 | WB | Large T | A0203 |
| 553 | YLRKSLQNS | 0.569 | 105 | WB | Large T | A0203 |
| 215 | KLCTFSFLI | 0.566 | 108 | WB | Large T | A0203 |
| 236 | ALTRDPYHI | 0.540 | 144 | WB | Large T | A0203 |
| 375 | LIFGAHGNA | 0.540 | 145 | WB | Large T | A0203 |
| 573 | GMTLLLLLI | 0.537 | 150 | WB | Large T | A0203 |
| 570 | LQSGMTLLL | 0.528 | 165 | WB | Large T | A0203 |
| 156 | TLACFAVYT | 0.527 | 166 | WB | Large T | A0203 |
| 648 | SQSQCSSQV | 0.520 | 179 | WB | Large T | A0203 |
| 391 | GVAWLHCLL | 0.517 | 185 | WB | Large T | A0203 |
| 398 | LLPKMDSVI | 0.516 | 188 | WB | Large T | A0203 |
| 394 | WLHCLLPKM | 0.513 | 194 | WB | Large T | A0203 |
| 464 | VAIDQYMVV | 0.512 | 195 | WB | Large T | A0203 |
| 188 | HMCAGHNII | 0.510 | 199 | WB | Large T | A0203 |
| 519 | TQIFPPGLV | 0.506 | 210 | WB | Large T | A0203 |
| 208 | AINNFCQKL | 0.501 | 220 | WB | Large T | A0203 |
| 368 | HILDKMDLI | 0.496 | 232 | WB | Large T | A0203 |
| 20 | RAAWGNLPL | 0.491 | 246 | WB | Large T | A0203 |
| 53 | RMNTLYKKM | 0.490 | 249 | WB | Large T | A0203 |
| 568 | RILQSGMTL | 0.485 | 263 | WB | Large T | A0203 |
| 538 | LQARFVRQI | 0.458 | 352 | WB | Large T | A0203 |
| 289 | LLGMYLEFQ | 0.456 | 360 | WB | Large T | A0203 |
| 557 | SLQNSEFLL | 0.447 | 396 | WB | Large T | A0203 |
| 596 | RIVEWKERL | 0.441 | 423 | WB | Large T | A0203 |
| 463 | GVAIDQYMV | 0.432 | 464 | WB | Large T | A0203 |
| 198 | FLTPHRHRV | 0.766 | 12 | SB | Large T | A0204 |
| 409 | FLHCVVFNV | 0.744 | 15 | SB | Large T | A0204 |
| 405 | VIFDFLHCV | 0.645 | 46 | SB | Large T | A0204 |
| 578 | LLLIWFRPV | 0.640 | 48 | SB | Large T | A0204 |
| 384 | VLEQYMAGV | 0.607 | 70 | WB | Large T | A0204 |
| 464 | VAIDQYMVV | 0.564 | 111 | WB | Large T | A0204 |
| 557 | SLQNSEFLL | 0.552 | 127 | WB | Large T | A0204 |
| 59 | KKMEQDVKV | 0.514 | 191 | WB | Large T | A0204 |
| 526 | LVTMNEYPV | 0.512 | 196 | WB | Large T | A0204 |
| 435 | TLAAGLLDL | 0.489 | 251 | WB | Large T | A0204 |
| 292 | MYLEFQYNV | 0.488 | 255 | WB | Large T | A0204 |
| 569 | ILQSGMTLL | 0.485 | 264 | WB | Large T | A0204 |
| 208 | AINNFCQKL | 0.474 | 296 | WB | Large T | A0204 |
| 397 | CLLPKMDSV | 0.468 | 315 | WB | Large T | A0204 |
| 175 | KLMEKYSVT | 0.464 | 329 | WB | Large T | A0204 |
| 361 | MLTERFNHI | 0.447 | 395 | WB | Large T | A0204 |
| 236 | ALTRDPYHI | 0.447 | 398 | WB | Large T | A0204 |
| 215 | KLCTFSFLI | 0.445 | 404 | WB | Large T | A0204 |
| 361 | MLTERFNHI | 0.848 | 5 | SB | Large T | A0206 |
| 397 | CLLPKMDSV | 0.834 | 6 | SB | Large T | A0206 |
| 409 | FLHCVVFNV | 0.819 | 7 | SB | Large T | A0206 |
| 578 | LLLIWFRPV | 0.801 | 8 | SB | Large T | A0206 |
| 198 | FLTPHRHRV | 0.793 | 9 | SB | Large T | A0206 |
| 405 | VIFDFLHCV | 0.746 | 15 | SB | Large T | A0206 |
| 544 | RQIDFRPKI | 0.739 | 16 | SB | Large T | A0206 |
| 648 | SQSQCSSQV | 0.729 | 18 | SB | Large T | A0206 |
| 384 | VLEQYMAGV | 0.692 | 27 | SB | Large T | A0206 |
| 570 | LQSGMTLLL | 0.683 | 30 | SB | Large T | A0206 |
| 596 | RIVEWKERL | 0.674 | 34 | SB | Large T | A0206 |
| 568 | RILQSGMTL | 0.638 | 50 | WB | Large T | A0206 |
| 20 | RAAWGNLPL | 0.634 | 52 | WB | Large T | A0206 |
| 435 | TLAAGLLDL | 0.583 | 91 | WB | Large T | A0206 |
| 215 | KLCTFSFLI | 0.560 | 116 | WB | Large T | A0206 |
| 464 | VAIDQYMVV | 0.560 | 117 | WB | Large T | A0206 |
| 368 | HILDKMDLI | 0.550 | 130 | WB | Large T | A0206 |
| 339 | QQAVDTVLA | 0.549 | 131 | WB | Large T | A0206 |
| 569 | ILQSGMTLL | 0.520 | 180 | WB | Large T | A0206 |
| 111 | FASDEEATA | 0.520 | 180 | WB | Large T | A0206 |
| 267 | KQVSWKLIT | 0.516 | 188 | WB | Large T | A0206 |
| 579 | LLIWFRPVA | 0.507 | 206 | WB | Large T | A0206 |
| 458 | LTFELGVAI | 0.503 | 216 | WB | Large T | A0206 |
| 10 | MELMDLLGL | 0.496 | 233 | WB | Large T | A0206 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pospeptide | logscore | affinity (nM) | Bind Level | Protein Name | Allele |
|---|---|---|---|---|---|
| 391 GVAWLHCLL | 0.476 | 291 | WB | Large T | A0206 |
| 287 FLLLGMYLE | 0.473 | 298 | WB | Large T | A0206 |
| 519 TQIFPPGLV | 0.470 | 308 | WB | Large T | A0206 |
| 288 LLLGMYLEF | 0.469 | 312 | WB | Large T | A0206 |
| 447 KALNVNLPM | 0.457 | 357 | WB | Large T | A0206 |
| 21 AAWGNLPLM | 0.457 | 357 | WB | Large T | A0206 |
| 394 WLHCLLPKM | 0.451 | 379 | WB | Large T | A0206 |
| 526 LVTMNEYPV | 0.441 | 421 | WB | Large T | A0206 |
| 175 KLMEKYSVT | 0.439 | 432 | WB | Large T | A0206 |
| 148 SQAVFSNRT | 0.438 | 437 | WB | Large T | A0206 |
| 198 FLTPHRHRV | 0.978 | 1 | SB | Large T | A0211 |
| 405 VIFDFLHCV | 0.968 | 1 | SB | Large T | A0211 |
| 409 FLHCVVFNV | 0.933 | 2 | SB | Large T | A0211 |
| 397 CLLPKMDSV | 0.929 | 2 | SB | Large T | A0211 |
| 384 VLEQYMAGV | 0.926 | 2 | SB | Large T | A0211 |
| 557 SLQNSEFLL | 0.912 | 2 | SB | Large T | A0211 |
| 494 NLDSLRDYL | 0.903 | 2 | SB | Large T | A0211 |
| 569 ILQSGMTLL | 0.890 | 3 | SB | Large T | A0211 |
| 435 TLAAGLLDL | 0.890 | 3 | SB | Large T | A0211 |
| 215 KLCTFSFLI | 0.876 | 3 | SB | Large T | A0211 |
| 578 LLLIWFRPV | 0.862 | 4 | SB | Large T | A0211 |
| 563 FLLEKRILQ | 0.862 | 4 | SB | Large T | A0211 |
| 579 LLIWFRPVA | 0.849 | 5 | SB | Large T | A0211 |
| 292 MYLEFQYNV | 0.832 | 6 | SB | Large T | A0211 |
| 388 YMAGVAWLH | 0.799 | 8 | SB | Large T | A0211 |
| 463 GVAIDQYMV | 0.796 | 9 | SB | Large T | A0211 |
| 428 PIDSGKTTL | 0.778 | 11 | SB | Large T | A0211 |
| 573 GMTLLLLLI | 0.771 | 11 | SB | Large T | A0211 |
| 500 DYLDGSVKV | 0.751 | 14 | SB | Large T | A0211 |
| 454 PMERLTFEL | 0.736 | 17 | SB | Large T | A0211 |
| 288 LLLGMYLEF | 0.733 | 17 | SB | Large T | A0211 |
| 526 LVTMNEYPV | 0.733 | 18 | SB | Large T | A0211 |
| 391 GVAWLHCLL | 0.725 | 19 | SB | Large T | A0211 |
| 464 VAIDQYMVV | 0.721 | 20 | SB | Large T | A0211 |
| 568 RILQSGMTL | 0.720 | 20 | SB | Large T | A0211 |
| 142 DLHQFLSQA | 0.703 | 24 | SB | Large T | A0211 |
| 361 MLTERFNHI | 0.692 | 28 | SB | Large T | A0211 |
| 236 ALTRDPYHI | 0.685 | 30 | SB | Large T | A0211 |
| 596 RIVEWKERL | 0.685 | 30 | SB | Large T | A0211 |
| 156 TLACFAVYT | 0.663 | 38 | SB | Large T | A0211 |
| 287 FLLLGMYLE | 0.659 | 40 | SB | Large T | A0211 |
| 208 AINNFCQKL | 0.637 | 50 | WB | Large T | A0211 |
| 575 TLLLLLIWF | 0.632 | 53 | WB | Large T | A0211 |
| 20 RAAWGNLPL | 0.620 | 61 | WB | Large T | A0211 |
| 14 DLLGLERAA | 0.614 | 65 | WB | Large T | A0211 |
| 289 LLGMYLEFQ | 0.602 | 74 | WB | Large T | A0211 |
| 603 RLDSEISMY | 0.592 | 82 | WB | Large T | A0211 |
| 368 HILDKMDLI | 0.590 | 84 | WB | Large T | A0211 |
| 576 LLLLLIWFR | 0.575 | 99 | WB | Large T | A0211 |
| 394 WLHCLLPKM | 0.569 | 106 | WB | Large T | A0211 |
| 353 TLHMTREEM | 0.558 | 119 | WB | Large T | A0211 |
| 273 LITEYAVET | 0.545 | 137 | WB | Large T | A0211 |
| 398 LLPKMDSVI | 0.535 | 152 | WB | Large T | A0211 |
| 401 KMDSVIFDF | 0.531 | 160 | WB | Large T | A0211 |
| 146 FLSQAVFSN | 0.527 | 166 | WB | Large T | A0211 |
| 188 HMCAGHNII | 0.524 | 172 | WB | Large T | A0211 |
| 406 IFDFLHCVV | 0.519 | 181 | WB | Large T | A0211 |
| 648 SQSQCSSQV | 0.514 | 191 | WB | Large T | A0211 |
| 458 LTFELGVAI | 0.508 | 204 | WB | Large T | A0211 |
| 497 SLRDYLDGS | 0.503 | 216 | WB | Large T | A0211 |
| 501 YLDGSVKVN | 0.501 | 220 | WB | Large T | A0211 |
| 171 ILYKKLMEK | 0.485 | 264 | WB | Large T | A0211 |
| 73 FGTWNSSEV | 0.481 | 274 | WB | Large T | A0211 |
| 609 SMYTFSRMK | 0.474 | 295 | WB | Large T | A0211 |
| 416 NVPKRRYWL | 0.464 | 330 | WB | Large T | A0211 |
| 109 DMFASDEEA | 0.459 | 346 | WB | Large T | A0211 |
| 139 FPSDLHQFL | 0.459 | 349 | WB | Large T | A0211 |
| 439 GLLDLCGGK | 0.452 | 377 | WB | Large T | A0211 |
| 465 AIDQYMVVF | 0.449 | 389 | WB | Large T | A0211 |
| 21 AAWGNLPLM | 0.448 | 394 | WB | Large T | A0211 |
| 521 IFPPGLVTM | 0.438 | 438 | WB | Large T | A0211 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 175 | KLMEKYSVT | 0.437 | 440 | WB | Large T | A0211 |
| 457 | RLTFELGVA | 0.430 | 478 | WB | Large T | A0211 |
| 150 | AVFSNRTLA | 0.428 | 486 | WB | Large T | A0211 |
| 198 | FLTPHRHRV | 0.950 | 1 | SB | Large T | A0212 |
| 405 | VIFDFLHCV | 0.944 | 1 | SB | Large T | A0212 |
| 384 | VLEQYMAGV | 0.915 | 2 | SB | Large T | A0212 |
| 397 | CLLPKMDSV | 0.909 | 2 | SB | Large T | A0212 |
| 409 | FLHCVVFNV | 0.905 | 2 | SB | Large T | A0212 |
| 435 | TLAAGLLDL | 0.836 | 5 | SB | Large T | A0212 |
| 569 | ILQSGMTLL | 0.822 | 6 | SB | Large T | A0212 |
| 292 | MYLEFQYNV | 0.776 | 11 | SB | Large T | A0212 |
| 578 | LLLIWFRPV | 0.774 | 11 | SB | Large T | A0212 |
| 557 | SLQNSEFLL | 0.763 | 12 | SB | Large T | A0212 |
| 563 | FLLEKRILQ | 0.736 | 17 | SB | Large T | A0212 |
| 464 | VAIDQYMVV | 0.723 | 20 | SB | Large T | A0212 |
| 494 | NLDSLRDYL | 0.711 | 22 | SB | Large T | A0212 |
| 361 | MLTERFNHI | 0.692 | 27 | SB | Large T | A0212 |
| 579 | LLIWFRPVA | 0.684 | 30 | SB | Large T | A0212 |
| 288 | LLLGMYLEF | 0.636 | 51 | WB | Large T | A0212 |
| 497 | SLRDYLDGS | 0.636 | 51 | WB | Large T | A0212 |
| 215 | KLCTFSFLI | 0.619 | 61 | WB | Large T | A0212 |
| 596 | RIVEWKERL | 0.610 | 68 | WB | Large T | A0212 |
| 388 | YMAGVAWLH | 0.607 | 69 | WB | Large T | A0212 |
| 287 | FLLLGMYLE | 0.598 | 77 | WB | Large T | A0212 |
| 428 | PIDSGKTTL | 0.561 | 115 | WB | Large T | A0212 |
| 14 | DLLGLERAA | 0.548 | 133 | WB | Large T | A0212 |
| 454 | PMERLTFEL | 0.545 | 137 | WB | Large T | A0212 |
| 526 | LVTMNEYPV | 0.533 | 155 | WB | Large T | A0212 |
| 458 | LTFELGVAI | 0.531 | 160 | WB | Large T | A0212 |
| 236 | ALTRDPYHI | 0.525 | 171 | WB | Large T | A0212 |
| 208 | AINNFCQKL | 0.521 | 177 | WB | Large T | A0212 |
| 500 | DYLDGSVKV | 0.517 | 185 | WB | Large T | A0212 |
| 111 | FASDEEATA | 0.507 | 206 | WB | Large T | A0212 |
| 289 | LLGMYLEFQ | 0.505 | 212 | WB | Large T | A0212 |
| 188 | HMCAGHNII | 0.504 | 214 | WB | Large T | A0212 |
| 368 | HILDKMDLI | 0.496 | 232 | WB | Large T | A0212 |
| 398 | LLPKMDSVI | 0.494 | 239 | WB | Large T | A0212 |
| 463 | GVAIDQYMV | 0.481 | 275 | WB | Large T | A0212 |
| 401 | KMDSVIFDF | 0.477 | 286 | WB | Large T | A0212 |
| 171 | ILYKKLMEK | 0.476 | 289 | WB | Large T | A0212 |
| 568 | RILQSGMTL | 0.453 | 370 | WB | Large T | A0212 |
| 139 | FPSDLHQFL | 0.450 | 385 | WB | Large T | A0212 |
| 394 | WLHCLLPKM | 0.439 | 434 | WB | Large T | A0212 |
| 198 | FLTPHRHRV | 0.957 | 1 | SB | Large T | A0216 |
| 405 | VIFDFLHCV | 0.924 | 2 | SB | Large T | A0216 |
| 384 | VLEQYMAGV | 0.898 | 2 | SB | Large T | A0216 |
| 397 | CLLPKMDSV | 0.898 | 3 | SB | Large T | A0216 |
| 409 | FLHCVVFNV | 0.881 | 3 | SB | Large T | A0216 |
| 569 | ILQSGMTLL | 0.861 | 4 | SB | Large T | A0216 |
| 494 | NLDSLRDYL | 0.860 | 4 | SB | Large T | A0216 |
| 557 | SLQNSEFLL | 0.844 | 5 | SB | Large T | A0216 |
| 454 | PMERLTFEL | 0.756 | 13 | SB | Large T | A0216 |
| 428 | PIDSGKTTL | 0.749 | 15 | SB | Large T | A0216 |
| 578 | LLLIWFRPV | 0.694 | 27 | SB | Large T | A0216 |
| 435 | TLAAGLLDL | 0.679 | 32 | SB | Large T | A0216 |
| 526 | LVTMNEYPV | 0.669 | 36 | SB | Large T | A0216 |
| 289 | LLGMYLEFQ | 0.657 | 40 | SB | Large T | A0216 |
| 215 | KLCTFSFLI | 0.657 | 41 | SB | Large T | A0216 |
| 142 | DLHQFLSQA | 0.655 | 41 | SB | Large T | A0216 |
| 292 | MYLEFQYNV | 0.655 | 41 | SB | Large T | A0216 |
| 563 | FLLEKRILQ | 0.646 | 45 | SB | Large T | A0216 |
| 596 | RIVEWKERL | 0.646 | 46 | SB | Large T | A0216 |
| 236 | ALTRDPYHI | 0.645 | 46 | SB | Large T | A0216 |
| 416 | NVPKRRYWL | 0.628 | 55 | WB | Large T | A0216 |
| 463 | GVAIDQYMV | 0.626 | 57 | WB | Large T | A0216 |
| 361 | MLTERFNHI | 0.601 | 74 | WB | Large T | A0216 |
| 156 | TLACFAVYT | 0.590 | 84 | WB | Large T | A0216 |
| 208 | AINNFCQKL | 0.578 | 96 | WB | Large T | A0216 |
| 568 | RILQSGMTL | 0.574 | 99 | WB | Large T | A0216 |
| 500 | DYLDGSVKV | 0.539 | 146 | WB | Large T | A0216 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 398 | LLPKMDSVI | 0.537 | 149 | WB | Large T | A0216 |
| 579 | LLIWFRPVA | 0.529 | 163 | WB | Large T | A0216 |
| 391 | GVAWLHCLL | 0.519 | 181 | WB | Large T | A0216 |
| 353 | TLHMTREEM | 0.510 | 200 | WB | Large T | A0216 |
| 619 | NICMGKCIL | 0.500 | 224 | WB | Large T | A0216 |
| 648 | SQSQCSSQV | 0.495 | 236 | WB | Large T | A0216 |
| 171 | ILYKKLMEK | 0.463 | 333 | WB | Large T | A0216 |
| 464 | VAIDQYMVV | 0.456 | 359 | WB | Large T | A0216 |
| 188 | HMCAGHNII | 0.440 | 428 | WB | Large T | A0216 |
| 368 | HILDKMDLI | 0.426 | 497 | WB | Large T | A0216 |
| 198 | FLTPHRHRV | 0.947 | 1 | SB | Large T | A0219 |
| 405 | VIFDFLHCV | 0.932 | 2 | SB | Large T | A0219 |
| 409 | FLHCVVFNV | 0.879 | 3 | SB | Large T | A0219 |
| 397 | CLLPKMDSV | 0.868 | 4 | SB | Large T | A0219 |
| 569 | ILQSGMTLL | 0.849 | 5 | SB | Large T | A0219 |
| 435 | TLAAGLLDL | 0.795 | 9 | SB | Large T | A0219 |
| 384 | VLEQYMAGV | 0.766 | 12 | SB | Large T | A0219 |
| 494 | NLDSLRDYL | 0.716 | 21 | SB | Large T | A0219 |
| 428 | PIDSGKTTL | 0.697 | 26 | SB | Large T | A0219 |
| 557 | SLQNSEFLL | 0.621 | 60 | WB | Large T | A0219 |
| 578 | LLLIWFRPV | 0.588 | 86 | WB | Large T | A0219 |
| 292 | MYLEFQYNV | 0.530 | 162 | WB | Large T | A0219 |
| 526 | LVTMNEYPV | 0.519 | 182 | WB | Large T | A0219 |
| 361 | MLTERFNHI | 0.518 | 183 | WB | Large T | A0219 |
| 500 | DYLDGSVKV | 0.508 | 205 | WB | Large T | A0219 |
| 21 | AAWGNLPLM | 0.506 | 209 | WB | Large T | A0219 |
| 454 | PMERLTFEL | 0.461 | 340 | WB | Large T | A0219 |
| 236 | ALTRDPYHI | 0.459 | 349 | WB | Large T | A0219 |
| 146 | FLSQAVFSN | 0.428 | 486 | WB | Large T | A0219 |
| 171 | ILYKKLMEK | 0.858 | 4 | SB | Large T | A0301 |
| 609 | SMYTFSRMK | 0.762 | 13 | SB | Large T | A0301 |
| 28 | LMRKAYLKK | 0.703 | 24 | SB | Large T | A0301 |
| 195 | IIFFLTPHR | 0.658 | 40 | SB | Large T | A0301 |
| 50 | KMKRMNTLY | 0.654 | 42 | SB | Large T | A0301 |
| 217 | CTFSFLICK | 0.640 | 49 | SB | Large T | A0301 |
| 221 | FLICKGVNK | 0.633 | 52 | WB | Large T | A0301 |
| 528 | TMNEYPVPK | 0.599 | 76 | WB | Large T | A0301 |
| 155 | RTLACFAVY | 0.595 | 79 | WB | Large T | A0301 |
| 27 | PLMRKAYLK | 0.578 | 96 | WB | Large T | A0301 |
| 226 | GVNKEYLLY | 0.545 | 137 | WB | Large T | A0301 |
| 121 | SQHSTPPKK | 0.490 | 248 | WB | Large T | A0301 |
| 231 | YLLYSALTR | 0.475 | 294 | WB | Large T | A0301 |
| 341 | AVDTVLAKK | 0.472 | 302 | WB | Large T | A0301 |
| 576 | LLLLLIWFR | 0.467 | 318 | WB | Large T | A0301 |
| 668 | HSQELHLCK | 0.464 | 331 | WB | Large T | A0301 |
| 504 | GSVKVNLEK | 0.452 | 376 | WB | Large T | A0301 |
| 509 | NLEKKHLNK | 0.452 | 377 | WB | Large T | A0301 |
| 350 | RVDTLHMTR | 0.444 | 409 | WB | Large T | A0301 |
| 603 | RLDSEISMY | 0.433 | 461 | WB | Large T | A0301 |
| 217 | CTFSFLICK | 0.826 | 6 | SB | Large T | A1101 |
| 528 | TMNEYPVPK | 0.817 | 7 | SB | Large T | A1101 |
| 609 | SMYTFSRMK | 0.802 | 8 | SB | Large T | A1101 |
| 207 | SAINNFCQK | 0.774 | 11 | SB | Large T | A1101 |
| 171 | ILYKKLMEK | 0.747 | 15 | SB | Large T | A1101 |
| 668 | HSQELHLCK | 0.730 | 18 | SB | Large T | A1101 |
| 341 | AVDTVLAKK | 0.703 | 24 | SB | Large T | A1101 |
| 195 | IIFFLTPHR | 0.686 | 30 | SB | Large T | A1101 |
| 504 | GSVKVNLEK | 0.679 | 32 | SB | Large T | A1101 |
| 121 | SQHSTPPKK | 0.674 | 33 | SB | Large T | A1101 |
| 147 | LSQAVFSNR | 0.654 | 42 | SB | Large T | A1101 |
| 536 | KTLQARFVR | 0.650 | 44 | SB | Large T | A1101 |
| 155 | RTLACFAVY | 0.646 | 46 | SB | Large T | A1101 |
| 340 | QAVDTVLAK | 0.602 | 74 | WB | Large T | A1101 |
| 505 | SVKVNLEKK | 0.583 | 91 | WB | Large T | A1101 |
| 27 | PLMRKAYLK | 0.576 | 98 | WB | Large T | A1101 |
| 120 | DSQHSTPPK | 0.567 | 108 | WB | Large T | A1101 |
| 393 | AWLHCLLPK | 0.566 | 109 | WB | Large T | A1101 |
| 413 | VVFNVPKRR | 0.559 | 118 | WB | Large T | A1101 |
| 439 | GLLDLCGGK | 0.551 | 129 | WB | Large T | A1101 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 324 | NAIIFAESK | 0.539 | 146 | WB | Large T | A1101 |
| 350 | RVDTLHMTR | 0.529 | 163 | WB | Large T | A1101 |
| 226 | GVNKEYLLY | 0.518 | 184 | WB | Large T | A1101 |
| 607 | EISMYTFSR | 0.496 | 233 | WB | Large T | A1101 |
| 274 | ITEYAVETK | 0.491 | 247 | WB | Large T | A1101 |
| 593 | IQSRIVEWK | 0.489 | 252 | WB | Large T | A1101 |
| 491 | GINNLDSLR | 0.488 | 254 | WB | Large T | A1101 |
| 296 | FQYNVEECK | 0.478 | 285 | WB | Large T | A1101 |
| 576 | LLLLLIWFR | 0.466 | 321 | WB | Large T | A1101 |
| 91 | SWWSSFNEK | 0.461 | 340 | WB | Large T | A1101 |
| 158 | ACFAVYTTK | 0.456 | 360 | WB | Large T | A1101 |
| 221 | FLICKGVNK | 0.446 | 399 | WB | Large T | A1101 |
| 32 | AYLKKCKEF | 0.708 | 23 | SB | Large T | A2301 |
| 581 | IWFRPVADF | 0.678 | 32 | SB | Large T | A2301 |
| 312 | PYHFKYHEK | 0.647 | 45 | SB | Large T | A2301 |
| 91 | SWWSSFNEK | 0.552 | 126 | WB | Large T | A2301 |
| 387 | QYMAGVAWL | 0.546 | 135 | WB | Large T | A2301 |
| 190 | CAGHNIIFF | 0.527 | 166 | WB | Large T | A2301 |
| 401 | KMDSVIFDF | 0.522 | 176 | WB | Large T | A2301 |
| 286 | VFLLLGMYL | 0.518 | 183 | WB | Large T | A2301 |
| 292 | MYLEFQYNV | 0.512 | 196 | WB | Large T | A2301 |
| 138 | DFPSDLHQF | 0.501 | 220 | WB | Large T | A2301 |
| 314 | HFKYHEKHF | 0.501 | 222 | WB | Large T | A2301 |
| 575 | TLLLLLIWF | 0.496 | 233 | WB | Large T | A2301 |
| 213 | CQKLCTFSF | 0.485 | 263 | WB | Large T | A2301 |
| 393 | AWLHCLLPK | 0.471 | 305 | WB | Large T | A2301 |
| 288 | LLLGMYLEF | 0.464 | 331 | WB | Large T | A2301 |
| 320 | KHFANAIIF | 0.463 | 334 | WB | Large T | A2301 |
| 327 | IFAESKNQK | 0.458 | 352 | WB | Large T | A2301 |
| 610 | MYTFSRMKY | 0.455 | 365 | WB | Large T | A2301 |
| 211 | NFCQKLCTF | 0.454 | 368 | WB | Large T | A2301 |
| 612 | TFSRMKYNI | 0.440 | 427 | WB | Large T | A2301 |
| 88 | EWESWWSSF | 0.597 | 78 | WB | Large T | A2402 |
| 387 | QYMAGVAWL | 0.587 | 87 | WB | Large T | A2402 |
| 138 | DFPSDLHQF | 0.544 | 138 | WB | Large T | A2402 |
| 241 | PYHIIEESI | 0.536 | 150 | WB | Large T | A2402 |
| 32 | AYLKKCKEF | 0.523 | 174 | WB | Large T | A2402 |
| 581 | IWFRPVADF | 0.503 | 216 | WB | Large T | A2402 |
| 468 | QYMVVFEDV | 0.502 | 219 | WB | Large T | A2402 |
| 612 | TFSRMKYNI | 0.451 | 381 | WB | Large T | A2402 |
| 286 | VFLLLGMYL | 0.434 | 456 | WB | Large T | A2402 |
| 417 | VPKRRYWLF | 0.432 | 466 | WB | Large T | A2402 |
| 32 | AYLKKCKEF | 0.859 | 4 | SB | Large T | A2403 |
| 387 | QYMAGVAWL | 0.773 | 11 | SB | Large T | A2403 |
| 138 | DFPSDLHQF | 0.618 | 62 | WB | Large T | A2403 |
| 320 | KHFANAIIF | 0.569 | 105 | WB | Large T | A2403 |
| 521 | IFPPGLVTM | 0.551 | 129 | WB | Large T | A2403 |
| 68 | AHQPDFGTW | 0.542 | 142 | WB | Large T | A2403 |
| 286 | VFLLLGMYL | 0.532 | 158 | WB | Large T | A2403 |
| 581 | IWFRPVADF | 0.506 | 209 | WB | Large T | A2403 |
| 401 | KMDSVIFDF | 0.462 | 338 | WB | Large T | A2403 |
| 190 | CAGHNIIFF | 0.458 | 351 | WB | Large T | A2403 |
| 468 | QYMVVFEDV | 0.446 | 400 | WB | Large T | A2403 |
| 211 | NFCQKLCTF | 0.433 | 461 | WB | Large T | A2403 |
| 285 | DVFLLLGMY | 0.689 | 29 | SB | Large T | A2601 |
| 265 | ETKQVSWKL | 0.506 | 209 | WB | Large T | A2601 |
| 8 | ESMELMDLL | 0.463 | 335 | WB | Large T | A2601 |
| 285 | DVFLLLGMY | 0.923 | 2 | SB | Large T | A2602 |
| 465 | AIDQYMVVF | 0.801 | 8 | SB | Large T | A2602 |
| 280 | ETKCEDVFL | 0.742 | 16 | SB | Large T | A2602 |
| 545 | QIDFRPKIY | 0.724 | 19 | SB | Large T | A2602 |
| 138 | DFPSDLHQF | 0.617 | 63 | WB | Large T | A2602 |
| 226 | GVNKEYLLY | 0.612 | 66 | WB | Large T | A2602 |
| 155 | RTLACFAVY | 0.609 | 68 | WB | Large T | A2602 |
| 152 | FSNRTLACF | 0.590 | 84 | WB | Large T | A2602 |
| 265 | ETKQVSWKL | 0.518 | 183 | WB | Large T | A2602 |
| 8 | ESMELMDLL | 0.476 | 290 | WB | Large T | A2602 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 103 | DLFCHEDMF | 0.457 | 358 | WB | Large T | A2602 |
| 450 | NVNLPMERL | 0.447 | 396 | WB | Large T | A2602 |
| 164 | TTKEKAQIL | 0.437 | 441 | WB | Large T | A2602 |
| 290 | LGMYLEFQY | 0.593 | 81 | WB | Large T | A2902 |
| 50 | KMKRMNTLY | 0.576 | 98 | WB | Large T | A2902 |
| 269 | VSWKLITEY | 0.552 | 127 | WB | Large T | A2902 |
| 285 | DVFLLLGMY | 0.538 | 148 | WB | Large T | A2902 |
| 226 | GVNKEYLLY | 0.508 | 204 | WB | Large T | A2902 |
| 610 | MYTFSRMKY | 0.474 | 295 | WB | Large T | A2902 |
| 414 | VFNVPKRRY | 0.429 | 480 | WB | Large T | A2902 |
| 28 | LMRKAYLKK | 0.830 | 6 | SB | Large T | A3001 |
| 51 | MKRMNTLYK | 0.827 | 6 | SB | Large T | A3001 |
| 36 | KCKEFHPDK | 0.817 | 7 | SB | Large T | A3001 |
| 418 | PKRRYWLFK | 0.813 | 7 | SB | Large T | A3001 |
| 121 | SQHSTPPKK | 0.755 | 14 | SB | Large T | A3001 |
| 682 | KRPKTPPPK | 0.723 | 19 | SB | Large T | A3001 |
| 528 | TMNEYPVPK | 0.716 | 21 | SB | Large T | A3001 |
| 677 | GFQCFKRPK | 0.683 | 30 | SB | Large T | A3001 |
| 120 | DSQHSTPPK | 0.675 | 33 | SB | Large T | A3001 |
| 674 | LCKGFQCFK | 0.669 | 36 | SB | Large T | A3001 |
| 129 | KKRKVEDPK | 0.666 | 37 | SB | Large T | A3001 |
| 158 | ACFAVYTTK | 0.657 | 40 | SB | Large T | A3001 |
| 536 | KTLQARFVR | 0.637 | 51 | WB | Large T | A3001 |
| 505 | SVKVNLEKK | 0.634 | 52 | WB | Large T | A3001 |
| 609 | SMYTFSRMK | 0.598 | 77 | WB | Large T | A3001 |
| 166 | KEKAQILYK | 0.579 | 95 | WB | Large T | A3001 |
| 312 | PYHFKYHEK | 0.574 | 100 | WB | Large T | A3001 |
| 195 | IIFFLTPHR | 0.569 | 105 | WB | Large T | A3001 |
| 393 | AWLHCLLPK | 0.519 | 181 | WB | Large T | A3001 |
| 50 | KMKRMNTLY | 0.501 | 220 | WB | Large T | A3001 |
| 340 | QAVDTVLAK | 0.481 | 273 | WB | Large T | A3001 |
| 274 | ITEYAVETK | 0.481 | 274 | WB | Large T | A3001 |
| 124 | STPPKKKRK | 0.478 | 282 | WB | Large T | A3001 |
| 171 | ILYKKLMEK | 0.467 | 318 | WB | Large T | A3001 |
| 411 | HCVVFNVPK | 0.465 | 325 | WB | Large T | A3001 |
| 27 | PLMRKAYLK | 0.439 | 431 | WB | Large T | A3001 |
| 544 | RQIDFRPKI | 0.437 | 440 | WB | Large T | A3001 |
| 668 | HSQELHLCK | 0.436 | 445 | WB | Large T | A3001 |
| 52 | KRMNTLYKK | 0.435 | 453 | WB | Large T | A3001 |
| 50 | KMKRMNTLY | 0.561 | 115 | WB | Large T | A3002 |
| 401 | KMDSVIFDF | 0.525 | 169 | WB | Large T | A3002 |
| 172 | LYKKLMEKY | 0.524 | 172 | WB | Large T | A3002 |
| 285 | DVFLLLGMY | 0.509 | 201 | WB | Large T | A3002 |
| 610 | MYTFSRMKY | 0.502 | 218 | WB | Large T | A3002 |
| 226 | GVNKEYLLY | 0.497 | 231 | WB | Large T | A3002 |
| 603 | RLDSEISMY | 0.483 | 269 | WB | Large T | A3002 |
| 536 | KTLQARFVR | 0.856 | 4 | SB | Large T | A3101 |
| 576 | LLLLLIWFR | 0.848 | 5 | SB | Large T | A3101 |
| 179 | KYSVTFISR | 0.844 | 5 | SB | Large T | A3101 |
| 541 | RFVRQIDFR | 0.836 | 5 | SB | Large T | A3101 |
| 147 | LSQAVFSNR | 0.821 | 6 | SB | Large T | A3101 |
| 547 | DFRPKIYLR | 0.799 | 8 | SB | Large T | A3101 |
| 195 | IIFFLTPHR | 0.720 | 20 | SB | Large T | A3101 |
| 528 | TMNEYPVPK | 0.713 | 22 | SB | Large T | A3101 |
| 350 | RVDTLHMTR | 0.712 | 22 | SB | Large T | A3101 |
| 197 | FFLTPHRHR | 0.682 | 31 | SB | Large T | A3101 |
| 491 | GINNLDSLR | 0.668 | 36 | SB | Large T | A3101 |
| 413 | VVFNVPKRR | 0.651 | 43 | SB | Large T | A3101 |
| 607 | EISMYTFSR | 0.604 | 72 | WB | Large T | A3101 |
| 155 | RTLACFAVY | 0.573 | 101 | WB | Large T | A3101 |
| 609 | SMYTFSRMK | 0.567 | 108 | WB | Large T | A3101 |
| 217 | CTFSFLICK | 0.563 | 113 | WB | Large T | A3101 |
| 50 | KMKRMNTLY | 0.540 | 144 | WB | Large T | A3101 |
| 91 | SWWSSFNEK | 0.515 | 190 | WB | Large T | A3101 |
| 123 | HSTPPKKKR | 0.487 | 257 | WB | Large T | A3101 |
| 292 | MYLEFQYNV | 0.476 | 289 | WB | Large T | A3101 |
| 677 | GFQCFKRPK | 0.472 | 301 | WB | Large T | A3101 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 231 | YLLYSALTR | 0.438 | 439 | WB | Large T | A3101 |
| 28 | LMRKAYLKK | 0.436 | 447 | WB | Large T | A3101 |
| 547 | DFRPKIYLR | 0.938 | 1 | SB | Large T | A3301 |
| 576 | LLLLLIWFR | 0.827 | 6 | SB | Large T | A3301 |
| 607 | EISMYTFSR | 0.826 | 6 | SB | Large T | A3301 |
| 195 | IIFFLTPHR | 0.692 | 27 | SB | Large T | A3301 |
| 588 | DFSKDIQSR | 0.669 | 35 | SB | Large T | A3301 |
| 197 | FFLTPHRHR | 0.615 | 64 | WB | Large T | A3301 |
| 147 | LSQAVFSNR | 0.592 | 82 | WB | Large T | A3301 |
| 231 | YLLYSALTR | 0.473 | 299 | WB | Large T | A3301 |
| 607 | EISMYTFSR | 0.908 | 2 | SB | Large T | A6801 |
| 412 | CVVFNVPKR | 0.851 | 5 | SB | Large T | A6801 |
| 195 | IIFFLTPHR | 0.838 | 5 | SB | Large T | A6801 |
| 217 | CTFSFLICK | 0.813 | 7 | SB | Large T | A6801 |
| 324 | NAIIFAESK | 0.796 | 9 | SB | Large T | A6801 |
| 207 | SAINNFCQK | 0.749 | 15 | SB | Large T | A6801 |
| 160 | FAVYTTKEK | 0.721 | 20 | SB | Large T | A6801 |
| 274 | ITEYAVETK | 0.648 | 44 | SB | Large T | A6801 |
| 147 | LSQAVFSNR | 0.643 | 47 | SB | Large T | A6801 |
| 536 | KTLQARFVR | 0.643 | 47 | SB | Large T | A6801 |
| 231 | YLLYSALTR | 0.628 | 56 | WB | Large T | A6801 |
| 616 | MKYNICMGK | 0.625 | 58 | WB | Large T | A6801 |
| 491 | GINNLDSLR | 0.625 | 58 | WB | Large T | A6801 |
| 413 | VVFNVPKRR | 0.622 | 60 | WB | Large T | A6801 |
| 560 | NSEFLLEKR | 0.620 | 61 | WB | Large T | A6801 |
| 609 | SMYTFSRMK | 0.595 | 80 | WB | Large T | A6801 |
| 167 | EKAQILYKK | 0.595 | 80 | WB | Large T | A6801 |
| 610 | MYTFSRMKY | 0.588 | 86 | WB | Large T | A6801 |
| 576 | LLLLLIWFR | 0.573 | 101 | WB | Large T | A6801 |
| 469 | YMVVFEDVK | 0.567 | 108 | WB | Large T | A6801 |
| 296 | FQYNVEECK | 0.534 | 153 | WB | Large T | A6801 |
| 123 | HSTPPKKKR | 0.530 | 162 | WB | Large T | A6801 |
| 340 | QAVDTVLAK | 0.527 | 167 | WB | Large T | A6801 |
| 668 | HSQELHLCK | 0.512 | 196 | WB | Large T | A6801 |
| 505 | SVKVNLEKK | 0.501 | 220 | WB | Large T | A6801 |
| 120 | DSQHSTPPK | 0.485 | 263 | WB | Large T | A6801 |
| 528 | TMNEYPVPK | 0.481 | 275 | WB | Large T | A6801 |
| 171 | ILYKKLMEK | 0.479 | 281 | WB | Large T | A6801 |
| 504 | GSVKVNLEK | 0.451 | 380 | WB | Large T | A6801 |
| 285 | DVFLLLGMY | 0.450 | 385 | WB | Large T | A6801 |
| 449 | LNVNLPMER | 0.448 | 390 | WB | Large T | A6801 |
| 350 | RVDTLHMTR | 0.441 | 422 | WB | Large T | A6801 |
| 403 | DSVIFDFLH | 0.439 | 432 | WB | Large T | A6801 |
| 388 | YMAGVAWLH | 0.437 | 440 | WB | Large T | A6801 |
| 588 | DFSKDIQSR | 0.437 | 444 | WB | Large T | A6801 |
| 547 | DFRPKIYLR | 0.427 | 492 | WB | Large T | A6801 |
| 8 | ESMELMDLL | 0.767 | 12 | SB | Large T | A6802 |
| 409 | FLHCVVFNV | 0.700 | 25 | SB | Large T | A6802 |
| 402 | MDSVIFDFL | 0.694 | 27 | SB | Large T | A6802 |
| 450 | NVNLPMERL | 0.691 | 28 | SB | Large T | A6802 |
| 219 | FSFLICKGV | 0.689 | 28 | SB | Large T | A6802 |
| 265 | ETKQVSWKL | 0.607 | 70 | WB | Large T | A6802 |
| 280 | ETKCEDVFL | 0.589 | 85 | WB | Large T | A6802 |
| 416 | NVPKRRYWL | 0.585 | 89 | WB | Large T | A6802 |
| 526 | LVTMNEYPV | 0.585 | 89 | WB | Large T | A6802 |
| 405 | VIFDFLHCV | 0.583 | 91 | WB | Large T | A6802 |
| 73 | FGTWNSSEV | 0.580 | 94 | WB | Large T | A6802 |
| 458 | LTFELGVAI | 0.577 | 96 | WB | Large T | A6802 |
| 371 | DKMDLIFGA | 0.565 | 110 | WB | Large T | A6802 |
| 589 | FSKDIQSRI | 0.558 | 119 | WB | Large T | A6802 |
| 198 | FLTPHRHRV | 0.543 | 140 | WB | Large T | A6802 |
| 519 | TQIFPPGLV | 0.515 | 189 | WB | Large T | A6802 |
| 377 | FGAHGNAVL | 0.502 | 218 | WB | Large T | A6802 |
| 156 | TLACFAVYT | 0.493 | 239 | WB | Large T | A6802 |
| 464 | VAIDQYMVV | 0.486 | 261 | WB | Large T | A6802 |
| 468 | QYMVVFEDV | 0.482 | 271 | WB | Large T | A6802 |
| 608 | ISMYTFSRM | 0.465 | 326 | WB | Large T | A6802 |
| 343 | DTVLAKKRV | 0.459 | 348 | WB | Large T | A6802 |
| 361 | MLTERFNHI | 0.450 | 382 | WB | Large T | A6802 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 191 | AGHNIIFFL | 0.447 | 396 | WB | Large T | A6802 |
| 154 | NRTLACFAV | 0.432 | 468 | WB | Large T | A6802 |
| 458 | LTFELGVAI | 0.702 | 25 | SB | Large T | A6901 |
| 405 | VIFDFLHCV | 0.691 | 28 | SB | Large T | A6901 |
| 409 | FLHCVVFNV | 0.683 | 30 | SB | Large T | A6901 |
| 578 | LLLIWFRPV | 0.630 | 54 | WB | Large T | A6901 |
| 8 | ESMELMDLL | 0.609 | 68 | WB | Large T | A6901 |
| 368 | HILDKMDLI | 0.587 | 87 | WB | Large T | A6901 |
| 139 | FPSDLHQFL | 0.553 | 125 | WB | Large T | A6901 |
| 292 | MYLEFQYNV | 0.522 | 176 | WB | Large T | A6901 |
| 21 | AAWGNLPLM | 0.483 | 267 | WB | Large T | A6901 |
| 198 | FLTPHRHRV | 0.481 | 274 | WB | Large T | A6901 |
| 265 | ETKQVSWKL | 0.457 | 355 | WB | Large T | A6901 |
| 500 | DYLDGSVKV | 0.449 | 389 | WB | Large T | A6901 |
| 464 | VAIDQYMVV | 0.431 | 472 | WB | Large T | A6901 |
| 20 | RAAWGNLPL | 0.721 | 20 | SB | Large T | B0702 |
| 26 | LPLMRKAYL | 0.719 | 20 | SB | Large T | B0702 |
| 200 | TPHRHRVSA | 0.662 | 38 | SB | Large T | B0702 |
| 532 | YPVPKTLQA | 0.651 | 43 | SB | Large T | B0702 |
| 399 | LPKMDSVIF | 0.516 | 187 | WB | Large T | B0702 |
| 568 | RILQSGMTL | 0.499 | 226 | WB | Large T | B0702 |
| 81 | VPTYGTEEW | 0.497 | 232 | WB | Large T | B0702 |
| 139 | FPSDLHQFL | 0.467 | 320 | WB | Large T | B0702 |
| 417 | VPKRRYWLF | 0.461 | 339 | WB | Large T | B0702 |
| 417 | VPKRRYWLF | 0.587 | 87 | WB | Large T | B0801 |
| 144 | HQFLSQAVF | 0.618 | 62 | WB | Large T | B1501 |
| 234 | YSALTRDPY | 0.569 | 105 | WB | Large T | B1501 |
| 50 | KMKRMNTLY | 0.561 | 115 | WB | Large T | B1501 |
| 213 | CQKLCTFSF | 0.528 | 165 | WB | Large T | B1501 |
| 155 | RTLACFAVY | 0.522 | 176 | WB | Large T | B1501 |
| 514 | HLNKRTQIF | 0.501 | 221 | WB | Large T | B1501 |
| 288 | LLLGMYLEF | 0.495 | 236 | WB | Large T | B1501 |
| 570 | LQSGMTLLL | 0.479 | 280 | WB | Large T | B1501 |
| 152 | FSNRTLACF | 0.468 | 315 | WB | Large T | B1501 |
| 176 | LMEKYSVTF | 0.466 | 324 | WB | Large T | B1501 |
| 20 | RAAWGNLPL | 0.444 | 411 | WB | Large T | B1501 |
| 388 | YMAGVAWLH | 0.439 | 434 | WB | Large T | B1501 |
| 10 | MELMDLLGL | 0.722 | 20 | SB | Large T | B1801 |
| 530 | NEYPVPKTL | 0.706 | 24 | SB | Large T | B1801 |
| 670 | QELHLCKGF | 0.692 | 27 | SB | Large T | B1801 |
| 229 | KEYLLYSAL | 0.571 | 104 | WB | Large T | B1801 |
| 664 | SENPHSQEL | 0.520 | 179 | WB | Large T | B1801 |
| 52 | KRMNTLYKK | 0.656 | 41 | SB | Large T | B2705 |
| 548 | FRPKIYLRK | 0.526 | 169 | WB | Large T | B2705 |
| 420 | RRYWLFKGP | 0.518 | 184 | WB | Large T | B2705 |
| 364 | ERFNHILDK | 0.460 | 343 | WB | Large T | B2705 |
| 614 | SRMKYNICM | 0.452 | 375 | WB | Large T | B2705 |
| 540 | ARFVRQIDF | 0.436 | 448 | WB | Large T | B2705 |
| 682 | KRPKTPPPK | 0.430 | 477 | WB | Large T | B2705 |
| 399 | LPKMDSVIF | 0.752 | 14 | SB | Large T | B3501 |
| 139 | FPSDLHQFL | 0.633 | 52 | WB | Large T | B3501 |
| 20 | RAAWGNLPL | 0.618 | 62 | WB | Large T | B3501 |
| 234 | YSALTRDPY | 0.565 | 111 | WB | Large T | B3501 |
| 447 | KALNVNLPM | 0.561 | 115 | WB | Large T | B3501 |
| 21 | AAWGNLPLM | 0.545 | 137 | WB | Large T | B3501 |
| 189 | MCAGHNIIF | 0.537 | 149 | WB | Large T | B3501 |
| 111 | FASDEEATA | 0.509 | 202 | WB | Large T | B3501 |
| 534 | VPKTLQARF | 0.498 | 229 | WB | Large T | B3501 |
| 81 | VPTYGTEEW | 0.486 | 260 | WB | Large T | B3501 |
| 269 | VSWKLITEY | 0.463 | 334 | WB | Large T | B3501 |
| 285 | DVFLLLGMY | 0.447 | 394 | WB | Large T | B3501 |
| 532 | YPVPKTLQA | 0.445 | 403 | WB | Large T | B3501 |
| 176 | LMEKYSVTF | 0.441 | 423 | WB | Large T | B3501 |
| 155 | RTLACFAVY | 0.434 | 455 | WB | Large T | B3501 |
| 666 | NPHSQELHL | 0.426 | 495 | WB | Large T | B3501 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 377 | FGAHGNAVL | 0.547 | 133 | WB | Large T | B3901 |
| 10 | MELMDLLGL | 0.751 | 14 | SB | Large T | B4001 |
| 229 | KEYLLYSAL | 0.690 | 28 | SB | Large T | B4001 |
| 664 | SENPHSQEL | 0.681 | 31 | SB | Large T | B4001 |
| 530 | NEYPVPKTL | 0.592 | 82 | WB | Large T | B4001 |
| 7 | EESMELMDL | 0.561 | 115 | WB | Large T | B4001 |
| 245 | IEESIQGGL | 0.552 | 127 | WB | Large T | B4001 |
| 561 | SEFLLEKRI | 0.498 | 227 | WB | Large T | B4001 |
| 18 | LERAAWGNL | 0.497 | 231 | WB | Large T | B4001 |
| 358 | REEMLTERF | 0.441 | 422 | WB | Large T | B4001 |
| 664 | SENPHSQEL | 0.630 | 54 | WB | Large T | B4002 |
| 229 | KEYLLYSAL | 0.583 | 91 | WB | Large T | B4002 |
| 606 | SEISMYTFS | 0.489 | 252 | WB | Large T | B4002 |
| 279 | VETKCEDVF | 0.469 | 314 | WB | Large T | B4002 |
| 177 | MEKYSVTFI | 0.462 | 335 | WB | Large T | B4002 |
| 606 | SEISMYTFS | 0.521 | 177 | WB | Large T | B4403 |
| 561 | SEFLLEKRI | 0.458 | 353 | WB | Large T | B4403 |
| 664 | SENPHSQEL | 0.446 | 403 | WB | Large T | B4403 |
| 329 | AESKNQKSI | 0.497 | 229 | WB | Large T | B4501 |
| 453 | LPMERLTFE | 0.451 | 378 | WB | Large T | B5101 |
| 139 | FPSDLHQFL | 0.438 | 437 | WB | Large T | B5101 |
| 81 | VPTYGTEEW | 0.673 | 34 | SB | Large T | B5301 |
| 399 | LPKMDSVIF | 0.628 | 55 | WB | Large T | B5301 |
| 26 | LPLMRKAYL | 0.625 | 57 | WB | Large T | B5301 |
| 666 | NPHSQELHL | 0.553 | 126 | WB | Large T | B5301 |
| 139 | FPSDLHQFL | 0.509 | 202 | WB | Large T | B5301 |
| 574 | MTLLLLLIW | 0.454 | 366 | WB | Large T | B5301 |
| 522 | FPPGLVTMN | 0.672 | 34 | SB | Large T | B5401 |
| 200 | TPHRHRVSA | 0.530 | 162 | WB | Large T | B5401 |
| 219 | FSFLICKGV | 0.453 | 373 | WB | Large T | B5401 |
| 453 | LPMERLTFE | 0.432 | 466 | WB | Large T | B5401 |
| 574 | MTLLLLLIW | 0.446 | 399 | WB | Large T | B5701 |
| 401 | KMDSVIFDF | 0.615 | 64 | WB | Large T | B5801 |
| 574 | MTLLLLLIW | 0.594 | 80 | WB | Large T | B5801 |
| 152 | FSNRTLACF | 0.562 | 114 | WB | Large T | B5801 |
| 84 | YGTEEWESW | 0.553 | 125 | WB | Large T | B5801 |
| 20 | RAAWGNLPL | 0.460 | 344 | WB | Large T | B5801 |
| 447 | KALNVNLPM | 0.442 | 419 | WB | Large T | B5801 |
| 269 | VSWKLITEY | 0.429 | 482 | WB | Large T | B5801 |
| | | | 10-mers | | | |
| 164 | TTKEKAQILY | 0.528 | 165 | WB | Large T | A0101 |
| 401 | KMDSVIFDFL | 0.830 | 6 | SB | Large T | A0201 |
| 291 | GMYLEFQYNV | 0.761 | 13 | SB | Large T | A0201 |
| 405 | VIFDFLHCVV | 0.679 | 32 | SB | Large T | A0201 |
| 525 | GLVTMNEYPV | 0.676 | 33 | SB | Large T | A0201 |
| 501 | YLDGSVKVNL | 0.671 | 35 | SB | Large T | A0201 |
| 569 | ILQSGMTLLL | 0.658 | 40 | SB | Large T | A0201 |
| 577 | LLLLIWFRPV | 0.657 | 40 | SB | Large T | A0201 |
| 383 | AVLEQYMAGV | 0.637 | 50 | WB | Large T | A0201 |
| 361 | MLTERFNHIL | 0.616 | 63 | WB | Large T | A0201 |
| 176 | LMEKYSVTFI | 0.609 | 68 | WB | Large T | A0201 |
| 404 | SVIFDFLHCV | 0.585 | 89 | WB | Large T | A0201 |
| 603 | RLDSEISMYT | 0.583 | 90 | WB | Large T | A0201 |
| 497 | SLRDYLDGSV | 0.570 | 104 | WB | Large T | A0201 |
| 272 | KLITEYAVET | 0.543 | 140 | WB | Large T | A0201 |
| 578 | LLLIWFRPVA | 0.503 | 216 | WB | Large T | A0201 |
| 563 | FLLEKRILQS | 0.500 | 222 | WB | Large T | A0201 |
| 56 | TLYKKMEQDV | 0.485 | 263 | WB | Large T | A0201 |
| 528 | TMNEYPVPKT | 0.457 | 354 | WB | Large T | A0201 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 12 | LMDLLGLERA | 0.456 | 361 | WB | Large T | A0201 |
| 568 | RILQSGMTLL | 0.454 | 367 | WB | Large T | A0201 |
| 288 | LLLGMYLEFQ | 0.448 | 391 | WB | Large T | A0201 |
| 3 | VLNREESMEL | 0.434 | 454 | WB | Large T | A0201 |
| 401 | KMDSVIFDFL | 0.773 | 11 | SB | Large T | A0202 |
| 603 | RLDSEISMYT | 0.720 | 20 | SB | Large T | A0202 |
| 569 | ILQSGMTLLL | 0.716 | 21 | SB | Large T | A0202 |
| 291 | GMYLEFQYNV | 0.681 | 31 | SB | Large T | A0202 |
| 525 | GLVTMNEYPV | 0.674 | 33 | SB | Large T | A0202 |
| 497 | SLRDYLDGSV | 0.665 | 37 | SB | Large T | A0202 |
| 405 | VIFDFLHCVV | 0.649 | 44 | SB | Large T | A0202 |
| 501 | YLDGSVKVNL | 0.648 | 44 | SB | Large T | A0202 |
| 288 | LLLGMYLEFQ | 0.645 | 46 | SB | Large T | A0202 |
| 577 | LLLLIWFRPV | 0.628 | 55 | WB | Large T | A0202 |
| 287 | FLLLGMYLEF | 0.618 | 62 | WB | Large T | A0202 |
| 570 | LQSGMTLLLL | 0.609 | 69 | WB | Large T | A0202 |
| 12 | LMDLLGLERA | 0.607 | 70 | WB | Large T | A0202 |
| 388 | YMAGVAWLHC | 0.582 | 91 | WB | Large T | A0202 |
| 156 | TLACFAVYTT | 0.566 | 109 | WB | Large T | A0202 |
| 175 | KLMEKYSVTF | 0.566 | 109 | WB | Large T | A0202 |
| 3 | VLNREESMEL | 0.562 | 114 | WB | Large T | A0202 |
| 397 | CLLPKMDSVI | 0.561 | 115 | WB | Large T | A0202 |
| 285 | DVFLLLGMYL | 0.560 | 117 | WB | Large T | A0202 |
| 435 | TLAAGLLDLC | 0.550 | 130 | WB | Large T | A0202 |
| 361 | MLTERFNHIL | 0.543 | 140 | WB | Large T | A0202 |
| 383 | AVLEQYMAGV | 0.535 | 153 | WB | Large T | A0202 |
| 353 | TLHMTREEML | 0.532 | 157 | WB | Large T | A0202 |
| 461 | ELGVAIDQYM | 0.520 | 180 | WB | Large T | A0202 |
| 56 | TLYKKMEQDV | 0.516 | 187 | WB | Large T | A0202 |
| 103 | DLFCHEDMFA | 0.516 | 187 | WB | Large T | A0202 |
| 463 | GVAIDQYMVV | 0.509 | 202 | WB | Large T | A0202 |
| 9 | SMELMDLLGL | 0.507 | 206 | WB | Large T | A0202 |
| 142 | DLHQFLSQAV | 0.497 | 230 | WB | Large T | A0202 |
| 611 | YTFSRMKYNI | 0.493 | 240 | WB | Large T | A0202 |
| 272 | KLITEYAVET | 0.492 | 243 | WB | Large T | A0202 |
| 375 | LIFGAHGNAV | 0.491 | 247 | WB | Large T | A0202 |
| 563 | FLLEKRILQS | 0.488 | 253 | WB | Large T | A0202 |
| 440 | LLDLCGGKAL | 0.488 | 255 | WB | Large T | A0202 |
| 25 | NLPLMRKAYL | 0.483 | 269 | WB | Large T | A0202 |
| 568 | RILQSGMTLL | 0.478 | 285 | WB | Large T | A0202 |
| 176 | LMEKYSVTFI | 0.471 | 305 | WB | Large T | A0202 |
| 236 | ALTRDPYHII | 0.461 | 341 | WB | Large T | A0202 |
| 493 | NNLDSLRDYL | 0.454 | 366 | WB | Large T | A0202 |
| 572 | SGMTLLLLLI | 0.453 | 371 | WB | Large T | A0202 |
| 148 | SQAVFSNRTL | 0.450 | 383 | WB | Large T | A0202 |
| 439 | GLLDLCGGKA | 0.445 | 406 | WB | Large T | A0202 |
| 609 | SMYTFSRMKY | 0.445 | 406 | WB | Large T | A0202 |
| 345 | VLAKKRVDTL | 0.445 | 407 | WB | Large T | A0202 |
| 360 | EMLTERFNHI | 0.440 | 427 | WB | Large T | A0202 |
| 578 | LLLIWFRPVA | 0.438 | 435 | WB | Large T | A0202 |
| 556 | KSLQNSEFLL | 0.437 | 441 | WB | Large T | A0202 |
| 213 | CQKLCTFSFL | 0.433 | 461 | WB | Large T | A0202 |
| 497 | SLRDYLDGSV | 0.883 | 3 | SB | Large T | A0203 |
| 361 | MLTERFNHIL | 0.815 | 7 | SB | Large T | A0203 |
| 291 | GMYLEFQYNV | 0.792 | 9 | SB | Large T | A0203 |
| 525 | GLVTMNEYPV | 0.769 | 12 | SB | Large T | A0203 |
| 383 | AVLEQYMAGV | 0.755 | 14 | SB | Large T | A0203 |
| 569 | ILQSGMTLLL | 0.731 | 18 | SB | Large T | A0203 |
| 375 | LIFGAHGNAV | 0.731 | 18 | SB | Large T | A0203 |
| 577 | LLLLIWFRPV | 0.708 | 23 | SB | Large T | A0203 |
| 56 | TLYKKMEQDV | 0.707 | 23 | SB | Large T | A0203 |
| 405 | VIFDFLHCVV | 0.674 | 34 | SB | Large T | A0203 |
| 3 | VLNREESMEL | 0.666 | 37 | SB | Large T | A0203 |
| 457 | RLTFELGVAI | 0.665 | 37 | SB | Large T | A0203 |
| 404 | SVIFDFLHCV | 0.654 | 42 | SB | Large T | A0203 |
| 501 | YLDGSVKVNL | 0.627 | 56 | WB | Large T | A0203 |
| 345 | VLAKKRVDTL | 0.625 | 57 | WB | Large T | A0203 |
| 176 | LMEKYSVTFI | 0.611 | 67 | WB | Large T | A0203 |
| 156 | TLACFAVYTT | 0.600 | 75 | WB | Large T | A0203 |
| 236 | ALTRDPYHII | 0.576 | 98 | WB | Large T | A0203 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 401 | KMDSVIFDFL | 0.549 | 132 | WB | Large T | A0203 |
| 537 | TLQARFVRQI | 0.548 | 132 | WB | Large T | A0203 |
| 439 | GLLDLCGGKA | 0.546 | 136 | WB | Large T | A0203 |
| 570 | LQSGMTLLLL | 0.542 | 142 | WB | Large T | A0203 |
| 568 | RILQSGMTLL | 0.541 | 143 | WB | Large T | A0203 |
| 397 | CLLPKMDSVI | 0.534 | 154 | WB | Large T | A0203 |
| 611 | YTFSRMKYNI | 0.521 | 177 | WB | Large T | A0203 |
| 142 | DLHQFLSQAV | 0.503 | 217 | WB | Large T | A0203 |
| 603 | RLDSEISMYT | 0.488 | 254 | WB | Large T | A0203 |
| 578 | LLLIWFRPVA | 0.485 | 261 | WB | Large T | A0203 |
| 272 | KLITEYAVET | 0.485 | 263 | WB | Large T | A0203 |
| 213 | CQKLCTFSFL | 0.480 | 277 | WB | Large T | A0203 |
| 463 | GVAIDQYMVV | 0.473 | 298 | WB | Large T | A0203 |
| 12 | LMDLLGLERA | 0.468 | 314 | WB | Large T | A0203 |
| 528 | TMNEYPVPKT | 0.465 | 326 | WB | Large T | A0203 |
| 9 | SMELMDLLGL | 0.462 | 338 | WB | Large T | A0203 |
| 333 | NQKSICQQAV | 0.456 | 361 | WB | Large T | A0203 |
| 336 | SICQQAVDTV | 0.435 | 451 | WB | Large T | A0203 |
| 383 | AVLEQYMAGV | 0.666 | 37 | SB | Large T | A0204 |
| 525 | GLVTMNEYPV | 0.603 | 73 | WB | Large T | A0204 |
| 577 | LLLLIWFRPV | 0.591 | 83 | WB | Large T | A0204 |
| 361 | MLTERFNHIL | 0.573 | 101 | WB | Large T | A0204 |
| 497 | SLRDYLDGSV | 0.565 | 110 | WB | Large T | A0204 |
| 336 | SICQQAVDTV | 0.557 | 120 | WB | Large T | A0204 |
| 3 | VLNREESMEL | 0.557 | 120 | WB | Large T | A0204 |
| 291 | GMYLEFQYNV | 0.549 | 132 | WB | Large T | A0204 |
| 405 | VIFDFLHCVV | 0.533 | 155 | WB | Large T | A0204 |
| 375 | LIFGAHGNAV | 0.515 | 190 | WB | Large T | A0204 |
| 537 | TLQARFVRQI | 0.496 | 234 | WB | Large T | A0204 |
| 236 | ALTRDPYHII | 0.494 | 238 | WB | Large T | A0204 |
| 401 | KMDSVIFDFL | 0.484 | 266 | WB | Large T | A0204 |
| 528 | TMNEYPVPKT | 0.473 | 300 | WB | Large T | A0204 |
| 345 | VLAKKRVDTL | 0.461 | 339 | WB | Large T | A0204 |
| 175 | KLMEKYSVTF | 0.451 | 380 | WB | Large T | A0204 |
| 569 | ILQSGMTLLL | 0.446 | 401 | WB | Large T | A0204 |
| 176 | LMEKYSVTFI | 0.437 | 440 | WB | Large T | A0204 |
| 463 | GVAIDQYMVV | 0.434 | 454 | WB | Large T | A0204 |
| 518 | RTQIFPPGLV | 0.431 | 473 | WB | Large T | A0204 |
| 383 | AVLEQYMAGV | 0.832 | 6 | SB | Large T | A0206 |
| 404 | SVIFDFLHCV | 0.773 | 11 | SB | Large T | A0206 |
| 401 | KMDSVIFDFL | 0.762 | 13 | SB | Large T | A0206 |
| 577 | LLLLIWFRPV | 0.744 | 15 | SB | Large T | A0206 |
| 570 | LQSGMTLLLL | 0.714 | 22 | SB | Large T | A0206 |
| 525 | GLVTMNEYPV | 0.698 | 26 | SB | Large T | A0206 |
| 291 | GMYLEFQYNV | 0.682 | 31 | SB | Large T | A0206 |
| 405 | VIFDFLHCVV | 0.674 | 33 | SB | Large T | A0206 |
| 568 | RILQSGMTLL | 0.670 | 35 | SB | Large T | A0206 |
| 361 | MLTERFNHIL | 0.650 | 43 | SB | Large T | A0206 |
| 375 | LIFGAHGNAV | 0.644 | 47 | SB | Large T | A0206 |
| 287 | FLLLGMYLEF | 0.607 | 70 | WB | Large T | A0206 |
| 497 | SLRDYLDGSV | 0.596 | 79 | WB | Large T | A0206 |
| 267 | KQVSWKLITE | 0.564 | 112 | WB | Large T | A0206 |
| 175 | KLMEKYSVTF | 0.553 | 125 | WB | Large T | A0206 |
| 148 | SQAVFSNRTL | 0.535 | 153 | WB | Large T | A0206 |
| 20 | RAAWGNLPLM | 0.518 | 184 | WB | Large T | A0206 |
| 388 | YMAGVAWLHC | 0.510 | 201 | WB | Large T | A0206 |
| 213 | CQKLCTFSFL | 0.505 | 212 | WB | Large T | A0206 |
| 272 | KLITEYAVET | 0.494 | 237 | WB | Large T | A0206 |
| 578 | LLLIWFRPVA | 0.494 | 238 | WB | Large T | A0206 |
| 336 | SICQQAVDTV | 0.493 | 242 | WB | Large T | A0206 |
| 501 | YLDGSVKVNL | 0.487 | 257 | WB | Large T | A0206 |
| 569 | ILQSGMTLLL | 0.483 | 269 | WB | Large T | A0206 |
| 520 | QIFPPGLVTM | 0.482 | 272 | WB | Large T | A0206 |
| 338 | CQQAVDTVLA | 0.481 | 275 | WB | Large T | A0206 |
| 277 | YAVETKCEDV | 0.480 | 278 | WB | Large T | A0206 |
| 155 | RTLACFAVYT | 0.469 | 312 | WB | Large T | A0206 |
| 563 | FLLEKRILQS | 0.454 | 368 | WB | Large T | A0206 |
| 603 | RLDSEISMYT | 0.445 | 405 | WB | Large T | A0206 |
| 397 | CLLPKMDSVI | 0.441 | 422 | WB | Large T | A0206 |
| 457 | RLTFELGVAI | 0.437 | 440 | WB | Large T | A0206 |

TABLE M-continued

Prediction of BK virus Large T protein specific MHC class1,
8-, 9-, 10-, 11-mer peptide binders for 42 MHC class 1 alleles
(see FIG. 11) using the www.cbs.dtu.dk/services/
NetMHC/ database. The MHC class 1 molecules for which
no binders were found are not listed.

| pos | peptide | logscore | affinity (nM) | Bind Level | Protein Name | Allele |
|---|---|---|---|---|---|---|
| 207 | SAINNFCQKL | 0.433 | 463 | WB | Large T | A0206 |
| 463 | GVAIDQYMVV | 0.429 | 481 | WB | Large T | A0206 |
| 501 | YLDGSVKVNL | 0.958 | 1 | SB | Large T | A0211 |
| 405 | VIFDFLHCVV | 0.936 | 2 | SB | Large T | A0211 |
| 525 | GLVTMNEYPV | 0.915 | 2 | SB | Large T | A0211 |
| 291 | GMYLEFQYNV | 0.909 | 2 | SB | Large T | A0211 |
| 569 | ILQSGMTLLL | 0.902 | 2 | SB | Large T | A0211 |
| 142 | DLHQFLSQAV | 0.898 | 3 | SB | Large T | A0211 |
| 497 | SLRDYLDGSV | 0.895 | 3 | SB | Large T | A0211 |
| 401 | KMDSVIFDFL | 0.890 | 3 | SB | Large T | A0211 |
| 577 | LLLLIWFRPV | 0.888 | 3 | SB | Large T | A0211 |
| 56 | TLYKKMEQDV | 0.875 | 3 | SB | Large T | A0211 |
| 361 | MLTERFNHIL | 0.874 | 3 | SB | Large T | A0211 |
| 383 | AVLEQYMAGV | 0.866 | 4 | SB | Large T | A0211 |
| 442 | DLCGGKALNV | 0.854 | 4 | SB | Large T | A0211 |
| 375 | LIFGAHGNAV | 0.829 | 6 | SB | Large T | A0211 |
| 3 | VLNREESMEL | 0.824 | 6 | SB | Large T | A0211 |
| 288 | LLLGMYLEFQ | 0.816 | 7 | SB | Large T | A0211 |
| 603 | RLDSEISMYT | 0.797 | 9 | SB | Large T | A0211 |
| 404 | SVIFDFLHCV | 0.791 | 9 | SB | Large T | A0211 |
| 236 | ALTRDPYHII | 0.782 | 10 | SB | Large T | A0211 |
| 388 | YMAGVAWLHC | 0.782 | 10 | SB | Large T | A0211 |
| 12 | LMDLLGLERA | 0.757 | 13 | SB | Large T | A0211 |
| 287 | FLLLGMYLEF | 0.747 | 15 | SB | Large T | A0211 |
| 463 | GVAIDQYMVV | 0.742 | 16 | SB | Large T | A0211 |
| 336 | SICQQAVDTV | 0.736 | 17 | SB | Large T | A0211 |
| 345 | VLAKKRVDTL | 0.725 | 19 | SB | Large T | A0211 |
| 353 | TLHMTREEML | 0.722 | 20 | SB | Large T | A0211 |
| 568 | RILQSGMTLL | 0.720 | 20 | SB | Large T | A0211 |
| 440 | LLDLCGGKAL | 0.713 | 22 | SB | Large T | A0211 |
| 578 | LLLIWFRPVA | 0.712 | 22 | SB | Large T | A0211 |
| 563 | FLLEKRILQS | 0.708 | 23 | SB | Large T | A0211 |
| 9 | SMELMDLLGL | 0.706 | 24 | SB | Large T | A0211 |
| 439 | GLLDLCGGKA | 0.690 | 28 | SB | Large T | A0211 |
| 520 | QIFPPGLVTM | 0.684 | 30 | SB | Large T | A0211 |
| 25 | NLPLMRKAYL | 0.682 | 31 | SB | Large T | A0211 |
| 457 | RLTFELGVAI | 0.675 | 33 | SB | Large T | A0211 |
| 156 | TLACFAVYTT | 0.669 | 35 | SB | Large T | A0211 |
| 435 | TLAAGLLDLC | 0.649 | 44 | SB | Large T | A0211 |
| 397 | CLLPKMDSVI | 0.648 | 44 | SB | Large T | A0211 |
| 197 | FFLTPHRHRV | 0.635 | 51 | WB | Large T | A0211 |
| 537 | TLQARFVRQI | 0.630 | 55 | WB | Large T | A0211 |
| 609 | SMYTFSRMKY | 0.624 | 58 | WB | Large T | A0211 |
| 176 | LMEKYSVTFI | 0.612 | 66 | WB | Large T | A0211 |
| 175 | KLMEKYSVTF | 0.575 | 98 | WB | Large T | A0211 |
| 103 | DLFCHEDMFA | 0.573 | 101 | WB | Large T | A0211 |
| 289 | LLGMYLEFQY | 0.539 | 146 | WB | Large T | A0211 |
| 428 | PIDSGKTTLA | 0.534 | 155 | WB | Large T | A0211 |
| 272 | KLITEYAVET | 0.531 | 160 | WB | Large T | A0211 |
| 545 | QIDFRPKIYL | 0.527 | 166 | WB | Large T | A0211 |
| 575 | TLLLLIWFR | 0.518 | 183 | WB | Large T | A0211 |
| 198 | FLTPHRHRVS | 0.517 | 185 | WB | Large T | A0211 |
| 528 | TMNEYPVPKT | 0.509 | 203 | WB | Large T | A0211 |
| 17 | GLERAAWGNL | 0.502 | 219 | WB | Large T | A0211 |
| 384 | VLEQYMAGVA | 0.492 | 244 | WB | Large T | A0211 |
| 277 | YAVETKCEDV | 0.480 | 278 | WB | Large T | A0211 |
| 124 | STPPKKKRKV | 0.477 | 287 | WB | Large T | A0211 |
| 360 | EMLTERFNHI | 0.458 | 351 | WB | Large T | A0211 |
| 171 | ILYKKLMEKY | 0.456 | 358 | WB | Large T | A0211 |
| 369 | ILDKMDLIFG | 0.442 | 418 | WB | Large T | A0211 |
| 215 | KLCTFSFLIC | 0.432 | 464 | WB | Large T | A0211 |
| 461 | ELGVAIDQYM | 0.429 | 479 | WB | Large T | A0211 |
| 501 | YLDGSVKVNL | 0.900 | 2 | SB | Large T | A0212 |
| 405 | VIFDFLHCVV | 0.897 | 3 | SB | Large T | A0212 |
| 56 | TLYKKMEQDV | 0.893 | 3 | SB | Large T | A0212 |
| 291 | GMYLEFQYNV | 0.886 | 3 | SB | Large T | A0212 |
| 497 | SLRDYLDGSV | 0.867 | 4 | SB | Large T | A0212 |
| 383 | AVLEQYMAGV | 0.855 | 4 | SB | Large T | A0212 |
| 525 | GLVTMNEYPV | 0.825 | 6 | SB | Large T | A0212 |
| 361 | MLTERFNHIL | 0.824 | 6 | SB | Large T | A0212 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 375 | LIFGAHGNAV | 0.806 | 8 | SB | Large T | A0212 |
| 142 | DLHQFLSQAV | 0.795 | 9 | SB | Large T | A0212 |
| 3 | VLNREESMEL | 0.788 | 9 | SB | Large T | A0212 |
| 401 | KMDSVIFDFL | 0.784 | 10 | SB | Large T | A0212 |
| 569 | ILQSGMTLLL | 0.783 | 10 | SB | Large T | A0212 |
| 577 | LLLLIWFRPV | 0.783 | 10 | SB | Large T | A0212 |
| 388 | YMAGVAWLHC | 0.765 | 12 | SB | Large T | A0212 |
| 345 | VLAKKRVDTL | 0.754 | 14 | SB | Large T | A0212 |
| 288 | LLLGMYLEFQ | 0.715 | 21 | SB | Large T | A0212 |
| 287 | FLLLGMYLEF | 0.683 | 30 | SB | Large T | A0212 |
| 563 | FLLEKRILQS | 0.666 | 37 | SB | Large T | A0212 |
| 442 | DLCGGKALNV | 0.657 | 40 | SB | Large T | A0212 |
| 397 | CLLPKMDSVI | 0.632 | 53 | WB | Large T | A0212 |
| 12 | LMDLLGLERA | 0.604 | 72 | WB | Large T | A0212 |
| 404 | SVIFDFLHCV | 0.604 | 72 | WB | Large T | A0212 |
| 9 | SMELMDLLGL | 0.579 | 95 | WB | Large T | A0212 |
| 603 | RLDSEISMYT | 0.573 | 101 | WB | Large T | A0212 |
| 236 | ALTRDPYHII | 0.570 | 104 | WB | Large T | A0212 |
| 277 | YAVETKCEDV | 0.569 | 106 | WB | Large T | A0212 |
| 578 | LLLIWFRPVA | 0.558 | 119 | WB | Large T | A0212 |
| 353 | TLHMTREEML | 0.552 | 126 | WB | Large T | A0212 |
| 197 | FFLTPHRHRV | 0.549 | 131 | WB | Large T | A0212 |
| 520 | QIFPPGLVTM | 0.543 | 139 | WB | Large T | A0212 |
| 176 | LMEKYSVTFI | 0.536 | 150 | WB | Large T | A0212 |
| 175 | KLMEKYSVTF | 0.528 | 165 | WB | Large T | A0212 |
| 463 | GVAIDQYMVV | 0.500 | 222 | WB | Large T | A0212 |
| 336 | SICQQAVDTV | 0.495 | 235 | WB | Large T | A0212 |
| 457 | RLTFELGVAI | 0.489 | 252 | WB | Large T | A0212 |
| 198 | FLTPHRHRVS | 0.484 | 266 | WB | Large T | A0212 |
| 609 | SMYTFSRMKY | 0.480 | 276 | WB | Large T | A0212 |
| 171 | ILYKKLMEKY | 0.477 | 285 | WB | Large T | A0212 |
| 25 | NLPLMRKAYL | 0.477 | 287 | WB | Large T | A0212 |
| 439 | GLLDLCGGKA | 0.476 | 288 | WB | Large T | A0212 |
| 611 | YTFSRMKYNI | 0.472 | 304 | WB | Large T | A0212 |
| 435 | TLAAGLLDLC | 0.461 | 342 | WB | Large T | A0212 |
| 440 | LLDLCGGKAL | 0.459 | 349 | WB | Large T | A0212 |
| 568 | RILQSGMTLL | 0.458 | 352 | WB | Large T | A0212 |
| 360 | EMLTERFNHI | 0.457 | 354 | WB | Large T | A0212 |
| 537 | TLQARFVRQI | 0.452 | 375 | WB | Large T | A0212 |
| 17 | GLERAAWGNL | 0.430 | 474 | WB | Large T | A0212 |
| 528 | TMNEYPVPKT | 0.428 | 488 | WB | Large T | A0212 |
| 525 | GLVTMNEYPV | 0.882 | 3 | SB | Large T | A0216 |
| 405 | VIFDFLHCVV | 0.863 | 4 | SB | Large T | A0216 |
| 497 | SLRDYLDGSV | 0.861 | 4 | SB | Large T | A0216 |
| 56 | TLYKKMEQDV | 0.842 | 5 | SB | Large T | A0216 |
| 291 | GMYLEFQYNV | 0.841 | 5 | SB | Large T | A0216 |
| 569 | ILQSGMTLLL | 0.838 | 5 | SB | Large T | A0216 |
| 501 | YLDGSVKVNL | 0.833 | 6 | SB | Large T | A0216 |
| 361 | MLTERFNHIL | 0.812 | 7 | SB | Large T | A0216 |
| 142 | DLHQFLSQAV | 0.809 | 7 | SB | Large T | A0216 |
| 401 | KMDSVIFDFL | 0.806 | 8 | SB | Large T | A0216 |
| 442 | DLCGGKALNV | 0.802 | 8 | SB | Large T | A0216 |
| 375 | LIFGAHGNAV | 0.773 | 11 | SB | Large T | A0216 |
| 3 | VLNREESMEL | 0.768 | 12 | SB | Large T | A0216 |
| 345 | VLAKKRVDTL | 0.765 | 12 | SB | Large T | A0216 |
| 577 | LLLLIWFRPV | 0.743 | 16 | SB | Large T | A0216 |
| 383 | AVLEQYMAGV | 0.739 | 16 | SB | Large T | A0216 |
| 336 | SICQQAVDTV | 0.721 | 20 | SB | Large T | A0216 |
| 25 | NLPLMRKAYL | 0.703 | 24 | SB | Large T | A0216 |
| 288 | LLLGMYLEFQ | 0.679 | 32 | SB | Large T | A0216 |
| 176 | LMEKYSVTFI | 0.675 | 33 | SB | Large T | A0216 |
| 236 | ALTRDPYHII | 0.671 | 35 | SB | Large T | A0216 |
| 353 | TLHMTREEML | 0.668 | 36 | SB | Large T | A0216 |
| 404 | SVIFDFLHCV | 0.647 | 45 | SB | Large T | A0216 |
| 603 | RLDSEISMYT | 0.630 | 54 | WB | Large T | A0216 |
| 197 | FFLTPHRHRV | 0.615 | 64 | WB | Large T | A0216 |
| 388 | YMAGVAWLHC | 0.602 | 73 | WB | Large T | A0216 |
| 568 | RILQSGMTLL | 0.598 | 77 | WB | Large T | A0216 |
| 156 | TLACFAVYTT | 0.567 | 108 | WB | Large T | A0216 |
| 397 | CLLPKMDSVI | 0.562 | 114 | WB | Large T | A0216 |
| 461 | ELGVAIDQYM | 0.550 | 130 | WB | Large T | A0216 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 17 | GLERAAWGNL | 0.545 | 137 | WB | Large T | A0216 |
| 103 | DLFCHEDMFA | 0.537 | 149 | WB | Large T | A0216 |
| 463 | GVAIDQYMVV | 0.534 | 155 | WB | Large T | A0216 |
| 537 | TLQARFVRQI | 0.528 | 165 | WB | Large T | A0216 |
| 563 | FLLEKRILQS | 0.511 | 198 | WB | Large T | A0216 |
| 545 | QIDFRPKIYL | 0.493 | 240 | WB | Large T | A0216 |
| 12 | LMDLLGLERA | 0.484 | 265 | WB | Large T | A0216 |
| 287 | FLLLGMYLEF | 0.483 | 270 | WB | Large T | A0216 |
| 289 | LLGMYLEFQY | 0.482 | 270 | WB | Large T | A0216 |
| 439 | GLLDLCGGKA | 0.477 | 287 | WB | Large T | A0216 |
| 9 | SMELMDLLGL | 0.468 | 316 | WB | Large T | A0216 |
| 673 | HLCKGFQCFK | 0.468 | 317 | WB | Large T | A0216 |
| 520 | QIFPPGLVTM | 0.463 | 334 | WB | Large T | A0216 |
| 190 | CAGHNIIFFL | 0.447 | 397 | WB | Large T | A0216 |
| 440 | LLDLCGGKAL | 0.445 | 406 | WB | Large T | A0216 |
| 124 | STPPKKKRKV | 0.438 | 439 | WB | Large T | A0216 |
| 578 | LLLIWFRPVA | 0.428 | 485 | WB | Large T | A0216 |
| 501 | YLDGSVKVNL | 0.885 | 3 | SB | Large T | A0219 |
| 569 | ILQSGMTLLL | 0.833 | 6 | SB | Large T | A0219 |
| 401 | KMDSVIFDPL | 0.761 | 13 | SB | Large T | A0219 |
| 361 | MLTERFNHIL | 0.747 | 15 | SB | Large T | A0219 |
| 405 | VIFDFLHCVV | 0.704 | 24 | SB | Large T | A0219 |
| 291 | GMYLEFQYNV | 0.679 | 32 | SB | Large T | A0219 |
| 142 | DLHQFLSQAV | 0.676 | 33 | SB | Large T | A0219 |
| 577 | LLLLIWFRPV | 0.646 | 45 | SB | Large T | A0219 |
| 525 | GLVTMNEYPV | 0.631 | 54 | WB | Large T | A0219 |
| 497 | SLRDYLDGSV | 0.622 | 59 | WB | Large T | A0219 |
| 388 | YMAGVAWLHC | 0.582 | 91 | WB | Large T | A0219 |
| 3 | VLNREESMEL | 0.573 | 101 | WB | Large T | A0219 |
| 288 | LLLGMYLEFQ | 0.572 | 102 | WB | Large T | A0219 |
| 56 | TLYKKMEQDV | 0.570 | 104 | WB | Large T | A0219 |
| 375 | LIFGAHGNAV | 0.565 | 110 | WB | Large T | A0219 |
| 442 | DLCGGKALNV | 0.557 | 120 | WB | Large T | A0219 |
| 383 | AVLEQYMAGV | 0.556 | 122 | WB | Large T | A0219 |
| 236 | ALTRDPYHII | 0.545 | 137 | WB | Large T | A0219 |
| 345 | VLAKKRVDTL | 0.515 | 189 | WB | Large T | A0219 |
| 603 | RLDSEISMYT | 0.498 | 227 | WB | Large T | A0219 |
| 12 | LMDLLGLERA | 0.486 | 260 | WB | Large T | A0219 |
| 397 | CLLPKMDSVI | 0.475 | 293 | WB | Large T | A0219 |
| 404 | SVIFDFLHCV | 0.474 | 294 | WB | Large T | A0219 |
| 435 | TLAAGLLDLC | 0.459 | 347 | WB | Large T | A0219 |
| 197 | FFLTPHRHRV | 0.449 | 389 | WB | Large T | A0219 |
| 353 | TLHMTREEML | 0.433 | 463 | WB | Large T | A0219 |
| 537 | TLQARFVRQI | 0.427 | 492 | WB | Large T | A0219 |
| 170 | QILYKKLMEK | 0.764 | 12 | SB | Large T | A0301 |
| 50 | KMKRMNTLYK | 0.754 | 14 | SB | Large T | A0301 |
| 615 | RMKYNICMGK | 0.751 | 14 | SB | Large T | A0301 |
| 608 | ISMYTFSRMK | 0.734 | 17 | SB | Large T | A0301 |
| 609 | SMYTFSRMKY | 0.707 | 23 | SB | Large T | A0301 |
| 527 | VTMNEYPVPK | 0.691 | 28 | SB | Large T | A0301 |
| 673 | HLCKGFQCFK | 0.668 | 36 | SB | Large T | A0301 |
| 27 | PLMRKAYLKK | 0.663 | 38 | SB | Large T | A0301 |
| 157 | LACFAVYTTK | 0.654 | 42 | SB | Large T | A0301 |
| 392 | VAWLHCLLPK | 0.582 | 92 | WB | Large T | A0301 |
| 575 | TLLLLIWFR | 0.574 | 100 | WB | Large T | A0301 |
| 220 | SFLICKGVNK | 0.554 | 124 | WB | Large T | A0301 |
| 22 | AWGNLPLMRK | 0.533 | 156 | WB | Large T | A0301 |
| 326 | IIFAESKNQK | 0.519 | 181 | WB | Large T | A0301 |
| 26 | LPLMRKAYLK | 0.500 | 222 | WB | Large T | A0301 |
| 558 | LQNSEFLLEK | 0.484 | 265 | WB | Large T | A0301 |
| 311 | QPYHFKYHEK | 0.465 | 326 | WB | Large T | A0301 |
| 417 | VPKRRYWLFK | 0.462 | 338 | WB | Large T | A0301 |
| 206 | VSAINNFCQK | 0.448 | 391 | WB | Large T | A0301 |
| 448 | ALNVNLPMER | 0.447 | 396 | WB | Large T | A0301 |
| 273 | LITEYAVETK | 0.446 | 399 | WB | Large T | A0301 |
| 171 | ILYKKLMEKY | 0.433 | 462 | WB | Large T | A0301 |
| 527 | VTMNEYPVPK | 0.811 | 7 | SB | Large T | A1101 |
| 608 | ISMYTFSRMK | 0.760 | 13 | SB | Large T | A1101 |
| 392 | VAWLHCLLPK | 0.708 | 23 | SB | Large T | A1101 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 558 | LQNSEFLLEK | 0.705 | 24 | SB | Large T | A1101 |
| 50 | KMKRMNTLYK | 0.700 | 25 | SB | Large T | A1101 |
| 326 | IIFAESKNQK | 0.695 | 27 | SB | Large T | A1101 |
| 206 | VSAINNFCQK | 0.692 | 28 | SB | Large T | A1101 |
| 609 | SMYTFSRMKY | 0.665 | 37 | SB | Large T | A1101 |
| 575 | TLLLLLIWFR | 0.648 | 45 | SB | Large T | A1101 |
| 170 | QILYKKLMEK | 0.643 | 47 | SB | Large T | A1101 |
| 157 | LACFAVYTTK | 0.635 | 51 | WB | Large T | A1101 |
| 673 | HLCKGFQCFK | 0.622 | 59 | WB | Large T | A1101 |
| 90 | ESWWSSFNEK | 0.565 | 110 | WB | Large T | A1101 |
| 615 | RMKYNICMGK | 0.556 | 121 | WB | Large T | A1101 |
| 121 | SQHSTPPKKK | 0.552 | 127 | WB | Large T | A1101 |
| 504 | GSVKVNLEKK | 0.541 | 143 | WB | Large T | A1101 |
| 339 | QQAVDTVLAK | 0.540 | 145 | WB | Large T | A1101 |
| 340 | QAVDTVLAKK | 0.534 | 154 | WB | Large T | A1101 |
| 448 | ALNVNLPMER | 0.528 | 165 | WB | Large T | A1101 |
| 194 | NIIFFLTPHR | 0.516 | 188 | WB | Large T | A1101 |
| 27 | PLMRKAYLKK | 0.478 | 284 | WB | Large T | A1101 |
| 21 | AAWGNLPLMR | 0.475 | 293 | WB | Large T | A1101 |
| 273 | LITEYAVETK | 0.470 | 310 | WB | Large T | A1101 |
| 120 | DSQHSTPPKK | 0.450 | 383 | WB | Large T | A1101 |
| 22 | AWGNLPLMRK | 0.449 | 387 | WB | Large T | A1101 |
| 220 | SFLICKGVNK | 0.445 | 404 | WB | Large T | A1101 |
| 468 | QYMVVFEDVK | 0.626 | 57 | WB | Large T | A2301 |
| 151 | VFSNRTLACF | 0.608 | 69 | WB | Large T | A2301 |
| 287 | FLLLGMYLEF | 0.575 | 99 | WB | Large T | A2301 |
| 582 | WFRPVADFSK | 0.548 | 133 | WB | Large T | A2301 |
| 57 | LYKKMEQDVK | 0.531 | 160 | WB | Large T | A2301 |
| 574 | MTLLLLLIWF | 0.524 | 171 | WB | Large T | A2301 |
| 83 | TYGTEEWESW | 0.500 | 224 | WB | Large T | A2301 |
| 406 | IFDFLHCVVF | 0.486 | 260 | WB | Large T | A2301 |
| 416 | NVPKRRYWLF | 0.477 | 288 | WB | Large T | A2301 |
| 220 | SFLICKGVNK | 0.469 | 311 | WB | Large T | A2301 |
| 159 | CFAVYTTKEK | 0.465 | 326 | WB | Large T | A2301 |
| 203 | RHRVSAINNF | 0.458 | 351 | WB | Large T | A2301 |
| 295 | EFQYNVEECK | 0.447 | 396 | WB | Large T | A2301 |
| 175 | KLMEKYSVTF | 0.446 | 401 | WB | Large T | A2301 |
| 91 | SWWSSFNEKW | 0.436 | 447 | WB | Large T | A2301 |
| 464 | SVAIDQYMVVF | 0.430 | 478 | WB | Large T | A2301 |
| 212 | FCQKLCTFSF | 0.426 | 499 | WB | Large T | A2301 |
| 151 | VFSNRTLACF | 0.606 | 71 | WB | Large T | A2402 |
| 162 | VYTTKEKAQI | 0.518 | 183 | WB | Large T | A2402 |
| 617 | KYNICMGKCI | 0.510 | 200 | WB | Large T | A2402 |
| 416 | NVPKRRYWLF | 0.506 | 209 | WB | Large T | A2402 |
| 406 | IFDFLHCVVF | 0.483 | 269 | WB | Large T | A2402 |
| 83 | TYGTEEWESW | 0.472 | 301 | WB | Large T | A2402 |
| 138 | DFPSDLHQFL | 0.430 | 477 | WB | Large T | A2402 |
| 83 | TYGTEEWESW | 0.622 | 59 | WB | Large T | A2403 |
| 513 | KHLNKRTQIF | 0.548 | 132 | WB | Large T | A2403 |
| 287 | FLLLGMYLEF | 0.533 | 155 | WB | Large T | A2403 |
| 212 | FCQKLCTFSF | 0.510 | 201 | WB | Large T | A2403 |
| 162 | VYTTKEKAQI | 0.492 | 243 | WB | Large T | A2403 |
| 175 | KLMEKYSVTF | 0.491 | 245 | WB | Large T | A2403 |
| 151 | VFSNRTLACF | 0.479 | 280 | WB | Large T | A2403 |
| 313 | YHFKYHEKHF | 0.456 | 358 | WB | Large T | A2403 |
| 406 | IFDFLHCVVF | 0.453 | 370 | WB | Large T | A2403 |
| 416 | NVPKRRYWLF | 0.449 | 389 | WB | Large T | A2403 |
| 203 | RHRVSAINNF | 0.444 | 408 | WB | Large T | A2403 |
| 574 | MTLLLLLIWF | 0.429 | 480 | WB | Large T | A2403 |
| 164 | TTKEKAQILY | 0.552 | 127 | WB | Large T | A2601 |
| 607 | EISMYTFSRM | 0.466 | 322 | WB | Large T | A2601 |
| 607 | EISMYTFSRM | 0.857 | 4 | SB | Large T | A2602 |
| 520 | QIFPPGLVTM | 0.811 | 7 | SB | Large T | A2602 |
| 268 | QVSWKLITEY | 0.726 | 19 | SB | Large T | A2602 |
| 164 | TTKEKAQILY | 0.721 | 20 | SB | Large T | A2602 |
| 416 | NVPKRRYWLF | 0.714 | 22 | SB | Large T | A2602 |
| 533 | PVPKTLQARF | 0.685 | 30 | SB | Large T | A2602 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 64 | DVKVAHQPDF | 0.665 | 37 | SB | Large T | A2602 |
| 280 | ETKCEDVFLL | 0.646 | 46 | SB | Large T | A2602 |
| 285 | DVFLLLGMYL | 0.612 | 66 | WB | Large T | A2602 |
| 368 | HILDKMDLIF | 0.589 | 85 | WB | Large T | A2602 |
| 80 | EVPTYGTEEW | 0.587 | 86 | WB | Large T | A2602 |
| 184 | FISRHMCAGH | 0.532 | 158 | WB | Large T | A2602 |
| 163 | YTTKEKAQIL | 0.514 | 192 | WB | Large T | A2602 |
| 284 | EDVFLLLGMY | 0.470 | 308 | WB | Large T | A2602 |
| 138 | DFPSDLHQFL | 0.465 | 326 | WB | Large T | A2602 |
| 611 | YTFSRMKYNI | 0.465 | 327 | WB | Large T | A2602 |
| 574 | MTLLLLLIWF | 0.463 | 333 | WB | Large T | A2602 |
| 464 | VAIDQYMVVF | 0.457 | 354 | WB | Large T | A2602 |
| 404 | SVIFDFLHCV | 0.451 | 380 | WB | Large T | A2602 |
| 609 | SMYTFSRMKY | 0.700 | 25 | SB | Large T | A2902 |
| 413 | VVFNVPKRRY | 0.524 | 172 | WB | Large T | A2902 |
| 171 | ILYKKLMEKY | 0.501 | 221 | WB | Large T | A2902 |
| 289 | LLGMYLEFQY | 0.496 | 232 | WB | Large T | A2902 |
| 75 | TWNSSEVPTY | 0.466 | 321 | WB | Large T | A2902 |
| 268 | QVSWKLITEY | 0.455 | 364 | WB | Large T | A2902 |
| 50 | KMKRMNTLYK | 0.848 | 5 | SB | Large T | A3001 |
| 676 | KGFQCFKRPK | 0.733 | 17 | SB | Large T | A3001 |
| 681 | FKRPKTPPPK | 0.723 | 20 | SB | Large T | A3001 |
| 51 | MKRMNTLYKK | 0.685 | 30 | SB | Large T | A3001 |
| 615 | RMKYNICMGK | 0.677 | 33 | SB | Large T | A3001 |
| 527 | VTMNEYPVPK | 0.661 | 39 | SB | Large T | A3001 |
| 417 | VPKRRYWLFK | 0.637 | 50 | WB | Large T | A3001 |
| 121 | SQHSTPPKKK | 0.623 | 59 | WB | Large T | A3001 |
| 582 | WFRPVADFSK | 0.622 | 59 | WB | Large T | A3001 |
| 542 | FVRQIDFRPK | 0.556 | 121 | WB | Large T | A3001 |
| 608 | ISMYTFSRMK | 0.552 | 126 | WB | Large T | A3001 |
| 128 | KKKRKVEDPK | 0.548 | 132 | WB | Large T | A3001 |
| 547 | DFRPKIYLRK | 0.507 | 207 | WB | Large T | A3001 |
| 307 | QKKDQPYHFK | 0.501 | 220 | WB | Large T | A3001 |
| 27 | PLMRKAYLKK | 0.500 | 224 | WB | Large T | A3001 |
| 356 | MTREEMLTER | 0.494 | 238 | WB | Large T | A3001 |
| 29 | MRKAYLKKCK | 0.488 | 255 | WB | Large T | A3001 |
| 119 | ADSQHSTPPK | 0.460 | 344 | WB | Large T | A3001 |
| 363 | TERFNHILDK | 0.445 | 405 | WB | Large T | A3001 |
| 166 | KEKAQILYKK | 0.442 | 418 | WB | Large T | A3001 |
| 164 | TTKEKAQILY | 0.439 | 432 | WB | Large T | A3001 |
| 120 | DSQHSTPPKK | 0.428 | 485 | WB | Large T | A3001 |
| 233 | LYSALTRDPY | 0.534 | 155 | WB | Large T | A3002 |
| 609 | SMYTFSRMKY | 0.528 | 165 | WB | Large T | A3002 |
| 268 | QVSWKLITEY | 0.485 | 262 | WB | Large T | A3002 |
| 75 | TWNSSEVPTY | 0.446 | 400 | WB | Large T | A3002 |
| 575 | TLLLLLIWFR | 0.750 | 14 | SB | Large T | A3101 |
| 230 | EYLLYSALTR | 0.642 | 48 | SB | Large T | A3101 |
| 50 | KMKRMNTLYK | 0.640 | 49 | SB | Large T | A3101 |
| 674 | LCKGFQCFKR | 0.638 | 50 | WB | Large T | A3101 |
| 609 | SMYTFSRMKY | 0.623 | 58 | WB | Large T | A3101 |
| 615 | RMKYNICMGK | 0.604 | 72 | WB | Large T | A3101 |
| 194 | NIIFFLTPHR | 0.586 | 88 | WB | Large T | A3101 |
| 448 | ALNVNLPMER | 0.583 | 90 | WB | Large T | A3101 |
| 673 | HLCKGFQCFK | 0.573 | 101 | WB | Large T | A3101 |
| 146 | FLSQAVFSNR | 0.570 | 104 | WB | Large T | A3101 |
| 412 | CVVFNVPKRR | 0.565 | 110 | WB | Large T | A3101 |
| 196 | IFFLTPHRHR | 0.550 | 130 | WB | Large T | A3101 |
| 356 | MTREEMLTER | 0.548 | 132 | WB | Large T | A3101 |
| 349 | KRVDTLHMTR | 0.530 | 161 | WB | Large T | A3101 |
| 220 | SFLICKGVNK | 0.524 | 172 | WB | Large T | A3101 |
| 51 | MKRMNTLYKK | 0.468 | 316 | WB | Large T | A3101 |
| 157 | LACFAVYTTK | 0.456 | 358 | WB | Large T | A3101 |
| 535 | PKTLQARFVR | 0.445 | 403 | WB | Large T | A3101 |
| 606 | SEISMYTFSR | 0.445 | 404 | WB | Large T | A3101 |
| 594 | QSRIVEWKER | 0.442 | 417 | WB | Large T | A3101 |
| 205 | RVSAINNFCQ | 0.434 | 458 | WB | Large T | A3101 |

TABLE M-continued

Prediction of BK virus Large T protein specific MHC class1,
8-, 9-, 10-, 11-mer peptide binders for 42 MHC class 1 alleles
(see FIG. 11) using the www.cbs.dtu.dk/services/
NetMHC/ database. The MHC class 1 molecules for which
no binders were found are not listed.

| pos | peptide | logscore | affinity (nM) | Bind Level | Protein Name | Allele |
|---|---|---|---|---|---|---|
| 230 | EYLLYSALTR | 0.653 | 42 | SB | Large T | A3301 |
| 575 | TLLLLLIWFR | 0.600 | 76 | WB | Large T | A3301 |
| 674 | LCKGFQCFKR | 0.537 | 150 | WB | Large T | A3301 |
| 196 | IFFLTPHRHR | 0.529 | 162 | WB | Large T | A3301 |
| 194 | NIIFFLTPHR | 0.529 | 163 | WB | Large T | A3301 |
| 11 | ELMDLLGLER | 0.512 | 196 | WB | Large T | A3301 |
| 146 | FLSQAVFSNR | 0.482 | 271 | WB | Large T | A3301 |
| 178 | EKYSVTFISR | 0.464 | 330 | WB | Large T | A3301 |
| 547 | DFRPKIYLRK | 0.429 | 482 | WB | Large T | A3301 |
| | | | | | Large T | A3301 |
| 194 | NIIFFLTPHR | 0.866 | 4 | SB | Large T | A6801 |
| 412 | CVVFNVPKRR | 0.785 | 10 | SB | Large T | A6801 |
| 356 | MTREEMLTER | 0.784 | 10 | SB | Large T | A6801 |
| 90 | ESWWSSFNEK | 0.756 | 13 | SB | Large T | A6801 |
| 146 | FLSQAVFSNR | 0.739 | 16 | SB | Large T | A6801 |
| 11 | ELMDLLGLER | 0.720 | 20 | SB | Large T | A6801 |
| 178 | EKYSVTFISR | 0.713 | 22 | SB | Large T | A6801 |
| 157 | LACFAVYTTK | 0.693 | 27 | SB | Large T | A6801 |
| 608 | ISMYTFSRMK | 0.660 | 39 | SB | Large T | A6801 |
| 673 | HLCKGFQCFK | 0.645 | 46 | SB | Large T | A6801 |
| 230 | EYLLYSALTR | 0.644 | 47 | SB | Large T | A6801 |
| 575 | TLLLLLIWFR | 0.643 | 47 | SB | Large T | A6801 |
| 326 | IIFAESKNQK | 0.639 | 49 | SB | Large T | A6801 |
| 273 | LITEYAVETK | 0.632 | 53 | WB | Large T | A6801 |
| 206 | VSAINNFCQK | 0.629 | 55 | WB | Large T | A6801 |
| 340 | QAVDTVLAKK | 0.623 | 59 | WB | Large T | A6801 |
| 490 | HGINNLDSLR | 0.593 | 81 | WB | Large T | A6801 |
| 475 | DVKGTGAESK | 0.581 | 93 | WB | Large T | A6801 |
| 606 | SEISMYTFSR | 0.572 | 102 | WB | Large T | A6801 |
| 592 | DIQSRIVEWK | 0.563 | 113 | WB | Large T | A6801 |
| 311 | QPYHFKYHEK | 0.556 | 122 | WB | Large T | A6801 |
| 527 | VTMNEYPVPK | 0.541 | 143 | WB | Large T | A6801 |
| 295 | EFQYNVEECK | 0.539 | 146 | WB | Large T | A6801 |
| 299 | NVEECKKCQK | 0.534 | 155 | WB | Large T | A6801 |
| 159 | CFAVYTTKEK | 0.524 | 171 | WB | Large T | A6801 |
| 296 | FQYNVEECKK | 0.510 | 200 | WB | Large T | A6801 |
| 196 | IFFLTPHRHR | 0.505 | 212 | WB | Large T | A6801 |
| 622 | MGKCILDITR | 0.480 | 277 | WB | Large T | A6801 |
| 542 | FVRQIDFRPK | 0.478 | 282 | WB | Large T | A6801 |
| 411 | HCVVFNVPKR | 0.476 | 290 | WB | Large T | A6801 |
| 120 | DSQHSTPPKK | 0.461 | 341 | WB | Large T | A6801 |
| 546 | IDFRPKIYLR | 0.437 | 443 | WB | Large T | A6801 |
| 164 | TTKEKAQILY | 0.433 | 460 | WB | Large T | A6801 |
| 404 | SVIFDFLHCV | 0.762 | 13 | SB | Large T | A6802 |
| 611 | YTFSRMKYNI | 0.677 | 32 | SB | Large T | A6802 |
| 285 | DVFLLLGMYL | 0.632 | 53 | WB | Large T | A6802 |
| 322 | FANAIIFAES | 0.613 | 66 | WB | Large T | A6802 |
| 280 | ETKCEDVFLL | 0.609 | 69 | WB | Large T | A6802 |
| 462 | LGVAIDQYMV | 0.574 | 100 | WB | Large T | A6802 |
| 607 | EISMYTFSRM | 0.562 | 114 | WB | Large T | A6802 |
| 375 | LIFGAHGNAV | 0.557 | 120 | WB | Large T | A6802 |
| 405 | VIFDFLHCVV | 0.536 | 151 | WB | Large T | A6802 |
| 647 | ESQSQCSSQV | 0.517 | 185 | WB | Large T | A6802 |
| 190 | CAGHNIIFFL | 0.488 | 253 | WB | Large T | A6802 |
| 383 | AVLEQYMAGV | 0.479 | 281 | WB | Large T | A6802 |
| 77 | NSSEVPTYGT | 0.467 | 320 | WB | Large T | A6802 |
| 19 | ERAAWGNLPL | 0.452 | 375 | WB | Large T | A6802 |
| 108 | EDMFASDEEA | 0.451 | 379 | WB | Large T | A6802 |
| 265 | ETKQVSWKLI | 0.451 | 380 | WB | Large T | A6802 |
| 207 | SAINNFCQKL | 0.440 | 428 | WB | Large T | A6802 |
| 463 | GVAIDQYMVV | 0.433 | 459 | WB | Large T | A6802 |
| 156 | TLACFAVYTT | 0.432 | 465 | WB | Large T | A6802 |
| 383 | AVLEQYMAGV | 0.745 | 15 | SB | Large T | A6901 |
| 404 | SVIFDFLHCV | 0.639 | 49 | SB | Large T | A6901 |
| 611 | YTFSRMKYNI | 0.596 | 79 | WB | Large T | A6901 |
| 375 | LIFGAHGNAV | 0.575 | 99 | WB | Large T | A6901 |
| 405 | VIFDFLHCVV | 0.552 | 127 | WB | Large T | A6901 |
| 360 | EMLTERFNHI | 0.545 | 137 | WB | Large T | A6901 |
| 520 | QIFPPPGLVTM | 0.541 | 143 | WB | Large T | A6901 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pospeptide | logscore | affinity (nM) | Bind Level | Protein Name | Allele |
|---|---|---|---|---|---|
| 453 LPMERLTFEL | 0.477 | 287 | WB | Large T | A6901 |
| 434 TTLAAGLLDL | 0.466 | 324 | WB | Large T | A6901 |
| 277 YAVETKCEDV | 0.458 | 352 | WB | Large T | A6901 |
| 197 FFLTPHRHRV | 0.452 | 374 | WB | Large T | A6901 |
| 577 LLLLIWFRPV | 0.435 | 451 | WB | Large T | A6901 |
| 285 DVFLLLGMYL | 0.431 | 470 | WB | Large T | A6901 |
| 549 RPKIYLRKSL | 0.785 | 10 | SB | Large T | B0702 |
| 200 TPHRHRVSAI | 0.752 | 14 | SB | Large T | B0702 |
| 453 LPMERLTFEL | 0.722 | 20 | SB | Large T | B0702 |
| 427 GPIDSGKTTL | 0.704 | 24 | SB | Large T | B0702 |
| 486 LPSGHGINNL | 0.573 | 101 | WB | Large T | B0702 |
| 584 RPVADFSKDI | 0.560 | 117 | WB | Large T | B0702 |
| 549 RPKIYLRKSL | 0.479 | 280 | WB | Large T | B0801 |
| 200 TPHRHRVSAI | 0.453 | 373 | WB | Large T | B0801 |
| 544 RQIDFRPKIY | 0.584 | 89 | WB | Large T | B1501 |
| 188 HMCAGHNIIF | 0.577 | 97 | WB | Large T | B1501 |
| 175 KLMEKYSVTF | 0.568 | 107 | WB | Large T | B1501 |
| 609 SMYTFSRMKY | 0.536 | 150 | WB | Large T | B1501 |
| 148 SQAVFSNRTL | 0.502 | 218 | WB | Large T | B1501 |
| 268 QVSWKLITEY | 0.478 | 284 | WB | Large T | B1501 |
| 287 FLLLGMYLEF | 0.475 | 292 | WB | Large T | B1501 |
| 249 IQGGLKEHDF | 0.467 | 318 | WB | Large T | B1501 |
| 464 VAIDQYMVVF | 0.445 | 406 | WB | Large T | B1501 |
| 570 LQSGMTLLLL | 0.439 | 434 | WB | Large T | B1501 |
| 460 FELGVAIDQY | 0.795 | 9 | SB | Large T | B1801 |
| 87 EEWESWWSSF | 0.653 | 42 | SB | Large T | B1801 |
| 455 MERLTFELGV | 0.576 | 98 | WB | Large T | B1801 |
| 574 MTLLLLLIWF | 0.498 | 227 | WB | Large T | B1801 |
| 420 RRYWLFKGPI | 0.605 | 71 | WB | Large T | B2705 |
| 52 KRMNTLYKKM | 0.591 | 83 | WB | Large T | B2705 |
| 567 KRILQSGMTL | 0.564 | 111 | WB | Large T | B2705 |
| 349 KRVDTLHMTR | 0.487 | 258 | WB | Large T | B2705 |
| 517 KRTQIFPPGL | 0.471 | 305 | WB | Large T | B2705 |
| 464 VAIDQYMVVF | 0.679 | 32 | SB | Large T | B3501 |
| 453 LPMERLTFEL | 0.600 | 75 | WB | Large T | B3501 |
| 20 RAAWGNLPLM | 0.595 | 80 | WB | Large T | B3501 |
| 268 QVSWKLITEY | 0.558 | 119 | WB | Large T | B3501 |
| 486 LPSGHGINNL | 0.549 | 131 | WB | Large T | B3501 |
| 287 FLLLGMYLEF | 0.479 | 279 | WB | Large T | B3501 |
| 523 PPGLVTMNEY | 0.479 | 281 | WB | Large T | B3501 |
| 532 YPVPKTLQAR | 0.470 | 310 | WB | Large T | B3501 |
| 139 FPSDLHQFLS | 0.459 | 347 | WB | Large T | B3501 |
| 189 MCAGHNIIFF | 0.451 | 379 | WB | Large T | B3501 |
| 389 MAGVAWLHCL | 0.449 | 390 | WB | Large T | B3501 |
| 262 EPEETKQVSW | 0.433 | 460 | WB | Large T | B3501 |
| 317 YHEKHFANAI | 0.608 | 69 | WB | Large T | B3901 |
| 148 SQAVFSNRTL | 0.545 | 137 | WB | Large T | B3901 |
| 19 ERAAWGNLPL | 0.539 | 147 | WB | Large T | B3901 |
| 501 YLDGSVKVNL | 0.498 | 228 | WB | Large T | B3901 |
| 6 REESMELMDL | 0.707 | 23 | SB | Large T | B4001 |
| 561 SEFLLEKRIL | 0.683 | 30 | SB | Large T | B4001 |
| 279 VETKCEDVFL | 0.502 | 218 | WB | Large T | B4001 |
| 264 EETKQVSWKL | 0.500 | 224 | WB | Large T | B4001 |
| 7 EESMELMDLL | 0.488 | 253 | WB | Large T | B4001 |
| 455 MERLTFELGV | 0.485 | 263 | WB | Large T | B4001 |
| 561 SEFLLEKRIL | 0.595 | 80 | WB | Large T | B4002 |
| 7 EESMELMDLL | 0.482 | 271 | WB | Large T | B4002 |
| 229 KEYLLYSALT | 0.482 | 272 | WB | Large T | B4002 |
| 279 VETKCEDVFL | 0.472 | 303 | WB | Large T | B4002 |
| 87 EEWESWWSSF | 0.458 | 353 | WB | Large T | B4002 |
| 561 SEFLLEKRIL | 0.496 | 233 | WB | Large T | B4403 |
| 606 SEISMYTFSR | 0.427 | 493 | WB | Large T | B4403 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos peptide | logscore | affinity (nM) | Bind Level | Protein Name | Allele |
|---|---|---|---|---|---|
| 453 LPMERLTFEL | 0.695 | 27 | SB | Large T | B5101 |
| 240 DPYHIIEESI | 0.492 | 244 | WB | Large T | B5101 |
| 486 LPSGHGINNL | 0.447 | 397 | WB | Large T | B5101 |
| 453 LPMERLTFEL | 0.721 | 20 | SB | Large T | B5301 |
| 262 EPEETKQVSW | 0.716 | 21 | SB | Large T | B5301 |
| 486 LPSGHGINNL | 0.585 | 89 | WB | Large T | B5301 |
| 427 GPIDSGKTTL | 0.470 | 308 | WB | Large T | B5301 |
| 200 TPHRHRVSAI | 0.457 | 356 | WB | Large T | B5301 |
| 139 FPSDLHQFLS | 0.584 | 89 | WB | Large T | B5401 |
| 26 LPLMRKAYLK | 0.511 | 197 | WB | Large T | B5401 |
| 160 FAVYTTKEKA | 0.489 | 252 | WB | Large T | B5401 |
| 453 LPMERLTFEL | 0.483 | 267 | WB | Large T | B5401 |
| 67 VAHQPDFGTW | 0.448 | 393 | WB | Large T | B5701 |
| 67 VAHQPDFGTW | 0.537 | 149 | WB | Large T | B5801 |
| 464 VAIDQYMVVF | 0.503 | 216 | WB | Large T | B5801 |
| 20 RAAWGNLPLM | 0.485 | 263 | WB | Large T | B5801 |
| 556 KSLQNSEFLL | 0.475 | 293 | WB | Large T | B5801 |
| 175 KLMEKYSVTF | 0.437 | 440 | WB | Large T | B5801 |
| 31 KAYLKKCKEF | 0.431 | 473 | WB | Large T | B5801 |
| 591 KDIQSRIVEW | 0.430 | 474 | WB | Large T | B5801 |
| 11-mers | | | | | |
| 163 YTTKEKAQILY | 0.682 | 31 | SB | Large T | A0101 |
| 388 YMAGVAWLHCL | 0.862 | 4 | SB | Large T | A0201 |
| 175 KLMEKYSVTFI | 0.854 | 4 | SB | Large T | A0201 |
| 576 LLLLLIWFRPV | 0.708 | 23 | SB | Large T | A0201 |
| 369 ILDKMDLIFGA | 0.641 | 48 | SB | Large T | A0201 |
| 569 ILQSGMTLLLL | 0.609 | 68 | WB | Large T | A0201 |
| 146 FLSQAVFSNRT | 0.563 | 113 | WB | Large T | A0201 |
| 198 FLTPHRHRVSA | 0.558 | 119 | WB | Large T | A0201 |
| 287 FLLLGMYLEFQ | 0.530 | 162 | WB | Large T | A0201 |
| 568 RILQSGMTLLL | 0.506 | 209 | WB | Large T | A0201 |
| 528 TMNEYPVPKTL | 0.501 | 222 | WB | Large T | A0201 |
| 439 GLLDLCGGKAL | 0.469 | 312 | WB | Large T | A0201 |
| 448 ALNVNLPMERL | 0.469 | 313 | WB | Large T | A0201 |
| 577 LLLLIWFRPVA | 0.462 | 336 | WB | Large T | A0201 |
| 11 ELMDLLGLERA | 0.458 | 351 | WB | Large T | A0201 |
| 217 CTFSFLICKGV | 0.447 | 398 | WB | Large T | A0201 |
| 152 FSNRTLACFAV | 0.439 | 431 | WB | Large T | A0201 |
| 269 VSWKLITEYAV | 0.439 | 432 | WB | Large T | A0201 |
| 570 LQSGMTLLLLL | 0.434 | 457 | WB | Large T | A0201 |
| 2 KVLNREESMEL | 0.432 | 467 | WB | Large T | A0201 |
| 388 YMAGVAWLHCL | 0.869 | 4 | SB | Large T | A0202 |
| 175 KLMEKYSVTFI | 0.858 | 4 | SB | Large T | A0202 |
| 189 MCAGHNIIFFL | 0.726 | 19 | SB | Large T | A0202 |
| 198 FLTPHRHRVSA | 0.718 | 21 | SB | Large T | A0202 |
| 146 FLSQAVFSNRT | 0.718 | 21 | SB | Large T | A0202 |
| 570 LQSGMTLLLLL | 0.667 | 36 | SB | Large T | A0202 |
| 569 ILQSGMTLLLL | 0.666 | 36 | SB | Large T | A0202 |
| 448 ALNVNLPMERL | 0.624 | 58 | WB | Large T | A0202 |
| 576 LLLLLIWFRPV | 0.621 | 60 | WB | Large T | A0202 |
| 152 FSNRTLACFAV | 0.601 | 74 | WB | Large T | A0202 |
| 287 FLLLGMYLEFQ | 0.593 | 82 | WB | Large T | A0202 |
| 528 TMNEYPVPKTL | 0.587 | 87 | WB | Large T | A0202 |
| 11 ELMDLLGLERA | 0.582 | 92 | WB | Large T | A0202 |
| 243 HIIEESIQGGL | 0.571 | 103 | WB | Large T | A0202 |
| 369 ILDKMDLIFGA | 0.561 | 115 | WB | Large T | A0202 |
| 212 FCQKLCTFSFL | 0.560 | 116 | WB | Large T | A0202 |
| 375 LIFGAHGNAVL | 0.541 | 142 | WB | Large T | A0202 |
| 461 ELGVAIDQYMV | 0.541 | 143 | WB | Large T | A0202 |
| 409 FLHCVVFNVPK | 0.524 | 171 | WB | Large T | A0202 |
| 439 GLLDLCGGKAL | 0.519 | 181 | WB | Large T | A0202 |
| 452 NLPMERLTFEL | 0.515 | 189 | WB | Large T | A0202 |
| 407 FDFLHCVVFNV | 0.493 | 239 | WB | Large T | A0202 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 3 | VLNREESMELM | 0.491 | 245 | WB | Large T | A0202 |
| 268 | QVSWKLITEYA | 0.488 | 255 | WB | Large T | A0202 |
| 290 | LGMYLEFQYNV | 0.481 | 273 | WB | Large T | A0202 |
| 217 | CTFSFLICKGV | 0.464 | 330 | WB | Large T | A0202 |
| 564 | LLEKRILQSGM | 0.447 | 398 | WB | Large T | A0202 |
| 222 | LICKGVNKEYL | 0.436 | 448 | WB | Large T | A0202 |
| 226 | GVNKEYLLYSA | 0.428 | 485 | WB | Large T | A0202 |
| 388 | YMAGVAWLHCL | 0.868 | 4 | SB | Large T | A0203 |
| 175 | KLMEKYSVTFI | 0.862 | 4 | SB | Large T | A0203 |
| 198 | FLTPHRHRVSA | 0.779 | 10 | SB | Large T | A0203 |
| 528 | TMNEYPVPKTL | 0.766 | 12 | SB | Large T | A0203 |
| 576 | LLLLLIWFRPV | 0.728 | 19 | SB | Large T | A0203 |
| 569 | ILQSGMTLLLL | 0.703 | 24 | SB | Large T | A0203 |
| 146 | FLSQAVFSNRT | 0.702 | 25 | SB | Large T | A0203 |
| 448 | ALNVNLPMERL | 0.668 | 36 | SB | Large T | A0203 |
| 11 | ELMDLLGLERA | 0.652 | 42 | SB | Large T | A0203 |
| 439 | GLLDLCGGKAL | 0.593 | 81 | WB | Large T | A0203 |
| 268 | QVSWKLITEYA | 0.577 | 97 | WB | Large T | A0203 |
| 570 | LQSGMTLLLLL | 0.548 | 132 | WB | Large T | A0203 |
| 226 | GVNKEYLLYSA | 0.540 | 144 | WB | Large T | A0203 |
| 243 | HIIEESIQGGL | 0.523 | 174 | WB | Large T | A0203 |
| 375 | LIFGAHGNAVL | 0.522 | 176 | WB | Large T | A0203 |
| 382 | NAVLEQYMAGV | 0.516 | 188 | WB | Large T | A0203 |
| 217 | CTFSFLICKGV | 0.515 | 190 | WB | Large T | A0203 |
| 374 | DLIFGAHGNAV | 0.511 | 197 | WB | Large T | A0203 |
| 404 | SVIFDFLHCVV | 0.498 | 229 | WB | Large T | A0203 |
| 152 | FSNRTLACFAV | 0.491 | 245 | WB | Large T | A0203 |
| 3 | VLNREESMELM | 0.473 | 298 | WB | Large T | A0203 |
| 287 | FLLLGMYLEFQ | 0.469 | 312 | WB | Large T | A0203 |
| 452 | NLPMERLTFEL | 0.465 | 327 | WB | Large T | A0203 |
| 369 | ILDKMDLIFGA | 0.464 | 328 | WB | Large T | A0203 |
| 568 | RILQSGMTLLL | 0.457 | 356 | WB | Large T | A0203 |
| 199 | LTPHRHRVSAI | 0.453 | 373 | WB | Large T | A0203 |
| 471 | VVFEDVKGTGA | 0.450 | 383 | WB | Large T | A0203 |
| 469 | YMVVFEDVKGT | 0.450 | 385 | WB | Large T | A0203 |
| 388 | YMAGVAWLHCL | 0.691 | 28 | SB | Large T | A0204 |
| 528 | TMNEYPVPKTL | 0.687 | 29 | SB | Large T | A0204 |
| 175 | KLMEKYSVTFI | 0.670 | 35 | SB | Large T | A0204 |
| 576 | LLLLLIWFRPV | 0.616 | 63 | WB | Large T | A0204 |
| 198 | FLTPHRHRVSA | 0.583 | 91 | WB | Large T | A0204 |
| 2 | KVLNREESMEL | 0.525 | 170 | WB | Large T | A0204 |
| 569 | ILQSGMTLLLL | 0.449 | 386 | WB | Large T | A0204 |
| 336 | SICQQAVDTVL | 0.431 | 472 | WB | Large T | A0204 |
| 544 | RQIDFRPKIYL | 0.801 | 8 | SB | Large T | A0206 |
| 388 | YMAGVAWLHCL | 0.796 | 9 | SB | Large T | A0206 |
| 175 | KLMEKYSVTFI | 0.743 | 16 | SB | Large T | A0206 |
| 576 | LLLLLIWFRPV | 0.738 | 16 | SB | Large T | A0206 |
| 570 | LQSGMTLLLLL | 0.711 | 22 | SB | Large T | A0206 |
| 198 | FLTPHRHRVSA | 0.706 | 24 | SB | Large T | A0206 |
| 404 | SVIFDFLHCVV | 0.688 | 29 | SB | Large T | A0206 |
| 152 | FSNRTLACFAV | 0.646 | 46 | SB | Large T | A0206 |
| 568 | RILQSGMTLLL | 0.644 | 47 | SB | Large T | A0206 |
| 369 | ILDKMDLIFGA | 0.622 | 59 | WB | Large T | A0206 |
| 2 | KVLNREESMEL | 0.620 | 61 | WB | Large T | A0206 |
| 148 | SQAVFSNRTLA | 0.618 | 62 | WB | Large T | A0206 |
| 335 | KSICQQAVDTV | 0.568 | 106 | WB | Large T | A0206 |
| 382 | NAVLEQYMAGV | 0.548 | 133 | WB | Large T | A0206 |
| 519 | TQIFPPGLVTM | 0.539 | 146 | WB | Large T | A0206 |
| 243 | HIIEESIQGGL | 0.519 | 182 | WB | Large T | A0206 |
| 287 | FLLLGMYLEFQ | 0.515 | 191 | WB | Large T | A0206 |
| 146 | FLSQAVFSNRT | 0.506 | 210 | WB | Large T | A0206 |
| 569 | ILQSGMTLLLL | 0.487 | 256 | WB | Large T | A0206 |
| 439 | GLLDLCGGKAL | 0.478 | 284 | WB | Large T | A0206 |
| 213 | CQKLCTFSFLI | 0.469 | 312 | WB | Large T | A0206 |
| 542 | FVRQIDFRPKI | 0.464 | 330 | WB | Large T | A0206 |
| 267 | KQVSWKLITEY | 0.462 | 336 | WB | Large T | A0206 |
| 471 | VVFEDVKGTGA | 0.460 | 343 | WB | Large T | A0206 |
| 383 | AVLEQYMAGVA | 0.445 | 407 | WB | Large T | A0206 |
| 577 | LLLLIWFRPVA | 0.444 | 408 | WB | Large T | A0206 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 155 | RTLACFAVYTT | 0.442 | 419 | WB | Large T | A0206 |
| 268 | QVSWKLITEYA | 0.438 | 437 | WB | Large T | A0206 |
| 375 | LIFGAHGNAVL | 0.437 | 441 | WB | Large T | A0206 |
| 452 | NLPMERLTFEL | 0.429 | 479 | WB | Large T | A0206 |
| 296 | FQYNVEECKKC | 0.427 | 490 | WB | Large T | A0206 |
| 388 | YMAGVAWLHCL | 0.966 | 1 | SB | Large T | A0211 |
| 198 | FLTPHRHRVSA | 0.943 | 1 | SB | Large T | A0211 |
| 576 | LLLLLIWFRPV | 0.898 | 3 | SB | Large T | A0211 |
| 569 | ILQSGMTLLLL | 0.893 | 3 | SB | Large T | A0211 |
| 439 | GLLDLCGGKAL | 0.887 | 3 | SB | Large T | A0211 |
| 452 | NLPMERLTFEL | 0.875 | 3 | SB | Large T | A0211 |
| 369 | ILDKMDLIFGA | 0.868 | 4 | SB | Large T | A0211 |
| 528 | TMNEYPVPKTL | 0.858 | 4 | SB | Large T | A0211 |
| 461 | ELGVAIDQYMV | 0.854 | 4 | SB | Large T | A0211 |
| 287 | FLLLGMYLEFQ | 0.832 | 6 | SB | Large T | A0211 |
| 454 | PMERLTFELGV | 0.823 | 6 | SB | Large T | A0211 |
| 11 | ELMDLLGLERA | 0.815 | 7 | SB | Large T | A0211 |
| 360 | EMLTERFNHIL | 0.779 | 10 | SB | Large T | A0211 |
| 374 | DLIFGAHGNAV | 0.775 | 11 | SB | Large T | A0211 |
| 175 | KLMEKYSVTFI | 0.773 | 11 | SB | Large T | A0211 |
| 577 | LLLLIWFRPVA | 0.765 | 12 | SB | Large T | A0211 |
| 568 | RILQSGMTLLL | 0.755 | 14 | SB | Large T | A0211 |
| 288 | LLLGMYLEFQY | 0.753 | 14 | SB | Large T | A0211 |
| 341 | AVDTVLAKKRV | 0.752 | 14 | SB | Large T | A0211 |
| 448 | ALNVNLPMERL | 0.747 | 15 | SB | Large T | A0211 |
| 375 | LIFGAHGNAVL | 0.691 | 28 | SB | Large T | A0211 |
| 603 | RLDSEISMYTF | 0.681 | 31 | SB | Large T | A0211 |
| 404 | SVIFDPLHCVV | 0.671 | 35 | SB | Large T | A0211 |
| 12 | LMDLLGLERAA | 0.669 | 35 | SB | Large T | A0211 |
| 146 | FLSQAVFSNRT | 0.648 | 45 | SB | Large T | A0211 |
| 485 | DLPSGHGINNL | 0.644 | 47 | SB | Large T | A0211 |
| 563 | FLLEKRILQSG | 0.601 | 74 | WB | Large T | A0211 |
| 2 | KVLNREESMEL | 0.597 | 77 | WB | Large T | A0211 |
| 501 | YLDGSVKVNLE | 0.596 | 78 | WB | Large T | A0211 |
| 189 | MCAGHNIIFFL | 0.591 | 83 | WB | Large T | A0211 |
| 428 | PIDSGKTTLAA | 0.577 | 97 | WB | Large T | A0211 |
| 405 | VIFDPLHCVVF | 0.563 | 112 | WB | Large T | A0211 |
| 196 | IFFLTPHRHRV | 0.551 | 128 | WB | Large T | A0211 |
| 217 | CTFSFLICKGV | 0.550 | 130 | WB | Large T | A0211 |
| 269 | VSWKLITEYAV | 0.549 | 132 | WB | Large T | A0211 |
| 109 | DMFASDEEATA | 0.544 | 138 | WB | Large T | A0211 |
| 544 | RQIDFRPKIYL | 0.542 | 141 | WB | Large T | A0211 |
| 3 | VLNREESMELM | 0.535 | 153 | WB | Large T | A0211 |
| 557 | SLQNSEFLLEK | 0.517 | 186 | WB | Large T | A0211 |
| 533 | PVPKTLQARFV | 0.511 | 198 | WB | Large T | A0211 |
| 243 | HIIEESIQGGL | 0.500 | 224 | WB | Large T | A0211 |
| 401 | KMDSVIFDFLH | 0.486 | 260 | WB | Large T | A0211 |
| 222 | LICKGVNKEYL | 0.462 | 338 | WB | Large T | A0211 |
| 353 | TLHMTREEMLT | 0.459 | 349 | WB | Large T | A0211 |
| 232 | LLYSALTRDPY | 0.435 | 449 | WB | Large T | A0211 |
| 215 | KLCTFSFLICK | 0.435 | 452 | WB | Large T | A0211 |
| 573 | GMTLLLLLIWF | 0.433 | 459 | WB | Large T | A0211 |
| 423 | WLFKGPIDSGK | 0.428 | 487 | WB | Large T | A0211 |
| 388 | YMAGVAWLHCL | 0.936 | 1 | SB | Large T | A0212 |
| 198 | FLTPHRHRVSA | 0.906 | 2 | SB | Large T | A0212 |
| 439 | GLLDLCGGKAL | 0.823 | 6 | SB | Large T | A0212 |
| 528 | TMNEYPVPKTL | 0.817 | 7 | SB | Large T | A0212 |
| 576 | LLLLLIWFRPV | 0.817 | 7 | SB | Large T | A0212 |
| 454 | PMERLTFELGV | 0.806 | 8 | SB | Large T | A0212 |
| 569 | ILQSGMTLLLL | 0.801 | 8 | SB | Large T | A0212 |
| 287 | FLLLGMYLEFQ | 0.777 | 11 | SB | Large T | A0212 |
| 369 | ILDKMDLIFGA | 0.756 | 13 | SB | Large T | A0212 |
| 374 | DLIFGAHGNAV | 0.706 | 24 | SB | Large T | A0212 |
| 360 | EMLTERFNHIL | 0.682 | 31 | SB | Large T | A0212 |
| 461 | ELGVAIDQYMV | 0.658 | 40 | SB | Large T | A0212 |
| 288 | LLLGMYLEFQY | 0.655 | 41 | SB | Large T | A0212 |
| 11 | ELMDLLGLERA | 0.654 | 42 | SB | Large T | A0212 |
| 452 | NLPMERLTFEL | 0.645 | 46 | SB | Large T | A0212 |
| 563 | FLLEKRILQSG | 0.643 | 47 | SB | Large T | A0212 |
| 375 | LIFGAHGNAVL | 0.631 | 54 | WB | Large T | A0212 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 175 | KLMEKYSVTFI | 0.620 | 60 | WB | Large T | A0212 |
| 577 | LLLLIWFRPVA | 0.601 | 74 | WB | Large T | A0212 |
| 269 | VSWKLITEYAV | 0.598 | 77 | WB | Large T | A0212 |
| 12 | LMDLLGLERAA | 0.577 | 96 | WB | Large T | A0212 |
| 146 | FLSQAVFSNRT | 0.577 | 97 | WB | Large T | A0212 |
| 448 | ALNVNLPMERL | 0.574 | 100 | WB | Large T | A0212 |
| 341 | AVDTVLAKKRV | 0.549 | 132 | WB | Large T | A0212 |
| 485 | DLPSGHGINNL | 0.537 | 149 | WB | Large T | A0212 |
| 405 | VIFDFLHCVVF | 0.536 | 151 | WB | Large T | A0212 |
| 3 | VLNREESMELM | 0.514 | 192 | WB | Large T | A0212 |
| 423 | WLFKGPIDSGK | 0.499 | 225 | WB | Large T | A0212 |
| 2 | KVLNREESMEL | 0.481 | 273 | WB | Large T | A0212 |
| 404 | SVIFDFLHCVV | 0.458 | 350 | WB | Large T | A0212 |
| 564 | LLEKRILQSGM | 0.452 | 374 | WB | Large T | A0212 |
| 469 | YMVVFEDVKGT | 0.452 | 377 | WB | Large T | A0212 |
| 243 | HIIEESIQGGL | 0.441 | 421 | WB | Large T | A0212 |
| 222 | LICKGVNKEYL | 0.440 | 428 | WB | Large T | A0212 |
| 217 | CTFSFLICKGV | 0.437 | 444 | WB | Large T | A0212 |
| 196 | IFFLTPHRHRV | 0.436 | 445 | WB | Large T | A0212 |
| 189 | MCAGHNIIFFL | 0.432 | 469 | WB | Large T | A0212 |
| 471 | VVFEDVKGTGA | 0.426 | 495 | WB | Large T | A0212 |
| 388 | YMAGVAWLHCL | 0.907 | 2 | SB | Large T | A0216 |
| 198 | FLTPHRHRVSA | 0.867 | 4 | SB | Large T | A0216 |
| 461 | ELGVAIDQYMV | 0.859 | 4 | SB | Large T | A0216 |
| 569 | ILQSGMTLLLL | 0.824 | 6 | SB | Large T | A0216 |
| 452 | NLPMERLTFEL | 0.778 | 11 | SB | Large T | A0216 |
| 454 | PMERLTFELGV | 0.771 | 11 | SB | Large T | A0216 |
| 576 | LLLLLIWFRPV | 0.754 | 14 | SB | Large T | A0216 |
| 528 | TMNEYPVPKTL | 0.752 | 14 | SB | Large T | A0216 |
| 374 | DLIFGAHGNAV | 0.737 | 17 | SB | Large T | A0216 |
| 287 | FLLLGMYLEFQ | 0.712 | 22 | SB | Large T | A0216 |
| 341 | AVDTVLAKKRV | 0.711 | 22 | SB | Large T | A0216 |
| 369 | ILDKMDLIFGA | 0.696 | 26 | SB | Large T | A0216 |
| 448 | ALNVNLPMERL | 0.693 | 27 | SB | Large T | A0216 |
| 175 | KLMEKYSVTFI | 0.691 | 28 | SB | Large T | A0216 |
| 439 | GLLDLCGGKAL | 0.678 | 32 | SB | Large T | A0216 |
| 146 | FLSQAVFSNRT | 0.661 | 39 | SB | Large T | A0216 |
| 11 | ELMDLLGLERA | 0.650 | 43 | SB | Large T | A0216 |
| 485 | DLPSGHGINNL | 0.642 | 48 | SB | Large T | A0216 |
| 375 | LIFGAHGNAVL | 0.639 | 49 | SB | Large T | A0216 |
| 360 | EMLTERFNHIL | 0.631 | 54 | WB | Large T | A0216 |
| 222 | LICKGVNKEYL | 0.620 | 60 | WB | Large T | A0216 |
| 568 | RILQSGMTLLL | 0.559 | 118 | WB | Large T | A0216 |
| 196 | IFFLTPHRHRV | 0.554 | 124 | WB | Large T | A0216 |
| 533 | PVPKTLQARFV | 0.551 | 128 | WB | Large T | A0216 |
| 404 | SVIFDFLHCVV | 0.528 | 165 | WB | Large T | A0216 |
| 189 | MCAGHNIIFFL | 0.523 | 173 | WB | Large T | A0216 |
| 288 | LLLGMYLEFQY | 0.517 | 186 | WB | Large T | A0216 |
| 2 | KVLNREESMEL | 0.514 | 191 | WB | Large T | A0216 |
| 577 | LLLLIWFRPVA | 0.493 | 240 | WB | Large T | A0216 |
| 544 | RQIDFRPKIYL | 0.485 | 264 | WB | Large T | A0216 |
| 269 | VSWKLITEYAV | 0.483 | 267 | WB | Large T | A0216 |
| 161 | AVYTTKEKAQI | 0.475 | 293 | WB | Large T | A0216 |
| 109 | DMFASDEEATA | 0.457 | 355 | WB | Large T | A0216 |
| 388 | YMAGVAWLHCL | 0.952 | 1 | SB | Large T | A0219 |
| 569 | ILQSGMTLLLL | 0.841 | 5 | SB | Large T | A0219 |
| 198 | FLTPHRHRVSA | 0.685 | 30 | SB | Large T | A0219 |
| 576 | LLLLLIWFRPV | 0.681 | 31 | SB | Large T | A0219 |
| 287 | FLLLGMYLEFQ | 0.664 | 37 | SB | Large T | A0219 |
| 461 | ELGVAIDQYMV | 0.655 | 41 | SB | Large T | A0219 |
| 369 | ILDKMDLIFGA | 0.647 | 45 | SB | Large T | A0219 |
| 11 | ELMDLLGLERA | 0.602 | 73 | WB | Large T | A0219 |
| 454 | PMERLTFELGV | 0.584 | 90 | WB | Large T | A0219 |
| 448 | ALNVNLPMERL | 0.562 | 114 | WB | Large T | A0219 |
| 146 | FLSQAVFSNRT | 0.559 | 118 | WB | Large T | A0219 |
| 374 | DLIFGAHGNAV | 0.556 | 121 | WB | Large T | A0219 |
| 360 | EMLTERFNHIL | 0.537 | 149 | WB | Large T | A0219 |
| 528 | TMNEYPVPKTL | 0.532 | 157 | WB | Large T | A0219 |
| 485 | DLPSGHGINNL | 0.524 | 172 | WB | Large T | A0219 |
| 452 | NLPMERLTFEL | 0.507 | 206 | WB | Large T | A0219 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 341 | AVDTVLAKKRV | 0.499 | 226 | WB | Large T | A0219 |
| 439 | GLLDLCGGKAL | 0.485 | 262 | WB | Large T | A0219 |
| 189 | MCAGHNIIFFL | 0.462 | 337 | WB | Large T | A0219 |
| 175 | KLMEKYSVTFI | 0.454 | 367 | WB | Large T | A0219 |
| 269 | VSWKLITEYAV | 0.448 | 394 | WB | Large T | A0219 |
| 156 | TLACFAVYTTK | 0.728 | 18 | SB | Large T | A0301 |
| 409 | FLHCVVFNVPK | 0.709 | 23 | SB | Large T | A0301 |
| 215 | KLCTFSFLICK | 0.671 | 35 | SB | Large T | A0301 |
| 50 | KMKRMNTLYKK | 0.667 | 36 | SB | Large T | A0301 |
| 391 | GVAWLHCLLPK | 0.656 | 41 | SB | Large T | A0301 |
| 205 | RVSAINNFCQK | 0.650 | 44 | SB | Large T | A0301 |
| 56 | TLYKKMEQDVK | 0.645 | 46 | SB | Large T | A0301 |
| 507 | KVNLEKKHLNK | 0.586 | 88 | WB | Large T | A0301 |
| 219 | FSFLICKGVNK | 0.581 | 92 | WB | Large T | A0301 |
| 195 | IIFFLTPHRHR | 0.575 | 99 | WB | Large T | A0301 |
| 164 | TTKEKAQILYK | 0.549 | 131 | WB | Large T | A0301 |
| 557 | SLQNSEFLLEK | 0.539 | 146 | WB | Large T | A0301 |
| 272 | KLITEYAVETK | 0.533 | 156 | WB | Large T | A0301 |
| 21 | AAWGNLPLMRK | 0.508 | 205 | WB | Large T | A0301 |
| 416 | NVPKRRYWLFK | 0.507 | 206 | WB | Large T | A0301 |
| 608 | ISMYTFSRMKY | 0.491 | 247 | WB | Large T | A0301 |
| 574 | MTLLLLLIWFR | 0.485 | 261 | WB | Large T | A0301 |
| 673 | HLCKGFQCFKR | 0.459 | 348 | WB | Large T | A0301 |
| 28 | LMRKAYLKKCK | 0.454 | 369 | WB | Large T | A0301 |
| 244 | IIEESIQGGLK | 0.448 | 393 | WB | Large T | A0301 |
| 497 | SLRDYLDGSVK | 0.443 | 416 | WB | Large T | A0301 |
| 423 | WLFKGPIDSGK | 0.432 | 464 | WB | Large T | A0301 |
| 401 | KMDSVIFDFLH | 0.427 | 490 | WB | Large T | A0301 |
| 391 | GVAWLHCLLPK | 0.825 | 6 | SB | Large T | A1101 |
| 215 | KLCTFSFLICK | 0.800 | 8 | SB | Large T | A1101 |
| 557 | SLQNSEFLLEK | 0.791 | 9 | SB | Large T | A1101 |
| 205 | RVSAINNFCQK | 0.784 | 10 | SB | Large T | A1101 |
| 574 | MTLLLLLIWFR | 0.768 | 12 | SB | Large T | A1101 |
| 21 | AAWGNLPLMRK | 0.742 | 16 | SB | Large T | A1101 |
| 164 | TTKEKAQILYK | 0.721 | 20 | SB | Large T | A1101 |
| 156 | TLACFAVYTTK | 0.719 | 20 | SB | Large T | A1101 |
| 526 | LVTMNEYPVPK | 0.716 | 21 | SB | Large T | A1101 |
| 507 | KVNLEKKHLNK | 0.706 | 24 | SB | Large T | A1101 |
| 325 | AIIFAESKNQK | 0.702 | 25 | SB | Large T | A1101 |
| 169 | AQILYKKLMEK | 0.699 | 25 | SB | Large T | A1101 |
| 118 | TADSQHSTPPK | 0.677 | 32 | SB | Large T | A1101 |
| 416 | NVPKRRYWLFK | 0.651 | 43 | SB | Large T | A1101 |
| 56 | TLYKKMEQDVK | 0.640 | 49 | SB | Large T | A1101 |
| 50 | KMKRMNTLYKK | 0.634 | 52 | WB | Large T | A1101 |
| 447 | KALNVNLPMER | 0.627 | 56 | WB | Large T | A1101 |
| 322 | FANAIIFAESK | 0.620 | 61 | WB | Large T | A1101 |
| 608 | ISMYTFSRMKY | 0.609 | 68 | WB | Large T | A1101 |
| 219 | FSFLICKGVNK | 0.594 | 80 | WB | Large T | A1101 |
| 338 | CQQAVDTVLAK | 0.593 | 81 | WB | Large T | A1101 |
| 362 | LTERFNHILDK | 0.588 | 86 | WB | Large T | A1101 |
| 409 | FLHCVVFNVPK | 0.555 | 122 | WB | Large T | A1101 |
| 195 | IIFFLTPHRHR | 0.547 | 134 | WB | Large T | A1101 |
| 437 | AAGLLDLCGGK | 0.547 | 134 | WB | Large T | A1101 |
| 20 | RAAWGNLPLMR | 0.531 | 160 | WB | Large T | A1101 |
| 272 | KLITEYAVETK | 0.526 | 169 | WB | Large T | A1101 |
| 607 | EISMYTFSRMK | 0.523 | 174 | WB | Large T | A1101 |
| 244 | IIEESIQGGLK | 0.506 | 209 | WB | Large T | A1101 |
| 339 | QQAVDTVLAKK | 0.471 | 307 | WB | Large T | A1101 |
| 467 | DQYMVVFEDVK | 0.445 | 404 | WB | Large T | A1101 |
| 497 | SLRDYLDGSVK | 0.436 | 448 | WB | Large T | A1101 |
| 581 | IWFRPVADFSK | 0.434 | 454 | WB | Large T | A1101 |
| 312 | PYHFKYHEKHF | 0.709 | 23 | SB | Large T | A2301 |
| 286 | VFLLLGMYLEF | 0.704 | 24 | SB | Large T | A2301 |
| 610 | MYTFSRMKYNI | 0.668 | 36 | SB | Large T | A2301 |
| 581 | IWFRPVADFSK | 0.626 | 57 | WB | Large T | A2301 |
| 500 | DYLDGSVKVNL | 0.598 | 77 | WB | Large T | A2301 |
| 211 | NFCQKLCTFSF | 0.575 | 99 | WB | Large T | A2301 |
| 83 | TYGTEEWESWW | 0.560 | 116 | WB | Large T | A2301 |
| 187 | RHMCAGHNIIF | 0.491 | 245 | WB | Large T | A2301 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 179 | KYSVTFISRHM | 0.485 | 263 | WB | Large T | A2301 |
| 316 | KYHEKHFANAI | 0.478 | 282 | WB | Large T | A2301 |
| 295 | EFQYNVEECKK | 0.478 | 283 | WB | Large T | A2301 |
| 617 | KYNICMGKCIL | 0.477 | 288 | WB | Large T | A2301 |
| 95 | SFNEKWDEDLF | 0.476 | 289 | WB | Large T | A2301 |
| 553 | YLRKSLQNSEF | 0.468 | 316 | WB | Large T | A2301 |
| 162 | VYTTKEKAQIL | 0.451 | 380 | WB | Large T | A2301 |
| 405 | VIFDFLHCVVF | 0.442 | 417 | WB | Large T | A2301 |
| 316 | KYHEKHFANAI | 0.677 | 33 | SB | Large T | A2402 |
| 286 | VFLLLGMYLEF | 0.676 | 33 | SB | Large T | A2402 |
| 312 | PYHFKYHEKHF | 0.617 | 62 | WB | Large T | A2402 |
| 610 | MYTFSRMKYNI | 0.570 | 105 | WB | Large T | A2402 |
| 83 | TYGTEEWESWW | 0.514 | 192 | WB | Large T | A2402 |
| 179 | KYSVTFISRHM | 0.513 | 193 | WB | Large T | A2402 |
| 162 | VYTTKEKAQIL | 0.482 | 272 | WB | Large T | A2402 |
| 211 | NFCQKLCTFSF | 0.461 | 341 | WB | Large T | A2402 |
| 286 | VFLLLGMYLEF | 0.742 | 16 | SB | Large T | A2403 |
| 316 | KYHEKHFANAI | 0.713 | 22 | SB | Large T | A2403 |
| 83 | TYGTEEWESWW | 0.653 | 42 | SB | Large T | A2403 |
| 312 | PYHFKYHEKHF | 0.613 | 66 | WB | Large T | A2403 |
| 397 | CLLPKMDSVIF | 0.571 | 103 | WB | Large T | A2403 |
| 162 | VYTTKEKAQIL | 0.563 | 112 | WB | Large T | A2403 |
| 365 | RFNHILDKMDL | 0.554 | 124 | WB | Large T | A2403 |
| 553 | YLRKSLQNSEF | 0.528 | 165 | WB | Large T | A2403 |
| 617 | KYNICMGKCIL | 0.509 | 202 | WB | Large T | A2403 |
| 211 | NFCQKLCTFSF | 0.504 | 213 | WB | Large T | A2403 |
| 95 | SFNEKWDEDLF | 0.478 | 285 | WB | Large T | A2403 |
| 187 | RHMCAGHNIIF | 0.466 | 321 | WB | Large T | A2403 |
| 163 | YTTKEKAQILY | 0.631 | 54 | WB | Large T | A2601 |
| 8 | ESMELMDLLGL | 0.474 | 297 | WB | Large T | A2601 |
| 163 | YTTKEKAQILY | 0.728 | 19 | SB | Large T | A2602 |
| 150 | AVFSNRTLACF | 0.703 | 24 | SB | Large T | A2602 |
| 170 | QILYKKLMEKY | 0.637 | 51 | WB | Large T | A2602 |
| 405 | VIFDFLHCVVF | 0.629 | 55 | WB | Large T | A2602 |
| 280 | ETKCEDVFLLL | 0.628 | 56 | WB | Large T | A2602 |
| 463 | GVAIDQYMVVF | 0.624 | 58 | WB | Large T | A2602 |
| 243 | HIIEESIQGGL | 0.535 | 153 | WB | Large T | A2602 |
| 356 | MTREEMLTERF | 0.491 | 247 | WB | Large T | A2602 |
| 142 | DLHQFLSQAVF | 0.472 | 304 | WB | Large T | A2602 |
| 450 | NVNLPMERLTF | 0.453 | 372 | WB | Large T | A2602 |
| 553 | YLRKSLQNSEF | 0.450 | 382 | WB | Large T | A2602 |
| 74 | GTWNSSEVPTY | 0.435 | 453 | WB | Large T | A2602 |
| 8 | ESMELMDLLGL | 0.433 | 462 | WB | Large T | A2602 |
| 221 | FLICKGVNKEY | 0.621 | 60 | WB | Large T | A2902 |
| 288 | LLLGMYLEFQY | 0.600 | 75 | WB | Large T | A2902 |
| 163 | YTTKEKAQILY | 0.475 | 293 | WB | Large T | A2902 |
| 286 | VFLLLGMYLEF | 0.470 | 307 | WB | Large T | A2902 |
| 170 | QILYKKLMEKY | 0.430 | 478 | WB | Large T | A2902 |
| 405 | VIFDFLHCVVF | 0.427 | 492 | WB | Large T | A2902 |
| 50 | KMKRMNTLYKK | 0.760 | 13 | SB | Large T | A3001 |
| 28 | LMRKAYLKKCK | 0.745 | 15 | SB | Large T | A3001 |
| 164 | TTKEKAQILYK | 0.727 | 19 | SB | Large T | A3001 |
| 507 | KVNLEKKHLNK | 0.707 | 23 | SB | Large T | A3001 |
| 680 | CFKRPKTPPPK | 0.688 | 29 | SB | Large T | A3001 |
| 409 | FLHCVVFNVPK | 0.668 | 36 | SB | Large T | A3001 |
| 497 | SLRDYLDGSVK | 0.662 | 38 | SB | Large T | A3001 |
| 158 | ACFAVYTTKEK | 0.661 | 39 | SB | Large T | A3001 |
| 416 | NVPKRRYWLFK | 0.594 | 80 | WB | Large T | A3001 |
| 541 | RFVRQIDFRPK | 0.587 | 87 | WB | Large T | A3001 |
| 215 | KLCTFSFLICK | 0.567 | 107 | WB | Large T | A3001 |
| 348 | KKRVDTLHMTR | 0.563 | 112 | WB | Large T | A3001 |
| 205 | RVSAINNFCQK | 0.546 | 136 | WB | Large T | A3001 |
| 526 | LVTMNEYPVPK | 0.536 | 151 | WB | Large T | A3001 |
| 306 | CQKKDQPYHFK | 0.508 | 204 | WB | Large T | A3001 |
| 118 | TADSQHSTPPK | 0.505 | 211 | WB | Large T | A3001 |
| 272 | KLITEYAVETK | 0.489 | 252 | WB | Large T | A3001 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 156 | TLACFAVYTTK | 0.486 | 259 | WB | Large T | A3001 |
| 557 | SLQNSEFLLEK | 0.482 | 271 | WB | Large T | A3001 |
| 169 | AQILYKKLMEK | 0.470 | 309 | WB | Large T | A3001 |
| 539 | QARFVRQIDFR | 0.458 | 353 | WB | Large T | A3001 |
| 581 | IWFRPVADFSK | 0.451 | 378 | WB | Large T | A3001 |
| 574 | MTLLLLLIWFR | 0.433 | 462 | WB | Large T | A3001 |
| 34 | LKKCKEFHPDK | 0.429 | 482 | WB | Large T | A3001 |
| 267 | KQVSWKLITEY | 0.523 | 175 | WB | Large T | A3002 |
| 170 | QILYKKLMEKY | 0.442 | 420 | WB | Large T | A3002 |
| 574 | MTLLLLLIWFR | 0.869 | 4 | SB | Large T | A3101 |
| 50 | KMKRMNTLYKK | 0.838 | 5 | SB | Large T | A3101 |
| 447 | KALNVNLPMER | 0.794 | 9 | SB | Large T | A3101 |
| 145 | QFLSQAVFSNR | 0.744 | 15 | SB | Large T | A3101 |
| 195 | IIFFLTPHRHR | 0.736 | 17 | SB | Large T | A3101 |
| 673 | HLCKGFQCFKR | 0.670 | 35 | SB | Large T | A3101 |
| 539 | QARFVRQIDFR | 0.653 | 42 | SB | Large T | A3101 |
| 355 | HMTREEMLTER | 0.647 | 45 | SB | Large T | A3101 |
| 205 | RVSAINNFCQK | 0.637 | 50 | WB | Large T | A3101 |
| 558 | LQNSEFLLEKR | 0.626 | 57 | WB | Large T | A3101 |
| 541 | RFVRQIDFRPK | 0.624 | 58 | WB | Large T | A3101 |
| 20 | RAAWGNLPLMR | 0.617 | 63 | WB | Large T | A3101 |
| 121 | SQHSTPPKKKR | 0.607 | 70 | WB | Large T | A3101 |
| 621 | CMGKCILDITR | 0.587 | 87 | WB | Large T | A3101 |
| 177 | MEKYSVTFISR | 0.582 | 91 | WB | Large T | A3101 |
| 215 | KLCTFSFLICK | 0.554 | 124 | WB | Large T | A3101 |
| 164 | TTKEKAQILYK | 0.536 | 151 | WB | Large T | A3101 |
| 680 | CFKRPKTPPPK | 0.526 | 169 | WB | Large T | A3101 |
| 534 | VPKTLQARFVR | 0.518 | 183 | WB | Large T | A3101 |
| 193 | HNIIFFLTPHR | 0.500 | 223 | WB | Large T | A3101 |
| 507 | KVNLEKKHLNK | 0.492 | 244 | WB | Large T | A3101 |
| 306 | CQKKDQPYHFK | 0.486 | 259 | WB | Large T | A3101 |
| 526 | LVTMNEYPVPK | 0.467 | 319 | WB | Large T | A3101 |
| 229 | KEYLLYSALTR | 0.466 | 321 | WB | Large T | A3101 |
| 593 | IQSRIVEWKER | 0.449 | 389 | WB | Large T | A3101 |
| 31 | KAYLKKCKEFH | 0.448 | 392 | WB | Large T | A3101 |
| 545 | QIDFRPKIYLR | 0.448 | 393 | WB | Large T | A3101 |
| 401 | KMDSVIFDFLH | 0.443 | 415 | WB | Large T | A3101 |
| 605 | DSEISMYTFSR | 0.438 | 435 | WB | Large T | A3101 |
| 28 | LMRKAYLKKCK | 0.433 | 461 | WB | Large T | A3101 |
| 574 | MTLLLLLIWFR | 0.838 | 5 | SB | Large T | A3301 |
| 195 | IIFFLTPHRHR | 0.685 | 30 | SB | Large T | A3301 |
| 605 | DSEISMYTFSR | 0.684 | 30 | SB | Large T | A3301 |
| 539 | QARFVRQIDFR | 0.650 | 44 | SB | Large T | A3301 |
| 145 | QFLSQAVFSNR | 0.639 | 49 | SB | Large T | A3301 |
| 355 | HMTREEMLTER | 0.625 | 57 | WB | Large T | A3301 |
| 673 | HLCKGFQCFKR | 0.606 | 70 | WB | Large T | A3301 |
| 531 | EYPVPKTLQAR | 0.582 | 92 | WB | Large T | A3301 |
| 545 | QIDFRPKIYLR | 0.484 | 264 | WB | Large T | A3301 |
| 285 | DVFLLLGMYLE | 0.462 | 337 | WB | Large T | A3301 |
| 416 | NVPKRRYWLFK | 0.441 | 424 | WB | Large T | A3301 |
| 177 | MEKYSVTFISR | 0.440 | 428 | WB | Large T | A3301 |
| 574 | MTLLLLLIWFR | 0.820 | 7 | SB | Large T | A6801 |
| 607 | EISMYTFSRMK | 0.808 | 7 | SB | Large T | A6801 |
| 322 | FANAIIFAESK | 0.780 | 10 | SB | Large T | A6801 |
| 605 | DSEISMYTFSR | 0.765 | 12 | SB | Large T | A6801 |
| 195 | IIFFLTPHRHR | 0.762 | 13 | SB | Large T | A6801 |
| 156 | TLACFAVYTTK | 0.756 | 14 | SB | Large T | A6801 |
| 205 | RVSAINNFCQK | 0.712 | 22 | SB | Large T | A6801 |
| 539 | QARFVRQIDFR | 0.695 | 27 | SB | Large T | A6801 |
| 219 | FSFLICKGVNK | 0.676 | 33 | SB | Large T | A6801 |
| 193 | HNIIFFLTPHR | 0.673 | 34 | SB | Large T | A6801 |
| 673 | HLCKGFQCFKR | 0.665 | 37 | SB | Large T | A6801 |
| 164 | TTKEKAQILYK | 0.656 | 41 | SB | Large T | A6801 |
| 355 | HMTREEMLTER | 0.654 | 42 | SB | Large T | A6801 |
| 526 | LVTMNEYPVPK | 0.641 | 48 | SB | Large T | A6801 |
| 416 | NVPKRRYWLFK | 0.635 | 51 | WB | Large T | A6801 |
| 340 | QAVDTVLAKKR | 0.620 | 61 | WB | Large T | A6801 |
| 409 | FLHCVVFNVPK | 0.589 | 85 | WB | Large T | A6801 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos peptide | logscore | affinity (nM) | Bind Level | Protein Name | Allele |
|---|---|---|---|---|---|
| 20 RAAWGNLPLMR | 0.562 | 114 | WB | Large T | A6801 |
| 325 AIIFAESKNQK | 0.554 | 124 | WB | Large T | A6801 |
| 56 TLYKKMEQDVK | 0.549 | 131 | WB | Large T | A6801 |
| 163 YTTKEKAQILY | 0.548 | 132 | WB | Large T | A6801 |
| 467 DQYMVVFEDVK | 0.534 | 155 | WB | Large T | A6801 |
| 391 GVAWLHCLLPK | 0.521 | 178 | WB | Large T | A6801 |
| 608 ISMYTFSRMKY | 0.493 | 240 | WB | Large T | A6801 |
| 295 EFQYNVEECKK | 0.489 | 251 | WB | Large T | A6801 |
| 25 NLPLMRKAYLK | 0.482 | 272 | WB | Large T | A6801 |
| 447 KALNVNLPMER | 0.477 | 288 | WB | Large T | A6801 |
| 545 QIDFRPKIYLR | 0.471 | 305 | WB | Large T | A6801 |
| 362 LTERFNHILDK | 0.463 | 332 | WB | Large T | A6801 |
| 177 MEKYSVTFISR | 0.463 | 335 | WB | Large T | A6801 |
| 145 QFLSQAVFSNR | 0.460 | 343 | WB | Large T | A6801 |
| 423 WLFKGPIDSGK | 0.456 | 361 | WB | Large T | A6801 |
| 118 TADSQHSTPPK | 0.435 | 450 | WB | Large T | A6801 |
| 557 SLQNSEFLLEK | 0.430 | 477 | WB | Large T | A6801 |
| 189 MCAGHNIIFFL | 0.792 | 9 | SB | Large T | A6802 |
| 217 CTFSFLICKGV | 0.752 | 14 | SB | Large T | A6802 |
| 404 SVIFDFLHCVV | 0.734 | 17 | SB | Large T | A6802 |
| 382 NAVLEQYMAGV | 0.680 | 31 | SB | Large T | A6802 |
| 403 DSVIFDFLHCV | 0.654 | 42 | SB | Large T | A6802 |
| 8 ESMELMDLLGL | 0.653 | 42 | SB | Large T | A6802 |
| 152 FSNRTLACFAV | 0.617 | 62 | WB | Large T | A6802 |
| 290 LGMYLEFQYNV | 0.606 | 70 | WB | Large T | A6802 |
| 462 LGVAIDQYMVV | 0.591 | 83 | WB | Large T | A6802 |
| 268 QVSWKLITEYA | 0.576 | 98 | WB | Large T | A6802 |
| 280 ETKCEDVFLLL | 0.573 | 101 | WB | Large T | A6802 |
| 11 ELMDLLGLERA | 0.570 | 105 | WB | Large T | A6802 |
| 234 YSALTRDPYHI | 0.549 | 132 | WB | Large T | A6802 |
| 388 YMAGVAWLHCL | 0.531 | 159 | WB | Large T | A6802 |
| 243 HIIEESIQGGL | 0.507 | 206 | WB | Large T | A6802 |
| 181 SVTFISRHMCA | 0.503 | 216 | WB | Large T | A6802 |
| 407 FDFLHCVVFNV | 0.489 | 251 | WB | Large T | A6802 |
| 374 DLIFGAHGNAV | 0.480 | 277 | WB | Large T | A6802 |
| 542 FVRQIDFRPKI | 0.446 | 400 | WB | Large T | A6802 |
| 212 FCQKLCTFSFL | 0.433 | 460 | WB | Large T | A6802 |
| 461 ELGVAIDQYMV | 0.429 | 484 | WB | Large T | A6802 |
| 388 YMAGVAWLHCL | 0.652 | 42 | SB | Large T | A6901 |
| 461 ELGVAIDQYMV | 0.575 | 99 | WB | Large T | A6901 |
| 374 DLIFGAHGNAV | 0.573 | 102 | WB | Large T | A6901 |
| 8 ESMELMDLLGL | 0.560 | 116 | WB | Large T | A6901 |
| 152 FSNRTLACFAV | 0.541 | 143 | WB | Large T | A6901 |
| 11 ELMDLLGLERA | 0.539 | 145 | WB | Large T | A6901 |
| 576 LLLLLIWFRPV | 0.519 | 182 | WB | Large T | A6901 |
| 404 SVIFDFLHCVV | 0.512 | 196 | WB | Large T | A6901 |
| 360 EMLTERFNHIL | 0.498 | 228 | WB | Large T | A6901 |
| 189 MCAGHNIIFFL | 0.474 | 297 | WB | Large T | A6901 |
| 243 HIIEESIQGGL | 0.472 | 303 | WB | Large T | A6901 |
| 382 NAVLEQYMAGV | 0.470 | 309 | WB | Large T | A6901 |
| 217 CTFSFLICKGV | 0.457 | 355 | WB | Large T | A6901 |
| 269 VSWKLITEYAV | 0.443 | 414 | WB | Large T | A6901 |
| 55 NTLYKKMEQDV | 0.432 | 464 | WB | Large T | A6901 |
| 532 YPVPKTLQARF | 0.646 | 46 | SB | Large T | B0702 |
| 553 YLRKSLQNSEF | 0.492 | 244 | WB | Large T | B0801 |
| 267 KQVSWKLITEY | 0.566 | 109 | WB | Large T | B1501 |
| 538 LQARFVRQIDF | 0.565 | 110 | WB | Large T | B1501 |
| 553 YLRKSLQNSEF | 0.561 | 116 | WB | Large T | B1501 |
| 188 HMCAGHNIIFF | 0.554 | 124 | WB | Large T | B1501 |
| 388 YMAGVAWLHCL | 0.542 | 141 | WB | Large T | B1501 |
| 221 FLICKGVNKEY | 0.541 | 142 | WB | Large T | B1501 |
| 544 RQIDFRPKIYL | 0.521 | 178 | WB | Large T | B1501 |
| 579 LLIWFRPVADF | 0.518 | 183 | WB | Large T | B1501 |
| 519 TQIFPPGLVTM | 0.480 | 276 | WB | Large T | B1501 |
| 232 LLYSALTRDPY | 0.478 | 283 | WB | Large T | B1501 |
| 405 VIFDFLHCVVF | 0.474 | 295 | WB | Large T | B1501 |
| 608 ISMYTFSRMKY | 0.450 | 384 | WB | Large T | B1501 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/ NetMHC/ database. The MHC class 1 molecules for which no binders were found are not listed.

| pos | peptide | logscore | affinity (nM) | Bind Level | Protein Name | Allele |
|---|---|---|---|---|---|---|
| 150 | AVFSNRTLACF | 0.434 | 457 | WB | Large T | B1501 |
| 570 | LQSGMTLLLLL | 0.429 | 483 | WB | Large T | B1501 |
| 668 | HSQELHLCKGF | 0.426 | 495 | WB | Large T | B1501 |
| 86 | TEEWESWWSSF | 0.650 | 44 | SB | Large T | B1801 |
| 460 | FELGVAIDQYM | 0.643 | 47 | SB | Large T | B1801 |
| 318 | HEKHFANAIIF | 0.625 | 57 | WB | Large T | B1801 |
| 18 | LERAAWGNLPL | 0.572 | 102 | WB | Large T | B1801 |
| 79 | SEVPTYGTEEW | 0.556 | 122 | WB | Large T | B1801 |
| 601 | KERLDSEISMY | 0.505 | 210 | WB | Large T | B1801 |
| 664 | SENPHSQELHL | 0.497 | 230 | WB | Large T | B1801 |
| 532 | YPVPKTLQARF | 0.461 | 341 | WB | Large T | B1801 |
| 614 | SRMKYNICMGK | 0.547 | 134 | WB | Large T | B2705 |
| 567 | KRILQSGMTLL | 0.507 | 207 | WB | Large T | B2705 |
| 544 | RQIDFRPKIYL | 0.450 | 382 | WB | Large T | B2705 |
| 548 | FRPKIYLRKSL | 0.450 | 385 | WB | Large T | B2705 |
| 522 | FPPGLVTMNEY | 0.812 | 7 | SB | Large T | B3501 |
| 532 | YPVPKTLQARF | 0.780 | 10 | SB | Large T | B3501 |
| 277 | YAVETKCEDVF | 0.742 | 16 | SB | Large T | B3501 |
| 399 | LPKMDSVIFDF | 0.560 | 116 | WB | Large T | B3501 |
| 41 | HPDKGGDEDKM | 0.545 | 136 | WB | Large T | B3501 |
| 392 | VAWLHCLLPKM | 0.532 | 158 | WB | Large T | B3501 |
| 139 | FPSDLHQFLSQ | 0.494 | 238 | WB | Large T | B3501 |
| 232 | LLYSALTRDPY | 0.453 | 371 | WB | Large T | B3501 |
| 459 | TFELGVAIDQY | 0.442 | 417 | WB | Large T | B3501 |
| 317 | YHEKHFANAII | 0.586 | 88 | WB | Large T | B3901 |
| 388 | YMAGVAWLHCL | 0.549 | 130 | WB | Large T | B3901 |
| 6 | REESMELMDLL | 0.673 | 34 | SB | Large T | B4001 |
| 664 | SENPHSQELHL | 0.668 | 36 | SB | Large T | B4001 |
| 18 | LERAAWGNLPL | 0.630 | 54 | WB | Large T | B4001 |
| 385 | LEQYMAGVAWL | 0.562 | 114 | WB | Large T | B4001 |
| 460 | FELGVAIDQYM | 0.552 | 126 | WB | Large T | B4001 |
| 279 | VETKCEDVFLL | 0.540 | 145 | WB | Large T | B4001 |
| 606 | SEISMYTFSRM | 0.498 | 228 | WB | Large T | B4001 |
| 133 | VEDPKDFPSDL | 0.446 | 399 | WB | Large T | B4001 |
| 166 | KEKAQILYKKL | 0.440 | 428 | WB | Large T | B4001 |
| 47 | DEDKMKRMNTL | 0.434 | 458 | WB | Large T | B4001 |
| 664 | SENPHSQELHL | 0.540 | 144 | WB | Large T | B4002 |
| 6 | REESMELMDLL | 0.511 | 198 | WB | Large T | B4002 |
| 264 | EETKQVSWKLI | 0.502 | 219 | WB | Large T | B4002 |
| 318 | HEKHFANAIIF | 0.459 | 347 | WB | Large T | B4002 |
| 359 | EEMLTERFNHI | 0.445 | 403 | WB | Large T | B4002 |
| 279 | VETKCEDVFLL | 0.432 | 464 | WB | Large T | B4002 |
| 79 | SEVPTYGTEEW | 0.512 | 196 | WB | Large T | B4402 |
| 261 | EEPEETKQVSW | 0.484 | 267 | WB | Large T | B4402 |
| 561 | SEFLLEKRILQ | 0.477 | 287 | WB | Large T | B4403 |
| 664 | SENPHSQELHL | 0.464 | 331 | WB | Large T | B4403 |
| 606 | SEISMYTFSRM | 0.457 | 356 | WB | Large T | B4403 |
| 79 | SEVPTYGTEEW | 0.452 | 375 | WB | Large T | B4403 |
| 261 | EEPEETKQVSW | 0.438 | 438 | WB | Large T | B4403 |
| 359 | EEMLTERFNHI | 0.482 | 271 | WB | Large T | B4501 |
| 115 | EEATADSQHST | 0.450 | 383 | WB | Large T | B4501 |
| 453 | LPMERLTFELG | 0.470 | 309 | WB | Large T | B5101 |
| 532 | YPVPKTLQARF | 0.433 | 463 | WB | Large T | B5101 |
| 522 | FPPGLVTMNEY | 0.689 | 28 | SB | Large T | B5301 |
| 532 | YPVPKTLQARF | 0.645 | 46 | SB | Large T | B5301 |
| 399 | LPKMDSVIFDF | 0.555 | 122 | WB | Large T | B5301 |
| 277 | YAVETKCEDVF | 0.474 | 296 | WB | Large T | B5301 |
| 453 | LPMERLTFELG | 0.580 | 93 | WB | Large T | B5401 |
| 522 | FPPGLVTMNEY | 0.544 | 138 | WB | Large T | B5401 |
| 427 | GPIDSGKTTLA | 0.508 | 204 | WB | Large T | B5401 |

TABLE M-continued

Prediction of BK virus Large T protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 82 | PTYGTEEWESW | 0.576 | 98 | WB | Large T | B5701 |
| 90 | ESWWSSFNEKW | 0.678 | 32 | SB | Large T | B5801 |
| 66 | KVAHQPDFGTW | 0.658 | 40 | SB | Large T | B5801 |
| 572 | SGMTLLLLLIW | 0.539 | 146 | WB | Large T | B5801 |
| 413 | VVFNVPKRRYW | 0.527 | 167 | WB | Large T | B5801 |
| 277 | YAVETKCEDVF | 0.495 | 235 | WB | Large T | B5801 |
| 608 | ISMYTFSRMKY | 0.487 | 258 | WB | Large T | B5801 |
| 82 | PTYGTEEWESW | 0.458 | 353 | WB | Large T | B5801 |

SEQ ID NOS.: 55454-58054

Preferred BK virus fragments of agnoprotein capable of interacting with one or more MHC class 1 molecules are listed in Table N.

TABLE N

Prediction of BK virus Agnoprotein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| | | 8-mers | | | | |
| 36 | FIFILELL | 0.641 | 48 | SB | Agno | A0201 |
| 59 | STTALPAV | 0.453 | 373 | WB | Agno | A0201 |
| 36 | FIFILELL | 0.785 | 10 | SB | Agno | A0202 |
| 12 | QLSRQASV | 0.702 | 25 | SB | Agno | A0202 |
| 12 | QLSRQASV | 0.712 | 22 | SB | Agno | A0203 |
| 59 | STTALPAV | 0.537 | 149 | WB | Agno | A0203 |
| 36 | FIFILELL | 0.524 | 171 | WB | Agno | A0203 |
| 32 | AQRIFIFI | 0.503 | 216 | WB | Agno | A0203 |
| 6 | NLVVLRQL | 0.431 | 473 | WB | Agno | A0203 |
| 12 | QLSRQASV | 0.508 | 206 | WB | Agno | A0204 |
| 59 | STTALPAV | 0.489 | 252 | WB | Agno | A0204 |
| 32 | AQRIFIFI | 0.646 | 46 | SB | Agno | A0206 |
| 36 | FIFILELL | 0.585 | 89 | WB | Agno | A0206 |
| 59 | STTALPAV | 0.582 | 92 | WB | Agno | A0206 |
| 12 | QLSRQASV | 0.479 | 281 | WB | Agno | A0206 |
| 38 | FILELLLE | 0.474 | 297 | WB | Agno | A0206 |
| 12 | QLSRQASV | 0.883 | 3 | SB | Agno | A0211 |
| 36 | FIFILELL | 0.782 | 10 | SB | Agno | A0211 |
| 59 | STTALPAV | 0.695 | 27 | SB | Agno | A0211 |
| 6 | NLVVLRQL | 0.688 | 29 | SB | Agno | A0211 |
| 12 | QLSRQASV | 0.825 | 6 | SB | Agno | A0212 |
| 36 | FIFILELL | 0.705 | 24 | SB | Agno | A0212 |
| 59 | STTALPAV | 0.504 | 214 | WB | Agno | A0212 |
| 46 | FCRGEDSV | 0.502 | 219 | WB | Agno | A0212 |
| 12 | QLSRQASV | 0.877 | 3 | SB | Agno | A0216 |
| 36 | FIFILELL | 0.643 | 47 | SB | Agno | A0216 |
| 6 | NLVVLRQL | 0.580 | 93 | WB | Agno | A0216 |
| 59 | STTALPAV | 0.474 | 294 | WB | Agno | A0216 |
| 1 | FCEPKNLV | 0.427 | 494 | WB | Agno | A0216 |
| 12 | QLSRQASV | 0.746 | 15 | SB | Agno | A0219 |
| 59 | STTALPAV | 0.455 | 364 | WB | Agno | A0219 |
| 23 | KTWTGTKK | 0.662 | 38 | SB | Agno | A0301 |
| 60 | TTALPAVK | 0.568 | 107 | WB | Agno | A0301 |
| 8 | VVLRQLSR | 0.444 | 408 | WB | Agno | A0301 |
| 13 | LSRQASVK | 0.436 | 444 | WB | Agno | A0301 |
| 60 | TTALPAVK | 0.785 | 10 | SB | Agno | A1101 |
| 23 | KTWTGTKK | 0.637 | 50 | WB | Agno | A1101 |
| 8 | VVLRQLSR | 0.554 | 124 | WB | Agno | A1101 |
| 16 | QASVKVGK | 0.458 | 351 | WB | Agno | A1101 |
| 35 | IFIFILEL | 0.573 | 101 | WB | Agno | A2301 |
| 31 | RAQRIFIF | 0.514 | 191 | WB | Agno | A2301 |
| 37 | IFILELLL | 0.454 | 367 | WB | Agno | A2301 |
| 37 | IFILELLL | 0.536 | 150 | WB | Agno | A2402 |
| 35 | IFIFILEL | 0.478 | 284 | WB | Agno | A2402 |
| 31 | RAQRIFIF | 0.431 | 472 | WB | Agno | A2402 |
| 31 | RAQRIFIF | 0.449 | 386 | WB | Agno | A2403 |
| 13 | LSRQASVK | 0.690 | 28 | SB | Agno | A3001 |
| 23 | KTWTGTKK | 0.659 | 40 | SB | Agno | A3001 |
| 27 | GTKKRAQR | 0.803 | 8 | SB | Agno | A3101 |
| 23 | KTWTGTKK | 0.648 | 45 | SB | Agno | A3101 |
| 8 | VVLRQLSR | 0.587 | 87 | WB | Agno | A3101 |
| 41 | ELLLEFCR | 0.701 | 25 | SB | Agno | A3301 |
| 27 | GTKKRAQR | 0.564 | 111 | WB | Agno | A3301 |
| 8 | VVLRQLSR | 0.466 | 323 | WB | Agno | A3301 |
| 60 | TTALPAVK | 0.774 | 11 | SB | Agno | A6801 |
| 41 | ELLLEFCR | 0.627 | 56 | WB | Agno | A6801 |
| 27 | GTKKRAQR | 0.537 | 150 | WB | Agno | A6801 |
| 16 | QASVKVGK | 0.459 | 349 | WB | Agno | A6801 |
| 51 | DSVDGKNK | 0.431 | 473 | WB | Agno | A6801 |
| 59 | STTALPAV | 0.655 | 42 | SB | Agno | A6802 |
| 33 | QRIFIFIL | 0.552 | 127 | WB | Agno | A6802 |
| 36 | FIFILELL | 0.512 | 195 | WB | Agno | A6802 |

TABLE N-continued

Prediction of BK virus Agnoprotein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 59 | STTALPAV | 0.674 | 34 | SB | Agno | A6901 |
| 36 | FIFILELL | 0.441 | 424 | WB | Agno | A6901 |
| 63 | LPAVKDSV | 0.582 | 91 | WB | Agno | B0702 |
| 3 | EPKNLVVL | 0.427 | 490 | WB | Agno | B0702 |
| 33 | QRIFIFIL | 0.431 | 472 | WB | Agno | B2705 |
| 3 | EPKNLVVL | 0.518 | 184 | WB | Agno | B3501 |
| 63 | LPAVKDSV | 0.585 | 88 | WB | Agno | B5101 |
| 3 | EPKNLVVL | 0.456 | 358 | WB | Agno | B5301 |
| 63 | LPAVKDSV | 0.745 | 15 | SB | Agno | B5401 |
| 31 | RAQRIFIF | 0.503 | 215 | WB | Agno | B5801 |

9-mers

| pos | peptide | logscore | affinity (nM) | Bind Level | Protein Name | Allele |
|---|---|---|---|---|---|---|
| 34 | RIFIFILEL | 0.674 | 34 | SB | Agno | A0201 |
| 36 | FIFILELLL | 0.613 | 66 | WB | Agno | A0201 |
| 11 | RQLSRQASV | 0.561 | 115 | WB | Agno | A0201 |
| 62 | ALPAVKDSV | 0.503 | 215 | WB | Agno | A0201 |
| 38 | FILELLLEF | 0.448 | 392 | WB | Agno | A0201 |
| 36 | FIFILELLL | 0.698 | 26 | SB | Agno | A0202 |
| 62 | ALPAVKDSV | 0.609 | 68 | WB | Agno | A0202 |
| 34 | RIFIFILEL | 0.540 | 144 | WB | Agno | A0202 |
| 11 | RQLSRQASV | 0.688 | 29 | SB | Agno | A0203 |
| 62 | ALPAVKDSV | 0.667 | 36 | SB | Agno | A0203 |
| 9 | VLRQLSRQA | 0.455 | 362 | WB | Agno | A0203 |
| 34 | RIFIFILEL | 0.439 | 433 | WB | Agno | A0203 |
| 62 | ALPAVKDSV | 0.515 | 190 | WB | Agno | A0204 |
| 11 | RQLSRQASV | 0.855 | 4 | SB | Agno | A0206 |
| 38 | FILELLLEF | 0.731 | 18 | SB | Agno | A0206 |
| 62 | ALPAVKDSV | 0.588 | 86 | WB | Agno | A0206 |
| 32 | AQRIFIFIL | 0.561 | 116 | WB | Agno | A0206 |
| 58 | KSTTALPAV | 0.559 | 118 | WB | Agno | A0206 |
| 34 | RIFIFILEL | 0.506 | 208 | WB | Agno | A0206 |
| 31 | RAQRIFIFI | 0.487 | 256 | WB | Agno | A0206 |
| 36 | FIFILELLL | 0.455 | 365 | WB | Agno | A0206 |
| 62 | ALPAVKDSV | 0.927 | 2 | SB | Agno | A0211 |
| 34 | RIFIFILEL | 0.836 | 5 | SB | Agno | A0211 |
| 36 | FIFILELLL | 0.796 | 9 | SB | Agno | A0211 |
| 38 | FILELLLEF | 0.621 | 60 | WB | Agno | A0211 |
| 9 | VLRQLSRQA | 0.546 | 135 | WB | Agno | A0211 |
| 11 | RQLSRQASV | 0.445 | 405 | WB | Agno | A0211 |
| 62 | ALPAVKDSV | 0.904 | 2 | SB | Agno | A0212 |
| 36 | FIFILELLL | 0.746 | 15 | SB | Agno | A0212 |
| 34 | RIFIFILEL | 0.679 | 32 | SB | Agno | A0212 |
| 38 | FILELLLEF | 0.614 | 65 | WB | Agno | A0212 |
| 11 | RQLSRQASV | 0.545 | 138 | WB | Agno | A0212 |
| 1 | FCEPKNLVV | 0.473 | 300 | WB | Agno | A0212 |
| 42 | LLLEFCRGE | 0.465 | 327 | WB | Agno | A0212 |
| 9 | VLRQLSRQA | 0.442 | 416 | WB | Agno | A0212 |
| 62 | ALPAVKDSV | 0.922 | 2 | SB | Agno | A0216 |
| 34 | RIFIFILEL | 0.732 | 18 | SB | Agno | A0216 |
| 36 | FIFILELLL | 0.654 | 42 | SB | Agno | A0216 |
| 11 | RQLSRQASV | 0.490 | 247 | WB | Agno | A0216 |
| 62 | ALPAVKDSV | 0.778 | 11 | SB | Agno | A0219 |
| 12 | QLSRQASVK | 0.643 | 47 | SB | Agno | A0301 |
| 15 | RQASVKVGK | 0.538 | 148 | WB | Agno | A0301 |
| 59 | STTALPAVK | 0.461 | 341 | WB | Agno | A0301 |
| 59 | STTALPAVK | 0.825 | 6 | SB | Agno | A1101 |
| 15 | RQASVKVGK | 0.624 | 58 | WB | Agno | A1101 |
| 7 | LVVLRQLSR | 0.460 | 345 | WB | Agno | A1101 |
| 35 | IFIFILELL | 0.514 | 192 | WB | Agno | A2301 |
| 38 | FILELLLEF | 0.473 | 300 | WB | Agno | A2301 |
| 35 | IFIFILELL | 0.610 | 67 | WB | Agno | A2402 |
| 38 | FILELLLEF | 0.532 | 157 | WB | Agno | A2403 |
| 38 | FILELLLEF | 0.598 | 77 | WB | Agno | A2602 |
| 38 | FILELLLEF | 0.463 | 334 | WB | Agno | A2902 |
| 21 | VGKTWTGTK | 0.528 | 165 | WB | Agno | A3001 |
| 59 | STTALPAVK | 0.477 | 285 | WB | Agno | A3001 |
| 29 | KKRAQRIFI | 0.452 | 377 | WB | Agno | A3001 |
| 23 | KTWTGTKKR | 0.727 | 19 | SB | Agno | A3101 |
| 15 | RQASVKVGK | 0.617 | 62 | WB | Agno | A3101 |
| 26 | TGTKKRAQR | 0.524 | 172 | WB | Agno | A3101 |
| 7 | LVVLRQLSR | 0.506 | 210 | WB | Agno | A3101 |
| 59 | STTALPAVK | 0.486 | 260 | WB | Agno | A3101 |
| 7 | LVVLRQLSR | 0.666 | 37 | SB | Agno | A3301 |
| 3 | EPKNLVVLR | 0.510 | 201 | WB | Agno | A3301 |
| 59 | STTALPAVK | 0.728 | 19 | SB | Agno | A6801 |
| 3 | EPKNLVVLR | 0.667 | 36 | SB | Agno | A6801 |
| 7 | LVVLRQLSR | 0.664 | 37 | SB | Agno | A6801 |
| 31 | RAQRIFIFI | 0.609 | 68 | WB | Agno | A6802 |
| 38 | FILELLLEF | 0.453 | 371 | WB | Agno | B1801 |
| 15 | RQASVKVGK | 0.566 | 109 | WB | Agno | B2705 |
| 30 | KRAQRIFIF | 0.523 | 174 | WB | Agno | B2705 |
| 11 | RQLSRQASV | 0.449 | 390 | WB | Agno | B2705 |
| 38 | FILELLLEF | 0.505 | 211 | WB | Agno | B3501 |
| 2 | CEPKNLVVL | 0.521 | 179 | WB | Agno | B4001 |
| 17 | ASVKVGKTW | 0.443 | 414 | WB | Agno | B5701 |
| 17 | ASVKVGKTW | 0.572 | 103 | WB | Agno | B5801 |

10-mers

| pos | peptide | logscore | affinity (nM) | Bind Level | Protein Name | Allele |
|---|---|---|---|---|---|---|
| 34 | RIFIFILELL | 0.605 | 71 | WB | Agno | A0201 |
| 38 | FILELLLEFC | 0.449 | 388 | WB | Agno | A0201 |
| 34 | RIFIFILELL | 0.719 | 20 | SB | Agno | A0202 |
| 38 | FILELLLEFC | 0.622 | 59 | WB | Agno | A0202 |
| 12 | QLSRQASVKV | 0.449 | 386 | WB | Agno | A0202 |
| 12 | QLSRQASVKV | 0.588 | 86 | WB | Agno | A0203 |
| 34 | RIFIFILELL | 0.456 | 359 | WB | Agno | A0203 |
| 12 | QLSRQASVKV | 0.503 | 215 | WB | Agno | A0204 |
| 38 | FILELLLEFC | 0.656 | 41 | SB | Agno | A0206 |
| 34 | RIFIFILELL | 0.549 | 131 | WB | Agno | A0206 |
| 61 | TALPAVKDSV | 0.450 | 382 | WB | Agno | A0206 |
| 12 | QLSRQASVKV | 0.859 | 4 | SB | Agno | A0211 |

TABLE N-continued

Prediction of BK virus Agnoprotein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| pos | peptide | logscore | affinity (nM) | Bind Level | Protein Name | Allele |
|---|---|---|---|---|---|---|
| 34 | RIFIFILELL | 0.772 | 11 | SB | Agno | A0211 |
| 38 | FILELLLEFC | 0.626 | 57 | WB | Agno | A0211 |
| 61 | TALPAVKDSV | 0.569 | 106 | WB | Agno | A0211 |
| 12 | QLSRQASVKV | 0.754 | 14 | SB | Agno | A0212 |
| 38 | FILELLLEFC | 0.627 | 56 | WB | Agno | A0212 |
| 34 | RIFIFILELL | 0.497 | 231 | WB | Agno | A0212 |
| 61 | TALPAVKDSV | 0.433 | 461 | WB | Agno | A0212 |
| 12 | QLSRQASVKV | 0.843 | 5 | SB | Agno | A0216 |
| 34 | RIFIFILELL | 0.581 | 92 | WB | Agno | A0216 |
| 61 | TALPAVKDSV | 0.550 | 130 | WB | Agno | A0216 |
| 12 | QLSRQASVKV | 0.632 | 53 | WB | Agno | A0219 |
| 61 | TALPAVKDSV | 0.549 | 131 | WB | Agno | A0219 |
| 11 | RQLSRQASVK | 0.636 | 51 | WB | Agno | A0301 |
| 58 | KSTTALPAVK | 0.532 | 158 | WB | Agno | A0301 |
| 20 | KVGKTWTGTK | 0.496 | 234 | WB | Agno | A0301 |
| 62 | ALPAVKDSVK | 0.452 | 375 | WB | Agno | A0301 |
| 58 | KSTTALPAVK | 0.688 | 29 | SB | Agno | A1101 |
| 20 | KVGKTWTGTK | 0.671 | 35 | SB | Agno | A1101 |
| 11 | RQLSRQASVK | 0.620 | 60 | WB | Agno | A1101 |
| 62 | ALPAVKDSVK | 0.445 | 404 | WB | Agno | A1101 |
| 37 | IFILELLLEF | 0.695 | 27 | SB | Agno | A2301 |
| 35 | IFIFILELLL | 0.487 | 256 | WB | Agno | A2301 |
| 37 | IFILELLLEF | 0.663 | 38 | SB | Agno | A2402 |
| 35 | IFIFILELLL | 0.622 | 59 | WB | Agno | A2402 |
| 37 | IFILELLLEF | 0.663 | 38 | SB | Agno | A2403 |
| 37 | IFILELLLEF | 0.470 | 309 | WB | Agno | A2902 |
| 20 | KVGKTWTGTK | 0.787 | 10 | SB | Agno | A3001 |
| 58 | KSTTALPAVK | 0.557 | 120 | WB | Agno | A3001 |
| 11 | RQLSRQASVK | 0.509 | 202 | WB | Agno | A3001 |
| 6 | NLVVLRQLSR | 0.567 | 108 | WB | Agno | A3101 |
| 39 | ILELLLEFCR | 0.521 | 177 | WB | Agno | A3101 |
| 25 | WTGTKKRAQR | 0.504 | 214 | WB | Agno | A3101 |
| 39 | ILELLLEFCR | 0.523 | 173 | WB | Agno | A3301 |
| 6 | NLVVLRQLSR | 0.485 | 262 | WB | Agno | A3301 |
| 6 | NLVVLRQLSR | 0.604 | 72 | WB | Agno | A6801 |
| 39 | ILELLLEFCR | 0.479 | 279 | WB | Agno | A6801 |
| 25 | WTGTKKRAQR | 0.465 | 326 | WB | Agno | A6801 |
| 33 | QRIFIFILEL | 0.528 | 164 | WB | Agno | A6802 |
| 61 | TALPAVKDSV | 0.473 | 301 | WB | Agno | A6802 |
| 34 | RIFIFILELL | 0.467 | 321 | WB | Agno | A6802 |
| 61 | TALPAVKDSV | 0.448 | 394 | WB | Agno | A6901 |
| 11 | RQLSRQASVK | 0.534 | 154 | WB | Agno | B2705 |
| 14 | SRQASVKVGK | 0.516 | 188 | WB | Agno | B2705 |
| 33 | QRIFIFILEL | 0.469 | 312 | WB | Agno | B2705 |
| 16 | QASVKVGKTW | 0.632

TABLE O

Predicted MHC class 2 BK virus peptide sequences. Prediction of 13-, 14-, 15-,16-mers from all 6 reading frames of the genome (access no #V01108) obtained using the program displayed in FIG. 2.

BK virus, reading frame 1

13 mers:

FCKNCKRIGISPN; CKNCKRIGISPNS; KNCKRIGISPNSF;
NCKRIGISPNSFA; CKRIGISPNSFAR; KRIGISPNSFARP;
RIGISPNSFARPQ; IGISPNSFARPQK; GISPNSFARPQKK;
ISPNSFARPQKKP; SPNSFARPQKKPP; PNSFARPQKKPPH;
NSFARPQKKPPHP; SFARPQKKPPHPY; FARPQKKPPHPYY;
ARPQKKPPHPYYL; RPQKKPPHPYYLR; PQKKPPHPYYLRE;
QKKPPHPYYLRER; KKPPHPYYLRERV; KPPHPYYLRERVE;
PPHPYYLRERVEA; PHPYYLRERVEAE; HPYYLRERVEAEA;
PYYLRERVEAEAA; YYLRERVEAEAAS; YLRERVEAEAASA;
LRERVEAEAASAS; RERVEAEAASASY; ERVEAEAASASYI;
RVEAEAASASYIL; KKRPQGGAAYPWN; KRPQGGAAYPWNA;
RPQGGAAYPWNAA; PQGGAAYPWNAAK; QGGAAYPWNAAKP;
PQEGKCMTHRGMQ; QEGKCMTHRGMQP; EGKCMTHRGMQPN;
GKCMTHRGMQPNH; KCMTHRGMQPNHD; CMTHRGMQPNHDL;
MTHRGMQPNHDLR; THRGMQPNHDLRK; HRGMQPNHDLRKE;
RGMQPNHDLRKES; GMQPNHDLRKESA; LTGRSCLPMECSQ;
TGRSCLPMECSQT; GRSCLPMECSQTM; RSCLPMECSQTMT;
SCLPMECSQTMTS; CLPMECSQTMTSG; LPMECSQTMTSGR;
PMECSQTMTSGRK; MECSQTMTSGRKV; ECSQTMTSGRKVH;
CSQTMTSGRKVHD; SQTMTSGRKVHDR; QTMTSGRKVHDRH;
TMTSGRKVHDRHV; MTSGRKVHDRHVL; TSGRKVHDRHVLR;
SGRKVHDRHVLRA; ESWPCPQLNWTKA; SWPCPQLNWTKAM;
WPCPQLNWTKAMV; PCPQLNWTKAMVL; CPQLNWTKAMVLR;
PQLNWTKAMVLRQ; QLNWTKAMVLRQL; LNWTKAMVLRQLS;
NWTKAMVLRQLSR; WTKAMVLRQLSRQ; TKAMVLRQLSRQA;
KAMVLRQLSRQAS; AMVLRQLSRQASV; MVLRQLSRQASVK;
VLRQLSRQASVKV; LRQLSRQASVKVG; RQLSRQASVKVGK;
QLSRQASVKVGKT; LSRQASVKVGKTW; SRQASVKVGKTWT;
RQASVKVGKTWTG; QASVKVGKTWTGT; ASVKVGKTWTGTK;
SVKVGKTWTGTKK; VKVGKTWTGTKKR; KVGKTWTGTKKRA;
VGKTWTGTKKRAQ; GKTWTGTKKRAQR; KTWTGTKKRAQRI;
TWTGTKKRAQRIF; WTGTKKRAQRIFI; TGTKKRAQRIFIF;
GTKKRAQRIFIFI; TKKRAQRIFIFIL; KKRAQRIFIFILE;
KRAQRIFIFILEL; RAQRIFIFILELL; AQRIFIFILELLL;
QRIFIFILELLLE; RIFIFILELLLEF; IFIFILELLLEFC;
FIFILELLLEFCR; IFILELLLEFCRG; FILELLLEFCRGE;
ILELLLEFCRGED; LELLLEFCRGEDS; ELLLEFCRGEDSV;
LLLEFCRGEDSVD; LLEFCRGEDSVDG; LEFCRGEDSVDGK;
EFCRGEDSVDGKN; FCRGEDSVDGKNK; CRGEDSVDGKNKS;
RGEDSVDGKNKST; GEDSVDGKNKSTT; EDSVDGKNKSTTA;
DSVDGKNKSTTAL; SVDGKNKSTTALP; VDGKNKSTTALPA;
DGKNKSTTALPAV; GKNKSTTALPAVK; KNKSTTALPAVKD;
NKSTTALPAVKDS; KSTTALPAVKDSV; STTALPAVKDSVK;
TTALPAVKDSVKD; TALPAVKDSVKDS; VSNPFFFVFPGSW;
SNPFFFVFPGSWV; NPFFFVFPGSWVL; PFFFVFPGSWVLL;
LPVYLRLLLPQDF; PVYLRLLLPQDFQ; VYLRLLLPQDFQW;
YLRLLLPQDFQWL; LRLLLPQDFQWLK; RLLLPQDFQWLKL;
LLLPQDFQWLKLL; LLPQDFQWLKLLL; LPQDFQWLKLLLG;
PQDFQWLKLLLGR; QDFQWLKLLLGRL; DFQWLKLLLGRLL;
FQWLKLLLGRLLL; QWLKLLLGRLLLL; LLVLLGLLLGLLL;
GISSLMIGITKFP; ISSLMIGITKFPL; ASISNQAWLWNCL;
SISNQAWLWNCLT; ISNQAWLWNCLTQ; SNQAWLWNCLTQM;
NQAWLWNCLTQMS; QAWLWNCLTQMST; AWLWNCLTQMSTM;
WLWNCLTQMSTMI; LWNCLTQMSTMIF; WNCLTQMSTMIFC;
NCLTQMSTMIFCF; CLTQMSTMIFCFL; LTQMSTMIFCFLV;
ILLLIIFNTLILG; LLLIIFNTLILGI; LLIIFNTLILGIG;
LIIFNTLILGIGV; IIFNTLILGIGVL; IFNTLILGIGVLL;
FNTLILGIGVLLC; NTLILGIGVLLCL; TLILGIGVLLCLL;
LILGIGVLLCLLL; ILGIGVLLCLLLF; LGIGVLLCLLLFP;
GIGVLLCLLLFPR; IGVLLCLLLFPRL; GVLLCLLLFPRLC;
VLLCLLLFPRLCG; LLCLLLFPRLCGM; LCLLLFPRLCGML;
CLLLFPRLCGMLL; LLLFPRLCGMLLG; LLFPRLCGMLLGM;
LFPRLCGMLLGMI; FPRLCGMLLGMIY; PRLCGMLLGMIYL;
RLCGMLLGMIYLL; PHRNCREEQKDFL; HRNCREEQKDFLE;
RNCREEQKDFLET; NCREEQKDFLETP; CREEQKDFLETPW;
REEQKDFLETPWL; EEQKDFLETPWLD; EQKDFLETPWLDF;
QKDFLETPWLDFW; KDFLETPWLDFWR; DFLETPWLDFWRK;
FLETPWLDFWRKL; LETPWLDFWRKLP; ETPWLDFWRKLPG;
TPWLDFWRKLPGQ; PWLDFWRKLPGQL; TFIIIFNNIILIF;
FIIIFNNIILIFP; IIIFNNIILIFPL; IIFNNIILIFPLL;

IFNNIILIFPLLG; FNNIILIFPLLGP; NNIILIFPLLGPQ;
NIILIFPLLGPQW; IILIFPLLGPQWL; ILIFPLLGPQWLD;
LIFPLLGPQWLDK; LKGKVPVYILAIL; KGKVPVYILAILI;
GKVPVYILAILIV; KKLLPQEVLIKEL; KLLPQEVLIKELL;
LLPQEVLIKELLL; LPQEVLIKELLLN; PQEVLIKELLLNG;
QEVLIKELLLNGC; EVLIKELLLNGCC; VLIKELLLNGCCL;
LIKELLLNGCCLY; IKELLLNGCCLYF; HLLLKHMKMAPTK;
LLLKHMKMAPTKR; LLKHMKMAPTKRK; LKHMKMAPTKRKG;
KHMKMAPTKRKGE; HMKMAPTKRKGEC; MKMAPTKRKGECP;
KMAPTKRKGECPG; MAPTKRKGECPGA; APTKRKGECPGAA;
PTKRKGECPGAAP; TKRKGECPGAAPK; KRKGECPGAAPKK;
RKGECPGAAPKKP; KGECPGAAPKKPK; GECPGAAPKKPKE;
ECPGAAPKKPKEP; CPGAAPKKPKEPV; PGAAPKKPKEPVQ;
GAAPKKPKEPVQV; AAPKKPKEPVQVP; APKKPKEPVQVPK;
PKKPKEPVQVPKL; KKPKEPVQVPKLL; KPKEPVQVPKLLI;
PKEPVQVPKLLIK; KEPVQVPKLLIKG; EPVQVPKLLIKGG;
PVQVPKLLIKGGV; VQVPKLLIKGGVE; QVPKLLIKGGVEV;
VPKLLIKGGVEVL; PKLLIKGGVEVLE; KLLIKGGVEVLEV;
LLIKGGVEVLEVK; LIKGGVEVLEVKT; IKGGVEVLEVKTG;
KGGVEVLEVKTGV; GGVEVLEVKTGVD; GVEVLEVKTGVDA;
VEVLEVKTGVDAI; EVLEVKTGVDAIT; VLEVKTGVDAITE;
LEVKTGVDAITEV; EVKTGVDAITEVE; VKTGVDAITEVEC;
KTGVDAITEVECF; TGVDAITEVECFL; GVDAITEVECFLN;
VDAITEVECFLNP; DAITEVECFLNPE; AITEVECFLNPEM;
ITEVECFLNPEMG; TEVECFLNPEMGD; EVECFLNPEMGDP;
VECFLNPEMGDPD; ECFLNPEMGDPDE; CFLNPEMGDPDEN;
FLNPEMGDPDENL; LNPEMGDPDENLR; NPEMGDPDENLRG;
PEMGDPDENLRGF; EMGDPDENLRGFS; MGDPDENLRGFSL;
GDPDENLRGFSLK; DPDENLRGFSLKL; PDENLRGFSLKLS;
DENLRGFSLKLSA; ENLRGFSLKLSAE; NLRGFSLKLSAEN;
LRGFSLKLSAEND; RGFSLKLSAENDF; GFSLKLSAENDFS;
FSLKLSAENDFSS; SLKLSAENDFSSD; LKLSAENDFSSDS;
KLSAENDFSSDSP; LSAENDFSSDSPE; SAENDFSSDSPER;
AENDFSSDSPERK; ENDFSSDSPERKM; NDFSSDSPERKML;
DFSSDSPERKMLP; FSSDSPERKMLPC; SSDSPERKMLPCY;
SDSPERKMLPCYS; DSPERKMLPCYST; SPERKMLPCYSTA;
PERKMLPCYSTAR; ERKMLPCYSTARI; RKMLPCYSTARIP;
KMLPCYSTARIPL; MLPCYSTARIPLP; LPCYSTARIPLPN;
PCYSTARIPLPNL; CYSTARIPLPNLN; YSTARIPLPNLNE;
STARIPLPNLNED; TARIPLPNLNEDL; ARIPLPNLNEDLT;
RIPLPNLNEDLTC; IPLPNLNEDLTCG; PLPNLNEDLTCGN;
LPNLNEDLTCGNL; PNLNEDLTCGNLL; NLNEDLTCGNLLM;
LNEDLTCGNLLMW; NEDLTCGNLLMWE; EDLTCGNLLMWEA;
DLTCGNLLMWEAV; LTCGNLLMWEAVT; TCGNLLMWEAVTV;
CGNLLMWEAVTVQ; GNLLMWEAVTVQT; NLLMWEAVTVQTE;
LLMWEAVTVQTEV; LMWEAVTVQTEVI; MWEAVTVQTEVIG;
WEAVTVQTEVIGI; EAVTVQTEVIGIT; AVTVQTEVIGITS;
VTVQTEVIGITSM; TVQTEVIGITSML; VQTEVIGITSMLN;
QTEVIGITSMLNL; TEVIGITSMLNLH; EVIGITSMLNLHA;
VIGITSMLNLHAG; IGITSMLNLHAGS; GITSMLNLHAGSQ;
ITSMLNLHAGSQK; TSMLNLHAGSQKV; SMLNLHAGSQKVH;
MLNLHAGSQKVHE; LNLHAGSQKVHEH; NLHAGSQKVHEHG;
LHAGSQKVHEHGG; HAGSQKVHEHGGG; AGSQKVHEHGGGK;
GSQKVHEHGGGKP; SQKVHEHGGGKPI; QKVHEHGGGKPIQ;
KVHEHGGGKPIQG; VHEHGGGKPIQGS; HEHGGGKPIQGSN;
EHGGGKPIQGSNF; HGGGKPIQGSNFH; GGGKPIQGSNFHF;
GGKPIQGSNFHFF; GKPIQGSNFHFFA; KPIQGSNFHFFAV;
PIQGSNFHFFAVG; IQGSNFHFFAVGG; QGSNFHFFAVGGE;
GSNFHFFAVGGEP; SNFHFFAVGGEPL; NFHFFAVGGEPLE;
FHFFAVGGEPLEM; HFFAVGGEPLEMQ; FFAVGGEPLEMQG;
FAVGGEPLEMQGV; AVGGEPLEMQGVL; VGGEPLEMQGVLM;
GGEPLEMQGVLMN; GEPLEMQGVLMNY; EPLEMQGVLMNYR;
PLEMQGVLMNYRS; LEMQGVLMNYRSK; EMQGVLMNYRSKY;
MQGVLMNYRSKYP; QGVLMNYRSKYPD; GVLMNYRSKYPDG;
VLMNYRSKYPDGT; LMNYRSKYPDGTI; MNYRSKYPDGTIT;
NYRSKYPDGTITP; YRSKYPDGTITPK; RSKYPDGTITPKN;
SKYPDGTITPKNP; KYPDGTITPKNPT; YPDGTITPKNPTA;
PDGTITPKNPTAQ; DGTITPKNPTAQS; GTITPKNPTAQSQ;
TITPKNPTAQSQV; ITPKNPTAQSQVM; TPKNPTAQSQVMN;
PKNPTAQSQVMNT; KNPTAQSQVMNTD; NPTAQSQVMNTDH;
PTAQSQVMNTDHK; TAQSQVMNTDHKA; AQSQVMNTDHKAY;
QSQVMNTDHKAYL; SQVMNTDHKAYLD; QVMNTDHKAYLDK;
VMNTDHKAYLDKN; MNTDHKAYLDKNN; NTDHKAYLDKNNA;
TDHKAYLDKNNAY; DHKAYLDKNNAYP; HKAYLDKNNAYPV;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

KAYLDKNNAYPVE; AYLDKNNAYPVEC; YLDKNNAYPVECW;
LDKNNAYPVECWV; DKNNAYPVECWVP; KNNAYPVECWVPD;
NNAYPVECWVPDP; NAYPVECWVPDPS; AYPVECWVPDPSR;
YPVECWVPDPSRN; PVECWVPDPSRNE; VECWVPDPSRNEN;
ECWVPDPSRNENA; CWVPDPSRNENAR; WVPDPSRNENARY;
VPDPSRNENARYF; PDPSRNENARYFG; DPSRNENARYFGT;
PSRNENARYFGTF; SRNENARYFGTFT; RNENARYFGTFTG;
NENARYFGTFTGG; ENARYFGTFTGGE; NARYFGTFTGGEN;
ARYFGTFTGGENV; RYFGTFTGGENVP; YFGTFTGGENVPP;
FGTFTGGENVPPV; GTFTGGENVPPVL; TFTGGENVPPVLH;
FTGGENVPPVLHV; TGGENVPPVLHVT; GGENVPPVLHVTN;
GENVPPVLHVTNT; ENVPPVLHVTNTA; NVPPVLHVTNTAT;
VPPVLHVTNTATT; PPVLHVTNTATTV; PVLHVTNTATTVL;
VLHVTNTATTVLL; LHVTNTATTVLLD; HVTNTATTVLLDE;
VTNTATTVLLDEQ; TNTATTVLLDEQG; NTATTVLLDEQGV;
TATTVLLDEQGVG; ATTVLLDEQGVGP; TTVLLDEQGVGPL;
TVLLDEQGVGPLC; VLLDEQGVGPLCK; LLDEQGVGPLCKA;
LDEQGVGPLCKAD; DEQGVGPLCKADS; EQGVGPLCKADSL;
QGVGPLCKADSLY; GVGPLCKADSLYV; VGPLCKADSLYVS;
GPLCKADSLYVSA; PLCKADSLYVSAA; LCKADSLYVSAAD;
CKADSLYVSAADI; KADSLYVSAADIC; ADSLYVSAADICG;
DSLYVSAADICGL; SLYVSAADICGLF; LYVSAADICGLFT;
YVSAADICGLFTN; VSAADICGLFTNS; SAADICGLFTNSS;
AADICGLFTNSSG; ADICGLFTNSSGT; DICGLFTNSSGTQ;
ICGLFTNSSGTQQ; CGLFTNSSGTQQW; GLFTNSSGTQQWR;
LFTNSSGTQQWRG; FTNSSGTQQWRGL; TNSSGTQQWRGLA;
NSSGTQQWRGLAR; SSGTQQWRGLARY; SGTQQWRGLARYF;
GTQQWRGLARYFK; TQQWRGLARYFKI; QQWRGLARYFKIR;
QWRGLARYFKIRL; WRGLARYFKIRLR; RGLARYFKIRLRK;
GLARYFKIRLRKR; LARYFKIRLRKRS; ARYFKIRLRKRSV;
RYFKIRLRKRSVK; YFKIRLRKRSVKN; FKIRLRKRSVKNP;
KIRLRKRSVKNPY; IRLRKRSVKNPYP; RLRKRSVKNPYPI;
LRKRSVKNPYPIS; RKRSVKNPYPISF; KRSVKNPYPISFL;
RSVKNPYPISFLL; SVKNPYPISFLLS; VKNPYPISFLLSD;
KNPYPISFLLSDL; NPYPISFLLSDLI; PYPISFLLSDLIN;
YPISFLLSDLINR; PISFLLSDLINRR; ISFLLSDLINRRT;
SFLLSDLINRRTQ; FLLSDLINRRTQR; LLSDLINRRTQRV;
LSDLINRRTQRVD; SDLINRRTQRVDG; DLINRRTQRVDGQ;
LINRRTQRVDGQP; INRRTQRVDGQPM; NRRTQRVDGQPMY;
RRTQRVDGQPMYG; RTQRVDGQPMYGM; TQRVDGQPMYGME;
QRVDGQPMYGMES; RVDGQPMYGMESQ; VDGQPMYGMESQV;
DGQPMYGMESQVE; GQPMYGMESQVEE; QPMYGMESQVEEV;
PMYGMESQVEEVR; MYGMESQVEEVRV; YGMESQVEEVRVF;
GMESQVEEVRVFD; MESQVEEVRVFDG; ESQVEEVRVFDGT;
SQVEEVRVFDGTE; QVEEVRVFDGTER; VEEVRVFDGTERL;
EEVRVFDGTERLP; EVRVFDGTERLPG; VRVFDGTERLPGD;
RVFDGTERLPGDP; VFDGTERLPGDPD; FDGTERLPGDPDM;
DGTERLPGDPDMI; GTERLPGDPDMIR; TERLPGDPDMIRY;
ERLPGDPDMIRYI; RLPGDPDMIRYID; LPGDPDMIRYIDK;
PGDPDMIRYIDKQ; GDPDMIRYIDKQG; DPDMIRYIDKQGQ;
PDMIRYIDKQGQL; DMIRYIDKQGQLQ; MIRYIDKQGQLQT;
IRYIDKQGQLQTK; RYIDKQGQLQTKM; YIDKQGQLQTKML;
TGAFIVHIHLINA; GAFIVHIHLINAA; AFIVHIHLINAAF;
FIVHIHLINAAFV; ATFKLVLFWGWCF; TFKLVLFWGWCFR;
FKLVLFWGWCFRP; KLVLFWGWCFRPF; LVLFWGWCFRPFK;
VLFWGWCFRPFKT; LFWGWCFRPFKTL; FWGWCFRPFKTLK;
WGWCFRPFKTLKA; GWCFRPFKTLKAF; WCFRPFKTLKAFT;
CFRPFKTLKAFTQ; FRPFKTLKAFTQM; RPFKTLKAFTQMQ;
PFKTLKAFTQMQL; FKTLKAFTQMQLL; KTLKAFTQMQLLT;
TLKAFTQMQLLTM; LKAFTQMQLLTMG; KAFTQMQLLTMGV;
ILFSCNIKNTFPH; LFSCNIKNTFPHA; FSCNIKNTFPHAY;
SCNIKNTFPHAYI; CNIKNTFPHAYII; NIKNTFPHAYIIF;
IKNTFPHAYIIFH; KNTFPHAYIIFHP; KSIHTYLRIQPFL;
SIHTYLRIQPFLP; IHTYLRIQPFLPF; HTYLRIQPFLPFN;
TYLRIQPFLPFNN; YLRIQPFLPFNNS; LRIQPFLPFNNSR;
RIQPFLPFNNSRL; IQPFLPFNNSRLY; QPFLPFNNSRLYI;
PFLPFNNSRLYIS; FLPFNNSRLYISC; LPFNNSRLYISCK;
PFNNSRLYISCKI; FNNSRLYISCKIS; NNSRLYISCKISY;
NSRLYISCKISYR; SRLYISCKISYRP; RLYISCKISYRPK;
LYISCKISYRPKP; YISCKISYRPKPN; ISCKISYRPKPNI;
YFGPKIYLSYKSS; FGPKIYLSYKSSL; GPKIYLSYKSSLQ;
PKIYLSYKSSLQG; KIYLSYKSSLQGF; IYLSYKSSLQGFR;
YLSYKSSLQGFRD; LSYKSSLQGFRDR; SYKSSLQGFRDRI;
YKSSLQGFRDRIL; KSSLQGFRDRILI; SSLQGFRDRILIH;

SLQGFRDRILIHC; LQGFRDRILIHCN; QGFRDRILIHCNQ;
GFRDRILIHCNQA; FRDRILIHCNQAW; RDRILIHCNQAWW;
DRILIHCNQAWWK; RILIHCNQAWWKY; ILIHCNQAWWKYL;
LIHCNQAWWKYLG; IHCNQAWWKYLGS; HCNQAWWKYLGSF;
CNQAWWKYLGSFV; FSSCPFYIFKNNH; SSCPFYIFKNNHV;
SCPFYIFKNNHVL; CPFYIFKNNHVLI; PFYIFKNNHVLIY;
FYIFKNNHVLIYS; YIFKNNHVLIYSY; IFKNNHVLIYSYT;
PVSSFRYIENNTV; VSSFRYIENNTVQ; SSFRYIENNTVQK;
SFRYIENNTVQKI; FRYIENNTVQKIK; RYIENNTVQKIKY;
YIENNTVQKIKYY; IENNTVQKIKYYR; ENNTVQKIKYYRI;
NNTVQKIKYYRIH; NTVQKIKYYRIHF; TVQKIKYYRIHFR;
QTVQPSNTCHILF; HFFPGHMKGIYSF; FFPGHMKGIYSFF;
FPGHMKGIYSFFS; NCIYCLLTNTFLI; CIYCLLTNTFLIF;
IYCLLTNTFLIFT; YCLLTNTFLIFTF; CLLTNTFLIFTFC;
LLTNTFLIFTFCK; LTNTFLIFTFCKN; TNTFLIFTFCKNN;
NTFLIFTFCKNNS; TFLIFTFCKNNSI; FLIFTFCKNNSIC;
LIFTFCKNNSICK; IFTFCKNNSICKV; FTFCKNNSICKVL;
TFCKNNSICKVLF; FCKNNSICKVLFM; CKNNSICKVLFMI;
KNNSICKVLFMIL; NNSICKVLFMILK; NSICKVLFMILKV;
SICKVLFMILKVI; ICKVLFMILKVIR; CKVLFMILKVIRL;
KVLFMILKVIRLV; VLFMILKVIRLVF; LFMILKVIRLVFF;
FMILKVIRLVFFL; MILKVIRLVFFLT; ILKVIRLVFFLTL;
LKVIRLVFFLTLF; KVIRLVFFLTLFT; VIRLVFFLTLFTL;
IRLVFFLTLFTLL; RLVFFLTLFTLLY; LVFFLTLFTLLYI;
VFFLTLFTLLYIV; FFLTLFTLLYIVL; FLTLFTLLYIVLK;
LTLFTLLYIVLKF; KHILTLCLYCILS; HILTLCLYCILSN;
FPRHLLCFFRLFW; PRHLLCFFRLFWA; RHLLCFFRLFWAK;
HLLCFFRLFWAKI; LLCFFRLFWAKIM; LCFFRLFWAKIML;
CFFRLFWAKIMLL; APLNAFFYSMVWI; PLNAFFYSMVWIS;
LNAFFYSMVWISS; KTKGTQLLTEIIN; TKGTQLLTEIINC;
KGTQLLTEIINCR; GTQLLTEIINCRN; TQLLTEIINCRNS;
QLLTEIINCRNSM; LLTEIINCRNSMS; LTEIINCRNSMSM;
TEIINCRNSMSMW; EIINCRNSMSMWS; KEYNIMPSTHVST;
EYNIMPSTHVSTN; YNIMPSTHVSTNK; NIMPSTHVSTNKS;
IMPSTHVSTNKSY; MPSTHVSTNKSYR; PSTHVSTNKSYRI;
STHVSTNKSYRIF; THVSTNKSYRIFF; HVSTNKSYRIFFH;
VSTNKSYRIFFHK; STNKSYRIFFHKF; TNKSYRIFFHKFF;
NKSYRIFFHKFFI; KSYRIFFHKFFIQ; SYRIFFHKFFIQN;
YRIFFHKFFIQNL; RIFFHKFFIQNLS; IFFHKFFIQNLSF;
FFHKFFIQNLSFF; FHKFFIQNLSFFF; HKFFIQNLSFFFS;
KFFIQNLSFFFSS; FFIQNLSFFFSSI; FIQNLSFFFSSIH;
IQNLSFFFSSIHS; QNLSFFFSSIHSK; NLSFFFSSIHSKA;
LSFFFSSIHSKAG; SFFFSSIHSKAGK; FFFSSIHSKAGKG;
FFSSIHSKAGKGS; FSSIHSKAGKGSI; SSIHSKAGKGSIT;
SIHSKAGKGSITK; IHSKAGKGSITKY; HSKAGKGSITKYS;
SKAGKGSITKYSL; KAGKGSITKYSLT; AGKGSITKYSLTK;
GKGSITKYSLTKK; KGSITKYSLTKKL; GSITKYSLTKKLV;
IRGKVFRVFYLSF; RGKVFRVFYLSFF; GKVFRVFYLSFFF;
KVFRVFYLSFFFG; VFRVFYLSFFFGW; FRVFYLSFFFGWC;
VLRICCCFFITGK; LRICCCFFITGKH; RICCCFFITGKHI;
ICCCFFITGKHIF; CCCFFITGKHIFM; CCFFITGKHIFMA;
CFFITGKHIFMAK; IFIPPFIKGTPPG; FIPPFIKGTPPGL;
IPPFIKGTPPGLP; PFFIKGTPPGLPL; FFIKGTPPGLPLF;
FIKGTPPGLPLFC; IKGTPPGLPLFCS; KGTPPGLPLFCSI;
GTPPGLPLFCSIG; TPPGLPLFCSIGW; PPGLPLFCSIGWH;
PGLPLFCSIGWHL; SFRSLKGVSPIIW; FRSLKGVSPIIWT;
RSLKGVSPIIWTH; SLKGVSPIIWTHH; LKGVSPIIWTHHC;
KGVSPIIWTHHCR; GVSPIIWTHHCRV; VSPIIWTHHCRVS;
SPIIWTHHCRVSS; PIIWTHHCRVSSV; IIWTHHCRVSSVR;
IWTHHCRVSSVRS; WTHHCRVSSVRSK; THHCRVSSVRSKP;
HHCRVSSVRSKPN; HCRVSSVRSKPNH; CRVSSVRSKPNHC;
RVSSVRSKPNHCV; VSSVRSKPNHCVK; SSVRSKPNHCVKQ;
SVRSKPNHCVKQS; VRSKPNHCVKQSM; RSKPNHCVKQSMQ;
QSIQTKGSFLKNF; SIQTKGSFLKNFL; IQTKGSFLKNFLF;
QTKGSFLKNFLFK; TKGSFLKNFLFKC; KGSFLKNFLFKCL;
GSFLKNFLFKCLN; SFLKNFLFKCLNL; FLKNFLFKCLNLS;
HSMQGQCTEGFLE; SMQGQCTEGFLEQ; MQGQCTEGFLEQI;
QGQCTEGFLEQIG; GQCTEGFLEQIGH; QCTEGFLEQIGHS;
CTEGFLEQIGHSL; TEGFLEQIGHSLQ; EGFLEQIGHSLQY;
GFLEQIGHSLQYR; FLEQIGHSLQYRV; LEQIGHSLQYRVS;
EQIGHSLQYRVSG; QIGHSLQYRVSGQ; IGHSLQYRVSGQR;
GHSLQYRVSGQRG; HSLQYRVSGQRGK; SLQYRVSGQRGKS;
LQYRVSGQRGKSA; QYRVSGQRGKSAQ; YRVSGQRGKSAQT;
RVSGQRGKSAQTS; VSGQRGKSAQTSE; SGQRGKSAQTSEL;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GQRGKSAQTSELL; QRGKSAQTSELLQ; RGKSAQTSELLQV;
GKSAQTSELLQVP; KSAQTSELLQVPK; SAQTSELLQVPKS;
AQTSELLQVPKSG; ATFTSCSIFLYKV; TFTSCSIFLYKVF;
FTSCSIFLYKVFI; TSCSIFLYKVFIL; SCSIFLYKVFILF;
CSIFLYKVFILFI; SIFLYKVFILFIL; IFLYKVFILFILS;
FLYKVFILFILSS; LYKVFILFILSSS; YKVFILFILSSSP;
KVFILFILSSSPP; VFILFILSSSPPL; FILFILSSSPPLS;
ILFILSSSPPLSG; AFLIKGRFPQAAL; FLIKGRFPQAALS;
LIKGRFPQAALSR; IKGRFPQAALSRP; KGRFPQAALSRPK;
GRFPQAALSRPKR; RFPQAALSRPKRS; FPQAALSRPKRSM;
PQAALSRPKRSMS; QAALSRPKRSMSS; AALSRPKRSMSSM;
ALSRPKRSMSSMD; LSRPKRSMSSMDS; SRPKRSMSSMDSS;
RPKRSMSSMDSSL; PKRSMSSMDSSLL; KRSMSSMDSSLLR;
RSMSSMDSSLLRT; SMSSMDSSLLRTL; MSSMDSSLLRTLS 14 mers:

FCKNCKRIGISPNS; CKNCKRIGISPNSF; KNCKRIGISPNSFA;
NCKRIGISPNSFAR; CKRIGISPNSFARP; KRIGISPNSFARPQ;
RIGISPNSFARPQK; IGISPNSFARPQKK; GISPNSFARPQKKP;
ISPNSFARPQKKPP; SPNSFARPQKKPPH; PNSFARPQKKPPHP;
NSFARPQKKPPHPY; SFARPQKKPPHPYY; FARPQKKPPHPYYL;
ARPQKKPPHPYYLR; RPQKKPPHPYYLRE; PQKKPPHPYYLRER;
QKKPPHPYYLRERV; KKPPHPYYLRERVE; KPPHPYYLRERVEA;
PPHPYYLRERVEAE; PHPYYLRERVEAEA; HPYYLRERVEAEAA;
PYYLRERVEAEAAS; YYLRERVEAEAASA; YLRERVEAEAASAS;
LRERVEAEAASASY; RERVEAEAASASYI; ERVEAEAASASYIL;
KKRPQGGAAYPWNA; KRPQGGAAYPWNAA; RPQGGAAYPWNAAK;
PQGGAAYPWNAAKP; PQEGKCMTHRGMQP; QEGKCMTHRGMQPN;
EGKCMTHRGMQPNH; GKCMTHRGMQPNHD; KCMTHRGMQPNHDL;
CMTHRGMQPNHDLR; MTHRGMQPNHDLRK; THRGMQPNHDLRKE;
HRGMQPNHDLRKES; RGMQPNHDLRKESA; LTGRSCLPMECSQT;
TGRSCLPMECSQTM; GRSCLPMECSQTMT; RSCLPMECSQTMTS;
SCLPMECSQTMTSG; CLPMECSQTMTSGR; LPMECSQTMTSGRK;
PMECSQTMTSGRKV; MECSQTMTSGRKVH; ECSQTMTSGRKVHD;
CSQTMTSGRKVHDR; SQTMTSGRKVHDRH; QTMTSGRKVHDRHV;
TMTSGRKVHDRHVL; MTSGRKVHDRHVLR; TSGRKVHDRHVLRA;
ESWPCPQLNWTKAM; SWPCPQLNWTKAMV; WPCPQLNWTKAMVL;
PCPQLNWTKAMVLR; CPQLNWTKAMVLRQ; PQLNWTKAMVLRQL;
QLNWTKAMVLRQLS; LNWTKAMVLRQLSR; NWTKAMVLRQLSRQ;
WTKAMVLRQLSRQA; TKAMVLRQLSRQAS; KAMVLRQLSRQASV;
AMVLRQLSRQASVK; MVLRQLSRQASVKV; VLRQLSRQASVKVG;
LRQLSRQASVKVGK; RQLSRQASVKVGKT; QLSRQASVKVGKTW;
LSRQASVKVGKTWT; SRQASVKVGKTWTG; RQASVKVGKTWTGT;
QASVKVGKTWTGTK; ASVKVGKTWTGTKK; SVKVGKTWTGTKKR;
VKVGKTWTGTKKRA; KVGKTWTGTKKRAQ; VGKTWTGTKKRAQR;
GKTWTGTKKRAQRI; KTWTGTKKRAQRIF; TWTGTKKRAQRIFI;
WTGTKKRAQRIFIF; TGTKKRAQRIFIFI; GTKKRAQRIFIFIL;
TKKRAQRIFIFILE; KKRAQRIFIFILEL; KRAQRIFIFILELL;
RAQRIFIFILELLL; AQRIFIFILELLLE; QRIFIFILELLLEF;
RIFIFILELLLEFC; IFIFILELLLEFCR; FIFILELLLEFCRG;
IFILELLLEFCRGE; FILELLLEFCRGED; ILELLLEFCRGEDS;
LELLLEFCRGEDSV; ELLLEFCRGEDSVD; LLLEFCRGEDSVDG;
LLEFCRGEDSVDGK; LEFCRGEDSVDGKN; EFCRGEDSVDGKNK;
FCRGEDSVDGKNKS; CRGEDSVDGKNKST; RGEDSVDGKNKSTT;
GEDSVDGKNKSTTA; EDSVDGKNKSTTAL; DSVDGKNKSTTALP;
SVDGKNKSTTALPA; VDGKNKSTTALPAV; DGKNKSTTALPAVK;
GKNKSTTALPAVKD; KNKSTTALPAVKDS; NKSTTALPAVKDSV;
KSTTALPAVKDSVK; STTALPAVKDSVKD; TTALPAVKDSVKDS;
VSNPFFFVFPGSWV; SNPFFFVFPGSWVL; NPFFFVFPGSWVLL;
LPVYLRLLLPQDFQ; PVYLRLLLPQDFQW; VYLRLLLPQDFQWL;
YLRLLLPQDFQWLK; LRLLLPQDFQWLKL; RLLLPQDFQWLKLL;
LLLPQDFQWLKLLL; LLPQDFQWLKLLLG; LPQDFQWLKLLLGR;
PQDFQWLKLLLGRL; QDFQWLKLLLGRLL; DFQWLKLLLGRLLL;
FQWLKLLLGRLLLL; GISSLMIGITKFPL; ASISNQAWLWNCLT;
SISNQAWLWNCLTQ; ISNQAWLWNCLTQM; SNQAWLWNCLTQMS;
NQAWLWNCLTQMST; QAWLWNCLTQMSTM; AWLWNCLTQMSTMI;
WLWNCLTQMSTMIF; LWNCLTQMSTMIFC; WNCLTQMSTMIFCF;
NCLTQMSTMIFCFL; CLTQMSTMIFCFLV; LTQMSTMIFCFLVI;
LLLIIFNTLILGIG; LLIIFNTLILGIGV; LIIFNTLILGIGVL;
IIFNTLILGIGVLL; IFNTLILGIGVLLC; FNTLILGIGVLLCL;
NTLILGIGVLLCLL; TLILGIGVLLCLLL; LILGIGVLLCLLLF;
ILGIGVLLCLLLFP; LGIGVLLCLLLFPR; GIGVLLCLLLFPRL;
IGVLLCLLLFPRLC; GVLLCLLLFPRLCG; VLLCLLLFPRLCGM;

LLCLLLFPRLCGML; LCLLLFPRLCGMLL; CLLLFPRLCGMLLG;
LLLFPRLCGMLLGM; LLFPRLCGMLLGMI; LFPRLCGMLLGMIY;
FPRLCGMLLGMIYL; PRLCGMLLGMIYLL; PHRNCREEQKDFLE;
HRNCREEQKDFLET; RNCREEQKDFLETP; NCREEQKDFLETPW;
CREEQKDFLETPWL; REEQKDFLETPWLD; EEQKDFLETPWLDF;
EQKDFLETPWLDFW; QKDFLETPWLDFWR; KDFLETPWLDFWRK;
DFLETPWLDFWRKL; FLETPWLDFWRKLP; LETPWLDFWRKLPG;
ETPWLDFWRKLPGQ; TPWLDFWRKLPGQL; TFIIIFNNIILIFP;
FIIIFNNIILIFPL; IIIFNNIILIFPLL; IIFNNIILIFPLLG;
IFNNIILIFPLLGP; FNNIILIFPLLGPQ; NNIILIFPLLGPQW;
NIILIFPLLGPQWL; IILIFPLLGPQWLD; ILIFPLLGPQWLDK;
LKGKVPVYILAILI; KGKVPVYILAILIV; KKLLPQEVLIKELL;
KLLPQEVLIKELLL; LLPQEVLIKELLLN; LPQEVLIKELLLNG;
PQEVLIKELLLNGC; QEVLIKELLLNGCC; EVLIKELLLNGCCL;
VLIKELLLNGCCLY; LIKELLLNGCCLYF; HLLLKHMKMAPTKR;
LLLKHMKMAPTKRK; LLKHMKMAPTKRKG; LKHMKMAPTKRKGE;
KHMKMAPTKRKGEC; HMKMAPTKRKGECP; MKMAPTKRKGECPG;
KMAPTKRKGECPGA; MAPTKRKGECPGAA; APTKRKGECPGAAP;
PTKRKGECPGAAPK; TKRKGECPGAAPKK; KRKGECPGAAPKKP;
RKGECPGAAPKKPK; KGECPGAAPKKPKE; GECPGAAPKKPKEP;
ECPGAAPKKPKEPV; CPGAAPKKPKEPVQ; PGAAPKKPKEPVQV;
GAAPKKPKEPVQVP; AAPKKPKEPVQVPK; APKKPKEPVQVPKL;
PKKPKEPVQVPKLL; KKPKEPVQVPKLLI; KPKEPVQVPKLLIK;
PKEPVQVPKLLIKG; KEPVQVPKLLIKGG; EPVQVPKLLIKGGV;
PVQVPKLLIKGGVE; VQVPKLLIKGGVEV; QVPKLLIKGGVEVL;
VPKLLIKGGVEVLE; PKLLIKGGVEVLEV; KLLIKGGVEVLEVK;
LLIKGGVEVLEVKT; LIKGGVEVLEVKTG; IKGGVEVLEVKTGV;
KGGVEVLEVKTGVD; GGVEVLEVKTGVDA; GVEVLEVKTGVDAI;
VEVLEVKTGVDAIT; EVLEVKTGVDAITE; VLEVKTGVDAITEV;
LEVKTGVDAITEVE; EVKTGVDAITEVEC; VKTGVDAITEVECF;
KTGVDAITEVECFL; TGVDAITEVECFLN; GVDAITEVECFLNP;
VDAITEVECFLNPE; DAITEVECFLNPEM; AITEVECFLNPEMG;
ITEVECFLNPEMGD; TEVECFLNPEMGDP; EVECFLNPEMGDPD;
VECFLNPEMGDPDE; ECFLNPEMGDPDEN; CFLNPEMGDPDENL;
FLNPEMGDPDENLR; LNPEMGDPDENLRG; NPEMGDPDENLRGF;
PEMGDPDENLRGFS; EMGDPDENLRGFSL; MGDPDENLRGFSLK;
GDPDENLRGFSLKL; DPDENLRGFSLKLS; PDENLRGFSLKLSA;
DENLRGFSLKLSAE; ENLRGFSLKLSAEN; NLRGFSLKLSAEND;
LRGFSLKLSAENDF; RGFSLKLSAENDFS; GFSLKLSAENDFSS;
FSLKLSAENDFSSD; SLKLSAENDFSSDS; LKLSAENDFSSDSP;
KLSAENDFSSDSPE; LSAENDFSSDSPER; SAENDFSSDSPERK;
AENDFSSDSPERKM; ENDFSSDSPERKML; NDFSSDSPERKMLP;
DFSSDSPERKMLPC; FSSDSPERKMLPCY; SSDSPERKMLPCYS;
SDSPERKMLPCYST; DSPERKMLPCYSTA; SPERKMLPCYSTAR;
PERKMLPCYSTARI; ERKMLPCYSTARIP; RKMLPCYSTARIPL;
KMLPCYSTARIPLP; MLPCYSTARIPLPN; LPCYSTARIPLPNL;
PCYSTARIPLPNLN; CYSTARIPLPNLNE; YSTARIPLPNLNED;
STARIPLPNLNEDL; TARIPLPNLNEDLT; ARIPLPNLNEDLTC;
RIPLPNLNEDLTCG; IPLPNLNEDLTCGN; PLPNLNEDLTCGNL;
LPNLNEDLTCGNLL; PNLNEDLTCGNLLM; NLNEDLTCGNLLMW;
LNEDLTCGNLLMWE; NEDLTCGNLLMWEA; EDLTCGNLLMWEAV;
DLTCGNLLMWEAVT; LTCGNLLMWEAVTV; TCGNLLMWEAVTVQ;
CGNLLMWEAVTVQT; GNLLMWEAVTVQTE; NLLMWEAVTVQTEV;
LLMWEAVTVQTEVI; LMWEAVTVQTEVIG; MWEAVTVQTEVIGI;
WEAVTVQTEVIGIT; EAVTVQTEVIGITS; AVTVQTEVIGITSM;
VTVQTEVIGITSML; TVQTEVIGITSMLN; VQTEVIGITSMLNL;
QTEVIGITSMLNLH; TEVIGITSMLNLHA; EVIGITSMLNLHAG;
VIGITSMLNLHAGS; IGITSMLNLHAGSQ; GITSMLNLHAGSQK;
ITSMLNLHAGSQKV; TSMLNLHAGSQKVH; SMLNLHAGSQKVHE;
MLNLHAGSQKVHEH; LNLHAGSQKVHEHG; NLHAGSQKVHEHGG;
LHAGSQKVHEHGGG; HAGSQKVHEHGGGK; AGSQKVHEHGGGKP;
GSQKVHEHGGGKPI; SQKVHEHGGGKPIQ; QKVHEHGGGKPIQG;
KVHEHGGGKPIQGS; VHEHGGGKPIQGSN; HEHGGGKPIQGSNF;
EHGGGKPIQGSNFH; HGGGKPIQGSNFHF; GGGKPIQGSNFHFF;
GGKPIQGSNFHFFA; GKPIQGSNFHFFAV; KPIQGSNFHFFAVG;
PIQGSNFHFFAVGG; IQGSNFHFFAVGGE; QGSNFHFFAVGGEP;
GSNFHFFAVGGEPL; SNFHFFAVGGEPLE; NFHFFAVGGEPLEM;
FHFFAVGGEPLEMQ; HFFAVGGEPLEMQG; FFAVGGEPLEMQGV;
FAVGGEPLEMQGVL; AVGGEPLEMQGVLM; VGGEPLEMQGVLMN;
GGEPLEMQGVLMNY; GEPLEMQGVLMNYR; EPLEMQGVLMNYRS;
PLEMQGVLMNYRSK; LEMQGVLMNYRSKY; EMQGVLMNYRSKYP;
MQGVLMNYRSKYPD; QGVLMNYRSKYPDG; GVLMNYRSKYPDGT;
VLMNYRSKYPDGTI; LMNYRSKYPDGTIT; MNYRSKYPDGTITP;
NYRSKYPDGTITPK; YRSKYPDGTITPKN; RSKYPDGTITPKNP;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

SKYPDGTITPKNPT; KYPDGTITPKNPTA; YPDGTITPKNPTAQ;
PDGTITPKNPTAQS; DGTITPKNPTAQSQ; GTITPKNPTAQSQV;
TITPKNPTAQSQVM; ITPKNPTAQSQVMN; TPKNPTAQSQVMNT;
PKNPTAQSQVMNTD; KNPTAQSQVMNTDH; NPTAQSQVMNTDHK;
PTAQSQVMNTDHKA; TAQSQVMNTDHKAY; AQSQVMNTDHKAYL;
QSQVMNTDHKAYLD; SQVMNTDHKAYLDK; QVMNTDHKAYLDKN;
VMNTDHKAYLDKNN; MNTDHKAYLDKNNA; NTDHKAYLDKNNAY;
TDHKAYLDKNNAYP; DHKAYLDKNNAYPV; HKAYLDKNNAYPVE;
KAYLDKNNAYPVEC; AYLDKNNAYPVECW; YLDKNNAYPVECWV;
LDKNNAYPVECWVP; DKNNAYPVECWVPD; KNNAYPVECWVPDP;
NNAYPVECWVPDPS; NAYPVECWVPDPSR; AYPVECWVPDPSRN;
YPVECWVPDPSRNE; PVECWVPDPSRNEN; VECWVPDPSRNENA;
ECWVPDPSRNENAR; CWVPDPSRNENARY; WVPDPSRNENARYF;
VPDPSRNENARYFG; PDPSRNENARYFGT; DPSRNENARYFGTF;
PSRNENARYFGTFT; SRNENARYFGTFTG; RNENARYFGTFTGG;
NENARYFGTFTGGE; ENARYFGTFTGGEN; NARYFGTFTGGENV;
ARYFGTFTGGENVP; RYFGTFTGGENVPP; YFGTFTGGENVPPV;
FGTFTGGENVPPVL; GTFTGGENVPPVLH; TFTGGENVPPVLHV;
FTGGENVPPVLHVT; TGGENVPPVLHVTN; GGENVPPVLHVTNT;
GENVPPVLHVTNTA; ENVPPVLHVTNTAT; NVPPVLHVTNTATT;
VPPVLHVTNTATTV; PPVLHVTNTATTVL; PVLHVTNTATTVLL;
VLHVTNTATTVLLD; LHVTNTATTVLLDE; HVTNTATTVLLDEQ;
VTNTATTVLLDEQG; TNTATTVLLDEQGV; NTATTVLLDEQGVG;
TATTVLLDEQGVGP; ATTVLLDEQGVGPL; TTVLLDEQGVGPLC;
TVLLDEQGVGPLCK; VLLDEQGVGPLCKA; LLDEQGVGPLCKAD;
LDEQGVGPLCKADS; DEQGVGPLCKADSL; EQGVGPLCKADSLY;
QGVGPLCKADSLYV; GVGPLCKADSLYVS; VGPLCKADSLYVSA;
GPLCKADSLYVSAA; PLCKADSLYVSAAD; LCKADSLYVSAADI;
CKADSLYVSAADIC; KADSLYVSAADICG; ADSLYVSAADICGL;
DSLYVSAADICGLF; SLYVSAADICGLFT; LYVSAADICGLFTN;
YVSAADICGLFTNS; VSAADICGLFTNSS; SAADICGLFTNSSG;
AADICGLFTNSSGT; ADICGLFTNSSGTQ; DICGLFTNSSGTQQ;
ICGLFTNSSGTQQW; CGLFTNSSGTQQWR; GLFTNSSGTQQWRG;
LFTNSSGTQQWRGL; FTNSSGTQQWRGLA; TNSSGTQQWRGLAR;
NSSGTQQWRGLARY; SSGTQQWRGLARYF; SGTQQWRGLARYFK;
GTQQWRGLARYFKI; TQQWRGLARYFKIR; QQWRGLARYFKIRL;
QWRGLARYFKIRLR; WRGLARYFKIRLRK; RGLARYFKIRLRKR;
GLARYFKIRLRKRS; LARYFKIRLRKRSV; ARYFKIRLRKRSVK;
RYFKIRLRKRSVKN; YFKIRLRKRSVKNP; FKIRLRKRSVKNPY;
KIRLRKRSVKNPYP; IRLRKRSVKNPYPI; RLRKRSVKNPYPIS;
LRKRSVKNPYPISF; RKRSVKNPYPISFL; KRSVKNPYPISFLL;
RSVKNPYPISFLLS; SVKNPYPISFLLSD; VKNPYPISFLLSDL;
KNPYPISFLLSDLI; NPYPISFLLSDLIN; PYPISFLLSDLINR;
YPISFLLSDLINRR; PISFLLSDLINRRT; ISFLLSDLINRRTQ;
SFLLSDLINRRTQR; FLLSDLINRRTQRV; LLSDLINRRTQRVD;
LSDLINRRTQRVDG; SDLINRRTQRVDGQ; DLINRRTQRVDGQP;
LINRRTQRVDGQPM; INRRTQRVDGQPMY; NRRTQRVDGQPMYG;
RRTQRVDGQPMYGM; RTQRVDGQPMYGME; TQRVDGQPMYGMES;
QRVDGQPMYGMESQ; RVDGQPMYGMESQV; VDGQPMYGMESQVE;
DGQPMYGMESQVEE; GQPMYGMESQVEEV; QPMYGMESQVEEVR;
PMYGMESQVEEVRV; MYGMESQVEEVRVF; YGMESQVEEVRVFD;
GMESQVEEVRVFDG; MESQVEEVRVFDGT; ESQVEEVRVFDGTE;
SQVEEVRVFDGTER; QVEEVRVFDGTERL; VEEVRVFDGTERLP;
EEVRVFDGTERLPG; EVRVFDGTERLPGD; VRVFDGTERLPGDP;
RVFDGTERLPGDPD; VFDGTERLPGDPDM; FDGTERLPGDPDMI;
DGTERLPGDPDMIR; GTERLPGDPDMIRY; TERLPGDPDMIRYI;
ERLPGDPDMIRYID; RLPGDPDMIRYIDK; LPGDPDMIRYIDKQ;
PGDPDMIRYIDKQG; GDPDMIRYIDKQGQ; DPDMIRYIDKQGQL;
PDMIRYIDKQGQLQ; DMIRYIDKQGQLQT; MIRYIDKQGQLQTK;
IRYIDKQGQLQTKM; RYIDKQGQLQTKML; TGAFIVHIHLINAA;
GAFIVHIHLINAAF; AFIVHIHLINAAFV; FIVHIHLINAAFVT;
TFKLVLFWGWCFRP; FKLVLFWGWCFRPF; KLVLFWGWCFRPFK;
LVLFWGWCFRPFKT; VLFWGWCFRPFKTL; LFWGWCFRPFKTLK;
FWGWCFRPFKTLKA; WGWCFRPFKTLKAF; GWCFRPFKTLKAFT;
WCFRPFKTLKAFTQ; CFRPFKTLKAFTQM; FRPFKTLKAFTQMQ;
RPFKTLKAFTQMQL; PFKTLKAFTQMQLL; FKTLKAFTQMQLLT;
KTLKAFTQMQLLTM; TLKAFTQMQLLTMG; LKAFTQMQLLTMGV;
ILFSCNIKNTFPHA; LFSCNIKNTFPHAY; FSCNIKNTFPHAYI;
SCNIKNTFPHAYII; CNIKNTFPHAYIIH; NIKNTFPHAYIIHP;
IKNTFPHAYIIHPF; KSIHTYLRIQPFLP; SIHTYLRIQPFLPF;
IHTYLRIQPFLPFN; HTYLRIQPFLPFNN; TYLRIQPFLPFNNS;
YLRIQPFLPFNNSR; LRIQPFLPFNNSRL; RIQPFLPFNNSRLY;
IQPFLPFNNSRLYI; QPFLPFNNSRLYIS; PFLPFNNSRLYISC;
FLPFNNSRLYISCK; LPFNNSRLYISCKI; PFNNSRLYISCKIS;
FNNSRLYISCKISY; NNSRLYISCKISYR; NSRLYISCKISYRP;
SRLYISCKISYRPK; RLYISCKISYRPKP; LYISCKISYRPKPN;
IYFGPKIYLSYKSS; YFGPKIYLSYKSSL; FGPKIYLSYKSSLQ;
GPKIYLSYKSSLQG; PKIYLSYKSSLQGF; KIYLSYKSSLQGFR;
IYLSYKSSLQGFRD; YLSYKSSLQGFRDR; LSYKSSLQGFRDRI;
SYKSSLQGFRDRIL; YKSSLQGFRDRILI; KSSLQGFRDRILIH;
SSLQGFRDRILIHC; SLQGFRDRILIHCN; LQGFRDRILIHCNQ;
QGFRDRILIHCNQA; GFRDRILIHCNQAW; FRDRILIHCNQAWW;
RDRILIHCNQAWWK; DRILIHCNQAWWKY; RILIHCNQAWWKYL;
ILIHCNQAWWKYLG; LIHCNQAWWKYLGS; IHCNQAWWKYLGSF;
HCNQAWWKYLGSFV; FSSCPFYIFKNNHV; SSCPFYIFKNNHVL;
SCPFYIFKNNHVLI; CPFYIFKNNHVLIY; PFYIFKNNHVLIYS;
FYIFKNNHVLIYSY; YIFKNNHVLIYSYT; PVSSFRYIENNTVQ;
VSSFRYIENNTVQK; SSFRYIENNTVQKI; SFRYIENNTVQKIK;
FRYIENNTVQKIKY; RYIENNTVQKIKYY; YIENNTVQKIKYYR;
IENNTVQKIKYYRI; ENNTVQKIKYYRIH; NNTVQKIKYYRIHF;
NTVQKIKYYRIHFR; HFPPGHMKGIYSFF; FPPGHMKGIYSFFS;
NCIYCLLTNTFLIF; CIYCLLTNTFLIFT; IYCLLTNTFLIFTF;
YCLLTNTFLIFTFC; CLLTNTFLIFTFCK; LLTNTFLIFTFCKN;
LTNTFLIFTFCKNN; TNTFLIFTFCKNNS; NTFLIFTFCKNNSI;
TFLIFTFCKNNSIC; FLIFTFCKNNSICK; LIFTFCKNNSICKV;
IFTFCKNNSICKVL; FTFCKNNSICKVLF; TFCKNNSICKVLFM;
FCKNNSICKVLFMI; CKNNSICKVLFMIL; KNNSICKVLFMILK;
NNSICKVLFMILKV; NSICKVLFMILKVI; SICKVLFMILKVIR;
ICKVLFMILKVIRL; CKVLFMILKVIRLV; KVLFMILKVIRLVF;
VLFMILKVIRLVFF; LFMILKVIRLVFFL; FMILKVIRLVFFLT;
MILKVIRLVFFLTL; ILKVIRLVFFLTLF; LKVIRLVFFLTLFT;
KVIRLVFFLTLFTL; VIRLVFFLTLFTLL; IRLVFFLTLFTLLY;
RLVFFLTLFTLLYI; LVFFLTLFTLLYIV; VFFLTLFTLLYIVL;
FFLTLFTLLYIVLK; FLTLFTLLYIVLKF; KHILTLCLYCILSN;
FPRHLLCFFRLFWA; PRHLLCFFRLFWAK; RHLLCFFRLFWAKI;
HLLCFFRLFWAKIM; LLCFFRLFWAKIML; LCFFRLFWAKIMLL;
APLNAFFYSMVWIS; PLNAFFYSMVWISS; KTKGTQLLTEIINC;
TKGTQLLTEIINCR; KGTQLLTEIINCRN; GTQLLTEIINCRNS;
TQLLTEIINCRNSM; QLLTEIINCRNSMS; LLTEIINCRNSMSM;
LTEIINCRNSMSMW; TEIINCRNSMSMWS; KEYNIMPSTHVSTN;
EYNIMPSTHVSTNK; YNIMPSTHVSTNKS; NIMPSTHVSTNKSY;
IMPSTHVSTNKSYR; MPSTHVSTNKSYRI; PSTHVSTNKSYRIF;
STHVSTNKSYRIFF; THVSTNKSYRIFFH; HVSTNKSYRIFFHK;
VSTNKSYRIFFHKF; STNKSYRIFFHKFF; TNKSYRIFFHKFFI;
NKSYRIFFHKFFIQ; KSYRIFFHKFFIQN; SYRIFFHKFFIQNL;
YRIFFHKFFIQNLS; RIFFHKFFIQNLSF; IFFHKFFIQNLSFF;
FFHKFFIQNLSFFF; FHKFFIQNLSFFFS; HKFFIQNLSFFFSS;
KFFIQNLSFFFSSI; FFIQNLSFFFSSIH; FIQNLSFFFSSIHS;
IQNLSFFFSSIHSK; QNLSFFFSSIHSKA; NLSFFFSSIHSKAG;
LSFFFSSIHSKAGK; SFFFSSIHSKAGKG; FFFSSIHSKAGKGS;
FFSSIHSKAGKGSI; FSSIHSKAGKGSIT; SSIHSKAGKGSITK;
SIHSKAGKGSITKY; IHSKAGKGSITKYS; HSKAGKGSITKYSL;
SKAGKGSITKYSLT; KAGKGSITKYSLTK; AGKGSITKYSLTKK;
GKGSITKYSLTKKL; KGSITKYSLTKKLV; IRGKVFRVFYLSFF;
RGKVFRVFYLSFFF; GKVFRVFYLSFFFG; KVFRVFYLSFFFGW;
VFRVFYLSFFFGWC; VLRICCCFFITGKH; LRICCCFFITGKHI;
RICCCFFITGKHIF; ICCCFFITGKHIFM; CCCFFITGKHIFMA;
CCFFITGKHIFMAK; IFIPFFIKGTPPGL; FIPFFIKGTPPGLP;
IPFFIKGTPPGLPL; PFFIKGTPPGLPLF; FFIKGTPPGLPLFC;
FIKGTPPGLPLFCS; IKGTPPGLPLFCSI; KGTPPGLPLFCSIG;
GTPPGLPLFCSIGW; TPPGLPLFCSIGWH; PPGLPLFCSIGWHL;
SFRSLKGVSPIIWT; FRSLKGVSPIIWTH; RSLKGVSPIIWTHH;
SLKGVSPIIWTHHC; LKGVSPIIWTHHCR; KGVSPIIWTHHCRV;
GVSPIIWTHHCRVS; VSPIIWTHHCRVSS; SPIIWTHHCRVSSV;
PIIWTHHCRVSSVR; IIWTHHCRVSSVRS; IWTHHCRVSSVRSK;
WTHHCRVSSVRSKP; THHCRVSSVRSKPN; HHCRVSSVRSKPNH;
HCRVSSVRSKPNHC; CRVSSVRSKPNHCV; RVSSVRSKPNHCVK;
VSSVRSKPNHCVKQ; SSVRSKPNHCVKQS; SVRSKPNHCVKQSM;
VRSKPNHCVKQSMQ; QSIQTKGSFLKNFL; SIQTKGSFLKNFLF;
IQTKGSFLKNFLFK; QTKGSFLKNFLFKC; TKGSFLKNFLFKCL;
KGSFLKNFLFKCLN; GSFLKNFLFKCLNL; SFLKNFLFKCLNLS;
HSMQGQCTEGFLEQ; SMQGQCTEGFLEQI; MQGQCTEGFLEQIG;
QGQCTEGFLEQIGS; GQCTEGFLEQIGSL; QCTEGFLEQIGSLQ;
CTEGFLEQIGSLQY; TEGFLEQIGSLQYR; EGFLEQIGSLQYRV;
GFLEQIGSLQYRVS; FLEQIGSLQYRVSG; LEQIGSLQYRVSGQ;
EQIGSLQYRVSGQR; QIGSLQYRVSGQRG; IGSLQYRVSGQRGK;
GHSLQYRVSGQRGK; HSLQYRVSGQRGKS; SLQYRVSGQRGKSA;
LQYRVSGQRGKSAQ; QYRVSGQRGKSAQT; YRVSGQRGKSAQTS;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

RVSGQRGKSAQTSE; VSGQRGKSAQTSEL; SGQRGKSAQTSELL;
GQRGKSAQTSELLQ; QRGKSAQTSELLQV; RGKSAQTSELLQVP;
GKSAQTSELLQVPK; KSAQTSELLQVPKS; SAQTSELLQVPKSG;
ATFTSCSIFLYKVF; TFTSCSIFLYKVFI; FTSCSIFLYKVFIL;
TSCSIFLYKVFILF; SCSIFLYKVFILFI; CSIFLYKVFILFIL;
SIFLYKVFILFILS; IFLYKVFILFILSS; FLYKVFILFILSSS;
LYKVFILFILSSSP; YKVFILFILSSSPP; KVFILFILSSSPPL;
VFILFILSSSPPLS; FILFILSSSPPLSG; AFLIKGRFPQAALS;
FLIKGRFPQAALSR; LIKGRFPQAALSRP; IKGRFPQAALSRPK;
KGRFPQAALSRPKR; GRFPQAALSRPKRS; RFPQAALSRPKRSM;
FPQAALSRPKRSMS; PQAALSRPKRSMSS; QAALSRPKRSMSSM;
AALSRPKRSMSSMD; ALSRPKRSMSSMDS; LSRPKRSMSSMDSS;
SRPKRSMSSMDSSL; RPKRSMSSMDSSLL; PKRSMSSMDSSLLR;
KRSMSSMDSSLLRT; RSMSSMDSSLLRTL; SMSSMDSSLLRTLS 15 mers:

FCKNCKRIGISPNSF; CKNCKRIGISPNSFA; KNCKRIGISPNSFAR;
NCKRIGISPNSFARP; CKRIGISPNSFARPQ; KRIGISPNSFARPQK;
RIGISPNSFARPQKK; IGISPNSFARPQKKP; GISPNSFARPQKKPP;
ISPNSFARPQKKPPH; SPNSFARPQKKPPHP; PNSFARPQKKPPHPY;
NSFARPQKKPPHPYY; SFARPQKKPPHPYYL; FARPQKKPPHPYYLR;
ARPQKKPPHPYYLRE; RPQKKPPHPYYLRER; PQKKPPHPYYLRERV;
QKKPPHPYYLRERVE; KKPPHPYYLRERVEA; KPPHPYYLRERVEAE;
PPHPYYLRERVEAEA; PHPYYLRERVEAEAA; HPYYLRERVEAEAAS;
PYYLRERVEAEAASA; YYLRERVEAEAASAS; YLRERVEAEAASASY;
LRERVEAEAASASYI; RERVEAEAASASYIL; KKRPQGGAAYPWNAA;
KRPQGGAAYPWNAAK; RPQGGAAYPWNAAKP; PQEGKCMTHRGMQPN;
QEGKCMTHRGMQPNH; EGKCMTHRGMQPNHD; GKCMTHRGMQPNHDL;
KCMTHRGMQPNHDLR; CMTHRGMQPNHDLRK; MTHRGMQPNHDLRKE;
THRGMQPNHDLRKES; HRGMQPNHDLRKESA; LTGRSCLPMECSQTM;
TGRSCLPMECSQTMT; GRSCLPMECSQTMTS; RSCLPMECSQTMTSG;
SCLPMECSQTMTSGR; CLPMECSQTMTSGRK; LPMECSQTMTSGRKV;
PMECSQTMTSGRKVH; MECSQTMTSGRKVHD; ECSQTMTSGRKVHDR;
CSQTMTSGRKVHDRH; SQTMTSGRKVHDRHV; QTMTSGRKVHDRHVL;
TMTSGRKVHDRHVLR; MTSGRKVHDRHVLRA; ESWPCPQLNWTKAMV;
SWPCPQLNWTKAMVL; WPCPQLNWTKAMVLR; PCPQLNWTKAMVLRQ;
CPQLNWTKAMVLRQL; PQLNWTKAMVLRQLS; QLNWTKAMVLRQLSR;
LNWTKAMVLRQLSRQ; NWTKAMVLRQLSRQA; WTKAMVLRQLSRQAS;
TKAMVLRQLSRQASV; KAMVLRQLSRQASVK; AMVLRQLSRQASVKV;
MVLRQLSRQASVKVG; VLRQLSRQASVKVGK; LRQLSRQASVKVGKT;
RQLSRQASVKVGKTW; QLSRQASVKVGKTWT; LSRQASVKVGKTWTG;
SRQASVKVGKTWTGT; RQASVKVGKTWTGTK; QASVKVGKTWTGTKK;
ASVKVGKTWTGTKKR; SVKVGKTWTGTKKRA; VKVGKTWTGTKKRAQ;
KVGKTWTGTKKRAQR; VGKTWTGTKKRAQRI; GKTWTGTKKRAQRIF;
KTWTGTKKRAQRIFI; TWTGTKKRAQRIFIF; WTGTKKRAQRIFIFI;
TGTKKRAQRIFIFIL; GTKKRAQRIFIFILE; TKKRAQRIFIFILEL;
KKRAQRIFIFILELL; KRAQRIFIFILELLE; RAQRIFIFILELLLE;
AQRIFIFILELLLEF; QRIFIFILELLLEFC; RIFIFILELLLEFCR;
IFIFILELLLEFCRG; FIFILELLLEFCRGE; IFILELLLEFCRGED;
FILELLLEFCRGEDS; ILELLLEFCRGEDSV; LELLLEFCRGEDSVD;
ELLLEFCRGEDSVDG; LLLEFCRGEDSVDGK; LLEFCRGEDSVDGKN;
LEFCRGEDSVDGKNK; EFCRGEDSVDGKNKS; FCRGEDSVDGKNKST;
CRGEDSVDGKNKSTT; RGEDSVDGKNKSTTA; GEDSVDGKNKSTTAL;
EDSVDGKNKSTTALP; DSVDGKNKSTTALPA; SVDGKNKSTTALPAV;
VDGKNKSTTALPAVK; DGKNKSTTALPAVKD; GKNKSTTALPAVKDS;
KNKSTTALPAVKDSV; NKSTTALPAVKDSVK; KSTTALPAVKDSVKD;
STTALPAVKDSVKDS; VSNPFFFVFPGSWVL; SNPFFFVFPGSWVLL;
LPVYLRLLLPQDFQW; PVYLRLLLPQDFQWL; VYLRLLLPQDFQWLK;
YLRLLLPQDFQWLKL; LRLLLPQDFQWLKLL; RLLLPQDFQWLKLLL;
LLLPQDFQWLKLLLG; LLPQDFQWLKLLLGR; LPQDFQWLKLLLGRL;
PQDFQWLKLLLGRLL; QDFQWLKLLLGRLLL; DFQWLKLLLGRLLLL;
ASISNQAWLWNCLTQ; SISNQAWLWNCLTQM; ISNQAWLWNCLTQMS;
SNQAWLWNCLTQMST; NQAWLWNCLTQMSTM; QAWLWNCLTQMSTMI;
AWLWNCLTQMSTMIF; WLWNCLTQMSTMIFC; LWNCLTQMSTMIFCF;
WNCLTQMSTMIFCFL; NCLTQMSTMIFCFLV; ILLLIIFNTLILGIG;
LLLIIFNTLILGIGV; LLIIFNTLILGIGVL; LIIFNTLILGIGVLL;
IIFNTLILGIGVLLC; IFNTLILGIGVLLCL; FNTLILGIGVLLCLL;
NTLILGIGVLLCLLL; TLILGIGVLLCLLLF; LILGIGVLLCLLLFP;
ILGIGVLLCLLLFPR; LGIGVLLCLLLFPRL; GIGVLLCLLLFPRLC;
IGVLLCLLLFPRLCG; GVLLCLLLFPRLCGM; VLLCLLLFPRLCGML;
LLCLLLFPRLCGMLL; LCLLLFPRLCGMLLG; CLLLFPRLCGMLLGM;
LLLFPRLCGMLLGMI; LLFPRLCGMLLGMIY; LFPRLCGMLLGMIYL;
FPRLCGMLLGMIYLL; PHRNCREEQKDFLET; HRNCREEQKDFLETP;
RNCREEQKDFLETPW; NCREEQKDFLETPWL; CREEQKDFLETPWLD;
REEQKDFLETPWLDF; EEQKDFLETPWLDFW; EQKDFLETPWLDFWR;
QKDFLETPWLDFWRK; KDFLETPWLDFWRKL; DFLETPWLDFWRKLP;
FLETPWLDFWRKLPG; LETPWLDFWRKLPGQ; ETPWLDFWRKLPGQL;
TFIIIFNNIILIFPL; FIIIFNNIILIFPLL; IIIFNNIILIFPLLG;
IIFNNIILIFPLLGP; IFNNIILIFPLLGPQ; FNNIILIFPLLGPQW;
NNIILIFPLLGPQWL; NIILIFPLLGPQWLD; IILIFPLLGPQWLDK;
LKGKVPVYILAILIV; KKLLPQEVLIKELLL; KLLPQEVLIKELLLN;
LLPQEVLIKELLLNG; LPQEVLIKELLLNGC; PQEVLIKELLLNGCC;
QEVLIKELLLNGCCL; EVLIKELLLNGCCLY; VLIKELLLNGCCLYF;
HLLLKHMKMAPTKRK; LLLKHMKMAPTKRKG; LLKHMKMAPTKRKGE;
LKHMKMAPTKRKGEC; KHMKMAPTKRKGECP; HMKMAPTKRKGECPG;
MKMAPTKRKGECPGA; KMAPTKRKGECPGAA; MAPTKRKGECPGAAP;
APTKRKGECPGAAPK; PTKRKGECPGAAPKK; TKRKGECPGAAPKKP;
KRKGECPGAAPKKPK; RKGECPGAAPKKPKE; KGECPGAAPKKPKEP;
GECPGAAPKKPKEPV; ECPGAAPKKPKEPVQ; CPGAAPKKPKEPVQV;
PGAAPKKPKEPVQVP; GAAPKKPKEPVQVPK; AAPKKPKEPVQVPKL;
APKKPKEPVQVPKLL; PKKPKEPVQVPKLLI; KKPKEPVQVPKLLIK;
KPKEPVQVPKLLIKG; PKEPVQVPKLLIKGG; KEPVQVPKLLIKGGV;
EPVQVPKLLIKGGVE; PVQVPKLLIKGGVEV; VQVPKLLIKGGVEVL;
QVPKLLIKGGVEVLE; VPKLLIKGGVEVLEV; PKLLIKGGVEVLEVK;
KLLIKGGVEVLEVKT; LLIKGGVEVLEVKTG; LIKGGVEVLEVKTGV;
IKGGVEVLEVKTGVD; KGGVEVLEVKTGVDA; GGVEVLEVKTGVDAI;
GVEVLEVKTGVDAIT; VEVLEVKTGVDAITE; EVLEVKTGVDAITEV;
VLEVKTGVDAITEVE; LEVKTGVDAITEVEC; EVKTGVDAITEVECF;
VKTGVDAITEVECFL; KTGVDAITEVECFLN; TGVDAITEVECFLNP;
GVDAITEVECFLNPE; VDAITEVECFLNPEM; DAITEVECFLNPEMG;
AITEVECFLNPEMGD; ITEVECFLNPEMGDP; TEVECFLNPEMGDPD;
EVECFLNPEMGDPDE; VECFLNPEMGDPDEN; ECFLNPEMGDPDENL;
CFLNPEMGDPDENLR; FLNPEMGDPDENLRG; LNPEMGDPDENLRGF;
NPEMGDPDENLRGFS; PEMGDPDENLRGFSL; EMGDPDENLRGFSLK;
MGDPDENLRGFSLKL; GDPDENLRGFSLKLS; DPDENLRGFSLKLSA;
PDENLRGFSLKLSAE; DENLRGFSLKLSAEN; ENLRGFSLKLSAEND;
NLRGFSLKLSAENDF; LRGFSLKLSAENDFS; RGFSLKLSAENDFSS;
GFSLKLSAENDFSSD; FSLKLSAENDFSSDS; SLKLSAENDFSSDSP;
LKLSAENDFSSDSPE; KLSAENDFSSDSPER; LSAENDFSSDSPERK;
SAENDFSSDSPERKM; AENDFSSDSPERKML; ENDFSSDSPERKMLP;
NDFSSDSPERKMLPC; DFSSDSPERKMLPCY; FSSDSPERKMLPCYS;
SSDSPERKMLPCYST; SDSPERKMLPCYSTA; DSPERKMLPCYSTAR;
SPERKMLPCYSTARI; PERKMLPCYSTARIP; ERKMLPCYSTARIPL;
RKMLPCYSTARIPLP; KMLPCYSTARIPLPN; MLPCYSTARIPLPNL;
LPCYSTARIPLPNLN; PCYSTARIPLPNLNE; CYSTARIPLPNLNED;
YSTARIPLPNLNEDL; STARIPLPNLNEDLT; TARIPLPNLNEDLTC;
ARIPLPNLNEDLTCG; RIPLPNLNEDLTCGN; IPLPNLNEDLTCGNL;
PLPNLNEDLTCGNLL; LPNLNEDLTCGNLLM; PNLNEDLTCGNLLMW;
NLNEDLTCGNLLMWE; LNEDLTCGNLLMWEA; NEDLTCGNLLMWEAV;
EDLTCGNLLMWEAVT; DLTCGNLLMWEAVTV; LTCGNLLMWEAVTVQ;
TCGNLLMWEAVTVQT; CGNLLMWEAVTVQTE; GNLLMWEAVTVQTEV;
NLLMWEAVTVQTEVI; LLMWEAVTVQTEVIG; LMWEAVTVQTEVIGI;
MWEAVTVQTEVIGIT; WEAVTVQTEVIGITS; EAVTVQTEVIGITSM;
AVTVQTEVIGITSML; VTVQTEVIGITSMLN; TVQTEVIGITSMLNL;
VQTEVIGITSMLNLH; QTEVIGITSMLNLHA; TEVIGITSMLNLHAG;
EVIGITSMLNLHAGS; VIGITSMLNLHAGSQ; IGITSMLNLHAGSQK;
GITSMLNLHAGSQKV; ITSMLNLHAGSQKVH; TSMLNLHAGSQKVHE;
SMLNLHAGSQKVHEH; MLNLHAGSQKVHEHG; LNLHAGSQKVHEHGG;
NLHAGSQKVHEHGGG; LHAGSQKVHEHGGGK; HAGSQKVHEHGGGKP;
AGSQKVHEHGGGKPI; GSQKVHEHGGGKPIQ; SQKVHEHGGGKPIQG;
QKVHEHGGGKPIQGS; KVHEHGGGKPIQGSN; VHEHGGGKPIQGSNF;
HEHGGGKPIQGSNFH; EHGGGKPIQGSNFHF; HGGGKPIQGSNFHFF;
GGGKPIQGSNFHFFA; GGKPIQGSNFHFFAV; GKPIQGSNFHFFAVG;
KPIQGSNFHFFAVGG; PIQGSNFHFFAVGGE; IQGSNFHFFAVGGEP;
QGSNFHFFAVGGEPL; GSNFHFFAVGGEPLE; SNFHFFAVGGEPLEM;
NFHFFAVGGEPLEMQ; FHFFAVGGEPLEMQG; HFFAVGGEPLEMQGV;
FFAVGGEPLEMQGVL; FAVGGEPLEMQGVLM; AVGGEPLEMQGVLMN;
VGGEPLEMQGVLMNY; GGEPLEMQGVLMNYR; GEPLEMQGVLMNYRS;
EPLEMQGVLMNYRSK; PLEMQGVLMNYRSKY; LEMQGVLMNYRSKYP;
EMQGVLMNYRSKYPD; MQGVLMNYRSKYPDG; QGVLMNYRSKYPDGT;
GVLMNYRSKYPDGTI; VLMNYRSKYPDGTIT; LMNYRSKYPDGTITP;
MNYRSKYPDGTITPK; NYRSKYPDGTITPKN; YRSKYPDGTITPKNP;
RSKYPDGTITPKNPT; SKYPDGTITPKNPTA; KYPDGTITPKNPTAQ;
YPDGTITPKNPTAQS; PDGTITPKNPTAQSQ; DGTITPKNPTAQSQV;
GTITPKNPTAQSQVM; TITPKNPTAQSQVMN; ITPKNPTAQSQVMNT;
TPKNPTAQSQVMNTD; PKNPTAQSQVMNTDH; KNPTAQSQVMNTDHK;
NPTAQSQVMNTDHKA; PTAQSQVMNTDHKAY; TAQSQVMNTDHKAYL;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

AQSQVMNTDHKAYLD; QSQVMNTDHKAYLDK; SQVMNTDHKAYLDKN;
QVMNTDHKAYLDKNN; VMNTDHKAYLDKNNA; MNTDHKAYLDKNNAY;
NTDHKAYLDKNNAYP; TDHKAYLDKNNAYPV; DHKAYLDKNNAYPVE;
HKAYLDKNNAYPVEC; KAYLDKNNAYPVECW; AYLDKNNAYPVECWV;
YLDKNNAYPVECWVP; LDKNNAYPVECWVPD; DKNNAYPVECWVPDP;
KNNAYPVECWVPDPS; NNAYPVECWVPDPSR; NAYPVECWVPDPSRN;
AYPVECWVPDPSRNE; YPVECWVPDPSRNEN; PVECWVPDPSRNENA;
VECWVPDPSRNENAR; ECWVPDPSRNENARY; CWVPDPSRNENARYF;
WVPDPSRNENARYFG; VPDPSRNENARYFGT; PDPSRNENARYFGTF;
DPSRNENARYFGTFT; PSRNENARYFGTFTG; SRNENARYFGTFTGG;
RNENARYFGTFTGGE; NENARYFGTFTGGEN; ENARYFGTFTGGENV;
NARYFGTFTGGENVP; ARYFGTFTGGENVPP; RYFGTFTGGENVPPV;
YFGTFTGGENVPPVL; FGTFTGGENVPPVLH; GTFTGGENVPPVLHV;
TFTGGENVPPVLHVT; FTGGENVPPVLHVTN; TGGENVPPVLHVTNT;
GGENVPPVLHVTNTA; GENVPPVLHVTNTAT; ENVPPVLHVTNTATT;
NVPPVLHVTNTATTV; VPPVLHVTNTATTVL; PPVLHVTNTATTVLL;
PVLHVTNTATTVLLD; VLHVTNTATTVLLDE; LHVTNTATTVLLDEQ;
HVTNTATTVLLDEQG; VTNTATTVLLDEQGV; TNTATTVLLDEQGVG;
NTATTVLLDEQGVGP; TATTVLLDEQGVGPL; ATTVLLDEQGVGPLC;
TTVLLDEQGVGPLCK; TVLLDEQGVGPLCKA; VLLDEQGVGPLCKAD;
LLDEQGVGPLCKADS; LDEQGVGPLCKADSL; DEQGVGPLCKADSLY;
EQGVGPLCKADSLYV; QGVGPLCKADSLYVS; GVGPLCKADSLYVSA;
VGPLCKADSLYVSAA; GPLCKADSLYVSAAD; PLCKADSLYVSAADI;
LCKADSLYVSAADIC; CKADSLYVSAADICG; KADSLYVSAADICGL;
ADSLYVSAADICGLF; DSLYVSAADICGLFT; SLYVSAADICGLFTN;
LYVSAADICGLFTNS; YVSAADICGLFTNSS; VSAADICGLFTNSSG;
SAADICGLFTNSSGT; AADICGLFTNSSGTQ; ADICGLFTNSSGTQQ;
DICGLFTNSSGTQQW; ICGLFTNSSGTQQWR; CGLFTNSSGTQQWRG;
GLFTNSSGTQQWRGL; LFTNSSGTQQWRGLA; FTNSSGTQQWRGLAR;
TNSSGTQQWRGLARY; NSSGTQQWRGLARYF; SSGTQQWRGLARYFK;
SGTQQWRGLARYFKI; GTQQWRGLARYFKIR; TQQWRGLARYFKIRL;
QQWRGLARYFKIRLR; QWRGLARYFKIRLRK; WRGLARYFKIRLRKR;
RGLARYFKIRLRKRS; GLARYFKIRLRKRSV; LARYFKIRLRKRSVK;
ARYFKIRLRKRSVKN; RYFKIRLRKRSVKNP; YFKIRLRKRSVKNPY;
FKIRLRKRSVKNPYP; KIRLRKRSVKNPYPI; IRLRKRSVKNPYPIS;
RLRKRSVKNPYPISF; LRKRSVKNPYPISFL; RKRSVKNPYPISFLL;
KRSVKNPYPISFLLS; RSVKNPYPISFLLSD; SVKNPYPISFLLSDL;
VKNPYPISFLLSDLI; KNPYPISFLLSDLIN; NPYPISFLLSDLINR;
PYPISFLLSDLINRR; YPISFLLSDLINRRT; PISFLLSDLINRRTQ;
ISFLLSDLINRRTQR; SFLLSDLINRRTQRV; FLLSDLINRRTQRVD;
LLSDLINRRTQRVDG; LSDLINRRTQRVDGQ; SDLINRRTQRVDGQP;
DLINRRTQRVDGQPM; LINRRTQRVDGQPMY; INRRTQRVDGQPMYG;
NRRTQRVDGQPMYGM; RRTQRVDGQPMYGME; RTQRVDGQPMYGMES;
TQRVDGQPMYGMESQ; QRVDGQPMYGMESQV; RVDGQPMYGMESQVE;
VDGQPMYGMESQVEE; DGQPMYGMESQVEEV; GQPMYGMESQVEEVR;
QPMYGMESQVEEVRV; PMYGMESQVEEVRVF; MYGMESQVEEVRVFD;
YGMESQVEEVRVFDG; GMESQVEEVRVFDGT; MESQVEEVRVFDGTE;
ESQVEEVRVFDGTER; SQVEEVRVFDGTERL; QVEEVRVFDGTERLP;
VEEVRVFDGTERLPG; EEVRVFDGTERLPGD; EVRVFDGTERLPGDP;
VRVFDGTERLPGDPD; RVFDGTERLPGDPDM; VFDGTERLPGDPDMI;
FDGTERLPGDPDMIR; DGTERLPGDPDMIRY; GTERLPGDPDMIRYI;
TERLPGDPDMIRYID; ERLPGDPDMIRYIDK; RLPGDPDMIRYIDKQ;
LPGDPDMIRYIDKQG; PGDPDMIRYIDKQGQ; GDPDMIRYIDKQGQL;
DPDMIRYIDKQGQLQ; PDMIRYIDKQGQLQT; DMIRYIDKQGQLQTK;
MIRYIDKQGQLQTKM; IRYIDKQGQLQTKML; TGAFIVIHLINAAF;
GAFIVIHLINAAFV; ATFKLVLFWGWCFRP; TFKLVLFWGWCFRPF;
FKLVLFWGWCFRPFK; KLVLFWGWCFRPFKT; LVLFWGWCFRPFKTL;
VLFWGWCFRPFKTLK; LFWGWCFRPFKTLKA; FWGWCFRPFKTLKAF;
WGWCFRPFKTLKAFT; GWCFRPFKTLKAFTQ; WCFRPFKTLKAFTQM;
CFRPFKTLKAFTQMQ; FRPFKTLKAFTQMQL; RPFKTLKAFTQMQLL;
PFKTLKAFTQMQLLT; FKTLKAFTQMQLLTM; KTLKAFTQMQLLTMG;
TLKAFTQMQLLTMGV; ILFSCNIKNTFPHAY; LFSCNIKNTFPHAYI;
FSCNIKNTFPHAYII; SCNIKNTFPHAYIIF; CNIKNTFPHAYIIFH;
NIKNTFPHAYIIFHP; KSIHTYLRIQPFLPF; SIHTYLRIQPFLPFN;
IHTYLRIQPFLPFNN; HTYLRIQPFLPFNNS; TYLRIQPFLPFNNSR;
YLRIQPFLPFNNSRL; LRIQPFLPFNNSRLY; RIQPFLPFNNSRLYI;
IQPFLPFNNSRLYIS; QPFLPFNNSRLYISC; PFLPFNNSRLYISCK;
FLPFNNSRLYISCKI; LPFNNSRLYISCKIS; PFNNSRLYISCKISY;
FNNSRLYISCKISYR; NNSRLYISCKISYRP; NSRLYISCKISYRPK;
SRLYISCKISYRPKP; RLYISCKISYRPKPN; LYISCKISYRPKPNI;
YISCKISYRPKPNIY; ISCKISYRPKPNIYF; SCKISYRPKPNIYFG;
CKISYRPKPNIYFGP; KISYRPKPNIYFGPK; ISYRPKPNIYFGPKI;
SYRPKPNIYFGPKIY; YRPKPNIYFGPKIYL; RPKPNIYFGPKIYLS;
PKPNIYFGPKIYLSY; KPNIYFGPKIYLSYK; PNIYFGPKIYLSYKS;
NIYFGPKIYLSYKSS; IYFGPKIYLSYKSSL; YFGPKIYLSYKSSLQ; FGPKIYLSYKSSLQG; GPKIYLSYKSSLQGF;
PKIYLSYKSSLQGFR; KIYLSYKSSLQGFRD; IYLSYKSSLQGFRDR;
YLSYKSSLQGFRDRI; LSYKSSLQGFRDRIL; SYKSSLQGFRDRILI;
YKSSLQGFRDRILIH; KSSLQGFRDRILIHC; SSLQGFRDRILIHCN;
SLQGFRDRILIHCNQ; LQGFRDRILIHCNQA; QGFRDRILIHCNQAW;
GFRDRILIHCNQAWW; FRDRILIHCNQAWWK; RDRILIHCNQAWWKY;
DRILIHCNQAWWKYL; RILIHCNQAWWKYLG; ILIHCNQAWWKYLGS;
LIHCNQAWWKYLGSF; IHCNQAWWKYLGSFV; FSSCPFYIFKNNHVL;
SSCPFYIFKNNHVLI; SCPFYIFKNNHVLIY; CPFYIFKNNHVLIYS;
PFYIFKNNHVLIYSY; FYIFKNNHVLIYSYT; PVSSFRYIENNTVQK;
VSSFRYIENNTVQKI; SSFRYIENNTVQKIK; SFRYIENNTVQKIKY;
FRYIENNTVQKIKYY; RYIENNTVQKIKYYR; YIENNTVQKIKYYRI;
IENNTVQKIKYYRIH; ENNTVQKIKYYRIHF; NNTVQKIKYYRIHFR;
HFFPGHMKGIYSFFS; NCIYCLLTNTFLIFT; CIYCLLTNTFLIFTF;
IYCLLTNTFLIFTFC; YCLLTNTFLIFTFCK; CLLTNTFLIFTFCKN;
LLTNTFLIFTFCKNN; LTNTFLIFTFCKNNS; TNTFLIFTFCKNNSI;
NTFLIFTFCKNNSIC; TFLIFTFCKNNSICK; FLIFTFCKNNSICKV;
LIFTFCKNNSICKVL; IFTFCKNNSICKVLF; FTFCKNNSICKVLFM;
TFCKNNSICKVLFMI; FCKNNSICKVLFMIL; CKNNSICKVLFMILK;
KNNSICKVLFMILKV; NNSICKVLFMILKVI; NSICKVLFMILKVIR;
SICKVLFMILKVIRL; ICKVLFMILKVIRLV; CKVLFMILKVIRLVF;
KVLFMILKVIRLVFF; VLFMILKVIRLVFFL; LFMILKVIRLVFFLT;
FMILKVIRLVFFLTL; MILKVIRLVFFLTLF; ILKVIRLVFFLTLFT;
LKVIRLVFFLTLFTL; KVIRLVFFLTLFTLL; VIRLVFFLTLFTLLY;
IRLVFFLTLFTLLYI; RLVFFLTLFTLLYIV; LVFFLTLFTLLYIVL;
VFFLTLFTLLYIVLK; FFLTLFTLLYIVLKF; FPRHLLCFFRLFWAK;
PRHLLCFFRLFWAKI; RHLLCFFRLFWAKIM; HLLCFFRLFWAKIML;
LLCFFRLFWAKIMLL; APLNAFFYSMVWISS; KTKGTQLLTEIINCR;
TKGTQLLTEIINCRN; KGTQLLTEIINCRNS; GTQLLTEIINCRNSM;
TQLLTEIINCRNSMS; QLLTEIINCRNSMSM; LLTEIINCRNSMSMW;
LTEIINCRNSMSMWG; KEYNIMPSTHVSTNK; EYNIMPSTHVSTNKS;
YNIMPSTHVSTNKSY; NIMPSTHVSTNKSYR; IMPSTHVSTNKSYRI;
MPSTHVSTNKSYRIF; PSTHVSTNKSYRIFF; STHVSTNKSYRIFFH;
THVSTNKSYRIFFHK; HVSTNKSYRIFFHKF; VSTNKSYRIFFHKFF;
STNKSYRIFFHKFFI; TNKSYRIFFHKFFIQ; NKSYRIFFHKFFIQN;
KSYRIFFHKFFIQNL; SYRIFFHKFFIQNLS; YRIFFHKFFIQNLSF;
RIFFHKFFIQNLSFF; IFFHKFFIQNLSFFF; FFHKFFIQNLSFFFS;
FHKFFIQNLSFFFSS; HKFFIQNLSFFFSSI; KFFIQNLSFFFSSIH;
FFIQNLSFFFSSIHS; FIQNLSFFFSSIHSK; IQNLSFFFSSIHSKA;
QNLSFFFSSIHSKAG; NLSFFFSSIHSKAGK; LSFFFSSIHSKAGKG;
SFFFSSIHSKAGKGS; FFFSSIHSKAGKGSI; FFSSIHSKAGKGSIT;
FSSIHSKAGKGSITK; SSIHSKAGKGSITKY; SIHSKAGKGSITKYS;
IHSKAGKGSITKYSL; HSKAGKGSITKYSLT; SKAGKGSITKYSLTK;
KAGKGSITKYSLTKK; AGKGSITKYSLTKKL; GKGSITKYSLTKKLY;
IRGKVFRVFYLSFFF; RGKVFRVFYLSFFFG; GKVFRVFYLSFFFGW;
KVFRVFYLSFFFGWC; VLRICCCFFITGKHI; LRICCCFFITGKHIF;
RICCCFFITGKHIFM; ICCCFFITGKHIFMA; CCCFFITGKHIFMAK;
IFIPFFIKGTPPGLP; FIPFFIKGTPPGLPL; IPFFIKGTPPGLPLF;
PFFIKGTPPGLPLFC; FFIKGTPPGLPLFCS; FIKGTPPGLPLFCSI;
IKGTPPGLPLFCSIG; KGTPPGLPLFCSIGW; GTPPGLPLFCSIGWH;
TPPGLPLFCSIGWHL; SFRSLKGVSPIIWTH; FRSLKGVSPIIWTHH;
RSLKGVSPIIWTHHC; SLKGVSPIIWTHHCR; LKGVSPIIWTHHCRV;
KGVSPIIWTHHCRVS; GVSPIIWTHHCRVSS; VSPIIWTHHCRVSSV;
SPIIWTHHCRVSSVR; PIIWTHHCRVSSVRS; IIWTHHCRVSSVRSK;
IWTHHCRVSSVRSKP; WTHHCRVSSVRSKPN; THHCRVSSVRSKPNH;
HHCRVSSVRSKPNHC; HCRVSSVRSKPNHCV; CRVSSVRSKPNHCVK;
RVSSVRSKPNHCVKQ; VSSVRSKPNHCVKQS; SSVRSKPNHCVKQSM;
SVRSKPNHCVKQSMQ; QSIQTKGSFLKNFLF; SIQTKGSFLKNFLFK;
IQTKGSFLKNFLFKC; QTKGSFLKNFLFKCL; TKGSFLKNFLFKCLN;
KGSFLKNFLFKCLNL; GSFLKNFLFKCLNLS; HSMQGQCTEGFLEQI;
SMQGQCTEGFLEQIG; MQGQCTEGFLEQIGH; QGQCTEGFLEQIGHS;
GQCTEGFLEQIGHSL; QCTEGFLEQIGHSLQ; CTEGFLEQIGHSLQY;
TEGFLEQIGHSLQYR; EGFLEQIGHSLQYRV; GFLEQIGHSLQYRVS;
FLEQIGHSLQYRVSG; LEQIGHSLQYRVSGQ; EQIGHSLQYRVSGQR;
QIGHSLQYRVSGQRG; IGHSLQYRVSGQRGK; GHSLQYRVSGQRGKS;
HSLQYRVSGQRGKSA; SLQYRVSGQRGKSAQ; LQYRVSGQRGKSAQT;
QYRVSGQRGKSAQTS; YRVSGQRGKSAQTSE; RVSGQRGKSAQTSEL;
VSGQRGKSAQTSELL; SGQRGKSAQTSELLQ; GQRGKSAQTSELLQV;
QRGKSAQTSELLQVP; RGKSAQTSELLQVPK; GKSAQTSELLQVPKS;
KSAQTSELLQVPKSG; ATFTSCSIFLYKVFI; TFTSCSIFLYKVFIL;
FTSCSIFLYKVFILF; TSCSIFLYKVFILFI; SCSIFLYKVFILFIL;
CSIFLYKVFILFILS; SIFLYKVFILFILSS; IFLYKVFILFILSSS;
FLYKVFILFILSSSP; LYKVFILFILSSSPP; YKVFILFILSSSPPL;
KVFILFILSSSPPLS; VFILFILSSSPPLSG; AFLIKGRFPQAALSR;
FLIKGRFPQAALSRP; LIKGRFPQAALSRPK; IKGRFPQAALSRPKR;
KGRFPQAALSRPKRS; GRFPQAALSRPKRSM; RFPQAALSRPKRSMS;
FPQAALSRPKRSMSS; PQAALSRPKRSMSSM; QAALSRPKRSMSSMD;
AALSRPKRSMSSMDS; ALSRPKRSMSSMDSS; LSRPKRSMSSMDSSL;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

SRPKRSMSSMDSSLL; RPKRSMSSMDSSLLR; PKRSMSSMDSSLLRT;
KRSMSSMDSSLLRTL; RSMSSMDSSLLRTLS 16 mers:

FCKNCKRIGISPNSFA; CKNCKRIGISPNSFAR;
KNCKRIGISPNSFARP; NCKRIGISPNSFARPQ;
CKRIGISPNSFARPQK; KRIGISPNSFARPQKK;
RIGISPNSFARPQKKP; IGISPNSFARPQKKPP;
GISPNSFARPQKKPPH; ISPNSFARPQKKPPHP;
SPNSFARPQKKPPHPY; PNSFARPQKKPPHPYY;
NSFARPQKKPPHPYYL; SFARPQKKPPHPYYLR;
FARPQKKPPHPYYLRE; ARPQKKPPHPYYLRER;
RPQKKPPHPYYLRERV; PQKKPPHPYYLRERVE;
QKKPPHPYYLRERVEA; KKPPHPYYLRERVEAE;
KPPHPYYLRERVEAEA; PPHPYYLRERVEAEAA;
PHPYYLRERVEAEAAS; HPYYLRERVEAEAASA;
PYYLRERVEAEAASAS; YYLRERVEAEAASASY;
YLRERVEAEAASASYI; LRERVEAEAASASYIL;
KKRPQGGAAYPWNAAK; KRPQGGAAYPWNAAKP;
PQEGKCMTHRGMQPNH; QEGKCMTHRGMQPNHD;
EGKCMTHRGMQPNHDL; GKCMTHRGMQPNHDLR;
KCMTHRGMQPNHDLRK; CMTHRGMQPNHDLRKE;
MTHRGMQPNHDLRKES; THRGMQPNHDLRKESA;
LTGRSCLPMECSQTMT; TGRSCLPMECSQTMTS;
GRSCLPMECSQTMTSG; RSCLPMECSQTMTSGR;
SCLPMECSQTMTSGRK; CLPMECSQTMTSGRKV;
LPMECSQTMTSGRKVH; PMECSQTMTSGRKVHD;
MECSQTMTSGRKVHDR; ECSQTMTSGRKVHDRH;
CSQTMTSGRKVHDRHV; SQTMTSGRKVHDRHVL;
QTMTSGRKVHDRHVLR; TMTSGRKVHDRHVLRA;
ESWPCPQLNWTKAMVL; SWPCPQLNWTKAMVLR;
WPCPQLNWTKAMVLRQ; PCPQLNWTKAMVLRQL;
CPQLNWTKAMVLRQLS; PQLNWTKAMVLRQLSR;
QLNWTKAMVLRQLSRQ; LNWTKAMVLRQLSRQA;
NWTKAMVLRQLSRQAS; WTKAMVLRQLSRQASV;
TKAMVLRQLSRQASVK; KAMVLRQLSRQASVKV;
AMVLRQLSRQASVKVG; MVLRQLSRQASVKVGK;
VLRQLSRQASVKVGKT; LRQLSRQASVKVGKTW;
RQLSRQASVKVGKTWT; QLSRQASVKVGKTWTG;
LSRQASVKVGKTWTGT; SRQASVKVGKTWTGTK;
RQASVKVGKTWTGTKK; QASVKVGKTWTGTKKR;
ASVKVGKTWTGTKKRA; SVKVGKTWTGTKKRAQ;
VKVGKTWTGTKKRAQR; KVGKTWTGTKKRAQRI;
VGKTWTGTKKRAQRIF; GKTWTGTKKRAQRIFI;
KTWTGTKKRAQRIFIF; TWTGTKKRAQRIFIFI;
WTGTKKRAQRIFIFIL; TGTKKRAQRIFIFILE;
GTKKRAQRIFIFILEL; TKKRAQRIFIFILELL;
KKRAQRIFIFILELLL; KRAQRIFIFILELLLE;
RAQRIFIFILELLLEF; AQRIFIFILELLLEFC;
QRIFIFILELLLEFCR; RIFIFILELLLEFCRG;
IFIFILELLLEFCRGE; FIFILELLLEFCRGED;
IFILELLLEFCRGEDS; FILELLLEFCRGEDSV;
ILELLLEFCRGEDSVD; LELLLEFCRGEDSVDG;
ELLLEFCRGEDSVDGK; LLLEFCRGEDSVDGKN;
LLEFCRGEDSVDGKNK; LEFCRGEDSVDGKNKS;
EFCRGEDSVDGKNKST; FCRGEDSVDGKNKSTT;
CRGEDSVDGKNKSTTA; RGEDSVDGKNKSTTAL;
GEDSVDGKNKSTTALP; EDSVDGKNKSTTALPA;
DSVDGKNKSTTALPAV; SVDGKNKSTTALPAVK;
VDGKNKSTTALPAVKD; DGKNKSTTALPAVKDS;
GKNKSTTALPAVKDSV; KNKSTTALPAVKDSVK;
NKSTTALPAVKDSVKD; KSTTALPAVKDSVKDS;
VSNPFFFVFPGSWVLL; LPVYLRLLLPQDFQWL;
PVYLRLLLPQDFQWLK; VYLRLLLPQDFQWLKL;
YLRLLLPQDFQWLKLL; LRLLLPQDFQWLKLLL;
RLLLPQDFQWLKLLLG; LLLPQDFQWLKLLLGR;
LLPQDFQWLKLLLGRL; LPQDFQWLKLLLGRLL;
PQDFQWLKLLLGRLLL; QDFQWLKLLLGRLLLL;
ASISNQAWLWNCLTQM; SISNQAWLWNCLTQMS;
ISNQAWLWNCLTQMST; SNQAWLWNCLTQMSTM;
NQAWLWNCLTQMSTMI; QAWLWNCLTQMSTMIF;
AWLWNCLTQMSTMIFC; WLWNCLTQMSTMIFCF;
LWNCLTQMSTMIFCFL; WNCLTQMSTMIFCFLV;
ILLLIIFNTLILGIGV; LLLIIFNTLILGIGVL;
LLIIFNTLILGIGVLL; LIIFNTLILGIGVLLC;
IIFNTLILGIGVLLCL; IFNTLILGIGVLLCLL;
FNTLILGIGVLLCLLL; NTLILGIGVLLCLLLF;
TLILGIGVLLCLLLFP; LILGIGVLLCLLLFPR;
ILGIGVLLCLLLFPRL; LGIGVLLCLLLFPRLC;
GIGVLLCLLLFPRLCG; IGVLLCLLLFPRLCGM;
GVLLCLLLFPRLCGML; VLLCLLLFPRLCGMLL;
LLCLLLFPRLCGMLLG; LCLLLFPRLCGMLLGM;
CLLLFPRLCGMLLGMI; LLLFPRLCGMLLGMIY;
LLFPRLCGMLLGMIYL; LFPRLCGMLLGMIYLL;
PHRNCREEQKDFLETP; HRNCREEQKDFLETPW;
RNCREEQKDFLETPWL; NCREEQKDFLETPWLD;
CREEQKDFLETPWLDF; REEQKDFLETPWLDFW;
EEQKDFLETPWLDFWR; EQKDFLETPWLDFWRK;
QKDFLETPWLDFWRKL; KDFLETPWLDFWRKLP;
DFLETPWLDFWRKLPG; FLETPWLDFWRKLPGQ;
LETPWLDFWRKLPGQL; TFIIIFNNIILIFPLL;
FIIIFNNIILIFPLLG; IIIFNNIILIFPLLGP;
IIFNNIILIFPLLGPQ; IFNNIILIFPLLGPQW;
FNNIILIFPLLGPQWL; NNIILIFPLLGPQWLD;
NIILIFPLLGPQWLDK; KKLLPQEVLIKELLLN;
KLLPQEVLIKELLLNG; LLPQEVLIKELLLNGC;
LPQEVLIKELLLNGCC; PQEVLIKELLLNGCCL;
QEVLIKELLLNGCCLY; EVLIKELLLNGCCLYF;
HLLLKHMKMAPTKRKG; LLLKHMKMAPTKRKGE;
LLKHMKMAPTKRKGEC; LKHMKMAPTKRKGECP;
KHMKMAPTKRKGECPG; HMKMAPTKRKGECPGA;
MKMAPTKRKGECPGAA; KMAPTKRKGECPGAAP;
MAPTKRKGECPGAAPK; APTKRKGECPGAAPKK;
PTKRKGECPGAAPKKP; TKRKGECPGAAPKKPK;
KRKGECPGAAPKKPKE; RKGECPGAAPKKPKEP;
KGECPGAAPKKPKEPV; GECPGAAPKKPKEPVQ;
ECPGAAPKKPKEPVQV; CPGAAPKKPKEPVQVP;
PGAAPKKPKEPVQVPK; GAAPKKPKEPVQVPKL;
AAPKKPKEPVQVPKLL; APKKPKEPVQVPKLLI;
PKKPKEPVQVPKLLIK; KKPKEPVQVPKLLIKG;
KPKEPVQVPKLLIKGG; PKEPVQVPKLLIKGGV;
KEPVQVPKLLIKGGVE; EPVQVPKLLIKGGVEV;
PVQVPKLLIKGGVEVL; VQVPKLLIKGGVEVLE;
QVPKLLIKGGVEVLEV; VPKLLIKGGVEVLEVK;
PKLLIKGGVEVLEVKT; KLLIKGGVEVLEVKTG;
LLIKGGVEVLEVKTGV; LIKGGVEVLEVKTGVD;
IKGGVEVLEVKTGVDA; KGGVEVLEVKTGVDAI;
GGVEVLEVKTGVDAIT; GVEVLEVKTGVDAITE;
VEVLEVKTGVDAITEV; EVLEVKTGVDAITEVE;
VLEVKTGVDAITEVEC; LEVKTGVDAITEVECF;
EVKTGVDAITEVECFL; VKTGVDAITEVECFLN;
KTGVDAITEVECFLNP; TGVDAITEVECFLNPE;
GVDAITEVECFLNPEM; VDAITEVECFLNPEMG;
DAITEVECFLNPEMGD; AITEVECFLNPEMGDP;
ITEVECFLNPEMGDPD; TEVECFLNPEMGDPDE;
EVECFLNPEMGDPDEN; VECFLNPEMGDPDENL;
ECFLNPEMGDPDENLR; CFLNPEMGDPDENLRG;
FLNPEMGDPDENLRGF; LNPEMGDPDENLRGFS;
NPEMGDPDENLRGFSL; PEMGDPDENLRGFSLK;
EMGDPDENLRGFSLKL; MGDPDENLRGFSLKLS;
GDPDENLRGFSLKLSA; DPDENLRGFSLKLSAE;
PDENLRGFSLKLSAEN; DENLRGFSLKLSAEND;
ENLRGFSLKLSAENDF; NLRGFSLKLSAENDFS;
LRGFSLKLSAENDFSS; RGFSLKLSAENDFSSD;
GFSLKLSAENDFSSDS; FSLKLSAENDFSSDSP;
SLKLSAENDFSSDSPE; LKLSAENDFSSDSPER;
KLSAENDFSSDSPERK; LSAENDFSSDSPERKM;
SAENDFSSDSPERKML; AENDFSSDSPERKMLP;
ENDFSSDSPERKMLPC; NDFSSDSPERKMLPCY;
DFSSDSPERKMLPCYS; FSSDSPERKMLPCYST;
SSDSPERKMLPCYSTA; SDSPERKMLPCYSTAR;
DSPERKMLPCYSTARI; SPERKMLPCYSTARIP;
PERKMLPCYSTARIPL; ERKMLPCYSTARIPLP;
RKMLPCYSTARIPLPN; KMLPCYSTARIPLPNL;
MLPCYSTARIPLPNLN; LPCYSTARIPLPNLNE;
PCYSTARIPLPNLNED; CYSTARIPLPNLNEDL;
YSTARIPLPNLNEDLT; STARIPLPNLNEDLTC;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

TARIPLPNLNEDLTCG; ARIPLPNLNEDLTCGN;
RIPLPNLNEDLTCGNL; IPLPNLNEDLTCGNLL;
PLPNLNEDLTCGNLLM; LPNLNEDLTCGNLLMW;
PNLNEDLTCGNLLMWE; NLNEDLTCGNLLMWEA;
LNEDLTCGNLLMWEAV; NEDLTCGNLLMWEAVT;
EDLTCGNLLMWEAVTV; DLTCGNLLMWEAVTVQ;
LTCGNLLMWEAVTVQT; TCGNLLMWEAVTVQTE;
CGNLLMWEAVTVQTEV; GNLLMWEAVTVQTEVI;
NLLMWEAVTVQTEVIG; LLMWEAVTVQTEVIGI;
LMWEAVTVQTEVIGIT; MWEAVTVQTEVIGITS;
WEAVTVQTEVIGITSM; EAVTVQTEVIGITSML;
AVTVQTEVIGITSMLN; VTVQTEVIGITSMLNL;
TVQTEVIGITSMLNLH; VQTEVIGITSMLNLHA;
QTEVIGITSMLNLHAG; TEVIGITSMLNLHAGS;
EVIGITSMLNLHAGSQ; VIGITSMLNLHAGSQK;
IGITSMLNLHAGSQKV; GITSMLNLHAGSQKVH;
ITSMLNLHAGSQKVHE; TSMLNLHAGSQKVHEH;
SMLNLHAGSQKVHEHG; MLNLHAGSQKVHEHGG;
LNLHAGSQKVHEHGGG; NLHAGSQKVHEHGGGK;
LHAGSQKVHEHGGGKP; HAGSQKVHEHGGGKPI;
AGSQKVHEHGGGKPIQ; GSQKVHEHGGGKPIQG;
SQKVHEHGGGKPIQGS; QKVHEHGGGKPIQGSN;
KVHEHGGGKPIQGSNF; VHEHGGGKPIQGSNFH;
HEHGGGKPIQGSNFHF; EHGGGKPIQGSNFHFF;
HGGGKPIQGSNFHFFA; GGGKPIQGSNFHFFAV;
GGKPIQGSNFHFFAVG; GKPIQGSNFHFFAVGG;
KPIQGSNFHFFAVGGE; PIQGSNFHFFAVGGEP;
IQGSNFHFFAVGGEPL; QGSNFHFFAVGGEPLE;
GSNFHFFAVGGEPLEM; SNFHFFAVGGEPLEMQ;
NFHFFAVGGEPLEMQG; FHFFAVGGEPLEMQGV;
HFFAVGGEPLEMQGVL; FFAVGGEPLEMQGVLM;
FAVGGEPLEMQGVLMN; AVGGEPLEMQGVLMNY;
VGGEPLEMQGVLMNYR; GGEPLEMQGVLMNYRS;
GEPLEMQGVLMNYRSK; EPLEMQGVLMNYRSKY;
PLEMQGVLMNYRSKYP; LEMQGVLMNYRSKYPD;
EMQGVLMNYRSKYPDG; MQGVLMNYRSKYPDGT;
QGVLMNYRSKYPDGTI; GVLMNYRSKYPDGTIT;
VLMNYRSKYPDGTITP; LMNYRSKYPDGTITPK;
MNYRSKYPDGTITPKN; NYRSKYPDGTITPKNP;
YRSKYPDGTITPKNPT; RSKYPDGTITPKNPTA;
SKYPDGTITPKNPTAQ; KYPDGTITPKNPTAQS;
YPDGTITPKNPTAQSQ; PDGTITPKNPTAQSQV;
DGTITPKNPTAQSQVM; GTITPKNPTAQSQVMN;
TITPKNPTAQSQVMNT; ITPKNPTAQSQVMNTD;
TPKNPTAQSQVMNTDH; PKNPTAQSQVMNTDHK;
KNPTAQSQVMNTDHKA; NPTAQSQVMNTDHKAY;
PTAQSQVMNTDHKAYL; TAQSQVMNTDHKAYLD;
AQSQVMNTDHKAYLDK; QSQVMNTDHKAYLDKN;
SQVMNTDHKAYLDKNN; QVMNTDHKAYLDKNNA;
VMNTDHKAYLDKNNAY; MNTDHKAYLDKNNAYP;
NTDHKAYLDKNNAYPV; TDHKAYLDKNNAYPVE;
DHKAYLDKNNAYPVEC; HKAYLDKNNAYPVECW;
KAYLDKNNAYPVECWV; AYLDKNNAYPVECWVP;
YLDKNNAYPVECWVPD; LDKNNAYPVECWVPDP;
DKNNAYPVECWVPDPS; KNNAYPVECWVPDPSR;
NNAYPVECWVPDPSRN; NAYPVECWVPDPSRNE;
AYPVECWVPDPSRNEN; YPVECWVPDPSRNENA;
PVECWVPDPSRNENAR; VECWVPDPSRNENARY;
ECWVPDPSRNENARYF; CWVPDPSRNENARYFG;
WVPDPSRNENARYFGT; VPDPSRNENARYFGTF;
PDPSRNENARYFGTFT; DPSRNENARYFGTFTG;
PSRNENARYFGTFTGG; SRNENARYFGTFTGGE;
RNENARYFGTFTGGEN; NENARYFGTFTGGENV;
ENARYFGTFTGGENVP; NARYFGTFTGGENVPP;
ARYFGTFTGGENVPPV; RYFGTFTGGENVPPVL;
YFGTFTGGENVPPVLH; FGTFTGGENVPPVLHV;
GTFTGGENVPPVLHVT; TFTGGENVPPVLHVTN;
FTGGENVPPVLHVTNT; TGGENVPPVLHVTNTA;
GGENVPPVLHVTNTAT; GENVPPVLHVTNTATT;
ENVPPVLHVTNTATTV; NVPPVLHVTNTATTVL;
VPPVLHVTNTATTVLL; PPVLHVTNTATTVLLD;
PVLHVTNTATTVLLDE; VLHVTNTATTVLLDEQ;
LHVTNTATTVLLDEQG; HVTNTATTVLLDEQGV;
VTNTATTVLLDEQGVG; TNTATTVLLDEQGVGP;

NTATTVLLDEQGVGPL; TATTVLLDEQGVGPLC;
ATTVLLDEQGVGPLCK; TTVLLDEQGVGPLCKA;
TVLLDEQGVGPLCKAD; VLLDEQGVGPLCKADS;
LLDEQGVGPLCKADSL; LDEQGVGPLCKADSLY;
DEQGVGPLCKADSLYV; EQGVGPLCKADSLYVS;
QGVGPLCKADSLYVSA; GVGPLCKADSLYVSAA;
VGPLCKADSLYVSAAD; GPLCKADSLYVSAADI;
PLCKADSLYVSAADIC; LCKADSLYVSAADICG;
CKADSLYVSAADICGL; KADSLYVSAADICGLF;
ADSLYVSAADICGLFT; DSLYVSAADICGLFTN;
SLYVSAADICGLFTNS; LYVSAADICGLFTNSS;
YVSAADICGLFTNSSG; VSAADICGLFTNSSGT;
SAADICGLFTNSSGTQ; AADICGLFTNSSGTQQ;
ADICGLFTNSSGTQQW; DICGLFTNSSGTQQWR;
ICGLFTNSSGTQQWRG; CGLFTNSSGTQQWRGL;
GLFTNSSGTQQWRGLA; LFTNSSGTQQWRGLAR;
FTNSSGTQQWRGLARY; TNSSGTQQWRGLARYF;
NSSGTQQWRGLARYFK; SSGTQQWRGLARYFKI;
SGTQQWRGLARYFKIR; GTQQWRGLARYFKIRL;
TQQWRGLARYFKIRLR; QQWRGLARYFKIRLRK;
QWRGLARYFKIRLRKR; WRGLARYFKIRLRKRS;
RGLARYFKIRLRKRSV; GLARYFKIRLRKRSVK;
LARYFKIRLRKRSVKN; ARYFKIRLRKRSVKNP;
RYFKIRLRKRSVKNPY; YFKIRLRKRSVKNPYP;
FKIRLRKRSVKNPYPI; KIRLRKRSVKNPYPIS;
IRLRKRSVKNPYPISF; RLRKRSVKNPYPISFL;
LRKRSVKNPYPISFLL; RKRSVKNPYPISFLLS;
KRSVKNPYPISFLLSD; RSVKNPYPISFLLSDL;
SVKNPYPISFLLSDLI; VKNPYPISFLLSDLIN;
KNPYPISFLLSDLINR; NPYPISFLLSDLINRR;
PYPISFLLSDLINRRT; YPISFLLSDLINRRTQ;
PISFLLSDLINRRTQR; ISFLLSDLINRRTQRV;
SFLLSDLINRRTQRVD; FLLSDLINRRTQRVDG;
LLSDLINRRTQRVDGQ; LSDLINRRTQRVDGQP;
SDLINRRTQRVDGQPM; DLINRRTQRVDGQPMY;
LINRRTQRVDGQPMYG; INRRTQRVDGQPMYGM;
NRRTQRVDGQPMYGME; RRTQRVDGQPMYGMES;
RTQRVDGQPMYGMESQ; TQRVDGQPMYGMESQV;
QRVDGQPMYGMESQVE; RVDGQPMYGMESQVEE;
VDGQPMYGMESQVEEV; DGQPMYGMESQVEEVR;
GQPMYGMESQVEEVRV; QPMYGMESQVEEVRVF;
PMYGMESQVEEVRVFD; MYGMESQVEEVRVFDG;
YGMESQVEEVRVFDGT; GMESQVEEVRVFDGTE;
MESQVEEVRVFDGTER; ESQVEEVRVFDGTERL;
SQVEEVRVFDGTERLP; QVEEVRVFDGTERLPG;
VEEVRVFDGTERLPGD; EEVRVFDGTERLPGDP;
EVRVFDGTERLPGDPD; VRVFDGTERLPGDPDM;
RVFDGTERLPGDPDMI; VFDGTERLPGDPDMIR;
FDGTERLPGDPDMIRY; DGTERLPGDPDMIRYI;
GTERLPGDPDMIRYID; TERLPGDPDMIRYIDK;
ERLPGDPDMIRYIDKQ; RLPGDPDMIRYIDKQG;
LPGDPDMIRYIDKQGQ; PGDPDMIRYIDKQGQL;
GDPDMIRYIDKQGQLQ; DPDMIRYIDKQGQLQT;
PDMIRYIDKQGQLQTK; DMIRYIDKQGQLQTKM;
MIRYIDKQGQLQTKML; TGAFIVHIHLINAAFV;
ATFKLVLFWGWCFRPF; TFKLVLFWGWCFRPFK;
FKLVLFWGWCFRPFKT; KLVLFWGWCFRPFKTL;
LVLFWGWCFRPFKTLK; VLFWGWCFRPFKTLKA;
LFWGWCFRPFKTLKAF; FWGWCFRPFKTLKAFT;
WGWCFRPFKTLKAFTQ; GWCFRPFKTLKAFTQM;
WCFRPFKTLKAFTQMQ; CFRPFKTLKAFTQMQL;
FRPFKTLKAFTQMQLL; RPFKTLKAFTQMQLLT;
PFKTLKAFTQMQLLTM; PKTLKAFTQMQLLTMG;
KTLKAFTQMQLLTMGV; ILFSCNIKNTFPHAYI;
LFSCNIKNTFPHAYII; FSCNIKNTFPHAYIIF;
SCNIKNTFPHAYIIFH; CNIKNTFPHAYIIFHP;
KSIHTYLRIQPFLPFN; SIHTYLRIQPFLPFNN;
IHTYLRIQPFLPFNNS; HTYLRIQPFLPFNNSR;
TYLRIQPFLPFNNSRL; YLRIQPFLPFNNSRLY;
LRIQPFLPFNNSRLYI; RIQPFLPFNNSRLYIS;
IQPFLPFNNSRLYISC; QPFLPFNNSRLYISCK;
PFLPFNNSRLYISCKI; FLPFNNSRLYISCKIS;
LPFNNSRLYISCKISY; PFNNSRLYISCKISYR;
FNNSRLYISCKISYRP; NNSRLYISCKISYRPK;

TABLE O-continued

Predicted MHC class 2 BK virus peptide sequences. Prediction of 13-, 14-, 15-, 16-mers from all 6 reading frames of the genome (access no #V01108) obtained using the program displayed in FIG. 2.

NSRLYISCKISYRPKP; SRLYISCKISYRPKPN;
IYFGPKIYLSYKSSLQ; YFGPKIYLSYKSSLQG;
FGPKIYLSYKSSLQGF; GPKIYLSYKSSLQGFR;
PKIYLSYKSSLQGFRD; KIYLSYKSSLQGFRDR;
IYLSYKSSLQGFRDRI; YLSYKSSLQGFRDRIL;
LSYKSSLQGFRDRILI; SYKSSLQGFRDRILIH;
YKSSLQGFRDRILIHC; KSSLQGFRDRILIHCN;
SSLQGFRDRILIHCNQ; SLQGFRDRILIHCNQA;
LQGFRDRILIHCNQAW; QGFRDRILIHCNQAWW;
GFRDRILIHCNQAWWK; FRDRILIHCNQAWWKY;
RDRILIHCNQAWWKYL; DRILIHCNQAWWKYLG;
RILIHCNQAWWKYLGS; ILIHCNQAWWKYLGSF;
LIHCNQAWWKYLGSFV; FSSCPFYIFKNNHVLI;
SSCPFYIFKNNHVLIY; SCPFYIFKNNHVLIYS;
CPFYIFKNNHVLIYSY; PFYIFKNNHVLIYSYT;
PVSSFRYIENNTVQKI; VSSFRYIENNTVQKIK;
SSFRYIENNTVQKIKY; SFRYIENNTVQKIKYY;
FRYIENNTVQKIKYYR; RYIENNTVQKIKYYRI;
YIENNTVQKIKYYRIH; IENNTVQKIKYYRIHF;
ENNTVQKIKYYRIHFR; NCIYCLLTNTFLIFTF;
CIYCLLTNTFLIFTFC; IYCLLTNTFLIFTFCK;
YCLLTNTFLIFTFCKN; CLLTNTFLIFTFCKNN;
LLTNTFLIFTFCKNNS; LTNTFLIFTFCKNNSI;
TNTFLIFTFCKNNSIC; NTFLIFTFCKNNSICK;
TFLIFTFCKNNSICKV; FLIFTFCKNNSICKVL;
LIFTFCKNNSICKVLF; IFTFCKNNSICKVLFM;
FTFCKNNSICKVLFMI; TFCKNNSICKVLFMIL;
FCKNNSICKVLFMILK; CKNNSICKVLFMILKV;
KNNSICKVLFMILKVI; NNSICKVLFMILKVIR;
NSICKVLFMILKVIRL; SICKVLFMILKVIRLV;
ICKVLFMILKVIRLVF; CKVLFMILKVIRLVFF;
KVLFMILKVIRLVFFL; VLFMILKVIRLVFFLT;
LFMILKVIRLVFFLTL; FMILKVIRLVFFLTLF;
MILKVIRLVFFLTLFT; ILKVIRLVFFLTLFTL;
LKVIRLVFFLTLFTLL; KVIRLVFFLTLFTLLY;
VIRLVFFLTLFTLLYI; IRLVFFLTLFTLLYIV;
RLVFFLTLFTLLYIVL; LVFFLTLFTLLYIVLK;
VFFLTLFTLLYIVLKF; FPRHLLCFFRLFWAKI;
PRHLLCFFRLFWAKIM; RHLLCFFRLFWAKIML;
HLLCFFRLFWAKIMLL; KTKGTQLLTEIINCRN;
TKGTQLLTEIINCRNS; KGTQLLTEIINCRNSM;
GTQLLTEIINCRNSMS; TQLLTEIINCRNSMSM;
QLLTEIINCRNSMSMW; LLTEIINCRNSMSMWS;
KEYNIMPSTHVSTNKS; EYNIMPSTHVSTNKSY;
YNIMPSTHVSTNKSYR; NIMPSTHVSTNKSYRI;
IMPSTHVSTNKSYRIF; MPSTHVSTNKSYRIFF;
PSTHVSTNKSYRIFFH; STHVSTNKSYRIFFHK;
THVSTNKSYRIFFHKF; HVSTNKSYRIFFHKFF;
VSTNKSYRIFFHKFFI; STNKSYRIFFHKFFIQ;
TNKSYRIFFHKFFIQN; NKSYRIFFHKFFIQNL;
KSYRIFFHKFFIQNLS; SYRIFFHKFFIQNLSF;
YRIFFHKFFIQNLSFF; RIFFHKFFIQNLSFFF;
IFFHKFFIQNLSFFFS; FFHKFFIQNLSFFFSS;
FHKFFIQNLSFFFSSI; HKFFIQNLSFFFSSIH;
KFFIQNLSFFFSSIHS; FFIQNLSFFFSSIHSK;
FIQNLSFFFSSIHSKA; IQNLSFFFSSIHSKAG;
QNLSFFFSSIHSKAGK; NLSFFFSSIHSKAGKG;
LSFFFSSIHSKAGKGS; SFFFSSIHSKAGKGSI;
FFFSSIHSKAGKGSIT; FFSSIHSKAGKGSITK;
FSSIHSKAGKGSITKY; SSIHSKAGKGSITKYS;
SIHSKAGKGSITKYSL; IHSKAGKGSITKYSLT;
HSKAGKGSITKYSLTK; SKAGKGSITKYSLTKK;
KAGKGSITKYSLTKKL; AGKGSITKYSLTKKLV;
IRGKVFRVFYLSFFFG; RGKVFRVFYLSFFFGW;
GKVFRVFYLSFFFGWC; VLRICCCFFITGKHIF;
LRICCCFFITGKHIFM; RICCCFFITGKHIFMA;
ICCCFFITGKHIFMAK; IFIPFFIKGTPPGLPL;
FIPFFIKGTPPGLPLF; IPFFIKGTPPGLPLFC;
PPFFIKGTPPGLPLFCS; FFIKGTPPGLPLFCSI;
FIKGTPPGLPLFCSIG; IKGTPPGLPLFCSIGW;
KGTPPGLPLFCSIGWH; GTPPGLPLFCSIGWHL;
SFRSLKGVSPIIWTHH; FRSLKGVSPIIWTHHC;
RSLKGVSPIIWTHHCR; SLKGVSPIIWTHHCRV;
LKGVSPIIWTHHCRVS; KGVSPIIWTHHCRVSS;
GVSPIIWTHHCRVSSV; VSPIIWTHHCRVSSVR;
SPIIWTHHCRVSSVRS; PIIWTHHCRVSSVRSK;
IIWTHHCRVSSVRSKP; IWTHHCRVSSVRSKPN;
WTHHCRVSSVRSKPNH; THHCRVSSVRSKPNHC;
HHCRVSSVRSKPNHCV; HCRVSSVRSKPNHCVK;
CRVSSVRSKPNHCVKQ; RVSSVRSKPNHCVKQS;
VSSVRSKPNHCVKQSM; SSVRSKPNHCVKQSMQ;
QSIQTKGSFLKNFLFK; SIQTKGSFLKNFLFKC;
IQTKGSFLKNFLFKCL; QTKGSFLKNFLFKCLN;
TKGSFLKNFLFKCLNL; KGSFLKNFLFKCLNLS;
HSMQGQCTEGFLEQIG; SMQGQCTEGFLEQIGH;
MQGQCTEGFLEQIGHS; QGQCTEGFLEQIGHSL;
GQCTEGFLEQIGHSLQ; QCTEGFLEQIGHSLQY;
CTEGFLEQIGHSLQYR; TEGFLEQIGHSLQYRV;
EGFLEQIGHSLQYRVS; GFLEQIGHSLQYRVSG;
FLEQIGHSLQYRVSGQ; LEQIGHSLQYRVSGQR;
EQIGHSLQYRVSGQRG; QIGHSLQYRVSGQRGK;
IGHSLQYRVSGQRGKS; GHSLQYRVSGQRGKSA;
HSLQYRVSGQRGKSAQ; SLQYRVSGQRGKSAQT;
LQYRVSGQRGKSAQTS; QYRVSGQRGKSAQTSE;
YRVSGQRGKSAQTSEL; RVSGQRGKSAQTSELL;
VSGQRGKSAQTSELLQ; SGQRGKSAQTSELLQV;
GQRGKSAQTSELLQVP; QRGKSAQTSELLQVPK;
RGKSAQTSELLQVPKS; GKSAQTSELLQVPKSG;
ATFTSCSIFLYKVFIL; TFTSCSIFLYKVFILF;
FTSCSIFLYKVFILFI; TSCSIFLYKVFILFIL;
SCSIFLYKVFILFILS; CSIFLYKVFILFILSS;
SIFLYKVFILFILSSS; IFLYKVFILFILSSSP;
FLYKVFILFILSSSPP; LYKVFILFILSSSPPL;
YKVFILFILSSSPPLS; KVFILFILSSSPPLSG;
AFLIKGRFPQAALSRP; FLIKGRFPQAALSRPK;
LIKGRFPQAALSRPKR; IKGRFPQAALSRPKRS;
KGRFPQAALSRPKRSM; GRFPQAALSRPKRSMS;
RFPQAALSRPKRSMSS; FPQAALSRPKRSMSSM;
PQAALSRPKRSMSSMD; QAALSRPKRSMSSMDS;
AALSRPKRSMSSMDSS; ALSRPKRSMSSMDSSL;
LSRPKRSMSSMDSSLL; SRPKRSMSSMDSSLLR;
RPKRSMSSMDSSLLRT; PKRSMSSMDSSLLRTL;
KRSMSSMDSSLLRTLS

---

BK virus, reading frame 2

13 mers:

GFPQIVLLGLRKS; FPQIVLLGLRKSL; PQIVLLGLRKSLH;
QIVLLGLRKSLHT; IVLLGLRKSLHTL; VLLGLRKSLHTLT;
LLGLRKSLHTLTT; LGLRKSLHTLTTT; EKGWRQRRPRPLI; KGWRQRRPRPLIY;
GWRQRRPRPLIYY; WRQRRPRPLIYYK; RQRRPRPLIYYKK;
QRRPRPLIYYKKK; RRPRPLIYYKKKG; RPRPLIYYKKKGH;
PRPLIYYKKKGHR; RPLIYYKKKGHRE; PLIYYKKKGHREE;
LIYYKKKGHREEL; IYYKKKGHREELL; YYKKKGHREELLT;
YKKKGHREELLTH; KKKGHREELLTHG; KKGHREELLTHGM;
KGHREELLTHGMQ; GHREELLTHGMQP; HREELLTHGMQPN;
REELLTHGMQPNH; EELLTHGMQPNHD; ELLTHGMQPNHDL;
LLTHGMQPNHDLR; LTHGMQPNHDLRK; THGMQPNHDLRKE;
HGMQPNHDLRKES; GMQPNHDLRKESA; LTGECSQTMTSGR;
TGECSQTMTSGRK; GECSQTMTSGRKV; ECSQTMTSGRKVH;
CSQTMTSGRKVHD; SQTMTSGRKVHDS; QTMTSGRKVHDSQ;
TMTSGRKVHDSQG; MTSGRKVHDSQGG; TSGRKVHDSQGGA;
SGRKVHDSQGGAA; GRKVHDSQGGAAY; RKVHDSQGGAAYP;
KVHDSQGGAAYPW; VHDSQGGAAYPWN; HDSQGGAAYPWNA;
DSQGGAAYPWNAA; SQGGAAYPWNAAK; QGGAAYPWNAAKP;
PQEGKCMTDMFCE; QEGKCMTDMFCEP; EGKCMTDMFCEPR;
GKCMTDMFCEPRN; KCMTDMFCEPRNL; CMTDMFCEPRNLG;
MTDMFCEPRNLGL; TDMFCEPRNLGLV; DMFCEPRNLGLVP;
MFCEPRNLGLVPS; TGQRPWFCASCHD; GQRPWFCASCHDK;
QRPWFCASCHDKL; RPWFCASCHDKLQ; KLVKPGLEQKKEL;
LVKPGLEQKKELR; VKPGLEQKKELRG; KPGLEQKKELRGF;
PGLEQKKELRGFL; GLEQKKELRGFLF; LEQKKELRGFLFL;
EQKKELRGFLFLF; VIPFFLYFQVHGC; IPFFLYFQVHGCC;
PFFLYFQVHGCCS; FFLYFQVHGCCSS; FLYFQVHGCCSST;
LYFQVHGCCSSTF; YFQVHGCCSSTFG; FQVHGCCSSTFGG;
QVHGCCSSTFGGP; VHGCCSSTFGGPS; HGCCSSTFGGPSC;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GCCSSTFGGPSCQ; CCSSTFGGPSCQC; CSSTFGGPSCQCI;
NCCWGGCCCYRSS; CCWGGCCCYRSSN; CWGGCCCYRSSNC;
WGGCCCYRSSNCI; GGCCCYRSSNCIP; GCCCYRSSNCIPC;
CCCYRSSNCIPCY; CCYRSSNCIPCYC; CYRSSNCIPCYCR;
YRSSNCIPCYCRG; RSSNCIPCYCRGH; SSNCIPCYCRGHN;
SNCIPCYCRGHNK; NCIPCYCRGHNKY; CIPCYCRGHNKYL;
IPCYCRGHNKYLR; PCYCRGHNKYLRG; CYCRGHNKYLRGY;
YCRGHNKYLRGYS; CRGHNKYLRGYSC; RGHNKYLRGYSCY;
GHNKYLRGYSCYR; HNKYLRGYSCYRP; NKYLRGYSCYRPN;
KYLRGYSCYRPNS; YLRGYSCYRPNSS; LRGYSCYRPNSSN;
RGYSCYRPNSSNI; GYSCYRPNSSNIC; YSCYRPNSSNICC;
SCYRPNSSNICCN; CYRPNSSNICCNC; YRPNSSNICCNCW;
RPNSSNICCNCWC; PNSSNICCNCWCS; NSSNICCNCWCSW;
SSNICCNCWCSWG; SNICCNCWCSWGY; NICCNCWCSWGYC;
ICCNCWCSWGYCW; CCNCWCSWGYCWV; CNCWCSWGYCWVC;
NCWCSWGYCWVCC; CWCSWGYCWVCCF; WCSWGYCWVCCFN;
CSWGYCWVCCFNS; SWGYCWVCCFNSN; WGYCWVCCFNSNC;
LGSQSFHCRPLSA; GSQSFHCRPLSAI; SQSFHCRPLSAIR;
QSFHCRPLSAIRH; SFHCRPLSAIRHG; PHCRPLSAIRHGF;
HCRPLSAIRHGFG; CRPLSAIRHGFGI; RPLSAIRHGFGIV;
ALGSFFVCYYFPG; LGSFFVCYYFPGF; GSFFVCYYFPGFV;
SFFVCYYFPGFVA; FFVCYYFPGFVAC; FVCYYFPGFVACY;
YTFYNLTGIAEKN; TFYNLTGIAEKNR; FYNLTGIAEKNRK;
YNLTGIAEKNRKI; NLTGIAEKNRKIF; IFGGNYLDNCKCP;
FGGNYLDNCKCPY; GGNYLDNCKCPYK; GNYLDNCKCPYKL;
NYLDNCKCPYKLL; QYRRSYTKNGLKK; YRRSYTKNGLKKS;
RRSYTKNGLKKST; RSYTKNGLKKSTK; SYTKNGLKKSTKC;
YTKNGLKKSTKCT; TKNGLKKSTKCTF; KNGLKKSTKCTFR;
NGLKKSTKCTFRR; GLKKSTKCTFRRV; LKKSTKCTFRRVY;
KKSTKCTFRRVYR; KSTKCTFRRVYRK; STKCTFRRVYRKN;
TKCTFRRVYRKNY; KCTFRRVYRKNYC; CTFRRVYRKNYCP;
TFRRVYRKNYCPR; FRRVYRKNYCPRR; RRVYRKNYCPRRC;
SKNCSSMDVAFTS; KNCSSMDVAFTSR; NCSSMDVAFTSRP;
CSSMDVAFTSRPV; SSMDVAFTSRPVR; SMDVAFTSRPVRD;
MDVAFTSRPVRDC; DVAFTSRPVRDCN; VAFTSRPVRDCNT;
AFTSRPVRDCNTC; FTSRPVRDCNTCS; RWPQPKEKESVQG;
WPQPKEKESVQGQ; PQPKEKESVQGQL; QPKEKESVQGQLP;
PKEKESVQGQLPK; KEKESVQGQLPKS; EKESVQGQLPKSQ;
KESVQGQLPKSQR; ESVQGQLPKSQRN; SVQGQLPKSQRNP;
VQGQLPKSQRNPC; QGQLPKSQRNPCK; GQLPKSQRNPCKC;
QLPKSQRNPCKCQ; LPKSQRNPCKCQN; PKSQRNPCKCQNY;
TQKWGIQMKTLGA; QKWGIQMKTLGAL; KWGIQMKTLGALV;
VLKMTLAVIAQRE; LKMTLAVIAQREK; KMTLAVIAQREKC;
MTLAVIAQREKCF; TLAVIAQREKCFP; LAVIAQREKCFPV;
AVIAQREKCFPVT; VIAQREKCFPVTA; IAQREKCFPVTAQ;
AQREKCFPVTAQQ; QREKCFPVTAQQE; REKCFPVTAQQEF;
EKCFPVTAQQEFP; KCFPVTAQQEFPS; CFPVTAQQEFPSP;
FPVTAQQEFPSPI; LACLTFMQGHKKC; ACLTFMQGHKKCM;
CLTFMQGHKKCMS; LTFMQGHKKCMSM; TFMQGHKKCMSMV;
FMQGHKKCMSMVE; MQGHKKCMSMVEE; QGHKKCMSMVEEN;
GHKKCMSMVEENL; HKKCMSMVEENLF; KKCMSMVEENLFK;
KCMSMVEENLFKA; CMSMVEENLFKAV; MSMVEENLFKAVI;
SMVEENLFKAVIS; MVEENLFKAVIST; VEENLFKAVISTS;
EENLFKAVISTSL; ENLFKAVISTSLL; ILTIRPIWTKTML;
LTIRPIWTKTMLI; TIRPIWTKTMLIQ; IRPIWTKTMLIQL;
RPIWTKTMLIQLS; PIWTKTMLIQLSA; IWTKTMLIQLSAG;
WTKTMLIQLSAGY; TKTMLIQLSAGYL; KTMLIQLSAGYLI;
TMLIQLSAGYLIP; MLIQLSAGYLIPV; LIQLSAGYLIPVE;
IQLSAGYLIPVEM; QLSAGYLIPVEMK; LSAGYLIPVEMKM;
SAGYLIPVEMKML; AGYLIPVEMKMLG; GYLIPVEMKMLGI;
YLIPVEMKMLGIL; LIPVEMKMLGILG; IPVEMKMLGILGL;
PVEMKMLGILGLS; VEMKMLGILGLSQ; EMKMLGILGLSQE;
MKMLGILGLSQEG; KMLGILGLSQEGK; MLGILGLSQEGKM;
LGILGLSQEGKMF; GILGLSQEGKMFP; ILGLSQEGKMFPQ;
LGLSQEGKMFPQY; GLSQEGKMFPQYF; LSQEGKMFPQYFS;
MNRVWGLFVKLIA; NRVWGLFVKLIAC; RVWGLFVKLIACM;
VWGLFVKLIACMF; WGLFVKLIACMFQ; GLFVKLIACMFQL;
LFVKLIACMFQLL; FVKLIACMFQLLI; VKLIACMFQLLIF;
KLIACMFQLLIFV; LIACMFQLLIFVA; IACMFQLLIFVAC;
ACMFQLLIFVACL; CMFQLLIFVACLL; MFQLLIFVACLLT;
FQLLIFVACLLTA; QLLIFVACLLTAL; LLIFVACLLTALE;
LIFVACLLTALEH; IFVACLLTALEHN; FVACLLTALEHNS;
VACLLTALEHNSG; ACLLTALEHNSGE; CLLTALEHNSGEA;
LLTALEHNSGEAL; LTALEHNSGEALQ; TALEHNSGEALQD;
ALEHNSGEALQDI; LEHNSGEALQDIL; EHNSGEALQDILR;
HNSGEALQDILRS; NSGEALQDILRSA; TGEPREWMGSLCM;
GEPREWMGSLCMV; EPREWMGSLCMVW; PREWMGSLCMVWN;
REWMGSLCMVWNP; EWMGSLCMVWNPR; KRLGCLMAQKDFQ;
RLGCLMAQKDFQG; LGCLMAQKDFQGT; GCLMAQKDFQGTQ;
CLMAQKDFQGTQI; DILTNRDNCKPKC; ILTNRDNCKPKCF;
LTNRDNCKPKCFK; TNRDNCKPKCFKQ; NRDNCKPKCFKQV;
RDNCKPKCFKQVL; DNCKPKCFKQVLL; NCKPKCFKQVLLL;
CKPKCFKQVLLLY; KPKCFKQVLLLYI; PKCFKQVLLLYIY;
KCFKQVLLLYIYI; MLLLYKPLLSLCY; LLLYKPLLSLCYF;
LLYKPLLSLCYFG; LYKPLLSLCYFGG; YKPLLSLCYFGGG;
KPLLSLCYFGGGV; PLLSLCYFGGGVL; LLSLCYFGGGVLG;
LSLCYFGGGVLGL; SLCYFGGGVLGLL; LCYFGGGVLGLLK;
CYFGGGVLGLLKH; LWGSDLWESSAGA; WGSDLWESSAGAE;
GSDLWESSAGAEV; SDLWESSAGAEVS; DLWESSAGAEVSE;
LWESSAGAEVSET; WESSAGAEVSETW; ESSAGAEVSETWE;
SSAGAEVSETWEE; SAGAEVSETWEEH; AGAEVSETWEEHC;
GAEVSETWEEHCD; AEVSETWEEHCDW; EVSETWEEHCDWD;
VSETWEEHCDWDS; SETWEEHCDWDSV; ETWEEHCDWDSVL;
TWEEHCDWDSVLD; WEEHCDWDSVLDP; EEHCDWDSVLDPC;
EHCDWDSVLDPCP; HCDWDSVLDPCPE; CDWDSVLDPCPES;
DWDSVLDPCPESS; WDSVLDPCPESSV; DSVLDPCPESSVS;
SVLDPCPESSVSE; VLDPCPESSVSES; LDPCPESSVSESS;
DPCPESSVSESSS; PCPESSVSESSSL; CPESSVSESSSLV;
PESSVSESSSLVI; ESSVSESSSLVIS; SSVSESSSLVISR;
SVSESSSLVISRI; VSESSSLVISRIH; SESSSLVISRIHF;
ESSSLVISRIHFP; SSSLVISRIHFPM; SSLVISRIHFPMH;
SLVISRIHFPMHI; LVISRIHFPMHIL; VISRIHFPMHILY;
ISRIHFPMHILYF; SRIHFPMHILYFI; RIHFPMHILYFIL;
IHFPMHILYFILE; HFPMHILYFILEK; FPMHILYFILEKV;
PMHILYFILEKVY; MHILYFILEKVYI; HILYFILEKVYIL;
ILYFILEKVYILI; LYFILEKVYILIS; YFILEKVYILISE;
FILEKVYILISES; ILEKVYILISESS; LEKVYILISESSL;
EKVYILISESSLS; KVYILISESSLSF; VYILISESSLSFH;
YILISESSLSFHS; ILISESSLSFHST; LISESSLSFHSTI;
ISESSLSFHSTIL; SESSLSFHSTILD; ESSLSFHSTILDC;
SSLSFHSTILDCI; SLSFHSTILDCIS; LSFHSTILDCISV;
SFHSTILDCISVA; FHSTILDCISVAK; HSTILDCISVAKS;
STILDCISVAKSA; TILDCISVAKSAT; ILDCISVAKSATG;
LDCISVAKSATGL; DCISVAKSATGLN; CISVAKSATGLNQ;
ISVAKSATGLNQI; SVAKSATGLNQIS; VAKSATGLNQISS;
AKSATGLNQISSS; KSATGLNQISSSN; SATGLNQISSSNK;
ATGLNQISSSNKV; TGLNQISSSNKVI; GLNQISSSNKVIP;
LNQISSSNKVIPL; NQISSSNKVIPLC; QISSSNKVIPLCK;
ISSSNKVIPLCKI; SSSNKVIPLCKIL; SSNKVIPLCKILF;
SNKVIPLCKILFS; NKVIPLCKILFSS; KVIPLCKILFSSK;
VIPLCKILFSSKN; IPLCKILFSSKNS; PLCKILFSSKNSE;
LCKILFSSKNSEF; CKILFSSKNSEFC; KILFSSKNSEFCK;
ILFSSKNSEFCKD; LFSSKNSEFCKDF; FSSKNSEFCKDFL;
SSKNSEFCKDFLK; SKNSEFCKDFLKY; KNSEFCKDFLKYI;
NSEFCKDFLKYIL; SEFCKDFLKYILG; EFCKDFLKYILGL;
FCKDFLKYILGLK; CKDFLKYILGLKS; KDFLKYILGLKSI;
DFLKYILGLKSIC; FLKYILGLKSICL; LKYILGLKSICLT;
KYILGLKSICLTN; YILGLKSICLTNL; ILGLKSICLTNLA;
LGLKSICLTNLAC; GLKSICLTNLACR; LKSICLTNLACRV;
KSICLTNLACRVL; SICLTNLACRVLG; ICLTNLACRVLGT;
CLTNLACRVLGTY; LTNLACRVLGTYG; TNLACRVLGTYGS;
NLACRVLGTYGSF; LACRVLGTYGSFI; ACRVLGTYGSFIV;
CRVLGTYGSFIVT; RVLGTYGSFIVTK; VLGTYGSFIVTKP;
LGTGYSFIVTKPG; GTGYSFIVTKPGG; TGYSFIVTKPGGN;
GYSFIVTKPGGNI; YSFIVTKPGGNIW; SFIVTKPGGNIWV;
FIVTKPGGNIWVL; IVTKPGGNIWVLL; VTKPGGNIWVLLF;
TKPGGNIWVLLFK; KPGGNIWVLLFKC; PGGNIWVLLFKCF;
GGNIWVLLFKCFF; GNIWVLLFKCFFS; NIWVLLFKCFFSK;
IWVLLFKCFFSKF; WVLLFKCFFSKFT; VLLFKCFFSKFTL;
LLFKCFFSKFTLT; LFKCFFSKFTLTL; FKCFFSKFTLTLP;
KCFFSKFTLTLPS; CFFSKFTLTLPSK; SLKLSKLFIPCPE;
LKLSKLFIPCPEG; KLSKLFIPCPEGK; LSKLFIPCPEGKS;
SKLFIPCPEGKSF; KLFIPCPEGKSFD; LFIPCPEGKSFDS;
FIPCPEGKSFDSA; IPCPEGKSFDSAP; PCPEGKSFDSAPV;
CPEGKSFDSAPVP; PEGKSFDSAPVPF; EGKSFDSAPVPFT;
GKSFDSAPVPFTS; KSFDSAPVPFTSS; SFDSAPVPFTSSK;
FDSAPVPFTSSKT; DSAPVPFTSSKTT; SAPVPFTSSKTTM;
APVPFTSSKTTMY; SIATPSSKVSLSM; IATPSSKVSLSMG;

TABLE O-continued

Predicted MHC class 2 BK virus peptide sequences. Prediction of 13-, 14-, 15-, 16-mers from all 6 reading frames of the genome (access no #V01108) obtained using the program displayed in FIG. 2.

ATPSSKVSLSMGR; TPSSKVSLSMGRF; PSSKVSLSMGRFT;
SSKVSLSMGRFTF; SKVSLSMGRFTFK; KVSLSMGRFTFKA;
VSLSMGRFTFKAL; SLSMGRFTFKALP; LSMGRFTFKALPP;
SMGRFTFKALPPH; MGRFTFKALPPHK; GRFTFKALPPHKS;
RFTFKALPPHKSN; FTFKALPPHKSNN; TFKALPPHKSNNP;
FKALPPHKSNNPA; KALPPHKSNNPAA; ALPPHKSNNPAAS;
LPPHKSNNPAASV; PPHKSNNPAASVV; PHKSNNPAASVVF;
HKSNNPAASVVFP; KSNNPAASVVFPL; SNNPAASVVFPLS;
NNPAASVVFPLSM; NPAASVVFPLSMG; PAASVVFPLSMGP;
AASVVFPLSMGPL; ASVVFPLSMGPLN; SVVFPLSMGPLNN;
VVFPLSMGPLNNQ; VFPLSMGPLNNQY; FPLSMGPLNNQYL;
PLSMGPLNNQYLL; LSMGPLNNQYLLL; SMGPLNNQYLLLG;
MGPLNNQYLLLGT; GPLNNQYLLLGTL; PLNNQYLLLGTLK;
LNNQYLLLGTLKT; NNQYLLLGTLKTI; NQYLLLGTLKTIQ;
QYLLLGTLKTIQC; YLLLGTLKTIQCK; LLLGTLKTIQCKK;
LLGTLKTIQCKKS; LGTLKTIQCKKSN; GTLKTIQCKKSNI;
TLKTIQCKKSNIT; LKTIQCKKSNITE; KTIQCKKSNITES;
TIQCKKSNITESI; IQCKKSNITESIL; QCKKSNITESILG;
CKKSNITESILGS; KKSNITESILGSK; KSNITESILGSKQ;
SNITESILGSKQC; NITESILGSKQCS; ITESILGSKQCSQ;
TESILGSKQCSQA; ESILGSKQCSQAT; SILGSKQCSQATP;
ILGSKQCSQATPA; LGSKQCSQATPAI; GSKQCSQATPAIY;
SKQCSQATPAIYC; KQCSQATPAIYCS; QCSQATPAIYCSS;
CSQATPAIYCSST; SQATPAIYCSSTA; QATPAIYCSSTAF;
ATPAIYCSSTAFP; RVSTLFLAKTVST; VSTLFLAKTVSTA;
STLFLAKTVSTAC; FLLSAKIIAFAKC; LLSAKIIAFAKCF;
LSAKIIAFAKCFS; NSKYIPNNKNTSS; SKYIPNNKNTSSH;
KYIPNNKNTSSHF; YIPNNKNTSSHFV; IPNNKNTSSHFVS;
PNNKNTSSHFVST; NNKNTSSHFVSTA; NKNTSSHFVSTAY;
KNTSSHFVSTAYS; NTSSHFVSTAYSV; TSSHFVSTAYSVI;
SSHFVSTAYSVIN; SHFVSTAYSVINF; HFVSTAYSVINFQ;
FVSTAYSVINFQD; VSTAYSVINFQDT; STAYSVINFQDTC;
TAYSVINFQDTCF; AYSVINFQDTCFV; YSVINFQDTCFVS;
SVINFQDTCFVSS; VINFQDTCFVSSG; INFQDTCFVSSGS;
NFQDTCFVSSGSS; FQDTCFVSSGSSG; QDTCFVSSGSSGL;
DTCFVSSGSSGLK; TCFVSSGSSGLKS; CFVSSGSSGLKSC;
FVSSGSSGLKSCS; VSSGSSGLKSCSF; SSGSSGLKSCSFK;
SGSSGLKSCSFKP; GSSGLKSCSFKPP; MLSSIVWYGSLVK;
LSSIVWYGSLVKA; SSIVWYGSLVKAL; SIVWYGSLVKALY;
IVWYGSLVKALYS; VWYGSLVKALYSK; WYGSLVKALYSKY;
YGSLVKALYSKYS; GSLVKALYSKYSL; SLVKALYSKYSLL;
LVKALYSKYSLLT; VKALYSKYSLLTP; KALYSKYSLLTPL;
ALYSKYSLLTPLQ; LYSKYSLLTPLQI; YSKYSLLTPLQIK;
SKYSLLTPLQIKK; KYSLLTPLQIKKL; YSLLTPLQIKKLV;
SLLTPLQIKKLVH; LLTPLQIKKLVHS; LTPLQIKKLVHSF;
TPLQIKKLVHSF; QKLLIAETLCLCG; KLLIAETLCLCGV;
LLIAETLCLCGVK; LIAETLCLCGVKK; IAETLCLCGVKKN;
AETLCLCGVKKNI; ETLCLCGVKKNII; TLCLCGVKKNIIL;
LCLCGVKKNIILC; CLCGVKKNIILCP; LCGVKKNIILCPA;
CGVKKNIILCPAH; GVKKNIILCPAHM; VKKNIILCPAHMC;
KKNIILCPAHMCL; KNIILCPAHMCLL; NIILCPAHMCLLI;
IILCPAHMCLLIK; ILCPAHMCLLIKV; LCPAHMCLLIKVT;
CPAHMCLLIKVTE; PAHMCLLIKVTEY; AHMCLLIKVTEYF;
HMCLLIKVTEYFS; MCLLIKVTEYFSI; CLLIKVTEYFSIS;
LLIKVTEYFSISF; LIKVTEYFSISFL; IKVTEYFSISFLY;
KVTEYFSISFLYR; VTEYFSISFLYRI; AFSLVVYTAKQAR;
FSLVVYTAKQARV; SLVVYTAKQARVL; LVVYTAKQARVLL;
VVYTAKQARVLLL; VYTAKQARVLLLN; YTAKQARVLLLNT;
TAKQARVLLLNTA; LRNWCRSEGKSLG; RNWCRSEGKSLGS;
NWCRSEGKSLGSS; WCRSEGKSLGSST; CRSEGKSLGSSTF;
RSEGKSLGSSTFL; SEGKSLGSSTFLF; EGKSLGSSTFLFF;
GKSLGSSTFLFFL; KSLGSSTFLFFLG; SLGSSTFLFFLGG;
LGSSTFLFFLGGV; GSSTFLFFLGGVE; SSTFLFFLGGVEC;
ESAVASSSLANIS; SAVASSSLANISS; AVASSSLANISSW;
VASSSLANISSWQ; ASSSLANISSWQN; SSSLANISSWQNK;
SSLANISSWQNKS; SLANISSWQNKSS; LANISSWQNKSSS;
ANISSWQNKSSSH; NISSWQNKSSSHF; ISSWQNKSSSHFS;
SSWQNKSSSHFSL; SWQNKSSSHFSLK; WQNKSSSHFSLKE;
QNKSSSHFSLKEL; NKSSSHFSLKELH; KSSSHFSLKELHQ;
SSSHFSLKELHQD; SSHFSLKELHQDS; SHFSLKELHQDSH;
HFSLKELHQDSHS; FSLKELHQDSHSS; SLKELHQDSHSSV;
LKELHQDSHSSVP; VGTYKKNNYLGPF; GTYKKNNYLGPFN;
TYKKNNYLGPFNI; YKKNNYLGPFNIL; KKNNYLGPFNILL;
KNNYLGPFNILLF; NNYLGPFNILLFI; REFLQLFGPTIAE;

EFLQLFGPTIAEF; FLQLFGPTIAEFL; LQLFGPTIAEFLQ;
QLFGPTIAEFLQL; LFGPTIAEFLQLG; FGPTIAEFLQLGL;
GPTIAEFLQLGLS; PTIAEFLQLGLSQ; TIAEFLQLGLSQT;
IAEFLQLGLSQTT; AEFLQLGLSQTTV; SSQCSSNLSKPRA;
SQCSSNLSKPRAL; QCSSNLSKPRALF; CSSNLSKPRALFL;
SSNLSKPRALFLK; SNLSKPRALFLKI; NLSKPRALFLKIF;
LSKPRALFLKIFY; SKPRALFLKIFYL; KPRALFLKIFYLN;
PRALFLKIFYLNA; RALFLKIFYLNAL; ALFLKIFYLNALI;
ADIACKGSAQKAF; DIACKGSAQKAFW; IACKGSAQKAFWN;
ACKGSAQKAFWNK; AIPCSTGYLGKEE; IPCSTGYLGKEEN;
PCSTGYLGKEENQ; CSTGYLGKEENQH; STGYLGKEENQHK;
TGYLGKEENQHKP; GYLGKEENQHKPL; YLGKEENQHKPLS;
LGKEENQHKPLSY; GKEENQHKPLSYS; KEENQHKPLSYSR;
EENQHKPLSYSRF; ENQHKPLSYSRFQ; NQHKPLSYSRFQN;
QHKPLSYSRFQNQ; HKPLSYSRFQNQA; KPLSYSRFQNQAD;
PLSYSRFQNQADE; LSYSRFQNQADEL; SYSRFQNQADELP;
YSRFQNQADELPL; SRFQNQADELPLH; RFQNQADELPLHP;
FQNQADELPLHPA; QNQADELPLHPAP; NQADELPLHPAPF;
QADELPLHPAPFF; ADELPLHPAPFFY; DELPLHPAPFFYT;
ELPLHPAPFFYTK; LPLHPAPFFYTKY; PLHPAPFFYTKYS;
LHPAPFFYTKYSF; HPAPFFYTKYSFS; PAPFFYTKYSFSS;
APFFYTKYSFSSF; PFFYTKYSFSSFY; FFYTKYSFSSFYP;
FYTKYSFSSFYPR; YTKYSFSSFYPRR; TKYSFSSFYPRRP;
KYSFSSFYPRRPL; YSFSSFYPRRPLC; SFSSFYPRRPLCQ;
FSSFYPRRPLCQG; SSFYPRRPLCQGE; SFYPRRPLCQGEI;
FYPRRPLCQGEIP; YPRRPLCQGEIPY; PRRPLCQGEIPYT;
RRPLCQGEIPYTS; RPLCQGEIPYTSL; PLCQGEIPYTSLN;
LCQGEIPYTSLNK; CQGEIPYTSLNKL; QGEIPYTSLNKLF;
GEIPYTSLNKLFS; EIPYTSLNKLFSL; IPYTSLNKLFSLR;
PYTSLNKLFSLRE; YTSLNKLFSLRED; TSLNKLFSLREDF;
SLNKLFSLREDFP; LNKLFSLREDFPR; NKLFSLREDFPRQ;
KLFSLREDFPRQL; LFSLREDFPRQLF; FSLREDFPRQLFQ;
SLREDFPRQLFQG; LREDFPRQLFQGL; REDFPRQLFQGLK;
EDFPRQLFQGLKG; DFPRQLFQGLKGP 14 mers:

GFPQIVLLGLRKSL; FPQIVLLGLRKSLH; PQIVLLGLRKSLHT;
QIVLLGLRKSLHTL; IVLLGLRKSLHTLT; VLLGLRKSLHTLTT;
EKGWRQRRPRPLIY; KGWRQRRPRPLIYY; GWRQRRPRPLIYYK;
WRQRRPRPLIYYKK; RQRRPRPLIYYKKK; QRRPRPLIYYKKKG;
RRPRPLIYYKKKGH; RPRPLIYYKKKGHR; PRPLIYYKKKGHRE;
RPLIYYKKKGHREE; PLIYYKKKGHREEL; LIYYKKKGHREELL;
IYYKKKGHREELLT; YYKKKGHREELLTH; YKKKGHREELLTHG;
KKKGHREELLTHGM; KKGHREELLTHGMQ; KGHREELLTHGMQP;
GHREELLTHGMQPN; HREELLTHGMQPNH; REELLTHGMQPNHD;
EELLTHGMQPNHDL; ELLTHGMQPNHDLR; LLTHGMQPNHDLRK;
LTHGMQPNHDLRKE; THGMQPNHDLRKES; HGMQPNHDLRKESA;
LTGECSQTMTSGRK; TGECSQTMTSGRKV; GECSQTMTSGRKVH;
ECSQTMTSGRKVHD; CSQTMTSGRKVHDS; SQTMTSGRKVHDSQ;
QTMTSGRKVHDSQG; TMTSGRKVHDSQGG; MTSGRKVHDSQGGA;
TSGRKVHDSQGGAA; SGRKVHDSQGGAAY; GRKVHDSQGGAAYP;
RKVHDSQGGAAYPW; KVHDSQGGAAYPWN; VHDSQGGAAYPWNA;
HDSQGGAAYPWNAA; DSQGGAAYPWNAAK; SQGGAAYPWNAAKP;
PQEGKCMTDMFCEP; QEGKCMTDMFCEPR; EGKCMTDMFCEPRN;
GKCMTDMFCEPRNL; KCMTDMFCEPRNLG; CMTDMFCEPRNLGL;
MTDMFCEPRNLGLV; TDMFCEPRNLGLVP; DMFCEPRNLGLVPS;
TGQRPWFCASCHDK; GQRPWFCASCHDKL; QRPWFCASCHDKLQ;
KLVKPGLEQKKELR; LVKPGLEQKKELRG; VKPGLEQKKELRGF;
KPGLEQKKELRGFL; PGLEQKKELRGFLF; GLEQKKELRGFLFL;
EQKKELRGFLFLF; VIPPFLYFQVHGCC; IPPFLYFQVHGCCS;
PPFLYFQVHGCCSS; PFLYFQVHGCCSST; FLYFQVHGCCSSTF;
LYFQVHGCCSSTFG; YFQVHGCCSSTFGG; FQVHGCCSSTFGGP;
QVHGCCSSTFGGPS; VHGCCSSTFGGPSC; HGCCSSTFGGPSCQ;
GCCSSTFGGPSCQC; CCSSTFGGPSCQCI; NCCWGGCCCYRSSN;
CCWGGCCCYRSSNC; CWGGCCCYRSSNCI; WGGCCCYRSSNCIP;
GGCCCYRSSNCIPC; GCCCYRSSNCIPCY; CCCYRSSNCIPCYC;
CCYRSSNCIPCYCR; CYRSSNCIPCYCRG; YRSSNCIPCYCRGH;
RSSNCIPCYCRGHN; SSNCIPCYCRGHNK; SNCIPCYCRGHNKY;
NCIPCYCRGHNKYL; CIPCYCRGHNKYLR; IPCYCRGHNKYLRG;
PCYCRGHNKYLRGY; CYCRGHNKYLRGYS; YCRGHNKYLRGYSC;
CRGHNKYLRGYSCY; RGHNKYLRGYSCYR; GHNKYLRGYSCYRP;
HNKYLRGYSCYRPN; NKYLRGYSCYRPNS; KYLRGYSCYRPNSS;
YLRGYSCYRPNSSN; LRGYSCYRPNSSNI; RGYSCYRPNSSNIC;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GYSCYRPNSSNICC; YSCYRPNSSNICCN; SCYRPNSSNICCNC;
CYRPNSSNICCNCW; YRPNSSNICCNCWC; RPNSSNICCNCWCS;
PNSSNICCNCWCSW; NSSNICCNCWCSWG; SSNICCNCWCSWGY;
SNICCNCWCSWGYC; NICCNCWCSWGYCW; ICCNCWCSWGYCWV;
CCNCWCSWGYCWVC; CNCWCSWGYCWVCC; NCWCSWGYCWVCCF;
CWCSWGYCWVCCFN; WCSWGYCWVCCFNS; CSWGYCWVCCFNSN;
SWGYCWVCCFNSNC; LGSQSFHCRPLSAI; GSQSFHCRPLSAIR;
SQSFHCRPLSAIRH; QSFHCRPLSAIRHG; SFHCRPLSAIRHGF;
FHCRPLSAIRHGFG; HCRPLSAIRHGFGI; CRPLSAIRHGFGIV;
ALGSFFVCYYFPGF; LGSFFVCYYFPGFV; GSFFVCYYFPGFVA;
SFFVCYYFPGFVAC; FFVCYYFPGFVACY; YTFYNLTGIAEKNR;
TFYNLTGIAEKNRK; FYNLTGIAEKNRKI; YNLTGIAEKNRKIF;
IFGGNYLDNCKPY; FGGNYLDNCKPYK; GGNYLDNCKPYKL;
GNYLDNCKPYKLL; QYRRSYTKNGLKKS; YRRSYTKNGLKKST;
RRSYTKNGLKKSTK; RSYTKNGLKKSTKC; SYTKNGLKKSTKCT;
YTKNGLKKSTKCTF; TKNGLKKSTKCTFR; KNGLKKSTKCTFRR;
NGLKKSTKCTFRRV; GLKKSTKCTFRRVY; LKKSTKCTFRRVYR;
KKSTKCTFRRVYRK; KSTKCTFRRVYRKN; STKCTFRRVYRKNY;
TKCTFRRVYRKNYC; KCTFRRVYRKNYCP; CTFRRVYRKNYCPR;
TFRRVYRKNYCPRR; FRRVYRKNYCPRRC; SKNCSSMDVAFTSR;
KNCSSMDVAFTSRP; NCSSMDVAFTSRPV; CSSMDVAFTSRPVR;
SSMDVAFTSRPVRD; SMDVAFTSRPVRDC; MDVAFTSRPVRDCN;
DVAFTSRPVRDCNT; VAFTSRPVRDCNTC; AFTSRPVRDCNTCS;
RWPQPKEKESVQGQ; WPQPKEKESVQGQL; PQPKEKESVQGQLP;
QPKEKESVQGQLPK; PKEKESVQGQLPKS; KEKESVQGQLPKSQ;
EKESVQGQLPKSQR; KESVQGQLPKSQRN; ESVQGQLPKSQRNP;
SVQGQLPKSQRNPC; VQGQLPKSQRNPCK; QGQLPKSQRNPCKQ;
GQLPKSQRNPCKCQ; QLPKSQRNPCKCQN; LPKSQRNPCKCQNY;
TQKWGIQMKTLGAL; QKWGIQMKTLGALV; VLKMTLAVIAQREK;
LKMTLAVIAQREKC; KMTLAVIAQREKCF; MTLAVIAQREKCFP;
TLAVIAQREKCFPV; LAVIAQREKCFPVT; AVIAQREKCFPVTA;
VIAQREKCFPVTAQ; IAQREKCFPVTAQQ; AQREKCFPVTAQQE;
QREKCFPVTAQQEF; REKCFPVTAQQEFP; EKCFPVTAQQEFPS;
KCFPVTAQQEFPSP; CFPVTAQQEFPSPI; LACLTFMQGHKKCM;
ACLTFMQGHKKCMS; CLTFMQGHKKCMSM; LTFMQGHKKCMSMV;
TFMQGHKKCMSMVE; FMQGHKKCMSMVEE; MQGHKKCMSMVEEN;
QGHKKCMSMVEENL; GHKKCMSMVEENLF; HKKCMSMVEENLFK;
KKCMSMVEENLFKA; KCMSMVEENLFKAV; CMSMVEENLFKAVI;
MSMVEENLFKAVIS; SMVEENLFKAVIST; MVEENLFKAVISTS;
VEENLFKAVISTSL; EENLFKAVISTSLL; ILTIRPIWTKTMLI;
LTIRPIWTKTMLIQ; TIRPIWTKTMLIQL; IRPIWTKTMLIQLS;
RPIWTKTMLIQLSA; PIWTKTMLIQLSAG; IWTKTMLIQLSAGY;
WTKTMLIQLSAGYL; TKTMLIQLSAGYLI; KTMLIQLSAGYLIP;
TMLIQLSAGYLIPV; MLIQLSAGYLIPVE; LIQLSAGYLIPVEM;
IQLSAGYLIPVEMK; QLSAGYLIPVEMKM; LSAGYLIPVEMKML;
SAGYLIPVEMKMLG; AGYLIPVEMKMLGI; GYLIPVEMKMLGIL;
YLIPVEMKMLGILG; LIPVEMKMLGILGL; IPVEMKMLGILGLS;
PVEMKMLGILGLSQ; VEMKMLGILGLSQE; EMKMLGILGLSQEG;
MKMLGILGLSQEGK; KMLGILGLSQEGKM; MLGILGLSQEGKMF;
LGILGLSQEGKMFP; GILGLSQEGKMFPQ; ILGLSQEGKMFPQY;
LGLSQEGKMFPQYF; GLSQEGKMFPQYFM; MNRVWGLFVKLIAC;
NRVWGLFVKLIACM; RVWGLFVKLIACMF; VWGLFVKLIACMFQ;
WGLFVKLIACMFQL; GLFVKLIACMFQLL; LFVKLIACMFQLLI;
FVKLIACMFQLLIF; VKLIACMFQLLIFV; KLIACMFQLLIFVA;
LIACMFQLLIFVAC; IACMFQLLIFVACL; ACMFQLLIFVACLL;
CMFQLLIFVACLLT; MFQLLIFVACLLTA; FQLLIFVACLLTAL;
QLLIFVACLLTALE; LLIFVACLLTALEH; LIFVACLLTALEHN;
IFVACLLTALEHNS; FVACLLTALEHNSG; VACLLTALEHNSGE;
ACLLTALEHNSGEA; CLLTALEHNSGEAL; LLTALEHNSGEALQ;
LTALEHNSGEALQD; TALEHNSGEALQDI; ALEHNSGEALQDIL;
LEHNSGEALQDILR; EHNSGEALQDILRS; HNSGEALQDILRSA;
TGEPREWMGSLCMV; GEPREWMGSLCMVW; EPREWMGSLCMVWN;
PREWMGSLCMVWNP; REWMGSLCMVWNPR; KRLGCLMAQKDFQG;
RLGCLMAQKDFQGT; LGCLMAQKDFQGTQ; GCLMAQKDFQGTQI;
DILTNRDNCKPKCF; ILTNRDNCKPKCFK; LTNRDNCKPKCFKQ;
TNRDNCKPKCFKQV; NRDNCKPKCFKQVL; RDNCKPKCFKQVLL;
DNCKPKCFKQVLLL; NCKPKCFKQVLLLY; CKPKCFKQVLLLYI;
KPKCFKQVLLLYIY; PKCFKQVLLLYIYI; MLLLYKPLLSLCYF;
LLLYKPLLSLCYFG; LLYKPLLSLCYFGG; LYKPLLSLCYFGGG;
YKPLLSLCYFGGGV; KPLLSLCYFGGGVL; PLLSLCYFGGGVLG;
LLSLCYFGGGVLGL; LSLCYFGGGVLGLL; SLCYFGGGVLGLLK;
LCYFGGGVLGLLKH; LWGSDLWESSAGAE; WGSDLWESSAGAEV;
GSDLWESSAGAEVS; SDLWESSAGAEVSE; DLWESSAGAEVSET;
LWESSAGAEVSETW; WESSAGAEVSETWE; ESSAGAEVSETWEE;
SSAGAEVSETWEEH; SAGAEVSETWEEHC; AGAEVSETWEEHCD;
GAEVSETWEEHCDW; AEVSETWEEHCDWD; EVSETWEEHCDWDS;
VSETWEEHCDWDSV; SETWEEHCDWDSVL; ETWEEHCDWDSVLD;
TWEEHCDWDSVLDP; WEEHCDWDSVLDPC; EEHCDWDSVLDPCP;
EHCDWDSVLDPCPE; HCDWDSVLDPCPES; CDWDSVLDPCPESS;
DWDSVLDPCPESSV; WDSVLDPCPESSVS; DSVLDPCPESSVSE;
SVLDPCPESSVSES; VLDPCPESSVSESS; LDPCPESSVSESSS;
DPCPESSVSESSSL; PCPESSVSESSSLV; CPESSVSESSSLVI;
PESSVSESSSLVIS; ESSVSESSSLVISR; SSVSESSSLVISRI;
SVSESSSLVISRIH; VSESSSLVISRIHF; SESSSLVISRIHFP;
ESSSLVISRIHFPM; SSSLVISRIHFPMH; SSLVISRIHFPMHI;
SLVISRIHFPMHIL; LVISRIHFPMHILY; VISRIHFPMHILYF;
ISRIHFPMHILYFI; SRIHFPMHILYFIL; RIHFPMHILYFILE;
IHFPMHILYFILEK; HFPMHILYFILEKV; FPMHILYFILEKVY;
PMHILYFILEKVYI; MHILYFILEKVYIL; HILYFILEKVYILI;
ILYFILEKVYILIS; LYFILEKVYILISE; YFILEKVYILISES;
FILEKVYILISESS; ILEKVYILISESSL; LEKVYILISESSLS;
EKVYILISESSLSF; KVYILISESSLSFH; VYILISESSLSFHS;
YILISESSLSFHST; ILISESSLSFHSTI; LISESSLSFHSTIL;
ISESSLSFHSTILD; SESSLSFHSTILDC; ESSLSFHSTILDCI;
SSLSFHSTILDCIS; SLSFHSTILDCISV; LSFHSTILDCISVA;
SFHSTILDCISVAK; FHSTILDCISVAKS; HSTILDCISVAKSA;
STILDCISVAKSAT; TILDCISVAKSATG; ILDCISVAKSATGL;
LDCISVAKSATGLN; DCISVAKSATGLNQ; CISVAKSATGLNQI;
ISVAKSATGLNQIS; SVAKSATGLNQISS; VAKSATGLNQISSS;
AKSATGLNQISSSN; KSATGLNQISSSNK; SATGLNQISSSNKV;
ATGLNQISSSNKVI; TGLNQISSSNKVIP; GLNQISSSNKVIPL;
LNQISSSNKVIPLC; NQISSSNKVIPLCK; QISSSNKVIPLCKI;
ISSSNKVIPLCKIL; SSSNKVIPLCKILF; SSNKVIPLCKILFS;
SNKVIPLCKILFSS; NKVIPLCKILFSSK; KVIPLCKILFSSKN;
VIPLCKILFSSKNS; IPLCKILFSSKNSE; PLCKILFSSKNSEF;
LCKILFSSKNSEFC; CKILFSSKNSEFCK; KILFSSKNSEFCKD;
ILFSSKNSEFCKDF; LFSSKNSEFCKDFL; FSSKNSEFCKDFLK;
SSKNSEFCKDFLKY; SKNSEFCKDFLKYI; KNSEFCKDFLKYIL;
NSEFCKDFLKYILG; SEFCKDFLKYILGL; EFCKDFLKYILGLK;
FCKDFLKYILGLKS; CKDFLKYILGLKSI; KDFLKYILGLKSIC;
DFLKYILGLKSICL; FLKYILGLKSICLT; LKYILGLKSICLTN;
KYILGLKSICLTNL; YILGLKSICLTNLA; ILGLKSICLTNLAC;
LGLKSICLTNLACR; GLKSICLTNLACRV; LKSICLTNLACRVL;
KSICLTNLACRVLG; SICLTNLACRVLGT; ICLTNLACRVLGTY;
CLTNLACRVLGTGY; LTNLACRVLGTGYS; TNLACRVLGTGYSF;
NLACRVLGTGYSFI; LACRVLGTGYSFIV; ACRVLGTGYSFIVT;
CRVLGTGYSFIVTK; RVLGTGYSFIVTKP; VLGTGYSFIVTKPG;
LGTGYSFIVTKPGG; GTGYSFIVTKPGGN; TGYSFIVTKPGGNI;
GYSFIVTKPGGNIW; YSFIVTKPGGNIWV; SFIVTKPGGNIWVL;
FIVTKPGGNIWVLL; IVTKPGGNIWVLLF; VTKPGGNIWVLLFK;
TKPGGNIWVLLFKC; KPGGNIWVLLFKCF; PGGNIWVLLFKCFF;
GGNIWVLLFKCFFS; GNIWVLLFKCFFSK; NIWVLLFKCFFSKF;
IWVLLFKCFFSKFT; WVLLFKCFFSKFTL; VLLFKCFFSKFTLT;
LLFKCFFSKFTLTL; LFKCFFSKFTLTLP; FKCFFSKFTLTLPS;
KCFFSKFTLTLPSK; SLKLSKLFIPCPEG; LKLSKLFIPCPEGK;
KLSKLFIPCPEGKS; LSKLFIPCPEGKSF; SKLFIPCPEGKSFD;
KLFIPCPEGKSFDS; LFIPCPEGKSFDSA; FIPCPEGKSFDSAP;
IPCPEGKSFDSAPV; PCPEGKSFDSAPVP; CPEGKSFDSAPVPF;
PEGKSFDSAPVPFT; EGKSFDSAPVPFTS; GKSFDSAPVPFTSS;
KSFDSAPVPFTSSK; SFDSAPVPFTSSKT; FDSAPVPFTSSKTT;
DSAPVPFTSSKTTM; SAPVPFTSSKTTMY; SIATPSSKVSLSMG;
IATPSSKVSLSMGR; ATPSSKVSLSMGRF; TPSSKVSLSMGRFT;
PSSKVSLSMGRFTF; SSKVSLSMGRFTFK; SKVSLSMGRFTFKA;
KVSLSMGRFTFKAL; VSLSMGRFTFKALP; SLSMGRFTFKALPP;
LSMGRFTFKALPPH; SMGRFTFKALPPHK; MGRFTFKALPPHKS;
GRFTFKALPPHKSN; RFTFKALPPHKSNN; FTFKALPPHKSNNP;
TFKALPPHKSNNPA; FKALPPHKSNNPAA; KALPPHKSNNPAAS;
ALPPHKSNNPAASV; LPPHKSNNPAASVV; PPHKSNNPAASVVF;
PHKSNNPAASVVFP; HKSNNPAASVVFPL; KSNNPAASVVFPLS;
SNNPAASVVFPLSM; NNPAASVVFPLSMG; NPAASVVFPLSMGP;
PAASVVFPLSMGPL; AASVVFPLSMGPLN; ASVVFPLSMGPLNN;
SVVFPLSMGPLNNQ; VVFPLSMGPLNNQY; VFPLSMGPLNNQYL;
FPLSMGPLNNQYLL; PLSMGPLNNQYLLL; LSMGPLNNQYLLLG;
SMGPLNNQYLLLGT; MGPLNNQYLLLGTL; GPLNNQYLLLGTLK;
PLNNQYLLLGTLKT; LNNQYLLLGTLKTI; NNQYLLLGTLKTIQ;
NQYLLLGTLKTIQC; QYLLLGTLKTIQCK; YLLLGTLKTIQCKK;
LLLGTLKTIQCKKS; LLGTLKTIQCKKSN; LGTLKTIQCKKSNI;
GTLKTIQCKKSNIT; TLKTIQCKKSNITE; LKTIQCKKSNITES;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

KTIQCKKSNITESI; TIQCKKSNITESIL; IQCKKSNITESILG;
QCKKSNITESILGS; CKKSNITESILGSK; KKSNITESILGSKQ;
KSNITESILGSKQC; SNITESILGSKQCS; NITESILGSKQCSQ;
ITESILGSKQCSQA; TESILGSKQCSQAT; ESILGSKQCSQATP;
SILGSKQCSQATPA; ILGSKQCSQATPAI; LGSKQCSQATPAIY;
GSKQCSQATPAIYC; SKQCSQATPAIYCS; KQCSQATPAIYCSS;
QCSQATPAIYCSST; CSQATPAIYCSSTA; SQATPAIYCSSTAF;
QATPAIYCSSTAFP; RVSTLFLAKTVSTA; VSTLFLAKTVSTAC;
FLLSAKIIAFAKCF; LLSAKIIAFAKCFS; NSKYIPNNKNTSSH;
SKYIPNNKNTSSHF; KYIPNNKNTSSHFV; YIPNNKNTSSHFVS;
IPNNKNTSSHFVST; PNNKNTSSHFVSTA; NNKNTSSHFVSTAY;
NKNTSSHFVSTAYS; KNTSSHFVSTAYSV; NTSSHFVSTAYSVI;
TSSHFVSTAYSVIN; SSHFVSTAYSVINF; SHFVSTAYSVINFQ;
HFVSTAYSVINFQD; FVSTAYSVINFQDT; VSTAYSVINFQDTC;
STAYSVINFQDTCF; TAYSVINFQDTCFV; AYSVINFQDTCFVS;
YSVINFQDTCFVSS; SVINFQDTCFVSSG; VINFQDTCFVSSGS;
INFQDTCFVSSGSS; NFQDTCFVSSGSSG; FQDTCFVSSGSSGL;
QDTCFVSSGSSGLK; DTCFVSSGSSGLKS; TCFVSSGSSGLKSC;
CFVSSGSSGLKSCS; FVSSGSSGLKSCSF; VSSGSSGLKSCSFK;
SSGSSGLKSCSFKP; SGSSGLKSCSFKPP; MLSSIVWYGSLVKA;
LSSIVWYGSLVKAL; SSIVWYGSLVKALY; SIVWYGSLVKALYS;
IVWYGSLVKALYSK; VWYGSLVKALYSKY; WYGSLVKALYSKYS;
YGSLVKALYSKYSL; GSLVKALYSKYSLL; SLVKALYSKYSLLT;
LVKALYSKYSLLTP; VKALYSKYSLLTPL; KALYSKYSLLTPLQ;
ALYSKYSLLTPLQI; LYSKYSLLTPLQIK; YSKYSLLTPLQIKK;
SKYSLLTPLQIKKL; KYSLLTPLQIKKLK; YSLLTPLQIKKLKV;
SLLTPLQIKKLKVH; LLTPLQIKKLKVHS; LTPLQIKKLKVHSF;
QKLLIAETLCLCGV; KLLIAETLCLCGVK; LLIAETLCLCGVKK;
LIAETLCLCGVKKN; IAETLCLCGVKKNI; AETLCLCGVKKNII;
ETLCLCGVKKNIIL; TLCLCGVKKNIILC; LCLCGVKKNIILCP;
CLCGVKKNIILCPA; LCGVKKNIILCPAH; CGVKKNIILCPAHM;
GVKKNIILCPAHMC; VKKNIILCPAHMCL; KKNIILCPAHMCLL;
KNIILCPAHMCLLI; NIILCPAHMCLLIK; IILCPAHMCLLIKV;
ILCPAHMCLLIKVT; LCPAHMCLLIKVTE; CPAHMCLLIKVTEY;
PAHMCLLIKVTEYF; AHMCLLIKVTEYFS; HMCLLIKVTEYFSI;
MCLLIKVTEYFSIS; CLLIKVTEYFSISF; LLIKVTEYFSISFL;
LIKVTEYFSISFLY; IKVTEYFSISFLYR; KVTEYFSISFLYRI;
AFSLVVYTAKQARV; FSLVVYTAKQARVL; SLVVYTAKQARVLL;
LVVYTAKQARVLLL; VVYTAKQARVLLLN; VYTAKQARVLLLNT;
YTAKQARVLLLNTA; LRNWCRSEGKSLGS; RNWCRSEGKSLGSS;
NWCRSEGKSLGSST; WCRSEGKSLGSSTF; CRSEGKSLGSSTFL;
RSEGKSLGSSTFLF; SEGKSLGSSTFLFF; EGKSLGSSTFLFFL;
GKSLGSSTFLFFLG; KSLGSSTFLFFLGG; SLGSSTFLFFLGGV;
LGSSTFLFFLGGVE; GSSTFLFFLGGVEC; ESAVASSSLANISS;
SAVASSSLANISSW; AVASSSLANISSWQ; VASSSLANISSWQN;
ASSSLANISSWQNK; SSSLANISSWQNKS; SSLANISSWQNKSS;
SLANISSWQNKSSS; LANISSWQNKSSSH; ANISSWQNKSSSHF;
NISSWQNKSSSHFS; ISSWQNKSSSHFSL; SSWQNKSSSHFSLK;
SWQNKSSSHFSLKE; WQNKSSSHFSLKEL; QNKSSSHFSLKELH;
NKSSSHFSLKELHQ; KSSSHFSLKELHQD; SSSHFSLKELHQDS;
SSHFSLKELHQDSH; SHFSLKELHQDSHS; HFSLKELHQDSHSS;
FSLKELHQDSHSSV; SLKELHQDSHSSVP; VGTYKKNNYLGPFN;
GTYKKNNYLGPFNI; TYKKNNYLGPFNIL; YKKNNYLGPFNILL;
KKNNYLGPFNILLF; KNNYLGPFNILLFI; REFLQLFGPTIAEF;
EFLQLFGPTIAEFL; FLQLFGPTIAEFLQ; LQLFGPTIAEFLQL;
QLFGPTIAEFLQLG; LFGPTIAEFLQLGL; FGPTIAEFLQLGLS;
GPTIAEFLQLGLSQ; PTIAEFLQLGLSQT; TIAEFLQLGLSQTT;
IAEFLQLGLSQTTV; SSQCSSNLSKPRAL; SQCSSNLSKPRALF;
QCSSNLSKPRALFL; CSSNLSKPRALFLK; SSNLSKPRALFLKI;
SNLSKPRALFLKIF; NLSKPRALFLKIFY; LSKPRALFLKIFYL;
SKPRALFLKIFYLN; KPRALFLKIFYLNA; PRALFLKIFYLNAL;
RALFLKIFYLNALI; ADIACKGSAQKAFW; DIACKGSAQKAFWN;
IACKGSAQKAFWNK; AIPCSTGYLGKEEN; IPCSTGYLGKEENQ;
PCSTGYLGKEENQH; CSTGYLGKEENQHK; STGYLGKEENQHKP;
TGYLGKEENQHKPL; GYLGKEENQHKPLS; YLGKEENQHKPLSY;
LGKEENQHKPLSYS; GKEENQHKPLSYSR; KEENQHKPLSYSRF;
EENQHKPLSYSRFQ; ENQHKPLSYSRFQN; NQHKPLSYSRFQNQ;
QHKPLSYSRFQNQA; HKPLSYSRFQNQAD; KPLSYSRFQNQADE;
PLSYSRFQNQADEL; LSYSRFQNQADELP; SYSRFQNQADELPL;
YSRFQNQADELPLH; SRFQNQADELPLHP; RFQNQADELPLHPA;
FQNQADELPLHPAP; QNQADELPLHPAPF; NQADELPLHPAPFF;
QADELPLHPAPFFY; ADELPLHPAPFFYT; DELPLHPAPFFYTK;
ELPLHPAPFFYTKY; LPLHPAPFFYTKYS; PLHPAPFFYTKYSF;
LHPAPFFYTKYSFS; HPAPFFYTKYSFSS; PAPFFYTKYSFSSF;
APFFYTKYSFSSFY; PFFYTKYSFSSFYP; FFYTKYSFSSFYPR;
FYTKYSFSSFYPRR; YTKYSFSSFYPRRP; TKYSFSSFYPRRPL;
KYSFSSFYPRRPLC; YSFSSFYPRRPLCQ; SFSSFYPRRPLCQG;
FSSFYPRRPLCQGE; SSFYPRRPLCQGEI; SFYPRRPLCQGEIP;
FYPRRPLCQGEIPY; YPRRPLCQGEIPYT; PRRPLCQGEIPYTS;
RRPLCQGEIPYTSL; RPLCQGEIPYTSLN; PLCQGEIPYTSLNK;
LCQGEIPYTSLNKL; CQGEIPYTSLNKLF; QGEIPYTSLNKLFS;
GEIPYTSLNKLFSL; EIPYTSLNKLFSLR; IPYTSLNKLFSLRE;
PYTSLNKLFSLRED; YTSLNKLFSLREDF; TSLNKLFSLREDFP;
SLNKLFSLREDFPR; LNKLFSLREDFPRQ; NKLFSLREDFPRQL;
KLFSLREDFPRQLF; LFSLREDFPRQLFQ; FSLREDFPRQLFQG;
SLREDFPRQLFQGL; LREDFPRQLFQGLK; REDFPRQLFQGLKG;
EDFPRQLFQGLKGP 15 mers:

GFPQIVLLGLRKSLH; FPQIVLLGLRKSLHT; PQIVLLGLRKSLHTL;
QIVLLGLRKSLHTLT; IVLLGLRKSLHTLTT; EKGWRQRRPRPLIYY;
KGWRQRRPRPLIYYK; GWRQRRPRPLIYYKK; WRQRRPRPLIYYKKK;
RQRRPRPLIYYKKKG; QRRPRPLIYYKKKGH; RRPRPLIYYKKKGHR;
RPRPLIYYKKKGHRE; PRPLIYYKKKGHREE; RPLIYYKKKGHREEL;
PLIYYKKKGHREELL; LIYYKKKGHREELLT; IYYKKKGHREELLTH;
YYKKKGHREELLTHG; YKKKGHREELLTHGM; KKKGHREELLTHGMQ;
KKGHREELLTHGMQP; KGHREELLTHGMQPN; GHREELLTHGMQPNH;
HREELLTHGMQPNHD; REELLTHGMQPNHDL; EELLTHGMQPNHDLR;
ELLTHGMQPNHDLRK; LLTHGMQPNHDLRKE; LTHGMQPNHDLRKES;
THGMQPNHDLRKESA; LTGECSQTMTSGRKV; TGECSQTMTSGRKVH;
GECSQTMTSGRKVHD; ECSQTMTSGRKVHDS; CSQTMTSGRKVHDSQ;
SQTMTSGRKVHDSQG; QTMTSGRKVHDSQGG; TMTSGRKVHDSQGGA;
MTSGRKVHDSQGGAA; TSGRKVHDSQGGAAY; SGRKVHDSQGGAAYP;
GRKVHDSQGGAAYPW; RKVHDSQGGAAYPWN; KVHDSQGGAAYPWNA;
VHDSQGGAAYPWNAA; HDSQGGAAYPWNAAK; DSQGGAAYPWNAAKP;
PQEGKCMTDMFCEPR; QEGKCMTDMFCEPRN; EGKCMTDMFCEPRNL;
GKCMTDMFCEPRNLG; KCMTDMFCEPRNLGL; CMTDMFCEPRNLGLV;
MTDMFCEPRNLGLVP; TDMFCEPRNLGLVPS; TGQRPWFCASCHDKL;
GQRPWFCASCHDKLG; KLVKPGLEQKKELRG; LVKPGLEQKKELRGF;
VKPGLEQKKELRGFL; KPGLEQKKELRGFLF; PGLEQKKELRGFLFL;
GLEQKKELRGFLFLF; VIPFFLYFQVHGCCS; IPFFLYFQVHGCCSS;
PFFLYFQVHGCCSST; FFLYFQVHGCCSSTF; FLYFQVHGCCSSTFG;
LYFQVHGCCSSTFGG; YFQVHGCCSSTFGGP; FQVHGCCSSTFGGPS;
QVHGCCSSTFGGPSC; VHGCCSSTFGGPSCQ; HGCCSSTFGGPSCQC;
GCCSSTFGGPSCQCI; NCCWGGCCCYRSSNC; CCWGGCCCYRSSNCI;
CWGGCCCYRSSNCIP; WGGCCCYRSSNCIPC; GGCCCYRSSNCIPCY;
GCCCYRSSNCIPCYC; CCCYRSSNCIPCYCR; CCYRSSNCIPCYCRG;
CYRSSNCIPCYCRGH; YRSSNCIPCYCRGHN; RSSNCIPCYCRGHNK;
SSNCIPCYCRGHNKY; SNCIPCYCRGHNKYL; NCIPCYCRGHNKYLR;
CIPCYCRGHNKYLRG; IPCYCRGHNKYLRGY; PCYCRGHNKYLRGYS;
CYCRGHNKYLRGYSC; YCRGHNKYLRGYSCY; CRGHNKYLRGYSCYR;
RGHNKYLRGYSCYRP; GHNKYLRGYSCYRPN; HNKYLRGYSCYRPNS;
NKYLRGYSCYRPNSS; KYLRGYSCYRPNSSN; YLRGYSCYRPNSSNI;
LRGYSCYRPNSSNIC; RGYSCYRPNSSNICC; GYSCYRPNSSNICCN;
YSCYRPNSSNICCNC; SCYRPNSSNICCNCW; CYRPNSSNICCNCWC;
YRPNSSNICCNCWCS; RPNSSNICCNCWCSW; PNSSNICCNCWCSWG;
NSSNICCNCWCSWGY; SSNICCNCWCSWGYC; SNICCNCWCSWGYCW;
NICCNCWCSWGYCWV; ICCNCWCSWGYCWVC; CCNCWCSWGYCWVCC;
CNCWCSWGYCWVCCF; NCWCSWGYCWVCCFN; CWCSWGYCWVCCFNS;
WCSWGYCWVCCFNSN; CSWGYCWVCCFNSNC; LGSQSFHCRPLSAIR;
GSQSFHCRPLSAIRH; SQSFHCRPLSAIRHG; QSFHCRPLSAIRHGF;
SFHCRPLSAIRHGFG; FHCRPLSAIRHGFGI; HCRPLSAIRHGFGIV;
ALGSFFVCYYFPGFV; LGSFFVCYYFPGFVA; GSFFVCYYFPGFVAC;
SFFVCYYFPGFVACY; YTFYNLTGIAEKNRK; TFYNLTGIAEKNRKI;
FYNLTGIAEKNRKIF; IFGGNYLDNCKCPYK; FGGNYLDNCKCPYKL;
GGNYLDNCKCPYKLL; QYRRSYTKNGLKKST; YRRSYTKNGLKKSTK;
RRSYTKNGLKKSTKC; RSYTKNGLKKSTKCT; SYTKNGLKKSTKCTF;
YTKNGLKKSTKCTFR; TKNGLKKSTKCTFRR; KNGLKKSTKCTFRRV;
NGLKKSTKCTFRRVY; GLKKSTKCTFRRVYR; LKKSTKCTFRRVYRK;
KKSTKCTFRRVYRKN; KSTKCTFRRVYRKNY; STKCTFRRVYRKNYC;
TKCTFRRVYRKNYCP; KCTFRRVYRKNYCPR; CTFRRVYRKNYCPRR;
TFRRVYRKNYCPRRC; SKNCSSMDVAFTSRP; KNCSSMDVAFTSRPV;
NCSSMDVAFTSRPVR; CSSMDVAFTSRPVRD; SSMDVAFTSRPVRDC;
SMDVAFTSRPVRDCN; MDVAFTSRPVRDCNT; DVAFTSRPVRDCNTC;
VAFTSRPVRDCNTCS; RWPQPKEKESVQGQL; WPQPKEKESVQGQLP;
PQPKEKESVQGQLPK; QPKEKESVQGQLPKS; PKEKESVQGQLPKSQ;
KEKESVQGQLPKSQR; EKESVQGQLPKSQRN; KESVQGQLPKSQRNP;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

ESVQGQLPKSQRNPC; SVQGQLPKSQRNPCK; VQGQLPKSQRNPCKC;
QGQLPKSQRNPCKCQ; GQLPKSQRNPCKCQN; QLPKSQRNPCKCQNY;
TQKWGIQMKTLGALV; VLKMTLAVIAQREKC; LKMTLAVIAQREKCF;
KMTLAVIAQREKCFP; MTLAVIAQREKCFPV; TLAVIAQREKCFPVT;
LAVIAQREKCFPVTA; AVIAQREKCFPVTAQ; VIAQREKCFPVTAQQ;
IAQREKCFPVTAQQE; AQREKCFPVTAQQEF; QREKCFPVTAQQEFP;
REKCFPVTAQQEFPS; EKCFPVTAQQEFPSP; KCFPVTAQQEFPSPI;
LACLTFMQGHKKCMS; ACLTFMQGHKKCMSM; CLTFMQGHKKCMSMV;
LTFMQGHKKCMSMVE; TFMQGHKKCMSMVEE; FMQGHKKCMSMVEEN;
MQGHKKCMSMVEENL; QGHKKCMSMVEENLF; GHKKCMSMVEENLFK;
HKKCMSMVEENLFKA; KKCMSMVEENLFKAV; KCMSMVEENLFKAVI;
CMSMVEENLFKAVIS; MSMVEENLFKAVIST; SMVEENLFKAVISTS;
MVEENLFKAVISTSL; VEENLFKAVISTSLL; ILTIRPIWTKTMLIQ;
LTIRPIWTKTMLIQL; TIRPIWTKTMLIQLS; IRPIWTKTMLIQLSA;
RPIWTKTMLIQLSAG; PIWTKTMLIQLSAGY; IWTKTMLIQLSAGYL;
WTKTMLIQLSAGYLI; TKTMLIQLSAGYLIP; KTMLIQLSAGYLIPV;
TMLIQLSAGYLIPVE; MLIQLSAGYLIPVEM; LIQLSAGYLIPVEMK;
IQLSAGYLIPVEMKM; QLSAGYLIPVEMKML; LSAGYLIPVEMKMLG;
SAGYLIPVEMKMLGI; AGYLIPVEMKMLGIL; GYLIPVEMKMLGILG;
YLIPVEMKMLGILGL; LIPVEMKMLGILGLS; IPVEMKMLGILGLSQ;
PVEMKMLGILGLSQE; VEMKMLGILGLSQEG; EMKMLGILGLSQEGK;
MKMLGILGLSQEGKM; KMLGILGLSQEGKMF; MLGILGLSQEGKMFP;
LGILGLSQEGKMFPQ; GILGLSQEGKMFPQY; ILGLSQEGKMFPQYF;
LGLSQEGKMFPQYFM; MNRVWGLFVKLIACM; NRVWGLFVKLIACMF;
RVWGLFVKLIACMFQ; VWGLFVKLIACMFQL; WGLFVKLIACMFQLL;
GLFVKLIACMFQLLI; LFVKLIACMFQLLIF; FVKLIACMFQLLIFV;
VKLIACMFQLLIFVA; KLIACMFQLLIFVAC; LIACMFQLLIFVACL;
IACMFQLLIFVACLL; ACMFQLLIFVACLLT; CMFQLLIFVACLLTA;
MFQLLIFVACLLTAL; FQLLIFVACLLTALE; QLLIFVACLLTALEH;
LLIFVACLLTALEHN; LIFVACLLTALEHNS; IFVACLLTALEHNSG;
FVACLLTALEHNSGE; VACLLTALEHNSGEA; ACLLTALEHNSGEAL;
CLLTALEHNSGEALQ; LLTALEHNSGEALQD; LTALEHNSGEALQDI;
TALEHNSGEALQDIL; ALEHNSGEALQDILR; LEHNSGEALQDILRS;
EHNSGEALQDILRSA; TGEPREWMGSLCMVW; GEPREWMGSLCMVWN;
EPREWMGSLCMVWNP; PREWMGSLCMVWNPR; KRLGCLMAQKDFQGT;
RLGCLMAQKDFQGTQ; LGCLMAQKDFQGTQI; DILTNRDNCKPKCFK;
ILTNRDNCKPKCFKQ; LTNRDNCKPKCFKQV; TNRDNCKPKCFKQVL;
NRDNCKPKCFKQVLL; RDNCKPKCFKQVLLL; DNCKPKCFKQVLLLY;
NCKPKCFKQVLLLYI; CKPKCFKQVLLLYIY; KPKCFKQVLLLYIYI;
MLLLYKPLLSLCYFG; LLLYKPLLSLCYFGG; LLYKPLLSLCYFGGG;
LYKPLLSLCYFGGGV; YKPLLSLCYFGGGVL; KPLLSLCYFGGGVLG;
PLLSLCYFGGGVLGL; LLSLCYFGGGVLGLL; LSLCYFGGGVLGLLK;
SLCYFGGGVLGLLKH; LWGSDLWESSAGAEV; WGSDLWESSAGAEVS;
GSDLWESSAGAEVSE; SDLWESSAGAEVSET; DLWESSAGAEVSETW;
LWESSAGAEVSETWE; WESSAGAEVSETWEE; ESSAGAEVSETWEEH;
SSAGAEVSETWEEHC; SAGAEVSETWEEHCD; AGAEVSETWEEHCDW;
GAEVSETWEEHCDWD; AEVSETWEEHCDWDS; EVSETWEEHCDWDSV;
VSETWEEHCDWDSVL; SETWEEHCDWDSVLD; ETWEEHCDWDSVLDP;
TWEEHCDWDSVLDPC; WEEHCDWDSVLDPCP; EEHCDWDSVLDPCPE;
EHCDWDSVLDPCPES; HCDWDSVLDPCPESS; CDWDSVLDPCPESSV;
DWDSVLDPCPESSVS; WDSVLDPCPESSVSE; DSVLDPCPESSVSES;
SVLDPCPESSVSESS; VLDPCPESSVSESSS; LDPCPESSVSESSSL;
DPCPESSVSESSSLV; PCPESSVSESSSLVI; CPESSVSESSSLVIS;
PESSVSESSSLVISR; ESSVSESSSLVISRI; SSVSESSSLVISRIH;
SVSESSSLVISRIHF; VSESSSLVISRIHFP; SESSSLVISRIHFPM;
ESSSLVISRIHFPMH; SSSLVISRIHFPMHI; SSLVISRIHFPMHIL;
SLVISRIHFPMHILY; LVISRIHFPMHILYF; VISRIHFPMHILYFI;
ISRIHFPMHILYFIL; SRIHFPMHILYFILE; RIHFPMHILYFILEK;
IHFPMHILYFILEKV; HFPMHILYFILEKVY; FPMHILYFILEKVYI;
PMHILYFILEKVYIL; MHILYFILEKVYILI; HILYFILEKVYILIS;
ILYFILEKVYILISE; LYFILEKVYILISES; YFILEKVYILISESS;
FILEKVYILISESSL; ILEKVYILISESSLS; LEKVYILISESSLSF;
EKVYILISESSLSFH; KVYILISESSLSFHS; VYILISESSLSFHST;
YILISESSLSFHSTI; ILISESSLSFHSTIL; LISESSLSFHSTILD;
ISESSLSFHSTILDC; SESSLSFHSTILDCI; ESSLSFHSTILDCIS;
SSLSFHSTILDCISV; SLSFHSTILDCISVA; LSFHSTILDCISVAK;
SFHSTILDCISVAKS; FHSTILDCISVAKSA; HSTILDCISVAKSAT;
STILDCISVAKSATG; TILDCISVAKSATGL; ILDCISVAKSATGLN;
LDCISVAKSATGLNQ; DCISVAKSATGLNQI; CISVAKSATGLNQIS;
ISVAKSATGLNQISS; SVAKSATGLNQISSS; VAKSATGLNQISSSN;
AKSATGLNQISSSNK; KSATGLNQISSSNKV; SATGLNQISSSNKVI;
ATGLNQISSSNKVIP; TGLNQISSSNKVIPL; GLNQISSSNKVIPLC;
LNQISSSNKVIPLCK; NQISSSNKVIPLCKI; QISSSNKVIPLCKIL;
ISSSNKVIPLCKILF; SSSNKVIPLCKILFS; SSNKVIPLCKILFSS;
SNKVIPLCKILFSSK; NKVIPLCKILFSSKN; KVIPLCKILFSSKNS;
VIPLCKILFSSKNSE; IPLCKILFSSKNSEF; PLCKILFSSKNSEFC;
LCKILFSSKNSEFCK; CKILFSSKNSEFCKD; KILFSSKNSEFCKDF;
ILFSSKNSEFCKDFL; LFSSKNSEFCKDFLK; FSSKNSEFCKDFLKY;
SSKNSEFCKDFLKYI; SKNSEFCKDFLKYIL; KNSEFCKDFLKYILG;
NSEFCKDFLKYILGL; SEFCKDFLKYILGLK; EFCKDFLKYILGLKS;
FCKDFLKYILGLKSI; CKDFLKYILGLKSIC; KDFLKYILGLKSICL;
DFLKYILGLKSICLT; FLKYILGLKSICLTN; LKYILGLKSICLTNL;
KYILGLKSICLTNLA; YILGLKSICLTNLAC; ILGLKSICLTNLACR;
LGLKSICLTNLACRV; GLKSICLTNLACRVL; LKSICLTNLACRVLG;
KSICLTNLACRVLGT; SICLTNLACRVLGTG; ICLTNLACRVLGTGY;
CLTNLACRVLGTGYS; LTNLACRVLGTGYSF; TNLACRVLGTGYSFI;
NLACRVLGTGYSFIV; LACRVLGTGYSFIVT; ACRVLGTGYSFIVTK;
CRVLGTGYSFIVTKP; RVLGTGYSFIVTKPG; VLGTGYSFIVTKPGG;
LGTGYSFIVTKPGGN; GTGYSFIVTKPGGNI; TGYSFIVTKPGGNIW;
GYSFIVTKPGGNIWV; YSFIVTKPGGNIWVL; SFIVTKPGGNIWVLL;
FIVTKPGGNIWVLLF; IVTKPGGNIWVLLFK; VTKPGGNIWVLLFKC;
TKPGGNIWVLLFKCF; KPGGNIWVLLFKCFF; PGGNIWVLLFKCFFS;
GGNIWVLLFKCFFSK; GNIWVLLFKCFFSKF; NIWVLLFKCFFSKFT;
IWVLLFKCFFSKFTL; WVLLFKCFFSKFTLT; VLLFKCFFSKFTLTL;
LLFKCFFSKFTLTLP; LFKCFFSKFTLTLPS; FKCFFSKFTLTLPSK;
SLKLSKLFIPCPEGK; LKLSKLFIPCPEGKS; KLSKLFIPCPEGKSF;
LSKLFIPCPEGKSFD; SKLFIPCPEGKSFDS; KLFIPCPEGKSFDSA;
LFIPCPEGKSFDSAP; FIPCPEGKSFDSAPV; IPCPEGKSFDSAPVP;
PCPEGKSFDSAPVPF; CPEGKSFDSAPVPFT; PEGKSFDSAPVPFTS;
EGKSFDSAPVPFTSS; GKSFDSAPVPFTSSK; KSFDSAPVPFTSSKT;
SFDSAPVPFTSSKTT; FDSAPVPFTSSKTTM; DSAPVPFTSSKTTMS;
SIATPSSKVSLSMGR; IATPSSKVSLSMGRF; ATPSSKVSLSMGRFT;
TPSSKVSLSMGRFTP; PSSKVSLSMGRFTFK; SSKVSLSMGRFTFKA;
SKVSLSMGRFTFKAL; KVSLSMGRFTFKALP; VSLSMGRFTFKALPP;
SLSMGRFTFKALPPH; LSMGRFTFKALPPHK; SMGRFTFKALPPHKS;
MGRFTFKALPPHKSN; GRFTFKALPPHKSNN; RFTFKALPPHKSNNP;
FTFKALPPHKSNNPA; TFKALPPHKSNNPAA; FKALPPHKSNNPAAS;
KALPPHKSNNPAASV; ALPPHKSNNPAASVV; LPPHKSNNPAASVVF;
PPHKSNNPAASVVFP; PHKSNNPAASVVFPL; HKSNNPAASVVFPLS;
KSNNPAASVVFPLSM; SNNPAASVVFPLSMG; NNPAASVVFPLSMGP;
NPAASVVFPLSMGPL; PAASVVFPLSMGPLN; AASVVFPLSMGPLNN;
ASVVFPLSMGPLNNQ; SVVFPLSMGPLNNQY; VVFPLSMGPLNNQYL;
VFPLSMGPLNNQYLL; FPLSMGPLNNQYLLL; PLSMGPLNNQYLLLG;
LSMGPLNNQYLLLGT; SMGPLNNQYLLLGTL; MGPLNNQYLLLGTLK;
GPLNNQYLLLGTLKT; PLNNQYLLLGTLKTI; LNNQYLLLGTLKTIQ;
NNQYLLLGTLKTIQC; NQYLLLGTLKTIQCK; QYLLLGTLKTIQCKK;
YLLLGTLKTIQCKKS; LLLGTLKTIQCKKSN; LLGTLKTIQCKKSNI;
LGTLKTIQCKKSNIT; GTLKTIQCKKSNITE; TLKTIQCKKSNITES;
LKTIQCKKSNITESI; KTIQCKKSNITESIL; TIQCKKSNITESILG;
IQCKKSNITESILGS; QCKKSNITESILGSK; CKKSNITESILGSKQ;
KKSNITESILGSKQC; KSNITESILGSKQCS; SNITESILGSKQCSQ;
NITESILGSKQCSQA; ITESILGSKQCSQAT; TESILGSKQCSQATP;
ESILGSKQCSQATPA; SILGSKQCSQATPAI; ILGSKQCSQATPAIY;
LGSKQCSQATPAIYC; GSKQCSQATPAIYCS; SKQCSQATPAIYCSS;
KQCSQATPAIYCSST; QCSQATPAIYCSSTA; CSQATPAIYCSSTAF;
SQATPAIYCSSTAFP; RVSTLFLAKTVSTAC; FLLSAKIIAFAKCFS;
NSKYIPNNKNTSSHF; SKYIPNNKNTSSHFV; KYIPNNKNTSSHFVS;
YIPNNKNTSSHFVST; IPNNKNTSSHFVSTA; PNNKNTSSHFVSTAY;
NNKNTSSHFVSTAYS; NKNTSSHFVSTAYSV; KNTSSHFVSTAYSVI;
NTSSHFVSTAYSVIN; TSSHFVSTAYSVINF; SSHFVSTAYSVINFQ;
SHFVSTAYSVINFQD; HFVSTAYSVINFQDT; FVSTAYSVINFQDTC;
VSTAYSVINFQDTCF; STAYSVINFQDTCFV; TAYSVINFQDTCFVS;
AYSVINFQDTCFVSS; YSVINFQDTCFVSSG; SVINFQDTCFVSSGS;
VINFQDTCFVSSGSS; INFQDTCFVSSGSSG; NFQDTCFVSSGSSGL;
FQDTCFVSSGSSGLK; QDTCFVSSGSSGLKS; DTCFVSSGSSGLKSC;
TCFVSSGSSGLKSCS; CFVSSGSSGLKSCSF; FVSSGSSGLKSCSFK;
VSSGSSGLKSCSFKP; SSGSSGLKSCSFKPP; MLSSIVWYGSLVKAL;
LSSIVWYGSLVKALY; SSIVWYGSLVKALYS; SIVWYGSLVKALYSK;
IVWYGSLVKALYSKY; VWYGSLVKALYSKYS; WYGSLVKALYSKYSL;
YGSLVKALYSKYSLL; GSLVKALYSKYSLLT; SLVKALYSKYSLLTP;
LVKALYSKYSLLTPL; VKALYSKYSLLTPLQ; KALYSKYSLLTPLQI;
ALYSKYSLLTPLQIK; LYSKYSLLTPLQIKK; YSKYSLLTPLQIKKL;
SKYSLLTPLQIKKLV; KYSLLTPLQIKKLVK; YSLLTPLQIKKLKVH;
SLLTPLQIKKLKVHS; LLTPLQIKKLKVHSF; QKLLIAETLCLCGVK;
KLLIAETLCLCGVKK; LLIAETLCLCGVKKN; LIAETLCLCGVKKNI;
IAETLCLCGVKKNII; AETLCLCGVKKNIIL; ETLCLCGVKKNIILC;
TLCLCGVKKNIILCP; LCLCGVKKNIILCPA; CLCGVKKNIILCPAH;
LCGVKKNIILCPAHM; CGVKKNIILCPAHMC; GVKKNIILCPAHMCL;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

VKKNIILCPAHMCLL; KKNIILCPAHMCLLI; KNIILCPAHMCLLIK;
NIILCPAHMCLLIKV; IILCPAHMCLLIKVT; ILCPAHMCLLIKVTE;
LCPAHMCLLIKVTEY; CPAHMCLLIKVTEYF; PAHMCLLIKVTEYFS;
AHMCLLIKVTEYFSI; HMCLLIKVTEYFSIS; MCLLIKVTEYFSISF;
CLLIKVTEYFSISFL; LLIKVTEYFSISFLY; LIKVTEYFSISFLYR;
IKVTEYFSISFLYRI; AFSLVVYTAKQARVL; FSLVVYTAKQARVLL;
SLVVYTAKQARVLLL; LVVYTAKQARVLLLN; VVYTAKQARVLLLNT;
VYTAKQARVLLLNTA; LRNWCRSEGKSLGSS; RNWCRSEGKSLGSST;
NWCRSEGKSLGSSTF; WCRSEGKSLGSSTFL; CRSEGKSLGSSTFLF;
RSEGKSLGSSTFLFF; SEGKSLGSSTFLFFL; EGKSLGSSTFLFFLG;
GKSLGSSTFLFFLGG; KSLGSSTFLFFLGGV; SLGSSTFLFFLGGVE;
LGSSTFLFFLGGVEC; ESAVASSSLANISSW; SAVASSSLANISSWQ;
AVASSSLANISSWQN; VASSSLANISSWQNK; ASSSLANISSWQNKS;
SSSLANISSWQNKSS; SSLANISSWQNKSSS; SLANISSWQNKSSSH;
LANISSWQNKSSSHF; ANISSWQNKSSSHFS; NISSWQNKSSSHFSL;
ISSWQNKSSSHFSLK; SSWQNKSSSHFSLKE; SWQNKSSSHFSLKEL;
WQNKSSSHFSLKELH; QNKSSSHFSLKELHQ; NKSSSHFSLKELHQD;
KSSSHFSLKELHQDS; SSSHFSLKELHQDSH; SSHFSLKELHQDSHS;
SHFSLKELHQDSHSS; HFSLKELHQDSHSSV; FSLKELHQDSHSSVG;
VGTYKKNNYLGPFNI; GTYKKNNYLGPFNIL; TYKKNNYLGPFNILL;
YKKNNYLGPFNILLF; KKNNYLGPFNILLFI; REFLQLFGPTIAEFL;
EFLQLFGPTIAEFLQ; FLQLFGPTIAEFLQL; LQLFGPTIAEFLQLG;
QLFGPTIAEFLQLGL; LFGPTIAEFLQLGLS; FGPTIAEFLQLGLSQ;
GPTIAEFLQLGLSQT; PTIAEFLQLGLSQTT; TIAEFLQLGLSQTTV;
SSQCSSNLSKPRALF; SQCSSNLSKPRALFL; QCSSNLSKPRALFLK;
CSSNLSKPRALFLKI; SSNLSKPRALFLKIF; SNLSKPRALFLKIFY;
NLSKPRALFLKIFYL; LSKPRALFLKIFYLN; SKPRALFLKIFYLNS;
KPRALFLKIFYLNAL; PRALFLKIFYLNALI; ADIACKGSAQKAFWN;
DIACKGSAQKAFWNK; AIPCSTGYLGKEENQ; IPCSTGYLGKEENQH;
PCSTGYLGKEENQHK; CSTGYLGKEENQHKP; STGYLGKEENQHKPL;
TGYLGKEENQHKPLS; GYLGKEENQHKPLSY; YLGKEENQHKPLSYS;
LGKEENQHKPLSYSR; GKEENQHKPLSYSRF; KEENQHKPLSYSRFQ;
EENQHKPLSYSRFQN; ENQHKPLSYSRFQNQ; NQHKPLSYSRFQNQA;
QHKPLSYSRFQNQAD; HKPLSYSRFQNQADE; KPLSYSRFQNQADEL;
PLSYSRFQNQADELP; LSYSRFQNQADELPL; SYSRFQNQADELPLH;
YSRFQNQADELPLHP; SRFQNQADELPLHPA; RFQNQADELPLHPAP;
FQNQADELPLHPAPF; QNQADELPLHPAPFF; NQADELPLHPAPFFY;
QADELPLHPAPFFYT; ADELPLHPAPFFYTK; DELPLHPAPFFYTKY;
ELPLHPAPFFYTKYS; LPLHPAPFFYTKYSF; PLHPAPFFYTKYSFS;
LHPAPFFYTKYSFSS; HPAPFFYTKYSFSSF; PAPFFYTKYSFSSFY;
APFFYTKYSFSSFYP; PFFYTKYSFSSFYPR; FFYTKYSFSSFYPRR;
FYTKYSFSSFYPRRP; YTKYSFSSFYPRRPL; TKYSFSSFYPRRPLC;
KYSFSSFYPRRPLCQ; YSFSSFYPRRPLCQG; SFSSFYPRRPLCQGE;
FSSFYPRRPLCQGEI; SSFYPRRPLCQGEIP; SFYPRRPLCQGEIPY;
FYPRRPLCQGEIPYT; YPRRPLCQGEIPYTS; PRRPLCQGEIPYTSL;
RRPLCQGEIPYTSLN; RPLCQGEIPYTSLNK; PLCQGEIPYTSLNKL;
LCQGEIPYTSLNKLF; CQGEIPYTSLNKLFS; QGEIPYTSLNKLFSL;
GEIPYTSLNKLFSLR; EIPYTSLNKLFSLRE; IPYTSLNKLFSLRED;
PYTSLNKLFSLREDF; YTSLNKLFSLREDFP; TSLNKLFSLREDFPR;
SLNKLFSLREDFPRQ; LNKLFSLREDFPRQL; NKLFSLREDFPRQLF;
KLFSLREDFPRQLFQ; LFSLREDFPRQLFQG; FSLREDFPRQLFQGL;
SLREDFPRQLFQGLK; LREDFPRQLFQGLKG; REDFPRQLFQGLKGP 16 mers:

GFPQIVLLGLRKSLHT; FPQIVLLGLRKSLHTL;
PQIVLLGLRKSLHTLT; QIVLLGLRKSLHTLTT;
EKGWRQRRPRPLIYYK; KGWRQRRPRPLIYYKK;
GWRQRRPRPLIYYKKK; WRQRRPRPLIYYKKKG;
RQRRPRPLIYYKKKGH; QRRPRPLIYYKKKGHR;
RRPRPLIYYKKKGHRE; RPRPLIYYKKKGHREE;
PRPLIYYKKKGHREEL; RPLIYYKKKGHREELL;
PLIYYKKKGHREELLT; LIYYKKKGHREELLTH;
IYYKKKGHREELLTHG; YYKKKGHREELLTHGM;
YKKKGHREELLTHGMQ; KKKGHREELLTHGMQP;
KKGHREELLTHGMQPN; KGHREELLTHGMQPNH;
GHREELLTHGMQPNHD; HREELLTHGMQPNHDL;
REELLTHGMQPNHDLR; EELLTHGMQPNHDLRK;
ELLTHGMQPNHDLRKE; LLTHGMQPNHDLRKES;
LTHGMQPNHDLRKESA; LTGECSQTMTSGRKVH;
TGECSQTMTSGRKVHD; GECSQTMTSGRKVHDS;
ECSQTMTSGRKVHDSQ; CSQTMTSGRKVHDSQG;
SQTMTSGRKVHDSQGG; QTMTSGRKVHDSQGGA;
TMTSGRKVHDSQGGAA; MTSGRKVHDSQGGAAY;

TSGRKVHDSQGGAAYP; SGRKVHDSQGGAAYPW;
GRKVHDSQGGAAYPWN; RKVHDSQGGAAYPWNA;
KVHDSQGGAAYPWNAA; VHDSQGGAAYPWNAAK;
HDSQGGAAYPWNAAKP; PQEGKCMTDMFCEPRN;
QEGKCMTDMFCEPRNL; EGKCMTDMFCEPRNLG;
GKCMTDMFCEPRNLGL; KCMTDMFCEPRNLGLV;
CMTDMFCEPRNLGLVP; MTDMFCEPRNLGLVPS;
TGQRPWFCASCHDKLQ; KLVKPGLEQKKELRGF;
LVKPGLEQKKELRGFL; VKPGLEQKKELRGFLF;
KPGLEQKKELRGFLFL; PGLEQKKELRGFLFLF;
VIPPFLYFQVHGCCSS; IPFFLYFQVHGCCSST;
PFFLYFQVHGCCSSTF; FFLYFQVHGCCSSTFG;
FLYFQVHGCCSSTFGG; LYFQVHGCCSSTFGGP;
YFQVHGCCSSTFGGPS; FQVHGCCSSTFGGPSC;
QVHGCCSSTFGGPSCQ; VHGCCSSTFGGPSCQC;
HGCCSSTFGGPSCQCI; NCCWGGCCCYRSSNCI;
CCWGGCCCYRSSNCIP; CWGGCCCYRSSNCIPC;
WGGCCCYRSSNCIPCY; GGCCCYRSSNCIPCYC;
GCCCYRSSNCIPCYCR; CCCYRSSNCIPCYCRG;
CCYRSSNCIPCYCRGH; CYRSSNCIPCYCRGHN;
YRSSNCIPCYCRGHNK; RSSNCIPCYCRGHNKY;
SSNCIPCYCRGHNKYL; SNCIPCYCRGHNKYLR;
NCIPCYCRGHNKYLRG; CIPCYCRGHNKYLRGY;
IPCYCRGHNKYLRGYS; PCYCRGHNKYLRGYSC;
CYCRGHNKYLRGYSCY; YCRGHNKYLRGYSCYR;
CRGHNKYLRGYSCYRP; RGHNKYLRGYSCYRPN;
GHNKYLRGYSCYRPNS; HNKYLRGYSCYRPNSS;
NKYLRGYSCYRPNSSN; KYLRGYSCYRPNSSNI;
YLRGYSCYRPNSSNIC; LRGYSCYRPNSSNICC;
RGYSCYRPNSSNICCN; GYSCYRPNSSNICCNC;
YSCYRPNSSNICCNCW; SCYRPNSSNICCNCWC;
CYRPNSSNICCNCWCS; YRPNSSNICCNCWCSW;
RPNSSNICCNCWCSWG; PNSSNICCNCWCSWGY;
NSSNICCNCWCSWGYC; SSNICCNCWCSWGYCW;
SNICCNCWCSWGYCWV; NICCNCWCSWGYCWVC;
ICCNCWCSWGYCWVCC; CCNCWCSWGYCWVCCF;
CNCWCSWGYCWVCCFN; NCWCSWGYCWVCCFNS;
CWCSWGYCWVCCFNSN; WCSWGYCWVCCFNSNC;
LGSQSFHCRPLSAIRH; GSQSFHCRPLSAIRHG;
SQSFHCRPLSAIRHGF; QSFHCRPLSAIRHGFG;
SFHCRPLSAIRHGFGI; FHCRPLSAIRHGFGIV;
ALGSFFVCYYFPGFVA; LGSFFVCYYFPGFVAC;
GSFFVCYYFPGFVACY; SFFVCYYFPGFVACYT;
FFVCYYFPGFVACYTY; YTFYNLTGIAEKNRKI;
TFYNLTGIAEKNRKIF; IFGGNYLDNCKCPYKL;
FGGNYLDNCKCPYKLL; QYRRSYTKNGLKKSTK;
YRRSYTKNGLKKSTKC; RRSYTKNGLKKSTKCT;
RSYTKNGLKKSTKCTF; SYTKNGLKKSTKCTFR;
YTKNGLKKSTKCTFRR; TKNGLKKSTKCTFRRV;
KNGLKKSTKCTFRRVY; NGLKKSTKCTFRRVYR;
GLKKSTKCTFRRVYRK; LKKSTKCTFRRVYRKN;
KKSTKCTFRRVYRKNY; KSTKCTFRRVYRKNYC;
STKCTFRRVYRKNYCP; TKCTFRRVYRKNYCPR;
KCTFRRVYRKNYCPRR; CTFRRVYRKNYCPRRC;
SKNCSSMDVAFTSRPV; KNCSSMDVAFTSRPVR;
NCSSMDVAFTSRPVRD; CSSMDVAFTSRPVRDC;
SSMDVAFTSRPVRDCN; SMDVAFTSRPVRDCNT;
MDVAFTSRPVRDCNTC; DVAFTSRPVRDCNTCS;
RWPQPKEKESVQGQLP; WPQPKEKESVQGQLPK;
PQPKEKESVQGQLPKS; QPKEKESVQGQLPKSQ;
PKEKESVQGQLPKSQR; KEKESVQGQLPKSQRN;
EKESVQGQLPKSQRNP; KESVQGQLPKSQRNPC;
ESVQGQLPKSQRNPCK; SVQGQLPKSQRNPCKC;
VQGQLPKSQRNPCKCQ; QGQLPKSQRNPCKCQN;
GQLPKSQRNPCKCQNY; VLKMTLAVIAQREKCF;
LKMTLAVIAQREKCFP; KMTLAVIAQREKCFPV;
MTLAVIAQREKCFPVT; TLAVIAQREKCFPVTA;
LAVIAQREKCFPVTAQ; AVIAQREKCFPVTAQQ;
VIAQREKCFPVTAQQE; IAQREKCFPVTAQQEF;
AQREKCFPVTAQQEFP; QREKCFPVTAQQEFPS;
REKCFPVTAQQEFPSP; EKCFPVTAQQEFPSPI;
LACLTFMQGHKKCMSM; ACLTFMQGHKKCMSMV;
CLTFMQGHKKCMSMVE; LTFMQGHKKCMSMVEE;
TFMQGHKKCMSMVEEN; FMQGHKKCMSMVEENL;
MQGHKKCMSMVEENLF; QGHKKCMSMVEENLFK;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GHKKCMSMVEENLFKA; HKKCMSMVEENLFKAV;
KKCMSMVEENLFKAVI; KCMSMVEENLFKAVIS;
CMSMVEENLFKAVIST; MSMVEENLFKAVISTS;
SMVEENLFKAVISTSL; MVEENLFKAVISTSLL;
ILTIRPIWTKTMLIQL; LTIRPIWTKTMLIQLS;
TIRPIWTKTMLIQLSA; IRPIWTKTMLIQLSAG;
RPIWTKTMLIQLSAGY; PIWTKTMLIQLSAGYL;
IWTKTMLIQLSAGYLI; WTKTMLIQLSAGYLIP;
TKTMLIQLSAGYLIPV; KTMLIQLSAGYLIPVE;
TMLIQLSAGYLIPVEM; MLIQLSAGYLIPVEMK;
LIQLSAGYLIPVEMKM; IQLSAGYLIPVEMKML;
QLSAGYLIPVEMKMLG; LSAGYLIPVEMKMLGI;
SAGYLIPVEMKMLGIL; AGYLIPVEMKMLGILG;
GYLIPVEMKMLGILGL; YLIPVEMKMLGILGLS;
LIPVEMKMLGILGLSQ; IPVEMKMLGILGLSQE;
PVEMKMLGILGLSQEG; VEMKMLGILGLSQEGK;
EMKMLGILGLSQEGKM; MKMLGILGLSQEGKMF;
KMLGILGLSQEGKMFP; MLGILGLSQEGKMFPQ;
LGILGLSQEGKMFPQY; GILGLSQEGKMFPQYF;
ILGLSQEGKMFPQYFM; MNRVWGLFVKLIACMF;
NRVWGLFVKLIACMFQ; RVWGLFVKLIACMFQL;
VWGLFVKLIACMFQLL; WGLFVKLIACMFQLLI;
GLFVKLIACMFQLLIF; LFVKLIACMFQLLIFV;
FVKLIACMFQLLIFVA; VKLIACMFQLLIFVAC;
KLIACMFQLLIFVACL; LIACMFQLLIFVACLL;
IACMFQLLIFVACLLT; ACMFQLLIFVACLLTA;
CMFQLLIFVACLLTAL; MFQLLIFVACLLTALE;
FQLLIFVACLLTALEH; QLLIFVACLLTALEHN;
LLIFVACLLTALEHNS; LIFVACLLTALEHNSG;
IFVACLLTALEHNSGE; FVACLLTALEHNSGEA;
VACLLTALEHNSGEAL; ACLLTALEHNSGEALQ;
CLLTALEHNSGEALQD; LLTALEHNSGEALQDI;
LTALEHNSGEALQDIL; TALEHNSGEALQDILR;
ALEHNSGEALQDILRS; LEHNSGEALQDILRSA;
TGEPREWMGSLCMVWN; GEPREWMGSLCMVWNP;
EPREWMGSLCMVWNPR; KRLGCLMAQKDFQGTQ;
RLGCLMAQKDFQGTQI; DILTNRDNCKPKCFKQ;
ILTNRDNCKPKCFKQV; LTNRDNCKPKCFKQVL;
TNRDNCKPKCFKQVLL; NRDNCKPKCFKQVLLL;
RDNCKPKCFKQVLLLY; DNCKPKCFKQVLLLYI;
NCKPKCFKQVLLLYIY; CKPKCFKQVLLLYIYI;
MLLLYKPLLSLCYFGG; LLLYKPLLSLCYFGGG;
LLYKPLLSLCYFGGGV; LYKPLLSLCYFGGGVL;
YKPLLSLCYFGGGVLG; KPLLSLCYFGGGVLGL;
PLLSLCYFGGGVLGLL; LLSLCYFGGGVLGLLK;
LSLCYFGGGVLGLLKH; LWGSDLWESSAGAEVS;
WGSDLWESSAGAEVSE; GSDLWESSAGAEVSET;
SDLWESSAGAEVSETW; DLWESSAGAEVSETWE;
LWESSAGAEVSETWEE; WESSAGAEVSETWEEH;
ESSAGAEVSETWEEHC; SSAGAEVSETWEEHCD;
SAGAEVSETWEEHCDW; AGAEVSETWEEHCDWD;
GAEVSETWEEHCDWDS; AEVSETWEEHCDWDSV;
EVSETWEEHCDWDSVL; VSETWEEHCDWDSVLD;
SETWEEHCDWDSVLDP; ETWEEHCDWDSVLDPC;
TWEEHCDWDSVLDPCP; WEEHCDWDSVLDPCPE;
EEHCDWDSVLDPCPES; EHCDWDSVLDPCPESS;
HCDWDSVLDPCPESSV; CDWDSVLDPCPESSVS;
DWDSVLDPCPESSVSE; WDSVLDPCPESSVSES;
DSVLDPCPESSVSESS; SVLDPCPESSVSESSS;
VLDPCPESSVSESSSL; LDPCPESSVSESSSLV;
DPCPESSVSESSSLVI; PCPESSVSESSSLVIS;
CPESSVSESSSLVISR; PESSVSESSSLVISRI;
ESSVSESSSLVISRIH; SSVSESSSLVISRIHF;
SVSESSSLVISRIHFP; VSESSSLVISRIHFPM;
SESSSLVISRIHFPMH; ESSSLVISRIHFPMHI;
SSSLVISRIHFPMHIL; SSLVISRIHFPMHILY;
SLVISRIHFPMHILYF; LVISRIHFPMHILYFI;
VISRIHFPMHILYFIL; ISRIHFPMHILYFILE;
SRIHFPMHILYFILEK; RIHFPMHILYFILEKV;
IHFPMHILYFILEKVY; HFPMHILYFILEKVYI;
FPMHILYFILEKVYIL; PMHILYFILEKVYILI;
MHILYFILEKVYILIS; HILYFILEKVYILISE;
ILYFILEKVYILISES; LYFILEKVYILISESS;
YFILEKVYILISESSL; FILEKVYILISESSLS;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

ILEKVYILISESSLSF; LEKVYILISESSLSFH;
EKVYILISESSLSFHS; KVYILISESSLSFHST;
VYILISESSLSFHSTI; YILISESSLSFHSTIL;
ILISESSLSFHSTILD; LISESSLSFHSTILDC;
ISESSLSFHSTILDCI; SESSLSFHSTILDCIS;
ESSLSFHSTILDCISV; SSLSFHSTILDCISVA;
SLSFHSTILDCISVAK; LSFHSTILDCISVAKS;
SFHSTILDCISVAKSA; FHSTILDCISVAKSAT;
HSTILDCISVAKSATG; STILDCISVAKSATGL;
TILDCISVAKSATGLN; ILDCISVAKSATGLNQ;
LDCISVAKSATGLNQI; DCISVAKSATGLNQIS;
CISVAKSATGLNQISS; ISVAKSATGLNQISSS;
SVAKSATGLNQISSSN; VAKSATGLNQISSSNK;
AKSATGLNQISSSNKV; KSATGLNQISSSNKVI;
SATGLNQISSSNKVIP; ATGLNQISSSNKVIPL;
TGLNQISSSNKVIPLC; GLNQISSSNKVIPLCK;
LNQISSSNKVIPLCKI; NQISSSNKVIPLCKIL;
QISSSNKVIPLCKILF; ISSSNKVIPLCKILFS;
SSSNKVIPLCKILFSS; SSNKVIPLCKILFSSK;
SNKVIPLCKILFSSKN; NKVIPLCKILFSSKNS;
KVIPLCKILFSSKNSE; VIPLCKILFSSKNSEF;
IPLCKILFSSKNSEFC; PLCKILFSSKNSEFCK;
LCKILFSSKNSEFCKD; CKILFSSKNSEFCKDF;
KILFSSKNSEFCKDFL; ILFSSKNSEFCKDFLK;
LFSSKNSEFCKDFLKY; FSSKNSEFCKDFLKYI;
SSKNSEFCKDFLKYIL; SKNSEFCKDFLKYILG;
KNSEFCKDFLKYILGL; NSEFCKDFLKYILGLK;
SEFCKDFLKYILGLKS; EFCKDFLKYILGLKSI;
FCKDFLKYILGLKSIC; CKDFLKYILGLKSICL;
KDFLKYILGLKSICLT; DFLKYILGLKSICLTN;
FLKYILGLKSICLTNL; LKYILGLKSICLTNLA;
KYILGLKSICLTNLAC; YILGLKSICLTNLACR;
ILGLKSICLTNLACRV; LGLKSICLTNLACRVL;
GLKSICLTNLACRVLG; LKSICLTNLACRVLGT;
KSICLTNLACRVLGTG; SICLTNLACRVLGTGY;
ICLTNLACRVLGTGYS; CLTNLACRVLGTGYSF;
LTNLACRVLGTGYSFI; TNLACRVLGTGYSFIV;
NLACRVLGTGYSFIVT; LACRVLGTGYSFIVTK;
ACRVLGTGYSFIVTKP; CRVLGTGYSFIVTKPG;
RVLGTGYSFIVTKPGG; VLGTGYSFIVTKPGGN;
LGTGYSFIVTKPGGNI; GTGYSFIVTKPGGNIW;
TGYSFIVTKPGGNIWV; GYSFIVTKPGGNIWVL;
YSFIVTKPGGNIWVLL; SFIVTKPGGNIWVLLF;
FIVTKPGGNIWVLLFK; IVTKPGGNIWVLLFKC;
VTKPGGNIWVLLFKCF; TKPGGNIWVLLFKCFF;
KPGGNIWVLLFKCFFS; PGGNIWVLLFKCFFSK;
GGNIWVLLFKCFFSKF; GNIWVLLFKCFFSKFT;
NIWVLLFKCFFSKFTL; IWVLLFKCFFSKFTLT;
WVLLFKCFFSKFTLTL; VLLFKCFFSKFTLTLP;
LLFKCFFSKFTLTLPS; LFKCFFSKFTLTLPSK;
SLKLSKLFIPCPEGKS; LKLSKLFIPCPEGKSF;
KLSKLFIPCPEGKSFD; LSKLFIPCPEGKSFDS;
SKLFIPCPEGKSFDSA; KLFIPCPEGKSFDSAP;
LFIPCPEGKSFDSAPV; FIPCPEGKSFDSAPVP;
IPCPEGKSFDSAPVPF; PCPEGKSFDSAPVPFT;
CPEGKSFDSAPVPFTS; PEGKSFDSAPVPFTSS;
EGKSFDSAPVPFTSSK; GKSFDSAPVPFTSSKT;
KSFDSAPVPFTSSKTT; SFDSAPVPFTSSKTTM;
FDSAPVPFTSSKTTMY; SIATPSSKVSLSMGRF;
IATPSSKVSLSMGRFT; ATPSSKVSLSMGRFTF;
TPSSKVSLSMGRFTFK; PSSKVSLSMGRFTFKA;
SSKVSLSMGRFTFKAL; SKVSLSMGRFTFKALP;
KVSLSMGRFTFKALPP; VSLSMGRFTFKALPPH;
SLSMGRFTFKALPPHK; LSMGRFTFKALPPHKS;
SMGRFTFKALPPHKSN; MGRFTFKALPPHKSNN;
GRFTFKALPPHKSNNP; RFTFKALPPHKSNNPA;
FTFKALPPHKSNNPAA; TFKALPPHKSNNPAAS;
FKALPPHKSNNPAASV; KALPPHKSNNPAASVV;
ALPPHKSNNPAASVVF; LPPHKSNNPAASVVFP;
PPHKSNNPAASVVFPL; PHKSNNPAASVVFPLS;
HKSNNPAASVVFPLSM; KSNNPAASVVFPLSMG;
SNNPAASVVFPLSMGP; NNPAASVVFPLSMGPL;
NPAASVVFPLSMGPLN; PAASVVFPLSMGPLNN;
AASVVFPLSMGPLNNQ; ASVVFPLSMGPLNNQY;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

SVVFPLSMGPLNNQYL; VVFPLSMGPLNNQYLL;
VFPLSMGPLNNQYLLL; FPLSMGPLNNQYLLLG;
PLSMGPLNNQYLLLGT; LSMGPLNNQYLLLGTL;
SMGPLNNQYLLLGTLK; MGPLNNQYLLLGTLKT;
GPLNNQYLLLGTLKTI; PLNNQYLLLGTLKTIQ;
LNNQYLLLGTLKTIQC; NNQYLLLGTLKTIQCK;
NQYLLLGTLKTIQCKK; QYLLLGTLKTIQCKKS;
YLLLGTLKTIQCKKSN; LLLGTLKTIQCKKSNI;
LLGTLKTIQCKKSNIT; LGTLKTIQCKKSNITE;
GTLKTIQCKKSNITES; TLKTIQCKKSNITESI;
LKTIQCKKSNITESIL; KTIQCKKSNITESILG;
TIQCKKSNITESILGS; IQCKKSNITESILGSK;
QCKKSNITESILGSKQ; CKKSNITESILGSKQC;
KKSNITESILGSKQCS; KSNITESILGSKQCSQ;
SNITESILGSKQCSQA; NITESILGSKQCSQAT;
ITESILGSKQCSQATP; TESILGSKQCSQATPA;
ESILGSKQCSQATPAI; SILGSKQCSQATPAIY;
ILGSKQCSQATPAIYC; LGSKQCSQATPAIYCS;
GSKQCSQATPAIYCSS; SKQCSQATPAIYCSST;
KQCSQATPAIYCSSTA; QCSQATPAIYCSSTAF;
CSQATPAIYCSSTAFP; NSKYIPNNKNTSSHFV;
SKYIPNNKNTSSHFVS; KYIPNNKNTSSHFVST;
YIPNNKNTSSHFVSTA; IPNNKNTSSHFVSTAY;
PNNKNTSSHFVSTAYS; NNKNTSSHFVSTAYSV;
NKNTSSHFVSTAYSVI; KNTSSHFVSTAYSVIN;
NTSSHFVSTAYSVINF; TSSHFVSTAYSVINFQ;
SSHFVSTAYSVINFQD; SHFVSTAYSVINFQDT;
HFVSTAYSVINFQDTC; FVSTAYSVINFQDTCF;
VSTAYSVINFQDTCFV; STAYSVINFQDTCFVS;
TAYSVINFQDTCFVSS; AYSVINFQDTCFVSSG;
YSVINFQDTCFVSSGS; SVINFQDTCFVSSGSS;
VINFQDTCFVSSGSSG; INFQDTCFVSSGSSGL;
NFQDTCFVSSGSSGLK; FQDTCFVSSGSSGLKS;
QDTCFVSSGSSGLKSC; DTCFVSSGSSGLKSCS;
TCFVSSGSSGLKSCSF; CFVSSGSSGLKSCSFK;
FVSSGSSGLKSCSFKP; VSSGSSGLKSCSFKPP;
MLSSIVWYGSLVKALY; LSSIVWYGSLVKALYS;
SSIVWYGSLVKALYSK; SIVWYGSLVKALYSKY;
IVWYGSLVKALYSKYS; VWYGSLVKALYSKYSL;
WYGSLVKALYSKYSLL; YGSLVKALYSKYSLLT;
GSLVKALYSKYSLLTP; SLVKALYSKYSLLTPL;
LVKALYSKYSLLTPLQ; VKALYSKYSLLTPLQI;
KALYSKYSLLTPLQIK; ALYSKYSLLTPLQIKK;
LYSKYSLLTPLQIKKL; YSKYSLLTPLQIKKLK;
SKYSLLTPLQIKKLKV; KYSLLTPLQIKKLKVH;
YSLLTPLQIKKLKVHS; SLLTPLQIKKLKVHSF;
QKLLIAETLCLCGVKK; KLLIAETLCLCGVKKN;
LLIAETLCLCGVKKNI; LIAETLCLCGVKKNII;
IAETLCLCGVKKNIIL; AETLCLCGVKKNIILC;
ETLCLCGVKKNIILCP; TLCLCGVKKNIILCPA;
LCLCGVKKNIILCPAH; CLCGVKKNIILCPAHM;
LCGVKKNIILCPAHMC; CGVKKNIILCPAHMCL;
GVKKNIILCPAHMCLL; VKKNIILCPAHMCLLI;
KKNIILCPAHMCLLIK; KNIILCPAHMCLLIKV;
NIILCPAHMCLLIKVT; IILCPAHMCLLIKVTE;
ILCPAHMCLLIKVTEY; LCPAHMCLLIKVTEYF;
CPAHMCLLIKVTEYFS; PAHMCLLIKVTEYFSI;
AHMCLLIKVTEYFSIS; HMCLLIKVTEYFSISF;
MCLLIKVTEYFSISFL; CLLIKVTEYFSISFLY;
LLIKVTEYFSISFLYR; LIKVTEYFSISFLYRI;
APFSLVVYTAKQARVLL; FSLVVYTAKQARVLLL;
SLVVYTAKQARVLLLN; LVVYTAKQARVLLLNT;
VVYTAKQARVLLLNTA; LRNWCRSEGKSLGSST;
RNWCRSEGKSLGSSTF; NWCRSEGKSLGSSTFL;
WCRSEGKSLGSSTFLF; CRSEGKSLGSSTFLFF;
RSEGKSLGSSTFLFFL; SEGKSLGSSTFLFFLG;
EGKSLGSSTFLFFLGG; GKSLGSSTFLFFLGGV;
KSLGSSTFLFFLGGVE; SLGSSTFLFFLGGVEC;
ESAVASSSLANISSWQ; SAVASSSLANISSWQN;
AVASSSLANISSWQNK; VASSSLANISSWQNKS;
ASSSLANISSWQNKSS; SSSLANISSWQNKSSS;
SSLANISSWQNKSSSH; SLANISSWQNKSSSHF;
LANISSWQNKSSSHFS; ANISSWQNKSSSHFSL;
NISSWQNKSSSHFSLK; ISSWQNKSSSHFSLKE;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

SSWQNKSSSHFSLKEL; SWQNKSSSHFSLKELH;
WQNKSSSHFSLKELHQ; QNKSSSHFSLKELHQD;
NKSSSHFSLKELHQDS; KSSSHFSLKELHQDSH;
SSSHFSLKELHQDSHS; SSHFSLKELHQDSHSS;
SHFSLKELHQDSHSSV; HFSLKELHQDSHSSVP;
VGTYKKNNYLGPFNIL; GTYKKNNYLGPFNILL;
TYKKNNYLGPFNILLF; YKKNNYLGPFNILLFI;
REFLQLFGPTIAEFLQ; EFLQLFGPTIAEFLQL;
FLQLFGPTIAEFLQLG; LQLFGPTIAEFLQLGL;
QLFGPTIAEFLQLGLS; LFGPTIAEFLQLGLSQ;
FGPTIAEFLQLGLSQT; GPTIAEFLQLGLSQTT;
PTIAEFLQLGLSQTTV; SSQCSSNLSKPRALFL;
SQCSSNLSKPRALFLK; QCSSNLSKPRALFLKI;
CSSNLSKPRALFLKIF; SSNLSKPRALFLKIFY;
SNLSKPRALFLKIFYL; NLSKPRALFLKIFYLN;
LSKPRALFLKIFYLNA; SKPRALFLKIFYLNAL;
KPRALFLKIFYLNALI; ADIACKGSAQKAFWNK;
AIPCSTGYLGKEENQH; IPCSTGYLGKEENQHK;
PCSTGYLGKEENQHKP; CSTGYLGKEENQHKPL;
STGYLGKEENQHKPLS; TGYLGKEENQHKPLSY;
GYLGKEENQHKPLSYS; YLGKEENQHKPLSYSR;
LGKEENQHKPLSYSRF; GKEENQHKPLSYSRFQ;
KEENQHKPLSYSRFQN; EENQHKPLSYSRFQNQ;
ENQHKPLSYSRFQNQA; NQHKPLSYSRFQNQAD;
QHKPLSYSRFQNQADE; HKPLSYSRFQNQADEL;
KPLSYSRFQNQADELP; PLSYSRFQNQADELPL;
LSYSRFQNQADELPLH; SYSRFQNQADELPLHP;
YSRFQNQADELPLHPA; SRFQNQADELPLHPAP;
RFQNQADELPLHPAPF; FQNQADELPLHPAPFF;
QNQADELPLHPAPFFY; NQADELPLHPAPFFYT;
QADELPLHPAPFFYTK; ADELPLHPAPFFYTKY;
DELPLHPAPFFYTKYS; ELPLHPAPFFYTKYSF;
LPLHPAPFFYTKYSFS; PLHPAPFFYTKYSFSS;
LHPAPFFYTKYSFSSF; HPAPFFYTKYSFSSFY;
PAPFFYTKYSFSSFYP; APFFYTKYSFSSFYPR;
PFFYTKYSFSSFYPRR; FFYTKYSFSSFYPRRP;
FYTKYSFSSFYPRRPL; YTKYSFSSFYPRRPLC;
TKYSFSSFYPRRPLCQ; KYSFSSFYPRRPLCQG;
YSFSSFYPRRPLCQGE; SFSSFYPRRPLCQGEI;
FSSFYPRRPLCQGEIP; SSFYPRRPLCQGEIPY;
SFYPRRPLCQGEIPYT; FYPRRPLCQGEIPYTS;
YPRRPLCQGEIPYTSL; PRRPLCQGEIPYTSLN;
RRPLCQGEIPYTSLNK; RPLCQGEIPYTSLNKL;
PLCQGEIPYTSLNKLF; LCQGEIPYTSLNKLFS;
CQGEIPYTSLNKLFSL; QGEIPYTSLNKLFSLR;
GEIPYTSLNKLFSLRE; EIPYTSLNKLFSLRED;
IPYTSLNKLFSLREDF; PYTSLNKLFSLREDFP;
YTSLNKLFSLREDFPR; TSLNKLFSLREDFPRQ;
SLNKLFSLREDFPRQL; LNKLFSLREDFPRQLF;
NKLFSLREDFPRQLFQ; KLFSLREDFPRQLFQG;
LFSLREDFPRQLFQGL; FSLREDFPRQLFQGLK;
SLREDFPRQLFQGLKG; LREDFPRQLFQGLKGP;

BK virus, reading frame 3

13 mers:

ASEKASTPLLLER; SEKASTPLLLERK; EKASTPLLLERKG;
KASTPLLLERKGG; ASTPLLLERKGGG; STPLLLERKGGGR;
TPLLLERKGGGRG; PLLLERKGGGRGG; LLLERKGGGRGGL;
LLERKGGGRGGLG; LERKGGGRGGLGL; ERKGGGRGGLGLL;
RKGGGRGGLGLLY; KGGGRGGLGLLYI; GGGRGGLGLLYII;
GGRGGLGLLYIIK; GRGGLGLLYIIKK; RGGLGLLYIIKKK;
GGLLLYIIKKKA; GLGLLYIIKKAT; LGLLYIIKKKATG;
GLLYIIKKKATGR; LLYIIKKKATGRS; LYIIKKKATGRSC;
YIIKKKATGRSCL; IIKKKATGRSCLP; IKKKATGRSCLPM;
KKKATGRSCLPME; KKATGRSCLPMEC; KATGRSCLPMECS;
ATGRSCLPMECSQ; TGRSCLPMECSQT; GRSCLPMECSQTM;
RSCLPMECSQTMT; SCLPMECSQTMTS; CLPMECSQTMTSG;
LPMECSQTMTSGR; PMECSQTMTSGRK; MECSQTMTSGRKV;
ECSQTMTSGRKVH; CSQTMTSGRKVHD; SQTMTSGRKVHDS;
QTMTSGRKVHDSQ; TMTSGRKVHDSQG; MTSGRKVHDSQGN;
TSGRKVHDSQGNA; SGRKVHDSQGNAA; GRKVHDSQGNAAK;

TABLE O-continued

Predicted MHC class 2 BK virus peptide sequences. Prediction of 13-, 14-, 15-, 16-mers from all 6 reading frames of the genome (access no #V01108) obtained using the program displayed in FIG. 2.

RKVHDSQGNAAKP; PQEGKCMTHREEL; QEGKCMTHREELL;
EGKCMTHREELLT; GKCMTHREELLTH; KCMTHREELLTHG;
CMTHREELLTHGM; MTHREELLTHGMQ; THREELLTHGMQP;
HREELLTHGMQPN; REELLTHGMQPNH; EELLTHGMQPNHD;
ELLTHGMQPNHDL; LLTHGMQPNHDLR; LTHGMQPNHDLRK;
THGMQPNHDLRKE; HGMQPNHDLRKES; GMQPNHDLRKESA;
QTCFASLGILALS; TCFASLGILALSP; CFASLGILALSPV;
FASLGILALSPVK; ASLGILALSPVKL; SLGILALSPVKLD;
LGILALSPVKLDK; GILALSPVKLDKG; ILALSPVKLDKGH;
LALSPVKLDKGHG; ALSPVKLDKGHGS; LSPVKLDKGHGSA;
SPVKLDKGHGSAP; PVKLDKGHGSAPA; VKLDKGHGSAPAV;
KLDKGHGSAPAVT; LDKGHGSAPAVTT; DKGHGSAPAVTTS;
KGHGSAPAVTTSF; GHGSAPAVTTSFS; HGSAPAVTTSFSE;
GSAPAVTTSFSES; SAPAVTTSFSESW; NLDWNKKKSSEDF;
LDWNKKKSSEDFY; DWNKKKSSEDFYF; WNKKKSSEDFYFY;
NKKKSSEDFYFYF; KKKSSEDFYFYFR; KKSSEDFYFYFRA;
KSSEDFYFYFRAF; SSEDFYFYFRAFA; SEDFYFYFRAFAG;
EDFYFYFRAFAGI; DFYFYFRAFAGIL; RQCRREKQKYHCF;
QCRREKQKYHCFT; CRREKQKYHCFTC; RREKQKYHCFTCC;
REKQKYHCFTCCK; EKQKYHCFTCCKR; KQKYHCFTCCKRL;
QKYHCFTCCKRLC; KYHCFTCCKRLCK; YHCFTCCKRLCKR;
HCFTCCKRLCKRL; CFTCCKRLCKRLL; FTCCKRLCKRLLG;
TCCKRLCKRLLGK; SLFFCISRFMGAA; LFFCISRFMGAAL;
FFCISRFMGAALA; FCISRFMGAALAL; CISRFMGAALALL;
ISRFMGAALALLG; SRFMGAALALLGD; RFMGAALALLGDL;
FMGAALALLGDLV; MGAALALLGDLVA; GAALALLGDLVAS;
AALALLGDLVASV; ALALLGDLVASVS; LALLGDLVASVSE;
ALLGDLVASVSEA; LLGDLVASVSEAA; LGDLVASVSEAAA;
GDLVASVSEAAAA; DLVASVSEAAAAT; LVASVSEAAAATG;
VASVSEAAAATGF; ASVSEAAAATGFS; SVSEAAAATGFSV;
VSEAAAATGFSVA; SEAAAATGFSVAE; EAAAATGFSVAEI;
AAAATGFSVAEIA; AAATGFSVAEIAA; AATGFSVAEIAAG;
ATGFSVAEIAAGE; TGFSVAEIAAGEA; GFSVAEIAAGEAA;
FSVAEIAAGEAAA; SVAEIAAGEAAAA; VAEIAAGEAAAAI;
AEIAAGEAAAAIE; EIAAGEAAAAIEV; IAAGEAAAAIEVQ;
AAGEAAAAIEVQI; AGEAAAAIEVQIA; GEAAAAIEVQIAS;
EAAAAIEVQIASL; AAAAIEVQIASLA; AAAIEVQIASLAT;
AAIEVQIASLATV; AIEVQIASLATVE; IEVQIASLATVEG;
EVQIASLATVEGI; VQIASLATVEGIT; QIASLATVEGITS;
IASLATVEGITST; ASLATVEGITSTS; SLATVEGITSTSE;
LATVEGITSTSEA; ATVEGITSTSEAI; TVEGITSTSEAIA;
VEGITSTSEAIAA; EGITSTSEAIAAI; GITSTSEAIAAIG;
ITSTSEAIAAIGL; TSTSEAIAAIGLT; STSEAIAAIGLTP;
TSEAIAAIGLTPQ; SEAIAAIGLTPQT; EAIAAIGLTPQTY;
AIAAIGLTPQTYA; IAAIGLTPQTYAV; AAIGLTPQTYAVI;
AIGLTPQTYAVIA; IGLTPQTYAVIAG; GLTPQTYAVIAGA;
LTPQTYAVIAGAP; TPQTYAVIAGAPG; PQTYAVIAGAPGA;
QTYAVIAGAPGAI; TYAVIAGAPGAIA; YAVIAGAPGAIAG;
AVIAGAPGAIAGF; VIAGAPGAIAGFA; IAGAPGAIAGFAA;
AGAPGAIAGFAAL; GAPGAIAGFAALI; APGAIAGFAALIQ;
PGAIAGFAALIQT; GAIAGFAALIQTV; AIAGFAALIQTVS;
IAGFAALIQTVSG; AGFAALIQTVSGI; GFAALIQTVSGIS;
FAALIQTVSGISS; AALIQTVSGISSL; ALIQTVSGISSLA;
LIQTVSGISSLAQ; IQTVSGISSLAQV; QTVSGISSLAQVG;
TVSGISSLAQVGY; VSGISSLAQVGYK; SGISSLAQVGYKF;
GISSLAQVGYKFF; ISSLAQVGYKFFD; SSLAQVGYKFFDD;
SLAQVGYKFFDDW; LAQVGYKFFDDWD; AQVGYKFFDDWDH;
QVGYKFFDDWDHK; VGYKFFDDWDHKV; GYKFFDDWDHKVS;
YKFFDDWDHKVST; KFFDDWDHKVSTV; FFDDWDHKVSTVG;
FDDWDHKVSTVGL; DDWDHKVSTVGLY; DWDHKVSTVGLYQ;
WDHKVSTVGLYQQ; DHKVSTVGLYQQS; HKVSTVGLYQQSG;
KVSTVGLYQQSGM; VSTVGLYQQSGMA; STVGLYQQSGMAL;
TVGLYQQSGMALE; VGLYQQSGMALEL; GLYQQSGMALELF;
LYQQSGMALELFN; YQQSGMALELFNP; QQSGMALELFNPD;
QSGMALELFNPDE; SGMALELFNPDEY; GMALELFNPDEYY;
MALELFNPDEYYD; ALELFNPDEYYDI; LELFNPDEYYDIL;
ELFNPDEYYDILF; LFNPDEYYDILFP; FNPDEYYDILFPG;
NPDEYYDILFPGV; PDEYYDILFPGVN; DEYYDILFPGVNT;
EYYDILFPGVNTF; YYDILFPGVNTFV; YDILFPGVNTFVN;
DILFPGVNTFVNN; ILFPGVNTFVNNI; LFPGVNTFVNNIQ;
FPGVNTFVNNIQY; PGVNTFVNNIQYL; GVNTFVNNIQYLD;
VNTFVNNIQYLDP; NTFVNNIQYLDPR; TFVNNIQYLDPRH;
FVNNIQYLDPRHW; VNNIQYLDPRHWG; NNIQYLDPRHWGP;
NIQYLDPRHWGPS; IQYLDPRHWGPSL; QYLDPRHWGPSLF;
YLDPRHWGPSLFA; LDPRHWGPSLFAT; DPRHWGPSLFATI;
PRHWGPSLFATIS; RHWGPSLFATISQ; HWGPSLFATISQA;
WGPSLFATISQAL; GPSLFATISQALW; PSLFATISQALWH;
SLFATISQALWHV; LFATISQALWHVI; FATISQALWHVIR;
ATISQALWHVIRD; TISQALWHVIRDD; ISQALWHVIRDDI;
SQALWHVIRDDIP; QALWHVIRDDIPS; ALWHVIRDDIPSI;
LWHVIRDDIPSIT; WHVIRDDIPSITS; HVIRDDIPSITSQ;
VIRDDIPSITSQE; IRDDIPSITSQEL; RDDIPSITSQELQ;
DDIPSITSQELQR; DIPSITSQELQRR; IPSITSQELQRRT;
PSITSQELQRRTE; SITSQELQRRTER; ITSQELQRRTERF;
TSQELQRRTERFF; SQELQRRTERFFR; QELQRRTERFFRD;
ELQRRTERFFRDS; LQRRTERFFRDSL; QRRTERFFRDSLA;
RRTERFFRDSLAR; RTERFFRDSLARF; TERFFRDSLARFL;
ERFFRDSLARFLE; RFFRDSLARFLEE; FFRDSLARFLEET;
FRDSLARFLEETT; RDSLARFLEETTW; DSLARFLEETTWT;
SLARFLEETTWTI; LARFLEETTWTIV; ARFLEETTWTIVN;
RFLEETTWTIVNA; FLEETTWTIVNAP; LEETTWTIVNAPI;
EETTWTIVNAPIN; ETTWTIVNAPINF; TTWTIVNAPINFY;
TWTIVNAPINFYN; WTIVNAPINFYNY; TIVNAPINFYNYI;
IVNAPINFYNYIQ; VNAPINFYNYIQQ; NAPINFYNYIQQY;
APINFYNYIQQYY; PINFYNYIQQYYS; INFYNYIQQYYSD;
NFYNYIQQYYSDL; FYNYIQQYYSDLS; YNYIQQYYSDLSP;
NYIQQYYSDLSPI; YIQQYYSDLSPIR; IQQYYSDLSPIRP;
QQYYSDLSPIRPS; QYYSDLSPIRPSM; YYSDLSPIRPSMV;
YSDLSPIRPSMVR; SDLSPIRPSMVRQ; DLSPIRPSMVRQV;
LSPIRPSMVRQVA; SPIRPSMVRQVAE; PIRPSMVRQVAER;
IRPSMVRQVAERE; RPSMVRQVAEREG; PSMVRQVAEREGT;
SMVRQVAEREGTR; MVRQVAEREGTRV; VRQVAEREGTRVH;
RQVAEREGTRVHF; QVAEREGTRVHFG; VAEREGTRVHFGH;
AEREGTRVHFGHT; EREGTRVHFGHTY; REGTRVHFGHTYS;
EGTRVHFGHTYSI; GTRVHFGHTYSID; TRVHFGHTYSIDD;
RVHFGHTYSIDDA; VHFGHTYSIDDAD; HFGHTYSIDDADS;
FGHTYSIDDADSI; GHTYSIDDADSIE; HTYSIDDADSIEE;
TYSIDDADSIEEV; YSIDDADSIEEVT; SIDDADSIEEVTQ;
IDDADSIEEVTQR; DDADSIEEVTQRM; DADSIEEVTQRMD;
ADSIEEVTQRMDL; DSIEEVTQRMDLR; SIEEVTQRMDLRN;
IEEVTQRMDLRNQ; EEVTQRMDLRNQQ; EVTQRMDLRNQQS;
VTQRMDLRNQQSV; TQRMDLRNQQSVH; QRMDLRNQQSVHS;
RMDLRNQQSVHSG; MDLRNQQSVHSGE; DLRNQQSVHSGEF;
LRNQQSVHSGEFI; RNQQSVHSGEFIE; NQQSVHSGEFIEK;
QQSVHSGEFIEKT; QSVHSGEFIEKTI; SVHSGEFIEKTIA;
VHSGEFIEKTIAP; HSGEFIEKTIAPG; SGEFIEKTIAPGG;
GEFIEKTIAPGGA; EFIEKTIAPGGAN; FIEKTIAPGGANQ;
IEKTIAPGGANQR; EKTIAPGGANQRT; KTIAPGGANQRTA;
TIAPGGANQRTAP; IAPGGANQRTAPQ; APGGANQRTAPQW;
PGGANQRTAPQWM; GGANQRTAPQWML; GANQRTAPQWMLP;
ANQRTAPQWMLPL; NQRTAPQWMLPLL; QRTAPQWMLPLLL;
RTAPQWMLPLLLG; TAPQWMLPLLLGL; APQWMLPLLLGLY;
PQWMLPLLLGLYG; QWMLPLLLGLYGT; WMLPLLLGLYGTV;
MLPLLLGLYGTVT; LPLLLGLYGTVTP; PLLLGLYGTVTPA;
LLLGLYGTVTPAL; LLGLYGTVTPALE; LGLYGTVTPALEA;
GLYGTVTPALEAY; LYGTVTPALEAYE; YGTVTPALEAYED;
GTVTPALEAYEDG; TVTPALEAYEDGP; VTPALEAYEDGPN;
TPALEAYEDGPNQ; PALEAYEDGPNQK; ALEAYEDGPNQKK;
LEAYEDGPNQKKR; EAYEDGPNQKKRR; AYEDGPNQKKRRV;
YEDGPNQKKRRVS; EDGPNQKKRRVSR; DGPNQKKRRVSRG;
GPNQKKRRVSRGS; PNQKKRRVSRGSS; NQKKRRVSRGSSQ;
QKKRRVSRGSSQK; KKRRVSRGSSQKA; KRRVSRGSSQKAK;
RRVSRGSSQKAKG; RVSRGSSQKAKGT; VSRGSSQKAKGTR;
SRGSSQKAKGTRA; RGSSQKAKGTRAS; GSSQKAKGTRASA;
SSQKAKGTRASAK; SQKAKGTRASAKT; QKAKGTRASAKTT;
KAKGTRASAKTTN; AKGTRASAKTTNK; KGTRASAKTTNKR;
GTRASAKTTNKRR; TRASAKTTNKRRS; RASAKTTNKRRSR;
ASAKTTNKRRSRS; SAKTTNKRRSRSS; AKTTNKRRSRSSR;
KTTNKRRSRSSRS; NWGRCYYRGRMLP; WGRCYYRGRMLPK;
GRCYYRGRMLPKP; RCYYRGRMLPKPR; CYYRGRMLPKPRN;
YYRGRMLPKPRNG; YRGRMLPKPRNGG; RGRMLPKPRNGGS;
GRMLPKPRNGGSR; PREKNASLLQHSK; REKNASLLQHSKN;
EKNASLLQHSKNS; KNASLLQHSKNSP; NASLLQHSKNSPP;
ASLLQHSKNSPPQ; SLLQHSKNSPPQF; LLQHSKNSPPQFK;
GPNLWKSTDVGGC; PNLWKSTDVGGCN; NLWKSTDVGGCNC;
LWKSTDVGGCNCT; WKSTDVGGCNCTN; KSTDVGGCNCTNR;
STDVGGCNCTNRG; TDVGGCNCTNRGY; DVGGCNCTNRGYW;
VGGCNCTNRGYWN; GGCNCTNRGYWNN; FPLLCCRWRTLGN;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

PLLCCRWRTLGNA; LLCCRWRTLGNAG; LCCRWRTLGNAGS;
CCRWRTLGNAGSA; CRWRTLGNAGSAN; RWRTLGNAGSANE;
WRTLGNAGSANEL; RTLGNAGSANELQ; TLGNAGSANELQV;
LGNAGSANELQVK; GNAGSANELQVKV; NAGSANELQVKVP;
VFWDFHRRGKCSP; FWDFHRRGKCSPS; WDFHRRGKCSPST;
DFHRRGKCSPSTS; FHRRGKCSPSTSC; HRRGKCSPSTSCD;
RRGKCSPSTSCDQ; RGKCSPSTSCDQH; GKCSPSTSCDQHS;
KCSPSTSCDQHSY; CSPSTSCDQHSYH; SPSTSCDQHSYHS;
PSTSCDQHSYHSV; STSCDQHSYHSVA; TSCDQHSYHSVAR;
QLWNTTVERPCKI; LWNTTVERPCKIF; DPPEKKICKESLP;
PPEKKICKESLPN; PEKKICKESLPNF; EKKICKESLPNFL;
KKICKESLPNFLF; KICKESLPNFLFA; ICKESLPNFLFAK;
PYKQENPESGWAA; YKQENPESGWAAY; KQENPESGWAAYV;
QENPESGWAAYVW; ENPESGWAAYVWY; NPESGWAAYVWYG;
PESGWAAYVWYGI; ESGWAAYVWYGIP; SGWAAYVWYGIPG;
GWAAYVWYGIPGR; WAAYVWYGIPGRR; AAYVWYGIPGRRG;
WHRKTSRGPRYDK; HRKTSRGPRYDKI; RKTSRGPRYDKIY;
QTGTIANQNALNR; TGTIANQNALNRC; GTIANQNALNRCF;
TIANQNALNRCFY; IANQNALNRCFYC; ANQNALNRCFYCT;
NQNALNRCFYCTY; QNALNRCFYCTYT; NALNRCFYCTYTF;
ALNRCFYCTYTFN; LNRCFYCTYTFNK; NRCFYCTYTFNKC;
RCFYCTYTFNKCC; CFYCTYTFNKCCF; FYCTYTFNKCCFC;
YCTYTFNKCCFCI; CTYTFNKCCFCIS; TYTFNKCCFCISH;
YTFNKCCFCISHF; NTESLYTNATLDY; TESLYTNATLDYG;
ESLYTNATLDYGG; SLYTNATLDYGGL; LYTNATLDYGGLT;
YTNATLDYGGLTF; TNATLDYGGLTFG; NATLDYGGLTFGN;
ATLDYGGLTFGNL; TLDYGGLTFGNLQ; LDYGGLTFGNLQQ;
DYGGLTFGNLQQG; YGGLTFGNLQQGL; GGLTFGNLQQGLK;
GLTFGNLQQGLKY; LTFGNLQQGLKYL; TFGNLQQGLKYLR;
FGNLQQGLKYLRL; GNLQQGLKYLRLG; NLQQGLKYLRLGK;
LQQGLKYLRLGKS; QQGLKYLRLGKSI; QGLKYLRLGKSIV;
GLKYLRLGKSIVI; LKYLRLGKSIVIG; KYLRLGKSIVIGI;
YLRLGKSIVIGIQ; LRLGKSIVIGIQC; RLGKSIVIGIQCL;
LGKSIVIGIQCLI; GKSIVIGIQCLIH; KSIVIGIQCLIHV;
SIVIGIQCLIHVQ; IVIGIQCLIHVQS; VIGIQCLIHVQSL;
IGIQCLIHVQSLQ; GIQCLIHVQSLQF; IQCLIHVQSLQFL;
QCLIHVQSLQFLN; CLIHVQSLQFLNP; LIHVQSLQFLNPL;
IHVQSLQFLNPLL; HVQSLQFLNPLLL; YQEYISPCIYYIS;
QEYISPCIYYISS; EYISPCIYYISSL; YISPCIYYISSLK;
ISPCIYYISSLKK; SPCIYYISSLKKY; PCIYYISSLKKYT;
CIYYISSLKKYTY; IYYISSLKKYTYL; YYISSLKKYTYLS;
YISSLKKYTYLSQ; ISSLKKYTYLSQN; SSLKKYTYLSQNP;
SLKKYTYLSQNPA; LKKYTYLSQNPAF; KKYTYLSQNPAFP;
KYTYLSQNPAFPS; YTYLSQNPAFPSI; TYLSQNPAFPSIQ;
YLSQNPAFPSIQQ; LSQNPAFPSIQQF; TKLAVATRSFHFV;
KLAVATRSFHFVK; LAVATRSFHFVKF; AVATRSFHFVKFF;
VATRSFHFVKFFF; ATRSFHFVKFFFQ; TRSFHFVKFFFQV;
RSFHFVKFFFQVR; SFHFVKFFFQVRT; FHFVKFFFQVRTL;
HFVKFFFQVRTLS; FVKFFFQVRTLSF; VKFFFQVRTLSFV;
KFFFQVRTLSFVR; FFFQVRTLSFVRI; FFQVRTLSFVRIF;
FQVRTLSFVRIFL; QVRTLSFVRIFLN; VRTLSFVRIFLNI;
RTLSFVRIFLNIF; TLSFVRIFLNIFW; LSFVRIFLNIFWA;
PSLVEIFGFFCLN; SLVEIFGFFCLNV; LVEIFGFFCLNVS;
VEIFGFFCLNVSF; EIFGFFCLNVSFL; IFGFFCLNVSFLN;
FGFFCLNVSFLNL; GFFCLNVSFLNLP; HFHLNNLSNCLNC;
FHLNNLSNCLNCL; HLNNLSNCLNCLF; LNNLSNCLNCLFH;
NNLSNCLNCLFHV; NLSNCLNCLFHVL; LSNCLNCLFHVLK;
SNCLNCLFHVLKA; NCLNCLFHVLKAN; CLNCLFHVLKANP;
LNCLFHVLKANPL; NCLFHVLKANPLI; CLFHVLKANPLIQ;
LFHVLKANPLIQL; FHVLKANPLIQLL; HVLKANPLIQLLS;
VLKANPLIQLLSL; LKANPLIQLLSLL; KANPLIQLLSLLH;
ANPLIQLLSLLHL; NPLIQLLSLLHLQ; PLIQLLSLLHLQK;
LIQLLSLLHLQKQ; IQLLSLLHLQKQP; QLLSLLHLQKQPC;
LLSLLHLQKQPCT; LSLLHLQKQPCTD; SLLHLQKQPCTDL;
LHLAQRLAFPWVG; HLAQRLAFPWVGL; LAQRLAFPWVGLH;
AQRLAFPWVGLHL; QRLAFPWVGLHLR; RLAFPWVGLHLRL;
LAFPWVGLHLRLY; AFPWVGLHLRLYH; FPWVGLHLRLYHH;
PWVGLHLRLYHHT; WVGLHLRLYHHTN; VGLHLRLYHHTNL;
GLHLRLYHHTNLI; LHLRLYHHTNLIT; HLRLYHHTNLITL;
LRLYHHTNLITLQ; RLYHHTNLITLQL; LYHHTNLITLQLV;
YHHTNLITLQLVL; HHTNLITLQLVLF; HTNLITLQLVLFF;
TNLITLQLVLFFH; NLITLQLVLFFHY; LITLQLVLFFHYQ;
ITLQLVLFFHYQW; TLQLVLFFHYQWD; LQLVLFFHYQWDL;
KQYSAKNQILQNP; QYSAKNQILQNPF; VANSAAKQHLPYI;

ANSAAKQHLPYIV; NSAAKQHLPYIVL; SAAKQHLPYIVLV;
AAKQHLPYIVLVQ; AKQHLPYIVLVQH; KQHLPYIVLVQHF;
QHLPYIVLVQHFH; HLPYIVLVQHFHE; LPYIVLVQHFHEL;
PYIVLVQHFHELQ; YIVLVQHFHELQI; IVLVQHFHELQIL;
VLVQHFHELQILN; LVQHFHELQILNP; VQHFHELQILNPF;
QHFHELQILNPFY; HFHELQILNPFYL; FHELQILNPFYLI;
HELQILNPFYLIY; ELQILNPFYLIYD; IFLLAFLPWSYEG;
FLLAFLPWSYEGY; LLAFLPWSYEGYL; LAFLPWSYEGYLL;
AFLPWSYEGYLLF; FLPWSYEGYLLFF; LKLYLLLADKYFF;
KLYLLLADKYFFD; LYLLLADKYFFDF; YLLLADKYFFDFY;
LLLADKYFFDFYF; LLADKYFFDFYFL; LADKYFFDFYFLQ;
ADKYFFDFYFLQK; SDKAGLFSDTFYT; DKAGLFSDTFYTP;
KAGLFSDTFYTPL; AGLFSDTFYTPLH; GLFSDTFYTPLHC;
LFSDTFYTPLHCI; FSDTFYTPLHCIE; SDTFYTPLHCIEI;
DTFYTPLHCIEIL; TFYTPLHCIEILN; FYTPLHCIEILNT;
YTPLHCIEILNTY; TPLHCIEILNTYL; PLHCIEILNTYLI;
LHCIEILNTYLII; HCIEILNTYLIIK; CIEILNTYLIIKT;
IEILNTYLIIKTH; EILNTYLIIKTHP; ILNTYLIIKTHPH;
LNTYLIIKTHPHT; NTYLIIKTHPHTL; TYLIIKTHPHTLS;
YLIIKTHPHTLSL; LIIKTHPHTLSLL; IIKTHPHTLSLLH;
IKTHPHTLSLLHT; KTHPHTLSLLHTQ; LISKTPALFLQAL;
ISKTPALFLQALL; SKTPALFLQALLG; NHAPLSPLECFLL;
LQKLYVVELKRI; GLLPFFFWVVLS; LLPFFFFWVVLSV;
LPFFFFWVVLSVE; PFFFFWVVLSVEN; FFFFWVVLSVENL;
FFFWVVLSVENLL; FFWVVLSVENLLL; FWVVLSVENLLLL;
WVVLSVENLLLLL; VVLSVENLLLLLH; VLSVENLLLLLHH;
LSVENLLLLLHHW; SVENLLLLLHHWQ; VENLLLLLHHWQT;
ENLLLLLHHWQTY; NLLLLLHHWQTYL; LLLLLHHWQTYLH;
LLLLHHWQTYLHG; LLLHHWQTYLHGK; LLHHWQTYLHGKI;
LHHWQTYLHGKIN; HHWQTYLHGKINL; HWQTYLHGKINLH;
WQTYLHGKINLHP; QTYLHGKINLHPI; TYLHGKINLHPIF;
YLHGKINLHPIFH; RNSTRTPTLLFHR; NSTRTPTLLFHRL;
STRTPTLLFHRLA; TRTPTLLFHRLAP; RTPTLLFHRLAPI;
TPTLLFHRLAPIK; PTLLFHRLAPIKK; TLLFHRLAPIKKI;
LLFHRLAPIKKII; LFHRLAPIKKIIT; GLLIFYYLSKYKL;
LLIFYYLSKYKLV; LIFYYLSKYKLVT; IFYYLSKYKLVTL;
FYYLSKYKLVTLK; YYLSKYKLVTLKL; ISEGSFSNYLDPP;
SEGSFSNYLDPPL; EGSFSNYLDPPLQ; GSFSNYLDPPLQS;
SFSNYLDPPLQSF; FSNYLDPPLQSFF; SNYLDPPLQSFFS;
AKPLCEAVNAVAI; KPLCEAVNAVAIY; PLCEAVNAVAIYP;
LCEAVNAVAIYPN; CEAVNAVAIYPNQ; EAVNAVAIYPNQG;
AVNAVAIYPNQGL; VNAVAIYPNQGLF; NAVAIYPNQGLFS;
HARAVHRRLFGTN; ARAVHRRLFGTNR; RAVHRRLFGTNRP;
AVHRRLFGTNRPF; VHRRLFGTNRPFL; HRRLFGTNRPFLA;
RRLFGTNRPFLAV; RLFGTNRPFLAVQ; LFGTNRPFLAVQG;
FGTNRPFLAVQGI; GTNRPFLAVQGIW; TNRPFLAVQGIWA;
NRPFLAVQGIWAK; RPFLAVQGIWAKR; PFLAVQGIWAKRK;
FLAVQGIWAKRKI; LAVQGIWAKRKIS; AVQGIWAKRKIST;
VQGIWAKRKISTN; QGIWAKRKISTNL; ATPGSKIRLMSYL;
TPGSKIRLMSYLY; PGSKIRLMSYLYI; GSKIRLMSYLYIL;
SKIRLMSYLYILL; KIRLMSYLYILLH; IRLMSYLYILLHF;
RLMSYLYILLHFF; LMSYLYILLHFFI; MSYLYILLHFFIQ;
SYLYILLHFFIQS; YLYILLHFFIQSI; LYILLHFFIQSIH;
YILLHFFIQSIHS; ILLHFFIQSIHSL; LLHFFIQSIHSLH;
LHFFIQSIHSLHF; HFFIQSIHSLHFI; FFIQSIHSLHFIL;
FIQSIHSLHFILV; IQSIHSLHFILVA; QSIHSLHFILVAP;
SIHSLHFILVAPF; IHSLHFILVAPFV; HSLHFILVAPFVR;
SLHFILVAPFVRV; LHFILVAPFVRVK; HFILVAPFVRVKF;
FILVAPFVRVKFL; ILVAPFVRVKFLT 14 mers:

ASEKASTPLLLERK; SEKASTPLLLERKG; EKASTPLLLERKGG;
KASTPLLLERKGGG; ASTPLLLERKGGGR; STPLLLERKGGGRG;
TPLLLERKGGGRGG; PLLLERKGGGRGGL; LLLERKGGGRGGLG;
LLERKGGGRGGLGL; LERKGGGRGGLGLL; ERKGGGRGGLGLLY;
RKGGGRGGLGLLYI; KGGGRGGLGLLYII; GGGRGGLGLLYIIK;
GGRGGLGLLYIIKK; GRGGLGLLYIIKKK; RGGLGLLYIIKKKA;
GGLGLLYIIKKKAT; GLGLLYIIKKKATG; LGLLYIIKKKATGR;
GLLYIIKKKATGRS; LLYIIKKKATGRSC; LYIIKKKATGRSCL;
YIIKKKATGRSCLP; IIKKKATGRSCLPM; IKKKATGRSCLPME;
KKKATGRSCLPMEC; KKATGRSCLPMECS; KATGRSCLPMECSQ;
ATGRSCLPMECSQT; TGRSCLPMECSQTM; GRSCLPMECSQTMT;
RSCLPMECSQTMTS; SCLPMECSQTMTSG; CLPMECSQTMTSGR;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

LPMECSQTMTSGRK; PMECSQTMTSGRKV; MECSQTMTSGRKVH;
ECSQTMTSGRKVHD; CSQTMTSGRKVHDS; SQTMTSGRKVHDSQ;
QTMTSGRKVHDSQG; TMTSGRKVHDSQGN; MTSGRKVHDSQGNA;
TSGRKVHDSQGNAA; SGRKVHDSQGNAAK; GRKVHDSQGNAAKP;
PQEGKCMTHREELL; QEGKCMTHREELLT; EGKCMTHREELLTH;
GKCMTHREELLTHG; KCMTHREELLTHGM; CMTHREELLTHGMQ;
MTHREELLTHGMQP; THREELLTHGMQPN; HREELLTHGMQPNH;
REELLTHGMQPNHD; EELLTHGMQPNHDL; ELLTHGMQPNHDLR;
LLTHGMQPNHDLRK; LTHGMQPNHDLRKE; THGMQPNHDLRKES;
HGMQPNHDLRKESA; QTCFASLGILALSP; TCFASLGILALSPV;
CFASLGILALSPVK; FASLGILALSPVKL; ASLGILALSPVKLD;
SLGILALSPVKLDK; LGILALSPVKLDKG; GILALSPVKLDKGH;
ILALSPVKLDKGHG; LALSPVKLDKGHGS; ALSPVKLDKGHGSA;
LSPVKLDKGHGSAP; SPVKLDKGHGSAPA; PVKLDKGHGSAPAV;
VKLDKGHGSAPAVT; KLDKGHGSAPAVTT; LDKGHGSAPAVTTS;
DKGHGSAPAVTTSF; KGHGSAPAVTTSFS; GHGSAPAVTTSFSE;
HGSAPAVTTSFSES; GSAPAVTTSFSESW; NLDWNKKKSSEDFY;
LDWNKKKSSEDFYF; DWNKKKSSEDFYFY; WNKKKSSEDFYFYF;
NKKKSSEDFYFYFR; KKKSSEDFYFYFRA; KKSSEDFYFYFRAF;
KSSEDFYFYFRAFA; SSEDFYFYFRAFAG; SEDFYFYFRAFAGI;
EDFYFYFRAFAGIL; RQCRREKQKYHCFT; QCRREKQKYHCFTC;
CRREKQKYHCFTCC; RREKQKYHCFTCCK; REKQKYHCFTCCKR;
EKQKYHCFTCCKRL; KQKYHCFTCCKRLC; QKYHCFTCCKRLCK;
KYHCFTCCKRLCKR; YHCFTCCKRLCKRL; HCFTCCKRLCKRLL;
CFTCCKRLCKRLLG; FTCCKRLCKRLLGK; SLFFCISRFMGAAL;
LFFCISRFMGAALA; FFCISRFMGAALAL; FCISRFMGAALALL;
CISRFMGAALALLG; ISRFMGAALALLGD; SRFMGAALALLGDL;
RFMGAALALLGDLV; FMGAALALLGDLVA; MGAALALLGDLVAS;
GAALALLGDLVASV; AALALLGDLVASVS; ALALLGDLVASVSE;
LALLGDLVASVSEA; ALLGDLVASVSEAA; LLGDLVASVSEAAA;
LGDLVASVSEAAAA; GDLVASVSEAAAAT; DLVASVSEAAAATG;
LVASVSEAAAATGF; VASVSEAAAATGFS; ASVSEAAAATGFSV;
SVSEAAAATGFSVA; VSEAAAATGFSVAE; SEAAAATGFSVAEI;
EAAAATGFSVAEIA; AAAATGFSVAEIAA; AAATGFSVAEIAAG;
AATGFSVAEIAAGE; ATGFSVAEIAAGEA; TGFSVAEIAAGEAA;
GFSVAEIAAGEAAA; FSVAEIAAGEAAAA; SVAEIAAGEAAAAI;
VAEIAAGEAAAAIE; AEIAAGEAAAAIEV; EIAAGEAAAAIEVQ;
IAAGEAAAAIEVQI; AAGEAAAAIEVQIA; AGEAAAAIEVQIAS;
GEAAAAIEVQIASL; EAAAAIEVQIASLA; AAAAIEVQIASLAT;
AAAIEVQIASLATV; AAIEVQIASLATVE; AIEVQIASLATVEG;
IEVQIASLATVEGI; EVQIASLATVEGIT; VQIASLATVEGITS;
QIASLATVEGITST; IASLATVEGITSTS; ASLATVEGITSTSE;
SLATVEGITSTSEA; LATVEGITSTSEAI; ATVEGITSTSEAIA;
TVEGITSTSEAIAA; VEGITSTSEAIAAI; EGITSTSEAIAAIG;
GITSTSEAIAAIGL; ITSTSEAIAAIGLT; TSTSEAIAAIGLTP;
STSEAIAAIGLTPQ; TSEAIAAIGLTPQT; SEAIAAIGLTPQTY;
EAIAAIGLTPQTYA; AIAAIGLTPQTYAV; IAAIGLTPQTYAVI;
AAIGLTPQTYAVIA; AIGLTPQTYAVIAG; IGLTPQTYAVIAGA;
GLTPQTYAVIAGAP; LTPQTYAVIAGAPG; TPQTYAVIAGAPGA;
PQTYAVIAGAPGAI; QTYAVIAGAPGAIA; TYAVIAGAPGAIAG;
YAVIAGAPGAIAGF; AVIAGAPGAIAGFA; VIAGAPGAIAGFAA;
IAGAPGAIAGFAAL; AGAPGAIAGFAALI; GAPGAIAGFAALIQ;
APGAIAGFAALIQT; PGAIAGFAALIQTV; GAIAGFAALIQTVS;
AIAGFAALIQTVSG; IAGFAALIQTVSGI; AGFAALIQTVSGIS;
GFAALIQTVSGISS; FAALIQTVSGISSL; AALIQTVSGISSLA;
ALIQTVSGISSLAQ; LIQTVSGISSLAQV; IQTVSGISSLAQVG;
QTVSGISSLAQVGY; TVSGISSLAQVGYK; VSGISSLAQVGYKF;
SGISSLAQVGYKFF; GISSLAQVGYKFFD; ISSLAQVGYKFFDD;
SSLAQVGYKFFDDW; SLAQVGYKFFDDWD; LAQVGYKFFDDWDH;
AQVGYKFFDDWDHK; QVGYKFFDDWDHKV; VGYKFFDDWDHKVS;
GYKFFDDWDHKVST; YKFFDDWDHKVSTV; KFFDDWDHKVSTVG;
FFDDWDHKVSTVGL; FDDWDHKVSTVGLY; DDWDHKVSTVGLYQ;
DWDHKVSTVGLYQQ; WDHKVSTVGLYQQS; DHKVSTVGLYQQSG;
HKVSTVGLYQQSGM; KVSTVGLYQQSGMA; VSTVGLYQQSGMAL;
STVGLYQQSGMALE; TVGLYQQSGMALEL; VGLYQQSGMALELF;
GLYQQSGMALELFN; LYQQSGMALELFNP; YQQSGMALELFNPD;
QQSGMALELFNPDE; QSGMALELFNPDEY; SGMALELFNPDEYY;
GMALELFNPDEYYD; MALELFNPDEYYDI; ALELFNPDEYYDIL;
LELFNPDEYYDILF; ELFNPDEYYDILFP; LFNPDEYYDILFPG;
FNPDEYYDILFPGV; NPDEYYDILFPGVN; PDEYYDILFPGVNT;
DEYYDILFPGVNTF; EYYDILFPGVNTFV; YYDILFPGVNTFVN;
YDILFPGVNTFVNN; DILFPGVNTFVNNI; ILFPGVNTFVNNIQ;
LFPGVNTFVNNIQY; FPGVNTFVNNIQYL; PGVNTFVNNIQYLD;
GVNTFVNNIQYLDP; VNTFVNNIQYLDPR; NTFVNNIQYLDPRH;
TFVNNIQYLDPRHW; FVNNIQYLDPRHWG; VNNIQYLDPRHWGP;
NNIQYLDPRHWGPS; NIQYLDPRHWGPSL; IQYLDPRHWGPSLF;
QYLDPRHWGPSLFA; YLDPRHWGPSLFAT; LDPRHWGPSLFATI;
DPRHWGPSLFATIS; PRHWGPSLFATISQ; RHWGPSLFATISQA;
HWGPSLFATISQAL; WGPSLFATISQALW; GPSLFATISQALWH;
PSLFATISQALWHV; SLFATISQALWHVI; LFATISQALWHVIR;
FATISQALWHVIRD; ATISQALWHVIRDD; TISQALWHVIRDDI;
ISQALWHVIRDDIP; SQALWHVIRDDIPS; QALWHVIRDDIPSI;
ALWHVIRDDIPSIT; LWHVIRDDIPSITS; WHVIRDDIPSITSQ;
HVIRDDIPSITSQE; VIRDDIPSITSQEL; IRDDIPSITSQELQ;
RDDIPSITSQELQR; DDIPSITSQELQRR; DIPSITSQELQRRT;
IPSITSQELQRRTE; PSITSQELQRRTER; SITSQELQRRTERF;
ITSQELQRRTERFF; TSQELQRRTERFFR; SQELQRRTERFFRD;
QELQRRTERFFRDS; ELQRRTERFFRDSL; LQRRTERFFRDSLA;
QRRTERFFRDSLAR; RRTERFFRDSLARF; RTERFFRDSLARFL;
TERFFRDSLARFLE; ERFFRDSLARFLEE; RFFRDSLARFLEET;
FFRDSLARFLEETT; FRDSLARFLEETTW; RDSLARFLEETTWT;
DSLARFLEETTWTI; SLARFLEETTWTIV; LARFLEETTWTIVN;
ARFLEETTWTIVNA; RFLEETTWTIVNAP; FLEETTWTIVNAPI;
LEETTWTIVNAPIN; EETTWTIVNAPINF; ETTWTIVNAPINFY;
TTWTIVNAPINFYN; TWTIVNAPINFYNY; WTIVNAPINFYNYI;
TIVNAPINFYNYIQ; IVNAPINFYNYIQQ; VNAPINFYNYIQQY;
NAPINFYNYIQQYS; APINFYNYIQQYYS; PINFYNYIQQYYSD;
INFYNYIQQYYSDL; NFYNYIQQYYSDLS; FYNYIQQYYSDLSP;
YNYIQQYYSDLSPI; NYIQQYYSDLSPIR; YIQQYYSDLSPIRP;
IQQYYSDLSPIRPS; QQYYSDLSPIRPSM; QYYSDLSPIRPSMV;
YYSDLSPIRPSMVR; YSDLSPIRPSMVRQ; SDLSPIRPSMVRQV;
DLSPIRPSMVRQVA; LSPIRPSMVRQVAE; SPIRPSMVRQVAER;
PIRPSMVRQVAERE; IRPSMVRQVAEREG; RPSMVRQVAEREGT;
PSMVRQVAEREGTR; SMVRQVAEREGTRV; MVRQVAEREGTRVH;
VRQVAEREGTRVHF; RQVAEREGTRVHFG; QVAEREGTRVHFGH;
VAEREGTRVHFGHT; AEREGTRVHFGHTY; EREGTRVHFGHTYS;
REGTRVHFGHTYSI; EGTRVHFGHTYSID; GTRVHFGHTYSIDD;
TRVHFGHTYSIDDA; RVHFGHTYSIDDAD; VHFGHTYSIDDADS;
HFGHTYSIDDADSI; FGHTYSIDDADSIE; GHTYSIDDADSIEE;
HTYSIDDADSIEEV; TYSIDDADSIEEVT; YSIDDADSIEEVTQ;
SIDDADSIEEVTQR; IDDADSIEEVTQRM; DDADSIEEVTQRMD;
DADSIEEVTQRMDL; ADSIEEVTQRMDLR; DSIEEVTQRMDLRN;
SIEEVTQRMDLRNQ; IEEVTQRMDLRNQQ; EEVTQRMDLRNQQS;
EVTQRMDLRNQQSV; VTQRMDLRNQQSVH; TQRMDLRNQQSVHS;
QRMDLRNQQSVHSG; RMDLRNQQSVHSGE; MDLRNQQSVHSGEF;
DLRNQQSVHSGEFI; LRNQQSVHSGEFIE; RNQQSVHSGEFIEK;
NQQSVHSGEFIEKT; QQSVHSGEFIEKTI; QSVHSGEFIEKTIA;
SVHSGEFIEKTIAP; VHSGEFIEKTIAPG; HSGEFIEKTIAPGG;
SGEFIEKTIAPGGA; GEFIEKTIAPGGAN; EFIEKTIAPGGANQ;
FIEKTIAPGGANQR; IEKTIAPGGANQRT; EKTIAPGGANQRTA;
KTIAPGGANQRTAP; TIAPGGANQRTAPQ; IAPGGANQRTAPQW;
APGGANQRTAPQWM; PGGANQRTAPQWML; GGANQRTAPQWMLP;
GANQRTAPQWMLPL; ANQRTAPQWMLPLL; NQRTAPQWMLPLLL;
QRTAPQWMLPLLLG; RTAPQWMLPLLLGL; TAPQWMLPLLLGLY;
APQWMLPLLLGLYG; PQWMLPLLLGLYGT; QWMLPLLLGLYGTV;
WMLPLLLGLYGTVT; MLPLLLGLYGTVTP; LPLLLGLYGTVTPA;
PLLLGLYGTVTPAL; LLLGLYGTVTPALE; LLGLYGTVTPALEA;
LGLYGTVTPALEAY; GLYGTVTPALEAYE; LYGTVTPALEAYED;
YGTVTPALEAYEDG; GTVTPALEAYEDGP; TVTPALEAYEDGPN;
VTPALEAYEDGPNQ; TPALEAYEDGPNQK; PALEAYEDGPNQKK;
ALEAYEDGPNQKKR; LEAYEDGPNQKKRV; EAYEDGPNQKKRRV;
AYEDGPNQKKRRVS; YEDGPNQKKRRVSR; EDGPNQKKRRVSRG;
DGPNQKKRRVSRGS; GPNQKKRRVSRGSS; PNQKKRRVSRGSSQ;
NQKKRRVSRGSSQK; QKKRRVSRGSSQKA; KKRRVSRGSSQKAK;
KRRVSRGSSQKAKG; RRVSRGSSQKAKGT; RVSRGSSQKAKGTR;
VSRGSSQKAKGTRA; SRGSSQKAKGTRAS; RGSSQKAKGTRASA;
GSSQKAKGTRASAK; SSQKAKGTRASAKT; SQKAKGTRASAKTT;
QKAKGTRASAKTTN; KAKGTRASAKTTNK; AKGTRASAKTTNKR;
KGTRASAKTTNKRR; GTRASAKTTNKRRS; TRASAKTTNKRRSS;
RASAKTTNKRRSRS; ASAKTTNKRRSRSS; SAKTTNKRRSRSSR;
AKTTNKRRSRSSRS; NWGRCYYRGRMLPK; WGRCYYRGRMLPKP;
GRCYYRGRMLPKPR; RCYYRGRMLPKPRN; CYYRGRMLPKPRNG;
YYRGRMLPKPRNGG; YRGRMLPKPRNGGS; RGRMLPKPRNGGSR;
PREKNASLLQHSKN; REKNASLLQHSKNS; EKNASLLQHSKNSP;
KNASLLQHSKNSPP; NASLLQHSKNSPPQ; ASLLQHSKNSPPQF;
SLLQHSKNSPPQFK; GPNLWKSTDVGGCN; PNLWKSTDVGGCNC;
NLWKSTDVGGCNCT; LWKSTDVGGCNCTN; WKSTDVGGCNCTNR;
KSTDVGGCNCTNRG; STDVGGCNCTNRGY; TDVGGCNCTNRGYW;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

DVGGCNCTNRGYWN; VGGCNCTNRGYWNN; FPLLCCRWRTLGNA;
PLLCCRWRTLGNAG; LLCCRWRTLGNAGS; LCCRWRTLGNAGSA;
CCRWRTLGNAGSAN; CRWRTLGNAGSANE; RWRTLGNAGSANEL;
WRTLGNAGSANELQ; RTLGNAGSANELQV; TLGNAGSANELQVK;
LGNAGSANELQVKV; GNAGSANELQVKVP; VFWDFHRRGKCSPS;
FWDFHRRGKCSPST; WDFHRRGKCSPSTS; DFHRRGKCSPSTSC;
FHRRGKCSPSTSCD; HRRGKCSPSTSCDQ; RRGKCSPSTSCDQH;
RGKCSPSTSCDQHS; GKCSPSTSCDQHSY; KCSPSTSCDQHSYH;
CSPSTSCDQHSYHS; SPSTSCDQHSYHSV; PSTSCDQHSYHSVA;
STSCDQHSYHSVAR; QLWNTTVERPCKIF; DPPEKKICKESLPN;
PPEKKICKESLPNF; PEKKICKESLPNFL; EKKICKESLPNFLF;
KKICKESLPNFLFA; KICKESLPNFLFAK; PYKQENPESGWAAY;
YKQENPESGWAAYV; KQENPESGWAAYVW; QENPESGWAAYVWY;
ENPESGWAAYVWYG; NPESGWAAYVWYGI; PESGWAAYVWYGIP;
ESGWAAYVWYGIPG; SGWAAYVWYGIPGR; GWAAYVWYGIPGRR;
WAAYVWYGIPGRRG; WHRKTSRGPRYDKI; HRKTSRGPRYDKIY;
QTGTIANQNALNRC; TGTIANQNALNRCF; GTIANQNALNRCFY;
TIANQNALNRCFYC; IANQNALNRCFYCT; ANQNALNRCFYCTY;
NQNALNRCFYCTYT; QNALNRCFYCTYTF; NALNRCFYCTYTFN;
ALNRCFYCTYTFNK; LNRCFYCTYTFNKC; NRCFYCTYTFNKCC;
RCFYCTYTFNKCCF; CFYCTYTFNKCCFC; FYCTYTFNKCCFCI;
YCTYTFNKCCFCIS; CTYTFNKCCFCISH; TYTFNKCCFCISHF;
NTESLYTNATLDYG; TESLYTNATLDYGG; ESLYTNATLDYGGL;
SLYTNATLDYGGLT; LYTNATLDYGGLTF; YTNATLDYGGLTFG;
TNATLDYGGLTFGN; NATLDYGGLTFGNL; ATLDYGGLTFGNLQ;
TLDYGGLTFGNLQQ; LDYGGLTFGNLQQG; DYGGLTFGNLQQGL;
YGGLTFGNLQQGLK; GGLTFGNLQQGLKY; GLTFGNLQQGLKYL;
LTFGNLQQGLKYLR; TFGNLQQGLKYLRL; FGNLQQGLKYLRLG;
GNLQQGLKYLRLGK; NLQQGLKYLRLGKS; LQQGLKYLRLGKSI;
QQGLKYLRLGKSIV; QGLKYLRLGKSIVI; GLKYLRLGKSIVIG;
LKYLRLGKSIVIGI; KYLRLGKSIVIGIQ; YLRLGKSIVIGIQC;
LRLGKSIVIGIQCL; RLGKSIVIGIQCLI; LGKSIVIGIQCLIH;
GKSIVIGIQCLIHV; KSIVIGIQCLIHVQ; SIVIGIQCLIHVQS;
IVIGIQCLIHVQSL; VIGIQCLIHVQSLQ; IGIQCLIHVQSLQF;
GIQCLIHVQSLQFL; IQCLIHVQSLQFLN; QCLIHVQSLQFLNP;
CLIHVQSLQFLNPL; LIHVQSLQFLNPLL; IHVQSLQFLNPLLL;
YQEYISPCIYYISS; QEYISPCIYYISSL; EYISPCIYYISSLK;
YISPCIYYISSLKK; ISPCIYYISSLKKY; SPCIYYISSLKKYT;
PCIYYISSLKKYTY; CIYYISSLKKYTYL; IYYISSLKKYTYLS;
YYISSLKKYTYLSQ; YISSLKKYTYLSQN; ISSLKKYTYLSQNP;
SSLKKYTYLSQNPA; SLKKYTYLSQNPAF; LKKYTYLSQNPAFP;
KKYTYLSQNPAFPS; KYTYLSQNPAFPSI; YTYLSQNPAFPSIQ;
TYLSQNPAFPSIQQ; YLSQNPAFPSIQQF; TKLAVATRSFHFVK;
KLAVATRSFHFVKF; LAVATRSFHFVKFF; AVATRSFHFVKFFF;
VATRSFHFVKFFFQ; ATRSFHFVKFFFQV; TRSFHFVKFFFQVR;
RSFHFVKFFFQVRT; SFHFVKFFFQVRTL; FHFVKFFFQVRTLS;
HFVKFFFQVRTLSF; FVKFFFQVRTLSFV; VKFFFQVRTLSFVR;
KFFFQVRTLSFVRI; FFFQVRTLSFVRIF; FFQVRTLSFVRIFL;
FQVRTLSFVRIFLN; QVRTLSFVRIFLNI; VRTLSFVRIFLNIF;
RTLSFVRIFLNIFW; TLSFVRIFLNIFWA; PSLVEIFGFFCLNV;
SLVEIFGFFCLNVS; LVEIFGFFCLNVSF; VEIFGFFCLNVSFL;
EIFGFFCLNVSFLN; IFGFFCLNVSFLNL; FGFFCLNVSFLNLP;
HFHLNNLSNCLNCL; FHLNNLSNCLNCLF; HLNNLSNCLNCLFH;
LNNLSNCLNCLFHV; NNLSNCLNCLFHVL; NLSNCLNCLFHVLK;
LSNCLNCLFHVLKA; SNCLNCLFHVLKAN; NCLNCLFHVLKANP;
CLNCLFHVLKANPL; LNCLFHVLKANPLI; NCLFHVLKANPLIQ;
CLFHVLKANPLIQL; LFHVLKANPLIQLL; FHVLKANPLIQLLS;
HVLKANPLIQLLSL; VLKANPLIQLLSLL; LKANPLIQLLSLLH;
KANPLIQLLSLLHL; ANPLIQLLSLLHLQ; NPLIQLLSLLHLQK;
PLIQLLSLLHLQKQ; LIQLLSLLHLQKQP; IQLLSLLHLQKQPC;
QLLSLLHLQKQPCT; LLSLLHLQKQPCTD; LSLLHLQKQPCTDL;
LHLAQRLAFPWVGL; HLAQRLAFPWVGLH; LAQRLAFPWVGLHL;
AQRLAFPWVGLHLR; QRLAFPWVGLHLRL; RLAFPWVGLHLRLY;
LAFPWVGLHLRLYH; AFPWVGLHLRLYHH; FPWVGLHLRLYHHT;
PWVGLHLRLYHHTN; WVGLHLRLYHHTNL; VGLHLRLYHHTNLI;
GLHLRLYHHTNLIT; LHLRLYHHTNLITL; HLRLYHHTNLITLQ;
LRLYHHTNLITLQL; RLYHHTNLITLQLV; LYHHTNLITLQLVL;
YHHTNLITLQLVLF; HHTNLITLQLVLFF; HTNLITLQLVLFFH;
TNLITLQLVLFFHY; NLITLQLVLFFHYQ; LITLQLVLFFHYQW;
ITLQLVLFFHYQWD; TLQLVLFFHYQWDL; KQYSAKNQILQNPF;
VANSAAKQHLPYIV; ANSAAKQHLPYIVL; NSAAKQHLPYIVLV;
SAAKQHLPYIVLVQ; AAKQHLPYIVLVQH; AKQHLPYIVLVQHF;
KQHLPYIVLVQHFH; QHLPYIVLVQHFHE; HLPYIVLVQHFHEL;
LPYIVLVQHFHELQ; PYIVLVQHFHELQI; YIVLVQHFHELQIL;

IVLVQHFHELQILN; VLVQHFHELQILNP; LVQHFHELQILNPF;
VQHFHELQILNPFY; QHFHELQILNPFYL; HFHELQILNPFYLI;
FHELQILNPFYLIY; HELQILNPFYLIYD; IFLLAFLPWSYEGY;
FLLAFLPWSYEGYL; LLAFLPWSYEGYLL; LAFLPWSYEGYLLF;
AFLPWSYEGYLLFF; LKLYLLLADKYFFD; KLYLLLADKYFFDF;
LYLLLADKYFFDFY; YLLLADKYFFDFYF; LLLADKYFFDFYFL;
LLADKYFFDFYFLQ; LADKYFFDFYFLQK; SDKAGLFSDTFYTP;
DKAGLFSDTFYTPL; KAGLFSDTFYTPLH; AGLFSDTFYTPLHC;
GLFSDTFYTPLHCI; LFSDTFYTPLHCIE; FSDTFYTPLHCIEI;
SDTFYTPLHCIEIL; DTFYTPLHCIEILN; TFYTPLHCIEILNT;
FYTPLHCIEILNTY; YTPLHCIEILNTYL; TPLHCIEILNTYLI;
PLHCIEILNTYLII; LHCIEILNTYLIIK; HCIEILNTYLIIKT;
CIEILNTYLIIKTH; IEILNTYLIIKTHP; EILNTYLIIKTHPH;
ILNTYLIIKTHPHT; LNTYLIIKTHPHTL; NTYLIIKTHPHTLS;
TYLIIKTHPHTLSL; YLIIKTHPHTLSLL; LIIKTHPHTLSLLH;
IIKTHPHTLSLLHT; IKTHPHTLSLLHTQ; LISKTPALFLQALL;
ISKTPALFLQALLG; GLLPFFFFWVVLSV; LLPFFFFWVVLSVE;
LPFFFFWVVLSVEN; PFFFFWVVLSVENL; FFFFWVVLSVENLL;
FFFWVVLSVENLLL; FFWVVLSVENLLLL; FWVVLSVENLLLLL;
WVVLSVENLLLLLH; VVLSVENLLLLLHH; VLSVENLLLLLHHW;
LSVENLLLLLHHWQ; SVENLLLLLHHWQT; VENLLLLLHHWQTY;
ENLLLLLHHWQTYL; NLLLLLHHWQTYLH; LLLLLHHWQTYLHG;
LLLLHHWQTYLHGK; LLLHHWQTYLHGKI; LLHHWQTYLHGKIN;
LHHWQTYLHGKINL; HHWQTYLHGKINLH; HWQTYLHGKINLHP;
WQTYLHGKINLHPI; QTYLHGKINLHPIF; TYLHGKINLHPIFH;
RNSTRTPTLLFHRL; NSTRTPTLLFHRLA; STRTPTLLFHRLAP;
TRTPTLLFHRLAPI; RTPTLLFHRLAPIK; TPTLLFHRLAPIKK;
PTLLFHRLAPIKKI; TLLFHRLAPIKKII; LLFHRLAPIKKIIT;
GLLIFYYLSKYKLV; LLIFYYLSKYKLVT; LIFYYLSKYKLVTL;
IFYYLSKYKLVTLK; FYYLSKYKLVTLKL; ISEGSFSNYLDPPL;
SEGSFSNYLDPPLQ; EGSFSNYLDPPLQS; GSFSNYLDPPLQSF;
SFSNYLDPPLQSFF; FSNYLDPPLQSFFS; AKPLCEAVNAVAIY;
KPLCEAVNAVAIYP; PLCEAVNAVAIYPN; LCEAVNAVAIYPNQ;
CEAVNAVAIYPNQG; EAVNAVAIYPNQGL; AVNAVAIYPNQGLF;
VNAVAIYPNQGLFS; HARAVHRRLFGTNR; ARAVHRRLFGTNRP;
RAVHRRLFGTNRPF; AVHRRLFGTNRPFL; VHRRLFGTNRPFLA;
HRRLFGTNRPFLAV; RRLFGTNRPFLAVQ; RLFGTNRPFLAVQG;
LFGTNRPFLAVQGI; FGTNRPFLAVQGIW; GTNRPFLAVQGIWA;
TNRPFLAVQGIWAK; NRPFLAVQGIWAKR; RPFLAVQGIWAKRK;
PFLAVQGIWAKRKI; FLAVQGIWAKRKIS; LAVQGIWAKRKIST;
AVQGIWAKRKISTN; VQGIWAKRKISTNL; ATPGSKIRLMSYLY;
TPGSKIRLMSYLYI; PGSKIRLMSYLYIL; GSKIRLMSYLYILL;
SKIRLMSYLYILLH; KIRLMSYLYILLHF; IRLMSYLYILLHFF;
RLMSYLYILLHFFI; LMSYLYILLHFFIQ; MSYLYILLHFFIQS;
SYLYILLHFFIQSI; YLYILLHFFIQSIH; LYILLHFFIQSIHS;
YILLHFFIQSIHSL; ILLHFFIQSIHSLH; LLHFFIQSIHSLHF;
LHFFIQSIHSLHFI; HFFIQSIHSLHFIL; FFIQSIHSLHFILV;
FIQSIHSLHFILVA; IQSIHSLHFILVAP; QSIHSLHFILVAPF;
SIHSLHFILVAPFV; IHSLHFILVAPFVR; HSLHFILVAPFVRV;
SLHFILVAPFVRVK; LHFILVAPFVRVKF; HFILVAPFVRVKFL;
FILVAPFVRVKFLT 15 mers:

ASEKASTPLLLERKG; SEKASTPLLLERKGG; EKASTPLLLERKGGG;
KASTPLLLERKGGGR; ASTPLLLERKGGGRG; STPLLLERKGGGRGG;
TPLLLERKGGGRGGL; PLLLERKGGGRGGLG; LLLERKGGGRGGLGL;
LLERKGGGRGGLGLL; LERKGGGRGGLGLLY; ERKGGGRGGLGLLYI;
RKGGGRGGLGLLYII; KGGGRGGLGLLYIIK; GGGRGGLGLLYIIKK;
GGRGGLGLLYIIKKK; GRGGLGLLYIIKKKA; RGGLGLLYIIKKKAT;
GGLGLLYIIKKKATG; GLGLLYIIKKKATGR; LGLLYIIKKKATGRS;
GLLYIIKKKATGRSC; LLYIIKKKATGRSCL; LYIIKKKATGRSCLP;
YIIKKKATGRSCLPM; IIKKKATGRSCLPME; IKKKATGRSCLPMEC;
KKKATGRSCLPMECS; KKATGRSCLPMECSQ; KATGRSCLPMECSQT;
ATGRSCLPMECSQTM; TGRSCLPMECSQTMT; GRSCLPMECSQTMTS;
RSCLPMECSQTMTSG; SCLPMECSQTMTSGR; CLPMECSQTMTSGRK;
LPMECSQTMTSGRKV; PMECSQTMTSGRKVH; MECSQTMTSGRKVHD;
ECSQTMTSGRKVHDS; CSQTMTSGRKVHDSQ; SQTMTSGRKVHDSQG;
QTMTSGRKVHDSQGN; TMTSGRKVHDSQGNA; MTSGRKVHDSQGNAA;
TSGRKVHDSQGNAAK; SGRKVHDSQGNAAKP; PQEGKCMTHREELLT;
QEGKCMTHREELLTH; EGKCMTHREELLTHG; GKCMTHREELLTHGM;
KCMTHREELLTHGMQ; CMTHREELLTHGMQP; MTHREELLTHGMQPN;
THREELLTHGMQPNH; HREELLTHGMQPNHD; REELLTHGMQPNHDL;
EELLTHGMQPNHDLR; ELLTHGMQPNHDLRK; LLTHGMQPNHDLRKE;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

LTHGMQPNHDLRKES; THGMQPNHDLRKESA; QTCFASLGILALSPV;
TCFASLGILALSPVK; CFASLGILALSPVKL; FASLGILALSPVKLD;
ASLGILALSPVKLDK; SLGILALSPVKLDKG; LGILALSPVKLDKGH;
GILALSPVKLDKGHG; ILALSPVKLDKGHGS; LALSPVKLDKGHGSA;
ALSPVKLDKGHGSAP; LSPVKLDKGHGSAPA; SPVKLDKGHGSAPAV;
PVKLDKGHGSAPAVT; VKLDKGHGSAPAVTT; KLDKGHGSAPAVTTS;
LDKGHGSAPAVTTSF; DKGHGSAPAVTTSFS; KGHGSAPAVTTSFSE;
GHGSAPAVTTSFSES; HGSAPAVTTSFSESW; NLDWNKKKSSEDFYF;
LDWNKKKSSEDFYFY; DWNKKKSSEDFYFYF; WNKKKSSEDFYFYFR;
NKKKSSEDFYFYFRA; KKKSSEDFYFYFRAF; KKSSEDFYFYFRAFA;
KSSEDFYFYFRAFAG; SSEDFYFYFRAFAGI; SEDFYFYFRAFAGIL;
RQCRREKQKYHCFTC; QCRREKQKYHCFTCC; CRREKQKYHCFTCCK;
RREKQKYHCFTCCKR; REKQKYHCFTCCKRL; EKQKYHCFTCCKRLC;
KQKYHCFTCCKRLCK; QKYHCFTCCKRLCKR; KYHCFTCCKRLCKRL;
YHCFTCCKRLCKRLL; HCFTCCKRLCKRLLG; CFTCCKRLCKRLLGD;
SLFFCISRFMGAALA; LFFCISRFMGAALAL; FFCISRFMGAALALL;
FCISRFMGAALALLG; CISRFMGAALALLGD; ISRFMGAALALLGDL;
SRFMGAALALLGDLV; RFMGAALALLGDLVA; FMGAALALLGDLVAS;
MGAALALLGDLVASV; GAALALLGDLVASVS; AALALLGDLVASVSE;
ALALLGDLVASVSEA; LALLGDLVASVSEAA; ALLGDLVASVSEAAA;
LLGDLVASVSEAAAA; LGDLVASVSEAAAAT; GDLVASVSEAAAATG;
DLVASVSEAAAATGF; LVASVSEAAAATGFS; VASVSEAAAATGFSV;
ASVSEAAAATGFSVA; SVSEAAAATGFSVAE; VSEAAAATGFSVAEI;
SEAAAATGFSVAEIA; EAAAATGFSVAEIAA; AAAATGFSVAEIAAG;
AAATGFSVAEIAAGE; AATGFSVAEIAAGEA; ATGFSVAEIAAGEAA;
TGFSVAEIAAGEAAA; GFSVAEIAAGEAAAA; FSVAEIAAGEAAAAI;
SVAEIAAGEAAAAIE; VAEIAAGEAAAAIEV; AEIAAGEAAAAIEVQ;
EIAAGEAAAAIEVQI; IAAGEAAAAIEVQIA; AAGEAAAAIEVQIAS;
AGEAAAAIEVQIASL; GEAAAAIEVQIASLA; EAAAAIEVQIASLAT;
AAAAIEVQIASLATV; AAAIEVQIASLATVE; AAIEVQIASLATVEG;
AIEVQIASLATVEGI; IEVQIASLATVEGIT; EVQIASLATVEGITS;
VQIASLATVEGITST; QIASLATVEGITSTS; IASLATVEGITSTSE;
ASLATVEGITSTSEA; SLATVEGITSTSEAI; LATVEGITSTSEAIA;
ATVEGITSTSEAIAA; TVEGITSTSEAIAAI; VEGITSTSEAIAAIG;
EGITSTSEAIAAIGL; GITSTSEAIAAIGLT; ITSTSEAIAAIGLTP;
TSTSEAIAAIGLTPQ; STSEAIAAIGLTPQT; TSEAIAAIGLTPQTY;
SEAIAAIGLTPQTYA; EAIAAIGLTPQTYAV; AIAAIGLTPQTYAVI;
IAAIGLTPQTYAVIA; AAIGLTPQTYAVIAG; AIGLTPQTYAVIAGA;
IGLTPQTYAVIAGAP; GLTPQTYAVIAGAPG; LTPQTYAVIAGAPGA;
TPQTYAVIAGAPGAI; PQTYAVIAGAPGAIA; QTYAVIAGAPGAIAG;
TYAVIAGAPGAIAGF; YAVIAGAPGAIAGFA; AVIAGAPGAIAGFAA;
VIAGAPGAIAGFAAL; IAGAPGAIAGFAALI; AGAPGAIAGFAALIQ;
GAPGAIAGFAALIQT; APGAIAGFAALIQTV; PGAIAGFAALIQTVS;
GAIAGFAALIQTVSG; AIAGFAALIQTVSGI; IAGFAALIQTVSGIS;
AGFAALIQTVSGISS; GFAALIQTVSGISSL; FAALIQTVSGISSLA;
AALIQTVSGISSLAQ; ALIQTVSGISSLAQV; LIQTVSGISSLAQVG;
IQTVSGISSLAQVGY; QTVSGISSLAQVGYK; TVSGISSLAQVGYKF;
VSGISSLAQVGYKFF; SGISSLAQVGYKFFD; GISSLAQVGYKFFDD;
ISSLAQVGYKFFDDW; SSLAQVGYKFFDDWD; SLAQVGYKFFDDWDH;
LAQVGYKFFDDWDHK; AQVGYKFFDDWDHKV; QVGYKFFDDWDHKVS;
VGYKFFDDWDHKVST; GYKFFDDWDHKVSTV; YKFFDDWDHKVSTVG;
KFFDDWDHKVSTVGL; FFDDWDHKVSTVGLY; FDDWDHKVSTVGLYQ;
DDWDHKVSTVGLYQQ; DWDHKVSTVGLYQQS; WDHKVSTVGLYQQSG;
DHKVSTVGLYQQSGM; HKVSTVGLYQQSGMA; KVSTVGLYQQSGMAL;
VSTVGLYQQSGMALE; STVGLYQQSGMALEL; TVGLYQQSGMALELF;
VGLYQQSGMALELFN; GLYQQSGMALELFNP; LYQQSGMALELFNPD;
YQQSGMALELFNPDE; QQSGMALELFNPDEY; QSGMALELFNPDEYY;
SGMALELFNPDEYYD; GMALELFNPDEYYDI; MALELFNPDEYYDIL;
ALELFNPDEYYDILF; LELFNPDEYYDILFP; ELFNPDEYYDILFPG;
LFNPDEYYDILFPGV; FNPDEYYDILFPGVN; NPDEYYDILFPGVNT;
PDEYYDILFPGVNTF; DEYYDILFPGVNTFV; EYYDILFPGVNTFVN;
YYDILFPGVNTFVNN; YDILFPGVNTFVNNI; DILFPGVNTFVNNIQ;
ILFPGVNTFVNNIQY; LFPGVNTFVNNIQYL; FPGVNTFVNNIQYLD;
PGVNTFVNNIQYLDP; GVNTFVNNIQYLDPR; VNTFVNNIQYLDPRH;
NTFVNNIQYLDPRHW; TFVNNIQYLDPRHWG; FVNNIQYLDPRHWGP;
VNNIQYLDPRHWGPS; NNIQYLDPRHWGPSL; NIQYLDPRHWGPSLF;
IQYLDPRHWGPSLFA; QYLDPRHWGPSLFAT; YLDPRHWGPSLFATI;
LDPRHWGPSLFATIS; DPRHWGPSLFATISQ; PRHWGPSLFATISQA;
RHWGPSLFATISQAL; HWGPSLFATISQALW; WGPSLFATISQALWH;
GPSLFATISQALWHV; PSLFATISQALWHVI; SLFATISQALWHVIR;
LFATISQALWHVIRD; FATISQALWHVIRDD; ATISQALWHVIRDDI;
TISQALWHVIRDDIP; ISQALWHVIRDDIPS; SQALWHVIRDDIPSI;
QALWHVIRDDIPSIT; ALWHVIRDDIPSITS; LWHVIRDDIPSITSQ;
WHVIRDDIPSITSQE; HVIRDDIPSITSQEL; VIRDDIPSITSQELQ;
IRDDIPSITSQELQR; RDDIPSITSQELQRR; DDIPSITSQELQRRT;
DIPSITSQELQRRTE; IPSITSQELQRRTER; PSITSQELQRRTERF;
SITSQELQRRTERFF; ITSQELQRRTERFFR; TSQELQRRTERFFRD;
SQELQRRTERFFRDS; QELQRRTERFFRDSL; ELQRRTERFFRDSLA;
LQRRTERFFRDSLAR; QRRTERFFRDSLARF; RRTERFFRDSLARFL;
RTERFFRDSLARFLE; TERFFRDSLARFLEE; ERFFRDSLARFLEET;
RFFRDSLARFLEETT; FFRDSLARFLEETTW; FRDSLARFLEETTWT;
RDSLARFLEETTWTI; DSLARFLEETTWTIV; SLARFLEETTWTIVN;
LARFLEETTWTIVNA; ARFLEETTWTIVNAP; RFLEETTWTIVNAPI;
FLEETTWTIVNAPIN; LEETTWTIVNAPINF; EETTWTIVNAPINFY;
ETTWTIVNAPINFYN; TTWTIVNAPINFYNY; TWTIVNAPINFYNYI;
WTIVNAPINFYNYIQ; TIVNAPINFYNYIQQ; IVNAPINFYNYIQQY;
VNAPINFYNYIQQYY; NAPINFYNYIQQYYS; APINFYNYIQQYYSD;
PINFYNYIQQYYSDL; INFYNYIQQYYSDLS; NFYNYIQQYYSDLSP;
FYNYIQQYYSDLSPI; YNYIQQYYSDLSPIR; NYIQQYYSDLSPIRP;
YIQQYYSDLSPIRPS; IQQYYSDLSPIRPSM; QQYYSDLSPIRPSMV;
QYYSDLSPIRPSMVR; YYSDLSPIRPSMVRQ; YSDLSPIRPSMVRQV;
SDLSPIRPSMVRQVA; DLSPIRPSMVRQVAE; LSPIRPSMVRQVAER;
SPIRPSMVRQVAERE; PIRPSMVRQVAEREG; IRPSMVRQVAEREGT;
RPSMVRQVAEREGTR; PSMVRQVAEREGTRV; SMVRQVAEREGTRVH;
MVRQVAEREGTRVHF; VRQVAEREGTRVHFG; RQVAEREGTRVHFGH;
QVAEREGTRVHFGHT; VAEREGTRVHFGHTY; AEREGTRVHFGHTYS;
EREGTRVHFGHTYSI; REGTRVHFGHTYSID; EGTRVHFGHTYSIDD;
GTRVHFGHTYSIDDA; TRVHFGHTYSIDDAD; RVHFGHTYSIDDADS;
VHFGHTYSIDDADSI; HFGHTYSIDDADSIE; FGHTYSIDDADSIEE;
GHTYSIDDADSIEEV; HTYSIDDADSIEEVT; TYSIDDADSIEEVTQ;
YSIDDADSIEEVTQR; SIDDADSIEEVTQRM; IDDADSIEEVTQRMD;
DDADSIEEVTQRMDL; DADSIEEVTQRMDLR; ADSIEEVTQRMDLRN;
DSIEEVTQRMDLRNQ; SIEEVTQRMDLRNQQ; IEEVTQRMDLRNQQS;
EEVTQRMDLRNQQSV; EVTQRMDLRNQQSVH; VTQRMDLRNQQSVHS;
TQRMDLRNQQSVHSG; QRMDLRNQQSVHSGE; RMDLRNQQSVHSGEF;
MDLRNQQSVHSGEFI; DLRNQQSVHSGEFIE; LRNQQSVHSGEFIEK;
RNQQSVHSGEFIEKT; NQQSVHSGEFIEKTI; QQSVHSGEFIEKTIA;
QSVHSGEFIEKTIAP; SVHSGEFIEKTIAPG; VHSGEFIEKTIAPGG;
HSGEFIEKTIAPGGA; SGEFIEKTIAPGGAN; GEFIEKTIAPGGANQ;
EFIEKTIAPGGANQR; FIEKTIAPGGANQRT; IEKTIAPGGANQRTA;
EKTIAPGGANQRTAP; KTIAPGGANQRTAPG; TIAPGGANQRTAPGW;
IAPGGANQRTAPQWM; APGGANQRTAPQWML; PGGANQRTAPQWMLP;
GGANQRTAPQWMLPL; GANQRTAPQWMLPLL; ANQRTAPQWMLPLLL;
NQRTAPQWMLPLLLG; QRTAPQWMLPLLLGL; RTAPQWMLPLLLGLY;
TAPQWMLPLLLGLYG; APQWMLPLLLGLYGT; PQWMLPLLLGLYGTV;
QWMLPLLLGLYGTVT; WMLPLLLGLYGTVTP; MLPLLLGLYGTVTPA;
LPLLLGLYGTVTPAL; PLLLGLYGTVTPALE; LLLGLYGTVTPALEA;
LLGLYGTVTPALEAY; LGLYGTVTPALEAYE; GLYGTVTPALEAYED;
LYGTVTPALEAYEDG; YGTVTPALEAYEDGP; GTVTPALEAYEDGPN;
TVTPALEAYEDGPNQ; VTPALEAYEDGPNQK; TPALEAYEDGPNQKK;
PALEAYEDGPNQKKR; ALEAYEDGPNQKKRR; LEAYEDGPNQKKRRV;
EAYEDGPNQKKRRVS; AYEDGPNQKKRRVSR; YEDGPNQKKRRVSRG;
EDGPNQKKRRVSRGS; DGPNQKKRRVSRGSS; GPNQKKRRVSRGSSQ;
PNQKKRRVSRGSSQK; NQKKRRVSRGSSQKA; QKKRRVSRGSSQKAK;
KKRRVSRGSSQKAKG; KRRVSRGSSQKAKGT; RRVSRGSSQKAKGTR;
RVSRGSSQKAKGTRA; VSRGSSQKAKGTRAS; SRGSSQKAKGTRASA;
RGSSQKAKGTRASAK; GSSQKAKGTRASAKT; SSQKAKGTRASAKTT;
SQKAKGTRASAKTTN; QKAKGTRASAKTTNK; KAKGTRASAKTTNKR;
AKGTRASAKTTNKRR; KGTRASAKTTNKRRS; GTRASAKTTNKRRSR;
TRASAKTTNKRRSRS; RASAKTTNKRRSRSS; ASAKTTNKRRSRSSR;
SAKTTNKRRSRSSRS; NWGRCYYRGRMLPKP; WGRCYYRGRMLPKPR;
GRCYYRGRMLPKPRN; RCYYRGRMLPKPRNG; CYYRGRMLPKPRNGG;
YYRGRMLPKPRNGGS; YRGRMLPKPRNGGSR; PREKNASLLQHSKNS;
REKNASLLQHSKNSP; EKNASLLQHSKNSPP; KNASLLQHSKNSPPQ;
NASLLQHSKNSPPQF; ASLLQHSKNSPPQFG; GPNLWKSTDVGGCNC;
PNLWKSTDVGGCNCT; NLWKSTDVGGCNCTN; LWKSTDVGGCNCTNR;
WKSTDVGGCNCTNRG; KSTDVGGCNCTNRGY; STDVGGCNCTNRGYW;
TDVGGCNCTNRGYWN; DVGGCNCTNRGYWNN; FPLLCCRWRTLGNAG;
PLLCCRWRTLGNAGS; LLCCRWRTLGNAGSA; LCCRWRTLGNAGSAN;
CCRWRTLGNAGSANE; CRWRTLGNAGSANEL; RWRTLGNAGSANELQ;
WRTLGNAGSANELQV; RTLGNAGSANELQVK; TLGNAGSANELQVKV;
LGNAGSANELQVKVP; VFWDFHRRGKCSPST; FWDFHRRGKCSPSTS;
WDFHRRGKCSPSTSC; DFHRRGKCSPSTSCD; DFHRRGKCSPSTSCDH;
HRRGKCSPSTSCDQH; RRGKCSPSTSCDQHS; RGKCSPSTSCDQHSY;
GKCSPSTSCDQHSYH; KCSPSTSCDQHSYHS; CSPSTSCDQHSYHSV;
SPSTSCDQHSYHSVA; PSTSCDQHSYHSVAR; DPPEKKICKESLPNF;
PPEKKICKESLPNFL; PEKKICKESLPNFLF; EKKICKESLPNFLFA;
KKICKESLPNFLFAK; PYKQENPESGWAAYV; YKQENPESGWAAYVW;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

KQENPESGWAAYVWY; QENPESGWAAYVWYG; ENPESGWAAYVWYGI;
NPESGWAAYVWYGIP; PESGWAAYVWYGIPG; ESGWAAYVWYGIPGR;
SGWAAYVWYGIPGRR; GWAAYVWYGIPGRRG; WHRKTSRGPRYDKIY;
QTGTIANQNALNRCF; TGTIANQNALNRCFY; GTIANQNALNRCFYC;
TIANQNALNRCFYCT; IANQNALNRCFYCTY; ANQNALNRCFYCTYT;
NQNALNRCFYCTYTF; QNALNRCFYCTYTFN; NALNRCFYCTYTFNK;
ALNRCFYCTYTFNKC; LNRCFYCTYTFNKCC; NRCFYCTYTFNKCCF;
RCFYCTYTFNKCCFC; CFYCTYTFNKCCFCI; FYCTYTFNKCCFCIS;
YCTYTFNKCCFCISH; CTYTFNKCCFCISHF; NTESLYTNATLDYGG;
TESLYTNATLDYGGL; ESLYTNATLDYGGLT; SLYTNATLDYGGLTF;
LYTNATLDYGGLTFG; YTNATLDYGGLTFGN; TNATLDYGGLTFGNL;
NATLDYGGLTFGNLQ; ATLDYGGLTFGNLQQ; TLDYGGLTFGNLQQG;
LDYGGLTFGNLQQGL; DYGGLTFGNLQQGLK; YGGLTFGNLQQGLKY;
GGLTFGNLQQGLKYL; GLTFGNLQQGLKYLR; LTFGNLQQGLKYLRL;
TFGNLQQGLKYLRLG; FGNLQQGLKYLRLGK; GNLQQGLKYLRLGKS;
NLQQGLKYLRLGKSI; LQQGLKYLRLGKSIV; QQGLKYLRLGKSIVI;
QGLKYLRLGKSIVIG; GLKYLRLGKSIVIGI; LKYLRLGKSIVIGIQ;
KYLRLGKSIVIGIQC; YLRLGKSIVIGIQCL; LRLGKSIVIGIQCLI;
RLGKSIVIGIQCLIH; LGKSIVIGIQCLIHV; GKSIVIGIQCLIHVQ;
KSIVIGIQCLIHVQS; SIVIGIQCLIHVQSL; IVIGIQCLIHVQSLQ;
VIGIQCLIHVQSLQF; IGIQCLIHVQSLQFL; GIQCLIHVQSLQFLN;
IQCLIHVQSLQFLNP; QCLIHVQSLQFLNPL; CLIHVQSLQFLNPLL;
LIHVQSLQFLNPLLL; YQEYISPCIYYISSL; QEYISPCIYYISSLK;
EYISPCIYYISSLKK; YISPCIYYISSLKKY; ISPCIYYISSLKKYT;
SPCIYYISSLKKYTY; PCIYYISSLKKYTYL; CIYYISSLKKYTYLS;
IYYISSLKKYTYLSQ; YYISSLKKYTYLSQN; YISSLKKYTYLSQNP;
ISSLKKYTYLSQNPA; SSLKKYTYLSQNPAF; SLKKYTYLSQNPAFP;
LKKYTYLSQNPAFPS; KKYTYLSQNPAFPSI; KYTYLSQNPAFPSIQ;
YTYLSQNPAFPSIQQ; TYLSQNPAFPSIQQF; TKLAVATRSFHFVKF;
KLAVATRSFHFVKFF; LAVATRSFHFVKFFF; AVATRSFHFVKFFFQ;
VATRSFHFVKFFFQV; ATRSFHFVKFFFQVR; TRSFHFVKFFFQVRT;
RSFHFVKFFFQVRTL; SFHFVKFFFQVRTLS; FHFVKFFFQVRTLSF;
HFVKFFFQVRTLSFV; FVKFFFQVRTLSFVR; VKFFFQVRTLSFVRI;
KFFFQVRTLSFVRIF; FFFQVRTLSFVRIFL; FFQVRTLSFVRIFLN;
FQVRTLSFVRIFLNI; QVRTLSFVRIFLNIF; VRTLSFVRIFLNIFW;
RTLSFVRIFLNIFWA; PSLVEIFGFFCLNVS; SLVEIFGFFCLNVSF;
LVEIFGFFCLNVSFL; VEIFGFFCLNVSFLN; EIFGFFCLNVSFLNL;
IFGFFCLNVSFLNLP; HFHLNNLSNCLNCLF; PHLNNLSNCLNCLFH;
HLNNLSNCLNCLFHV; LNNLSNCLNCLFHVL; NNLSNCLNCLFHVLK;
NLSNCLNCLFHVLKA; LSNCLNCLFHVLKAN; SNCLNCLFHVLKANP;
NCLNCLFHVLKANPL; CLNCLFHVLKANPLI; LNCLFHVLKANPLIQ;
NCLFHVLKANPLIQL; CLFHVLKANPLIQLL; LFHVLKANPLIQLLS;
FHVLKANPLIQLLSL; HVLKANPLIQLLSLL; VLKANPLIQLLSLLH;
LKANPLIQLLSLLHL; KANPLIQLLSLLHLQ; ANPLIQLLSLLHLQK;
NPLIQLLSLLHLQKQ; PLIQLLSLLHLQKQP; LIQLLSLLHLQKQPC;
IQLLSLLHLQKQPCT; QLLSLLHLQKQPCTD; LLSLLHLQKQPCTDL;
LHLAQRLAFPWVGLH; HLAQRLAFPWVGLHL; LAQRLAFPWVGLHLR;
AQRLAFPWVGLHLRL; QRLAFPWVGLHLRLY; RLAFPWVGLHLRLYH;
LAFPWVGLHLRLYHH; AFPWVGLHLRLYHHT; FPWVGLHLRLYHHTN;
PWVGLHLRLYHHTNL; WVGLHLRLYHHTNLI; VGLHLRLYHHTNLIT;
GLHLRLYHHTNLITL; LHLRLYHHTNLITLQ; HLRLYHHTNLITLQL;
LRLYHHTNLITLQLV; RLYHHTNLITLQLVL; LYHHTNLITLQLVLF;
YHHTNLITLQLVLFF; HHTNLITLQLVLFFH; HTNLITLQLVLFFHY;
TNLITLQLVLFFHYQ; NLITLQLVLFFHYQW; LITLQLVLFFHYQWD;
ITLQLVLFFHYQWDL; VANSAAKQHLPYIVL; ANSAAKQHLPYIVLV;
NSAAKQHLPYIVLVQ; SAAKQHLPYIVLVQH; AAKQHLPYIVLVQHF;
AKQHLPYIVLVQHFH; KQHLPYIVLVQHFHE; QHLPYIVLVQHFHEL;
HLPYIVLVQHFHELQ; LPYIVLVQHFHELQI; PYIVLVQHFHELQIL;
YIVLVQHFHELQILN; IVLVQHFHELQILNP; VLVQHFHELQILNPF;
LVQHFHELQILNPFY; VQHFHELQILNPFYL; QHFHELQILNPFYLI;
HFHELQILNPFYLIY; FHELQILNPFYLIYD; IFLLAFLPWSYEGYL;
FLLAFLPWSYEGYLL; LLAFLPWSYEGYLLF; LAFLPWSYEGYLLFF;
LKLYLLLADKYFFDF; KLYLLLADKYFFDFY; LYLLLADKYFFDFYF;
YLLLADKYFFDFYFL; LLLADKYFFDFYFLQ; LLADKYFFDFYFLQK;
SDKAGLFSDTFYTPL; DKAGLFSDTFYTPLH; KAGLFSDTFYTPLHC;
AGLFSDTFYTPLHCI; GLFSDTFYTPLHCIE; LFSDTFYTPLHCIEI;
FSDTFYTPLHCIEIL; SDTFYTPLHCIEILN; DTFYTPLHCIEILNT;
TFYTPLHCIEILNTY; FYTPLHCIEILNTYL; YTPLHCIEILNTYLI;
TPLHCIEILNTYLII; PLHCIEILNTYLIIK; LHCIEILNTYLIIKT;
HCIEILNTYLIIKTH; CIEILNTYLIIKTHP; IEILNTYLIIKTHPH;
EILNTYLIIKTHPHT; ILNTYLIIKTHPHTL; LNTYLIIKTHPHTLS;
NTYLIIKTHPHTLSL; TYLIIKTHPHTLSLL; YLIIKTHPHTLSLLH;
LIIKTHPHTLSLLHT; IIKTHPHTLSLLHTQ; LISKTPALFLQALLG;
GLLPFFFFWVVLSVE; LLPFFFFWVVLSVEN; LPFFFFWVVLSVENL;
PFFFFWVVLSVENLL; FFFFWVVLSVENLLL; FFFWVVLSVENLLLL;
FFWVVLSVENLLLLL; FWVVLSVENLLLLLH; WVVLSVENLLLLLHH;
VVLSVENLLLLLHHW; VLSVENLLLLLHHWQ; LSVENLLLLLHHWQT;
SVENLLLLLHHWQTY; VENLLLLLHHWQTYL; ENLLLLLHHWQTYLH;
NLLLLLHHWQTYLHG; LLLLLHHWQTYLHGK; LLLLHHWQTYLHGKI;
LLLHHWQTYLHGKIN; LLHHWQTYLHGKINL; LHHWQTYLHGKINLH;
HHWQTYLHGKINLHP; HWQTYLHGKINLHPI; WQTYLHGKINLHPIF;
QTYLHGKINLHPIFH; RNSTRTPTLLFHRLA; NSTRTPTLLFHRLAP;
STRTPTLLFHRLAPI; TRTPTLLFHRLAPIK; RTPTLLFHRLAPIKK;
TPTLLFHRLAPIKKI; PTLLFHRLAPIKKII; TLLFHRLAPIKKIIT;
GLLIFYYLSKYKLVT; LLIFYYLSKYKLVTL; LIFYYLSKYKLVTLK;
IFYYLSKYKLVTLKL; ISEGSFSNYLDPPLQ; SEGSFSNYLDPPLQS;
EGSFSNYLDPPLQSF; GSFSNYLDPPLQSFF; SFSNYLDPPLQSFFS;
AKPLCEAVNAVAIYP; KPLCEAVNAVAIYPN; PLCEAVNAVAIYPNQ;
LCEAVNAVAIYPNQG; CEAVNAVAIYPNQGL; EAVNAVAIYPNQGLF;
AVNAVAIYPNQGLFS; HARAVHRRLFGTNRP; ARAVHRRLFGTNRPF;
RAVHRRLFGTNRPFL; AVHRRLFGTNRPFLA; VHRRLFGTNRPFLAV;
HRRLFGTNRPFLAVQ; RRLFGTNRPFLAVQG; RLFGTNRPFLAVQGI;
LFGTNRPFLAVQGIW; FGTNRPFLAVQGIWA; GTNRPFLAVQGIWAK;
TNRPFLAVQGIWAKR; NRPFLAVQGIWAKRK; RPFLAVQGIWAKRKI;
PFLAVQGIWAKRKIS; FLAVQGIWAKRKIST; LAVQGIWAKRKISTN;
AVQGIWAKRKISTNL; ATPGSKIRLMSYLYI; TPGSKIRLMSYLYIL;
PGSKIRLMSYLYILL; GSKIRLMSYLYILLH; SKIRLMSYLYILLHF;
KIRLMSYLYILLHFF; IRLMSYLYILLHFFI; RLMSYLYILLHFFIQ;
LMSYLYILLHFFIQS; MSYLYILLHFFIQSI; SYLYILLHFFIQSIH;
YLYILLHFFIQSIHS; LYILLHFFIQSIHSL; YILLHFFIQSIHSLH;
ILLHFFIQSIHSLHF; LLHFFIQSIHSLHFI; LHFFIQSIHSLHFIL;
HFFIQSIHSLHFILV; FFIQSIHSLHFILVA; FIQSIHSLHFILVAP;
IQSIHSLHFILVAPF; QSIHSLHFILVAPFV; SIHSLHFILVAPFVR;
IHSLHFILVAPFVRV; HSLHFILVAPFVRVK; SLHFILVAPFVRVKF;
LHFILVAPFVRVKFL; HFILVAPFVRVKFLT; KVHELHGFFPVKNFI;
VHELHGFFPVKNFIH 16 mers:

ASEKASTPLLLERKGG; SEKASTPLLLERKGGG;
EKASTPLLLERKGGGR; KASTPLLLERKGGGRG;
ASTPLLLERKGGGRGG; STPLLLERKGGGRGGL;
TPLLLERKGGGRGGLG; PLLLERKGGGRGGLGL;
LLLERKGGGRGGLGLL; LLERKGGGRGGLGLLY;
LERKGGGRGGLGLLYI; ERKGGGRGGLGLLYII;
RKGGGRGGLGLLYIIK; KGGGRGGLGLLYIIKK;
GGGRGGLGLLYIIKKK; GGRGGLGLLYIIKKKA;
GRGGLGLLYIIKKKAT; RGGLGLLYIIKKKATG;
GGLGLLYIIKKKATGR; GLGLLYIIKKKATGRS;
LGLLYIIKKKATGRSC; GLLYIIKKKATGRSCL;
LLYIIKKKATGRSCLP; LYIIKKKATGRSCLPM;
YIIKKKATGRSCLPME; IIKKKATGRSCLPMEC;
IKKKATGRSCLPMECS; KKKATGRSCLPMECSQ;
KKATGRSCLPMECSQT; KATGRSCLPMECSQTM;
ATGRSCLPMECSQTMT; TGRSCLPMECSQTMTS;
GRSCLPMECSQTMTSG; RSCLPMECSQTMTSGR;
SCLPMECSQTMTSGRK; CLPMECSQTMTSGRKV;
LPMECSQTMTSGRKVH; PMECSQTMTSGRKVHD;
MECSQTMTSGRKVHDS; ECSQTMTSGRKVHDSQ;
CSQTMTSGRKVHDSQG; SQTMTSGRKVHDSQGN;
QTMTSGRKVHDSQGNA; TMTSGRKVHDSQGNAA;
MTSGRKVHDSQGNAAK; TSGRKVHDSQGNAAKP;
PQEGKCMTHREELLTH; QEGKCMTHREELLTHG;
EGKCMTHREELLTHGM; GKCMTHREELLTHGMQ;
KCMTHREELLTHGMQP; CMTHREELLTHGMQPN;
MTHREELLTHGMQPNH; THREELLTHGMQPNHD;
HREELLTHGMQPNHDL; REELLTHGMQPNHDLR;
EELLTHGMQPNHDLRK; ELLTHGMQPNHDLRKE;
LLTHGMQPNHDLRKES; LTHGMQPNHDLRKESA;
QTCFASLGILALSPVK; TCFASLGILALSPVKL;
CFASLGILALSPVKLD; FASLGILALSPVKLDK;
ASLGILALSPVKLDKG; SLGILALSPVKLDKGH;
LGILALSPVKLDKGHG; GILALSPVKLDKGHGS;
ILALSPVKLDKGHGSA; LALSPVKLDKGHGSAP;
ALSPVKLDKGHGSAPA; LSPVKLDKGHGSAPAV;
SPVKLDKGHGSAPAVT; PVKLDKGHGSAPAVTT;
VKLDKGHGSAPAVTTS; KLDKGHGSAPAVTTSF;
LDKGHGSAPAVTTSFS; DKGHGSAPAVTTSFSE;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

KGHGSAPAVTTSFSES; GHGSAPAVTTSFSESW;
NLDWNKKKSSEDFYFY; LDWNKKKSSEDFYFYF;
DWNKKKSSEDFYFYFR; WNKKKSSEDFYFYFRA;
NKKKSSEDFYFYFRAF; KKKSSEDFYFYFRAFA;
KKSSEDFYFYFRAFAG; KSSEDFYFYFRAFAGI;
SSEDFYFYFRAFAGIL; RQCRREKQKYHCFTCC;
QCRREKQKYHCFTCCK; CRREKQKYHCFTCCKR;
RREKQKYHCFTCCKRL; REKQKYHCFTCCKRLC;
EKQKYHCFTCCKRLCK; KQKYHCFTCCKRLCKR;
QKYHCFTCCKRLCKRL; KYHCFTCCKRLCKRLL;
YHCFTCCKRLCKRLLG; HCFTCCKRLCKRLLGK;
SLFFCISRFMGAALAL; LFFCISRFMGAALALL;
FFCISRFMGAALALLG; FCISRFMGAALALLGD;
CISRFMGAALALLGDL; ISRFMGAALALLGDLV;
SRFMGAALALLGDLVA; RFMGAALALLGDLVAS;
FMGAALALLGDLVASV; MGAALALLGDLVASVS;
GAALALLGDLVASVSE; AALALLGDLVASVSEA;
ALALLGDLVASVSEAA; LALLGDLVASVSEAAA;
ALLGDLVASVSEAAAA; LLGDLVASVSEAAAAT;
LGDLVASVSEAAAATG; GDLVASVSEAAAATGF;
DLVASVSEAAAATGFS; LVASVSEAAAATGFSV;
VASVSEAAAATGFSVA; ASVSEAAAATGFSVAE;
SVSEAAAATGFSVAEI; VSEAAAATGFSVAEIA;
SEAAAATGFSVAEIAA; EAAAATGFSVAEIAAG;
AAAATGFSVAEIAAGE; AAATGFSVAEIAAGEA;
AATGFSVAEIAAGEAA; ATGFSVAEIAAGEAAA;
TGFSVAEIAAGEAAAA; GFSVAEIAAGEAAAAI;
FSVAEIAAGEAAAAIE; SVAEIAAGEAAAAIEV;
VAEIAAGEAAAAIEVQ; AEIAAGEAAAAIEVQI;
EIAAGEAAAAIEVQIA; IAAGEAAAAIEVQIAS;
AAGEAAAAIEVQIASL; AGEAAAAIEVQIASLA;
GEAAAAIEVQIASLAT; EAAAAIEVQIASLATV;
AAAAIEVQIASLATVE; AAAIEVQIASLATVEG;
AAIEVQIASLATVEGI; AIEVQIASLATVEGIT;
IEVQIASLATVEGITS; EVQIASLATVEGITST;
VQIASLATVEGITSTS; QIASLATVEGITSTSE;
IASLATVEGITSTSEA; ASLATVEGITSTSEAI;
SLATVEGITSTSEAIA; LATVEGITSTSEAIAA;
ATVEGITSTSEAIAAI; TVEGITSTSEAIAAIG;
VEGITSTSEAIAAIGL; EGITSTSEAIAAIGLT;
GITSTSEAIAAIGLTP; ITSTSEAIAAIGLTPQ;
TSTSEAIAAIGLTPQT; STSEAIAAIGLTPQTY;
TSEAIAAIGLTPQTYA; SEAIAAIGLTPQTYAV;
EAIAAIGLTPQTYAVI; AIAAIGLTPQTYAVIA;
IAAIGLTPQTYAVIAG; AAIGLTPQTYAVIAGA;
AIGLTPQTYAVIAGAP; IGLTPQTYAVIAGAPG;
GLTPQTYAVIAGAPGA; LTPQTYAVIAGAPGAI;
TPQTYAVIAGAPGAIA; PQTYAVIAGAPGAIAG;
QTYAVIAGAPGAIAGF; TYAVIAGAPGAIAGFA;
YAVIAGAPGAIAGFAA; AVIAGAPGAIAGFAAL;
VIAGAPGAIAGFAALI; IAGAPGAIAGFAALIQ;
AGAPGAIAGFAALIQT; GAPGAIAGFAALIQTV;
APGAIAGFAALIQTVS; PGAIAGFAALIQTVSG;
GAIAGFAALIQTVSGI; AIAGFAALIQTVSGIS;
IAGFAALIQTVSGISS; AGFAALIQTVSGISSL;
GFAALIQTVSGISSLA; FAALIQTVSGISSLAQ;
AALIQTVSGISSLAQV; ALIQTVSGISSLAQVG;
LIQTVSGISSLAQVGY; IQTVSGISSLAQVGYK;
QTVSGISSLAQVGYKF; TVSGISSLAQVGYKFF;
VSGISSLAQVGYKFFD; SGISSLAQVGYKFFDD;
GISSLAQVGYKFFDDW; ISSLAQVGYKFFDDWD;
SSLAQVGYKFFDDWDH; SLAQVGYKFFDDWDHK;
LAQVGYKFFDDWDHKV; AQVGYKFFDDWDHKVS;
QVGYKFFDDWDHKVST; VGYKFFDDWDHKVSTV;
GYKFFDDWDHKVSTVG; YKFFDDWDHKVSTVGL;
KFFDDWDHKVSTVGLY; FFDDWDHKVSTVGLYQ;
FDDWDHKVSTVGLYQQ; DDWDHKVSTVGLYQQS;
DWDHKVSTVGLYQQSG; WDHKVSTVGLYQQSGM;
DHKVSTVGLYQQSGMA; HKVSTVGLYQQSGMAL;
KVSTVGLYQQSGMALE; VSTVGLYQQSGMALEL;
STVGLYQQSGMALELF; TVGLYQQSGMALELFN;
VGLYQQSGMALELFNP; GLYQQSGMALELFNPD;
LYQQSGMALELFNPDE; YQQSGMALELFNPDEY;
QQSGMALELFNPDEYY; QSGMALELFNPDEYYD;

SGMALELFNPDEYYDI; GMALELFNPDEYYDIL;
MALELFNPDEYYDILF; ALELFNPDEYYDILFP;
LELFNPDEYYDILFPG; ELFNPDEYYDILFPGV;
LFNPDEYYDILFPGVN; FNPDEYYDILFPGVNT;
NPDEYYDILFPGVNTF; PDEYYDILFPGVNTFV;
DEYYDILFPGVNTFVN; EYYDILFPGVNTFVNN;
YYDILFPGVNTFVNNI; YDILFPGVNTFVNNIQ;
DILFPGVNTFVNNIQY; ILFPGVNTFVNNIQYL;
LFPGVNTFVNNIQYLD; FPGVNTFVNNIQYLDP;
PGVNTFVNNIQYLDPR; GVNTFVNNIQYLDPRH;
VNTFVNNIQYLDPRHW; NTFVNNIQYLDPRHWG;
TFVNNIQYLDPRHWGP; FVNNIQYLDPRHWGPS;
VNNIQYLDPRHWGPSL; NNIQYLDPRHWGPSLF;
NIQYLDPRHWGPSLFA; IQYLDPRHWGPSLFAT;
QYLDPRHWGPSLFATI; YLDPRHWGPSLFATIS;
LDPRHWGPSLFATISQ; DPRHWGPSLFATISQA;
PRHWGPSLFATISQAL; RHWGPSLFATISQALW;
HWGPSLFATISQALWH; WGPSLFATISQALWHV;
GPSLFATISQALWHVI; PSLFATISQALWHVIR;
SLFATISQALWHVIRD; LFATISQALWHVIRDD;
FATISQALWHVIRDDI; ATISQALWHVIRDDIP;
TISQALWHVIRDDIPS; ISQALWHVIRDDIPSI;
SQALWHVIRDDIPSIT; QALWHVIRDDIPSITS;
ALWHVIRDDIPSITSQ; LWHVIRDDIPSITSQE;
WHVIRDDIPSITSQEL; HVIRDDIPSITSQELQ;
VIRDDIPSITSQELQR; IRDDIPSITSQELQRR;
RDDIPSITSQELQRRT; DDIPSITSQELQRRTE;
DIPSITSQELQRRTER; IPSITSQELQRRTERF;
PSITSQELQRRTERFF; SITSQELQRRTERFFR;
ITSQELQRRTERFFRD; TSQELQRRTERFFRDS;
SQELQRRTERFFRDSL; QELQRRTERFFRDSLA;
ELQRRTERFFRDSLAR; LQRRTERFFRDSLARF;
QRRTERFFRDSLARFL; RRTERFFRDSLARFLE;
RTERFFRDSLARFLEE; TERFFRDSLARFLEET;
ERFFRDSLARFLEETT; RFFRDSLARFLEETTW;
FFRDSLARFLEETTWT; FRDSLARFLEETTWTI;
RDSLARFLEETTWTIV; DSLARFLEETTWTIVN;
SLARFLEETTWTIVNA; LARFLEETTWTIVNAP;
ARFLEETTWTIVNAPI; RFLEETTWTIVNAPIN;
FLEETTWTIVNAPINF; LEETTWTIVNAPINFY;
EETTWTIVNAPINFYN; ETTWTIVNAPINFYNY;
TTWTIVNAPINFYNYI; TWTIVNAPINFYNYIQ;
WTIVNAPINFYNYIQQ; TIVNAPINFYNYIQQY;
IVNAPINFYNYIQQYY; VNAPINFYNYIQQYYS;
NAPINFYNYIQQYYSD; APINFYNYIQQYYSDL;
PINFYNYIQQYYSDLS; INFYNYIQQYYSDLSP;
NFYNYIQQYYSDLSPI; FYNYIQQYYSDLSPIR;
YNYIQQYYSDLSPIRP; NYIQQYYSDLSPIRPS;
YIQQYYSDLSPIRPSM; IQQYYSDLSPIRPSMV;
QQYYSDLSPIRPSMVR; QYYSDLSPIRPSMVRQ;
YYSDLSPIRPSMVRQV; YSDLSPIRPSMVRQVA;
SDLSPIRPSMVRQVAE; DLSPIRPSMVRQVAER;
LSPIRPSMVRQVAERE; SPIRPSMVRQVAEREG;
PIRPSMVRQVAEREGT; IRPSMVRQVAEREGTR;
RPSMVRQVAEREGTRV; PSMVRQVAEREGTRVH;
SMVRQVAEREGTRVHF; MVRQVAEREGTRVHFG;
VRQVAEREGTRVHFGH; RQVAEREGTRVHFGHT;
QVAEREGTRVHFGHTY; VAEREGTRVHFGHTYS;
AEREGTRVHFGHTYSI; EREGTRVHFGHTYSID;
REGTRVHFGHTYSIDD; EGTRVHFGHTYSIDDA;
GTRVHFGHTYSIDDAD; TRVHFGHTYSIDDADS;
RVHFGHTYSIDDADSI; VHFGHTYSIDDADSIE;
HFGHTYSIDDADSIEE; FGHTYSIDDADSIEEV;
GHTYSIDDADSIEEVT; HTYSIDDADSIEEVTQ;
TYSIDDADSIEEVTQR; YSIDDADSIEEVTQRM;
SIDDADSIEEVTQRMD; IDDADSIEEVTQRMDL;
DDADSIEEVTQRMDLR; DADSIEEVTQRMDLRN;
ADSIEEVTQRMDLRNQ; DSIEEVTQRMDLRNQQ;
SIEEVTQRMDLRNQQS; IEEVTQRMDLRNQQSV;
EEVTQRMDLRNQQSVH; EVTQRMDLRNQQSVHS;
VTQRMDLRNQQSVHSG; TQRMDLRNQQSVHSGE;
QRMDLRNQQSVHSGEF; RMDLRNQQSVHSGEFI;
MDLRNQQSVHSGEFIE; DLRNQQSVHSGEFIEK;
LRNQQSVHSGEFIEKT; RNQQSVHSGEFIEKTI;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

NQQSVHSGEFIEKTIA; QQSVHSGEFIEKTIAP;
QSVHSGEFIEKTIAPG; SVHSGEFIEKTIAPGG;
VHSGEFIEKTIAPGGA; HSGEFIEKTIAPGGAN;
SGEFIEKTIAPGGANQ; GEFIEKTIAPGGANQR;
EFIEKTIAPGGANQRT; FIEKTIAPGGANQRTA;
IEKTIAPGGANQRTAP; EKTIAPGGANQRTAPQ;
KTIAPGGANQRTAPQW; TIAPGGANQRTAPQWM;
IAPGGANQRTAPQWML; APGGANQRTAPQWMLP;
PGGANQRTAPQWMLPL; GGANQRTAPQWMLPLL;
GANQRTAPQWMLPLLL; ANQRTAPQWMLPLLLG;
NQRTAPQWMLPLLLGL; QRTAPQWMLPLLLGLY;
RTAPQWMLPLLLGLYG; TAPQWMLPLLLGLYGT;
APQWMLPLLLGLYGTV; PQWMLPLLLGLYGTVT;
QWMLPLLLGLYGTVTP; WMLPLLLGLYGTVTPA;
MLPLLLGLYGTVTPAL; LPLLLGLYGTVTPALE;
PLLLGLYGTVTPALEA; LLLGLYGTVTPALEAY;
LLGLYGTVTPALEAYE; LGLYGTVTPALEAYED;
GLYGTVTPALEAYEDG; LYGTVTPALEAYEDGP;
YGTVTPALEAYEDGPN; GTVTPALEAYEDGPNQ;
TVTPALEAYEDGPNQK; VTPALEAYEDGPNQKK;
TPALEAYEDGPNQKKR; PALEAYEDGPNQKKRR;
ALEAYEDGPNQKKRRV; LEAYEDGPNQKKRRVS;
EAYEDGPNQKKRRVSR; AYEDGPNQKKRRVSRG;
YEDGPNQKKRRVSRGS; EDGPNQKKRRVSRGSS;
DGPNQKKRRVSRGSSQ; GPNQKKRRVSRGSSQK;
PNQKKRRVSRGSSQKA; NQKKRRVSRGSSQKAK;
QKKRRVSRGSSQKAKG; KKRRVSRGSSQKAKGT;
KRRVSRGSSQKAKGTR; RRVSRGSSQKAKGTRA;
RVSRGSSQKAKGTRAS; VSRGSSQKAKGTRASA;
SRGSSQKAKGTRASAK; RGSSQKAKGTRASAKT;
GSSQKAKGTRASAKTT; SSQKAKGTRASAKTTN;
SQKAKGTRASAKTTNK; QKAKGTRASAKTTNKR;
KAKGTRASAKTTNKRR; AKGTRASAKTTNKRRS;
KGTRASAKTTNKRRSR; GTRASAKTTNKRRSRS;
TRASAKTTNKRRSRSS; RASAKTTNKRRSRSSR;
ASAKTTNKRRSRSSRS; NWGRCYYRGRMLPKPR;
WGRCYYRGRMLPKPRN; GRCYYRGRMLPKPRNG;
RCYYRGRMLPKPRNGG; CYYRGRMLPKPRNGGS;
YYRGRMLPKPRNGGSR; PREKNASLLQHSKNSP;
REKNASLLQHSKNSPP; EKNASLLQHSKNSPPQ;
KNASLLQHSKNSPPQF; NASLLQHSKNSPPQFK;
GPNLWKSTDVGGCNCT; PNLWKSTDVGGCNCTN;
NLWKSTDVGGCNCTNR; LWKSTDVGGCNCTNRG;
WKSTDVGGCNCTNRGY; KSTDVGGCNCTNRGYW;
STDVGGCNCTNRGYWN; TDVGGCNCTNRGYWNN;
FPLLCCRWRTLGNAGS; PLLCCRWRTLGNAGSA;
LLCCRWRTLGNAGSAN; LCCRWRTLGNAGSANE;
CCRWRTLGNAGSANEL; CRWRTLGNAGSANELQ;
RWRTLGNAGSANELQV; WRTLGNAGSANELQVK;
RTLGNAGSANELQVKV; TLGNAGSANELQVKVP;
VFWDFHRRGKCSPSTS; FWDFHRRGKCSPSTSC;
WDFHRRGKCSPSTSCD; DFHRRGKCSPSTSCDQ;
FHRRGKCSPSTSCDQH; HRRGKCSPSTSCDQHS;
RRGKCSPSTSCDQHSY; RGKCSPSTSCDQHSYH;
GKCSPSTSCDQHSYHS; KCSPSTSCDQHSYHSV;
CSPSTSCDQHSYHSVA; SPSTSCDQHSYHSVAR;
DPPEKKICKESLPNFL; PPEKKICKESLPNFLF;
PEKKICKESLPNFLFA; EKKICKESLPNFLFAK;
PYKQENPESGWAAYVW; YKQENPESGWAAYVWY;
KQENPESGWAAYVWYG; QENPESGWAAYVWYGI;
ENPESGWAAYVWYGIP; NPESGWAAYVWYGIPG;
PESGWAAYVWYGIPGR; ESGWAAYVWYGIPGRR;
SGWAAYVWYGIPGRRG; QTGTIANQNALNRCFY;
TGTIANQNALNRCFYC; GTIANQNALNRCFYCT;
TIANQNALNRCFYCTY; IANQNALNRCFYCTYT;
ANQNALNRCFYCTYTF; NQNALNRCFYCTYTFN;
QNALNRCFYCTYTFNK; NALNRCFYCTYTFNKC;
ALNRCFYCTYTFNKCC; LNRCFYCTYTFNKCCF;
NRCFYCTYTFNKCCFC; RCFYCTYTFNKCCFCI;
CFYCTYTFNKCCFCIS; FYCTYTFNKCCFCISH;
YCTYTFNKCCFCISHF; NTESLYTNATLDYGGL;
TESLYTNATLDYGGLT; ESLYTNATLDYGGLTF;
SLYTNATLDYGGLTFG; LYTNATLDYGGLTFGN;
YTNATLDYGGLTFGNL; TNATLDYGGLTFGNLQ;

NATLDYGGLTFGNLQQ; ATLDYGGLTFGNLQQG;
TLDYGGLTFGNLQQGL; LDYGGLTFGNLQQGLK;
DYGGLTFGNLQQGLKY; YGGLTFGNLQQGLKYL;
GGLTFGNLQQGLKYLR; GLTFGNLQQGLKYLRL;
LTFGNLQQGLKYLRLG; TFGNLQQGLKYLRLGK;
FGNLQQGLKYLRLGKS; GNLQQGLKYLRLGKSI;
NLQQGLKYLRLGKSIV; LQQGLKYLRLGKSIVI;
QQGLKYLRLGKSIVIG; QGLKYLRLGKSIVIGI;
GLKYLRLGKSIVIGIQ; LKYLRLGKSIVIGIQC;
KYLRLGKSIVIGIQCL; YLRLGKSIVIGIQCLI;
LRLGKSIVIGIQCLIH; RLGKSIVIGIQCLIHV;
LGKSIVIGIQCLIHVQ; GKSIVIGIQCLIHVQS;
KSIVIGIQCLIHVQSL; SIVIGIQCLIHVQSLQ;
IVIGIQCLIHVQSLQF; VIGIQCLIHVQSLQFL;
IGIQCLIHVQSLQFLN; GIQCLIHVQSLQFLNP;
IQCLIHVQSLQFLNPL; QCLIHVQSLQFLNPLL;
CLIHVQSLQFLNPLLL; YQEYISPCIYYISSLK;
QEYISPCIYYISSLKK; EYISPCIYYISSLKKY;
YISPCIYYISSLKKYT; ISPCIYYISSLKKYTY;
SPCIYYISSLKKYTYL; PCIYYISSLKKYTYLS;
CIYYISSLKKYTYLSQ; IYYISSLKKYTYLSQN;
YYISSLKKYTYLSQNP; YISSLKKYTYLSQNPA;
ISSLKKYTYLSQNPAF; SSLKKYTYLSQNPAFP;
SLKKYTYLSQNPAFPS; LKKYTYLSQNPAFPSI;
KKYTYLSQNPAFPSIQ; KYTYLSQNPAFPSIQQ;
YTYLSQNPAFPSIQQF; TKLAVATRSFHFVKFF;
KLAVATRSFHFVKFFF; LAVATRSFHFVKFFFQ;
AVATRSFHFVKFFFQV; VATRSFHFVKFFFQVR;
ATRSFHFVKFFFQVRT; TRSFHFVKFFFQVRTL;
RSFHFVKFFFQVRTLS; SFHFVKFFFQVRTLSF;
FHFVKFFFQVRTLSFV; HFVKFFFQVRTLSFVR;
FVKFFFQVRTLSFVRI; VKFFFQVRTLSFVRIF;
KFFFQVRTLSFVRIFL; FFFQVRTLSFVRIFLN;
FFQVRTLSFVRIFLNI; FQVRTLSFVRIFLNIF;
QVRTLSFVRIFLNIFW; VRTLSFVRIFLNIFWA;
PSLVEIFGFFCLNVSF; SLVEIFGFFCLNVSFL;
LVEIFGFFCLNVSFLN; VEIFGFFCLNVSFLNL;
EIFGFFCLNVSFLNLP; HFHLNNLSNCLNCLFH;
FHLNNLSNCLNCLFHV; HLNNLSNCLNCLFHVL;
LNNLSNCLNCLFHVLK; NNLSNCLNCLFHVLKA;
NLSNCLNCLFHVLKAN; LSNCLNCLFHVLKANP;
SNCLNCLFHVLKANPL; NCLNCLFHVLKANPLI;
CLNCLFHVLKANPLIQ; LNCLFHVLKANPLIQL;
NCLFHVLKANPLIQLL; CLFHVLKANPLIQLLS;
LFHVLKANPLIQLLSL; FHVLKANPLIQLLSLL;
HVLKANPLIQLLSLLH; VLKANPLIQLLSLLHL;
LKANPLIQLLSLLHLQ; KANPLIQLLSLLHLQK;
ANPLIQLLSLLHLQKQ; NPLIQLLSLLHLQKQP;
PLIQLLSLLHLQKQPC; LIQLLSLLHLQKQPCT;
IQLLSLLHLQKQPCTD; QLLSLLHLQKQPCTDL;
LHLAQRLAFPWVGLHL; HLAQRLAFPWVGLHLR;
LAQRLAFPWVGLHLRL; AQRLAFPWVGLHLRLY;
QRLAFPWVGLHLRLYH; RLAFPWVGLHLRLYHH;
LAFPWVGLHLRLYHHT; AFPWVGLHLRLYHHTN;
FPWVGLHLRLYHHTNL; PWVGLHLRLYHHTNLI;
WVGLHLRLYHHTNLIT; VGLHLRLYHHTNLITL;
GLHLRLYHHTNLITLQ; LHLRLYHHTNLITLQL;
HLRLYHHTNLITLQLV; LRLYHHTNLITLQLVL;
RLYHHTNLITLQLVLF; LYHHTNLITLQLVLFF;
YHHTNLITLQLVLFFH; HHTNLITLQLVLFFHY;
HTNLITLQLVLFFHYQ; TNLITLQLVLFFHYQW;
NLITLQLVLFFHYQWD; LITLQLVLFFHYQWDL;
VANSAAKQHLPYIVLV; ANSAAKQHLPYIVLVQ;
NSAAKQHLPYIVLVQH; SAAKQHLPYIVLVQHF;
AAKQHLPYIVLVQHFH; AKQHLPYIVLVQHFHE;
KQHLPYIVLVQHFHEL; QHLPYIVLVQHFHELQ;
HLPYIVLVQHFHELQI; LPYIVLVQHFHELQIL;
PYIVLVQHFHELQILN; YIVLVQHFHELQILNP;
IVLVQHFHELQILNPF; VLVQHFHELQILNPFY;
LVQHFHELQILNPFYL; VQHFHELQILNPFYLI;
QHFHELQILNPFYLIY; HFHELQILNPFYLIYD;
IFLLAFLPWSYEGYLL; FLLAFLPWSYEGYLLF;
LLAFLPWSYEGYLLFF; LKLYLLLADKYFFDFY;
KLYLLLADKYFFDFYF; LYLLLADKYFFDFYFL;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

YLLLADKYFFDFYFLQ; LLLADKYFFDFYFLQK;
SDKAGLFSDTFYTPLH; DKAGLFSDTFYTPLHC;
KAGLFSDTFYTPLHCI; AGLFSDTFYTPLHCIE;
GLFSDTFYTPLHCIEI; LFSDTFYTPLHCIEIL;
FSDTFYTPLHCIEILN; SDTFYTPLHCIEILNT;
DTFYTPLHCIEILNTY; TFYTPLHCIEILNTYL;
FYTPLHCIEILNTYLI; YTPLHCIEILNTYLII;
TPLHCIEILNTYLIIK; PLHCIEILNTYLIIKT;
LHCIEILNTYLIIKTH; HCIEILNTYLIIKTHP;
CIEILNTYLIIKTHPH; IEILNTYLIIKTHPHT;
EILNTYLIIKTHPHTL; ILNTYLIIKTHPHTLS;
LNTYLIIKTHPHTLSL; NTYLIIKTHPHTLSLL;
TYLIIKTHPHTLSLLH; YLIIKTHPHTLSLLHT;
LIIKTHPHTLSLLHTQ; GLLPFFFFWVVLSVEN;
LLPFFFFWVVLSVENL; LPFFFFWVVLSVENLL;
PFFFFWVVLSVENLLL; FFFFWVVLSVENLLLL;
FFFWVVLSVENLLLLL; FFWVVLSVENLLLLLH;
FWVVLSVENLLLLLHH; WVVLSVENLLLLLHHW;
VVLSVENLLLLLHHWQ; VLSVENLLLLLHHWQT;
LSVENLLLLLHHWQTY; SVENLLLLLHHWQTYL;
VENLLLLLHHWQTYLH; ENLLLLLHHWQTYLHG;
NLLLLLHHWQTYLHGK; LLLLLHHWQTYLHGKI;
LLLLHHWQTYLHGKIN; LLLHHWQTYLHGKINL;
LLHHWQTYLHGKINLH; LHHWQTYLHGKINLHP;
HHWQTYLHGKINLHPI; HWQTYLHGKINLHPIF;
WQTYLHGKINLHPIFH; RNSTRTPTLLFHRLAP;
NSTRTPTLLFHRLAPI; STRTPTLLFHRLAPIK;
TRTPTLLFHRLAPIKK; RTPTLLFHRLAPIKKI;
TPTLLFHRLAPIKKII; PTLLFHRLAPIKKIIT;
GLLIFYYLSKYKLVTL; LLIFYYLSKYKLVTLK;
LIFYYLSKYKLVTLKL; ISEGSFSNYLDPPLQS;
SEGSFSNYLDPPLQSF; EGSFSNYLDPPLQSFF;
GSFSNYLDPPLQSFFS; AKPLCEAVNAVAIYPN;
KPLCEAVNAVAIYPNQ; PLCEAVNAVAIYPNQG;
LCEAVNAVAIYPNQGL; CEAVNAVAIYPNQGLF;
EAVNAVAIYPNQGLFS; HARAVHRRLFGTNRPF;
ARAVHRRLFGTNRPFL; RAVHRRLFGTNRPFLA;
AVHRRLFGTNRPFLAV; VHRRLFGTNRPFLAVQ;
HRRLFGTNRPFLAVQG; RRLFGTNRPFLAVQGI;
RLFGTNRPFLAVQGIW; LFGTNRPFLAVQGIWA;
FGTNRPFLAVQGIWAK; GTNRPFLAVQGIWAKR;
TNRPFLAVQGIWAKRK; NRPFLAVQGIWAKRKI;
RPFLAVQGIWAKRKIS; PFLAVQGIWAKRKIST;
FLAVQGIWAKRKISTN; LAVQGIWAKRKISTNL;
ATPGSKIRLMSYLYIL; TPGSKIRLMSYLYILL;
PGSKIRLMSYLYILLH; GSKIRLMSYLYILLHF;
SKIRLMSYLYILLHFF; KIRLMSYLYILLHFFI;
IRLMSYLYILLHFFIQ; RLMSYLYILLHFFIQS;
LMSYLYILLHFFIQSI; MSYLYILLHFFIQSIH;
SYLYILLHFFIQSIHS; YLYILLHFFIQSIHSL;
LYILLHFFIQSIHSLH; YILLHFFIQSIHSLHF;
ILLHFFIQSIHSLHFI; LLHFFIQSIHSLHFIL;
LHFFIQSIHSLHFILV; HFFIQSIHSLHFILVA;
FFIQSIHSLHFILVAP; FIQSIHSLHFILVAPF;
IQSIHSLHFILVAPFV; QSIHSLHFILVAPFVR;
SIHSLHFILVAPFVRV; IHSLHFILVAPFVRVK;
HSLHFILVAPFVRVKF; SLHFILVAPFVRVKFL;
LHFILVAPFVRVKFLT; HFILVAPFVRVKFLT

---

BK virus reverse reading frame 1

13 mers:

MDKVLNREESMEL; DKVLNREESMELM; KVLNREESMELMD;
VLNREESMELMDL; LNREESMELMDLL; NREESMELMDLLG;
REESMELMDLLGL; EESMELMDLLGLE; ESMELMDLLGLER;
SMELMDLLGLERA; MELMDLLGLERAA; ELMDLLGLERAAW;
LMDLLGLERAAWG; MDLLGLERAAWGN; DLLGLERAAWGNL;
LLGLERAAWGNLP; LGLERAAWGNLPL; GLERAAWGNLPLM;
LERAAWGNLPLMR; ERAAWGNLPLMRK; RAAWGNLPLMRKA;
AAWGNLPLMRKAY; AWGNLPLMRKAYL; WGNLPLMRKAYLR;
GNLPLMRKAYLRK; NLPLMRKAYLRKC; LPLMRKAYLRKCK;
PLMRKAYLRKCKE; LMRKAYLRKCKEF; MRKAYLRKCKEFH;

RKAYLRKCKEFHP; KAYLRKCKEFHPD; AYLRKCKEFHPDK;
YLRKCKEFHPDKG; LRKCKEFHPDKGG; RKCKEFHPDKGGD;
KCKEFHPDKGGDE; CKEFHPDKGGDED; KEFHPDKGGDEDK;
EFHPDKGGDEDKM; FHPDKGGDEDKMK; HPDKGGDEDKMKR;
PDKGGDEDKMKRM; DKGGDEDKMKRMN; KGGDEDKMKRMNT;
GGDEDKMKRMNTL; GDEDKMKRMNTLY; DEDKMKRMNTLYK;
EDKMKRMNTLYKK; DKMKRMNTLYKKM; KMKRMNTLYKKME;
MKRMNTLYKKMEQ; KRMNTLYKKMEQD; RMNTLYKKMEQDV;
MNTLYKKMEQDVK; NTLYKKMEQDVKV; TLYKKMEQDVKVA;
LYKKMEQDVKVAH; YKKMEQDVKVAHQ; KKMEQDVKVAHQP;
KMEQDVKVAHQPD; MEQDVKVAHQPDF; EQDVKVAHQPDFG;
QDVKVAHQPDFGT; DVKVAHQPDFGTW; VKVAHQPDFGTWS;
KVAHQPDFGTWSS; VAHQPDFGTWSSS; AHQPDFGTWSSSE;
HQPDFGTWSSSEV; QPDFGTWSSSEVC; PDFGTWSSSEVCA;
DFGTWSSSEVCAD; FGTWSSSEVCADF; GTWSSSEVCADFP;
TWSSSEVCADFPL; WSSSEVCADFPLC; SSSEVCADFPLCP;
SSEVCADFPLCPD; SEVCADFPLCPDT; EVCADFPLCPDTL;
VCADFPLCPDTLY; CADFPLCPDTLYC; ADFPLCPDTLYCK;
DFPLCPDTLYCKE; FPLCPDTLYCKEW; PLCPDTLYCKEWP;
LCPDTLYCKEWPI; CPDTLYCKEWPIC; PDTLYCKEWPICS;
DTLYCKEWPICSK; TLYCKEWPICSKK; LYCKEWPICSKKP;
YCKEWPICSKKPS; CKEWPICSKKPSV; KEWPICSKKPSVH;
EWPICSKKPSVHC; WPICSKKPSVHCP; PICSKKPSVHCPC;
ICSKKPSVHCPCM; CSKKPSVHCPCML; SKKPSVHCPCMLC;
KKPSVHCPCMLCQ; KPSVHCPCMLCQL; PSVHCPCMLCQLR;
SVHCPCMLCQLRL; VHCPCMLCQLRLR; HCPCMLCQLRLRH;
CPCMLCQLRLRHL; PCMLCQLRLRHLN; CMLCQLRLRHLNR;
MLCQLRLRHLNRK; LCQLRLRHLNRKF; CQLRLRHLNRKFL;
QLRLRHLNRKFLR; LRLRHLNRKFLRK; RLRHLNRKFLRKE;
LRHLNRKFLRKEP; RHLNRKFLRKEPL; HLNRKFLRKEPLV;
LNRKFLRKEPLVW; NRKFLRKEPLVWI; RKFLRKEPLVWID;
KFLRKEPLVWIDC; FLRKEPLVWIDCY; LRKEPLVWIDCYC;
RKEPLVWIDCYCI; KEPLVWIDCYCID; EPLVWIDCYCIDC;
PLVWIDCYCIDCF; LVWIDCYCIDCFT; VWIDCYCIDCFTQ;
WIDCYCIDCFTQW; IDCYCIDCFTQWF; DCYCIDCFTQWFG;
CYCIDCFTQWFGL; YCIDCFTQWFGLD; CIDCFTQWFGLDL;
IDCFTQWFGLDLT; DCFTQWFGLDLTE; CFTQWFGLDLTEE;
FTQWFGLDLTEET; TQWFGLDLTEETL; QWFGLDLTEETLQ;
WFGLDLTEETLQW; FGLDLTEETLQWW; GLDLTEETLQWWV;
LDLTEETLQWWVQ; DLTEETLQWWVQI; LTEETLQWWVQII;
TEETLQWWVQIIG; EETLQWWVQIIGE; ETLQWWVQIIGET;
TLQWWVQIIGETP; LQWWVQIIGETPF; QWWVQIIGETPFR;
WWVQIIGETPFRD; WVQIIGETPFRDL; VQIIGETPFRDLK;
QIIGETPFRDLKL; KALSNYFFYRCQP; ALSNYFFYRCQPM;
LSNYFFYRCQPME; SNYFFYRCQPMEQ; NYFFYRCQPMEQK;
YFFYRCQPMEQKS; FFYRCQPMEQKSG; FYRCQPMEQKSGS;
YRCQPMEQKSGSP; RCQPMEQKSGSPG; CQPMEQKSGSPGG;
QPMEQKSGSPGGV; PMEQKSGSPGGVP; MEQKSGSPGGVPL;
EQKSGSPGGVPLM; QKSGSPGGVPLMK; KSGSPGGVPLMKN;
SGSPGGVPLMKNG; GSPGGVPLMKNGM; SPGGVPLMKNGMK;
PGGVPLMKNGMKI; GGVPLMKNGMKIY; GVPLMKNGMKIYF;
VPLMKNGMKIYFA; PLMKNGMKIYFAM; LMKNGMKIYFAMK;
MKNGMKIYFAMKI; KNGMKIYFAMKIC; NGMKIYFAMKICL;
GMKIYFAMKICLP; MKIYFAMKICLPV; KIYFAMKICLPVM;
IYFAMKICLPVMK; YFAMKICLPVMKK; FAMKICLPVMKKQ;
AMKICLPVMKKQQ; MKICLPVMKKQQQ; KICLPVMKKQQQI;
ICLPVMKKQQQIL; CLPVMKKQQQILN; LPVMKKQQQILNT;
PVMKKQQQILNTQ; VMKKQQQILNTQH; MKKQQQILNTQHH;
KKQQQILNTQHHP; KQQQILNTQHHPK; QQQILNTQHHPKK;
QQILNTQHHPKKK; QILNTQHHPKKKE; ILNTQHHPKKKER;
KTLKTFPLIYTSF; TLKTFPLIYTSFL; LKTFPLIYTSFLV;
KTFPLIYTSFLVK; TFPLIYTSFLVKL; FPLIYTSFLVKLY;
PLIYTSFLVKLYL; LIYTSFLVKLYLV; IYTSFLVKLYLVI;
YTSFLVKLYLVIE; TSFLVKLYLVIEP; SFLVKLYLVIEPL;
FLVKLYLVIEPLP; LVKLYLVIEPLPA; VKLYLVIEPLPAL;
KLYLVIEPLPALL; LYLVIEPLPALLC; YLVIEPLPALLCI;
LVIEPLPALLCIL; VIEPLPALLCILL; IEPLPALLCILLK;
EPLPALLCILLKK; PLPALLCILLKKK; LPALLCILLKKKL;
PALLCILLKKKLK; ALLCILLKKKLKF; LLCILLKKKLKFC;
LCILLKKKLKFCI; CILLKKKLKFCIK; ILLKKKLKFCIKN;
LLKKKLKFCIKNL; LKKKLKFCIKNLW; KKKLKFCIKNLWK;
KKLKFCIKNLWKN; KLKFCIKNLWKNI; LKFCIKNLWKNIL;
LLLVDTCVLGIIL; LLVDTCVLGIILY; LVDTCVLGIILYS;
VDTCVLGIILYSF; LHIDIEFLQLIIS; HIDIEFLQLIISV;

TABLE O-continued

Predicted MHC class 2 BK virus peptide sequences. Prediction of 13-, 14-, 15-, 16-mers from all 6 reading frames of the genome (access no #V01108) obtained using the program displayed in FIG. 2.

IDIEFLQLIISVK; DIEFLQLIISVKS; IEFLQLIISVKSC;
EFLQLIISVKSCV; FLQLIISVKSCVP; LQLIISVKSCVPL;
QLIISVKSCVPLV; LIISVKSCVPLVF; FVRVLIRNTYYIV;
VRVLIRNTYYIVP; RSMILAQKSLKKQ; SMILAQKSLKKQS;
MILAQKSLKKQSR; ILAQKSLKKQSRC; LAQKSLKKQSRCL;
AQKSLKKQSRCLG; QKSLKKQSRCLGN; RSVKSVRKKTSLI;
SVKSVRKKTSLIT; VKSVRKKTSLITL; KSVRKKTSLITLS;
SVRKKTSLITLSI; VRKKTSLITLSIM; RKKTSLITLSIMK;
KKTSLITLSIMKS; KTSLITLSIMKST; TSLITLSIMKSTL;
SLITLSIMKSTLQ; LITLSIMKSTLQM; ITLSIMKSTLQML;
TLSIMKSTLQMLL; LSIMKSTLQMLLF; SIMKSTLQMLLFL;
IMKSTLQMLLFLQ; MKSTLQMLLFLQK; KSTLQMLLFLQKV;
STLQMLLFLQKVK; TLQMLLFLQKVKI; LQMLLFLQKVKIK;
QMLLFLQKVKIKK; MLLFLQKVKIKKV; LLFLQKVKIKKVF;
LFLQKVKIKKVFV; FLQKVKIKKVFVS; LQKVKIKKVFVSK;
QKVKIKKVFVSKQ; NNIWQVLLGCTVC; NIWQVLLGCTVCY;
IWQVLLGCTVCYL; WQVLLGCTVCYLK; QVLLGCTVCYLKW;
VLLGCTVCYLKWI; LLGCTVCYLKWIL; YLIFCTVLFSMYL;
LIFCTVLFSMYLK; IFCTVLFSMYLKE; FCTVLFSMYLKED;
CTVLFSMYLKEDT; TVLFSMYLKEDTG; VLFSMYLKEDTGY;
LFSMYLKEDTGYL; FSMYLKEDTGYLK; SMYLKEDTGYLKV;
MYLKEDTGYLKVP; YLKEDTGYLKVPL; LKEDTGYLKVPLI;
KEDTGYLKVPLIV; EDTGYLKVPLIVE; DTGYLKVPLIVEK;
TGYLKVPLIVEKQ; GYLKVPLIVEKQH; KGQELNQRICLQD;
GQELNQRICLQDM; QELNQRICLQDME; TKEPKYFHQAWLQ;
MSILSLKPCKLDL; ENPYKTQSSYLKK; NPYKTQSSYLKKE;
PYKTQSSYLKKEF; YKTQSSYLKKEFY; KTQSSYLKKEFYK;
TQSSYLKKEFYKV; QSSYLKKEFYKVE; LILQLIYNLELLN;
ILQLIYNLELLNG; LQLIYNLELLNGR; QLIYNLELLNGRK;
LIYNLELLNGRKG; IYNLELLNGRKGW; YNLELLNGRKGWI;
NLELLNGRKGWIL; LELLNGRKGWILR; NIIYAWGNVFLIL;
IIYAWGNVFLILQ; IYAWGNVFLILQE; YAWGNVFLILQEK;
AWGNVFLILQEKR; WGNVFLILQEKRI; GNVFLILQEKRIQ;
NVFLILQEKRIQK; VFLILQEKRIQKL; FLILQEKRIQKLK;
LILQEKRIQKLKT; ILQEKRIQKLKTL; LQEKRIQKLKTLD;
QEKRIQKLKTLDM; EKRIQKLKTLDMD; KRIQKLKTLDMDQ;
RIQKLKTLDMDQA; IQKLKTLDMDQAL; QKLKTLDMDQALN;
KLKTLDMDQALNP; LKTLDMDQALNPN; KTLDMDQALNPNH;
TLDMDQALNPNHN; LDMDQALNPNHNA; DMDQALNPNHNAL;
MDQALNPNHNALP; DQALNPNHNALPK; QALNPNHNALPKS;
ALNPNHNALPKSQ; LNPNHNALPKSQI; NPNHNALPKSQIL;
PNHNALPKSQILQ; NHNALPKSQILQP; HNALPKSQILQPL;
NALPKSQILQPLL; ALPKSQILQPLLK; LPKSQILQPLLKI;
PKSQILQPLLKIP; KSQILQPLLKIPK; SQILQPLLKIPKG;
QILQPLLKIPKGQ; ILQPLLKIPKGQT; LQPLLKIPKGQTP;
QPLLKIPKGQTPI; PLLKIPKGQTPIV; LLKIPKGQTPIVK;
LKIPKGQTPIVKS; KIPKGQTPIVKSC; IPKGQTPIVKSCI;
PKGQTPIVKSCIC; KGQTPIVKSCICV; GQTPIVKSCICVK;
QTPIVKSCICVKA; TPIVKSCICVKAF; PIVKSCICVKAFS;
IVKSCICVKAFSV; VKSCICVKAFSVL; KSCICVKAFSVLK;
SCICVKAFSVLKG; CICVKAFSVLKGL; ICVKAFSVLKGLK;
CVKAFSVLKGLKH; VKAFSVLKGLKHH; KAFSVLKGLKHHP;
AFSVLKGLKHHPQ; FSVLKGLKHHPQN; SVLKGLKHHPQNN;
VLKGLKHHPQNNT; LKGLKHHPQNNTS; KGLKHHPQNNTSL;
GLKHHPQNNTSLK; LKHHPQNNTSLKV; KHHPQNNTSLKVA;
HHPQNNTSLKVAY; HPQNNTSLKVAYT; PQNNTSLKVAYTK;
QNNTSLKVAYTKA; NNTSLKVAYTKAA; NTSLKVAYTKAAF;
TSLKVAYTKAAFI; SLKVAYTKAAFIK; LKVAYTKAAFIKC;
KVAYTKAAFIKCI; VAYTKAAFIKCIC; AYTKAAFIKCICT;
YTKAAFIKCICTI; TKAAFIKCICTIK; KAAFIKCICTIKA;
AAFIKCICTIKAP; AFIKCICTIKAPV; SILVCNCPCLSIY;
ILVCNCPCLSIYL; LVCNCPCLSIYLI; VCNCPCLSIYLII;
CNCPCLSIYLIIS; NCPCLSIYLIISG; CPCLSIYLIISGS;
PCLSIYLIISGSP; CLSIYLIISGSPG; LSIYLIISGSPGS;
SIYLIISGSPGSL; IYLIISGSPGSLS; YLIISGSPGSLSV;
LIISGSPGSLSVP; IISGSPGSLSVPS; ISGSPGSLSVPSN;
SGSPGSLSVPSNT; GSPGSLSVPSNTL; SPGSLSVPSNTLT;
PGSLSVPSNTLTS; GSLSVPSNTLTSS; SLSVPSNTLTSST;
LSVPSNTLTSSTW; SVPSNTLTSSTWD; PSNTLTSSTWDSI;
SNTLTSSTWDSIP; NTLTSSTWDSIPY; TLTSSTWDSIPYI;
LTSSTWDSIPYIG; TSSTWDSIPYIGC; SSTWDSIPYIGCP;
STWDSIPYIGCPS; TWDSIPYIGCPST;
WDSIPYIGCPSTL; DSIPYIGCPSTLW; SIPYIGCPSTLWV;
IPYIGCPSTLWVL; PYIGCPSTLWVLL; YIGCPSTLWVLLF;
IGCPSTLWVLLFI; GCPSTLWVLLFIR; CPSTLWVLLFIRS;
PSTLWVLLFIRSL; STLWVLLFIRSLS; TLWVLLFIRSLSK;
LWVLLFIRSLSKK; WVLLFIRSLSKKE; VLLFIRSLSKKEI;
LLFIRSLSKKEIG; GFFTDLFLRRILK; FFTDLFLRRILKY;
FTDLFLRRILKYL; TDLFLRRILKYLA; DLFLRRILKYLAR;
LFLRRILKYLARP; FLRRILKYLARPL; LRRILKYLARPLH;
RRILKYLARPLHC; RILKYLARPLHCC; ILKYLARPLHCCV;
LKYLARPLHCCVP; KYLARPLHCCVPE; YLARPLHCCVPEL;
LARPLHCCVPELL; ARPLHCCVPELLV; RPLHCCVPELLVN;
PLHCCVPELLVNR; LHCCVPELLVNRP; HCCVPELLVNRPQ;
CCVPELLVNRPQI; CVPELLVNRPQIS; VPELLVNRPQISA;
PELLVNRPQISAA; ELLVNRPQISAAE; LLVNRPQISAAET;
LVNRPQISAAETY; VNRPQISAAETYR; NRPQISAAETYRL;
RPQISAAETYRLS; PQISAAETYRLSA; QISAAETYRLSAL;
ISAAETYRLSALQ; SAAETYRLSALQR; AAETYRLSALQRG;
AETYRLSALQRGP; ETYRLSALQRGPT; TYRLSALQRGPTP;
YRLSALQRGPTPC; RLSALQRGPTPCS; LSALQRGPTPCSS;
SALQRGPTPCSSS; ALQRGPTPCSSSN; LQRGPTPCSSSNT;
QRGPTPCSSSNTV; RGPTPCSSSNTVV; GPTPCSSSNTVVA;
PTPCSSSNTVVAV; TPCSSSNTVVAVL; PCSSSNTVVAVLV;
CSSSNTVVAVLVT; STGGTFSPPVKVP; TGGTFSPPVKVPK;
GGTFSPPVKVPKY; GTFSPPVKVPKYL; TFSPPVKVPKYLA;
FSPPVKVPKYLAF; SPPVKVPKYLAFS; PPVKVPKYLAFSF;
PVKVPKYLAFSFL; VKVPKYLAFSFLL; KVPKYLAFSFLLG;
VPKYLAFSFLLGS; PKYLAFSFLLGSG; KYLAFSFLLGSGT;
YLAFSFLLGSGTQ; LAFSFLLGSGTQH; AFSFLLGSGTQHS;
FSFLLGSGTQHST; SFLLGSGTQHSTG; ALWSVFITWDWAV;
LWSVFITWDWAVG; WSVFITWDWAVGF; SVFITWDWAVGFL;
VFITWDWAVGFLG; FITWDWAVGFLGV; ITWDWAVGFLGVI;
TWDWAVGFLGVIV; WDWAVGFLGVIVP; DWAVGFLGVIVPS;
WAVGFLGVIVPSG; AVGFLGVIVPSGY; VGFLGVIVPSGYF;
GFLGVIVPSGYFD; FLGVIVPSGYFDL; FISTPCISKGSPP;
ISTPCISKGSPPT; STPCISKGSPPTA; TPCISKGSPPTAK;
PCISKGSPPTAKK; CISKGSPPTAKKW; ISKGSPPTAKKWK;
SKGSPPTAKKWKL; KGSPPTAKKWKLL; GSPPTAKKWKLLP;
IGFPPPCSCTFCD; GFPPPCSCTFCDP; FPPPCSCTFCDPA;
RLSMLVIPITSVC; LSMLVIPITSVCT; SMLVIPITSVCTV;
MLVIPITSVCTVT; LVIPITSVCTVTA; VIPITSVCTVTAS;
IPITSVCTVTASH; PITSVCTVTASHI; ITSVCTVTASHIS;
TSVCTVTASHISR; SVCTVTASHISRF; VCTVTASHISRFP;
CTVTASHISRFPQ; TVTASHISRFPQV; VTASHISRFPQVR;
TASHISRFPQVRS; ASHISRFPQVRSS; SHISRFPQVRSSF;
HISRFPQVRSSFK; ISRFPQVRSSFKL; SRFPQVRSSFKLG;
RFPQVRSSFKLGR; FPQVRSSFKLGRG; PQVRSSFKLGRGI;
QVRSSFKLGRGIL; VRSSFKLGRGILA; RSSFKLGRGILAV;
SSFKLGRGILAVL; QGSIFLSGLSLLK; GSIFLSGLSLLKS;
SIFLSGLSLLKSF; IFLSGLSLLKSFS; FLSGLSLLKSFSA;
LSGLSLLKSFSAL; SGLSLLKSFSALS; GLSLLKSFSALSF;
LSLLKSFSALSFR; SLLKSFSALSFRL; LLKSFSALSFRLK;
LKSFSALSFRLKP; KSFSALSFRLKPL; SFSALSFRLKPLR;
FSALSFRLKPLRF; SALSFRLKPLRFS; ALSFRLKPLRFSS;
LSFRLKPLRFSSG; SFRLKPLRFSSGS; FRLKPLRFSSGSP;
RLKPLRFSSGSPI; LKPLRFSSGSPIS; KPLRFSSGSPISG;
PLRFSSGSPISGF; LRFSSGSPISGFR; RFSSGSPISGFRK;
FSSGSPISGFRKH; SSGSPISGFRKHS; SGSPISGFRKHST;
GSPISGFRKHSTS; SPISGFRKHSTSV; PISGFRKHSTSVI;
ISGFRKHSTSVIA; SGFRKHSTSVIAS; GFRKHSTSVIAST;
FRKHSTSVIASTP; RKHSTSVIASTPV; KHSTSVIASTPVL;
HSTSVIASTPVLT; STSVIASTPVLTS; TSVIASTPVLTSR;
SVIASTPVLTSRT; VIASTPVLTSRTS; IASTPVLTSRTST;
ASTPVLTSRTSTP; STPVLTSRTSTPP; TPVLTSRTSTPPF;
PVLTSRTSTPPFI; VLTSRTSTPPFIS; LTSRTSTPPFISS;
TSRTSTPPFISSF; SRTSTPPFISSFG; RTSTPPFISSFGT;
TSTPPFISSFGTC; STPPFISSFGTCT; TPPFISSFGTCTG;
PPFISSFGTCTGS; PFISSFGTCTGSF; FISSFGTCTGSFG;
ISSFGTCTGSFGF; SSFGTCTGSFGFL; SFGTCTGSFGFLG;
FGTCTGSFGFLGA; GTCTGSFGFLGAA; TCTGSFGFLGAAP;
CTGSFGFLGAAPG; TGSFGFLGAAPGH; GSFGFLGAAPGHS;
SFGFLGAAPGHSP; FGFLGAAPGHSPF; GFLGAAPGHSPFL;
FLGAAPGHSPFLL; LGAAPGHSPFLLV; GAAPGHSPFLLVG;
AAPGHSPFLLVGA; APGHSPFLLVGAI; PGHSPFLLVGAIF;
GHSPFLLVGAIFI; HSPFLLVGAIFIC; SPFLLVGAIFICF;
PFLLVGAIFICFK; FLLVGAIFICFKS; LLVGAIFICFKSR;
LVGAIFICFKSRC; VGAIFICFKSRCY; GAIFICFKSRCYS;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

AIFICFKSRCYSP; IFICFKSRCYSPV; FICFKSRCYSPVQ;
ICFKSRCYSPVQA; RQHPLRSSSLIST; QHPLRSSSLISTS;
HPLRSSSLISTSW; PLRSSSLISTSWG; LRSSSLISTSWGN;
RSSSLISTSWGNS; SSSLISTSWGNSF; SSLISTSWGNSFF;
SLISTSWGNSFFY; LISTSWGNSFFYK; ISTSWGNSFFYKL;
STSWGNSFFYKLS; VHSLCNFFYTVSI; HSLCNFFYTVSII;
SLCNFFYTVSIIY; LCNFFYTVSIIYT; CNFFYTVSIIYTI;
NFFYTVSIIYTIS; FFYTVSIIYTISM; FYTVSIIYTISMA;
YTVSIIYTISMAK; TVSIIYTISMAKM; VSIIYTISMAKMY;
SIIYTISMAKMYT; IIYTISMAKMYTG; IYTISMAKMYTGT;
YTISMAKMYTGTF; TISMAKMYTGTFP; ISMAKMYTGTFPF;
SMAKMYTGTFPFS; MAKMYTGTFPFSY; AKMYTGTFPFSYL;
KMYTGTFPFSYLS; MYTGTFPFSYLSN; YTGTFPFSYLSNH;
GPNRGKIRIILLN; PNRGKIRIILLNI; NRGKIRIILLNII;
RGKIRIILLNIII; GKIRIILLNIIIK; KIRIILLNIIIKV;
IRIILLNIIIKVY; RIILLNIIIKVYR; IILLNIIIKVYRG;
ILLNIIIKVYRGI; LLNIIIKVYRGIY; LNIIIKVYRGIYN;
NIIIKVYRGIYNC; IIIKVYRGIYNCP; IIKVYRGIYNCPG;
IKVYRGIYNCPGS; KVYRGIYNCPGSF; VYRGIYNCPGSFL;
YRGIYNCPGSFLQ; RGIYNCPGSFLQK; GIYNCPGSFLQKS;
IYNCPGSFLQKSS; YNCPGSFLQKSSQ; NCPGSFLQKSSQG;
CPGSFLQKSSQGV; PGSFLQKSSQGVS; GSFLQKSSQGVSK;
SFLQKSSQGVSKK; FLQKSSQGVSKKS; LQKSSQGVSKKSF;
QKSSQGVSKKSFC; KSSQGVSKKSFCS; SSQGVSKKSFCSS;
SQGVSKKSFCSSL; QGVSKKSFCSSLQ; GVSKKSFCSSLQF;
VSKKSFCSSLQFL; GYRRYIIPNNMPQ; YRRYIIPNNMPQS;
RRYIIPNNMPQSL; RYIIPNNMPQSLG; YIIPNNMPQSLGN;
IIPNNMPQSLGNS; IPNNMPQSLGNSS; PNNMPQSLGNSSK;
NNMPQSLGNSSKQ; NMPQSLGNSSKQR; MPQSLGNSSKQRR;
PQSLGNSSKQRRT; QSLGNSSKQRRTP; SLGNSSKQRRTPM;
LGNSSKQRRTPMP; GNSSKQRRTPMPR; NSSKQRRTPMPRI;
SSKQRRTPMPRIK; SKQRRTPMPRIKV; KQRRTPMPRIKVL;
QRRTPMPRIKVLN; RRTPMPRIKVLNI; RTPMPRIKVLNII;
TPMPRIKVLNIIN; PMPRIKVLNIINK; MPRIKVLNIINKS;
PRIKVLNIINKSI; RIKVLNIINKSIY; IKVLNIINKSIYT;
KVLNIINKSIYTR; VLNIINKSIYTRK; LNIINKSIYTRKQ;
NIINKSIYTRKQN; IINKSIYTRKQNI; INKSIYTRKQNII;
NKSIYTRKQNIIV; KSIYTRKQNIIVL; SIYTRKQNIIVLI;
IYTRKQNIIVLIW; YTRKQNIIVLIWV; TRKQNIIVLIWVK;
RKQNIIVLIWVKQ; KQNIIVLIWVKQF; QNIIVLIWVKQFQ;
NIIVLIWVKQFQS; IIVLIWVKQFQSH; IVLIWVKQFQSHA;
LLIEAYSGNFVIP; LIEAYSGNFVIPI; IEAYSGNFVIPII;
EAYSGNFVIPIIK; AYSGNFVIPIIKE; YSGNFVIPIIKEL;
SGNFVIPIIKELI; GNFVIPIIKELIP; NFVIPIIKELIPY;
FVIPIIKELIPYL; VIPIIKELIPYLS; SSKPSNSPRSTSN;
SKPSNSPRSTSNY; KPSNSPRSTSNYS; PSNSPRSTSNYSI;
SNSPRSTSNYSIC; NSPRSTSNYSICL; SPRSTSNYSICLR;
PRSTSNYSICLRS; GTCYALYSSKGCN; TCYALYSSKGCNL;
CYALYSSKGCNLN; YALYSSKGCNLNF; ALYSSKGCNLNFY;
LYSSKGCNLNFYS; YSSKGCNLNFYSS; SSKGCNLNFYSSS;
SKGCNLNFYSSSS; KGCNLNFYSSSSL; GCNLNFYSSSSLP;
CNLNFYSSSSLPS; NLNFYSSSSLPSS; LNFYSSSSLPSSS;
NFYSSSSLPSSNF; FYSSSSLPSSNFS; YSSSSLPSSNFSH;
KSCGSSSLRYTGN; SSTHEPGNTKKKG; STHEPGNTKKKGL;
THEPGNTKKKGLL; HEPGNTKKKGLLT; ESFTESFTAGKAV;
SPTESFTAGKAVV; FTESFTAGKAVVL; TESFTAGKAVVLL;
ESFTAGKAVVLLF; SFTAGKAVVLLFF; FTAGKAVVLLFFP;
TAGKAVVLLFFPS; AGKAVVLLFFPST; GKAVVLLFFPSTL;
KAVVLLFFPSTLS; AVVLLFFPSTLSS; VVLLFFPSTLSSP;
VLLFFPSTLSSPL; LLFFPSTLSSPLQ; LFFPSTLSSPLQN;
FFPSTLSSPLQNS; FPSTLSSPLQNSS; PSTLSSPLQNSSK;
STLSSPLQNSSKS; TLSSPLQNSSKSS; LSSPLQNSSKSSK;
SSPLQNSSKSSKI; SPLQNSSKSSKIK; PLQNSSKSSKIKI;
LQNSSKSSKIKIK; QNSSKSSKIKIKI; NSSKSSKIKIKIL;
ALFFVPVQVLPTF; LFFVPVQVLPTFT; FFVPVQVLPTFTE;
FVPVQVLPTFTEA; VPVQVLPTFTEAC; PVQVLPTFTEACR;
VQVLPTFTEACRD; QVLPTFTEACRDS; VLPTFTEACRDSW;
LPTFTEACRDSWR; PTFTEACRDSWRR; TFTEACRDSWRRT;
FTEACRDSWRRTM; TEACRDSWRRTMA; EACRDSWRRTMAF;
ACRDSWRRTMAFV; CRDSWRRTMAFVQ; RDSWRRTMAFVQF;
DSWRRTMAFVQFN; SWRRTMAFVQFNW; WRRTMAFVQFNWG;
RRTMAFVQFNWGQ; RTMAFVQFNWGQG; TMAFVQFNWGQGQ;
MAFVQFNWGQGQD; AFVQFNWGQGQDS; ARKTCLSCTFLPE;
RKTCLSCTFLPEV; KTCLSCTFLPEVM; TCLSCTFLPEVMV;
CLSCTFLPEVMVW; LSCTFLPEVMVWL; SCTFLPEVMVWLH;
CTFLPEVMVWLHS; TFLPEVMVWLHSM; FLPEVMVWLHSMG;
LPEVMVWLHSMGK; PEVMVWLHSMGKQ; EVMVWLHSMGKQL;
VMVWLHSMGKQLL; MVWLHSMGKQLLP; VWLHSMGKQLLPV;
WLHSMGKQLLPVS; LHSMGKQLLPVSH; HSMGKQLLPVSHA;
SMGKQLLPVSHAL; MGKQLLPVSHALS; GKQLLPVSHALSF;
KQLLPVSHALSFL; QLLPVSHALSFLR; LLPVSHALSFLRS;
LPVSHALSFLRSW; PVSHALSFLRSWF; VSHALSFLRSWFG;
SHALSFLRSWFGC; HALSFLRSWFGCI; ALSFLRSWFGCIP;
LSFLRSWFGCIPL; EAEAASASTLSLK; GLAKLFGEIPILL;
LAKLFGEIPILLQ; AKLFGEIPILLQF; KLFGEIPILLQFL;
LFGEIPILLQFLQ 14 mers:

MDKVLNREESMELM; DKVLNREESMELMD; KVLNREESMELMDL;
VLNREESMELMDLL; LNREESMELMDLLG; NREESMELMDLLGL;
REESMELMDLLGLE; EESMELMDLLGLER; ESMELMDLLGLERA;
SMELMDLLGLERAA; MELMDLLGLERAAW; ELMDLLGLERAAWG;
LMDLLGLERAAWGN; MDLLGLERAAWGNL; DLLGLERAAWGNLP;
LLGLERAAWGNLPL; LGLERAAWGNLPLM; GLERAAWGNLPLMR;
LERAAWGNLPLMRK; ERAAWGNLPLMRKA; RAAWGNLPLMRKAY;
AAWGNLPLMRKAYL; AWGNLPLMRKAYLR; WGNLPLMRKAYLRK;
GNLPLMRKAYLRKC; NLPLMRKAYLRKCK; LPLMRKAYLRKCKE;
PLMRKAYLRKCKEF; LMRKAYLRKCKEFH; MRKAYLRKCKEFHP;
RKAYLRKCKEFHPD; KAYLRKCKEFHPDK; AYLRKCKEFHPDKG;
YLRKCKEFHPDKGG; LRKCKEFHPDKGGD; RKCKEFHPDKGGDE;
KCKEFHPDKGGDED; CKEFHPDKGGDEDK; KEFHPDKGGDEDKM;
EFHPDKGGDEDKMK; FHPDKGGDEDKMKR; HPDKGGDEDKMKRM;
PDKGGDEDKMKRMN; DKGGDEDKMKRMNT; KGGDEDKMKRMNTL;
GGDEDKMKRMNTLY; GDEDKMKRMNTLYK; DEDKMKRMNTLYKK;
EDKMKRMNTLYKKM; DKMKRMNTLYKKME; KMKRMNTLYKKMEQ;
MKRMNTLYKKMEQD; KRMNTLYKKMEQDV; RMNTLYKKMEQDVK;
MNTLYKKMEQDVKV; NTLYKKMEQDVKVA; TLYKKMEQDVKVAH;
LYKKMEQDVKVAHQ; YKKMEQDVKVAHQP; KKMEQDVKVAHQPD;
KMEQDVKVAHQPDF; MEQDVKVAHQPDFG; EQDVKVAHQPDFGT;
QDVKVAHQPDFGTW; DVKVAHQPDFGTWS; VKVAHQPDFGTWSS;
KVAHQPDFGTWSSS; VAHQPDFGTWSSSE; AHQPDFGTWSSSEV;
HQPDFGTWSSSEVC; QPDFGTWSSSEVCA; PDFGTWSSSEVCAD;
DFGTWSSSEVCADF; FGTWSSSEVCADFP; GTWSSSEVCADFPL;
TWSSSEVCADFPLC; WSSSEVCADFPLCP; SSSEVCADFPLCPD;
SSEVCADFPLCPDT; SEVCADFPLCPDTL; EVCADFPLCPDTLY;
VCADFPLCPDTLYC; CADFPLCPDTLYCK; ADFPLCPDTLYCKE;
DFPLCPDTLYCKEW; FPLCPDTLYCKEWP; PLCPDTLYCKEWPI;
LCPDTLYCKEWPIC; CPDTLYCKEWPICS; PDTLYCKEWPICSK;
DTLYCKEWPICSKK; TLYCKEWPICSKKP; LYCKEWPICSKKPS;
YCKEWPICSKKPSV; CKEWPICSKKPSVH; KEWPICSKKPSVHC;
EWPICSKKPSVHCP; WPICSKKPSVHCPC; PICSKKPSVHCPCM;
ICSKKPSVHCPCML; CSKKPSVHCPCMLC; SKKPSVHCPCMLCQ;
KKPSVHCPCMLCQL; KPSVHCPCMLCQLR; PSVHCPCMLCQLRL;
SVHCPCMLCQLRLR; VHCPCMLCQLRLRH; HCPCMLCQLRLRHL;
CPCMLCQLRLRHLN; PCMLCQLRLRHLNR; CMLCQLRLRHLNRK;
MLCQLRLRHLNRKF; LCQLRLRHLNRKFL; CQLRLRHLNRKFLR;
QLRLRHLNRKFLRK; LRLRHLNRKFLRKE; RLRHLNRKFLRKEP;
LRHLNRKFLRKEPL; RHLNRKFLRKEPLV; HLNRKFLRKEPLVW;
LNRKFLRKEPLVWI; NRKFLRKEPLVWID; RKFLRKEPLVWIDC;
KFLRKEPLVWIDCY; FLRKEPLVWIDCYC; LRKEPLVWIDCYCI;
RKEPLVWIDCYCID; KEPLVWIDCYCIDC; EPLVWIDCYCIDCF;
PLVWIDCYCIDCFT; LVWIDCYCIDCFTQ; VWIDCYCIDCFTQW;
WIDCYCIDCFTQWF; IDCYCIDCFTQWFG; DCYCIDCFTQWFGL;
CYCIDCFTQWFGLD; YCIDCFTQWFGLDL; CIDCFTQWFGLDLT;
IDCFTQWFGLDLTE; DCFTQWFGLDLTEE; CFTQWFGLDLTEET;
FTQWFGLDLTEETL; TQWFGLDLTEETLQ; QWFGLDLTEETLQW;
WFGLDLTEETLQWW; FGLDLTEETLQWWV; GLDLTEETLQWWVQ;
LDLTEETLQWWVQI; DLTEETLQWWVQII; LTEETLQWWVQIIG;
TEETLQWWVQIIGE; EETLQWWVQIIGET; ETLQWWVQIIGETP;
TLQWWVQIIGETPF; LQWWVQIIGETPFR; QWWVQIIGETPFRD;
WWVQIIGETPFRDL; WVQIIGETPFRDLK; VQIIGETPFRDLKL;
KALSNYFFYRCQPM; ALSNYFFYRCQPME; LSNYFFYRCQPMEQ;
SNYFFYRCQPMEQK; NYFFYRCQPMEQKS; YFFYRCQPMEQKSG;
FFYRCQPMEQKSGS; FYRCQPMEQKSGSP; YRCQPMEQKSGSPG;
RCQPMEQKSGSPGG; CQPMEQKSGSPGGV; QPMEQKSGSPGGVP;
PMEQKSGSPGGVPL; MEQKSGSPGGVPLM; EQKSGSPGGVPLMK;
QKSGSPGGVPLMKN; KSGSPGGVPLMKNG; SGSPGGVPLMKNGM;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GSPGGVPLMKNGMK; SPGGVPLMKNGMKI; PGGVPLMKNGMKIY;
GGVPLMKNGMKIYF; GVPLMKNGMKIYFA; VPLMKNGMKIYFAM;
PLMKNGMKIYFAMK; LMKNGMKIYFAMKI; MKNGMKIYFAMKIC;
KNGMKIYFAMKICL; NGMKIYFAMKICLP; GMKIYFAMKICLPV;
MKIYFAMKICLPVM; KIYFAMKICLPVMK; IYFAMKICLPVMKK;
YFAMKICLPVMKKQ; FAMKICLPVMKKQQ; AMKICLPVMKKQQQ;
MKICLPVMKKQQQI; KICLPVMKKQQQIL; ICLPVMKKQQQILN;
CLPVMKKQQQILNT; LPVMKKQQQILNTQ; PVMKKQQQILNTQH;
VMKKQQQILNTQHH; MKKQQQILNTQHHP; KKQQQILNTQHHPK;
KQQQILNTQHHPKK; QQQILNTQHHPKKK; QQILNTQHHPKKKE;
QILNTQHHPKKKER; KTLKTFPLIYTSFL; TLKTFPLIYTSFLV;
LKTFPLIYTSFLVK; KTFPLIYTSFLVKL; TFPLIYTSFLVKLY;
FPLIYTSFLVKLYL; PLIYTSFLVKLYLV; LIYTSFLVKLYLVI;
IYTSFLVKLYLVIE; YTSFLVKLYLVIEP; TSFLVKLYLVIEPL;
SFLVKLYLVIEPLA; FLVKLYLVIEPLPA; LVKLYLVIEPLPAL;
VKLYLVIEPLPALL; KLYLVIEPLPALLC; LYLVIEPLPALLCI;
YLVIEPLPALLCIL; LVIEPLPALLCILL; VIEPLPALLCILLK;
IEPLPALLCILLKK; EPLPALLCILLKKK; PLPALLCILLKKKL;
LPALLCILLKKKLK; PALLCILLKKKLKF; ALLCILLKKKLKFC;
LLCILLKKKLKFCI; LCILLKKKLKFCIK; CILLKKKLKFCIKN;
ILLKKKLKFCIKNL; LLKKKLKFCIKNLW; LKKKLKFCIKNLWK;
KKKLKFCIKNLWKN; KKLKFCIKNLWKNI; KLKFCIKNLWKNIL;
LLLVDTCVLGIILY; LLVDTCVLGIILYS; LVDTCVLGIILYSF;
LHIDIEFLQLIISV; HIDIEFLQLIISVK; IDIEFLQLIISVKS;
DIEFLQLIISVKSC; IEFLQLIISVKSCV; EFLQLIISVKSCVP;
FLQLIISVKSCVPL; LQLIISVKSCVPLV; QLIISVKSCVPLVF;
FVRVLIRNTYYIVP; RSMILAQKSLKKQS; SMILAQKSLKKQSR;
MILAQKSLKKQSRC; ILAQKSLKKQSRCL; LAQKSLKKQSRCLG;
AQKSLKKQSRCLGN; RSVKSVRKKTSLIT; SVKSVRKKTSLITL;
VKSVRKKTSLITLS; KSVRKKTSLITLSI; SVRKKTSLITLSIM;
VRKKTSLITLSIMK; RKKTSLITLSIMKS; KKTSLITLSIMKST;
KTSLITLSIMKSTL; TSLITLSIMKSTLQ; SLITLSIMKSTLQM;
LITLSIMKSTLQML; ITLSIMKSTLQMLL; TLSIMKSTLQMLLF;
LSIMKSTLQMLLFL; SIMKSTLQMLLFLQ; IMKSTLQMLLFLQK;
MKSTLQMLLFLQKV; KSTLQMLLFLQKVK; STLQMLLFLQKVKI;
TLQMLLFLQKVKIK; LQMLLFLQKVKIKK; QMLLFLQKVKIKKV;
MLLFLQKVKIKKVF; LLFLQKVKIKKVFV; LFLQKVKIKKVFVS;
FLQKVKIKKVFVSK; LQKVKIKKVFVSKQ; NNIWQVLLGCTVCY;
NIWQVLLGCTVCYL; IWQVLLGCTVCYLK; WQVLLGCTVCYLKW;
QVLLGCTVCYLKWI; VLLGCTVCYLKWIK; LLGCTVCYLKWIKE;
LIFCTVLFSMYLKE; IFCTVLFSMYLKED; FCTVLFSMYLKEDT;
CTVLFSMYLKEDTG; TVLFSMYLKEDTGY; VLFSMYLKEDTGYL;
LFSMYLKEDTGYLK; FSMYLKEDTGYLKV; SMYLKEDTGYLKVP;
MYLKEDTGYLKVPL; YLKEDTGYLKVPLI; LKEDTGYLKVPLIV;
KEDTGYLKVPLIVE; EDTGYLKVPLIVEK; DTGYLKVPLIVEKQ;
TGYLKVPLIVEKQH; KGQELNQRICLQDM; GQELNQRICLQDME;
ENPYKTQSSYLKKE; NPYKTQSSYLKKEF; PYKTQSSYLKKEFY;
YKTQSSYLKKEFYK; KTQSSYLKKEFYKE; TQSSYLKKEFYKEP;
LILQLIYNLELLNG; ILQLIYNLELLNGR; LQLIYNLELLNGRK;
QLIYNLELLNGRKG; LIYNLELLNGRKGW; IYNLELLNGRKGWI;
YNLELLNGRKGWIL; NLELLNGRKGWILR; NIIYAWGNVFLILQ;
IIYAWGNVFLILQE; IYAWGNVFLILQEK; YAWGNVFLILQEKR;
AWGNVFLILQEKRI; WGNVFLILQEKRIQ; GNVFLILQEKRIQK;
NVFLILQEKRIQKL; VFLILQEKRIQKLK; FLILQEKRIQKLKT;
LILQEKRIQKLKTL; ILQEKRIQKLKTLD; LQEKRIQKLKTLDM;
QEKRIQKLKTLDMD; EKRIQKLKTLDMDQ; KRIQKLKTLDMDQA;
RIQKLKTLDMDQAL; IQKLKTLDMDQALN; QKLKTLDMDQALNP;
KLKTLDMDQALNPN; LKTLDMDQALNPNH; KTLDMDQALNPNHN;
TLDMDQALNPNHNA; LDMDQALNPNHNAL; DMDQALNPNHNALP;
MDQALNPNHNALPK; DQALNPNHNALPKS; QALNPNHNALPKSQ;
ALNPNHNALPKSQI; LNPNHNALPKSQIL; NPNHNALPKSQILQ;
PNHNALPKSQILQP; NHNALPKSQILQPL; HNALPKSQILQPLL;
NALPKSQILQPLLK; ALPKSQILQPLLKI; LPKSQILQPLLKIP;
PKSQILQPLLKIPK; KSQILQPLLKIPKG; SQILQPLLKIPKGQ;
QILQPLLKIPKGQT; ILQPLLKIPKGQTP; LQPLLKIPKGQTPI;
QPLLKIPKGQTPIV; PLLKIPKGQTPIVK; LLKIPKGQTPIVKS;
LKIPKGQTPIVKSC; KIPKGQTPIVKSCI; IPKGQTPIVKSCIC;
PKGQTPIVKSCICV; KGQTPIVKSCICVK; GQTPIVKSCICVKA;
QTPIVKSCICVKAF; TPIVKSCICVKAFS; PIVKSCICVKAFSV;
IVKSCICVKAFSVL; VKSCICVKAFSVLK; KSCICVKAFSVLKG;
SCICVKAFSVLKGL; CICVKAFSVLKGLK; ICVKAFSVLKGLKH;
CVKAFSVLKGLKHH; VKAFSVLKGLKHHP; KAFSVLKGLKHHPQ;
AFSVLKGLKHHPQN; FSVLKGLKHHPQNN; SVLKGLKHHPQNNT;
VLKGLKHHPQNNTS; LKGLKHHPQNNTSL; KGLKHHPQNNTSLK;
GLKHHPQNNTSLKV; LKHHPQNNTSLKVA; KHHPQNNTSLKVAY;
HHPQNNTSLKVAYT; HPQNNTSLKVAYTK; PQNNTSLKVAYTKA;
QNNTSLKVAYTKAA; NNTSLKVAYTKAAF; NTSLKVAYTKAAFI;
TSLKVAYTKAAFIK; SLKVAYTKAAFIKC; LKVAYTKAAFIKCI;
KVAYTKAAFIKCIC; VAYTKAAFIKCICT; AYTKAAFIKCICTI;
YTKAAFIKCICTIK; TKAAFIKCICTIKA; KAAFIKCICTIKAP;
AAFIKCICTIKAPV; SILVCNCPCLSIYL; ILVCNCPCLSIYLI;
LVCNCPCLSIYLII; VCNCPCLSIYLIIS; CNCPCLSIYLIISG;
NCPCLSIYLIISGS; CPCLSIYLIISGSP; PCLSIYLIISGSPG;
CLSIYLIISGSPGS; LSIYLIISGSPGSL; SIYLIISGSPGSLS;
IYLIISGSPGSLSV; YLIISGSPGSLSVP; LIISGSPGSLSVPS;
IISGSPGSLSVPSN; ISGSPGSLSVPSNT; SGSPGSLSVPSNTL;
GSPGSLSVPSNTLT; SPGSLSVPSNTLTS; PGSLSVPSNTLTSS;
GSLSVPSNTLTSST; SLSVPSNTLTSSTW; LSVPSNTLTSSTWD;
SVPSNTLTSSTWDS; VPSNTLTSSTWDSI; PSNTLTSSTWDSIP;
SNTLTSSTWDSIPY; NTLTSSTWDSIPYI; TLTSSTWDSIPYIG;
LTSSTWDSIPYIGC; TSSTWDSIPYIGCP; SSTWDSIPYIGCPS;
STWDSIPYIGCPST; TWDSIPYIGCPSTL; WDSIPYIGCPSTLW;
DSIPYIGCPSTLWV; SIPYIGCPSTLWVL; IPYIGCPSTLWVLL;
PYIGCPSTLWVLLF; YIGCPSTLWVLLFI; IGCPSTLWVLLFIR;
GCPSTLWVLLFIRS; CPSTLWVLLFIRSL; PSTLWVLLFIRSLS;
STLWVLLFIRSLSK; TLWVLLFIRSLSKK; LWVLLFIRSLSKKE;
WVLLFIRSLSKKEI; VLLFIRSLSKKEIG; GFFTDLFLRRILKY;
FFTDLFLRRILKYL; FTDLFLRRILKYLA; TDLFLRRILKYLAR;
DLFLRRILKYLARP; LFLRRILKYLARPL; FLRRILKYLARPLH;
LRRILKYLARPLHC; RRILKYLARPLHCC; RILKYLARPLHCCV;
ILKYLARPLHCCVP; LKYLARPLHCCVPE; KYLARPLHCCVPEL;
YLARPLHCCVPELL; LARPLHCCVPELLV; ARPLHCCVPELLVN;
RPLHCCVPELLVNR; PLHCCVPELLVNRP; LHCCVPELLVNRPQ;
HCCVPELLVNRPQI; CCVPELLVNRPQIS; CVPELLVNRPQISA;
VPELLVNRPQISAA; PELLVNRPQISAAE; ELLVNRPQISAAET;
LLVNRPQISAAETY; LVNRPQISAAETYR; VNRPQISAAETYRL;
NRPQISAAETYRLS; RPQISAAETYRLSA; PQISAAETYRLSAL;
QISAAETYRLSALQ; ISAAETYRLSALQR; SAAETYRLSALQRG;
AAETYRLSALQRGP; AETYRLSALQRGPT; ETYRLSALQRGPTP;
TYRLSALQRGPTPC; YRLSALQRGPTPCS; RLSALQRGPTPCSS;
LSALQRGPTPCSSS; SALQRGPTPCSSSN; ALQRGPTPCSSSNT;
LQRGPTPCSSSNTV; QRGPTPCSSSNTVV; RGPTPCSSSNTVVA;
GPTPCSSSNTVVAV; PTPCSSSNTVVAVL; TPCSSSNTVVAVLV;
PCSSSNTVVAVLVT; STGGTFSPPVKVPK; TGGTFSPPVKVPKY;
GGTFSPPVKVPKYL; GTFSPPVKVPKYLA; TFSPPVKVPKYLAF;
FSPPVKVPKYLAFS; SPPVKVPKYLAFSF; PPVKVPKYLAFSFL;
PVKVPKYLAFSFLL; VKVPKYLAFSFLLG; KVPKYLAFSFLLGS;
VPKYLAFSFLLGSG; PKYLAFSFLLGSGT; KYLAFSFLLGSGTQ;
YLAFSFLLGSGTQH; LAFSFLLGSGTQHS; AFSFLLGSGTQHST;
FSFLLGSGTQHSTG; ALWSVFITWDWAVG; LWSVFITWDWAVGF;
WSVFITWDWAVGFL; SVFITWDWAVGFLG; VFITWDWAVGFLGV;
FITWDWAVGFLGVI; ITWDWAVGFLGVIV; TWDWAVGFLGVIVP;
WDWAVGFLGVIVPS; DWAVGFLGVIVPSG; WAVGFLGVIVPSGY;
AVGFLGVIVPSGYF; VGFLGVIVPSGYFD; GFLGVIVPSGYFDL;
FISTPCISKGSPPT; ISTPCISKGSPPTA; STPCISKGSPPTAK;
TPCISKGSPPTAKK; PCISKGSPPTAKKW; CISKGSPPTAKKWK;
ISKGSPPTAKKWKL; SKGSPPTAKKWKLL; KGSPPTAKKWKLLP;
IGFPPPCSCTFCDP; GFPPPCSCTFCDPA; RLSMLVIPITSVCT;
LSMLVIPITSVCTV; SMLVIPITSVCTVT; MLVIPITSVCTVTA;
LVIPITSVCTVTAS; VIPITSVCTVTASH; IPITSVCTVTASHI;
PITSVCTVTASHIS; ITSVCTVTASHISR; TSVCTVTASHISRF;
SVCTVTASHISRFP; VCTVTASHISRFPQ; CTVTASHISRFPQV;
TVTASHISRFPQVR; VTASHISRFPQVRS; TASHISRFPQVRSS;
ASHISRFPQVRSSF; SHISRFPQVRSSFK; HISRFPQVRSSFKL;
ISRFPQVRSSFKLG; SRFPQVRSSFKLGR; RFPQVRSSFKLGRG;
FPQVRSSFKLGRGI; PQVRSSFKLGRGIL; QVRSSFKLGRGILA;
VRSSFKLGRGILAV; RSSFKLGRGILAVL; QGSIFLSGLSLLKS;
GSIFLSGLSLLKSF; SIFLSGLSLLKSFS; IFLSGLSLLKSFSA;
FLSGLSLLKSFSAL; LSGLSLLKSFSALS; SGLSLLKSFSALSF;
GLSLLKSFSALSFR; LSLLKSFSALSFRL; SLLKSFSALSFRLK;
LLKSFSALSFRLKP; LKSFSALSFRLKPL; KSFSALSFRLKPLR;
SFSALSFRLKPLRF; FSALSFRLKPLRFS; SALSFRLKPLRFSS;
ALSFRLKPLRFSSG; LSFRLKPLRFSSGS; SFRLKPLRFSSGSP;
FRLKPLRFSSGSPI; RLKPLRFSSGSPIS; LKPLRFSSGSPISG;
KPLRFSSGSPISGF; PLRFSSGSPISGFR; LRFSSGSPISGFRK;
RFSSGSPISGFRKH; FSSGSPISGFRKHS; SSGSPISGFRKHST;
SGSPISGFRKHSTS; GSPISGFRKHSTSV; SPISGFRKHSTSVI;
PISGFRKHSTSVIA; ISGFRKHSTSVIAS; SGFRKHSTSVIAST;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GFRKHSTSVIASTP; FRKHSTSVIASTPV; RKHSTSVIASTPVL;
KHSTSVIASTPVLT; HSTSVIASTPVLTS; STSVIASTPVLTSR;
TSVIASTPVLTSRT; SVIASTPVLTSRTS; VIASTPVLTSRTST;
IASTPVLTSRTSTP; ASTPVLTSRTSTPP; STPVLTSRTSTPPF;
TPVLTSRTSTPPFI; PVLTSRTSTPPFIS; VLTSRTSTPPFISS;
LTSRTSTPPFISSF; TSRTSTPPFISSFG; SRTSTPPFISSFGT;
RTSTPPFISSFGTC; TSTPPFISSFGTCT; STPPFISSFGTCTG;
TPPFISSFGTCTGS; PPFISSFGTCTGSF; PFISSFGTCTGSFG;
FISSFGTCTGSFGF; ISSFGTCTGSFGFL; SSFGTCTGSFGFLG;
SFGTCTGSFGFLGA; FGTCTGSFGFLGAA; GTCTGSFGFLGAAP;
TCTGSFGFLGAAPG; CTGSFGFLGAAPGH; TGSFGFLGAAPGHS;
GSFGFLGAAPGHSP; SFGFLGAAPGHSPF; FGFLGAAPGHSPFL;
GFLGAAPGHSPFLL; FLGAAPGHSPFLLV; LGAAPGHSPFLLVG;
GAAPGHSPFLLVGA; AAPGHSPFLLVGAI; APGHSPFLLVGAIF;
PGHSPFLLVGAIFI; GHSPFLLVGAIFIC; HSPFLLVGAIFICF;
SPFLLVGAIFICFK; PFLLVGAIFICFKS; FLLVGAIFICFKSR;
LLVGAIFICFKSRC; LVGAIFICFKSRCY; VGAIFICFKSRCYS;
GAIFICFKSRCYSP; AIFICFKSRCYSPV; IFICFKSRCYSPVQ;
FICFKSRCYSPVQA; RQHPLRSSSLISTS; QHPLRSSSLISTSW;
HPLRSSSLISTSWG; PLRSSSLISTSWGN; LRSSSLISTSWGNS;
RSSSLISTSWGNSF; SSSLISTSWGNSFF; SSLISTSWGNSFFY;
SLISTSWGNSFFYK; LISTSWGNSFFYKL; ISTSWGNSFFYKLS;
VHSLCNFFYTVSII; HSLCNFFYTVSIIY; SLCNFFYTVSIIYT;
LCNFFYTVSIIYTI; CNFFYTVSIIYTIS; NFFYTVSIIYTISM;
FFYTVSIIYTISMA; FYTVSIIYTISMAK; YTVSIIYTISMAKM;
TVSIIYTISMAKMY; VSIIYTISMAKMYT; SIIYTISMAKMYTG;
IIYTISMAKMYTGT; IYTISMAKMYTGTF; YTISMAKMYTGTFP;
TISMAKMYTGTFPP; ISMAKMYTGTFPPS; SMAKMYTGTFPPSY;
MAKMYTGTFPPSYL; AKMYTGTFPPSYLS; KMYTGTFPPSYLSN;
MYTGTFPPSYLSNH; GPNRGKIRIILLNI; PNRGKIRIILLNII;
NRGKIRIILLNIII; RGKIRIILLNIIIK; GKIRIILLNIIIKV;
KIRIILLNIIIKVY; IRIILLNIIIKVYR; RIILLNIIIKVYRG;
IILLNIIIKVYRGI; ILLNIIIKVYRGIY; LLNIIIKVYRGIYN;
LNIIIKVYRGIYNC; NIIIKVYRGIYNCP; IIIKVYRGIYNCPG;
IIKVYRGIYNCPGS; IKVYRGIYNCPGSF; KVYRGIYNCPGSFL;
VYRGIYNCPGSFLQ; YRGIYNCPGSFLQK; RGIYNCPGSFLQKS;
GIYNCPGSFLQKSS; IYNCPGSFLQKSSQ; YNCPGSFLQKSSQG;
NCPGSFLQKSSQGV; CPGSFLQKSSQGVS; PGSFLQKSSQGVSK;
GSFLQKSSQGVSKK; SFLQKSSQGVSKKS; FLQKSSQGVSKKSF;
LQKSSQGVSKKSFC; QKSSQGVSKKSFCS; KSSQGVSKKSFCSS;
SSQGVSKKSFCSSL; SQGVSKKSFCSSLQ; QGVSKKSFCSSLQF;
GVSKKSFCSSLQFL; GYRRYIIPNNMPQS; YRRYIIPNNMPQSL;
RRYIIPNNMPQSLG; RYIIPNNMPQSLGN; YIIPNNMPQSLGNS;
IIPNNMPQSLGNSS; IPNNMPQSLGNSSK; PNNMPQSLGNSSKQ;
NNMPQSLGNSSKQR; NMPQSLGNSSKQRR; MPQSLGNSSKQRRT;
PQSLGNSSKQRRTP; QSLGNSSKQRRTPM; SLGNSSKQRRTPMP;
LGNSSKQRRTPMPR; GNSSKQRRTPMPRI; NSSKQRRTPMPRIK;
SSKQRRTPMPRIKV; SKQRRTPMPRIKVL; KQRRTPMPRIKVLN;
QRRTPMPRIKVLNI; RRTPMPRIKVLNII; RTPMPRIKVLNIIN;
TPMPRIKVLNIIIK; PMPRIKVLNIINKS; MPRIKVLNIINKSI;
PRIKVLNIINKSIY; RIKVLNIINKSIYT; IKVLNIINKSIYTR;
KVLNIINKSIYTRK; VLNIINKSIYTRKQ; LNIINKSIYTRKQN;
NIINKSIYTRKQNI; IINKSIYTRKQNII; INKSIYTRKQNIIV;
NKSIYTRKQNIIVL; KSIYTRKQNIIVLI; SIYTRKQNIIVLIW;
IYTRKQNIIVLIWV; YTRKQNIIVLIWVK; TRKQNIIVLIWVKQ;
RKQNIIVLIWVKQF; KQNIIVLIWVKQFQ; QNIIVLIWVKQFQS;
NIIVLIWVKQFQSH; IIVLIWVKQFQSHA; LLIEAYSGNFVIPI;
LIEAYSGNFVIPII; IEAYSGNFVIPIIK; EAYSGNFVIPIIKE;
AYSGNFVIPIIKEL; YSGNFVIPIIKELI; SGNFVIPIIKELIP;
GNFVIPIIKELIPY; NFVIPIIKELIPYL; FVIPIIKELIPYLS;
SSKPSNSPRSTSNY; SKPSNSPRSTSNYS; KPSNSPRSTSNYSI;
PSNSPRSTSNYSIC; SNSPRSTSNYSICL; NSPRSTSNYSICLR;
SPRSTSNYSICLRS; GTCYALYSSKGCNL; TCYALYSSKGCNLN;
CYALYSSKGCNLNF; YALYSSKGCNLNFY; ALYSSKGCNLNFYS;
LYSSKGCNLNFYSS; YSSKGCNLNFYSSS; SSKGCNLNFYSSSS;
SKGCNLNFYSSSSL; KGCNLNFYSSSSLP; GCNLNFYSSSSLPS;
CNLNFYSSSSLPSS; NLNFYSSSLPSSN; LNFYSSSLPSSNF;
NFYSSSLPSSNFS; FYSSSSLPSSNFSH; SSTHEPGNTKKKGL;
STHEPGNTKKKGLL; THEPGNTKKKGLLT; ESFTESFTAGKAVV;
SFTESFTAGKAVVL; FTESFTAGKAVVLL; TESFTAGKAVVLLF;
ESFTAGKAVVLLFF; SFTAGKAVVLLFFP; FTAGKAVVLLFFPS;
TAGKAVVLLFFPST; AGKAVVLLFFPSTL; GKAVVLLFFPSTLS;
KAVVLLFFPSTLSS; AVVLLFFPSTLSSP; VVLLFFPSTLSSPL;
VLLFFPSTLSSPLQ; LLFFPSTLSSPLQN; LFFPSTLSSPLQNS;
FFPSTLSSPLQNSS; FPSTLSSPLQNSSK; PSTLSSPLQNSSKS;
STLSSPLQNSSKSS; TLSSPLQNSSKSSK; LSSPLQNSSKSSKI;
SSPLQNSSKSSKIK; SPLQNSSKSSKIKI; PLQNSSKSSKIKIK;
LQNSSKSSKIKIKI; QNSSKSSKIKIKIL; ALFFVPVQVLPTFT;
LFFVPVQVLPTFTE; FFVPVQVLPTFTEA; FVPVQVLPTFTEAC;
VPVQVLPTFTEACR; PVQVLPTFTEACRD; VQVLPTFTEACRDS;
QVLPTFTEACRDSW; VLPTFTEACRDSWR; LPTFTEACRDSWRR;
PTFTEACRDSWRRT; TFTEACRDSWRRTM; FTEACRDSWRRTMA;
TEACRDSWRRTMAF; EACRDSWRRTMAFV; ACRDSWRRTMAFVQ;
CRDSWRRTMAFVQF; RDSWRRTMAFVQFN; DSWRRTMAFVQFNW;
SWRRTMAFVQFNWG; WRRTMAFVQFNWGQ; RRTMAFVQFNWGQG;
RTMAFVQFNWGQGQ; TMAFVQFNWGQGQD; MAFVQFNWGQGQDS;
ARKTCLSCTFLPEV; RKTCLSCTFLPEVM; KTCLSCTFLPEVMV;
TCLSCTFLPEVMVW; CLSCTFLPEVMVWL; LSCTFLPEVMVWLH;
SCTFLPEVMVWLHS; CTFLPEVMVWLHSM; TFLPEVMVWLHSMG;
FLPEVMVWLHSMGK; LPEVMVWLHSMGKQ; PEVMVWLHSMGKQL;
EVMVWLHSMGKQLL; VMVWLHSMGKQLLP; MVWLHSMGKQLLPV;
VWLHSMGKQLLPVS; WLHSMGKQLLPVSH; LHSMGKQLLPVSHA;
HSMGKQLLPVSHAL; SMGKQLLPVSHALS; MGKQLLPVSHALSF;
GKQLLPVSHALSFL; KQLLPVSHALSFLR; QLLPVSHALSFLRS;
LLPVSHALSFLRSW; LPVSHALSFLRSWF; PVSHALSFLRSWFG;
VSHALSFLRSWFGC; SHALSFLRSWFGCI; HALSFLRSWFGCIP;
ALSFLRSWFGCIPL; GLAKLFGEIPILLQ; LAKLFGEIPILLQF;
AKLFGEIPILLQFL; KLFGEIPILLQFLQ 15 mers:

MDKVLNREESMELMD; DKVLNREESMELMDL; KVLNREESMELMDLL;
VLNREESMELMDLLG; LNREESMELMDLLGL; NREESMELMDLLGLE;
REESMELMDLLGLER; EESMELMDLLGLERA; ESMELMDLLGLERAA;
SMELMDLLGLERAAW; MELMDLLGLERAAWG; ELMDLLGLERAAWGN;
LMDLLGLERAAWGNL; MDLLGLERAAWGNLP; DLLGLERAAWGNLPL;
LLGLERAAWGNLPLM; LGLERAAWGNLPLMR; GLERAAWGNLPLMRK;
LERAAWGNLPLMRKA; ERAAWGNLPLMRKAY; RAAWGNLPLMRKAYL;
AAWGNLPLMRKAYLR; AWGNLPLMRKAYLRK; WGNLPLMRKAYLRKC;
GNLPLMRKAYLRKCK; NLPLMRKAYLRKCKE; LPLMRKAYLRKCKEF;
PLMRKAYLRKCKEFH; LMRKAYLRKCKEFHP; MRKAYLRKCKEFHPD;
RKAYLRKCKEFHPDK; KAYLRKCKEFHPDKG; AYLRKCKEFHPDKGG;
YLRKCKEFHPDKGGD; LRKCKEFHPDKGGDE; RKCKEFHPDKGGDED;
KCKEFHPDKGGDEDK; CKEFHPDKGGDEDKM; KEFHPDKGGDEDKMK;
EFHPDKGGDEDKMKR; FHPDKGGDEDKMKRM; HPDKGGDEDKMKRMN;
PDKGGDEDKMKRMNT; DKGGDEDKMKRMNTL; KGGDEDKMKRMNTLY;
GGDEDKMKRMNTLYK; GDEDKMKRMNTLYKK; DEDKMKRMNTLYKKM;
EDKMKRMNTLYKKME; DKMKRMNTLYKKMEQ; KMKRMNTLYKKMEQD;
MKRMNTLYKKMEQDV; KRMNTLYKKMEQDVK; RMNTLYKKMEQDVKV;
MNTLYKKMEQDVKVA; NTLYKKMEQDVKVAH; TLYKKMEQDVKVAHQ;
LYKKMEQDVKVAHQP; YKKMEQDVKVAHQPD; KKMEQDVKVAHQPDF;
KMEQDVKVAHQPDFG; MEQDVKVAHQPDFGT; EQDVKVAHQPDFGTW;
QDVKVAHQPDFGTWS; DVKVAHQPDFGTWSS; VKVAHQPDFGTWSSS;
KVAHQPDFGTWSSSE; VAHQPDFGTWSSSEV; AHQPDFGTWSSSEVC;
HQPDFGTWSSSEVCA; QPDFGTWSSSEVCAD; PDFGTWSSSEVCADF;
DFGTWSSSEVCADFP; FGTWSSSEVCADFPL; GTWSSSEVCADFPLC;
TWSSSEVCADFPLCP; WSSSEVCADFPLCPD; SSSEVCADFPLCPDT;
SSEVCADFPLCPDTL; SEVCADFPLCPDTLY; EVCADFPLCPDTLYC;
VCADFPLCPDTLYCK; CADFPLCPDTLYCKE; ADFPLCPDTLYCKEW;
DFPLCPDTLYCKEWP; FPLCPDTLYCKEWPI; PLCPDTLYCKEWPIC;
LCPDTLYCKEWPICS; CPDTLYCKEWPICSK; PDTLYCKEWPICSKK;
DTLYCKEWPICSKKP; TLYCKEWPICSKKPS; LYCKEWPICSKKPSV;
YCKEWPICSKKPSVH; CKEWPICSKKPSVHC; KEWPICSKKPSVHCP;
EWPICSKKPSVHCPC; WPICSKKPSVHCPCM; PICSKKPSVHCPCML;
ICSKKPSVHCPCMLC; CSKKPSVHCPCMLCQ; SKKPSVHCPCMLCQL;
KKPSVHCPCMLCQLR; KPSVHCPCMLCQLRL; PSVHCPCMLCQLRLR;
SVHCPCMLCQLRLRH; VHCPCMLCQLRLRHL; HCPCMLCQLRLRHLN;
CPCMLCQLRLRHLNR; PCMLCQLRLRHLNRK; CMLCQLRLRHLNRKF;
MLCQLRLRHLNRKFL; LCQLRLRHLNRKFLR; CQLRLRHLNRKFLRK;
QLRLRHLNRKFLRKE; LRLRHLNRKFLRKEP; RLRHLNRKFLRKEPL;
LRHLNRKFLRKEPLV; RHLNRKFLRKEPLVW; HLNRKFLRKEPLVWI;
LNRKFLRKEPLVWID; NRKFLRKEPLVWIDC; RKFLRKEPLVWIDCY;
KFLRKEPLVWIDCYC; FLRKEPLVWIDCYCI; LRKEPLVWIDCYCID;
RKEPLVWIDCYCIDC; KEPLVWIDCYCIDCF; EPLVWIDCYCIDCFT;
PLVWIDCYCIDCFTQ; LVWIDCYCIDCFTQW; VWIDCYCIDCFTQWF;
WIDCYCIDCFTQWFG; IDCYCIDCFTQWFGL; DCYCIDCFTQWFGLD;
CYCIDCFTQWFGLDL; YCIDCFTQWFGLDLT; CIDCFTQWFGLDLTE;
IDCFTQWFGLDLTEE; DCFTQWFGLDLTEET; CFTQWFGLDLTEETL;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

FTQWFGLDLTEETLQ; TQWFGLDLTEETLQW; QWFGLDLTEETLQWW;
WFGLDLTEETLQWWV; FGLDLTEETLQWWVQ; GLDLTEETLQWWVQI;
LDLTEETLQWWVQII; DLTEETLQWWVQIIG; LTEETLQWWVQIIGE;
TEETLQWWVQIIGET; EETLQWWVQIIGETP; ETLQWWVQIIGETPF;
TLQWWVQIIGETPFR; LQWWVQIIGETPFRD; QWWVQIIGETPFRDL;
WWVQIIGETPFRDLK; WVQIIGETPFRDLKL; KALSNYFFYRCQPME;
ALSNYFFYRCQPMEQ; LSNYFFYRCQPMEQK; SNYFFYRCQPMEQKS;
NYFFYRCQPMEQKSG; YFFYRCQPMEQKSGS; FFYRCQPMEQKSGSP;
FYRCQPMEQKSGSPG; YRCQPMEQKSGSPGG; RCQPMEQKSGSPGGV;
CQPMEQKSGSPGGVP; QPMEQKSGSPGGVPL; PMEQKSGSPGGVPLM;
MEQKSGSPGGVPLMK; EQKSGSPGGVPLMKN; QKSGSPGGVPLMKNG;
KSGSPGGVPLMKNGM; SGSPGGVPLMKNGMK; GSPGGVPLMKNGMKI;
SPGGVPLMKNGMKIY; PGGVPLMKNGMKIYF; GGVPLMKNGMKIYFA;
GVPLMKNGMKIYFAM; VPLMKNGMKIYFAMK; PLMKNGMKIYFAMKI;
LMKNGMKIYFAMKIC; MKNGMKIYFAMKICL; KNGMKIYFAMKICLP;
NGMKIYFAMKICLPV; GMKIYFAMKICLPVM; MKIYFAMKICLPVMK;
KIYFAMKICLPVMKK; IYFAMKICLPVMKKQ; YFAMKICLPVMKKQQ;
FAMKICLPVMKKQQQ; AMKICLPVMKKQQQI; MKICLPVMKKQQQIL;
KICLPVMKKQQQILN; ICLPVMKKQQQILNT; CLPVMKKQQQILNTQ;
LPVMKKQQQILNTQH; PVMKKQQQILNTQHH; VMKKQQQILNTQHHP;
MKKQQQILNTQHHPK; KKQQQILNTQHHPKK; KQQQILNTQHHPKKK;
QQQILNTQHHPKKKE; QQILNTQHHPKKKER; KTLKTFPLIYTSFLV;
TLKTFPLIYTSFLVK; LKTFPLIYTSFLVKL; KTFPLIYTSFLVKLY;
TFPLIYTSFLVKLYL; FPLIYTSFLVKLYLV; PLIYTSFLVKLYLVI;
LIYTSFLVKLYLVIE; IYTSFLVKLYLVIEP; YTSFLVKLYLVIEPL;
TSFLVKLYLVIEPLP; SFLVKLYLVIEPLPA; FLVKLYLVIEPLPAL;
LVKLYLVIEPLPALL; VKLYLVIEPLPALLC; KLYLVIEPLPALLCI;
LYLVIEPLPALLCIL; YLVIEPLPALLCILL; LVIEPLPALLCILLK;
VIEPLPALLCILLKK; IEPLPALLCILLKKK; EPLPALLCILLKKKL;
PLPALLCILLKKKLK; LPALLCILLKKKLKF; PALLCILLKKKLKFC;
ALLCILLKKKLKFCI; LLCILLKKKLKFCIK; LCILLKKKLKFCIKN;
CILLKKKLKFCIKNL; ILLKKKLKFCIKNLW; LLKKKLKFCIKNLWK;
LKKKLKFCIKNLWKN; KKKLKFCIKNLWKNI; KKLKFCIKNLWKNIL;
LLLVDTCVLGIILYS; LLVDTCVLGIILYSF; LHIDIEFLQLIISVK;
HIDIEFLQLIISVKS; IDIEFLQLIISVKSC; DIEFLQLIISVKSCV;
IEFLQLIISVKSCVP; EFLQLIISVKSCVPL; FLQLIISVKSCVPLV;
LQLIISVKSCVPLVF; RSMILAQKSLKKQSR; SMILAQKSLKKQSRC;
MILAQKSLKKQSRCL; ILAQKSLKKQSRCLG; LAQKSLKKQSRCLGN;
RSVKSVRKKTSLITL; SVKSVRKKTSLITLS; VKSVRKKTSLITLSI;
KSVRKKTSLITLSIM; SVRKKTSLITLSIMK; VRKKTSLITLSIMKS;
RKKTSLITLSIMKST; KKTSLITLSIMKSTL; KTSLITLSIMKSTLQ;
TSLITLSIMKSTLQM; SLITLSIMKSTLQML; LITLSIMKSTLQMLL;
ITLSIMKSTLQMLLF; TLSIMKSTLQMLLFL; LSIMKSTLQMLLFLQ;
SIMKSTLQMLLFLQK; IMKSTLQMLLFLQKV; MKSTLQMLLFLQKVK;
KSTLQMLLFLQKVKI; STLQMLLFLQKVKIK; TLQMLLFLQKVKIKK;
LQMLLFLQKVKIKKV; QMLLFLQKVKIKKVF; MLLFLQKVKIKKVFV;
LLFLQKVKIKKVFVS; LFLQKVKIKKVFVSK; FLQKVKIKKVFVSKQ;
NNIWQVLLGCTVCYL; NIWQVLLGCTVCYLK; IWQVLLGCTVCYLKI;
WQVLLGCTVCYLKWI; QVLLGCTVCYLKWIL; YLIFCTVLFSMYLKE;
LIFCTVLFSMYLKED; IFCTVLFSMYLKEDT; FCTVLFSMYLKEDTG;
CTVLFSMYLKEDTGY; TVLFSMYLKEDTGYL; VLFSMYLKEDTGYLK;
LFSMYLKEDTGYLKV; FSMYLKEDTGYLKVP; SMYLKEDTGYLKVPL;
MYLKEDTGYLKVPLI; YLKEDTGYLKVPLIV; LKEDTGYLKVPLIVE;
KEDTGYLKVPLIVEK; EDTGYLKVPLIVEKQ; DTGYLKVPLIVEKQH;
KGQELNQRICLQDME; ENPYKTQSSYLKKEF; NPYKTQSSYLKKEFY;
PYKTQSSYLKKEFYK; YKTQSSYLKKEFYKV; KTQSSYLKKEFYKVE;
LILQLIYNLELLNGR; ILQLIYNLELLNGRK; LQLIYNLELLNGRKG;
QLIYNLELLNGRKGW; LIYNLELLNGRKGWI; IYNLELLNGRKGWIL;
YNLELLNGRKGWILR; NIIYAWGNVFLILQE; IIYAWGNVFLILQEK;
IYAWGNVFLILQEKR; YAWGNVFLILQEKRI; AWGNVFLILQEKRIQ;
WGNVFLILQEKRIQK; GNVFLILQEKRIQKL; NVFLILQEKRIQKLK;
VFLILQEKRIQKLKT; FLILQEKRIQKLKTL; LILQEKRIQKLKTLD;
ILQEKRIQKLKTLDM; LQEKRIQKLKTLDMD; QEKRIQKLKTLDMDQ;
EKRIQKLKTLDMDQA; KRIQKLKTLDMDQAL; RIQKLKTLDMDQALN;
IQKLKTLDMDQALNP; QKLKTLDMDQALNPN; KLKTLDMDQALNPNH;
LKTLDMDQALNPNHN; KTLDMDQALNPNHNA; TLDMDQALNPNHNAL;
LDMDQALNPNHNALP; DMDQALNPNHNALPK; MDQALNPNHNALPKS;
DQALNPNHNALPKSQ; QALNPNHNALPKSQI; ALNPNHNALPKSQIL;
LNPNHNALPKSQILQ; NPNHNALPKSQILQP; PNHNALPKSQILQPL;
NHNALPKSQILQPLL; HNALPKSQILQPLLK; NALPKSQILQPLLKI;
ALPKSQILQPLLKIP; LPKSQILQPLLKIPK; PKSQILQPLLKIPKG;
KSQILQPLLKIPKGQ; SQILQPLLKIPKGQT; QILQPLLKIPKGQTP;
ILQPLLKIPKGQTPI; LQPLLKIPKGQTPIV; QPLLKIPKGQTPIVK;
PLLKIPKGQTPIVKS; LLKIPKGQTPIVKSC; LKIPKGQTPIVKSCI;
KIPKGQTPIVKSCIC; IPKGQTPIVKSCICV; PKGQTPIVKSCICVK;
KGQTPIVKSCICVKA; GQTPIVKSCICVKAF; QTPIVKSCICVKAFS;
TPIVKSCICVKAFSV; PIVKSCICVKAFSVL; IVKSCICVKAFSVLK;
VKSCICVKAFSVLKG; KSCICVKAFSVLKGL; SCICVKAFSVLKGLK;
CICVKAFSVLKGLKH; ICVKAFSVLKGLKHH; CVKAFSVLKGLKHHP;
VKAFSVLKGLKHHPQ; KAFSVLKGLKHHPQN; AFSVLKGLKHHPQNN;
FSVLKGLKHHPQNNT; SVLKGLKHHPQNNTS; VLKGLKHHPQNNTSL;
LKGLKHHPQNNTSLK; KGLKHHPQNNTSLKV; GLKHHPQNNTSLKVA;
LKHHPQNNTSLKVAY; KHHPQNNTSLKVAYT; HHPQNNTSLKVAYTK;
HPQNNTSLKVAYTKA; PQNNTSLKVAYTKAA; QNNTSLKVAYTKAAF;
NNTSLKVAYTKAAFI; NTSLKVAYTKAAFIK; TSLKVAYTKAAFIKC;
SLKVAYTKAAFIKCI; LKVAYTKAAFIKCIC; KVAYTKAAFIKCICT;
VAYTKAAFIKCICTI; AYTKAAFIKCICTIK; YTKAAFIKCICTIKA;
TKAAFIKCICTIKAP; KAAFIKCICTIKAPV; SILVCNCPCLSIYLI;
ILVCNCPCLSIYLII; LVCNCPCLSIYLIIS; VCNCPCLSIYLIISG;
CNCPCLSIYLIISGS; NCPCLSIYLIISGSP; CPCLSIYLIISGSPG;
PCLSIYLIISGSPGS; CLSIYLIISGSPGSL; LSIYLIISGSPGSLS;
SIYLIISGSPGSLSV; IYLIISGSPGSLSVP; YLIISGSPGSLSVPS;
LIISGSPGSLSVPSN; IISGSPGSLSVPSNT; ISGSPGSLSVPSNTL;
SGSPGSLSVPSNTLT; GSPGSLSVPSNTLTS; SPGSLSVPSNTLTSS;
PGSLSVPSNTLTSST; GSLSVPSNTLTSSTW; SLSVPSNTLTSSTWD;
LSVPSNTLTSSTWDS; SVPSNTLTSSTWDSI; VPSNTLTSSTWDSIP;
PSNTLTSSTWDSIPY; SNTLTSSTWDSIPYI; NTLTSSTWDSIPYIG;
TLTSSTWDSIPYIGC; LTSSTWDSIPYIGCP; TSSTWDSIPYIGCPS;
SSTWDSIPYIGCPST; STWDSIPYIGCPSTL; TWDSIPYIGCPSTLW;
WDSIPYIGCPSTLWV; DSIPYIGCPSTLWVL; SIPYIGCPSTLWVLL;
IPYIGCPSTLWVLLF; PYIGCPSTLWVLLFI; YIGCPSTLWVLLFIR;
IGCPSTLWVLLFIRS; GCPSTLWVLLFIRSL; CPSTLWVLLFIRSLS;
PSTLWVLLFIRSLSK; STLWVLLFIRSLSKK; TLWVLLFIRSLSKKE;
LWVLLFIRSLSKKEI; WVLLFIRSLSKKEIG; GFFTDLFLRRILKYL;
FFTDLFLRRILKYLA; FTDLFLRRILKYLAR; TDLFLRRILKYLARP;
DLFLRRILKYLARPL; LFLRRILKYLARPLH; FLRRILKYLARPLHC;
LRRILKYLARPLHCC; RRILKYLARPLHCCV; RILKYLARPLHCCVP;
ILKYLARPLHCCVPE; LKYLARPLHCCVPEL; KYLARPLHCCVPELL;
YLARPLHCCVPELLV; LARPLHCCVPELLVN; ARPLHCCVPELLVNR;
RPLHCCVPELLVNRP; PLHCCVPELLVNRPQ; LHCCVPELLVNRPQI;
HCCVPELLVNRPQIS; CCVPELLVNRPQISA; CVPELLVNRPQISAA;
VPELLVNRPQISAAE; PELLVNRPQISAAET; ELLVNRPQISAAETY;
LLVNRPQISAAETYR; LVNRPQISAAETYRL; VNRPQISAAETYRLS;
NRPQISAAETYRLSA; RPQISAAETYRLSAL; PQISAAETYRLSALQ;
QISAAETYRLSALQR; ISAAETYRLSALQRG; SAAETYRLSALQRGP;
AAETYRLSALQRGPT; AETYRLSALQRGPTP; ETYRLSALQRGPTPC;
TYRLSALQRGPTPCS; YRLSALQRGPTPCSS; RLSALQRGPTPCSSS;
LSALQRGPTPCSSSN; SALQRGPTPCSSSNT; ALQRGPTPCSSSNTV;
LQRGPTPCSSSNTVV; QRGPTPCSSSNTVVA; RGPTPCSSSNTVVAV;
GPTPCSSSNTVVAVL; PTPCSSSNTVVAVLV; TPCSSSNTVVAVLVT;
STGGTFSPPVKVPKY; TGGTFSPPVKVPKYL; GGTFSPPVKVPKYLA;
GTFSPPVKVPKYLAF; TFSPPVKVPKYLAFS; FSPPVKVPKYLAFSF;
SPPVKVPKYLAFSFL; PPVKVPKYLAFSFLL; PVKVPKYLAFSFLLG;
VKVPKYLAFSFLLGS; KVPKYLAFSFLLGSG; VPKYLAFSFLLGSGT;
PKYLAFSFLLGSGTQ; KYLAFSFLLGSGTQH; YLAFSFLLGSGTQHS;
LAFSFLLGSGTQHST; AFSFLLGSGTQHSTG; ALWSVFITWDWAVGF;
LWSVFITWDWAVGFL; WSVFITWDWAVGFLG; SVFITWDWAVGFLGV;
VFITWDWAVGFLGVI; FITWDWAVGFLGVIV; ITWDWAVGFLGVIVP;
TWDWAVGFLGVIVPS; WDWAVGFLGVIVPSG; DWAVGFLGVIVPSGY;
WAVGFLGVIVPSGYF; AVGFLGVIVPSGYFD; VGFLGVIVPSGYFDL;
FISTPCISKGSPPTA; ISTPCISKGSPPTAK; STPCISKGSPPTAKK;
TPCISKGSPPTAKKW; PCISKGSPPTAKKWK; CISKGSPPTAKKWKL;
ISKGSPPTAKKWKLL; SKGSPPTAKKWKLLP; IGFPPPCSCTFCDPA;
RLSMLVIPITSVCTV; LSMLVIPITSVCTVT; SMLVIPITSVCTVTA;
MLVIPITSVCTVTAS; LVIPITSVCTVTASH; VIPITSVCTVTASHI;
IPITSVCTVTASHIS; PITSVCTVTASHISR; ITSVCTVTASHISRF;
TSVCTVTASHISRFP; SVCTVTASHISRFPQ; VCTVTASHISRFPQV;
CTVTASHISRFPQVR; TVTASHISRFPQVRS; VTASHISRFPQVRSS;
TASHISRFPQVRSSF; ASHISRFPQVRSSFK; SHISRFPQVRSSFKL;
HISRFPQVRSSFKLG; ISRFPQVRSSFKLGR; SRFPQVRSSFKLGRG;
RFPQVRSSFKLGRGI; FPQVRSSFKLGRGIL; PQVRSSFKLGRGILA;
QVRSSFKLGRGILAV; VRSSFKLGRGILAVL; QGSIFLSGLSLLKSF;
GSIFLSGLSLLKSFS; SIFLSGLSLLKSFSA; IFLSGLSLLKSFSAL;
FLSGLSLLKSFSALS; LSGLSLLKSFSALSF; SGLSLLKSFSALSFR;
GLSLLKSFSALSFRL; LSLLKSFSALSFRLK; SLLKSFSALSFRLKP;
LLKSFSALSFRLKPL; LKSFSALSFRLKPLR; KSFSALSFRLKPLRF;
SFSALSFRLKPLRFS; FSALSFRLKPLRFSS; SALSFRLKPLRFSSG;
ALSFRLKPLRFSSGS; LSFRLKPLRFSSGSP; SFRLKPLRFSSGSPI;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

FRLKPLRFSSGSPIS; RLKPLRFSSGSPISG; LKPLRFSSGSPISGF;
KPLRFSSGSPISGFR; PLRFSSGSPISGFRK; LRFSSGSPISGFRKH;
RFSSGSPISGFRKHS; FSSGSPISGFRKHST; SSGSPISGFRKHSTS;
SGSPISGFRKHSTSV; GSPISGFRKHSTSVI; SPISGFRKHSTSVIA;
PISGFRKHSTSVIAS; ISGFRKHSTSVIAST; SGFRKHSTSVIASTP;
GFRKHSTSVIASTPV; FRKHSTSVIASTPVL; RKHSTSVIASTPVLT;
KHSTSVIASTPVLTS; HSTSVIASTPVLTSR; STSVIASTPVLTSRT;
TSVIASTPVLTSRTS; SVIASTPVLTSRTST; VIASTPVLTSRTSTP;
IASTPVLTSRTSTPP; ASTPVLTSRTSTPPF; STPVLTSRTSTPPFI;
TPVLTSRTSTPPFIS; PVLTSRTSTPPFISS; VLTSRTSTPPFISSF;
LTSRTSTPPFISSFG; TSRTSTPPFISSFGT; SRTSTPPFISSFGTC;
RTSTPPFISSFGTCT; TSTPPFISSFGTCTG; STPPFISSFGTCTGS;
TPPFISSFGTCTGSF; PPFISSFGTCTGSFG; PFISSFGTCTGSFGF;
FISSFGTCTGSFGFL; ISSFGTCTGSFGFLG; SSFGTCTGSFGFLGA;
SFGTCTGSFGFLGAA; FGTCTGSFGFLGAAP; GTCTGSFGFLGAAPG;
TCTGSFGFLGAAPGH; CTGSFGFLGAAPGHS; TGSFGFLGAAPGHSP;
GSFGFLGAAPGHSPF; SFGFLGAAPGHSPFL; FGFLGAAPGHSPFLL;
GFLGAAPGHSPFLLV; FLGAAPGHSPFLLVG; LGAAPGHSPFLLVGA;
GAAPGHSPFLLVGAI; AAPGHSPFLLVGAIF; APGHSPFLLVGAIFI;
PGHSPFLLVGAIFIC; GHSPFLLVGAIFICF; HSPFLLVGAIFICFK;
SPFLLVGAIFICFKS; PFLLVGAIFICFKSR; FLLVGAIFICFKSRC;
LLVGAIFICFKSRCY; LVGAIFICFKSRCYS; VGAIFICFKSRCYSP;
GAIFICFKSRCYSPV; AIFICFKSRCYSPVQ; IFICFKSRCYSPVQA;
RQHPLRSSSLISTSW; QHPLRSSSLISTSWG; HPLRSSSLISTSWGN;
PLRSSSLISTSWGNS; LRSSSLISTSWGNSF; RSSSLISTSWGNSFF;
SSSLISTSWGNSFFY; SSLISTSWGNSFFYK; SLISTSWGNSFFYKL;
LISTSWGNSFFYKLS; VHSLCNFFYTVSIIY; HSLCNFFYTVSIIYT;
SLCNFFYTVSIIYTI; LCNFFYTVSIIYTIS; CNFFYTVSIIYTISM;
NFFYTVSIIYTISMA; FFYTVSIIYTISMAK; FYTVSIIYTISMAKM;
YTVSIIYTISMAKMY; TVSIIYTISMAKMYT; VSIIYTISMAKMYTG;
SIIYTISMAKMYTGT; IIYTISMAKMYTGTF; IYTISMAKMYTGTFP;
YTISMAKMYTGTFPF; TISMAKMYTGTFPFS; ISMAKMYTGTFPFSY;
SMAKMYTGTFPFSYL; MAKMYTGTFPFSYLS; AKMYTGTFPFSYLSN;
KMYTGTFPFSYLSNH; GPNRGKIRIILLNII; PNRGKIRIILLNIII;
NRGKIRIILLNIIIK; RGKIRIILLNIIIKV; GKIRIILLNIIIKVY;
KIRIILLNIIIKVYR; IRIILLNIIIKVYRG; RIILLNIIIKVYRGI;
IILLNIIIKVYRGIY; ILLNIIIKVYRGIYN; LLNIIIKVYRGIYNC;
LNIIIKVYRGIYNCP; NIIIKVYRGIYNCPG; IIIKVYRGIYNCPGS;
IIKVYRGIYNCPGSF; IKVYRGIYNCPGSFL; KVYRGIYNCPGSFLQ;
VYRGIYNCPGSFLQK; YRGIYNCPGSFLQKS; RGIYNCPGSFLQKSS;
GIYNCPGSFLQKSSQ; IYNCPGSFLQKSSQG; YNCPGSFLQKSSQGV;
NCPGSFLQKSSQGVS; CPGSFLQKSSQGVSK; PGSFLQKSSQGVSKK;
GSFLQKSSQGVSKKS; SFLQKSSQGVSKKSF; FLQKSSQGVSKKSFC;
LQKSSQGVSKKSFCS; QKSSQGVSKKSFCSS; KSSQGVSKKSFCSSL;
SSQGVSKKSFCSSLQ; SQGVSKKSFCSSLQF; QGVSKKSFCSSLQFL;
GYRRYIIPNNMPQSL; YRRYIIPNNMPQSLG; RRYIIPNNMPQSLGN;
RYIIPNNMPQSLGNS; YIIPNNMPQSLGNSS; IIPNNMPQSLGNSSK;
IPNNMPQSLGNSSKQ; PNNMPQSLGNSSKQR; NNMPQSLGNSSKQRR;
NMPQSLGNSSKQRRT; MPQSLGNSSKQRRTP; PQSLGNSSKQRRTPM;
QSLGNSSKQRRTPMP; SLGNSSKQRRTPMPR; LGNSSKQRRTPMPRI;
GNSSKQRRTPMPRIK; NSSKQRRTPMPRIKV; SSKQRRTPMPRIKVL;
SKQRRTPMPRIKVLN; KQRRTPMPRIKVLNI; QRRTPMPRIKVLNII;
RRTPMPRIKVLNIIN; RTPMPRIKVLNIINK; TPMPRIKVLNIINKS;
PMPRIKVLNIINKSI; MPRIKVLNIINKSIY; PRIKVLNIINKSIYT;
RIKVLNIINKSIYTR; IKVLNIINKSIYTRK; KVLNIINKSIYTRKQ;
VLNIINKSIYTRKQN; LNIINKSIYTRKQNI; NIINKSIYTRKQNII;
IINKSIYTRKQNIIV; INKSIYTRKQNIIVL; NKSIYTRKQNIIVLI;
KSIYTRKQNIIVLIW; SIYTRKQNIIVLIWV; IYTRKQNIIVLIWVK;
YTRKQNIIVLIWVKQ; TRKQNIIVLIWVKQF; RKQNIIVLIWVKQFQ;
KQNIIVLIWVKQFQS; QNIIVLIWVKQFQSH; NIIVLIWVKQFQSHA;
LLIEAYSGNFVIPII; LIEAYSGNFVIPIIK; IEAYSGNFVIPIIKE;
EAYSGNFVIPIIKEL; AYSGNFVIPIIKELI; YSGNFVIPIIKELIP;
SGNFVIPIIKELIPY; GNFVIPIIKELIPYL; NFVIPIIKELIPYLS;
SSKPSNSPRSTSNYS; SKPSNSPRSTSNYSI; KPSNSPRSTSNYSIC;
PSNSPRSTSNYSICL; SNSPRSTSNYSICLR; NSPRSTSNYSICLRS;
GTCYALYSSKGCNLN; TCYALYSSKGCNLNF; CYALYSSKGCNLNFY;
YALYSSKGCNLNFYS; ALYSSKGCNLNFYSS; LYSSKGCNLNFYSSS;
YSSKGCNLNFYSSSS; SSKGCNLNFYSSSSL; SKGCNLNFYSSSSLP;
KGCNLNFYSSSSLPS; GCNLNFYSSSSLPSS; CNLNFYSSSSLPSSN;
NLNFYSSSSLPSSNF; LNFYSSSSLPSSNFS; NFYSSSSLPSSNFSH;
SSTHEPGNTKKKGLL; STHEPGNTKKKGLLT; ESFTESFTAGKAVVL;
SFTESFTAGKAVVLL; FTESFTAGKAVVLLF; TESFTAGKAVVLLFF;
ESFTAGKAVVLLFFP; SFTAGKAVVLLFFPS; FTAGKAVVLLFFPST;
TAGKAVVLLFFPSTL; AGKAVVLLFFPSTLS; GKAVVLLFFPSTLSS;
KAVVLLFFPSTLSSP; AVVLLFFPSTLSSPL; VVLLFFPSTLSSPLQ;
VLLFFPSTLSSPLQN; LLFFPSTLSSPLQNS; LFFPSTLSSPLQNSS;
FFPSTLSSPLQNSSK; FPSTLSSPLQNSSKS; PSTLSSPLQNSSKSS;
STLSSPLQNSSKSSK; TLSSPLQNSSKSSKI; LSSPLQNSSKSSKIK;
SSPLQNSSKSSKIKI; SPLQNSSKSSKIKIK; PLQNSSKSSKIKIKI;
LQNSSKSSKIKIKIL; ALFFVPVQVLPTFTE; LFFVPVQVLPTFTEA;
FFVPVQVLPTFTEAC; FVPVQVLPTFTEACR; VPVQVLPTFTEACRD;
PVQVLPTFTEACRDS; VQVLPTFTEACRDSW; QVLPTFTEACRDSWR;
VLPTFTEACRDSWRR; LPTFTEACRDSWRRT; PTFTEACRDSWRRTM;
TFTEACRDSWRRTMA; FTEACRDSWRRTMAF; TEACRDSWRRTMAFV;
EACRDSWRRTMAFVQ; ACRDSWRRTMAFVQF; CRDSWRRTMAFVQFN;
RDSWRRTMAFVQFNW; DSWRRTMAFVQFNWG; SWRRTMAFVQFNWGQ;
WRRTMAFVQFNWGQG; RRTMAFVQFNWGQGQ; RTMAFVQFNWGQGQD;
TMAFVQFNWGQGQDS; ARKTCLSCTFLPEVM; RKTCLSCTFLPEVMV;
KTCLSCTFLPEVMVW; TCLSCTFLPEVMVWL; CLSCTFLPEVMVWLH;
LSCTFLPEVMVWLHS; SCTFLPEVMVWLHSM; CTFLPEVMVWLHSMG;
TFLPEVMVWLHSMGK; FLPEVMVWLHSMGKQ; LPEVMVWLHSMGKQL;
PEVMVWLHSMGKQLL; EVMVWLHSMGKQLLP; VMVWLHSMGKQLLPV;
MVWLHSMGKQLLPVS; VWLHSMGKQLLPVSH; WLHSMGKQLLPVSHA;
LHSMGKQLLPVSHAL; HSMGKQLLPVSHALS; SMGKQLLPVSHALSF;
MGKQLLPVSHALSFL; GKQLLPVSHALSFLR; KQLLPVSHALSFLRS;
QLLPVSHALSFLRSW; LLPVSHALSFLRSWF; LPVSHALSFLRSWFG;
PVSHALSFLRSWFGC; VSHALSFLRSWFGCI; SHALSFLRSWFGCIP;
HALSFLRSWFGCIPL; GLAKLFGEIPILLQF; LAKLFGEIPILLQFL;
AKLFGEIPILLQFLQ 16 mers:

MDKVLNREESMELMDL; DKVLNREESMELMDLL;
KVLNREESMELMDLLG; VLNREESMELMDLLGL;
LNREESMELMDLLGLE; NREESMELMDLLGLER;
REESMELMDLLGLERA; EESMELMDLLGLERAA;
ESMELMDLLGLERAAW; SMELMDLLGLERAAWG;
MELMDLLGLERAAWGN; ELMDLLGLERAAWGNL;
LMDLLGLERAAWGNLP; MDLLGLERAAWGNLPL;
DLLGLERAAWGNLPLM; LLGLERAAWGNLPLMR;
LGLERAAWGNLPLMRK; GLERAAWGNLPLMRKA;
LERAAWGNLPLMRKAY; ERAAWGNLPLMRKAYL;
RAAWGNLPLMRKAYLR; AAWGNLPLMRKAYLRK;
AWGNLPLMRKAYLRKC; WGNLPLMRKAYLRKCK;
GNLPLMRKAYLRKCKE; NLPLMRKAYLRKCKEF;
LPLMRKAYLRKCKEFH; PLMRKAYLRKCKEFHP;
LMRKAYLRKCKEFHPD; MRKAYLRKCKEFHPDK;
RKAYLRKCKEFHPDKG; KAYLRKCKEFHPDKGG;
AYLRKCKEFHPDKGGD; YLRKCKEFHPDKGGDE;
LRKCKEFHPDKGGDED; RKCKEFHPDKGGDEDK;
KCKEFHPDKGGDEDKM; CKEFHPDKGGDEDKMK;
KEFHPDKGGDEDKMKR; EFHPDKGGDEDKMKRM;
FHPDKGGDEDKMKRMN; HPDKGGDEDKMKRMNT;
PDKGGDEDKMKRMNTL; DKGGDEDKMKRMNTLY;
KGGDEDKMKRMNTLYK; GGDEDKMKRMNTLYKK;
GDEDKMKRMNTLYKKM; DEDKMKRMNTLYKKME;
EDKMKRMNTLYKKMEQ; DKMKRMNTLYKKMEQD;
KMKRMNTLYKKMEQDV; MKRMNTLYKKMEQDVK;
KRMNTLYKKMEQDVKV; RMNTLYKKMEQDVKVA;
MNTLYKKMEQDVKVAH; NTLYKKMEQDVKVAHQ;
TLYKKMEQDVKVAHQP; LYKKMEQDVKVAHQPD;
YKKMEQDVKVAHQPDF; KKMEQDVKVAHQPDFG;
KMEQDVKVAHQPDFGT; MEQDVKVAHQPDFGTW;
EQDVKVAHQPDFGTWS; QDVKVAHQPDFGTWSS;
DVKVAHQPDFGTWSSS; VKVAHQPDFGTWSSSE;
KVAHQPDFGTWSSSEV; VAHQPDFGTWSSSEVC;
AHQPDFGTWSSSEVCA; HQPDFGTWSSSEVCAD;
QPDFGTWSSSEVCADF; PDFGTWSSSEVCADFP;
DFGTWSSSEVCADFPL; FGTWSSSEVCADFPLC;
GTWSSSEVCADFPLCP; TWSSSEVCADFPLCPD;
WSSSEVCADFPLCPDT; SSSEVCADFPLCPDTL;
SSEVCADFPLCPDTLY; SEVCADFPLCPDTLYC;
EVCADFPLCPDTLYCK; VCADFPLCPDTLYCKE;
CADFPLCPDTLYCKEW; ADFPLCPDTLYCKEWP;
DFPLCPDTLYCKEWPI; FPLCPDTLYCKEWPIC;
PLCPDTLYCKEWPICS; LCPDTLYCKEWPICSK;
CPDTLYCKEWPICSKK; PDTLYCKEWPICSKKP;
DTLYCKEWPICSKKPS; TLYCKEWPICSKKPSV;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

LYCKEWPICSKKPSVH; YCKEWPICSKKPSVHC;
CKEWPICSKKPSVHCP; KEWPICSKKPSVHCPC;
EWPICSKKPSVHCPCM; WPICSKKPSVHCPCML;
PICSKKPSVHCPCMLC; ICSKKPSVHCPCMLCQ;
CSKKPSVHCPCMLCQL; SKKPSVHCPCMLCQLR;
KKPSVHCPCMLCQLRL; KPSVHCPCMLCQLRLR;
PSVHCPCMLCQLRLRH; SVHCPCMLCQLRLRHL;
VHCPCMLCQLRLRHLN; HCPCMLCQLRLRHLNR;
CPCMLCQLRLRHLNRK; PCMLCQLRLRHLNRKF;
CMLCQLRLRHLNRKFL; MLCQLRLRHLNRKFLR;
LCQLRLRHLNRKFLRK; CQLRLRHLNRKFLRKE;
QLRLRHLNRKFLRKEP; LRLRHLNRKFLRKEPL;
RLRHLNRKFLRKEPLV; LRHLNRKFLRKEPLVW;
RHLNRKFLRKEPLVWI; HLNRKFLRKEPLVWID;
LNRKFLRKEPLVWIDC; NRKFLRKEPLVWIDCY;
RKFLRKEPLVWIDCYC; KFLRKEPLVWIDCYCI;
FLRKEPLVWIDCYCID; LRKEPLVWIDCYCIDC;
RKEPLVWIDCYCIDCF; KEPLVWIDCYCIDCFT;
EPLVWIDCYCIDCFTQ; PLVWIDCYCIDCFTQW;
LVWIDCYCIDCFTQWF; VWIDCYCIDCFTQWFG;
WIDCYCIDCFTQWFGL; IDCYCIDCFTQWFGLD;
DCYCIDCFTQWFGLDL; CYCIDCFTQWFGLDLT;
YCIDCFTQWFGLDLTE; CIDCFTQWFGLDLTEE;
IDCFTQWFGLDLTEET; DCFTQWFGLDLTEETL;
CFTQWFGLDLTEETLQ; FTQWFGLDLTEETLQW;
TQWFGLDLTEETLQWW; QWFGLDLTEETLQWWV;
WFGLDLTEETLQWWVQ; FGLDLTEETLQWWVQI;
GLDLTEETLQWWVQII; LDLTEETLQWWVQIIG;
DLTEETLQWWVQIIGE; LTEETLQWWVQIIGET;
TEETLQWWVQIIGETP; EETLQWWVQIIGETPF;
ETLQWWVQIIGETPFR; TLQWWVQIIGETPFRD;
LQWWVQIIGETPFRDL; QWWVQIIGETPFRDLK;
WWVQIIGETPFRDLKL; KALSNYFFYRCQPMEQ;
ALSNYFFYRCQPMEQK; LSNYFFYRCQPMEQKS;
SNYFFYRCQPMEQKSG; NYFFYRCQPMEQKSGS;
YFFYRCQPMEQKSGSP; FFYRCQPMEQKSGSPG;
FYRCQPMEQKSGSPGG; YRCQPMEQKSGSPGGV;
RCQPMEQKSGSPGGVP; CQPMEQKSGSPGGVPL;
QPMEQKSGSPGGVPLM; PMEQKSGSPGGVPLMK;
MEQKSGSPGGVPLMKN; EQKSGSPGGVPLMKNG;
QKSGSPGGVPLMKNGM; KSGSPGGVPLMKNGMK;
SGSPGGVPLMKNGMKI; GSPGGVPLMKNGMKIY;
SPGGVPLMKNGMKIYF; PGGVPLMKNGMKIYFA;
GGVPLMKNGMKIYFAM; GVPLMKNGMKIYFAMK;
VPLMKNGMKIYFAMKI; PLMKNGMKIYFAMKIC;
LMKNGMKIYFAMKICL; MKNGMKIYFAMKICLP;
KNGMKIYFAMKICLPV; NGMKIYFAMKICLPVM;
GMKIYFAMKICLPVMK; MKIYFAMKICLPVMKK;
KIYFAMKICLPVMKKQ; IYFAMKICLPVMKKQQ;
YFAMKICLPVMKKQQQ; FAMKICLPVMKKQQQI;
AMKICLPVMKKQQQIL; MKICLPVMKKQQQILN;
KICLPVMKKQQQILNT; ICLPVMKKQQQILNTQ;
CLPVMKKQQQILNTQH; LPVMKKQQQILNTQHH;
PVMKKQQQILNTQHHP; VMKKQQQILNTQHHPK;
MKKQQQILNTQHHPKK; KKQQQILNTQHHPKKK;
KQQQILNTQHHPKKKE; QQQILNTQHHPKKKER;
KTLKTFPLIYTSFLVK; TLKTFPLIYTSFLVKL;
LKTFPLIYTSFLVKLY; KTFPLIYTSFLVKLYL;
TFPLIYTSFLVKLYLV; FPLIYTSFLVKLYLVI;
PLIYTSFLVKLYLVIE; LIYTSFLVKLYLVIEP;
IYTSFLVKLYLVIEPL; YTSFLVKLYLVIEPLP;
TSFLVKLYLVIEPLPA; SFLVKLYLVIEPLPAL;
FLVKLYLVIEPLPALL; LVKLYLVIEPLPALLC;
VKLYLVIEPLPALLCI; KLYLVIEPLPALLCIL;
LYLVIEPLPALLCILL; YLVIEPLPALLCILLK;
LVIEPLPALLCILLKK; VIEPLPALLCILLKKK;
IEPLPALLCILLKKKL; EPLPALLCILLKKKLK;
PLPALLCILLKKKLKF; LPALLCILLKKKLKFC;
PALLCILLKKKLKFCI; ALLCILLKKKLKFCIK;
LLCILLKKKLKFCIKN; LCILLKKKLKFCIKNL;
CILLKKKLKFCIKNLW; ILLKKKLKFCIKNLWK;
LLKKKLKFCIKNLWKN; LKKKLKFCIKNLWKNI;
KKKLKFCIKNLWKNIL; LLLVDTCVLGIILYSF;
LHIDIEFLQLIISVKS; HIDIEFLQLIISVKSC;
IDIEFLQLIISVKSCV; DIEFLQLIISVKSCVP;
IEFLQLIISVKSCVPL; EFLQLIISVKSCVPLV;
FLQLIISVKSCVPLVF; RSMILAQKSLKKQSRC;
SMILAQKSLKKQSRCL; MILAQKSLKKQSRCLG;
ILAQKSLKKQSRCLGN; RSVKSVRKKTSLITLS;
SVKSVRKKTSLITLSI; VKSVRKKTSLITLSIM;
KSVRKKTSLITLSIMK; SVRKKTSLITLSIMKS;
VRKKTSLITLSIMKST; RKKTSLITLSIMKSTL;
KKTSLITLSIMKSTLQ; KTSLITLSIMKSTLQM;
TSLITLSIMKSTLQML; SLITLSIMKSTLQMLL;
LITLSIMKSTLQMLLF; ITLSIMKSTLQMLLFL;
TLSIMKSTLQMLLFLQ; LSIMKSTLQMLLFLQK;
SIMKSTLQMLLFLQKV; IMKSTLQMLLFLQKVK;
MKSTLQMLLFLQKVKI; KSTLQMLLFLQKVKIK;
STLQMLLFLQKVKIKV; TLQMLLFLQKVKIKKV;
LQMLLFLQKVKIKKVF; QMLLFLQKVKIKKVFV;
MLLFLQKVKIKKVFVS; LLFLQKVKIKKVFVSK;
LFLQKVKIKKVFVSKQ; NNIWQVLLGCTVCYLK;
NIWQVLLGCTVCYLKI; IWQVLLGCTVCYLKWI;
WQVLLGCTVCYLKWIL; YLIFCTVLFSMYLKED;
LIFCTVLFSMYLKEDT; IFCTVLFSMYLKEDTG;
FCTVLFSMYLKEDTGY; CTVLFSMYLKEDTGYL;
TVLFSMYLKEDTGYLK; VLFSMYLKEDTGYLKV;
LFSMYLKEDTGYLKVP; FSMYLKEDTGYLKVPL;
SMYLKEDTGYLKVPLI; MYLKEDTGYLKVPLIV;
YLKEDTGYLKVPLIVE; LKEDTGYLKVPLIVEK;
KEDTGYLKVPLIVEKQ; EDTGYLKVPLIVEKQH;
ENPYKTQSSYLKKEFY; NPYKTQSSYLKKEFYK;
PYKTQSSYLKKEFYKV; YKTQSSYLKKEFYKVE;
LILQLIYNLELLNGRK; ILQLIYNLELLNGRKG;
LQLIYNLELLNGRKGW; QLIYNLELLNGRKGWI;
LIYNLELLNGRKGWIL; IYNLELLNGRKGWILR;
NIIYAWGNVFLILQEK; IIYAWGNVFLILQEKR;
IYAWGNVFLILQEKRI; YAWGNVFLILQEKRIQ;
AWGNVFLILQEKRIQK; WGNVFLILQEKRIQKL;
GNVFLILQEKRIQKLK; NVFLILQEKRIQKLKT;
VFLILQEKRIQKLKTL; FLILQEKRIQKLKTLD;
LILQEKRIQKLKTLDM; ILQEKRIQKLKTLDMD;
LQEKRIQKLKTLDMDQ; QEKRIQKLKTLDMDQA;
EKRIQKLKTLDMDQAL; KRIQKLKTLDMDQALN;
RIQKLKTLDMDQALNP; IQKLKTLDMDQALNPN;
QKLKTLDMDQALNPNH; KLKTLDMDQALNPNHN;
LKTLDMDQALNPNHNA; KTLDMDQALNPNHNAL;
TLDMDQALNPNHNALP; LDMDQALNPNHNALPK;
DMDQALNPNHNALPKS; MDQALNPNHNALPKSQ;
DQALNPNHNALPKSQI; QALNPNHNALPKSQIL;
ALNPNHNALPKSQILQ; LNPNHNALPKSQILQP;
NPNHNALPKSQILQPL; PNHNALPKSQILQPLL;
NHNALPKSQILQPLLK; HNALPKSQILQPLLKI;
NALPKSQILQPLLKIP; ALPKSQILQPLLKIPK;
LPKSQILQPLLKIPKG; PKSQILQPLLKIPKGQ;
KSQILQPLLKIPKGQT; SQILQPLLKIPKGQTP;
QILQPLLKIPKGQTPI; ILQPLLKIPKGQTPIV;
LQPLLKIPKGQTPIVK; QPLLKIPKGQTPIVKS;
PLLKIPKGQTPIVKSC; LLKIPKGQTPIVKSCI;
LKIPKGQTPIVKSCIC; KIPKGQTPIVKSCICV;
IPKGQTPIVKSCICVK; PKGQTPIVKSCICVKA;
KGQTPIVKSCICVKAF; GQTPIVKSCICVKAFS;
QTPIVKSCICVKAFSV; TPIVKSCICVKAFSVL;
PIVKSCICVKAFSVLK; IVKSCICVKAFSVLKG;
VKSCICVKAFSVLKGL; KSCICVKAFSVLKGLK;
SCICVKAFSVLKGLKH; CICVKAFSVLKGLKHH;
ICVKAFSVLKGLKHHP; CVKAFSVLKGLKHHPQ;
VKAFSVLKGLKHHPQN; KAFSVLKGLKHHPQNN;
AFSVLKGLKHHPQNNT; FSVLKGLKHHPQNNTS;
SVLKGLKHHPQNNTSL; VLKGLKHHPQNNTSLK;
LKGLKHHPQNNTSLKV; KGLKHHPQNNTSLKVA;
GLKHHPQNNTSLKVAY; LKHHPQNNTSLKVAYT;
KHHPQNNTSLKVAYTK; HHPQNNTSLKVAYTKA;
HPQNNTSLKVAYTKAA; PQNNTSLKVAYTKAAF;
QNNTSLKVAYTKAAFI; NNTSLKVAYTKAAFIK;
NTSLKVAYTKAAFIKC; TSLKVAYTKAAFIKCI;
SLKVAYTKAAFIKCIC; LKVAYTKAAFIKCICT;
KVAYTKAAFIKCICTI; VAYTKAAFIKCICTIK;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

AYTKAAFIKCICTIKA; YTKAAFIKCICTIKAP;
TKAAFIKCICTIKAPV; SILVCNCPCLSIYLII;
ILVCNCPCLSIYLIIS; LVCNCPCLSIYLIISG;
VCNCPCLSIYLIISGS; CNCPCLSIYLIISGSP;
NCPCLSIYLIISGSPG; CPCLSIYLIISGSPGS;
PCLSIYLIISGSPGSL; CLSIYLIISGSPGSLS;
LSIYLIISGSPGSLSV; SIYLIISGSPGSLSVP;
IYLIISGSPGSLSVPS; YLIISGSPGSLSVPSN;
LIISGSPGSLSVPSNT; IISGSPGSLSVPSNTL;
ISGSPGSLSVPSNTLT; SGSPGSLSVPSNTLTS;
GSPGSLSVPSNTLTSS; SPGSLSVPSNTLTSST;
PGSLSVPSNTLTSSTW; GSLSVPSNTLTSSTWD;
SLSVPSNTLTSSTWDS; LSVPSNTLTSSTWDSI;
SVPSNTLTSSTWDSIP; VPSNTLTSSTWDSIPY;
PSNTLTSSTWDSIPYI; SNTLTSSTWDSIPYIG;
NTLTSSTWDSIPYIGC; TLTSSTWDSIPYIGCP;
LTSSTWDSIPYIGCPS; TSSTWDSIPYIGCPST;
SSTWDSIPYIGCPSTL; STWDSIPYIGCPSTLW;
TWDSIPYIGCPSTLWV; WDSIPYIGCPSTLWVL;
DSIPYIGCPSTLWVLL; SIPYIGCPSTLWVLLF;
IPYIGCPSTLWVLLFI; PYIGCPSTLWVLLFIR;
YIGCPSTLWVLLFIRS; IGCPSTLWVLLFIRSL;
GCPSTLWVLLFIRSLS; CPSTLWVLLFIRSLSK;
PSTLWVLLFIRSLSKK; STLWVLLFIRSLSKKE;
TLWVLLFIRSLSKKEI; LWVLLFIRSLSKKEIG;
GFFTDLFLRRILKYLA; FFTDLFLRRILKYLAR;
FTDLFLRRILKYLARP; TDLFLRRILKYLARPL;
DLFLRRILKYLARPLH; LFLRRILKYLARPLHC;
FLRRILKYLARPLHCC; LRRILKYLARPLHCCV;
RRILKYLARPLHCCVP; RILKYLARPLHCCVPE;
ILKYLARPLHCCVPEL; LKYLARPLHCCVPELL;
KYLARPLHCCVPELLV; YLARPLHCCVPELLVN;
LARPLHCCVPELLVNR; ARPLHCCVPELLVNRP;
RPLHCCVPELLVNRPQ; PLHCCVPELLVNRPQI;
LHCCVPELLVNRPQIS; HCCVPELLVNRPQISA;
CCVPELLVNRPQISAA; CVPELLVNRPQISAAE;
VPELLVNRPQISAAET; PELLVNRPQISAAETY;
ELLVNRPQISAAETYR; LLVNRPQISAAETYRL;
LVNRPQISAAETYRLS; VNRPQISAAETYRLSA;
NRPQISAAETYRLSAL; RPQISAAETYRLSALQ;
PQISAAETYRLSALQR; QISAAETYRLSALQRG;
ISAAETYRLSALQRGP; SAAETYRLSALQRGPT;
AAETYRLSALQRGPTP; AETYRLSALQRGPTPC;
ETYRLSALQRGPTPCS; TYRLSALQRGPTPCSS;
YRLSALQRGPTPCSSS; RLSALQRGPTPCSSSN;
LSALQRGPTPCSSSNT; SALQRGPTPCSSSNTV;
ALQRGPTPCSSSNTVV; LQRGPTPCSSSNTVVA;
QRGPTPCSSSNTVVAV; RGPTPCSSSNTVVAVL;
GPTPCSSSNTVVAVLV; PTPCSSSNTVVAVLVT;
STGGTFSPPVKVPKYL; TGGTFSPPVKVPKYLA;
GGTFSPPVKVPKYLAF; GTFSPPVKVPKYLAFS;
TFSPPVKVPKYLAFSF; FSPPVKVPKYLAFSFL;
SPPVKVPKYLAFSFLL; PPVKVPKYLAFSFLLG;
PVKVPKYLAFSFLLGS; VKVPKYLAFSFLLGSG;
KVPKYLAFSFLLGSGT; VPKYLAFSFLLGSGTQ;
PKYLAFSFLLGSGTQH; KYLAFSFLLGSGTQHS;
YLAFSFLLGSGTQHST; LAFSFLLGSGTQHSTG;
ALWSVFITWDWAVGFL; LWSVFITWDWAVGFLG;
WSVFITWDWAVGFLGV; SVFITWDWAVGFLGVI;
VFITWDWAVGFLGVIV; FITWDWAVGFLGVIVP;
ITWDWAVGFLGVIVPS; TWDWAVGFLGVIVPSG;
WDWAVGFLGVIVPSGY; DWAVGFLGVIVPSGYF;
WAVGFLGVIVPSGYFD; AVGFLGVIVPSGYFDL;
FISTPCISKGSPPTAK; ISTPCISKGSPPTAKK;
STPCISKGSPPTAKKW; TPCISKGSPPTAKKWK;
PCISKGSPPTAKKWKL; CISKGSPPTAKKWKLL;
ISKGSPPTAKKWKLLP; RLSMLVIPITSVCTVT;
LSMLVIPITSVCTVTA; SMLVIPITSVCTVTAS;
MLVIPITSVCTVTASH; LVIPITSVCTVTASHI;
VIPITSVCTVTASHIS; IPITSVCTVTASHISR;
PITSVCTVTASHISRF; ITSVCTVTASHISRFP;
TSVCTVTASHISRFPQ; SVCTVTASHISRFPQV;
VCTVTASHISRFPQVR; CTVTASHISRFPQVRS;
TVTASHISRFPQVRSS; VTASHISRFPQVRSSF;

TASHISRFPQVRSSFK; ASHISRFPQVRSSFKL;
SHISRFPQVRSSFKLG; HISRFPQVRSSFKLGR;
ISRFPQVRSSFKLGRG; SRFPQVRSSFKLGRGI;
RFPQVRSSFKLGRGIL; FPQVRSSFKLGRGILA;
PQVRSSFKLGRGILAV; QVRSSFKLGRGILAVL;
QGSIFLSGLSLLKSFS; GSIFLSGLSLLKSFSA;
SIFLSGLSLLKSFSAL; IFLSGLSLLKSFSALS;
FLSGLSLLKSFSALSF; LSGLSLLKSFSALSFR;
SGLSLLKSFSALSFRL; GLSLLKSFSALSFRLK;
LSLLKSFSALSFRLKP; SLLKSFSALSFRLKPL;
LLKSFSALSFRLKPLR; LKSFSALSFRLKPLRF;
KSFSALSFRLKPLRFS; SFSALSFRLKPLRFSS;
FSALSFRLKPLRFSSG; SALSFRLKPLRFSSGS;
ALSFRLKPLRFSSGSP; LSFRLKPLRFSSGSPI;
SFRLKPLRFSSGSPIS; FRLKPLRFSSGSPISG;
RLKPLRFSSGSPISGF; LKPLRFSSGSPISGFR;
KPLRFSSGSPISGFRK; PLRFSSGSPISGFRKH;
LRFSSGSPISGFRKHS; RFSSGSPISGFRKHST;
FSSGSPISGFRKHSTS; SSGSPISGFRKHSTSV;
SGSPISGFRKHSTSVI; GSPISGFRKHSTSVIA;
SPISGFRKHSTSVIAS; PISGFRKHSTSVIAST;
ISGFRKHSTSVIASTP; SGFRKHSTSVIASTPV;
GFRKHSTSVIASTPVL; FRKHSTSVIASTPVLT;
RKHSTSVIASTPVLTS; KHSTSVIASTPVLTSR;
HSTSVIASTPVLTSRT; STSVIASTPVLTSRTS;
TSVIASTPVLTSRTST; SVIASTPVLTSRTSTP;
VIASTPVLTSRTSTPP; IASTPVLTSRTSTPPF;
ASTPVLTSRTSTPPFI; STPVLTSRTSTPPFIS;
TPVLTSRTSTPPFISS; PVLTSRTSTPPFISSF;
VLTSRTSTPPFISSFG; LTSRTSTPPFISSFGT;
TSRTSTPPFISSFGTC; SRTSTPPFISSFGTCT;
RTSTPPFISSFGTCTG; TSTPPFISSFGTCTGS;
STPPFISSFGTCTGSF; TPPFISSFGTCTGSFG;
PPFISSFGTCTGSFGF; PFISSFGTCTGSFGFL;
FISSFGTCTGSFGFLG; ISSFGTCTGSFGFLGA;
SSFGTCTGSFGFLGAA; SFGTCTGSFGFLGAAP;
FGTCTGSFGFLGAAPG; GTCTGSFGFLGAAPGH;
TCTGSFGFLGAAPGHS; CTGSFGFLGAAPGHSP;
TGSFGFLGAAPGHSPF; GSFGFLGAAPGHSPFL;
SFGFLGAAPGHSPFLL; FGFLGAAPGHSPFLLV;
GFLGAAPGHSPFLLVG; FLGAAPGHSPFLLVGA;
LGAAPGHSPFLLVGAI; GAAPGHSPFLLVGAIF;
AAPGHSPFLLVGAIFI; APGHSPFLLVGAIFIC;
PGHSPFLLVGAIFICF; GHSPFLLVGAIFICFK;
HSPFLLVGAIFICFKS; SPFLLVGAIFICFKSR;
PFLLVGAIFICFKSRC; FLLVGAIFICFKSRCY;
LLVGAIFICFKSRCYS; LVGAIFICFKSRCYSP;
VGAIFICFKSRCYSPV; GAIFICFKSRCYSPVQ;
AIFICFKSRCYSPVQA; RQHPLRSSSLISTSWG;
QHPLRSSSLISTSWGN; HPLRSSSLISTSWGNS;
PLRSSSLISTSWGNSF; LRSSSLISTSWGNSFF;
RSSSLISTSWGNSFFY; SSSLISTSWGNSFFYK;
SSLISTSWGNSFFYKL; SLISTSWGNSFFYKLS;
VHSLCNFFYTVSIIYT; HSLCNFFYTVSIIYTI;
SLCNFFYTVSIIYTIS; LCNFFYTVSIIYTISM;
CNFFYTVSIIYTISMA; NFFYTVSIIYTISMAK;
FFYTVSIIYTISMAKM; FYTVSIIYTISMAKMY;
YTVSIIYTISMAKMYT; TVSIIYTISMAKMYTG;
VSIIYTISMAKMYTGT; SIIYTISMAKMYTGTF;
IIYTISMAKMYTGTFP; IYTISMAKMYTGTFPF;
YTISMAKMYTGTFPFS; TISMAKMYTGTFPFSY;
ISMAKMYTGTFPFSYL; SMAKMYTGTFPFSYLS;
MAKMYTGTFPFSYLSN; AKMYTGTFPFSYLSNH;
GPNRGKIRIILLNIII; PNRGKIRIILLNIIIK;
NRGKIRIILLNIIIKV; RGKIRIILLNIIIKVY;
GKIRIILLNIIIKVYR; KIRIILLNIIIKVYRG;
IRIILLNIIIKVYRGI; RIILLNIIIKVYRGIY;
IILLNIIIKVYRGIYN; ILLNIIIKVYRGIYNC;
LLNIIIKVYRGIYNCP; LNIIIKVYRGIYNCPG;
NIIIKVYRGIYNCPGS; IIIKVYRGIYNCPGSF;
IIKVYRGIYNCPGSFL; IKVYRGIYNCPGSFLQ;
KVYRGIYNCPGSFLQK; VYRGIYNCPGSFLQKS;
YRGIYNCPGSFLQKSS; RGIYNCPGSFLQKSSQ;
GIYNCPGSFLQKSSQG; IYNCPGSFLQKSSQGV;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

YNCPGSFLQKSSQGVS; NCPGSFLQKSSQGVSK;
CPGSFLQKSSQGVSKK; PGSFLQKSSQGVSKKS;
GSFLQKSSQGVSKKSF; SFLQKSSQGVSKKSFC;
FLQKSSQGVSKKSFCS; LQKSSQGVSKKSFCSS;
QKSSQGVSKKSFCSSL; KSSQGVSKKSFCSSLQ;
SSQGVSKKSFCSSLQF; SQGVSKKSFCSSLQFL;
GYRRYIIPNNMPQSLG; YRRYIIPNNMPQSLGN;
RRYIIPNNMPQSLGNS; RYIIPNNMPQSLGNSS;
YIIPNNMPQSLGNSSK; IIPNNMPQSLGNSSKQ;
IPNNMPQSLGNSSKQR; PNNMPQSLGNSSKQRR;
NNMPQSLGNSSKQRRT; NMPQSLGNSSKQRRTP;
MPQSLGNSSKQRRTPM; PQSLGNSSKQRRTPMP;
QSLGNSSKQRRTPMPR; SLGNSSKQRRTPMPRI;
LGNSSKQRRTPMPRIK; GNSSKQRRTPMPRIKV;
NSSKQRRTPMPRIKVL; SSKQRRTPMPRIKVLN;
SKQRRTPMPRIKVLNI; KQRRTPMPRIKVLNII;
QRRTPMPRIKVLNIIN; RRTPMPRIKVLNIIINK;
RTPMPRIKVLNIINKS; TPMPRIKVLNIINKSI;
PMPRIKVLNIINKSIY; MPRIKVLNIINKSIYT;
PRIKVLNIINKSIYTR; RIKVLNIINKSIYTRK;
IKVLNIINKSIYTRKQ; KVLNIINKSIYTRKQN;
VLNIINKSIYTRKQNI; LNIINKSIYTRKQNII;
NIINKSIYTRKQNIIV; IINKSIYTRKQNIIVL;
INKSIYTRKQNIIVLI; NKSIYTRKQNIIVLIW;
KSIYTRKQNIIVLIWV; SIYTRKQNIIVLIWVK;
IYTRKQNIIVLIWVKQ; YTRKQNIIVLIWVKQF;
TRKQNIIVLIWVKQFQ; RKQNIIVLIWVKQFQS;
KQNIIVLIWVKQFQSH; QNIIVLIWVKQFQSHA;
LLIEAYSGNFVIPIIK; LIEAYSGNFVIPIIKE;
IEAYSGNFVIPIIKEL; EAYSGNFVIPIIKELI;
AYSGNFVIPIIKELIP; YSGNFVIPIIKELIPY;
SGNFVIPIIKELIPYL; GNFVIPIIKELIPYLS;
SSKPSNSPRSTSNYSI; SKPSNSPRSTSNYSIC;
KPSNSPRSTSNYSICL; PSNSPRSTSNYSICLR;
SNSPRSTSNYSICLRS; GTCYALYSSKGCNLNF;
TCYALYSSKGCNLNFY; CYALYSSKGCNLNFYS;
YALYSSKGCNLNFYSS; ALYSSKGCNLNFYSSS;
LYSSKGCNLNFYSSSS; YSSKGCNLNFYSSSSL;
SSKGCNLNFYSSSSLP; SKGCNLNFYSSSSLPS;
KGCNLNFYSSSSLPSS; GCNLNFYSSSSLPSSN;
CNLNFYSSSSLPSSNF; NLNFYSSSSLPSSNFS;
LNFYSSSSLPSSNFSH; SSTHEPGNTKKKGLLT;
ESFTESFTAGKAVVLL; SFTESFTAGKAVVLLF;
FTESFTAGKAVVLLFF; TESFTAGKAVVLLFFP;
ESFTAGKAVVLLFFPS; SFTAGKAVVLLFFPST;
FTAGKAVVLLFFPSTL; TAGKAVVLLFFPSTLS;
AGKAVVLLFFPSTLSS; GKAVVLLFFPSTLSSP;
KAVVLLFFPSTLSSPL; AVVLLFFPSTLSSPLQ;
VVLLFFPSTLSSPLQN; VLLFFPSTLSSPLQNS;
LLFFPSTLSSPLQNSS; LFFPSTLSSPLQNSSK;
FFPSTLSSPLQNSSKS; FPSTLSSPLQNSSKSS;
PSTLSSPLQNSSKSSK; STLSSPLQNSSKSSKI;
TLSSPLQNSSKSSKIK; LSSPLQNSSKSSKIKI;
SSPLQNSSKSSKIKIK; SPLQNSSKSSKIKIKI;
PLQNSSKSSKIKIKIL; ALFFVPVQVLPTFTEA;
LFFVPVQVLPTFTEAC; FFVPVQVLPTFTEACR;
FVPVQVLPTFTEACRD; VPVQVLPTFTEACRDS;
PVQVLPTFTEACRDSW; VQVLPTFTEACRDSWR;
QVLPTFTEACRDSWRR; VLPTFTEACRDSWRRT;
LPTFTEACRDSWRRTM; PTFTEACRDSWRRTMA;
TFTEACRDSWRRTMAF; FTEACRDSWRRTMAFV;
TEACRDSWRRTMAFVQ; EACRDSWRRTMAFVQF;
ACRDSWRRTMAFVQFN; CRDSWRRTMAFVQFNW;
RDSWRRTMAFVQFNWG; DSWRRTMAFVQFNWGQ;
SWRRTMAFVQFNWGQG; WRRTMAFVQFNWGQGQ;
RRTMAFVQFNWGQGQD; RTMAFVQFNWGQGQDS;
ARKTCLSCTFLPEVMV; RKTCLSCTFLPEVMVW;
KTCLSCTFLPEVMVWL; TCLSCTFLPEVMVWLH;
CLSCTFLPEVMVWLHS; LSCTFLPEVMVWLHSM;
SCTFLPEVMVWLHSMG; CTFLPEVMVWLHSMGK;
TFLPEVMVWLHSMGKQ; FLPEVMVWLHSMGKQL;
LPEVMVWLHSMGKQLL; PEVMVWLHSMGKQLLP;
EVMVWLHSMGKQLLPV; VMVWLHSMGKQLLPVS;
MVWLHSMGKQLLPVSH; VWLHSMGKQLLPVSHA;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

WLHSMGKQLLPVSHAL; LHSMGKQLLPVSHALS;
HSMGKQLLPVSHALSF; SMGKQLLPVSHALSFL;
MGKQLLPVSHALSFLR; GKQLLPVSHALSFLRS;
KQLLPVSHALSFLRSW; QLLPVSHALSFLRSWF;
LLPVSHALSFLRSWFG; LPVSHALSFLRSWFGC;
PVSHALSFLRSWFGCI; VSHALSFLRSWFGCIP;
SHALSFLRSWFGCIPL; GLAKLFGEIPILLQFL;
LAKLFGEIPILLQFLQ

BK virus reverse reading frame 2

13 mers:

WIKFLTGKNPWSS; IKFLTGKNPWSSW; KFLTGKNPWSSWT;
FLTGKNPWSSWTF; GSVRNFTLTKGAT; SVRNFTLTKGATR;
VRNFTLTKGATRI; RNFTLTKGATRIK; LISLILEPGVAQR;
ISLILEPGVAQRF; SLILEPGVAQRFV; LILEPGVAQRFVL;
ILEPGVAQRFVLI; LEPGVAQRFVLIF; EPGVAQRFVLIFL;
PGVAQRFVLIFLF; GVAQRFVLIFLFA; VAQRFVLIFLFAQ;
AQRFVLIFLFAQI; QRFVLIFLFAQIP; RFVLIFLFAQIPC;
FVLIFLFAQIPCT; VLIFLFAQIPCTA; LIFLFAQIPCTAR;
IFLFAQIPCTARN; FLFAQIPCTARNG; LFAQIPCTARNGL;
FAQIPCTARNGLF; AQIPCTARNGLFV; QIPCTARNGLFVP;
IPCTARNGLFVPK; PCTARNGLFVPKS; CTARNGLFVPKSL;
TARNGLFVPKSLL; ARNGLFVPKSLLC; RNGLFVPKSLLCT;
NGLFVPKSLLCTA; GLFVPKSLLCTAL; LFVPKSLLCTALA;
FVPKSLLCTALAC; VPKSLLCTALACY; PKSLLCTALACYV;
KSLLCTALACYVS; SLLCTALACYVSL; LLCTALACYVSLD;
IATALTASHSGLA; VIIFFIGANLWNR; IIFFIGANLWNRR;
IFFIGANLWNRRV; FFIGANLWNRRVG; FIGANLWNRRVGV;
IGANLWNRRVGVL; GANLWNRRVGVLV; ANLWNRRVGVLVE;
NLWNRRVGVLVEF; LWNRRVGVLVEFL; RSNSRFSTLNTTQ;
SNSRFSTLNTTQK; NSRFSTLNTTQKK; SRFSTLNTTQKKK;
RFSTLNTTQKKKK; FSTLNTTQKKKKG; STLNTTQKKKKGR;
TLNTTQKKKKGRR; LNTTQKKKKGRRP; NTTQKKKKGRRPS;
SIPYYRRKHSRGL; IPYYRRKHSRGLK; PYYRRKHSRGLKG;
YYRRKHSRGLKGA; GCVFIIRYVFRIS; CVFIIRYVFRISI;
VFIIRYVFRISIQ; FIIRYVFRISIQC; IIRYVFRISIQCR;
IRYVFRISIQCRG; RYVFRISIQCRGV; KSKKYLSASSRYS;
SKKYLSASSRYSF; KKYLSASSRYSFS; KKSRYPSYDQGRN;
KSRYPSYDQGRNA; SRYPSYDQGRNAN; RYPSYDQGRNANR;
YPSYDQGRNANRK; PSYDQGRNANRKI; SYDQGRNANRKIQ;
YDQGRNANRKIQS; DQGRNANRKIQSY; QGRNANRKIQSYI;
GRNANRKIQSYIR; NGFNIWSSWKCCT; GFNIWSSWKCCTR;
FNIWSSWKCCTRT; NIWSSWKCCTRTI; IWSSWKCCTRTIY;
WSSWKCCTRTIYG; SSWKCCTRTIYGR; SWKCCTRTIYGRC;
WKCCTRTIYGRCC; KCCTRTIYGRCCL; CCTRTIYGRCCLA;
CTRTIYGRCCLAA; TRTIYGRCCLAAL; RTIYGRCCLAALF;
TIYGRCCLAALFA; IYGRCCLAALFAT; WKNNTSCRVIRFV;
KNNTSCRVIRFVW; NNTSCRVIRFVWW; SLKCKPTHGKANL;
IKGFAFRTWNKQF; KGFAFRTWNKQFR; GFAFRTWNKQFRQ;
FAFRTWNKQFRQF; AFRTWNKQFRQFE; FRTWNKQFRQFER;
RTWNKQFRQFERL; TWNKQFRQFERLF; WNKQFRQFERLFR;
NKQFRQFERLFRW; KQFRQFERLFRWK; QFRQFERLFRWKC;
GKFRKETFKQKNP; KFRKETFKQKNPN; FRKETFKQKNPNI;
RKETFKQKNPNIS; KETFKQKNPNIST; ETFKQKNPNISTR;
TFKQKNPNISTRL; FKQKNPNISTRLG; KQKNPNISTRLGY;
QKNPNISTRLGYN; KNPNISTRLGYNE; AQNIFKKILTKLR;
QNIFKKILTKLRV; NIFKKILTKLRVL; IFKKILTKLRVLT;
KKNFTKWNDLVAT; KNFTKWNDLVATA; NFTKWNDLVATAN;
FTKWNDLVATANL; TKWNDLVATANLV; IPITMLFPSLRYF;
PITMLFPSLRYFS; ITMLFPSLRYFSP; TMLFPSLRYFSPC;
KWLIQKQHLLNVY; WLIQKQHLLNVYV; LIQKQHLLNVYVQ;
KHLFKAFWFAIVP; HLFKAFWFAIVPV; LFKAFWFAIVPVC;
FKAFWFAIVPVCQ; KAFWFAIVPVCQY; AFWFAIVPVCQYI;
FWFAIVPVCQYIL; WFAIVPVCQYILS; FAIVPVCQYILSY;
AIVPVCQYILSYL; IVPVCQYILSYLG; VPVCQYILSYLGP;
PVCQYILSYLGPL; VCQYILSYLGPLE; CQYILSYLGPLEV;
QYILSYLGPLEVF; YILSYLGPLEVFL; ILSYLGPLEVFLC;
LSYLGPLEVFLCH; SYLGPLEVFLCHQ; YLGPLEVFLCHQT;
LGPLEVFLCHQTP; GHLAKRKLGKDSL; HLAKRKLGKDSLQ;
LAKRKLGKDSLQI; AKRKLGKDSLQIF; KRKLGKDSLQIFF;
RKLGKDSLQIFFS; KLGKDSLQIFFSG; LGKDSLQIFFSGG;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GKDSLQIFFSGGS; NILQGLSTVVFQS; ILQGLSTVVFQSC;
TGHKYQQLKHTGY; GHKYQQLKHTGYQ; HKYQQLKHTGYQL;
KYQQLKHTGYQLY; YQQLKHTGYQLYK; QQLKHTGYQLYKE;
QLKHTGYQLYKEA; LKHTGYQLYKEAP; KHTGYQLYKEAPH;
HTGYQLYKEAPHP; TGYQLYKEAPHPV; GYQLYKEAPHPVH;
YQLYKEAPHPVHL; QLYKEAPHPVHLA; LYKEAPHPVHLAT;
YKEAPHPVHLATL; KEAPHPVHLATLW; LCWSHEVLGEHFP;
CWSHEVLGEHFPL; WSHEVLGEHFPLL; HFHFYWDQVPSTQ;
FHFYWDQVPSTQL; HFYWDQVPSTQLD; FYWDQVPSTQLDK;
YWDQVPSTQLDKH; WDQVPSTQLDKHC; DQVPSTQLDKHCF;
QVPSTQLDKHCFC; VPSTQLDKHCFCP; PSTQLDKHCFCPN;
STQLDKHCFCPNR; TQLDKHCFCPNRP; QLDKHCFCPNRPY;
LDKHCFCPNRPYG; DKHCFCPNRPYGQ; KHCFCPNRPYGQY;
HCFCPNRPYGQYS; CFCPNRPYGQYSL; FCPNRPYGQYSLP;
CPNRPYGQYSLPG; PNRPYGQYSLPGT; NRPYGQYSLPGTG;
RPYGQYSLPGTGL; PYGQYSLPGTGLL; YGQYSLPGTGLLG;
GQYSLPGTGLLGF; YHQGTLTCNSLAL; HQGTLTCNSLALP;
QGTLTCNSLALPA; GTLTCNSLALPAF; TLTCNSLALPAFP;
LTCNSLALPAFPR; TCNSLALPAFPRV; CNSLALPAFPRVL;
NSLALPAFPRVLH; SLALPAFPRVLHL; LALPAFPRVLHLQ;
ALPAFPRVLHLQQ; LPAFPRVLHLQQR; PAFPRVLHLQQRS;
AFPRVLHLQQRSG; FPRVLHLQQRSGN; PRVLHLQQRSGNY;
RVLHLQQRSGNYC; VLHLQQRSGNYCL; LHLQQRSGNYCLE;
VFLHHAHALFVTL; FLHHAHALFVTLH; LHHAHALFVTLHE;
HHAHALFVTLHEG; PLFVQLQPPTSVD; LFVQLQPPTSVDF;
FVQLQPPTSVDFH; VQLQPPTSVDFHR; QLQPPTSVDFHRL;
LQPPTSVDFHRLG; QPPTSVDFHRLGP; PPTSVDFHRLGPH;
PTSVDFHRLGPHL; TSVDFHRLGPHLN; SVDFHRLGPHLNW;
VDFHRLGPHLNWG; DFHRLGPHLNWGG; FHRLGPHLNWGGE;
HRLGPHLNWGGEF; RLGPHLNWGGEFL; LGPHLNWGGEFLL;
GPHLNWGGEFLLC; PHLNWGGEFLLCC; HLNWGGEFLLCCN;
LNWGGEFLLCCNR; NWGGEFLLCCNRE; WGGEFLLCCNREA;
GGEFLLCCNREAF; GEFLLCCNREAFF; EFLLCCNREAFFS;
FLLCCNREAFFSL; LLCCNREAFFSLG; LCCNREAFFSLGY;
CCNREAFFSLGYH; CNREAFFSLGYHC; GFHLDPPFLGLGS;
FHLDPPFLGLGSI; HLDPPFLGLGSIL; LDPPFLGLGSILP;
DPPFLGLGSILPL; LLELLLLLLLVVL; LELLLLLLVVLA;
ELLLLLLLVVLAL; LLLLLLLVVLALA; LLLLLLVVLALAR;
LLLLLVVLALARV; LLLLVVLALARVP; LLLVVLALARVPL;
LLVVLALARVPLA; LVVLALARVPLAF; VVLALARVPLAFW;
VLALARVPLAFWE; LALARVPLAFWEL; ALARVPLAFWELP;
LARVPLAFWELPL; ARVPLAFWELPLD; RVPLAFWELPLDT;
VPLAFWELPLDTL; PLAFWELPLDTLL; LAFWELPLDTLLF;
AFWELPLDTLLFF; FWELPLDTLLFFW; WELPLDTLLFFWL;
ELPLDTLLFFWLG; LPLDTLLFFWLGP; PLDTLLFFWLGPS;
LDTLLFFWLGPSS; DTLLFFWLGPSSY; TLLFFWLGPSSYA;
LLFFWLGPSSYAS; LFFWLGPSSYASR; FFWLGPSSYASRA;
FWLGPSSYASRAG; WLGPSSYASRAGV; LGPSSYASRAGVT;
GPSSYASRAGVTV; PSSYASRAGVTVP; SSYASRAGVTVPY;
SYASRAGVTVPYR; YASRAGVTVPYRP; ASRAGVTVPYRPR;
SRAGVTVPYRPRS; RAGVTVPYRPRSK; AGVTVPYRPRSKG;
GVTVPYRPRSKGN; VTVPYRPRSKGNI; TVPYRPRSKGNIH;
LAPPGAIVFSINS; APPGAIVFSINSP; PPGAIVFSINSPE;
PGAIVFSINSPEC; GAIVFSINSPECT; AIVFSINSPECTL;
IVFSINSPECTLC; FLKSILCVTSSIL; LKSILCVTSSILS;
KSILCVTSSILSA; SILCVTSSILSAS; ILCVTSSILSASS;
LCVTSSILSASSI; CVTSSILSASSIL; VWPKCTRVPSLSA;
WPKCTRVPSLSAT; PKCTRVPSLSATC; KCTRVPSLSATCL;
CTRVPSLSATCLT; TRVPSLSATCLTI; RVPSLSATCLTIE;
VPSLSATCLTIEG; PSLSATCLTIEGL; SLSATCLTIEGLI;
LSATCLTIEGLIG; SATCLTIEGLIGE; ATCLTIEGLIGER;
TCLTIEGLIGERS; CLTIEGLIGERSE; KFIGAFTIVQVVS;
FIGAFTIVQVVSS; IGAFTIVQVVSSK; GAFTIVQVVSSKN;
AFTIVQVVSSKNL; FTIVQVVSSKNLA; TIVQVVSSKNLAK;
IVQVVSSKNLAKE; VQVVSSKNLAKES; QVVSSKNLAKESL;
VVSSKNLAKESLK; VSSKNLAKESLKN; SSKNLAKESLKNL;
SKNLAKESLKNLS; KNLAKESLKNLSV; NLAKESLKNLSVL;
LAKESLKNLSVLL; AKESLKNLSVLLC; KESLKNLSVLLCN;
ESLKNLSVLLCNS; SLKNLSVLLCNSC; LKNLSVLLCNSCE;
KNLSVLLCNSCEV; NLSVLLCNSCEVI; LSVLLCNSCEVIE;
SVLLCNSCEVIEG; VLLCNSCEVIEGI; LLCNSCEVIEGIS;
LCNSCEVIEGISS; CNSCEVIEGISSL; NSCEVIEGISSLI;
SCEVIEGISSLIT; CEVIEGISSLITC; EVIEGISSLITCH;
VIEGISSLITCHK; IEGISSLITCHKA; EGISSLITCHKAW;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GISSLITCHKAWE; ISSLITCHKAWEI; SSLITCHKAWEIV;
SLITCHKAWEIVA; LITCHKAWEIVAN; ITCHKAWEIVANK;
TCHKAWEIVANKE; CHKAWEIVANKEG; HKAWEIVANKEGP;
KAWEIVANKEGPQ; AWEIVANKEGPQC; WEIVANKEGPQCL;
EIVANKEGPQCLG; IVANKEGPQCLGS; VANKEGPQCLGSR;
ANKEGPQCLGSRY; ILLTKVFTPGNRI; LLTKVFTPGNRIS;
YSSGLNNSKAMPD; SSGLNNSKAMPDC; IKAANPAIAPGAP;
KAANPAIAPGAPA; AANPAIAPGAPAI; ANPAIAPGAPAIT;
NPAIAPGAPAITA; PAIAPGAPAITAY; AIAPGAPAITAYV;
GVRPIAAIASEVL; VRPIAAIASEVLV; RPIAAIASEVLVM;
PIAAIASEVLVMP; IAAIASEVLVMPS; AAIASEVLVMPST;
AIASEVLVMPSTV; IASEVLVMPSTVA; ASEVLVMPSTVAR;
SEVLVMPSTVARD; EVLVMPSTVARDA; VLVMPSTVARDAI;
TSIAAAASPAAIS; SIAAAASPAAISA; IAAAASPAAISAT;
AAAASPAAISATE; AAASPAAISATEN; AASPAAISATENP;
ASPAAISATENPV; SPAAISATENPVA; PAAISATENPVAA;
AAISATENPVAAA; AISATENPVAAAA; ISATENPVAAAAS;
SATENPVAAAASD; ATENPVAAAASDT; TENPVAAAASDTL;
ENPVAAAASDTLA; NPVAAAASDTLAT; PVAAAASDTLATR;
VAAAASDTLATRS; AAAASDTLATRSP; AAASDTLATRSPK;
AASDTLATRSPKS; ASDTLATRSPKSA; SDTLATRSPKSAR;
DTLATRSPKSARA; TLATRSPKSARAA; LATRSPKSARAAP;
ATRSPKSARAAPM; TRSPKSARAAPMN; RSPKSARAAPMNL;
SPKSARAAPMNLE; PKSARAAPMNLEI; KSARAAPMNLEIQ;
SARAAPMNLEIQK; ARAAPMNLEIQKK; RAAPMNLEIQKKR;
AAPMNLEIQKKRD; APMNLEIQKKRDY; PMNLEIQKKRDYL;
MNLEIQKKRDYLP; NLEIQKKRDYLPR; LEIQKKRDYLPRS;
EIQKKRDYLPRSL; IQKKRDYLPRSLL; QKKRDYLPRSLLQ;
KKRDYLPRSLLQS; KRDYLPRSLLQSL; RDYLPRSLLQSLL;
DYLPRSLLQSLLQ; YLPRSLLQSLLQQ; LPRSLLQSLLQQV;
PRSLLQSLLQQVK; RSLLQSLLQQVKQ; SLLQSLLQQVKQW;
LLQSLLQQVKQWY; LQSLLQQVKQWYF; QSLLQQVKQWYFC;
SLLQQVKQWYFCF; LLQQVKQWYFCFS; LQQVKQWYFCFSR;
QQVKQWYFCFSRL; QVKQWYFCFSRLH; VKQWYFCFSRLHC;
KQWYFCFSRLHCL; QWYFCFSRLHCLH; WYFCFSRLHCLHL;
YFCFSRLHCLHLY; FCFSRLHCLHLYK; CFSRLHCLHLYKI;
FSRLHCLHLYKIP; SRLHCLHLYKIPA; RLHCLHLYKIPAK;
LHCLHLYKIPAKA; HCLHLYKIPAKAL; CLHLYKIPAKALK;
KSSELFFLFQSRF; SSELFFLFQSRFY; SELFFLFQSRFYQ;
ELFFLFQSRFYQL; LFFLFQSRFYQLS; FFLFQSRFYQLSL;
FLFQSRFYQLSLK; LFQSRFYQLSLKL; FQSRFYQLSLKLV;
QSRFYQLSLKLVV; SRFYQLSLKLVVT; RFYQLSLKLVVTA;
FYQLSLKLVVTAG; YQLSLKLVVTAGA; QLSLKLVVTAGAE;
LSLKLVVTAGAEP; SLKLVVTAGAEPW; LKLVVTAGAEPWP;
KLVVTAGAEPWPL; LVVTAGAEPWPLS; VVTAGAEPWPLSS;
VTAGAEPWPLSSL; TAGAEPWPLSSLT; AGAEPWPLSSLTG;
GAEPWPLSSLTGD; AEPWPLSSLTGDK; EPWPLSSLTGDKA;
PWPLSSLTGDKAK; WPLSSLTGDKAKI; PLSSLTGDKAKIP;
LSSLTGDKAKIPR; SSLTGDKAKIPRL; SLTGDKAKIPRLA;
LTGDKAKIPRLAK; TGDKAKIPRLAKH; GDKAKIPRLAKHV;
DKAKIPRLAKHVC; KAKIPRLAKHVCH; AKIPRLAKHVCHA;
KIPRLAKHVCHAL; IPRLAKHVCHALS; PRLAKHVCHALSF;
RLAKHVCHALSFL; LAKHVCHALSFLR; AKHVCHALSFLRS;
KHVCHALSFLRSW; HVCHALSFLRSWF; VCHALSFLRSWFG;
CHALSFLRSWFGC; HALSFLRSWFGCI; ALSFLRSWFGCIP;
LSFLRSWFGCIPW; SFLRSWFGCIPWV; FLRSWFGCIPWVS;
LRSWFGCIPWVSS; RSWFGCIPWVSSS; SWFGCIPWVSSSS;
WFGCIPWVSSSSL; GHGLAAFPCESCT; HGLAAFPCESCTF;
GLAAFPCESCTFL; LAAFPCESCTFLP; AAFPCESCTFLPE;
AFPCESCTFLPEV; FPCESCTFLPEVM; PCESCTFLPEVMV;
CESCTFLPEVMVW; ESCTFLPEVMVWL; SCTFLPEVMVWLH;
CTFLPEVMVWLHS; TFLPEVMVWLHSM; FLPEVMVWLHSMG;
LPEVMVWLHSMGK; PEVMVWLHSMGKQ; EVMVWLHSMGKQL;
VMVWLHSMGKQLL; MVWLHSMGKQLLP; VWLHSMGKQLLPV;
WLHSMGKQLLPVA; LHSMGKQLLPVAF; HSMGKQLLPVAFF;
SMGKQLLPVAFFF; MGKQLLPVAFFFI; GKQLLPVAFFFII;
KQLLPVAFFFIIY; QLLPVAFFFIIYK; LLPVAFFFIIYKR;
LPVAFFFIIYKRP; PVAFFFIIYKRPR; VAFFFIIYKRPRP;
AFFFIIYKRPRPP; FFFIIYKRPRPPL; FFIIYKRPRPPLP;
FIIYKRPRPPLPP; IIYKRPRPPLPPP; IYKRPRPPLPPPF;
YKRPRPPLPPPFL; KRPRPPLPPPFLS; RPRPPLPPPFLSS;
PRPPLPPPFLSSS; RPPLPPPFLSSSK; PPLPPPFLSSSKG;
PLPPPFLSSSKGV; LPPPFLSSSKGVE; PPPFLSSSKGVEA;
PPFLSSSKGVEAF; PFLSSSKGVEAFS; FLSSSKGVEAFSE;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

LSSSKGVEAFSEA; QNYLGKSLFFCNF; NYLGKSLFFCNFC; YLGKSLFFCNFCK 14 mers:

WIKFLTGKNPWSSW; IKFLTGKNPWSSWT; KFLTGKNPWSSWTF;
GSVRNFTLTKGATR; SVRNFTLTKGATRI; VRNFTLTKGATRIK;
LISLILEPGVAQRF; ISLILEPGVAQRFV; SLILEPGVAQRFVL;
LILEPGVAQRFVLI; ILEPGVAQRFVLIF; LEPGVAQRFVLIFL;
EPGVAQRFVLIFLF; PGVAQRFVLIFLFA; GVAQRFVLIFLFAQ;
VAQRFVLIFLFAQI; AQRFVLIFLFAQIP; QRFVLIFLFAQIPC;
RFVLIFLFAQIPCT; FVLIFLFAQIPCTA; VLIFLFAQIPCTAR;
LIFLFAQIPCTARN; IFLFAQIPCTARNG; FLFAQIPCTARNGL;
LFAQIPCTARNGLF; FAQIPCTARNGLFV; AQIPCTARNGLFVP;
QIPCTARNGLFVPK; IPCTARNGLFVPKS; PCTARNGLFVPKSL;
CTARNGLFVPKSLL; TARNGLFVPKSLLC; ARNGLFVPKSLLCT;
RNGLFVPKSLLCTA; NGLFVPKSLLCTAL; GLFVPKSLLCTALA;
LFVPKSLLCTALAC; FVPKSLLCTALACY; VPKSLLCTALACYV;
PKSLLCTALACYVS; KSLLCTALACYVSL; SLLCTALACYVSLD;
VIIFFIGANLWNRR; IIFFIGANLWNRRV; IFFIGANLWNRRVG;
FFIGANLWNRRVGV; FIGANLWNRRVGVL; IGANLWNRRVGVLV;
GANLWNRRVGVLVE; ANLWNRRVGVLVEF; NLWNRRVGVLVEFL;
RSNSRFSTLNTTQK; SNSRFSTLNTTQKK; NSRFSTLNTTQKKK;
SRFSTLNTTQKKKK; RFSTLNTTQKKKKG; FSTLNTTQKKKKGR;
STLNTTQKKKKGRR; TLNTTQKKKKGRRP; RSIPYYRRKHSRGL;
SIPYYRRKHSRGLK; IPYYRRKHSRGLKG; PYYRRKHSRGLKGA;
GCVFIIRYVFRISI; CVFIIRYVFRISIQ; VFIIRYVFRISIQC;
FIIRYVFRISIQCR; IIRYVFRISIQCRG; IRYVFRISIQCRGV;
KSKKYLSASSRYSF; SKKYLSASSRYSFS; KKSRYPSYDQGRNA;
KSRYPSYDQGRNAN; SRYPSYDQGRNANR; RYPSYDQGRNANRK;
YPSYDQGRNANRKI; PSYDQGRNANRKIQ; SYDQGRNANRKIQS;
YDQGRNANRKIQSY; DQGRNANRKIQSYI; QGRNANRKIQSYIR;
NGFNIWSSWKCCTR; GFNIWSSWKCCTRT; FNIWSSWKCCTRTI;
NIWSSWKCCTRTIY; IWSSWKCCTRTIYG; WSSWKCCTRTIYGR;
SSWKCCTRTIYGRC; SWKCCTRTIYGRCC; WKCCTRTIYGRCCL;
KCCTRTIYGRCCLA; CCTRTIYGRCCLAA; CTRTIYGRCCLAAL;
TRTIYGRCCLAALF; RTIYGRCCLAALFA; TIYGRCCLAALFAT;
WKNNTSCRVIRFVW; KNNTSCRVIRFVWW; IKGFAFRTWNKQFR;
KGFAFRTWNKQFRQ; GFAFRTWNKQFRQF; FAFRTWNKQFRQFE;
AFRTWNKQFRQFER; FRTWNKQFRQFERL; RTWNKQFRQFERLF;
TWNKQFRQFERLFR; WNKQFRQFERLFRW; NKQFRQFERLFRWK;
KQFRQFERLFRWKC; GKFRKETFKQKNPN; KFRKETFKQKNPNI;
FRKETFKQKNPNIS; RKETFKQKNPNIST; KETFKQKNPNISTR;
ETFKQKNPNISTRL; TFKQKNPNISTRLG; FKQKNPNISTRLGY;
KQKNPNISTRLGYN; QKNPNISTRLGYNE; AQNIFKKILTKLRV;
QNIFKKILTKLRVL; NIFKKILTKLRVLT; KKNFTKWNDLVATA;
KNFTKWNDLVATAN; NFTKWNDLVATANL; FTKWNDLVATANLV;
IPITMLFPSLRYFS; PITMLFPSLRYFSP; ITMLFPSLRYFSPC;
KWLIQKQHLLNVYV; WLIQKQHLLNVYVQ; KHLFKAFWFAIVPV;
HLFKAFWFAIVPVC; LFKAFWFAIVPVCQ; FKAFWFAIVPVCQY;
KAFWFAIVPVCQYI; AFWFAIVPVCQYIL; FWFAIVPVCQYILS;
WFAIVPVCQYILSY; FAIVPVCQYILSYL; AIVPVCQYILSYLG;
IVPVCQYILSYLGP; VPVCQYILSYLGPL; PVCQYILSYLGPLE;
VCQYILSYLGPLEV; CQYILSYLGPLEVF; QYILSYLGPLEVFL;
YILSYLGPLEVFLC; ILSYLGPLEVFLCH; LSYLGPLEVFLCHQ;
SYLGPLEVFLCHQT; YLGPLEVFLCHQTP; GHLAKRKLGKDSLQ;
HLAKRKLGKDSLQI; LAKRKLGKDSLQIF; AKRKLGKDSLQIFF;
KRKLGKDSLQIFFS; RKLGKDSLQIFFSG; KLGKDSLQIFFSGG;
LGKDSLQIFFSGGS; NILQGLSTVVFQSC; TGHKYQQLKHTGYQ;
GHKYQQLKHTGYQL; HKYQQLKHTGYQLY; KYQQLKHTGYQLYK;
YQQLKHTGYQLYKE; QQLKHTGYQLYKEA; QLKHTGYQLYKEAP;
LKHTGYQLYKEAPH; KHTGYQLYKEAPHP; HTGYQLYKEAPHPV;
TGYQLYKEAPHPVH; GYQLYKEAPHPVHL; YQLYKEAPHPVHLA;
QLYKEAPHPVHLAT; LYKEAPHPVHLATL; YKEAPHPVHLATLW;
LCWSHEVLGEHPPL; CWSHEVLGEHPPLL; HFHFYWDQVPSTQL;
FHFYWDQVPSTQLD; HFYWDQVPSTQLDK; FYWDQVPSTQLDKH;
YWDQVPSTQLDKHC; WDQVPSTQLDKHCF; DQVPSTQLDKHCFC;
QVPSTQLDKHCFCP; VPSTQLDKHCFCPN; PSTQLDKHCFCPNR;
STQLDKHCFCPNRP; TQLDKHCFCPNRPY; QLDKHCFCPNRPYG;
LDKHCFCPNRPYGQ; DKHCFCPNRPYGQY; KHCFCPNRPYGQYS;
HCFCPNRPYGQYSL; CFCPNRPYGQYSLP; FCPNRPYGQYSLPG;
CPNRPYGQYSLPGT; PNRPYGQYSLPGTG; NRPYGQYSLPGTGL;
RPYGQYSLPGTGLL; PYGQYSLPGTGLLG; YGQYSLPGTGLLGF;
YHQGTLTCNSLALP; HQGTLTCNSLALPA; QGTLTCNSLALPAF;
GTLTCNSLALPAFP; TLTCNSLALPAFPR; LTCNSLALPAFPRV;
TCNSLALPAFPRVL; CNSLALPAFPRVLH; NSLALPAFPRVLHL;
SLALPAFPRVLHLQ; LALPAFPRVLHLQQ; ALPAFPRVLHLQQR;
LPAFPRVLHLQQRS; PAFPRVLHLQQRSG; AFPRVLHLQQRSGN;
FPRVLHLQQRSGNY; PRVLHLQQRSGNYC; RVLHLQQRSGNYCL;
VLHLQQRSGNYCLE; VFLHHAHALFVTLH; FLHHAHALFVTLHE;
LHHAHALFVTLHEG; PLFVQLQPPTSVDF; LFVQLQPPTSVDFH;
FVQLQPPTSVDFHR; VQLQPPTSVDFHRL; QLQPPTSVDFHRLG;
LQPPTSVDFHRLGP; QPPTSVDFHRLGPH; PPTSVDFHRLGPHL;
PTSVDFHRLGPHLN; TSVDFHRLGPHLNW; SVDFHRLGPHLNWG;
VDFHRLGPHLNWGG; DFHRLGPHLNWGGE; FHRLGPHLNWGGEF;
HRLGPHLNWGGEFL; RLGPHLNWGGEFLL; LGPHLNWGGEFLLC;
GPHLNWGGEFLLCC; PHLNWGGEFLLCCN; HLNWGGEFLLCCNR;
LNWGGEFLLCCNRE; NWGGEFLLCCNREA; WGGEFLLCCNREAF;
GGEFLLCCNREAFF; GEFLLCCNREAFFS; EFLLCCNREAFFSL;
FLLCCNREAFFSLG; LLCCNREAFFSLGY; LCCNREAFFSLGYH;
CCNREAFFSLGYHC; GFHLDPPFLGLGSI; FHLDPPFLGLGSIL;
HLDPPFLGLGSILP; LDPPFLGLGSILPL; LLELLLLLLVVLA;
LELLLLLLVVLAL; ELLLLLLVVLALA; LLLLLLVVLALAR;
LLLLLVVLALARV; LLLLVVLALARVP; LLLVVLALARVPL;
LLVVLALARVPLA; LVVLALARVPLAF; VVLALARVPLAFW;
VLALARVPLAFWE; LALARVPLAFWEL; ALARVPLAFWELP;
ALARVPLAFWELPL; LARVPLAFWELPLD; ARVPLAFWELPLDT;
RVPLAFWELPLDTL; VPLAFWELPLDTLL; PLAFWELPLDTLLF;
LAFWELPLDTLLFF; AFWELPLDTLLFFW; FWELPLDTLLFFWL;
WELPLDTLLFFWLG; ELPLDTLLFFWLGP; LPLDTLLFFWLGPS;
PLDTLLFFWLGPSS; LDTLLFFWLGPSSY; DTLLFFWLGPSSYA;
TLLFFWLGPSSYAS; LLFFWLGPSSYASR; LFFWLGPSSYASRA;
FFWLGPSSYASRAG; FWLGPSSYASRAGV; WLGPSSYASRAGVT;
LGPSSYASRAGVTV; GPSSYASRAGVTVP; PSSYASRAGVTVPY;
SSYASRAGVTVPYR; SYASRAGVTVPYRP; YASRAGVTVPYRPR;
ASRAGVTVPYRPRS; SRAGVTVPYRPRSK; RAGVTVPYRPRSKG;
AGVTVPYRPRSKGN; GVTVPYRPRSKGNI; VTVPYRPRSKGNIH;
LAPPGAIVFSINSP; APPGAIVFSINSPE; PPGAIVFSINSPEC;
PGAIVFSINSPECT; GAIVFSINSPECTL; AIVFSINSPECTLC;
FLKSILCVTSSILS; LKSILCVTSSILSA; KSILCVTSSILSAS;
SILCVTSSILSASS; ILCVTSSILSASSI; LCVTSSILSASSIL;
VWPKCTRVPSLSAT; WPKCTRVPSLSATC; PKCTRVPSLSATCL;
KCTRVPSLSATCLT; CTRVPSLSATCLTI; TRVPSLSATCLTIE;
RVPSLSATCLTIEG; VPSLSATCLTIEGL; PSLSATCLTIEGLI;
SLSATCLTIEGLIG; LSATCLTIEGLIGE; SATCLTIEGLIGER;
ATCLTIEGLIGERS; TCLTIEGLIGERSE; KFIGAFTIVQVSS;
FIGAFTIVQVSSK; IGAFTIVQVSSKN; GAFTIVQVSSKNL;
AFTIVQVSSKNLA; FTIVQVSSKNLAK; TIVQVSSKNLAKE;
IVQVVSSKNLAKES; VQVVSSKNLAKESL; QVVSSKNLAKESLK;
VVSSKNLAKESLKN; VSSKNLAKESLKNL; SSKNLAKESLKNLS;
SKNLAKESLKNLSV; KNLAKESLKNLSVL; NLAKESLKNLSVLL;
LAKESLKNLSVLLC; AKESLKNLSVLLCN; KESLKNLSVLLCNS;
ESLKNLSVLLCNSC; SLKNLSVLLCNSCE; LKNLSVLLCNSCEV;
KNLSVLLCNSCEVI; NLSVLLCNSCEVIE; LSVLLCNSCEVIEG;
SVLLCNSCEVIEGI; VLLCNSCEVIEGIS; LLCNSCEVIEGISS;
LCNSCEVIEGISSL; CNSCEVIEGISSLI; NSCEVIEGISSLIT;
SCEVIEGISSLITC; CEVIEGISSLITCH; EVIEGISSLITCHK;
VIEGISSLITCHKA; IEGISSLITCHKAW; EGISSLITCHKAWE;
GISSLITCHKAWEI; ISSLITCHKAWEIV; SSLITCHKAWEIVA;
SLITCHKAWEIVAN; LITCHKAWEIVANK; ITCHKAWEIVANKE;
TCHKAWEIVANKEG; CHKAWEIVANKEGP; HKAWEIVANKEGPQ;
KAWEIVANKEGPQC; AWEIVANKEGPQCL; WEIVANKEGPQCLG;
EIVANKEGPQCLGS; IVANKEGPQCLGSR; VANKEGPQCLGSRY;
ILLTKVFTPGNRIS; YSSGLNNSKAMPDC; IKAANPAIAPGAPA;
KAANPAIAPGAPAI; AANPAIAPGAPAIT; ANPAIAPGAPAITA;
NPAIAPGAPAITAY; PAIAPGAPAITAYV; GVRPIAAIASEVLV;
VRPIAAIASEVLVM; RPIAAIASEVLVMP; PIAAIASEVLVMPS;
IAAIASEVLVMPST; AAIASEVLVMPSTV; AIASEVLVMPSTVA;
IASEVLVMPSTVAR; ASEVLVMPSTVARD; SEVLVMPSTVARDA;
EVLVMPSTVARDAI; TSIAAAASPAAISA; SIAAAASPAAISAT;
IAAAASPAAISATE; AAAASPAAISATEN; AAASPAAISATENP;
AASPAAISATENPV; ASPAAISATENPVA; SPAAISATENPVAA;
PAAISATENPVAAA; AAISATENPVAAAS; AISATENPVAAAAS;
ISATENPVAAAASD; SATENPVAAAASDT; ATENPVAAAASDTL;
TENPVAAAASDTLA; ENPVAAAASDTLAT; NPVAAAASDTLATR;
PVAAAASDTLATRS; VAAAASDTLATRSP; AAAASDTLATRSPK;
AAASDTLATRSPKS; AASDTLATRSPKSA; ASDTLATRSPKSAR;
SDTLATRSPKSARA; DTLATRSPKSARAA; TLATRSPKSARAAP;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

LATRSPKSARAAPM; ATRSPKSARAAPMN; TRSPKSARAAPMNL;
RSPKSARAAPMNLE; SPKSARAAPMNLEI; PKSARAAPMNLEIQ;
KSARAAPMNLEIQK; SARAAPMNLEIQKK; ARAAPMNLEIQKKR;
RAAPMNLEIQKKRD; AAPMNLEIQKKRDY; APMNLEIQKKRDYL;
PMNLEIQKKRDYLP; MNLEIQKKRDYLPR; NLEIQKKRDYLPRS;
LEIQKKRDYLPRSL; EIQKKRDYLPRSLL; IQKKRDYLPRSLLQ;
QKKRDYLPRSLLQS; KKRDYLPRSLLQSL; KRDYLPRSLLQSLL;
RDYLPRSLLQSLLQ; DYLPRSLLQSLLQQ; YLPRSLLQSLLQQV;
LPRSLLQSLLQQVK; PRSLLQSLLQQVKQ; RSLLQSLLQQVKQW;
SLLQSLLQQVKQWY; LLQSLLQQVKQWYF; LQSLLQQVKQWYFC;
QSLLQQVKQWYFCF; SLLQQVKQWYFCFS; LLQQVKQWYFCFSR;
LQQVKQWYFCFSRL; QQVKQWYFCFSRLH; QVKQWYFCFSRLHC;
VKQWYFCFSRLHCL; KQWYFCFSRLHCLH; QWYFCFSRLHCLHL;
WYFCFSRLHCLHLY; YFCFSRLHCLHLYK; FCFSRLHCLHLYKI;
CFSRLHCLHLYKIP; FSRLHCLHLYKIPA; SRLHCLHLYKIPAK;
RLHCLHLYKIPAKA; LHCLHLYKIPAKAL; HCLHLYKIPAKALK;
KSSELFFLFQSRFY; SSELFFLFQSRFYQ; SELFFLFQSRFYQL;
ELFFLFQSRFYQLS; LFFLFQSRFYQLSL; FFLFQSRFYQLSLK;
FLFQSRFYQLSLKL; LFQSRFYQLSLKLV; FQSRFYQLSLKLVV;
QSRFYQLSLKLVVT; SRFYQLSLKLVVTA; RFYQLSLKLVVTAG;
FYQLSLKLVVTAGA; YQLSLKLVVTAGAE; QLSLKLVVTAGAEP;
LSLKLVVTAGAEPW; SLKLVVTAGAEPWP; LKLVVTAGAEPWPL;
KLVVTAGAEPWPLS; LVVTAGAEPWPLSS; VVTAGAEPWPLSSL;
VTAGAEPWPLSSLT; TAGAEPWPLSSLTG; AGAEPWPLSSLTGD;
GAEPWPLSSLTGDK; AEPWPLSSLTGDKA; EPWPLSSLTGDKAK;
PWPLSSLTGDKAKI; WPLSSLTGDKAKIP; PLSSLTGDKAKIPR;
LSSLTGDKAKIPRL; SSLTGDKAKIPRLA; SLTGDKAKIPRLAK;
LTGDKAKIPRLAKH; TGDKAKIPRLAKHV; GDKAKIPRLAKHVC;
DKAKIPRLAKHVCH; KAKIPRLAKHVCHA; AKIPRLAKHVCHAL;
KIPRLAKHVCHALS; IPRLAKHVCHALSF; PRLAKHVCHALSFL;
RLAKHVCHALSFLR; LAKHVCHALSFLRS; AKHVCHALSFLRSW;
KHVCHALSFLRSWF; HVCHALSFLRSWFG; VCHALSFLRSWFGC;
CHALSFLRSWFGCI; HALSFLRSWFGCIP; ALSFLRSWFGCIPW;
LSFLRSWFGCIPWV; SFLRSWFGCIPWVS; FLRSWFGCIPWVSS;
LRSWFGCIPWVSSS; RSWFGCIPWVSSSS; SWFGCIPWVSSSSL;
GHGLAAFPCESCTF; HGLAAFPCESCTFL; GLAAFPCESCTFLP;
LAAFPCESCTFLPE; AAFPCESCTFLPEV; AFPCESCTFLPEVM;
FPCESCTFLPEVMV; PCESCTFLPEVMVW; CESCTFLPEVMVWL;
ESCTFLPEVMVWLH; SCTFLPEVMVWLHS; CTFLPEVMVWLHSM;
TFLPEVMVWLHSMG; FLPEVMVWLHSMGK; LPEVMVWLHSMGKQ;
PEVMVWLHSMGKQL; EVMVWLHSMGKQLL; VMVWLHSMGKQLLP;
MVWLHSMGKQLLPV; VWLHSMGKQLLPVA; WLHSMGKQLLPVAF;
LHSMGKQLLPVAFF; HSMGKQLLPVAFFF; SMGKQLLPVAFFFI;
MGKQLLPVAFFFII; GKQLLPVAFFFIIY; KQLLPVAFFFIIYK;
QLLPVAFFFIIYKR; LLPVAFFFIIYKRP; LPVAFFFIIYKRPR;
PVAFFFIIYKRPRP; VAFFFIIYKRPRPP; AFFFIIYKRPRPPL;
FFFIIYKRPRPPLP; FFIIYKRPRPPLPP; FIIYKRPRPPLPPP;
IIYKRPRPPLPPPL; IYKRPRPPLPPPFL; YKRPRPPLPPPFLS;
KRPRPPLPPPFLSS; RPRPPLPPPFLSSS; PRPPLPPPFLSSSK;
RPPLPPPFLSSSKG; PPLPPPFLSSSKGV; PLPPPFLSSSKGVE;
LPPPFLSSSKGVEA; PPPFLSSSKGVEAF; PPFLSSSKGVEAFS;
PFLSSSKGVEAFSE; FLSSSKGVEAFSEA; QNYLGKSLFFCNFC;
NYLGKSLFFCNFCK 15 mers:

WIKFLTGKNPWSSWT; IKFLTGKNPWSSWTF; GSVRNFTLTKGATRI;
SVRNFTLTKGATRIK; LISLILEPGVAQRFV; ISLILEPGVAQRFVL;
SLILEPGVAQRFVLI; LILEPGVAQRFVLIF; ILEPGVAQRFVLIFL;
LEPGVAQRFVLIFLF; EPGVAQRFVLIFLFA; PGVAQRFVLIFLAQ;
GVAQRFVLIFLFAQI; VAQRFVLIFLFAQIP; AQRFVLIFLFAQIPC;
QRFVLIFLFAQIPCT; RFVLIFLFAQIPCTA; FVLIFLFAQIPCTAR;
VLIFLFAQIPCTARN; LIFLFAQIPCTARNG; IFLFAQIPCTARNGL;
FLFAQIPCTARNGLF; LFAQIPCTARNGLFV; FAQIPCTARNGLFVP;
AQIPCTARNGLFVPK; QIPCTARNGLFVPKS; IPCTARNGLFVPKSL;
PCTARNGLFVPKSLL; CTARNGLFVPKSLLC; TARNGLFVPKSLLCT;
ARNGLFVPKSLLCTA; RNGLFVPKSLLCTAL; NGLFVPKSLLCTALA;
GLFVPKSLLCTALAC; LFVPKSLLCTALACY; FVPKSLLCTALACYV;
VPKSLLCTALACYVS; PKSLLCTALACYVSL; KSLLCTALACYVSLD;
VIIFFIGANLWNRRV; IIFFIGANLWNRRVG; IFFIGANLWNRRVGV;
FFIGANLWNRRVGVL; FIGANLWNRRVGVLV; IGANLWNRRVGVLVE;
GANLWNRRVGVLVEF; ANLWNRRVGVLVEFL; RSNSRFSTLNTTQKK;
SNSRFSTLNTTQKKK; NSRFSTLNTTQKKKK; SRFSTLNTTQKKKKG;
RFSTLNTTQKKKKGR; FSTLNTTQKKKKGRR; STLNTTQKKKKGRRP;

RSIPYYRRKHSRGLK; SIPYYRRKHSRGLKG; IPYYRRKHSRGLKGA;
GCVFIIRYVFRISIQ; CVFIIRYVFRISIQC; VFIIRYVFRISIQCR;
FIIRYVFRISIQCRG; IIRYVFRISIQCRGV; KSKKYLSASSRYSFS;
KKSRYPSYDQGRNAN; KSRYPSYDQGRNANR; SRYPSYDQGRNANRK;
RYPSYDQGRNANRKI; YPSYDQGRNANRKIQ; PSYDQGRNANRKIQS;
SYDQGRNANRKIQSY; YDQGRNANRKIQSYI; DQGRNANRKIQSYIR;
NGFNIWSSWKCCTRT; GFNIWSSWKCCTRTI; FNIWSSWKCCTRTIY;
NIWSSWKCCTRTIYG; IWSSWKCCTRTIYGR; WSSWKCCTRTIYGRC;
SSWKCCTRTIYGRCC; SWKCCTRTIYGRCCL; WKCCTRTIYGRCCLA;
KCCTRTIYGRCCLAA; CCTRTIYGRCCLAAL; CTRTIYGRCCLAALF;
TRTIYGRCCLAALFA; RTIYGRCCLAALFAT; WKNNTSCRVIRFVWW;
IKGFAFRTWNKQFRQ; KGFAFRTWNKQFRQF; GFAFRTWNKQFRQFE;
FAFRTWNKQFRQFER; AFRTWNKQFRQFERL; FRTWNKQFRQFERLF;
RTWNKQFRQFERLFR; TWNKQFRQFERLFRW; WNKQFRQFERLFRWK;
NKQFRQFERLFRWKC; GKFRKETFKQKNPNI; KFRKETFKQKNPNIS;
FRKETFKQKNPNIST; RKETFKQKNPNISTR; KETFKQKNPNISTRL;
ETFKQKNPNISTRLG; TFKQKNPNISTRLGY; FKQKNPNISTRLGYN;
KQKNPNISTRLGYNE; AQNIFKKILTKLRVL; QNIFKKILTKLRVLT;
KKNFTKWNDLVATAN; KNFTKWNDLVATANL; NFTKWNDLVATANLV;
IPITMLFPSLRYFSP; PITMLFPSLRYFSPC; KWLIQKQHLLNVYVQ;
KHLFKAFWFAIVPVC; HLFKAFWFAIVPVCQ; LFKAFWFAIVPVCQY;
FKAFWFAIVPVCQYI; KAFWFAIVPVCQYIL; AFWFAIVPVCQYILS;
FWFAIVPVCQYILSY; WFAIVPVCQYILSYL; FAIVPVCQYILSYLG;
AIVPVCQYILSYLGP; IVPVCQYILSYLGPL; VPVCQYILSYLGPLE;
PVCQYILSYLGPLEV; VCQYILSYLGPLEVF; CQYILSYLGPLEVFL;
QYILSYLGPLEVFLC; YILSYLGPLEVFLCH; ILSYLGPLEVFLCHQ;
LSYLGPLEVFLCHQT; SYLGPLEVFLCHQTP; GHLAKRKLGKDSLQI;
HLAKRKLGKDSLQIF; LAKRKLGKDSLQIFF; AKRKLGKDSLQIFFS;
KRKLGKDSLQIFFSG; RKLGKDSLQIFFSGG; KLGKDSLQIFFSGGS;
TGHKYQQLKHTGYQL; GHKYQQLKHTGYQLY; HKYQQLKHTGYQLYK;
KYQQLKHTGYQLYKE; YQQLKHTGYQLYKEA; QQLKHTGYQLYKEAP;
QLKHTGYQLYKEAPH; LKHTGYQLYKEAPHP; KHTGYQLYKEAPHPV;
HTGYQLYKEAPHPVH; TGYQLYKEAPHPVHL; GYQLYKEAPHPVHLA;
YQLYKEAPHPVHLAT; QLYKEAPHPVHLATL; LYKEAPHPVHLATLW;
LCWSHEVLGEHFPLL; HFHFYWDQVPSTQLD; FHFYWDQVPSTQLDK;
HFYWDQVPSTQLDKH; FYWDQVPSTQLDKHC; YWDQVPSTQLDKHCF;
WDQVPSTQLDKHCFC; DQVPSTQLDKHCFCP; QVPSTQLDKHCFCPN;
VPSTQLDKHCFCPNR; PSTQLDKHCFCPNRP; STQLDKHCFCPNRPY;
TQLDKHCFCPNRPYG; QLDKHCFCPNRPYGQ; LDKHCFCPNRPYGQY;
DKHCFCPNRPYGQYS; KHCFCPNRPYGQYSL; HCFCPNRPYGQYSLP;
CFCPNRPYGQYSLPG; FCPNRPYGQYSLPGT; CPNRPYGQYSLPGTG;
PNRPYGQYSLPGTGL; NRPYGQYSLPGTGLL; RPYGQYSLPGTGLLG;
PYGQYSLPGTGLLGF; YHQGTLTCNSLALPA; HQGTLTCNSLALPAF;
QGTLTCNSLALPAFP; GTLTCNSLALPAFPR; TLTCNSLALPAFPRV;
LTCNSLALPAFPRVL; TCNSLALPAFPRVLH; CNSLALPAFPRVLHL;
NSLALPAFPRVLHLQ; SLALPAFPRVLHLQQ; LALPAFPRVLHLQQR;
ALPAFPRVLHLQQRS; LPAFPRVLHLQQRSG; PAFPRVLHLQQRSGN;
AFPRVLHLQQRSGNY; FPRVLHLQQRSGNYC; PRVLHLQQRSGNYCL;
RVLHLQQRSGNYCLE; VFLHHAHALFVTLHE; FLHHAHALFVTLHEG;
PLFVQLQPPTSVDFH; LFVQLQPPTSVDFHR; FVQLQPPTSVDFHRL;
VQLQPPTSVDFHRLG; QLQPPTSVDFHRLGP; LQPPTSVDFHRLGPH;
QPPTSVDFHRLGPHL; PPTSVDFHRLGPHLN; PTSVDFHRLGPHLNW;
TSVDFHRLGPHLNWG; SVDFHRLGPHLNWGG; VDFHRLGPHLNWGGE;
DFHRLGPHLNWGGEF; FHRLGPHLNWGGEFL; HRLGPHLNWGGEFLL;
RLGPHLNWGGEFLLC; LGPHLNWGGEFLLCC; GPHLNWGGEFLLCCN;
PHLNWGGEFLLCCNR; HLNWGGEFLLCCNRE; LNWGGEFLLCCNREA;
NWGGEFLLCCNREAF; WGGEFLLCCNREAFF; GGEFLLCCNREAFFS;
GEFLLCCNREAFFSL; EFLLCCNREAFFSLG; FLLCCNREAFFSLGY;
LLCCNREAFFSLGYH; LCCNREAFFSLGYHC; GFHLDPPFLGLGSIL;
FHLDPPFLGLGSILP; HLDPPFLGLGSILPL; LLELLLLLLLVVLAL;
LELLLLLLLVVLALA; ELLLLLLLVVLALAR; LLLLLLLVVLALARV;
LLLLLLVVLALARVP; LLLLLVVLALARVPL; LLLLVVLALARVPLA;
LLLVVLALARVPLAF; LLVVLALARVPLAFW; LVVLALARVPLAFWE;
VVLALARVPLAFWEL; VLALARVPLAFWELP; LALARVPLAFWELPL;
ALARVPLAFWELPLD; LARVPLAFWELPLDT; ARVPLAFWELPLDTL;
RVPLAFWELPLDTLL; VPLAFWELPLDTLLF; PLAFWELPLDTLLFF;
LAFWELPLDTLLFFW; AFWELPLDTLLFFWL; FWELPLDTLLFFWLG;
WELPLDTLLFFWLGP; ELPLDTLLFFWLGPS; LPLDTLLFFWLGPSS;
PLDTLLFFWLGPSSY; LDTLLFFWLGPSSYA; DTLLFFWLGPSSYAS;
TLLFFWLGPSSYASR; LLFFWLGPSSYASRA; LFFWLGPSSYASRAG;
FFWLGPSSYASRAGV; FWLGPSSYASRAGVT; WLGPSSYASRAGVTV;
LGPSSYASRAGVTVP; GPSSYASRAGVTVPY; PSSYASRAGVTVPYR;
SSYASRAGVTVPYRP; SYASRAGVTVPYRPR; YASRAGVTVPYRPRS;
ASRAGVTVPYRPRSK; SRAGVTVPYRPRSKG; RAGVTVPYRPRSKGN;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

AGVTVPYRPRSKGNI; GVTVPYRPRSKGNIH; LAPPGAIVFSINSPE;
APPGAIVFSINSPEC; PPGAIVFSINSPECT; PGAIVFSINSPECTL;
GAIVFSINSPECTLC; FLKSILCVTSSILSA; LKSILCVTSSILSAS;
KSILCVTSSILSASS; SILCVTSSILSASSI; ILCVTSSILSASSIL;
VWPKCTRVPSLSATC; WPKCTRVPSLSATCL; PKCTRVPSLSATCLT;
KCTRVPSLSATCLTI; CTRVPSLSATCLTIE; TRVPSLSATCLTIEG;
RVPSLSATCLTIEGL; VPSLSATCLTIEGLI; PSLSATCLTIEGLIG;
SLSATCLTIEGLIGE; LSATCLTIEGLIGER; SATCLTIEGLIGERS;
ATCLTIEGLIGERSE; KFIGAFTIVQVVSSK; FIGAFTIVQVVSSKN;
IGAFTIVQVVSSKNL; GAFTIVQVVSSKNLA; AFTIVQVVSSKNLAK;
FTIVQVVSSKNLAKE; TIVQVVSSKNLAKES; IVQVVSSKNLAKESL;
VQVVSSKNLAKESLK; QVVSSKNLAKESLKN; VVSSKNLAKESLKNL;
VSSKNLAKESLKNLS; SSKNLAKESLKNLSV; SKNLAKESLKNLSVL;
KNLAKESLKNLSVLL; NLAKESLKNLSVLLC; LAKESLKNLSVLLCN;
AKESLKNLSVLLCNS; KESLKNLSVLLCNSC; ESLKNLSVLLCNSCE;
SLKNLSVLLCNSCEV; LKNLSVLLCNSCEVI; KNLSVLLCNSCEVIE;
NLSVLLCNSCEVIEG; LSVLLCNSCEVIEGI; SVLLCNSCEVIEGIS;
VLLCNSCEVIEGISS; LLCNSCEVIEGISSL; LCNSCEVIEGISSLI;
CNSCEVIEGISSLIT; NSCEVIEGISSLITC; SCEVIEGISSLITCH;
CEVIEGISSLITCHK; EVIEGISSLITCHKA; VIEGISSLITCHKAW;
IEGISSLITCHKAWE; EGISSLITCHKAWEI; GISSLITCHKAWEIV;
ISSLITCHKAWEIVA; SSLITCHKAWEIVAN; SLITCHKAWEIVANK;
LITCHKAWEIVANKE; ITCHKAWEIVANKEG; TCHKAWEIVANKEGP;
CHKAWEIVANKEGPQ; HKAWEIVANKEGPQC; KAWEIVANKEGPQCL;
AWEIVANKEGPQCLG; WEIVANKEGPQCLGS; EIVANKEGPQCLGSR;
IVANKEGPQCLGSRY; IKAANPAIAPGAPAI; KAANPAIAPGAPAIT;
AANPAIAPGAPAITA; ANPAIAPGAPAITAY; NPAIAPGAPAITAYN;
GVRPIAAIASEVLVM; VRPIAAIASEVLVMP; RPIAAIASEVLVMPS;
PIAAIASEVLVMPST; IAAIASEVLVMPSTV; AAIASEVLVMPSTVA;
AIASEVLVMPSTVAR; IASEVLVMPSTVARD; ASEVLVMPSTVARDA;
SEVLVMPSTVARDAI; TSIAAAASPAAISAT; SIAAAASPAAISATE;
IAAAASPAAISATEN; AAAASPAAISATENP; AAASPAAISATENPV;
AASPAAISATENPVA; ASPAAISATENPVAA; SPAAISATENPVAAA;
PAAISATENPVAAAA; AAISATENPVAAAAS; AISATENPVAAAASD;
ISATENPVAAAASDT; SATENPVAAAASDTL; ATENPVAAAASDTLA;
TENPVAAAASDTLAT; ENPVAAAASDTLATR; NPVAAAASDTLATRS;
PVAAAASDTLATRSP; VAAAASDTLATRSPK; AAAASDTLATRSPKS;
AAASDTLATRSPKSA; AASDTLATRSPKSAR; ASDTLATRSPKSARA;
SDTLATRSPKSARAA; DTLATRSPKSARAAP; TLATRSPKSARAAPM;
LATRSPKSARAAPMN; ATRSPKSARAAPMNL; TRSPKSARAAPMNLE;
RSPKSARAAPMNLEI; SPKSARAAPMNLEIQ; PKSARAAPMNLEIQK;
KSARAAPMNLEIQKK; SARAAPMNLEIQKKR; ARAAPMNLEIQKKRD;
RAAPMNLEIQKKRDY; AAPMNLEIQKKRDYL; APMNLEIQKKRDYLP;
PMNLEIQKKRDYLPR; MNLEIQKKRDYLPRS; NLEIQKKRDYLPRSL;
LEIQKKRDYLPRSLL; EIQKKRDYLPRSLLQ; IQKKRDYLPRSLLQS;
QKKRDYLPRSLLQSL; KKRDYLPRSLLQSLL; KRDYLPRSLLQSLLQ;
RDYLPRSLLQSLLQQ; DYLPRSLLQSLLQQV; YLPRSLLQSLLQQVK;
LPRSLLQSLLQQVKQ; PRSLLQSLLQQVKQW; RSLLQSLLQQVKQWY;
SLLQSLLQQVKQWYF; LLQSLLQQVKQWYFC; LQSLLQQVKQWYFCF;
QSLLQQVKQWYFCFS; SLLQQVKQWYFCFSR; LLQQVKQWYFCFSRL;
LQQVKQWYFCFSRLH; QQVKQWYFCFSRLHC; QVKQWYFCFSRLHCL;
VKQWYFCFSRLHCLH; KQWYFCFSRLHCLHL; QWYFCFSRLHCLHLY;
WYFCFSRLHCLHLYK; YFCFSRLHCLHLYKI; FCFSRLHCLHLYKIP;
CFSRLHCLHLYKIPA; FSRLHCLHLYKIPAK; SRLHCLHLYKIPAKA;
RLHCLHLYKIPAKAL; LHCLHLYKIPAKALK; KSSELFFLFQSRFYQ;
SSELFFLFQSRFYQL; SELFFLFQSRFYQLS; ELFFLFQSRFYQLSL;
LFFLFQSRFYQLSLK; FFLFQSRFYQLSLKL; FLFQSRFYQLSLKLV;
LFQSRFYQLSLKLVV; FQSRFYQLSLKLVVT; QSRFYQLSLKLVVTA;
SRFYQLSLKLVVTAG; RFYQLSLKLVVTAGA; FYQLSLKLVVTAGAE;
YQLSLKLVVTAGAEP; QLSLKLVVTAGAEPW; LSLKLVVTAGAEPWP;
SLKLVVTAGAEPWPL; LKLVVTAGAEPWPLS; KLVVTAGAEPWPLSS;
LVVTAGAEPWPLSSL; VVTAGAEPWPLSSLT; VTAGAEPWPLSSLTG;
TAGAEPWPLSSLTGD; AGAEPWPLSSLTGDK; GAEPWPLSSLTGDKA;
AEPWPLSSLTGDKAK; EPWPLSSLTGDKAKI; PWPLSSLTGDKAKIP;
WPLSSLTGDKAKIPR; PLSSLTGDKAKIPRL; LSSLTGDKAKIPRLA;
SSLTGDKAKIPRLAK; SLTGDKAKIPRLAKH; LTGDKAKIPRLAKHV;
TGDKAKIPRLAKHVC; GDKAKIPRLAKHVCH; DKAKIPRLAKHVCHA;
KAKIPRLAKHVCHAL; AKIPRLAKHVCHALS; KIPRLAKHVCHALSF;
IPRLAKHVCHALSFL; PRLAKHVCHALSFLR; RLAKHVCHALSFLRS;
LAKHVCHALSFLRSW; AKHVCHALSFLRSWF; KHVCHALSFLRSWFG;
HVCHALSFLRSWFGC; VCHALSFLRSWFGCI; CHALSFLRSWFGCIP;
HALSFLRSWFGCIPW; ALSFLRSWFGCIPWV; LSFLRSWFGCIPWVS;
SFLRSWFGCIPWVSS; FLRSWFGCIPWVSSS; LRSWFGCIPWVSSSS;
RSWFGCIPWVSSSSL; GHGLAAFPCESCTFL; HGLAAFPCESCTFLP;
GLAAFPCESCTFLPE; LAAFPCESCTFLPEV; AAFPCESCTFLPEVM;
AFPCESCTFLPEVMV; FPCESCTFLPEVMVW; PCESCTFLPEVMVWL;
CESCTFLPEVMVWLH; ESCTFLPEVMVWLHS; SCTFLPEVMVWLHSM;
CTFLPEVMVWLHSMG; TFLPEVMVWLHSMGK; FLPEVMVWLHSMGKQ;
LPEVMVWLHSMGKQL; PEVMVWLHSMGKQLL; EVMVWLHSMGKQLLP;
VMVWLHSMGKQLLPV; MVWLHSMGKQLLPVA; VWLHSMGKQLLPVAF;
WLHSMGKQLLPVAFF; LHSMGKQLLPVAFFF; HSMGKQLLPVAFFFI;
SMGKQLLPVAFFFII; MGKQLLPVAFFFIIY; GKQLLPVAFFFIIYK;
KQLLPVAFFFIIYKR; QLLPVAFFFIIYKRP; LLPVAFFFIIYKRPR;
LPVAFFFIIYKRPRP; PVAFFFIIYKRPRPP; VAFFFIIYKRPRPPL;
AFFFIIYKRPRPPLP; FFFIIYKRPRPPLPP; FFIIYKRPRPPLPPP;
FIIYKRPRPPLPPPF; IIYKRPRPPLPPPFL; IYKRPRPPLPPPFLS;
YKRPRPPLPPPFLSS; KRPRPPLPPPFLSSS; RPRPPLPPPFLSSSK;
PRPPLPPPFLSSSKG; RPPLPPPFLSSSKGV; PPLPPPFLSSSKGVE;
PLPPPFLSSSKGVEA; LPPPFLSSSKGVEAF; PPPFLSSSKGVEAFS;
PPFLSSSKGVEAFSE; PFLSSSKGVEAFSEA; QNYLGKSLFFCNFCK 16 mers:

WIKFLTGKNPWSSWTF; GSVRNFTLTKGATRIK;
LISLILEPGVAQRFVL; ISLILEPGVAQRFVLI;
SLILEPGVAQRFVLIF; LILEPGVAQRFVLIFL;
ILEPGVAQRFVLIFLF; LEPGVAQRFVLIFLFA;
EPGVAQRFVLIFLFAQ; PGVAQRFVLIFLFAQI;
GVAQRFVLIFLFAQIP; VAQRFVLIFLFAQIPC;
AQRFVLIFLFAQIPCT; QRFVLIFLFAQIPCTA;
RFVLIFLFAQIPCTAR; FVLIFLFAQIPCTARN;
VLIFLFAQIPCTARNG; LIFLFAQIPCTARNGL;
IFLFAQIPCTARNGLF; FLFAQIPCTARNGLFV;
LFAQIPCTARNGLFVP; FAQIPCTARNGLFVPK;
AQIPCTARNGLFVPKS; QIPCTARNGLFVPKSL;
IPCTARNGLFVPKSLL; PCTARNGLFVPKSLLC;
CTARNGLFVPKSLLCT; TARNGLFVPKSLLCTA;
ARNGLFVPKSLLCTAL; RNGLFVPKSLLCTALA;
NGLFVPKSLLCTALAC; GLFVPKSLLCTALACY;
LFVPKSLLCTALACYV; FVPKSLLCTALACYVS;
VPKSLLCTALACYVSL; PKSLLCTALACYVSLD;
VIIFFIGANLWNRRVG; IIFFIGANLWNRRVGV;
IFFIGANLWNRRVGVL; FFIGANLWNRRVGVLV;
FIGANLWNRRVGVLVE; IGANLWNRRVGVLVEF;
GANLWNRRVGVLVEFL; RSNSRFSTLNTTQKKK;
SNSRFSTLNTTQKKKK; NSRFSTLNTTQKKKKG;
SRFSTLNTTQKKKKGR; RFSTLNTTQKKKKGRR;
FSTLNTTQKKKKGRRP; RSIPYYRRKHSRGLKG;
SIPYYRRKHSRGLKGA; GCVFIIRYVFRISIQC;
CVFIIRYVFRISIQCR; VFIIRYVFRISIQCRG;
FIIRYVFRISIQCRGV; KKSRYPSYDQGRNANR;
KSRYPSYDQGRNANRK; SRYPSYDQGRNANRKI;
RYPSYDQGRNANRKIQ; YPSYDQGRNANRKIQS;
PSYDQGRNANRKIQSY; SYDQGRNANRKIQSYI;
YDQGRNANRKIQSYIR; NGFNIWSSWKCCTRTI;
GFNIWSSWKCCTRTIY; FNIWSSWKCCTRTIYG;
NIWSSWKCCTRTIYGR; IWSSWKCCTRTIYGRC;
WSSWKCCTRTIYGRCC; SSWKCCTRTIYGRCCL;
SWKCCTRTIYGRCCLA; WKCCTRTIYGRCCLAA;
KCCTRTIYGRCCLAAL; CCTRTIYGRCCLAALF;
CTRTIYGRCCLAALFA; TRTIYGRCCLAALFAT;
IKGFAFRTWNKQFRQF; KGFAFRTWNKQFRQFE;
GFAFRTWNKQFRQFER; FAFRTWNKQFRQFERL;
AFRTWNKQFRQFERLF; FRTWNKQFRQFERLFR;
RTWNKQFRQFERLFRW; TWNKQFRQFERLFRWK;
WNKQFRQFERLFRWKC; GKFRKETFKQKNPNIS;
KFRKETFKQKNPNIST; FRKETFKQKNPNISTR;
RKETFKQKNPNISTRL; KETFKQKNPNISTRLG;
ETFKQKNPNISTRLGY; TFKQKNPNISTRLGYN;
FKQKNPNISTRLGYNE; AQNIFKKILTKLRVLT;
KKNFTKWNDLVATANL; KNFTKWNDLVATANLV;
IPITMLFPSLRYFSPC; KHLFKAFWFAIVPVCQ;
HLFKAFWFAIVPVCQY; LFKAFWFAIVPVCQYI;
FKAFWFAIVPVCQYIL; KAFWFAIVPVCQYILS;
AFWFAIVPVCQYILSY; FWFAIVPVCQYILSYL;
WFAIVPVCQYILSYLG; FAIVPVCQYILSYLGP;
AIVPVCQYILSYLGPL; IVPVCQYILSYLGPLE;
VPVCQYILSYLGPLEV; PVCQYILSYLGPLEVF;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

VCQYILSYLGPLEVFL; CQYILSYLGPLEVFLC;
QYILSYLGPLEVFLCH; YILSYLGPLEVFLCHQ;
ILSYLGPLEVFLCHQT; LSYLGPLEVFLCHQTP;
GHLAKRKLGKDSLQIF; HLAKRKLGKDSLQIFF;
LAKRKLGKDSLQIFFS; AKRKLGKDSLQIFFSG;
KRKLGKDSLQIFFSGG; RKLGKDSLQIFFSGGS;
TGHKYQQLKHTGYQLY; GHKYQQLKHTGYQLYK;
HKYQQLKHTGYQLYKE; KYQQLKHTGYQLYKEA;
YQQLKHTGYQLYKEAP; QQLKHTGYQLYKEAPH;
QLKHTGYQLYKEAPHP; LKHTGYQLYKEAPHPV;
KHTGYQLYKEAPHPVH; HTGYQLYKEAPHPVHL;
TGYQLYKEAPHPVHLA; GYQLYKEAPHPVHLAT;
YQLYKEAPHPVHLATL; QLYKEAPHPVHLATLW;
HFHFYWDQVPSTQLDK; FHFYWDQVPSTQLDKH;
HFYWDQVPSTQLDKHC; FYWDQVPSTQLDKHCF;
YWDQVPSTQLDKHCFC; WDQVPSTQLDKHCFCP;
DQVPSTQLDKHCFCPN; QVPSTQLDKHCFCPNR;
VPSTQLDKHCFCPNRP; PSTQLDKHCFCPNRPY;
STQLDKHCFCPNRPYG; TQLDKHCFCPNRPYGQ;
QLDKHCFCPNRPYGQY; LDKHCFCPNRPYGQYS;
DKHCFCPNRPYGQYSL; KHCFCPNRPYGQYSLP;
HCFCPNRPYGQYSLPG; CFCPNRPYGQYSLPGT;
FCPNRPYGQYSLPGTG; CPNRPYGQYSLPGTGL;
PNRPYGQYSLPGTGLL; NRPYGQYSLPGTGLLG;
RPYGQYSLPGTGLLGF; YHQGTLTCNSLALPAF;
HQGTLTCNSLALPAFP; QGTLTCNSLALPAFPR;
GTLTCNSLALPAFPRV; TLTCNSLALPAFPRVL;
LTCNSLALPAFPRVLH; TCNSLALPAFPRVLHL;
CNSLALPAFPRVLHLQ; NSLALPAFPRVLHLQQ;
SLALPAFPRVLHLQQR; LALPAFPRVLHLQQRS;
ALPAFPRVLHLQQRSG; LPAFPRVLHLQQRSGN;
PAFPRVLHLQQRSGNY; AFPRVLHLQQRSGNYC;
FPRVLHQQRSGNYCL; PRVLHQQRSGNYCLE;
VFLHHAHALFVTLHEG; PLFVQLQPPTSVDFHR;
LFVQLQPPTSVDFHRL; FVQLQPPTSVDFHRLG;
VQLQPPTSVDFHRLGP; QLQPPTSVDFHRLGPH;
LQPPTSVDFHRLGPHL; QPPTSVDFHRLGPHLN;
PPTSVDFHRLGPHLNW; PTSVDFHRLGPHLNWG;
TSVDFHRLGPHLNWGG; SVDFHRLGPHLNWGGE;
VDFHRLGPHLNWGGEF; DFHRLGPHLNWGGEFL;
FHRLGPHLNWGGEFLL; HRLGPHLNWGGEFLLC;
RLGPHLNWGGEFLLCC; LGPHLNWGGEFLLCCN;
GPHLNWGGEFLLCCNR; PHLNWGGEFLLCCNRE;
HLNWGGEFLLCCNREA; LNWGGEFLLCCNREAF;
NWGGEFLLCCNREAFF; WGGEFLLCCNREAFFS;
GGEFLLCCNREAFFSL; GEFLLCCNREAFFSLG;
EFLLCCNREAFFSLGY; FLLCCNREAFFSLGYH;
LLCCNREAFFSLGYHC; GFHLDPPFLGLGSILP;
FHLDPPFLGLGSILPL; LLELLLLLLVVLALA;
LELLLLLLLVVLALAR; ELLLLLLLVVLALARV;
LLLLLLLVVLALARVP; LLLLLLVVLALARVPL;
LLLLLVVLALARVPLA; LLLLVVLALARVPLAF;
LLLVVLALARVPLAFW; LLVVLALARVPLAFWE;
LVVLALARVPLAFWEL; VVLALARVPLAFWELP;
VLALARVPLAFWELPL; LALARVPLAFWELPLD;
ALARVPLAFWELPLDT; LARVPLAFWELPLDTL;
ARVPLAFWELPLDTLL; RVPLAFWELPLDTLLF;
VPLAFWELPLDTLLFF; PLAFWELPLDTLLFFW;
LAFWELPLDTLLFFWL; AFWELPLDTLLFFWLG;
FWELPLDTLLFFWLGP; WELPLDTLLFFWLGPS;
ELPLDTLLFFWLGPSS; LPLDTLLFFWLGPSSY;
PLDTLLFFWLGPSSYA; LDTLLFFWLGPSSYAS;
DTLLFFWLGPSSYASR; TLLFFWLGPSSYASRA;
LLFFWLGPSSYASRAG; LFFWLGPSSYASRAGV;
FFWLGPSSYASRAGVT; FWLGPSSYASRAGVTV;
WLGPSSYASRAGVTVP; LGPSSYASRAGVTVPY;
GPSSYASRAGVTVPYR; PSSYASRAGVTVPYRP;
SSYASRAGVTVPYRPR; SYASRAGVTVPYRPRS;
YASRAGVTVPYRPRSK; ASRAGVTVPYRPRSKG;
SRAGVTVPYRPRSKGN; RAGVTVPYRPRSKGNI;
AGVTVPYRPRSKGNIH; LAPPGAIVFSINSPEC;
APPGAIVFSINSPECT; PPGAIVFSINSPECTL;
PGAIVFSINSPECTLC; FLKSILCVTSSILSAS;
LKSILCVTSSILSASS; KSILCVTSSILSASSI;
SILCVTSSILSASSIL; VWPKCTRVPSLSATCL;
WPKCTRVPSLSATCLT; PKCTRVPSLSATCLTI;
KCTRVPSLSATCLTIE; CTRVPSLSATCLTIEG;
TRVPSLSATCLTIEGL; RVPSLSATCLTIEGLI;
VPSLSATCLTIEGLIG; PSLSATCLTIEGLIGE;
SLSATCLTIEGLIGER; LSATCLTIEGLIGERS;
SATCLTIEGLIGERSE; KFIGAFTIVQVVSSKN;
FIGAFTIVQVVSSKNL; IGAFTIVQVVSSKNLA;
GAFTIVQVVSSKNLAK; AFTIVQVVSSKNLAKE;
FTIVQVVSSKNLAKES; TIVQVVSSKNLAKESL;
IVQVVSSKNLAKESLK; VQVVSSKNLAKESLKN;
QVVSSKNLAKESLKNL; VVSSKNLAKESLKNLS;
VSSKNLAKESLKNLSV; SSKNLAKESLKNLSVL;
SKNLAKESLKNLSVLL; KNLAKESLKNLSVLLC;
NLAKESLKNLSVLLCN; LAKESLKNLSVLLCNS;
AKESLKNLSVLLCNSC; KESLKNLSVLLCNSCE;
ESLKNLSVLLCNSCEV; SLKNLSVLLCNSCEVI;
LKNLSVLLCNSCEVIE; KNLSVLLCNSCEVIEG;
NLSVLLCNSCEVIEGI; LSVLLCNSCEVIEGIS;
SVLLCNSCEVIEGISS; VLLCNSCEVIEGISSL;
LLCNSCEVIEGISSLI; LCNSCEVIEGISSLIT;
CNSCEVIEGISSLITC; NSCEVIEGISSLITCH;
SCEVIEGISSLITCHK; CEVIEGISSLITCHKA;
EVIEGISSLITCHKAW; VIEGISSLITCHKAWE;
IEGISSLITCHKAWEI; EGISSLITCHKAWEIV;
GISSLITCHKAWEIVA; ISSLITCHKAWEIVAN;
SSLITCHKAWEIVANK; SLITCHKAWEIVANKE;
LITCHKAWEIVANKEG; ITCHKAWEIVANKEGP;
TCHKAWEIVANKEGPQ; CHKAWEIVANKEGPQC;
HKAWEIVANKEGPQCL; KAWEIVANKEGPQCLG;
AWEIVANKEGPQCLGS; WEIVANKEGPQCLGSR;
EIVANKEGPQCLGSRY; IKAANPAIAPGAPAIT;
KAANPAIAPGAPAITA; AANPAIAPGAPAITAY;
ANPAIAPGAPAITAYV; GVRPIAAIASEVLVMP;
VRPIAAIASEVLVMPS; RPIAAIASEVLVMPST;
PIAAIASEVLVMPSTV; IAAIASEVLVMPSTVA;
AAIASEVLVMPSTVAR; AIASEVLVMPSTVARD;
IASEVLVMPSTVARDA; ASEVLVMPSTVARDAI;
TSIAAAASPAAISATE; SIAAAASPAAISATEN;
IAAAASPAAISATENP; AAAASPAAISATENPV;
AAASPAAISATENPVA; AASPAAISATENPVAA;
ASPAAISATENPVAAA; SPAAISATENPVAAAA;
PAAISATENPVAAAAS; AAISATENPVAAAASD;
AISATENPVAAAASDT; ISATENPVAAAASDTL;
SATENPVAAAASDTLA; ATENPVAAAASDTLAT;
TENPVAAAASDTLATR; ENPVAAAASDTLATRS;
NPVAAAASDTLATRSP; PVAAAASDTLATRSPK;
VAAAASDTLATRSPKS; AAAASDTLATRSPKSA;
AAASDTLATRSPKSAR; AASDTLATRSPKSARA;
ASDTLATRSPKSARAA; SDTLATRSPKSARAAP;
DTLATRSPKSARAAPM; TLATRSPKSARAAPMN;
LATRSPKSARAAPMNL; ATRSPKSARAAPMNLE;
TRSPKSARAAPMNLEI; RSPKSARAAPMNLEIQ;
SPKSARAAPMNLEIQK; PKSARAAPMNLEIQKK;
KSARAAPMNLEIQKKR; SARAAPMNLEIQKKRD;
ARAAPMNLEIQKKRDY; RAAPMNLEIQKKRDYL;
AAPMNLEIQKKRDYLP; APMNLEIQKKRDYLPR;
PMNLEIQKKRDYLPRS; MNLEIQKKRDYLPRSL;
NLEIQKKRDYLPRSLL; LEIQKKRDYLPRSLLQ;
EIQKKRDYLPRSLLQS; IQKKRDYLPRSLLQSL;
QKKRDYLPRSLLQSLL; KKRDYLPRSLLQSLLQ;
KRDYLPRSLLQSLLQQ; RDYLPRSLLQSLLQQV;
DYLPRSLLQSLLQQVK; YLPRSLLQSLLQQVKQ;
LPRSLLQSLLQQVKQW; PRSLLQSLLQQVKQWY;
RSLLQSLLQQVKQWYF; SLLQSLLQQVKQWYFC;
LLQSLLQQVKQWYFCF; LQSLLQQVKQWYFCFS;
QSLLQQVKQWYFCFSR; SLLQQVKQWYFCFSRL;
LLQQVKQWYFCFSRLH; LQQVKQWYFCFSRLHC;
QQVKQWYFCFSRLHCL; QVKQWYFCFSRLHCLH;
VKQWYFCFSRLHCLHL; KQWYFCFSRLHCLHLY;
QWYFCFSRLHCLHLYK; WYFCFSRLHCLHLYKI;
YFCFSRLHCLHLYKIP; FCFSRLHCLHLYKIPA;
CFSRLHCLHLYKIPAK; FSRLHCLHLYKIPAKA;
SRLHCLHLYKIPAKAL; RLHCLHLYKIPAKALK;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

KSSELFFLFQSRFYQL; SSELFFLFQSRFYQLS;
SELFFLFQSRFYQLSL; ELFFLFQSRFYQLSLK;
LFFLFQSRFYQLSLKL; FFLFQSRFYQLSLKLV;
FLFQSRFYQLSLKLVV; LFQSRFYQLSLKLVVT;
FQSRFYQLSLKLVVTA; QSRFYQLSLKLVVTAG;
SRFYQLSLKLVVTAGA; RFYQLSLKLVVTAGAE;
FYQLSLKLVVTAGAEP; YQLSLKLVVTAGAEPW;
QLSLKLVVTAGAEPWP; LSLKLVVTAGAEPWPL;
SLKLVVTAGAEPWPLS; LKLVVTAGAEPWPLSS;
KLVVTAGAEPWPLSSL; LVVTAGAEPWPLSSLT;
VVTAGAEPWPLSSLTG; VTAGAEPWPLSSLTGD;
TAGAEPWPLSSLTGDK; AGAEPWPLSSLTGDKA;
GAEPWPLSSLTGDKAK; AEPWPLSSLTGDKAKI;
EPWPLSSLTGDKAKIP; PWPLSSLTGDKAKIPR;
WPLSSLTGDKAKIPRL; PLSSLTGDKAKIPRLA;
LSSLTGDKAKIPRLAK; SSLTGDKAKIPRLAKH;
SLTGDKAKIPRLAKHV; LTGDKAKIPRLAKHVC;
TGDKAKIPRLAKHVCH; GDKAKIPRLAKHVCHA;
DKAKIPRLAKHVCHAL; KAKIPRLAKHVCHALS;
AKIPRLAKHVCHALSF; KIPRLAKHVCHALSFL;
IPRLAKHVCHALSFLR; PRLAKHVCHALSFLRS;
RLAKHVCHALSFLRSW; LAKHVCHALSFLRSWF;
AKHVCHALSFLRSWFG; KHVCHALSFLRSWFGC;
HVCHALSFLRSWFGCI; VCHALSFLRSWFGCIP;
CHALSFLRSWFGCIPW; HALSFLRSWFGCIPWV;
ALSFLRSWFGCIPWVS; LSFLRSWFGCIPWVSS;
SFLRSWFGCIPWVSSS; FLRSWFGCIPWVSSSL;
LRSWFGCIPWVSSSSL; GHGLAAFPCESCTFLP;
HGLAAFPCESCTFLPE; GLAAFPCESCTFLPEV;
LAAFPCESCTFLPEVM; AAFPCESCTFLPEVMV;
APFCESCTFLPEVMVW; FPCESCTFLPEVMVWL;
PCESCTFLPEVMVWLH; CESCTFLPEVMVWLHS;
ESCTFLPEVMVWLHSM; SCTFLPEVMVWLHSMG;
CTFLPEVMVWLHSMGK; TFLPEVMVWLHSMGKQ;
FLPEVMVWLHSMGKQL; LPEVMVWLHSMGKQLL;
PEVMVWLHSMGKQLLP; EVMVWLHSMGKQLLPV;
VMVWLHSMGKQLLPVA; MVWLHSMGKQLLPVAF;
VWLHSMGKQLLPVAFF; WLHSMGKQLLPVAFFF;
LHSMGKQLLPVAFFFI; HSMGKQLLPVAFFFII;
SMGKQLLPVAFFFIIY; MGKQLLPVAFFFIIYK;
GKQLLPVAFFFIIYKR; KQLLPVAFFFIIYKRP;
QLLPVAFFFIIYKRPR; LLPVAFFFIIYKRPRP;
LPVAFFFIIYKRPRPP; PVAFFFIIYKRPRPPL;
VAFFFIIYKRPRPPLP; AFFFIIYKRPRPPLPP;
FFFIIYKRPRPPLPPP; FFIIYKRPRPPLPPPF;
FIIYKRPRPPLPPPFL; IIYKRPRPPLPPPFLS;
IYKRPRPPLPPPFLSS; YKRPRPPLPPPFLSSS;
KRPRPPLPPPFLSSSK; RPRPPLPPPFLSSSKG;
PRPPLPPPFLSSSKGV; RPPLPPPFLSSSKGVE;
PPLPPPFLSSSKGVEA; PLPPPFLSSSKGVEAF;
LPPPFLSSSKGVEAFS; PPPFLSSSKGVEAFSE;
PPFLSSSKGVEAFSEA

BK virus, reverse reading frame 3

13 mers:

QGRIHGAHGPFRP; KSCLGKSSLNEKS; SCLGKSSLNEKSL;
CLGKSSLNEKSLF; LGKSSLNEKSLFK; GKSSLNEKSLFKE;
KSSLNEKSLFKEV; FSSLPRYPVLQGMA; SSLPRYPVLQGMAY;
SLPRYPVLQGMAY; LPRYPVLQGMAYL; PRYPVLQGMAYLF;
RYPVLQGMAYLFQ; YPVLQGMAYLFQK; PVLQGMAYLFQKA;
VLQGMAYLFQKAF; LQGMAYLFQKAFC; QGMAYLFQKAFCA;
GMAYLFQKAFCAL; MAYLFQKAFCALP; AYLFQKAFCALPL;
YLFQKAFCALPLH; LFQKAFCALPLHA; FQKAFCALPLHAM;
QKAFCALPLHAMS; KAFCALPLHAMSA; KIFKKRALGLDRL;
IFKKRALGLDRLL; FKKRALGLDRLLL; KKRALGLDRLLLH;
RNSAMVGPNNWRN; NSAMVGPNNWRNS; SAMVGPNNWRNSL;
AMVGPNNWRNSLQ; MVGPNNWRNSLQR; VGPNNWRNSLQRS;
GPNNWRNSLQRSK; PNNWRNSLQRSKA; NNWRNSLQRSKAL;
NWRNSLQRSKALR; VPTYGTEEWESWW; PTYGTEEWESWWS;
TYGTEEWESWWSS; YGTEEWESWWSSF; GTEEWESWWSSFN;
TEEWESWWSSFNE; EEWESWWSSFNEK; EWESWWSSFNEKW;
WESWWSSFNEKWD; ESWWSSFNEKWDE; SWWSSFNEKWDED;
WWSSFNEKWDEDL; WSSFNEKWDEDLF; SSFNEKWDEDLFC;
SFNEKWDEDLFCH; FNEKWDEDLFCHE; NEKWDEDLFCHED;
EKWDEDLFCHEDM; KWDEDLFCHEDMF; WDEDLFCHEDMFA;
DEDLFCHEDMFAS; EDLFCHEDMFASD; DLFCHEDMFASDE;
LFCHEDMFASDEE; FCHEDMFASDEEA; CHEDMFASDEEAT;
HEDMFASDEEATA; EDMFASDEEATAD; DMFASDEEATADS;
MFASDEEATADSQ; FASDEEATADSQH; ASDEEATADSQHS;
SDEEATADSQHST; DEEATADSQHSTP; EEATADSQHSTPP;
EATADSQHSTPPK; ATADSQHSTPPKK; TADSQHSTPPKKK;
ADSQHSTPPKKKR; DSQHSTPPKKKRK; SQHSTPPKKKRKV;
QHSTPPKKKRKVE; HSTPPKKKRKVED; STPPKKKRKVEDP;
TPPKKKRKVEDPK; PPKKKRKVEDPKD; PKKKRKVEDPKDF;
KKKRKVEDPKDFP; KKRKVEDPKDFPS; KRKVEDPKDFPSD;
RKVEDPKDFPSDL; KVEDPKDFPSDLH; VEDPKDFPSDLHQ;
EDPKDFPSDLHQF; DPKDFPSDLHQFL; PKDFPSDLHQFLS;
KDFPSDLHQFLSQ; DFPSDLHQFLSQA; FPSDLHQFLSQAV;
PSDLHQFLSQAVF; SDLHQFLSQAVFS; DLHQFLSQAVFSN;
LHQFLSQAVFSNR; HQFLSQAVFSNRT; QFLSQAVFSNRTL;
FLSQAVFSNRTLA; LSQAVFSNRTLAC; SQAVFSNRTLACF;
QAVFSNRTLACFA; AVFSNRTLACFAV; VFSNRTLACFAVY;
FSNRTLACFAVYT; SNRTLACFAVYTT; NRTLACFAVYTTK;
RTLACFAVYTTKE; TLACFAVYTTKEK; LACFAVYTTKEKA;
ACFAVYTTKEKAQ; CFAVYTTKEKAQI; FAVYTTKEKAQIL;
AVYTTKEKAQILY; VYTTKEKAQILYK; YTTKEKAQILYKK;
TTKEKAQILYKKL; TKEKAQILYKKLM; KEKAQILYKKLME;
EKAQILYKKLMEY; KAQILYKKLMEYS; AQILYKKLMEYSV;
QILYKKLMEYSVT; ILYKKLMEYSVTF;
YKKLMEYSVTFI; KKLMEYSVTFIS; KLMEYSVTFISR;
LMEKYSVTFISRH; MEKYSVTFISRHM; EKYSVTFISRHMC;
KYSVTFISRHMCA; YSVTFISRHMCAG; SVTFISRHMCAGH;
VTFISRHMCAGHN; TFISRHMCAGHNI; FISRHMCAGHNII;
ISRHMCAGHNIIF; SRHMCAGHNIIFF; RHMCAGHNIIFFL;
HMCAGHNIIFFLT; MCAGHNIIFFLTP; CAGHNIIFFLTPH;
AGHNIIFFLTPHR; GHNIIFFLTPHRH; HNIIFFLTPHRHR;
NIIFFLTPHRHRV; IIFFLTPHRHRVS; IFFLTPHRHRVSA;
FFLTPHRHRVSAI; FLTPHRHRVSAIN; LTPHRHRVSAINN;
TPHRHRVSAINNF; PHRHRVSAINNFC; HRHRVSAINNFCQ;
RHRVSAINNFCQK; HRVSAINNFCQKL; RVSAINNFCQKLC;
VSAINNFCQKLCT; SAINNFCQKLCTF; AINNFCQKLCTFS;
INNFCQKLCTFSF; NNFCQKLCTFSFL; NFCQKLCTFSFLI;
FCQKLCTFSFLIC; CQKLCTFSFLICK; QKLCTFSFLICKG;
KLCTFSFLICKGV; LCTFSFLICKGVN; CTFSFLICKGVNK;
TFSFLICKGVNKE; FSFLICKGVNKEY; SFLICKGVNKEYL;
FLICKGVNKEYLL; LICKGVNKEYLLY; ICKGVNKEYLLYS;
CKGVNKEYLLYSA; KGVNKEYLLYSAL; GVNKEYLLYSALT;
VNKEYLLYSALTR; NKEYLLYSALTRD; KEYLLYSALTRDP;
EYLLYSALTRDPY; YLLYSALTRDPYH; LLYSALTRDPYHT;
LYSALTRDPYHTI; YSALTRDPYHTIE; SALTRDPYHTIEE;
ALTRDPYHTIEES; LTRDPYHTIEESI; TRDPYHTIEESIQ;
RDPYHTIEESIQG; DPYHTIEESIQGG; PYHTIEESIQGGL;
YHTIEESIQGGLK; HTIEESIQGGLKE; TIEESIQGGLKEH;
IEESIQGGLKEHD; EESIQGGLKEHDF; ESIQGGLKEHDFS;
SIQGGLKEHDFSP; IQGGLKEHDFSPE; QGGLKEHDFSPEE;
GGLKEHDFSPEEP; GLKEHDFSPEEPE; LKEHDFSPEEPEE;
KEHDFSPEEPEET; EHDFSPEEPEETK; HDFSPEEPEETKQ;
DFSPEEPEETKQV; FSPEEPEETKQVS; SPEEPEETKQVSW;
PEEPEETKQVSWK; EEPEETKQVSWKL; EPEETKQVSWKLI;
PEETKQVSWKLIT; EETKQVSWKLITE; ETKQVSWKLITEY;
TKQVSWKLITEYA; KQVSWKLITEYAV; QVSWKLITEYAVE;
VSWKLITEYAVET; SWKLITEYAVETK; WKLITEYAVETKC;
KLITEYAVETKCE; LITEYAVETKCED; ITEYAVETKCEDV;
TEYAVETKCEDVF; EYAVETKCEDVFL; YAVETKCEDVFLL;
AVETKCEDVFLLL; VETKCEDVFLLLG; ETKCEDVFLLLGM;
TKCEDVFLLLGMY; KCEDVFLLLGMYL; CEDVFLLLGMYLE;
EDVFLLLGMYLEF; DVFLLLGMYLEFQ; VFLLLGMYLEFQY;
FLLLGMYLEFQYN; LLLGMYLEFQYNV; LLGMYLEFQYNVE;
LGMYLEFQYNVEE; GMYLEFQYNVEEC; MYLEFQYNVEECK;
YLEFQYNVEECKK; LEFQYNVEECKKC; EFQYNVEECKKCQ;
FQYNVEECKKCQK; QYNVEECKKCQKK; YNVEECKKCQKKD;
NVEECKKCQKKDQ; VEECKKCQKKDQP; EECKKCQKKDQPY;
ECKKCQKKDQPYH; CKKCQKKDQPYHF; KKCQKKDQPYHFK;
KCQKKDQPYHFKY; CQKKDQPYHFKYH; QKKDQPYHFKYHE;
KKDQPYHFKYHEK; KDQPYHFKYHEKH; DQPYHFKYHEKHF;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

QPYHFKYHEKHFA; PYHFKYHEKHFAN; YHFKYHEKHFANA;
HFKYHEKHFANAI; FKYHEKHFANAII; KYHEKHFANAIIF;
YHEKHFANAIIFA; HEKHFANAIIFAE; EKHFANAIIFAES;
KHFANAIIFAESK; HFANAIIFAESKN; FANAIIFAESKNQ;
ANAIIFAESKNQK; NAIIFAESKNQKS; AIIFAESKNQKSI;
IIFAESKNQKSIC; IFAESKNQKSICQ; FAESKNQKSICQQ;
AESKNQKSICQQA; ESKNQKSICQQAV; SKNQKSICQQAVD;
KNQKSICQQAVDT; NQKSICQQAVDTV; QKSICQQAVDTVL;
KSICQQAVDTVLA; SICQQAVDTVLAK; ICQQAVDTVLAKK;
CQQAVDTVLAKKR; QQAVDTVLAKKRV; QAVDTVLAKKRVD;
AVDTVLAKKRVDT; VDTVLAKKRVDTL; DTVLAKKRVDTLH;
TVLAKKRVDTLHM; VLAKKRVDTLHMT; LAKKRVDTLHMTR;
AKKRVDTLHMTRE; KKRVDTLHMTREE; KRVDTLHMTREEM;
RVDTLHMTREEML; VDTLHMTREEMLT; DTLHMTREEMLTE;
TLHMTREEMLTER; LHMTREEMLTERF; HMTREEMLTERFN;
MTREEMLTERFNH; TREEMLTERFNHI; REEMLTERFNHIL;
EEMLTERFNHILD; EMLTERFNHILDK; MLTERFNHILDKM;
LTERFNHILDKMD; TERFNHILDKMDL; ERFNHILDKMDLI;
RFNHILDKMDLIF; FNHILDKMDLIFG; NHILDKMDLIFGA;
HILDKMDLIFGAH; ILDKMDLIFGAHG; LDKMDLIFGAHGN;
DKMDLIFGAHGNA; KMDLIFGAHGNAV; MDLIFGAHGNAVL;
DLIFGAHGNAVLE; LIFGAHGNAVLEQ; IFGAHGNAVLEQY;
FGAHGNAVLEQYM; GAHGNAVLEQYMA; AHGNAVLEQYMAG;
HGNAVLEQYMAGV; GNAVLEQYMAGVA; NAVLEQYMAGVAW;
AVLEQYMAGVAWL; VLEQYMAGVAWLH; LEQYMAGVAWLHC;
EQYMAGVAWLHCL; QYMAGVAWLHCLL; YMAGVAWLHCLLP;
MAGVAWLHCLLPK; AGVAWLHCLLPKM; GVAWLHCLLPKMD;
VAWLHCLLPKMDS; AWLHCLLPKMDSV; WLHCLLPKMDSVI;
LHCLLPKMDSVIF; HCLLPKMDSVIFD; CLLPKMDSVIFDF;
LLPKMDSVIFDFL; LPKMDSVIFDFLH; PKMDSVIFDFLHC;
KMDSVIFDFLHCI; MDSVIFDFLHCIV; DSVIFDFLHCIVF;
SVIFDFLHCIVFN; VIFDFLHCIVFNV; IFDFLHCIVFNVP;
FDFLHCIVFNVPK; DFLHCIVFNVPKR; FLHCIVFNVPKRR;
LHCIVFNVPKRRY; HCIVFNVPKRRYW; CIVFNVPKRRYWL;
IVFNVPKRRYWLF; VFNVPKRRYWLFK; FNVPKRRYWLFKG;
NVPKRRYWLFKGP; VPKRRYWLFKGPI; PKRRYWLFKGPID;
KRRYWLFKGPIDS; RRYWLFKGPIDSG; RYWLFKGPIDSGK;
YWLFKGPIDSGKT; WLFKGPIDSGKTT; LFKGPIDSGKTTL;
FKGPIDSGKTTLA; KGPIDSGKTTLAA; GPIDSGKTTLAAG;
PIDSGKTTLAAGL; IDSGKTTLAAGLL; DSGKTTLAAGLLD;
SGKTTLAAGLLDL; GKTTLAAGLLDLC; KTTLAAGLLDLCG;
TTLAAGLLDLCGG; TLAAGLLDLCGGK; LAAGLLDLCGGKA;
AAGLLDLCGGKAL; AGLLDLCGGKALN; GLLDLCGGKALNV;
LLDLCGGKALNVN; LDLCGGKALNVNL; DLCGGKALNVNLP;
LCGGKALNVNLPM; CGGKALNVNLPME; GGKALNVNLPMER;
GKALNVNLPMERL; KALNVNLPMERLT; ALNVNLPMERLTF;
LNVNLPMERLTFE; NVNLPMERLTFEL; VNLPMERLTFELG;
NLPMERLTFELGV; LPMERLTFELGVA; PMERLTFELGVAI;
MERLTFELGVAID; ERLTFELGVAIDQ; RLTFELGVAIDQY;
LTFELGVAIDQYM; TFELGVAIDQYMV; FELGVAIDQYMVV;
ELGVAIDQYMVVF; LGVAIDQYMVVFE; GVAIDQYMVVFED;
VAIDQYMVVFEDV; AIDQYMVVFEDVK; IDQYMVVFEDVKG;
DQYMVVFEDVKGT; QYMVVFEDVKGTG; YMVVFEDVKGTGA;
MVVFEDVKGTGAE; VVFEDVKGTGAES; VFEDVKGTGAESK;
FEDVKGTGAESKD; EDVKGTGAESKDL; DVKGTGAESKDLP;
VKGTGAESKDLPS; KGTGAESKDLPSG; GTGAESKDLPSGH;
TGAESKDLPSGHG; GAESKDLPSGHGI; AESKDLPSGHGIN;
ESKDLPSGHGINN; SKDLPSGHGINNL; KDLPSGHGINNLD;
DLPSGHGINNLDS; LPSGHGINNLDSL; PSGHGINNLDSLR;
SGHGINNLDSLRD; GHGINNLDSLRDY; HGINNLDSLRDYL;
GINNLDSLRDYLD; INNLDSLRDYLDG; NNLDSLRDYLDGS;
NLDSLRDYLDGSV; LDSLRDYLDGSVK; DSLRDYLDGSVKV;
SLRDYLDGSVKVN; LRDYLDGSVKVNL; RDYLDGSVKVNLE;
DYLDGSVKVNLEK; YLDGSVKVNLEKK; LDGSVKVNLEKKH;
DGSVKVNLEKKHL; GSVKVNLEKKHLN; SVKVNLEKKHLNK;
VKVNLEKKHLNKR; KVNLEKKHLNKRT; VNLEKKHLNKRTQ;
NLEKKHLNKRTQI; LEKKHLNKRTQIF; EKKHLNKRTQIFP;
KKHLNKRTQIFPP; KHLNKRTQIFPPG; HLNKRTQIFPPGL;
LNKRTQIFPPGLV; NKRTQIFPPGLVT; KRTQIFPPGLVTM;
RTQIFPPGLVTMN; TQIFPPGLVTMNE; QIFPPGLVTMNEY;
IFPPGLVTMNEYP; FPPGLVTMNEYPV; PPGLVTMNEYPVP;
PGLVTMNEYPVPK; GLVTMNEYPVPKT; LVTMNEYPVPKTL;
VTMNEYPVPKTLQ; TMNEYPVPKTLQA; MNEYPVPKTLQAR;
NEYPVPKTLQARF; EYPVPKTLQARFV; YPVPKTLQARFVR;

PVPKTLQARFVRQ; VPKTLQARFVRQI; PKTLQARFVRQID;
KTLQARFVRQIDF; TLQARFVRQIDFR; LQARFVRQIDFRP;
QARFVRQIDFRPK; ARFVRQIDFRPKI; RFVRQIDFRPKIY;
FVRQIDFRPKIYL; VRQIDFRPKIYLR; RQIDFRPKIYLRK;
QIDFRPKIYLRKS; IDFRPKIYLRKSL; DFRPKIYLRKSLQ;
FRPKIYLRKSLQN; RPKIYLRKSLQNS; PKIYLRKSLQNSE;
KIYLRKSLQNSEF; IYLRKSLQNSEFL; YLRKSLQNSEFLL;
LRKSLQNSEFLLE; RKSLQNSEFLLEK; KSLQNSEFLLEKR;
SLQNSEFLLEKRI; LQNSEFLLEKRIL; QNSEFLLEKRILQ;
NSEFLLEKRILQS; SEFLLEKRILQSG; EFLLEKRILQSGM;
FLLEKRILQSGMT; LLEKRILQSGMTL; LEKRILQSGMTLL;
EKRILQSGMTLLL; KRILQSGMTLLLL; RILQSGMTLLLLL;
ILQSGMTLLLLLI; LQSGMTLLLLLIW; QSGMTLLLLLIWF;
SGMTLLLLLIWFR; GMTLLLLLIWFRP; MTLLLLLIWFRPV;
TLLLLLIWFRPVA; LLLLLIWFRPVAD; LLLLIWFRPVADF;
LLLIWFRPVADFA; LLIWFRPVADFAT; LIWFRPVADFATD;
IWFRPVADFATDI; WFRPVADFATDIQ; FRPVADFATDIQS;
RPVADFATDIQSR; PVADFATDIQSRI; VADFATDIQSRIV;
ADFATDIQSRIVE; DFATDIQSRIVEW; FATDIQSRIVEWK;
ATDIQSRIVEWKE; TDIQSRIVEWKER; DIQSRIVEWKERL;
IQSRIVEWKERLD; QSRIVEWKERLDS; SRIVEWKERLDSE;
RIVEWKERLDSEI; IVEWKERLDSEIS; VEWKERLDSEISM;
EWKERLDSEISMY; WKERLDSEISMYT; KERLDSEISMYTF;
ERLDSEISMYTFS; RLDSEISMYTFSR; LDSEISMYTFSRM;
DSEISMYTFSRMK; SEISMYTFSRMKY; EISMYTFSRMKYN;
ISMYTFSRMKYNI; SMYTFSRMKYNIC; MYTFSRMKYNICM;
YTFSRMKYNICMG; TFSRMKYNICMGK; FSRMKYNICMGKC;
SRMKYNICMGKCI; RMKYNICMGKCIL; MKYNICMGKCILD;
KYNICMGKCILDI; YNICMGKCILDIT; NICMGKCILDITR;
ICMGKCILDITRE; CMGKCILDITREE; MGKCILDITREED;
GKCILDITREEDS; KCILDITREEDSE; CILDITREEDSET;
ILDITREEDSETE; LDITREEDSETED; DITREEDSETEDS;
ITREEDSETEDSG; TREEDSETEDSGH; REEDSETEDSGHG;
EEDSETEDSGHGS; EDSETEDSGHGSS; DSETEDSGHGSST;
SETEDSGHGSSTE; ETEDSGHGSSTES; TEDSGHGSSTESQ;
EDSGHGSSTESQS; DSGHGSSTESQSQ; SGHGSSTESQSQC;
GHGSSTESQSQCS; HGSSTESQSQCSS; GSSTESQSQCSSQ;
SSTESQSQCSSQV; STESQSQCSSQVS; TESQSQCSSQVSD;
ESQSQCSSQVSDT; SQSQCSSQVSDTS; QSQCSSQVSDTSA;
SQCSSQVSDTSAP; QCSSQVSDTSAPA; CSSQVSDTSAPAE;
SSQVSDTSAPAED; SQVSDTSAPAEDS; QVSDTSAPAEDSQ;
VSDTSAPAEDSQR; SDTSAPAEDSQRS; DTSAPAEDSQRSD;
TSAPAEDSQRSDP; SAPAEDSQRSDPH; APAEDSQRSDPHS;
PAEDSQRSDPHSQ; AEDSQRSDPHSQE; EDSQRSDPHSQEL;
DSQRSDPHSQELH; SQRSDPHSQELHL; QRSDPHSQELHLC;
RSDPHSQELHLCK; SDPHSQELHLCKG; DPHSQELHLCKGF;
PHSQELHLCKGFQ; HSQELHLCKGFQC; SQELHLCKGFQCF;
QELHLCKGFQCFK; ELHLCKGFQCFKR; LHLCKGFQCFKRP;
HLCKGFQCFKRPK; LCKGFQCFKRPKT; CKGFQCFKRPKTP;
KGFQCFKRPKTPP; GFQCFKRPKTPPP; FQCFKRPKTPPPK;
HKLKSGLYKSSIY; MYMYNKSTCLKHF; YMYNKSTCLKHFG;
MYNKSTCLKHFGL; YNKSTCLKHFGLQ; NKSTCLKHFGLQL;
KSTCLKHFGLQLS; STCLKHFGLQLSL; TCLKHFGLQLSLF;
CLKHFGLQLSLFV; LKHFGLQLSLFVN; KHFGLQLSLFVNI;
HFGLQLSLFVNIS; FGLQLSLFVNISY; GLQLSLFVNISYH;
LQLSLFVNISYHI; QLSLFVNISYHIW; LSLFVNISYHIWV;
SLFVNISYHIWVP; LFVNISYHIWVPW; FVNISYHIWVPWK;
VNISYHIWVPWKS; NISYHIWVPWKSF; ISYHIWVPWKSFC;
SYHIWVPWKSFCA; YHIWVPWKSFCAI; HIWVPWKSFCAIK;
IWVPWKSFCAIKH; WVPWKSFCAIKHP; VPWKSFCAIKHPN;
PWKSFCAIKHPNL; WKSFCAIKHPNLF; KSFCAIKHPNLFY;
SFCAIKHPNLFYL; FCAIKHPNLFYLG; CAIKHPNLFYLGF;
AIKHPNLFYLGFH; IKHPNLFYLGFHT; KHPNLFYLGFHTI;
HPNLFYLGFHTIH; PNLFYLGFHTIHR; NLFYLGFHTIHRL;
LFYLGFHTIHRLP; FYLGFHTIHRLPI; YLGFHTIHRLPIH;
LGFHTIHRLPIHS; GFHTIHRLPIHSL; FHTIHRLPIHSLG;
HTIHRLPIHSLGS; TIHRLPIHSLGSP; IHRLPIHSLGSPV;
HRLPIHSLGSPVY; RLPIHSLGSPVYK; LPIHSLGSPVYKV;
PIHSLGSPVYKVT; QKGNWVRILYRSF; KGNWVRILYRSFS;
GNWVRILYRSFSQ; NWVRILYRSFSQA; WVRILYRSFSQAD;
VRILYRSFSQADL; RILYRSFSQADLK; ILYRSFSQADLKI;
LYRSFSQADLKIS; YRSFSQADLKISC; RSFSQADLKISCK;
SFSQADLKISCKA; FSQADLKISCKAS; SQADLKISCKASP;
QADLKISCKASPL; ADLKISCKASPLL; DLKISCKASPLLC;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

LKISCKASPLLCS; KISCKASPLLCSR; ISCKASPLLCSRA;
SCKASPLLCSRAV; CKASPLLCSRAVS; KASPLLCSRAVSK;
ASPLLCSRAVSKQ; SPLLCSRAVSKQA; PLLCSRAVSKQAT;
LLCSRAVSKQATN; LCSRAVSKQATNI; CSRAVSKQATNIS;
SRAVSKQATNISS; NIQAISFTKRPHT; IQAISFTKRPHTL;
QAISFTKRPHTLF; AISFTKRPHTLFI; QHCGSCVGHMKYW;
HCGSCVGHMKYWG; CGSCVGHMKYWGN; GSCVGHMKYWGNI;
SCVGHMKYWGNIF; CVGHMKYWGNIFP; VGHMKYWGNIFPS;
GHMKYWGNIFPSC; HMKYWGNIFPSCE; MKYWGNIFPSCES;
KYWGNIFPSCESP; YWGNIFPSCESPK; WGNIFPSCESPKI;
GNIFPSCESPKIP; NIFPSCESPKIPS; IFPSCESPKIPSI;
FPSCESPKIPSIF; PSCESPKIPSIFI; SCESPKIPSIFIS;
CESPKIPSIFIST; ESPKIPSIFISTG; SPKIPSIFISTGI;
PKIPSIFISTGIR; KIPSIFISTGIRY; IPSIFISTGIRYP;
PSIFISTGIRYPA; SIFISTGIRYPAL; IFISTGIRYPALN;
FISTGIRYPALNW; ISTGIRYPALNWI; STGIRYPALNWIS;
TGIRYPALNWISI; GIRYPALNWISIV; IRYPALNWISIVF;
RYPALNWISIVFV; YPALNWISIVFVQ; PALNWISIVFVQI;
ALNWISIVFVQIG; LNWISIVFVQIGL; NWISIVFVQIGLM;
WISIVFVQIGLMV; ISIVFVQIGLMVS; SIVFVQIGLMVSI;
IVFVQIGLMVSIH; VFVQIGLMVSIHY; FVQIGLMVSIHYL;
VQIGLMVSIHYLG; QIGLMVSIHYLGL; IGLMVSIHYLGLG;
GLMVSIHYLGLGC; LMVSIHYLGLGCW; MVSIHYLGLGCWV;
VSIHYLGLGCWVF; SIHYLGLGCWVFR; IHYLGLGCWVFRG;
HYLGLGCWVFRGY; YLGLGCWVFRGYS; LGLGCWVFRGYST;
GLGCWVFRGYSTI; LGCWVFRGYSTIR; GCWVFRGYSTIRV;
CWVFRGYSTIRVL; HSLHFQGFSTYSK; SLHFQGFSTYSKE;
LHFQGFSTYSKEV; HFQGFSTYSKEVE; FQGFSTYSKEVEI;
QGFSTYSKEVEIT; GFSTYSKEVEITA; FSTYSKEVEITAL;
STYSKEVEITALN; TYSKEVEITALNR; YSKEVEITALNRF;
SKEVEITALNRFS; KEVEITALNRFSS; EVEITALNRFSST;
VEITALNRFSSTM; EITALNRFSSTML; ITALNRFSSTMLM;
TALNRFSSTMLMH; ALNRFSSTMLMHF; LNRFSSTMLMHFL;
PCMKVKHASYSNN; CMKVKHASYSNNL; MKVKHASYSNNLC;
KVKHASYSNNLCL; VKHASYSNNLCLY; KHASYSNNLCLYS;
HASYSNNLCLYSY; ASYSNNLCLYSYS; SYSNNLCLYSYSL;
YSNNLCLYSYSLP; SNNLCLYSYSLPH; NNLCLYSYSLPHQ;
IGEGNSCCAVTGK; GEGNSCCAVTGKH; EGNSCCAVTGKHF;
GNSCCAVTGKHFS; NSCCAVTGKHFSL; SCCAVTGKHFSLW;
CCAVTGKHFSLWA; CAVTGKHFSLWAI; AVTGKHFSLWAIT;
VTGKHFSLWAITA; TGKHFSLWAITAK; GKHFSLWAITAKV;
KHFSLWAITAKVI; HFSLWAITAKVIF; FSLWAITAKVIFS;
SLWAITAKVIFST; TKAPKVFIWIPHF; KAPKVFIWIPHFW;
APKVFIWIPHFWV; EAFYLCNSIYPSF; AFYLCNSIYPSFN;
FYLCNSIYPSFNF; FWHLHGFLWLFGS; WHLHGFLWLFGSC;
HLHGFLWLFGSCP; LHGFLWLFGSCPW; HGFLWLFGSCPWT;
GFLWLFGSCPWTL; FLWLFGSCPWTLS; LWLFGSCPWTLSF;
WLFGSCPWTLSFS; LFGSCPWTLSFSF; FGSCPWTLSFSFG;
GSCPWTLSFSFGW; SCPWTLSFSFGWG; CPWTLSFSFGWGH;
PWTLSFSFGWGHL; WTLSFSFGWGHLH; TLSFSFGWGHLHM;
LSFSFGWGHLHML; SFSFGWGHLHMLQ; FSFGWGHLHMLQE;
SFGWGHLHMLQEQ; FGWGHLHMLQEQV; GWGHLHMLQEQVL;
WGHLHMLQEQVLQ; GHLHMLQEQVLQS; HLHMLQEQVLQSR;
LHMLQEQVLQSRT; HMLQEQVLQSRTG; MLQEQVLQSRTGL;
LQEQVLQSRTGLE; QEQVLQSRTGLEV; EQVLQSRTGLEVK;
QVLQSRTGLEVKA; VLQSRTGLEVKAT; LQSRTGLEVKATS;
QSRTGLEVKATSI; SRTGLEVKATSIE; RTGLEVKATSIEE;
TGLEVKATSIEEQ; GLEVKATSIEEQF; LEVKATSIEEQFF;
EVKATSIEEQFFD; TLLNVHFVDFLSP; LLNVHFVDFLSPF;
LNVHFVDFLSPFF; NVHFVDFLSPFFV; LLLYCQHHLYYKY;
LLYCQHHLYYKYG; LYCQHHLYYKYGQ; YCQHHLYYKYGQN;
CQHHLYYKYGQNV; QHHLYYKYGQNVH; HHLYYKYGQNVHG;
HLYYKYGQNVHGY; LYYKYGQNVHGYL; YYKYGQNVHGYLP;
YKYGQNVHGYLPF; KYGQNVHGYLPFQ; YGQNVHGYLPFQL;
GQNVHGYLPFQLL; QNVHGYLPFQLLV; GKDQNNIVEYNYK;
KDQNNIVEYNYKS; DQNNIVEYNYKSL; KIFLFFSAIPVRL;
QKYLHQETEYHST; KYLHQETEYHSTH; YLHQETEYHSTHL;
LHQETEYHSTHLG; TIPKPCLIADRGL; IPKPCLIADRGLQ;
PKPCLIADRGLQW; KPCLIADRGLQWK; PCLIADRGLQWKL;
CLIADRGLQWKLC; LIADRGLQWKLCD; IADRGLQWKLCDP;
ADRGLQWKLCDPN; DRGLQWKLCDPNH; RGLQWKLCDPNHQ;
GLQWKLCDPNHQR; LQWKLCDPNHQRT; QWKLCDPNHQRTY;
WKLCDPNHQRTYT; KLCDPNHQRTYTL; LCDPNHQRTYTLL;
CDPNHQRTYTLLE; DPNHQRTYTLLEL; PNHQRTYTLLELR;
NHQRTYTLLELRN; PQEHQQLQHMFEE; QEHQQLQHMFEEL;
EHQQLQHMFEELG; HQQLQHMFEELGL; QQQPPQQQFQPLK;
QPPPQQQFQPLKI; QPPQQQFQPLKIL; PPQQQFQPLKILW;
PQQQFQPLKILWQ; QQQFQPLKILWQQ; QQFQPLKILWQQQ;
QFQPLKILWQQQP; FQPLKILWQQQPQ; QPLKILWQQQPQI;
PLKILWQQQPQIH; LKILWQQQPQIHW; KILWQQQPQIHWQ;
ILWQQQPQIHWQL; LWQQQPQIHWQLG; WQQQPQIHWQLGP;
QQQPQIHWQLGPP; QQPQIHWQLGPPK; QPQIHWQLGPPKV;
PQIHWQLGPPKVL; QIHWQLGPPKVLE; IHWQLGPPKVLEQ;
HWQLGPPKVLEQH; WQLGPPKVLEQHP; TWKYKKKGITYLG;
WKYKKKGITYLGV; KYKKKGITYLGVF; YKKKGITYLGVFY;
KKKGITYLGVFYR; KKGITYLGVFYRV; KGITYLGVFYRVF;
GITYLGVFYRVFY; ITYLGVFYRVFYS; TYLGVFYRVFYSR;
SSGTFVFPVYTVF; SGTFVFPVYTVFT; GTFVFPVYTVFTS;
TFVFPVYTVFTST; FVFPVYTVFTSTK; VFPVYTVFTSTKF;
FPVYTVFTSTKFQ; PVYTVFTSTKFQQ; VYTVFTSTKFQQK;
YTVFTSTKFQQKL; NKNKNPLSSFFCS; KNKNPLSSFFCSS;
NKNPLSSFFCSSP; KNPLSSFFCSSPG; NPLSSFFCSSPGF;
PLSSFFCSSPGFT; LSSFFCSSPGFTN; SSFFCSSPGFTNF;
SFFCSSPGFTNFH; FFCSSPGFTNFHG; GTRPRFLGSQNMS;
TRPRFLGSQNMSV; RPRFLGSQNMSVM; PRFLGSQNMSVMH;
RFLGSQNMSVMHF; FLGSQNMSVMHFP; LGSQNMSVMHFPS;
AAPPCESCTFLPE; APPCESCTFLPEV; PPCESCTFLPEVM;
PCESCTFLPEVMV; CESCTFLPEVMVW; ESCTFLPEVMVWL;
SCTFLPEVMVWLH; CTFLPEVMVWLHS; TFLPEVMVWLHSP;
FLPEVMVWLHSPV; LPEVMVWLHSPVS; PEVMVWLHSPVSH;
EVMVWLHSPVSHA; VMVWLHSPVSHAL; MVWLHSPVSHALS;
VWLHSPVSHALSF; WLHSPVSHALSFL; LHSPVSHALSFLR;
HSPVSHALSFLRS; SPVSHALSFLRSW; PVSHALSFLRSWF;
VSHALSFLRSWFG; SHALSFLRSWFGC; HALSFLRSWFGCI;
ALSFLRSWFGCIP; LSFLRSWFGCIPW; SFLRSWFGCIPWV;
FLRSWFGCIPWVS; LRSWFGCIPWVSS; RSWFGCIPWVSSS;
SWFGCIPWVSSSS; WFGCIPWVSSSSL; FGCIPWVSSSSLW;
GCIPWVSSSSLWP; CIPWVSSSSLWPF; IPWVSSSSLWPFF;
PWVSSSSLWPFFL; YIRGRGRLCLHPF; IRGRGRLCLHPFS;
RGRGRLCLHPFSQ; GRGRLCLHPFSQV; RGRLCLHPFSQVV;
GRLCLHPFSQVVR; RLCLHPFSQVVRV; LCLHPFSQVVRVW;
CLHPFSQVVRVWR; LHPFSQVVRVWRL; HPFSQVVRVWRLF;
PFSQVVRVWRLFL; FSQVVRVWRLFLR; SQVVRVWRLFLRP;
QVVRVWRLFLRPS; VVRVWRLFLRPSK; VRVWRLFLRPSKT;
RVWRLFLRPSKTI; VWRLFLRPSKTIW; WRLFLRPSKTIWG;
RLFLRPSKTIWGN; LFLRPSKTIWGNP; FLRPSKTIWGNPY;
LRPSKTIWGNPYS; RPSKTIWGNPYSF; PSKTIWGNPYSFA;
SKTIWGNPYSFAI; KTIWGNPYSFAIF; TIWGNPYSFAIFA;
IWGNPYSFAIFAK 14 mers:

KSCLGKSSLNEKSL; SCLGKSSLNEKSLF; CLGKSSLNEKSLFK;
LGKSSLNEKSLFKE; GKSSLNEKSLFKEV; FSSLPRYPVLQGMA;
SSLPRYPVLQGMAY; SLPRYPVLQGMAYL; LPRYPVLQGMAYLF;
PRYPVLQGMAYLFQ; RYPVLQGMAYLFQK; YPVLQGMAYLFQKA;
PVLQGMAYLFQKAF; VLQGMAYLFQKAFC; LQGMAYLFQKAFCA;
QGMAYLFQKAFCAL; GMAYLFQKAFCALP; MAYLFQKAFCALPL;
AYLFQKAFCALPLH; YLFQKAFCALPLHA; LFQKAFCALPLHAM;
FQKAFCALPLHAMS; QKAFCALPLHAMSA; KIPKKRALGLDRLL;
IFKKRALGLDRLLL; FKKRALGLDRLLLH; RNSAMVGPNNWRNS;
NSAMVGPNNWRNSL; SAMVGPNNWRNSLQ; AMVGPNNWRNSLQR;
MVGPNNWRNSLQRS; VGPNNWRNSLQRSK; GPNNWRNSLQRSKA;
PNNWRNSLQRSKAL; NNWRNSLQRSKALR; VPTYGTEEWESWWS;
PTYGTEEWESWWSS; TYGTEEWESWWSSF; YGTEEWESWWSSFN;
GTEEWESWWSSFNE; TEEWESWWSSFNEK; EEWESWWSSFNEKW;
EWESWWSSFNEKWD; WESWWSSFNEKWDE; ESWWSSFNEKWDED;
SWWSSFNEKWDEDL; WWSSFNEKWDEDLF; WSSFNEKWDEDLFC;
SSFNEKWDEDLFCH; SFNEKWDEDLFCHE; FNEKWDEDLFCHED;
NEKWDEDLFCHEDM; EKWDEDLFCHEDMF; KWDEDLFCHEDMFA;
WDEDLFCHEDMFAS; DEDLFCHEDMFASD; EDLFCHEDMFASDE;
DLFCHEDMFASDEE; LFCHEDMFASDEEA; FCHEDMFASDEEAT;
CHEDMFASDEEATA; HEDMFASDEEATAD; EDMFASDEEATADS;
DMFASDEEATADSQ; MFASDEEATADSQH; FASDEEATADSQHS;
ASDEEATADSQHST; SDEEATADSQHSTP; DEEATADSQHSTPP;
EEATADSQHSTPPK; EATADSQHSTPPKK; ATADSQHSTPPKKK;
TADSQHSTPPKKKR; ADSQHSTPPKKKRK; DSQHSTPPKKKRKV;
SQHSTPPKKKRKVE; QHSTPPKKKRKVED; HSTPPKKKRKVEDP;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

STPPKKKRKVEDPK; TPPKKKRKVEDPKD; PPKKKRKVEDPKDF;
PKKKRKVEDPKDFP; KKKRKVEDPKDFPS; KKRKVEDPKDFPSD;
KRKVEDPKDFPSDL; RKVEDPKDFPSDLH; KVEDPKDFPSDLHQ;
VEDPKDFPSDLHQF; EDPKDFPSDLHQFL; DPKDFPSDLHQFLS;
PKDFPSDLHQFLSQ; KDFPSDLHQFLSQA; DFPSDLHQFLSQAV;
FPSDLHQFLSQAVF; PSDLHQFLSQAVFS; SDLHQFLSQAVFSN;
DLHQFLSQAVFSNR; LHQFLSQAVFSNRT; HQFLSQAVFSNRTL;
QFLSQAVFSNRTLA; FLSQAVFSNRTLAC; LSQAVFSNRTLACF;
SQAVFSNRTLACFA; QAVFSNRTLACFAV; AVFSNRTLACFAVY;
VFSNRTLACFAVYT; FSNRTLACFAVYTT; SNRTLACFAVYTTK;
NRTLACFAVYTTKE; RTLACFAVYTTKEK; TLACFAVYTTKEKA;
LACFAVYTTKEKAQ; ACFAVYTTKEKAQI; CFAVYTTKEKAQIL;
FAVYTTKEKAQILY; AVYTTKEKAQILYK; VYTTKEKAQILYKK;
YTTKEKAQILYKKL; TTKEKAQILYKKLM; TKEKAQILYKKLME;
KEKAQILYKKLMEK; EKAQILYKKLMEKY; KAQILYKKLMEKYS;
AQILYKKLMEKYSV; QILYKKLMEKYSVT; ILYKKLMEKYSVTF;
LYKKLMEKYSVTFI; YKKLMEKYSVTFIS; KKLMEKYSVTFISR;
KLMEKYSVTFISRH; LMEKYSVTFISRHM; MEKYSVTFISRHMC;
EKYSVTFISRHMCA; KYSVTFISRHMCAG; YSVTFISRHMCAGH;
SVTFISRHMCAGHN; VTFISRHMCAGHNI; TFISRHMCAGHNII;
FISRHMCAGHNIIF; ISRHMCAGHNIIFF; SRHMCAGHNIIFFL;
RHMCAGHNIIFFLT; HMCAGHNIIFFLTP; MCAGHNIIFFLTPH;
CAGHNIIFFLTPHR; AGHNIIFFLTPHRH; GHNIIFFLTPHRHR;
HNIIFFLTPHRHRV; NIIFFLTPHRHRVS; IIFFLTPHRHRVSA;
IFFLTPHRHRVSAI; FFLTPHRHRVSAIN; FLTPHRHRVSAINN;
LTPHRHRVSAINNF; TPHRHRVSAINNFC; PHRHRVSAINNFCQ;
HRHRVSAINNFCQK; RHRVSAINNFCQKL; HRVSAINNFCQKLC;
RVSAINNFCQKLCT; VSAINNFCQKLCTF; SAINNFCQKLCTFS;
AINNFCQKLCTFSF; INNFCQKLCTFSFL; NNFCQKLCTFSFLI;
NFCQKLCTFSFLIC; FCQKLCTFSFLICK; CQKLCTFSFLICKG;
QKLCTFSFLICKGV; KLCTFSFLICKGVN; LCTFSFLICKGVNK;
CTFSFLICKGVNKE; TFSFLICKGVNKEY; FSFLICKGVNKEYL;
SFLICKGVNKEYLL; FLICKGVNKEYLLY; LICKGVNKEYLLYS;
ICKGVNKEYLLYSA; CKGVNKEYLLYSAL; KGVNKEYLLYSALT;
GVNKEYLLYSALTR; VNKEYLLYSALTRD; NKEYLLYSALTRDP;
KEYLLYSALTRDPY; EYLLYSALTRDPYH; YLLYSALTRDPYHT;
LLYSALTRDPYHTI; LYSALTRDPYHTIE; YSALTRDPYHTIEE;
SALTRDPYHTIEES; ALTRDPYHTIEESI; LTRDPYHTIEESIQ;
TRDPYHTIEESIQG; RDPYHTIEESIQGG; DPYHTIEESIQGGL;
PYHTIEESIQGGLK; YHTIEESIQGGLKE; HTIEESIQGGLKEH;
TIEESIQGGLKEHD; IEESIQGGLKEHDF; EESIQGGLKEHDFS;
ESIQGGLKEHDFSP; SIQGGLKEHDFSPE; IQGGLKEHDFSPEE;
QGGLKEHDFSPEEP; GGLKEHDFSPEEPE; GLKEHDFSPEEPEE;
LKEHDFSPEEPEET; KEHDFSPEEPEETK; EHDFSPEEPEETKQ;
HDFSPEEPEETKQV; DFSPEEPEETKQVS; FSPEEPEETKQVSW;
SPEEPEETKQVSWK; PEEPEETKQVSWKL; EEPEETKQVSWKLI;
EPEETKQVSWKLIT; PEETKQVSWKLITE; EETKQVSWKLITEY;
ETKQVSWKLITEYA; TKQVSWKLITEYAV; KQVSWKLITEYAVE;
QVSWKLITEYAVET; VSWKLITEYAVETK; SWKLITEYAVETKC;
WKLITEYAVETKCE; KLITEYAVETKCED; LITEYAVETKCEDV;
ITEYAVETKCEDVF; TEYAVETKCEDVFL; EYAVETKCEDVFLL;
YAVETKCEDVFLLL; AVETKCEDVFLLLG; VETKCEDVFLLLGM;
ETKCEDVFLLLGMY; TKCEDVFLLLGMYL; KCEDVFLLLGMYLE;
CEDVFLLLGMYLEF; EDVFLLLGMYLEFQ; DVFLLLGMYLEFQY;
VFLLLGMYLEFQYN; FLLLGMYLEFQYNV; LLLGMYLEFQYNVE;
LLGMYLEFQYNVEE; LGMYLEFQYNVEEC; GMYLEFQYNVEECK;
MYLEFQYNVEECKK; YLEFQYNVEECKKC; LEFQYNVEECKKCQ;
EFQYNVEECKKCQK; FQYNVEECKKCQKK; QYNVEECKKCQKKD;
YNVEECKKCQKKDQ; NVEECKKCQKKDQP; VEECKKCQKKDQPY;
EECKKCQKKDQPYH; ECKKCQKKDQPYHF; CKKCQKKDQPYHFK;
KKCQKKDQPYHFKY; KCQKKDQPYHFKYH; CQKKDQPYHFKYHE;
QKKDQPYHFKYHEK; KKDQPYHFKYHEKH; KDQPYHFKYHEKHF;
DQPYHFKYHEKHFA; QPYHFKYHEKHFAN; PYHFKYHEKHFANA;
YHFKYHEKHFANAI; HFKYHEKHFANAII; FKYHEKHFANAIIF;
KYHEKHFANAIIFA; YHEKHFANAIIFAE; HEKHFANAIIFAES;
EKHFANAIIFAESK; KHFANAIIFAESKN; HFANAIIFAESKNQ;
FANAIIFAESKNQK; ANAIIFAESKNQKS; NAIIFAESKNQKSI;
AIIFAESKNQKSIC; IIFAESKNQKSICQ; IFAESKNQKSICQQ;
FAESKNQKSICQQA; AESKNQKSICQQAV; ESKNQKSICQQAVD;
SKNQKSICQQAVDT; KNQKSICQQAVDTV; NQKSICQQAVDTVL;
QKSICQQAVDTVLA; KSICQQAVDTVLAK; SICQQAVDTVLAKK;
ICQQAVDTVLAKKR; CQQAVDTVLAKKRV; QQAVDTVLAKKRVD;
QAVDTVLAKKRVDT; AVDTVLAKKRVDTL; VDTVLAKKRVDTLH;
DTVLAKKRVDTLHM; TVLAKKRVDTLHMT; VLAKKRVDTLHMTR;
LAKKRVDTLHMTRE; AKKRVDTLHMTREE; KKRVDTLHMTREEM;
KRVDTLHMTREEML; RVDTLHMTREEMLT; VDTLHMTREEMLTE;
DTLHMTREEMLTER; TLHMTREEMLTERF; LHMTREEMLTERFN;
HMTREEMLTERFNH; MTREEMLTERFNHI; TREEMLTERFNHIL;
REEMLTERFNHILD; EEMLTERFNHILDK; EMLTERFNHILDKM;
MLTERFNHILDKMD; LTERFNHILDKMDL; TERFNHILDKMDLI;
ERFNHILDKMDLIF; RFNHILDKMDLIFG; FNHILDKMDLIFGA;
NHILDKMDLIFGAH; HILDKMDLIFGAHG; ILDKMDLIFGAHGN;
LDKMDLIFGAHGNA; DKMDLIFGAHGNAV; KMDLIFGAHGNAVL;
MDLIFGAHGNAVLE; DLIFGAHGNAVLEQ; LIFGAHGNAVLEQY;
IFGAHGNAVLEQYM; FGAHGNAVLEQYMA; GAHGNAVLEQYMAG;
AHGNAVLEQYMAGV; HGNAVLEQYMAGVA; GNAVLEQYMAGVAW;
NAVLEQYMAGVAWL; AVLEQYMAGVAWLH; VLEQYMAGVAWLHC;
LEQYMAGVAWLHCL; EQYMAGVAWLHCLL; QYMAGVAWLHCLLP;
YMAGVAWLHCLLPK; MAGVAWLHCLLPKM; AGVAWLHCLLPKMD;
GVAWLHCLLPKMDS; VAWLHCLLPKMDSV; AWLHCLLPKMDSVI;
WLHCLLPKMDSVIF; LHCLLPKMDSVIFD; HCLLPKMDSVIFDF;
CLLPKMDSVIFDFL; LLPKMDSVIFDFLH; LPKMDSVIFDFLHC;
PKMDSVIFDFLHCI; KMDSVIFDFLHCIV; MDSVIFDFLHCIVF;
DSVIFDFLHCIVFN; SVIFDFLHCIVFNV; VIFDFLHCIVFNVP;
IFDFLHCIVFNVPK; FDFLHCIVFNVPKR; DFLHCIVFNVPKRR;
FLHCIVFNVPKRRY; LHCIVFNVPKRRYW; HCIVFNVPKRRYWL;
CIVFNVPKRRYWLF; IVFNVPKRRYWLFK; VFNVPKRRYWLFKG;
FNVPKRRYWLFKGP; NVPKRRYWLFKGPI; VPKRRYWLFKGPID;
PKRRYWLFKGPIDS; KRRYWLFKGPIDSG; RRYWLFKGPIDSGK;
RYWLFKGPIDSGKT; YWLFKGPIDSGKTT; WLFKGPIDSGKTTL;
LFKGPIDSGKTTLA; FKGPIDSGKTTLAA; KGPIDSGKTTLAAG;
GPIDSGKTTLAAGL; PIDSGKTTLAAGLL; IDSGKTTLAAGLLD;
DSGKTTLAAGLLDL; SGKTTLAAGLLDLC; GKTTLAAGLLDLCG;
KTTLAAGLLDLCGG; TTLAAGLLDLCGGK; TLAAGLLDLCGGKA;
LAAGLLDLCGGKAL; AAGLLDLCGGKALN; AGLLDLCGGKALNV;
GLLDLCGGKALNVL; LLDLCGGKALNVLP; LDLCGGKALNVLPM;
DLCGGKALNVLPME; LCGGKALNVLPMER; CGGKALNVLPMERL;
GGKALNVLPMERLT; GKALNVLPMERLTF; KALNVLPMERLTFE;
ALNVLPMERLTFEL; LNVLPMERLTFELG; NVLPMERLTFELGV;
VNLPMERLTFELGV; NLPMERLTFELGVA; LPMERLTFELGVAI;
PMERLTFELGVAID; MERLTFELGVAIDQ; ERLTFELGVAIDQY;
RLTFELGVAIDQYM; LTFELGVAIDQYMV; TFELGVAIDQYMVV;
FELGVAIDQYMVVF; ELGVAIDQYMVVFE; LGVAIDQYMVVFED;
GVAIDQYMVVFEDV; VAIDQYMVVFEDVK; AIDQYMVVFEDVKG;
IDQYMVVFEDVKGT; DQYMVVFEDVKGTG; QYMVVFEDVKGTGA;
YMVVFEDVKGTGAE; MVVFEDVKGTGAES; VVFEDVKGTGAESK;
VFEDVKGTGAESKD; FEDVKGTGAESKDL; EDVKGTGAESKDLP;
DVKGTGAESKDLPS; VKGTGAESKDLPSG; KGTGAESKDLPSGH;
GTGAESKDLPSGHG; TGAESKDLPSGHGI; GAESKDLPSGHGIN;
AESKDLPSGHGINN; ESKDLPSGHGINNL; SKDLPSGHGINNLD;
KDLPSGHGINNLDS; DLPSGHGINNLDSL; LPSGHGINNLDSLR;
PSGHGINNLDSLRD; SGHGINNLDSLRDY; GHGINNLDSLRDYL;
HGINNLDSLRDYLD; GINNLDSLRDYLDG; INNLDSLRDYLDGS;
NNLDSLRDYLDGSV; NLDSLRDYLDGSVK; LDSLRDYLDGSVKV;
DSLRDYLDGSVKVN; SLRDYLDGSVKVNL; LRDYLDGSVKVNLE;
RDYLDGSVKVNLEK; DYLDGSVKVNLEKK; YLDGSVKVNLEKKH;
LDGSVKVNLEKKHL; DGSVKVNLEKKHLN; GSVKVNLEKKHLNK;
SVKVNLEKKHLNKR; VKVNLEKKHLNKRT; KVNLEKKHLNKRTQ;
VNLEKKHLNKRTQI; NLEKKHLNKRTQIF; LEKKHLNKRTQIFP;
EKKHLNKRTQIFPP; KKHLNKRTQIFPPG; KHLNKRTQIFPPGL;
HLNKRTQIFPPGLV; LNKRTQIFPPGLVT; NKRTQIFPPGLVTM;
KRTQIFPPGLVTMN; RTQIFPPGLVTMNE; TQIFPPGLVTMNEY;
QIFPPGLVTMNEYP; IFPPGLVTMNEYPV; FPPGLVTMNEYPVP;
PPGLVTMNEYPVPK; PGLVTMNEYPVPKT; GLVTMNEYPVPKTL;
LVTMNEYPVPKTLQ; VTMNEYPVPKTLQA; TMNEYPVPKTLQAR;
MNEYPVPKTLQARF; NEYPVPKTLQARFV; EYPVPKTLQARFVR;
YPVPKTLQARFVRQ; PVPKTLQARFVRQI; VPKTLQARFVRQID;
PKTLQARFVRQIDF; KTLQARFVRQIDFR; TLQARFVRQIDFRP;
LQARFVRQIDFRPK; QARFVRQIDFRPKI; ARFVRQIDFRPKIY;
RFVRQIDFRPKIYL; FVRQIDFRPKIYLR; VRQIDFRPKIYLRK;
RQIDFRPKIYLRKS; QIDFRPKIYLRKSL; IDFRPKIYLRKSLQ;
DFRPKIYLRKSLQN; FRPKIYLRKSLQNS; RPKIYLRKSLQNSE;
PKIYLRKSLQNSEF; KIYLRKSLQNSEFL; IYLRKSLQNSEFLL;
YLRKSLQNSEFLLE; LRKSLQNSEFLLEK; RKSLQNSEFLLEKR;
KSLQNSEFLLEKRI; SLQNSEFLLEKRIL; LQNSEFLLEKRILQ;
QNSEFLLEKRILQS; NSEFLLEKRILQSG; SEFLLEKRILQSGM;
EFLLEKRILQSGMT; FLLEKRILQSGMTL; LLEKRILQSGMTLL;
LEKRILQSGMTLLL; EKRILQSGMTLLLL; KRILQSGMTLLLLL;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

RILQSGMTLLLLLI; ILQSGMTLLLLLIW; LQSGMTLLLLLIWF;
QSGMTLLLLLIWFR; SGMTLLLLLIWFRP; GMTLLLLLIWFRPV;
MTLLLLLIWFRPVA; TLLLLLIWFRPVAD; LLLLLIWFRPVADF;
LLLLIWFRPVADFA; LLLIWFRPVADFAT; LLIWFRPVADFATD;
LIWFRPVADFATDI; IWFRPVADFATDIQ; WFRPVADFATDIQS;
FRPVADFATDIQSR; RPVADFATDIQSRI; PVADFATDIQSRIV;
VADFATDIQSRIVE; ADFATDIQSRIVEW; DFATDIQSRIVEWK;
FATDIQSRIVEWKE; ATDIQSRIVEWKER; TDIQSRIVEWKERL;
DIQSRIVEWKERLD; IQSRIVEWKERLDS; QSRIVEWKERLDSE;
SRIVEWKERLDSEI; RIVEWKERLDSEIS; IVEWKERLDSEISM;
VEWKERLDSEISMY; EWKERLDSEISMYT; WKERLDSEISMYTF;
KERLDSEISMYTFS; ERLDSEISMYTFSR; RLDSEISMYTFSRM;
LDSEISMYTFSRMK; DSEISMYTFSRMKY; SEISMYTFSRMKYN;
EISMYTFSRMKYNI; ISMYTFSRMKYNIC; SMYTFSRMKYNICM;
MYTFSRMKYNICMG; YTFSRMKYNICMGK; TFSRMKYNICMGKC;
FSRMKYNICMGKCI; SRMKYNICMGKCIL; RMKYNICMGKCILD;
MKYNICMGKCILDI; KYNICMGKCILDIT; YNICMGKCILDITR;
NICMGKCILDITRE; ICMGKCILDITREE; CMGKCILDITREED;
MGKCILDITREEDS; GKCILDITREEDSE; KCILDITREEDSET;
CILDITREEDSETE; ILDITREEDSETED; LDITREEDSETEDS;
DITREEDSETEDSG; ITREEDSETEDSGH; TREEDSETEDSGHG;
REEDSETEDSGHGS; EEDSETEDSGHGSS; EDSETEDSGHGSST;
DSETEDSGHGSSTE; SETEDSGHGSSTES; ETEDSGHGSSTESQ;
TEDSGHGSSTESQS; EDSGHGSSTESQSQ; DSGHGSSTESQSQC;
SGHGSSTESQSQCS; GHGSSTESQSQCSS; HGSSTESQSQCSSQ;
GSSTESQSQCSSQV; SSTESQSQCSSQVS; STESQSQCSSQVSD;
TESQSQCSSQVSDT; ESQSQCSSQVSDTS; SQSQCSSQVSDTSA;
QSQCSSQVSDTSAP; SQCSSQVSDTSAPA; QCSSQVSDTSAPAE;
CSSQVSDTSAPAED; SSQVSDTSAPAEDS; SQVSDTSAPAEDSQ;
QVSDTSAPAEDSQR; VSDTSAPAEDSQRS; SDTSAPAEDSQRSD;
DTSAPAEDSQRSDP; TSAPAEDSQRSDPH; SAPAEDSQRSDPHS;
APAEDSQRSDPHSQ; PAEDSQRSDPHSQE; AEDSQRSDPHSQEL;
EDSQRSDPHSQELH; DSQRSDPHSQELHL; SQRSDPHSQELHLC;
QRSDPHSQELHLCK; RSDPHSQELHLCKG; SDPHSQELHLCKGF;
DPHSQELHLCKGFQ; PHSQELHLCKGFQC; HSQELHLCKGFQCF;
SQELHLCKGFQCFK; QELHLCKGFQCFKR; ELHLCKGFQCFKRP;
LHLCKGFQCFKRPK; HLCKGFQCFKRPKT; LCKGFQCFKRPKTP;
CKGFQCFKRPKTPP; KGFQCFKRPKTPPP; GFQCFKRPKTPPPK;
MYMYNKSTCLKHFG; YMYNKSTCLKHFGL; MYNKSTCLKHFGLQ;
YNKSTCLKHFGLQL; NKSTCLKHFGLQLS; KSTCLKHFGLQLSL;
STCLKHFGLQLSLF; TCLKHFGLQLSLFV; CLKHFGLQLSLFVN;
LKHFGLQLSLFVNI; KHFGLQLSLFVNIS; HFGLQLSLFVNISY;
FGLQLSLFVNISYH; GLQLSLFVNISYHI; LQLSLFVNISYHIW;
QLSLFVNISYHIWV; LSLFVNISYHIWVP; SLFVNISYHIWVPW;
LFVNISYHIWVPWK; FVNISYHIWVPWKS; VNISYHIWVPWKSF;
NISYHIWVPWKSFC; ISYHIWVPWKSFCA; SYHIWVPWKSFCAI;
YHIWVPWKSFCAIK; HIWVPWKSFCAIKH; IWVPWKSFCAIKHP;
WVPWKSFCAIKHPN; VPWKSFCAIKHPNL; PWKSFCAIKHPNLF;
WKSFCAIKHPNLFY; KSFCAIKHPNLFYL; SFCAIKHPNLFYLG;
FCAIKHPNLFYLGF; CAIKHPNLFYLGFH; AIKHPNLFYLGFHT;
IKHPNLFYLGFHTI; KHPNLFYLGFHTIH; HPNLFYLGFHTIHR;
PNLFYLGFHTIHRL; NLFYLGFHTIHRLP; LFYLGFHTIHRLPI;
FYLGFHTIHRLPIH; YLGFHTIHRLPIHS; LGFHTIHRLPIHSL;
GFHTIHRLPIHSLG; FHTIHRLPIHSLGS; HTIHRLPIHSLGSP;
TIHRLPIHSLGSPV; IHRLPIHSLGSPVY; HRLPIHSLGSPVYK;
RLPIHSLGSPVYKV; LPIHSLGSPVYKVT; QKGNWVRILYRSFS;
KGNWVRILYRSFSQ; GNWVRILYRSFSQA; NWVRILYRSFSQAD;
WVRILYRSFSQADL; VRILYRSFSQADLK; RILYRSFSQADLKI;
ILYRSFSQADLKIS; LYRSFSQADLKISC; YRSFSQADLKISCK;
RSFSQADLKISCKA; SFSQADLKISCKAS; FSQADLKISCKASP;
SQADLKISCKASPL; QADLKISCKASPLL; ADLKISCKASPLLC;
DLKISCKASPLLCS; LKISCKASPLLCSR; KISCKASPLLCSRA;
ISCKASPLLCSRAV; SCKASPLLCSRAVS; CKASPLLCSRAVSK;
KASPLLCSRAVSKQ; ASPLLCSRAVSKQA; SPLLCSRAVSKQAT;
PLLCSRAVSKQATN; LLCSRAVSKQATNI; LCSRAVSKQATNIS;
CSRAVSKQATNISS; NIQAISFTKRPHTL; IQAISFTKRPHTLF;
QAISFTKRPHTLFI; QHCGSCVGHMKYWG; HCGSCVGHMKYWGN;
CGSCVGHMKYWGNI; GSCVGHMKYWGNIF; SCVGHMKYWGNIFP;
CVGHMKYWGNIFPS; VGHMKYWGNIFPSC; GHMKYWGNIFPSCE;
HMKYWGNIFPSCES; MKYWGNIFPSCESP; KYWGNIFPSCESPK;
YWGNIFPSCESPKI; WGNIFPSCESPKIP; GNIFPSCESPKIPS;
NIFPSCESPKIPSI; IFPSCESPKIPSIF; FPSCESPKIPSIFI;
PSCESPKIPSIFIS; SCESPKIPSIFIST; CESPKIPSIFISTG;
ESPKIPSIFISTGI; SPKIPSIFISTGIR; PKIPSIFISTGIRY;
KIPSIFISTGIRYP; IPSIFISTGIRYPA; PSIFISTGIRYPAL;
SIFISTGIRYPALN; IFISTGIRYPALNW; FISTGIRYPALNWI;
ISTGIRYPALNWIS; STGIRYPALNWISI; TGIRYPALNWISIV;
GIRYPALNWISIVF; IRYPALNWISIVFV; RYPALNWISIVFVQ;
YPALNWISIVFVQI; PALNWISIVFVQIG; ALNWISIVFVQIGL;
LNWISIVFVQIGLM; NWISIVFVQIGLMV; WISIVFVQIGLMVS;
ISIVFVQIGLMVSI; SIVFVQIGLMVSIH; IVFVQIGLMVSIHY;
VFVQIGLMVSIHYL; FVQIGLMVSIHYLG; VQIGLMVSIHYLGL;
QIGLMVSIHYLGLG; IGLMVSIHYLGLGC; GLMVSIHYLGLGCW;
LMVSIHYLGLGCWV; MVSIHYLGLGCWVF; VSIHYLGLGCWVFR;
SIHYLGLGCWVFRG; IHYLGLGCWVFRGY; HYLGLGCWVFRGYS;
YLGLGCWVFRGYST; LGLGCWVFRGYSTI; GLGCWVFRGYSTIR;
LGCWVFRGYSTIRV; GCWVFRGYSTIRVL; HSLHFQGFSTYSKE;
SLHFQGFSTYSKEV; LHFQGFSTYSKEVE; HFQGFSTYSKEVEI;
FQGFSTYSKEVEIT; QGFSTYSKEVEITA; GFSTYSKEVEITAL;
FSTYSKEVEITALN; STYSKEVEITALNR; TYSKEVEITALNRF;
YSKEVEITALNRFS; SKEVEITALNRFSS; KEVEITALNRFSST;
EVEITALNRFSSTM; VEITALNRFSSTML; EITALNRFSSTMLM;
ITALNRFSSTMLMH; TALNRFSSTMLMHF; ALNRFSSTMLMHFL;
PCMKVKHASYSNNL; CMKVKHASYSNNLC; MKVKHASYSNNLCL;
KVKHASYSNNLCLY; VKHASYSNNLCLYS; KHASYSNNLCLYSY;
HASYSNNLCLYSYS; ASYSNNLCLYSYSL; SYSNNLCLYSYSLP;
YSNNLCLYSYSLPH; SNNLCLYSYSLPHQ; NNLCLYSYSLPHQI;
IGEGNSCCAVTGKH; GEGNSCCAVTGKHF; EGNSCCAVTGKHFS; GNSCCAVTGKHFSL;
NSCCAVTGKHFSLW; SCCAVTGKHFSLWA; CCAVTGKHFSLWAI;
CAVTGKHFSLWAIT; AVTGKHFSLWAITA; VTGKHFSLWAITAK;
TGKHFSLWAITAKV; GKHFSLWAITAKVI; KHFSLWAITAKVIF;
HFSLWAITAKVIFS; FSLWAITAKVIFST; TKAPKVFIWIPHFW;
KAPKVFIWIPHFWV; EAFYLCNSIYPSFN; AFYLCNSIYPSFNF;
FWHLHGFLWLFGSC; WHLHGFLWLFGSCP; HLHGFLWLFGSCPW;
LHGFLWLFGSCPWT; HGFLWLFGSCPWTL; GFLWLFGSCPWTLS;
FLWLFGSCPWTLSF; LWLFGSCPWTLSFS; WLFGSCPWTLSFSF;
LFGSCPWTLSFSFG; FGSCPWTLSFSFGW; GSCPWTLSFSFGWG;
SCPWTLSFSFGWGH; CPWTLSFSFGWGHL; PWTLSFSFGWGHLH;
WTLSFSFGWGHLHM; TLSFSFGWGHLHML; LSFSFGWGHLHMLQ;
SFSFGWGHLHMLQE; FSFGWGHLHMLQEQ; SFGWGHLHMLQEQV;
FGWGHLHMLQEQVL; GWGHLHMLQEQVLQ; WGHLHMLQEQVLQS;
GHLHMLQEQVLQSR; HLHMLQEQVLQSRT; LHMLQEQVLQSRTG;
HMLQEQVLQSRTGL; MLQEQVLQSRTGLE; LQEQVLQSRTGLEV;
QEQVLQSRTGLEVK; EQVLQSRTGLEVKA; QVLQSRTGLEVKAT;
VLQSRTGLEVKATS; LQSRTGLEVKATSI; QSRTGLEVKATSIE;
SRTGLEVKATSIEE; RTGLEVKATSIEEQ; TGLEVKATSIEEQF;
GLEVKATSIEEQFF; LEVKATSIEEQFFD; TLLNVHFVDFLSPF;
LLNVHFVDFLSPFV; LNVHFVDFLSPFFV; LLLYCQHHLYYKYG;
LLYCQHHLYYKYGQ; LYCQHHLYYKYGQN; YCQHHLYYKYGQNV;
CQHHLYYKYGQNVH; QHHLYYKYGQNVHG; HHLYYKYGQNVHGY;
HLYYKYGQNVHGYL; LYYKYGQNVHGYLP; YYKYGQNVHGYLPF;
YKYGQNVHGYLPFQ; KYGQNVHGYLPFQL; YGQNVHGYLPFQLL;
GQNVHGYLPFQLLV; GKDQNNIVEYNYKS; KDQNNIVEYNYKSL;
QKYLHQETEYHSTH; KYLHQETEYHSTHL; YLHQETEYHSTHLG;
TIPKPCLIADRGLQ; IPKPCLIADRGLQW; PKPCLIADRGLQWK;
KPCLIADRGLQWKL; PCLIADRGLQWKLC; CLIADRGLQWKLCD;
LIADRGLQWKLCDP; IADRGLQWKLCDPN; ADRGLQWKLCDPNH;
DRGLQWKLCDPNHQ; RGLQWKLCDPNHQR; GLQWKLCDPNHQRT;
LQWKLCDPNHQRTY; QWKLCDPNHQRTYT; WKLCDPNHQRTYTL;
KLCDPNHQRTYTLL; LCDPNHQRTYTLLE; CDPNHQRTYTLLEL;
DPNHQRTYTLLELR; PNHQRTYTLLELRN; PQEHQQLQHMFEEL;
QEHQQLQHMFEELG; EHQQLQHMFEELGL; QQQPPQQQFQPLKI;
QQPPQQQFQPLKIL; QPPQQQFQPLKILW; PPQQQFQPLKILWQ;
PQQQFQPLKILWQQ; QQQFQPLKILWQQQ; QQFQPLKILWQQQP;
QFQPLKILWQQQPQ; FQPLKILWQQQPQI; QPLKILWQQQPQIH;
PLKILWQQQPQIHW; LKILWQQQPQIHWQ; KILWQQQPQIHWQL;
ILWQQQPQIHWQLG; LWQQQPQIHWQLGP; WQQQPQIHWQLGPP;
QQQPQIHWQLGPPK; QQPQIHWQLGPPKV; QPQIHWQLGPPKVL;
PQIHWQLGPPKVLE; QIHWQLGPPKVLEQ; IHWQLGPPKVLEQH;
HWQLGPPKVLEQHP; TWKYKKKGITYLGV; WKYKKKGITYLGVF;
KYKKKGITYLGVFY; YKKKGITYLGVFYR; KKKGITYLGVFYRV;
KKGITYLGVFYRVF; KGITYLGVFYRVFY; GITYLGVFYRVFYS;
ITYLGVFYRVFYST; YLGVFYRVFYSTFV; SSGTFVFPVYTVFT; SGTFVFPVYTVFTS;
GTFVFPVYTVFTST; TFVFPVYTVFTSTK; FVFPVYTVFTSTKF;
VFPVYTVFTSTKFQ; FPVYTVFTSTKFQQ; PVYTVFTSTKFQQK;
VYTVFTSTKFQQKL; NKNKNPLSSFFCSS; KNKNPLSSFFCSSP;
NKNPLSSFFCSSPG; KNPLSSFFCSSPGF; NPLSSFFCSSPGFT;
PLSSFFCSSPGFTN; LSSFFCSSPGFTNF; SSFFCSSPGFTNFH;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

LGTRPRFLGSQNMS; GTRPRFLGSQNMSV; TRPRFLGSQNMSVM;
RPRFLGSQNMSVMH; PRFLGSQNMSVMHF; RFLGSQNMSVMHFP;
FLGSQNMSVMHFPS; AAPPCESCTFLPEV; APPCESCTFLPEVM;
PPCESCTFLPEVMV; PCESCTFLPEVMVW; CESCTFLPEVMVWL;
ESCTFLPEVMVWLH; SCTFLPEVMVWLHS; CTFLPEVMVWLHSP;
TFLPEVMVWLHSPV; FLPEVMVWLHSPVS; LPEVMVWLHSPVSH;
PEVMVWLHSPVSHA; EVMVWLHSPVSHAL; VMVWLHSPVSHALS;
MVWLHSPVSHALSF; VWLHSPVSHALSFL; WLHSPVSHALSFLR;
LHSPVSHALSFLRS; HSPVSHALSFLRSW; SPVSHALSFLRSWF;
PVSHALSFLRSWFG; VSHALSFLRSWFGC; SHALSFLRSWFGCI;
HALSFLRSWFGCIP; ALSFLRSWFGCIPW; LSFLRSWFGCIPWV;
SFLRSWFGCIPWVS; FLRSWFGCIPWVSS; LRSWFGCIPWVSSS;
RSWFGCIPWVSSSS; SWFGCIPWVSSSSL; WFGCIPWVSSSSLW;
FGCIPWVSSSSLWP; GCIPWVSSSSLWPF; CIPWVSSSSLWPFF;
IPWVSSSSLWPFFL; YIRGRGRLCLHPFS; IRGRGRLCLHPFSQ;
RGRGRLCLHPFSQV; GRGRLCLHPFSQVV; RGRLCLHPFSQVVR;
GRLCLHPFSQVVRV; RLCLHPFSQVVRVW; LCLHPFSQVVRVWR;
CLHPFSQVVRVWRL; LHPFSQVVRVWRLF; HPFSQVVRVWRLFL;
PFSQVVRVWRLFLR; FSQVVRVWRLFLRP; SQVVRVWRLFLRPS;
QVVRVWRLFLRPSK; VVRVWRLFLRPSKT; VRVWRLFLRPSKTI;
RVWRLFLRPSKTIW; VWRLFLRPSKTIWG; WRLFLRPSKTIWGN;
RLFLRPSKTIWGNP; LFLRPSKTIWGNPY; FLRPSKTIWGNPYS;
LRPSKTIWGNPYSF; RPSKTIWGNPYSFA; PSKTIWGNPYSFAI;
SKTIWGNPYSFAIF; KTIWGNPYSFAIFA; TIWGNPYSFAIFAK 15 mers:

KSCLGKSSLNEKSLF; SCLGKSSLNEKSLFK; CLGKSSLNEKSLFKE;
LGKSSLNEKSLFKEV; FSSLPRYPVLQGMAY; SSLPRYPVLQGMAYL;
SLPRYPVLQGMAYLF; LPRYPVLQGMAYLFQ; PRYPVLQGMAYLFQK;
RYPVLQGMAYLFQKA; YPVLQGMAYLFQKAF; PVLQGMAYLFQKAFC;
VLQGMAYLFQKAFCA; LQGMAYLFQKAFCAL; QGMAYLFQKAFCALP;
GMAYLFQKAFCALPL; MAYLFQKAFCALPLH; AYLFQKAFCALPLHA;
YLFQKAFCALPLHAM; LFQKAFCALPLHAMS; FQKAFCALPLHAMSA;
KIFKKRALGLDRLLL; IFKKRALGLDRLLLH; RNSAMVGPNNWRNSL;
NSAMVGPNNWRNSLQ; SAMVGPNNWRNSLQR; AMVGPNNWRNSLQRS;
MVGPNNWRNSLQRSK; VGPNNWRNSLQRSKA; GPNNWRNSLQRSKAL;
PNNWRNSLQRSKALR; VPTYGTEEWESWWSS; PTYGTEEWESWWSSF;
TYGTEEWESWWSSFN; YGTEEWESWWSSFNE; GTEEWESWWSSFNEK;
TEEWESWWSSFNEKW; EEWESWWSSFNEKWD; EWESWWSSFNEKWDE;
WESWWSSFNEKWDED; ESWWSSFNEKWDEDL; SWWSSFNEKWDEDLF;
WWSSFNEKWDEDLFC; WSSFNEKWDEDLFCH; SSFNEKWDEDLFCHE;
SFNEKWDEDLFCHED; FNEKWDEDLFCHEDM; NEKWDEDLFCHEDMF;
EKWDEDLFCHEDMFA; KWDEDLFCHEDMFAS; WDEDLFCHEDMFASD;
DEDLFCHEDMFASDE; EDLFCHEDMFASDEE; DLFCHEDMFASDEEA;
LFCHEDMFASDEEAT; FCHEDMFASDEEATA; CHEDMFASDEEATAD;
HEDMFASDEEATADS; EDMFASDEEATADSQ; DMFASDEEATADSQH;
MFASDEEATADSQHS; FASDEEATADSQHST; ASDEEATADSQHSTP;
SDEEATADSQHSTPP; DEEATADSQHSTPPK; EEATADSQHSTPPKK;
EATADSQHSTPPKKK; ATADSQHSTPPKKKR; TADSQHSTPPKKKRK;
ADSQHSTPPKKKRKV; DSQHSTPPKKKRKVE; SQHSTPPKKKRKVED;
QHSTPPKKKRKVEDP; HSTPPKKKRKVEDPK; STPPKKKRKVEDPKD;
TPPKKKRKVEDPKDF; PPKKKRKVEDPKDFP; PKKKRKVEDPKDFPS;
KKKRKVEDPKDFPSD; KKRKVEDPKDFPSDL; KRKVEDPKDFPSDLH;
RKVEDPKDFPSDLHQ; KVEDPKDFPSDLHQF; VEDPKDFPSDLHQFL;
EDPKDFPSDLHQFLS; DPKDFPSDLHQFLSQ; PKDFPSDLHQFLSQA;
KDFPSDLHQFLSQAV; DFPSDLHQFLSQAVF; FPSDLHQFLSQAVFS;
PSDLHQFLSQAVFSN; SDLHQFLSQAVFSNR; DLHQFLSQAVFSNRT;
LHQFLSQAVFSNRTL; HQFLSQAVFSNRTLA; QFLSQAVFSNRTLAC;
FLSQAVFSNRTLACF; LSQAVFSNRTLACFA; SQAVFSNRTLACFAV;
QAVFSNRTLACFAVY; AVFSNRTLACFAVYT; VFSNRTLACFAVYTT;
FSNRTLACFAVYTTK; SNRTLACFAVYTTKE; NRTLACFAVYTTKEK;
RTLACFAVYTTKEKA; TLACFAVYTTKEKAQ; LACFAVYTTKEKAQI;
ACFAVYTTKEKAQIL; CFAVYTTKEKAQILY; FAVYTTKEKAQILYK;
AVYTTKEKAQILYKK; VYTTKEKAQILYKKL; YTTKEKAQILYKKLM;
TTKEKAQILYKKLME; TKEKAQILYKKLMEK; KEKAQILYKKLMEKY;
EKAQILYKKLMEKYS; KAQILYKKLMEKYSV; AQILYKKLMEKYSVT;
QILYKKLMEKYSVTF; ILYKKLMEKYSVTFI; LYKKLMEKYSVTFIS;
YKKLMEKYSVTFISR; KKLMEKYSVTFISRH; KLMEKYSVTFISRHM;
LMEKYSVTFISRHMC; MEKYSVTFISRHMCA; EKYSVTFISRHMCAG;
KYSVTFISRHMCAGH; YSVTFISRHMCAGHN; SVTFISRHMCAGHNI;
VTFISRHMCAGHNII; TFISRHMCAGHNIIF; FISRHMCAGHNIIFF;
ISRHMCAGHNIIFFL; SRHMCAGHNIIFFLT; RHMCAGHNIIFFLTP;
HMCAGHNIIFFLTPH; MCAGHNIIFFLTPHR; CAGHNIIFFLTPHRH;

AGHNIIFFLTPHRHR; GHNIIFFLTPHRHRV; HNIIFFLTPHRHRVS;
NIIFFLTPHRHRVSA; IIFFLTPHRHRVSAI; IFFLTPHRHRVSAIN;
FFLTPHRHRVSAINN; FLTPHRHRVSAINNF; LTPHRHRVSAINNFC;
TPHRHRVSAINNFCQ; PHRHRVSAINNFCQK; HRHRVSAINNFCQKL;
RHRVSAINNFCQKLC; HRVSAINNFCQKLCT; RVSAINNFCQKLCTF;
VSAINNFCQKLCTFS; SAINNFCQKLCTFSF; AINNFCQKLCTFSFL;
INNFCQKLCTFSFLI; NNFCQKLCTFSFLIC; NFCQKLCTFSFLICK;
FCQKLCTFSFLICKG; CQKLCTFSFLICKGV; QKLCTFSFLICKGVN;
KLCTFSFLICKGVNK; LCTFSFLICKGVNKE; CTFSFLICKGVNKEY;
TFSFLICKGVNKEYL; FSFLICKGVNKEYLL; SFLICKGVNKEYLLY;
FLICKGVNKEYLLYS; LICKGVNKEYLLYSA; ICKGVNKEYLLYSAL;
CKGVNKEYLLYSALT; KGVNKEYLLYSALTR; GVNKEYLLYSALTRD;
VNKEYLLYSALTRDP; NKEYLLYSALTRDPY; KEYLLYSALTRDPYH;
EYLLYSALTRDPYHT; YLLYSALTRDPYHTI; LLYSALTRDPYHTIE;
LYSALTRDPYHTIEE; YSALTRDPYHTIEES; SALTRDPYHTIEESI;
ALTRDPYHTIEESIQ; LTRDPYHTIEESIQG; TRDPYHTIEESIQGG;
RDPYHTIEESIQGGL; DPYHTIEESIQGGLK; PYHTIEESIQGGLKE;
YHTIEESIQGGLKEH; HTIEESIQGGLKEHD; TIEESIQGGLKEHDF;
IEESIQGGLKEHDFS; EESIQGGLKEHDFSP; ESIQGGLKEHDFSPE;
SIQGGLKEHDFSPEE; IQGGLKEHDFSPEEP; QGGLKEHDFSPEEPE;
GGLKEHDFSPEEPEE; GLKEHDFSPEEPEET; LKEHDFSPEEPEETK;
KEHDFSPEEPEETKQ; EHDFSPEEPEETKQV; HDFSPEEPEETKQVS;
DFSPEEPEETKQVSW; FSPEEPEETKQVSWK; SPEEPEETKQVSWKL;
PEEPEETKQVSWKLI; EEPEETKQVSWKLIT; EPEETKQVSWKLITE;
PEETKQVSWKLITEY; EETKQVSWKLITEYA; ETKQVSWKLITEYAV;
TKQVSWKLITEYAVE; KQVSWKLITEYAVET; QVSWKLITEYAVETK;
VSWKLITEYAVETKC; SWKLITEYAVETKCE; WKLITEYAVETKCED;
KLITEYAVETKCEDV; LITEYAVETKCEDVF; ITEYAVETKCEDVFL;
TEYAVETKCEDVFLL; EYAVETKCEDVFLLL; YAVETKCEDVFLLLG;
AVETKCEDVFLLLGM; VETKCEDVFLLLGMY; ETKCEDVFLLLGMYL;
TKCEDVFLLLGMYLE; KCEDVFLLLGMYLEF; CEDVFLLLGMYLEFQ;
EDVFLLLGMYLEFQY; DVFLLLGMYLEFQYN; VFLLLGMYLEFQYNV;
FLLLGMYLEFQYNVE; LLLGMYLEFQYNVEE; LLGMYLEFQYNVEEC;
LGMYLEFQYNVEECK; GMYLEFQYNVEECKK; MYLEFQYNVEECKKC;
YLEFQYNVEECKKCQ; LEFQYNVEECKKCQK; EFQYNVEECKKCQKK;
FQYNVEECKKCQKKD; QYNVEECKKCQKKDQ; YNVEECKKCQKKDQP;
NVEECKKCQKKDQPY; VEECKKCQKKDQPYH; EECKKCQKKDQPYHF;
ECKKCQKKDQPYHFK; CKKCQKKDQPYHFKY; KKCQKKDQPYHFKYH;
KCQKKDQPYHFKYHE; CQKKDQPYHFKYHEK; QKKDQPYHFKYHEKH;
KKDQPYHFKYHEKHF; KDQPYHFKYHEKHFA; DQPYHFKYHEKHFAN;
QPYHFKYHEKHFANA; PYHFKYHEKHFANAI; YHFKYHEKHFANAII;
HFKYHEKHFANAIIF; FKYHEKHFANAIIFA; KYHEKHFANAIIFAE;
YHEKHFANAIIFAES; HEKHFANAIIFAESK; EKHFANAIIFAESKN;
KHFANAIIFAESKNQ; HFANAIIFAESKNQS; FANAIIFAESKNQSI;
ANAIIFAESKNQSIC; NAIIFAESKNQSICQ; AIIFAESKNQSICQQ;
IIFAESKNQSICQQQ; IFAESKNQSICQQA; FAESKNQSICQQAV;
AESKNQSICQQAVD; ESKNQSICQQAVDT; SKNQSICQQAVDTV;
KNQSICQQAVDTVL; NQSICQQAVDTVLA; QSICQQAVDTVLAK;
KSICQQAVDTVLAKK; SICQQAVDTVLAKKR; ICQQAVDTVLAKKRV;
CQQAVDTVLAKKRVD; QQAVDTVLAKKRVDT; QAVDTVLAKKRVDTL;
AVDTVLAKKRVDTLH; VDTVLAKKRVDTLHM; DTVLAKKRVDTLHMT;
TVLAKKRVDTLHMTR; VLAKKRVDTLHMTRE; LAKKRVDTLHMTREE;
AKKRVDTLHMTREEM; KKRVDTLHMTREEML; KRVDTLHMTREEMLT;
RVDTLHMTREEMLTE; VDTLHMTREEMLTER; DTLHMTREEMLTERF;
TLHMTREEMLTERFN; LHMTREEMLTERFNH; HMTREEMLTERFNHI;
MTREEMLTERFNHIL; TREEMLTERFNHILD; REEMLTERFNHILDK;
EEMLTERFNHILDKM; EMLTERFNHILDKMD; MLTERFNHILDKMDL;
LTERFNHILDKMDLI; TERFNHILDKMDLIF; ERFNHILDKMDLIFG;
RFNHILDKMDLIFGA; FNHILDKMDLIFGAH; NHILDKMDLIFGAHG;
HILDKMDLIFGAHGN; ILDKMDLIFGAHGNA; LDKMDLIFGAHGNAV;
DKMDLIFGAHGNAVL; KMDLIFGAHGNAVLE; MDLIFGAHGNAVLEQ;
DLIFGAHGNAVLEQY; LIFGAHGNAVLEQYM; IFGAHGNAVLEQYMA;
FGAHGNAVLEQYMAG; GAHGNAVLEQYMAGV; AHGNAVLEQYMAGVA;
HGNAVLEQYMAGVAW; GNAVLEQYMAGVAWL; NAVLEQYMAGVAWLH;
AVLEQYMAGVAWLHC; VLEQYMAGVAWLHCL; LEQYMAGVAWLHCLL;
EQYMAGVAWLHCLLP; QYMAGVAWLHCLLPK; YMAGVAWLHCLLPKM;
MAGVAWLHCLLPKMD; AGVAWLHCLLPKMDS; GVAWLHCLLPKMDSV;
VAWLHCLLPKMDSVI; AWLHCLLPKMDSVIF; WLHCLLPKMDSVIFD;
LHCLLPKMDSVIFDF; HCLLPKMDSVIFDFL; CLLPKMDSVIFDFLH;
LLPKMDSVIFDFLHC; LPKMDSVIFDFLHCI; PKMDSVIFDFLHCIV;
KMDSVIFDFLHCIVF; MDSVIFDFLHCIVFN; DSVIFDFLHCIVFNV;
SVIFDFLHCIVFNVP; VIFDFLHCIVFNVPK; IFDFLHCIVFNVPKR;
FDFLHCIVFNVPKRR; DFLHCIVFNVPKRRY; FLHCIVFNVPKRRYW;
LHCIVFNVPKRRYWL; HCIVFNVPKRRYWLF; CIVFNVPKRRYWLFK;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

IVFNVPKRRYWLFKG; VFNVPKRRYWLFKGP; FNVPKRRYWLFKGPI;
NVPKRRYWLFKGPID; VPKRRYWLFKGPIDS; PKRRYWLFKGPIDSG;
KRRYWLFKGPIDSGK; RRYWLFKGPIDSGKT; RYWLFKGPIDSGKTT;
YWLFKGPIDSGKTTL; WLFKGPIDSGKTTLA; LFKGPIDSGKTTLAA;
FKGPIDSGKTTLAAG; KGPIDSGKTTLAAGL; GPIDSGKTTLAAGLL;
PIDSGKTTLAAGLLD; IDSGKTTLAAGLLDL; DSGKTTLAAGLLDLC;
SGKTTLAAGLLDLCG; GKTTLAAGLLDLCGG; KTTLAAGLLDLCGGK;
TTLAAGLLDLCGGKA; TLAAGLLDLCGGKAL; LAAGLLDLCGGKALN;
AAGLLDLCGGKALNV; AGLLDLCGGKALNVN; GLLDLCGGKALNVNL;
LLDLCGGKALNVNLP; LDLCGGKALNVNLPM; DLCGGKALNVNLPME;
LCGGKALNVNLPMER; CGGKALNVNLPMERL; GGKALNVNLPMERLT;
GKALNVNLPMERLTF; KALNVNLPMERLTFE; ALNVNLPMERLTFEL;
LNVNLPMERLTFELG; NVNLPMERLTFELGV; VNLPMERLTFELGVA;
NLPMERLTFELGVAI; LPMERLTFELGVAID; PMERLTFELGVAIDQ;
MERLTFELGVAIDQY; ERLTFELGVAIDQYM; RLTFELGVAIDQYMV;
LTFELGVAIDQYMVV; TFELGVAIDQYMVVF; FELGVAIDQYMVVFE;
ELGVAIDQYMVVFED; LGVAIDQYMVVFEDV; GVAIDQYMVVFEDVK;
VAIDQYMVVFEDVKG; AIDQYMVVFEDVKGT; IDQYMVVFEDVKGTG;
DQYMVVFEDVKGTGA; QYMVVFEDVKGTGAE; YMVVFEDVKGTGAES;
MVVFEDVKGTGAESK; VVFEDVKGTGAESKD; VFEDVKGTGAESKDL;
FEDVKGTGAESKDLP; EDVKGTGAESKDLPS; DVKGTGAESKDLPSG;
VKGTGAESKDLPSGH; KGTGAESKDLPSGHG; GTGAESKDLPSGHGI;
TGAESKDLPSGHGIN; GAESKDLPSGHGINN; AESKDLPSGHGINNL;
ESKDLPSGHGINNLD; SKDLPSGHGINNLDS; KDLPSGHGINNLDSL;
DLPSGHGINNLDSLR; LPSGHGINNLDSLRD; PSGHGINNLDSLRDY;
SGHGINNLDSLRDYL; GHGINNLDSLRDYLD; HGINNLDSLRDYLDG;
GINNLDSLRDYLDGS; INNLDSLRDYLDGSV; NNLDSLRDYLDGSVK;
NLDSLRDYLDGSVKV; LDSLRDYLDGSVKVN; DSLRDYLDGSVKVNL;
SLRDYLDGSVKVNLE; LRDYLDGSVKVNLEK; RDYLDGSVKVNLEKK;
DYLDGSVKVNLEKKH; YLDGSVKVNLEKKHL; LDGSVKVNLEKKHLN;
DGSVKVNLEKKHLNK; GSVKVNLEKKHLNKR; SVKVNLEKKHLNKRT;
VKVNLEKKHLNKRTQ; KVNLEKKHLNKRTQI; VNLEKKHLNKRTQIF;
NLEKKHLNKRTQIFP; LEKKHLNKRTQIFPP; EKKHLNKRTQIFPPG;
KKHLNKRTQIFPPGL; KHLNKRTQIFPPGLV; HLNKRTQIFPPGLVT;
LNKRTQIFPPGLVTM; NKRTQIFPPGLVTMN; KRTQIFPPGLVTMNE;
RTQIFPPGLVTMNEY; TQIFPPGLVTMNEYP; QIFPPGLVTMNEYPV;
IFPPGLVTMNEYPVP; FPPGLVTMNEYPVPK; PPGLVTMNEYPVPKT;
PGLVTMNEYPVPKTL; GLVTMNEYPVPKTLQ; LVTMNEYPVPKTLQA;
VTMNEYPVPKTLQAR; TMNEYPVPKTLQARF; MNEYPVPKTLQARFV;
NEYPVPKTLQARFVR; EYPVPKTLQARFVRQ; YPVPKTLQARFVRQI;
PVPKTLQARFVRQID; VPKTLQARFVRQIDF; PKTLQARFVRQIDFR;
KTLQARFVRQIDFRP; TLQARFVRQIDFRPK; LQARFVRQIDFRPKI;
QARFVRQIDFRPKIY; ARFVRQIDFRPKIYL; RFVRQIDFRPKIYLR;
FVRQIDFRPKIYLRK; VRQIDFRPKIYLRKS; RQIDFRPKIYLRKSL;
QIDFRPKIYLRKSLQ; IDFRPKIYLRKSLQN; DFRPKIYLRKSLQNS;
FRPKIYLRKSLQNSE; RPKIYLRKSLQNSEF; PKIYLRKSLQNSEFL;
KIYLRKSLQNSEFLL; IYLRKSLQNSEFLLE; YLRKSLQNSEFLLEK;
LRKSLQNSEFLLEKR; RKSLQNSEFLLEKRI; KSLQNSEFLLEKRIL;
SLQNSEFLLEKRILQ; LQNSEFLLEKRILQS; QNSEFLLEKRILQSG;
NSEFLLEKRILQSGM; SEFLLEKRILQSGMT; EFLLEKRILQSGMTL;
FLLEKRILQSGMTLL; LLEKRILQSGMTLLL; LEKRILQSGMTLLLL;
EKRILQSGMTLLLLL; KRILQSGMTLLLLLI; RILQSGMTLLLLLIW;
ILQSGMTLLLLLIWF; LQSGMTLLLLLIWFR; QSGMTLLLLLIWFRP;
SGMTLLLLLIWFRPV; GMTLLLLLIWFRPVA; MTLLLLLIWFRPVAD;
TLLLLLIWFRPVADF; LLLLLIWFRPVADFA; LLLLIWFRPVADFAT;
LLLIWFRPVADFATD; LLIWFRPVADFATDI; LIWFRPVADFATDIQ;
IWFRPVADFATDIQS; WFRPVADFATDIQSR; FRPVADFATDIQSRI;
RPVADFATDIQSRIV; PVADFATDIQSRIVE; VADFATDIQSRIVEW;
ADFATDIQSRIVEWK; DFATDIQSRIVEWKE; FATDIQSRIVEWKER;
ATDIQSRIVEWKERL; TDIQSRIVEWKERLD; DIQSRIVEWKERLDS;
IQSRIVEWKERLDSE; QSRIVEWKERLDSEI; SRIVEWKERLDSEIS;
RIVEWKERLDSEISM; IVEWKERLDSEISMY; VEWKERLDSEISMYT;
EWKERLDSEISMYTF; WKERLDSEISMYTFS; KERLDSEISMYTFSR;
ERLDSEISMYTFSRM; RLDSEISMYTFSRMK; LDSEISMYTFSRMKY;
DSEISMYTFSRMKYN; SEISMYTFSRMKYNI; EISMYTFSRMKYNIC;
ISMYTFSRMKYNICM; SMYTFSRMKYNICMG; MYTFSRMKYNICMGK;
YTFSRMKYNICMGKC; TFSRMKYNICMGKCI; FSRMKYNICMGKCIL;
SRMKYNICMGKCILD; RMKYNICMGKCILDI; MKYNICMGKCILDIT;
KYNICMGKCILDITR; YNICMGKCILDITRE; NICMGKCILDITREE;
ICMGKCILDITREED; CMGKCILDITREEDS; MGKCILDITREEDSE;
GKCILDITREEDSET; KCILDITREEDSETE; CILDITREEDSETED;
ILDITREEDSETEDS; LDITREEDSETEDSG; DITREEDSETEDSGH;
ITREEDSETEDSGHG; TREEDSETEDSGHGS; REEDSETEDSGHGSS;
EEDSETEDSGHGSST; EDSETEDSGHGSSTE; DSETEDSGHGSSTES;
SETEDSGHGSSTESQ; ETEDSGHGSSTESQS; TEDSGHGSSTESQSQ;
EDSGHGSSTESQSQC; DSGHGSSTESQSQCS; SGHGSSTESQSQCSS;
GHGSSTESQSQCSSQ; HGSSTESQSQCSSQV; GSSTESQSQCSSQVS;
SSTESQSQCSSQVSD; STESQSQCSSQVSDT; TESQSQCSSQVSDTS;
ESQSQCSSQVSDTSA; SQSQCSSQVSDTSAP; QSQCSSQVSDTSAPA;
SQCSSQVSDTSAPAE; QCSSQVSDTSAPAED; CSSQVSDTSAPAEDS;
SSQVSDTSAPAEDSQ; SQVSDTSAPAEDSQR; QVSDTSAPAEDSQRS;
VSDTSAPAEDSQRSD; SDTSAPAEDSQRSDP; DTSAPAEDSQRSDPH;
TSAPAEDSQRSDPHS; SAPAEDSQRSDPHSQ; APAEDSQRSDPHSQE;
PAEDSQRSDPHSQEL; AEDSQRSDPHSQELH; EDSQRSDPHSQELHL;
DSQRSDPHSQELHLC; SQRSDPHSQELHLCK; QRSDPHSQELHLCKG;
RSDPHSQELHLCKGF; SDPHSQELHLCKGFQ; DPHSQELHLCKGFQC;
PHSQELHLCKGFQCF; HSQELHLCKGFQCFK; SQELHLCKGFQCFKR;
QELHLCKGFQCFKRP; ELHLCKGFQCFKRPK; LHLCKGFQCFKRPKT;
HLCKGFQCFKRPKTP; LCKGFQCFKRPKTPP; CKGFQCFKRPKTPPP;
KGFQCFKRPKTPPPK; MYMYNKSTCLKHFGL; YMYNKSTCLKHFGLQ;
MYNKSTCLKHFGLQL; YNKSTCLKHFGLQLS; NKSTCLKHFGLQLSL;
KSTCLKHFGLQLSLF; STCLKHFGLQLSLFV; TCLKHFGLQLSLFVN;
CLKHFGLQLSLFVNI; LKHFGLQLSLFVNIS; KHFGLQLSLFVNISY;
HFGLQLSLFVNISYH; FGLQLSLFVNISYHI; GLQLSLFVNISYHIW;
LQLSLFVNISYHIWV; QLSLFVNISYHIWVP; LSLFVNISYHIWVPW;
SLFVNISYHIWVPWK; LFVNISYHIWVPWKS; FVNISYHIWVPWKSF;
VNISYHIWVPWKSFC; NISYHIWVPWKSFCA; ISYHIWVPWKSFCAI;
SYHIWVPWKSFCAIK; YHIWVPWKSFCAIKH; HIWVPWKSFCAIKHP;
IWVPWKSFCAIKHPN; WVPWKSFCAIKHPNL; VPWKSFCAIKHPNLF;
PWKSFCAIKHPNLFY; WKSFCAIKHPNLFYL; KSFCAIKHPNLFYLG;
SFCAIKHPNLFYLGF; FCAIKHPNLFYLGFH; CAIKHPNLFYLGFHT;
AIKHPNLFYLGFHTI; IKHPNLFYLGFHTIH; KHPNLFYLGFHTIHR;
HPNLFYLGFHTIHRL; PNLFYLGFHTIHRLP; NLFYLGFHTIHRLPI;
LFYLGFHTIHRLPIH; FYLGFHTIHRLPIHS; YLGFHTIHRLPIHSL;
LGFHTIHRLPIHSLG; GFHTIHRLPIHSLGS; FHTIHRLPIHSLGSP;
HTIHRLPIHSLGSPV; TIHRLPIHSLGSPVY; IHRLPIHSLGSPVYK;
HRLPIHSLGSPVYKV; RLPIHSLGSPVYKVT; QKGNWVRILYRSFSQ;
KGNWVRILYRSFSQA; GNWVRILYRSFSQAD; NWVRILYRSFSQADL;
WVRILYRSFSQADLK; VRILYRSFSQADLKI; RILYRSFSQADLKIS;
ILYRSFSQADLKISC; LYRSFSQADLKISCK; YRSFSQADLKISCKA;
RSFSQADLKISCKAS; SFSQADLKISCKASP; FSQADLKISCKASPL;
SQADLKISCKASPLL; QADLKISCKASPLLC; ADLKISCKASPLLCS;
DLKISCKASPLLCSR; LKISCKASPLLCSRA; KISCKASPLLCSRAV;
ISCKASPLLCSRAVS; SCKASPLLCSRAVSK; CKASPLLCSRAVSKQ;
KASPLLCSRAVSKQA; ASPLLCSRAVSKQAT; SPLLCSRAVSKQATN;
PLLCSRAVSKQATNI; LLCSRAVSKQATNIS; LCSRAVSKQATNISS;
NIQAISFTKRPHTLF; IQAISFTKRPHTLFI; QHCGSCVGHMKYWGN;
HCGSCVGHMKYWGNI; CGSCVGHMKYWGNIF; GSCVGHMKYWGNIFP;
SCVGHMKYWGNIFPS; CVGHMKYWGNIFPSC; VGHMKYWGNIFPSCE;
GHMKYWGNIFPSCES; HMKYWGNIFPSCESP; MKYWGNIFPSCESPK;
KYWGNIFPSCESPKI; YWGNIFPSCESPKIP; WGNIFPSCESPKIPS;
GNIFPSCESPKIPSI; NIFPSCESPKIPSIF; IFPSCESPKIPSIFI;
FPSCESPKIPSIFIS; PSCESPKIPSIFIST; SCESPKIPSIFISTG;
CESPKIPSIFISTGI; ESPKIPSIFISTGIR; SPKIPSIFISTGIRY;
PKIPSIFISTGIRYP; KIPSIFISTGIRYPA; IPSIFISTGIRYPAL;
PSIFISTGIRYPALN; SIFISTGIRYPALNW; IFISTGIRYPALNWI;
FISTGIRYPALNWIS; ISTGIRYPALNWISI; STGIRYPALNWISIV;
TGIRYPALNWISIVF; GIRYPALNWISIVFV; IRYPALNWISIVFVQ;
RYPALNWISIVFVQI; YPALNWISIVFVQIG; PALNWISIVFVQIGL;
ALNWISIVFVQIGLM; LNWISIVFVQIGLMV; NWISIVFVQIGLMVS;
WISIVFVQIGLMVSI; ISIVFVQIGLMVSIH; SIVFVQIGLMVSIHY;
IVFVQIGLMVSIHYL; VFVQIGLMVSIHYLG; FVQIGLMVSIHYLGL;
VQIGLMVSIHYLGLG; QIGLMVSIHYLGLGC; IGLMVSIHYLGLGCW;
GLMVSIHYLGLGCWV; LMVSIHYLGLGCWVF; MVSIHYLGLGCWVFR;
VSIHYLGLGCWVFRG; SIHYLGLGCWVFRGY; IHYLGLGCWVFRGYS;
HYLGLGCWVFRGYST; YLGLGCWVFRGYSTI; LGLGCWVFRGYSTIR;
GLGCWVFRGYSTIRV; LGCWVFRGYSTIRVL; HSLHFQGFSTYSKEV;
SLHFQGFSTYSKEVE; LHFQGFSTYSKEVEI; HFQGFSTYSKEVEIT;
FQGFSTYSKEVEITA; QGFSTYSKEVEITAL; GFSTYSKEVEITALN;
FSTYSKEVEITALNR; STYSKEVEITALNRF; TYSKEVEITALNRFS;
YSKEVEITALNRFSS; SKEVEITALNRFSST; KEVEITALNRFSSTM;
EVEITALNRFSSTML; VEITALNRFSSTMLM; EITALNRFSSTMLMH;
ITALNRFSSTMLMHF; TALNRFSSTMLMHFL; PCMKVKHASYSNNLC;
CMKVKHASYSNNLCL; MKVKHASYSNNLCLY; KVKHASYSNNLCLYS;
VKHASYSNNLCLYSY; KHASYSNNLCLYSYS; HASYSNNLCLYSYSL;
ASYSNNLCLYSYSLP; SYSNNLCLYSYSLPH; YSNNLCLYSYSLPHQ;
IGEGNSCCAVTGKHF; GEGNSCCAVTGKHFS; EGNSCCAVTGKHFSL;
GNSCCAVTGKHFSLW; NSCCAVTGKHFSLWA; SCCAVTGKHFSLWAI;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

CCAVTGKHFSLWAIT; CAVTGKHFSLWAITA; AVTGKHFSLWAITAK;
VTGKHFSLWAITAKV; TGKHFSLWAITAKVI; GKHFSLWAITAKVIF;
KHFSLWAITAKVIFS; HFSLWAITAKVIFST; TKAPKVFIWIPHFWV;
EAFYLCNSIYPSFNF; FWHLHGFLWLFGSCP; WHLHGFLWLFGSCPW;
HLHGFLWLFGSCPWT; LHGFLWLFGSCPWTL; HGFLWLFGSCPWTLS;
GFLWLFGSCPWTLSF; FLWLFGSCPWTLSFS; LWLFGSCPWTLSFSF;
WLFGSCPWTLSFSFG; LFGSCPWTLSFSFGW; FGSCPWTLSFSFGWG;
GSCPWTLSFSFGWGH; SCPWTLSFSFGWGHL; CPWTLSFSFGWGHLH;
PWTLSFSFGWGHLHM; WTLSFSFGWGHLHML; TLSFSFGWGHLHMLQ;
LSFSFGWGHLHMLQE; SFSFGWGHLHMLQEQ; FSFGWGHLHMLQEQV;
SFGWGHLHMLQEQVL; FGWGHLHMLQEQVLQ; GWGHLHMLQEQVLQS;
WGHLHMLQEQVLQSR; GHLHMLQEQVLQSRT; HLHMLQEQVLQSRTG;
LHMLQEQVLQSRTGL; HMLQEQVLQSRTGLE; MLQEQVLQSRTGLEV;
LQEQVLQSRTGLEVK; QEQVLQSRTGLEVKA; EQVLQSRTGLEVKAT;
QVLQSRTGLEVKATS; VLQSRTGLEVKATSI; LQSRTGLEVKATSIE;
QSRTGLEVKATSIEE; SRTGLEVKATSIEEQ; RTGLEVKATSIEEQF;
TGLEVKATSIEEQFF; GLEVKATSIEEQFFD; TLLNVHFVDFLSPFF;
LLNVHFVDFLSPFFV; LLLYCQHHLYYKYGQ; LLYCQHHLYYKYGQN;
LYCQHHLYYKYGQNV; YCQHHLYYKYGQNVH; CQHHLYYKYGQNVHG;
QHHLYYKYGQNVHGY; HHLYYKYGQNVHGYL; HLYYKYGQNVHGYLP;
LYYKYGQNVHGYLPF; YYKYGQNVHGYLPFQ; YKYGQNVHGYLPFQL;
KYGQNVHGYLPFQLL; YGQNVHGYLPFQLLV; GKDQNNIVEYNYKSL;
QKYLHQETEYHSTHL; KYLHQETEYHSTHLG; TIPKPCLIADRGLQW;
IPKPCLIADRGLQWK; PKPCLIADRGLQWKL; KPCLIADRGLQWKLC;
PCLIADRGLQWKLCD; CLIADRGLQWKLCDP; LIADRGLQWKLCDPN;
IADRGLQWKLCDPNH; ADRGLQWKLCDPNHQ; DRGLQWKLCDPNHQR;
RGLQWKLCDPNHQRT; GLQWKLCDPNHQRTY; LQWKLCDPNHQRTYT;
QWKLCDPNHQRTYTL; WKLCDPNHQRTYTLL; KLCDPNHQRTYTLLE;
LCDPNHQRTYTLLEL; CDPNHQRTYTLLELR; DPNHQRTYTLLELRN;
PQEHQQLQHMFEELG; QEHQQLQHMFEELGL; QQQPPQQQFQPLKIL;
QQPPQQQFQPLKILW; QPPQQQFQPLKILWQ; PPQQQFQPLKILWQQ;
PQQQFQPLKILWQQQ; QQQFQPLKILWQQQP; QQFQPLKILWQQQPQ;
QFQPLKILWQQQPQI; FQPLKILWQQQPQIH; QPLKILWQQQPQIHW;
PLKILWQQQPQIHWQ; LKILWQQQPQIHWQL; KILWQQQPQIHWQLG;
ILWQQQPQIHWQLGP; LWQQQPQIHWQLGPP; WQQQPQIHWQLGPPK;
QQQPQIHWQLGPPKV; QQPQIHWQLGPPKVL; QPQIHWQLGPPKVLE;
PQIHWQLGPPKVLEQ; QIHWQLGPPKVLEQH; IHWQLGPPKVLEQHP;
TWKYKKKGITYLGVF; WKYKKKGITYLGVFY; KYKKKGITYLGVFYR;
YKKKGITYLGVFYRV; KKKGITYLGVFYRVF; KKGITYLGVFYRVFY;
KGITYLGVFYRVFYS; GITYLGVFYRVFYSR; SSGTFVFPVYTVFTS;
SGTFVFPVYTVFTST; GTFVFPVYTVFTSTK; TFVFPVYTVFTSTKF;
FVFPVYTVFTSTKFQ; VFPVYTVFTSTKFQQ; FPVYTVFTSTKFQQK;
PVYTVFTSTKFQQKL; NKNKNPLSSFFCSSP; KNKNPLSSFFCSSPG;
NKNPLSSFFCSSPGF; KNPLSSFFCSSPGFT; NPLSSFFCSSPGFTN;
PLSSFFCSSPGFTNF; LSSFFCSSPGFTNFH; LGTRPRFLGSQNMSV;
GTRPRFLGSQNMSVM; TRPRFLGSQNMSVMH; RPRFLGSQNMSVMHF;
PRFLGSQNMSVMHFP; RFLGSQNMSVMHFPS; AAPPCESCTFLPEVM;
APPCESCTFLPEVMV; PPCESCTFLPEVMVW; PCESCTFLPEVMVWL;
CESCTFLPEVMVWLH; ESCTFLPEVMVWLHS; SCTFLPEVMVWLHSP;
CTFLPEVMVWLHSPV; TFLPEVMVWLHSPVS; FLPEVMVWLHSPVSH;
LPEVMVWLHSPVSHA; PEVMVWLHSPVSHAL; EVMVWLHSPVSHALS;
VMVWLHSPVSHALSF; MVWLHSPVSHALSFL; VWLHSPVSHALSFLR;
WLHSPVSHALSFLRS; LHSPVSHALSFLRSW; HSPVSHALSFLRSWF;
SPVSHALSFLRSWFG; PVSHALSFLRSWFGC; VSHALSFLRSWFGCI;
SHALSFLRSWFGCIP; HALSFLRSWFGCIPW; ALSFLRSWFGCIPWV;
LSFLRSWFGCIPWVS; SFLRSWFGCIPWVSS; FLRSWFGCIPWVSSS;
LRSWFGCIPWVSSSS; RSWFGCIPWVSSSSL; SWFGCIPWVSSSSLW;
WFGCIPWVSSSSLWP; FGCIPWVSSSSLWPF; GCIPWVSSSSLWPFF;
CIPWVSSSSLWPFFL; YIRGRGRLCLHPFSQ; IRGRGRLCLHPFSQV;
RGRGRLCLHPFSQVV; GRGRLCLHPFSQVVR; RGRLCLHPFSQVVRV;
GRLCLHPFSQVVRVW; RLCLHPFSQVVRVWR; LCLHPFSQVVRVWRL;
CLHPFSQVVRVWRLF; LHPFSQVVRVWRLFL; HPFSQVVRVWRLFLR;
PFSQVVRVWRLFLRP; FSQVVRVWRLFLRPS; SQVVRVWRLFLRPSK;
QVVRVWRLFLRPSKT; VVRVWRLFLRPSKTI; VRVWRLFLRPSKTIW;
RVWRLFLRPSKTIWG; VWRLFLRPSKTIWGN; WRLFLRPSKTIWGNP;
RLFLRPSKTIWGNPY; LFLRPSKTIWGNPYS; FLRPSKTIWGNPYSF;
LRPSKTIWGNPYSFA; RPSKTIWGNPYSFAI; PSKTIWGNPYSFAIF;
SKTIWGNPYSFAIFA; KTIWGNPYSFAIFAK

16 mers:

KSCLGKSSLNEKSLFK; SCLGKSSLNEKSLFKE;
CLGKSSLNEKSLFKEV; FSSLPRYPVLQGMAYL;
SSLPRYPVLQGMAYLF; SLPRYPVLQGMAYLFQ;
LPRYPVLQGMAYLFQK; PRYPVLQGMAYLFQKA;
RYPVLQGMAYLFQKAF; YPVLQGMAYLFQKAFC;
PVLQGMAYLFQKAFCA; VLQGMAYLFQKAFCAL;
LQGMAYLFQKAFCALP; QGMAYLFQKAFCALPL;
GMAYLFQKAFCALPLH; MAYLFQKAFCALPLHA;
AYLFQKAFCALPLHAM; YLFQKAFCALPLHAMS;
LFQKAFCALPLHAMSA; KIFKKRALGLDRLLLH;
RNSAMVGPNNWRNSLQ; NSAMVGPNNWRNSLQR;
SAMVGPNNWRNSLQRS; AMVGPNNWRNSLQRSK;
MVGPNNWRNSLQRSKA; VGPNNWRNSLQRSKAL;
GPNNWRNSLQRSKALR; VPTYGTEEWESWWSSF;
PTYGTEEWESWWSSFN; TYGTEEWESWWSSFNE;
YGTEEWESWWSSFNEK; GTEEWESWWSSFNEKW;
TEEWESWWSSFNEKWD; EEWESWWSSFNEKWDE;
EWESWWSSFNEKWDED; WESWWSSFNEKWDEDL;
ESWWSSFNEKWDEDLF; SWWSSFNEKWDEDLFC;
WWSSFNEKWDEDLFCH; WSSFNEKWDEDLFCHE;
SSFNEKWDEDLFCHED; SFNEKWDEDLFCHEDM;
FNEKWDEDLFCHEDMF; NEKWDEDLFCHEDMFA;
EKWDEDLFCHEDMFAS; KWDEDLFCHEDMFASD;
WDEDLFCHEDMFASDE; DEDLFCHEDMFASDEE;
EDLFCHEDMFASDEEA; DLFCHEDMFASDEEAT;
LFCHEDMFASDEEATA; FCHEDMFASDEEATAD;
CHEDMFASDEEATADS; HEDMFASDEEATADSQ;
EDMFASDEEATADSQH; DMFASDEEATADSQHS;
MFASDEEATADSQHST; FASDEEATADSQHSTP;
ASDEEATADSQHSTPP; SDEEATADSQHSTPPK;
DEEATADSQHSTPPKK; EEATADSQHSTPPKKK;
EATADSQHSTPPKKKR; ATADSQHSTPPKKKRK;
TADSQHSTPPKKKRKV; ADSQHSTPPKKKRKVE;
DSQHSTPPKKKRKVED; SQHSTPPKKKRKVEDP;
QHSTPPKKKRKVEDPK; HSTPPKKKRKVEDPKD;
STPPKKKRKVEDPKDF; TPPKKKRKVEDPKDFP;
PPKKKRKVEDPKDFPS; PKKKRKVEDPKDFPSD;
KKKRKVEDPKDFPSDL; KKRKVEDPKDFPSDLH;
KRKVEDPKDFPSDLHQ; RKVEDPKDFPSDLHQF;
KVEDPKDFPSDLHQFL; VEDPKDFPSDLHQFLS;
EDPKDFPSDLHQFLSQ; DPKDFPSDLHQFLSQA;
PKDFPSDLHQFLSQAV; KDFPSDLHQFLSQAVF;
DFPSDLHQFLSQAVFS; FPSDLHQFLSQAVFSN;
PSDLHQFLSQAVFSNR; SDLHQFLSQAVFSNRT;
DLHQFLSQAVFSNRTL; LHQFLSQAVFSNRTLA;
HQFLSQAVFSNRTLAC; QFLSQAVFSNRTLACF;
FLSQAVFSNRTLACFA; LSQAVFSNRTLACFAV;
SQAVFSNRTLACFAVY; QAVFSNRTLACFAVYT;
AVFSNRTLACFAVYTT; VFSNRTLACFAVYTTK;
FSNRTLACFAVYTTKE; SNRTLACFAVYTTKEK;
NRTLACFAVYTTKEKA; RTLACFAVYTTKEKAQ;
TLACFAVYTTKEKAQI; LACFAVYTTKEKAQIL;
ACFAVYTTKEKAQILY; CFAVYTTKEKAQILYK;
FAVYTTKEKAQILYKK; AVYTTKEKAQILYKKL;
VYTTKEKAQILYKKLM; YTTKEKAQILYKKLME;
TTKEKAQILYKKLMEK; TKEKAQILYKKLMEKY;
KEKAQILYKKLMEKYS; EKAQILYKKLMEKYSV;
KAQILYKKLMEKYSVT; AQILYKKLMEKYSVTF;
QILYKKLMEKYSVTFI; ILYKKLMEKYSVTFIS;
LYKKLMEKYSVTFISR; YKKLMEKYSVTFISRH;
KKLMEKYSVTFISRHM; KLMEKYSVTFISRHMC;
LMEKYSVTFISRHMCA; MEKYSVTFISRHMCAG;
EKYSVTFISRHMCAGH; KYSVTFISRHMCAGHN;
YSVTFISRHMCAGHNI; SVTFISRHMCAGHNII;
VTFISRHMCAGHNIIF; TFISRHMCAGHNIIFF;
FISRHMCAGHNIIFFL; ISRHMCAGHNIIFFLT;
SRHMCAGHNIIFFLTP; RHMCAGHNIIFFLTPH;
HMCAGHNIIFFLTPHR; MCAGHNIIFFLTPHRH;
CAGHNIIFFLTPHRHR; AGHNIIFFLTPHRHRV;
GHNIIFFLTPHRHRVS; HNIIFFLTPHRHRVSA;
NIIFFLTPHRHRVSAI; IIFFLTPHRHRVSAIN;
IFFLTPHRHRVSAINN; FFLTPHRHRVSAINNF;
FLTPHRHRVSAINNFC; LTPHRHRVSAINNFCQ;
TPHRHRVSAINNFCQK; PHRHRVSAINNFCQKL;
HRHRVSAINNFCQKLC; RHRVSAINNFCQKLCT;
HRVSAINNFCQKLCTF; RVSAINNFCQKLCTFS;
VSAINNFCQKLCTFSF; SAINNFCQKLCTFSFL;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

AINNFCQKLCTFSFLI; INNFCQKLCTFSFLIC;
NNFCQKLCTFSFLICK; NFCQKLCTFSFLICKG;
FCQKLCTFSFLICKGV; CQKLCTFSFLICKGVN;
QKLCTFSFLICKGVNK; KLCTFSFLICKGVNKE;
LCTFSFLICKGVNKEY; CTFSFLICKGVNKEYL;
TFSFLICKGVNKEYLL; FSFLICKGVNKEYLLY;
SFLICKGVNKEYLLYS; FLICKGVNKEYLLYSA;
LICKGVNKEYLLYSAL; ICKGVNKEYLLYSALT;
CKGVNKEYLLYSALTR; KGVNKEYLLYSALTRD;
GVNKEYLLYSALTRDP; VNKEYLLYSALTRDPY;
NKEYLLYSALTRDPYH; KEYLLYSALTRDPYHT;
EYLLYSALTRDPYHTI; YLLYSALTRDPYHTIE;
LLYSALTRDPYHTIEE; LYSALTRDPYHTIEES;
YSALTRDPYHTIEESI; SALTRDPYHTIEESIQ;
ALTRDPYHTIEESIQG; LTRDPYHTIEESIQGG;
TRDPYHTIEESIQGGL; RDPYHTIEESIQGGLK;
DPYHTIEESIQGGLKE; PYHTIEESIQGGLKEH;
YHTIEESIQGGLKEHD; HTIEESIQGGLKEHDF;
TIEESIQGGLKEHDFS; IEESIQGGLKEHDFSP;
EESIQGGLKEHDFSPE; ESIQGGLKEHDFSPEE;
SIQGGLKEHDFSPEEP; IQGGLKEHDFSPEEPE;
QGGLKEHDFSPEEPEE; GGLKEHDFSPEEPEET;
GLKEHDFSPEEPEETK; LKEHDFSPEEPEETKQ;
KEHDFSPEEPEETKQV; EHDFSPEEPEETKQVS;
HDFSPEEPEETKQVSW; DFSPEEPEETKQVSWK;
FSPEEPEETKQVSWKL; SPEEPEETKQVSWKLI;
PEEPEETKQVSWKLIT; EEPEETKQVSWKLITE;
EPEETKQVSWKLITEY; PEETKQVSWKLITEYA;
EETKQVSWKLITEYAV; ETKQVSWKLITEYAVE;
TKQVSWKLITEYAVET; KQVSWKLITEYAVETK;
QVSWKLITEYAVETKC; VSWKLITEYAVETKCE;
SWKLITEYAVETKCED; WKLITEYAVETKCEDV;
KLITEYAVETKCEDVF; LITEYAVETKCEDVFL;
ITEYAVETKCEDVFLL; TEYAVETKCEDVFLLL;
EYAVETKCEDVFLLLG; YAVETKCEDVFLLLGM;
AVETKCEDVFLLLGMY; VETKCEDVFLLLGMYL;
ETKCEDVFLLLGMYLE; TKCEDVFLLLGMYLEF;
KCEDVFLLLGMYLEFQ; CEDVFLLLGMYLEFQY;
EDVFLLLGMYLEFQYN; DVFLLLGMYLEFQYNV;
VFLLLGMYLEFQYNVE; FLLLGMYLEFQYNVEE;
LLLGMYLEFQYNVEEC; LLGMYLEFQYNVEECK;
LGMYLEFQYNVEECKK; GMYLEFQYNVEECKKC;
MYLEFQYNVEECKKCQ; YLEFQYNVEECKKCQK;
LEFQYNVEECKKCQKK; EFQYNVEECKKCQKKD;
FQYNVEECKKCQKKDQ; QYNVEECKKCQKKDQP;
YNVEECKKCQKKDQPY; NVEECKKCQKKDQPYH;
VEECKKCQKKDQPYHF; EECKKCQKKDQPYHFK;
ECKKCQKKDQPYHFKY; CKKCQKKDQPYHFKYH;
KKCQKKDQPYHFKYHE; KCQKKDQPYHFKYHEK;
CQKKDQPYHFKYHEKH; QKKDQPYHFKYHEKHF;
KKDQPYHFKYHEKHFA; KDQPYHFKYHEKHFAN;
DQPYHFKYHEKHFANA; QPYHFKYHEKHFANAI;
PYHFKYHEKHFANAII; YHFKYHEKHFANAIIF;
HFKYHEKHFANAIIFA; FKYHEKHFANAIIFAE;
KYHEKHFANAIIFAES; YHEKHFANAIIFAESK;
HEKHFANAIIFAESKN; EKHFANAIIFAESKNQ;
KHFANAIIFAESKNQK; HFANAIIFAESKNQKS;
FANAIIFAESKNQKSI; ANAIIFAESKNQKSIC;
NAIIFAESKNQKSICQ; AIIFAESKNQKSICQQ;
IIFAESKNQKSICQQA; IFAESKNQKSICQQAV;
FAESKNQKSICQQAVD; AESKNQKSICQQAVDT;
ESKNQKSICQQAVDTV; SKNQKSICQQAVDTVL;
KNQKSICQQAVDTVLA; NQKSICQQAVDTVLAK;
QKSICQQAVDTVLAKK; KSICQQAVDTVLAKKR;
SICQQAVDTVLAKKRV; ICQQAVDTVLAKKRVD;
CQQAVDTVLAKKRVDT; QQAVDTVLAKKRVDTL;
QAVDTVLAKKRVDTLH; AVDTVLAKKRVDTLHM;
VDTVLAKKRVDTLHMT; DTVLAKKRVDTLHMTR;
TVLAKKRVDTLHMTRE; VLAKKRVDTLHMTREE;
LAKKRVDTLHMTREEM; AKKRVDTLHMTREEML;
KKRVDTLHMTREEMLT; KRVDTLHMTREEMLTE;
RVDTLHMTREEMLTER; VDTLHMTREEMLTERF;
DTLHMTREEMLTERFN; TLHMTREEMLTERFNH;
LHMTREEMLTERFNHI; HMTREEMLTERFNHIL;
MTREEMLTERFNHILD; TREEMLTERFNHILDK;
REEMLTERFNHILDKM; EEMLTERFNHILDKMD;
EMLTERFNHILDKMDL; MLTERFNHILDKMDLI;
LTERFNHILDKMDLIF; TERFNHILDKMDLIFG;
ERFNHILDKMDLIFGA; RFNHILDKMDLIFGAH;
FNHILDKMDLIFGAHG; NHILDKMDLIFGAHGN;
HILDKMDLIFGAHGNA; ILDKMDLIFGAHGNAV;
LDKMDLIFGAHGNAVL; DKMDLIFGAHGNAVLE;
KMDLIFGAHGNAVLEQ; MDLIFGAHGNAVLEQY;
DLIFGAHGNAVLEQYM; LIFGAHGNAVLEQYMA;
IFGAHGNAVLEQYMAG; FGAHGNAVLEQYMAGV;
GAHGNAVLEQYMAGVA; AHGNAVLEQYMAGVAW;
HGNAVLEQYMAGVAWL; GNAVLEQYMAGVAWLH;
NAVLEQYMAGVAWLHC; AVLEQYMAGVAWLHCL;
VLEQYMAGVAWLHCLL; LEQYMAGVAWLHCLLP;
EQYMAGVAWLHCLLPK; QYMAGVAWLHCLLPKM;
YMAGVAWLHCLLPKMD; MAGVAWLHCLLPKMDS;
AGVAWLHCLLPKMDSV; GVAWLHCLLPKMDSVI;
VAWLHCLLPKMDSVIF; AWLHCLLPKMDSVIFD;
WLHCLLPKMDSVIFDF; LHCLLPKMDSVIFDFL;
HCLLPKMDSVIFDFLH; CLLPKMDSVIFDFLHC;
LLPKMDSVIFDFLHCI; LPKMDSVIFDFLHCIV;
PKMDSVIFDFLHCIVF; KMDSVIFDFLHCIVFN;
MDSVIFDFLHCIVFNV; DSVIFDFLHCIVFNVP;
SVIFDFLHCIVFNVPK; VIFDFLHCIVFNVPKR;
IFDFLHCIVFNVPKRR; FDFLHCIVFNVPKRRY;
DFLHCIVFNVPKRRYW; FLHCIVFNVPKRRYWL;
LHCIVFNVPKRRYWLF; HCIVFNVPKRRYWLFK;
CIVFNVPKRRYWLFKG; IVFNVPKRRYWLFKGP;
VFNVPKRRYWLFKGPI; FNVPKRRYWLFKGPID;
NVPKRRYWLFKGPIDS; VPKRRYWLFKGPIDSG;
PKRRYWLFKGPIDSGK; KRRYWLFKGPIDSGKT;
RRYWLFKGPIDSGKTT; RYWLFKGPIDSGKTTL;
YWLFKGPIDSGKTTLA; WLFKGPIDSGKTTLAA;
LFKGPIDSGKTTLAAG; FKGPIDSGKTTLAAGL;
KGPIDSGKTTLAAGLL; GPIDSGKTTLAAGLLD;
PIDSGKTTLAAGLLDL; IDSGKTTLAAGLLDLC;
DSGKTTLAAGLLDLCG; SGKTTLAAGLLDLCGG;
GKTTLAAGLLDLCGGK; KTTLAAGLLDLCGGKA;
TTLAAGLLDLCGGKAL; TLAAGLLDLCGGKALN;
LAAGLLDLCGGKALNV; AAGLLDLCGGKALNVN;
AGLLDLCGGKALNVNL; GLLDLCGGKALNVNLP;
LLDLCGGKALNVNLPM; LDLCGGKALNVNLPME;
DLCGGKALNVNLPMER; LCGGKALNVNLPMERL;
CGGKALNVNLPMERLT; GGKALNVNLPMERLTF;
GKALNVNLPMERLTFE; KALNVNLPMERLTFEL;
ALNVNLPMERLTFELG; LNVNLPMERLTFELGV;
NVNLPMERLTFELGVA; VNLPMERLTFELGVAI;
NLPMERLTFELGVAID; LPMERLTFELGVAIDQ;
PMERLTFELGVAIDQY; MERLTFELGVAIDQYM;
ERLTFELGVAIDQYMV; RLTFELGVAIDQYMVV;
LTFELGVAIDQYMVVF; TFELGVAIDQYMVVFE;
FELGVAIDQYMVVFED; ELGVAIDQYMVVFEDV;
LGVAIDQYMVVFEDVK; GVAIDQYMVVFEDVKG;
VAIDQYMVVFEDVKGT; AIDQYMVVFEDVKGTG;
IDQYMVVFEDVKGTGA; DQYMVVFEDVKGTGAE;
QYMVVFEDVKGTGAES; YMVVFEDVKGTGAESK;
MVVFEDVKGTGAESKD; VVFEDVKGTGAESKDL;
VFEDVKGTGAESKDLP; FEDVKGTGAESKDLPS;
EDVKGTGAESKDLPSG; DVKGTGAESKDLPSGH;
VKGTGAESKDLPSGHG; KGTGAESKDLPSGHGI;
GTGAESKDLPSGHGIN; TGAESKDLPSGHGINN;
GAESKDLPSGHGINNL; AESKDLPSGHGINNLD;
ESKDLPSGHGINNLDS; SKDLPSGHGINNLDSL;
KDLPSGHGINNLDSLR; DLPSGHGINNLDSLRD;
LPSGHGINNLDSLRDY; PSGHGINNLDSLRDYL;
SGHGINNLDSLRDYLD; GHGINNLDSLRDYLDG;
HGINNLDSLRDYLDGS; GINNLDSLRDYLDGSV;
INNLDSLRDYLDGSVK; NNLDSLRDYLDGSVKV;
NLDSLRDYLDGSVKVN; LDSLRDYLDGSVKVNL;
DSLRDYLDGSVKVNLE; SLRDYLDGSVKVNLEK;
LRDYLDGSVKVNLEKK; RDYLDGSVKVNLEKKH;
DYLDGSVKVNLEKKHL; YLDGSVKVNLEKKHLN;
LDGSVKVNLEKKHLNK; DGSVKVNLEKKHLNKR;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

GSVKVNLEKKHLNKRT; SVKVNLEKKHLNKRTQ;
VKVNLEKKHLNKRTQI; KVNLEKKHLNKRTQIF;
VNLEKKHLNKRTQIFP; NLEKKHLNKRTQIFPP;
LEKKHLNKRTQIFPPG; EKKHLNKRTQIFPPGL;
KKHLNKRTQIFPPGLV; KHLNKRTQIFPPGLVT;
HLNKRTQIFPPGLVTM; LNKRTQIFPPGLVTMN;
NKRTQIFPPGLVTMNE; KRTQIFPPGLVTMNEY;
RTQIFPPGLVTMNEYP; TQIFPPGLVTMNEYPV;
QIFPPGLVTMNEYPVP; IFPPGLVTMNEYPVPK;
FPPGLVTMNEYPVPKT; PPGLVTMNEYPVPKTL;
PGLVTMNEYPVPKTLQ; GLVTMNEYPVPKTLQA;
LVTMNEYPVPKTLQAR; VTMNEYPVPKTLQARF;
TMNEYPVPKTLQARFV; MNEYPVPKTLQARFVR;
NEYPVPKTLQARFVRQ; EYPVPKTLQARFVRQI;
YPVPKTLQARFVRQID; PVPKTLQARFVRQIDF;
VPKTLQARFVRQIDFR; PKTLQARFVRQIDFRP;
KTLQARFVRQIDFRPK; TLQARFVRQIDFRPKI;
LQARFVRQIDFRPKIY; QARFVRQIDFRPKIYL;
ARFVRQIDFRPKIYLR; RFVRQIDFRPKIYLRK;
FVRQIDFRPKIYLRKS; VRQIDFRPKIYLRKSL;
RQIDFRPKIYLRKSLQ; QIDFRPKIYLRKSLQN;
IDFRPKIYLRKSLQNS; DFRPKIYLRKSLQNSE;
FRPKIYLRKSLQNSEF; RPKIYLRKSLQNSEFL;
PKIYLRKSLQNSEFLL; KIYLRKSLQNSEFLLE;
IYLRKSLQNSEFLLEK; YLRKSLQNSEFLLEKR;
LRKSLQNSEFLLEKRI; RKSLQNSEFLLEKRIL;
KSLQNSEFLLEKRILQ; SLQNSEFLLEKRILQS;
LQNSEFLLEKRILQSG; QNSEFLLEKRILQSGM;
NSEFLLEKRILQSGMT; SEFLLEKRILQSGMTL;
EFLLEKRILQSGMTLL; FLLEKRILQSGMTLLL;
LLEKRILQSGMTLLLL; LEKRILQSGMTLLLLL;
EKRILQSGMTLLLLLI; KRILQSGMTLLLLLIW;
RILQSGMTLLLLLIWF; ILQSGMTLLLLLIWFR;
LQSGMTLLLLLIWFRP; QSGMTLLLLLIWFRPV;
SGMTLLLLLIWFRPVA; GMTLLLLLIWFRPVAD;
MTLLLLLIWFRPVADF; TLLLLLIWFRPVADFA;
LLLLLIWFRPVADFAT; LLLLIWFRPVADFATD;
LLLIWFRPVADFATDI; LLIWFRPVADFATDIQ;
LIWFRPVADFATDIQS; IWFRPVADFATDIQSR;
WFRPVADFATDIQSRI; FRPVADFATDIQSRIV;
RPVADFATDIQSRIVE; PVADFATDIQSRIVEW;
VADFATDIQSRIVEWK; ADFATDIQSRIVEWKE;
DFATDIQSRIVEWKER; FATDIQSRIVEWKERL;
ATDIQSRIVEWKERLD; TDIQSRIVEWKERLDS;
DIQSRIVEWKERLDSE; IQSRIVEWKERLDSEI;
QSRIVEWKERLDSEIS; SRIVEWKERLDSEISM;
RIVEWKERLDSEISMY; IVEWKERLDSEISMYT;
VEWKERLDSEISMYTF; EWKERLDSEISMYTFS;
WKERLDSEISMYTFSR; KERLDSEISMYTFSRM;
ERLDSEISMYTFSRMK; RLDSEISMYTFSRMKY;
LDSEISMYTFSRMKYN; DSEISMYTFSRMKYNI;
SEISMYTFSRMKYNIC; EISMYTFSRMKYNICM;
ISMYTFSRMKYNICMG; SMYTFSRMKYNICMGK;
MYTFSRMKYNICMGKC; YTFSRMKYNICMGKCI;
TFSRMKYNICMGKCIL; FSRMKYNICMGKCILD;
SRMKYNICMGKCILDI; RMKYNICMGKCILDIT;
MKYNICMGKCILDITR; KYNICMGKCILDITRE;
YNICMGKCILDITREE; NICMGKCILDITREED;
ICMGKCILDITREEDS; CMGKCILDITREEDSE;
MGKCILDITREEDSET; GKCILDITREEDSETE;
KCILDITREEDSETED; CILDITREEDSETEDS;
ILDITREEDSETEDSG; LDITREEDSETEDSGH;
DITREEDSETEDSGHG; ITREEDSETEDSGHGS;
TREEDSETEDSGHGSS; REEDSETEDSGHGSST;
EEDSETEDSGHGSSTE; EDSETEDSGHGSSTES;
DSETEDSGHGSSTESQ; SETEDSGHGSSTESQS;
ETEDSGHGSSTESQSQ; TEDSGHGSSTESQSQC;
EDSGHGSSTESQSQCS; DSGHGSSTESQSQCSS;
SGHGSSTESQSQCSSQ; GHGSSTESQSQCSSQV;
HGSSTESQSQCSSQVS; GSSTESQSQCSSQVSD;
SSTESQSQCSSQVSDT; STESQSQCSSQVSDTS;
TESQSQCSSQVSDTSA; ESQSQCSSQVSDTSAP;
SQSQCSSQVSDTSAPA; QSQCSSQVSDTSAPAE;
SQCSSQVSDTSAPAED; QCSSQVSDTSAPAEDS;
CSSQVSDTSAPAEDSQ; SSQVSDTSAPAEDSQR;
SQVSDTSAPAEDSQRS; QVSDTSAPAEDSQRSD;
VSDTSAPAEDSQRSDP; SDTSAPAEDSQRSDPH;
DTSAPAEDSQRSDPHS; TSAPAEDSQRSDPHSQ;
SAPAEDSQRSDPHSQE; APAEDSQRSDPHSQEL;
PAEDSQRSDPHSQELH; AEDSQRSDPHSQELHL;
EDSQRSDPHSQELHLC; DSQRSDPHSQELHLCK;
SQRSDPHSQELHLCKG; QRSDPHSQELHLCKGF;
RSDPHSQELHLCKGFQ; SDPHSQELHLCKGFQC;
DPHSQELHLCKGFQCF; PHSQELHLCKGFQCFK;
HSQELHLCKGFQCFKR; SQELHLCKGFQCFKRP;
QELHLCKGFQCFKRPK; ELHLCKGFQCFKRPKT;
LHLCKGFQCFKRPKTP; HLCKGFQCFKRPKTPP;
LCKGFQCFKRPKTPPP; CKGFQCFKRPKTPPPK;
MYMYNKSTCLKHFGLQ; YMYNKSTCLKHFGLQL;
MYNKSTCLKHFGLQLS; YNKSTCLKHFGLQLSL;
NKSTCLKHFGLQLSLF; KSTCLKHFGLQLSLFV;
STCLKHFGLQLSLFVN; TCLKHFGLQLSLFVNI;
CLKHFGLQLSLFVNIS; LKHFGLQLSLFVNISY;
KHFGLQLSLFVNISYH; HFGLQLSLFVNISYHI;
FGLQLSLFVNISYHIW; GLQLSLFVNISYHIWV;
LQLSLFVNISYHIWVP; QLSLFVNISYHIWVPW;
LSLFVNISYHIWVPWK; SLFVNISYHIWVPWKS;
LFVNISYHIWVPWKSF; FVNISYHIWVPWKSFC;
VNISYHIWVPWKSFCA; NISYHIWVPWKSFCAI;
ISYHIWVPWKSFCAIK; SYHIWVPWKSFCAIKH;
YHIWVPWKSFCAIKHP; HIWVPWKSFCAIKHPN;
IWVPWKSFCAIKHPNL; WVPWKSFCAIKHPNLF;
VPWKSFCAIKHPNLFY; PWKSFCAIKHPNLFYL;
WKSFCAIKHPNLFYLG; KSFCAIKHPNLFYLGF;
SFCAIKHPNLFYLGFH; FCAIKHPNLFYLGFHT;
CAIKHPNLFYLGFHTI; AIKHPNLFYLGFHTIH;
IKHPNLFYLGFHTIHR; KHPNLFYLGFHTIHRL;
HPNLFYLGFHTIHRLP; PNLFYLGFHTIHRLPI;
NLFYLGFHTIHRLPIH; LFYLGFHTIHRLPIHS;
FYLGFHTIHRLPIHSL; YLGFHTIHRLPIHSLG;
LGFHTIHRLPIHSLGS; GFHTIHRLPIHSLGSP;
FHTIHRLPIHSLGSPV; HTIHRLPIHSLGSPVY;
TIHRLPIHSLGSPVYK; IHRLPIHSLGSPVYKV;
HRLPIHSLGSPVYKVT; QKGNWVRILYRSFSQA;
KGNWVRILYRSFSQAD; GNWVRILYRSFSQADL;
NWVRILYRSFSQADLK; WVRILYRSFSQADLKI;
VRILYRSFSQADLKIS; RILYRSFSQADLKISC;
ILYRSFSQADLKISCK; LYRSFSQADLKISCKA;
YRSFSQADLKISCKAS; RSFSQADLKISCKASP;
SFSQADLKISCKASPL; FSQADLKISCKASPLL;
SQADLKISCKASPLLC; QADLKISCKASPLLCS;
ADLKISCKASPLLCSR; DLKISCKASPLLCSRA;
LKISCKASPLLCSRAV; KISCKASPLLCSRAVS;
ISCKASPLLCSRAVSK; SCKASPLLCSRAVSKQ;
CKASPLLCSRAVSKQA; KASPLLCSRAVSKQAT;
ASPLLCSRAVSKQATN; SPLLCSRAVSKQATNI;
PLLCSRAVSKQATNIS; LLCSRAVSKQATNISS;
NIQAISFTKRPHTLFI; QHCGSCVGHMKYWGNI;
HCGSCVGHMKYWGNIF; CGSCVGHMKYWGNIFP;
GSCVGHMKYWGNIFPS; SCVGHMKYWGNIFPSC;
CVGHMKYWGNIFPSCE; VGHMKYWGNIFPSCES;
GHMKYWGNIFPSCESP; HMKYWGNIFPSCESPK;
MKYWGNIFPSCESPKI; KYWGNIFPSCESPKIP;
YWGNIFPSCESPKIPS; WGNIFPSCESPKIPSI;
GNIFPSCESPKIPSIF; NIFPSCESPKIPSIFI;
IFPSCESPKIPSIFIS; FPSCESPKIPSIFIST;
PSCESPKIPSIFISTG; SCESPKIPSIFISTGI;
CESPKIPSIFISTGIR; ESPKIPSIFISTGIRY;
SPKIPSIFISTGIRYP; PKIPSIFISTGIRYPA;
KIPSIFISTGIRYPAL; IPSIFISTGIRYPALN;
PSIFISTGIRYPALNW; SIFISTGIRYPALNWI;
IFISTGIRYPALNWIS; FISTGIRYPALNWISI;
ISTGIRYPALNWISIV; STGIRYPALNWISIVF;
TGIRYPALNWISIVFV; GIRYPALNWISIVFVQ;
IRYPALNWISIVFVQI; RYPALNWISIVFVQIG;
YPALNWISIVFVQIGL; PALNWISIVFVQIGLM;
ALNWISIVFVQIGLMV; LNWISIVFVQIGLMVS;
NWISIVFVQIGLMVSI; WISIVFVQIGLMVSIH;

TABLE O-continued

Predicted MHC class 2 BK virus peptide sequences. Prediction of 13-, 14-, 15-,16-mers from all 6 reading frames of the genome (access no #V01108) obtained using the program displayed in FIG. 2.

ISIVFVQIGLMVSIHY; SIVFVQIGLMVSIHYL;
IVFVQIGLMVSIHYLG; VFVQIGLMVSIHYLGL;
FVQIGLMVSIHYLGLG; VQIGLMVSIHYLGLGC;
QIGLMVSIHYLGLGCW; IGLMVSIHYLGLGCWV;
GLMVSIHYLGLGCWVF; LMVSIHYLGLGCWVFR;
MVSIHYLGLGCWVFRG; VSIHYLGLGCWVFRGY;
SIHYLGLGCWVFRGYS; IHYLGLGCWVFRGYST;
HYLGLGCWVFRGYSTI; YLGLGCWVFRGYSTIR;
LGLGCWVFRGYSTIRV; GLGCWVFRGYSTIRVL;
HSLHFQGFSTYSKEVE; SLHFQGFSTYSKEVEI;
LHFQGFSTYSKEVEIT; HFQGFSTYSKEVEITA;
FQGFSTYSKEVEITAL; QGFSTYSKEVEITALN;
GFSTYSKEVEITALNR; FSTYSKEVEITALNRF;
STYSKEVEITALNRFS; TYSKEVEITALNRFSS;
YSKEVEITALNRFSST; SKEVEITALNRFSSTM;
KEVEITALNRFSSTML; EVEITALNRFSSTMLM;
VEITALNRFSSTMLMH; EITALNRFSSTMLMHF;
ITALNRFSSTMLMHFL; PCMKVKHASYSNNLCL;
CMKVKHASYSNNLCLY; MKVKHASYSNNLCLYS;
KVKHASYSNNLCLYSY; VKHASYSNNLCLYSYS;
KHASYSNNLCLYSYSL; HASYSNNLCLYSYSLP;
ASYSNNLCLYSYSLPH; SYSNNLCLYSYSLPHQ;
IGEGNSCCAVTGKHFS; GEGNSCCAVTGKHFSL;
EGNSCCAVTGKHFSLW; GNSCCAVTGKHFSLWA;
NSCCAVTGKHFSLWAI; SCCAVTGKHFSLWAIT;
CCAVTGKHFSLWAITA; CAVTGKHFSLWAITAK;
AVTGKHFSLWAITAKV; VTGKHFSLWAITAKVI;
TGKHFSLWAITAKVIF; GKHFSLWAITAKVIFS;
KHFSLWAITAKVIFST; FWHLHGFLWLFGSCPW;
WHLHGFLWLFGSCPWT; HLHGFLWLFGSCPWTL;
LHGFLWLFGSCPWTLS; HGFLWLFGSCPWTLSF;
GFLWLFGSCPWTLSFS; FLWLFGSCPWTLSFSF;
LWLFGSCPWTLSFSFG; WLFGSCPWTLSFSFGW;
LFGSCPWTLSFSFGWG; FGSCPWTLSFSFGWGH;
GSCPWTLSFSFGWGHL; SCPWTLSFSFGWGHLH;
CPWTLSFSFGWGHLHM; PWTLSFSFGWGHLHML;
WTLSFSFGWGHLHMLQ; TLSFSFGWGHLHMLQE;
LSFSFGWGHLHMLQEQ; SFSFGWGHLHMLQEQV;
FSFGWGHLHMLQEQVL; SFGWGHLHMLQEQVLQ;
FGWGHLHMLQEQVLQS; GWGHLHMLQEQVLQSR;
WGHLHMLQEQVLQSRT; GHLHMLQEQVLQSRTG;
HLHMLQEQVLQSRTGL; LHMLQEQVLQSRTGLE;
HMLQEQVLQSRTGLEV; MLQEQVLQSRTGLEVK;
LQEQVLQSRTGLEVKA; QEQVLQSRTGLEVKAT;
EQVLQSRTGLEVKATS; QVLQSRTGLEVKATSI;
VLQSRTGLEVKATSIE; LQSRTGLEVKATSIEE;
QSRTGLEVKATSIEEQ; SRTGLEVKATSIEEQF;
RTGLEVKATSIEEQFF; TGLEVKATSIEEQFFD;
TLLNVHFVDFLSPFFV; LLLYCQHHLYYKYGQN;
LLYCQHHLYYKYGQNV; LYCQHHLYYKYGQNVH;
YCQHHLYYKYGQNVHG; CQHHLYYKYGQNVHGY;
QHHLYYKYGQNVHGYL; HHLYYKYGQNVHGYLP;
HLYYKYGQNVHGYLPF; LYYKYGQNVHGYLPFQ;
YYKYGQNVHGYLPFQL; YKYGQNVHGYLPFQLL;
KYGQNVHGYLPFQLLV; QKYLHQETEYHSTHLG;
TIPKPCLIADRGLQWK; IPKPCLIADRGLQWKL;
PKPCLIADRGLQWKLC; KPCLIADRGLQWKLCD;
PCLIADRGLQWKLCDP; CLIADRGLQWKLCDPN;
LIADRGLQWKLCDPNH; IADRGLQWKLCDPNHQ;
ADRGLQWKLCDPNHQR; DRGLQWKLCDPNHQRT;
RGLQWKLCDPNHQRTY; GLQWKLCDPNHQRTYT;
LQWKLCDPNHQRTYTL; QWKLCDPNHQRTYTLL;
WKLCDPNHQRTYTLLE; KLCDPNHQRTYTLLEL;
LCDPNHQRTYTLLELR; CDPNHQRTYTLLELRN;
PQEHQQLQHMFEELGL; QQQPPQQQFQPLKILW;
QQPPQQQFQPLKILWQ; QPPQQQFQPLKILWQQ;
PPQQQFQPLKILWQQQ; PQQQFQPLKILWQQQP;
QQQFQPLKILWQQQPQ; QQFQPLKILWQQQPQI;
QFQPLKILWQQQPQIH; FQPLKILWQQQPQIHW;
QPLKILWQQQPQIHWQ; PLKILWQQQPQIHWQL;
LKILWQQQPQIHWQLG; KILWQQQPQIHWQLGP;
ILWQQQPQIHWQLGPP; LWQQQPQIHWQLGPPK;
WQQQPQIHWQLGPPKV; QQQPQIHWQLGPPKVL;
QQPQIHWQLGPPKVLE; QPQIHWQLGPPKVLEQ;
PQIHWQLGPPKVLEQH; QIHWQLGPPKVLEQHP;
TWKYKKKGITYLGVFY; WKYKKKGITYLGVFYR;
KYKKKGITYLGVFYRV; YKKKGITYLGVFYRVF;
KKKGITYLGVFYRVFY; KKGITYLGVFYRVFYS;
KGITYLGVFYRVFYSR; SSGTFVFPVYTVFTST;
SGTFVFPVYTVFTSTK; GTFVFPVYTVFTSTKF;
TFVFPVYTVFTSTKFQ; FVFPVYTVFTSTKFQQ;
VFPVYTVFTSTKFQQK; FPVYTVFTSTKFQQKL;
NKNKNPLSSFFCSSPG; KNKNPLSSFFCSSPGF;
NKNPLSSFFCSSPGFT; KNPLSSFFCSSPGFTN;
NPLSSFFCSSPGFTNF; PLSSFFCSSPGFTNFH;
LGTRPRFLGSQNMSVM; GTRPRFLGSQNMSVMH;
TRPRFLGSQNMSVMHF; RPRFLGSQNMSVMHFP;
PRFLGSQNMSVMHFPS; AAPPCESCTFLPEVMV;
APPCESCTFLPEVMVW; PPCESCTFLPEVMVWL;
PCESCTFLPEVMVWLH; CESCTFLPEVMVWLHS;
ESCTFLPEVMVWLHSP; SCTFLPEVMVWLHSPV;
CTFLPEVMVWLHSPVS; TFLPEVMVWLHSPVSH;
FLPEVMVWLHSPVSHA; LPEVMVWLHSPVSHAL;
PEVMVWLHSPVSHALS; EVMVWLHSPVSHALSF;
VMVWLHSPVSHALSFL; MVWLHSPVSHALSFLR;
VWLHSPVSHALSFLRS; WLHSPVSHALSFLRSW;
LHSPVSHALSFLRSWF; HSPVSHALSFLRSWFG;
SPVSHALSFLRSWFGC; PVSHALSFLRSWFGCI;
VSHALSFLRSWFGCIP; SHALSFLRSWFGCIPW;
HALSFLRSWFGCIPWV; ALSFLRSWFGCIPWVS;
LSFLRSWFGCIPWVSS; SFLRSWFGCIPWVSSS;
FLRSWFGCIPWVSSSS; LRSWFGCIPWVSSSSL;
RSWFGCIPWVSSSSLW; SWFGCIPWVSSSSLWP;
WFGCIPWVSSSSLWPF; FGCIPWVSSSSLWPFF;
GCIPWVSSSSLWPFFL; YIRGRGRLCLHPFSQV;
IRGRGRLCLHPFSQVV; RGRGRLCLHPFSQVVR;
GRGRLCLHPFSQVVRV; RGRLCLHPFSQVVRVW;
GRLCLHPFSQVVRVWR; RLCLHPFSQVVRVWRL;
LCLHPFSQVVRVWRLF; CLHPFSQVVRVWRLFL;
LHPFSQVVRVWRLFLR; HPFSQVVRVWRLFLRP;
PFSQVVRVWRLFLRPS; FSQVVRVWRLFLRPSK;
SQVVRVWRLFLRPSKT; QVVRVWRLFLRPSKTI;
VVRVWRLFLRPSKTIW; VRVWRLFLRPSKTIWG;
RVWRLFLRPSKTIWGN; VWRLFLRPSKTIWGNP;
WRLFLRPSKTIWGNPY; RLFLRPSKTIWGNPYS;
LFLRPSKTIWGNPYSF; FLRPSKTIWGNPYSFA;
LRPSKTIWGNPYSFAI; RPSKTIWGNPYSFAIF;
PSKTIWGNPYSFAIFA; SKTIWGNPYSFAIFAK

SEQ ID NOS.: 24957-44888

Preferred BK virus fragments of VP2-3 capable of interacting with one or more MHC class 2 molecules are listed in Table P.

TABLE P

Prediction of BK virus VP2-3 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0101 | 36 AAIEVQIASLATVEG | VQIASLATV | 0.7655 | 13 | SB | BK VP2-3 |
| DRB1_0101 | 37 AIEVQIASLATVEGI | IASLATVEG | 0.7653 | 13 | SB | BK VP2-3 |
| DRB1_0101 | 38 IEVQIASLATVEGIT | IASLATVEG | 0.7535 | 14 | SB | BK VP2-3 |
| DRB1_0101 | 39 EVQIASLATVEGITT | IASLATVEG | 0.7419 | 16 | SB | BK VP2-3 |
| DRB1_0101 | 216 QDYYSNLSPIRPSMV | YSNLSPIRP | 0.7369 | 17 | SB | BK VP2-3 |
| DRB1_0101 | 258 VTQRMDLRNKESVHS | VTQRMDLRN | 0.7362 | 17 | SB | BK VP2-3 |
| DRB1_0101 | 259 TQRMDLRNKESVHSG | LRNKESVHS | 0.7390 | 17 | SB | BK VP2-3 |
| DRB1_0101 | 260 QRMDLRNKESVHSGE | LRNKESVHS | 0.7399 | 17 | SB | BK VP2-3 |
| DRB1_0101 | 261 RMDLRNKESVHSGEF | LRNKESVHS | 0.7383 | 17 | SB | BK VP2-3 |
| DRB1_0101 | 262 MDLRNKESVHSGEFI | LRNKESVHS | 0.7362 | 17 | SB | BK VP2-3 |
| DRB1_0101 | 217 DYYSNLSPIRPSMVR | YSNLSPIRP | 0.7308 | 18 | SB | BK VP2-3 |
| DRB1_0101 | 82 AALIQTVTGISSLAQ | IQTVTGISS | 0.7316 | 18 | SB | BK VP2-3 |
| DRB1_0101 | 83 ALIQTVTGISSLAQV | VTGISSLAQ | 0.7288 | 19 | SB | BK VP2-3 |
| DRB1_0101 | 40 VQIASLATVEGITTT | IASLATVEG | 0.7231 | 20 | SB | BK VP2-3 |
| DRB1_0101 | 66 QTYAVIAGAPGAIAG | IAGAPGAIA | 0.7250 | 20 | SB | BK VP2-3 |
| DRB1_0101 | 65 PQTYAVIAGAPGAIA | VIAGAPGAI | 0.7203 | 21 | SB | BK VP2-3 |
| DRB1_0101 | 67 TYAVIAGAPGAIAGF | IAGAPGAIA | 0.7196 | 21 | SB | BK VP2-3 |
| DRB1_0101 | 68 YAVIAGAPGAIAGFA | IAGAPGAIA | 0.7188 | 21 | SB | BK VP2-3 |
| DRB1_0101 | 213 NYIQDYYSNLSPIRP | YYSNLSPIR | 0.7087 | 23 | SB | BK VP2-3 |
| DRB1_0101 | 214 YIQDYYSNLSPIRPS | YSNLSPIRP | 0.7104 | 23 | SB | BK VP2-3 |
| DRB1_0101 | 215 IQDYYSNLSPIRPSM | YSNLSPIRP | 0.7116 | 23 | SB | BK VP2-3 |
| DRB1_0101 | 219 YSNLSPIRPSMVRQV | YSNLSPIRP | 0.7018 | 25 | SB | BK VP2-3 |
| DRB1_0101 | 84 LIQTVTGISSLAQVG | VTGISSLAQ | 0.7012 | 25 | SB | BK VP2-3 |
| DRB1_0101 | 69 AVIAGAPGAIAGFAA | IAGAPGAIA | 0.6972 | 26 | SB | BK VP2-3 |
| DRB1_0101 | 85 IQTVTGISSLAQVGY | VTGISSLAQ | 0.7004 | 26 | SB | BK VP2-3 |
| DRB1_0101 | 24 FSVAEIAAGEAAAAI | IAAGEAAAA | 0.6947 | 27 | SB | BK VP2-3 |
| DRB1_0101 | 26 VAEIAAGEAAAAIEV | IAAGEAAAA | 0.6967 | 27 | SB | BK VP2-3 |
| DRB1_0101 | 27 AEIAAGEAAAAIEVQ | IAAGEAAAA | 0.6963 | 27 | SB | BK VP2-3 |
| DRB1_0101 | 25 SVAEIAAGEAAAAIE | IAAGEAAAA | 0.6933 | 28 | SB | BK VP2-3 |
| DRB1_0101 | 34 AAAAIEVQIASLATV | EVQIASLAT | 0.6919 | 28 | SB | BK VP2-3 |
| DRB1_0101 | 35 AAAIEVQIASLATVE | VQIASLATV | 0.6928 | 28 | SB | BK VP2-3 |
| DRB1_0101 | 23 GFSVAEIAAGEAAAA | VAEIAAGEA | 0.6867 | 30 | SB | BK VP2-3 |
| DRB1_0101 | 292 QWMLPLLLGLYGTVT | QWMLPLLLG | 0.6800 | 32 | SB | BK VP2-3 |
| DRB1_0101 | 1 MGAALALLGDLVASV | MGAALALLG | 0.6779 | 33 | SB | BK VP2-3 |
| DRB1_0101 | 296 PLLLGLYGTVTPALE | LLGLYGTVT | 0.6771 | 33 | SB | BK VP2-3 |
| DRB1_0101 | 289 TAPQWMLPLLLGLYG | PQWMLPLLL | 0.6746 | 34 | SB | BK VP2-3 |
| DRB1_0101 | 295 LPLLLGLYGTVTPAL | LLGLYGTVT | 0.6709 | 35 | SB | BK VP2-3 |
| DRB1_0101 | 218 YYSNLSPIRPSMVRQ | YSNLSPIRP | 0.6689 | 36 | SB | BK VP2-3 |
| DRB1_0101 | 293 WMLPLLLGLYGTVTP | LLGLYGTVT | 0.6559 | 41 | SB | BK VP2-3 |
| DRB1_0101 | 294 MLPLLLGLYGTVTPA | LLGLYGTVT | 0.6545 | 42 | SB | BK VP2-3 |
| DRB1_0101 | 220 SNLSPIRPSMVRQVA | IRPSMVRQV | 0.6515 | 43 | SB | BK VP2-3 |
| DRB1_0101 | 288 RTAPQWMLPLLLGLY | PQWMLPLLL | 0.6514 | 43 | SB | BK VP2-3 |
| DRB1_0101 | 86 QTVTGISSLAQVGGAATG | VTGISSLAQ | 0.6515 | 43 | SB | BK VP2-3 |
| DRB1_0101 | 9 GDLVASVSEAAATG | LVASVSEAA | 0.6476 | 45 | SB | BK VP2-3 |
| DRB1_0101 | 287 QRTAPQWMLPLLLGL | PQWMLPLLL | 0.6469 | 46 | SB | BK VP2-3 |
| DRB1_0101 | 290 APQWMLPLLLGLYGT | QWMLPLLLG | 0.6444 | 47 | SB | BK VP2-3 |
| DRB1_0101 | 263 DLRNKESVHSGEFIE | LRNKESVHS | 0.6362 | 51 | WB | BK VP2-3 |
| DRB1_0101 | 264 LRNKESVHSGEFIEK | LRNKESVHS | 0.6346 | 52 | WB | BK VP2-3 |
| DRB1_0101 | 42 IASLATVEGITTTSE | IASLATVEG | 0.6326 | 53 | WB | BK VP2-3 |
| DRB1_0101 | 5 LALLGDLVASVSEAA | LGDLVASVS | 0.6322 | 53 | WB | BK VP2-3 |
| DRB1_0101 | 170 RDDIPAITSQELQRR | IPAITSQEL | 0.6313 | 54 | WB | BK VP2-3 |
| DRB1_0101 | 171 DDIPAITSQELQRRT | IPAITSQEL | 0.6309 | 54 | WB | BK VP2-3 |
| DRB1_0101 | 186 ERFFRDSLARFLEET | FRDSLARFL | 0.6320 | 54 | WB | BK VP2-3 |
| DRB1_0101 | 184 RTERFFRDSLARFLE | FRDSLARFL | 0.6295 | 55 | WB | BK VP2-3 |
| DRB1_0101 | 185 TERFFRDSLARFLEE | FRDSLARFL | 0.6304 | 55 | WB | BK VP2-3 |
| DRB1_0101 | 183 RRTERFFRDSLARFL | FFRDSLARF | 0.6285 | 56 | WB | BK VP2-3 |
| DRB1_0101 | 187 RFFRDSLARFLEETT | FRDSLARFL | 0.6286 | 56 | WB | BK VP2-3 |
| DRB1_0101 | 70 VIAGAPGAIAGFAAL | IAGAPGAIA | 0.6277 | 56 | WB | BK VP2-3 |
| DRB1_0101 | 75 PGAIAGFAALIQTVT | IAGFAALIQ | 0.6288 | 56 | WB | BK VP2-3 |
| DRB1_0101 | 76 GAIAGFAALIQTVTG | FAALIQTVT | 0.6280 | 56 | WB | BK VP2-3 |
| DRB1_0101 | 41 QIASLATVEGITTTS | IASLATVEG | 0.6263 | 57 | WB | BK VP2-3 |
| DRB1_0101 | 6 ALLGDLVASVSEAAA | LVASVSEAA | 0.6253 | 58 | WB | BK VP2-3 |
| DRB1_0101 | 221 NLSPIRPSMVRQVAE | IRPSMVRQV | 0.6218 | 60 | WB | BK VP2-3 |
| DRB1_0101 | 297 LLGLYGTVTPALEAY | LLGLYGTVT | 0.6216 | 60 | WB | BK VP2-3 |
| DRB1_0101 | 222 LSPIRPSMVRQVAER | IRPSMVRQV | 0.6206 | 61 | WB | BK VP2-3 |
| DRB1_0101 | 291 PQWMLPLLLGLYGTV | PQWMLPLLL | 0.6197 | 61 | WB | BK VP2-3 |
| DRB1_0101 | 298 LLGLYGTVTPALEAY | LLGLYGTVT | 0.6201 | 61 | WB | BK VP2-3 |
| DRB1_0101 | 79 AGFAALIQTVTGISS | FAALIQTVT | 0.6202 | 61 | WB | BK VP2-3 |
| DRB1_0101 | 8 LGDLVASVSEAAAAT | LVASVSEAA | 0.6196 | 61 | WB | BK VP2-3 |
| DRB1_0101 | 155 PSLFATISQALWHVI | LFATISQAL | 0.6154 | 64 | WB | BK VP2-3 |
| DRB1_0101 | 28 EIAAGEAAAAIEVQI | IAAGEAAAA | 0.6146 | 65 | WB | BK VP2-3 |
| DRB1_0101 | 286 NQRTAPQWMLPLLLG | PQWMLPLLL | 0.6139 | 65 | WB | BK VP2-3 |
| DRB1_0101 | 151 RHWGPSLFATISQAL | RHWGPSLFA | 0.6126 | 66 | WB | BK VP2-3 |

TABLE P-continued

Prediction of BK virus VP2-3 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. Identity |
|---|---|---|---|---|---|
| DRB1_0101 | 275 FIEKTIAPGGANQRT | IAPGGANQR | 0.6093 | 69 | WB BK VP2-3 |
| DRB1_0101 | 29 IAAGEAAAAIEVQIA | IAAGEAAAA | 0.6093 | 69 | WB BK VP2-3 |
| DRB1_0101 | 7 LLGDLVASVSEAAAA | LVASVSEAA | 0.6068 | 70 | WB BK VP2-3 |
| DRB1_0101 | 11 LVASVSEAAAATGFS | VSEAAAATG | 0.6048 | 72 | WB BK VP2-3 |
| DRB1_0101 | 152 HWGPSLFATISQALW | LFATISQAL | 0.6052 | 72 | WB BK VP2-3 |
| DRB1_0101 | 276 IEKTIAPGGANQRTA | IAPGGANQR | 0.6053 | 72 | WB BK VP2-3 |
| DRB1_0101 | 154 GPSLFATISQALWHV | LFATISQAL | 0.6040 | 73 | WB BK VP2-3 |
| DRB1_0101 | 111 TVGLYQQSGMALELF | LYQQSGMAL | 0.6024 | 74 | WB BK VP2-3 |
| DRB1_0101 | 10 DLVASVSEAAAATGF | VSEAAAATG | 0.6015 | 75 | WB BK VP2-3 |
| DRB1_0101 | 112 VGLYQQSGMALELFN | LYQQSGMAL | 0.6010 | 75 | WB BK VP2-3 |
| DRB1_0101 | 277 EKTIAPGGANQRTAP | IAPGGANQR | 0.6011 | 75 | WB BK VP2-3 |
| DRB1_0101 | 71 IAGAPGAIAGFAALI | IAGAPGAIA | 0.6015 | 75 | WB BK VP2-3 |
| DRB1_0101 | 153 WGPSLFATISQALWH | LFATISQAL | 0.5994 | 76 | WB BK VP2-3 |
| DRB1_0101 | 223 SPIRPSMVRQVAERE | IRPSMVRQV | 0.6003 | 76 | WB BK VP2-3 |
| DRB1_0101 | 110 STVGLYQQSGMALEL | LYQQSGMAL | 0.5977 | 78 | WB BK VP2-3 |
| DRB1_0101 | 78 IAGFAALIQTVTGIS | FAALIQTVT | 0.5963 | 79 | WB BK VP2-3 |
| DRB1_0101 | 77 AIAGFAALIQTVTGI | FAALIQTVT | 0.5949 | 80 | WB BK VP2-3 |
| DRB1_0101 | 278 KTIAPGGANQRTAPQ | IAPGGANQR | 0.5943 | 81 | WB BK VP2-3 |
| DRB1_0101 | 2 GAALALLGDLVASVS | LALLGDLVA | 0.5930 | 82 | WB BK VP2-3 |
| DRB1_0101 | 3 AALALLGDLVASVSE | LGDLVASVS | 0.5912 | 83 | WB BK VP2-3 |
| DRB1_0101 | 81 FAALIQTVTGISSLA | IQTVTGISS | 0.5912 | 83 | WB BK VP2-3 |
| DRB1_0101 | 173 IPAITSQELQRRTER | ITSQELQRR | 0.5853 | 89 | WB BK VP2-3 |
| DRB1_0101 | 172 DIPAITSQELQRRTE | ITSQELQRR | 0.5840 | 90 | WB BK VP2-3 |
| DRB1_0101 | 88 VTGISSLAQVGYRFF | VTGISSLAQ | 0.5828 | 91 | WB BK VP2-3 |
| DRB1_0101 | 80 GFAALIQTVTGISSL | IQTVTGISS | 0.5817 | 92 | WB BK VP2-3 |
| DRB1_0101 | 274 EFIEKTIAPGGANQR | IEKTIAPGG | 0.5781 | 96 | WB BK VP2-3 |
| DRB1_0101 | 320 KRRVSRGSSQKAKGT | VSRGSSQKA | 0.5786 | 96 | WB BK VP2-3 |
| DRB1_0101 | 167 HVIRDDIPAITSQEL | IRDDIPAIT | 0.5761 | 98 | WB BK VP2-3 |
| DRB1_0101 | 109 VSTVGLYQQSGMALE | LYQQSGMAL | 0.5756 | 99 | WB BK VP2-3 |
| DRB1_0101 | 64 TPQTYAVIAGAPGAI | YAVIAGAPG | 0.5756 | 99 | WB BK VP2-3 |
| DRB1_0101 | 321 RRVSRGSSQKAKGTR | VSRGSSQKA | 0.5746 | 100 | WB BK VP2-3 |
| DRB1_0101 | 323 VSRGSSQKAKGTRAS | VSRGSSQKA | 0.5730 | 101 | WB BK VP2-3 |
| DRB1_0101 | 319 KKRRVSRGSSQKAKG | VSRGSSQKA | 0.5712 | 104 | WB BK VP2-3 |
| DRB1_0101 | 318 QKKRRVSRGSSQKAK | VSRGSSQKA | 0.5695 | 105 | WB BK VP2-3 |
| DRB1_0101 | 87 TVTGISSLAQVGYRF | VTGISSLAQ | 0.5702 | 105 | WB BK VP2-3 |
| DRB1_0101 | 299 LGLYGTVTPALEAYE | LYGTVTPAL | 0.5689 | 106 | WB BK VP2-3 |
| DRB1_0101 | 4 ALALLGDLVASVSEA | LGDLVASVS | 0.5688 | 106 | WB BK VP2-3 |
| DRB1_0101 | 317 NQKKRRVSRGSSQKA | RVSRGSSQK | 0.5685 | 107 | WB BK VP2-3 |
| DRB1_0101 | 12 VASVSEAAAATGFSV | VSEAAAATG | 0.5666 | 109 | WB BK VP2-3 |
| DRB1_0101 | 169 IRDDIPAITSQELQR | IPAITSQEL | 0.5628 | 113 | WB BK VP2-3 |
| DRB1_0101 | 285 ANQRTAPQWMLPLLL | RTAPQWMLP | 0.5629 | 113 | WB BK VP2-3 |
| DRB1_0101 | 33 EAAAAIEVQIASLAT | IEVQIASLA | 0.5628 | 113 | WB BK VP2-3 |
| DRB1_0101 | 74 APGAIAGFAALIQTV | IAGFAALIQ | 0.5631 | 113 | WB BK VP2-3 |
| DRB1_0101 | 168 VIRDDIPAITSQELQ | IPAITSQEL | 0.5596 | 117 | WB BK VP2-3 |
| DRB1_0101 | 212 YNYIQDYYSNLSPIR | IQDYYSNLS | 0.5601 | 117 | WB BK VP2-3 |
| DRB1_0101 | 72 AGAPGAIAGFAALIQ | AIAGFAALI | 0.5598 | 117 | WB BK VP2-3 |
| DRB1_0101 | 73 GAPGAIAGFAALIQT | IAGFAALIQ | 0.5602 | 117 | WB BK VP2-3 |
| DRB1_0101 | 108 KVSTVGLYQQSGMAL | TVGLYQQSG | 0.5550 | 123 | WB BK VP2-3 |
| DRB1_0101 | 156 SLFATISQALWHVIR | LFATISQAL | 0.5526 | 127 | WB BK VP2-3 |
| DRB1_0101 | 13 ASVSEAAAATGFSVA | VSEAAAATG | 0.5482 | 133 | WB BK VP2-3 |
| DRB1_0101 | 113 GLYQQSGMALELFNP | LYQQSGMAL | 0.5426 | 141 | WB BK VP2-3 |
| DRB1_0101 | 157 LFATISQALWHVIRD | LFATISQAL | 0.5415 | 143 | WB BK VP2-3 |
| DRB1_0101 | 188 FFRDSLARFLEETTW | FRDSLARFL | 0.5345 | 154 | WB BK VP2-3 |
| DRB1_0101 | 43 ASLATVEGITTTSEA | LATVEGITT | 0.5345 | 154 | WB BK VP2-3 |
| DRB1_0101 | 149 DPRHWGPSLFATISQ | RHWGPSLFA | 0.5298 | 162 | WB BK VP2-3 |
| DRB1_0101 | 148 LDPRHWGPSLFATIS | RHWGPSLFA | 0.5294 | 163 | WB BK VP2-3 |
| DRB1_0101 | 57 AIAAIGLTPQTYAVI | IAAIGLTPQ | 0.5280 | 165 | WB BK VP2-3 |
| DRB1_0101 | 189 FRDSLARFLEETTWT | FRDSLARFL | 0.5271 | 167 | WB BK VP2-3 |
| DRB1_0101 | 279 TIAPGGANQRTAPQW | IAPGGANQR | 0.5252 | 170 | WB BK VP2-3 |
| DRB1_0101 | 174 PAITSQELQRRTERF | ITSQELQRR | 0.5214 | 177 | WB BK VP2-3 |
| DRB1_0101 | 114 LYQQSGMALELFNPD | LYQQSGMAL | 0.5213 | 178 | WB BK VP2-3 |
| DRB1_0101 | 199 ETTWTIVNAPINFYN | IVNAPINFY | 0.5209 | 178 | WB BK VP2-3 |
| DRB1_0101 | 58 IAAIGLTPQTYAVIA | LTPQTYAVI | 0.5203 | 180 | WB BK VP2-3 |
| DRB1_0101 | 147 YLDPRHWGPSLFATI | RHWGPSLFA | 0.5192 | 182 | WB BK VP2-3 |
| DRB1_0101 | 56 EAIAAIGLTPQTYAV | IAAIGLTPQ | 0.5190 | 182 | WB BK VP2-3 |
| DRB1_0101 | 200 TTWTIVNAPINFYNY | IVNAPINFY | 0.5185 | 183 | WB BK VP2-3 |
| DRB1_0101 | 198 EETTWTIVNAPINFY | WTIVNAPIN | 0.5179 | 184 | WB BK VP2-3 |
| DRB1_0101 | 224 PIRPSMVRQVAEREG | IRPSMVRQV | 0.5170 | 186 | WB BK VP2-3 |
| DRB1_0101 | 63 LTPQTYAVIAGAPGA | YAVIAGAPG | 0.5172 | 186 | WB BK VP2-3 |
| DRB1_0101 | 225 IRPSMVRQVAEREGT | IRPSMVRQV | 0.5152 | 190 | WB BK VP2-3 |
| DRB1_0101 | 209 INFYNYIQDYYSNLS | YNYIQDYYS | 0.5135 | 193 | WB BK VP2-3 |
| DRB1_0101 | 55 SEAIAAIGLTPQTYA | IAAIGLTPQ | 0.5133 | 194 | WB BK VP2-3 |
| DRB1_0101 | 210 NFYNYIQDYYSNLSP | IQDYYSNLS | 0.5129 | 195 | WB BK VP2-3 |

TABLE P-continued

Prediction of BK virus VP2-3 protein specific MHC class 2, 15-mer
peptide binders for 14 MHC class 2 alleles (see

TABLE P-continued

Prediction of BK virus VP2-3 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0401 | 217 DYYSNLSPIRPSMVR | YSNLSPIR | 0.4779 | 284 | WB | BK VP2-3 |
| DRB1_0401 | 83 ALIQTVTGISSLAQV | VTGISSLAQ | 0.4763 | 289 | WB | BK VP2-3 |
| DRB1_0401 | 84 LIQTVTGISSLAQVG | VTGISSLAQ | 0.4711 | 306 | WB | BK VP2-3 |
| DRB1_0401 | 218 YYSNLSPIRPSMVRQ | YSNLSPIR | 0.4694 | 312 | WB | BK VP2-3 |
| DRB1_0401 | 198 EETTWTIVNAPINFY | WTIVNAPIN | 0.4557 | 361 | WB | BK VP2-3 |
| DRB1_0401 | 199 ETTWTIVNAPINFYN | IVNAPINFY | 0.4556 | 362 | WB | BK VP2-3 |
| DRB1_0401 | 200 TTWTIVNAPINFYNY | IVNAPINFY | 0.4527 | 373 | WB | BK VP2-3 |
| DRB1_0401 | 85 IQTVTGISSLAQVGY | VTGISSLAQ | 0.4432 | 414 | WB | BK VP2-3 |
| DRB1_0401 | 202 WTIVNAPINFYNYIQ | IVNAPINFY | 0.4421 | 418 | WB | BK VP2-3 |
| DRB1_0401 | 201 TWTIVNAPINFYNYI | IVNAPINFY | 0.4401 | 427 | WB | BK VP2-3 |
| DRB1_0401 | 81 FAALIQTVTGISSLA | LIQTVTGIS | 0.4399 | 428 | WB | BK VP2-3 |
| DRB1_0401 | 36 AAIEVQIASLATVEG | IEVQIASLA | 0.4327 | 463 | WB | BK VP2-3 |
| DRB1_0401 | 132 DILFPGVNTFVNNIQ | GVNTFVNNI | 0.4289 | 483 | WB | BK VP2-3 |
| DRB1_0404 | 213 NYIQDYYSNLSPIRP | IQDYYSNLS | 0.5128 | 195 | WB | BK VP2-3 |
| DRB1_0404 | 82 AALIQTVTGISSLAQ | LIQTVTGIS | 0.4868 | 258 | WB | BK VP2-3 |
| DRB1_0404 | 198 EETTWTIVNAPINFY | TTWTIVNAP | 0.4822 | 271 | WB | BK VP2-3 |
| DRB1_0404 | 215 IQDYYSNLSPIRPSM | IQDYYSNLS | 0.4815 | 273 | WB | BK VP2-3 |
| DRB1_0404 | 295 LPLLLGLYGTVTPAL | LLGLYGTVT | 0.4754 | 292 | WB | BK VP2-3 |
| DRB1_0404 | 214 YIQDYYSNLSPIRPS | IQDYYSNLS | 0.4645 | 328 | WB | BK VP2-3 |
| DRB1_0404 | 296 PLLLGLYGTVTPALE | LLGLYGTVT | 0.4620 | 337 | WB | BK VP2-3 |
| DRB1_0404 | 293 WMLPLLLGLYGTVTP | LLGLYGTVT | 0.4571 | 356 | WB | BK VP2-3 |
| DRB1_0404 | 294 MLPLLLGLYGTVTPA | LLGLYGTVT | 0.4547 | 365 | WB | BK VP2-3 |
| DRB1_0404 | 36 AAIEVQIASLATVEG | IEVQIASLA | 0.4515 | 378 | WB | BK VP2-3 |
| DRB1_0404 | 200 TTWTIVNAPINFYNY | IVNAPINFY | 0.4472 | 396 | WB | BK VP2-3 |
| DRB1_0404 | 194 ARFLEETTWTIVNAP | FLEETTWTI | 0.4467 | 398 | WB | BK VP2-3 |
| DRB1_0404 | 212 YNYIQDYYSNLSPIR | IQDYYSNLS | 0.4449 | 406 | WB | BK VP2-3 |
| DRB1_0404 | 199 ETTWTIVNAPINFYN | IVNAPINFY | 0.4444 | 408 | WB | BK VP2-3 |
| DRB1_0404 | 81 FAALIQTVTGISSLA | LIQTVTGIS | 0.4428 | 415 | WB | BK VP2-3 |
| DRB1_0404 | 292 QWMLPLLLGLYGTVT | MLPLLLGLY | 0.4376 | 439 | WB | BK VP2-3 |
| DRB1_0404 | 297 LLLGLYGTVTPALEA | LGLYGTVTP | 0.4365 | 445 | WB | BK VP2-3 |
| DRB1_0404 | 84 LIQTVTGISSLAQVG | LIQTVTGIS | 0.4287 | 483 | WB | BK VP2-3 |
| DRB1_0404 | 38 IEVQIASLATVEGIT | IASLATVEG | 0.4281 | 487 | WB | BK VP2-3 |
| DRB1_0404 | 78 IAGFAALIQTVTGIS | AALIQTVTG | 0.4270 | 493 | WB | BK VP2-3 |
| DRB1_0404 | 196 FLEETTWTIVNAPIN | TTWTIVNAP | 0.4258 | 499 | WB | BK VP2-3 |
| DRB1_0405 | 213 NYIQDYYSNLSPIRP | IQDYYSNLS | 0.5630 | 113 | WB | BK VP2-3 |
| DRB1_0405 | 212 YNYIQDYYSNLSPIR | IQDYYSNLS | 0.5391 | 146 | WB | BK VP2-3 |
| DRB1_0405 | 209 INFYNYIQDYYSNLS | YNYIQDYYS | 0.5339 | 155 | WB | BK VP2-3 |
| DRB1_0405 | 96 QVGYRFFSDWDHKVS | YRFFSDWDH | 0.5285 | 164 | WB | BK VP2-3 |
| DRB1_0405 | 210 NFYNYIQDYYSNLSP | IQDYYSNLS | 0.5274 | 166 | WB | BK VP2-3 |
| DRB1_0405 | 196 FLEETTWTIVNAPIN | EETTWTIVN | 0.5259 | 169 | WB | BK VP2-3 |
| DRB1_0405 | 214 YIQDYYSNLSPIRPS | IQDYYSNLS | 0.5183 | 184 | WB | BK VP2-3 |
| DRB1_0405 | 215 IQDYYSNLSPIRPSM | IQDYYSNLS | 0.5155 | 189 | WB | BK VP2-3 |
| DRB1_0405 | 135 FPGVNTFVNNIQYLD | VNTFVNNIQ | 0.5129 | 194 | WB | BK VP2-3 |
| DRB1_0405 | 211 FYNYIQDYYSNLSPI | IQDYYSNLS | 0.5093 | 202 | WB | BK VP2-3 |
| DRB1_0405 | 198 EETTWTIVNAPINFY | WTIVNAPIN | 0.5089 | 203 | WB | BK VP2-3 |
| DRB1_0405 | 136 PGVNTFVNNIQYLDP | VNTFVNNIQ | 0.5073 | 207 | WB | BK VP2-3 |
| DRB1_0405 | 95 AQVGYRFFSDWDHKV | YRFFSDWDH | 0.5059 | 210 | WB | BK VP2-3 |
| DRB1_0405 | 132 DILFPGVNTFVNNIQ | FPGVNTFVN | 0.5008 | 222 | WB | BK VP2-3 |
| DRB1_0405 | 133 ILFPGVNTFVNNIQY | VNTFVNNIQ | 0.4983 | 228 | WB | BK VP2-3 |
| DRB1_0405 | 97 VGYRFFSDWDHKVST | YRFFSDWDH | 0.4930 | 241 | WB | BK VP2-3 |
| DRB1_0405 | 194 ARFLEETTWTIVNAP | EETTWTIVN | 0.4887 | 253 | WB | BK VP2-3 |
| DRB1_0405 | 197 LEETTWTIVNAPINF | WTIVNAPIN | 0.4832 | 268 | WB | BK VP2-3 |
| DRB1_0405 | 199 ETTWTIVNAPINFYN | WTIVNAPIN | 0.4813 | 274 | WB | BK VP2-3 |
| DRB1_0405 | 195 RFLEETTWTIVNAPI | EETTWTIVN | 0.4799 | 278 | WB | BK VP2-3 |
| DRB1_0405 | 94 LAQVGYRFFSDWDHK | GYRFFSDWD | 0.4772 | 286 | WB | BK VP2-3 |
| DRB1_0405 | 93 SLAQVGYRFFSDWDH | GYRFFSDWD | 0.4758 | 291 | WB | BK VP2-3 |
| DRB1_0405 | 134 LFPGVNTFVNNIQYL | VNTFVNNIQ | 0.4752 | 292 | WB | BK VP2-3 |
| DRB1_0405 | 193 LARFLEETTWTIVNA | EETTWTIVN | 0.4694 | 312 | WB | BK VP2-3 |
| DRB1_0405 | 158 FATISQALWHVIRDD | QALWHVIRD | 0.4626 | 335 | WB | BK VP2-3 |
| DRB1_0405 | 157 LFATISQALWHVIRD | SQALWHVIR | 0.4616 | 339 | WB | BK VP2-3 |
| DRB1_0405 | 200 TTWTIVNAPINFYNY | IVNAPINFY | 0.4599 | 345 | WB | BK VP2-3 |
| DRB1_0405 | 98 GYRFFSDWDHKVSTV | YRFFSDWDH | 0.4557 | 361 | WB | BK VP2-3 |
| DRB1_0405 | 192 SLARFLEETTWTIVN | FLEETTWTI | 0.4451 | 405 | WB | BK VP2-3 |
| DRB1_0405 | 137 GVNTFVNNIQYLDPR | VNTFVNNIQ | 0.4315 | 469 | WB | BK VP2-3 |
| DRB1_0405 | 138 VNTFVNNIQYLDPRH | VNTFVNNIQ | 0.4315 | 469 | WB | BK VP2-3 |
| DRB1_0701 | 155 PSLFATISQALWHVI | LFATISQAL | 0.6499 | 44 | SB | BK VP2-3 |
| DRB1_0701 | 154 GPSLFATISQALWHV | LFATISQAL | 0.6324 | 53 | WB | BK VP2-3 |
| DRB1_0701 | 153 WGPSLFATISQALWH | LFATISQAL | 0.6252 | 58 | WB | BK VP2-3 |
| DRB1_0701 | 152 HWGPSLFATISQALW | LFATISQAL | 0.6229 | 59 | WB | BK VP2-3 |
| DRB1_0701 | 151 RHWGPSLFATISQAL | WGPSLFATI | 0.6204 | 61 | WB | BK VP2-3 |

TABLE P-continued

Prediction of BK virus VP2-3 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0701 | 219 YSNLSPIRPSMVRQV | LSPIRPSMV | 0.6186 | 62 | WB | BK VP2-3 |
| DRB1_0701 | 220 SNLSPIRPSMVRQVA | LSPIRPSMV | 0.6184 | 62 | WB | BK VP2-3 |
| DRB1_0701 | 216 QDYYSNLSPIRPSMV | YYSNLSPIR | 0.6145 | 65 | WB | BK VP2-3 |
| DRB1_0701 | 217 DYYSNLSPIRPSMVR | LSPIRPSMV | 0.6117 | 67 | WB | BK VP2-3 |
| DRB1_0701 | 218 YYSNLSPIRPSMVRQ | LSPIRPSMV | 0.6108 | 67 | WB | BK VP2-3 |
| DRB1_0701 | 194 ARFLEETTWTIVNAP | FLEETTWTI | 0.6047 | 72 | WB | BK VP2-3 |
| DRB1_0701 | 191 DSLARFLEETTWTIV | FLEETTWTI | 0.6040 | 73 | WB | BK VP2-3 |
| DRB1_0701 | 193 LARFLEETTWTIVNA | FLEETTWTI | 0.6028 | 73 | WB | BK VP2-3 |
| DRB1_0701 | 192 SLARFLEETTWTIVN | FLEETTWTI | 0.6024 | 74 | WB | BK VP2-3 |
| DRB1_0701 | 156 SLFATISQALWHVIR | LFATISQAL | 0.5732 | 101 | WB | BK VP2-3 |
| DRB1_0701 | 157 LFATISQALWHVIRD | LFATISQAL | 0.5709 | 104 | WB | BK VP2-3 |
| DRB1_0701 | 195 RFLEETTWTIVNAPI | LEETTWTIV | 0.5523 | 127 | WB | BK VP2-3 |
| DRB1_0701 | 221 NLSPIRPSMVRQVAE | LSPIRPSMV | 0.5258 | 169 | WB | BK VP2-3 |
| DRB1_0701 | 222 LSPIRPSMVRQVAER | LSPIRPSMV | 0.5249 | 171 | WB | BK VP2-3 |
| DRB1_0701 | 196 FLEETTWTIVNAPIN | FLEETTWTI | 0.5082 | 205 | WB | BK VP2-3 |
| DRB1_0701 | 58 IAAIGLTPQTYAVIA | LTPQTYAVI | 0.4999 | 224 | WB | BK VP2-3 |
| DRB1_0701 | 57 AIAAIGLTPQTYAVI | AIGLTPQTY | 0.4992 | 226 | WB | BK VP2-3 |
| DRB1_0701 | 59 AAIGLTPQTYAVIAG | LTPQTYAVI | 0.4959 | 234 | WB | BK VP2-3 |
| DRB1_0701 | 60 AIGLTPQTYAVIAGA | LTPQTYAVI | 0.4955 | 235 | WB | BK VP2-3 |
| DRB1_0701 | 61 IGLTPQTYAVIAGAP | LTPQTYAVI | 0.4924 | 243 | WB | BK VP2-3 |
| DRB1_0701 | 190 RDSLARFLEETTWTI | RDSLARFLE | 0.4903 | 248 | WB | BK VP2-3 |
| DRB1_0701 | 167 HVIRDDIPAITSQEL | VIRDDIPAI | 0.4747 | 294 | WB | BK VP2-3 |
| DRB1_0701 | 131 YDILFPGVNTFVNNI | LFPGVNTFV | 0.4730 | 299 | WB | BK VP2-3 |
| DRB1_0701 | 168 VIRDDIPAITSQELQ | IPAITSQEL | 0.4729 | 300 | WB | BK VP2-3 |
| DRB1_0701 | 132 DILFPGVNTFVNNIQ | LFPGVNTFV | 0.4725 | 301 | WB | BK VP2-3 |
| DRB1_0701 | 169 IRDDIPAITSQELQR | IPAITSQEL | 0.4681 | 316 | WB | BK VP2-3 |
| DRB1_0701 | 170 RDDIPAITSQELQRR | IPAITSQEL | 0.4671 | 319 | WB | BK VP2-3 |
| DRB1_0701 | 171 DDIPAITSQELQRRT | IPAITSQEL | 0.4635 | 332 | WB | BK VP2-3 |
| DRB1_0701 | 129 EYYDILFPGVNTFVN | LFPGVNTFV | 0.4503 | 383 | WB | BK VP2-3 |
| DRB1_0701 | 130 YYDILFPGVNTFVNN | FPGVNTFVN | 0.4488 | 389 | WB | BK VP2-3 |
| DRB1_0701 | 133 ILFPGVNTFVNNIQY | FPGVNTFVN | 0.4334 | 459 | WB | BK VP2-3 |
| DRB1_0701 | 158 FATISQALWHVIRDD | ISQALWHVI | 0.4279 | 488 | WB | BK VP2-3 |
| DRB1_0802 | 214 YIQDYYSNLSPIRPS | YSNLSPIRP | 0.4370 | 442 | WB | BK VP2-3 |
| DRB1_0802 | 213 NYIQDYYSNLSPIRP | YYSNLSPIR | 0.4360 | 447 | WB | BK VP2-3 |
| DRB1_0802 | 215 IQDYYSNLSPIRPSM | YSNLSPIRP | 0.4360 | 447 | WB | BK VP2-3 |
| DRB1_0802 | 216 QDYYSNLSPIRPSMV | YSNLSPIRP | 0.4358 | 448 | WB | BK VP2-3 |
| DRB1_0901 | 110 STVGLYQQSGMALEL | YQQSGMALE | 0.4827 | 270 | WB | BK VP2-3 |
| DRB1_0901 | 111 TVGLYQQSGMALELF | YQQSGMALE | 0.4750 | 293 | WB | BK VP2-3 |
| DRB1_0901 | 112 VGLYQQSGMALELFN | YQQSGMALE | 0.4750 | 293 | WB | BK VP2-3 |
| DRB1_0901 | 109 VSTVGLYQQSGMALE | LYQQSGMAL | 0.4737 | 297 | WB | BK VP2-3 |
| DRB1_0901 | 36 AAIEVQIASLATVEG | VQIASLATV | 0.4709 | 306 | WB | BK VP2-3 |
| DRB1_0901 | 35 AAAIEVQIASLATVE | VQIASLATV | 0.4664 | 322 | WB | BK VP2-3 |
| DRB1_0901 | 198 EETTWTIVNAPINFY | WTIVNAPIN | 0.4656 | 324 | WB | BK VP2-3 |
| DRB1_0901 | 199 ETTWTIVNAPINFYN | WTIVNAPIN | 0.4657 | 324 | WB | BK VP2-3 |
| DRB1_0901 | 37 AIEVQIASLATVEGI | VQIASLATV | 0.4650 | 326 | WB | BK VP2-3 |
| DRB1_0901 | 34 AAAAIEVQIASLATV | IEVQIASLA | 0.4647 | 328 | WB | BK VP2-3 |
| DRB1_0901 | 38 IEVQIASLATVEGIT | VQIASLATV | 0.4639 | 331 | WB | BK VP2-3 |
| DRB1_0901 | 297 LLLGLYGTVTPALEA | LYGTVTPAL | 0.4627 | 335 | WB | BK VP2-3 |
| DRB1_0901 | 200 TTWTIVNAPINFYNY | WTIVNAPIN | 0.4612 | 340 | WB | BK VP2-3 |
| DRB1_0901 | 296 PLLLGLYGTVTPALE | LYGTVTPAL | 0.4611 | 341 | WB | BK VP2-3 |
| DRB1_0901 | 299 LGLYGTVTPALEAYE | LYGTVTPAL | 0.4598 | 346 | WB | BK VP2-3 |
| DRB1_0901 | 298 LLGLYGTVTPALEAY | LYGTVTPAL | 0.4531 | 372 | WB | BK VP2-3 |
| DRB1_0901 | 113 GLYQQSGMALELFNP | YQQSGMALE | 0.4451 | 405 | WB | BK VP2-3 |
| DRB1_0901 | 183 RRTERFFRDSLARFL | FFRDSLARF | 0.4413 | 422 | WB | BK VP2-3 |
| DRB1_0901 | 184 RTERFFRDSLARFLE | FRDSLARFL | 0.4404 | 426 | WB | BK VP2-3 |
| DRB1_0901 | 186 ERFFRDSLARFLEET | FRDSLARFL | 0.4393 | 431 | WB | BK VP2-3 |
| DRB1_0901 | 185 TERFFRDSLARFLEE | FRDSLARFL | 0.4382 | 436 | WB | BK VP2-3 |
| DRB1_0901 | 187 RFFRDSLARFLEETT | FRDSLARFL | 0.4306 | 474 | WB | BK VP2-3 |
| DRB1_0901 | 295 LPLLLGLYGTVTPAL | LGLYGTVTP | 0.4290 | 482 | WB | BK VP2-3 |
| DRB1_0901 | 65 PQTYAVIAGAPGAIA | VIAGAPGAI | 0.4281 | 487 | WB | BK VP2-3 |
| DRB1_0901 | 66 QTYAVIAGAPGAIAG | VIAGAPGAI | 0.4279 | 488 | WB | BK VP2-3 |
| DRB1_0901 | 67 TYAVIAGAPGAIAGF | VIAGAPGAI | 0.4259 | 499 | WB | BK VP2-3 |
| DRB1_1302 | 135 FPGVNTFVNNIQYLD | VNTFVNNIQ | 0.7008 | 25 | SB | BK VP2-3 |
| DRB1_1302 | 136 PGVNTFVNNIQYLDP | FVNNIQYLD | 0.6940 | 27 | SB | BK VP2-3 |
| DRB1_1302 | 137 GVNTFVNNIQYLDPR | FVNNIQYLD | 0.6861 | 30 | SB | BK VP2-3 |
| DRB1_1302 | 138 VNTFVNNIQYLDPRH | FVNNIQYLD | 0.6825 | 31 | SB | BK VP2-3 |
| DRB1_1302 | 139 NTFVNNIQYLDPRHW | FVNNIQYLD | 0.6608 | 39 | SB | BK VP2-3 |
| DRB1_1302 | 213 NYIQDYYSNLSPIRP | IQDYYSNLS | 0.6338 | 53 | WB | BK VP2-3 |
| DRB1_1302 | 216 QDYYSNLSPIRPSMV | YSNLSPIRP | 0.6265 | 57 | WB | BK VP2-3 |
| DRB1_1302 | 215 IQDYYSNLSPIRPSM | YSNLSPIRP | 0.6245 | 58 | WB | BK VP2-3 |

TABLE P-continued

Prediction of BK virus VP2-3 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. Identity |
|---|---|---|---|---|---|
| DRB1_1302 | 214 YIQDYYSNLSPIRPS | YSNLSPIRP | 0.6230 | 59 | WB BK VP2-3 |
| DRB1_1302 | 217 DYYSNLSPIRPSMVR | YSNLSPIRP | 0.6216 | 60 | WB BK VP2-3 |
| DRB1_1302 | 293 WMLPLLLGLYGTVTP | LLGLYGTVT | 0.6200 | 61 | WB BK VP2-3 |
| DRB1_1302 | 296 PLLLGLYGTVTPALE | LGLYGTVTP | 0.6167 | 63 | WB BK VP2-3 |
| DRB1_1302 | 294 MLPLLLGLYGTVTPA | LGLYGTVTP | 0.6126 | 66 | WB BK VP2-3 |
| DRB1_1302 | 295 LPLLLGLYGTVTPAL | LGLYGTVTP | 0.6083 | 69 | WB BK VP2-3 |
| DRB1_1302 | 297 LLLGLYGTVTPALEA | LGLYGTVTP | 0.6067 | 70 | WB BK VP2-3 |
| DRB1_1302 | 140 TFVNNIQYLDPRHWG | FVNNIQYLD | 0.5962 | 79 | WB BK VP2-3 |
| DRB1_1302 | 36 AAIEVQIASLATVEG | VQIASLATV | 0.5884 | 86 | WB BK VP2-3 |
| DRB1_1302 | 141 FVNNIQYLDPRHWGP | FVNNIQYLD | 0.5710 | 104 | WB BK VP2-3 |
| DRB1_1302 | 37 AIEVQIASLATVEGI | VQIASLATV | 0.5647 | 111 | WB BK VP2-3 |
| DRB1_1302 | 38 IEVQIASLATVEGIT | VQIASLATV | 0.5646 | 111 | WB BK VP2-3 |
| DRB1_1302 | 218 YYSNLSPIRPSMVRQ | YSNLSPIRP | 0.5481 | 133 | WB BK VP2-3 |
| DRB1_1302 | 199 ETTWTIVNAPINFYN | IVNAPINFY | 0.5463 | 135 | WB BK VP2-3 |
| DRB1_1302 | 200 TTWTIVNAPINFYNY | IVNAPINFY | 0.5452 | 137 | WB BK VP2-3 |
| DRB1_1302 | 198 EETTWTIVNAPINFY | WTIVNAPIN | 0.5445 | 138 | WB BK VP2-3 |
| DRB1_1302 | 298 LLGLYGTVTPALEAY | LGLYGTVTP | 0.5383 | 148 | WB BK VP2-3 |
| DRB1_1302 | 219 YSNLSPIRPSMVRQV | YSNLSPIRP | 0.5366 | 150 | WB BK VP2-3 |
| DRB1_1302 | 201 TWTIVNAPINFYNYI | IVNAPINFY | 0.5349 | 153 | WB BK VP2-3 |
| DRB1_1302 | 79 AGFAALIQTVTGISS | FAALIQTVT | 0.5306 | 161 | WB BK VP2-3 |
| DRB1_1302 | 34 AAAAIEVQIASLATV | IEVQIASLA | 0.5257 | 169 | WB BK VP2-3 |
| DRB1_1302 | 202 WTIVNAPINFYNYIQ | IVNAPINFY | 0.5240 | 172 | WB BK VP2-3 |
| DRB1_1302 | 35 AAAIEVQIASLATVE | VQIASLATV | 0.5233 | 174 | WB BK VP2-3 |
| DRB1_1302 | 299 LGLYGTVTPALEAYE | LGLYGTVTP | 0.5095 | 202 | WB BK VP2-3 |
| DRB1_1302 | 40 VQIASLATVEGITTT | IASLATVEG | 0.5094 | 202 | WB BK VP2-3 |
| DRB1_1302 | 80 GFAALIQTVTGISSL | IQTVTGISS | 0.5080 | 205 | WB BK VP2-3 |
| DRB1_1302 | 39 EVQIASLATVEGITT | IASLATVEG | 0.5076 | 206 | WB BK VP2-3 |
| DRB1_1302 | 81 FAALIQTVTGISSLA | IQTVTGISS | 0.5054 | 211 | WB BK VP2-3 |
| DRB1_1302 | 78 IAGFAALIQTVTGIS | FAALIQTVT | 0.4783 | 283 | WB BK VP2-3 |
| DRB1_1302 | 82 AALIQTVTGISSLAQ | IQTVTGISS | 0.4693 | 312 | WB BK VP2-3 |
| DRB1_1302 | 83 ALIQTVTGISSLAQV | IQTVTGISS | 0.4437 | 411 | WB BK VP2-3 |
| DRB1_1302 | 109 VSTVGLYQQSGMALE | VGLYQQSGM | 0.4417 | 420 | WB BK VP2-3 |
| DRB1_1302 | 132 DILFPGVNTFVNNIQ | FPGVNTFVN | 0.4394 | 431 | WB BK VP2-3 |
| DRB1_1302 | 133 ILFPGVNTFVNNIQY | VNTFVNNIQ | 0.4339 | 457 | WB BK VP2-3 |
| DRB1_1302 | 203 TIVNAPINFYNYIQD | IVNAPINFY | 0.4317 | 468 | WB BK VP2-3 |
| DRB1_1302 | 110 STVGLYQQSGMALEL | VGLYQQSGM | 0.4274 | 490 | WB BK VP2-3 |
| DRB1_1501 | 259 TQRMDLRNKESVHSG | LRNKESVHS | 0.5055 | 211 | WB BK VP2-3 |
| DRB1_1501 | 258 VTQRMDLRNKESVHS | TQRMDLRNK | 0.4963 | 233 | WB BK VP2-3 |
| DRB1_1501 | 260 QRMDLRNKESVHSGE | LRNKESVHS | 0.4888 | 252 | WB BK VP2-3 |
| DRB1_1501 | 261 RMDLRNKESVHSGEF | LRNKESVHS | 0.4818 | 272 | WB BK VP2-3 |
| DRB1_1501 | 292 QWMLPLLLGLYGTVT | MLPLLLGLY | 0.4818 | 272 | WB BK VP2-3 |
| DRB1_1501 | 293 WMLPLLLGLYGTVTP | LLGLYGTVT | 0.4703 | 308 | WB BK VP2-3 |
| DRB1_1501 | 262 MDLRNKESVHSGEFI | LRNKESVHS | 0.4652 | 326 | WB BK VP2-3 |
| DRB1_1501 | 294 MLPLLLGLYGTVTPA | LLGLYGTVT | 0.4567 | 357 | WB BK VP2-3 |
| DRB1_1501 | 295 LPLLLGLYGTVTPAL | LLGLYGTVT | 0.4514 | 378 | WB BK VP2-3 |
| DRB1_1501 | 296 PLLLGLYGTVTPALE | LLGLYGTVT | 0.4387 | 434 | WB BK VP2-3 |
| DRB4_0101 | 213 NYIQDYYSNLSPIRP | IQDYYSNLS | 0.4336 | 458 | WB BK VP2-3 |
| DRB5_0101 | 216 QDYYSNLSPIRPSMV | YYSNLSPIR | 0.5417 | 142 | WB BK VP2-3 |
| DRB5_0101 | 214 YIQDYYSNLSPIRPS | YSNLSPIRP | 0.5315 | 159 | WB BK VP2-3 |
| DRB5_0101 | 215 IQDYYSNLSPIRPSM | YSNLSPIRP | 0.5316 | 159 | WB BK VP2-3 |
| DRB5_0101 | 213 NYIQDYYSNLSPIRP | YYSNLSPIR | 0.5308 | 160 | WB BK VP2-3 |
| DRB5_0101 | 217 DYYSNLSPIRPSMVR | YSNLSPIRP | 0.5081 | 205 | WB BK VP2-3 |
| DRB5_0101 | 218 YYSNLSPIRPSMVRQ | YYSNLSPIR | 0.4623 | 336 | WB BK VP2-3 |
| DRB5_0101 | 174 PAITSQELQRRTERF | ITSQELQRR | 0.4449 | 406 | WB BK VP2-3 |
| DRB5_0101 | 173 IPAITSQELQRRTER | ITSQELQRR | 0.4422 | 418 | WB BK VP2-3 |

SEQ ID NOS.: 58312-59135

Preferred BK virus fragments of VP1 capable of interacting with one or more MHC class 2 molecules are listed in Table Q.

TABLE Q

Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB1_0101 | 164 QGVLMNYRTKYPQGT | LMNYRTKYP | 0.7782 | 11 | SB | VP1 |
| DRB1_0101 | 165 GVLMNYRTKYPQGTI | YRTKYPQGT | 0.7768 | 11 | SB | VP1 |
| DRB1_0101 | 166 VLMNYRTKYPQGTIT | YRTKYPQGT | 0.7796 | 11 | SB | VP1 |
| DRB1_0101 | 167 LMNYRTKYPQGTITP | YRTKYPQGT | 0.7798 | 11 | SB | VP1 |
| DRB1_0101 | 168 MNYRTKYPQGTITPK | YRTKYPQGT | 0.7778 | 11 | SB | VP1 |
| DRB1_0101 | 118 KTEVIGITSMLNLHA | VIGITSMLN | 0.7623 | 13 | SB | VP1 |
| DRB1_0101 | 119 TEVIGITSMLNLHAG | VIGITSMLN | 0.7621 | 13 | SB | VP1 |
| DRB1_0101 | 233 PPVLHVTNTATTVLL | VTNTATTVL | 0.7280 | 19 | SB | VP1 |
| DRB1_0101 | 234 PVLHVTNTATTVLLD | VTNTATTVL | 0.7252 | 20 | SB | VP1 |
| DRB1_0101 | 235 VLHVTNTATTVLLDE | VTNTATTVL | 0.7244 | 20 | SB | VP1 |
| DRB1_0101 | 232 VPPVLHVTNTATTVL | VLHVTNTAT | 0.7197 | 21 | SB | VP1 |
| DRB1_0101 | 236 LHVTNTATTVLLDEQ | VTNTATTVL | 0.7207 | 21 | SB | VP1 |
| DRB1_0101 | 121 VIGITSMLNLHAGSQ | VIGITSMLN | 0.7107 | 23 | SB | VP1 |
| DRB1_0101 | 120 EVIGITSMLNLHAGS | VIGITSMLN | 0.7035 | 25 | SB | VP1 |
| DRB1_0101 | 266 ADICGLFTNSSGTQQ | ICGLFTNSS | 0.7009 | 25 | SB | VP1 |
| DRB1_0101 | 262 YVSAADICGLFTNSS | YVSAADICG | 0.6956 | 27 | SB | VP1 |
| DRB1_0101 | 117 VKTEVIGITSMLNLH | VIGITSMLN | 0.6913 | 28 | SB | VP1 |
| DRB1_0101 | 116 TVKTEVIGITSMLNL | VIGITSMLN | 0.6903 | 29 | SB | VP1 |
| DRB1_0101 | 115 VTVKTEVIGITSMLN | EVIGITSML | 0.6842 | 30 | SB | VP1 |
| DRB1_0101 | 169 NYRTKYPQGTITPKN | YRTKYPQGT | 0.6853 | 30 | SB | VP1 |
| DRB1_0101 | 265 AADICGLFTNSSGTQ | ICGLFTNSS | 0.6859 | 30 | SB | VP1 |
| DRB1_0101 | 170 YRTKYPQGTITPKNP | YRTKYPQGT | 0.6835 | 31 | SB | VP1 |
| DRB1_0101 | 264 SAADICGLFTNSSGT | ICGLFTNSS | 0.6829 | 31 | SB | VP1 |
| DRB1_0101 | 263 VSAADICGLFTNSSG | ICGLFTNSS | 0.6809 | 32 | SB | VP1 |
| DRB1_0101 | 305 FLLSDLINRRTQKVD | LINRRTQKV | 0.6730 | 34 | SB | VP1 |
| DRB1_0101 | 304 SFLLSDLINRRTQKV | LSDLINRRT | 0.6723 | 35 | SB | VP1 |
| DRB1_0101 | 105 TCGNLLMWEAVTVKT | LLMWEAVTV | 0.6651 | 37 | SB | VP1 |
| DRB1_0101 | 106 CGNLLMWEAVTVKTE | LLMWEAVTV | 0.6660 | 37 | SB | VP1 |
| DRB1_0101 | 107 GNLLMWEAVTVKTEV | LLMWEAVTV | 0.6675 | 37 | SB | VP1 |
| DRB1_0101 | 306 LLSDLINRRTQKVDG | LINRRTQKV | 0.6610 | 39 | SB | VP1 |
| DRB1_0101 | 307 LSDLINRRTQKVDGQ | LINRRTQKV | 0.6620 | 39 | SB | VP1 |
| DRB1_0101 | 308 SDLINRRTQKVDGQP | LINRRTQKV | 0.6493 | 44 | SB | VP1 |
| DRB1_0101 | 122 IGITSMLNLHAGSQK | ITSMLNLHA | 0.6472 | 45 | SB | VP1 |
| DRB1_0101 | 108 NLLMWEAVTVKTEVI | MWEAVTVKT | 0.6381 | 50 | WB | VP1 |
| DRB1_0101 | 237 HVTNTATTVLLDEQG | VTNTATTVL | 0.6362 | 51 | WB | VP1 |
| DRB1_0101 | 267 DICGLFTNSSGTQQW | ICGLFTNSS | 0.6283 | 56 | WB | VP1 |
| DRB1_0101 | 268 ICGLFTNSSGTQQWR | ICGLFTNSS | 0.6286 | 56 | WB | VP1 |
| DRB1_0101 | 104 LTCGNLLMWEAVTVK | LLMWEAVTV | 0.6269 | 57 | WB | VP1 |
| DRB1_0101 | 317 KVDGQPMYGMESQVE | VDGQPMYGM | 0.6232 | 59 | WB | VP1 |
| DRB1_0101 | 318 VDGQPMYGMESQVEE | MYGMESQVE | 0.6230 | 59 | WB | VP1 |

TABLE Q-continued

Prediction of BK virus VP1 protein specific MHC class 2, 15-mer peptide binders for 14 MHC class 2 alleles (see TABLE Q-continued Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB1_0101 | 295 RSVKNPYPIS-FLLSD | VKNPYPISF | 0.5161 | 188 | WB | VP1 |
| DRB1_0101 | 312 NRRTQKVDGQP-MYGM | KVDGQPMYG | 0.5163 | 188 | WB | VP1 |
| DRB1_0101 | 160 PLEMQGVLM-NYRTKY | MQGVLMNYR | 0.5148 | 190 | WB | VP1 |
| DRB1_0101 | 269 CGLFTNSS-GTQQWRG | FTNSSGTQQ | 0.5138 | 193 | WB | VP1 |
| DRB1_0101 | 292 LRKRSVKNPYP-ISFL | VKNPYPISF | 0.5094 | 202 | WB | VP1 |
| DRB1_0101 | 163 MQGVLMNYRT-KYPQG | LMNYRTKYP | 0.5072 | 207 | WB | VP1 |
| DRB1_0101 | 230 ENVPPVLHVTNT-ATT | VLHVTNTAT | 0.5053 | 211 | WB | VP1 |
| DRB1_0101 | 293 RKRSVKNPYPIS-FLL | VKNPYPISF | 0.5053 | 211 | WB | VP1 |
| DRB1_0101 | 270 GLFTNSS-GTQQWRGL | FTNSSGTQQ | 0.5035 | 215 | WB | VP1 |
| DRB1_0101 | 175 PQGTITP-KNPTAQSQ | ITPKNPTAQ | 0.5026 | 217 | WB | VP1 |
| DRB1_0101 | 176 QGTITP-KNPTAQSQV | ITPKNPTAQ | 0.5007 | 222 | WB | VP1 |
| DRB1_0101 | 291 RLRKRSVKNPYP-ISF | LRKRSVKNP | 0.5005 | 222 | WB | VP1 |
| DRB1_0101 | 125 TSMLNLHAGSQK-VHE | MLNLHAGSQ | 0.4968 | 231 | WB | VP1 |
| DRB1_0101 | 62 DNLRGYSQHL-SAENA | LRGYSQHLS | 0.4929 | 241 | WB | VP1 |
| DRB1_0101 | 83 DRKMLPCYSTAR-IPL | MLPCYSTAR | 0.4902 | 249 | WB | VP1 |
| DRB1_0101 | 87 LPCYSTAR-IPLPNLN | YSTARIPLP | 0.4891 | 252 | WB | VP1 |
| DRB1_0101 | 85 KMLPCYSTAR-IPLPN | YSTARIPLP | 0.4865 | 259 | WB | VP1 |
| DRB1_0101 | 349 IRYIDRQGQLQT-KMV | YIDRQGQLQ | 0.4856 | 261 | WB | VP1 |
| DRB1_0101 | 111 MWEAVTVKTE-VIGIT | MWEAVTVKT | 0.4847 | 264 | WB | VP1 |
| DRB1_0101 | 88 PCYSTARIPLPN-LNE | YSTARIPLP | 0.4819 | 272 | WB | VP1 |
| DRB1_0101 | 86 MLPCYSTAR-IPLPNL | YSTARIPLP | 0.4817 | 273 | WB | VP1 |
| DRB1_0101 | 23 VQVPKLLIKG-GVEVL | LLIKGGVEV | 0.4803 | 277 | WB | VP1 |
| DRB1_0101 | 61 DDNLRGYSQHL-SAEN | LRGYSQHLS | 0.4800 | 278 | WB | VP1 |
| DRB1_0101 | 179 ITP-KNPTAQSVMNT | ITPKNPTAQ | 0.4786 | 282 | WB | VP1 |
| DRB1_0101 | 285 ARYFKIRLRKRS-VKN | FKIRLRKRS | 0.4787 | 282 | WB | VP1 |
| DRB1_0101 | 155 AVGGDPLEMQGV-LMN | GDPLEMQGV | 0.4780 | 284 | WB | VP1 |
| DRB1_0101 | 284 LARYFKIRL-RKRSVK | FKIRLRKRS | 0.4764 | 289 | WB | VP1 |
| DRB1_0101 | 178 TITP-KNPTAQSVMN | ITPKNPTAQ | 0.4755 | 291 | WB | VP1 |
| DRB1_0101 | 282 RGLARYFKIRL-RKRS | YFKIRLRKR | 0.4754 | 292 | WB | VP1 |
| DRB1_0101 | 283 GLARYFKIRL-RKRSV | FKIRLRKRS | 0.4744 | 295 | WB | VP1 |
| DRB1_0101 | 173 KYPQGTITP-KNPTAQ | PQGTITPKN | 0.4716 | 304 | WB | VP1 |
| DRB1_0101 | 174 YPQGTITP-KNPTAQS | ITPKNPTAQ | 0.4716 | 304 | WB | VP1 |
| DRB1_0101 | 224 GTYTGGENVPPV-LHV | YTGGENVPP | 0.4697 | 310 | WB | VP1 |
| DRB1_0101 | 322 PMYGMESQVEEVRVF | MYGMESQVE | 0.4691 | 312 | WB | VP1 |
| DRB1_0101 | 156 VGGDPLEMQGV-LMNY | LEMQGVLMN | 0.4685 | 314 | WB | VP1 |
| DRB1_0101 | 25 VPKLLIKGGVEV-LEV | LLIKGGVEV | 0.4678 | 317 | WB | VP1 |
| DRB1_0101 | 24 QVPKLLIKG-GVEVLE | LLIKGGVEV | 0.4674 | 318 | WB | VP1 |
| DRB1_0101 | 22 PVQVPKLLIKG-GVEV | VPKLLIKGG | 0.4668 | 320 | WB | VP1 |
| DRB1_0101 | 261 LYVSAADICGLFTNS | YVSAADICG | 0.4665 | 321 | WB | VP1 |
| DRB1_0101 | 26 PKLLIKGGVEV-LEVK | LLIKGGVEV | 0.4633 | 332 | WB | VP1 |

TABLE Q-continued

Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB1_0101 | 151 FHFFAVGGD-PLEMQG | VGGDPLEMQ | 0.4633 | 333 | WB | VP1 |
| DRB1_0101 | 323 MYGMESQVEEVRVFDMYGMESQVE | | 0.4626 | 335 | WB | VP1 |
| DRB1_0101 | 150 NFHFFAVGGD-PLEMQ | AVGGDPLEM | 0.4611 | 340 | WB | VP1 |
| DRB1_0101 | 223 FGTYTGGENVP-PVLH | YTGGENVPP | 0.4596 | 346 | WB | VP1 |
| DRB1_0101 | 297 VKNPYPISFLLS-DLI | VKNPYPISF | 0.4588 | 349 | WB | VP1 |
| DRB1_0101 | 63 NLRGYSQHLSAE-NAF | YSQHLSAEN | 0.4583 | 351 | WB | VP1 |
| DRB1_0101 | 152 HFFAVGGD-PLEMQGV | VGGDPLEMQ | 0.4576 | 354 | WB | VP1 |
| DRB1_0101 | 286 RYFKIRLRKRS-VKNP | FKIRLRKRS | 0.4564 | 358 | WB | VP1 |
| DRB1_0101 | 64 LRGYSQHLSAE-NAFE | YSQHLSAEN | 0.4559 | 360 | WB | VP1 |
| DRB1_0101 | 220 TRYFGTYTGGEN-VPP | YFGTYTGGE | 0.4546 | 365 | WB | VP1 |
| DRB1_0101 | 301 YPISFLLSDLIN-RRT | ISFLLSDLI | 0.4540 | 368 | WB | VP1 |
| DRB1_0101 | 126 SMLNLHAGSQK-VHEN | MLNLHAGSQ | 0.4520 | 376 | WB | VP1 |
| DRB1_0101 | 34 VEVLEVKTGV-DAITE | VKTGVDAIT | 0.4507 | 381 | WB | VP1 |
| DRB1_0101 | 33 GVEVLEVKTGV-DAIT | VEVLEVKTG | 0.4499 | 385 | WB | VP1 |
| DRB1_0101 | 226 YTGGENVPPVL-HVTN | YTGGENVPP | 0.4471 | 397 | WB | VP1 |
| DRB1_0101 | 303 ISFLLSDLIN-RRTQK | LSDLINRRT | 0.4468 | 397 | WB | VP1 |
| DRB1_0101 | 153 FFAVGGD-PLEMQGVL | VGGDPLEMQ | 0.4446 | 407 | WB | VP1 |
| DRB1_0101 | 225 TYTGGENVPPVL-HVT | YTGGENVPP | 0.4439 | 410 | WB | VP1 |
| DRB1_0101 | 302 PISFLLSDLIN-RRTQ | LSDLINRRT | 0.4439 | 411 | WB | VP1 |
| DRB1_0101 | 36 VLEVKTGVDAIT-EVE | VKTGVDAIT | 0.4399 | 429 | WB | VP1 |
| DRB1_0101 | 35 EVLEVKTGV-DAITEV | VKTGVDAIT | 0.4395 | 430 | WB | VP1 |
| DRB1_0101 | 37 LEVKTGVDAIT-EVEC | VKTGVDAIT | 0.4381 | 437 | WB | VP1 |
| DRB1_0101 | 127 MLNLHAGSQK-VHENG | MLNLHAGSQ | 0.4375 | 440 | WB | VP1 |
| DRB1_0101 | 229 GENVPPVL-HVTNTAT | NVPPVLHVT | 0.4368 | 443 | WB | VP1 |
| DRB1_0101 | 60 PDDNLRGYSQHL-SAE | LRGYSQHLS | 0.4346 | 454 | WB | VP1 |
| DRB1_0101 | 59 DPDDNLR-GYSQHLSA | LRGYSQHLS | 0.4337 | 458 | WB | VP1 |
| DRB1_0101 | 65 RGYSQHLSAE-NAFES | YSQHLSAEN | 0.4335 | 459 | WB | VP1 |
| DRB1_0101 | 27 KLLIKGGVEV-LEVKT | LIKGGVEVL | 0.4331 | 461 | WB | VP1 |
| DRB1_0101 | 221 RYFGTYTGGEN-VPPV | YTGGENVPP | 0.4318 | 468 | WB | VP1 |
| DRB1_0101 | 296 SVKNPYPIS-FLLSDL | VKNPYPISF | 0.4317 | 468 | WB | VP1 |
| DRB1_0101 | 222 YFGTYTGGENVP-PVL | YTGGENVPP | 0.4313 | 470 | WB | VP1 |
| DRB1_0101 | 271 LFTNSSGTQQWR-GLA | FTNSSGTQQ | 0.4313 | 470 | WB | VP1 |
| DRB1_0101 | 58 GDPDDNLR-GYSQHLS | NLRGYSQHL | 0.4305 | 474 | WB | VP1 |
| DRB1_0101 | 281 WRGLARYFKIRL-RKR | WRGLARYFK | 0.4285 | 485 | WB | VP1 |
| DRB1_0101 | 276 SGTQQWRGLARY-FKI | WRGLARYFK | 0.4263 | 496 | WB | VP1 |
| DRB1_0101 | 154 FAVGGD-PLEMQGVLM | VGGDPLEMQ | 0.4261 | 498 | WB | VP1 |
| DRB1_0101 | 277 GTQQWRGLARY-FKIR | WRGLARYFK | 0.4259 | 498 | WB | VP1 |
| DRB1_0101 | 275 SSGTQQWR-GLARYFK | QQWRGLARY | 0.4258 | 499 | WB | VP1 |
| DRB1_0401 | 118 KTEVIGITSMLN-LHA | VIGITSMLN | 0.5278 | 165 | WB | VP1 |

TABLE Q-continued

Prediction of BK virus VP1 protein specific MHC class 2, 15-mer peptide binders for 14 MHC class 2 alleles (see TABLE Q-continued Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB1_0404 | 265 AADICGLFTNSSGTQ | ICGLFTNSS | 0.5081 | 205 | WB | VP1 |
| DRB1_0404 | 167 LMNYRTKYPQGTITP | LMNYRTKYP | 0.5069 | 208 | WB | VP1 |
| DRB1_0404 | 304 SFLLSDLINRRTQKV | LLSDLINRR | 0.4931 | 241 | WB | VP1 |
| DRB1_0404 | 301 YPISFLLSDLINRRT | LLSDLINRR | 0.4876 | 256 | WB | VP1 |
| DRB1_0404 | 119 TEVIGITSMLNLHAG | ITSMLNLHA | 0.4851 | 263 | WB | VP1 |
| DRB1_0404 | 302 PISFLLSDLINRRTQ | LLSDLINRR | 0.4821 | 271 | WB | VP1 |
| DRB1_0404 | 303 ISFLLSDLINRRTQK | LLSDLINRR | 0.4816 | 273 | WB | VP1 |
| DRB1_0404 | 118 KTEVIGITSMLNLHA | VIGITSMLN | 0.4807 | 275 | WB | VP1 |
| DRB1_0404 | 46 ITEVECFLNPEMGDP | TEVECFLNP | 0.4807 | 275 | WB | VP1 |
| DRB1_0404 | 47 TEVECFLNPEMGDPD | FLNPEMGDP | 0.4801 | 277 | WB | VP1 |
| DRB1_0404 | 48 EVECFLNPEMGDPDD | FLNPEMGDP | 0.4754 | 292 | WB | VP1 |
| DRB1_0404 | 50 ECFLNPEMGDPDDNL | FLNPEMGDP | 0.4751 | 293 | WB | VP1 |
| DRB1_0404 | 49 VECFLNPEMGDPDDN | FLNPEMGDP | 0.4745 | 295 | WB | VP1 |
| DRB1_0404 | 267 DICGLFTNSSGTQQW | LFTNSSGTQ | 0.4682 | 315 | WB | VP1 |
| DRB1_0404 | 268 ICGLFTNSSGTQQWR | LFTNSSGTQ | 0.4665 | 321 | WB | VP1 |
| DRB1_0404 | 84 RKMLPCYSTARIPLP | MLPCYSTAR | 0.4629 | 334 | WB | VP1 |
| DRB1_0404 | 105 TCGNLLMWEAVTVKT | LMWEAVTVK | 0.4618 | 338 | WB | VP1 |
| DRB1_0404 | 106 CGNLLMWEAVTVKTE | LMWEAVTVK | 0.4597 | 346 | WB | VP1 |
| DRB1_0404 | 232 VPPVLHVTNTATTVL | LHVTNTATT | 0.4584 | 351 | WB | VP1 |
| DRB1_0404 | 300 PYPISFLLSDLINRR | FLLSDLINR | 0.4582 | 351 | WB | VP1 |
| DRB1_0404 | 120 EVIGITSMLNLHAGS | ITSMLNLHA | 0.4575 | 354 | WB | VP1 |
| DRB1_0404 | 107 GNLLMWEAVTVKTEV | LMWEAVTVK | 0.4552 | 363 | WB | VP1 |
| DRB1_0404 | 233 PPVLHVTNTATTVLL | LHVTNTATT | 0.4466 | 398 | WB | VP1 |
| DRB1_0404 | 230 ENVPPVLHVTNTATT | VLHVTNTAT | 0.4465 | 399 | WB | VP1 |
| DRB1_0404 | 108 NLLMWEAVTVKTEVI | LMWEAVTVK | 0.4456 | 403 | WB | VP1 |
| DRB1_0404 | 305 FLLSDLINRRTQKVD | LLSDLINRR | 0.4431 | 414 | WB | VP1 |
| DRB1_0404 | 192 NTDHKAYLDKNNAYP | KAYLDKNNA | 0.4422 | 418 | WB | VP1 |
| DRB1_0404 | 193 TDHKAYLDKNNAYPV | YLDKNNAYP | 0.4402 | 427 | WB | VP1 |
| DRB1_0404 | 231 NVPPVLHVTNTATTV | LHVTNTATT | 0.4401 | 428 | WB | VP1 |
| DRB1_0404 | 194 DHKAYLDKNNAYPVE | YLDKNNAYP | 0.4393 | 431 | WB | VP1 |
| DRB1_0404 | 85 KMLPCYSTARIPLPN | YSTARIPLP | 0.4335 | 459 | WB | VP1 |
| DRB1_0404 | 234 PVLHVTNTATTVLLD | LHVTNTATT | 0.4328 | 463 | WB | VP1 |
| DRB1_0404 | 195 HKAYLDKNNAYPVEC | YLDKNNAYP | 0.4303 | 476 | WB | VP1 |
| DRB1_0404 | 196 KAYLDKNNAYPVECW | YLDKNNAYP | 0.4288 | 483 | WB | VP1 |
| DRB1_0404 | 104 LTCGNLLMWEAVTVK | LLMWEAVTV | 0.4272 | 492 | WB | VP1 |
| DRB1_0405 | 205 YPVECWIPDPSRNEN | WIPDPSRNE | 0.4758 | 291 | WB | VP1 |
| DRB1_0405 | 204 AYPVECWIPDPSRNE | ECWIPDPSR | 0.4737 | 297 | WB | VP1 |
| DRB1_0405 | 118 KTEVIGITSMLNLHA | VIGITSMLN | 0.4649 | 327 | WB | VP1 |

TABLE Q-continued

Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB1_0405 | 119 TEVIGITSMLNLHAG | VIGITSMLN | 0.4617 | 338 | WB | VP1 |
| DRB1_0405 | 88 PCYSTARIPLPNLNE | YSTARIPLP | 0.4515 | 378 | WB | VP1 |
| DRB1_0405 | 206 PVECWIPDPSRNENT | WIPDPSRNE | 0.4387 | 434 | WB | VP1 |
| DRB1_0405 | 115 VTVKTEVIGITSMLN | TVKTEVIGI | 0.4272 | 492 | WB | VP1 |
| DRB1_0701 | 232 VPPVLHVTNTATTVL | VLHVTNTAT | 0.7832 | 10 | SB | VP1 |
| DRB1_0701 | 233 PPVLHVTNTATTVLL | VTNTATTVL | 0.7867 | 10 | SB | VP1 |
| DRB1_0701 | 234 PVLHVTNTATTVLLD | VTNTATTVL | 0.7821 | 11 | SB | VP1 |
| DRB1_0701 | 235 VLHVTNTATTVLLDE | VTNTATTVL | 0.7792 | 11 | SB | VP1 |
| DRB1_0701 | 236 LHVTNTATTVLLDEQ | VTNTATTVL | 0.7807 | 11 | SB | VP1 |
| DRB1_0701 | 237 HVTNTATTVLLDEQG | VTNTATTVL | 0.6865 | 30 | SB | VP1 |
| DRB1_0701 | 238 VTNTATTVLLDEQGV | VTNTATTVL | 0.6833 | 31 | SB | VP1 |
| DRB1_0701 | 304 SFLLSDLINRRTQKV | LSDLINRRT | 0.5382 | 148 | WB | VP1 |
| DRB1_0701 | 308 SDLINRRTQKVDGQP | LINRRTQKV | 0.5370 | 150 | WB | VP1 |
| DRB1_0701 | 305 FLLSDLINRRTQKVD | LINRRTQKV | 0.5365 | 151 | WB | VP1 |
| DRB1_0701 | 306 LLSDLINRRTQKVDG | LINRRTQKV | 0.5340 | 155 | WB | VP1 |
| DRB1_0701 | 307 LSDLINRRTQKVDGQ | LINRRTQKV | 0.5332 | 156 | WB | VP1 |
| DRB1_0701 | 231 NVPPVLHVTNTATTV | VLHVTNTAT | 0.4751 | 293 | WB | VP1 |
| DRB1_0701 | 107 GNLLMWEAVTVKTEV | LLMWEAVTV | 0.4593 | 347 | WB | VP1 |
| DRB1_0701 | 105 TCGNLLMWEAVTVKT | LLMWEAVTV | 0.4539 | 368 | WB | VP1 |
| DRB1_0701 | 106 CGNLLMWEAVTVKTE | LLMWEAVTV | 0.4530 | 372 | WB | VP1 |
| DRB1_0701 | 104 LTCGNLLMWEAVTVK | LLMWEAVTV | 0.4517 | 377 | WB | VP1 |
| DRB1_0701 | 103 DLTCGNLLMWEAVTV | LTCGNLLMW | 0.4475 | 395 | WB | VP1 |
| DRB1_0701 | 230 ENVPPVLHVTNTATT | VLHVTNTAT | 0.4461 | 401 | WB | VP1 |
| DRB1_0701 | 309 DLINRRTQKVDGQPM | LINRRTQKV | 0.4383 | 436 | WB | VP1 |
| DRB1_0701 | 310 LINRRTQKVDGQPMY | LINRRTQKV | 0.4370 | 442 | WB | VP1 |
| DRB1_0701 | 285 ARYFKIRLRKRSVKN | YFKIRLRKR | 0.4289 | 483 | WB | VP1 |
| DRB1_0701 | 249 EQGVGPLCKADSLYV | PLCKADSLY | 0.4260 | 498 | WB | VP1 |
| DRB1_0802 | 282 RGLARYFKIRLRKRS | RGLARYFKI | 0.5826 | 91 | WB | VP1 |
| DRB1_0802 | 283 GLARYFKIRLRKRSV | FKIRLRKRS | 0.5827 | 91 | WB | VP1 |
| DRB1_0802 | 284 LARYFKIRLRKRSVK | FKIRLRKRS | 0.5824 | 92 | WB | VP1 |
| DRB1_0802 | 285 ARYFKIRLRKRSVKN | FKIRLRKRS | 0.5816 | 92 | WB | VP1 |
| DRB1_0802 | 286 RYFKIRLRKRSVKNP | FKIRLRKRS | 0.5825 | 92 | WB | VP1 |
| DRB1_0802 | 287 YFKIRLRKRSVKNPY | FKIRLRKRS | 0.4907 | 247 | WB | VP1 |
| DRB1_0802 | 288 FKIRLRKRSVKNPYP | FKIRLRKRS | 0.4905 | 248 | WB | VP1 |
| DRB1_0901 | 84 RKMLPCYSTARIPLP | LPCYSTARI | 0.5150 | 190 | WB | VP1 |
| DRB1_0901 | 85 KMLPCYSTARIPLPN | YSTARIPLP | 0.5124 | 195 | WB | VP1 |
| DRB1_0901 | 86 MLPCYSTARIPLPNL | YSTARIPLP | 0.4991 | 226 | WB | VP1 |
| DRB1_0901 | 87 LPCYSTARIPLPNLN | YSTARIPLP | 0.4968 | 231 | WB | VP1 |

TABLE Q-continued

Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB1_0901 | 88 PCYSTARIPLPN-LNE | YSTARIPLP | 0.4598 | 345 | WB | VP1 |
| DRB1_1101 | 276 SGTQQWRGLARY-FKI | WRGLARYFK | 0.5202 | 180 | WB | VP1 |
| DRB1_1101 | 277 GTQQWRGLARY-FKIR | WRGLARYFK | 0.5200 | 180 | WB | VP1 |
| DRB1_1101 | 278 TQQWRGLARY-FKIRL | WRGLARYFK | 0.5165 | 187 | WB | VP1 |
| DRB1_1101 | 275 SSGTQQWR-GLARYFK | QQWRGLARY | 0.5148 | 191 | WB | VP1 |
| DRB1_1101 | 279 QQWRGLARY-FKIRLR | WRGLARYFK | 0.5146 | 191 | WB | VP1 |
| DRB1_1101 | 281 WRGLARYFKIRL-RKR | WRGLARYFK | 0.4569 | 357 | WB | VP1 |
| DRB1_1101 | 280 QWRGLARY-FKIRLRK | WRGLARYFK | 0.4404 | 426 | WB | VP1 |
| DRB1_1302 | 161 LEMQGVLMNYRT-KYP | VLMNYRTKY | 0.6366 | 51 | WB | VP1 |
| DRB1_1302 | 162 EMQGVLMNYRT-KYPQ | VLMNYRTKY | 0.6357 | 51 | WB | VP1 |
| DRB1_1302 | 163 MQGVLMNYRT-KYPQG | VLMNYRTKY | 0.6190 | 62 | WB | VP1 |
| DRB1_1302 | 164 QGVLMNYRT-KYPQGT | VLMNYRTKY | 0.6178 | 63 | WB | VP1 |
| DRB1_1302 | 160 PLEMQGVLM-NYRTKY | QGVLMNYRT | 0.6118 | 67 | WB | VP1 |
| DRB1_1302 | 233 PPVLHVTNTATT-VLL | VTNTATTVL | 0.6016 | 75 | WB | VP1 |
| DRB1_1302 | 234 PVLHVTNTATTV-LLD | VTNTATTVL | 0.5831 | 91 | WB | VP1 |
| DRB1_1302 | 232 VPPVLHVTNTAT-TVL | VLHVTNTAT | 0.5808 | 93 | WB | VP1 |
| DRB1_1302 | 235 VLHVTNTATTV-LLDE | VTNTATTVL | 0.5658 | 110 | WB | VP1 |
| DRB1_1302 | 284 LARYFKIRL-RKRSVK | FKIRLRKRS | 0.5521 | 127 | WB | VP1 |
| DRB1_1302 | 165 GVLMNYRT-KYPQGTI | VLMNYRTKY | 0.5482 | 133 | WB | VP1 |
| DRB1_1302 | 285 ARYFKIRLRKRS-VKN | FKIRLRKRS | 0.5453 | 137 | WB | VP1 |
| DRB1_1302 | 286 RYFKIRLRKRS-VKNP | FKIRLRKRS | 0.5448 | 138 | WB | VP1 |
| DRB1_1302 | 287 YFKIRLRKRS-VKNPY | IRLRKRSVK | 0.5427 | 141 | WB | VP1 |
| DRB1_1302 | 236 LHVTNTATTVLL-DEQ | VTNTATTVL | 0.5416 | 143 | WB | VP1 |
| DRB1_1302 | 288 FKIRLRKRSVKN-PYP | IRLRKRSVK | 0.5351 | 153 | WB | VP1 |
| DRB1_1302 | 117 VKTEVIG-ITSMLNLH | IGITSMLNL | 0.5226 | 175 | WB | VP1 |
| DRB1_1302 | 166 VLMNYRT-KYPQGTIT | VLMNYRTKY | 0.5220 | 176 | WB | VP1 |
| DRB1_1302 | 116 TVKTEVIG-ITSMLNL | EVIGITSML | 0.5120 | 196 | WB | VP1 |
| DRB1_1302 | 282 RGLARYFKIRL-RKRS | LARYFKIRL | 0.4951 | 236 | WB | VP1 |
| DRB1_1302 | 118 KTEVIGITSMLN-LHA | IGITSMLNL | 0.4947 | 237 | WB | VP1 |
| DRB1_1302 | 283 GLARYFKIRL-RKRSV | FKIRLRKRS | 0.4916 | 245 | WB | VP1 |
| DRB1_1302 | 304 SFLLSDLIN-RRTQKV | LLSDLINRR | 0.4893 | 251 | WB | VP1 |
| DRB1_1302 | 305 FLLSDLIN-RRTQKVD | LINRRTQKV | 0.4877 | 255 | WB | VP1 |
| DRB1_1302 | 119 TEVIGITSMLNL-HAG | IGITSMLNL | 0.4792 | 280 | WB | VP1 |
| DRB1_1302 | 120 EVIGITSMLNL-HAGS | IGITSMLNL | 0.4786 | 282 | WB | VP1 |
| DRB1_1302 | 91 STARIPLPN-LNEDLT | ARIPLPNLN | 0.4726 | 301 | WB | VP1 |
| DRB1_1302 | 237 HVTNTATTVLLD-EQG | VTNTATTVL | 0.4703 | 308 | WB | VP1 |
| DRB1_1302 | 95 IPLPN-LNEDLTCGNL | LPNLNEDLT | 0.4680 | 316 | WB | VP1 |
| DRB1_1302 | 93 ARIPLPN-LNEDLTCG | LPNLNEDLT | 0.4675 | 318 | WB | VP1 |

TABLE Q-continued

Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB1_1302 | 94 RIPLPNLNEDLTCGN | LPNLNEDLT | 0.4673 | 318 | WB | VP1 |
| DRB1_1302 | 159 DPLEMQGVLMNYRTK | QGVLMNYRT | 0.4669 | 320 | WB | VP1 |
| DRB1_1302 | 92 TARIPLPNLNEDLTC | LPNLNEDLT | 0.4645 | 328 | WB | VP1 |
| DRB1_1302 | 158 GDPLEMQGVLMNYRT | LEMQGVLMN | 0.4643 | 329 | WB | VP1 |
| DRB1_1302 | 289 KIRLRKRSVKNPYPI | RKRSVKNPY | 0.4576 | 354 | WB | VP1 |
| DRB1_1302 | 290 IRLRKRSVKNPYPIS | RKRSVKNPY | 0.4565 | 358 | WB | VP1 |
| DRB1_1302 | 306 LLSDLINRRTQKVDG | LINRRTQKV | 0.4527 | 373 | WB | VP1 |
| DRB1_1302 | 122 IGITSMLNLHAGSQK | IGITSMLNL | 0.4502 | 383 | WB | VP1 |
| DRB1_1302 | 115 VTVKTEVIGITSMLN | VKTEVIGIT | 0.4481 | 392 | WB | VP1 |
| DRB1_1302 | 114 AVTVKTEVIGITSML | VKTEVIGIT | 0.4425 | 417 | WB | VP1 |
| DRB1_1302 | 238 VTNTATTVLLDEQGV | VTNTATTVL | 0.4366 | 444 | WB | VP1 |
| DRB1_1302 | 307 LSDLINRRTQKVDGQ | LINRRTQKV | 0.4354 | 450 | WB | VP1 |
| DRB1_1302 | 23 VQVPKLLIKGGVEVL | LLIKGGVEV | 0.4322 | 466 | WB | VP1 |
| DRB1_1302 | 266 ADICGLFTNSSGTQQ | LFTNSSGTQ | 0.4320 | 466 | WB | VP1 |
| DRB1_1302 | 267 DICGLFTNSSGTQQW | FTNSSGTQQ | 0.4291 | 481 | WB | VP1 |
| DRB1_1501 | 283 GLARYFKIRLRKRSV | YFKIRLRKR | 0.6573 | 41 | SB | VP1 |
| DRB1_1501 | 282 RGLARYFKIRLRKRS | YFKIRLRKR | 0.6478 | 45 | SB | VP1 |
| DRB1_1501 | 284 LARYFKIRLRKRSVK | YFKIRLRKR | 0.6478 | 45 | SB | VP1 |
| DRB1_1501 | 285 ARYFKIRLRKRSVKN | YFKIRLRKR | 0.6480 | 45 | SB | VP1 |
| DRB1_1501 | 281 WRGLARYFKIRLRKR | ARYFKIRLR | 0.6307 | 54 | WB | VP1 |
| DRB1_1501 | 286 RYFKIRLRKRSVKNP | YFKIRLRKR | 0.5738 | 101 | WB | VP1 |
| DRB1_1501 | 279 QQWRGLARYFKIRLR | WRGLARYFK | 0.5664 | 109 | WB | VP1 |
| DRB1_1501 | 287 YFKIRLRKRSVKNPY | YFKIRLRKR | 0.5644 | 111 | WB | VP1 |
| DRB1_1501 | 301 YPISFLLSDLINRRT | FLLSDLINR | 0.5442 | 139 | WB | VP1 |
| DRB1_1501 | 280 QWRGLARYFKIRLRK | ARYFKIRLR | 0.5432 | 140 | WB | VP1 |
| DRB1_1501 | 302 PISFLLSDLINRRTQ | FLLSDLINR | 0.5326 | 157 | WB | VP1 |
| DRB1_1501 | 303 ISFLLSDLINRRTQK | FLLSDLINR | 0.5312 | 160 | WB | VP1 |
| DRB1_1501 | 304 SFLLSDLINRRTQKV | LLSDLINRR | 0.5284 | 165 | WB | VP1 |
| DRB1_1501 | 300 PYPISFLLSDLINRR | FLLSDLINR | 0.5247 | 171 | WB | VP1 |
| DRB1_1501 | 305 FLLSDLINRRTQKVD | FLLSDLINR | 0.5067 | 208 | WB | VP1 |
| DRB1_1501 | 104 LTCGNLLMWEAVTVK | LLMWEAVTV | 0.5050 | 212 | WB | VP1 |
| DRB1_1501 | 105 TCGNLLMWEAVTVKT | LLMWEAVTV | 0.5048 | 212 | WB | VP1 |
| DRB1_1501 | 107 GNLLMWEAVTVKTEV | LLMWEAVTV | 0.5033 | 216 | WB | VP1 |
| DRB1_1501 | 106 CGNLLMWEAVTVKTE | LLMWEAVTV | 0.5029 | 217 | WB | VP1 |
| DRB1_1501 | 161 LEMQGVLMNYRTKYP | MQGVLMNYR | 0.4970 | 231 | WB | VP1 |
| DRB1_1501 | 278 TQQWRGLARYFKIRL | WRGLARYFK | 0.4915 | 245 | WB | VP1 |
| DRB1_1501 | 275 SSGTQQWRGLARYFK | TQQWRGLAR | 0.4823 | 271 | WB | VP1 |
| DRB1_1501 | 276 SGTQQWRGLARYFKI | TQQWRGLAR | 0.4818 | 272 | WB | VP1 |

TABLE Q-continued

Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB1_1501 | 163 MQGVLMNYRT-KYPQG | MQGVLMNYR | 0.4769 | 287 | WB | VP1 |
| DRB1_1501 | 299 NPYPISFLLS-DLINR | ISFLLSDLI | 0.4742 | 296 | WB | VP1 |
| DRB1_1501 | 162 EMQGVLMNYRT-KYPQ | MQGVLMNYR | 0.4707 | 307 | WB | VP1 |
| DRB1_1501 | 288 FKIRLRKRSVKN-PYP | IRLRKRSVK | 0.4578 | 353 | WB | VP1 |
| DRB1_1501 | 277 GTQQWRGLARY-FKIR | WRGLARYFK | 0.4564 | 358 | WB | VP1 |
| DRB1_1501 | 108 NLLMWEAVTVK-TEVI | LLMWEAVTV | 0.4524 | 374 | WB | VP1 |
| DRB1_1501 | 160 PLEMQGVLM-NYRTKY | MQGVLMNYR | 0.4445 | 408 | WB | VP1 |
| DRB1_1501 | 122 IGITSMLNLHAG-SQK | ITSMLNLHA | 0.4316 | 469 | WB | VP1 |
| DRB4_0101 | 205 YPVECWIP-DPSRNEN | VECWIPDPS | 0.5233 | 174 | WB | VP1 |
| DRB4_0101 | 203 NAYPVECWIP-DPSRN | VECWIPDPS | 0.5154 | 189 | WB | VP1 |
| DRB4_0101 | 204 AYPVECWIP-DPSRNE | VECWIPDPS | 0.5145 | 191 | WB | VP1 |
| DRB4_0101 | 202 NNAYPVECWIP-DPSR | VECWIPDPS | 0.5002 | 223 | WB | VP1 |
| DRB4_0101 | 201 KNNAYPVECWIP-DPS | YPVECWIPD | 0.4824 | 271 | WB | VP1 |
| DRB4_0101 | 206 PVECWIPDPSR-NENT | VECWIPDPS | 0.4517 | 377 | WB | VP1 |
| DRB4_0101 | 207 VECWIPDPSR-NENTR | VECWIPDPS | 0.4492 | 388 | WB | VP1 |
| DRB5_0101 | 285 ARYFKIRLRKRS-VKN | FKIRLRKRS | 0.6288 | 55 | WB | VP1 |
| DRB5_0101 | 284 LARYFKIRL-RKRSVK | FKIRLRKRS | 0.6287 | 56 | WB | VP1 |
| DRB5_0101 | 282 RGLARYFKIRL-RKRS | YFKIRLRKR | 0.6211 | 60 | WB | VP1 |
| DRB5_0101 | 283 GLARYFKIRL-RKRSV | FKIRLRKRS | 0.6196 | 61 | WB | VP1 |
| DRB5_0101 | 286 RYFKIRLRKRS-VKNP | FKIRLRKRS | 0.5991 | 77 | WB | VP1 |
| DRB5_0101 | 287 YFKIRLRKRS-VKNPY | FKIRLRKRS | 0.5403 | 145 | WB | VP1 |
| DRB5_0101 | 281 WRGLARYFKIRL-RKR | WRGLARYFK | 0.4956 | 235 | WB | VP1 |
| DRB5_0101 | 288 FKIRLRKRSVKN-PYP | FKIRLRKRS | 0.4834 | 267 | WB | VP1 |
| DRB5_0101 | 164 QGVLMNYRT-KYPQGT | LMNYRTKYP | 0.4622 | 337 | WB | VP1 |
| DRB5_0101 | 165 GVLMNYRT-KYPQGTI | YRTKYPQGT | 0.4558 | 361 | WB | VP1 |
| DRB5_0101 | 177 GTITP-KNPTAQSQVM | ITPKNPTAQ | 0.4497 | 386 | WB | VP1 |
| DRB5_0101 | 71 LSAENAFESDSP-DRK | AFESDSPDR | 0.4477 | 394 | WB | VP1 |
| DRB5_0101 | 72 SAENAFESDSP-DRKM | FESDSPDRK | 0.4472 | 396 | WB | VP1 |
| DRB5_0101 | 73 AENAFESDSP-DRKML | FESDSPDRK | 0.4469 | 397 | WB | VP1 |
| DRB5_0101 | 173 KYPQGTITP-KNPTAQ | QGTITPKNP | 0.4468 | 398 | WB | VP1 |
| DRB5_0101 | 74 ENAFESDSPDRK-MLP | FESDSPDRK | 0.4464 | 400 | WB | VP1 |
| DRB5_0101 | 275 SSGTQQWR-GLARYFK | TQQWRGLAR | 0.4455 | 403 | WB | VP1 |
| DRB5_0101 | 174 YPQGTITP-KNPTAQS | ITPKNPTAQ | 0.4442 | 409 | WB | VP1 |
| DRB5_0101 | 276 SGTQQWRGLARY-FKI | WRGLARYFK | 0.4440 | 410 | WB | VP1 |
| DRB5_0101 | 279 QQWRGLARY-FKIRLR | WRGLARYFK | 0.4423 | 417 | WB | VP1 |
| DRB5_0101 | 277 GTQQWRGLARY-FKIR | WRGLARYFK | 0.4408 | 424 | WB | VP1 |
| DRB5_0101 | 278 TQQWRGLARY-FKIRL | WRGLARYFK | 0.4408 | 424 | WB | VP1 |
| DRB5_0101 | 176 QGTITP-KNPTAQSQV | ITPKNPTAQ | 0.4392 | 432 | WB | VP1 |

TABLE Q-continued

Prediction of BK virus VP1 protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allel | pospeptide | core | 1-log50k(aff) | aff(nM) | Bind level | Identity |
|---|---|---|---|---|---|---|
| DRB5_0101 | 175 PQGTITP-KNPTAQSQ | ITPKNPTAQ | 0.4390 | 433 | WB | VP1 |
| DRB5_0101 | 166 VLMNYRT-KYPQGTIT | YRTKYPQGT | 0.4344 | 455 | WB | VP1 |
| DRB5_0101 | 168 MNYRT-KYPQGTITPK | YRTKYPQGT | 0.4342 | 456 | WB | VP1 |
| DRB5_0101 | 75 NAFESDSPDRKM-LPC | FESDSPDRK | 0.4294 | 480 | WB | VP1 |

SEQ ID NOS.: 59136-59917

Preferred BK virus fragments of small T antigen capable of interacting with one or more MHC class 2 molecules are listed in Table R.

TABLE R

Prediction of BK virus small t protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0101 | 21 RAAWGNLPLMR-KAYL | WGNLPLMRK | 0.6972 | 26 | SB | Small t |
| DRB1_0101 | 19 LERAAWGNLPLM-RKA | WGNLPLMRK | 0.6958 | 27 | SB | Small t |
| DRB1_0101 | 20 ERAAWGNLPLMR-KAY | WGNLPLMRK | 0.6940 | 27 | SB | Small t |
| DRB1_0101 | 22 AAWGNLPLMR-KAYLK | WGNLPLMRK | 0.6954 | 27 | SB | Small t |
| DRB1_0101 | 18 GLERAAWGNL-PLMRK | ERAAWGNLP | 0.6928 | 28 | SB | Small t |
| DRB1_0101 | 24 WGNLPLMRKAY-LKKC | WGNLPLMRK | 0.6020 | 74 | WB | Small t |
| DRB1_0101 | 23 AWGNLPLMRKAY-LKK | WGNLPLMRK | 0.6000 | 76 | WB | Small t |
| DRB1_0101 | 110 PCMLCQLRLRHL-NRK | LCQLRLRHL | 0.5884 | 86 | WB | Small t |
| DRB1_0101 | 111 CMLCQLRLRHLN-RKF | LCQLRLRHL | 0.5833 | 91 | WB | Small t |
| DRB1_0101 | 108 HCPCMLCQLRL-RHLN | LCQLRLRHL | 0.5732 | 101 | WB | Small t |
| DRB1_0101 | 107 VHCPCMLCQLRL-RHL | PCMLCQLRL | 0.5712 | 104 | WB | Small t |
| DRB1_0101 | 109 CPCMLCQLRL-RHLNR | LCQLRLRHL | 0.5711 | 104 | WB | Small t |
| DRB1_0101 | 11 MELMDLLGLER-AAWG | MDLLGLERA | 0.5102 | 200 | WB | Small t |
| DRB1_0101 | 113 LCQLRLRHLNRK-FLR | LCQLRLRHL | 0.5082 | 205 | WB | Small t |
| DRB1_0101 | 112 MLCQLRLRHLN-RKFL | LCQLRLRHL | 0.5077 | 206 | WB | Small t |
| DRB1_0101 | 121 LNRKFLRKE-PLVWID | LRKEPLVWI | 0.4900 | 249 | WB | Small t |
| DRB1_0101 | 120 HLNRKFLRKE-PLVWI | FLRKEPLVW | 0.4888 | 252 | WB | Small t |
| DRB1_0101 | 12 ELMDLLGLER-AAWGN | MDLLGLERA | 0.4876 | 256 | WB | Small t |
| DRB1_0101 | 122 NRKFLRKE-PLVWIDC | LRKEPLVWI | 0.4836 | 267 | WB | Small t |
| DRB1_0101 | 8 EESMELMDLL-GLERA | LMDLLGLER | 0.4834 | 268 | WB | Small t |
| DRB1_0101 | 123 RKFLRKE-PLVWIDCY | LRKEPLVWI | 0.4822 | 271 | WB | Small t |
| DRB1_0101 | 9 ESMELMDLL-GLERAA | LMDLLGLER | 0.4823 | 271 | WB | Small t |
| DRB1_0101 | 48 DEDKMKRMNT-LYKKM | MKRMNTLYK | 0.4796 | 279 | WB | Small t |
| DRB1_0101 | 47 GDEDKMKRMNT-LYKK | MKRMNTLYK | 0.4754 | 292 | WB | Small t |
| DRB1_0101 | 10 SMELMDLLGLER-AAW | MDLLGLERA | 0.4730 | 299 | WB | Small t |

TABLE R-continued

Prediction of BK virus small t protein specific MHC class 2, 15-mer peptide binders for 14 MHC class 2 alleles (see TABLE R-continued Prediction of BK virus small t protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0405 | 18 GLERAAWGNLPLMRK | RAAWGNLPL | 0.5095 | 202 | WB | Small t |
| DRB1_0405 | 19 LERAAWGNLPLMRKA | RAAWGNLPL | 0.4956 | 235 | WB | Small t |
| DRB1_0405 | 137 YCIDCFTQWFGLDLT | FTQWFGLDL | 0.4951 | 236 | WB | Small t |
| DRB1_0405 | 139 IDCFTQWFGLDLTEE | TQWFGLDLT | 0.4864 | 259 | WB | Small t |
| DRB1_0405 | 51 KMKRMNTLYKKMEQD | MKRMNTLYK | 0.4857 | 261 | WB | Small t |
| DRB1_0405 | 52 MKRMNTLYKKMEQDV | MKRMNTLYK | 0.4857 | 261 | WB | Small t |
| DRB1_0405 | 138 CIDCFTQWFGLDLTE | TQWFGLDLT | 0.4851 | 263 | WB | Small t |
| DRB1_0405 | 155 LQWWVQIIGETPFRD | LQWWVQIIG | 0.4691 | 312 | WB | Small t |
| DRB1_0405 | 140 DCFTQWFGLDLTEET | TQWFGLDLT | 0.4671 | 319 | WB | Small t |
| DRB1_0405 | 69 AHQPDFGTWNSSEVC | FGTWNSSEV | 0.4648 | 327 | WB | Small t |
| DRB1_0405 | 68 VAHQPDFGTWNSSEV | QPDFGTWNS | 0.4624 | 336 | WB | Small t |
| DRB1_0405 | 20 ERAAWGNLPLMRKAY | WGNLPLMRK | 0.4570 | 356 | WB | Small t |
| DRB1_0405 | 71 QPDFGTWNSSEVCAD | FGTWNSSEV | 0.4550 | 364 | WB | Small t |
| DRB1_0405 | 17 LGLERAAWGNLPLMR | RAAWGNLPL | 0.4515 | 378 | WB | Small t |
| DRB1_0405 | 70 HQPDFGTWNSSEVCA | FGTWNSSEV | 0.4467 | 398 | WB | Small t |
| DRB1_0405 | 154 TLQWWVQIIGETPFR | LQWWVQIIG | 0.4465 | 399 | WB | Small t |
| DRB1_0405 | 16 LLGLERAAWGNLPLM | RAAWGNLPL | 0.4465 | 399 | WB | Small t |
| DRB1_0405 | 15 DLLGLERAAWGNLPL | ERAAWGNLP | 0.4401 | 427 | WB | Small t |
| DRB1_0405 | 136 CYCIDCFTQWFGLDL | IDCFTQWFG | 0.4322 | 465 | WB | Small t |
| DRB1_0405 | 141 CFTQWFGLDLTEETL | TQWFGLDLT | 0.4323 | 465 | WB | Small t |
| DRB1_0405 | 72 PDFGTWNSSEVCADF | FGTWNSSEV | 0.4300 | 477 | WB | Small t |
| DRB1_0701 | 95 CKEWPICSKKPSVHC | ICSKKPSVH | 0.4880 | 255 | WB | Small t |
| DRB1_0701 | 96 KEWPICSKKPSVHCP | ICSKKPSVH | 0.4829 | 269 | WB | Small t |
| DRB1_0701 | 97 EWPICSKKPSVHCPC | ICSKKPSVH | 0.4823 | 271 | WB | Small t |
| DRB1_0701 | 98 WPICSKKPSVHCPCM | ICSKKPSVH | 0.4807 | 276 | WB | Small t |
| DRB1_0701 | 94 YCKEWPICSKKPSVH | PICSKKPSV | 0.4738 | 297 | WB | Small t |
| DRB1_0701 | 70 HQPDFGTWNSSEVCA | FGTWNSSEV | 0.4721 | 303 | WB | Small t |
| DRB1_0701 | 71 QPDFGTWNSSEVCAD | FGTWNSSEV | 0.4716 | 304 | WB | Small t |
| DRB1_0701 | 68 VAHQPDFGTWNSSEV | DFGTWNSSE | 0.4709 | 306 | WB | Small t |
| DRB1_0701 | 69 AHQPDFGTWNSSEVC | FGTWNSSEV | 0.4705 | 308 | WB | Small t |
| DRB1_0701 | 72 PDFGTWNSSEVCADF | FGTWNSSEV | 0.4685 | 314 | WB | Small t |
| DRB1_1101 | 47 GDEDKMKRMNTLYKK | MKRMNTLYK | 0.4550 | 364 | WB | Small t |
| DRB1_1101 | 49 EDKMKRMNTLYKKME | MKRMNTLYK | 0.4498 | 385 | WB | Small t |
| DRB1_1101 | 48 DEDKMKRMNTLYKKM | MKRMNTLYK | 0.4495 | 386 | WB | Small t |
| DRB1_1101 | 50 DKMKRMNTLYKKMEQ | MKRMNTLYK | 0.4483 | 391 | WB | Small t |
| DRB1_1101 | 46 GGDEDKMKRMNTLYK | EDKMKRMNT | 0.4433 | 413 | WB | Small t |
| DRB1_1101 | 18 GLERAAWGNLPLMRK | AWGNLPLMR | 0.4312 | 471 | WB | Small t |
| DRB1_1101 | 19 LERAAWGNLPLMRKA | WGNLPLMRK | 0.4311 | 471 | WB | Small t |

TABLE R-continued

Prediction of BK virus small t protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. | Identity |
|---|---|---|---|---|---|---|
| DRB1_1101 | 21 RAAWGNLPLMR-KAYL | WGNLPLMRK | 0.4288 | 483 | WB | Small t |
| DRB1_1101 | 20 ERAAWGNLPLMR-KAY | WGNLPLMRK | 0.4279 | 488 | WB | Small t |
| DRB1_1302 | 18 GLERAAWGNL-PLMRK | LERAAWGNL | 0.5752 | 99 | WB | Small t |
| DRB1_1302 | 21 RAAWGNLPLMR-KAYL | WGNLPLMRK | 0.5714 | 103 | WB | Small t |
| DRB1_1302 | 22 AAWGNLPLMR-KAYLK | WGNLPLMRK | 0.5704 | 104 | WB | Small t |
| DRB1_1302 | 19 LERAAWGNLPLM-RKA | WGNLPLMRK | 0.5702 | 105 | WB | Small t |
| DRB1_1302 | 20 ERAAWGNLPLMR-KAY | WGNLPLMRK | 0.5531 | 126 | WB | Small t |
| DRB1_1302 | 48 DEDKMKRMNT-LYKKM | MKRMNTLYK | 0.5012 | 221 | WB | Small t |
| DRB1_1302 | 49 EDKMKRMNTLYK-KME | MKRMNTLYK | 0.4986 | 227 | WB | Small t |
| DRB1_1302 | 50 DKMKRMNTLYK-KMEQ | MKRMNTLYK | 0.4966 | 232 | WB | Small t |
| DRB1_1302 | 47 GDEDKMKRMNT-LYKK | MKRMNTLYK | 0.4940 | 239 | WB | Small t |
| DRB1_1302 | 24 WGNLPLMRKAY-LKKC | WGNLPLMRK | 0.4926 | 242 | WB | Small t |
| DRB1_1302 | 23 AWGNLPLMRKAY-LKK | WGNLPLMRK | 0.4885 | 253 | WB | Small t |
| DRB1_1302 | 153 ETLQWWVQI-IGETPF | WWVQIIGET | 0.4827 | 270 | WB | Small t |
| DRB1_1302 | 46 GGDEDKMKRMNT-LYK | DKMKRMNTL | 0.4800 | 278 | WB | Small t |
| DRB1_1302 | 155 LQWWVQIIGETP-FRD | VQIIGETPF | 0.4679 | 317 | WB | Small t |
| DRB1_1302 | 154 TLQWWVQIIGET-PFR | VQIIGETPF | 0.4659 | 323 | WB | Small t |
| DRB1_1302 | 113 LCQLRLRHLNRK-FLR | LRLRHLNRK | 0.4607 | 342 | WB | Small t |
| DRB1_1302 | 112 MLCQLRLRHLN-RKFL | LRLRHLNRK | 0.4561 | 360 | WB | Small t |
| DRB1_1302 | 114 CQLRLRHLNRK-FLRK | LRLRHLNRK | 0.4549 | 364 | WB | Small t |
| DRB1_1302 | 156 QWWVQIIGETP-FRDL | VQIIGETPF | 0.4401 | 427 | WB | Small t |
| DRB1_1302 | 51 KMKRMNTLYK-KMEQD | MKRMNTLYK | 0.4272 | 492 | WB | Small t |
| DRB1_1501 | 111 CMLCQLRLRHLN-RKF | LRLRHLNRK | 0.5327 | 157 | WB | Small t |
| DRB1_1501 | 110 PCMLCQLRLRHL-NRK | QLRLRHLNR | 0.5274 | 166 | WB | Small t |
| DRB1_1501 | 48 DEDKMKRMNT-LYKKM | MKRMNTLYK | 0.5229 | 174 | WB | Small t |
| DRB1_1501 | 49 EDKMKRMNTLYK-KME | MKRMNTLYK | 0.5190 | 182 | WB | Small t |
| DRB1_1501 | 24 WGNLPLMRKAY-LKKC | LMRKAYLKK | 0.5176 | 185 | WB | Small t |
| DRB1_1501 | 113 LCQLRLRHLNRK-FLR | LRLRHLNRK | 0.5166 | 187 | WB | Small t |
| DRB1_1501 | 50 DKMKRMNTLYK-KMEQ | MKRMNTLYK | 0.5153 | 190 | WB | Small t |
| DRB1_1501 | 47 GDEDKMKRMNT-LYKK | MKRMNTLYK | 0.5147 | 191 | WB | Small t |
| DRB1_1501 | 112 MLCQLRLRHLN-RKFL | LRLRHLNRK | 0.5140 | 192 | WB | Small t |
| DRB1_1501 | 23 AWGNLPLMRKAY-LKK | LPLMRKAYL | 0.5076 | 206 | WB | Small t |
| DRB1_1501 | 25 GNLPLMRKAYLK-KCK | LMRKAYLKK | 0.5063 | 209 | WB | Small t |
| DRB1_1501 | 46 GGDEDKMKRMNT-LYK | DKMKRMNTL | 0.5026 | 217 | WB | Small t |
| DRB1_1501 | 26 NLPLMRKAYLK-KCKE | LMRKAYLKK | 0.4961 | 233 | WB | Small t |
| DRB1_1501 | 114 CQLRLRHLNRK-FLRK | LRLRHLNRK | 0.4919 | 244 | WB | Small t |
| DRB1_1501 | 27 LPLMRKAYLK-KCKEF | LMRKAYLKK | 0.4850 | 263 | WB | Small t |
| DRB1_1501 | 13 LMDLLGLER-AAWGNL | LMDLLGLER | 0.4683 | 315 | WB | Small t |

TABLE R-continued

Prediction of BK virus small t protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k(aff) | aff(nM) | B.L. | Identity |
|---|---|---|---|---|---|---|
| DRB1_1501 | 11 MELMDLLGLER-AAWG | LMDLLGLER | 0.4651 | 326 | WB | Small t |
| DRB1_1501 | 115 QLRLRHLNRKFL-RKE | LRLRHLNRK | 0.4643 | 329 | WB | Small t |
| DRB1_1501 | 120 HLNRKFLRKE-PLVWI | FLRKEPLVW | 0.4621 | 337 | WB | Small t |
| DRB1_1501 | 121 LNRKFLRKE-PLVWID | FLRKEPLVW | 0.4374 | 440 | WB | Small t |
| DRB1_1501 | 28 PLMRKAYLKKCK-EFH | LMRKAYLKK | 0.4332 | 461 | WB | Small t |
| DRB1_1501 | 51 KMKRMNTLYK-KMEQD | MKRMNTLYK | 0.4331 | 461 | WB | Small t |
| DRB1_1501 | 123 RKFLRKE-PLVWIDCY | FLRKEPLVW | 0.4300 | 477 | WB | Small t |
| DRB1_1501 | 10 SMELMDLLGLER-AAW | LMDLLGLER | 0.4261 | 497 | WB | Small t |
| DRB4_0101 | 94 YCKEWPICSK-KPSVH | YCKEWPICS | 0.5706 | 104 | WB | Small t |
| DRB4_0101 | 112 MLCQLRLRHLN-RKFL | LRLRHLNRK | 0.5364 | 151 | WB | Small t |
| DRB4_0101 | 113 LCQLRLRHLNRK-FLR | LRLRHLNRK | 0.5342 | 155 | WB | Small t |
| DRB4_0101 | 111 CMLCQLRLRHLN-RKF | LRLRHLNRK | 0.5331 | 156 | WB | Small t |
| DRB4_0101 | 110 PCMLCQLRLRHL-NRK | LCQLRLRHL | 0.5322 | 158 | WB | Small t |
| DRB4_0101 | 95 CKEWPICSKKPS-VHC | ICSKKPSVH | 0.5323 | 158 | WB | Small t |
| DRB4_0101 | 114 CQLRLRHLNRK-FLRK | LRLRHLNRK | 0.5291 | 163 | WB | Small t |
| DRB4_0101 | 96 KEWPICSKKPS-VHCP | ICSKKPSVH | 0.5267 | 167 | WB | Small t |
| DRB4_0101 | 97 EWPICSKKPSVH-CPC | ICSKKPSVH | 0.5247 | 171 | WB | Small t |
| DRB4_0101 | 98 WPICSKKPSVH-CPCM | ICSKKPSVH | 0.5172 | 186 | WB | Small t |
| DRB4_0101 | 115 QLRLRHLNRKFL-RKE | LRLRHLNRK | 0.4556 | 361 | WB | Small t |
| DRB4_0101 | 116 LRLRHLNRKFL-RKEP | LRLRHLNRK | 0.4510 | 380 | WB | Small t |
| DRB4_0101 | 100 ICSKKPSVHCPC-MLC | ICSKKPSVH | 0.4432 | 413 | WB | Small t |
| DRB4_0101 | 99 PICSKKPSVHCP-CML | ICSKKPSVH | 0.4374 | 440 | WB | Small t |
| DRB5_0101 | 49 EDKMKRMNTLYK-KME | MKRMNTLYK | 0.4763 | 289 | WB | Small t |
| DRB5_0101 | 50 DKMKRMNTLYK-KMEQ | MKRMNTLYK | 0.4758 | 290 | WB | Small t |
| DRB5_0101 | 48 DEDKMKRMNT-LYKKM | MKRMNTLYK | 0.4726 | 301 | WB | Small t |
| DRB5_0101 | 47 GDEDKMKRMNT-LYKK | MKRMNTLYK | 0.4617 | 338 | WB | Small t |
| DRB5_0101 | 46 GGDEDKMKRMNT-LYK | DKMKRMNTL | 0.4567 | 357 | WB | Small t |
| DRB5_0101 | 112 MLCQLRLRHLN-RKFL | LRLRHLNRK | 0.4397 | 429 | WB | Small t |
| DRB5_0101 | 114 CQLRLRHLNRK-FLRK | LRHLNRKFL | 0.4398 | 429 | WB | Small t |
| DRB5_0101 | 53 KRMNTLYK-KMEQDVK | KRMNTLYKK | 0.4284 | 485 | WB | Small t |
| DRB5_0101 | 22 AAWGNLPLMR-KAYLK | WGNLPLMRK | 0.4268 | 494 | WB | Small t |

SEQ ID NOS.: 59918-60257

Preferred BK virus fragments of large T antigen capable of interacting with one or more MHC class 2 molecules are listed in Table S.

TABLE S

Prediction of BK virus Large T protein specific MHC class 2, 15-mer peptide binders for 14 MHC class 2 alleles (see FIG. 11) using the www.cbs.dtu.dk/services/NetMHCII/database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0101 | 566 LEKRILQSGMTLLLL | LQSGMTLLL | 0.7526 | 15 | SB | Large T |
| DRB1_0101 | 567 EKRILQSGMTLLLLL | LQSGMTLLL | 0.7519 | 15 | SB | Large T |
| DRB1_0101 | 568 KRILQSGMTLLLLLI | LQSGMTLLL | 0.7525 | 15 | SB | Large T |
| DRB1_0101 | 569 RILQSGMTLLLLLIW | LQSGMTLLL | 0.7504 | 15 | SB | Large T |
| DRB1_0101 | 565 LLEKRILQSGMTLLL | KRILQSGMT | 0.7441 | 16 | SB | Large T |
| DRB1_0101 | 21 RAAWGNLPLMRKAYL | WGNLPLMRK | 0.6972 | 26 | SB | Large T |
| DRB1_0101 | 19 LERAAWGNLPLMRKA | WGNLPLMRK | 0.6958 | 27 | SB | Large T |
| DRB1_0101 | 20 ERAAWGNLPLMRKAY | WGNLPLMRK | 0.6940 | 27 | SB | Large T |
| DRB1_0101 | 22 AAWGNLPLMRKAYLK | WGNLPLMRK | 0.6954 | 27 | SB | Large T |
| DRB1_0101 | 18 GLERAAWGNLPLMRK | ERAAWGNLP | 0.6928 | 28 | SB | Large T |
| DRB1_0101 | 570 ILQSGMTLLLLLIWF | LQSGMTLLL | 0.6646 | 38 | SB | Large T |
| DRB1_0101 | 571 LQSGMTLLLLLIWFR | LQSGMTLLL | 0.6561 | 41 | SB | Large T |
| DRB1_0101 | 383 NAVLEQYMAGVAWLH | EQYMAGVAW | 0.6528 | 43 | SB | Large T |
| DRB1_0101 | 387 EQYMAGVAWLHCLLP | YMAGVAWLH | 0.6516 | 43 | SB | Large T |
| DRB1_0101 | 385 VLEQYMAGVAWLHCL | YMAGVAWLH | 0.6507 | 44 | SB | Large T |
| DRB1_0101 | 384 AVLEQYMAGVAWLHC | YMAGVAWLH | 0.6486 | 45 | SB | Large T |
| DRB1_0101 | 386 LEQYMAGVAWLHCLL | YMAGVAWLH | 0.6483 | 45 | SB | Large T |
| DRB1_0101 | 441 LLDLCGGKALNVNLP | LCGGKALNV | 0.6340 | 52 | WB | Large T |
| DRB1_0101 | 144 LHQFLSQAVFSNRTL | LHQFLSQAV | 0.6329 | 53 | WB | Large T |
| DRB1_0101 | 143 DLHQFLSQAVFSNRT | LHQFLSQAV | 0.6318 | 54 | WB | Large T |
| DRB1_0101 | 442 LDLCGGKALNVNLPM | LCGGKALNV | 0.6310 | 54 | WB | Large T |
| DRB1_0101 | 439 AGLLDLCGGKALNVN | LCGGKALNV | 0.6263 | 57 | WB | Large T |
| DRB1_0101 | 440 GLLDLCGGKALNVNL | LCGGKALNV | 0.6223 | 60 | WB | Large T |
| DRB1_0101 | 438 AAGLLDLCGGKALNV | LLDLCGGKA | 0.6207 | 61 | WB | Large T |
| DRB1_0101 | 142 SDLHQFLSQAVFSNR | LHQFLSQAV | 0.6178 | 62 | WB | Large T |
| DRB1_0101 | 141 PSDLHQFLSQAVFSN | LHQFLSQAV | 0.6165 | 63 | WB | Large T |
| DRB1_0101 | 533 YPVPKTLQARFVRQI | PKTLQARFV | 0.6160 | 64 | WB | Large T |
| DRB1_0101 | 534 PVPKTLQARFVRQID | LQARFVRQI | 0.6136 | 65 | WB | Large T |
| DRB1_0101 | 140 FPSDLHQFLSQAVFS | LHQFLSQAV | 0.6083 | 69 | WB | Large T |
| DRB1_0101 | 138 KDFPSDLHQFLSQAV | FPSDLHQFL | 0.6036 | 73 | WB | Large T |
| DRB1_0101 | 139 DFPSDLHQFLSQAVF | LHQFLSQAV | 0.6019 | 74 | WB | Large T |
| DRB1_0101 | 24 WGNLPLMRKAYLKKC | WGNLPLMRK | 0.6020 | 74 | WB | Large T |
| DRB1_0101 | 23 AWGNLPLMRKAYLKK | WGNLPLMRK | 0.6000 | 76 | WB | Large T |
| DRB1_0101 | 517 NKRTQIFPPGLVTMN | IFPPGLVTM | 0.5951 | 80 | WB | Large T |
| DRB1_0101 | 518 KRTQIFPPGLVTMNE | IFPPGLVTM | 0.5907 | 84 | WB | Large T |
| DRB1_0101 | 428 GPIDSGKTTLAAGLL | IDSGKTTLA | 0.5880 | 86 | WB | Large T |
| DRB1_0101 | 519 RTQIFPPGLVTMNEY | IFPPGLVTM | 0.5871 | 87 | WB | Large T |
| DRB1_0101 | 520 TQIFPPGLVTMNEYP | IFPPGLVTM | 0.5843 | 90 | WB | Large T |
| DRB1_0101 | 268 KQVSWKLITEYAVET | WKLITEYAV | 0.5795 | 95 | WB | Large T |
| DRB1_0101 | 269 QVSWKLITEYAVETK | LITEYAVET | 0.5780 | 96 | WB | Large T |
| DRB1_0101 | 284 CEDVFLLLGMYLEFQ | VFLLLGMYL | 0.5771 | 97 | WB | Large T |
| DRB1_0101 | 285 EDVFLLLGMYLEFQY | VFLLLGMYL | 0.5774 | 97 | WB | Large T |
| DRB1_0101 | 535 VPKTLQARFVRQIDF | LQARFVRQI | 0.5743 | 100 | WB | Large T |
| DRB1_0101 | 536 PKTLQARFVRQIDFR | LQARFVRQI | 0.5746 | 100 | WB | Large T |
| DRB1_0101 | 270 VSWKLITEYAVETKC | LITEYAVET | 0.5715 | 103 | WB | Large T |
| DRB1_0101 | 147 FLSQAVFSNRTLACF | SQAVFSNRT | 0.5698 | 105 | WB | Large T |
| DRB1_0101 | 388 QYMAGVAWLHCLLPK | YMAGVAWLH | 0.5680 | 107 | WB | Large T |
| DRB1_0101 | 603 ERLDSEISMYTFSRM | LDSEISMYT | 0.5669 | 108 | WB | Large T |
| DRB1_0101 | 389 YMAGVAWLHCLLPKM | YMAGVAWLH | 0.5664 | 109 | WB | Large T |
| DRB1_0101 | 448 KALNVNLPMERLTFE | LNVNLPMER | 0.5655 | 110 | WB | Large T |
| DRB1_0101 | 444 LCGGKALNVNLPMER | LCGGKALNV | 0.5641 | 112 | WB | Large T |
| DRB1_0101 | 446 GGKALNVNLPMERLT | LNVNLPMER | 0.5640 | 112 | WB | Large T |
| DRB1_0101 | 425 LFKGPIDSGKTTLAA | IDSGKTTLA | 0.5627 | 113 | WB | Large T |
| DRB1_0101 | 447 GKALNVNLPMERLTF | LNVNLPMER | 0.5619 | 114 | WB | Large T |
| DRB1_0101 | 427 KGPIDSGKTTLAAGL | IDSGKTTLA | 0.5613 | 115 | WB | Large T |
| DRB1_0101 | 599 VEWKERLDSEISMYT | KERLDSEIS | 0.5611 | 115 | WB | Large T |
| DRB1_0101 | 445 CGGKALNVNLPMERL | LNVNLPMER | 0.5598 | 117 | WB | Large T |
| DRB1_0101 | 490 GHGINNLDSLRDYLD | INNLDSLRD | 0.5597 | 117 | WB | Large T |
| DRB1_0101 | 271 SWKLITEYAVETKCE | LITEYAVET | 0.5583 | 119 | WB | Large T |
| DRB1_0101 | 489 SGHGINNLDSLRDYL | INNLDSLRD | 0.5574 | 120 | WB | Large T |
| DRB1_0101 | 491 HGINNLDSLRDYLDG | INNLDSLRD | 0.5573 | 120 | WB | Large T |
| DRB1_0101 | 424 WLFKGPIDSGKTTLA | KGPIDSGKT | 0.5567 | 121 | WB | Large T |
| DRB1_0101 | 487 LPSGHGINNLDSLRD | LPSGHGINN | 0.5568 | 121 | WB | Large T |
| DRB1_0101 | 530 MNEYPVPKTLQARFV | YPVPKTLQA | 0.5570 | 121 | WB | Large T |
| DRB1_0101 | 426 FKGPIDSGKTTLAAG | IDSGKTTLA | 0.5562 | 122 | WB | Large T |
| DRB1_0101 | 600 EWKERLDSEISMYTF | LDSEISMYT | 0.5562 | 122 | WB | Large T |
| DRB1_0101 | 602 KERLDSEISMYTFSR | LDSEISMYT | 0.5560 | 122 | WB | Large T |
| DRB1_0101 | 488 PSGHGINNLDSLRDY | INNLDSLRD | 0.5554 | 123 | WB | Large T |
| DRB1_0101 | 601 WKERLDSEISMYTFS | LDSEISMYT | 0.5538 | 125 | WB | Large T |
| DRB1_0101 | 272 WKLITEYAVETKCED | LITEYAVET | 0.5514 | 128 | WB | Large T |
| DRB1_0101 | 531 NEYPVPKTLQARFVR | PKTLQARFV | 0.5518 | 128 | WB | Large T |
| DRB1_0101 | 521 QIFPPGLVTMNEYPV | FPPGLVTMN | 0.5507 | 129 | WB | Large T |
| DRB1_0101 | 443 DLCGGKALNVNLPME | LCGGKALNV | 0.5488 | 132 | WB | Large T |

TABLE S-continued

Prediction of BK virus Large T protein specific MHC class 2, 15-mer peptide binders for 14 MHC class 2 alleles (see FIG. 11) using the www.cbs.dtu.dk/services/NetMHCII/database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0101 | 228 VNKEYLLYSALTRDP | YLLYSALTR | 0.5454 | 137 | WB | Large T |
| DRB1_0101 | 145 HQFLSQAVFSNRTLA | SQAVFSNRT | 0.5437 | 139 | WB | Large T |
| DRB1_0101 | 374 MDLIFGAHGNAVLEQ | IFGAHGNAV | 0.5440 | 139 | WB | Large T |
| DRB1_0101 | 375 DLIFGAHGNAVLEQY | IFGAHGNAV | 0.5439 | 139 | WB | Large T |
| DRB1_0101 | 229 NKEYLLYSALTRDPY | LYSALTRDP | 0.5434 | 140 | WB | Large T |
| DRB1_0101 | 146 QFLSQAVFSNRTLAC | SQAVFSNRT | 0.5423 | 141 | WB | Large T |
| DRB1_0101 | 373 KMDLIFGAHGNAVLE | IFGAHGNAV | 0.5366 | 150 | WB | Large T |
| DRB1_0101 | 564 FLLEKRILQSGMTLL | KRILQSGMT | 0.5369 | 150 | WB | Large T |
| DRB1_0101 | 372 DKMDLIFGAHGNAVL | IFGAHGNAV | 0.5366 | 151 | WB | Large T |
| DRB1_0101 | 230 KEYLLYSALTRDPYH | LYSALTRDP | 0.5334 | 156 | WB | Large T |
| DRB1_0101 | 449 ALNVNLPMERLTFEL | NVNLPMERL | 0.5320 | 158 | WB | Large T |
| DRB1_0101 | 286 DVFLLLGMYLEFQYN | LLGMYLEFQ | 0.5310 | 160 | WB | Large T |
| DRB1_0101 | 232 YLLYSALTRDPYHII | LYSALTRDP | 0.5298 | 162 | WB | Large T |
| DRB1_0101 | 338 ICQQAVDTVLAKKRV | QQAVDTVLA | 0.5273 | 166 | WB | Large T |
| DRB1_0101 | 430 IDSGKTTLAAGLLDL | IDSGKTTLA | 0.5269 | 167 | WB | Large T |
| DRB1_0101 | 149 SQAVFSNRTLACFAV | FSNRTLACF | 0.5259 | 169 | WB | Large T |
| DRB1_0101 | 337 SICQQAVDTVLAKKR | QQAVDTVLA | 0.5252 | 170 | WB | Large T |
| DRB1_0101 | 148 LSQAVFSNRTLACFA | FSNRTLACF | 0.5244 | 172 | WB | Large T |
| DRB1_0101 | 231 EYLLYSALTRDPYHI | LYSALTRDP | 0.5238 | 173 | WB | Large T |
| DRB1_0101 | 522 IFPPGLVTMNEYPVP | IFPPGLVTM | 0.5236 | 173 | WB | Large T |
| DRB1_0101 | 532 EYPVPKTLQARFVRQ | PKTLQARFV | 0.5222 | 176 | WB | Large T |
| DRB1_0101 | 429 PIDSGKTTLAAGLLD | IDSGKTTLA | 0.5198 | 180 | WB | Large T |
| DRB1_0101 | 516 LNKRTQIFPPGLVTM | RTQIFPPGL | 0.5156 | 189 | WB | Large T |
| DRB1_0101 | 287 VFLLLGMYLEFQYNV | VFLLLGMYL | 0.5144 | 191 | WB | Large T |
| DRB1_0101 | 11 MELMDLLGLERAAWG | MDLLGLERA | 0.5102 | 200 | WB | Large T |
| DRB1_0101 | 473 VFEDVKGTGAESKDL | VKGTGAESK | 0.5100 | 201 | WB | Large T |
| DRB1_0101 | 474 FEDVKGTGAESKDLP | VKGTGAESK | 0.5088 | 203 | WB | Large T |
| DRB1_0101 | 537 KTLQARFVRQIDFRP | LQARFVRQI | 0.5092 | 203 | WB | Large T |
| DRB1_0101 | 475 EDVKGTGAESKDLPS | VKGTGAESK | 0.5068 | 208 | WB | Large T |
| DRB1_0101 | 195 NIIFFLTPHRHRVSA | IFFLTPHRH | 0.5062 | 209 | WB | Large T |
| DRB1_0101 | 335 QKSICQQAVDTVLAK | ICQQAVDTV | 0.5063 | 209 | WB | Large T |
| DRB1_0101 | 194 HNIIFFLTPHRHRVS | IFFLTPHRH | 0.5053 | 211 | WB | Large T |
| DRB1_0101 | 336 KSICQQAVDTVLAKK | ICQQAVDTV | 0.5051 | 212 | WB | Large T |
| DRB1_0101 | 334 NQKSICQQAVDTVLA | ICQQAVDTV | 0.5035 | 215 | WB | Large T |
| DRB1_0101 | 450 LNVNLPMERLTFELG | NVNLPMERL | 0.5031 | 216 | WB | Large T |
| DRB1_0101 | 527 LVTMNEYPVPKTLQA | MNEYPVPKT | 0.5027 | 217 | WB | Large T |
| DRB1_0101 | 528 VTMNEYPVPKTLQAR | YPVPKTLQA | 0.5012 | 221 | WB | Large T |
| DRB1_0101 | 371 LDKMDLIFGAHGNAV | LDKMDLIFG | 0.4990 | 226 | WB | Large T |
| DRB1_0101 | 572 QSGMTLLLLLIWFRP | MTLLLLLIW | 0.4975 | 230 | WB | Large T |
| DRB1_0101 | 282 TKCEDVFLLLGMYLE | VFLLLGMYL | 0.4937 | 239 | WB | Large T |
| DRB1_0101 | 283 KCEDVFLLLGMYLEF | VFLLLGMYL | 0.4920 | 244 | WB | Large T |
| DRB1_0101 | 376 LIFGAHGNAVLEQYM | FGAHGNAVL | 0.4919 | 244 | WB | Large T |
| DRB1_0101 | 394 AWLHCLLPKMDSVIF | LLPKMDSVI | 0.4910 | 246 | WB | Large T |
| DRB1_0101 | 604 RLDSEISMYTFSRMK | LDSEISMYT | 0.4900 | 249 | WB | Large T |
| DRB1_0101 | 605 LDSEISMYTFSRMKY | LDSEISMYT | 0.4889 | 252 | WB | Large T |
| DRB1_0101 | 12 ELMDLLGLERAAWGN | MDLLGLERA | 0.4876 | 256 | WB | Large T |
| DRB1_0101 | 472 VVFEDVKGTGAESKD | VKGTGAESK | 0.4858 | 261 | WB | Large T |
| DRB1_0101 | 471 MVVFEDVKGTGAESK | FEDVKGTGA | 0.4853 | 262 | WB | Large T |
| DRB1_0101 | 340 QQAVDTVLAKKRVDT | VDTVLAKKR | 0.4843 | 265 | WB | Large T |
| DRB1_0101 | 172 ILYKKLMEKYSVTFI | YKKLMEKYS | 0.4836 | 267 | WB | Large T |
| DRB1_0101 | 339 CQQAVDTVLAKKRVD | VDTVLAKKR | 0.4837 | 267 | WB | Large T |
| DRB1_0101 | 8 EESMELMDLLGLERA | LMDLLGLER | 0.4834 | 268 | WB | Large T |
| DRB1_0101 | 9 ESMELMDLLGLERAA | LMDLLGLER | 0.4823 | 271 | WB | Large T |
| DRB1_0101 | 395 WLHCLLPKMDSVIFD | LPKMDSVIF | 0.4815 | 273 | WB | Large T |
| DRB1_0101 | 256 EHDFNPEEPEETKQV | FNPEEPEET | 0.4804 | 276 | WB | Large T |
| DRB1_0101 | 152 VFSNRTLACFAVYTT | TLACFAVYT | 0.4803 | 277 | WB | Large T |
| DRB1_0101 | 257 HDFNPEEPEETKQVS | FNPEEPEET | 0.4796 | 279 | WB | Large T |
| DRB1_0101 | 48 DEDKMKRMNTLYKKM | MKRMNTLYK | 0.4796 | 279 | WB | Large T |
| DRB1_0101 | 255 KEHDFNPEEPEETKQ | FNPEEPEET | 0.4792 | 280 | WB | Large T |
| DRB1_0101 | 396 LHCLLPKMDSVIFDF | LPKMDSVIF | 0.4778 | 284 | WB | Large T |
| DRB1_0101 | 254 LKEHDFNPEEPEETK | FNPEEPEET | 0.4775 | 285 | WB | Large T |
| DRB1_0101 | 150 QAVFSNRTLACFAVY | FSNRTLACF | 0.4767 | 288 | WB | Large T |
| DRB1_0101 | 563 EFLLEKRILQSGMTL | KRILQSGMT | 0.4767 | 288 | WB | Large T |
| DRB1_0101 | 226 KGVNKEYLLYSALTR | EYLLYSALT | 0.4763 | 289 | WB | Large T |
| DRB1_0101 | 548 DFRPKIYLRKSLQNS | FRPKIYLRK | 0.4755 | 291 | WB | Large T |
| DRB1_0101 | 47 GDEDKMKRMNTLYKK | MKRMNTLYK | 0.4754 | 292 | WB | Large T |
| DRB1_0101 | 549 FRPKIYLRKSLQNSE | YLRKSLQNS | 0.4751 | 293 | WB | Large T |
| DRB1_0101 | 171 QILYKKLMEKYSVTF | YKKLMEKYS | 0.4745 | 295 | WB | Large T |
| DRB1_0101 | 253 GLKEHDFNPEEPEET | GLKEHDFNP | 0.4744 | 295 | WB | Large T |
| DRB1_0101 | 196 IIFFLTPHRHRVSAI | LTPHRHRVS | 0.4734 | 298 | WB | Large T |
| DRB1_0101 | 397 HCLLPKMDSVIFDFL | LPKMDSVIF | 0.4735 | 298 | WB | Large T |
| DRB1_0101 | 10 SMELMDLLGLERAAW | MDLLGLERA | 0.4730 | 299 | WB | Large T |
| DRB1_0101 | 578 LLLLIWFRPVADFSK | LIWFRPVAD | 0.4729 | 300 | WB | Large T |

TABLE S-continued

Prediction of BK virus Large T protein specific MHC class 2, 15-mer peptide binders for 14 MHC class 2 alleles (see FIG. 11) using the www.cbs.dtu.dk/services/NetMHCII/database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0101 | 49 EDKMKRMNTLYKKME | MKRMNTLYK | 0.4724 | 302 | WB | Large T |
| DRB1_0101 | 562 SEFLLEKRILQSGMT | LEKRILQSG | 0.4722 | 302 | WB | Large T |
| DRB1_0101 | 579 LLLIWFRPVADFSKD | LIWFRPVAD | 0.4723 | 302 | WB | Large T |
| DRB1_0101 | 551 PKIYLRKSLQNSEFL | YLRKSLQNS | 0.4719 | 303 | WB | Large T |
| DRB1_0101 | 523 FPPGLVTMNEYPVPK | FPPGLVTMN | 0.4709 | 306 | WB | Large T |
| DRB1_0101 | 197 IFFLTPHRHRVSAIN | LTPHRHRVS | 0.4697 | 310 | WB | Large T |
| DRB1_0101 | 50 DKMKRMNTLYKKMEQ | MKRMNTLYK | 0.4699 | 310 | WB | Large T |
| DRB1_0101 | 550 RPKIYLRKSLQNSEF | YLRKSLQNS | 0.4698 | 310 | WB | Large T |
| DRB1_0101 | 46 GGDEDKMKRMNTLYK | DKMKRMNTL | 0.4690 | 313 | WB | Large T |
| DRB1_0101 | 2 DKVLNREESMELMDL | LNREESMEL | 0.4683 | 315 | WB | Large T |
| DRB1_0101 | 577 LLLLLIWFRPVADFS | LIWFRPVAD | 0.4684 | 315 | WB | Large T |
| DRB1_0101 | 153 FSNRTLACFAVYTTK | LACFAVYTT | 0.4677 | 317 | WB | Large T |
| DRB1_0101 | 3 KVLNREESMELMDLL | LNREESMEL | 0.4672 | 319 | WB | Large T |
| DRB1_0101 | 281 ETKCEDVFLLLGMYL | EDVFLLLGM | 0.4666 | 321 | WB | Large T |
| DRB1_0101 | 573 SGMTLLLLLIWFRPV | MTLLLLLIW | 0.4649 | 327 | WB | Large T |
| DRB1_0101 | 493 INNLDSLRDYLDGSV | INNLDSLRD | 0.4638 | 331 | WB | Large T |
| DRB1_0101 | 524 PPGLVTMNEYPVPKT | LVTMNEYPV | 0.4635 | 332 | WB | Large T |
| DRB1_0101 | 525 PGLVTMNEYPVPKTL | MNEYPVPKT | 0.4633 | 333 | WB | Large T |
| DRB1_0101 | 151 AVFSNRTLACFAVYT | FSNRTLACF | 0.4625 | 336 | WB | Large T |
| DRB1_0101 | 492 GINNLDSLRDYLDGS | INNLDSLRD | 0.4622 | 336 | WB | Large T |
| DRB1_0101 | 227 GVNKEYLLYSALTRD | YLLYSALTR | 0.4619 | 338 | WB | Large T |
| DRB1_0101 | 529 TMNEYPVPKTLQARF | YPVPKTLQA | 0.4598 | 345 | WB | Large T |
| DRB1_0101 | 459 LTFELGVAIDQYMVV | LGVAIDQYM | 0.4589 | 349 | WB | Large T |
| DRB1_0101 | 457 ERLTFELGVAIDQYM | LTFELGVAI | 0.4584 | 351 | WB | Large T |
| DRB1_0101 | 398 CLLPKMDSVIFDFLH | LPKMDSVIF | 0.4578 | 353 | WB | Large T |
| DRB1_0101 | 552 KIYLRKSLQNSEFLL | YLRKSLQNS | 0.4575 | 354 | WB | Large T |
| DRB1_0101 | 13 LMDLLGLERAAWGNL | LGLERAAWG | 0.4572 | 355 | WB | Large T |
| DRB1_0101 | 575 MTLLLLLIWFRPVAD | MTLLLLLIW | 0.4574 | 355 | WB | Large T |
| DRB1_0101 | 451 NVNLPMERLTFELGV | NVNLPMERL | 0.4555 | 362 | WB | Large T |
| DRB1_0101 | 193 GHNIIFFLTPHRHRV | IFFLTPHRH | 0.4529 | 372 | WB | Large T |
| DRB1_0101 | 1 MDKVLNREESMELMD | LNREESMEL | 0.4521 | 376 | WB | Large T |
| DRB1_0101 | 432 SGKTTLAAGLLDLCG | KTTLAAGLL | 0.4504 | 382 | WB | Large T |
| DRB1_0101 | 233 LLYSALTRDPYHIIE | LYSALTRDP | 0.4500 | 384 | WB | Large T |
| DRB1_0101 | 377 IFGAHGNAVLEQYMA | IFGAHGNAV | 0.4493 | 387 | WB | Large T |
| DRB1_0101 | 273 KLITEYAVETKCEDV | LITEYAVET | 0.4490 | 388 | WB | Large T |
| DRB1_0101 | 458 RLTFELGVAIDQYMV | LGVAIDQYM | 0.4476 | 394 | WB | Large T |
| DRB1_0101 | 234 LYSALTRDPYHIIEE | LYSALTRDP | 0.4472 | 396 | WB | Large T |
| DRB1_0101 | 422 RYWLFKGPIDSGKTT | WLFKGPIDS | 0.4473 | 396 | WB | Large T |
| DRB1_0101 | 421 RRYWLFKGPIDSGKT | WLFKGPIDS | 0.4465 | 399 | WB | Large T |
| DRB1_0101 | 274 LITEYAVETKCEDVF | LITEYAVET | 0.4460 | 401 | WB | Large T |
| DRB1_0101 | 14 MDLLGLERAAWGNLP | LGLERAAWG | 0.4451 | 405 | WB | Large T |
| DRB1_0101 | 476 DVKGTGAESKDLPSG | VKGTGAESK | 0.4428 | 415 | WB | Large T |
| DRB1_0101 | 477 VKGTGAESKDLPSGH | VKGTGAESK | 0.4412 | 422 | WB | Large T |
| DRB1_0101 | 526 GLVTMNEYPVPKTLQ | MNEYPVPKT | 0.4408 | 424 | WB | Large T |
| DRB1_0101 | 174 YKKLMEKYSVTFISR | LMEKYSVTF | 0.4406 | 425 | WB | Large T |
| DRB1_0101 | 390 MAGVAWLHCLLPKMD | VAWLHCLLP | 0.4407 | 425 | WB | Large T |
| DRB1_0101 | 173 LYKKLMEKYSVTFIS | LMEKYSVTF | 0.4405 | 426 | WB | Large T |
| DRB1_0101 | 5 LNREESMELMDLLGL | LNREESMEL | 0.4397 | 429 | WB | Large T |
| DRB1_0101 | 580 LLIWFRPVADFSKDI | WFRPVADFS | 0.4370 | 442 | WB | Large T |
| DRB1_0101 | 391 AGVAWLHCLLPKMDS | VAWLHCLLP | 0.4368 | 443 | WB | Large T |
| DRB1_0101 | 7 REESMELMDLLGLER | MELMDLLGL | 0.4355 | 449 | WB | Large T |
| DRB1_0101 | 341 QAVDTVLAKKRVDTL | VDTVLAKKR | 0.4341 | 456 | WB | Large T |
| DRB1_0101 | 431 DSGKTTLAAGLLDLC | KTTLAAGLL | 0.4339 | 457 | WB | Large T |
| DRB1_0101 | 155 NRTLACFAVYTTKEK | LACFAVYTT | 0.4312 | 471 | WB | Large T |
| DRB1_0101 | 192 AGHNIIFFLTPHRHR | IFFLTPHRH | 0.4310 | 472 | WB | Large T |
| DRB1_0101 | 538 TLQARFVRQIDFRPK | LQARFVRQI | 0.4309 | 472 | WB | Large T |
| DRB1_0101 | 266 ETKQVSWKLITEYAV | VSWKLITEY | 0.4307 | 473 | WB | Large T |
| DRB1_0101 | 267 TKQVSWKLITEYAVE | WKLITEYAV | 0.4303 | 475 | WB | Large T |
| DRB1_0101 | 539 LQARFVRQIDFRPKI | LQARFVRQI | 0.4290 | 482 | WB | Large T |
| DRB1_0101 | 225 CKGVNKEYLLYSALT | VNKEYLLYS | 0.4288 | 483 | WB | Large T |
| DRB1_0101 | 677 KGFQCFKRPKTPPPK | FKRPKTPPP | 0.4281 | 487 | WB | Large T |
| DRB1_0101 | 333 KNQKSICQQAVDTVL | ICQQAVDTV | 0.4261 | 498 | WB | Large T |
| DRB1_0101 | 72 PDFGTWNSSEVPTYG | FGTWNSSEV | 0.4258 | 499 | WB | Large T |
| DRB1_0401 | 47 GDEDKMKRMNTLYKK | MKRMNTLYK | 0.5015 | 220 | WB | Large T |
| DRB1_0401 | 48 DEDKMKRMNTLYKKM | MKRMNTLYK | 0.4994 | 225 | WB | Large T |
| DRB1_0401 | 46 GGDEDKMKRMNTLYK | KMKRMNTLY | 0.4992 | 226 | WB | Large T |
| DRB1_0401 | 49 EDKMKRMNTLYKKME | MKRMNTLYK | 0.4991 | 226 | WB | Large T |
| DRB1_0401 | 50 DKMKRMNTLYKKMEQ | MKRMNTLYK | 0.4948 | 237 | WB | Large T |
| DRB1_0401 | 192 AGHNIIFFLTPHRHR | IIFFLTPHR | 0.4859 | 261 | WB | Large T |
| DRB1_0401 | 194 HNIIFFLTPHRHRVS | IIFFLTPHR | 0.4856 | 261 | WB | Large T |
| DRB1_0401 | 193 GHNIIFFLTPHRHRV | IIFFLTPHR | 0.4820 | 272 | WB | Large T |

TABLE S-continued

Prediction of BK virus Large T protein specific MHC class 2, 15-mer peptide binders for 14 MHC class 2 alleles (see FIG. 11) using the www.cbs.dtu.dk/services/NetMHCII/database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0401 | 191CAGHNIIFFLTPHRH | IIFFLTPHR | 0.4700 | 309 | WB | Large T |
| DRB1_0401 | 190MCAGHNIIFFLTPHR | MCAGHNIIF | 0.4533 | 371 | WB | Large T |
| DRB1_0404 | 194HNIIFFLTPHRHRVS | IIFFLTPHR | 0.5594 | 118 | WB | Large T |
| DRB1_0404 | 193GHNIIFFLTPHRHRV | IIFFLTPHR | 0.5580 | 119 | WB | Large T |
| DRB1_0404 | 284CEDVFLLLGMYLEFQ | FLLLGMYLE | 0.5487 | 132 | WB | Large T |
| DRB1_0404 | 286DVFLLLGMYLEFQYN | LLGMYLEFQ | 0.5479 | 133 | WB | Large T |
| DRB1_0404 | 285EDVFLLLGMYLEFQY | LLGMYLEFQ | 0.5470 | 135 | WB | Large T |
| DRB1_0404 | 288FLLLGMYLEFQYNVE | LLGMYLEFQ | 0.5425 | 141 | WB | Large T |
| DRB1_0404 | 287VFLLLGMYLEFQYNV | LLGMYLEFQ | 0.5417 | 142 | WB | Large T |
| DRB1_0404 | 192AGHNIIFFLTPHRHR | IIFFLTPHR | 0.5303 | 161 | WB | Large T |
| DRB1_0404 | 191CAGHNIIFFLTPHRH | IIFFLTPHR | 0.5272 | 167 | WB | Large T |
| DRB1_0404 | 575MTLLLLLIWFRPVAD | LLLLIWFRP | 0.5188 | 182 | WB | Large T |
| DRB1_0404 | 389YMAGVAWLHCLLPKM | VAWLHCLLP | 0.5113 | 198 | WB | Large T |
| DRB1_0404 | 387EQYMAGVAWLHCLLP | YMAGVAWLH | 0.5087 | 203 | WB | Large T |
| DRB1_0404 | 576TLLLLLIWFRPVADF | LLLLIWFRP | 0.5091 | 203 | WB | Large T |
| DRB1_0404 | 190MCAGHNIIFFLTPHR | HNIIFFLTP | 0.5052 | 211 | WB | Large T |
| DRB1_0404 | 390MAGVAWLHCLLPKMD | VAWLHCLLP | 0.5054 | 211 | WB | Large T |
| DRB1_0404 | 175KKLMEKYSVTFISRH | LMEKYSVTF | 0.5033 | 216 | WB | Large T |
| DRB1_0404 | 391AGVAWLHCLLPKMDS | VAWLHCLLP | 0.5004 | 223 | WB | Large T |
| DRB1_0404 | 577LLLLLIWFRPVADFS | LLIWFRPVA | 0.5001 | 223 | WB | Large T |
| DRB1_0404 | 388QYMAGVAWLHCLLPK | VAWLHCLLP | 0.4995 | 225 | WB | Large T |
| DRB1_0404 | 195NIIFFLTPHRHRVSA | IIFFLTPHR | 0.4985 | 227 | WB | Large T |
| DRB1_0404 | 179EKYSVTFISRHMCAG | YSVTFISRH | 0.4981 | 228 | WB | Large T |
| DRB1_0404 | 177LMEKYSVTFISRHMC | YSVTFISRH | 0.4969 | 231 | WB | Large T |
| DRB1_0404 | 176KLMEKYSVTFISRHM | YSVTFISRH | 0.4952 | 236 | WB | Large T |
| DRB1_0404 | 178MEKYSVTFISRHMCA | YSVTFISRH | 0.4940 | 239 | WB | Large T |
| DRB1_0404 | 578LLLLIWFRPVADFSK | LLIWFRPVA | 0.4909 | 247 | WB | Large T |
| DRB1_0404 | 196IIFFLTPHRHRVSAI | IIFFLTPHR | 0.4866 | 258 | WB | Large T |
| DRB1_0404 | 574GMTLLLLLIWFRPVA | LLLLIWFRP | 0.4835 | 267 | WB | Large T |
| DRB1_0404 | 371LDKMDLIFGAHGNAV | MDLIFGAHG | 0.4592 | 348 | WB | Large T |
| DRB1_0404 | 290LLGMYLEFQYNVEEC | LLGMYLEFQ | 0.4448 | 406 | WB | Large T |
| DRB1_0404 | 289LLLGMYLEFQYNVEE | LLGMYLEFQ | 0.4447 | 407 | WB | Large T |
| DRB1_0404 | 372DKMDLIFGAHGNAVL | IFGAHGNAV | 0.4437 | 411 | WB | Large T |
| DRB1_0405 | 575MTLLLLLIWFRPVAD | LLIWFRPVA | 0.7757 | 11 | SB | Large T |
| DRB1_0405 | 576TLLLLLIWFRPVADF | LIWFRPVAD | 0.7721 | 12 | SB | Large T |
| DRB1_0405 | 577LLLLLIWFRPVADFS | LIWFRPVAD | 0.7733 | 12 | SB | Large T |
| DRB1_0405 | 578LLLLIWFRPVADFSK | LIWFRPVAD | 0.7738 | 12 | SB | Large T |
| DRB1_0405 | 579LLLIWFRPVADFSKD | LIWFRPVAD | 0.7712 | 12 | SB | Large T |
| DRB1_0405 | 85YGTEEWESWWSSFNE | WESWWSSFN | 0.7453 | 16 | SB | Large T |
| DRB1_0405 | 87TEEWESWWSSFNEKW | WESWWSSFN | 0.7451 | 16 | SB | Large T |
| DRB1_0405 | 86GTEEWESWWSSFNEK | WESWWSSFN | 0.7381 | 17 | SB | Large T |
| DRB1_0405 | 88EEWESWWSSFNEKWD | WESWWSSFN | 0.7402 | 17 | SB | Large T |
| DRB1_0405 | 84TYGTEEWESWWSSFN | TEEWESWWS | 0.7216 | 20 | SB | Large T |
| DRB1_0405 | 580LLIWFRPVADFSKDI | LIWFRPVAD | 0.6804 | 32 | SB | Large T |
| DRB1_0405 | 581LIWFRPVADFSKDIQ | LIWFRPVAD | 0.6771 | 33 | SB | Large T |
| DRB1_0405 | 89EWESWWSSFNEKWDE | WESWWSSFN | 0.6771 | 33 | SB | Large T |
| DRB1_0405 | 90WESWWSSFNEKWDED | WESWWSSFN | 0.6504 | 44 | SB | Large T |
| DRB1_0405 | 49EDKMKRMNTLYKKME | MKRMNTLYK | 0.5687 | 106 | WB | Large T |
| DRB1_0405 | 50DKMKRMNTLYKKMEQ | MKRMNTLYK | 0.5662 | 109 | WB | Large T |
| DRB1_0405 | 47GDEDKMKRMNTLYKK | MKRMNTLYK | 0.5447 | 138 | WB | Large T |
| DRB1_0405 | 46GGDEDKMKRMNTLYK | DKMKRMNTL | 0.5432 | 140 | WB | Large T |
| DRB1_0405 | 48DEDKMKRMNTLYKKM | MKRMNTLYK | 0.5413 | 143 | WB | Large T |
| DRB1_0405 | 490GHGINNLDSLRDYLD | INNLDSLRD | 0.5182 | 184 | WB | Large T |
| DRB1_0405 | 491HGINNLDSLRDYLDG | INNLDSLRD | 0.5113 | 198 | WB | Large T |
| DRB1_0405 | 18GLERAAWGNLPLMRK | RAAWGNLPL | 0.5095 | 202 | WB | Large T |
| DRB1_0405 | 487LPSGHGINNLDSLRD | GHGINNLDS | 0.4979 | 229 | WB | Large T |
| DRB1_0405 | 19LERAAWGNLPLMRKA | RAAWGNLPL | 0.4956 | 235 | WB | Large T |
| DRB1_0405 | 488PSGHGINNLDSLRDY | INNLDSLRD | 0.4948 | 237 | WB | Large T |
| DRB1_0405 | 489SGHGINNLDSLRDYL | INNLDSLRD | 0.4858 | 261 | WB | Large T |
| DRB1_0405 | 51KMRMNTLYKKMEQD | MKRMNTLYK | 0.4857 | 261 | WB | Large T |
| DRB1_0405 | 52MKRMNTLYKKMEQDV | MKRMNTLYK | 0.4857 | 261 | WB | Large T |
| DRB1_0405 | 391AGVAWLHCLLPKMDS | VAWLHCLLP | 0.4831 | 269 | WB | Large T |
| DRB1_0405 | 91ESWWSSFNEKWDEDL | WSSFNEKWD | 0.4812 | 274 | WB | Large T |
| DRB1_0405 | 390MAGVAWLHCLLPKMD | VAWLHCLLP | 0.4697 | 310 | WB | Large T |
| DRB1_0405 | 387EQYMAGVAWLHCLLP | YMAGVAWLH | 0.4648 | 327 | WB | Large T |
| DRB1_0405 | 68VAHQPDFGTWNSSEV | QPDFGTWNS | 0.4624 | 336 | WB | Large T |
| DRB1_0405 | 418VPKRRYWLFKGPIDS | YWLFKGPID | 0.4620 | 337 | WB | Large T |
| DRB1_0405 | 388QYMAGVAWLHCLLPK | VAWLHCLLP | 0.4614 | 339 | WB | Large T |
| DRB1_0405 | 420KRRYWLFKGPIDSGK | YWLFKGPID | 0.4599 | 345 | WB | Large T |
| DRB1_0405 | 419PKRRYWLFKGPIDSG | YWLFKGPID | 0.4586 | 350 | WB | Large T |
| DRB1_0405 | 20ERAAWGNLPLMRKAY | WGNLPLMRK | 0.4570 | 356 | WB | Large T |

TABLE S-continued

Prediction of BK virus Large T protein specific MHC class 2, 15-mer peptide binders for 14 MHC class 2 alleles (see FIG. 11) using the www.cbs.dtu.dk/services/NetMHCII/database. The MHC class 2 molecules for which no binders were found are not listed.

| Allele | pospeptide | core | 1-log50k(aff) | aff(nM) | B.L. | Identity |
|---|---|---|---|---|---|---|
| DRB1_0405 | 69 AHQPDFGTWNSSEVP | FGTWNSSEV | 0.4571 | 356 | WB | Large T |
| DRB1_0405 | 389 YMAGVAWLHCLLPKM | VAWLHCLLP | 0.4547 | 365 | WB | Large T |
| DRB1_0405 | 421 RRYWLFKGPIDSGKT | YWLFKGPID | 0.4540 | 368 | WB | Large T |
| DRB1_0405 | 417 NVPKRRYWLFKGPID | RYWLFKGPI | 0.4530 | 372 | WB | Large T |
| DRB1_0405 | 17 LGLERAAWGNLPLMR | RAAWGNLPL | 0.4515 | 378 | WB | Large T |
| DRB1_0405 | 16 LLGLERAAWGNLPLM | RAAWGNLPL | 0.4465 | 399 | WB | Large T |
| DRB1_0405 | 493 INNLDSLRDYLDGSV | INNLDSLRD | 0.4409 | 424 | WB | Large T |
| DRB1_0405 | 492 GINNLDSLRDYLDGS | INNLDSLRD | 0.4405 | 426 | WB | Large T |
| DRB1_0405 | 15 DLLGLERAAWGNLPL | ERAAWGNLP | 0.4401 | 427 | WB | Large T |
| DRB1_0405 | 70 HQPDFGTWNSSEVPT | FGTWNSSEV | 0.4392 | 432 | WB | Large T |
| DRB1_0405 | 653 CSSQVSDTSAPDSEN | QVSDTSAPD | 0.4296 | 479 | WB | Large T |
| DRB1_0405 | 654 SSQVSDTSAPDSENP | QVSDTSAPD | 0.4282 | 486 | WB | Large T |
| DRB1_0701 | 412 HCVVFNVPKRRYWLF | VFNVPKRRY | 0.5438 | 139 | WB | Large T |
| DRB1_0701 | 413 CVVFNVPKRRYWLFK | VPKRRYWLF | 0.5406 | 144 | WB | Large T |
| DRB1_0701 | 414 VVFNVPKRRYWLFKG | VPKRRYWLF | 0.5149 | 190 | WB | Large T |
| DRB1_0701 | 415 VFNVPKRRYWLFKGP | VPKRRYWLF | 0.5009 | 221 | WB | Large T |
| DRB1_0701 | 71 QPDFGTWNSSEVPTY | FGTWNSSEV | 0.4820 | 272 | WB | Large T |
| DRB1_0701 | 72 PDFGTWNSSEVPTYG | FGTWNSSEV | 0.4789 | 281 | WB | Large T |
| DRB1_0701 | 68 VAHQPDFGTWNSSEV | DFGTWNSSE | 0.4709 | 306 | WB | Large T |
| DRB1_0701 | 69 AHQPDFGTWNSSEVP | FGTWNSSEV | 0.4658 | 324 | WB | Large T |
| DRB1_0701 | 70 HQPDFGTWNSSEVPT | FGTWNSSEV | 0.4657 | 324 | WB | Large T |
| DRB1_0701 | 416 FNVPKRRYWLFKGPI | VPKRRYWLF | 0.4627 | 335 | WB | Large T |
| DRB1_0701 | 194 HNIIFFLTPHRHRVS | IFFLTPHRH | 0.4550 | 364 | WB | Large T |
| DRB1_0701 | 195 NIIFFLTPHRHRVSA | IFFLTPHRH | 0.4521 | 375 | WB | Large T |
| DRB1_0701 | 193 GHNIIFFLTPHRHRV | IFFLTPHRH | 0.4386 | 434 | WB | Large T |
| DRB1_0701 | 176 KLMEKYSVTFISRHM | YSVTFISRH | 0.4346 | 454 | WB | Large T |
| DRB1_0701 | 196 IIFFLTPHRHRVSAI | IFFLTPHRH | 0.4331 | 461 | WB | Large T |
| DRB1_0701 | 177 LMEKYSVTFISRHMC | YSVTFISRH | 0.4315 | 469 | WB | Large T |
| DRB1_0701 | 387 EQYMAGVAWLHCLLP | YMAGVAWLH | 0.4303 | 475 | WB | Large T |
| DRB1_0701 | 386 LEQYMAGVAWLHCLL | YMAGVAWLH | 0.4292 | 481 | WB | Large T |
| DRB1_0701 | 192 AGHNIIFFLTPHRHR | IFFLTPHRH | 0.4288 | 483 | WB | Large T |
| DRB1_0701 | 197 IFFLTPHRHRVSAIN | IFFLTPHRH | 0.4289 | 483 | WB | Large T |
| DRB1_0901 | 229 NKEYLLYSALTRDPY | YLLYSALTR | 0.4376 | 439 | WB | Large T |
| DRB1_0901 | 230 KEYLLYSALTRDPYH | YLLYSALTR | 0.4372 | 441 | WB | Large T |
| DRB1_0901 | 72 PDFGTWNSSEVPTYG | WNSSEVPTY | 0.4364 | 445 | WB | Large T |
| DRB1_0901 | 71 QPDFGTWNSSEVPTY | FGTWNSSEV | 0.4355 | 449 | WB | Large T |
| DRB1_0901 | 228 VNKEYLLYSALTRDP | YLLYSALTR | 0.4325 | 464 | WB | Large T |
| DRB1_0901 | 384 AVLEQYMAGVAWLHC | LEQYMAGVA | 0.4270 | 493 | WB | Large T |
| DRB1_0901 | 383 NAVLEQYMAGVAWLH | LEQYMAGVA | 0.4259 | 499 | WB | Large T |
| DRB1_1101 | 232 YLLYSALTRDPYHII | YSALTRDPY | 0.4594 | 347 | WB | Large T |
| DRB1_1101 | 233 LLYSALTRDPYHIIE | YSALTRDPY | 0.4586 | 350 | WB | Large T |
| DRB1_1101 | 231 EYLLYSALTRDPYHI | YSALTRDPY | 0.4552 | 363 | WB | Large T |
| DRB1_1101 | 229 NKEYLLYSALTRDPY | YLLYSALTR | 0.4548 | 364 | WB | Large T |
| DRB1_1101 | 47 GDEDKMKRMNTLYKK | MKRMNTLYK | 0.4550 | 364 | WB | Large T |
| DRB1_1101 | 230 KEYLLYSALTRDPYH | YSALTRDPY | 0.4537 | 369 | WB | Large T |
| DRB1_1101 | 49 EDKMKRMNTLYKKME | MKRMNTLYK | 0.4498 | 385 | WB | Large T |
| DRB1_1101 | 48 DEDKMKRMNTLYKKM | MKRMNTLYK | 0.4495 | 386 | WB | Large T |
| DRB1_1101 | 50 DKMKRMNTLYKKMEQ | MKRMNTLYK | 0.4483 | 391 | WB | Large T |
| DRB1_1101 | 46 GGDEDKMKRMNTLYK | EDKMKRMNT | 0.4433 | 413 | WB | Large T |
| DRB1_1101 | 18 GLERAAWGNLPLMRK | AWGNLPLMR | 0.4312 | 471 | WB | Large T |
| DRB1_1101 | 19 LERAAWGNLPLMRKA | WGNLPLMRK | 0.4311 | 471 | WB | Large T |
| DRB1_1101 | 21 RAAWGNLPLMRKAYL | WGNLPLMRK | 0.4288 | 483 | WB | Large T |
| DRB1_1101 | 20 ERAAWGNLPLMRKAY | WGNLPLMRK | 0.4279 | 488 | WB | Large T |
| DRB1_1302 | 18 GLERAAWGNLPLMRK | LERAAWGNL | 0.5752 | 99 | WB | Large T |
| DRB1_1302 | 21 RAAWGNLPLMRKAYL | WGNLPLMRK | 0.5714 | 103 | WB | Large T |
| DRB1_1302 | 22 AAWGNLPLMRKAYLK | WGNLPLMRK | 0.5704 | 104 | WB | Large T |
| DRB1_1302 | 19 LERAAWGNLPLMRKA | WGNLPLMRK | 0.5702 | 105 | WB | Large T |
| DRB1_1302 | 20 ERAAWGNLPLMRKAY | WGNLPLMRK | 0.5531 | 126 | WB | Large T |
| DRB1_1302 | 285 EDVFLLLGMYLEFQY | FLLLGMYLE | 0.5498 | 130 | WB | Large T |
| DRB1_1302 | 445 CGGKALNVNLPMERL | LNVNLPMER | 0.5476 | 134 | WB | Large T |
| DRB1_1302 | 446 GGKALNVNLPMERLT | LNVNLPMER | 0.5454 | 137 | WB | Large T |
| DRB1_1302 | 566 LEKRILQSGMTLLLL | ILQSGMTLL | 0.5431 | 140 | WB | Large T |
| DRB1_1302 | 444 LCGGKALNVNLPMER | GKALNVNLP | 0.5427 | 141 | WB | Large T |
| DRB1_1302 | 565 LLEKRILQSGMTLLL | ILQSGMTLL | 0.5420 | 142 | WB | Large T |
| DRB1_1302 | 447 GKALNVNLPMERLTF | LNVNLPMER | 0.5392 | 146 | WB | Large T |
| DRB1_1302 | 284 CEDVFLLLGMYLEFQ | FLLLGMYLE | 0.5383 | 148 | WB | Large T |
| DRB1_1302 | 283 KCEDVFLLLGMYLEF | FLLLGMYLE | 0.5363 | 151 | WB | Large T |
| DRB1_1302 | 567 EKRILQSGMTLLLLL | ILQSGMTLL | 0.5327 | 157 | WB | Large T |
| DRB1_1302 | 282 TKCEDVFLLLGMYLE | VFLLLGMYL | 0.5292 | 163 | WB | Large T |

TABLE S-continued

Prediction of BK virus Large T protein specific MHC class 2, 15-mer peptide binders for 14 MHC class 2 alleles (see FIG. 11) using the www.cbs.dtu.dk/services/NetMHCII/database. The MHC class 2 molecules for which no binders were found are not listed.

| Allele | pospeptide | core | 1-log50k(aff) | aff(nM) | B.L. | Identity |
|---|---|---|---|---|---|---|
| DRB1_1302 | 568 KRILQSGMTLLLLLI | ILQSGMTLL | 0.5282 | 165 | WB | Large T |
| DRB1_1302 | 286 DVFLLLGMYLEFQYN | FLLLGMYLE | 0.5258 | 169 | WB | Large T |
| DRB1_1302 | 409 DFLHCVVFNVPKRRY | VVFNVPKRR | 0.5112 | 198 | WB | Large T |
| DRB1_1302 | 411 LHCVVFNVPKRRYWL | VFNVPKRRY | 0.5079 | 205 | WB | Large T |
| DRB1_1302 | 410 FLHCVVFNVPKRRYW | VFNVPKRRY | 0.5074 | 206 | WB | Large T |
| DRB1_1302 | 48 DEDKMKRMNTLYKKM | MKRMNTLYK | 0.5012 | 221 | WB | Large T |
| DRB1_1302 | 448 KALNVNLPMERLTFE | LNVNLPMER | 0.4996 | 225 | WB | Large T |
| DRB1_1302 | 49 EDKMKRMNTLYKKME | MKRMNTLYK | 0.4986 | 227 | WB | Large T |
| DRB1_1302 | 609 ISMYTFSRMKYNICM | MYTFSRMKY | 0.4969 | 231 | WB | Large T |
| DRB1_1302 | 50 DKMKRMNTLYKKMEQ | MKRMNTLYK | 0.4966 | 232 | WB | Large T |
| DRB1_1302 | 412 HCVVFNVPKRRYWLF | VFNVPKRRY | 0.4955 | 235 | WB | Large T |
| DRB1_1302 | 47 GDEDKMKRMNTLYKK | MKRMNTLYK | 0.4940 | 239 | WB | Large T |
| DRB1_1302 | 564 FLLEKRILQSGMTLL | KRILQSGMT | 0.4938 | 239 | WB | Large T |
| DRB1_1302 | 608 EISMYTFSRMKYNIC | ISMYTFSRM | 0.4935 | 240 | WB | Large T |
| DRB1_1302 | 24 WGNLPLMRKAYLKKC | WGNLPLMRK | 0.4926 | 242 | WB | Large T |
| DRB1_1302 | 23 AWGNLPLMRKAYLKK | WGNLPLMRK | 0.4885 | 253 | WB | Large T |
| DRB1_1302 | 46 GGDEDKMKRMNTLYK | DKMKRMNTL | 0.4800 | 278 | WB | Large T |
| DRB1_1302 | 487 LPSGHGINNLDSLRD | HGINNLDSL | 0.4764 | 289 | WB | Large T |
| DRB1_1302 | 489 SGHGINNLDSLRDYL | INNLDSLRD | 0.4752 | 293 | WB | Large T |
| DRB1_1302 | 488 PSGHGINNLDSLRDY | INNLDSLRD | 0.4736 | 298 | WB | Large T |
| DRB1_1302 | 569 RILQSGMTLLLLLIW | LQSGMTLLL | 0.4720 | 303 | WB | Large T |
| DRB1_1302 | 287 VFLLLGMYLEFQYNV | FLLLGMYLE | 0.4711 | 306 | WB | Large T |
| DRB1_1302 | 413 CVVFNVPKRRYWLFK | VFNVPKRRY | 0.4581 | 352 | WB | Large T |
| DRB1_1302 | 522 IFPPGLVTMNEYPVP | PGLVTMNEY | 0.4560 | 360 | WB | Large T |
| DRB1_1302 | 490 GHGINNLDSLRDYLD | INNLDSLRD | 0.4532 | 371 | WB | Large T |
| DRB1_1302 | 523 FPPGLVTMNEYPVPK | PGLVTMNEY | 0.4489 | 389 | WB | Large T |
| DRB1_1302 | 232 YLLYSALTRDPYHII | YSALTRDPY | 0.4367 | 444 | WB | Large T |
| DRB1_1302 | 491 HGINNLDSLRDYLDG | INNLDSLRD | 0.4358 | 448 | WB | Large T |
| DRB1_1302 | 570 ILQSGMTLLLLLIWF | ILQSGMTLL | 0.4330 | 462 | WB | Large T |
| DRB1_1302 | 449 ALNVNLPMERLTFEL | LNVNLPMER | 0.4326 | 463 | WB | Large T |
| DRB1_1302 | 607 SEISMYTFSRMKYNI | ISMYTFSRM | 0.4327 | 463 | WB | Large T |
| DRB1_1302 | 51 KMKRMNTLYKKMEQD | MKRMNTLYK | 0.4272 | 492 | WB | Large T |
| DRB1_1501 | 192 AGHNIIFFLTPHRHR | IIFFLTPHR | 0.6526 | 43 | SB | Large T |
| DRB1_1501 | 193 GHNIIFFLTPHRHRV | IIFFLTPHR | 0.6507 | 44 | SB | Large T |
| DRB1_1501 | 575 MTLLLLLIWFRPVAD | LLLLLIWFR | 0.6509 | 44 | SB | Large T |
| DRB1_1501 | 574 GMTLLLLLIWFRPVA | LLLLLIWFR | 0.6462 | 46 | SB | Large T |
| DRB1_1501 | 191 CAGHNIIFFLTPHRH | IIFFLTPHR | 0.6427 | 48 | SB | Large T |
| DRB1_1501 | 194 HNIIFFLTPHRHRVS | IIFFLTPHR | 0.6416 | 48 | SB | Large T |
| DRB1_1501 | 576 TLLLLLIWFRPVADF | LLLLLIWFR | 0.6127 | 66 | WB | Large T |
| DRB1_1501 | 577 LLLLLIWFRPVADFS | LLIWFRPVA | 0.5958 | 79 | WB | Large T |
| DRB1_1501 | 190 MCAGHNIIFFLTPHR | NIIFFLTPH | 0.5914 | 83 | WB | Large T |
| DRB1_1501 | 573 SGMTLLLLLIWFRPV | LLLLLIWFR | 0.5875 | 87 | WB | Large T |
| DRB1_1501 | 195 NIIFFLTPHRHRVSA | IIFFLTPHR | 0.5848 | 89 | WB | Large T |
| DRB1_1501 | 572 QSGMTLLLLLIWFRP | LLLLLIWFR | 0.5640 | 112 | WB | Large T |
| DRB1_1501 | 196 IIFFLTPHRHRVSAI | IIFFLTPHR | 0.5515 | 128 | WB | Large T |
| DRB1_1501 | 578 LLLLIWFRPVADFSK | LLIWFRPVA | 0.5410 | 144 | WB | Large T |
| DRB1_1501 | 571 LQSGMTLLLLLIWFR | TLLLLLIWF | 0.5272 | 167 | WB | Large T |
| DRB1_1501 | 48 DEDKMKRMNTLYKKM | MKRMNTLYK | 0.5229 | 174 | WB | Large T |
| DRB1_1501 | 49 EDKMKRMNTLYKKME | MKRMNTLYK | 0.5190 | 182 | WB | Large T |
| DRB1_1501 | 24 WGNLPLMRKAYLKKC | LMRKAYLKK | 0.5176 | 185 | WB | Large T |
| DRB1_1501 | 50 DKMKRMNTLYKKMEQ | MKRMNTLYK | 0.5153 | 190 | WB | Large T |
| DRB1_1501 | 47 GDEDKMKRMNTLYKK | MKRMNTLYK | 0.5147 | 191 | WB | Large T |
| DRB1_1501 | 23 AWGNLPLMRKAYLKK | LPLMRKAYL | 0.5076 | 206 | WB | Large T |
| DRB1_1501 | 25 GNLPLMRKAYLKKCK | LMRKAYLKK | 0.5063 | 209 | WB | Large T |
| DRB1_1501 | 46 GGDEDKMKRMNTLYK | DKMKRMNTL | 0.5026 | 217 | WB | Large T |
| DRB1_1501 | 26 NLPLMRKAYLKKCKE | LMRKAYLKK | 0.4961 | 233 | WB | Large T |
| DRB1_1501 | 548 DFRPKIYLRKSLQNS | DFRPKIYLR | 0.4942 | 238 | WB | Large T |
| DRB1_1501 | 227 GVNKEYLLYSALTRD | YLLYSALTR | 0.4878 | 255 | WB | Large T |
| DRB1_1501 | 228 VNKEYLLYSALTRDP | YLLYSALTR | 0.4864 | 259 | WB | Large T |
| DRB1_1501 | 229 NKEYLLYSALTRDPY | YLLYSALTR | 0.4863 | 259 | WB | Large T |
| DRB1_1501 | 230 KEYLLYSALTRDPYH | YLLYSALTR | 0.4859 | 260 | WB | Large T |
| DRB1_1501 | 27 LPLMRKAYLKKCKEF | LMRKAYLKK | 0.4850 | 263 | WB | Large T |
| DRB1_1501 | 409 DFLHCVVFNVPKRRY | CVVFNVPKR | 0.4823 | 271 | WB | Large T |
| DRB1_1501 | 410 FLHCVVFNVPKRRYW | CVVFNVPKR | 0.4819 | 272 | WB | Large T |
| DRB1_1501 | 226 KGVNKEYLLYSALTR | VNKEYLLYS | 0.4792 | 280 | WB | Large T |
| DRB1_1501 | 411 LHCVVFNVPKRRYWL | CVVFNVPKR | 0.4791 | 280 | WB | Large T |
| DRB1_1501 | 543 FVRQIDFRPKIYLRK | DFRPKIYLR | 0.4749 | 293 | WB | Large T |
| DRB1_1501 | 544 VRQIDFRPKIYLRKS | DFRPKIYLR | 0.4739 | 297 | WB | Large T |
| DRB1_1501 | 542 RFVRQIDFRPKIYLR | VRQIDFRPK | 0.4731 | 299 | WB | Large T |
| DRB1_1501 | 408 FDFLHCVVFNVPKRR | CVVFNVPKR | 0.4728 | 300 | WB | Large T |
| DRB1_1501 | 579 LLLIWFRPVADFSKD | LLIWFRPVA | 0.4695 | 311 | WB | Large T |
| DRB1_1501 | 13 LMDLLGLERAAWGNL | LMDLLGLER | 0.4683 | 315 | WB | Large T |

TABLE S-continued

Prediction of BK virus Large T protein specific MHC class 2, 15-mer
peptide binders for 14 MHC class 2 alleles (see FIG. 11) using the
www.cbs.dtu.dk/services/NetMHCII/database. The MHC class 2
molecules for which no binders were found are not listed.

| Allele | pospeptide | core | 1-log50k(aff) | aff(nM) | B.L. | Identity |
|---|---|---|---|---|---|---|
| DRB1_1501 | 549 FRPKIYLRKSLQNSE | YLRKSLQNS | 0.4683 | 315 | WB | Large T |
| DRB1_1501 | 11 MELMDLLGLERAAWG | LMDLLGLER | 0.4651 | 326 | WB | Large T |
| DRB1_1501 | 142 SDLHQFLSQAVFSNR | LHQFLSQAV | 0.4611 | 341 | WB | Large T |
| DRB1_1501 | 413 CVVFNVPKRRYWLFK | CVVFNVPKR | 0.4554 | 362 | WB | Large T |
| DRB1_1501 | 169 KAQILYKKLMEKYSV | ILYKKLMEK | 0.4523 | 375 | WB | Large T |
| DRB1_1501 | 170 AQILYKKLMEKYSVT | ILYKKLMEK | 0.4511 | 379 | WB | Large T |
| DRB1_1501 | 546 QIDFRPKIYLRKSLQ | DFRPKIYLR | 0.4502 | 383 | WB | Large T |
| DRB1_1501 | 419 PKRRYWLFKGPIDSG | WLFKGPIDS | 0.4498 | 385 | WB | Large T |
| DRB1_1501 | 418 VPKRRYWLFKGPIDS | KRRYWLFKG | 0.4458 | 402 | WB | Large T |
| DRB1_1501 | 547 IDFRPKIYLRKSLQN | FRPKIYLRK | 0.4373 | 440 | WB | Large T |
| DRB1_1501 | 420 KRRYWLFKGPIDSGK | WLFKGPIDS | 0.4350 | 452 | WB | Large T |
| DRB1_1501 | 414 VVFNVPKRRYWLFKG | PKRRYWLFK | 0.4334 | 460 | WB | Large T |
| DRB1_1501 | 28 PLMRKAYLKKCKEFH | LMRKAYLKK | 0.4332 | 461 | WB | Large T |
| DRB1_1501 | 51 KMKRMNTLYKKMEQD | MKRMNTLYK | 0.4331 | 461 | WB | Large T |
| DRB1_1501 | 172 ILYKKLMEKYSVTFI | ILYKKLMEK | 0.4319 | 467 | WB | Large T |
| DRB1_1501 | 550 RPKIYLRKSLQNSEF | YLRKSLQNS | 0.4316 | 469 | WB | Large T |
| DRB1_1501 | 545 RQIDFRPKIYLRKSL | DFRPKIYLR | 0.4312 | 471 | WB | Large T |
| DRB1_1501 | 580 LLIWFRPVADFSKDI | LLIWFRPVA | 0.4297 | 479 | WB | Large T |
| DRB1_1501 | 412 HCVVFNVPKRRYWLF | CVVFNVPKR | 0.4294 | 480 | WB | Large T |
| DRB1_1501 | 10 SMELMDLLGLERAAW | LMDLLGLER | 0.4261 | 497 | WB | Large T |
| DRB4_0101 | 609 ISMYTFSRMKYNICM | FSRMKYNIC | 0.5682 | 107 | WB | Large T |
| DRB4_0101 | 611 MYTFSRMKYNICMGK | FSRMKYNIC | 0.5289 | 163 | WB | Large T |
| DRB4_0101 | 608 EISMYTFSRMKYNIC | ISMYTFSRM | 0.5272 | 167 | WB | Large T |
| DRB4_0101 | 612 YTFSRMKYNICMGKC | FSRMKYNIC | 0.5271 | 167 | WB | Large T |
| DRB4_0101 | 610 SMYTFSRMKYNICMG | FSRMKYNIC | 0.5243 | 172 | WB | Large T |
| DRB4_0101 | 576 TLLLLLIWFRPVADF | LIWFRPVAD | 0.4721 | 302 | WB | Large T |
| DRB4_0101 | 194 HNIIFFLTPHRHRVS | IFFLTPHRH | 0.4700 | 309 | WB | Large T |
| DRB4_0101 | 193 GHNIIFFLTPHRHRV | IFFLTPHRH | 0.4668 | 320 | WB | Large T |
| DRB4_0101 | 192 AGHNIIFFLTPHRHR | IFFLTPHRH | 0.4660 | 323 | WB | Large T |
| DRB4_0101 | 195 NIIFFLTPHRHRVSA | IFFLTPHRH | 0.4640 | 330 | WB | Large T |
| DRB4_0101 | 541 ARFVRQIDFRPKIYL | VRQIDFRPK | 0.4637 | 331 | WB | Large T |
| DRB4_0101 | 577 LLLLLIWFRPVADFS | LIWFRPVAD | 0.4628 | 334 | WB | Large T |
| DRB4_0101 | 191 CAGHNIIFFLTPHRH | IIFFLTPHR | 0.4583 | 351 | WB | Large T |
| DRB4_0101 | 613 TFSRMKYNICMGKCI | FSRMKYNIC | 0.4575 | 354 | WB | Large T |
| DRB4_0101 | 542 RFVRQIDFRPKIYLR | VRQIDFRPK | 0.4556 | 362 | WB | Large T |
| DRB4_0101 | 578 LLLLIWFRPVADFSK | LIWFRPVAD | 0.4526 | 373 | WB | Large T |
| DRB4_0101 | 614 FSRMKYNICMGKCIL | FSRMKYNIC | 0.4368 | 443 | WB | Large T |
| DRB4_0101 | 579 LLLIWFRPVADFSKD | LIWFRPVAD | 0.4362 | 446 | WB | Large T |
| DRB4_0101 | 539 LQARFVRQIDFRPKI | VRQIDFRPK | 0.4355 | 449 | WB | Large T |
| DRB4_0101 | 575 MTLLLLLIWFRPVAD | LLLIWFRPV | 0.4344 | 455 | WB | Large T |
| DRB4_0101 | 538 TLQARFVRQIDFRPK | FVRQIDFRP | 0.4341 | 456 | WB | Large T |
| DRB4_0101 | 540 QARFVRQIDFRPKIY | VRQIDFRPK | 0.4260 | 498 | WB | Large T |
| DRB5_0101 | 543 FVRQIDFRPKIYLRK | RQIDFRPKI | 0.6349 | 52 | WB | Large T |
| DRB5_0101 | 544 VRQIDFRPKIYLRKS | FRPKIYLRK | 0.6346 | 52 | WB | Large T |
| DRB5_0101 | 545 RQIDFRPKIYLRKSL | FRPKIYLRK | 0.6343 | 52 | WB | Large T |
| DRB5_0101 | 546 QIDFRPKIYLRKSLQ | FRPKIYLRK | 0.6326 | 53 | WB | Large T |
| DRB5_0101 | 547 IDFRPKIYLRKSLQN | FRPKIYLRK | 0.6322 | 53 | WB | Large T |
| DRB5_0101 | 411 LHCVVFNVPKRRYWL | VVFNVPKRR | 0.5655 | 110 | WB | Large T |
| DRB5_0101 | 412 HCVVFNVPKRRYWLF | VVFNVPKRR | 0.5631 | 113 | WB | Large T |
| DRB5_0101 | 410 FLHCVVFNVPKRRYW | VVFNVPKRR | 0.5614 | 115 | WB | Large T |
| DRB5_0101 | 409 DFLHCVVFNVPKRRY | VVFNVPKRR | 0.5437 | 139 | WB | Large T |
| DRB5_0101 | 548 DFRPKIYLRKSLQNS | FRPKIYLRK | 0.5361 | 151 | WB | Large T |
| DRB5_0101 | 549 FRPKIYLRKSLQNSE | FRPKIYLRK | 0.5359 | 152 | WB | Large T |
| DRB5_0101 | 255 KEHDFNPEEPEETKQ | FNPEEPEET | 0.5183 | 183 | WB | Large T |
| DRB5_0101 | 254 LKEHDFNPEEPEETK | FNPEEPEET | 0.5181 | 184 | WB | Large T |
| DRB5_0101 | 256 EHDFNPEEPEETKQV | FNPEEPEET | 0.5168 | 186 | WB | Large T |
| DRB5_0101 | 253 GLKEHDFNPEEPEET | GLKEHDFNP | 0.5161 | 188 | WB | Large T |
| DRB5_0101 | 257 HDFNPEEPEETKQVS | FNPEEPEET | 0.5162 | 188 | WB | Large T |
| DRB5_0101 | 408 FDFLHCVVFNVPKRR | CVVFNVPKR | 0.5052 | 211 | WB | Large T |
| DRB5_0101 | 413 CVVFNVPKRRYWLFK | VVFNVPKRR | 0.5006 | 222 | WB | Large T |
| DRB5_0101 | 84 TYGTEEWESWWSSFN | TEEWESWWS | 0.4988 | 227 | WB | Large T |
| DRB5_0101 | 85 YGTEEWESWWSSFNE | WESWWSSFN | 0.4977 | 229 | WB | Large T |
| DRB5_0101 | 88 EEWESWWSSFNEKWD | WESWWSSFN | 0.4975 | 230 | WB | Large T |
| DRB5_0101 | 87 TEEWESWWSSFNEKW | WESWWSSFN | 0.4963 | 233 | WB | Large T |
| DRB5_0101 | 86 GTEEWESWWSSFNEK | WESWWSSFN | 0.4952 | 235 | WB | Large T |
| DRB5_0101 | 677 KGFQCFKRPKTPPPK | FQCFKRPKT | 0.4816 | 273 | WB | Large T |
| DRB5_0101 | 49 EDKMKRMNTLYKKME | MKRMNTLYK | 0.4763 | 289 | WB | Large T |
| DRB5_0101 | 50 DKMKRMNTLYKKMEQ | MKRMNTLYK | 0.4758 | 290 | WB | Large T |
| DRB5_0101 | 48 DEDKMKRMNTLYKKM | MKRMNTLYK | 0.4726 | 301 | WB | Large T |
| DRB5_0101 | 414 VVFNVPKRRYWLFKG | VVFNVPKRR | 0.4695 | 311 | WB | Large T |
| DRB5_0101 | 47 GDEDKMKRMNTLYKK | MKRMNTLYK | 0.4617 | 338 | WB | Large T |

TABLE S-continued

Prediction of BK virus Large T protein specific MHC class 2, 15-mer peptide binders for 14 MHC class 2 alleles (see FIG. 11) using the www.cbs.dtu.dk/services/NetMHCII/database. The MHC class 2 molecules for which no binders were found are not listed.

| Allele | pospeptide | core | 1-log50k(aff) | aff(nM) | B.L. | Identity |
|---|---|---|---|---|---|---|
| DRB5_0101 | 194 HNIIFFLTPHRHRVS | FFLTPHRHR | 0.4587 | 350 | WB | Large T |
| DRB5_0101 | 46 GGDEDKMKRMNTLYK | DKMKRMNTL | 0.4567 | 357 | WB | Large T |
| DRB5_0101 | 193 GHNIIFFLTPHRHRV | FFLTPHRHR | 0.4542 | 367 | WB | Large T |
| DRB5_0101 | 195 NIIFFLTPHRHRVSA | FFLTPHRHR | 0.4419 | 419 | WB | Large T |
| DRB5_0101 | 119 TADSQHSTPPKKKRK | QHSTPPKKK | 0.4363 | 446 | WB | Large T |
| DRB5_0101 | 120 ADSQHSTPPKKKRKV | QHSTPPKKK | 0.4331 | 461 | WB | Large T |
| DRB5_0101 | 259 FNPEEPEETKQVSWK | FNPEEPEET | 0.4320 | 467 | WB | Large T |
| DRB5_0101 | 53 KRMNTLYKKMEQDVK | KRMNTLYKK | 0.4284 | 485 | WB | Large T |
| DRB5_0101 | 22 AAWGNLPLMRKAYLK | WGNLPLMRK | 0.4268 | 494 | WB | Large T |

SEQ ID NOS.: 60258-61275

Preferred BK virus fragments of Agnoprotein capable of interacting with one or more MHC class 2 molecules are listed in Table T.

TABLE T

Prediction of BK virus Agnoprotein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k (aff) | affinity (nM) | Bind Level | Identity |
|---|---|---|---|---|---|---|
| DRB1_0101 | 8 LVVLRQLSRQAS-VKV | LRQLSRQAS | 0.6877 | 29 | SB | Agno |
| DRB1_0101 | 9 VVLRQLSRQAS-VKVG | LSRQASVKV | 0.6820 | 31 | SB | Agno |
| DRB1_0101 | 10 VLRQLSRQASVK-VGK | LSRQASVKV | 0.6587 | 40 | SB | Agno |
| DRB1_0101 | 11 LRQLSRQASVK-VGKT | LSRQASVKV | 0.6595 | 40 | SB | Agno |
| DRB1_0101 | 5 PKNLVVL-RQLSRQAS | VLRQLSRQA | 0.6455 | 46 | SB | Agno |
| DRB1_0101 | 7 NLVVL-RQLSRQASVK | VLRQLSRQA | 0.6439 | 47 | SB | Agno |
| DRB1_0101 | 6 KNLVVL-RQLSRQASV | VLRQLSRQA | 0.6410 | 49 | SB | Agno |
| DRB1_0101 | 12 RQLSRQASVKVG-KTW | LSRQASVKV | 0.6369 | 51 | WB | Agno |
| DRB1_0101 | 14 LSRQASVKVGK-TWTG | LSRQASVKV | 0.6206 | 61 | WB | Agno |
| DRB1_0101 | 18 ASVKVGKTWTGT-KKR | VKVGKTWTG | 0.5679 | 107 | WB | Agno |
| DRB1_0101 | 17 QASVKVGKTWT-GTKK | VKVGKTWTG | 0.5669 | 108 | WB | Agno |
| DRB1_0101 | 15 SRQASVKVGK-TWTGT | VKVGKTWTG | 0.5640 | 112 | WB | Agno |
| DRB1_0101 | 16 RQASVKVGKTWT-GTK | VKVGKTWTG | 0.5640 | 112 | WB | Agno |
| DRB1_0101 | 4 EPKNLVVL-RQLSRQA | PKNLVVLRQ | 0.5604 | 116 | WB | Agno |
| DRB1_0101 | 13 QLSRQASVKVGK-TWT | LSRQASVKV | 0.5447 | 138 | WB | Agno |
| DRB1_0101 | 19 SVKVGKTWTGTK-KRA | VKVGKTWTG | 0.4852 | 263 | WB | Agno |
| DRB1_0101 | 20 VKVGKTWTGTK-KRAQ | VKVGKTWTG | 0.4749 | 293 | WB | Agno |
| DRB1_0401 | 8 LVVLRQLSRQAS-VKV | VLRQLSRQA | 0.4745 | 295 | WB | Agno |
| DRB1_0401 | 10 VLRQLSRQASVK-VGK | LSRQASVKV | 0.4500 | 384 | WB | Agno |
| DRB1_0401 | 9 VVLRQLSRQAS-VKVG | LSRQASVKV | 0.4476 | 394 | WB | Agno |
| DRB1_0401 | 11 LRQLSRQASVK-VGKT | LSRQASVKV | 0.4393 | 431 | WB | Agno |
| DRB1_0401 | 12 RQLSRQASVKVG-KTW | LSRQASVKV | 0.4380 | 437 | WB | Agno |
| DRB1_0405 | 55 DGKNKSTTAL-PAVKD | NKSTTALPA | 0.4704 | 308 | WB | Agno |
| DRB1_0405 | 56 GKNKSTTAL-PAVKDS | TTALPAVKD | 0.4657 | 324 | WB | Agno |

TABLE T-continued

Prediction of BK virus Agnoprotein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | pospeptide | core | 1-log50k affinity (aff) | Bind (nM) | Identity Level | |
|---|---|---|---|---|---|---|
| DRB1_0405 | 57 KNKSTTAL-PAVKDSV | TTALPAVKD | 0.4367 | 443 | WB | Agno |
| DRB1_0405 | 58 NKSTTAL-PAVKDSVK | TTALPAVKD | 0.4330 | 462 | WB | Agno |
| DRB1_1101 | 8 LVVLRQLSRQAS-VKV | LRQLSRQAS | 0.4614 | 340 | WB | Agno |
| DRB1_1101 | 5 PKNLVVL-RQLSRQAS | PKNLVVLRQ | 0.4605 | 343 | WB | Agno |
| DRB1_1101 | 6 KNLVVL-RQLSRQASV | LRQLSRQAS | 0.4594 | 347 | WB | Agno |
| DRB1_1101 | 9 VVLRQLSRQAS-VKVG | LRQLSRQAS | 0.4595 | 347 | WB | Agno |
| DRB1_1101 | 7 NLVVL-RQLSRQASVK | LRQLSRQAS | 0.4579 | 352 | WB | Agno |
| DRB1_1302 | 5 PKNLVVL-RQLSRQAS | VVLRQLSRQ | 0.5120 | 196 | WB | Agno |
| DRB1_1302 | 8 LVVLRQLSRQAS-VKV | LRQLSRQAS | 0.5035 | 215 | WB | Agno |
| DRB1_1302 | 6 KNLVVL-RQLSRQASV | LRQLSRQAS | 0.5031 | 216 | WB | Agno |
| DRB1_1302 | 9 VVLRQLSRQAS-VKVG | LRQLSRQAS | 0.4904 | 248 | WB | Agno |
| DRB1_1302 | 7 NLVVL-RQLSRQASVK | LRQLSRQAS | 0.4893 | 251 | WB | Agno |
| DRB1_1302 | 3 CEPKNLVVL-RQLSRQ | LVVLRQLSR | 0.4329 | 462 | WB | Agno |
| DRB1_1501 | 5 PKNLVVL-RQLSRQAS | LVVLRQLSR | 0.6754 | 34 | SB | Agno |
| DRB1_1501 | 6 KNLVVL-RQLSRQASV | LVVLRQLSR | 0.6742 | 34 | SB | Agno |
| DRB1_1501 | 4 EPKNLVVL-RQLSRQA | LVVLRQLSR | 0.6596 | 40 | SB | Agno |
| DRB1_1501 | 3 CEPKNLVVL-RQLSRQ | LVVLRQLSR | 0.6209 | 60 | WB | Agno |
| DRB1_1501 | 7 NLVVL-RQLSRQASVK | LVVLRQLSR | 0.6093 | 69 | WB | Agno |
| DRB1_1501 | 8 LVVLRQLSRQAS-VKV | LVVLRQLSR | 0.6010 | 75 | WB | Agno |
| DRB1_1501 | 2 FCEPKNLVVL-RQLSR | NLVVLRQLS | 0.5977 | 78 | WB | Agno |
| DRB1_1501 | 9 VVLRQLSRQAS-VKVG | LRQLSRQAS | 0.4406 | 425 | WB | Agno |
| DRB4_0101 | 35 RIFI-FILELLLEFCR | ILELLLEFC | 0.4266 | 494 | WB | Agno |

SEQ ID NOS: 61276-61367

Preferred *Borrelia afzelli* fragments of Osp C capable of interacting with one or more MHC class 1 and/or MHC class 2 molecules are listed in Table U.

TABLE U

Prediction of MHC class 1 and 2 *Borrelia afzelii* OspC peptide binders. Prediction of 8-, 9-, 10-, 11-, 13-, 14-, 15-, 16-mer peptides were using the program displayed in FIG. 2

8 mers:

MKKNTLSA; KKNTLSAI; KNTLSAIL; NTLSAILM; TLSAILMT; LSAILMTL;
SAILMTLF; AILMTLFL; ILMTLFLF; LMTLFLFI; MTLFLFIS; TLFLFISC;
LFLFISCN; FLFISCNN; LFISCNNS; FISCNNSG; ISCNNSGK; SCNNSGKG;
CNNSGKGG; NNSGKGGD; NSGKGGDS; SGKGGDSA; GKGGDSAS; KGGDSAST;
GGDSASTN; GDSASTNP; DSASTNPA; SASTNPAD; ASTNPADE; STNPADES;
TNPADESA; NPADESAK; PADESAKG; ADESAKGP; DESAKGPN; ESAKGPNL;
SAKGPNLT; AKGPNLTE; KGPNLTEI; GPNLTEIS; PNLTEISK; NLTEISKK;
LTEISKKI; TEISKKIT; EISKKITD; ISKKITDS; SKKITDSN; KKITDSNA;
KITDSNAF; ITDSNAFV; TDSNAFVL; DSNAFVLA; SNAFVLAV; NAFVLAVK;
AFVLAVKE; FVLAVKEV; VLAVKEVE; LAVKEVET; AVKEVETL; VKEVETLV;
KEVETLVS; EVETLVSS; VETLVSSI; ETLVSSID; TLVSSIDE; LVSSIDEL;
VSSIDELA; SSIDELAN; SIDELANK; IDELANKA; DELANKAI; ELANKAIG;
LANKAIGK; ANKAIGKK; NKAIGKKI; KAIGKKIQ; AIGKKIQQ; IGKKIQQN;

TABLE U-continued

Prediction of MHC class 1 and 2 *Borrelia afzelii* OspC peptide binders. Prediction of 8-, 9-, 10-, 11-, 13-, 14-, 15-, 16-mer peptides were using the program displayed in FIG. 2

GKKIQQNG; KKIQQNGL; KIQQNGLG; IQQNGLGA; QQNGLGAE; QNGLGAEA;
NGLGAEAN; GLGAEANR; LGAEANRN; GAEANRNE; AEANRNES; EANRNESL;
ANRNESLL; NRNESLLA; RNESLLAG; NESLLAGV; ESLLAGVH; SLLAGVHE;
LLAGVHEI; LAGVHEIS; AGVHEIST; GVHEISTL; VHEISTLI; HEISTLIT;
EISTLITE; ISTLITEK; STLITEKL; TLITEKLS; LITEKLSK; ITEKLSKL;
TEKLSKLK; EKLSKLKN; KLSKLKNS; LSKLKNSG; SKLKNSGE; KLKNSGEL;
LKNSGELK; KNSGELKA; NSGELKAK; SGELKAKI; GELKAKIE; ELKAKIED;
LKAKIEDA; KAKIEDAK; AKIEDAKK; KIEDAKKC; IEDAKKCS; EDAKKCSE;
DAKKCSEE; AKKCSEEF; KKCSEEFT; KCSEEFTN; CSEEFTNK; SEEFTNKL;
EEFTNKLR; EFTNKLRV; FTNKLRVS; TNKLRVSH; NKLRVSHA; KLRVSHAD;
LRVSHADL; RVSHADLG; VSHADLGK; SHADLGKQ; HADLGKQG; ADLGKQGV;
DLGKQGVN; LGKQGVND; GKQGVNDD; KQGVNDDD; QGVNDDDA; GVNDDDAK;
VNDDDAKK; NDDDAKKA; DDDAKKAI; DDAKKAIL; DAKKAILK; AKKAILKT;
KKAILKTN; KAILKTNA; AILKTNAD; ILKTNADK; LKTNADKT; KTNADKTK;
TNADKTKG; NADKTKGA; ADKTKGAE; DKTKGAEE; KTKGAEEL; TKGAEELG;
KGAEELGK; GAEELGKL; AEELGKLF; EELGKLFK; ELGKLFKS; LGKLFKSV;
GKLFKSVE; KLFKSVEG; LFKSVEGL; FKSVEGLV; KSVEGLVK; SVEGLVKA;
VEGLVKAA; EGLVKAAQ; GLVKAAQE; LVKAAQEA; VKAAQEAL; KAAQEALT;
AAQEALTN; AQEALTNS; QEALTNSV; EALTNSVK; ALTNSVKE; LTNSVKEL;
TNSVKELT; NSVKELTS; SVKELTSP; VKELTSPV; KELTSPVV; ELTSPVVA;
LTSPVVAE; TSPVVAES; SPVVAESP; PVVAESPK; VVAESPKK; VAESPKKP 9 mers:

MKKNTLSAI; KKNTLSAIL; KNTLSAILM; NTLSAILMT; TLSAILMTL;
LSAILMTLF; SAILMTLFL; AILMTLFLF; ILMTLFLFI; LMTLFLFIS;
MTLFLFISC; TLFLFISCN; LFLFISCNN; FLFISCNNS; LFISCNNSG;
FISCNNSGK; ISCNNSGKG; SCNNSGKGG; CNNSGKGGD; NNSGKGGDS;
NSGKGGDSA; SGKGGDSAS; GKGGDSAST; KGGDSASTN; GGDSASTNP;
GDSASTNPA; DSASTNPAD; SASTNPADE; ASTNPADES; STNPADESA;
TNPADESAK; NPADESAKG; PADESAKGP; ADESAKGPN; DESAKGPNL;
ESAKGPNLT; SAKGPNLTE; AKGPNLTEI; KGPNLTEIS; GPNLTEISK;
PNLTEISKK; NLTEISKKI; LTEISKKIT; TEISKKITD; EISKKITDS;
ISKKITDSN; SKKITDSNA; KKITDSNAF; KITDSNAFV; ITDSNAFVL;
TDSNAFVLA; DSNAFVLAV; SNAFVLAVK; NAFVLAVKE; AFVLAVKEV;
FVLAVKEVE; VLAVKEVET; LAVKEVETL; AVKEVETLV; VKEVETLVS;
KEVETLVSS; EVETLVSSI; VETLVSSID; ETLVSSIDE; TLVSSIDEL;
LVSSIDELA; VSSIDELAN; SSIDELANK; SIDELANKA; IDELANKAI;
DELANKAIG; ELANKAIGK; LANKAIGKK; ANKAIGKKI; NKAIGKKIQ;
KAIGKKIQQ; AIGKKIQQN; IGKKIQQNG; GKKIQQNGL; KKIQQNGLG;
KIQQNGLGA; IQQNGLGAE; QQNGLGAEA; QNGLGAEAN; NGLGAEANR;
GLGAEANRN; LGAEANRNE; GAEANRNES; AEANRNESL; EANRNESLL;
ANRNESLLA; NRNESLLAG; RNESLLAGV; NESLLAGVH; ESLLAGVHE;
SLLAGVHEI; LLAGVHEIS; LAGVHEIST; AGVHEISTL; GVHEISTLI;
VHEISTLIT; HEISTLITE; EISTLITEK; ISTLITEKL; STLITEKLS;
TLITEKLSK; LITEKLSKL; ITEKLSKLK; TEKLSKLKN; EKLSKLKNS;
KLSKLKNSG; LSKLKNSGE; SKLKNSGEL; KLKNSGELK; LKNSGELKA;
KNSGELKAK; NSGELKAKI; SGELKAKIE; GELKAKIED; ELKAKIEDA;
LKAKIEDAK; KAKIEDAKK; AKIEDAKKC; KIEDAKKCS; IEDAKKCSE;
EDAKKCSEE; DAKKCSEEF; AKKCSEEFT; KKCSEEFTN; KCSEEFTNK;
CSEEFTNKL; SEEFTNKLR; EEFTNKLRV; EFTNKLRVS; FTNKLRVSH;
TNKLRVSHA; NKLRVSHAD; KLRVSHADL; LRVSHADLG; RVSHADLGK;
VSHADLGKQ; SHADLGKQG; HADLGKQGV; ADLGKQGVN; DLGKQGVND;
LGKQGVNDD; GKQGVNDDD; KQGVNDDDA; QGVNDDDAK; GVNDDDAKK;
VNDDDAKKA; NDDDAKKAI; DDDAKKAIL; DDAKKAILK; DAKKAILKT;
AKKAILKTN; KKAILKTNA; KAILKTNAD; AILKTNADK; ILKTNADKT;
LKTNADKTK; KTNADKTKG; TNADKTKGA; NADKTKGAE; ADKTKGAEE;
DKTKGAEEL; KTKGAEELG; TKGAEELGK; KGAEELGKL; GAEELGKLF;
AEELGKLFK; EELGKLFKS; ELGKLFKSV; LGKLFKSVE; GKLFKSVEG;
KLFKSVEGL; LFKSVEGLV; FKSVEGLVK; KSVEGLVKA; SVEGLVKAA;
VEGLVKAAQ; EGLVKAAQE; GLVKAAQEA; LVKAAQEAL; VKAAQEALT;
KAAQEALTN; AAQEALTNS; AQEALTNSV; QEALTNSVK; EALTNSVKE;
ALTNSVKEL; LTNSVKELT; TNSVKELTS; NSVKELTSP; SVKELTSPV;
VKELTSPVV; KELTSPVVA; ELTSPVVAE; LTSPVVAES; TSPVVAESP;
SPVVAESPK; PVVAESPKK; VVAESPKKP 10 mers:

MKKNTLSAIL; KKNTLSAILM; KNTLSAILMT; NTLSAILMTL; TLSAILMTLF;
LSAILMTLFL; SAILMTLFLF; AILMTLFLFI; ILMTLFLFIS; LMTLFLFISC;
MTLFLFISCN; TLFLFISCNN; LFLFISCNNS; FLFISCNNSG; LFISCNNSGK;
FISCNNSGKG; ISCNNSGKGG; SCNNSGKGGD; CNNSGKGGDS; NNSGKGGDSA;
NSGKGGDSAS; SGKGGDSAST; GKGGDSASTN; KGGDSASTNP; GGDSASTNPA;
GDSASTNPAD; DSASTNPADE; SASTNPADES; ASTNPADESA; STNPADESAK;
TNPADESAKG; NPADESAKGP; PADESAKGPN; ADESAKGPNL; DESAKGPNLT;

TABLE U-continued

Prediction of MHC class 1 and 2 *Borrelia afzelii* OspC peptide binders. Prediction of 8-, 9-, 10-, 11-, 13-, 14-, 15-, 16-mer peptides were using the program displayed in FIG. 2

ESAKGPNLTE; SAKGPNLTEI; AKGPNLTEIS; KGPNLTEISK; GPNLTEISKK;
PNLTEISKKI; NLTEISKKIT; LTEISKKITD; TEISKKITDS; EISKKITDSN;
ISKKITDSNA; SKKITDSNAF; KKITDSNAFV; KITDSNAFVL; ITDSNAFVLA;
TDSNAFVLAV; DSNAFVLAVK; SNAFVLAVKE; NAFVLAVKEV; AFVLAVKEVE;
FVLAVKEVET; VLAVKEVETL; LAVKEVETLV; AVKEVETLVS; VKEVETLVSS;
KEVETLVSSI; EVETLVSSID; VETLVSSIDE; ETLVSSIDEL; TLVSSIDELA;
LVSSIDELAN; VSSIDELANK; SSIDELANKA; SIDELANKAI; IDELANKAIG;
DELANKAIGK; ELANKAIGKK; LANKAIGKKI; ANKAIGKKIQ; NKAIGKKIQQ;
KAIGKKIQQN; AIGKKIQQNG; IGKKIQQNGL; GKKIQQNGLG; KKIQQNGLGA;
KIQQNGLGAE; IQQNGLGAEA; QQNGLGAEAN; QNGLGAEANR; NGLGAEANRN;
GLGAEANRNE; LGAEANRNES; GAEANRNESL; AEANRNESLL; EANRNESLLA;
ANRNESLLAG; NRNESLLAGV; RNESLLAGVH; NESLLAGVHE; ESLLAGVHEI;
SLLAGVHEIS; LLAGVHEIST; LAGVHEISTL; AGVHEISTLI; GVHEISTLIT;
VHEISTLITE; HEISTLITEK; EISTLITEKL; ISTLITEKLS; STLITEKLSK;
TLITEKLSKL; LITEKLSKLK; ITEKLSKLKN; TEKLSKLKNS; EKLSKLKNSG;
KLSKLKNSGE; LSKLKNSGEL; SKLKNSGELK; KLKNSGELKA; LKNSGELKAK;
KNSGELKAKI; NSGELKAKIE; SGELKAKIED; GELKAKIEDA; ELKAKIEDAK;
LKAKIEDAKK; KAKIEDAKKC; AKIEDAKKCS; KIEDAKKCSE; IEDAKKCSEE;
EDAKKCSEEF; DAKKCSEEFT; AKKCSEEFTN; KKCSEEFTNK; KCSEEFTNKL;
CSEEFTNKLR; SEEFTNKLRV; EEFTNKLRVS; EFTNKLRVSH; FTNKLRVSHA;
TNKLRVSHAD; NKLRVSHADL; KLRVSHADLG; LRVSHADLGK; RVSHADLGKQ;
VSHADLGKQG; SHADLGKQGV; HADLGKQGVN; ADLGKQGVND; DLGKQGVNDD;
LGKQGVNDDD; GKQGVNDDDA; KQGVNDDDAK; QGVNDDDAKK; GVNDDDAKKA;
VNDDDAKKAI; NDDDAKKAIL; DDDAKKAILK; DDAKKAILKT; DAKKAILKTN;
AKKAILKTNA; KKAILKTNAD; KAILKTNADK; AILKTNADKT; ILKTNADKTK;
LKTNADKTKG; KTNADKTKGA; TNADKTKGAE; NADKTKGAEE; ADKTKGAEEL;
DKTKGAEELG; KTKGAEELGK; TKGAEELGKL; KGAEELGKLF; GAEELGKLFK;
AEELGKLFKS; EELGKLFKSV; ELGKLFKSVE; LGKLFKSVEG; GKLFKSVEGK;
KLFKSVEGLV; LFKSVEGLVK; FKSVEGLVKA; KSVEGLVKAA; SVEGLVKAAQ;
VEGLVKAAQE; EGLVKAAQEA; GLVKAAQEAL; LVKAAQEALT; VKAAQEALTN;
KAAQEALTNS; AAQEALTNSV; AQEALTNSVK; QEALTNSVKE; EALTNSVKEL;
ALTNSVKELT; LTNSVKELTS; TNSVKELTSP; NSVKELTSPV; SVKELTSPVV;
VKELTSPVVA; KELTSPVVAE; ELTSPVVAES; LTSPVVAESP; TSPVVAESPK;
SPVVAESPKK; PVVAESPKKP 11 mers:

MKKNTLSAILM; KKNTLSAILMT; KNTLSAILMTL; NTLSAILMTLF;
TLSAILMTLFL; LSAILMTLFLF; SAILMTLFLFI; AILMTLFLFIS;
ILMTLFLFISC; LMTLFLFISCN; MTLFLFISCNN; TLFLFISCNNS;
LFLFISCNNSG; FLFISCNNSGK; LFISCNNSGKG; FISCNNSGKGG;
ISCNNSGKGGD; SCNNSGKGGDS; CNNSGKGGDSA; NNSGKGGDSAS;
NSGKGGDSAST; SGKGGDSASTN; GKGGDSASTNP; KGGDSASTNPA;
GGDSASTNPAD; GDSASTNPADE; DSASTNPADES; SASTNPADESA;
ASTNPADESAK; STNPADESAKG; TNPADESAKGP; NPADESAKGPN;
PADESAKGPNL; ADESAKGPNLT; DESAKGPNLTE; ESAKGPNLTEI;
SAKGPNLTEIS; AKGPNLTEISK; KGPNLTEISKK; GPNLTEISKKI;
PNLTEISKKIT; NLTEISKKITD; LTEISKKITDS; TEISKKITDSN;
EISKKITDSNA; ISKKITDSNAF; SKKITDSNAFV; KKITDSNAFVL;
KITDSNAFVLA; ITDSNAFVLAV; TDSNAFVLAVK; DSNAFVLAVKE;
SNAFVLAVKEV; NAFVLAVKEVE; AFVLAVKEVET; FVLAVKEVETL;
VLAVKEVETLV; LAVKEVETLVS; AVKEVETLVSS; VKEVETLVSSI;
KEVETLVSSID; EVETLVSSIDE; VETLVSSIDEL; ETLVSSIDELA;
TLVSSIDELAN; LVSSIDELANK; VSSIDELANKA; SSIDELANKAI;
SIDELANKAIG; IDELANKAIGK; DELANKAIGKK; ELANKAIGKKI;
LANKAIGKKIQ; ANKAIGKKIQQ; NKAIGKKIQQN; KAIGKKIQQNG;
AIGKKIQQNGL; IGKKIQQNGLG; GKKIQQNGLGA; KKIQQNGLGAE;
KIQQNGLGAEA; IQQNGLGAEAN; QQNGLGAEANR; QNGLGAEANRN;
NGLGAEANRNE; GLGAEANRNES; LGAEANRNESL; GAEANRNESLL;
AEANRNESLLA; EANRNESLLAG; ANRNESLLAGV; NRNESLLAGVH;
RNESLLAGVHE; NESLLAGVHEI; ESLLAGVHEIS; SLLAGVHEIST;
LLAGVHEISTL; LAGVHEISTLI; AGVHEISTLIT; GVHEISTLITE;
VHEISTLITEK; HEISTLITEKL; EISTLITEKLS; ISTLITEKLSK;
STLITEKLSKL; TLITEKLSKLK; LITEKLSKLKN; ITEKLSKLKNS;
TEKLSKLKNSG; EKLSKLKNSGE; KLSKLKNSGEL; LSKLKNSGELK;
SKLKNSGELKA; KLKNSGELKAK; LKNSGELKAKI; KNSGELKAKIE;
NSGELKAKIED; SGELKAKIEDA; GELKAKIEDAK; ELKAKIEDAKK;
LKAKIEDAKKC; KAKIEDAKKCS; AKIEDAKKCSE; KIEDAKKCSEE;
IEDAKKCSEEF; EDAKKCSEEFT; DAKKCSEEFTN; AKKCSEEFTNK;
KKCSEEFTNKL; KCSEEFTNKLR; CSEEFTNKLRV; SEEFTNKLRVS;
EEFTNKLRVSH; EFTNKLRVSHA; FTNKLRVSHAD; TNKLRVSHADL;
NKLRVSHADLG; KLRVSHADLGK; LRVSHADLGKQ; RVSHADLGKQG;
VSHADLGKQGV; SHADLGKQGVN; HADLGKQGVND; ADLGKQGVNDD;
DLGKQGVNDDD; LGKQGVNDDDA; GKQGVNDDDAK; KQGVNDDDAKK;
QGVNDDDAKKA; GVNDDDAKKAI; VNDDDAKKAIL; NDDDAKKAILK;

TABLE U-continued

Prediction of MHC class 1 and 2 *Borrelia afzelii* OspC peptide binders. Prediction of 8-, 9-, 10-, 11-, 13-, 14-, 15-, 16-mer peptides were using the program displayed in FIG. 2

DDDAKKAILKT; DDAKKAILKTN; DAKKAILKTNA; AKKAILKTNAD;
KKAILKTNADK; KAILKTNADKT; AILKTNADKTK; ILKTNADKTKG;
LKTNADKTKGA; KTNADKTKGAE; TNADKTKGAEE; NADKTKGAEEL;
ADKTKGAEELG; DKTKGAEELGK; KTKGAEELGKL; TKGAEELGKLF;
KGAEELGKLFK; GAEELGKLFKS; AEELGKLFKSV; EELGKLFKSVE;
ELGKLFKSVEG; LGKLFKSVEGL; GKLFKSVEGLV; KLFKSVEGLVK;
LFKSVEGLVKA; FKSVEGLVKAA; KSVEGLVKAAQ; SVEGLVKAAQE;
VEGLVKAAQEA; EGLVKAAQEAL; GLVKAAQEALT; LVKAAQEALTN;
VKAAQEALTNS; KAAQEALTNSV; AAQEALTNSVK; AQEALTNSVKE;
QEALTNSVKEL; EALTNSVKELT; ALTNSVKELTS; LTNSVKELTSP;
TNSVKELTSPV; NSVKELTSPVV; SVKELTSPVVA; VKELTSPVVAE;
KELTSPVVAES; ELTSPVVAESP; LTSPVVAESPK; TSPVVAESPKK;
SPVVAESPKKP;

13 mers:

MKKNTLSAILMTL; KKNTLSAILMTLF; KNTLSAILMTLFL; NTLSAILMTLFLF;
TLSAILMTLFLFI; LSAILMTLFLFIS; SAILMTLFLFISC; AILMTLFLFISCN;
ILMTLFLFISCNN; LMTLFLFISCNNS; MTLFLFISCNNSG; TLFLFISCNNSGK;
LFLFISCNNSGKG; FLFISCNNSGKGG; LFISCNNSGKGGD; FISCNNSGKGGDS;
ISCNNSGKGGDSA; SCNNSGKGGDSAS; CNNSGKGGDSAST; NNSGKGGDSASTN;
NSGKGGDSASTNP; SGKGGDSASTNPA; GKGGDSASTNPAD; KGGDSASTNPADE;
GGDSASTNPADES; GDSASTNPADESA; DSASTNPADESAK; SASTNPADESAKG;
ASTNPADESAKGP; STNPADESAKGPN; TNPADESAKGPNL; NPADESAKGPNLT;
PADESAKGPNLTE; ADESAKGPNLTEI; DESAKGPNLTEIS; ESAKGPNLTEISK;
SAKGPNLTEISKK; AKGPNLTEISKKI; KGPNLTEISKKIT; GPNLTEISKKITD;
PNLTEISKKITDS; NLTEISKKITDSN; LTEISKKITDSNA; TEISKKITDSNAF;
EISKKITDSNAFV; ISKKITDSNAFVL; SKKITDSNAFVLA; KKITDSNAFVLAV;
KITDSNAFVLAVK; ITDSNAFVLAVKE; TDSNAFVLAVKEV; DSNAFVLAVKEVE;
SNAFVLAVKEVET; NAFVLAVKEVETL; AFVLAVKEVETLV; FVLAVKEVETLVS;
VLAVKEVETLVSS; LAVKEVETLVSSI; AVKEVETLVSSID; VKEVETLVSSIDE;
KEVETLVSSIDEL; EVETLVSSIDELA; VETLVSSIDELAN; ETLVSSIDELANK;
TLVSSIDELANKA; LVSSIDELANKAI; VSSIDELANKAIG; SSIDELANKAIGK;
SIDELANKAIGKK; IDELANKAIGKKI; DELANKAIGKKIQ; ELANKAIGKKIQQ;
LANKAIGKKIQQN; ANKAIGKKIQQNG; NKAIGKKIQQNGL; KAIGKKIQQNGLG;
AIGKKIQQNGLGA; IGKKIQQNGLGAE; GKKIQQNGLGAEA; KKIQQNGLGAEAN;
KIQQNGLGAEANR; IQQNGLGAEANRN; QQNGLGAEANRNE; QNGLGAEANRNES;
NGLGAEANRNESL; GLGAEANRNESLL; LGAEANRNESLLA; GAEANRNESLLAG;
AEANRNESLLAGV; EANRNESLLAGVH; ANRNESLLAGVHE; NRNESLLAGVHEI;
RNESLLAGVHEIS; NESLLAGVHEIST; ESLLAGVHEISTL; SLLAGVHEISTLI;
LLAGVHEISTLIT; LAGVHEISTLITE; AGVHEISTLITEK; GVHEISTLITEKL;
VHEISTLITEKLS; HEISTLITEKLSK; EISTLITEKLSKL; ISTLITEKLSKLK;
STLITEKLSKLKN; TLITEKLSKLKNS; LITEKLSKLKNSG; ITEKLSKLKNSGE;
TEKLSKLKNSGEL; EKLSKLKNSGELK; KLSKLKNSGELKA; LSKLKNSGELKAK;
SKLKNSGELKAKI; KLKNSGELKAKIE; LKNSGELKAKIED; KNSGELKAKIEDA;
NSGELKAKIEDAK; SGELKAKIEDAKK; GELKAKIEDAKKC; ELKAKIEDAKKCS;
LKAKIEDAKKCSE; KAKIEDAKKCSEE; AKIEDAKKCSEEF; KIEDAKKCSEEFT;
IEDAKKCSEEFTN; EDAKKCSEEFTNK; DAKKCSEEFTNKL; AKKCSEEFTNKLR;
KKCSEEFTNKLRV; KCSEEFTNKLRVS; CSEEFTNKLRVSH; SEEFTNKLRVSHA;
EEFTNKLRVSHAD; EFTNKLRVSHADL; FTNKLRVSHADLG; TNKLRVSHADLGK;
NKLRVSHADLGKQ; KLRVSHADLGKQG; LRVSHADLGKQGV; RVSHADLGKQGVN;
VSHADLGKQGVND; SHADLGKQGVNDD; HADLGKQGVNDDD; ADLGKQGVNDDDA;
DLGKQGVNDDDAK; LGKQGVNDDDAKK; GKQGVNDDDAKKA; KQGVNDDDAKKAI;
QGVNDDDAKKAIL; GVNDDDAKKAILK; VNDDDAKKAILKT; NDDDAKKAILKTN;
DDDAKKAILKTNA; DDAKKAILKTNAD; DAKKAILKTNADK; AKKAILKTNADKT;
KKAILKTNADKTK; KAILKTNADKTKG; AILKTNADKTKGA; ILKTNADKTKGAE;
LKTNADKTKGAEE; KTNADKTKGAEEL; TNADKTKGAEELG; NADKTKGAEELGK;
ADKTKGAEELGKL; DKTKGAEELGKLF; KTKGAEELGKLFK; TKGAEELGKLFKS;
KGAEELGKLFKSV; GAEELGKLFKSVE; AEELGKLFKSVEG; EELGKLFKSVEGL;
ELGKLFKSVEGLV; LGKLFKSVEGLVK; GKLFKSVEGLVKA; KLFKSVEGLVKAA;
LFKSVEGLVKAAQ; FKSVEGLVKAAQE; KSVEGLVKAAQEA; SVEGLVKAAQEAL;
VEGLVKAAQEALT; EGLVKAAQEALTN; GLVKAAQEALTNS; LVKAAQEALTNSV;
VKAAQEALTNSVK; KAAQEALTNSVKE; AAQEALTNSVKEL; AQEALTNSVKELT;
QEALTNSVKELTS; EALTNSVKELTSP; ALTNSVKELTSPV; LTNSVKELTSPVV;
TNSVKELTSPVVA; NSVKELTSPVVAE; SVKELTSPVVAES; VKELTSPVVAESP;
KELTSPVVAESPK; ELTSPVVAESPKK; LTSPVVAESPKKP

14 mers:

MKKNTLSAILMTLF; KKNTLSAILMTLFL; KNTLSAILMTLFLF;
NTLSAILMTLFLFI; TLSAILMTLFLFIS; LSAILMTLFLFISC;
SAILMTLFLFISCN; AILMTLFLFISCNN; ILMTLFLFISCNNS;
LMTLFLFISCNNSG; MTLFLFISCNNSGK; TLFLFISCNNSGKG;
LFLFISCNNSGKGG; FLFISCNNSGKGGD; LFISCNNSGKGGDS;
FISCNNSGKGGDSA; ISCNNSGKGGDSAS; SCNNSGKGGDSAST;

TABLE U-continued

Prediction of MHC class 1 and 2 Borrelia afzelii OspC peptide binders. Prediction of 8-, 9-, 10-, 11-, 13-, 14-, 15-, 16-mer peptides were using the program displayed in FIG. 2

CNNSGKGGDSASTN; NNSGKGGDSASTNP; NSGKGGDSASTNPA;
SGKGGDSASTNPAD; GKGGDSASTNPADE; KGGDSASTNPADES;
GGDSASTNPADESA; GDSASTNPADESAK; DSASTNPADESAKG;
SASTNPADESAKGP; ASTNPADESAKGPN; STNPADESAKGPNL;
TNPADESAKGPNLT; NPADESAKGPNLTE; PADESAKGPNLTEI;
ADESAKGPNLTEIS; DESAKGPNLTEISK; ESAKGPNLTEISKK;
SAKGPNLTEISKKI; AKGPNLTEISKKIT; KGPNLTEISKKITD;
GPNLTEISKKITDS; PNLTEISKKITDSN; NLTEISKKITDSNA;
LTEISKKITDSNAF; TEISKKITDSNAFV; EISKKITDSNAFVL;
ISKKITDSNAFVLA; SKKITDSNAFVLAV; KKITDSNAFVLAVK;
KITDSNAFVLAVKE; ITDSNAFVLAVKEV; TDSNAFVLAVKEVE;
DSNAFVLAVKEVET; SNAFVLAVKEVETL; NAFVLAVKEVETLV;
AFVLAVKEVETLVS; FVLAVKEVETLVSS; VLAVKEVETLVSSI;
LAVKEVETLVSSID; AVKEVETLVSSIDE; VKEVETLVSSIDEL;
KEVETLVSSIDELA; EVETLVSSIDELAN; VETLVSSIDELANK;
ETLVSSIDELANKA; TLVSSIDELANKAI; LVSSIDELANKAIG;
VSSIDELANKAIGK; SSIDELANKAIGKK; SIDELANKAIGKKI;
IDELANKAIGKKIQ; DELANKAIGKKIQQ; ELANKAIGKKIQQN;
LANKAIGKKIQQNG; ANKAIGKKIQQNGL; NKAIGKKIQQNGLG;
KAIGKKIQQNGLGA; AIGKKIQQNGLGAE; IGKKIQQNGLGAEA;
GKKIQQNGLGAEAN; KKIQQNGLGAEANR; KIQQNGLGAEANRN;
IQQNGLGAEANRNE; QQNGLGAEANRNES; QNGLGAEANRNESL;
NGLGAEANRNESLL; GLGAEANRNESLLA; LGAEANRNESLLAG;
GAEANRNESLLAGV; AEANRNESLLAGVH; EANRNESLLAGVHE;
ANRNESLLAGVHEI; NRNESLLAGVHEIS; RNESLLAGVHEIST;
NESLLAGVHEISTL; ESLLAGVHEISTLI; SLLAGVHEISTLIT;
LLAGVHEISTLITE; LAGVHEISTLITEK; AGVHEISTLITEKL;
GVHEISTLITEKLS; VHEISTLITEKLSK; HEISTLITEKLSKL;
EISTLITEKLSKLK; ISTLITEKLSKLKN; STLITEKLSKLKNS;
TLITEKLSKLKNSG; LITEKLSKLKNSGE; ITEKLSKLKNSGEL;
TEKLSKLKNSGELK; EKLSKLKNSGELKA; KLSKLKNSGELKAK;
LSKLKNSGELKAKI; SKLKNSGELKAKIE; KLKNSGELKAKIED;
LKNSGELKAKIEDA; KNSGELKAKIEDAK; NSGELKAKIEDAKK;
SGELKAKIEDAKKC; GELKAKIEDAKKCS; ELKAKIEDAKKCSE;
LKAKIEDAKKCSEE; KAKIEDAKKCSEEF; AKIEDAKKCSEEFT;
KIEDAKKCSEEFTN; IEDAKKCSEEFTNK; EDAKKCSEEFTNKL;
DAKKCSEEFTNKLR; AKKCSEEFTNKLRV; KKCSEEFTNKLRVS;
KCSEEFTNKLRVSH; CSEEFTNKLRVSHA; SEEFTNKLRVSHAD;
EEFTNKLRVSHADL; EFTNKLRVSHADLG; FTNKLRVSHADLGK;
TNKLRVSHADLGKQ; NKLRVSHADLGKQG; KLRVSHADLGKQGV;
LRVSHADLGKQGVN; RVSHADLGKQGVND; VSHADLGKQGVNDD;
SHADLGKQGVNDDD; HADLGKQGVNDDDA; ADLGKQGVNDDDAK;
DLGKQGVNDDDAKK; LGKQGVNDDDAKKA; GKQGVNDDDAKKAI;
KQGVNDDDAKKAIL; QGVNDDDAKKAILK; GVNDDDAKKAILKT;
VNDDDAKKAILKTN; NDDDAKKAILKTNA; DDDAKKAILKTNAD;
DDAKKAILKTNADK; DAKKAILKTNADKT; AKKAILKTNADKTK;
KKAILKTNADKTKG; KAILKTNADKTKGA; AILKTNADKTKGAE;
ILKTNADKTKGAEE; LKTNADKTKGAEEL; KTNADKTKGAEELG;
TNADKTKGAEELGK; NADKTKGAEELGKL; ADKTKGAEELGKLF;
DKTKGAEELGKLFK; KTKGAEELGKLFKS; TKGAEELGKLFKSV;
KGAEELGKLFKSVE; GAEELGKLFKSVEG; AEELGKLFKSVEGL;
EELGKLFKSVEGLV; ELGKLFKSVEGLVK; LGKLFKSVEGLVKA;
GKLFKSVEGLVKAA; KLFKSVEGLVKAAQ; LFKSVEGLVKAAQE;
FKSVEGLVKAAQEA; KSVEGLVKAAQEAL; SVEGLVKAAQEALT;
VEGLVKAAQEALTN; EGLVKAAQEALTNS; GLVKAAQEALTNSV;
LVKAAQEALTNSVK; VKAAQEALTNSVKE; KAAQEALTNSVKEL;
AAQEALTNSVKELT; AQEALTNSVKELTS; QEALTNSVKELTSP;
EALTNSVKELTSPV; ALTNSVKELTSPVV; LTNSVKELTSPVVA;
TNSVKELTSPVVAE; NSVKELTSPVVAES; SVKELTSPVVAESP;
VKELTSPVVAESPK; KELTSPVVAESPKK; ELTSPVVAESPKKP 15 mers:

MKKNTLSAILMTLFL; KKNTLSAILMTLFLF; KNTLSAILMTLFLFI;
NTLSAILMTLFLFIS; TLSAILMTLFLFISC; LSAILMTLFLFISCN;
SAILMTLFLFISCNN; AILMTLFLFISCNNS; ILMTLFLFISCNNSG;
LMTLFLFISCNNSGK; MTLFLFISCNNSGKG; TLFLFISCNNSGKGG;
LFLFISCNNSGKGGD; FLFISCNNSGKGGDS; LFISCNNSGKGGDSA;
FISCNNSGKGGDSAS; ISCNNSGKGGDSAST; SCNNSGKGGDSASTN;
CNNSGKGGDSASTNP; NNSGKGGDSASTNPA; NSGKGGDSASTNPAD;
SGKGGDSASTNPADE; GKGGDSASTNPADES; KGGDSASTNPADESA;
GGDSASTNPADESAK; GDSASTNPADESAKG; DSASTNPADESAKGP;
SASTNPADESAKGPN; ASTNPADESAKGPNL; STNPADESAKGPNLT;
TNPADESAKGPNLTE; NPADESAKGPNLTEI; PADESAKGPNLTEIS;
ADESAKGPNLTEISK; DESAKGPNLTEISKK; ESAKGPNLTEISKKI;

TABLE U-continued

Prediction of MHC class 1 and 2 *Borrelia afzelii* OspC peptide binders. Prediction of 8-, 9-, 10-, 11-, 13-, 14-, 15-, 16-mer peptides were using the program displayed in FIG. 2

SAKGPNLTEISKKIT; AKGPNLTEISKKITD; KGPNLTEISKKITDS;
GPNLTEISKKITDSN; PNLTEISKKITDSNA; NLTEISKKITDSNAF;
LTEISKKITDSNAFV; TEISKKITDSNAFVL; EISKKITDSNAFVLA;
ISKKITDSNAFVLAV; SKKITDSNAFVLAVK; KKITDSNAFVLAVKE;
KITDSNAFVLAVKEV; ITDSNAFVLAVKEVE; TDSNAFVLAVKEVET;
DSNAFVLAVKEVETL; SNAFVLAVKEVETLV; NAFVLAVKEVETLVS;
AFVLAVKEVETLVSS; FVLAVKEVETLVSSI; VLAVKEVETLVSSID;
LAVKEVETLVSSIDE; AVKEVETLVSSIDEL; VKEVETLVSSIDELA;
KEVETLVSSIDELAN; EVETLVSSIDELANK; VETLVSSIDELANKA;
ETLVSSIDELANKAI; TLVSSIDELANKAIG; LVSSIDELANKAIGK;
VSSIDELANKAIGKK; SSIDELANKAIGKKI; SIDELANKAIGKKIQ;
IDELANKAIGKKIQQ; DELANKAIGKKIQQN; ELANKAIGKKIQQNG;
LANKAIGKKIQQNGL; ANKAIGKKIQQNGLG; NKAIGKKIQQNGLGA;
KAIGKKIQQNGLGAE; AIGKKIQQNGLGAEA; IGKKIQQNGLGAEAN;
GKKIQQNGLGAEANR; KKIQQNGLGAEANRN; KIQQNGLGAEANRNE;
IQQNGLGAEANRNES; QQNGLGAEANRNESL; QNGLGAEANRNESLL;
NGLGAEANRNESLLA; GLGAEANRNESLLAG; LGAEANRNESLLAGV;
GAEANRNESLLAGVH; AEANRNESLLAGVHE; EANRNESLLAGVHEI;
ANRNESLLAGVHEIS; NRNESLLAGVHEIST; RNESLLAGVHEISTL;
NESLLAGVHEISTLI; ESLLAGVHEISTLIT; SLLAGVHEISTLITE;
LLAGVHEISTLITEK; LAGVHEISTLITEKL; AGVHEISTLITEKLS;
GVHEISTLITEKLSK; VHEISTLITEKLSKL; HEISTLITEKLSKLK;
EISTLITEKLSKLKN; ISTLITEKLSKLKNS; STLITEKLSKLKNSG;
TLITEKLSKLKNSGE; LITEKLSKLKNSGEL; ITEKLSKLKNSGELK;
TEKLSKLKNSGELKA; EKLSKLKNSGELKAK; KLSKLKNSGELKAKI;
LSKLKNSGELKAKIE; SKLKNSGELKAKIED; KLKNSGELKAKIEDA;
LKNSGELKAKIEDAK; KNSGELKAKIEDAKK; NSGELKAKIEDAKKC;
SGELKAKIEDAKKCS; GELKAKIEDAKKCSE; ELKAKIEDAKKCSEE;
LKAKIEDAKKCSEEF; KAKIEDAKKCSEEFT; AKIEDAKKCSEEFTN;
KIEDAKKCSEEFTNK; IEDAKKCSEEFTNKL; EDAKKCSEEFTNKLR;
DAKKCSEEFTNKLRV; AKKCSEEFTNKLRVS; KKCSEEFTNKLRVSH;
KCSEEFTNKLRVSHA; CSEEFTNKLRVSHAD; SEEFTNKLRVSHADL;
EEFTNKLRVSHADLG; EFTNKLRVSHADLGK; FTNKLRVSHADLGKQ;
TNKLRVSHADLGKQG; NKLRVSHADLGKQGV; KLRVSHADLGKQGVN;
LRVSHADLGKQGVND; RVSHADLGKQGVNDD; VSHADLGKQGVNDDD;
SHADLGKQGVNDDDA; HADLGKQGVNDDDAK; ADLGKQGVNDDDAKK;
DLGKQGVNDDDAKKA; LGKQGVNDDDAKKAI; GKQGVNDDDAKKAIL;
KQGVNDDDAKKAILK; QGVNDDDAKKAILKT; GVNDDDAKKAILKTN;
VNDDDAKKAILKTNA; NDDDAKKAILKTNAD; DDDAKKAILKTNADK;
DDAKKAILKTNADKT; DAKKAILKTNADKTK; AKKAILKTNADKTKG;
KKAILKTNADKTKGA; KAILKTNADKTKGAE; AILKTNADKTKGAEE;
ILKTNADKTKGAEEL; LKTNADKTKGAEELG; KTNADKTKGAEELGK;
TNADKTKGAEELGKL; NADKTKGAEELGKLF; ADKTKGAEELGKLFK;
DKTKGAEELGKLFKS; KTKGAEELGKLFKSV; TKGAEELGKLFKSVE;
KGAEELGKLFKSVEG; GAEELGKLFKSVEGL; AEELGKLFKSVEGLV;
EELGKLFKSVEGLVK; ELGKLFKSVEGLVKA; LGKLFKSVEGLVKAA;
GKLFKSVEGLVKAAQ; KLFKSVEGLVKAAQE; LFKSVEGLVKAAQEA;
FKSVEGLVKAAQEAL; KSVEGLVKAAQEALT; SVEGLVKAAQEALTN;
VEGLVKAAQEALTNS; EGLVKAAQEALTNSV; GLVKAAQEALTNSVK;
LVKAAQEALTNSVKE; VKAAQEALTNSVKEL; KAAQEALTNSVKELT;
AAQEALTNSVKELTS; AQEALTNSVKELTSP; QEALTNSVKELTSPV;
EALTNSVKELTSPVV; ALTNSVKELTSPVVA; LTNSVKELTSPVVAE;
TNSVKELTSPVVAES; NSVKELTSPVVAESP; SVKELTSPVVAESPK;
VKELTSPVVAESPKK; KELTSPVVAESPKKP 16 mers:

MKKNTLSAILMTLFLF; KKNTLSAILMTLFLFI; KNTLSAILMTLFLFIS;
NTLSAILMTLFLFISC; TLSAILMTLFLFISCN; LSAILMTLFLFISCNN;
SAILMTLFLFISCNNS; AILMTLFLFISCNNSG; ILMTLFLFISCNNSGK;
LMTLFLFISCNNSGKG; MTLFLFISCNNSGKGG; TLFLFISCNNSGKGGD;
LFLFISCNNSGKGGDS; FLFISCNNSGKGGDSA; LFISCNNSGKGGDSAS;
FISCNNSGKGGDSAST; ISCNNSGKGGDSASTN; SCNNSGKGGDSASTNP;
CNNSGKGGDSASTNPA; NNSGKGGDSASTNPAD; NSGKGGDSASTNPADE;
SGKGGDSASTNPADES; GKGGDSASTNPADESA; KGGDSASTNPADESAK;
GGDSASTNPADESAKG; GDSASTNPADESAKGP; DSASTNPADESAKGPN;
SASTNPADESAKGPNL; ASTNPADESAKGPNLT; STNPADESAKGPNLTE;
TNPADESAKGPNLTEI; NPADESAKGPNLTEIS; PADESAKGPNLTEISK;
ADESAKGPNLTEISKK; DESAKGPNLTEISKKI; ESAKGPNLTEISKKIT;
SAKGPNLTEISKKITD; AKGPNLTEISKKITDS; KGPNLTEISKKITDSN;
GPNLTEISKKITDSNA; PNLTEISKKITDSNAF; NLTEISKKITDSNAFV;
LTEISKKITDSNAFVL; TEISKKITDSNAFVLA; EISKKITDSNAFVLAV;
ISKKITDSNAFVLAVK; SKKITDSNAFVLAVKE; KKITDSNAFVLAVKEV;
KITDSNAFVLAVKEVE; ITDSNAFVLAVKEVET; TDSNAFVLAVKEVETL;
DSNAFVLAVKEVETLV; SNAFVLAVKEVETLVS; NAFVLAVKEVETLVSS;

TABLE U-continued

Prediction of MHC class 1 and 2 *Borrelia afzelii* OspC peptide binders. Prediction of 8-, 9-, 10-, 11-, 13-, 14-, 15-, 16-mer peptides were using the program displayed in FIG. 2

AFVLAVKEVETLVSSI; FVLAVKEVETLVSSID; VLAVKEVETLVSSIDE;
LAVKEVETLVSSIDEL; AVKEVETLVSSIDELA; VKEVETLVSSIDELAN;
KEVETLVSSIDELANK; EVETLVSSIDELANKA; VETLVSSIDELANKAI;
ETLVSSIDELANKAIG; TLVSSIDELANKAIGK; LVSSIDELANKAIGKK;
VSSIDELANKAIGKKI; SSIDELANKAIGKKIQ; SIDELANKAIGKKIQQ;
IDELANKAIGKKIQQN; DELANKAIGKKIQQNG; ELANKAIGKKIQQNGL;
LANKAIGKKIQQNGLG; ANKAIGKKIQQNGLGA; NKAIGKKIQQNGLGAE;
KAIGKKIQQNGLGAEA; AIGKKIQQNGLGAEAN; IGKKIQQNGLGAEANR;
GKKIQQNGLGAEANRN; KKIQQNGLGAEANRNE; KIQQNGLGAEANRNES;
IQQNGLGAEANRNESL; QQNGLGAEANRNESLL; QNGLGAEANRNESLLA;
NGLGAEANRNESLLAG; GLGAEANRNESLLAGV; LGAEANRNESLLAGVH;
GAEANRNESLLAGVHE; AEANRNESLLAGVHEI; EANRNESLLAGVHEIS;
ANRNESLLAGVHEIST; NRNESLLAGVHEISTL; RNESLLAGVHEISTLI;
NESLLAGVHEISTLIT; ESLLAGVHEISTLITE; SLLAGVHEISTLITEK;
LLAGVHEISTLITEKL; LAGVHEISTLITEKLS; AGVHEISTLITEKLSK;
GVHEISTLITEKLSKL; VHEISTLITEKLSKLK; HEISTLITEKLSKLKN;
EISTLITEKLSKLKNS; ISTLITEKLSKLKNSG; STLITEKLSKLKNSGE;
TLITEKLSKLKNSGEL; LITEKLSKLKNSGELK; ITEKLSKLKNSGELKA;
TEKLSKLKNSGELKAK; EKLSKLKNSGELKAKI; KLSKLKNSGELKAKIE;
LSKLKNSGELKAKIED; SKLKNSGELKAKIEDA; KLKNSGELKAKIEDAK;
LKNSGELKAKIEDAKK; KNSGELKAKIEDAKKC; NSGELKAKIEDAKKCS;
SGELKAKIEDAKKCSE; GELKAKIEDAKKCSEE; ELKAKIEDAKKCSEEF;
LKAKIEDAKKCSEEFT; KAKIEDAKKCSEEFTN; AKIEDAKKCSEEFTNK;
KIEDAKKCSEEFTNKL; IEDAKKCSEEFTNKLR; EDAKKCSEEFTNKLRV;
DAKKCSEEFTNKLRVS; AKKCSEEFTNKLRVSH; KKCSEEFTNKLRVSHA;
KCSEEFTNKLRVSHAD; CSEEFTNKLRVSHADL; SEEFTNKLRVSHADLG;
EEFTNKLRVSHADLGK; EFTNKLRVSHADLGKQ; FTNKLRVSHADLGKQG;
TNKLRVSHADLGKQGV; NKLRVSHADLGKQGVN; KLRVSHADLGKQGVND;
LRVSHADLGKQGVNDD; RVSHADLGKQGVNDDD; VSHADLGKQGVNDDDA;
SHADLGKQGVNDDDAK; HADLGKQGVNDDDAKK; ADLGKQGVNDDDAKKA;
DLGKQGVNDDDAKKAI; LGKQGVNDDDAKKAIL; GKQGVNDDDAKKAILK;
KQGVNDDDAKKAILKT; QGVNDDDAKKAILKTN; GVNDDDAKKAILKTNA;
VNDDDAKKAILKTNAD; NDDDAKKAILKTNADK; DDDAKKAILKTNADKT;
DDAKKAILKTNADKTK; DAKKAILKTNADKTKG; AKKAILKTNADKTKGA;
KKAILKTNADKTKGAE; KAILKTNADKTKGAEE; AILKTNADKTKGAEEL;
ILKTNADKTKGAEELG; LKTNADKTKGAEELGK; KTNADKTKGAEELGKL;
TNADKTKGAEELGKLF; NADKTKGAEELGKLFK; ADKTKGAEELGKLFKS;
DKTKGAEELGKLFKSV; KTKGAEELGKLFKSVE; TKGAEELGKLFKSVEG;
KGAEELGKLFKSVEGL; GAEELGKLFKSVEGLV; AEELGKLFKSVEGLVK;
EELGKLFKSVEGLVKA; ELGKLFKSVEGLVKAA; LGKLFKSVEGLVKAAQ;
GKLFKSVEGLVKAAQE; KLFKSVEGLVKAAQEA; LFKSVEGLVKAAQEAL;
FKSVEGLVKAAQEALT; KSVEGLVKAAQEALTN; SVEGLVKAAQEALTNS;
VEGLVKAAQEALTNSV; EGLVKAAQEALTNSVK; GLVKAAQEALTNSVKE;
LVKAAQEALTNSVKEL; VKAAQEALTNSVKELT; KAAQEALTNSVKELTS;
AAQEALTNSVKELTSP; AQEALTNSVKELTSPV; QEALTNSVKELTSPVV;
EALTNSVKELTSPVVA; ALTNSVKELTSPVVAE; LTNSVKELTSPVVAES;
TNSVKELTSPVVAESP; NSVKELTSPVVAESPK; SVKELTSPVVAESPKK;
VKELTSPVVAESPKKP

SEQ ID NOS: 49527-51126

Preferred *Borrelia burgdorferi* fragments of Osp A capable of interacting with one or more MHC molecules are listed in Table V.

TABLE V

Prediction of *Borrelia burgdorferi* OspA protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| | | |
|---|---|---|
| CAA44492.1\|Outer surface protein A [*Borrelia burgdorferi*] Seq9 | HLA-A0101 | |
| | HLA-A0201 | YLLGIGLIL |
| | | FTLEGTLAA |
| | | KTSTLTISV |
| | | FTKEDTITV |
| | | ALIACKQNV |
| | | LLGIGLILA |

TABLE V-continued

Prediction of *Borrelia burgdorferi* OspA protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

SLEATVDKL
ILKSGEITV
KVTEGTVVL
STLDEKNSV
TLVSKKVTL
GIGLILALI
YLLGIGLILA
TLDEKNSVSV
ALDDSDTTQA
LLGIGLILAL
NILKSGEITV
TLAADGKTTL

TABLE V-continued

Prediction of *Borrelia burgdorferi* OspA protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

| | |
|---|---|
| | VLKDFTLEGT |
| | YSLEATVDKL |
| | YLLGIGLILAL |
| | LVFTKEDTITV |
| | LLGIGLILALI |
| | ILALIACKQNV |
| | STLDEKNSVSV |
| | ALDDSDTTQAT |
| | VLKDFTLEGTL |
| | SLEATVDKLEL |
| | ILKSGEITVAL |
| | ALIACKQNVST |
| | TTLKVTEGTVV |
| | LAADGKTTLKV |
| | LIACKQNVSTL |
| HLA-A0301 | VVLSKNILK |
| | KTKNLVFTK |
| | LVSKKVTLK |
| | LILALIACK |
| | LTISVNSQK |
| | KAVEITTLK |
| | AADGKTTLK |
| | ISVNSQKTK |
| | RANGTRLEY |
| | SQTKFEIFK |
| | KSDGSGKAK |
| | TQATKKTGK |
| | MTELVSKEK |
| | TLVSKKVTLK |
| | TLTISVNSQK |
| | TVVLSKNILK |
| | GLILALIACK |
| | TLKELKNALK |
| | LSQTKFEIFK |
| | LAADGKTTLK |
| | VTEGTVVLSK |
| | KLELKGTSDK |
| | TTQATKKTGK |
| | GMTELVSKEK |
| | KYSLEATVDK |
| | KQNVSTLDEK |
| | TIADDLSQTK |
| | TISVNSQKTK |
| | KEDAKTLVSK |
| | GSGKAKEVLK |
| | KTIVRANGTR |
| | GTLEGEKTDK |
| | GKAVEITTLK |
| | GTRLEYTDIK |
| | VSKKVTLKDK |
| | IKSDGSGKAK |
| | TLAADGKTTLK |
| | STLTISVNSQK |
| | KTLVSKKVTLK |
| | KVTEGTVVLSK |
| | TTLKELKNALK |
| | LTISVNSQKTK |
| | GTVVLSKNILK |
| | FTKEDTITVQK |
| | IVRANGTRLEY |
| | TLKDKSSTEEK |
| | LVSKKVTLKDK |
| | KFNEKGETSEK |
| | LTIADDLSQTK |
| | SQKTKNLVFTK |
| | KSSTEEKFNEK |
| | ATKKTGKWDSK |
| HLA-A1101 | VVLSKNILK |
| | KTKNLVFTK |
| | SQTKFEIFK |
| | LTISVNSQK |
| | ATVDKLELK |
| | LILALIACK |
| | STEEKFNEK |
| | KAVEITTLK |
| | LVSKKVTLK |
| | MTELVSKEK |
| | AADGKTTLK |
| | SAGTNLEGK |
| | YSLEATVDK |
| | GSGTLEGEK |
| | TQATKKTGK |
| | RANGTRLEY |
| | IADDLSQTK |
| | ISVNSQKTK |
| | KSDGSGKAK |
| | GGMTELVSK |
| | TEGTVVLSK |
| | EITTLKELK |
| | TIVRANGTR |
| | TVVLSKNILK |
| | TTQATKKTGK |
| | TIADDLSQTK |
| | VTEGTVVLSK |
| | LSQTKFEIFK |
| | SSTEEKFNEK |
| | GLILALIACK |
| | KQNVSTLDEK |
| | TLTISVNSQK |
| | TLVSKKVTLK |
| | TISVNSQKTK |
| | LAADGKTTLK |
| | GMTELVSKEK |
| | TLKELKNALK |
| | KTIVRANGTR |
| | GSGKAKEVLK |
| | GTLEGEKTDK |
| | VSKKVTLKDK |
| | GTRLEYTDIK |
| | KLELKGTSDK |
| | DSAGTNLEGK |
| | STLTISVNSQK |
| | TTLKELKNALK |
| | KVTEGTVVLSK |
| | KTLVSKKVTLK |
| | GTVVLSKNILK |
| | LTIADDLSQTK |
| | TLAADGKTTLK |
| | AVEITTLKELK |
| | LTISVNSQKTK |
| | SQKTKNLVFTK |
| | KSSTEEKFNEK |
| | ATKKTGKWDSK |
| | TLKDKSSTEEK |
| | FTKEDTITVQK |
| | TLEGTLAADGK |
| | LVSKKVTLKDK |
| | MTELVSKEKDK |
| | DLSQTKFEIFK |
| | YTDIKSDGSGK |
| | LVSKEKDKDGK |
| | KFNEKGETSEK |
| | IGLILALIACK |
| HLA-A2402 | KYLLGIGLI |
| | KWDSKTSTL |
| | KYDSAGTNL |
| | KYLLGIGLIL |
| | KWDSKTSTLTI |
| | KYSLEATVDKL |
| HLA-A2902 | IVRANGTRLEY |
| | TIADDLSQTKF |
| HLA-A6801 | LTISVNSQK |
| | ETSEKTIVR |
| | MTELVSKEK |

TABLE V-continued

Prediction of *Borrelia burgdorferi* OspA protein specific MHC class1, 8-, 9-, 10-, 11-mer peptide binders for 42 MHC class 1 alleles (see FIG. 11) using the www.cbs.dtu.dk/services/NetMHC/ database. The MHC class 1 molecules for which no binders were found are not listed.

|  |  |
|---|---|
|  | EITTLKELK |
|  | TIVRANGTR |
|  | KAVEITTLK |
|  | DAKTLVSKK |
|  | KTKNLVFTK |
|  | STEEKFNEK |
|  | ATVDKLELK |
|  | LVSKKVTLK |
|  | SQTKFEIFK |
|  | YSLEATVDK |
|  | EGTLAADGK |
|  | ISVNSQKTK |
|  | LILALIACK |
|  | DIKSDGSGK |
|  | VVLSKNILK |
|  | EDAKTLVSK |
|  | DSDTTQATK |
|  | SAGTNLEGK |
|  | TVVLSKNILK |
|  | TLTISVNSQK |
|  | EATVDKLELK |
|  | TIADDLSQTK |
|  | DSAGTNLEGK |
|  | TTQATKKTGK |
|  | LAADGKTTLK |
|  | KTIVRANGTR |
|  | TISVNSQKTK |
|  | TLVSKKVTLK |
|  | SSTEEKFNEK |
|  | TLKELKNALK |
|  | LSQTKFEIFK |
|  | VTEGTVVLSK |
|  | EDAKTLVSKK |
|  | DSDTTQATKK |
|  | GLILALIACK |
| HLA-B0702 | IVRANGTRL |
|  | KVTEGTVVL |
|  | LAADGKTTL |
|  | LPGGMTELV |
|  | TVVLSKNIL |
|  | KAVEITTLKEL |
| HLA-B0801 | TLKELKNAL |
|  | ILKSGEITVAL |
|  | YLLGIGLILAL |
|  | TLKVTEGTVVL |
| HLA-B1501 | SQKTKNLVF |
|  | RANGTRLEY |
|  | YLLGIGLIL |
|  | KVTEGTVVL |
|  | TLKELKNAL |
|  | KAKEVLKDF |
|  | IVRANGTRL |
|  | LGIGLILAL |
|  | TLAADGKTTL |
|  | IVRANGTRLEY |
|  | YLLGIGLILAL |
|  | VQKYDSAGTNL |
|  | ILKSGEITVAL |
|  | VSKEKDKDGKY |
|  | VLKDFTLEGTL |
|  | TLKVTEGTVVL |
|  | VNSQKTKNLVF |
| HLA-B2705 | KKYLLGIGL |
|  | VRANGTRLEY |
|  | GKWDSKTSTL |
|  | KKYLLGIGLIL |
| HLA-B3501 | LAADGKTTL |
|  | RANGTRLEY |
|  | FTLEGTLAA |
|  | TVVLSKNIL |
|  | VALDDSDTT |
|  | YLLGIGLIL |
|  | LPGGMTELV |
|  | IADDLSQTKF |
|  | LPGGMTELVS |
|  | LKVTEGTVVL |
|  | YSLEATVDKL |
|  | YLLGIGLILAL |
|  | NSVSVDLPGGM |
|  | IVRANGTRLEY |
|  | TIADDLSQTKF |
|  | KAVEITTLKEL |
| HLA-B4403 | KEVLKDFTL |
|  | GEITVALDD |
|  | KEKDKDGKY |
|  | KEDAKTLVS |
|  | GEITVALDDS |
|  | KEDTITVQKY |
|  | GEITVALDDSD |
|  | KEVLKDFTLEG |
| HLA-B5101 | LPGGMTELV |
| HLA-B5701 | TTQATKKTGKW |

SEQ ID NOS: 51127-51380

Preferred *Borrelia garinii* fragments of FlaB capable of interacting with one or more MHC molecules are listed in Table X.

TABLE X

Prediction of *Borrelia garinii* FlaB protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| BAD18055.1 FlaB protein [*Borrelia garinii*] Seq15 | HLA-A0101 | NQDEAIAVNIY |
|---|---|---|
|  |  | ELAVQSGNGTY |
|  | HLA-A0201 | SQASWTLRV |
|  |  | QLTDEINRI |
|  |  | AQAAQTAPV |
|  |  | AIAVNIYAA |
|  |  | SLAKIENAI |
|  |  | AVNIYAANV |
|  |  | AQYNQMHML |
|  |  | TTVDANTSL |
|  |  | SQGGVNSPV |
|  |  | QTAPVQEGV |
|  |  | NIYAANVANL |
|  |  | NLNEVEKVLV |
|  |  | VLVRMKELAV |
|  |  | QLTDEINRIA |
|  |  | NLFSGEGAQA |
|  |  | IAVNIYAANV |
|  |  | SLSGSQASWTL |
|  |  | MLSNKSASQNV |
|  |  | AIAVNIYAANV |
|  |  | SQASWTLRVHV |
|  |  | GMQPAKINTPA |
|  |  | KVLVRMKELAV |
|  |  | SLAKIENAIRM |
|  |  | NLFSGEGAQAA |
|  | HLA-A0301 | NQMHMLSNK |
|  |  | GSQASWTLR |
|  |  | TVDANTSLAK |
|  |  | YNQMHMLSNK |
|  |  | LSGSQASWTLR |

TABLE X-continued

Prediction of *Borrelia garinii* FlaB protein specific MHC class 2, 15-mer peptide binders for 14 MHC class 2 alleles (see FIG. 11) using the www.cbs.dtu.dk/services/NetMHCII/ database. The MHC class 2 molecules for which no binders were found are not listed.

| Allele | Peptide |
|---|---|
| HLA-A1101 | TTVDANTSLAK |
| | LSNKSASQNVR |
| | NQMHMLSNK |
| | GSQASWTLR |
| | AVQSGNGTY |
| | TVDANTSLAK |
| | YNQMHMLSNK |
| | EVEKVLVRMK |
| | TTVDANTSLAK |
| | TTEGNLNEVEK |
| | TAEELGMQPAK |
| | TSLAKIENAIR |
| | QYNQMHMLSNK |
| | LSGSQASWTLR |
| | LSNKSASQNVR |
| HLA-A2402 | IYAANVANL |
| | YAANVANLF |
| | IYAANVANLF |
| | TYSDADRGSI |
| | IYAANVANLFS |
| HLA-A2902 | AVQSGNGTY |
| | YAANVANLF |
| | ELAVQSGNGTY |
| | EINRIADQAQY |
| HLA-A6801 | LAKIENAIR |
| | EGNLNEVEK |
| | YAANVANLF |
| | NGTYSDADR |
| | GSQASWTLR |
| | NQMHMLSNK |
| | TSKAINFIQ |
| | NKSASQNVR |
| | EVEKVLVRMK |
| | SLAKIENAIR |
| | TVDANTSLAK |
| | NTSKAINFIQ |
| | SGSQASWTLR |
| | TTVDANTSLA |
| | TTVDANTSLAK |
| | TTEGNLNEVEK |
| | EIEQLTDEINR |
| | LSNKSASQNVR |
| | TSLAKIENAIR |
| | EINRIADQAQY |
| | NLNEVEKVLVR |
| | LSGSQASWTLR |
| | TAEELGMQPAK |
| | QYNQMHMLSNK |
| | NIYAANVANLF |
| | QTAPVQEGVQQ |
| HLA-B0702 | SPVNVTTTV |
| | QPAKINTPA |
| | QPAPATAPS |
| | LVRMKELAV |
| | TPASLSGSQ |
| | APSQGGVNS |
| | APATAPSQG |
| | APVQEGVQQ |
| | TPASLSGSQA |
| | SPVNVTTTVD |
| | APSQGGVNSP |
| | QPAKINTPAS |
| | APSQGGVNSPV |
| | QPAKINTPASL |
| | APATAPSQGGV |
| | SPVNVTTTVDA |
| | TPASLSGSQAS |
| HLA-B0801 | KVLVRMKEL |
| | VEKVLVRMKEL |
| HLA-B1501 | YAANVANLF |
| | AVQSGNGTY |
| | AQAAQTAPV |
| | AQYNQMHML |
| | SQGGVNSPV |
| | SLSGSQASW |
| | SQASWTLRV |
| | IQIEIEQLT |
| | LAVQSGNGTY |
| | SQASWTLRVH |
| | SQNVRTAEEL |
| | VQQEGAQQPA |
| | INRIADQAQY |
| | AQAAQTAPVQ |
| | MQPAKINTPA |
| | ELAVQSGNGTY |
| | NIYAANVANLF |
| | NQDEAIAVNIY |
| | SLSGSQASWTL |
| HLA-B2705 | NRIADQAQY |
| HLA-B3501 | YAANVANLF |
| | QPAPATAPS |
| | SPVNVTTTV |
| | DEAIAVNIY |
| | TTVDANTSL |
| | LAVQSGNGT |
| | QPAKINTPA |
| | AVQSGNGTY |
| | QASWTLRVH |
| | IAVNIYAAN |
| | LAVQSGNGTY |
| | IADQAQYNQM |
| | QPAKINTPAS |
| | LAKIENAIRM |
| | QPAPATAPSQ |
| | YAANVANLFS |
| | TAEELGMQPA |
| | EAIAVNIYAA |
| | QAQYNQMHML |
| | TPASLSGSQA |
| | SPVNVTTTVD |
| | TPASLSGSQAS |
| | ELAVQSGNGTY |
| | NQDEAIAVNIY |
| | QPAKINTPASL |
| | IAVNIYAANVA |
| | NIYAANVANLF |
| | SPVNVTTTVDA |
| | EINRIADQAQY |
| | IADQAQYNQMH |
| | APSQGGVNSPV |
| | LAVQSGNGTYS |
| HLA-B4403 | EELGMQPAKI |
| | NEVEKVLVRM |
| | DEINRIADQA |
| | DEINRIADQAQ |
| HLA-B5101 | SPVNVTTTV |
| | APATAPSQGGV |
| | APSQGGVNSPV |
| HLA-B5701 | ASLSGSQASW |

SEQ ID NOS: 51381-51540

Preferred *Mycobacterium tuberculosis* fragments of CFP10 protein (Rv3874) capable of interacting with one or more class 1 and/or one or more class 2 MHC molecules are listed in Table Y.

TABLE Y

Prediction of MHC class 1 and 2 *Mycobacterium tuberculosis* CFP10 peptide binders. Prediction of 8-, 9-, 10-, 11-, 13-, 14-, 15-, 16-mer peptides were using the program displayed in FIG. 2

8 mers:

MAEMKTDA; AEMKTDAA; EMKTDAAT; MKTDAATL; KTDAATLA; TDAATLAQ; DAATLAQE; AATLAQEA; ATLAQEAG; TLAQEAGN; LAQEAGNF; AQEAGNFE; QEAGNFER; EAGNFERI; AGNFERIS; GNFERISG; NFERISGD; FERISGDL; ERISGDLK; RISGDLKT; ISGDLKTQ; SGDLKTQI; GDLKTQID; DLKTQIDQ; LKTQIDQV; KTQIDQVE; TQIDQVES; QIDQVEST; IDQVESTA; DQVESTAG; QVESTAGS; VESTAGSL; ESTAGSLQ; STAGSLQG; TAGSLQGQ; AGSLQGQW; GSLQGQWR; SLQGQWRG; LQGQWRGA; QGQWRGAA; GQWRGAAG; QWRGAAGT; WRGAAGTA; RGAAGTAA; GAAGTAAQ; AAGTAAQA; AGTAAQAA; GTAAQAAV; TAAQAAVV; AAQAAVVR; AQAAVVRF; QAAVVRFQ; AAVVRFQE; AVVRFQEA; VVRFQEAA; VRFQEAAN; RFQEAANK; FQEAANKQ; QEAANKQK; EAANKQKQ; AANKQKQE; ANKQKQEL; NKQKQELD; KQKQELDE; QKQELDEI; KQELDEIS; QELDEIST; ELDEISTN; LDEISTNI; DEISTNIR; EISTNIRQ; ISTNIRQA; STNIRQAG; TNIRQAGV; NIRQAGVQ; IRQAGVQY; RQAGVQYS; QAGVQYSR; AGVQYSRA; GVQYSRAD; VQYSRADE; QYSRADEE; YSRADEEQ; SRADEEQQ; RADEEQQQ; ADEEQQQA; DEEQQQAL; EEQQQALS; EQQQALSS; QQQALSSQ; QQALSSQM; QALSSQMG; ALSSQMGF 9 mers:

MAEMKTDAA; AEMKTDAAT; EMKTDAATL; MKTDAATLA; KTDAATLAQ; TDAATLAQE; DAATLAQEA; AATLAQEAG; ATLAQEAGN; TLAQEAGNF; LAQEAGNFE; AQEAGNFER; QEAGNFERI; EAGNFERIS; AGNFERISG; GNFERISGD; NFERISGDL; FERISGDLK; ERISGDLKT; RISGDLKTQ; ISGDLKTQI; SGDLKTQID; GDLKTQIDQ; DLKTQIDQV; LKTQIDQVE; KTQIDQVES; TQIDQVEST; QIDQVESTA; IDQVESTAG; DQVESTAGS; QVESTAGSL; VESTAGSLQ; ESTAGSLQG; STAGSLQGQ; TAGSLQGQW; AGSLQGQWR; GSLQGQWRG; SLQGQWRGA; LQGQWRGAA; QGQWRGAAG; GQWRGAAGT; QWRGAAGTA; WRGAAGTAA; RGAAGTAAQ; GAAGTAAQA; AAGTAAQAA; AGTAAQAAV; GTAAQAAVV; TAAQAAVVR; AAQAAVVRF; AQAAVVRFQ; QAAVVRFQE; AAVVRFQEA; AVVRFQEAA; VVRFQEAAN; VRFQEAANK; RFQEAANKQ; FQEAANKQK; QEAANKQKQ; EAANKQKQE; AANKQKQEL; ANKQKQELD; NKQKQELDE; KQKQELDEI; QKQELDEIS; KQELDEIST; QELDEISTN; ELDEISTNI; LDEISTNIR; DEISTNIRQ; EISTNIRQA; ISTNIRQAG; STNIRQAGV; TNIRQAGVQ; NIRQAGVQY; IRQAGVQYS; RQAGVQYSR; QAGVQYSRA; AGVQYSRAD; GVQYSRADE; VQYSRADEE; QYSRADEEQ; YSRADEEQQ; SRADEEQQQ; RADEEQQQA; ADEEQQQAL; DEEQQQALS; EEQQQALSS; EQQQALSSQ; QQQALSSQM; QQALSSQMG; QALSSQMGF;

10 mers:

MAEMKTDAAT; AEMKTDAATL; EMKTDAATLA; MKTDAATLAQ; KTDAATLAQE; TDAATLAQEA; DAATLAQEAG; AATLAQEAGN; ATLAQEAGNF; TLAQEAGNFE; LAQEAGNFER; AQEAGNFERI; QEAGNFERIS; EAGNFERISG; AGNFERISGD; GNFERISGDL; NFERISGDLK; FERISGDLKT; ERISGDLKTQ; RISGDLKTQI; ISGDLKTQID; SGDLKTQIDQ; GDLKTQIDQV; DLKTQIDQVE; LKTQIDQVES; KTQIDQVEST; TQIDQVESTA; QIDQVESTAG; IDQVESTAGS; DQVESTAGSL; QVESTAGSLQ; VESTAGSLQG; ESTAGSLQGQ; STAGSLQGQW; TAGSLQGQWR; AGSLQGQWRG; GSLQGQWRGA; SLQGQWRGAA; LQGQWRGAAG; QGQWRGAAGT; GQWRGAAGTA; QWRGAAGTAA; WRGAAGTAAQ; RGAAGTAAQA; GAAGTAAQAA; AAGTAAQAAV; AGTAAQAAVV; GTAAQAAVVR; TAAQAAVVRF; AAQAAVVRFQ; AQAAVVRFQE; QAAVVRFQEA; AAVVRFQEAA; AVVRFQEAAN; VVRFQEAANK; VRFQEAANKQ; RFQEAANKQK; FQEAANKQKQ; QEAANKQKQE; EAANKQKQEL; AANKQKQELD; ANKQKQELDE; NKQKQELDEI; KQKQELDEIS; QKQELDEIST; KQELDEISTN; QELDEISTNI; ELDEISTNIR; LDEISTNIRQ; DEISTNIRQA; EISTNIRQAG; ISTNIRQAGV; STNIRQAGVQ; TNIRQAGVQY; NIRQAGVQYS; IRQAGVQYSR; RQAGVQYSRA; QAGVQYSRAD; AGVQYSRADE; GVQYSRADEE; VQYSRADEEQ; QYSRADEEQQ; YSRADEEQQQ; SRADEEQQQA; RADEEQQQAL; ADEEQQQALS; DEEQQQALSS; EEQQQALSSQ; EQQQALSSQM; QQQALSSQMG; QQALSSQMGF;

11 mers:

MAEMKTDAATL; AEMKTDAATLA; EMKTDAATLAQ; MKTDAATLAQE; KTDAATLAQEA; TDAATLAQEAG; DAATLAQEAGN; AATLAQEAGNF; ATLAQEAGNFE; TLAQEAGNFER; LAQEAGNFERI; AQEAGNFERIS; QEAGNFERISG; EAGNFERISGD; AGNFERISGDL; GNFERISGDLK; NFERISGDLKT; FERISGDLKTQ; ERISGDLKTQI; RISGDLKTQID; ISGDLKTQIDQ; SGDLKTQIDQV; GDLKTQIDQVE; DLKTQIDQVES; LKTQIDQVEST; KTQIDQVESTA; TQIDQVESTAG; QIDQVESTAGS; IDQVESTAGSL; DQVESTAGSLQ; QVESTAGSLQG; VESTAGSLQGQ; ESTAGSLQGQW; STAGSLQGQWR; TAGSLQGQWRG; AGSLQGQWRGA; GSLQGQWRGAA; SLQGQWRGAAG; LQGQWRGAAGT; QGQWRGAAGTA;

TABLE Y-continued

Prediction of MHC class 1 and 2 *Mycobacterium tuberculosis* CFP10 peptide binders. Prediction of 8-, 9-, 10-, 11-, 13

TABLE Y-continued

Prediction of MHC class 1 and 2 *Mycobacterium tuberculosis* CFP10 peptide binders. Prediction of 8-, 9-, 10-, 11-, 13-, -continued

INDEX TO SEQUENCE LIST

| | SEQ ID NO |
|---|---|
| Table D: BclX(L) fragments (class II) | 47134-47645 |
| Table O: BK 13-16 mers class II | 24957-44888 |
| Table P: BK 13-16 mers class II | 58312-59135 |
| Table Q: BK 13-16 mers class II | 59136-59917 |
| Table R: BK 13-16 mers class II | 59918-60257 |
| Table S: BK 13-16 mers class II | 60258-61275 |
| Table T: BK 13-16 mers class II | 61276-61367 |
| Table F: Survivin fragments (class I) | 47646-48180 |
| Table G: Mcl-1 fragments (class II) | 48181-49526 |
| Table U: *Borrelia* OspC 8-11 mers and 13-16 mers | 49527-51126 |
| Table V: *Borrelia* OspA fragments | 51127-51380 |
| Table X: *Borrelia* FlaB fragments | 51381-51540 |
| Table Y: *Mycobacterium tuberculosis* CFP10 8-11 mers and 13-16 mers | 51541-52252 |
| FIG. 7 | 61368-61663 |
| FIG. 8 and 9 | 61664 |
| FIG. 12 | 61665-61726 |
| FIG. 15, 16 and 17 | 61727 |
| FIG. 18 | 61728 |
| FIG. 19 | 61729 |
| FIG. 20 | 61730 |

EXAMPLES

Example 1

This example describes how to make a MHC class I complex with a peptide in the peptide binding-groove using in vitro refolding. The MHC-complex in this example consisted of light chain β2m, the MHC class I Heavy Chain allele HLA-A*0201 (a truncated version in which the intracellular and transmembrane domains have been deleted) and the peptide QLFEELQEL. MHC I-complexes consists of 3 components; Light Chain (β2m), Heavy Chain and a peptide of typically 8-10 amino acids. In this example MHC-complexes was generated by in vitro refolding of heavy chain, β2m and peptide in a buffer containing reduced and oxidized glutathione. By incubation in this buffer a non-covalent complex between Heavy Chain, β2m and peptide was formed. Heavy chain and β2m was expressed as inclusion bodies in *E. coli* prior to in vitro refolding following standard procedures as described in Garboczi et al., (1996), Nature 384, 134-141. Following refolding the MHC complexes was biotinylated using BirA enzyme able to biotinylate a specific amino acid residue in a recognition sequence fused to the C-terminal of the Heavy Chain by genetic fusion. Monomer MHC complexes was then purified by size exclusion chromatography.

1. 200 ml of refolding buffer (100 mM Tris, 400 mM L-arginin-HCL, 2 mM NaEDTA, 0.5 mM oxidized Gluthathione, 5 mM reduced Glutathione, pH 8.0) was supplied with protease inhibitors PMSF (phenylmethylsulphonyl fluoride), Pepstatin A and Leupeptin (to a final concentration of 1 mM, 1 mg/l and 1 mg/l, respectively). The refolding buffer was placed at 10° C. on a stirrer.
2. 12 mg of peptide QLFEELQEL was dissolved in DMSO or another suitable solvent (300-500 µl), and added drop-wise to the refolding buffer at vigorous stirring.
3. 4.4 mg of human Light Chain β2m was added drop-wise to the refolding buffer at vigorous stirring.
4. 6.2 mg of Heavy Chain HLA-A*0201 (supplied with DTT to a concentration of 0.1 mM) was added drop-wise to the refolding buffer at vigorous stirring.
5. The folding reaction was placed at 10° C. at slow stirring for 4-8 hours.
6. After 4-8 hours, step 3 and 4 was repeated and the folding reaction is placed at 10° C. at slow stirring O/N.
7. Step 3 and 4 was repeated, and the folding reaction is placed at 10° C. at slow stirring for 6-8 hours.
 Optionally, steps 5-7 may be done in less time, e.g. a total of 0.5-5 hours.
8. After 6-8 hours the folding reaction was filtrated through a 0.2 µm filter to remove aggregates.
9. The folding reaction was concentrated O/N at 10° C. shaking gently in a suitable concentrator with a 5000 mw cut-off filter. The folding reaction was concentrated to approximately 5-10 ml. (Optionally the filtrate can be stored at 4° C. and reused for another folding with the same peptide and heavy chain.)
10. The concentrated folding reaction was buffer-exchanged at least 8 times, into a MHC-buffer (20 mM Tris-HCl, 50 mM NaCl, pH 8.0) and concentrated (at 10° C. in a suitable concentrator with a 5000 mw cut-off filter) down to approximately 1 ml.
11. The heavy chain part of the MHC-complex was biotinylated by mixing the following components: approximately 1000 µl folded MHC-complex, 100 µl each of Biomix-A, Biomix-B and d-Biotin (all 3 from Biotin Protein Ligase Kit from Avidity, 10 µl birA enzyme (3 mg/ml, from Biotin Protein Ligase Kit from Avidity, 0.5 µl Pepstatin A (2 mg/ml) and 0.5 µl Leupeptin (2 mg/ml). The above was gently mixed and incubated O/N at room temperature.
12. The biotinylated and folded MHC-complex solution was centrifuged for 5 min. at 1700×g, room temperature.
13. Correctly folded MHC-complex was separated and purified from excess biotin, excess β2m, excess heavy chain and aggregates thereof, by size exclusion chromatography on a column that separates proteins in the 10-100 kDa range. Correctly folded monomer MHC-complex was eluted with a MHC-buffer (20 mM Tris-HCl, 50 mM NaCl, pH 8.0). The elution profile consisted of 4 peaks, corresponding to aggregated Heavy Chain, correctly folded monomer MHC-complex, β2m and excess biotin and peptide (See FIG. 8).
14. Fractions containing the folded MHC-complex were pooled and concentrated to approximately 1 ml in a suitable concentrator with a 5000 mw cut-off filter. The protein-concentration was estimated from its absorption at 280 nm.
15. Folded MHC-complex can optionally be stored at −170° C. before further use.
16. The grade of biotinylation was analyzed by a SDS PAGE SHIFT-assay with Streptavidin (FIG. 9) and correct folding was confirmed by ELISA, using the antibody W6/32 that recognizes correctly folded MHC-peptide complex.
17.

The above procedure may be used for folding any MHC I complexes consisting of any β2m, any heavy chain and any peptide approx. 8-11 amino acids long. Either of the components can be truncated or otherwise modified. The above procedure can also be used for generation of "empty" MHC I complexes consisting of β2m and heavy chain without peptide.

Example 2

This example describes how to generate soluble biotinylated MHC II complexes using a baculovirus expression system, where the MHC II complex was DR4 consisting of the α-chain DRA1*0101 and the β-chain DRB1*0401 as described by Svendsen et al., (2004), J. Immunol. 173(11): 7037-45. Briefly, The hydrophobic transmembrane regions of the DRα and DRβ chains of DR4 were replaced by leucine zipper dimerization domains from the transcription factors Fos and Jun to promote DR α/β assembly. This was done by ligating cytoplasmic cDNA sequences of DRA1*0101 and DRB1*0401 to fos- and jun-encoding sequences. A birA site GLNDIFEAQKIEWH was added to the 3' end of the DRA1*0101-fos template. Covalently bound peptide AGFKGEQGPKGEP derived from collagen II amino acid 261-273 were genetically attached by a flexible linker peptide to the N terminus of the DRβ-chain. Finally, the modified DRA1*0101 and DRB1*0401 inserts were cloned into the expression vector pAcAb3. The pAcAB3-DRA1*0101/DRB1*0401 plasmids were cotransfected with linearized baculovirus DNA (BD Pharmingen; BaculoGold kit) into Sf9 insect cells, according to the manufacturer's instructions. Following two rounds of plaque purification, clonal virus isolates were further amplified three times before preparation of high-titer virus ($10^8$-$10^{10}$/ ml). These stocks were used to infect High Five or serum-free Sf21 insect cells (Invitrogen Life Technologies, Carlsbad, Calif.) for protein production. Spinner cultures (2-3× $10^6$ cells/ml) were infected at a multiplicity of infection of 1-3 in a volume of 150 ml per 2 L spinner flask. Supernatants were harvested and proteinase inhibitor tablets (Roche, Basel, Switzerland) were added before affinity purification on MiniLeak-Low columns (Kem-En-Tec) coupled with the anti-HLA-DR monoclonal antibody L243. HLA-DR4 complexes were eluted with diethylamine (pH 11) into neutralization buffer (2 M Tris, pH 6.5) and immediately buffer exchanged and concentrated in PBS, 0.01% $NaN_3$, using Millipore (Bedford, Mass.) concentrators. The purity of protein was confirmed by SDS-PAGE. The purified DR4 complexes were biotinylated in vitro as described for MHC I complexes elsewhere herein. These complexes may now be used for coupling to any dimerization domain, e.g. divynylsulfone activated dextran 270 coupled with SA and a fluorochrome.

Example 3

This example describes how to generate empty biotinylated MHC II complexes using a baculovirus expression system, where the MHC II complex consist of any α-chain and any β-chain, including truncated and otherwise modified versions of the two. Briefly, The hydrophobic transmembrane regions of the DRα and DRβ chains of MHC II are replaced by leucine zipper dimerization domains from the transcription factors Fos and Jun to promote DR α/β assembly. This is done by ligating cytoplasmic cDNA sequences of DRα and DRβ to fos- and jun-encoding sequences. A birA site GLNDIFEAQKIEWH is added to the 3' end of either the DRα-fos/DRα-jun or the DRβ-jun/DRβ-fos template. The modified DRα and DRβ inserts is cloned into the expression vector pAcAb3 and cotransfected with linearized baculovirus DNA into Sf9 insect cells, according to the manufacturer's instructions. Following rounds of plaque purification, clonal virus isolates is further amplified before preparation of high-titer virus. These stocks are used to infect High Five or serum-free Sf21 insect cells (Invitrogen Life Technologies, Carlsbad, Calif.) for protein production, e.g. as Spinner cultures. Supernatants are harvested and proteinase inhibitors added before affinity purification, e.g. using a MiniLeak-Low columns (Kem-En-Tec) coupled with anti-MHC II antibody. The purified MHC II complexes is biotinylated in vitro as described for MHC I complexes elsewhere herein. These biotinylated MHC II complexes may now be used for coupling to any dimerization domain, e.g. divynylsulfone activated dextran 270 coupled with SA and a fluorochrome.

Example 4

This example describes how to generate biotinylated MHC II complexes using a cell based protein expression system, where the MHC II complex consist of any α-chain and any β-chain, including truncated and otherwise modified versions of the two. The MHC II complex may also have a peptide bound in the peptide binding cleft.

The hydrophobic transmembrane regions of the MHC II α-chain and MHC II β-chain are replaced by leucine zipper dimerization domains from the transcription factors Fos and Jun to promote α/β chain assembly. This is done by ligating cytoplasmic cDNA sequences of α-chain and β-chain to fos- and jun-encoding sequences. A birA site GLNDIFEAQKIEWH is added to the 3' end of the DRα-fos template. Optionally covalently bound peptide is genetically attached by a flexible linker peptide to the N terminus of the DRβ-chain. The modified DRα and DRβ inserts is cloned into a suitable expression vector and transfected into a cell line capable of protein expression, e.g. insect cells, CHO cells or similar. Transfected cells are grown in culture, supernatants are harvested and proteinase inhibitors added before affinity purification, e.g. using a MiniLeak-Low columns (Kem-En-Tec) coupled with anti-MHC II antibody. Alternatively the expressed MHC II complexes may be purified by anion- or cation-exchange chromatography. The purified MHC II complexes is biotinylated in vitro as described for MHC I complexes elsewhere herein. These biotinylated MHC II complexes may now be used for coupling to any dimerization domain, e.g. divynylsulfone activated dextran 270 coupled with SA and a fluorochrome.

Example 5

This is an example of how to make a MHC multimer that is a tetramer and where the MHC are attached to the multimerization domain through a non-covalent interaction The multimerization domain consist of Streptavidin. The MHC molecule was biotinylated DR4 consisting of the α-chain DRA1*0101 and the β-chain DRB1*0401 and the peptide AGFKGEQGPKGEP derived from collagen II amino acid 261-273. The biotinylated MHC-peptide complexes was generated as described in a previous example herein.

Fluorescent DR4-peptide tetramer complexes were assembled by addition of ultra-avidin-R-PE (Leinco Technologies, St. Louis, Mo.) at a final molar ratio of biotinylated to DR4-peptide ultra-avidin-R-PE of 6:1. The resulting DR4-peptide multimer complexes were subjected to size exclusion on a Superdex-200 column to separate the tetramer complexes from protein aggregates and lower molecular weight complexes and excess fre DR4-peptide. The tetramer complexes were concentrated using Centicon-30 concentrators and stored at 0.1-0.3 mg/ml in a mixture of protease inhibitors.

These complexes could be used to detect specific T cells in a flow cytometry assay as described by Svendsen et al. (2004) Tracking of Proinflammatory Collagen-Specific T cells in Early and Late Collagen-Induced Arthritis in Humanized mice. J. Immunol. 173:7037-7045.

Example 6

This example describes how an activated divinylsylfone-dextran (270 kDa) (VS-dex270) was coupled with streptavidin (SA) and Allophycocyanin (APC).

1. Streptavidin (approx. 100 mg SA/ml in 10 mM HEPES, 0.1M NaCl, pH 7.85) was dialysed with gentle stirring for 2 days against 10 mM HEPES, 0.1M NaCl, pH 7.85 (20 fold excess volume) at 2-8° C. with 1 buffer change/day.
2. 5 ml of APC from a homogen suspension (approx. 10 mg/ml) was centrifuged 40 min. at 3000 rpm. The supernatant was discharged and the precipitate dissolved in 5 ml of 10 mM HEPES, 0.1M NaCl, pH 7.85. This APC solution was dialysed with gentle stirring in the dark for 2 days against 10 mM HEPES, 0.1M NaCl, pH 7.85 (20 fold excess volume) at 2-8° C. with 1 buffer change/day.
3. The APC-solution was concentrated to 1 ml and the concentration measured to 47 g/L at UV 650 nm. The A650/A278-ratio was measured to 4.2.
4. The SA-solution was filtrated through a 0.45 µm filter and the protein concentration was measured to 61.8 g SA/L at UV 278 nm.
5. Conjugation: The reagents was mixed to a total volume of 500 µl in the following order with 8.1 mol SA/mol Dex and 27 mol APC/mol Dex.:
   a) 90 µl water
   b) 160 µl activated VS-dex270
   c) 23 µl SA (61.8 g/L)~8.1 equivalents,
   d) 177 µl APC (47 g/L)~27 equivalents,
   e) 50 µl of 100 mM HEPES, 1M NaCl, pH 8

The reaction was placed in a water bath with stirring at 30° C. in the dark for 18 hours.

6. The coupling was stopped by adding 50 µl 0.1M ethanolamine, pH 8.0.
7. The conjugate was purified on a Sephacryl S-200 column with 10 mM HEPES, 0.1M NaCl buffer, pH 7.2.
8. 3 peaks were collected (peak 1: APC-SA-dex270; peak 2: Free APC; peak 3: Free SA). Volume, UV A650 and UV A278 were measured.
9. The concentration of dextran270, APC/Dex and SA/Dex were calculated to $22.4 \times 10^{-8}$ M; 3.48 and 9.54 respectively.
10. The conjugate were added $NaN_3$ and BSA to a final concentration of 15 mM and 1% respectively. The volume was adjusted with 10 mM HEPES, 0.1M NaCl, pH 7.2 to a final concentration of $16 \times 10^{-8}$ M Dex270.
11. The conjugate were kept at 2-8° C. in dark until further use.

Example 7

This example describes how an activated divinylsylfone-dextran (270 kDa) (VS-dex270) was coupled with streptavidin (SA) and R-phycoerythrin (RPE).

The coupling procedure described for coupling of SA and APC to VS-dex270 (as described elsewhere herein) were followed with the exception that APC were replaced with RPE

Example 8

This example describes how to couple an empty MHC or a MHC-complex to a dextran multimerization domain through a non-covalent coupling, to generate a MHC-dextramer. The MHC-dextramer in this example consisted of APC-streptavidin (APC-SA)-conjugated 270 kDA dextran and a biotinylated, folded MHC-complex composed of β2m, HLA-A*0201 heavy chain and the peptide NLVPMVATV.

The APC-SA conjugated 270 kDA dextran contained 3.7 molecules of SA per dextran (each SA can bind 3 MHC-complexes) and the concentration was $16 \times 10^{-8}$ M. The concentration of the HLA-A*0201/NLVPMVATV-complex was 4 mg/ml (1 µg=20,663 pmol). The molecular concentration of the MHC-complex was $8.27 \times 10^{-5}$M.

The MHC-Complex was Attached to the Dextran by a Non-Covalent Biotin-Streptavidin Interaction Between the Biotinylated Heavy Chain Part of the MHC-Complex and the SA, Conjugated to Dextran.

Here follows a protocol for how to produce 1000 µl of a MHC-dextramer solution with a final concentration of approximately $32 \times 10^{-9}$M:

1. 200 µL 270 kDA vinylsulfone-activated dextran, corresponding to $3.2 \times 10^{-11}$ mol, and 4 µl MHC-complex, corresponding to $3.55 \times 10^{-10}$ mol was mixed and incubated at room temperature in the dark for 30 min.
2. A buffer of 0.05M Tris-HCl, 15 mM $NaN_3$, 1% BSA, pH 7.2 was added to a total volume of 1000 µl.
3. The resulting MHC-dextramer preparation may now be used in flow cytometry experiments.

Example 9

This is an example of how to make and use MHC multimers that are trimers consisting of a streptavidin multimerization domain with 3 biotinylated MHC complexes and 1 fluorophore molecule attached to the biotin binding pockets of streptavidin.

MHC complexes consisting of HLA-A*0201 heavy chain, beta2microglobulin and NLVPMVATV peptide or the negative control peptide GLAGDVSAV were generated as described elsewhere herein. The fluorophore in this example was Fluorescein-linker molecules as shown in FIG. 10. Each of these molecules consist of a linker-biotin molecule mounted with 4 trippel fluorescein-linker molecules. The linker-biotin molecule was here H-L30-Lys($NH_2$)-L30-Lys($NH_2$)-L30-Lys($NH_2$)L300Lys(caproylamidobiotin)-$NH_2$ where L30 was a 30 atom large linker and L300 was a 300 atom large linker. Both L30 and L300 was composed of multiple L15 linkers with the structure shown in FIG. 10B. Linker-biotin molecules were generated as follows: Downloaded Boc-L300-Lys(Fmoc) resin (100 mg) was deprotected and subjected to coupling with Boc-Lys(2ClZ)—OH, Boc-L30-OH, Boc-Lys(2ClZ)—OH, Boc-L30-OH, Boc-Lys(2ClZ)—OH then Boc-L30-OH. The resin was Fmoc deprotected and reacted twice (2×2 h) with caproylamido biotin NHS ester (25 mg in 0.5 mL NMP+25 microL DIPEA). The resin was washed with TFA and the product cleaved off with TFA:TFMSA:mCresol:thioanisol (6:2:1:1), 1 mL, precipitated with diethyl ether and purified by RP-HPLC. MS calculated for $C_{300}H_{544}N_{64}O_{137}S$ is 7272.009 Da, found 7271.19 Da.

Alternatively linker-biotin molecule was H-L60-Lys($NH_2$)-L60-Lys($NH_2$)-L60-Lys($NH_2$)L300Lys(caproylamidobiotin)-$NH_2$ and made from downloaded Boc-L300-Lys(Fmoc) resin (100 mg), and then prepared analogously to H-L30-Lys($NH_2$)-L30-Lys($NH_2$)-L30-Lys($NH_2$)L300Lys(caproylamidobiotin)-$NH_2$. MS calculated for $C_{360}H_{652}N_{76}O_{167}S$ is 8749.5848 Da and was found to be 7271.19 Da. Yield 3 mg.

The trippel fluorescein-linker molecules was here betaalanin-L90-Lys(Flu)-L90-Lys(Flu)-L90-Lys(Flu)-$NH_2$ where Lys=Lysine, Flu=Fluorescein and L90 is a 90 atom linker (se FIG. 10 for further details). The trippel-fluorescein-linker molecule was generated as follows:

Downloaded Boc-Lys(Fmoc) resin, 2 g, was Boc deprotected and subjected to 3× coupling with Boc-L30-OH, Boc-Lys(Fmoc)-OH, 3×Boc-L30-OH, Boc-Lys(Fmoc)-OH, 3×Boc-L30-OH. The three Fmoc groups were removed and carboxyfluorescein, 301 mg, activated with HATU, 274 mg, and DIPEA, 139 µL, in 8 mL NMP, was added to the resin twice for 30 min. The resin was Boc deprotected and subjected to 2×30 min coupling with beta-alanine-N,N-diacetic acid benzyl ester, followed by 5 min treatment with 20% piperidine in NMP. The resin was washed with DCM, then TFA and the product was cleaved off the resin, precipitated with diethyl ether and purified by RP-HPLC. Yield was 621 mg. MS calculated for $C_{268}H_{402}N_{44}O_{116}$ is 6096.384 Da, while MS found was 6096 Da.

Biotin-linker molecule were coupled together with 4 trippel fluorescein-linker molecules as follows: (500 nmol) was dissolved in 88 microliter NMP+2 µl pyridine and activated for 10 min at room temperature (conversion to cyclic anhydride) by addition of 10 µl N,N' diisopropylcarbodiimide. Following activation the trippel fluorescein-linker was precipitated with diethyl ether and redissolved in 100 microliter NMP containing 10 nmol biotin-linker Once dissolved the coupling was initiated by addition of 5 µl diisopropyl ethyl amine, and was complete after 30 min.

Streptavidin and Fluorescein-linker molecules are then mixed in a molar ration of 1:1 and incubated for ½ hour. Then MHC complexes are added in 3-fold molar excess in respect to streptavidin and incubated for another ½ hour. Alternatively, MHC complexes are added first, then Fluorescein-linker molecules or MHC complexes are mixed with Fluorescein-linker molecules before addition to Streptavidin.

These MHC multimers are then used to stain CMV specific T cells in a flow Cytometry experiment. 1×10$^6$ purified HPBMC from a donor with T cells specific for HLA-A*0201(NLVPMVATV) are incubated with 10 µl of each of the two HLA-A*0201(peptide)/Fluorescein constructs described above for 10 minutes in the dark at room temperature with a cell concentration of 2×10$^7$ cells/ml. 10 µl of mouse-anti-human CD8/PB (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The cells are resuspended in 400-500 µl PBS; pH=7.2 and analyzed on a flowcytometer.

In the above described example the Fluorescein-linker is as shown in FIG. 10 but the linker molecule can be any linker molecule as described in patent application WO 2007/015168 A2 (Lohse (2007)) or alternatively chemical biotinylated fluorochrom can be used instead of Fluorescein-linker molecules. The MHC complexes described in this example is a MHC I molecule composed of HLA-A*0201 heavy chain, beta2microglobulin and NLVPMVATV peptide but can in principle be any MHC complex or MHC like molecule as described elsewhere herein.

Example 10

This is an example of how to make MHC multimers consisting of a streptavidin multimerization domain with 3 biotinylated MHC complexes attached to the biotin binding pockets of streptavidin and how to use such trimer MHC complexes to detect specific T cells by direct detection of individual cells in a flow cytometry experiment by addition of a biotinylated fluorophore molecule. In this example the fluorophore is Fluorescein linker molecules constructed as described elsewhere herein.

MHC complexes consisting of HLA-A*0201 heavy chain, beta2microglobulin and peptide are generated as described elsewhere. MHC complexes are incubated with streptavidin in a molar ratio of 3:1 for ½ hour.

These trimer MHC multimers are then used to stain CMV specific T cells in a flow Cytometry experiment. 1×10$^6$ purified HPBMC from a donor with T cells specific for HLA-A*0201(NLVPMVATV) are incubated with 10 µl HLA-A*0201(peptide) multimer construct for 10 minutes in the dark at room temperature with a cell concentration of 2×10$^7$ cells/ml. Then Fluorescein linker molecules (as described in Example 42) are added and incubation continued for 5 minutes. 10 µl mouse-anti-human CD8/PB antibody (clone DK25 from Dako) is added and the incubation continued for another 20 minutes at 4° C. in the dark. The samples are then washed by addition of 2 ml PBS; pH=7.2 followed by centrifugation for 5 minutes at 200×g and the supernatant removed. Cells are resuspended in 400-500 µl PBS; pH=7.2 and analyzed on a flowcytometer.

In this example the Fluorescein-linker is as shown in FIG. 10 but the linker molecule can be any linker molecule as described in Lohse, Jesper, (2007), WO 2007/015168 A2 or alternative chemically biotinylated fluorochrome may be used. The MHC complexes described in this example is a MHC I molecule composed of HLA-A*0201 heavy chain, beta2microglobulin and NLVPMVATV peptide but can in principle be any MHC complex or MHC like molecule as described elsewhere herein.

Example 11

This is an example of how to make MHC multimers where the multimerization domain is dextran and the MHC complexes are chemically conjugated to the dextran multimerization domain.

MHC complexes consisting of HLA-A*0201 heavy chain, beta2microglobulin and NLVPMVATV peptide or the negative control peptide GLAGDVSAV are generated as described elsewhere herein. Dextran with a molecular weight of 270 kDa is activated with divinylsulfone. Activated Dextran is then incubated with MHC and RPE in a 0.05 M NaCHO$_3$ buffer; pH=9.5 with a molar ratio between MHC and Dextran of 30-60 and a molar ratio between RPE and dextran of 3-7:1 The mixture is placed in a water bath at 30° C. for 16 hours. Excess fluorochrome, MHC and dextran are removed by FPLC using a sephacryl S-300 column.

These MHC/RPE dextramers are then used to stain CMV specific T cells in a flow Cytometry experiment. Briefly, 1×10$^6$ purified HPBMC from a donor with T cells specific for HLA-A*0201(NLVPMVATV) are incubated with 10 µl of each of the two HLA-A*0201(peptide)/RPE constructs described above for 10 minutes in the dark at room temperature with a cell concentration of 2×10$^7$ cells/ml. 10 µl mouse-anti-human CD8/PB antibody (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The cells are then resuspended in 400-500 µl PBS; pH=7.2 and analyzed on a flow cytometer.

Example 12

This is an example of how to make MHC multimers where the multimerization domain is dextran and MHC complexes are MHC I molecules chemically conjugated to dextran multimerization domain and the dextran multimerization domain also have fluorochrome chemically coupled.

Human beta2microglobulin is coupled to dextran as follows. Dextran with a molecular weight of 270 kDa is activated with divinylsulfone. Activated dextran is incubated with human beta2microglobulin and RPE in a 0.05 M NaCHO$_3$ buffer; pH=9.5 with a molar ratio between beta2microglobulin and Dextran of 30-60 and a molar ratio between RPE and dextran of 3-7:1. The molar ratio of the final product is preferable 4-6 RPE and 15-24 beta2microglobulin per dextran. The mixture is placed in a water bath at 30° C. for 16 hours. Excess fluorochrome, beta2microglobulin and dextran are removed by FPLC using a sephacryl S-300 column. The beta2microglobulin-RPE-dextran construct is then refolded in vitro together with heavy chain and peptide using the following procedure. 200 ml refolding buffer (100 mM Tris, 400 mM L-arginin-HCL, 2 mM NaEDTA, 0.5 mM oxidized Gluthathione, 5 mM reduced Glutathione, pH 8.0) supplied with protease inhibitors PMSF, Pepstatin A and Leupeptin (to a final concentration of 1 mM, 1 mg/l and 1 mg/l, respectively) is made and cooled to 10° C. 12 mg NLVPMVATV peptide is dissolved in DMSO and added to the refolding buffer together with 20-30 mg beta2microglobulin-RPE-dex and 6 mg HLA-A*0201 heavy chain. Incubation at 10° C. for 4-8 hours, then 20-30 mg beta2microglobulin-RPE-dex and 6 mg HLA-A*0201 heavy chain is added and incubation continued for 4-8 hours. Another 20-30 mg beta2microglobulin-RPE-dex and 6 mg HLA-A*0201 heavy chain is added and incubation continued for 6-8 hours. The folding reaction is filtrated through a 0.2 µm filter to remove larger aggregates and then buffer exchanged into a buffer containing 20 mM Tris-HCl, 50 nM NaCl; pH=8.0 followed by concentration to 1-2 ml sample. Dextran-RPE-MHC complexes are then separated from excess heavy chain and peptide by size exclusion chromatography using a sephacryl S-300, S-400 or sephacryl S-500 column.

These MHC/RPE dextramers may be used to stain CMV specific T cells in a flow Cytometry experiment. Briefly, 1×10$^6$ purified HPBMC from a donor with T cells specific for HLA-A*0201(NLVPMVATV) are incubated with 10 µl of each of the two HLA-A*0201(peptide)/RPE constructs described above for 10 minutes in the dark at room temperature with a cell concentration of 2×10$^7$ cells/ml. 10 µl of mouse-anti-human CD8/PB antibody (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The cells are then resuspended in 400-500 µl PBS; pH=7.2 and analyzed on a flowcytometer.

Example 13

The preparation of a Pentamer is described in e.g. (United States Patent application 20040209295). Briefly, the following steps lead to a fluorescent Pentamer reagent:

The following is a detailed example for cloning, expressing, and purifying a pentameric class I MHC complex, which comprises a chimeric fusion of .beta.2m with COMP. The chimeric .beta.2m-COMP protein is expressed in insoluble inclusion bodies in *E. coli* and subsequently assembled as pentameric .beta.2m-COMP in vitro. The pentameric class I MHC peptide complex is then formed in a second refolding reaction by combining beta.2m-COMP pentamers and the human MHC class I .alpha. molecule known as HLA-A*0201, in the presence of an appropriate synthetic binding peptide representing the T cell antigen. In this example, a well characterized antigen derived from Epstein-Barr virus BMLF1 protein, GLCTLVAML (a.a. 289-297) [SEQ ID NO: 1], is used. The resultant complex is labelled with a fluorescent entity and used as a staining reagent for detecting antigen-specific T cells from a mixed lymphocyte population, in a flow cytometry application.

The strategy involves the sequential cloning into pET-24c vector of .beta.2m, yielding a construct referred to as pET-BMC01, followed by the insertion of the oligomerisation domain of cartilage oligomeric matrix protein (COMP) with a biotin acceptor sequence (BP) for site-specific biotinylation with the biotin-protein ligase BirA, yielding a construct referred to as pETBMC02. Thirdly a polyglycine linker is cloned in between .beta.2m and COMP, yielding a construct referred to as pETBMC03, and finally, a serine-residue is removed by site-directed mutagenesis, which serine residue precedes the poly-glycine linker, to give the final .beta.2m-COMP/pET-24c construct, referred to as pET-BMC04 (see also FIG. 3). Removal of the serine residue is carried out to avoid steric hindrance when the .beta.2m molecule is associated with the MHC class I chain protein.

The extracellular portion of .beta.2m comprises of 99 amino acids (equivalent to Ile1-Met99 of the mature protein) encoded by 74 bp-370 by of the DNA sequence. This region of the .beta.2m sequence is amplified from a normal human lymphocyte cDNA library, by polymerase chain reaction (PCR)

beta.2m PCR product is purified from the above reaction mix using a QIAquick® PCR purification kit according to the manufacturer's instructions (Qiagen). 200 ng of purified PCR product and 1.mu.g pET-24c vector (Novagen) are each digested with BamH I (10 U) and Nde I (10 U) restriction enzymes (New England Biolabs, NEB) for 4 h at 37.degree. C., in accordance with the manufacturer's instructions, and purified.

The gel-purified insert and vector DNA are ligated at a 1:3 molar ratio (vector: insert, 50 ng: 7.5 ng) using T4 DNA ligase (5 U; Bioline), in T4 DNA ligase buffer (as supplied) for 16 hrs at 16.degree. C.

The ligation mixtures and appropriate controls are subsequently transformed into XL1-Blue strain competent *E. coli* cells, according to the manufacturer's instructions (Stratagene). Successful transformants are selected by plating the cells on Luria-Bertani (LB) agar plates containing 30 .mu.g/ml kanamycin, and incubating overnight at 37.degree. C.

A selection of single colonies from the bacterial transformation plates are screened by PCR with T7 promoter [SEQ ID NO: 4] (1 .mu.M) and T7 terminator [SEQ ID NO: 5] (1 .mu.M) primers (Sigma Genosys, see Appendix I for primer sequences), which are complementary to regions of the pET vector flanking the cloning site. Amplification is carried out using Taq DNA polymerase (1 U, Bioline) in Taq reaction buffer (as supplied), supplemented with 2 mM MgSO.sub.4 and 0.2 mM dNTPs, using 25 thermal-cycling reactions as detailed above. Successful transformants generated a DNA fragment of approximately 500 bp, ascertained by 1.5% agarose gel electrophoresis.

Bacterial transformants that generated the correct size of PCR products are inoculated into 6 ml of sterile LB-kanamycin medium and incubated overnight at 37.degree. C. with 200 rpm shaking. pETBMC01 plasmid DNA is recovered from the bacterial cultures using a QIAprep® Spin Mini-prep kit according to the manufacturer's instructions (Qiagen). The presence of the .beta.2m fragment in these plasmids is further verified by automated DNA sequencing.

The sequence of the oligomerisation domain of COMP is obtained from the Genbank database (accession #1705995) and a region encoding the coiled-coil domain (amino acids 21-85) is selected based on self-association experiments of COMP (Efinov et al., FEBS Letters 341:54-58 (1994)). A biotin acceptor sequence 'BP': SLNDIFEAQKIEWHE [SEQ ID NO: 6] is incorporated at the C terminus and an additional 14 amino acid linker, PQPQPKPQPKPEPET [SEQ ID NO:7] is included to provide a physical separation between the COMP oligomerising domain and BP.

The whole region is synthesized using the overlapping complementary oligonucleotides, and purified COMP-BP and 1 /.mu.g pETBMC01 vector are digested for 4 hrs at 37.degree. C. using Hind III (10 U) and Xho I (10 U) restriction enzymes (NEB), as described in Section 1.1. The digestion products are purified, ligated, transformed and PCR screened as in Section 1.1. Plasmids positive from the screen are purified and sequenced as described in Section 1.1.

The poly-glycine linker is synthesized by annealing overlapping oligonucleotides. Since the nucleotide sequence of the polyGlycine linker only incorporates the 5' overhang of the cut BamH I restriction site, and the 3' overhang of the cut Hind III nucleotide recognition motifs, there is no need to digest the annealed product to produce the complementary single-stranded overhangs suitable for subsequent ligation. The oligonucleotides are phosphorylated and annealed as described in Section 1.2.

pETBMC02 is digested with BamH I (10 U) and Hind III (10 U). Ligation of the annealed poly-glycine linker into pETBMC02 was as described previously (Section 1.1), assuming 96 fmoles of annealed oligonucleotide/.mu.l. The transformation and PCR-screening reactions are as described in Section 1.1, but in addition, the presence of an inserted linker is verified by a restriction enzyme digestion of the PCR screen product to ascertain the presence or absence of a Sal I restriction site. Successful transformants are not susceptible to Sal I digestion, given the removal of the site from the plasmid vector backbone. Purification of pETBMC03 and automated sequencing is as described in Section 1.1.

Analysis of X-ray crystallography models of MHC class I molecules reveal that the C terminus of .beta.2m closely abuts the .alpha.3 domain of the .alpha. chain. It is therefore desirable to achieve maximum flexibility at the start of the poly-glycine linker.

The extracellular portion of HLA-A*0201 .alpha. chain (EMBL M84379) comprises of 276 amino acids (equivalent to Gly1-Pro276 of the mature protein) encoded by bases 73-900 of the messenger RNA sequence. This region of the A*0201 sequence is amplified from a normal human lymphocyte cDNA library by PCR, using the primers A2S#1 [SEQ ID NO: 20] and A2S#2 [SEQ ID NO: 21] which incorporated NcoI and BamHI restriction sites respectively. The procedure for cloning the A*0201 insert into Nco I/BamH I-digested pET-11d vector (Novagen) is essentially as described for .beta.2m in Section 1.1.

An identical procedure is carried out to produce either .beta.2m-COMP or A*0201 .alpha. chain proteins. Plasmid DNA is transformed into an E. coli expression host strain in preparation for a large scale bacterial prep. Protein is produced as insoluble inclusion bodies within the bacterial cells, and is recovered by sonication. Purified inclusion bodies are solubilised in denaturing buffer and stored at −80.degree. C. until required.

Purified plasmid DNA is transformed into the BL21(DE3) pLysS E. coli strain, which carries a chromosomal copy of the T7 RNA polymerase required to drive protein expression from pET-based constructs. Transformations into BL21 (DE3)pLysS competent cells (Stratagene) are carried out with appropriate controls.

A single bacterial transformant colony is innoculated into 60 ml sterile LB medium, containing appropriate antibiotics for selection, and left to stand overnight in a warm room (.about.24.degree. C.) The resulting overnight culture is added to 6 liters of LB and grown at 37.degree. C. with shaking (.about.240 rpm), up to mid-log phase (OD-.sub.600=0.3-0.4). Protein expression is induced at this stage by addition of 1.0 ml of 1M IPTG to each flask. The cultures are left for a further 4 h at 37.degree. C. with shaking, after which the cells are harvested by centrifugation and the supernatant discarded.

The bacterial cell pellet is resuspended in ice-cold balanced salt solution and sonicated (XL series sonicator; Misonix Inc., USA) in a small glass beaker on ice in order to lyse the cells and release the protein inclusion bodies. Once the cells are completely lysed the inclusion bodies are spun down in 50 ml polycarbonate Oak Ridge centrifuge tubes in a Beckman high-speed centrifuge (J2 series) at 15,000 rpm for 10 min. The inclusion bodies are then washed three times in chilled Triton® wash This is followed by a final wash in detergent-free wash buffer.

The resultant purified protein preparation is solubilised in 20-50 ml of 8 M urea buffer, containing 50 mM MES, pH 6.5, 0.1 mM EDTA and 1 mM DTT, and left on an end-over-end rotator overnight at 4.degree. C. Insoluble particles are removed by centrifugation and the protein yield is determined using Bradford's protein assay reagent (Bio-Rad Laboratories) and by comparison with known standards. Urea-solubilised protein is dispensed in 10 mg aliquots and stored at −80.degree. C. for future use.

Assembly of .beta.2m-COMP from the urea-solubilised inclusion bodies is performed by diluting the protein into 20 mM CAPS buffer, pH 11.0, containing 0.2 M sodium chloride and 1 mM EDTA, to give a final protein concentration of 1.5 mg/ml. The protein is oxidised at room temperature by addition of oxidised and reduced glutathione to final concentrations of 20 mM and 2 mM, respectively. Following an overnight incubation, disulphide bond formation is analysed by non-reducing SDS-PAGE on 10% bis-tricine gels (Invitrogen).

The protein mixture is subsequently buffer exchanged into 20 mM Tris, pH 8.0, 50 mM sodium chloride ('S200 buffer'), and concentrated to a final volume of 4.5 ml, in preparation for enzymatic biotinylation with BirA (Affinity, Denver, Colo.). 0.5 ml of 10.times. BirA reaction buffer (as supplied) is added, and recombinant BirA enzyme at 10 /.mu.M final concentration, supplemented with 10 mM ATP, pH 7.0. A selection of protease inhibitors is also used to preserve the proteins: 0.2 mM PMSF, 2 /.mu.g/ml pepstatin and 2 /.mu.g/ml leupeptin. The reaction is left for 4 hours at room temperature.

Biotinylated .beta.2m-COMP is purified by size exclusion chromatography (SEC) on a Superdex®200 HR 26/60 column (Amersham Biosciences), running S200 buffer.

500 ml of refolding buffer is prepared as follows: 100 mM Tris, pH 8.0, 400 mM Larginine hydrochloride, 2 mM EDTA, 5 mM reduced glutathione and 0.5 mM oxidised glutathione, dissolved in deionised water and left stirring at 4.degree. C. 15 mg of lyophilised synthetic peptide GLCTL- VAML is dissolved in 0.5 ml dimethylsulfoxide and added to the refolding buffer whilst stirring. 50 mg of biotinylated pentameric .beta.2m-COMP and 30 mg of A*0201 .alpha. chain is added sequentially, injected through a 23 gauge hypodermic needle directly into the vigorously-stirred buffer, to ensure adequate dispersion. The refolding mixture is then left stirring gently for 16 hours at 4.degree. C.

The protein refolding mixture is subsequently concentrated from 500 ml to 20 ml using a MiniKros hollow fibre ultrafiltration cartridge (Spectrum Labs, Rancho Dominguez, Calif.) with a 30 kD molecular weight cutoff. Further concentration of the complex from 20 ml to 5 ml is carried out in Centricon Plus-20 centrifugal concentrators (30 kD molecular weight cut-off) according to the manufacturers instructions, followed by buffer exchange into S200 buffer using disposable PD10 desalting columns (Amersham Biosciences), according to the manufacturer's instructions. Final volume is 7.5 ml. The concentrated protein refold mixture is first purified by SEC on a Superdex® 200 HR 26/60 gel filtration chromatography column, as in Section 4.2. Fractions containing protein complexes in the region of 310 kD is collected.

Fractions collected from SEC are pooled and subjected to further purification by anion exchange chromatography on a MonoQ® HR 5/5 column (Amersham Biosciences), running a salt gradient from 0-0.5 M sodium chloride in 20 mM Tris over 15 column volumes. The dominant peak is collected. Protein recovery is determined using the Bradford assay.

Since each streptavidin molecule is able to bind up to 4 biotin entities, final labelling with phycoerythrin (PE)-conjugated streptavidin is carried out in a molar ratio of 1:0.8, streptavidin to biotinylated pentamer complex respectively, taking into account the initial biotinylation efficiency measurement made for .beta.2m-COMP in Section 4.2. The total required amount of pentamer complex is subdivided (e.g. into 5 equal amounts) and titrated successively into streptavidin-PE. The concentration of A*0201 pentamer-streptavidin complex is adjusted to 1 mg/ml with phosphate buffered saline (PBS), supplemented with 0.01% azide and 1% BSA.

This resultant fluorescent Pentamer reagent is stored at 4.degree. C.

Example 14. Prediction of MHC Class 1 BK Virus Peptide Binders

This example describes the total approach, applied to the BK virus genome. It thus involves the translation of the genome in both directions, i.e. in six possible reading frames.

Prediction of MHC class 1 BK virus peptide sequences for use in construction of MHC'mers designed to be used for analytical, diagnostic, prognostic, therapeutic and vaccine purposes, through the interaction of the MHC'mers with BK virus-specific T-cells. Prediction is carried out using the total approach. Thus, the 8-, 9-, 10- and 11-mer peptide sequences are generated from six amino acid sequences representing direct translation of the BK virus genome sequence in all six reading frames. The 8-, 9-, 10- and 11-mer peptide sequences are derived from the genome sequence by application of the software program described in (FIG. 2). The 8-, 9-, 10- and 11-mer peptide sequences are shown in table I.

Example 15. Prediction of MHC Class 2 BK Virus Peptide Binders

This example describes the total approach, applied to the BK virus genome. It thus involves the translation of the genome in both directions, i.e. in six possible reading frames.

Prediction of MHC class 2 BK virus peptide sequences for use in construction of MHC'mers designed to be used for analytical, diagnostic, prognostic, therapeutic and vaccine purposes, through the interaction of the MHC'mers with BK virus-specific T-cells. Prediction is carried out using the total approach. Thus, the 13-, 14-, 15- and 16-mer peptide sequences are generated from six amino acid sequences representing direct translation of the BK virus genome sequence in all six reading frames. The 13-, 14-, 15- and 16-mer peptide sequences are derived from the genome sequence by application of the software program described in (FIG. 2). The 13-, 14-, 15- and 16-mer peptide sequences are shown in table O.

Example 16. Prediction of MHC Class 1 Peptide Binders for BK Agnoprotein Using Directed Approach This example describes the directed approach, applied to a known protein sequence, the Agnoprotein encoded by the BK virus genome. The purpose is to predict BK virus peptide sequences that binds to MHC class 1 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table N. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 17. Prediction of MHC Class 1 Peptide Binders for BK Small t Protein Using Directed Approach This example describes the directed approach, applied to a known protein sequence, the small t protein encoded by the BK virus genome. The purpose is to predict BK virus peptide sequences that binds to MHC class 1 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table L. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 18. Prediction of MHC Class 1 Peptide Binders for BK Large T Protein Using Directed Approach This example describes the directed approach, applied to a known protein sequence, the Large T protein encoded by the BK virus genome. The purpose is to predict BK virus peptide sequences that binds to MHC class 1 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table M. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 19. Prediction of MHC Class 1 Peptide Binders for BK VP1 Protein Using Directed Approach This example describes the directed approach, applied to a known protein sequence, the VP1 protein encoded by the BK virus genome. The purpose is to predict BK virus peptide sequences that binds to MHC class 1 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table K. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 20. Prediction of MHC Class 1 Peptide Binders for BK VP2-3 Protein Using Directed Approach This example describes the directed approach, applied to a known protein sequence, the VP2-3 protein encoded by the human genome. The purpose is to predict BK virus peptide sequences that binds to MHC class 1 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table J. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 21. Prediction of MHC Class 1 Peptide Binders for Human Cancer Protein Bcl-2 Using Directed Approach This example describes the directed approach, applied to a known protein sequence, the cancer protein Bcl-2 encoded by the human genome. The purpose is to predict Bcl-2 peptide sequences that binds to MHC class 1 molecules for use in construction of MHC'mers designed to be used for analytical, diagnostic, prognostic, therapeutic and vaccine purposes, through the interaction of the MHC'mers with human Bcl-2 specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table C. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 22. Prediction of MHC Class 1 Peptide Binders for Human Cancer Protein BclX(L) Using Directed Approach This example describes the directed approach, applied to a known protein sequence, the cancer protein BclX(L) encoded by the human genome. The purpose is to predict BclX(L) peptide sequences that binds to MHC class 1 molecules for use in construction of MHC'mers designed to be used for analytical, diagnostic, prognostic, therapeutic and vaccine purposes, through the interaction of the MHC-'mers with human BclX(L) specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table B. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 23. Prediction of MHC Class 1 Human Cancer Protein Survivin Peptide Binders This example describes the prediction of MHC class 1 human Survivin peptide sequences for use in construction of MHC'mers designed to be used for analytical, diagnostic, prognostic, therapeutic and vaccine purposes, through the interaction of the MHC'mers with human Survivin specific T-cells. Prediction of the 8-, 9-, 10- and 11-mer peptide sequences are carried out using the peptide generation software program described in FIG. 2. The outcome is shown in table F.

Example 24. Prediction of MHC Class 2 Peptide Binders for BK Agnoprotein Using Directed Approach This example describes the directed approach, applied to a known protein sequence, the Agnoprotein encoded by the BK virus genome. The purpose is to predict BK virus peptide sequences that binds to MHC class 2 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 14 HLA class 2 alleles included in the www.cbs.dtu.dk/services/NetMHC/ database (FIG. 11).

The result of the prediction software is used to find all strong and weak 15-mer peptide binders of the 14 HLA class 2 alleles. It also finds the important central nonamer core peptide sequence of each binding peptide. The result can be seen in table T. The MHC class 2 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 25. Prediction of MHC Class 2 Peptide Binders for BK Small t Protein Using Directed Approach This example describes the directed approach, applied to a known protein sequence, the small t protein encoded by the BK virus genome. The purpose is to predict BK virus peptide sequences that binds to MHC class 2 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 14 HLA class 2 alleles included in the www.cbs.dtu.dk/services/NetMHC/ database (FIG. 11).

The result of the prediction software is used to find all strong and weak 15-mer peptide binders of the 14 HLA class 2 alleles. It also finds the important central nonamer core peptide sequence of each binding peptide. The result can be seen in table R. The MHC class 2 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 26. Prediction of MHC Class 2 Peptide Binders for BK Large T Protein Using Directed Approach This example describes the directed approach, applied to a known protein sequence, the Large T protein encoded by the BK virus genome. The purpose is to predict BK virus peptide sequences that binds to MHC class 2 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 14 HLA class 2 alleles included in the www.cbs.dtu.dk/services/NetMHC/ database (FIG. 11).

The result of the prediction software is used to find all strong and weak 15-mer peptide binders of the 14 HLA class 2 alleles. It also finds the important central nonamer core peptide sequence of each binding peptide. The result can be seen in table S. The MHC class 2 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 27. Prediction of MHC Class 2 Peptide Binders for BK VP1 Protein Using Directed Approach This example describes the directed approach, applied to a known protein sequence, the VP1 protein encoded by the BK virus genome. The purpose is to predict BK virus peptide sequences that binds to MHC class 2 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 14 HLA class 2 alleles included in the www.cbs.dtu.dk/services/NetMHC/ database (FIG. 11).

The result of the prediction software is used to find all strong and weak 15-mer peptide binders of the 14 HLA class 2 alleles. It also finds the important central nonamer core peptide sequence of each binding peptide. The result can be seen in table Q. The MHC class 2 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 28. Prediction of MHC Class 2 Peptide Binders for BK VP2-3 Protein Using Directed Approach This example describes the directed approach, applied to a known protein sequence, the VP1 protein encoded by the BK virus genome. The purpose is to predict BK virus peptide sequences that binds to MHC class 2 molecules for use in construction of MHC'mers designed to be used for analytical, diagnostic, prognostic, therapeutic and vaccine purposes, through the interaction of the MHC'mers with BK virus specific T-cells. Prediction is carried out using the known preferences of the 14 HLA class 2 alleles included in the www.cbs.dtu.dk/services/NetMHC/ database (FIG. 11).

The result of the prediction software is used to find all strong and weak 15-mer peptide binders of the 14 HLA class 2 alleles. It also finds the important central nonamer core peptide sequence of each binding peptide. The result can be seen in table P. The MHC class 2 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 29. Prediction of MHC Class 2 Human Cancer Protein Mcl-1 Peptide Binders This example describes the prediction of MHC class 2 human Mcl-1 peptide sequences for use in construction of MHC'mers designed to be used for analytical, diagnostic, prognostic, therapeutic and vaccine purposes, through the interaction of the MHC'mers with human Mcl-1 specific T-cells. Prediction of the 13-, 14-, 15- and 16-mer peptide sequences are carried out using the peptide generation software program described in FIG. 2. The outcome is shown in table G.

Example 30. Prediction of MHC Class 2 Peptide Binders for Human Cancer Protein Bcl-2 Using Directed Approach This example describes the directed approach, applied to a known protein sequence, the cancer protein Bcl-2 encoded by the human genome. The purpose is to predict Bcl-2 peptide sequences that binds to MHC class 2 molecules for use in construction of MHC'mers designed to be used for analytical, diagnostic, prognostic, therapeutic and vaccine purposes, through the interaction of the MHC'mers with human Bcl-2 specific T-cells. Prediction is carried out using the known preferences of the 14 HLA class 2 alleles included in the www.cbs.dtu.dk/services/NetMHCII/ database (FIG. 11).

The result of the prediction software is used to find all strong and weak 15-mer peptide binders of the 14 HLA class 2 alleles. It also finds the important central nonamer core peptide sequence of each binding peptide. The result can be seen in table E. The MHC class 2 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 31. Prediction of MHC Class 2 Peptide Binders for Human Cancer Protein BclX(L) Using Directed Approach This example describes the directed approach, applied to a known protein sequence, the cancer protein BclX(L) encoded by the human genome. The purpose is to predict BclX(L) peptide sequences that binds to MHC class 2 molecules for use in construction of MHC'mers designed to be used for analytical, diagnostic, prognostic, therapeutic and vaccine purposes, through the interaction of the MHC'mers with human BclX(L) specific T-cells. Prediction is carried out using the known preferences of the 14 HLA class 2 alleles included in the www.cbs.dtu.dk/services/NetMHCII/ database (FIG. 11).

The result of the prediction software is used to find all strong and weak 15-mer peptide binders of the 14 HLA class 2 alleles. It also finds the important central nonamer core peptide sequence of each binding peptide. The result can be seen in table D. The MHC class 2 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 32. Prediction of MHC Class 1 and 2 *Borrelia afzelii* OspC Peptide Binders This example describes the prediction of MHC class 1 and 2 *Borrelia afzelii* OspC peptide sequences for use in construction of MHC'mers designed to be used for analytical, diagnostic, prognostic, therapeutic and vaccine purposes, through the interaction of the MHC'mers with *Borrelia afzelii* OspC specific T-cells. Prediction of the 8-, 9-, 10-, 11-, 13-, 14-, 15- and 16-mer peptide sequences are carried out using the peptide generation software program described in FIG. 2. The outcome is shown in table U.

Example 33. Prediction of MHC Class 1 *Borrelia burgdorferi* OspA Peptide Binders This example describes the directed approach, applied to a known protein sequence, the *Borrelia burgdorferi* protein OspA encoded by the *Borrelia* genome. The purpose is to predict OspA peptide sequences that binds to MHC class 1 molecules for use in construction of MHC'mers designed to be used for analytical, diagnostic, prognostic, therapeutic and vaccine purposes, through the interaction of the MHC'mers with human OspA specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table V. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 34. Prediction of MHC Class 1 *Borrelia garinii* Flab Peptide Binders This example describes the directed approach, applied to a known protein sequence, the *Borrelia garinii* protein FlaB encoded by the *Borrelia* genome. The purpose is to predict FlaB peptide sequences that binds to MHC class 1 molecules for use in construction of MHC'mers designed to be used for analytical, diagnostic, prognostic, therapeutic and vaccine purposes, through the interaction of the MHC'mers with human FlaB specific T-cells. Prediction is carried out using the known preferences of the 42 HLA class 1 alleles included in the www.cbs.dtu.dk/services/NetMHC/ database (FIG. 11).

The result of the prediction software is used to find all strong and weak 8-, 9-, 10- and 11-mer peptide binders of the 42 HLA class 1 alleles. The result can be seen in table X. The MHC class 1 alleles for whom no binders are predicted are omitted from the list. The listed peptides are ranked according to decreased binding affinity for the individual MHC alleles. Strong binders are defined as binders with an affinity value of less than 50 nM and weak binders with a value of less than 500 nM. Only peptides defined as weak or strong binders are shown.

Example 35. Prediction of MHC Class 1 and 2 *Mycobacterium tuberculosis* CFP10 Peptide Binders This example describes the prediction of MHC class 1 and 2 *Mycobacterium tuberculosis* CFP10 peptide sequences for use in construction of MHC'mers designed to be used for analytical, diagnostic, prognostic, therapeutic and vaccine purposes, through the interaction of the MHC'mers with *Mycobacterium tuberculosis* CFP10 specific T-cells. Prediction of the 8-, 9-, 10-, 11-, 13-, 14-, 15- and 16-mer peptide sequences are carried out using the peptide generation software program described in FIG. 2. The outcome is shown in table Y.

Example 36. Prediction of MHC Class 1 LCMV Gp1 Nonamer Peptide Binders for Mouse H-2Kd An Example of Non-Human MHC Peptide Binding Motifs.

This example describes the directed approach, applied to the known protein sequence of a mouse virus protein LCMV gp1 in context of mouse MHC class 1.

Prediction of LCMV gp1 peptide sequences that binds to the MHC class 1 molecule H-2Kd for use in construction of MHC'mers designed to be used for as analytical, diagnostic, prognostic, therapeutic and vaccine purposes, through the interaction of the MHC'mers with LCMV specific mouse T-cells. Prediction is carried out using the known preferences of the given H-2 molecules for peptide binding as laid down in the prediction program found on www.syfpeithi.de. The generated 9-mer peptides are ranked according to their binding efficiency to the individual HLA class 1 molecules. The output is shown in FIG. 2.

Example 37. Test of Predicted BclX(L) 10-mer Binding Peptide Functionality in Elispot In example 22 the best binding BclX(L) 10-mer peptide for HLA-A*0201 was identified to be YLNDHLEPWI (SEQ ID NO.: 46196). This peptide has then been tested in ELISPOT to see if it were able to detect the presence Bcl-X(L)-specific, CD8 positive T cells in PBL (Peripheral Blood Lymphocytes) from a breast cancer patient. PBL from a breast cancer patient was analyzed by ELISPOT ex vivo either with or without the Bcl-X(L)173-182 peptide (YLNDHLEPWI (SEQ ID NO.: 46196)), 106 PBL/well in doublets. The number of spots was counted using the Immunospot Series 2.0 Analyzer (CTL Analysers). The result is given as number of spots above the pictures of the result as shown in FIG. 15 and it clearly shows the presence of BclX(L) specific T-cells and thereby the functionality of the peptide as compared to the absence of added peptide.

Example 38. Test of Predicted BclX(L) 10-mer Binding Peptide Functionality in Flow Cytometry In example 22 the best binding BclX(L) 10-mer peptide for HLA-A*0201 was identified to be YLNDHLEPWI (SEQ ID NO.: 46196). In the present example the functionality of the peptide is shown in a flow cytometric analysis of PBL from the patient was analyzed ex vivo by Flow cytometry to identify Bcl-X(L)173-182 specific CD8 T cells using the dextramer complex HLA-A2/Bcl-X(L)173-182-APC, 7-AAD-PerCP, CD3-FITC, and CD8-APC-Cy7. The dextramer complex HLA-A2/HIV-1 pol476-484-APC was used as negative control. The result (FIG. 16) clearly demonstrate that a MHC Dextramer HLA-A*0201/YLNDHLEPWI (SEQ ID NO.: 46196) complex detects BclX(L) antigen specific CD-8 cells in the patient sample at a level of 0.03% as compared with the negative control using HIV specific MHC Dextramer.

Example 39. Use of BclX(L) Specific MHC Dextramer for Sorting of Antigen Specific CD8 T Cells from Patient Sample The antigen specific CD8 positive T-cells of example 38 were sorted out during the flow cytometric analysis using the MHC Dextramer HLA-A*0201/YLNDHLEPWI (SEQ ID NO.: 46196). The detectable population of dextramer positive CD8 T cells was sorted as single cells into 96 well plates using the following protocol:

Small lymphocytes were gated by forward and side scatter profile, before cloning according to CD8/MHC-multimer double staining. CD8/MHC-multimer double-positive cells were sorted as single cells into 96 well plates (Nunc) already containing $10^5$ cloning mix cells/well. The cloning mix was prepared containing $10^6$ irradiated (20 Gy) lymphocytes from three healthy donors per nil in X-vivo with 5% heat-inactivated human serum, 25 mM HEPES buffer (GibcoBRL), 1 μg/ml phytohemagglutinin (PHA) (Peprotech) and 120 U/ml IL-2. The cloning mix was incubated for two hours at 37° C./5% $CO_2$, prior to cloning. After cloning, the plates were incubated at 37° C./5% $CO_2$. Every 3-4 days 50 μL1 fresh media were added containing IL-2 to a final concentration of 120 U/ml. Following 10-14 days of incubation, growing clones were further expanded using cloning mix cells. Consequently, each of the growing clones were transferred (split) into two or three wells (depending on the number of growing cells) of a new 96 well plate containing $5\times10^4$ cloning mix cells/well. Clones that were not growing at this time were incubated for another week with IL-2, and then expanded. Subsequently, the specificity of the growing clones was tested in a $^{51}$Cr-release assay or by FACS.

Out of twenty-isolated dextramer positive CD8 T cells, ten were able to be expanded into T-cell clones.

Example 40. Demonstration of Specific Cytolytic Activity of Isolated BclX(L) Specific CD8 T-Cells The ten expanded T cell clones isolated by Flow sorting as shown in example 39 were tested for their specificity by analysis in a standard 51-Cr release assay. For this purpose, T2 cells loaded with either Bcl-X(L)173-182 peptide or an irrelevant peptide (BA4697-105, GLQHWVPEL) were used as target cells. Five CD8 T-cell clones (Clone 8, 9, 10, 11, and 12) effectively lysed T2 cells pulsed with Bcl-X(L)173-182 without killing of T2 cells pulsed with an irrelevant peptide (FIG. 17). One of these BclX(L)173-182 specific CD8 T-cell clones [Clone 9] were expanded for further analyses. The remaining five expanded clones (Clone 7, 13, 15, 17, and 18) did not show specific lysis against T2 cells pulsed with Bcl-X(L)173-182 peptide (FIG. 8).

Example 41. Demonstration of the Cytotoxic Capacity of a BclX(L)173-182 Specific CD8 T Cell Clone Isolated by Flow Aided Sorting of Antigen (HLA-A*0201/YLNDHLEPWI (SEQ ID NO.: 46196) Specific T Cells The Bcl-X(L)173-182 specific clone 9 was expanded for additional 2 weeks before the cytotoxic potential was examined further in 51Cr-release assays. Two assays were performed a Cell lysis of T2 cells pulsed with Bcl-X(L)173-182 peptide or an irrelevant peptide (BA4697-105, GLQHWVPEL) in three E:T ratios. b Cell lysis of T2 cells pulsed with different concentrations of Bcl-X(L)173-182 peptide at the E:T ratio 1:1 The result is given in FIG. 18. As can be seen

Example 42. Synthesis of a Comprehensive Library of Antigenic Peptides of Variable Size Derived from a Full-Length Antigen Sequence In this example it is described how virtually all of the possible 8'- to 20'-mer peptide epitopes of an antigen may be synthetically prepared by modification of the standard Fmoc peptide synthesis protocol.

N-☐-amino acids are incorporated into a peptide of the desired sequence with one end of the sequence remaining attached to a solid support matrix. All soluble reagents can be removed from the peptide-solid support matrix by filtration and washed away at the end of each coupling step. After each of the coupling steps, and after the removal of reagents, a fraction of the generated peptides are removed and recovered from the polymeric support by cleavage of the cleavable linker that links the growing peptide to solid support.

The solid support can be a synthetic polymer that bears reactive groups such as —OH. These groups are made so that they can react easily with the carboxyl group of an N-☐-protected amino acid, thereby covalently binding it to the polymer. The amino protecting group can then be removed and a second N-☐-protected amino acid can be coupled to the attached amino acid. These steps are repeated until the desired sequence is obtained. At the end of the synthesis, a different reagent is applied to cleave the bond between the C-terminal amino acid and the polymer support; the peptide then goes into solution and can be obtained from the solution.

Initially, the first Fmoc amino acid (starting at the C-terminal end of the antigen sequence) is coupled to a precursor molecule on an insoluble support resin via an acid labile linker. Deprotection of Fmoc is accomplished by treatment of the amino acid with a base, usually piperidine. Before coupling the next amino acid, a fraction of the synthesized peptide (for example 0.1%) is detached from the solid support, and recovered. Then additional beads carrying only the precursor molecule including the linker (for example corresponding to 0.1% of the total amount of solid support in the reaction) is added. Then the next Fmoc amino acid is coupled utilizing a pre-activated species or in situ activation.

This cycle of amino acid coupling, removal of reagents, detachment of a small fraction of synthesized peptide and recovery of these, and activation of the immobilized peptide to prepare for the next round of coupling, goes on until the entire antigen sequence has been processed.

The recovered peptides thus represent different fragments of the antigen, with varying lengths. The peptide pool thus contains most or all of the possible peptide epitopes of the antigen, and may be used in the preparation of MHC multimers as a pool.

The entire process, including the detachment of a fraction of the peptides after each round of coupling, follows standard Fmoc peptide synthesis protocols, and involves weak acids such as TFA or TMSBr, typical scavengers such as thiol compounds, phenol and water, and involves standard protecting groups.

Example 43

This is an example of how MHC multimers may be used for detection of cancer specific T cells in blood samples from patients.

In this example the MHC multimer used are MHC complexes coupled to fluorophor-labelled dextran (Dextramers). The dextramers are used for direct detection of TCR in flow Cytometry. The antigen origin is cancer, thus, immune monitoring of a cancer.

MHC multimers carrying cancer specific peptides is in this example used to detect the presence of cancer specific T cells in the blood from cancer patients.

Purified MHC-peptide complexes consisting of HLA-A*1101 heavy chain, human beta2microglobulin and peptide derived from a region in Survivin (Table F) or a negative control peptide were generated by in vitro refolding, purified and biotinylated as described elsewhere herein. Biotinylated MHC-peptide complexes were then coupled to a 270 kDa dextran multimerization domain labelled with APC by interaction with streptavidin (SA) on the dextran multimerization domain. The dextran-APC-SA multimerization domain was generated as described elsewhere herein. MHC-peptide complexes were added in an amount corresponding to a ratio of three MHC-peptide molecules per SA molecule and each molecule dextran contains 3.7 SA molecule and 8.95 molecules APC. The final concentration of dextran was 3.8× 10e-8 M. The following MHC(peptide)/APC dextran constructs were made:
1. APC-SA conjugated 270 kDa dextran coupled with HLA-A*1101 in complex with beta2microglobulin and the peptide DLAQCFFCFK derived from Survivin.
2. APC-SA conjugated 270 kDa dextran coupled with HLA-A*1101 in complex with beta2microglobulin and the non-sense peptide.

The binding of the above described MHC(peptide)/APC dextran was used to determine the presence of Survivin specific T cells in the blood from cancer patients by flow cytometry following a standard flow cytometry protocol.

Blood from a cancer patient is isolated and 100 ul of this blood is incubated with 10 µl of the MHC(peptide)/APC dextran constructs described above for 10 minutes in the dark at room temperature. 5 µl of each of each of the antibodies mouse-anti-human CD3/PB (clone UCHT1 from Dako), and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the MHC(peptide)/APC dextran construct 1 described above and thereby the presence of Survivin specific T cells in the blood. Blood analysed with MHC (peptide)/APC dextran construct 2 show no staining of CD3 and CD8 positive cells with this MHC(peptide)/APC dextran construct.

The sensitivity of the above described test may be enhanced by addition of labeled antibodies specific for activation markers expressed in or on the surface of the Survivin specific T cells.

We conclude that the MHC(peptide)/APC dextran constructs can be used to detect the presence of Survivin specific T cells in the blood of cancer.

Example 44

This is an example of how MHC multimers may be used for detection of cancer specific T cells in blood samples from patients.

In this example the MHC multimer used are MHC complexes coupled to fluorophor-labelled multimerisation domain Streptavidin (SA, used for direct detection of TCR in flow Cytometry. The antigen origin is cancer, thus, immune monitoring of a cancer.

MHC multimers carrying cancer specific peptides is in this example used to detect the presence of cancer specific T cells in the blood from cancer patients.

Purified MHC-peptide complexes consisting of HLA-A*1101 heavy chain, human beta2microglobulin and peptide derived from a region in Survivin (Table F) or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:
3. APC-SA coupled with HLA-A*1101 in complex with beta2microglobulin and the peptide DLAQCFFCFK derived from Survivin.
4. APC-SA coupled with HLA-A*1101 in complex with beta2microglobulin and the non-sense peptide.

The binding of the above described MHC(peptide)/APC dextran can be used to determine the presence of Survivin specific T cells in the blood from cancer patients by flow cytometry following a standard flow cytometry protocol.

Blood from a cancer patient is isolated and 100 ul of this blood is incubated with either of the SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the SA-MHC(peptide)/APC tetramers 3 described above and thereby the presence of Survivin specific T cells in the blood. Blood analysed with SA-MHC (peptide)/APC tetramers 4 should show no staining of CD3 and CD8 positive cells with this SA-MHC(peptide)/APC tetramer.

The sensitivity of the above described test may be enhanced by addition of labeled antibodies specific for activation markers expressed in or on the surface of the Survivin specific T cells.

We conclude that the APC-SA coupled MHC(peptide) constructs may be used to detect the presence of Survivin specific T cells in the blood of cancer patients.

Example 45

This is an example of how MHC multimers may be used for detection of cancer specific T cells in blood samples from patients.

In this example the MHC multimer used are MHC complexes coupled to any fluorophor-labelled multimerisation as described elsewhere herein. The MHC multimers are used for direct detection of TCR in flow Cytometry. The antigen origin is cancer, thus, immune monitoring of a cancer.

MHC multimers carrying cancer specific peptides is in this example used to detect the presence of cancer specific T cells in the blood from cancer patients.

Purified MHC-peptide complexes consisting of HLA-A*1101 heavy chain, human beta2microglobulin and peptide derived a region in Survivin (Table F) or a negative control peptide were generated by in vitro refolding and purified or purified from antigen presenting cells. MHC-peptide complexes are then coupled to a multimerisation domain together with APC.

The following MHC(peptide)/APC multimers are made:
5. APC-multimerisation domain coupled with HLA-A*1101 in complex with beta2microglobulin and the peptide DLAQCFFCFK derived from Survivin.
6. APC-multimerisation domain coupled with HLA-A*1101 in complex with beta2microglobulin and the non-sense peptide.

The binding of the above described MHC(peptide)/APC multimers can be used to determine the presence of Survivin specific T cells in the blood from cancer patients by flow cytometry following a standard flow cytometry protocol.

Blood from a cancer patient is isolated and 100 ul of this blood is incubated with either of the MHC(peptide)/APC multimers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the MHC(peptide)/APC multimers 5 described above and thereby the presence of Survivin specific T cells in the blood. Blood analysed with MHC(peptide)/APC multimer 6 should show no staining of CD3 and CD8 positive cells with this SA-MHC(peptide)/APC multimer.

The sensitivity of the above described test may be enhanced by addition of labeled antibodies specific for activation markers expressed in or on the surface of the Survivin specific T cells.

We conclude that the APC-multimerisation domain coupled MHC(peptide) constructs may be used to detect the presence of Survivin specific T cells in the blood of cancer patients.

Example 46

This is an example of how MHC multimers may be used for detection of Epstein-Barr Virus (EBV) specific T cells in blood samples from humans infected with EBV.

In this example the MHC multimer used are MHC complexes coupled to fluorophor-labelled dextran (Dextramers). The dextramers are used for direct detection of TCR in flow cytometry.

The antigen origin is EBV, thus, immune monitoring of EBV infection MHC multimers carrying EBV specific peptides is in this example used to detect the presence of EBV specific T cells in the blood of patients infected with Epstein-Barr virus.

Purified MHC-peptide complexes consisting of HLA-B*0702 heavy chain, human beta2microglobulin and peptide derived from a region in EBV nuclear antigen (EBNA) or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contains 3.7 SA molecule and 8.95 molecules APC. The final concentration of dextran is 3.8×10e-8 M. The following MHC(peptide)/APC dextran constructs are made:

7. APC-SA conjugated 270 kDa dextran coupled with HLA-B*0702 in complex with beta2microglobulin and the peptide RPPIFIRRL derived from EBNA 3A.
8. APC-SA conjugated 270 kDa dextran coupled with HLA-B*0702 in complex with beta2microglobulin and the peptide QPRAPIRPI derived from EBNA 6.
9. APC-SA conjugated 270 kDa dextran coupled with HLA-B*0702 in complex with beta2microglobulin and the HIV peptide TPGPGVRYPL.

The binding of the above described MHC(peptide)/APC dextran is used to determine the presence of EBV specific T cells in the blood from EBV infected individuals by flow cytometry following a standard flow cytometry protocol.

Blood from a patient with EBV infection is isolated and 100 ul of this blood is incubated with 10 µl of the MHC (peptide)/APC dextran constructs described above for 10 minutes in the dark at room temperature. 5 µl of each of each of the antibodies mouse-anti-human CD3/PB (clone UCHT1 from Dako), and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 300×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the MHC(peptide)/APC dextran construct 1 or 2 described above and thereby the presence of EBV specific T cells indicate that the patient are infected with Epstein-Barr virus. Blood analysed with MHC(peptide)/APC dextran construct 3 show no staining of CD3 and CD8 positive cells with this MHC(peptide)/APC dextran construct.

The sensitivity of the above described test may be enhanced by addition of labeled antibodies specific for activation markers expressed in or on the surface of the EBV specific T cells.

We conclude that the MHC(peptide)/APC dextran constructs can be used to detect the presence of EBV specific T cells in the blood of patients infected with Epstein-Barr virus.

Example 47

This is an example of how MHC multimers may be used for detection of Epstein-Barr Virus (EBV) specific T cells in blood samples from humans infected with EBV.

In this example the MHC multimer used are MHC complexes coupled to fluorophor-labelled multimerisation domain Streptavidin (SA), used for direct detection of TCR in flow cytometry. The antigen origin is EBV, thus, immune monitoring of EBV infection MHC multimers carrying EBV specific peptides is in this example used to detect the presence of EBV specific T cells in the blood of patients infected with Epstein-Barr virus.

Purified MHC-peptide complexes consisting of HLA-B*0702 heavy chain, human beta2microglobulin and peptide derived from a region in EBV nuclear antigen (EBNA) or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:

10. APC-SA coupled with HLA-B*0702 in complex with beta2microglobulin and the peptide RPPIFIRRL derived from EBNA 3A.
11. APC-SA coupled with HLA-B*0702 in complex with beta2microglobulin and the peptide QPRAPIRPI derived from EBNA 6.
12. APC-SA coupled with HLA-B*0702 in complex with beta2microglobulin and the HIV peptide TPGPGVRYPL.

The binding of the above described MHC(peptide)/APC dextran can be used to determine the presence of EBV specific T cells in the blood from Epstein-Barr virus infected individuals by flow cytometry following a standard flow cytometry protocol.

Blood from a patient with EBV is isolated and 100 ul of this blood is incubated with either of the SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the SA-MHC(peptide)/APC tetramers 4 or 5 described above and thereby the presence of EBV specific T cells will indicate that the patient are infected with Epstein-Barr virus. Blood analysed with SA-MHC(peptide)/APC tetramers 6 should show no staining of CD3 and CD8 positive cells with this SA-MHC(peptide)/APC tetramer.

The sensitivity of the above described test may be enhanced by addition of labeled antibodies specific for activation markers expressed in or on the surface of the EBV specific T cells.

We conclude that the APC-SA coupled MHC(peptide) constructs may be used to detect the presence of EBV specific T cells in the blood of patients infected with Epstein-Barr virus Example 48

This is an example of how MHC multimers may be used for detection of Epstein-Barr Virus (EBV) specific T cells in blood samples from humans infected with EBV.

In this example the MHC multimer used are MHC complexes coupled to any fluorophor-labelled multimerisation as described elsewhere herein. The MHC multimers are used for direct detection of TCR in flow cytometry. The antigen origin is EBV, thus, immune monitoring of EBV infection MHC multimers carrying EBV specific peptides is in this example used to detect the presence of EBV specific T cells in the blood of patients infected with Epstein-Barr virus.

Purified MHC-peptide complexes consisting of HLA-B*0702 heavy chain, human beta2microglobulin and peptide derived a region in EBV nuclear antigen (EBNA) or a negative control peptide were generated by in vitro refolding and purified or purified from antigen presenting cells. MHC-peptide complexes are then coupled to a multimerisation domain together with APC.

The following MHC(peptide)/APC multimers are made:
13. APC-multimerisation domain coupled with HLA-B*0702 in complex with beta2microglobulin and the peptide RPPIFIRRL derived from EBNA 3A.
14. APC-multimerisation domain coupled with HLA-B*0702 in complex with beta2microglobulin and the peptide QPRAPIRPI derived from EBNA 6.
15. APC-multimerisation domain coupled with HLA-A*0201 in complex with beta2microglobulin and the HIV peptide TPGPGVRYPL.

The binding of the above described MHC(peptide)/APC multimers can be used to determine the presence of EBV specific T cells in the blood from EBV infected individuals by flow cytometry following a standard flow cytometry protocol.

Blood from a patient with EBV infection is isolated and 100 ul of this blood is incubated with either of the MHC (peptide)/APC multimers described above for 10 minutes in the dark at room temperature. 5 μl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 μl PBS; pH=7.2 and analyzed on flowcytometer.

The presence of cells labeled with anti-CD3/PB, anti-CD8/PE and either of the MHC(peptide)/APC multimers 7 or 8 described above and thereby the presence of EBV specific T cells will indicate that the patient are infected with Epstein-Barr virus. Blood analysed with MHC(peptide)/APC multimer 9 should show no staining of CD3 and CD8 positive cells with this SA-MHC(peptide)/APC multimer.

The sensitivity of the above described test may be enhanced by addition of labeled antibodies specific for activation markers expressed in or on the surface of the EBV specific T cells.

We conclude that the APC-multimerisation domain coupled MHC(peptide) constructs may be used to detect the presence of EBV specific T cells in the blood of patients infected with Epstein-Barr virus.

Example 49

This is an example of how MHC multimers may be used for detection of influenza matrix peptide in blood samples from humans infected with influenza.

In this example the MHC multimer used are MHC complexes coupled to fluorophor-labelled dextran (Dextramers). The dextramers are used for direct detection of TCR in flow cytometry. The antigen origin is Influenza, thus, immune monitoring of influenza.

The MHC multimer used are MHC complexes coupled to labeled dextran.

MHC multimers carrying influenza specific peptides is in this example used to detect the presence of influenza specific T cells in the blood of patients infected with influenza virus.

Purified MHC-peptide complexes consisting of HLA-A*0201 heavy chain, human beta2microglobulin and peptide derived from a region in influenza matrix peptide (Flu-MP) or a negative control peptide were generated by in vitro refolding, purified and biotinylated as described elsewhere herein. Biotinylated MHC-peptide complexes were then coupled to a 270 kDa dextran multimerization domain labelled with APC by interaction with streptavidin (SA) on the dextran multimerization domain. The dextran-APC-SA multimerization domain was generated as described elsewhere herein. MHC-peptide complexes were added in an amount corresponding to a ratio of three MHC-peptide molecules per SA molecule and each molecule dextran contains 3.7 SA molecule and 8.95 molecules APC. The final concentration of dextran was 3.8×10e-8 M. The following MHC(peptide)/APC dextran constructs were made:
16. APC-SA conjugated 270 kDa dextran coupled with HLA-A*0201 in complex with beta2microglobulin and the peptide GILGFVFTL derived from Flu-MP.
17. APC-SA conjugated 270 kDa dextran coupled with HLA-A*0201 in complex with beta2microglobulin and the non-sense peptide GLAGDVSAV.

The binding of the above described MHC(peptide)/APC dextran was used to determine the presence of influenza specific T cells in the blood from influenza infected individuals by flow cytometry following a standard flow cytometry protocol.

Blood from a influenza infected patient is isolated and 100 ul of this blood is incubated with 10 μl of the MHC(peptide)/APC dextran constructs described above for 10 minutes in the dark at room temperature. 5 μl of each of each of the antibodies mouse-anti-human CD3/PB (clone UCHT1 from Dako), and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 μl PBS; pH=7.2 and analyzed on flowcytometer.

The presence of cells labeled with anti-CD3/PB, anti-CD8/PE and the MHC(peptide)/APC dextran construct 1 described above and thereby the presence of influenza specific T cells indicate that the patient are infected with influenza virus. Blood analysed with MHC(peptide)/APC dextran construct 2 show no staining of CD3 and CD8 positive cells with this MHC(peptide)/APC dextran construct.

The sensitivity of the above described test may be enhanced by addition of labeled antibodies specific for activation markers expressed in or on the surface of the influenza specific T cells.

We conclude that the MHC(peptide)/APC dextran constructs can be used to detect the presence of influenza specific T cells in the blood of patients infected with influenza virus.

Example 50

This is an example of how MHC multimers may be used for detection of influenza matrix peptide in blood samples from humans infected with influenza.

In this example the MHC multimer used are MHC complexes coupled to fluorophor-labelled multimerisation domain Streptavidin (SA), used for direct detection of TCR in flow cytometry. The antigen origin is Influenza, thus, immune monitoring of influenza.

The MHC multimer used are MHC complexes coupled to labeled dextran.

MHC multimers carrying influenza specific peptides is in this example used to detect the presence of influenza specific T cells in the blood of patients infected with influenza virus.

Purified MHC-peptide complexes consisting of HLA-A*0201 heavy chain, human beta2microglobulin and peptide derived from a region in influenza matrix peptide (Flu-MP) or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:
18. APC-SA coupled with HLA-A*0201 in complex with beta2microglobulin and the peptide GILGFVFTL derived from Flu-MP.
19. APC-SA coupled with HLA-A*0201 in complex with beta2microglobulin and the non-sense peptide GLAGDVSAV.

The binding of the above described MHC(peptide)/APC dextran can be used to determine the presence of influenza specific T cells in the blood from influenza infected individuals by flow cytometry following a standard flow cytometry protocol.

Blood from a cancer patient is isolated and 100 ul of this blood is incubated with either of the SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the SA-MHC(peptide)/APC tetramers 3 described above and thereby the presence of influenza specific T cells will indicate that the patient are infected with influenza virus. Blood analysed with SA-MHC(peptide)/APC tetramers 4 should show no staining of CD3 and CD8 positive cells with this SA-MHC(peptide)/APC tetramer.

The sensitivity of the above described test may be enhanced by addition of labeled antibodies specific for activation markers expressed in or on the surface of the influenza specific T cells.

We conclude that the APC-SA coupled MHC(peptide) constructs may be used to detect the presence of influenza specific T cells in the blood of patients infected with influenza virus.

Example 51

This is an example of how MHC multimers may be used for detection of influenza matrix peptide in blood samples from humans infected with influenza.

In this example the MHC multimer used are MHC complexes coupled to any fluorophor-labelled multimerisation as described elsewhere herein. The MHC multimers are used for direct detection of TCR in flow cytometry. The antigen origin is Influenza, thus, immune monitoring of influenza.

The MHC multimer used are MHC complexes coupled to labeled dextran.

MHC multimers carrying influenza specific peptides is in this example used to detect the presence of influenza specific T cells in the blood of patients infected with influenza virus.

Purified MHC-peptide complexes consisting of HLA-A*0201 heavy chain, human beta2microglobulin and peptide derived a region in influenza matrix peptide (Flu-MP) or a negative control peptide were generated by in vitro refolding and purified or purified from antigen presenting cells. MHC-peptide complexes are then coupled to a multimerisation domain together with APC.

The following MHC(peptide)/APC multimers are made:
20. APC-multimerisation domain coupled with HLA-A*0201 in complex with beta2microglobulin and the peptide GILGFVFTL derived from Flu-MP.
21. APC-multimerisation domain coupled with HLA-A*0201 in complex with beta2microglobulin and the non-sense peptide GLAGDVSAV.

The binding of the above described MHC(peptide)/APC multimers can be used to determine the presence of influenza specific T cells in the blood from influenza infected by flow cytometry following a standard flow cytometry protocol.

Blood from a influenza infected patient is isolated and 100 ul of this blood is incubated with either of the MHC (peptide)/APC multimers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the MHC(peptide)/APC multimers 5 described above and thereby the presence of influenza specific T cells will indicate that the patient are infected with influenza virus. Blood analysed with MHC(peptide)/APC multimer 6 should show no staining of CD3 and CD8 positive cells with this SA-MHC(peptide)/APC multimer.

The sensitivity of the above described test may be enhanced by addition of labeled antibodies specific for activation markers expressed in or on the surface of the influenza specific T cells.

We conclude that the APC-multimerisation domain coupled MHC(peptide) constructs may be used to detect the presence of influenza specific T cells in the blood of patients infected with influenza virus.

Example 52

This is an example of how MHC multimers may be used for detection of Multiple sclerosis (MS) specific T cells in blood samples from MS patients.

In this example the MHC multimer used are MHC complexes coupled to fluorophor-labelled dextran (Dextramers). The dextramers are used for direct detection of TCR in flow Cytometry. The antigen origin is MS, thus, immune monitoring of MS.

MHC multimers carrying MS specific peptides is in this example used to detect the presence of MS specific T cells in the blood of MS patients.

Purified MHC-peptide complexes consisting of HLA-DR2 heavy chains and peptide derived from a region in Myelin Basic Protein (MBP) in MS or a negative control peptide are generated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain was generated as described elsewhere herein. MHC-peptide complexes are added in an amount corresponding to a ratio of three MHC-peptide molecules per SA molecule and each molecule dextran contains 3.7 SA molecule and 8.95 molecules APC. The final concentration of dextran was 3.8×10e-8 M. The following MHC(peptide)/APC dextran constructs are made:

22. APC-SA conjugated 270 kDa dextran coupled with HLA-DR2 in complex with the peptide MBP 83-102 YDENPVVHFF KNIVTPRTPP derived from Multiple sclerosis.
23. APC-SA conjugated 270 kDa dextran coupled with HLA-DR2 in complex with the peptide MBP 144-163 VDAQGTLSKIFKLGGRDSRS derived from Multiple sclerosis.
24. APC-SA conjugated 270 kDa dextran coupled with HLA-DR2 in complex with a non-sense peptide.

The binding of the above described MHC(peptide)/APC dextran was used to determine the presence of MS specific T cells in the blood from MS patients by flow cytometry following a standard flow cytometry protocol.

Blood from a MS patient is isolated and 100 ul of this blood is incubated with 10 µl of the MHC(peptide)/APC dextran constructs described above for 10 minutes in the dark at room temperature. 5 µl of each of each of the antibodies mouse-anti-human CD3/PB (clone UCHT1 from Dako), and mouse-anti-human CD4/PE (clone MT310 from Dako) are added and the incubation continues for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD4/PE and either of the MHC(peptide)/APC dextran construct 1 or 2 described above and thereby the presence of MS specific T cells in the blood. Blood analysed with MHC (peptide)/APC dextran construct 3 show no staining of CD3 and CD4 positive cells with this MHC(peptide)/APC dextran construct.

The sensitivity of the above described test may be enhanced by addition of labeled antibodies specific for activation markers expressed in or on the surface of the MS specific T cells.

We conclude that the MHC(peptide)/APC dextran constructs can be used to detect the presence of MS specific T cells in the blood of MS patients.

Example 53

This is an example of how MHC multimers may be used for detection of Multiple sclerosis (MS) specific T cells in blood samples from MS patients.

In this example the MHC multimer used are MHC complexes coupled to fluorophor-labelled multimerisation domain Streptavidin (SA, used for direct detection of TCR in flow Cytometry. The antigen origin is MS, thus, immune monitoring of MS.

MHC multimers carrying MS specific peptides is in this example used to detect the presence of MS specific T cells in the blood of MS patients.

Purified MHC-peptide complexes consisting of HLA-DR2 heavy chains and peptide derived from a region in Myelin Basic Protein (MBP) in MS or a negative control peptide are generated as described elsewhere herein. Biotinylated MHC-peptide complexes are then coupled SA labelled with APC. MHC-peptide complexes are added in an amount corresponding to a ratio of 5 MHC-peptide molecules per SA molecule. Then SA/APC carrying four MHC complexes are purified from free SA, free monomeric MHC complex, SA carrying three, two and one MHC complexes.

The following SA-MHC(peptide)/APC tetramers are made:

25. APC-SA coupled with HLA-DR2 in complex with the peptide MBP 83-102 YDENPVVHFFKNIVTPRTPP derived from Multiple sclerosis.
26. APC-SA coupled with HLA-DR2 in complex with the peptide MBP 144-163 VDAQGTLSKIFKLGGRDSRS derived from Multiple sclerosis.
27. APC-SA coupled with HLA-DR2 in complex with a non-sense peptide.

The binding of the above described MHC(peptide)/APC dextran can be used to determine the presence of MS specific T cells in the blood from MS patients by flow cytometry following a standard flow cytometry protocol.

Blood from a MS patient is isolated and 100 ul of this blood is incubated with either of the SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD4/PE (clone MT310 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD4/PE and either of the SA-MHC(peptide)/APC tetramers 4 or 5 described above and thereby the presence of MS specific T cells in the blood. Blood analysed with SA-MHC (peptide)/APC tetramers 6 should show no staining of CD3 and CD4 positive cells with this SA-MHC(peptide)/APC tetramer.

The sensitivity of the above described test may be enhanced by addition of labeled antibodies specific for activation markers expressed in or on the surface of the MS specific T cells.

We conclude that the APC-SA coupled MHC(peptide) constructs may be used to detect the presence of MS specific T cells in the blood of MS patients.

Example 54

This is an example of how MHC multimers may be used for detection of Multiple sclerosis (MS) specific T cells in blood samples from MS patients.

In this example the MHC multimer used are MHC complexes coupled to any fluorophor-labelled multimerisation as described elsewhere herein. The MHC multimers are used for direct detection of TCR in flow Cytometry. The antigen origin is MS, thus, immune monitoring of MS.

MHC multimers carrying MS specific peptides is in this example used to detect the presence of MS specific T cells in the blood of MS patients.

Purified MHC-peptide complexes consisting of HLA-DR2 heavy chains and peptide derived from a region in Myelin Basic Protein (MBP) in MS or a negative control peptide are generated. MHC-peptide complexes are then coupled to a multimerisation domain together with APC.

The following MHC(peptide)/APC multimers are made:
28. APC-multimerisation domain coupled with HLA-DR2 in complex with the peptide MBP 83-102 YDENPVVHFFKNIVTPRTPP derived from Multiple sclerosis.
29. APC-multimerisation domain coupled with HLA-DR2 in complex with the peptide MBP 144-163 VDAQGTLSKIFKLGGRDSRS derived from Multiple sclerosis.
30. APC-multimerisation domain coupled with HLA-DR2 in complex with a non-sense peptide.

The binding of the above described MHC(peptide)/APC multimers can be used to determine the presence of MS specific T cells in the blood from MS patients by flow cytometry following a standard flow cytometry protocol.

Blood from a MS patient is isolated and 100 ul of this blood is incubated with either of the MHC(peptide)/APC multimers described above for 10 minutes in the dark at room temperature. 5 µl of each of each of the antibodies mouse-anti-human CD3/PB (clone UCHT1 from Dako) and mouse-anti-human CD4/PE (clone MT310 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD4/PE and either of the MHC(peptide)/APC multimers 7 or 8 described above and thereby the presence of MS specific T cells in the blood. Blood analysed with MHC(peptide)/APC multimer 9 should show no staining of CD3 and CD4 positive cells with this SA-MHC(peptide)/APC multimer.

The sensitivity of the above described test may be enhanced by addition of labeled antibodies specific for activation markers expressed in or on the surface of the MS specific T cells.

We conclude that the APC-multimerisation domain coupled MHC(peptide) constructs may be used to detect the presence of MS specific T cells in the blood of MS patients.

Example 55

This is an example of how MHC multimers may be used for detection of Rheumatoid arthritis (RA) specific T cells in blood samples from RA patients.

In this example the MHC multimer used are MHC complexes coupled to fluorophor-labelled dextran (Dextramers). The dextramers are used for direct detection of TCR in flow cytometry. The antigen origin is RA, thus, immune monitoring of RA.

MHC multimers carrying RA specific peptides is in this example used to detect the presence of RA specific T cells in the blood of MS patients.

Purified MHC-peptide complexes consisting of HLA-DR4 heavy chains and peptide derived from a region in Collagen Type II (CII) in RA or a negative control peptide are generated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain was generated as described elsewhere herein. MHC-peptide complexes are added in an amount corresponding to a ratio of three MHC-peptide molecules per SA molecule and each molecule dextran contains 3.7 SA molecule and 8.95 molecules APC. The final concentration of dextran was 3.8× 10e-8 M. The following MHC(peptide)/APC dextran constructs are made:
31. APC-SA conjugated 270 kDa dextran coupled with HLA-DR4 in complex with the peptide CII 261-273 AGFKGEQGPKGEP derived from Rheumatoid arthritis
32. APC-SA conjugated 270 kDa dextran coupled with HLA-DR4 in complex with a non-sense peptide.

The binding of the above described MHC(peptide)/APC dextran was used to determine the presence of RA specific T cells in the blood from RA patients by flow cytometry following a standard flow cytometry protocol.

Blood from a RA patient is isolated and 100 ul of this blood is incubated with 10 µl of the MHC(peptide)/APC dextran constructs described above for 10 minutes in the dark at room temperature. 5 µl of each of each of the antibodies mouse-anti-human CD3/PB (clone UCHT1 from Dako), and mouse-anti-human CD4/PE (clone MT310 from Dako) are added and the incubation continues for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD4/PE and the MHC(peptide)/APC dextran construct 1 described above and thereby the presence of RA specific T cells in the blood. Blood analysed with MHC(peptide)/APC dextran construct 2 show no staining of CD3 and CD4 positive cells with this MHC(peptide)/APC dextran construct.

The sensitivity of the above described test may be enhanced by addition of labeled antibodies specific for activation markers expressed in or on the surface of the RA specific T cells.

We conclude that the MHC(peptide)/APC dextran constructs can be used to detect the presence of RA specific T cells in the blood of RA patients.

Example 56

This is an example of how MHC multimers may be used for detection of Rheumatoid arthritis (RA) specific T cells in blood samples from RA patients In this example the MHC multimer used are MHC complexes coupled to fluorophor-labelled multimerisation domain Streptavidin (SA), used for direct detection of TCR in flow cytometry. The antigen origin is RA, thus, immune monitoring of RA.

MHC multimers carrying RA specific peptides is in this example used to detect the presence of RA specific T cells in the blood of RA patients.

Purified MHC-peptide complexes consisting of HLA-DR4 heavy chains and peptide derived from a region in Collagen type II (CII) in RA or a negative control peptide are generated as described elsewhere herein. Biotinylated MHC-peptide complexes are then coupled SA labelled with APC. MHC-peptide complexes are added in an amount corresponding to a ratio of 5 MHC-peptide molecules per SA molecule. Then SA/APC carrying four MHC complexes are purified from free SA, free monomeric MHC complex, SA carrying three, two and one MHC complexes.

The following SA-MHC(peptide)/APC tetramers are made:

33. APC-SA coupled with HLA-DR4 in complex with the peptide CII 261-273 AGFKGEQGPKGEP derived from Rheumatoid arthritis.
34. APC-SA coupled with HLA-DR4 in complex with a non-sense peptide.

The binding of the above described MHC(peptide)/APC dextran can be used to determine the presence of RA specific T cells in the blood from RA patients by flow cytometry following a standard flow cytometry protocol.

Blood from a RA patient is isolated and 100 ul of this blood is incubated with either of the SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD4/PE (clone MT310 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD4/PE and the SA-MHC(peptide)/APC tetramers 3 described above and thereby the presence of RA specific T cells in the blood. Blood analysed with SA-MHC(peptide)/APC tetramers 4 should show no staining of CD3 and CD4 positive cells with this SA-MHC(peptide)/APC tetramer.

The sensitivity of the above described test may be enhanced by addition of labeled antibodies specific for activation markers expressed in or on the surface of the RA specific T cells.

We conclude that the APC-SA coupled MHC(peptide) constructs may be used to detect the presence of RA specific T cells in the blood of RA patients.

Example 57

This is an example of how MHC multimers may be used for detection of Rheumatoid arthritis (RA) specific T cells in blood samples from RA patients.

In this example the MHC multimer used are MHC complexes coupled to any fluorophor-labelled multimerisation as described elsewhere herein. The MHC multimers are used for direct detection of TCR in flow cytometry. The antigen origin is RA, thus, immune monitoring of RA. MHC multimers carrying RA specific peptides is in this example used to detect the presence of RA specific T cells in the blood of MS patients.

This is an example of how MHC multimers may be used for detection of Rheumatoid arthritis (RA) specific T cells in blood samples from RA patients. The MHC multimer used are MHC complexes coupled to MHC multimers carrying RA specific peptides is in this example used to detect the presence of RA specific T cells in the blood of RA patients.

Purified MHC-peptide complexes consisting of HLA-DR4 heavy chains and peptide derived from a region in Myelin Basic Protein (MBP) in MS or a negative control peptide are generated. MHC-peptide complexes are then coupled to a multimerisation domain together with APC.

The following MHC(peptide)/APC multimers are made:

35. APC-multimerisation domain coupled with HLA-DR4 in complex with the peptide CII 261-273 AGFK-GEQGPKGEP derived from Rheumatoid arthritis.
36. APC-multimerisation domain coupled with HLA-DR4 in complex with a non-sense peptide.

The binding of the above described MHC(peptide)/APC multimers can be used to determine the presence of RA specific T cells in the blood from RA patients by flow cytometry following a standard flow cytometry protocol.

Blood from a RA patient is isolated and 100 ul of this blood is incubated with either of the MHC(peptide)/APC multimers described above for 10 minutes in the dark at room temperature. 5 µl of each of each of the antibodies mouse-anti-human CD3/PB (clone UCHT1 from Dako) and mouse-anti-human CD4/PE (clone MT310 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD4/PE and the MHC(peptide)/APC multimers 5 described above and thereby the presence of RA specific T cells in the blood. Blood analysed with MHC(peptide)/APC multimer 6 should show no staining of CD3 and CD4 positive cells with this SA-MHC(peptide)/APC multimers.

The sensitivity of the above described test may be enhanced by addition of labeled antibodies specific for activation markers expressed in or on the surface of the RA specific T cells.

We conclude that the APC-multimerisation domain coupled MHC(peptide) constructs may be used to detect the presence of RA specific T cells in the blood of RA patients.

Example 58

This is an example of how MHC multimers may be used for diagnosis of Tuberculosis (TB) in blood samples from humans infected with *Mycobacterium tuberculosis*.

In this example the MHC multimer used are MHC complexes coupled to fluorophor-labelled dextran (Dextramers). The dextramers are used for direct detection of TCR in flow cytometry. The antigen origin is TB, thus, immune monitoring of TB.

TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-A*0201 heavy chain, human beta2microglobulin and peptide derived from regions in *Mycobacterium tuberculosis* Antigen 85B (Ag85B) or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contained 3.7 SA molecule and 8.95 molecules APC. The final concentration of dextran was 3.8×10e-8 M. The following MHC(peptide)/APC dextran constructs are made:

37. APC-SA conjugated 270 kDa dextran coupled with HLA-A*0201 in complex with beta2microglobulin and the peptide KLVANNTRL derived from Ag85B.
38. APC-SA conjugated 270 kDa dextran coupled with HLA-A*0201 in complex with beta2microglobulin and the peptide YLLDGLRAQ derived from Ag85B.
39. APC-SA conjugated 270 kDa dextran coupled with HLA-A*0201 in complex with beta2microglobulin and the peptide FLTSELPQW derived from Ag85B.
40. APC-SA conjugated 270 kDa dextran coupled with HLA-A*0201 in complex with beta2microglobulin and the non-sense peptide GLAGDVSAV.

The binding of the above described MHC(peptide)/APC dextran can be used to determine the presence of Ag85B specific T cells in the blood from TB infected individuals by flow cytometry following a standard flow cytometry protocol.

Blood from a patient with TB is isolated and 100 ul of this blood is incubated with 10 µl of one of the MHC(peptide)/APC dextran constructs described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the MHC(peptide)/APC dextran constructs 1, 2 or 3 described above and thereby the presence of TB specific T cells will indicate that the patient are infected with *Mycobacterium tuberculosis*. Blood analysed with MHC(peptide)/APC dextran construct 4 should show no staining of CD3 and CD8 positive cells with this MHC (peptide)/APC dextran construct.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 59

This is an example of how MHC multimers may be used for diagnosis of Tuberculosis (TB) in blood samples from humans infected with *Mycobacterium tuberculosis*.

In this example the MHC multimer used are MHC complexes coupled to fluorophor-labelled the multimerisation domain Streptavidin (SA), used for direct detection of TCR in flow cytometry. The antigen origin is TB, thus, immune monitoring of TB.

TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-A*0201 heavy chain, human beta2microglobulin and peptide derived from regions in *Mycobacterium tuberculosis* Antigen 85B (Ag85B) or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:

41. APC-SA coupled with HLA-A*0201 in complex with beta2microglobulin and the peptide KLVANNTRL derived from Ag85B.
42. APC-SA coupled with HLA-A*0201 in complex with beta2microglobulin and the peptide YLLDGLRAQ derived from Ag85B.
43. APC-SA coupled with HLA-A*0201 in complex with beta2microglobulin and the peptide FLTSELPQW derived from Ag85B.
44. APC-SA coupled with HLA-A*0201 in complex with beta2microglobulin and the non-sense peptide GLAGDVSAV The binding of the above described MHC(peptide)/APC dextran can be used to determine the presence of Ag85B specific T cells in the blood from TB infected individuals by flow cytometry following a standard flow cytometry protocol.

Blood from a patient with TB is isolated and 100 ul of this blood is incubated with either of the four SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the SA-MHC(peptide)/APC tetramers 5, 6 or 7 described above and thereby the presence of TB specific T cells will indicate that the patient are infected with *Mycobacterium tuberculosis*. Blood analysed with SA-MHC (peptide)/APC tetramers 8 should show no staining of CD3 and CD8 positive cells with this SA-MHC(peptide)/APC tetramer.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 60

This is an example of how MHC multimers may be used for diagnosis of Tuberculosis (TB) in blood samples from humans infected with *Mycobacterium tuberculosis*.

In this example the MHC multimer used are MHC complexes coupled to any fluorophor-labelled multimerisation as described elsewhere herein. The MHC multimers are used for direct detection of TCR in flow cytometry. The antigen origin is TB, thus, immune monitoring of TB. TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

This is an example of how MHC multimers may be used for diagnosis of Tuberculosis (TB) in blood samples from humans infected with *Mycobacterium tuberculosis*. The MHC multimer used are MHC complexes coupled to TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-A*0201 heavy chain, human beta2microglobulin and peptide derived from regions in *Mycobacterium tuberculosis* Antigen 85B (Ag85B) or a negative control peptide are generated by in vitro refolding and purified or purified from antigen presenting cells. MHC-peptide complexes are then coupled to a multimerisation domain together with APC.

The following MHC(peptide)/APC multimers are made:
45. APC-multimerisation domain coupled with HLA-A*0201 in complex with beta2microglobulin and the peptide KLVANNTRL derived from Ag85B.
46. APC-multimerisation domain coupled with HLA-A*0201 in complex with beta2microglobulin and the peptide YLLDGLRAQ derived from Ag85B.
47. APC-multimerisation domain coupled with HLA-A*0201 in complex with beta2microglobulin and the peptide FLTSELPQW derived from Ag85B.
48. APC-multimerisation domain coupled with HLA-A*0201 in complex with beta2microglobulin and the non-sense peptide GLAGDVSAV The binding of the above described MHC(peptide)/APC multimers can be used to determine the presence of Ag85B specific T cells in the blood from TB infected individuals by flow cytometry following a standard flow cytometry protocol.

Blood from a patient with TB is isolated and 100 ul of this blood is incubated with either of the four MHC(peptide)/APC multimers described above for 10 minutes in the dark at room temperature. 5 μl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 μl PBS; pH=7.2 and analyzed on flowcytometer.

The presence of cells labeled with anti-CD3/PB, anti-CD8/PE and either of the MHC(peptide)/APC multimers 9, 10 or 11 described above and thereby the presence of TB specific T cells will indicate that the patient are infected with *Mycobacterium tuberculosis*. Blood analysed with MHC (peptide)/APC multimer 12 should show no staining of CD3 and CD8 positive cells with this SA-MHC(peptide)/APC multimer.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 61

This is an example of how MHC multimers may be used for diagnosis of Tuberculosis (TB) in blood samples from humans infected with *Mycobacterium tuberculosis*.

In this example the MHC multimer used are MHC complexes coupled to fluorophor-labelled dextran (Dextramers). The dextramers are used for direct detection of TCR in flow cytometry. The antigen origin is TB, thus, immune monitoring of TB.

TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-B*0801 heavy chain, human beta2microglobulin and peptide derived from regions in *Mycobacterium tuberculosis* Antigen 85B (Ag85B) or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contained 3.7 SA molecule and 8.95 molecules APC. The final concentration of dextran was 3.8×10e-8 M. The following MHC(peptide)/APC dextran constructs are made:
49. APC-SA conjugated 270 kDa dextran coupled with HLA-B*0801 in complex with beta2microglobulin and the peptide MGRDIKVQF derived from Ag85B.
50. APC-SA conjugated 270 kDa dextran coupled with HLA-B*0801 in complex with beta2microglobulin and the peptide DIKVQFQSG derived from Ag85B.
51. APC-SA conjugated 270 kDa dextran coupled with HLA-B*0801 in complex with beta2microglobulin and the peptide ENFVRSSNL derived from Ag85B.
52. APC-SA conjugated 270 kDa dextran coupled with HLA-B*0801 in complex with beta2microglobulin and the non-sense peptide.

The binding of the above described MHC(peptide)/APC dextran can be used to determine the presence of Ag85B specific T cells in the blood from TB infected individuals by flow cytometry following a standard flow cytometry protocol.

Blood from a patient with TB is isolated and 100 ul of this blood is incubated with 10 µl of one of the MHC(peptide)/APC dextran constructs described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the MHC(peptide)/APC dextran constructs 13, 14 or 15 described above and thereby the presence of TB specific T cells will indicate that the patient are infected with *Mycobacterium tuberculosis*. Blood analysed with MHC(peptide)/APC dextran construct 16 should show no staining of CD3 and CD8 positive cells with this MHC (peptide)/APC dextran construct.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 62

This is an example of how MHC multimers may be used for diagnosis of Tuberculosis (TB) in blood samples from humans infected with *Mycobacterium tuberculosis*.

In this example the MHC multimer used are MHC complexes coupled to fluorophor-labelled the multimerisation domain Streptavidin (SA), used for direct detection of TCR in flow cytometry. The antigen origin is TB, thus, immune monitoring of TB.

TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-A*0201 heavy chain, human beta2microglobulin and peptide derived from regions in *Mycobacterium tuberculosis* Antigen 85B (Ag85B) or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:
53. APC-SA coupled with HLA-B*0801 in complex with beta2microglobulin and the peptide MGRDIKVQF derived from Ag85B.
54. APC-SA coupled with HLA-B*0801 in complex with beta2microglobulin and the peptide DIKVQFQSG derived from Ag85B.
55. APC-SA coupled with HLA-B*0801 in complex with beta2microglobulin and the peptide ENFVRSSNL derived from Ag85B.
56. APC-SA coupled with HLA-B*0801 in complex with beta2microglobulin and the non-sense peptide.

The binding of the above described MHC(peptide)/APC dextran can be used to determine the presence of Ag85B specific T cells in the blood from TB infected individuals by flow cytometry following a standard flow cytometry protocol.

Blood from a patient with TB is isolated and 100 ul of this blood is incubated with either of the four SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the SA-MHC(peptide)/APC tetramers 17, 18 or 19 described above and thereby the presence of TB specific T cells will indicate that the patient are infected with *Mycobacterium tuberculosis*. Blood analysed with SA-MHC(peptide)/APC tetramers 20 should show no staining of CD3 and CD8 positive cells with this SA-MHC(peptide)/APC tetramer.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 63

This is an example of how MHC multimers may be used for diagnosis of Tuberculosis (TB) in blood samples from humans infected with *Mycobacterium tuberculosis*.

In this example the MHC multimer used are MHC complexes coupled to any fluorophor-labelled multimerisation as described elsewhere herein. The MHC multimers are used for direct detection of TCR in flow cytometry. The antigen origin is TB, thus, immune monitoring of TB. TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-B*0801 heavy chain, human beta2microglobulin and peptide derived from regions in *Mycobacterium tuberculosis* Antigen 85B (Ag85B) or a negative control peptide are generated by in vitro refolding and purified or purified from antigen presenting cells. MHC-peptide complexes are then coupled to a multimerisation domain together with APC.

The following MHC(peptide)/APC multimers are made:

57. APC-multimerisation domain coupled with HLA-B*0801 in complex with beta2microglobulin and the peptide MGRDIKVQF derived from Ag85B.
58. APC-multimerisation domain coupled with HLA-B*0801 in complex with beta2microglobulin and the peptide DIKVQFQSG derived from Ag85B.
59. APC-multimerisation domain coupled with HLA-B*0801 in complex with beta2microglobulin and the peptide ENFVRSSNL derived from Ag85B.
60. APC-multimerisation domain coupled with HLA-B*0801 in complex with beta2microglobulin and the non-sense peptide.

The binding of the above described MHC(peptide)/APC multimers can be used to determine the presence of Ag85B specific T cells in the blood from TB infected individuals by flow cytometry following a standard flow cytometry protocol.

Blood from a patient with TB is isolated and 100 ul of this blood is incubated with either of the four MHC(peptide)/APC multimers described above for 10 minutes in the dark at room temperature. 5 μl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 μl PBS; pH=7.2 and analyzed on flowcytometer.

The presence of cells labeled with anti-CD3/PB, anti-CD8/PE and either of the MHC(peptide)/APC multimers 21, 22 or 23 described above and thereby the presence of TB specific T cells will indicate that the patient are infected with *Mycobacterium tuberculosis*. Blood analysed with MHC (peptide)/APC multimer 24 should show no staining of CD3 and CD8 positive cells with this SA-MHC(peptide)/APC multimer.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 64

This is an example of how MHC multimers may be used for diagnosis of Tuberculosis (TB) in blood samples from humans infected with *Mycobacterium tuberculosis*.

In this example the MHC multimer used are MHC complexes coupled to fluorophor-labelled dextran (Dextramers). The dextramers are used for direct detection of TCR in flow cytometry. The antigen origin is TB, thus, immune monitoring of TB.

TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-B*44 heavy chain, human beta2microglobulin and peptide derived from regions in antigen Mtb39 or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contained 3.7 SA molecule and 8.95 molecules APC. The final concentration of dextran was 3.8×10e-8 M.

The following MHC(peptide)/APC dextran constructs are made:

61. APC-SA conjugated 270 kDa dextran coupled with HLA-B*44 in complex with beta2microglobulin and the peptide MWAQDAAAMF derived from Mtb39.
62. APC-SA conjugated 270 kDa dextran coupled with HLA-B*44 in complex with beta2microglobulin and the peptide AAERGPGQML derived from Mtb39.
63. APC-SA conjugated 270 kDa dextran coupled with HLA-B*44 in complex with beta2microglobulin and the non-sense peptide.

The binding of the above described MHC(peptide)/APC dextran can be used to determine the presence of Mtb39 specific T cells in the blood from TB infected individuals by flow cytometry following a standard flow cytometry protocol.

Blood from a patient with TB is isolated and 100 ul of this blood is incubated with 10 μl of one of the MHC(peptide)/APC dextran constructs described above for 10 minutes in the dark at room temperature. 5 μl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 μl PBS; pH=7.2 and analyzed on flowcytometer.

The presence of cells labeled with anti-CD3/PB, anti-CD8/PE and either of the MHC(peptide)/APC dextran constructs 25 or 26 described above and thereby the presence of TB specific T cells will indicate that the patient are infected with *Mycobacterium tuberculosis*. Blood analysed with MHC(peptide)/APC dextran construct 27 should show no staining of CD3 and CD8 positive cells with this MHC (peptide)/APC dextran construct.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 65

This is an example of how MHC multimers may be used for diagnosis of Tuberculosis (TB) in blood samples from humans infected with *Mycobacterium tuberculosis*.

In this example the MHC multimer used are MHC complexes coupled to fluorophor-labelled the multimerisation domain Streptavidin (SA), used for direct detection of TCR in flow cytometry. The antigen origin is TB, thus, immune monitoring of TB.

TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-B*44 heavy chain, human beta2microglobulin and peptide derived from regions in antigen Mtb39 or a negative control peptide are generated by in vitro refolding, purified and biotinylated as described elsewhere herein. Biotinylated MHC-peptide complexes are then coupled SA labelled with APC. MHC-peptide complexes are added in an amount corresponding to a ratio of 5 MHC-peptide molecules per SA molecule. Then SA/APC carrying four MHC complexes are purified from free SA, free monomeric MHC complex, SA carrying three, two and one MHC complexes.

The following SA-MHC(peptide)/APC tetramers are made:
64. APC-SA coupled with HLA-B*44 in complex with beta2microglobulin and the peptide MWAQDAAAMF derived from Ag85B.
65. APC-SA coupled with HLA-B*44 in complex with beta2microglobulin and the peptide AAERGPGQML derived from Ag85B.
66. APC-SA coupled with HLA-B*44 in complex with beta2microglobulin and the non-sense peptide.

The binding of the above described MHC(peptide)/APC dextran can be used to determine the presence of Mtb39 specific T cells in the blood from TB infected individuals by flow cytometry following a standard flow cytometry protocol.

Blood from a patient with TB is isolated and 100 ul of this blood is incubated with either of the four SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the SA-MHC(peptide)/APC tetramers 28 or 29 described above and thereby the presence of TB specific T cells will indicate that the patient are infected with *Mycobacterium tuberculosis*. Blood analysed with SA-MHC (peptide)/APC tetramers 30 should show no staining of CD3 and CD8 positive cells with this SA-MHC(peptide)/APC tetramer.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 66

This is an example of how MHC multimers may be used for diagnosis of Tuberculosis (TB) in blood samples from humans infected with *Mycobacterium tuberculosis*.

In this example the MHC multimer used are MHC complexes coupled to any fluorophor-labelled multimerisation as described elsewhere herein. The MHC multimers are used for direct detection of TCR in flow cytometry. The antigen origin is TB, thus, immune monitoring of TB. TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-B*44 heavy chain, human beta2microglobulin and peptide derived from regions in antigen Mtb39 or a negative control peptide are generated by in vitro refolding and purified or purified from antigen presenting cells. MHC-peptide complexes are then coupled to a multimerisation domain together with APC.

The following MHC(peptide)/APC multimers are made:
67. APC-multimerisation domain coupled with HLA-B*44 in complex with beta2microglobulin and the peptide MWAQDAAAMF derived from Mtb39.
68. APC-multimerisation domain coupled with HLA-B*44 in complex with beta2microglobulin and the peptide AAERGPGQML derived from Mtb39.
69. APC-multimerisation domain coupled with HLA-B*44 in complex with beta2microglobulin and the non-sense peptide.

The binding of the above described MHC(peptide)/APC multimers can be used to determine the presence of Mtb39 specific T cells in the blood from TB infected individuals by flow cytometry following a standard flow cytometry protocol.

Blood from a patient with TB is isolated and 100 ul of this blood is incubated with either of the four MHC(peptide)/APC multimers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the MHC(peptide)/APC multimers 31 or 32 described above and thereby the presence of TB specific T cells will indicate that the patient are infected with

*Mycobacterium tuberculosis*. Blood analysed with MHC (peptide)/APC multimer 33 should show no staining of CD3 and CD8 positive cells with this SA-MHC(peptide)/APC multimer.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 67

This is an example of how MHC multimers may be used for diagnosis of Tuberculosis (TB) in blood samples from humans infected with *Mycobacterium tuberculosis*.

In this example the MHC multimer used are MHC complexes coupled to fluorophor-labelled dextran (Dextramers). The dextramers are used for direct detection of TCR in flow cytometry. The antigen origin is TB, thus, immune monitoring of TB.

TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-B*14 heavy chain, human beta2microglobulin and peptide derived from regions in culture filtrate protein 10 (CFP10) antigen (Table Y) or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contained 3.7 SA molecule and 8.95 molecules APC. The final concentration of dextran was 3.8×10e-8 M. The following MHC (peptide)/APC dextran constructs are made:
- 70. APC-SA conjugated 270 kDa dextran coupled with HLA-B*14 in complex with beta2microglobulin and the peptide RADEEQQQAL derived from CFP10.
- 71. APC-SA conjugated 270 kDa dextran coupled with HLA-B*14 in complex with beta2microglobulin and the non-sense peptide.

The binding of the above described MHC(peptide)/APC dextran can be used to determine the presence of CFP10 specific T cells in the blood from TB infected individuals by flow cytometry following a standard flow cytometry protocol.

Blood from a patient with TB is isolated and 100 ul of this blood is incubated with 10 µl of one of the MHC(peptide)/APC dextran constructs described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the MHC(peptide)/APC dextran constructs 34 described above and thereby the presence of TB specific T cells will indicate that the patient are infected with *Mycobacterium tuberculosis*. Blood analysed with MHC(peptide)/APC dextran construct 25 should show no staining of CD3 and CD8 positive cells with this MHC(peptide)/APC dextran construct.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 68

This is an example of how MHC multimers may be used for diagnosis of Tuberculosis (TB) in blood samples from humans infected with *Mycobacterium tuberculosis*.

In this example the MHC multimer used are MHC complexes coupled to fluorophor-labelled the multimerisation domain Streptavidin (SA), used for direct detection of TCR in flow cytometry. The antigen origin is TB, thus, immune monitoring of TB.

TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-B*14 heavy chain, human beta2microglobulin and peptide derived from regions in culture filtrate protein 10 (CFP10) antigen (Table Y) or a negative control peptide are generated by in vitro refolding, purified and biotinylated as described elsewhere herein. Biotinylated MHC-peptide complexes are then coupled SA labelled with APC. MHC-peptide complexes are added in an amount corresponding to a ratio of 5 MHC-peptide molecules per SA molecule. Then SA/APC carrying four MHC complexes are purified from free SA, free monomeric MHC complex, SA carrying three, two and one MHC complexes.

The following SA-MHC(peptide)/APC tetramers are made:
- 72. APC-SA coupled with HLA-B*14 in complex with beta2microglobulin and the peptide RADEEQQQAL derived from CFP10.
- 73. APC-SA coupled with HLA-B*44 in complex with beta2microglobulin and the non-sense peptide.

The binding of the above described MHC(peptide)/APC dextran can be used to determine the presence of CFP10 specific T cells in the blood from TB infected individuals by flow cytometry following a standard flow cytometry protocol.

Blood from a patient with TB is isolated and 100 ul of this blood is incubated with either of the four SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the SA-MHC(peptide)/APC tetramers 36 described above and thereby the presence of TB specific T cells will indicate that the patient are infected with *Mycobacterium tuberculosis*. Blood analysed with SA-MHC(peptide)/APC tetramers 37 should show no staining of CD3 and CD8 positive cells with this SA-MHC(peptide)/APC tetramer.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 69

This is an example of how MHC multimers may be used for diagnosis of Tuberculosis (TB) in blood samples from humans infected with *Mycobacterium tuberculosis*.

In this example the MHC multimer used are MHC complexes coupled to any fluorophor-labelled multimerisation as described elsewhere herein. The MHC multimers are used for direct detection of TCR in flow cytometry. The antigen origin is TB, thus, immune monitoring of TB. TB is caused by infection by *Mycobacterium tuberculosis*. During acute infection TB specific activated T cells will be present in increased amounts in an activated state compared to healthy individuals. The presences of an increased amount of activated TB specific T cells may thereby act as a surrogate marker for infection with *Mycobacterium tuberculosis*. MHC multimers carrying TB specific peptides is in this example used to detect the presence of TB specific T cells in the blood of patients infected with *Mycobacterium tuberculosis*.

Purified MHC-peptide complexes consisting of HLA-B*14 heavy chain, human beta2microglobulin and peptide derived from regions in culture filtrate protein 10 (CFP10) antigen (Table Y) or a negative control peptide are generated by in vitro refolding and purified or purified from antigen presenting cells. MHC-peptide complexes are then coupled to a multimerisation domain together with APC.

The following MHC(peptide)/APC multimers are made:
74. APC-multimerisation domain coupled with HLA-B*14 in complex with beta2microglobulin and the peptide RADEEQQQAL derived from CFP10.
75. APC-multimerisation domain coupled with HLA-B*14 in complex with beta2microglobulin and the non-sense peptide.

The binding of the above described MHC(peptide)/APC multimers can be used to determine the presence of CFP10 specific T cells in the blood from TB infected individuals by flow cytometry following a standard flow cytometry protocol.

Blood from a patient with TB is isolated and 100 ul of this blood is incubated with either of the four MHC(peptide)/APC multimers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the MHC(peptide)/APC multimers 38 described above and thereby the presence of TB specific T cells will indicate that the patient are infected with *Mycobacterium tuberculosis*. Blood analysed with MHC(peptide)/APC multimer 39 should show no staining of CD3 and CD8 positive cells with this SA-MHC(peptide)/APC multimer.

The sensitivity of the above described diagnostic test may be enhanced by addition of labeled antibodies specific for activation markers expressed in or on the surface of the TB specific T cells.

We conclude that the MHC(peptide)/APC dextran constructs can be used to detect the presence of TB specific T cells in the blood of patients infected with *Mycobacterium tuberculosis*.

Example 70

This is an example of how MHC multimers may be used for diagnosis of Lyme Disease in blood samples from humans infected with *Borrelia* bacteria.

In this example the MHC multimer used are MHC complexes coupled to fluorophor-labelled dextran (Dextramers). The dextramers are used for direct detection of TCR in flow Cytometry. The antigen origin is *Borrelia*, thus, immune monitoring of a *Borrelia* infection.

Lyme disease is caused by infection by *Borrelia* bacteria. During acute infection *Borrelia* specific activated T cells will be present in increased amounts in an activated state compared to healthy individuals. The presences of an increased amount of activated *Borrelia* specific T cells may thereby act as a surrogate marker for infection with *Borrelia* bacterium. MHC multimers carrying *borrelia* specific peptides is in this example used to detect the presence of *Borrelia* specific T cells in the blood of patients infected with *Borrelia*.

Purified MHC-peptide complexes consisting of HLA-A*0201 heavy chain, human beta2microglobulin and peptide derived from regions in Outer surface protein A (Table V) or Flagellin B (Table X) conserved among the three species *Borrelia Burgdorferi*, *Borrelia Garinii* and *Borrelia Afzelii* or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contains 3.7 SA molecule and 8.95 molecules APC. The final concentration of dextran is 3.8×10e-8 M. The following MHC(peptide)/APC dextran constructs are made:

76. APC-SA conjugated 270 kDa dextran coupled with HLA-A*0201 in complex with beta2microglobulin and the peptide ALIACKQNV derived from OspA.
77. APC-SA conjugated 270 kDa dextran coupled with HLA-A*0201 in complex with beta2microglobulin and the peptide FTKEDTIT derived from OspA.
78. APC-SA conjugated 270 kDa dextran coupled with HLA-A*0201 in complex with beta2microglobulin and the peptide SIQIEIEQL derived from Fla B
79. APC-SA conjugated 270 kDa dextran coupled with HLA-A*0201 in complex with beta2microglobulin and the peptide NLNEVEKVL derived from Fla B
80. APC-SA conjugated 270 kDa dextran coupled with HLA-A*0201 in complex with beta2microglobulin and the peptide SLAKIENAI derived from Fla B
81. APC-SA conjugated 270 kDa dextran coupled with HLA-A*0201 in complex with beta2microglobulin and the non-sense peptide GLAGDVSAV The binding of the above described MHC(peptide)/APC dextran is used to determine the presence of Osp A or Fla B specific T cells in the blood from *Borrelia* infected individuals by flow cytometry following a standard flow cytometry protocol.

Blood from a patient with Lyme disease is isolated and 100 ul of this blood is incubated with 10 μl of each of the MHC(peptide)/APC dextran constructs described above for 10 minutes in the dark at room temperature. 5 μl of each of each of the antibodies mouse-anti-human CD3/PB (clone UCHT1 from Dako), mouse-anti-human CD4/FITC (clone MT310 from Dako) and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 300×g and the supernatant removed. The washing step is repeated twice. The washed cells are resuspended in 400-500 μl PBS+1% BSA; pH=7.2 and analyzed on flowcytometer.

The presence of cells labeled with anti-CD3/PB, anti-CD8/PE and the MHC(peptide)/APC dextran constructs 1, 2, 3, 4 and 5 described above and thereby the presence of *Borrelia* specific T cells indicate that the patient are infected with *Borrelia* bacteria. Blood analysed with MHC(peptide)/APC dextran construct 6 show no staining of CD3 and CD8 positive cells with this MHC(peptide)/APC dextran construct.

The result is shown in FIG. 19.

The sensitivity of the above described diagnostic test may be enhanced by addition of labeled antibodies specific for activation markers expressed in or on the surface of the *Borrelia* specific T cells.

We conclude that the MHC(peptide)/APC dextran constructs can be used to detect the presence of *Borrelia* specific T cells in the blood of patients infected with *Borrelia*.

Example 71

This is an example of how MHC multimers may be used for diagnosis of Lyme Disease in blood samples from humans infected with *Borrelia* bacteria.

In this example the MHC multimer used are MHC complexes coupled to the fluorophor-labelled multimerisation domain Streptavidin (SA), used for direct detection of TCR in flow Cytometry. The antigen origin is *Borrelia*, thus, immune monitoring of a *Borrelia* infection. Lyme disease is caused by infection by *Borrelia* bacteria. During acute infection *Borrelia* specific activated T cells will be present in increased amounts in an activated state compared to healthy individuals. The presences of an increased amount of activated *Borrelia* specific T cells may thereby act as a surrogate marker for infection with *Borrelia* bacterium. MHC multimers carrying *borrelia* specific peptides is in this example used to detect the presence of *Borrelia* specific T cells in the blood of patients infected with *Borrelia*.

Purified MHC-peptide complexes consisting of HLA-A*0201 heavy chain, human beta2microglobulin and peptide derived from regions in Outer surface protein A (Table V) or Flagellin B (Table X) conserved among the three species *Borrelia Burgdorferi*, *Borrelia Garinii* and *Borrelia Afzelii* or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:

82. APC-SA coupled with HLA-A*0201 in complex with beta2microglobulin and the peptide ALIACKQNV derived from OspA.
83. APC-SA coupled with HLA-A*0201 in complex with beta2microglobulin and the peptide FTKEDTIT derived from OspA.
84. APC-SA coupled with HLA-A*0201 in complex with beta2microglobulin and the peptide SIQIEIEQL derived from Fla B.
85. APC-SA coupled with HLA-A*0201 in complex with beta2microglobulin and the peptide NLNEVEKVL derived from Fla B.
86. APC-SA coupled with HLA-A*0201 in complex with beta2microglobulin and the peptide SLAKIENAI derived from Fla B.
87. APC-SA coupled with HLA-A*0201 in complex with beta2microglobulin and the non-sense peptide GLAGDVSAV The binding of the above described MHC(peptide)/APC dextran can be used to determine the presence of Osp A or Fla B specific T cells in the blood from *Borrelia* infected individuals by flow cytometry following a standard flow cytometry protocol.

Blood from a patient with Lyme disease is isolated and 100 ul of this blood is incubated with either of the four SA-MHC(peptide)/APC tetramers described above for 10 minutes in the dark at room temperature. 5 μl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 μl PBS; pH=7.2 and analyzed on flowcytometer.

The presence of cells labeled with anti-CD3/PB, anti-CD8/PE and either of the SA-MHC(peptide)/APC tetramers 7, 8, 9, 10 or 11 described above and thereby the presence of *Borrelia* specific T cells will indicate that the patient are infected with *Borrelia* bacteria. Blood analysed with SA- MHC(peptide)/APC tetramers 12 should show no staining of CD3 and CD8 positive cells with this SA-MHC(peptide)/APC tetramer.

The sensitivity of the above described diagnostic test may be enhanced by addition of labeled antibodies specific for activation markers expressed in or on the surface of the *Borrelia* specific T cells.

We conclude that the APC-SA coupled MHC(peptide) constructs may be used to detect the presence of *Borrelia* specific T cells in the blood of patients infected with *Borrelia*.

Example 72

This is an example of how MHC multimers may be used for diagnosis of Lyme Disease in blood samples from humans infected with *Borrelia* bacteria.

In this example the MHC multimer used are MHC complexes coupled to any fluorophor-labelled multimerisation as described elsewhere herein. The MHC multimers are used for direct detection of TCR in flow cytometry. The antigen origin is *Borrelia*, thus, immune monitoring of a *Borrelia* infection.

Lyme disease is caused by infection by *Borrelia* bacteria. During acute infection *Borrelia* specific activated T cells will be present in increased amounts in an activated state compared to healthy individuals. The presences of an increased amount of activated *Borrelia* specific T cells may thereby act as a surrogate marker for infection with *Borrelia* bacterium. MHC multimers carrying *borrelia* specific peptides is in this example used to detect the presence of *Borrelia* specific T cells in the blood of patients infected with *Borrelia*.

Purified MHC-peptide complexes consisting of HLA-A*0201 heavy chain, human beta2microglobulin and peptide derived from regions in Outer surface protein A (Table V) or Flagellin B (Table X) conserved among the three species *Borrelia Burgdorferi*, *Borrelia Garinii* and *Borrelia Afzelii* or a negative control peptide were generated by in vitro refolding and purified or purified from antigen presenting cells. MHC-peptide complexes are then coupled to a multimerisation domain together with APC.

The following MHC(peptide)/APC multimers are made:
88. APC-multimerisation domain coupled with HLA-A*0201 in complex with beta2microglobulin and the peptide ALIACKQNV derived from OspA.
89. APC-multimerisation domain coupled with HLA-A*0201 in complex with beta2microglobulin and the peptide FTKEDTIT derived from OspA.
90. APC-multimerisation domain coupled with HLA-A*0201 in complex with beta2microglobulin and the peptide SIQIEIEQL derived from Fla B.
91. APC-multimerisation domain coupled with HLA-A*0201 in complex with beta2microglobulin and the peptide NLNEVEKVL derived from Fla B.
92. APC-multimerisation domain coupled with HLA-A*0201 in complex with beta2microglobulin and the peptide SLAKIENAI derived from Fla B.
93. APC-multimerisation domain coupled with HLA-A*0201 in complex with beta2microglobulin and the non-sense peptide GLAGDVSAV The binding of the above described MHC(peptide)/APC multimers can be used to determine the presence of Osp A or Fla B specific T cells in the blood from *Borrelia* infected individuals by flow cytometry following a standard flow cytometry protocol.

Blood from a patient with Lyme disease is isolated and 100 ul of this blood is incubated with either of the four MHC(peptide)/APC multimers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flow-cytometer.

The presence of cells labeled with anti-CD3/PB, anti-CD8/PE and either of the MHC(peptide)/APC multimers 13, 14, 15, 16 or 17 described above and thereby the presence of *Borrelia* specific T cells will indicate that the patient are infected with *Borrelia* bacteria.

Blood analysed with MHC(peptide)/APC multimer 18 should show no staining of CD3 and CD8 positive cells with this SA-MHC(peptide)/APC multimer.

The sensitivity of the above described diagnostic test may be enhanced by addition of labeled antibodies specific for activation markers expressed in or on the surface of the *Borrelia* specific T cells.

We conclude that the APC-multimerisation domain coupled MHC(peptide) constructs may be used to detect the presence of *Borrelia* specific T cells in the blood of patients infected with *Borrelia*.

Example 73

This is an example of how MHC multimers may be used for diagnosis of Lyme Disease in blood samples from humans infected with *Borrelia* bacteria.

In this example the MHC multimer used are MHC complexes coupled to fluorophor-labelled dextran (Dextramers). The dextramers are used for direct detection of TCR in flow Cytometry. The antigen origin is *Borrelia*, thus, immune monitoring of a *Borrelia* infection.

Lyme disease is caused by infection by *Borrelia* bacteria. During acute infection *Borrelia* specific activated T cells will be present in increased amounts in an activated state compared to healthy individuals. The presences of an increased amount of activated *Borrelia* specific T cells may thereby act as a surrogate marker for infection with *Borrelia* bacterium. MHC multimers carrying *borrelia* specific peptides is in this example used to detect the presence of *Borrelia* specific T cells in the blood of patients infected with *Borrelia*.

Purified MHC-peptide complexes consisting of HLA-A*0301 heavy chain, human beta2microglobulin and peptide derived from regions in Outer surface protein C (Table U) conserved among the three species *Borrelia Burgdorferi*, *Borrelia Garinii* and *Borrelia Afzelii* or a negative control peptide were generated by in vitro refolding, purified and biotinylated as described elsewhere herein. Biotinylated MHC-peptide complexes were then coupled to a 270 kDa dextran multimerization domain labelled with APC by interaction with streptavidin (SA) on the dextran multimerization domain. The dextran-APC-SA multimerization domain was generated as described elsewhere herein. MHC-peptide complexes were added in an amount corresponding to a ratio of three MHC-peptide molecules per SA molecule and each molecule dextran contained 3.7 SA molecule and 8.95 molecules APC. The final concentration of dextran was 3.8×10e-8 M. The following MHC(peptide)/APC dextran constructs were made:
94. APC-SA conjugated 270 kDa dextran coupled with HLA-A*0301 in complex with beta2microglobulin and the peptide TLITEKLSK derived from OspC.
95. APC-SA conjugated 270 kDa dextran coupled with HLA-A*0301 in complex with beta2microglobulin and the peptide ELANKAIGK derived from OspC.
96. APC-SA conjugated 270 kDa dextran coupled with HLA-A*0301 in complex with beta2microglobulin and the HIV peptide QVPLRPMTYK.

The binding of the above described MHC(peptide)/APC dextran can be used to determine the presence of Osp C specific T cells in the blood from *Borrelia* infected individuals by flow cytometry following a standard flow cytometry protocol.

Blood from a patient with Lyme disease is isolated and 100 ul of this blood is incubated with 10 μl of one of the MHC(peptide)/APC dextran constructs described above for 10 minutes in the dark at room temperature. 5 μl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 μl PBS; pH=7.2 and analyzed on flowcytometer.

The presence of cells labeled with anti-CD3/PB, anti-CD8/PE and either of the MHC(peptide)/APC dextran constructs 19 or 20 described above and thereby the presence of *Borrelia* specific T cells will indicate that the patient are infected with *Borrelia* bacteria. Blood analysed with MHC(peptide)/APC dextran construct 21 should show no staining of CD3 and CD8 positive cells with this MHC(peptide)/APC dextran construct.

The sensitivity of the above described diagnostic test may be enhanced by addition of labeled antibodies specific for activation markers expressed in or on the surface of the *Borrelia* specific T cells.

We conclude that the APC-SA conjugated 270 kDa dextran coupled MHC(peptide) constructs may be used to detect the presence of *Borrelia* specific T cells in the blood of patients infected with *Borrelia*.

Example 74

This is an example of how MHC multimers may be used for diagnosis of Lyme Disease in blood samples from humans infected with *Borrelia* bacteria.

In this example the MHC multimer used are MHC complexes coupled to the fluorophor-labelled multimerisation domain Streptavidin (SA), used for direct detection of TCR in flow Cytometry. The antigen origin is *Borrelia*, thus, immune monitoring of a *Borrelia* infection. Lyme disease is caused by infection by *Borrelia* bacteria. During acute infection *Borrelia* specific activated T cells will be present in increased amounts in an activated state compared to healthy individuals. The presences of an increased amount of activated *Borrelia* specific T cells may thereby act as a surrogate marker for infection with *Borrelia* bacterium. MHC multimers carrying *borrelia* specific peptides is in this example used to detect the presence of *Borrelia* specific T cells in the blood of patients infected with *Borrelia*.

Purified MHC-peptide complexes consisting of HLA-A*0301 heavy chain, human beta2microglobulin and peptide derived from regions in Outer surface protein C (Table U) conserved among the three species *Borrelia Burgdorferi*, *Borrelia Garinii* and *Borrelia Afzelii* or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:
97. APC-SA coupled with HLA-A*0301 in complex with beta2microglobulin and the peptide TLITEKLSK derived from OspC.
98. APC-SA coupled with HLA-A*0301 in complex with beta2microglobulin and the peptide ELANKAIGK derived from OspC.
99. APC-SA coupled with HLA-A*0201 in complex with beta2microglobulin and the HIV peptide QVPLRPMTYK.

The binding of the above described MHC(peptide)/APC dextran can be used to determine the presence of Osp C specific T cells in the blood from *Borrelia* infected individuals by flow cytometry following a standard flow cytometry protocol.

Blood from a patient with Lyme disease is isolated and 100 ul of this blood is incubated with either of the four SA-MHC(peptide)/APC tetramers described above for 10 minutes in the dark at room temperature. 5 μl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 μl PBS; pH=7.2 and analyzed on flowcytometer.

The presence of cells labeled with anti-CD3/PB, anti-CD8/PE and either of the SA-MHC(peptide)/APC tetramers 22 or 23 described above and thereby the presence of *Borrelia* specific T cells will indicate that the patient are infected with *Borrelia* bacteria. Blood analysed with SA-MHC(peptide)/APC tetramers 24 should show no staining of CD3 and CD8 positive cells with this SA-MHC(peptide)/APC tetramer.

The sensitivity of the above described diagnostic test may be enhanced by addition of labeled antibodies specific for activation markers expressed in or on the surface of the *Borrelia* specific T cells.

We conclude that the APC-SA coupled MHC(peptide) constructs may be used to detect the presence of *Borrelia* specific T cells in the blood of patients infected with *Borrelia*.

Example 75

This is an example of how MHC multimers may be used for diagnosis of Lyme Disease in blood samples from humans infected with *Borrelia* bacteria.

In this example the MHC multimer used are MHC complexes coupled to any fluorophor-labelled multimerisation as described elsewhere herein. The MHC multimers are used for direct detection of TCR in flow cytometry. The antigen origin is *Borrelia*, thus, immune monitoring of a *Borrelia* infection.

Lyme disease is caused by infection by *Borrelia* bacteria. During acute infection *Borrelia* specific activated T cells will be present in increased amounts in an activated state compared to healthy individuals. The presences of an increased amount of activated *Borrelia* specific T cells may thereby act as a surrogate marker for infection with *Borrelia* bacterium. MHC multimers carrying *borrelia* specific peptides is in this example used to detect the presence of *Borrelia* specific T cells in the blood of patients infected with *Borrelia*.

Purified MHC-peptide complexes consisting of HLA-A*0201 heavy chain, human beta2microglobulin and peptide derived from regions in Outer surface protein C (Table U) conserved among the three species *Borrelia Burgdorferi*, *Borrelia Garinii* and *Borrelia Afzelii* or a negative control peptide were generated by in vitro refolding and purified or purified from antigen presenting cells. MHC-peptide complexes are then coupled to a multimerisation domain together with APC.

The following MHC(peptide)/APC multimers are made:
100. APC-multimerisation domain coupled with HLA-A*0201 in complex with beta2microglobulin and the peptide TLITEKLSK derived from OspC.
101. APC-multimerisation domain coupled with HLA-A*0201 in complex with beta2microglobulin and the peptide ELANKAIG derived from OspC.
102. APC-multimerisation domain coupled with HLA-A*0201 in complex with beta2microglobulin and the HIV peptide QVPLRPMTYK.

The binding of the above described MHC(peptide)/APC multimers can be used to determine the presence of Osp C specific T cells in the blood from *Borrelia* infected individuals by flow cytometry following a standard flow cytometry protocol.

Blood from a patient with Lyme disease is isolated and 100 ul of this blood is incubated with either of the four MHC(peptide)/APC multimers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the MHC(peptide)/APC multimers 25 or 26 described above and thereby the presence of *Borrelia* specific T cells will indicate that the patient are infected with *Borrelia* bacteria. Blood analysed with MHC(peptide)/APC multimer 27 should show no staining of CD3 and CD8 positive cells with this SA-MHC(peptide)/APC multimer.

The sensitivity of the above described diagnostic test may be enhanced by addition of labeled antibodies specific for activation markers expressed in or on the surface of the *Borrelia* specific T cells.

We conclude that the APC-multimerisation domain coupled MHC(peptide) constructs may be used to detect the presence of *Borrelia* specific T cells in the blood of patients infected with *Borrelia*.

Example 76

This is an example of how MHC multimers may be used for detection of Cytomegalovirus (CMV) specific T cells in blood samples from humans infected with CMV.

In this example the MHC multimer used are MHC complexes coupled to fluorophor-labelled dextran (Dextramers). The dextramers are used for direct detection of TCR in flow cytometry. The antigen origin is CMV, thus, immune monitoring of CMV.

MHC multimers carrying CMV specific peptides is in this example used to detect the presence of CMV specific T cells in the blood of patients infected with Cytomegalovirus.

Purified MHC-peptide complexes consisting of HLA-A*0201 heavy chain, human beta2microglobulin and peptide derived from a region in CMV internal matrix protein pp65 or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contains 3.7 SA molecule and 8.95 molecules APC. The final concentration of dextran is 3.8×10e-8 M. The following MHC(peptide)/APC dextran constructs are made:
103. APC-SA conjugated 270 kDa dextran coupled with HLA-A*0201 in complex with beta2microglobulin and the peptide NLVPMVATV derived from CMV pp65.
104. APC-SA conjugated 270 kDa dextran coupled with HLA-A*0201 in complex with beta2microglobulin and the non-sense peptide GLAGDVSAV The binding of the above described MHC(peptide)/APC dextran is used to determine the presence of CMV pp65 specific T cells in the blood from CMV infected individuals by flow cytometry following a standard flow cytometry protocol.

Blood from a patient with CMV infection is isolated and 100 ul of this blood is incubated with 10 µl of the MHC (peptide)/APC dextran constructs described above for 10 minutes in the dark at room temperature. 5 µl of each of each of the antibodies mouse-anti-human CD3/PB (clone UCHT1 from Dako), and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 300×g and the supernatant removed. The washing step is repeated twice. The washed cells are resuspended in 400-500 µl PBS+1% BSA; pH=7.2 and analyzed on flowcytometer. The presence of cells labeled with anti-CD3/PB, anti-CD8/PE and the MHC(peptide)/APC dextran construct 1 described above and thereby the presence of CMV specific T cells indicate that the patient are infected with Cytomegalovirus. Blood analysed with MHC (peptide)/APC dextran construct 2 show no staining of CD3 and CD8 positive cells with this MHC(peptide)/APC dextran construct. The result is shown I FIG. 20

The sensitivity of the above described test may be enhanced by addition of labeled antibodies specific for activation markers expressed in or on the surface of the CMV specific T cells.

We conclude that the MHC(peptide)/APC dextran constructs can be used to detect the presence of CMV specific T cells in the blood of patients infected with Cytomegalovirus.

Example 77

This is an example of how MHC multimers may be used for detection of Cytomegalovirus (CMV) specific T cells in blood samples from humans infected with CMV.

In this example the MHC multimer used are MHC complexes coupled to fluorophor-labelled multimerisation domain Streptavidin (SA), used for direct detection of TCR in flow cytometry. The antigen origin is CMV, thus, immune monitoring of CMV.

MHC multimers carrying CMV specific peptides is in this example used to detect the presence of CMV specific T cells in the blood of patients infected with Cytomegalovirus.

Purified MHC-peptide complexes consisting of HLA-A*0201 heavy chain, human beta2microglobulin and peptide derived from a region in CMV internal matrix protein pp65 or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:
- 105. APC-SA coupled with HLA-A*0201 in complex with beta2microglobulin and the peptide NLVPMVATV derived from CMV pp65.
- 106. APC-SA coupled with HLA-A*0201 in complex with beta2microglobulin and the non-sense peptide GLAGDVSAV The binding of the above described MHC(peptide)/APC dextran can be used to determine the presence of CMV pp65 specific T cells in the blood from Cytomegalovirus infected individuals by flow cytometry following a standard flow cytometry protocol.

Blood from a patient with CMV is isolated and 100 ul of this blood is incubated with either of the SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the SA-MHC(peptide)/APC tetramers 3 described above and thereby the presence of CMV specific T cells will indicate that the patient are infected with Cytomegalovirus. Blood analysed with SA-MHC(peptide)/APC tetramers 4 should show no staining of CD3 and CD8 positive cells with this SA-MHC(peptide)/APC tetramer.

The sensitivity of the above described test may be enhanced by addition of labeled antibodies specific for activation markers expressed in or on the surface of the CMV specific T cells.

We conclude that the APC-SA coupled MHC(peptide) constructs may be used to detect the presence of CMV specific T cells in the blood of patients infected with Cytomegalovirus.

Example 78

This is an example of how MHC multimers may be used for detection of Cytomegalovirus (CMV) specific T cells in blood samples from humans infected with CMV.

In this example the MHC multimer used are MHC complexes coupled to any fluorophor-labelled multimerisation as described elsewhere herein. The MHC multimers are used for direct detection of TCR in flow cytometry. The antigen origin is CMV, thus, immune monitoring of CMV.

MHC multimers carrying CMV specific peptides is in this example used to detect the presence of CMV specific T cells in the blood of patients infected with Cytomegalovirus.

Purified MHC-peptide complexes consisting of HLA-A*0201 heavy chain, human beta2microglobulin and peptide derived a region in CMV internal matrix protein pp65 or a negative control peptide were generated by in vitro refolding and purified or purified from antigen presenting cells. MHC-peptide complexes are then coupled to a multimerisation domain together with APC.

The following MHC(peptide)/APC multimers are made:
- 107. APC-multimerisation domain coupled with HLA-A*0201 in complex with beta2microglobulin and the peptide NLVPMVATV derived from CMV pp65.
- 108. APC-multimerisation domain coupled with HLA-A*0201 in complex with beta2microglobulin and the non-sense peptide GLAGDVSAV.

The binding of the above described MHC(peptide)/APC multimers can be used to determine the presence of CMV pp65 specific T cells in the blood from CMV infected individuals by flow cytometry following a standard flow cytometry protocol.

Blood from a patient with CMV infection is isolated and 100 ul of this blood is incubated with either of the MHC (peptide)/APC multimers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and the MHC(peptide)/APC multimers 5 described above and thereby the presence of CMV specific T cells will indicate that the patient are infected with Cytomegalovirus. Blood analysed with MHC(peptide)/APC multimer 6 should show no staining of CD3 and CD8 positive cells with this SA-MHC(peptide)/APC multimer.

The sensitivity of the above described test may be enhanced by addition of labeled antibodies specific for activation markers expressed in or on the surface of the CMV specific T cells.

We conclude that the APC-multimerisation domain coupled MHC(peptide) constructs may be used to detect the presence of CMV specific T cells in the blood of patients infected with Cytomegalovirus.

Example 79

This is an example of how MHC multimers may be used for detection of Cytomegalovirus (CMV) specific T cells in blood samples from humans infected with CMV.

In this example the MHC multimer used are MHC complexes coupled to fluorophor-labelled dextran (Dextramers). The dextramers are used for direct detection of TCR in flow cytometry. The antigen origin is CMV, thus, immune monitoring of CMV.

MHC multimers carrying CMV specific peptides is in this example used to detect the presence of CMV specific T cells in the blood of patients infected with Cytomegalovirus.

Purified MHC-peptide complexes consisting of HLA-A*2402 heavy chain, human beta2microglobulin and peptide derived from a region in CMV internal matrix protein pp65 or a negative control peptide are generated by in vitro refolding, purified and biotinylated as described elsewhere herein. Biotinylated MHC-peptide complexes are then coupled to a 270 kDa dextran multimerization domain labelled with APC by interaction with streptavidin (SA) on the dextran multimerization domain. The dextran-APC-SA multimerization domain is generated as described elsewhere herein. MHC-peptide complexes are added in an amount corresponding to a ratio of three MHC-peptide molecules per SA molecule and each molecule dextran contains 3.7 SA molecule and 8.95 molecules APC. The final concentration of dextran is 3.8×10e-8 M. The following MHC(peptide)/APC dextran constructs are made:

109. APC-SA conjugated 270 kDa dextran coupled with HLA-A*2402 in complex with beta2microglobulin and the peptide QYDPVAALF derived from CMV pp65.
110. APC-SA conjugated 270 kDa dextran coupled with HLA-A*2402 in complex with beta2microglobulin and the peptide VYALPLKML derived from CMV pp65.
111. APC-SA conjugated 270 kDa dextran coupled with HLA-A*2402 in complex with beta2microglobulin and the non-sense peptide.

The binding of the above described MHC(peptide)/APC dextran is used to determine the presence of CMV pp65 specific T cells in the blood from CMV infected individuals by flow cytometry following a standard flow cytometry protocol.

Blood from a patient with CMV infection is isolated and 100 ul of this blood is incubated with 10 µl of the MHC (peptide)/APC dextran constructs described above for 10 minutes in the dark at room temperature. 5 µl of each of each of the antibodies mouse-anti-human CD3/PB (clone UCHT1 from Dako), and mouse-anti-human CD8/PE (clone DK25 from Dako) are added and the incubation continues for another 20 minutes at 4° C. in the dark. The samples are then washed by adding 2 ml PBS; pH=7.2 followed by centrifugation for 5 minutes at 300×g and the supernatant removed. The washing step is repeated. The washed cells are resuspended in 400-500 µl PBS+1% BSA; pH=7.2 and analyzed on flowcytometer.

The presence of cells labeled with anti-CD3/PB, anti-CD8/PE and the MHC(peptide)/APC dextran constructs 7 or 8 described above and thereby the presence of CMV specific T cells indicate that the patient are infected with Cytomegalovirus. Blood analysed with MHC(peptide)/APC dextran construct 9 show no staining of CD3 and CD8 positive cells with this MHC(peptide)/APC dextran construct.

The sensitivity of the above described test may be enhanced by addition of labeled antibodies specific for activation markers expressed in or on the surface of the CMV specific T cells.

We conclude that the MHC(peptide)/APC dextran constructs can be used to detect the presence of CMV specific T cells in the blood of patients infected with Cytomegalovirus.

Example 80

This is an example of how MHC multimers may be used for detection of Cytomegalovirus (CMV) specific T cells in blood samples from humans infected with CMV.

In this example the MHC multimer used are MHC complexes coupled to fluorophor-labelled multimerisation domain Streptavidin (SA), used for direct detection of TCR in flow cytometry.

The antigen origin is CMV, thus, immune monitoring of CMV.

MHC multimers carrying CMV specific peptides is in this example used to detect the presence of CMV specific T cells in the blood of patients infected with Cytomegalovirus.

Purified MHC-peptide complexes consisting of HLA-A*2402 heavy chain, human beta2microglobulin and peptide derived from a region in CMV internal matrix protein pp65 or a negative control peptide were generated by in vitro refolding, purified and biotinylated as described elsewhere herein. Biotinylated MHC-peptide complexes are then coupled SA labelled with APC. MHC-peptide complexes were added in an amount corresponding to a ratio of 5 MHC-peptide molecules per SA molecule. Then SA/APC carrying four MHC complexes were purified from free SA, free monomeric MHC complex, SA carrying three, two and one MHC complexes.

The following SA-MHC(peptide)/APC tetramers are made:

112. APC-SA coupled with HLA-A*2402 in complex with beta2microglobulin and the peptide QYDPVAALF derived from CMV pp65.
113. APC-SA coupled with HLA-A*2402 in complex with beta2microglobulin and the peptide VYALPLKML derived from CMV pp65.
114. APC-SA coupled with HLA-A*2402 in complex with beta2microglobulin and the non-sense peptide.

The binding of the above described MHC(peptide)/APC dextran can be used to determine the presence of CMV pp65 specific T cells in the blood from Cytomegalovirus infected individuals by flow cytometry following a standard flow cytometry protocol.

Blood from a patient with CMV is isolated and 100 ul of this blood is incubated with either of the SA-MHC(peptide)/APC tetramers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the SA-MHC(peptide)/APC tetramers 10 or 11 described above and thereby the presence of CMV specific T cells will indicate that the patient are infected with Cytomegalovirus. Blood analysed with SA-MHC(peptide)/APC tetramers 12 should show no staining of CD3 and CD8 positive cells with this SA-MHC(peptide)/APC tetramer.

The sensitivity of the above described test may be enhanced by addition of labeled antibodies specific for activation markers expressed in or on the surface of the CMV specific T cells.

We conclude that the APC-SA coupled MHC(peptide) constructs may be used to detect the presence of CMV specific T cells in the blood of patients infected with Cytomegalovirus.

Example 81

This is an example of how MHC multimers may be used for detection of Cytomegalovirus (CMV) specific T cells in blood samples from humans infected with CMV.

In this example the MHC multimer used are MHC complexes coupled to any fluorophor-labelled multimerisation as described elsewhere herein. The MHC multimers are used for direct detection of TCR in flow cytometry. The antigen origin is CMV, thus, immune monitoring of CMV.

MHC multimers carrying CMV specific peptides is in this example used to detect the presence of CMV specific T cells in the blood of patients infected with Cytomegalovirus.

Purified MHC-peptide complexes consisting of HLA-A*2402 heavy chain, human beta2microglobulin and peptide derived a region in CMV internal matrix protein pp65 or a negative control peptide were generated by in vitro refolding and purified or purified from antigen presenting cells. MHC-peptide complexes are then coupled to a multimerisation domain together with APC.

The following MHC(peptide)/APC multimers are made:
115. APC-multimerisation domain coupled with HLA-A*2402 in complex with beta2microglobulin and the peptide QYDPVAALF derived from CMV pp65.
116. APC-multimerisation domain coupled with HLA-A*2402 in complex with beta2microglobulin and the peptide VYALPLKML derived from CMV pp65.
117. APC-multimerisation domain coupled with HLA-A*2402 in complex with beta2microglobulin and the non-sense peptide.

The binding of the above described MHC(peptide)/APC multimers can be used to determine the presence of CMV pp65 specific T cells in the blood from CMV infected individuals by flow cytometry following a standard flow cytometry protocol.

Blood from a patient with CMV infection is isolated and 100 ul of this blood is incubated with either of the MHC (peptide)/APC multimers described above for 10 minutes in the dark at room temperature. 5 µl of each of each of the antibodies mouse-anti-human CD3/PB (clone UCHT1 from Dako) and mouse-anti-human CD8/PE (clone DK25 from Dako) are added and the incubation continued for another 20 minutes at 4° C. in the dark. The samples are then washed by adding 2 ml PBS; pH=7.2 followed by centrifugation for 5 minutes at 200×g and the supernatant removed. The washing step is repeated. The washed cells are resuspended in 400-500 µl PBS; pH=7.2 and analyzed on flowcytometer.

The presence of cells labeled with anti-CD3/PB, anti-CD8/PE and either of the MHC(peptide)/APC multimers 13 or 14 described above and thereby the presence of CMV specific T cells will indicate that the patient are infected with Cytomegalovirus. Blood analysed with MHC(peptide)/APC multimer 15 should show no staining of CD3 and CD8 positive cells with this SA-MHC(peptide)/APC multimer.

The sensitivity of the above described test may be enhanced by addition of labeled antibodies specific for activation markers expressed in or on the surface of the CMV specific T cells.

We conclude that the APC-multimerisation domain coupled MHC(peptide) constructs may be used to detect the presence of CMV specific T cells in the blood of patients infected with Cytomegalovirus.

Example 82

This is an example of measurement of antigen reactive T-Cells by IFN-γ capture in blood samples by ELISPOT.

This is an example of indirect detection of TCR, where individual cells are immobilized and measured by a chromogen assay.

The example provides a sensitive assay for the detection of T-cells reactive to an antigen by detecting a soluble factor whose secretion is induced by stimulation of the T-cell by the antigen.

A summary flow chart of the method is shown in FIG. 20. In brief, peripheral blood is diluted threefold in Dulbecco's phosphate buffered saline (DPBS), underlain with 15 ml of Ficoll (Pharmacia Ficoll-Paque #17-0840-02, Piscataway, N.J.) per 40 ml diluted blood in a 50 ml polypropylene centrifuge tube, and spun at 2000 RPM for 20 minutes in a Beckman CS-6R centrifuge (Beckman Inc., Palo Alto, Calif.). The buffy layer at the DPBS/Ficoll interface is removed, washed twice with DPBS and once with human tissue culture medium (hTCM: αMEM+5% heat inactivated human AB serum (Ultraserum, BioWhittaker, Walkersville, Md.), penicillin/streptomycin, 1-glutamine) at low RCF to remove platelets. Sixty percent of the PBMCs are resuspended in freezing medium (10% dimethyl sulfoxide (Sigma Chemical Co., St. Louis, Mo.), 90% fetal bovine serum to a concentration of $5 \times 10^6$ cells/ml, frozen in a programmable Cryo-Med (New Baltimore, Mich.) cell freezer, and stored under liquid nitrogen until needed.

The purified PBMCs are plated at $2 \times 10^5$ cells/well at a volume of 0.1 ml in 96 well Costar cell culture plates. An equal volume of antigen at 10 µg/ml is added to triplicate or sextuplet sets of wells and the plate is incubated in a 37° C., 5% $CO_2$ incubator. On day five, 10 µl/well of 100 U/ml stock recombinant IL-2 (Advanced Biotechnologies Inc., Columbia, Md.) is added to each well. On day 8, frozen PBMCs are thawed, washed in DPBS+0.5% bovine serum albumin (BSA) to remove DMSO, resuspended to a concentration of $4 \times 10^6$ cells/ml in hTCM, and γ-irradiated (3,000 RADS). Fifty microliters/well are dispensed along with 50 µl of the appropriate antigen at a stock concentration of 40 µl/ml to give a final antigen concentration of 10 µg/ml.

To prepare a capture plate, IFN-γ capture antibody (monoclonal mouse anti-human IFN-g, Endogen #M700A, Cambridge, Mass.) is diluted to 10 µg/ml in sterile 0.1 M $Na(CO_3)_2$ pH 8.2 buffer, aliquotted at 50 µl/well in flat bottomed 96 well sterile microtiter plates (Corning Costar Corp.), and incubated at 4° C. for a minimum of 24 hours. Prior to use, excess antibody is removed and wells are washed twice with dPBS+1% Tween 20 (PBST). To block further nonspecific protein binding, plates are incubated with 250 µl/well of PBS+5% BSA at room temperature for 1 hour. After discarding the blocking solution, wells are washed once with PBST (0.1% Tween), followed by hTCM in preparation for the antigen stimulated cells.

On day 9 of the assay, twenty four hours after the second antigen stimulation, the stimulation plate is spun for 5 minutes at 1500 RPM in a Beckman CS-6R centrifuge and 90 µl of supernatant is carefully removed from each well with a micropipette. The pelleted cells are resuspended in 100 µl of hTCM, pooled in sterile tubes (Corning Costar corp sterile ClusterTAb #4411, Cambridge, Mass.), mixed and transferred into an equal number of wells of an anti IFN-γ capture plate. Capture plates are incubated undisturbed at 37° C. for 16-20 hours. At the end of the IFN-γ secretion phase, the cells are discarded and the plates are washed three times with 0.1% PBST. A final aliquot of PBST is added to the wells for ten minutes, removed, and 100 μl of a 1:500 dilution of rabbit anti-human IFN-γ polyclonal antibody (Endogen #P700, Cambridge, Mass.) in PBST+1% BSA is added to each well for 3.5 hours at room temperature with gentle rocking. Unbound anti-IFN-γ polyclonal antibody is removed by three washes with PBST, followed by a wash with 250 μl of 1×Tris-buffered saline+0.05% Tween 20 (TBST). Next, a 100 μl aliquot of 1:5000 alkaline phosphatase-conjugated mouse anti-rabbit polyclonal antibody (Jackson Immunological #211-055-109, West Grove, Pa.) diluted in TBST is added to each well and incubated at room temperature for 1.5-2 hours with gentle rocking. Excess enzyme-conjugated antibody is removed by three washes with PBST and two washes with alkaline phosphatase buffer (APB=0.1 M NaCl, 0.05 M MgCl.sub.2, 0.1 M Tris HCl, pH 9.5) followed by addition of the substrate mix of p-Toluidine salt and nitroblue tetrazolium chloride (BCIP/NBT, GIBCO BRL #18280-016, Gaithersburg, Md.). To stop the calorimetric reaction, plates were washed three times in $dH_2O$, inverted to minimize deposition of dust in the wells, and dried overnight at 28° C. in a dust free drying oven.

Images of the spots corresponding to the lymphokine secreted by individual antigen-stimulated T cells are captured with a CCD video camera and the image is analyzed by NIH image software. Captured images are enhanced using the Look Up Table which contrasts the images. Thresholding is then applied to every image and a wand tool is used to highlight the border to effectively subtract the edge of the well so that background counts won't be high and artificial. Density slicing over a narrow range is then used to highlight the spots produced from secreting cells. Pixel limits are set to subtract out small debris and large particles, and the number of spots falling within the prescribed pixel range are counted by the software program. Totals from each well are then manually recorded for future analysis. Alternatively, spots can be counted by other commercially available or customized software applications, or may be quantitated manually by a technician using standard light microscopy. Spots can also be counted manually under a light microscope.

We conclude that the protocol detailed above can be used for the enumeration of single IFN-γ secreting T cells.

Example 83

This is an example of measurement of antigen reactive T-Cells by IFN-γ capture in blood samples from Multiple Sclerosis (MS) patients by ELISPOT.

This is an example of indirect detection of TCR, where individual cells are immobilized and measured by a chromogen assay. The antigenic peptide origin is MS, thus, immune monitoring of MS.

The example provides a sensitive assay for the detection of T-cells reactive to the antigen Myelin Basic Protein (MBP), by detecting a soluble factor whose secretion is induced by stimulation of the T-cell by the antigen.

This example is similar to the experiment above. PBMCs from Multiple Sclerosis patients are isolated, prepared and stored as described in the example above.

The purified PBMCs are plated at $2\times10^5$ cells/well at a volume of 0.1 ml in 96 well Costar cell culture plates. An equal volume of antigen, MBP 83-102 (YDENPVVHFF KNIVTPRTPP) or 144-163 (VDAQGTLSKIFKLGGRD-SRS), at 10 μg/ml is added to triplicate or sextuplet sets of wells and the plate is incubated in a 37° C., 5% $CO_2$ incubator. On day five, 10 μl/well of 100 U/ml stock recombinant IL-2 is added to each well. On day 8, frozen PBMCs are thawed, washed in DPBS+0.5% BSA to remove DMSO, resuspended to a concentration of $4\times10^6$ cells/ml in hTCM, and γ-irradiated (3,000 RADS). 50 μl/well are dispensed along with 50 μl of the appropriate antigen at a stock concentration of 40 μl/ml to give a final antigen concentration of 10 μg/ml.

A capture plate with IFN-γ antibody is prepared, washed and blocked as described in the example above.

On day 9 of the assay, twenty four hours after the second antigen stimulation, the stimulation plate is spun for 5 minutes at 1500 RPM and 90 μl of supernatant is carefully removed from each well with a micropipette. The pelleted cells are resuspended in 100 μl of hTCM, pooled in sterile tubes, mixed and transferred into an equal number of wells of an anti IFN-γ capture plate. Capture plates are incubated undisturbed at 37° C. for 16-20 hours. At the end of the IFN-γ secretion phase, the cells are discarded and the plates are washed three times with 0.1% PBST. A final aliquot of PBST is added to the wells for ten minutes, removed, and 100 μl of a 1:500 dilution of rabbit anti-human IFN-γ polyclonal antibody in PBST+1% BSA is added to each well for 3.5 hours at room temperature with gentle rocking. Unbound anti-IFN-γ polyclonal antibody is removed by three washes with PBST, followed by a wash with 250 μl of 1×Tris-buffered saline+0.05% Tween 20 (TBST). Next, a 100 μl aliquot of 1:5000 alkaline phosphatase-conjugated mouse anti-rabbit polyclonal antibody diluted in TBST is added to each well and incubated at room temperature for 1.5-2 hours with gentle rocking. Excess enzyme-conjugated antibody is removed by three washes with PBST and two washes with alkaline phosphatase followed by addition of the substrate mix of p-Toluidine salt and nitroblue tetrazolium chloride. To stop the calorimetric reaction, plates were washed three times in $dH_2O$, inverted to minimize deposition of dust in the wells, and dried overnight at 28° C. in a dust free drying oven.

Images of the spots corresponding to the lymphokine secreted by individual antigen-stimulated T cells are captured with a CCD video camera and the image is analyzed as described in the example above We conclude that the experiment detailed above can be used for the enumeration of single IFN-γ secreting T cells in blood from Multiple Sclerosis patients.

Example 84

This is an example of measurement of antigen reactive T-Cells by IFN-γ capture in blood samples from Multiple Sclerosis (MS) patients by ELISPOT.

This is an example of indirect detection of TCR, where individual cells are immobilized and measured by a chromogen assay. Antigenic peptide origin is MS, thus, immune monitoring of MS.

The example provides a sensitive assay for the detection of T-cells reactive to the antigen Myelin Oligodendrocyte Glycoprotein (MOG), by detecting a soluble factor whose secretion is induced by stimulation of the T-cell by the antigen.

This example is similar to the experiment above PBMCs from Multiple Sclerosis patients are isolated, prepared and stored as described in the example above.

The purified PBMCs are plated at $2\times10^5$ cells/well at a volume of 0.1 ml in 96 well Costar cell culture plates. An equal volume of antigen, MOG 1-20 (GQFRVIGPRHPI- RALVGDEV) or 41-60 (RPPFSRVVHLYRNGKDQDGD), at 10 μg/ml is added to triplicate or sextuplet sets of wells and the plate is incubated in a 37° C., 5% $CO_2$ incubator. On day five, 10 μl/well of 100 U/ml stock recombinant IL-2 is added to each well. On day 8, frozen PBMCs are thawed, washed in DPBS+0.5% BSA to remove DMSO, resuspended to a concentration of $4 \times 10^6$ cells/ml in hTCM, and γ-irradiated (3,000 RADS). 50 μl/well are dispensed along with 50 μl of the appropriate antigen at a stock concentration of 40 μl/ml to give a final antigen concentration of 10 μg/ml.

A capture plate with IFN-γ antibody is prepared, washed and blocked as described in the example above.

On day 9 of the assay, twenty four hours after the second antigen stimulation, the stimulation plate is spun for 5 minutes at 1500 RPM and 90 μl of supernatant is carefully removed from each well with a micropipette. The pelleted cells are resuspended in 100 μl of hTCM, pooled in sterile tubes, mixed and transferred into an equal number of wells of an anti IFN-γ capture plate. Capture plates are incubated undisturbed at 37° C. for 16-20 hours. At the end of the IFN-γ secretion phase, the cells are discarded and the plates are washed three times with 0.1% PBST. A final aliquot of PBST is added to the wells for ten minutes, removed, and 100 μl of a 1:500 dilution of rabbit anti-human IFN-γ polyclonal antibody in PBST+1% BSA is added to each well for 3.5 hours at room temperature with gentle rocking. Unbound anti-IFN-γ polyclonal antibody is removed by three washes with PBST, followed by a wash with 250 μl of 1×Tris-buffered saline+0.05% Tween 20 (TBST). Next, a 100 μl aliquot of 1:5000 alkaline phosphatase-conjugated mouse anti-rabbit polyclonal antibody diluted in TBST is added to each well and incubated at room temperature for 1.5-2 hours with gentle rocking. Excess enzyme-conjugated antibody is removed by three washes with PBST and two washes with alkaline phosphatase followed by addition of the substrate mix of p-Toluidine salt and nitroblue tetrazolium chloride. To stop the calorimetric reaction, plates were washed three times in $dH_2O$, inverted to minimize deposition of dust in the wells, and dried overnight at 28° C. in a dust free drying oven.

Images of the spots corresponding to the lymphokine secreted by individual antigen-stimulated T cells are captured with a CCD video camera and the image is analyzed as described in the example above We conclude that the experiment detailed above can be used for the enumeration of single IFN-δ secreting T cells in blood from Multiple Sclerosis patients.

Example 85

This is an example of measurement of antigen reactive T-Cells by IFN-γ capture in blood samples from Rheumatoid Arthritis (RA) patients by ELISPOT.

This is an example of indirect detection of TCR, where individual cells are immobilized and measured by a chromogen assay. Antigenic peptide origin is RA, thus, immune monitoring of RA.

The example provides a sensitive assay for the detection of T-cells reactive to the antigen type II collagen (CII) 261-273, by detecting a soluble factor whose secretion is induced by stimulation of the T-cell by the antigen.

This example is similar to the experiment above. PBMCs from Rheumatoid Arthritis patients are isolated, prepared and stored as described in the example above.

The purified PBMCs are plated at $2 \times 10^5$ cells/well at a volume of 0.1 ml in 96 well Costar cell culture plates. An equal volume of antigen, CII 261-273 (AGFKGEQGPK-GEP), at 10 μg/ml is added to triplicate or sextuplet sets of wells and the plate is incubated in a 37° C., 5% $CO_2$ incubator. On day five, 10 μl/well of 100 U/ml stock recombinant IL-2 is added to each well. On day 8, frozen PBMCs are thawed, washed in DPBS+0.5% BSA to remove DMSO, resuspended to a concentration of $4 \times 10^6$ cells/ml in hTCM, and γ-irradiated (3,000 RADS). 50 μl/well are dispensed along with 50 μl of the appropriate antigen at a stock concentration of 40 μl/ml to give a final antigen concentration of 10 μg/ml.

A capture plate with IFN-γ antibody is prepared, washed and blocked as described in the example above.

On day 9 of the assay, twenty four hours after the second antigen stimulation, the stimulation plate is spun for 5 minutes at 1500 RPM and 90 μl of supernatant is carefully removed from each well with a micropipette. The pelleted cells are resuspended in 100 μl of hTCM, pooled in sterile tubes, mixed and transferred into an equal number of wells of an anti IFN-γ capture plate. Capture plates are incubated undisturbed at 37° C. for 16-20 hours. At the end of the IFN-γ secretion phase, the cells are discarded and the plates are washed three times with 0.1% PBST. A final aliquot of PBST is added to the wells for ten minutes, removed, and 100 μl of a 1:500 dilution of rabbit anti-human IFN-γ polyclonal antibody in PBST+1% BSA is added to each well for 3.5 hours at room temperature with gentle rocking. Unbound anti-IFN-γ polyclonal antibody is removed by three washes with PBST, followed by a wash with 250 μl of 1×Tris-buffered saline+0.05% Tween 20 (TBST). Next, a 100 μl aliquot of 1:5000 alkaline phosphatase-conjugated mouse anti-rabbit polyclonal antibody diluted in TBST is added to each well and incubated at room temperature for 1.5-2 hours with gentle rocking. Excess enzyme-conjugated antibody is removed by three washes with PBST and two washes with alkaline phosphatase followed by addition of the substrate mix of p-Toluidine salt and nitroblue tetrazolium chloride. To stop the calorimetric reaction, plates were washed three times in $dH_2O$, inverted to minimize deposition of dust in the wells, and dried overnight at 28° C. in a dust free drying oven.

Images of the spots corresponding to the lymphokine secreted by individual antigen-stimulated T cells are captured with a CCD video camera and the image is analyzed as described in the example above We conclude that the experiment detailed above can be used for the enumeration of single IFN-γ secreting T cells in blood from Rheumatoid Arthritis patients.'

Example 86

This is an example of measurement of antigen reactive T-Cells by IFN-γ capture in blood samples from Melanoma patients by ELISPOT.

This is an example of indirect detection of TCR, where individual cells are immobilized and measured by a chromogen assay. The antigenic peptide origin is Melanoma, thus, immune monitoring of cancer.

The example provides a sensitive assay for the detection of T-cells reactive to the antigen MELAN-A/MART-1 27-35, by detecting a soluble factor whose secretion is induced by stimulation of the T-cell by the antigen.

This example is similar to the experiment above. PBMCs from Melanoma patients are isolated, prepared and stored as described in the example above.

The purified PBMCs are plated at $2 \times 10^5$ cells/well at a volume of 0.1 ml in 96 well Costar cell culture plates. An equal volume of antigen, MELAN-A/MART-1 27-35 (AA- GIGILTV), at 10 µg/ml is added to triplicate or sextuplet sets of wells and the plate is incubated in a 37° C., 5% $CO_2$ incubator. On day five, 10 µl/well of 100 U/ml stock recombinant IL-2 is added to each well. On day 8, frozen PBMCs are thawed, washed in DPBS+0.5% BSA to remove DMSO, resuspended to a concentration of $4\times10^6$ cells/ml in hTCM, and γ-irradiated (3,000 RADS). 50 µl/well are dispensed along with 50 µl of the appropriate antigen at a stock concentration of 40 µl/ml to give a final antigen concentration of 10 µg/ml.

A capture plate with IFN-γ antibody is prepared, washed and blocked as described in the example above.

On day 9 of the assay, twenty four hours after the second antigen stimulation, the stimulation plate is spun for 5 minutes at 1500 RPM and 90 µl of supernatant is carefully removed from each well with a micropipette. The pelleted cells are resuspended in 100 µl of hTCM, pooled in sterile tubes, mixed and transferred into an equal number of wells of an anti IFN-γ capture plate. Capture plates are incubated undisturbed at 37° C. for 16-20 hours. At the end of the IFN-γ secretion phase, the cells are discarded and the plates are washed three times with 0.1% PBST. A final aliquot of PBST is added to the wells for ten minutes, removed, and 100 µl of a 1:500 dilution of rabbit anti-human IFN-γ polyclonal antibody in PBST+1% BSA is added to each well for 3.5 hours at room temperature with gentle rocking. Unbound anti-IFN-γ polyclonal antibody is removed by three washes with PBST, followed by a wash with 250 µl of 1×Tris-buffered saline+0.05% Tween 20 (TBST). Next, a 100 µl aliquot of 1:5000 alkaline phosphatase-conjugated mouse anti-rabbit polyclonal antibody diluted in TBST is added to each well and incubated at room temperature for 1.5-2 hours with gentle rocking. Excess enzyme-conjugated antibody is removed by three washes with PBST and two washes with alkaline phosphatase followed by addition of the substrate mix of p-Toluidine salt and nitroblue tetrazolium chloride. To stop the calorimetric reaction, plates were washed three times in $dH_2O$, inverted to minimize deposition of dust in the wells, and dried overnight at 28° C. in a dust free drying oven.

Images of the spots corresponding to the lymphokine secreted by individual antigen-stimulated T cells are captured with a CCD video camera and the image is analyzed as described in the example above We conclude that the experiment detailed above can be used for the enumeration of single IFN-γ secreting T cells in blood from Melanoma patients.

Example 87

This is an example of measurement of antigen reactive T-Cells by IFN-γ capture in blood samples by ELISPOT.

This is an example of indirect detection of TCR, where individual cells are immobilized and measured by a chromogen assay. The antigenic peptide origin is a library of antigens.

The example provides a sensitive assay for the detection of T-cells reactive to the antigen of a library generated as described in example 42, by detecting a soluble factor whose secretion is induced by stimulation of the T-cell by the antigen.

This example is similar to the experiment above. PMBC are isolated, prepared and stored as described in the example above.

The purified PBMCs are plated at $2\times10^5$ cells/well at a volume of 0.1 ml in 96 well Costar cell culture plates. An equal volume of antigens from the library, at 10 µg/ml is added to triplicate or sextuplet sets of wells and the plate is incubated in a 37° C., 5% $CO_2$ incubator. On day five, 10 µl/well of 100 U/ml stock recombinant IL-2 is added to each well. On day 8, frozen PBMCs are thawed, washed in DPBS+0.5% BSA to remove DMSO, resuspended to a concentration of $4\times10^6$ cells/ml in hTCM, and γ-irradiated (3,000 RADS). 50 µl/well are dispensed along with 50 µl of the appropriate antigen at a stock concentration of 40 µl/ml to give a final antigen concentration of 10 µg/ml.

A capture plate with IFN-γ antibody is prepared, washed and blocked as described in the example above.

On day 9 of the assay, twenty four hours after the second antigen stimulation, the stimulation plate is spun for 5 minutes at 1500 RPM and 90 µl of supernatant is carefully removed from each well with a micropipette. The pelleted cells are resuspended in 100 µl of hTCM, pooled in sterile tubes, mixed and transferred into an equal number of wells of an anti IFN-γ capture plate. Capture plates are incubated undisturbed at 37° C. for 16-20 hours. At the end of the IFN-γ secretion phase, the cells are discarded and the plates are washed three times with 0.1% PBST. A final aliquot of PBST is added to the wells for ten minutes, removed, and 100 µl of a 1:500 dilution of rabbit anti-human IFN-γ polyclonal antibody in PBST+1% BSA is added to each well for 3.5 hours at room temperature with gentle rocking. Unbound anti-IFN-γ polyclonal antibody is removed by three washes with PBST, followed by a wash with 250 µl of 1×Tris-buffered saline+0.05% Tween 20 (TBST). Next, a 100 µl aliquot of 1:5000 alkaline phosphatase-conjugated mouse anti-rabbit polyclonal antibody diluted in TBST is added to each well and incubated at room temperature for 1.5-2 hours with gentle rocking. Excess enzyme-conjugated antibody is removed by three washes with PBST and two washes with alkaline phosphatase followed by addition of the substrate mix of p-Toluidine salt and nitroblue tetrazolium chloride. To stop the calorimetric reaction, plates were washed three times in $dH_2O$, inverted to minimize deposition of dust in the wells, and dried overnight at 28° C. in a dust free drying oven.

Images of the spots corresponding to the lymphokine secreted by individual antigen-stimulated T cells are captured with a CCD video camera and the image is analyzed as described in the example above We conclude that the experiment detailed above can be used for the enumeration of single IFN-γ secreting T cells in blood.

Example 88

This is an example of how antigen specific T-cells can be detected using a direct detection method detecting T cell immobilized in solid tissue. In this example MHC dextramers are used to detect antigen specific T cells on frozen tissue sections using enzymatic chromogenic precipitation detection.

Equilibrate the cryosection tissue (e.g. section of spleen from transgenic mice) to −20° C. in the cryostate. Cut 5 µm sections and then dry sections on slides at room temperature. Store slides frozen until use at −20° C.

Equilibrate frozen sections to room temperature. Fix with acetone for 5 min.

Immediately after fixation transfer slides to TBS buffer (50 mM Tris-HCL pH 7.6, 150 mM NaCl) for 10 min.

Incubate slides with FITC-conjugated MHC-dextramers at appropriate dilution (1:40-1:80) and incubate for 30 min at room temperature. Other dilution ranges, as well as incubation time and temperature, may be desirable.

Decant solution and gently tap slides against filter paper, submerge in TBS buffer.

Decant and wash for 10 min in TBS buffer.

Incubate with rabbit polyclonal anti-FITC antibody (Dako P5100) at 1:100 dilution in TBS at room temperature for 30 min.

Repeat step 5 and 6.

Incubate with Envision anti-Rabbit HRP (Dako K4003) at room temperature for 30 min. Other visualization systems may be used.

Repeat step 5 and 6.

Develop with DAB+ (Dako K3468) in fume hood for 10 min. Other substrates may be used Rinse slides in tap-water for 5 min.

Counterstain with hematoxylin (Dako 53309) for 2 min.

Repeat step 12, mount slides.

The slides stained with MHC-Dextramers can now be evaluated by microscopy.

Example 89

This is an example of how antigen specific T-cells can be detected using a direct detection method detecting T cell immobilized in solid tissue. In this example MHC dextramers are used to detect antigen specific T cells on paraffin embedded tissue sections using enzymatic chromogenic precipitation detection.

Formaldehyde fixed paraffin-embedded tissue are cut in section and mounted on the glass slice, for subsequent IHC staining with MHC-dextramers. Tissue fixed and prepared according to other protocols may be used as well. E.g. fresh tissue, lightly fixed tissue section (e.g. tissue fixed in 2% formaldehyde) or formalin-fixed, paraffin-embedded tissue section.

Optimal staining may require target retrieval treatment with enzymes as well as heating in a suitable buffer before incubation with antibodies and MHC-dextramer.

The sample is stained for DNA using DAPI stain, followed by incubated with an antigen specific MHCdex/FITC reagent, followed by addition of anti-FITC antibody labeled with HRP. Then the substrate for HRP, "DAP" is added and the reaction allows to progress.

The sample is analyzed by light microscopy for the present of a colored precipitate on the cells (DAPI stained nucleus) positive for the specific MHC/dex reagent.

A digital image of the stained sample is obtained, and this can be analyzed manually in the same way as by microscopy. However, a digital image may be used for automatic determination of where and how many cells that are positive, related to the total amount of cells, determined by the DAPI staining, or other criteria or stainings.

Items

The present invention is further disclosed herein below by citation of the following, non-limiting items of the invention.

1. A MHC complex comprising one or more functional MHC molecule(s) capable of binding a peptide P,
wherein, when more than one MHC molecule is present, the MHC complex further comprises a multimerization domain preferably comprising at least one binding entity and/or a carrier,
wherein, when the multimerization domain is present, the more than one functional MHC molecules are attached either to the at least one binding entity and/or to the carrier, wherein, when the more than one functional MHC molecules are attached to the carrier, the MHC molecules are either attached directly to the carrier or attached to the carrier via one or more binding entities.

2. The MHC complex according to item 1, wherein the MHC molecule is a vertebrate MHC molecule such as a human, a murine, a rat, a porcine, a bovine or an avian molecule.

3. The MHC complex according to item 1 or 2, wherein the MHC molecule is a human MHC molecule.

4. The MHC complex according to any one of items 1-3, wherein the MHC molecule is a MHC Class I molecule selected from the group consisting of a heavy chain, a heavy chain combined with a $\beta_2$m, a heavy chain combined with a peptide, and a heavy chain/$\beta_2$m dimer with a peptide;
or a MHC Class II molecule selected from the group consisting of an $\alpha/\beta$ dimer, an $\alpha/\beta$ dimer with a peptide, $\alpha/\beta$ dimer combined through an affinity tag and a $\alpha/\beta$ dimer combined through an affinity tag with a peptide;
or a MHC Class I like molecule or MHC Class II like molecule.

5. The MHC complex according to any one of items 1-4, wherein the MHC molecule is a peptide free MHC molecule.

6. The MHC complex according to any one of items 1-5, wherein more than one MHC molecule is present, and wherein at least two of said MHC molecules are different.

7. The MHC complex according to any one of items 1-5, wherein more than one MHC molecule is present, and wherein the MHC molecules are the same.

8. The MHC complex according to any one of items 1-7, wherein at least two of the peptides harboured by the MHC complexes are different.

9. The MHC complex according to any one of items 1-7, wherein the peptides harboured by the MHC complexes are the same.

10. The MHC complex according to any one of items 1-9, wherein the MHC molecule(s) are attached to the carrier directly.

11. The MHC complex according to any one of items 1-9, wherein the MHC molecule(s) are attached to the carrier via one or more binding entities.

12. The MHC complex according to item 11, wherein each binding entity has attached thereto from 1 to 10 MHC molecules.

13. The MHC complex according to item 11, wherein each binding entity has attached thereto from 1 to 8 MHC molecules.

14. The MHC complex according to item 11, wherein each binding entity has attached thereto from 1 to 6 MHC molecules.

15. The MHC complex according to item 11, wherein each binding entity has attached thereto from 1 to 4 MHC molecules.

16. The MHC complex according to item 11, wherein each binding entity has attached thereto from 1 to 3 MHC molecules.

17. The MHC complex according to item 11, wherein each binding entity has attached thereto 1 or 2 MHC molecules.

18. The MHC complex according to any one of items 1-17, wherein the total number of MHC molecules of the construct is from 1 to 100.

19. The MHC complex according to any one of items 1-17, wherein the total number of MHC molecules of the construct is from 1 to 50.

20. The MHC complex according to any one of items 1-17, wherein the total number of MHC molecules of the construct is from 1 to 25.

21. The MHC complex according to item 1, wherein the binding entity is selected from streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

22. The MHC complex according to any one of items 1-21, further comprising one or more biologically active molecules.

23. The MHC complex according to claim 22, wherein the biologically active molecules is selected from proteins, co-stimulatory molecules, cell modulating molecules, receptors, accessory molecules, adhesion molecules, natural ligands, and toxic molecules, and antibodies and recombinant binding molecules thereto, and combinations thereof.

24. The MHC complex according to items 22 or 23, wherein the biologically active molecule is attached to the carrier either directly or via one or more of the binding entities.

25. The MHC complex according to any one of items 22-24, wherein the biologically active molecule is selected from proteins such as MHC Class I-like proteins like MIC A, MIC B, CD1d, HLA E, HLA F, HLA G, HLA H, ULBP-1, ULBP-2, and ULBP-3,
co-stimulatory molecules such as CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells,
cell modulating molecules such as CD16, NKp30, NKp44, NKp46, NKp80, 2B4, KIR, LIR, CD94/NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin,
accessory molecules such as LFA-1, CD11a/18, CD54 (ICAM-1), CD106 (VCAM), and CD49a,b,c,d,e,f/CD29 (VLA-4),
adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P,
toxic molecules such as cyclophosphamide, methrotrexate, Azathioprine, mizoribine, 15-deoxyspergualin, neomycin, staurosporine, genestein, herbimycin A, *Pseudomonas* exotoxin A, saporin, Rituxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin,
and antibodies thereto, or antibody derivatives or fragments thereof, and combinations thereof.

26. The MHC complex according to any of items 1-25 further comprising one or more labelling compounds.

27. The MHC complex according to item 26, wherein one or more labelling compounds are attached to the carrier.

28. The MHC complex according to item 26, wherein one or more labelling compounds are attached to one or more of the binding entities.

29. The MHC complex according to item 26, wherein one or more labelling compounds are attached to the MHC molecule(s).

30. The MHC complex according to item 26, wherein one or more labelling compounds are attached to the carrier and/or one or more of the binding entities and/or one or more of the MHC molecules.

31. The MHC complex according to any one of items 26-30, wherein the labelling compound is directly or indirectly detectable.

32. The MHC complex according to any of items 26-31, wherein the labelling compound is a fluorescent label, an enzyme label, a radioisotope, a chemiluminescent label, a bioluminescent label, a polymer, a metal particle, a hapten, an antibody, or a dye.

33. The MHC complex according to any one of items 26-32, wherein the labelling compound
is selected from fluorescent labels such as 5-(and 6)-carboxyfluorescein, 5- or 6-carboxyfluorescein, 6-(fluorescein)-5-(and 6)-carboxamido hexanoic acid, fluorescein isothiocyanate (F)TC), rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeston Red, Green fluorescent protein (GFP) and analogues thereof, and conjugates of R-phycoerythrin or allophycoerythrin and e.g. Cy5 or Texas Red, and inorganic fluorescent labels based on semiconductor nanocrystals (like quantum dot and Qdot™ nanocrystals), and time-resolved fluorescent labels based on lanthanides like Eu3+ and Sm3+,
from haptens such as DNP, biotin, and digoxiginin, or
is selected from enzymatic labels such as horse radish peroxidase (HRP), alkaline phosphatase (AP), beta-galactosidase (GAL), glucose-6-phosphate dehydrogenase, beta-N-acetyl-glucosaminidase, β-glucuronidase, invertase, Xanthine Oxidase, firefly luciferase and glucose oxidase (GO), or
is selected from luminescence labels such as luminol, isoluminol, acridinium esters, 1,2-dioxetanes and pyridopyridazines, or
is selected from radioactivity labels such as incorporated isotopes of iodide, cobalt, selenium, tritium, and phosphor.

34. The MHC complex according to any one of items 1-33, wherein the carrier is selected from
polysaccharides including dextrans, carboxy methyl dextran, dextran polyaldehyde, carboxymethyl dextran lactone, and cyclodextrins,
pullulans, schizophyllan, scleroglucan, xanthan, gellan, O-ethylamino guaran, chitins and chitosans including 6-O-carboxymethyl chitin and N-carboxymethyl chitosan,
derivatised cellolosics including carboxymethyl cellulose, carboxymethyl hydroxyethyl cellulose, hydroxyethyl cellulose, 6-amino-6-deoxy cellulose and O-ethylamine cellulose,
hydroxylated starch, hydroxypropyl starch, hydroxyethyl starch, carrageenans, alginates, and agarose, synthetic polysaccharides including ficoll and carboxymethylated ficoll, vinyl polymers including poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinyl-alcohol), poly(vinyl alcohol-co-vinyl chloroacetate), aminated poly (vinyl alcohol), and co block polymers thereof, poly ethylene glycol (PEG) or polypropylene glycol or poly(ethylene oxide-co-propylene oxides) containing polymer backbones including linear, comb-shaped or StarBurst™ dendrimers, poly amino acids including polylysines, polyglutamic acid, polyurethanes, poly(ethylene imines), pluriol.

proteins including albumins, immunoglobulins, and viruslike proteins (VLP), and polynucleotides, DNA, PNA, LNA, oligonucleotides and oligonucleotide dendrimer constructs.

35. The MHC complex according to any one of items 1-34, wherein the carrier is a soluble carrier.

36. The MHC complex according to any one of items 1-35 in soluble form.

37. The MHC complex according to any one of items 1-36 immobilised onto a solid or semi-solid support.

38. The MHC complex according to item 37, immobilised directly to the solid or semi-solid support.

39. The MHC complex according to item 37, immobilised to the solid or semi-solid support via a linker, a spacer, or an antibody, an antibody derivative or a fragment thereof.

40. The MHC complex according to any one of items 37-39, wherein the support is selected from particles, beads, biodegradable particles, sheets, gels, filters, membranes (e.g. nylon membranes), fibres, capillaries, needles, microtitre strips, tubes, plates or wells, combs, pipette tips, micro arrays, and chips.

41. The MHC complex according to item 40, wherein the support is selected from beads and particles.

42. The MHC complex according to item 41, wherein the beads and particles are polymeric beads, polymeric particles, magnetic beads, magnetic particles, supermagnetic beads, or supermagnetic particles.

43. The MHC complex according to any one of items 1-42 for use in a flow cytometric method.

44. The MHC complex according to any one of items 1-42 for use in a histological method.

45. The MHC complex according to any one of items 1-42 for use in a cytological method.

46. A method for detecting the presence of MHC recognising cells in a sample comprising the steps of
(a) providing a sample suspected of comprising MHC recognising cells,
(b) contacting the sample with a MHC complex according to items 1-42, and
(c) determining any binding of the MHC complex, which binding indicates the presence of MHC recognising cells.

47. A method for monitoring MHC recognising cells comprising the steps of
(a) providing a sample suspected of comprising MHC recognising cells,
(b) contacting the sample with a MHC complex according to items 1-42, and
(c) determining any binding of the MHC complex, thereby monitoring MHC recognising cells.

48. A method for establishing a prognosis of a disease involving MHC recognising cells comprising the steps of
(a) providing a sample suspected of comprising MHC recognising cells,
(b) contacting the sample with a MHC complex according to items 1-42, and
(c) determining any binding of the MHC complex, thereby establishing a prognosis of a disease involving MHC recognising cells.

49. A method for determining the status of a disease involving MHC recognising cells comprising the steps of
(a) providing a sample suspected of comprising MHC recognising cells,
(b) contacting the sample with a MHC complex according to items 1-42, and
(c) determining any binding of the MHC complex, thereby determining the status of a disease involving MHC recognising cells.

50. A method for diagnosing a disease involving MHC recognising cells comprising the steps of
(a) providing a sample suspected of comprising MHC recognising cells,
(b) contacting the sample with a MHC complex according to items 1-42, and
(c) determining any binding of the MHC complex, thereby diagnosing a disease involving MHC recognising cells.

51. A method for determining the effectiveness of a medicament against a disease involving MHC recognising cells comprising the steps of
(a) providing a sample from a subject receiving treatment with a medicament,
(b) contacting the sample with a MHC complex according to items 1-42, and
(c) determining any binding of the MHC complex, thereby determining the effectiveness of the medicament.

52. The method according to any one of items 46-51, wherein the MHC recognising cells are involved in a disease of inflammatory, auto-immune, allergic, viral, cancerous, infectious, allo- or xenogene (graft versus host and host versus graft) origin.

53. The method according to item 52, wherein the disease is a chronic inflammatory bowel disease such as Crohn's disease or ulcerative colitis, sclerosis, type I diabetes, rheumatoid arthritis, psoriasis, atopic dermatitis, asthma, malignant melanoma, renal carcinoma, breast cancer, lung cancer, cancer of the uterus, cervical cancer, prostatic cancer, brain cancer, head and neck cancer, leukaemia, cutaneous lymphoma, hepatic carcinoma, colorectal cancer, bladder cancer, rejection-related disease, Graft-versus-host-related disease, or a viral disease associated with hepatitis, AIDS, measles, pox, chicken pox, rubella or herpes.

54. The method according to any one of items 46-53, wherein the MHC recognising cells selected from subpopulations of CD3+ T-cells, gamma,delta T-cells, alpha,beta T-cells, CD4+ T-cells, T helper cells, CD8+ T-cells, Suppressor T-cells, CD8+ cytotoxic T-cells, CTLs, NK cells, NKT cells, LAK cells, and MAK.

55. The method according to any one of items 46-51, wherein the sample is selected from histological material, cytological material, primary tumours, secondary organ metastasis, fine needle aspirates, spleen tissue, bone marrow specimens, cell smears, exfoliative cytological specimens, touch preparations, oral swabs, laryngeal swabs, vaginal swabs, bronchial lavage, gastric lavage, from the umbilical cord, and from body fluids such as blood (e.g. from a peripheral blood mononuclear cell (PBMC) population isolated from blood or from other blood-derived preparations such as leukopheresis products), from sputum samples, expectorates, and bronchial aspirates.

56. The method according to any one of items 46-55, wherein the determination of the binding is carried out by inspection in a microscope, by light, by fluorescence, by electron transmission, or by flow cytometry.

57. The method according to any one of items 46-56, wherein the sample is mounted on a support.

58. The method according to item 57, wherein the support is a solid or semi-solid support.

59. The method according to item 57 or 58, wherein the support is selected from glass slides, microtiter plates having one or more wells, beads, particles, membranes, filters, filter membranes, polymer slides, polymer membranes, chamber slides, dishes, and petridishes.

60. A composition comprising a MHC complex according to any one of items 1-42 in a solubilising medium.

61. The composition according to item 60, wherein the MHC complex comprises peptide filled MHC molecules.

62. The composition according to item 60, wherein the MHC complex comprises peptide free MHC molecules.

63. The composition according to item 62, wherein peptides to fill the peptide free MHC molecules, and the MHC complex comprising peptide free molecules are provided separately.

64. A composition comprising a MHC complex according to any one of items 1-42, wherein the MHC complex is immobilised onto a solid or semi-solid support.

65. The composition according to item 64, wherein the support is selected from glass slides, microtiter plates having one or more wells, beads, particles, membranes, filters, filter membranes, polymer slides, polymer membranes, chamber slides, dishes, and petridishes.

66. The composition according to item 64 or 65, wherein the beads and particles are polymeric beads, polymeric particles, magnetic beads, magnetic particles, supermagnetic beads, or supermagnetic particles.

67. The composition according to item 64, wherein the MHC complex comprises peptide filled MHC molecules.

68. The composition according to item 64, wherein the MHC complex comprises peptide free MHC molecules.

69. The composition according to item 68, wherein peptides to fill the peptide free MHC molecules, and the MHC complex comprising peptide free molecules are provided separately.

70. Use of a MHC complex according to any one of items 1-42 as a detection system.

71. Use of a MHC complex according to any one of items 1-42 for diagnosing a disease involving MHC recognising cells.

72. Use of a MHC complex according to any one of items 1-42 for monitoring a disease involving MHC recognising cells.

73. Use of a MHC complex according to any one of items 1-42 for establishing a prognosis for a disease involving MHC recognising cells.

74. Use of a MHC complex according to any one of items 1-42 for determining the status of a disease involving MHC recognising cells.

75. Use of a MHC complex according to any one of items 1-42 for determining the effectiveness of a medicament against a disease involving MHC recognising cells.

76. Use according to any one of items 71, wherein the MHC recognising cells are involved in a disease of inflammatory, auto-immune, allergic, viral, cancerous, infectious, allo- or xenogene (graft-versus-host and host-versus-graft) origin.

77. Use according to item 76, wherein the disease is a chronic inflammatory bowel disease such as Crohn's disease or ulcerative colitis, sclerosis, type I diabetes, rheumatoid arthritis, psoriasis, atopic dermatitis, asthma, malignant melanoma, renal carcinoma, breast cancer, lung cancer, cancer of the uterus, cervical cancer, prostatic cancer, brain cancer, head and neck cancer, leukaemia, cutaneous lymphoma, hepatic carcinoma, colorectal cancer, bladder cancer, rejection-related disease, Graft-versus-host-related disease, or a viral disease associated with hepatitis, AIDS, measles, pox, chicken pox, rubella or herpes.

78. Use according to any one of items 70-77, wherein the MHC recognising cells are selected from subpopulations of CD3+ T-cells, gamma,delta T-cells, alpha,beta T-cells, CD4+ T-cells, T helper cells, CD8+ T-cells, Suppressor T-cells, CD8+ cytotoxic T-cells, CTLs, NK cells, NKT cells, LAK cells, and MAK.

79. The MHC complex according to any one of items 1-42 for use as a therapeutic composition.

80. The MHC complex according to any one of items 1-42 for use in in vivo therapy.

81. The MHC complex according to any one of items 1-42 for use in ex vivo therapy.

82. A therapeutic composition comprising as active ingredient a MHC complex as defined in any one of items 1-42.

83. The therapeutic composition according to item 82, wherein the MHC complex is immobilised to a biodegradable solid or semi-solid support.

84. The therapeutic composition according to item 82 or 83, wherein the MHC complex comprises
a carrier having attached thereto one or more MHC molecules, said MHC molecules being attached to the carrier either directly or via one or more binding entities.

85. The therapeutic composition according to item 82 or 83, wherein the MHC molecule is a vertebrate MHC molecule such as a human, a murine, a rat, a porcine, a bovine or an avian molecule.

86. The therapeutic composition according to any one of items 82-85, wherein the MHC molecule is a human MHC molecule.

87. The therapeutic composition according to any one of items 82-86, wherein the MHC molecule is
a MHC Class I molecule selected from the group consisting of a heavy chain, a heavy chain combined with a $\beta_2$m, a heavy chain combined with a peptide, and a heavy chain/ $\square_2$m dimer with a peptide;
or a MHC Class II molecule selected from the group consisting of an $\alpha/\beta$ dimer, an $\alpha/\beta$ dimer with a peptide, $\alpha/\beta$ dimer combined through an affinity tag and a $\alpha/\beta$ dimer combined through an affinity tag with a peptide
or a MHC Class I like molecule or a MHC Class II like molecule.

88. The therapeutic composition according to any one of items 82-87, wherein the MHC molecule is a peptide free MHC molecule.

89. The therapeutic composition according to any one of items 82-88, wherein at least two of the MHC molecules are different.

90. The therapeutic composition according to any one of items 82-88, wherein the MHC molecules are the same.

91. The therapeutic composition according to any one of items 82-88, wherein at least two of the peptides harboured by the MHC molecules are different.

92. The therapeutic composition according to any one of items 82-88, wherein the peptides harboured by the MHC molecules are the same.

93. The therapeutic composition according to any one of items 82-92, wherein the MHC molecules are attached to the carrier directly.

94. The therapeutic composition according to any one of items 82-92, wherein the MHC molecules are attached to the carrier via one or more binding entities.

95. The therapeutic composition according to item 94, wherein each binding entity has attached thereto from 1 to 10 MHC molecules.

96. The therapeutic composition according to item 94, wherein each binding entity has attached thereto from 1 to 8 MHC molecules.

97. The therapeutic composition according to item 94, wherein each binding entity has attached thereto from 1 to 6 MHC molecules.

98. The therapeutic composition according to item 94, wherein each binding entity has attached thereto from 1 to 4 MHC molecules.

99. The therapeutic composition according to item 94, wherein each binding entity has attached thereto from 1 to 3 MHC molecules.

100. The therapeutic composition according to item 94, wherein each binding entity has attached thereto 1 or 2 MHC molecules.

101. The therapeutic composition according to any one of items 82-100, wherein the total number of MHC molecules of the construct is from 1 to 100.

102. The therapeutic composition according to any one of items 82-100, wherein the total number of MHC molecules of the construct is from 1 to 50.

103. The therapeutic composition according to any one of items 82-100, wherein the total number of MHC molecules of the construct is from 1 to 25.

104. The therapeutic composition according to item 94, wherein the binding entity is selected from streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

105. The therapeutic composition according to any one of items 82-104 further comprising one or more biologically active molecules.

106. The therapeutic composition according to item 105, wherein the biologically active molecules is selected from proteins, co-stimulatory molecules, cell modulating molecules, receptors, accessory molecules, adhesion molecules, natural ligands, and toxic molecules, and antibodies and recombinant binding molecules thereto, and combinations thereof.

107. The therapeutic composition according to item 105 or 106, wherein the biologically active molecule is attached to the carrier either directly or via one or more of the binding entities.

108. The therapeutic composition according to any one of items 105-107, wherein the biologically active molecule is selected from proteins such as MHC Class I-like proteins like MIC A, MIC B, CD1d, HLA E, HLA F, HLA G, HLA H, ULBP-1, ULBP-2, and ULBP-3, co-stimulatory molecules such as CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells, cell modulating molecules such as CD16, NKp30, NKp44, NKp46, NKp80, 2B4, KIR, LIR, CD94/NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin, accessory molecules such as LFA-1, CD11a/18, CD54 (ICAM-1), CD106 (VCAM), and CD49a,b,c,d,e,f/CD29 (VLA-4), adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P, toxic molecules such as cyclophosphamide, methrotrexate, Azathioprine, mizoribine, 15-deoxuspergualin, neomycin, staurosporine, genestein, herbimycin A, *Pseudomonas* exotoxin A, saporin, Rituxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin, and antibodies thereto, or antibody derivatives or fragments thereof, and combinations thereof.

109. The therapeutic composition according to any one of items 82-108, wherein the carrier is selected from polysaccharides including dextrans, carboxy methyl dextran, dextran polyaldehyde, carboxymethyl dextran lactone, and cyclodextrins, pullulans, schizophyllan, scleroglucan, xanthan, gellan, O-ethylamino guaran, chitins and chitosans including 6-O-carboxymethyl chitin and N-carboxymethyl chitosan, derivatised cellolosics including carboxymethyl cellulose, carboxymethyl hydroxyethyl cellulose, hydroxyethyl cellulose, 6-amino-6-deoxy cellulose and O-ethylamine cellulose, hydroxylated starch, hydroxypropyl starch, hydroxyethyl starch, carrageenans, alginates, and agarose, synthetic polysaccharides including ficoll and carboxymethylated ficoll, vinyl polymers including poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinyl-alcohol), poly(vinyl alcohol-co-vinyl chloroacetate), aminated poly(vinyl alcohol), and co block polymers thereof, poly ethylene glycol (PEG) or polypropylene glycol or poly(ethylene oxide-co-propylene oxides) containing polymer backbones including linear, comb-shaped or Star-Burst™ dendrimers, poly amino acids including polylysines, polyglutamic acid, polyurethanes, poly(ethylene imines), pluriol.

proteins including albumins, immunoglobulins, and virus-like proteins (VLP), and polynucleotides, DNA, PNA, LNA, oligonucleotides and oligonucleotide dendrimer constructs.

110. The therapeutic composition according to any one of items 82-109, wherein the carrier is a soluble carrier.

111. The therapeutic composition according to any one of items 82-110 further comprising one or more adjuvants and/or excipients.

112. The therapeutic composition according to item 111, wherein the adjuvant is selected from saponins such as Quil A and Qs-21, oil in water emulsions such as MF59, MPL, PLG, PLGA, aluminium salts, calcium phosphate, water in oil emulsions such as IFA (Freund's incomplete adjuvant) and CFA (Freund's complete adjuvant), interleukins such as IL-1β, IL-2, IL-7, IL-12, and INFγ, Adju-Phos®, glucan, antigen formulation, biodegradable microparticles, Cholera Holotoxin, liposomes, DDE, DHEA, DMPC, DMPG, DOC/Alum Complex, ISCOMs®, muramyl dipeptide, monophosphoryl lipid A, muramyl tripeptide, and phospatidylethanolamine In a preferred embodiment, the adjuvant is selected from saponins such as Quil A and Qs-21, MF59, MPL, PLG, PLGA, calcium phosphate, and aluminium salts.

113. The therapeutic composition according to item 113, wherein the excipient is selected from diluents, buffers, suspending agents, wetting agents, solubilising agents, pH-adjusting agents, dispersing agents, preserving agents, and/or colorants.

114. The therapeutic composition according to any one of items 82-113 for the treatment, prevention, stabilisation, or alleviation of disease involving MHC recognising cells.

115. The therapeutic composition according to item 114, wherein the MHC recognising cells are involved in a disease of inflammatory, auto-immune, allergic, viral, cancerous, infectious, allo- or xenogene (graft versus host and host versus graft) origin.

116. The therapeutic composition according to item 115, wherein the disease is a chronic inflammatory bowel disease such as Crohn's disease or ulcerative colitis, sclerosis, type I diabetes, rheumatoid arthritis, psoriasis, atopic dermatitis, asthma, malignant melanoma, renal carcinoma, breast cancer, lung cancer, cancer of the uterus, prostatic cancer, brain cancer, head and neck cancer, leukaemia, cutaneous lymphoma, hepatic carcinoma, colorectal cancer, bladder cancer, rejection-related disease, Graft-versus-host-related disease, or a viral disease associated with hepatitis, AIDS, measles, pox, chicken pox, rubella or herpes.

117. The therapeutic composition according to any one of items 82-116 formulated for parenteral administration, including intravenous, intramuscular, intraarticular, subcutaneous, intradermal, epicutantous/transdermal, and intraperitoneal administration, for infusion, for oral administration, for nasal administration, for rectal administration, or for topic administration.

118. A therapeutic composition comprising as active ingredient an effective amount of MHC recognising cells, the MHC recognising cells being obtained by
bringing a sample from a subject comprising MHC recognising cells into contact with the MHC complex according to any one of items 1-42, whereby the MHC recognising cells become bound to the MHC complex,
isolating the bound MHC complex and the MHC recognising cells, and
expanding such MHC recognising cells to a clinically relevant number.

119. The therapeutic composition according to item 118, wherein the isolated MHC recognising cells are liberated from the MHC complex prior to expansion.

120. The therapeutic composition according to items 118 or 119, wherein the MHC complex is immobilised onto a solid or semi-solid support.

121. The therapeutic composition according to item 120, wherein the MHC complex is immobilised onto the solid or semi-solid support prior to contact with the sample.

122. The therapeutic composition according to item 120, wherein the MHC complex is immobilised onto the solid or semi-solid support following contact with the sample.

123. The therapeutic composition according to any one of items 118-122, wherein the expansion is carried out in the presence of one or more MHC complexes, optionally one or more biologically active molecules and optionally feeder cells such as dendritic cells or feeder cells.

124. The therapeutic composition according to any one of items 120-123, wherein the MHC complex is immobilised onto the solid or semi-solid support directly.

125. The therapeutic composition according to any one of items 120-124, wherein the MHC complex is immobilised to the solid or semi-solid support via a linker, a spacer, or an antibody, an antibody derivative or a fragment thereof.

126. The therapeutic composition according to any one of items 120-125, wherein the solid or semi-solid support is selected from particles, beads, biodegradable particles, sheets, gels, filters, membranes, fibres, capillaries, needles, microtitre strips, tubes, plates or wells, combs, pipette tips, micro arrays, chips, and microtiter plates having one or more wells.

127. The therapeutic composition according to any one of items 120-126, wherein the solid support is selected from particles and beads.

128. The therapeutic composition according to item 127, wherein the particles and beads are polymeric, magnetic or superparamagnetic.

129. The therapeutic composition according to any one of items 118-128, wherein the isolation is performed by applying a magnetic field or by flow cytometry.

130. The therapeutic composition according to any one of items 118-128, wherein the MHC complex comprises
a carrier having attached thereto one or more MHC molecules, said MHC molecules being attached to the carrier either directly or via one or more binding entities.

131. The therapeutic composition according to any one of items 118-130, wherein the MHC molecule is a vertebrate MHC molecule such as a human, a murine, a rat, a porcine, a bovine or an avian molecule.

132. The therapeutic composition according to any one of items 118-131, wherein the MHC molecule is a human MHC molecule.

133. The therapeutic composition according to any one of items 118-132, wherein the MHC molecule is
a MHC Class I molecule selected from the group consisting of a heavy chain, a heavy chain combined with a $\square_2$m, a heavy chain combined with a peptide, and a heavy chain/$\square_2$m dimer with a peptide;
or a MHC Class II molecule selected from the group consisting of an $\bar\alpha\square$ dimer, an $\bar\alpha\square$ dimer with a peptide, $\square\square$dimer combined through an affinity tag and a $\square\square$dimer combined through an affinity tag with a peptide;
or a MHC Class I like molecule or a MHC Class II molecule.

134. The therapeutic composition according to any one of items 118-133, wherein the MHC molecule is a peptide free MHC molecule.

135. The therapeutic composition according to any one of items 118-134, wherein at least two of the MHC molecules are different.

136. The therapeutic composition according to any one of items 118-135, wherein the MHC molecules are the same.

137. The therapeutic composition according to any one of items 118-136, wherein at least two of the peptides harboured by the MHC molecules are different.

138. The therapeutic composition according to any one of items 118-137, wherein the peptides harboured by the MHC molecules are the same.

139. The therapeutic composition according to any one of items 118-138, wherein the MHC molecules are attached to the carrier directly.

140. The therapeutic composition according to any one of items 118-138, wherein the MHC molecules are attached to the carrier via one or more binding entities.

141. The therapeutic composition according to item 140, wherein each binding entity has attached thereto from 1 to 10 MHC molecules.

142. The therapeutic composition according to item 140, wherein each binding entity has attached thereto from 1 to 8 MHC molecules.

143. The therapeutic composition according to item 140, wherein each binding entity has attached thereto from 1 to 6 MHC molecules.

144. The therapeutic composition according to item 140, wherein each binding entity has attached thereto from 1 to 4 MHC molecules.

145. The therapeutic composition according to item 140, wherein each binding entity has attached thereto from 1 to 3 MHC molecules.

146. The therapeutic composition according to item 140, wherein each binding entity has attached thereto 1 or 2 MHC molecules.

147. The therapeutic composition according to any one of items 118-146, wherein the total number of MHC molecules of the construct is from 1 to 100.

148. The therapeutic composition according to any one of items 118-146, wherein the total number of MHC molecules of the construct is from 1 to 50.

149. The therapeutic composition according to any one of items 118-146, wherein the total number of MHC molecules of the construct is from 1 to 25.

150. The therapeutic composition according to item 140, wherein the binding entity is selected from streptavidin streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

151. The therapeutic composition according to any one of items 118-150 further comprising one or more biologically active molecules.

152. The therapeutic composition according to item 151, wherein the biologically active molecules is selected from proteins, co-stimulatory molecules, cell modulating molecules, receptors, accessory molecules, adhesion molecules, natural ligands, and toxic molecules, and antibodies and recombinant binding molecules thereto, and combinations thereof.

153. The therapeutic composition according to item 150 or 151, wherein the biologically active molecule is attached to the carrier either directly or via one or more of the binding entities.

154. The therapeutic composition according to any one of items 151-153, wherein the biologically active molecule is selected from
proteins such as MHC Class I-like proteins like MICA, MIC B, CD1d, HLA E, HLA F, HLA G, HLA H, ULBP-1, ULBP-2, and ULBP-3,
co-stimulatory molecules such as CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells,
cell modulating molecules such as CD16, NKp30, NKp44, NKp46, NKp80, 2B4, KIR, LIR, CD94/NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin,
accessory molecules such as LFA-1, CD11a/18, CD54 (ICAM-1), CD106 (VCAM), and CD49a,b,c,d,e,f/CD29 (VLA-4), adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P,
toxic molecules such as cyclophosphamide, methrotrexate, Azathioprine, mizoribine, 15-deoxuspergualin, neomycin, staurosporine, genestein, herbimycin A, *Pseudomonas* exotoxin A, saporin, Rituxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin,
and antibodies thereto, or antibody derivatives or fragments thereof, and combinations thereof.

155. The therapeutic composition according to any one of items 118-154, wherein the carrier is selected from
polysaccharides including dextrans, carboxy methyl dextran, dextran polyaldehyde, carboxymethyl dextran lactone, and cyclodextrins,
pullulans, schizophyllan, scleroglucan, xanthan, gellan, O-ethylamino guaran, chitins and chitosans including 6-O-carboxymethyl chitin and N-carboxymethyl chitosan,
derivatised cellolosics including carboxymethyl cellulose, carboxymethyl hydroxyethyl cellulose, hydroxyethyl cellulose, 6-amino-6-deoxy cellulose and O-ethylamine cellulose,
hydroxylated starch, hydroxypropyl starch, hydroxyethyl starch, carrageenans, alginates, and agarose,
synthetic polysaccharides including ficoll and carboxymethylated ficoll,
vinyl polymers including poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinyl-alcohol), poly(vinyl alcohol-co-vinyl chloroacetate), aminated poly(vinyl alcohol), and co block polymers thereof, poly ethylene glycol (PEG) or polypropylene glycol or poly(ethylene oxide-co-propylene oxides) containing polymer backbones including linear, comb-shaped or StarBurst™ dendrimers, poly amino acids including polylysines, polyglutamic acid, polyurethanes, poly(ethylene imines), pluriol.

proteins including albumins, immunoglobulins, and virus-like proteins (VLP), and polynucleotides, DNA, PNA, LNA, oligonucleotides and oligonucleotide dendrimer constructs.

156. The therapeutic composition according to any one of items 118-155 further comprising one or more labelling compounds.

157. The therapeutic composition according to item 156, wherein one or more labelling compounds are attached to the carrier.

158. The therapeutic composition according to item 156, wherein one or more labelling compounds are attached to one or more of the binding entities.

159. The therapeutic composition according to item 156, wherein one or more labelling compounds are attached to the one or more MHC molecules.

160. The therapeutic composition according to item 156, wherein one or more labelling compounds are attached to the carrier and/or one or more of the binding entities and/or one or more of the MHC molecules.

161. The therapeutic composition according to any one of items 156-160, wherein the labelling compound is directly or indirectly detectable.

162. The therapeutic composition according to any one of items 156-161, wherein the labelling compound is a fluorescent label, an enzyme label, a radioisotope, a chemiluminescent label, a bioluminescent label, a polymer, a metal particle, a hapten, an antibody, or a dye.

163. The therapeutic composition according to any one of items 156-162, wherein the labelling compound is selected from fluorescent labels such as 5-(and 6)-carboxyfluorescein, 5- or 6-carboxyfluorescein, 6-(fluorescein)-5-(and 6)-carboxamido hexanoic acid, fluorescein isothiocyanate (FITC), rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, Green fluorescent protein (GFP) and analogues thereof, and conjugates of R-phycoerythrin or allophycoerythrin and e.g. Cy5 or Texas Red, and inorganic fluorescent labels based on semiconductor nanocrystals (like quantum dot and Qdot™ nanocrystals), and time-resolved fluorescent labels based on lanthanides like Eu3+ and Sm3+, from haptens such as DNP, biotin, and digoxiginin, or is selected from haptens such as DNP, fluorescein isothiocyanate (FITC), biotin, and digoxiginin, or is selected from enzymatic labels such as horse radish peroxidase (HRP), alkaline phosphatase (AP), beta-galactosidase (GAL), glucose-6-phosphate dehydrogenase, beta-N-acetyl-glucosaminidase, β-glucuronidase, invertase, Xanthine Oxidase, firefly luciferase and glucose oxidase (GO), or is selected from luminescence labels such as luminol, isoluminol, acridinium esters, 1,2-dioxetanes and pyridopyridazines, or is selected from radioactivity labels such as incorporated isotopes of iodide, cobalt, selenium, tritium, and phosphor.

164. The therapeutic composition according to any one of items 118-163, wherein the carrier is a soluble carrier.

165. The therapeutic composition according to any one of items 118-164 further comprising one or more excipients.

166. The therapeutic composition according to items 165, wherein the excipient is selected from diluents, buffers, suspending agents, wetting agents, solubilising agents, pH-adjusting agents, dispersing agents, preserving agents, and/or colorants.

167. The therapeutic composition according to any one of items 118-166 for the treatment, prevention, stabilisation, or alleviation of a disease involving MHC recognising cells.

168. The therapeutic composition according to item 167, wherein MHC recognising cells are involved in a disease of inflammatory, auto-immune, allergic, viral, cancerous, infectious, allo- or xenogene (graft versus host and host versus graft) origin.

169. The therapeutic composition according to item 167 or 168, wherein the disease is a chronic inflammatory bowel disease such as Crohn's disease or ulcerative colitis, sclerosis, type I diabetes, rheumatoid arthritis, psoriasis, atopic dermatitis, asthma, malignant melanoma, renal carcinoma, breast cancer, lung cancer, cancer of the uterus, prostatic cancer, brain cancer, head and neck cancer, leukaemia, cutaneous lymphoma, hepatic carcinoma, colorectal cancer, bladder cancer, rejection-related disease, Graft-versus-host-related disease, or a viral disease associated with hepatitis, AIDS, measles, pox, chicken pox, rubella or herpes.

170. The therapeutic composition according to any one of items 118-169 formulated for parenteral administration, including intravenous, intramuscular, intraarticular, subcutaneous, intradermal, epicutantous/transdermal, and intraperitoneal administration, for infusion, for oral administration, for nasal administration, for rectal administration, or for topic administration.

171. The therapeutic composition according to any one of items 82-170 for use in in vivo therapy.

172. A method of treating an animal, including a human being, comprising administering a therapeutic composition according to any one of items 82-170 in an effective amount.

173. A method of up-regulating, down-regulating, modulate an immune response in an animal, including a human being, comprising administering a therapeutic composition according to any one of items 82-170 in an effective amount.

174. A method of inducing anergy of a cell in an animal, including a human being, comprising administering a therapeutic composition according to any one of items 82-170 in an effective amount.

175. An adoptive cellular immunotherapeutic method comprising administrating to an animal, including a human being, a therapeutic composition according to any one of items 82-170.

176. A method of obtaining MHC recognising cells comprising bringing into contact a MHC complex according to any one of items 1-42 and a sample suspected of comprising MHC recognising cells under conditions whereby the MHC recognising cells bind to the MHC complex, and isolating the bound MHC complex and MHC recognising cells.

177. The method according to item 176, wherein the isolation is carried out by applying a magnetic field or by flow cytometry.

178. A method for producing a therapeutic composition according to any one of items 82-170, comprising providing a MHC complex as defined in items 1-42, solubilising or dispersing the MHC complex in a medium suitable for therapeutic substances,
and optionally adding other adjuvants and/or excipients.

179. A method for producing a therapeutic composition according to any one of items 118-170, comprising
obtaining MHC recognising cells using a MHC complex according to any one of items 1-42,
expanding such MHC recognising cells to a clinically relevant number,
formulating the obtained cells in a medium suitable for administration, and
optionally adding adjuvants and/or excipients.

180. Use of a MHC complex according to any one of items 1-42 for ex vivo expansion of MHC recognising cells.

181. Use according to item 180, wherein the MHC complex is in soluble form.

182. Use according to item 180, wherein the MHC complex is immobilised onto a solid or semi-solid support.

183. Use according to item 182, wherein the solid or semi-solid support is selected from particles, beads, biodegradable particles, sheets, gels, filters, membranes (e.g. nylon membranes), fibres, capillaries, needles, microtitre strips, tubes, plates or wells, combs, pipette tips, micro arrays, chips, and slides.

184. Use according to item 182 or 183, wherein the solid or semi-solid support is selected from beads and particles.

185. Use according to item 184, wherein the solid or semi-solid support is selected from polymeric, magnetic or superparamagnetic particles and beads.

186. Use according to any one of items 180-185, wherein the MHC complex further comprises one or more biologically active molecules.

187. Use according to any one of items 180-186, wherein the biologically active molecule is selected from
proteins such as MHC Class I-like proteins like MIC A, MIC B, CD1d, HLA E, HLA F, HLA G, HLA H, ULBP-1, ULBP-2, and ULBP-3,
co-stimulatory molecules such as CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells,
cell modulating molecules such as CD16, NKp30, NKp44, NKp46, NKp80, 2B4, KIR, LIR, CD94/NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin,
accessory molecules such as LFA-1, CD11a/18, CD54 (ICAM-1), CD106 (VCAM), and CD49a,b,c,d,e,f/CD29 (VLA-4),
adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P, toxic molecules such as cyclophosphamide, methrotrexate, Azathioprine, mizoribine, 15-deoxuspergualin, neomycin, staurosporine, genestein, herbimycin A, *Pseudomonas* exotoxin A, saporin, Rituxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin,
and antibodies thereto, or antibody derivatives or fragments thereof, and combinations thereof.

187. Use of a MHC molecule in a histological method.

188. Use of a MHC molecule in a cytological method.

189. Use of a MHC molecule according to item 187 or 188 in a method for determining the presence of MHC recognising cells in a sample, in which method the MHC recognising cells of the sample are mounted on a support.

190. Use of a MHC molecule according to item 187 or 188, in a method for monitoring the presence of MHC recognising cells in a sample, in which method the MHC recognising cells of the sample are mounted on a support.

191. Use of a MHC molecule according to item 187 or 188 in a method for determining the status of a disease involving MHC recognising cells, in which method the MHC recognising cells of the sample are mounted on a support.

192. Use of a MHC molecule according to item 187 or 188 in a method for establishing a prognosis of a disease involving MHC recognising cells, in which method the MHC recognising cells of the sample are mounted on a support.

193. Use of a MHC molecule according to any one of items 187-192, wherein the support is a solid or semi-solid support.

194. Use of a MHC molecule according to any one of items 187-193, wherein the support is selected from glass slides, membranes, filters, polymer slides, chamber slides, dishes, and petridishes.

195. Use according to any one of items 187-194, wherein the sample is selected from histological material, cytological material, primary tumours, secondary organ metastasis, fine needle aspirates, spleen tissue, bone marrow specimens, cell smears, exfoliative cytological specimens, touch preparations, oral swabs, laryngeal swabs, vaginal swabs, bronchial lavage, gastric lavage, from the umbilical cord, and from body fluids such as blood (e.g. from a peripheral blood mononuclear cell (PBMC) population isolated from blood or from other blood-derived preparations such as leukopheresis products), from sputum samples, expectorates, and bronchial aspirates.

196. The use according to any one of items 187-195, wherein the MHC molecule is
a MHC Class I molecule selected from the group consisting of a heavy chain, a heavy chain combined with a $\square_2$m, a heavy chain combined with a peptide, and a heavy chain/$\square_2$m dimer with a peptide;
or a MHC Class II molecule selected from the group consisting of an α/$\square$dimer, an α/$\square$ dimer with a peptide, $\square$/$\square$ dimer combined through an affinity tag and a $\square$/$\square$ dimer combined through an affinity tag with a peptide;
or a MHC Class I like molecule or a MHC Class II like molecule.

197. The use according to any one of items 187-196, wherein the MHC molecule is a vertebrate MHC molecule such as a human, a murine, a rat, a porcine, a bovine or an avian molecule.

198. The use according to any one of items 187-197, wherein the MHC molecule is a human MHC molecule.

199. The use according to any one of items 187-198, wherein the MHC molecule is a peptide free MHC molecule.

200. The use according to any one of items 187-199, wherein the MHC molecule is attached to a binding entity.

201. Use according to item 200, wherein the binding entity has attached thereto from 1 to 10 MHC molecules, such as from 1 to 9, from 1 to 8, from 1 to 7, from 1 to 6, from 1 to 5, from 1 to 4, from 1 to 3, or 1 or 2 MHC molecules.

202. Use according to item 200, wherein the binding entity is selected from streptavidin streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

203. Use according to any one of items 187-202, wherein the MHC molecule further comprises a labelling compound.

204. Use according to item 203, wherein the labelling compound can be detected directly or indirectly.

205. Use according to item 203 or 204, wherein the labelling compound is a fluorescent label, an enzyme label, a radioisotope, a chemiluminescent label, a bioluminescent label, a polymer, a metal particle, a hapten, an antibody, or a dye.

206. Use according to any one of items 203-205, wherein the labelling compound is selected from
5-(and 6)-carboxyfluorescein, 5- or 6-carboxyfluorescein, 6-(fluorescein)-5-(and 6)-carboxamido hexanoic acid, fluorescein isothiocyanate (FITC), rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, Green fluorescent protein (GFP) and analogues thereof, and conjugates of R-phycoerythrin or allophycoerythrin and e.g. Cy5 or Texas Red, and inorganic fluorescent labels based on semiconductor nanocrystals (like quantum dot and Qdot™ nanocrystals), and time-resolved fluorescent labels based on lanthanides like Eu3+ and Sm3+,
from haptens such as DNP, biotin, and digoxiginin, or
is selected from enzymatic labels such as horse radish peroxidase (HRP), alkaline phosphatase (AP), beta-galactosidase (GAL), glucose-6-phosphate dehydrogenase, beta-N-acetyl-glucosaminidase, β-glucuronidase, invertase, Xanthine Oxidase, firefly luciferase and glucose oxidase (GO), or
is selected from luminiscence labels such as luminol, isoluminol, acridinium esters, 1,2-dioxetanes and pyridopyridazines, or
is selected from radioactivity labels such as incorporated isotopes of iodide, cobalt, selenium, tritium, and phosphor.

207. The use according to any one of items 203-206, wherein the labelling compound is attached to the MHC molecule and/or the binding entity.

208. A method for detecting the presence of MHC recognising cells in a sample comprising the steps of
(a) providing a sample suspected of comprising MHC recognising cells mounted on a support,
(b) contacting the sample with a MHC molecule as defined in items 187-207, and
(c) determining any binding of the MHC molecule, which binding indicates the presence of MHC recognising cells.

209. A method for monitoring MHC recognising cells comprising the steps of
(a) providing a sample suspected comprising MHC recognising cells mounted on a support,
(b) contacting the sample with a MHC molecule as defined in items 187-207, and
(c) determining any binding of the MHC molecule, thereby monitoring MHC recognising cells.

210. A method for the prognosis of a disease involving MHC recognising cells comprising the steps of
(a) providing a sample suspected comprising MHC recognising cells mounted on a support,
(b) contacting the sample with a MHC molecule as defined in items 187-207, and
(c) determining any binding of the MHC molecule, thereby establishing a prognosis of a disease involving MHC recognising cells.

211. A method for determining the status of a disease involving MHC recognising cells comprising the steps of
(a) providing a sample suspected comprising MHC recognising cells mounted on a support,
(b) contacting the sample with a MHC molecule as defined in items 187-207, and
(c) determining any binding of the MHC molecule, thereby determining the status of a disease involving MHC recognising cells.

212. A method for the diagnosis of a disease involving MHC recognising cells comprising the steps of
(a) providing a sample suspected comprising MHC recognising cells mounted on a support,
(b) contacting the sample with a MHC molecule as defined in items 187-207, and
(c) determining any binding of the MHC molecule, thereby diagnosing a disease involving MHC recognising cells.

213. A method for the effectiveness of a medicament against a disease involving MHC recognising cells comprising the steps of
(a) providing a sample from a subject receiving treatment with a medicament mounted on a support,
(b) contacting the sample with a MHC molecule as defined in items 187-207, and
(c) determining any binding of the MHC molecule, thereby determining the effectiveness of the medicament.

214. The method according to any one of items 208-213, wherein the MHC recognising cells are involved in a disease of inflammatory, auto-immune, allergic, viral, cancerous, infectious, allo- or xenogene (graft-versus-host and host-versus-graft) origin.

215. The method according to item 214, wherein the disease is a chronic inflammatory bowel disease such as Crohn's disease or ulcerative colitis, sclerosis, type I diabetes, rheumatoid arthritis, psoriasis, atopic dermatitis, asthma, malignant melanoma, renal carcinoma, breast cancer, lung cancer, cancer of the uterus, cervical cancer, prostatic cancer, brain cancer, head and neck cancer, leukaemia, cutaneous lymphoma, hepatic carcinoma, colorectal cancer, bladder cancer, rejection-related disease, Graft-versus-host-related disease, or a viral disease associated with hepatitis, AIDS, measles, pox, chicken pox, rubella or herpes.

216. The method according to any one of items 208-214, wherein the MHC recognising cells are selected from sub-populations of CD3+ T-cells, gamma,delta T-cells, alpha, beta T-cells, CD4+ T-cells, T helper cells, CD8+ T-cells, Suppressor T-cells, CD8+ cytotoxic T-cells, CTLs, NK cells, NKT cells, LAK cells, and MAK.

217. The method or use according to any one of items 201-216, wherein the sample is selected from histological material, cytological material, primary tumours, secondary organ metastasis, fine needle aspirates, spleen tissue, bone marrow specimens, cell smears, exfoliative cytological specimens, touch preparations, oral swabs, laryngeal swabs, vaginal swabs, bronchial lavage, gastric lavage, from the umbilical cord, and from body fluids such as blood (e.g. from a peripheral blood mononuclear cell (PBMC) population isolated from blood or from other blood-derived preparations such as R

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10336808B2). An electronic copy of the "Sequence Listing" will also be available from the USPTO upon request and payment of the fee set forth in 37 CFR 1.19(b)(3).

The invention claimed is:

1. An isolated MHC multimer comprising $(a-b-P)_n$,
wherein n>1,
wherein a and b together form a functional MHC protein which is bound to the peptide P,
wherein (a-b-P) is the MHC peptide complex formed when the peptide P is bound to the functional MHC protein,
wherein each MHC peptide complex of the MHC multimer is associated with one or more multimerization domains selected from the group consisting of scaffolds, carriers, optionally substituted organic molecules, membranes, liposomes or micelles, polymers, polysaccharides, dextran moieties, IgG domains, coiled-coil polypeptide structures, DNA duplexes, nucleic acid duplexes, PNA-PNA, PNA-DNA, DNA-RNA, avidins, streptavidins, antibodies, small organic molecules, proteins, a solid support, and biological polymers, with the proviso that the one or more multimerization domains is not a cell,
wherein each MHC protein is an MHC class I molecule encoded by an HLA-A*02 allele, and
wherein in at least one MHC peptide complex, the sequence of P originates from a *Borrelia* OspC antigen, is capable of binding said MHC class I molecule encoded by an HLA-A*02 allele, and is selected from the group consisting of SEQ ID NOS:49735, 49739, 49779, 49795, 49921, and 49937.

2. The isolated MHC multimer according to claim 1, wherein n is in the range from 8 to 25.

3. The isolated MHC multimer according to claim 1, wherein n>10.

4. The isolated MHC multimer according to claim 1, wherein the MHC multimer comprises one or more covalently or non-covalently attached labels, and wherein said one or more labels can be selected from the group consisting of fluorescent labels, fluorophores, enzymes, radioisotopes, chemiluminescent labels, dyes, bioluminescent labels, metal particles, haptens, polymers, and antibodies.

5. A composition comprising a plurality of MHC multimers according to claim 1 and a carrier, wherein the MHC multimers are identical.

6. A composition comprising a plurality of MHC multimers according to claim 1 and a carrier, wherein the MHC multimers are different.

7. A kit comprising a MHC multimer according to claim 1, a positive control, and/or instructions for use.

8. The isolated MHC multimer according to claim 1, wherein the HLA*02 allele is selected from the group consisting of HLA-A*0201, HLA-A*0202, HLA-A*0203, HLA-A*0206, HLA-A*0211, HLA-A*0212, HLA-A*0216, HLA-A*0217, HLA-A*0219, and HLA-A*0250.

* * * * *